US010913727B2

(12) United States Patent
Pliushchev et al.

(10) Patent No.: US 10,913,727 B2
(45) Date of Patent: Feb. 9, 2021

(54) MODULATORS OF THE INTEGRATED STRESS PATHWAY

(71) Applicants: Calico Life Sciences LLC, South San Francisco, CA (US); AbbVie Inc., North Chicago, IL (US)

(72) Inventors: Marina Pliushchev, Vernon Hills, IL (US); Jennifer M. Frost, Gurnee, IL (US); Lawrence A. Black, Lahaina, HI (US); Xiangdong Xu, Vernon Hills, IL (US); Ramzi Farah Sweis, Lake Bluff, IL (US); Lei Shi, Vernon Hills, IL (US); Qingwei I. Zhang, Libertyville, IL (US); Yunsong Tong, Libertyville, IL (US); Charles W. Hutchins, Green Oaks, IL (US); Seungwon Chung, Libertyville, IL (US); Michael J. Dart, Highland Park, IL (US)

(73) Assignee: AbbVie Inc., North Chicago, IL (US)

( * ) Notice: Subject to any disclaimer, the term of this patent is extended or adjusted under 35 U.S.C. 154(b) by 0 days.

(21) Appl. No.: 16/098,679

(22) PCT Filed: May 5, 2017

(86) PCT No.: PCT/US2017/031393
§ 371 (c)(1),
(2) Date: Nov. 2, 2018

(87) PCT Pub. No.: WO2017/193063
PCT Pub. Date: Nov. 9, 2017

(65) Prior Publication Data
US 2019/0135772 A1 May 9, 2019

Related U.S. Application Data

(60) Provisional application No. 62/332,272, filed on May 5, 2016.

(51) Int. Cl.
*C07D 307/82* (2006.01)
*C07D 213/74* (2006.01)
*C07D 231/14* (2006.01)
*C07D 237/10* (2006.01)
*C07D 241/12* (2006.01)
*C07D 241/44* (2006.01)
*C07D 261/08* (2006.01)
*C07D 277/32* (2006.01)
*C07D 213/57* (2006.01)
*C07D 307/56* (2006.01)
*C07C 233/74* (2006.01)
*C07D 213/54* (2006.01)
*C07C 235/54* (2006.01)
*C07C 233/79* (2006.01)
*C07C 255/41* (2006.01)
*C07C 255/57* (2006.01)
*C07C 235/14* (2006.01)

(52) U.S. Cl.
CPC .......... *C07D 307/82* (2013.01); *C07C 233/74* (2013.01); *C07C 233/79* (2013.01); *C07C 235/14* (2013.01); *C07C 235/54* (2013.01); *C07C 255/41* (2013.01); *C07C 255/57* (2013.01); *C07D 213/54* (2013.01); *C07D 213/57* (2013.01); *C07D 213/74* (2013.01); *C07D 231/14* (2013.01); *C07D 237/10* (2013.01); *C07D 241/12* (2013.01); *C07D 241/44* (2013.01); *C07D 261/08* (2013.01); *C07D 277/32* (2013.01); *C07D 307/56* (2013.01); *C07C 2602/38* (2017.05); *C07C 2602/40* (2017.05); *C07C 2602/44* (2017.05)

(58) Field of Classification Search
CPC .................................................. C07C 233/74
See application file for complete search history.

(56) References Cited

U.S. PATENT DOCUMENTS

| 7,994,211 B2 | 8/2011 | Ray et al. |
| 2004/0133011 A1 | 7/2004 | Waddell et al. |
| 2006/0149070 A1 | 7/2006 | Rohde et al. |
| 2007/0185079 A1 | 8/2007 | Evertsson et al. |
| 2015/0057289 A1 | 2/2015 | Li et al. |
| 2016/0096800 A1 | 4/2016 | Walter et al. |

FOREIGN PATENT DOCUMENTS

| WO | WO-2011/087758 A1 | 7/2011 |
| WO | WO-2012/088365 A1 | 6/2012 |
| WO | WO-2014/144952 A2 | 9/2014 |
| WO | WO-2015/038778 A1 | 3/2015 |

OTHER PUBLICATIONS

André et al. "(S)-ABOC: A Rigid Bicyclic β-Amino Acid as Turn Inducer". Organic Letters (2012) vol. 14(4), pp. 960-963.
Database PubChem Compound [Online] Jul. 10, 2005, retrieved from NCBI, Database accession No. 1300563.
Database PubChem Compound [Online] Nov. 13, 2007, retrieved from NCBI, Database accession No. 17565335.
Database PubChem Compound [Online] Dec. 5, 2007, retrieved from NCBI, Database accession No. 20755106.
Database PubChem Compound [Online] Nov. 15, 2010, retrieved from NCBI, Database accession No. 46939935.
Database PubChem Compound [Online] Nov. 15, 2010, retrieved from NCBI, Database accession No. 46939936.
Database PubChem Compound [Online] May 3, 2011, retrieved from NCBI, Database accession No. 51064332.
Database PubChem Compound [Online] Nov. 30, 2012, retrieved from NCBI, Database accession No. 66910924.
Database PubChem Compound [Online] Nov. 30, 2012, retrieved from NCBI, Database accession No. 66910946.

(Continued)

*Primary Examiner* — Noble E Jarrell
(74) *Attorney, Agent, or Firm* — Goodwin Procter LLP

(57) ABSTRACT

Provided herein are compounds, compositions, and methods useful for modulating the integrated stress response (ISR) and for treating related diseases; disorders and conditions.

18 Claims, No Drawings

(56) References Cited

OTHER PUBLICATIONS

Database PubChem Compound [Online] Nov. 30, 2012, retrieved from NCBI, Database accession No. 66910949.
Database PubChem Compound [Online] Nov. 30, 2012, retrieved from NCBI, Database accession No. 68048074.
Database PubChem Compound [Online] Dec. 1, 2012, retrieved from NCBI, Database accession No. 69612403.
Database PubChem Compound [Online] Mar. 23, 2015, retrieved from NCBI, Database accession No. 91663862.
Database PubChem Compound [Online] Dec. 11, 2015, retrieved from NCBI, Database accession No. 98260962.
Database PubChem Compound [Online] Dec. 18, 2015, retrieved from NCBI, Database accession No. 101566942.
Database PubChem Compound [Online] Feb. 23, 2016, retrieved from NCBI, Database accession No. 118417886.
Fogli and Boespflug-Tanguy "The large spectrum of eIF2B-related diseases" Biochemical Society Transactions (2006) vol. 34, pp. 22-29.
Font et a. "Structural characteristics of novel symmetrical diaryl derivatives with nitrogenated functions. Requirements for cytotoxic activity" Bioorganic & Medicinal Chemistry (2006) vol. 14, pp. 1942-1948.
International Search Report and Written Opinion dated Jul. 10, 2017 for Application No. PCT/US2017/031352 (12 pages).
International Search Report and Written Opinion dated Jun. 26, 2017 for Application No. PCT/US2017/031360 (16 pages).
International Search Report and Written Opinion dated Jun. 26, 2017 for Application No. PCT/US2017/031367 (13 pages).
International Search Report and Written Opinion dated Jul. 3, 2017 for Application No. PCT/US2017/031393 (13 pages).
Patel et al. "Discovery of adamantine ethers as inhibitors of 11β-HSD-1: Synthesis and biological evaluation" Bioorganic & Medicinal Chemistry Letters (2007) vol. 17, pp. 750-755.
Smith et al. "Norbornyl Dipeptide Analogues: Mimics of Both a Transition State and a Torsionally Distorted Ground State" Bioorganic Chemistry (1995) vol. 23, pp. 397-414.
U.S. Appl. No. 16/098,675, Modulators of the Integrated Stress Pathway, filed Nov. 2, 2018, Published, US-2019-0144440-A1 Published on May 16, 2019.
U.S. Appl. No. 16/098,946, Modulators of the Integrated Stress Pathway, filed Nov. 5, 2018, Published, US-2019-0194135-A1 Published on Jun. 27, 2019.
U.S. Appl. No. 16/098,950, Modulators of the Integrated Stress Pathway, filed Nov. 5, 2018, Published, US-2019-0142806-A1 Published on May 16, 2019.

MODULATORS OF THE INTEGRATED STRESS PATHWAY

CROSS-REFERENCE TO RELATED APPLICATION

This application is a national stage filing under U.S.C. § 371 of PCT/US2017/031393, filed May 5, 2017, which claims the benefit of, and priority to U.S. provisional application No. 62/332,272, filed May 5, 2016, the content of each of which is hereby incorporated by reference in its entirety.

BACKGROUND

In metazoa, diverse stress signals converge at a single phosphorylation event at serine 51 of a common effector, the translation initiation factor eIF2α. This step is carried out by four eIF2α kinases in mammalian cells: PERK, which responds to an accumulation of unfolded proteins in the endoplasmic reticulum (ER), GCN2 to amino acid starvation and UV light, PKR to viral infection and metabolic stress, and HRI to heme deficiency. This collection of signaling pathways has been termed the "integrated stress response" (ISR), as they converge on the same molecular event. eIF2α phosphorylation results in an attenuation of translation with consequences that allow cells to cope with the varied stresses (Wek, R. C. et al, *Biochem Soc Trans* (2006) 34(Pt 1):7-11).

eIF2 (which is comprised of three subunits, α, β and γ) binds GTP and the initiator Met-tRNA to form the ternary complex (eIF2-GTP-Met-tRNA$_i$), which, in turn, associates with the 40S ribosomal subunit scanning the 5'UTR of mRNAs to select the initiating AUG codon. Upon phosphorylation of its α-subunit, eIF2 becomes a competitive inhibitor of its GTP-exchange factor (GEF), eIF2B (Hinnebusch, A. G. and Lorsch, J. R. *Cold Spring Harbor Perspect Biol* (2012) 4(10)). The tight and nonproductive binding of phosphorylated eIF2 to eIF2B prevents loading of the eIF2 complex with GTP, thus blocking ternary complex formation and reducing translation initiation (Krishnamoorthy, T. et al, *Mol Cell Biol* (2001) 21(15):5018-5030). Because eIF2B is less abundant than eIF2, phosphorylation of only a small fraction of the total eIF2 has a dramatic impact on eIF2B activity in cells.

eIF2B is a complex molecular machine, composed of five different subunits, eIF2B1 through eIF2B5. eIF2B5 catalyzes the GDP/GTP exchange reaction and, together with a partially homologous subunit eIF2B3, constitutes the "catalytic core" (Williams, D. D. et al, *J Biol Chem* (2001) 276:24697-24703). The three remaining subunits (eIF2B1, eIF2B2, and eIF2B4) are also highly homologous to one another and form a "regulatory sub-complex" that provides binding sites for eIF2B's substrate eIF2 (Dev, K. et al, *Mol Cell Biol* (2010) 30:5218-5233). The exchange of GDP with GTP in eIF2 is catalyzed by its dedicated guanine nucleotide exchange factor (GEF) eIF2B. eIF2B exists as a decamer (B1$_2$ B2$_2$ B3$_2$ B4$_2$ B5$_2$) or dimer of two pentamers in cells (Gordiyenko, Y. et al, *Nat Commun* (2014) 5:3902; Wortham, N.C. et al, *FASEB J* (2014) 28:2225-2237). Molecules such as ISRIB interact with and stabilize the eIF2B dimer conformation, thereby enhancing intrinsic GEF activity and making cells less sensitive to the cellular effects of phosphorylation of eIF2α (Sidrauski, C. et al, *eLife* (2015) e07314; Sekine, Y. et al, *Science* (2015) 348:1027-1030). As such, small molecule therapeutics that can modulate eIF2B activity may have the potential to attenuate the PERK branch of the UPR and the overall ISR, and therefore may be used in the prevention and/or treatment of various diseases, such as a neurodegenerative disease, a leukodystrophy, cancer, an inflammatory disease, a musculoskeletal disease, or a metabolic disease.

SUMMARY OF THE INVENTION

The present invention features compounds, compositions, and methods for the modulation of eIF2B (e.g., activation of eIF2B) and the attenuation of the ISR signaling pathway. In some embodiments, the present invention features an eIF2B modulator (e.g., an eIF2B activator) comprising a compound of Formula (I) or a pharmaceutically acceptable salt, solvate, hydrate, tautomer, or stereoisomer thereof. In other embodiments, the present invention features methods of using a compound of Formula (I) or a pharmaceutically acceptable salt, solvate, hydrate, tautomer, or stereoisomer thereof for the treatment of a disease or disorder, e.g., a neurodegenerative disease, a leukodystrophy, cancer, an inflammatory disease, a musculoskeletal disease, a metabolic disease, or a disease or disorder associated with impaired function of eIF2B or components in the ISR pathway (e.g., eIF2 pathway).

In one aspect, the present invention features a compound of Formula (I):

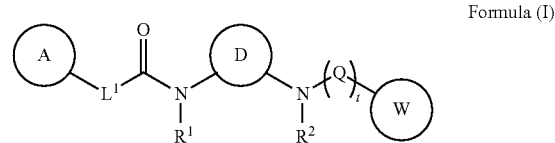

Formula (I)

or a pharmaceutically acceptable salt, solvate, hydrate, tautomer, or stereoisomer thereof, wherein D is a bridged monocyclic cycloalkyl, bridged monocyclic heterocyclyl, or cubanyl, wherein each bridged monocyclic cycloalkyl, bridged monocyclic heterocyclyl, or cubanyl is optionally substituted with 1-4 R$^X$; L$^1$ is C$_1$-C$_6$ alkylene, C$_1$-C$_6$ alkenylene, or 2-7-membered heteroalkylene, wherein each C$_1$-C$_6$ alkylene, C$_1$-C$_6$ alkenylene, or 2-7-membered heteroalkylene is optionally substituted with 1-5 R$^X$; R$^1$ and R$^2$ are each independently hydrogen, C$_1$-C$_6$ alkyl, C$_1$-C$_6$ alkoxy-C$_1$-C$_6$ alkyl, hydroxy-C$_1$-C$_6$ alkyl, or silyloxy-C$_1$-C$_6$ alkyl; Q is C(O) or S(O)$_2$; A and W are each independently phenyl or 5-6-membered heteroaryl, wherein each phenyl or 5-6-membered heteroaryl is optionally substituted with 1-5 R$^Y$; each R$^X$ is independently selected from the group consisting of C$_1$-C$_6$ alkyl, hydroxy-C$_1$-C$_6$ alkyl, halo-C$_1$-C$_6$ alkyl, amino-C$_1$-C$_6$ alkyl, cyano-C$_1$-C$_6$ alkyl, oxo, halo, cyano, —OR$^A$, —NR$^B$R$^C$, —NR$^B$C(O)R$^D$, —C(O)NR$^B$R$^C$, —C(O)R$^D$, —C(O)OH, —C(O)OR$^D$, —SR$^E$, —S(O)R$^D$, —S(O)$_2$R$^D$, and G$^2$; each R$^Y$ is independently selected from the group consisting of hydrogen, C$_1$-C$_6$ alkyl, C$_1$-C$_6$ alkenyl, hydroxy-C$_1$-C$_6$ alkyl, hydroxy-C$_1$-C$_6$ alkenyl, halo-C$_1$-C$_6$ alkyl, halo-C$_1$-C$_6$ alkoxy, amino-C$_1$-C$_6$ alkyl, amido-C$_1$-C$_6$ alkyl, cyano-C$_1$-C$_6$ alkyl, siloxy-C$_1$-C$_6$ alkoxy, hydroxyl-C$_1$-C$_6$ alkoxy, C$_1$-C$_6$ alkoxy-C$_1$-C$_6$ alkyl, C$_1$-C$_6$ alkoxy-C$_1$-C$_6$ alkenyl, C$_1$-C$_6$ alkoxy-C$_1$-C$_6$ alkoxy, oxo, halo, cyano, —OR$^A$, —NR$^B$R$^C$, —NR$^B$C(O)R$^D$, —C(O)NR$^B$R$^C$, —C(O)R$^D$, —C(O)OH, —C(O)OR$^D$, —S(R$^F$)$_m$, —S(O)R$^D$, —S(O)$_2$R$^D$, S(O)NR$^B$R$^C$, —NR$^B$S(O)$_2$R$^D$, —OS(O)R$^D$, —OS(O)$_2$R$^D$, R$^F$S—C$_1$-C$_6$ alkyl, R$^D$C(O)NR$^B$—C$_1$-C$_6$ alkyl, (R$^B$)(R$^C$)N—C$_1$-C$_6$ alkoxy, R$^D$OC(O)NR$^B$—C$_1$-C$_6$ alkyl, G$^1$, G$^1$-C$_1$-C$_6$ alkyl, G$^1$-N(R$^B$), G$^1$-C$_1$-C$_6$ alkenyl, $G^1$-O—, $G^1C(O)NR^B$—$C_1$-$C_6$ alkyl, and $G^1$-$NR^BC(O)$; or 2 $R^Y$ groups on adjacent atoms, together with the atoms to which they are attached form a fused phenyl, a 3-7-membered fused cycloalkyl ring, a 3-7-membered fused heterocyclyl ring, or a 5-6-membered fused heteroaryl ring, each optionally substituted with 1-5 $R^X$; each $G^1$ or $G^2$ is independently 3-7 membered cycloalkyl, 4-7-membered heterocyclyl, aryl, or 5-6-membered heteroaryl, wherein each 3-7 membered cycloalkyl, 4-7-membered heterocyclyl, aryl, or 5-6-membered heteroaryl is optionally substituted with 1-6$R^Z$; each $R^Z$ is independently selected from the group consisting of $C_1$-$C_6$ alkyl, hydroxy-$C_1$-$C_6$ alkyl, halo-$C_1$-$C_6$ alkyl, halo, cyano, oxo, —$OR^A$, —$NR^BR^C$, —$NR^BC(O)R^D$, —$C(O)NR^BR^C$, —$C(O)R^D$, —$C(O)OH$, —$C(O)OR^D$, and —$S(O)_2R^D$; $R^A$ is, at each occurrence, independently hydrogen, $C_1$-$C_6$ alkyl, halo-$C_1$-$C_6$ alkyl, —$ORA^1$, —$C(O)NR^BR^C$, —$C(O)R^D$, —$C(O)OH$, or —$C(O)OR^D$; each of $R^B$ and $R^C$ is independently hydrogen, $C_1$-$C_6$ alkyl, hydroxy-$C_1$-$C_6$ alkyl, $G^1$-$C_1$-$C_6$ alkyl, 3-7 membered cycloalkyl, or 4-7-membered heterocyclyl, wherein each alkyl, cycloalkyl, or heterocyclyl is optionally substituted with 1-6 $R^Z$; or $R^B$ and $R^C$ together with the atom to which they are attached form a 3-7-membered cycloalkyl or heterocyclyl ring optionally substituted with 1-6 $R^Z$; $R^D$ is, at each occurrence, independently $C_1$-$C_6$ alkyl, $C_1$-$C_6$ alkoxy-$C_1$-$C_6$ alkyl, or halo-$C_1$-$C_6$ alkyl; each $R^E$ is independently hydrogen $C_1$-$C_6$ alkyl, or halo-$C_1$-$C_6$ alkyl; each $R^F$ is independently hydrogen, $C_1$-$C_6$ alkyl, or halo; each $RA^1$ is hydrogen, $C_1$-$C_6$ alkyl, halo-$C_1$-$C_6$ alkyl, 3-7 membered cycloalkyl, or 4-7-membered heterocyclyl; m is 1, 3, or 5; and t is 0 or 1.

In some embodiments, D is a bridged monocyclic cycloalkyl optionally substituted with 1-4 $R^X$. In some embodiments, D is a bridged 4-6 membered cycloalkyl optionally substituted with 1-4 $R^X$. In some embodiments, D is selected from bicyclo[1.1.1]pentane, bicyclo[2.2.1]heptane, bicyclo[2.2.2]octane, or bicyclo[2.1.1]hexane, each of which is optionally substituted with 1-4 $R^X$. In some embodiments, D is selected from bicyclo[1.1.1]pentane, bicyclo[2.2.2]octane, or bicyclo[2.1.1]hexane, each of which is optionally substituted with 1-4 $R^X$. In some embodiments, D is selected from:

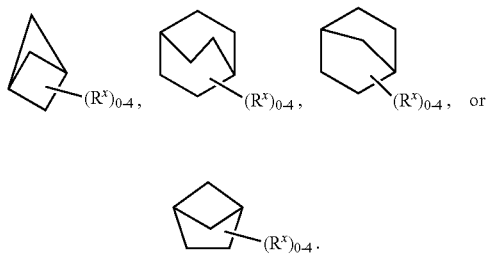

In some embodiments, D is selected from:

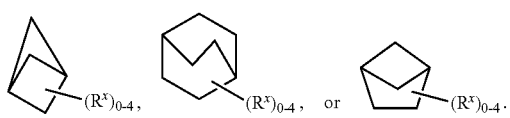

In some embodiments, D is selected from:

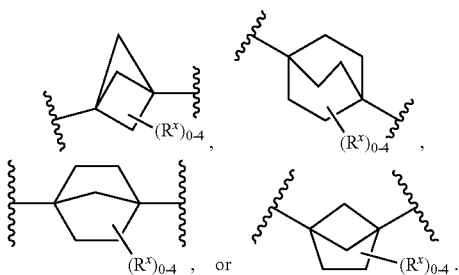

In some embodiments, D is selected from:

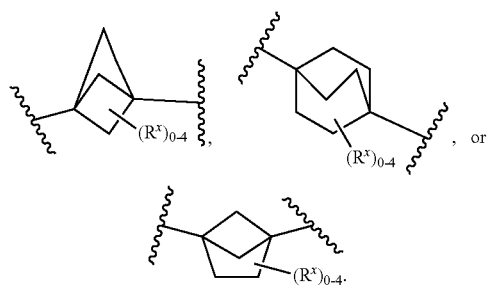

In some embodiments, D is substituted with 1 $R^X$. In some embodiments, D is substituted with one $R^X$, and $R^X$ is halo or —$OR^A$ (e.g., fluoro, OH). In some embodiments, D is substituted with 0 $R^X$. In some embodiments, D is

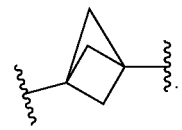 [SMILES: *C12CC(*)(C1)C2]

In some embodiments, $L^1$ is 2-7-membered heteroalkylene optionally substituted by 1-5 $R^X$. In some embodiments, $L^1$ is 2-7-membered heteroalkylene substituted by 0 $R^X$. In some embodiments, $L^1$ is $CH_2OCH_2$—*, $CH_2O$—*, wherein "—*" indicates the attachment point to A. In some embodiments, $L^1$ is $CH_2O$—*, wherein "—*" indicates the attachment point to A.

In some embodiments, Q is C(O). In some embodiments, Q is $S(O)_2$.

In some embodiments, t is 1. In some embodiments, t is 0.

In some embodiments, each of $R^1$ and $R^2$ is independently hydrogen or $C_1$-$C_6$ alkyl (e.g., $CH_3$). In some embodiments, each of $R^1$ and $R^2$ is independently hydrogen. In some embodiments, one of $R^1$ and $R^2$ is independently hydrogen and the other of $R^1$ and $R^2$ is independently is $C_1$-$C_6$ alkyl (e.g., $CH_3$).

In some embodiments, A is phenyl and W is independently phenyl or 5-6-membered heteroaryl. In some embodiments, each A and W is independently phenyl. In some embodiments, A is phenyl and W is 5-6-membered heteroaryl.

In some embodiments, W is a monocyclic 5-6-membered heteroaryl. In some embodiments, 2 $R^Y$ groups on adjacent atoms of W, together with the atoms to which they are attached form a 3-7-membered fused cycloalkyl or heterocyclyl optionally substituted with 1-5 $R^X$ forming a bicyclic heteroaryl. In some embodiments, W is a 10-membered heteroaryl, a 9-membered heteroaryl, a 6-membered heteroaryl, or a 5-membered heteroaryl. In some embodiments, W is a heteroaryl containing nitrogen, oxygen or sulfur as allowed by valence.

In some embodiments, each A and W is independently a phenyl or 5-6-membered heteroaryl optionally substituted with 1-5 $R^Y$, and each $R^Y$ is independently $C_1$-$C_6$ alkyl, hydroxy-$C_1$-$C_6$ alkyl, halo-$C_1$-$C_6$ alkyl, halo-$C_1$-$C_6$ alkoxy, $C_1$-$C_6$ alkoxy-$C_1$-$C_6$ alkyl, silyloxy-$C_1$-$C_6$ alkyl, halo, —$OR^A$, cycloalkyl, heterocyclyl, —C(O)OH, —C(O)$OR^D$, or $G^1$. In some embodiments, each of A and W is independently phenyl, pyridyl, pyrimidinyl, pyrazinyl, pyridazinyl, oxazolyl, isoxazolyl, furanyl, or pyrazolyl, each of which is optionally substituted with 1-5 $R^Y$ groups.

In some embodiments, each A and W is selected from:

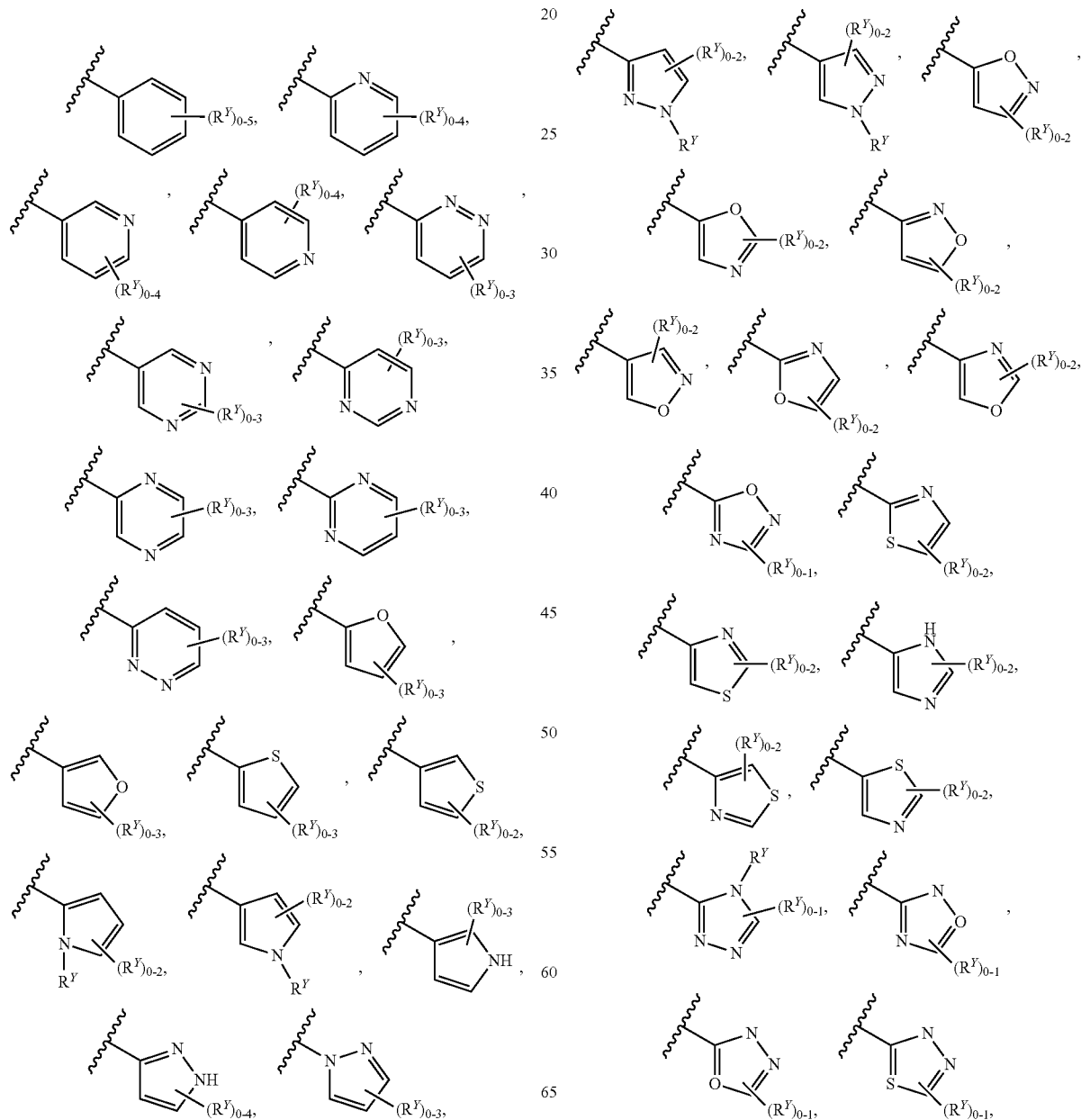

-continued
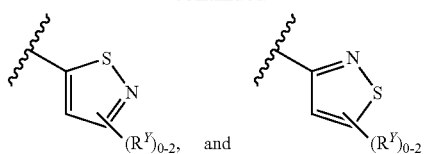
In some embodiments, each of A and W is selected from:
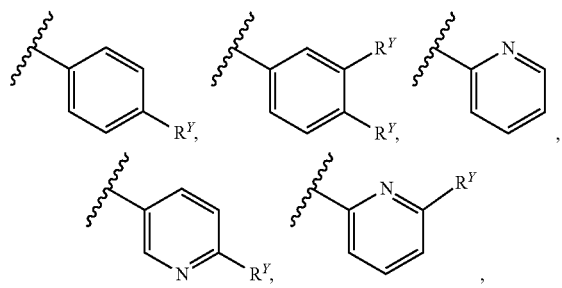
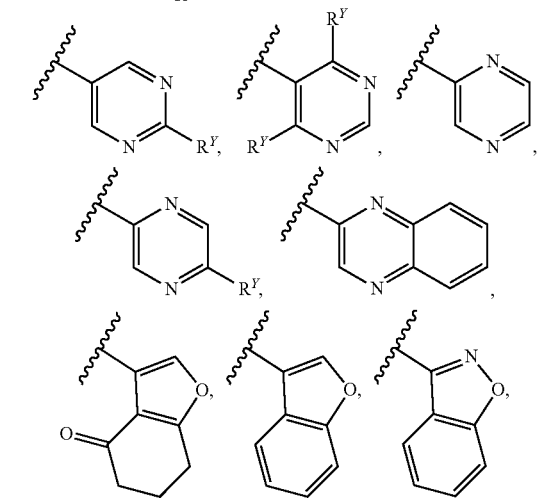
-continued
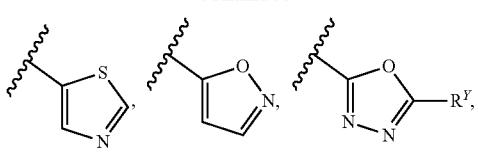
In some embodiments, each of A and W is selected from:

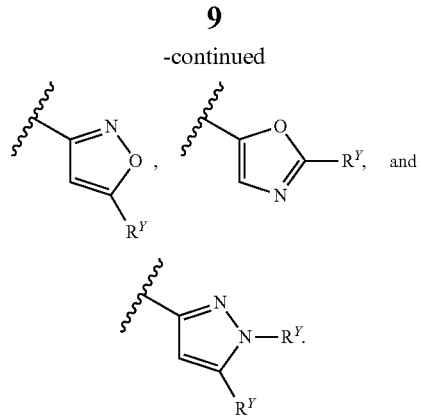

In some embodiments, A is phenyl or pyridyl and W is phenyl or 5-6-membered heteroaryl, each of A and W is optionally substituted with 1-5 $R^Y$, and each $R^Y$ is independently $C_1$-$C_6$ alkyl, hydroxy-$C_1$-$C_6$ alkyl, halo-$C_1$-$C_6$ alkyl, halo-$C_1$-$C_6$ alkoxy, siloxy-$C_1$-$C_6$ alkoxy, hydroxy $C_1$-$C_6$ alkoxy, halo, —$OR^A$, —C(O)OH, —C(O)$OR^D$, or $G^1$. In some embodiments, A is phenyl or pyridyl and W is phenyl, pyridyl, pyrimidinyl, pyrazinyl, pyridazinyl, oxazolyl, isoxazolyl, furanyl, or pyrazolyl, wherein A and W are each optionally substituted with 1-5 $R^Y$.

In some embodiments, A is

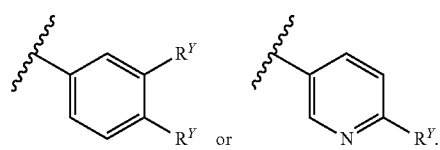

In some embodiments, A is

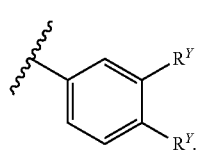

In some embodiments, W is selected from:

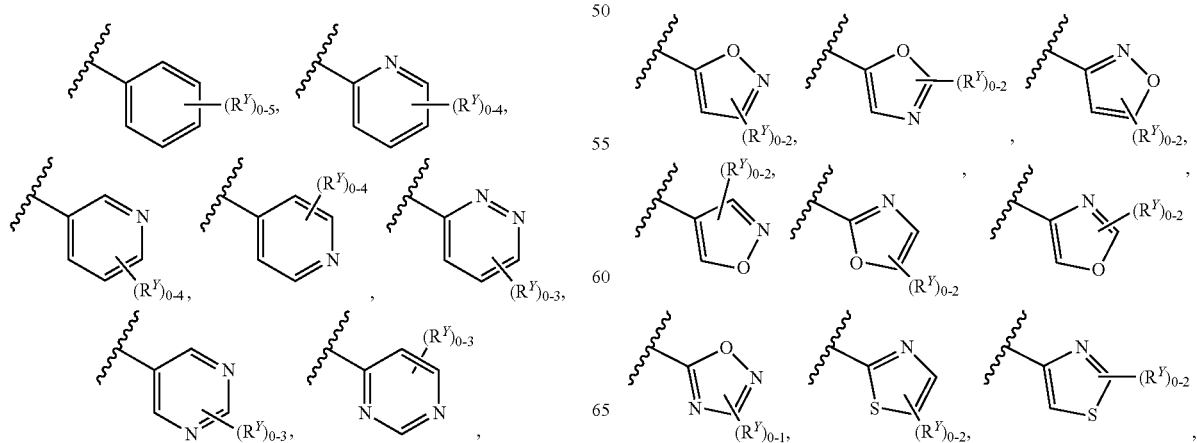

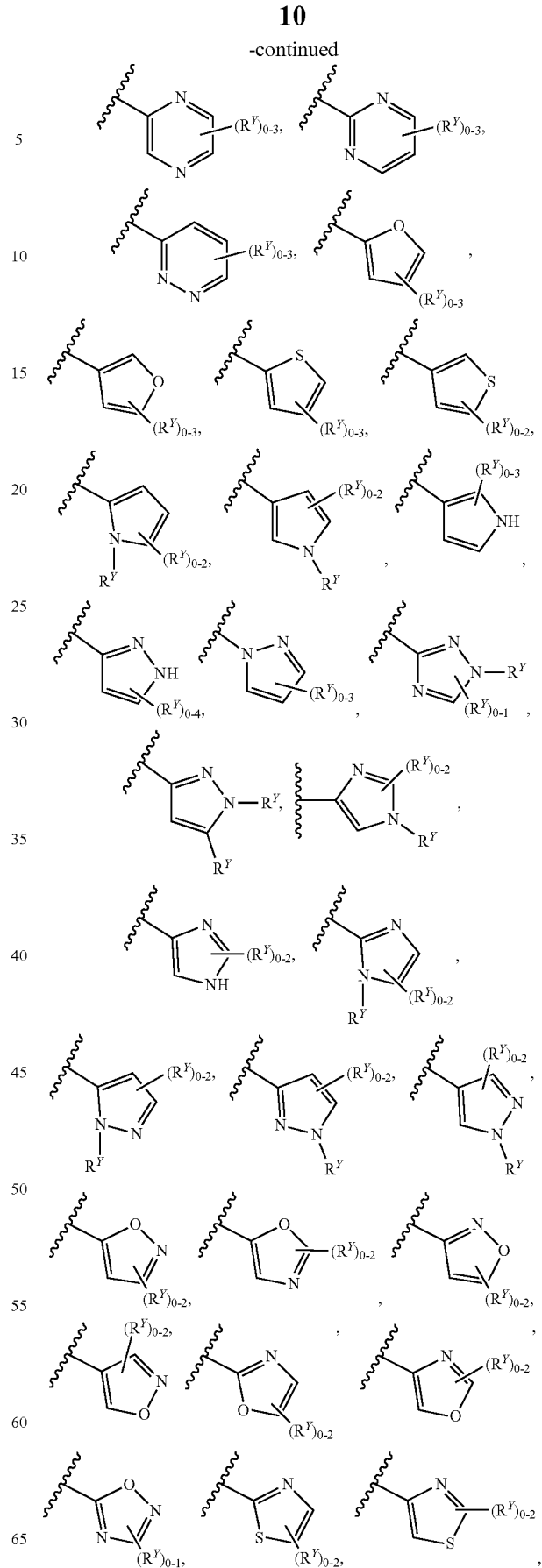

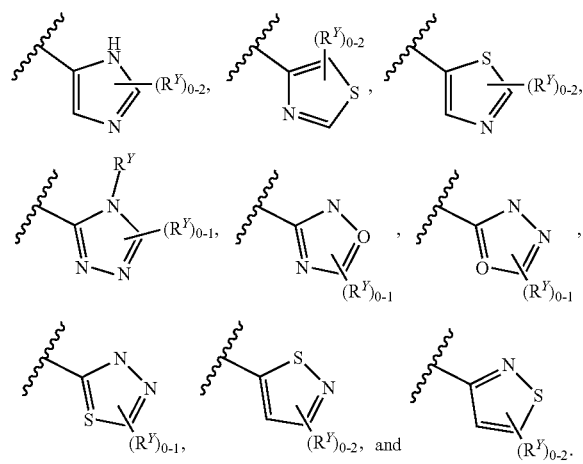

In some embodiments, W is selected from:

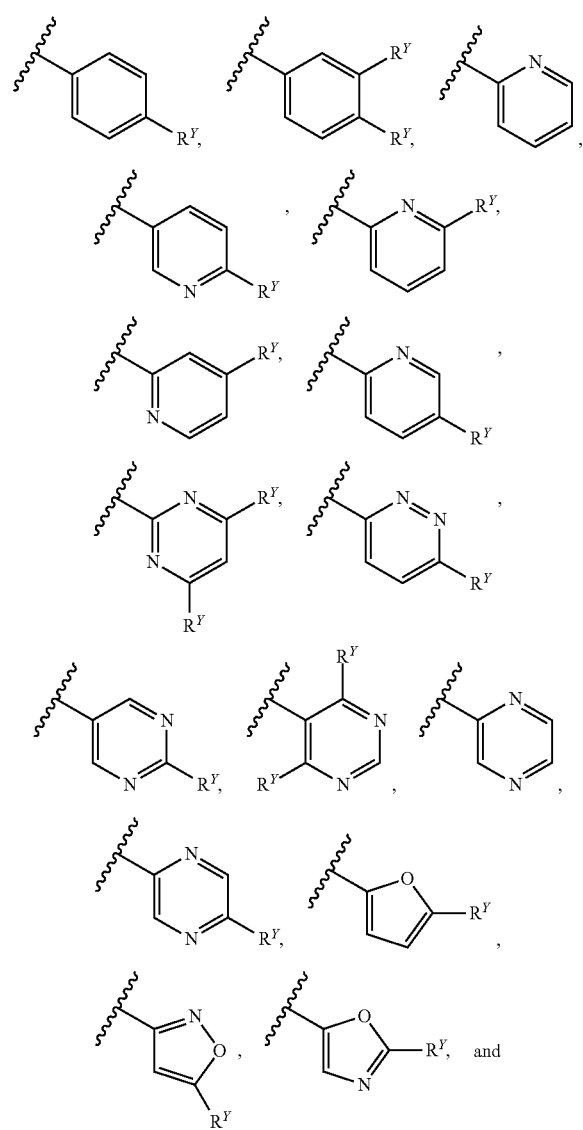

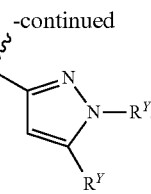

In some embodiments, each $R^Y$ is independently selected from chloro, fluoro, oxo, CN, OH, $CF_3$, $CHF_2$, $CH_3$, $CH_2CH_3$, $CH_2CH_2CH_2CH_3$, $CH=CHCH_2OH$, $CH_2CH_2OH$, $CH_2NH_2$, $NHCH_3$, $CH_2NHC(O)CH_3$, $N(CH_2CH_3)_2$, $CH2N(CH_3)_2$, $C(CH_3)_2OH$, $CH(CH_3)_2$, $CH_2CH_2CH_3$, $C(CH_3)_3$, $CH_2CH(CH_3)_2$, $CH_2CH_2OH$, $CH(OH)CH_3$, $CH_2CH_2CH_2OCH_3$, $CH_2CF_3$, $CH_2C(CH_3)_2OH$, $CH_2SCH_3$, $CH_2CN$, $CH_2CH_2CN$, $CH_2CH_2C(CH_3)_2OH$, $CH_2NHC(O)CH_3$, $OCH_3$, $OCH_2CH_3$, $OCH_2CH_2CH_3$, $OCH_2CH_2OCH_3$, $OCH(CH_3)_2$, $OCF_3$, $OCH_2CF_3$, $OCH_2CH_2N(CH_3)_2$, $CH_2OH$, $CH_2OCH_3$, $OCH_2CH_2OH$, $OCHF_2$, $OCF_3$, $OCH_3$, $CH_2OH$, $C(O)OH$, $C(O)CH_3$, $C(O)OCH_3$, $C(O)NH_2$, $C(O)NHCH_2CH_2CH_2OH$, $CH_2CN$, $C(O)OCH_2CH_3$, $C(O)NHCH_2CH_3$, $OCH_2CH_2OSi(CH_3)_2C(CH_3)_3$, $CH_2N(CH_3)_2$, $CH_2NHC(O)CH_3$, $CH_2NHC(O)OC(CH_3)_3$, $CH=CHCH_2OCH_3$, $CH=CHC(CH_3)_2OH$, $N(CH_3)_2$, $N(CH_2CH_3)_2$, $NHCH_2CH_3$, $NHC(O)CH_3$, $NHC(O)CH_2OCH_3$, $NHS(O)_2CH_3$, $SCH_3$, $SCH_2CH_3$, $SO_2NH_2$, $S(O)CH_3$, $S(O)_2CH_3$, $G^1$, $C(O)NHG^1$, $N(CH_3)CH_2G^1$, $NHG^1$, $OG^1$, $CH_2G^1$, $CH_2CH_2G^1$, $CH_2NHC(O)G^1$, or $CH=CHG^1$.

In some embodiments, each $R^Y$ is independently chloro, fluoro, CN, OH, $CF_3$, $CHF_2$, $CH_3$, $CH_2CH_3$, $CH_2CH_2CH_2CH_3$, $CH=CHCH_2OH$, $CH_2CH_2OH$, $CH_2NH_2$, $NHCH_3$, $CH_2NHC(O)CH_3$, $N(CH_2CH_3)_2$, $CH_2N(CH_3)_2$, $C(CH_3)_2OH$, $OCH_3$, $CH_2OH$, $CH_2OCH_3$, $OCH_2CH_2OH$, $OCHF_2$, $OCF_3$, $OCH_3$, $CH_2OH$, $C(O)OH$, $CH_2CN$, $C(O)OCH_2CH_3$, $C(O)NHCH_2CH_3$, $OCH_2CH_2OSi(CH_3)_2C(CH_3)_3$, or $G^1$.

In some embodiments, each of A and W is independently substituted with 2 $R^Y$ on adjacent atoms, and the 2 $R^Y$, together with the atoms to which they are attached, form a 3-7-membered fused heterocyclyl ring or 5-6-membered heteroaryl ring, each optionally substituted with 1-5 $R^X$. In some embodiments, the 2 $R^Y$ together with the atoms to which they are attached form a dioxolanyl, hexahydropyrimidinyl, pyridyl, or pyrimidinyl ring, each of which is optionally substituted with 1-5 $R^X$. In some embodiments, each $R^X$ is independently $C_1$-$C_6$ alkyl, fluoro, chloro, oxo, $OCH_3$, $C(O)OCH_3$, or $G^2$.

In some embodiments, $G^1$ or $G^2$ is pyrrolidinyl, azetidinyl, cyclopropyl, cyclohexyl, cyclohexenyl, tetrahydropyranyl, dihydropyranyl, tetrahydropyridinyl, piperidinyl, phenyl, pyridyl, pyrimidinyl, pyridazinyl, pyrazolyl, morpholino, furanyl, triazolyl, oxetanyl, or pyrazinyl, each of which is optionally substituted with 1-5 $R^Z$. In some embodiments, $G^1$ is pyrrolidinyl, cyclopropyl, cyclohexyl, cyclohexenyl, tetrahydropyranyl, dihydropyranyl, tetrahydropyridinyl, piperidinyl, phenyl, pyridyl, pyrimidinyl, pyridazinyl, or pyrazinyl, each of which is optionally substituted with 1-5 $R^Z$.

In some embodiments, $G^1$ is pyrrolidinyl, azetidinyl, cyclopropyl, cyclohexyl, cyclohexenyl, tetrahydropyranyl, dihydropyranyl, tetrahydropyridinyl, piperidinyl, phenyl, pyridyl, pyrimidinyl, pyridazinyl, pyrazolyl, morpholino, furanyl, triazolyl, oxetanyl, or pyrazinyl, each of which is optionally substituted with 1-5 $R^Z$. In some embodiments, $G^1$ is pyrrolidinyl, cyclopropyl, cyclohexyl, cyclohexenyl, tetrahydropyranyl, dihydropyranyl, tetrahydropyridinyl, piperidinyl, phenyl, pyridyl, pyrimidinyl, pyridazinyl, or pyrazinyl, each of which is optionally substituted with 1-5 $R^Z$.

In some embodiments, each $R^Z$ is independently $OR^A$, $C(O)R^D$, halo, halo $C_1$-$C_6$ alkyl, $C_1$-$C_6$ alkyl, $C(O)R^D$, or $C(O)OR^D$ (e.g., fluoro, chloro, OH, $OCH_3$, oxo, $CH_3$, $CHF_2$, $CF_3$, $C(O)CH_3$ or $C(O)OC(CH_3)_3$). In some embodiments, each $R^Z$ is independently $OR^A$, $C(O)R^D$, halo, halo $C_1$-$C_6$ alkyl, $C_1$-$C_6$ alkyl, or $C(O)OR^D$ (e.g., OH, $C(O)CH_3$ or $C(O)OC(CH_3)_3$).

In one aspect, the present invention features a compound of Formula (I-a):

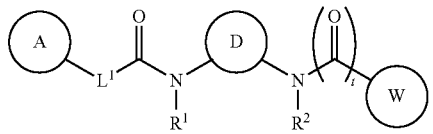

Formula (I-a)

or a pharmaceutically acceptable salt, solvate, hydrate, tautomer, or stereoisomer thereof, wherein D is a bridged monocyclic cycloalkyl, bridged monocyclic heterocyclyl, or cubanyl, wherein each bridged monocyclic cycloalkyl, bridged monocyclic heterocyclyl, or cubanyl is optionally substituted with 1-4 $R^X$; $L^1$ is $C_1$-$C_6$ alkylene or 2-7-membered heteroalkylene, wherein each $C_1$-$C_6$ alkylene or 2-7-membered heteroalkylene is optionally substituted with 1-5 $R^X$; $R^1$ and $R^2$ are each independently hydrogen, $C_1$-$C_6$ alkyl, $C_1$-$C_6$ alkoxy-$C_1$-$C_6$ alkyl, hydroxy-$C_1$-$C_6$ alkyl, or silyloxy-$C_1$-$C_6$ alkyl; A and W are each independently phenyl or 5-6-membered heteroaryl, wherein each phenyl or 5-6-membered heteroaryl is optionally substituted with 1-5 $R^Y$; each $R^X$ is independently selected from the group consisting of $C_1$-$C_6$ alkyl, hydroxy-$C_1$-$C_6$ alkyl, halo-$C_1$-$C_6$ alkyl, amino-$C_1$-$C_6$ alkyl, cyano-$C_1$-$C_6$ alkyl, oxo, halo, cyano, $—OR^A$, $—NR^BR^C$, $—NR^BC(O)R^D$, $—C(O)NR^BR^C$, $—C(O)R^D$, $—C(O)OH$, $—C(O)OR^D$, $—SR^E$, $—S(O)R^D$, and $—S(O)_2R^D$; each $R^Y$ is independently selected from the group consisting of hydrogen, $C_1$-$C_6$ alkyl, hydroxy-$C_1$-$C_6$ alkyl, halo-$C_1$-$C_6$ alkyl, halo-$C_1$-$C_6$ alkoxy, amino-$C_1$-$C_6$ alkyl, cyano-$C_1$-$C_6$ alkyl, siloxy-$C_1$-$C_6$ alkoxy, hydroxyl-$C_1$-$C_6$ alkoxy, oxo, halo, cyano, $—OR^A$, $—NR^BR^C$, $—NR^BC(O)R^D$, $—C(O)NR^BR^C$, $—C(O)R^D$, $—C(O)OH$, $—C(O)OR^D$, $—S(R^F)_m$, $—S(O)R^D$, $—S(O)_2R^D$, and $G^1$; or 2 $R^Y$ groups on adjacent atoms, together with the atoms to which they are attached form a 3-7-membered fused cycloalkyl ring, a 3-7-membered fused heterocyclyl ring, or a 5-6-membered fused heteroaryl ring, each optionally substituted with 1-5 $R^X$; each $G^1$ is independently 3-7 membered cycloalkyl, 4-7-membered heterocyclyl, aryl, or 5-6-membered heteroaryl, wherein each 3-7 membered cycloalkyl, 4-7-membered heterocyclyl, aryl, or 5-6-membered heteroaryl is optionally substituted with 1-3 $R^Z$; each $R^Z$ is independently selected from the group consisting of $C_1$-$C_6$ alkyl, hydroxy-$C_1$-$C_6$ alkyl, halo-$C_1$-$C_6$ alkyl, halo, cyano, $—OR^A$, $—NR^BR^C$, $—NR^BC(O)R^D$, $—C(O)NR^BR^C$, $—C(O)R^D$, $—C(O)OH$, $—C(O)OR^D$, and $—S(O)_2R^D$; $R^A$ is, at each occurrence, independently hydrogen, $C_1$-$C_6$ alkyl, halo-$C_1$-$C_6$ alkyl, $—C(O)NR^BR^C$, $—C(O)R^D$, $—C(O)OH$, or $—C(O)OR^D$; each of $R^B$ and $R^C$ is independently hydrogen or $C_1$-$C_6$ alkyl; or $R^B$ and $R^C$ together with the atom to which they are attached form a 3-7-membered cycloalkyl or heterocyclyl ring optionally substituted with 1-3 $R^Z$; $R^D$ is, at each occurrence, independently $C_1$-$C_6$ alkyl or halo-$C_1$-$C_6$ alkyl; each $R^E$ is independently hydrogen $C_1$-$C_6$ alkyl, or halo-$C_1$-$C_6$ alkyl; each $R^F$ is independently hydrogen, $C_1$-$C_6$ alkyl, or halo; m is 1, 3, or 5; and t is 0 or 1.

In some embodiments, D is a bridged monocyclic cycloalkyl optionally substituted with 1-4 $R^X$. In some embodiments, D is a bridged 4-6 membered cycloalkyl optionally substituted with 1-4 $R^X$. In some embodiments, D is selected from bicyclo[1.1.1]pentane, bicyclo[2.2.2]octane, or bicyclo[2.1.1]hexane, each of which is optionally substituted with 1-4 $R^X$. In some embodiments, D is selected from:

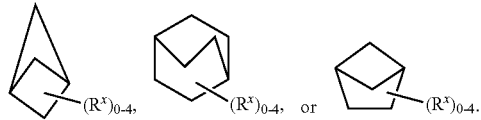

In some embodiments, D is selected from:

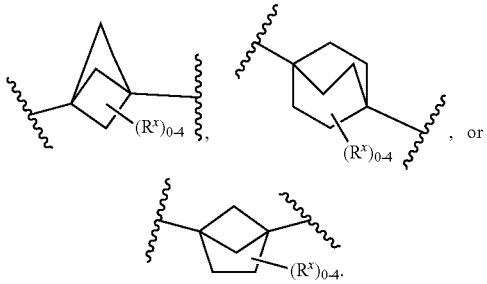

In some embodiments, D is substituted with 1 $R^X$. In some embodiments, D is substituted with one $R^X$, and $R^X$ is $—OR^A$ (e.g., OH). In some embodiments, D is substituted with 0 $R^X$. In some embodiments, D is

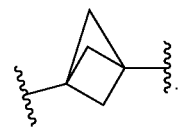 [SMILES: *C12CC(*)(C1)C2]

In some embodiments, $L^1$ is 2-7-membered heteroalkylene optionally substituted by 1-5 $R^X$. In some embodiments, $L^1$ is 2-7-membered heteroalkylene substituted by 0 $R^X$. In some embodiments, $L^1$ is $CH_2O—*$, wherein "—*" indicates the attachment point to A.

In some embodiments, t is 1. In some embodiments, t is 0.

In some embodiments, each of $R^1$ and $R^2$ is independently hydrogen.

In some embodiments, each A and W is independently a phenyl or 5-6-membered heteroaryl optionally substituted with 1-5 $R^Y$, and each $R^Y$ is independently $C_1$-$C_6$ alkyl, hydroxy-$C_1$-$C_6$ alkyl, halo-$C_1$-$C_6$ alkyl, halo-$C_1$-$C_6$ alkoxy, $C_1$-$C_6$ alkoxy-$C_1$-$C_6$ alkyl, silyloxy-$C_1$-$C_6$ alkyl, halo, $—OR^A$, cycloalkyl, heterocyclyl, $—C(O)OH$, $—C(O)OR^D$, or $G^1$. In some embodiments, each of A and W is independently phenyl, pyridyl, pyrimidinyl, pyrazinyl, pyridazinyl, oxazolyl, isoxazolyl, furanyl, or pyrazolyl, each of which is optionally substituted with 1-5 R groups. In some embodiments, each of A and W is selected from:

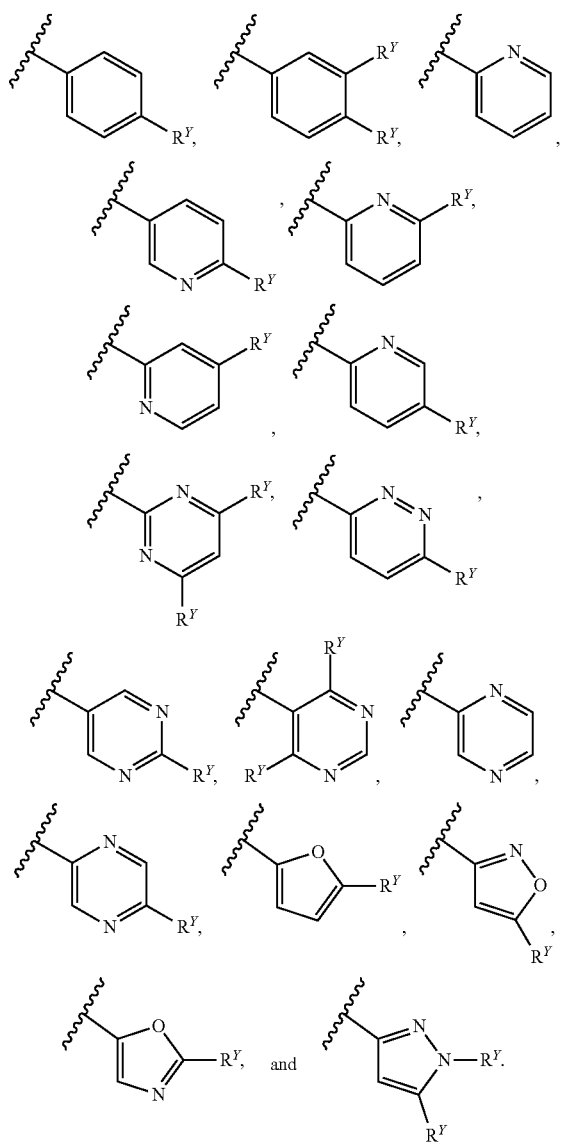

In some embodiments, A is phenyl or pyridyl and W is phenyl or 5-6-membered heteroaryl, each of A and W is optionally substituted with 1-5 $R^Y$, and each $R^Y$ is independently $C_1$-$C_6$ alkyl, hydroxy-$C_1$-$C_6$ alkyl, halo-$C_1$-$C_6$ alkyl, halo-$C_1$-$C_6$ alkoxy, siloxy-$C_1$-$C_6$ alkyl, hydroxy $C_1$-$C_6$ alkoxy, halo, —$OR^A$, —C(O)OH, —C(O)$OR^D$, or $G^1$. In some embodiments, A is phenyl or pyridyl and W is phenyl, pyridyl, pyrimidinyl, pyrazinyl, pyridazinyl, oxazolyl, isoxazolyl, furanyl, or pyrazolyl, wherein A and W are each optionally substituted with 1-5 $R^Y$.

In some embodiments, A is

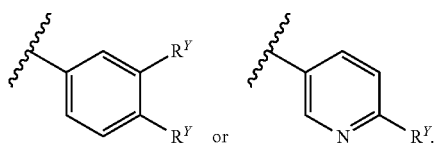

In some embodiments, W is selected from:

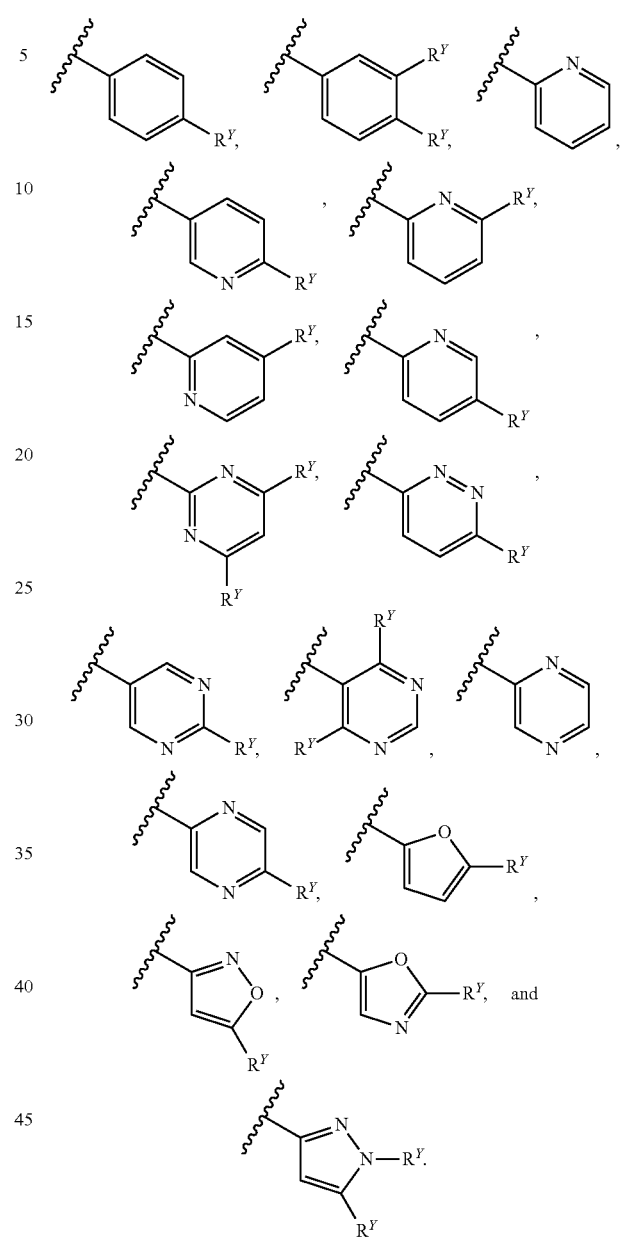

In some embodiments, each $R^Y$ is independently chloro, fluoro, $CF_3$, $CHF_2$, $CH_3$, $CH_2CH_3$, $CH_2CH_2CH_2CH_3$, $OCH_3$, $CH_2OH$, $OCH_2CH_2OH$, $OCHF_2$, $OCF_3$, C(O)OH, $OCH_2CH_2OSi(CH_3)_2C(CH_3)_3$, or $G^1$.

In some embodiments, each of A and W is independently substituted with 2 $R^Y$ on adjacent atoms, and the 2 $R^Y$, together with the atoms to which they are attached, form a 3-7-membered fused heterocyclyl ring or 5-6-membered heteroaryl ring, each optionally substituted with 1-5 $R^X$. In some embodiments, the 2 $R^Y$ together with the atoms to which they are attached form a dioxolanyl, hexahydropyrimidinyl, pyridyl, or pyrimidinyl ring, each of which is optionally substituted with 1-5 $R^X$. In some embodiments, each $R^X$ is independently fluoro.

In some embodiments, $G^1$ is pyrrolidinyl, cyclopropyl, cyclohexyl, cyclohexenyl, tetrahydropyranyl, dihydropyranyl, tetrahydropyridinyl, piperidinyl, phenyl, pyridyl, pyrimidinyl, pyridazinyl, or pyrazinyl, each of which is optionally substituted with 1-5 $R^Z$. In some embodiments, each $R^Z$ is independently $OR^A$, $C(O)R^D$, halo, halo $C_1$-$C_6$ alkyl, $C_1$-$C_6$ alkyl, or $C(O)OR^D$ (e.g., OH, $C(O)CH_3$ or $C(O)OC(CH_3)_3$).

In some embodiments, the compound of Formula (I) is a compound of Formula (I-b):

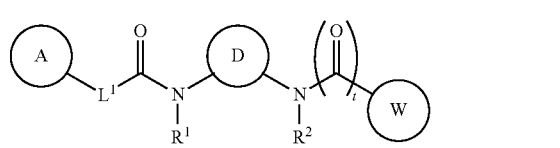

Formula (I-b)

or a pharmaceutically acceptable salt, solvate, hydrate, tautomer, or stereoisomer thereof, wherein D is bicyclo[1.1.1]pentane, bicyclo[2.2.1]heptane, bicyclo[2.2.2]octane, or bicyclo[2.1.1]hexane, each of which is optionally substituted with 1-4 $R^X$; $L^1$ $CH_2O$—*, wherein "—*" indicates the attachment point to A; $R^1$ and $R^2$ are each independently hydrogen or $C_1$-$C_6$ alkyl; A is phenyl optionally substituted with 1-2 $R^Y$; W is phenyl or 5-6 membered heteroaryl, wherein each phenyl or 5-6-membered heteroaryl is optionally substituted with 1-5 $R^Y$; each $R^X$ is independently $C_1$-$C_6$ alkyl, fluoro, chloro, oxo, $OCH_3$, $C(O)OCH_3$, or $G^2$; each $R^Y$ is independently chloro, fluoro, oxo, CN, OH, $CF_3$, $CHF_2$, $CH_3$, $CH_2CH_3$, $CH_2CH_2CH_2CH_3$, $CH=CHCH_2OH$, $CH_2CH_2OH$, $CH_2NH_2$, $NHCH_3$, $CH_2NHC(O)CH_3$, $N(CH_2CH_3)_2$, $CH_2N(CH_3)_2$, $C(CH_3)_2OH$, $CH(CH_3)_2$, $CH_2CH_2CH_3$, $C(CH_3)_3$, $CH_2CH(CH_3)_2$, $CH_2CH_2OH$, $CH(OH)CH_3$, $CH_2CH_2CH_2OCH_3$, $CH_2CF_3$, $CH_2C(CH_3)_2OH$, $CH_2SCH_3$, $CH_2CN$, $CH_2CH_2CN$, $CH_2CH_2C(CH_3)_2OH$, $CH_2NHC(O)CH_3$, $OCH_3$, $OCH_2CH_3$, $OCH_2CH_2CH_3$, $OCH_2CH_2OCH_3$, $OCH(CH_3)_2$, $OCF_3$, $OCH_2CF_3$, $OCH_2CH_2N(CH_3)_2$, $CH_2OH$, $CH_2OCH_3$, $OCH_2CH_2OH$, $OCHF_2$, $OCF_3$, $OCH_3$, $CH_2OH$, $C(O)OH$, $C(O)CH_3$, $C(O)OCH_3$, $C(O)NH_2$, $C(O)NHCH_2CH_2CH_2OH$, $CH_2CN$, $C(O)OCH_2CH_3$, $C(O)NHCH_2CH_3$, $OCH_2CH_2OSi(CH_3)_2C(CH_3)_3$, $CH_2N(CH_3)_2$, $CH_2NHC(O)CH_3$, $CH_2NHC(O)OC(CH_3)_3$, $CH=CHCH_2OCH_3$, $CH=CHC(CH_3)_2OH$, $N(CH_3)_2$, $N(CH_2CH_3)_2$, $NHCH_2CH_3$, $NHC(O)CH_3$, $NHC(O)CH_2OCH_3$, $NHS(O)_2CH_3$, $SCH_3$, $SCH_2CH_3$, $SO_2NH_2$, $S(O)CH_3$, $S(O)_2CH_3$, $G^1$, $C(O)NHG^1$, $N(CH_3)CH_2G^1$, $NHG^1$, $OG^1$, $CH_2G^1$, $CH_2CH_2G^1$, $CH_2NHC(O)G^1$, or $CH=CHG^1$; or 2 $R^Y$ groups on adjacent atoms, together with the atoms to which they are attached form a 5-7-membered fused heterocyclyl ring, 5-6-membered fused heteroaryl, a 5-6-membered fused cycloalkyl, or a fused phenyl, each optionally substituted with 1-5 $R^X$; and $G^1$ and $G^2$ are each independently pyrrolidinyl, azetidinyl, cyclopropyl, cyclohexyl, cyclohexenyl, tetrahydropyranyl, dihydropyranyl, tetrahydropyridinyl, piperidinyl, phenyl, pyridyl, pyrimidinyl, pyridazinyl, pyrazolyl, morphilino, furanyl, triazolyl, oxetanyl, or pyrazinyl, each of which is optionally substituted with 1-5 $R^Z$; each $R^Z$ is independently fluoro, chloro, OH, $OCH_3$, oxo, $CH_3$, $CHF_2$, $CF_3$, $C(O)CH_3$ or $C(O)OC(CH_3)_3$; and t is 0 or 1.

In some embodiments, the compound of Formula (I) is a compound of Formula (I-c):

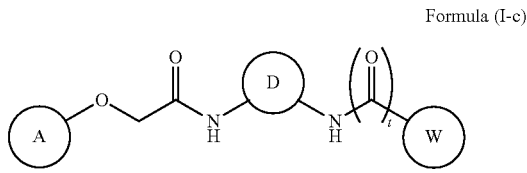

Formula (I-c)

or a pharmaceutically acceptable salt, solvate, hydrate, tautomer, or stereoisomer thereof, wherein each of A, W, D, and t is defined as for Formula (I).

In some embodiments, the compound of Formula (I) is a compound of Formula (I-d):

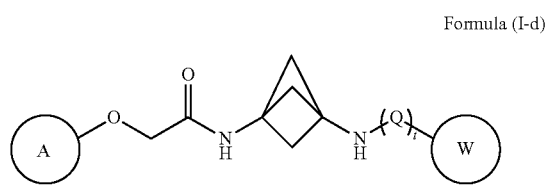

Formula (I-d)

or a pharmaceutically acceptable salt, solvate, hydrate, tautomer, or stereoisomer thereof, wherein each of A, W, Q, and t is defined as for Formula (I).

In some embodiments, the compound of Formula (I) is a compound of Formula (I-d):

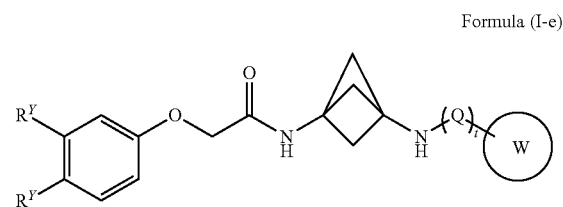

Formula (I-e)

or a pharmaceutically acceptable salt, solvate, hydrate, tautomer, or stereoisomer thereof, wherein each of W, Q, and t is defined as for Formula (I).

In some embodiments, the compound of Formula (I) is a compound of Formula (I-f):

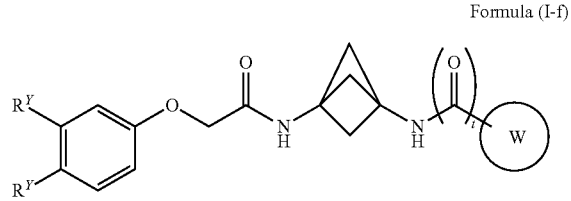

Formula (I-f)

or a pharmaceutically acceptable salt, solvate, hydrate, tautomer, or stereoisomer thereof, wherein each of W and t is defined as for Formula (I).

In some embodiments, the compound of Formula (I) is a compound of Formula (I-g):

Formula (I-g)

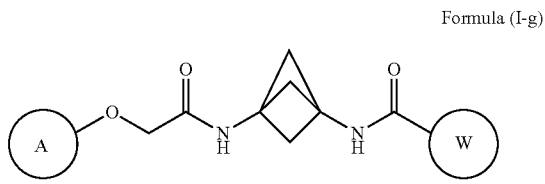

or a pharmaceutically acceptable salt, solvate, hydrate, tautomer, or stereoisomer thereof, wherein each of A and W is defined as for Formula (I).

In some embodiments, the compound of Formula (I) is a compound of Formula (I-h):

Formula (I-h)

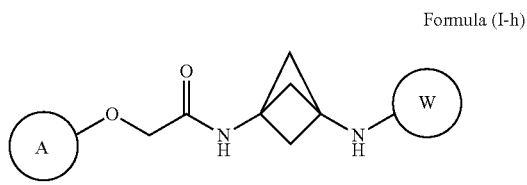

or a pharmaceutically acceptable salt, solvate, hydrate, tautomer, or stereoisomer thereof, wherein each of A and W is defined as for Formula (I).

In some embodiments, the compound of Formula (I) is a compound of Formula (I-i):

Formula (I-i)

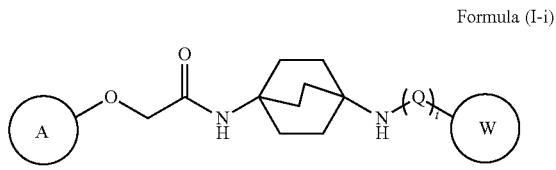

or a pharmaceutically acceptable salt, solvate, hydrate, tautomer, or stereoisomer thereof, wherein each of A, W, Q, and t is defined as for Formula (I).

In some embodiments, the compound of Formula (I) is a compound of Formula (I-j):

Formula (I-j)

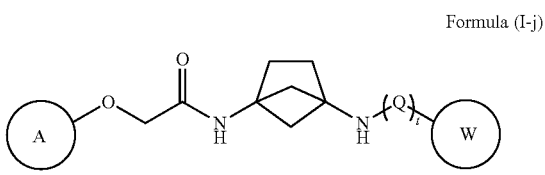

or a pharmaceutically acceptable salt, solvate, hydrate, tautomer, or stereoisomer thereof, wherein each of A, W, Q, and t is defined as for Formula (I).

In some embodiments, the compound is selected from any compound set forth in Table 1 or a pharmaceutically acceptable salt, solvate, hydrate, tautomer, or stereoisomer thereof.

In some embodiments, the compound of Formula (I) (e.g., a compound of Formula (I-a), (I-b), (I-c), (I-d), (I-e), (I-f), (I-g), (I-h), (I-i) or (I-j)) or a pharmaceutically acceptable salt thereof is formulated as a pharmaceutically acceptable composition comprising a compound of any one of the preceding claims and a pharmaceutically acceptable carrier.

In another aspect, the present invention features a method of treating a neurodegenerative disease, a leukodystrophy, cancer, an inflammatory disease, a musculoskeletal disease, a metabolic disease, or a disease or disorder associated with impaired function of eIF2B or components in the ISR pathway (e.g., eIF2 pathway) in a subject, wherein the method comprises administering a compound of Formula (I) or a pharmaceutically acceptable salt, solvate, hydrate, tautomer, or stereoisomer thereof, or a composition thereof, to a subject.

In some embodiments, the method comprises the treatment of a neurodegenerative disease. In some embodiments, the neurodegenerative disease comprises vanishing white matter disease, childhood ataxia with CNS hypo-myelination, a leukodystrophy, a leukoencephalopathy, hypomyelinating or demyelinating disease, an intellectual disability syndrome, Alzheimer's disease, amyotrophic lateral sclerosis, Creutzfeldt-Jakob disease, Frontotemporal dementia, Gerstmann-Straussler-Scheinker disease, Huntington's disease, dementia (e.g., HIV-associated dementia or Lewy body dementia), Kuru, Parkinson's disease, progressive nuclear palsy, a tauopathy, or a prion disease. In some embodiments, the neurodegenerative disease comprises vanishing white matter disease. In some embodiments, the neurodegenerative disease comprises a psychiatric disease such as agoraphobia, Alzheimer's disease, anorexia nervosa, amnesia, anxiety disorder, bipolar disorder, body dysmorphic disorder, bulimia nervosa, claustrophobia, depression, delusions, Diogenes syndrome, dyspraxia, insomnia, Munchausen's syndrome, narcolepsy, narcissistic personality disorder, obsessive-compulsive disorder, psychosis, phobic disorder, schizophrenia, seasonal affective disorder, schizoid personality disorder, sleepwalking, social phobia, substance abuse, tardive dyskinesia, Tourette syndrome, or trichotillomania. In some embodiments, the neurodegenerative disease comprises a disease or disorder with symptoms of cognitive impairment or cognitive decline such as Alzheimer's disease, Parkinson's disease, Huntington's disease, schizophrenia, autism, frontotemporal dementia, dementia (e.g., HIV-associated dementia or Lewy body dementia), age relaed dementia, chronic traumatic encephalopathy, HIV-induced neurocognitive impairment, a HIV-associated neurocognitive disorder, a hypoxic injury (e.g., premature brain injury, chronic perinatal hypoxia), traumatic brain injury, or postoperative cognitive dysfunction. In some embodiments, the neurodegenerative disease comprises an intellectual disability syndrome. In some embodiments, the neurodegenerative disease comprises mild cognitive impairment.

In some embodiments, the method comprises the treatment of cancer. In some embodiments, the cancer comprises pancreatic cancer, breast cancer, multiple myeloma, or a cancer of the secretory cells. In some embodiments, the method comprises the treatment of cancer in combination with a chemotherapeutic agent for the enhancement of memory (e.g., long term memory).

In some embodiments, the method comprises the treatment of an inflammatory disease. In some embodiments, the inflammatory disease comprises postoperative cognitive dysfunction, traumatic brain injury, arthritis (e.g., rheumatoid arthritis, psoriatic arthritis, or juvenile idiopathic arthritis), systemic lupus erythematosus (SLE), myasthenia gravis, diabetes (e.g., juvenile onset diabetes or diabetes mellitus type 1), Guillain-Barre syndrome, Hashimoto's encephalitis, Hashimoto's thyroiditis, ankylosing spondylitis, psoriasis, Sjogren's syndrome, vasculitis, glomerulonephritis, auto-immune thyroiditis, Behcet's disease, Crohn's disease, ulcerative colitis, bullous pemphigoid, sarcoidosis, ichthyosis, Graves ophthalmopathy, inflammatory bowel disease, Addison's disease, vitiligo, asthma (e.g., allergic asthma), acne vulgaris, celiac disease, chronic prostatitis, pelvic inflammatory disease, reperfusion injury, sarcoidosis, transplant rejection, interstitial cystitis, or atopic dermatitis.

In some embodiments, the method comprises the treatment of a musculoskeletal disease. In some embodiments, the musculoskeletal disease comprises muscular dystrophy, multiple sclerosis, Freidrich's ataxia, a muscle wasting disorder (e.g., muscle atrophy, sarcopenia, cachexia), inclusion body myopathy, progressive muscular atrophy, motor neuron disease, carpal tunnel syndrome, epicondylitis, tendinitis, back pain, muscle pain, muscle soreness, repetitive strain disorders, or paralysis.

In some embodiments, the method comprises the treatment of a metabolic disease. In some embodiments, the metabolic disease comprises non-alcoholic steatohepatitis (NASH), non-alcoholic fatty liver disease (NAFLD), liver fibrosis, obesity, heart disease, atherosclerosis, arthritis, cystinosis, phenylketonuria, proliferative retinopathy, or Kearns-Sayre disease.

In another aspect, the present invention features a method of treating a disease or disorder related to modulation (e.g., a decrease) in eIF2B activity or level, modulation (e.g., a decrease) of eIF2α activity or level, modulation (e.g., an increase) in eIF2α phosphorylation, modulation (e.g., an increase) of phosphorylated eIF2α pathway activity, or modulation (e.g., an increase) of ISR activity in a subject, wherein the method comprises administering a compound of Formula (I) or a pharmaceutically acceptable salt, solvate, hydrate, tautomer, or stereoisomer thereof, or a composition thereof, to a subject. In some embodiments, the disease may be caused by a mutation to a gene or protein sequence related to a member of the eIF2 pathway (e.g., the eIF2α signaling pathway or ISR pathway).

In another aspect, the present invention features a method of treating a leukodystrophy such as vanishing white matter disease (VWMD) or childhood ataxia with central nervous system hypomyelination. In some embodiments, the leukodystrophy is characterized by an amino acid mutation (e.g., an amino acid deletion, amino acid addition, or amino acid substitution) in a tRNA synthetase. In some embodiments, administration of a compound of Formula (I) enhances eIF2B activity in a subject with a leukodystrophy, such as vanishing white matter disease (VWMD) or childhood ataxia with central nervous system hypomyelination.

In another aspect, the present invention features a method of treating a disease or disorder related to an amino acid mutation (e.g., an amino acid deletion, amino acid addition, or amino acid substitution) in a gene or gene product (e.g., RNA or protein) that modulates (e.g., reduces) protein synthesis. In some embodiments, administration of a compound of Formula (I) enhances residual GEF activity of a mutant GEF complex in a subject.

In another aspect, the present invention features a composition for use in treating a neurodegenerative disease, a leukodystrophy, cancer, an inflammatory disease, a musculoskeletal disease, or a metabolic disease in a subject, wherein the composition comprises a compound of Formula (I) or a pharmaceutically acceptable salt, solvate, hydrate, tautomer, or stereoisomer thereof.

In some embodiments, the neurodegenerative disease comprises vanishing white matter disease, childhood ataxia with CNS hypo-myelination, a leukodystrophy, a leukoencephalopathy, hypomyelinating or demyelinating disease, an intellectual disability syndrome, Alzheimer's disease, amyotrophic lateral sclerosis, Creutzfeldt-Jakob disease, Fronto-temporal dementia, Gerstmann-Straussler-Scheinker disease, Huntington's disease, dementia (e.g., HIV-associated dementia or Lewy body dementia), Kuru, Parkinson's disease, progressive nuclear palsy, a tauopathy, or a prion disease. In some embodiments, the neurodegenerative disease comprises vanishing white matter disease. In some embodiments, the neurodegenerative disease comprises a psychiatric disease such as agoraphobia, Alzheimer's disease, anorexia nervosa, amnesia, anxiety disorder, bipolar disorder, body dysmorphic disorder, bulimia nervosa, claustrophobia, depression, delusions, Diogenes syndrome, dyspraxia, insomnia, Munchausen's syndrome, narcolepsy, narcissistic personality disorder, obsessive-compulsive disorder, psychosis, phobic disorder, schizophrenia, seasonal affective disorder, schizoid personality disorder, sleepwalking, social phobia, substance abuse, tardive dyskinesia, Tourette syndrome, or trichotillomania. In some embodiments, the neurodegenerative disease comprises a disease or disorder with symptoms of cognitive impairment or cognitive decline such as Alzheimer's disease, Parkinson's disease, Huntington's disease, schizophrenia, autism, frontotemporal dementia, dementia (e.g., HIV-associated dementia or Lewy body dementia), age related dementia, chronic traumatic encephalopathy, HIV-induced neurocognitive impairment, a HIV-associated neurocognitive disorder, a hypoxic injury (e.g., premature brain injury, chronic perinatal hypoxia), traumatic brain injury, or postoperative cognitive dysfunction. In some embodiments, the neurodegenerative disease comprises an intellectual disability syndrome. In some embodiments, the neurodegenerative disease comprises mild cognitive impairment.

In some embodiments, the cancer comprises pancreatic cancer, breast cancer, multiple myeloma, or a cancer of the secretory cells. In some embodiments, the method comprises the treatment of cancer in combination with a chemotherapeutic agent for the enhancement of memory (e.g., long term memory).

In some embodiments, the inflammatory disease comprises postoperative cognitive dysfunction, traumatic brain injury, arthritis (e.g., rheumatoid arthritis, psoriatic arthritis, or juvenile idiopathic arthritis), systemic lupus erythematosus (SLE), myasthenia gravis, diabetes (e.g., juvenile onset diabetes or diabetes mellitus type 1), Guillain-Barre syndrome, Hashimoto's encephalitis, Hashimoto's thyroiditis, ankylosing spondylitis, psoriasis, Sjogren's syndrome, vasculitis, glomerulonephritis, auto-immune thyroiditis, Behcet's disease, Crohn's disease, ulcerative colitis, bullous pemphigoid, sarcoidosis, ichthyosis, Graves' ophthalmopathy, inflammatory bowel disease, Addison's disease, vitiligo, asthma (e.g., allergic asthma), acne vulgaris, celiac disease, chronic prostatitis, pelvic inflammatory disease, reperfusion injury, sarcoidosis, transplant rejection, interstitial cystitis, or atopic dermatitis.

In some embodiments, the musculoskeletal disease comprises muscular dystrophy, multiple sclerosis, Freidrich's ataxia, a muscle wasting disorder (e.g., muscle atrophy, sarcopenia, cachexia), inclusion body myopathy, progressive muscular atrophy, motor neuron disease, carpal tunnel syndrome, epicondylitis, tendinitis, back pain, muscle pain, muscle soreness, repetitive strain disorders, or paralysis.

In some embodiments, the metabolic disease comprises non-alcoholic steatohepatitis (NASH), non-alcoholic fatty liver disease (NAFLD), liver fibrosis, obesity, heart disease, atherosclerosis, arthritis, cystinosis, phenylketonuria, proliferative retinopathy, or Kearns-Sayre disease.

In another aspect, the present invention features a composition for use in treating a disease or disorder related to modulation (e.g., a decrease) in eIF2B activity or level, modulation (e.g., a decrease) of eIF2α activity or level, modulation (e.g., an increase) in eIF2α phosphorylation, modulation (e.g., an increase) of phosphorylated eIF2α pathway activity, or modulation (e.g., an increase) of ISR activity in a subject, wherein the composition comprises a compound of Formula (I) or a pharmaceutically acceptable salt, solvate, hydrate, tautomer, or stereoisomer thereof. In some embodiments, the disease may be caused by a mutation to a gene or protein sequence related to a member of the eIF2 pathway (e.g., the eIF2α signaling pathway or ISR pathway).

In another aspect, the present invention features a composition for use in treating a leukodystrophy such as vanishing white matter disease (VWMD) or childhood ataxia with central nervous system hypomyelination. In some embodiments, the leukodystrophy is characterized by an amino acid mutation (e.g., an amino acid deletion, amino acid addition, or amino acid substitution) in a tRNA synthetase. In some embodiments, the composition comprising a compound of Formula (I) enhances eIF2B activity in a subject with a leukodystrophy, such as vanishing white matter disease (VWMD) or childhood ataxia with central nervous system hypomyelination.

In another aspect, the present invention features a composition for use in treating a disease or disorder related to an amino acid mutation (e.g., an amino acid deletion, amino acid addition, or amino acid substitution) in a gene or gene product (e.g., RNA or protein) that modulates (e.g., reduces) protein synthesis. In some embodiments, the composition comprising a compound of Formula (I) enhances residual GEF activity of a mutant GEF complex in a subject.

DETAILED DESCRIPTION OF THE INVENTION

The present invention features compounds, compositions, and methods comprising a compound of Formula (I) or a pharmaceutically acceptable salt, solvate, hydrate, tautomer, or stereoisomer thereof for use, e.g., in the modulation (e.g., activation) of eIF2B and the attenuation of the ISR signaling pathway.

Definitions

Chemical Definitions

Definitions of specific functional groups and chemical terms are described in more detail below. The chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in Thomas Sorrell, *Organic Chemistry*, University Science Books, Sausalito, 1999; Smith and March, *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987.

The abbreviations used herein have their conventional meaning within the chemical and biological arts. The chemical structures and formulae set forth herein are constructed according to the standard rules of chemical valency known in the chemical arts.

Compounds described herein can comprise one or more asymmetric centers, and thus can exist in various isomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, Stereochemistry of Carbon Compounds (McGraw-Hill, NY, 1962); and Wilen, *Tables of Resolving Agents and Optical Resolutions* p. 268 (E. L. Eliel, Ed., Univ. of Notre Dame Press, Notre Dame, Ind. 1972). The invention additionally encompasses compounds described herein as individual isomers substantially free of other isomers, and alternatively, as mixtures of various isomers.

As used herein a pure enantiomeric compound is substantially free from other enantiomers or stereoisomers of the compound (i.e., in enantiomeric excess). In other words, an "S" form of the compound is substantially free from the "R" form of the compound and is, thus, in enantiomeric excess of the "R" form. The term "enantiomerically pure" or "pure enantiomer" denotes that the compound comprises more than 75% by weight, more than 80% by weight, more than 85% by weight, more than 90% by weight, more than 91% by weight, more than 92% by weight, more than 93% by weight, more than 94% by weight, more than 95% by weight, more than 96% by weight, more than 97% by weight, more than 98% by weight, more than 99% by weight, more than 99.5% by weight, or more than 99.9% by weight, of the enantiomer. In certain embodiments, the weights are based upon total weight of all enantiomers or stereoisomers of the compound.

In the compositions provided herein, an enantiomerically pure compound can be present with other active or inactive ingredients. For example, a pharmaceutical composition comprising enantiomerically pure R-compound can comprise, for example, about 90% excipient and about 10% enantiomerically pure R-compound. In certain embodiments, the enantiomerically pure R-compound in such compositions can, for example, comprise, at least about 95% by weight R-compound and at most about 5% by weight S-compound, by total weight of the compound. For example, a pharmaceutical composition comprising enantiomerically pure S-compound can comprise, for example, about 90% excipient and about 10% enantiomerically pure S-compound. In certain embodiments, the enantiomerically pure S-compound in such compositions can, for example, comprise, at least about 95% by weight S-compound and at most about 5% by weight R-compound, by total weight of the compound. In certain embodiments, the active ingredient can be formulated with little or no excipient or carrier.

Compound described herein may also comprise one or more isotopic substitutions. For example, H may be in any isotopic form, including $^1$H, $^2$H (D or deuterium), and $^3$H (T or tritium); C may be in any isotopic form, including $^{12}$C, $^{13}$C, and $^{14}$C; O may be in any isotopic form, including $^{16}$O and $^{18}$O; and the like.

The articles "a" and "an" may be used herein to refer to one or to more than one (i.e. at least one) of the grammatical objects of the article. By way of example "an analogue" means one analogue or more than one analogue.

When a range of values is listed, it is intended to encompass each value and sub-range within the range. For example "$C_1$-$C_6$ alkyl" is intended to encompass, $C_1$, $C_2$, $C_3$, $C_4$, $C_5$, $C_6$, $C_1$-$C_6$, $C_1$-$C_5$, $C_1$-$C_4$, $C_1$-$C_3$, $C_1$-$C_2$, $C_2$-$C_6$, $C_2$-$C_5$, $C_2$-$C_4$, $C_2$-$C_3$, $C_3$-$C_6$, $C_3$-$C_5$, $C_3$-$C_4$, $C_4$-$C_6$, $C_4$-$C_5$, and $C_5$-$C_6$ alkyl.

The following terms are intended to have the meanings presented therewith below and are useful in understanding the description and intended scope of the present invention.

"Alkyl" refers to a radical of a straight-chain or branched saturated hydrocarbon group having from 1 to 20 carbon atoms ("$C_1$-$C_{20}$ alkyl"). In some embodiments, an alkyl group has 1 to 12 carbon atoms ("$C_1$-$C_{12}$ alkyl"). In some embodiments, an alkyl group has 1 to 8 carbon atoms ("$C_1$-$C_8$ alkyl"). In some embodiments, an alkyl group has 1 to 6 carbon atoms ("$C_1$-$C_6$ alkyl"). In some embodiments, an alkyl group has 1 to 5 carbon atoms ("$C_1$-$C_5$ alkyl"). In some embodiments, an alkyl group has 1 to 4 carbon atoms ("$C_1$-$C_4$alkyl"). In some embodiments, an alkyl group has 1 to 3 carbon atoms ("$C_1$-$C_3$ alkyl"). In some embodiments, an alkyl group has 1 to 2 carbon atoms ("$C_1$-$C_2$ alkyl"). In some embodiments, an alkyl group has 1 carbon atom ("$C_1$ alkyl"). In some embodiments, an alkyl group has 2 to 6 carbon atoms ("$C_2$-$C_6$alkyl"). Examples of $C_1$-$C_6$alkyl groups include methyl ($C_1$), ethyl ($C_2$), n-propyl ($C_3$), iso-propyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). Additional examples of alkyl groups include n-heptyl ($C_7$), n-octyl ($C_8$) and the like. Each instance of an alkyl group may be independently optionally substituted, i.e., unsubstituted (an "unsubstituted alkyl") or substituted (a "substituted alkyl") with one or more substituents; e.g., for instance from 1 to 5 substituents, 1 to 3 substituents, or 1 substituent. In certain embodiments, the alkyl group is unsubstituted $C_{1-10}$ alkyl (e.g., —$CH_3$). In certain embodiments, the alkyl group is substituted $C_{1-6}$ alkyl. Common alkyl abbreviations include Me (—$CH_3$), Et (—$CH_2CH_3$), iPr (—$CH(CH_3)_2$), nPr (—$CH_2CH_2CH_3$), n-Bu (—$CH_2CH_2CH_2CH_3$), or i-Bu (—$CH_2CH(CH_3)_2$).

The term "alkylene," by itself or as part of another substituent, means, unless otherwise stated, a divalent radical derived from an alkyl, as exemplified, but not limited by, —$CH_2CH_2CH_2CH_2$—. Typically, an alkyl (or alkylene) group will have from 1 to 24 carbon atoms, with those groups having 10 or fewer carbon atoms being preferred in the present invention. The term "alkenylene," by itself or as part of another substituent, means, unless otherwise stated, a divalent radical derived from an alkene. An alkylene group may be described as, e.g., a $C_1$-$C_6$-membered alkylene, wherein the term "membered" refers to the non-hydrogen atoms within the moiety.

"Alkenyl" refers to a radical of a straight-chain or branched hydrocarbon group having from 2 to 20 carbon atoms, one or more carbon-carbon double bonds, and no triple bonds ("$C_2$-$C_{20}$ alkenyl"). In some embodiments, an alkenyl group has 2 to 10 carbon atoms ("$C_2$-$C_{10}$ alkenyl"). In some embodiments, an alkenyl group has 2 to 8 carbon atoms ("$C_2$-$C_8$ alkenyl"). In some embodiments, an alkenyl group has 2 to 6 carbon atoms ("$C_2$-$C_6$ alkenyl"). In some embodiments, an alkenyl group has 2 to 5 carbon atoms ("$C_2$-$C_5$ alkenyl"). In some embodiments, an alkenyl group has 2 to 4 carbon atoms ("$C_2$-$C_4$ alkenyl"). In some embodiments, an alkenyl group has 2 to 3 carbon atoms ("$C_2$-$C_3$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_2$-$C_4$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_2$-$C_6$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Each instance of an alkenyl group may be independently optionally substituted, i.e., unsubstituted (an "unsubstituted alkenyl") or substituted (a "substituted alkenyl") with one or more substituents e.g., for instance from 1 to 5 substituents, 1 to 3 substituents, or 1 substituent. In certain embodiments, the alkenyl group is unsubstituted $C_{2-10}$ alkenyl. In certain embodiments, the alkenyl group is substituted $C_{2-6}$ alkenyl.

"Aryl" refers to a radical of a monocyclic or polycyclic (e.g., bicyclic or tricyclic) 4n+2 aromatic ring system (e.g., having 6, 10, or 14 π electrons shared in a cyclic array) having 6-14 ring carbon atoms and zero heteroatoms provided in the aromatic ring system ("$C_6$-$C_{14}$ aryl"). In some embodiments, an aryl group has six ring carbon atoms ("$C_6$ aryl"; e.g., phenyl). In some embodiments, an aryl group has ten ring carbon atoms ("$C_{10}$ aryl"; e.g., naphthyl such as 1-naphthyl and 2-naphthyl). In some embodiments, an aryl group has fourteen ring carbon atoms ("$C_{14}$ aryl"; e.g., anthracyl). An aryl group may be described as, e.g., a $C_6$-$C_{10}$-membered aryl, wherein the term "membered" refers to the non-hydrogen ring atoms within the moiety. Aryl groups include, but are not limited to, phenyl, naphthyl, indenyl, and tetrahydronaphthyl. Each instance of an aryl group may be independently optionally substituted, i.e., unsubstituted (an "unsubstituted aryl") or substituted (a "substituted aryl") with one or more substituents. In certain embodiments, the aryl group is unsubstituted $C_6$-$C_{14}$ aryl. In certain embodiments, the aryl group is substituted $C_6$-$C_{14}$ aryl.

In certain embodiments, an aryl group is substituted with one or more of groups selected from halo, $C_1$-$C_8$ alkyl, halo-$C_1$-$C_8$ alkyl, haloxy-$C_1$-$C_8$ alkyl, cyano, hydroxy, alkoxy $C_1$-$C_8$ alkyl, and amino.

Examples of representative substituted aryls include the following

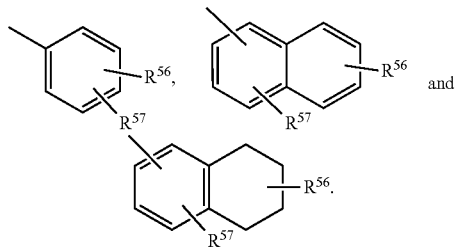

wherein one of $R^{56}$ and $R^{57}$ may be hydrogen and at least one of $R^{56}$ and $R^{57}$ is each independently selected from $C_1$-$C_8$ alkyl, halo-$C_1$-$C_8$ alkyl, 4-10 membered heterocyclyl, alkanoyl, alkoxy-$C_1$-$C_8$ alkyl, heteroaryloxy, alkylamino, arylamino, heteroarylamino, $NR^{58}COR^{59}$, $NR^{58}SOR^{59}$ $NR^{58}SO_2R^{59}$, C(O)Oalkyl, C(O)Oaryl, $CONR^{58}R^{59}$, $CONR^{58}OR^{59}$, $NR^{58}R^{59}$, $SO_2NR^{58}R^{59}$, S-alkyl, S(O)-alkyl, $S(O)_2$-alkyl, S-aryl, S(O)-aryl, $S(O_2)$-aryl; or $R^{56}$ and $R^{57}$ may be joined to form a cyclic ring (saturated or unsaturated) from 5 to 8 atoms, optionally containing one or more heteroatoms selected from the group N, O, or S.

Other representative aryl groups having a fused heterocyclyl group include the following:

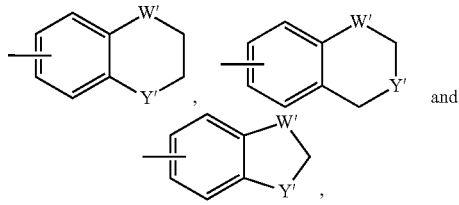

wherein each W is selected from $C(R^{66})_2$, $NR^{66}$, O, and S; and each Y is selected from carbonyl, $NR^{66}$, O and S; and $R^{66}$ is independently hydrogen, $C_1$-$C_8$ alkyl, $C_3$-$C_{10}$ cycloalkyl, 4-10 membered heterocyclyl, $C_6$-$C_{10}$ aryl, and 5-10 membered heteroaryl.

An "arylene" and a "heteroarylene," alone or as part of another substituent, mean a divalent radical derived from an aryl and heteroaryl, respectively. Non-limiting examples of heteroaryl groups include pyridinyl, pyrimidinyl, thiophenyl, thienyl, furanyl, indolyl, benzoxadiazolyl, benzodioxolyl, benzodioxanyl, thianaphthanyl, pyrrolopyridinyl, indazolyl, quinolinyl, quinoxalinyl, pyridopyrazinyl, quinazolinonyl, benzoisoxazolyl, imidazopyridinyl, benzofuranyl, benzothienyl, benzothiophenyl, phenyl, naphthyl, biphenyl, pyrrolyl, pyrazolyl, imidazolyl, pyrazinyl, oxazolyl, isoxazolyl, thiazolyl, furylthienyl, pyridyl, pyrimidyl, benzothiazolyl, purinyl, benzimidazolyl, isoquinolyl, thiadiazolyl, oxadiazolyl, pyrrolyl, diazolyl, triazolyl, tetrazolyl, benzothiadiazolyl, isothiazolyl, pyrazolopyrimidinyl, pyrrolopyrimidinyl, benzotriazolyl, benzoxazolyl, or quinolyl. The examples above may be substituted or unsubstituted and divalent radicals of each heteroaryl example above are non-limiting examples of heteroarylene.

"Halo" or "halogen," independently or as part of another substituent, mean, unless otherwise stated, a fluorine (F), chlorine (Cl), bromine (Br), or iodine (I) atom. The term "halide" by itself or as part of another substituent, refers to a fluoride, chloride, bromide, or iodide atom. In certain embodiments, the halo group is either fluorine or chlorine.

Additionally, terms such as "haloalkyl" are meant to include monohaloalkyl and polyhaloalkyl. For example, the term "halo-$C_1$-$C_6$ alkyl" includes, but is not limited to, fluoromethyl, difluoromethyl, trifluoromethyl, 2,2,2-trifluoroethyl, 4-chlorobutyl, 3-bromopropyl, and the like.

The term "heteroalkyl," by itself or in combination with another term, means, unless otherwise stated, a non-cyclic stable straight or branched chain, or combinations thereof, including at least one carbon atom and at least one heteroatom selected from the group consisting of O, N, P, Si, and S, and wherein the nitrogen and sulfur atoms may optionally be oxidized, and the nitrogen heteroatom may optionally be quaternized. The heteroatom(s) O, N, P, S, and Si may be placed at any interior position of the heteroalkyl group or at the position at which the alkyl group is attached to the remainder of the molecule. Exemplary heteroalkyl groups include, but are not limited to: —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH═CH—O—$CH_3$, —Si($CH_3$)$_3$, —$CH_2$—CH═N—$OCH_3$, —CH═CH—N($CH_3$)—$CH_3$, —O—$CH_3$, and —O—$CH_2$—$CH_3$. Up to two or three heteroatoms may be consecutive, such as, for example, —$CH_2$—NH—$OCH_3$ and —$CH_2$—O—Si($CH_3$)$_3$. Where "heteroalkyl" is recited, followed by recitations of specific heteroalkyl groups, such as —$CH_2$O, —$NR^BR^C$, or the like, it will be understood that the terms heteroalkyl and —$CH_2$O or —$NR^BR^C$ are not redundant or mutually exclusive. Rather, the specific heteroalkyl groups are recited to add clarity. Thus, the term "heteroalkyl" should not be interpreted herein as excluding specific heteroalkyl groups, such as —$CH_2$O, —$NR^BR^C$, or the like.

Similarly, the term "heteroalkylene," by itself or as part of another substituent, means, unless otherwise stated, a divalent radical derived from heteroalkyl, as exemplified, but not limited by, —$CH_2O$— and —$CH_2CH_2O$—. A heteroalkylene group may be described as, e.g., a 2-7-membered heteroalkylene, wherein the term "membered" refers to the non-hydrogen atoms within the moiety. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— may represent both —C(O)$_2$R'— and —R'C(O)$_2$—.

"Heteroaryl" refers to a radical of a 5-10 membered monocyclic or bicyclic 4n+2 aromatic ring system (e.g., having 6 or 10 π electrons shared in a cyclic array) having ring carbon atoms and 1-4 ring heteroatoms provided in the aromatic ring system, wherein each heteroatom is independently selected from nitrogen, oxygen and sulfur ("5-10 membered heteroaryl"). In heteroaryl groups that contain one or more nitrogen atoms, the point of attachment can be a carbon or nitrogen atom, as valency permits. Heteroaryl bicyclic ring systems can include one or more heteroatoms in one or both rings. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused (aryl/heteroaryl) ring system. Bicyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl). A heteroaryl group may be described as, e.g., a 6-10-membered heteroaryl, wherein the term "membered" refers to the non-hydrogen ring atoms within the moiety.

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Each instance of a heteroaryl group may be independently optionally substituted, i.e., unsubstituted (an "unsubstituted heteroaryl") or substituted (a "substituted heteroaryl") with one or more substituents. In certain embodiments, the heteroaryl group is unsubstituted 5-14 membered heteroaryl. In certain embodiments, the heteroaryl group is substituted 5-14 membered heteroaryl.

Exemplary 5-membered heteroaryl groups containing one heteroatom include, without limitation, pyrrolyl, furanyl and thiophenyl. Exemplary 5-membered heteroaryl groups containing two heteroatoms include, without limitation, imidazolyl, pyrazolyl, oxazolyl, isoxazolyl, thiazolyl, and isothiazolyl. Exemplary 5-membered heteroaryl groups containing three heteroatoms include, without limitation, triazolyl, oxadiazolyl, and thiadiazolyl. Exemplary 5-membered heteroaryl groups containing four heteroatoms include, without limitation, tetrazolyl. Exemplary 6-membered heteroaryl groups containing one heteroatom include, without limitation, pyridinyl. Exemplary 6-membered heteroaryl groups containing two heteroatoms include, without limitation, pyridazinyl, pyrimidinyl, and pyrazinyl. Exemplary 6-membered heteroaryl groups containing three or four heteroatoms include, without limitation, triazinyl and tetrazinyl, respectively. Exemplary 7-membered heteroaryl groups containing one heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl.

Examples of representative heteroaryls include the following formulae:

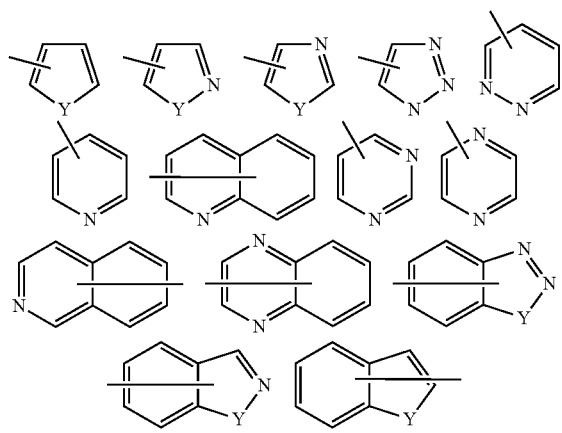

wherein each Y is selected from carbonyl, $NR^{65}$, O, and S; and $R^{65}$ is independently hydrogen, $C_1$-$C_8$ alkyl, $C_3$-$C_{10}$ cycloalkyl, 4-10 membered heterocyclyl, $C_6$-$C_{10}$ aryl, and 5-10 membered heteroaryl.

"Cycloalkyl" refers to a radical of a non-aromatic cyclic hydrocarbon group having from 3 to 10 ring carbon atoms ("$C_3$-$C_{10}$ cycloalkyl") and zero heteroatoms in the non-aromatic ring system. In some embodiments, a cycloalkyl group has 3 to 8 ring carbon atoms ("$C_3$-$C_8$ cycloalkyl"). In some embodiments, a cycloalkyl group has 3 to 6 ring carbon atoms ("$C_3$-$C_6$ cycloalkyl"). In some embodiments, a cycloalkyl group has 3 to 6 ring carbon atoms ("$C_3$-$C_6$ cycloalkyl"). In some embodiments, a cycloalkyl group has 5 to 10 ring carbon atoms ("$C_5$-$C_{10}$ cycloalkyl"). A cycloalkyl group may be described as, e.g., a $C_4$-$C_7$-membered cycloalkyl, wherein the term "membered" refers to the non-hydrogen ring atoms within the moiety. Exemplary $C_3$-$C_6$ cycloalkyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_3$-$C_8$ cycloalkyl groups include, without limitation, the aforementioned $C_3$-$C_6$ cycloalkyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), cubanyl ($C_8$), bicyclo[1.1.1]pentanyl ($C_5$), bicyclo[2.2.2]octanyl ($C_8$), bicyclo[2.1.1]hexanyl ($C_6$), bicyclo[3.1.1]heptanyl ($C_7$), and the like. Exemplary $C_3$-$C_{10}$ cycloalkyl groups include, without limitation, the aforementioned $C_3$-$C_8$ cycloalkyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. As the foregoing examples illustrate, in certain embodiments, the cycloalkyl group is either monocyclic ("monocyclic cycloalkyl") or contain a fused, bridged or spiro ring system such as a bicyclic system ("bicyclic cycloalkyl") and can be saturated or can be partially unsaturated. "Cycloalkyl" also includes ring systems wherein the cycloalkyl ring, as defined above, is fused with one or more aryl groups wherein the point of attachment is on the cycloalkyl ring, and in such instances, the number of carbons continue to designate the number of carbons in the cycloalkyl ring system. Each instance of a cycloalkyl group may be independently optionally substituted, i.e., unsubstituted (an "unsubstituted cycloalkyl") or substituted (a "substituted cycloalkyl") with one or more substituents. In certain embodiments, the cycloalkyl group is unsubstituted $C_3$-$C_{10}$ cycloalkyl. In certain embodiments, the cycloalkyl group is a substituted $C_3$-$C_{10}$ cycloalkyl.

In some embodiments, "cycloalkyl" is a monocyclic, saturated cycloalkyl group having from 3 to 10 ring carbon atoms ("$C_3$-$C_{10}$ cycloalkyl"). In some embodiments, a cycloalkyl group has 3 to 8 ring carbon atoms ("$C_3$-$C_8$ cycloalkyl"). In some embodiments, a cycloalkyl group has 3 to 6 ring carbon atoms ("$C_3$-$C_6$ cycloalkyl"). In some embodiments, a cycloalkyl group has 5 to 6 ring carbon atoms ("$C_5$-$C_6$ cycloalkyl"). In some embodiments, a cycloalkyl group has 5 to 10 ring carbon atoms ("$C_5$-$C_{10}$ cycloalkyl"). Examples of $C_5$-$C_6$ cycloalkyl groups include cyclopentyl ($C_5$) and cyclohexyl ($C_5$). Examples of $C_3$-$C_6$ cycloalkyl groups include the aforementioned $C_5$-$C_6$ cycloalkyl groups as well as cyclopropyl ($C_3$) and cyclobutyl ($C_4$). Examples of $C_3$-$C_8$ cycloalkyl groups include the aforementioned $C_3$-$C_6$ cycloalkyl groups as well as cycloheptyl ($C_7$) and cyclooctyl ($C_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is unsubstituted $C_3$-$C_{10}$ cycloalkyl. In certain embodiments, the cycloalkyl group is substituted $C_3$-$C_{10}$ cycloalkyl.

"Heterocyclyl" or "heterocyclic" refers to a radical of a 3- to 10-membered non-aromatic ring system having ring carbon atoms and 1 to 4 ring heteroatoms, wherein each heteroatom is independently selected from nitrogen, oxygen, sulfur, boron, phosphorus, and silicon ("3-10 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or a fused, bridged or spiro ring system such as a bicyclic system ("bicyclic heterocyclyl"), and can be saturated or can be partially unsaturated. Heterocyclyl bicyclic ring systems can include one or more heteroatoms in one or both rings. "Heterocyclyl" also includes ring systems wherein the heterocyclyl ring, as defined above, is fused with one or more cycloalkyl groups wherein the point of attachment is either on the cycloalkyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. A heterocyclyl group may be described as, e.g., a 3-7-membered heterocyclyl, wherein the term "membered" refers to the non-hydrogen ring atoms, i.e., carbon, nitrogen, oxygen, sulfur, boron, phosphorus, and silicon, within the moiety. Each instance of heterocyclyl may be independently optionally substituted, i.e., unsubstituted (an "unsubstituted heterocyclyl") or substituted (a "substituted heterocyclyl") with one or more substituents. In certain embodiments, the heterocyclyl group is unsubstituted 3-10 membered heterocyclyl. In certain embodiments, the heterocyclyl group is substituted 3-10 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, sulfur, boron, phosphorus, and silicon ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has one ring heteroatom selected from nitrogen, oxygen, and sulfur.

Exemplary 3-membered heterocyclyl groups containing one heteroatom include, without limitation, azirdinyl, oxiranyl, thiorenyl. Exemplary 4-membered heterocyclyl groups containing one heteroatom include, without limitation, azetidinyl, oxetanyl and thietanyl. Exemplary 5-membered heterocyclyl groups containing one heteroatom include, without limitation, tetrahydrofuranyl, dihydrofuranyl, tetrahydrothiophenyl, dihydrothiophenyl, pyrrolidinyl, dihydropyrrolyl and pyrrolyl-2,5-dione. Exemplary 5-membered heterocyclyl groups containing two heteroatoms include, without limitation, dioxolanyl, oxasulfuranyl, disulfuranyl, and oxazolidin-2-one. Exemplary 5-membered heterocyclyl groups containing three heteroatoms include, without limitation, triazolinyl, oxadiazolinyl, and thiadiazolinyl. Exemplary 6-membered heterocyclyl groups containing one heteroatom include, without limitation, piperidinyl, tetrahydropyranyl, dihydropyridinyl, and thianyl. Exemplary 6-membered heterocyclyl groups containing two heteroatoms include, without limitation, piperazinyl, morpholinyl, dithianyl, dioxanyl. Exemplary 6-membered heterocyclyl groups containing two heteroatoms include, without limitation, triazinanyl. Exemplary 7-membered heterocyclyl groups containing one heteroatom include, without limitation, azepanyl, oxepanyl and thiepanyl. Exemplary 8-membered heterocyclyl groups containing one heteroatom include, without limitation, azocanyl, oxecanyl and thiocanyl. Exemplary 5-membered heterocyclyl groups fused to a $C_6$ aryl ring (also referred to herein as a 5,6-bicyclic heterocyclic ring) include, without limitation, indolinyl, isoindolinyl, dihydrobenzofuranyl, dihydrobenzothienyl, benzoxazolinonyl, and the like. Exemplary 6-membered heterocyclyl groups fused to an aryl ring (also referred to herein as a 6,6-bicyclic heterocyclic ring) include, without limitation, tetrahydroquinolinyl, tetrahydroisoquinolinyl, and the like.

Particular examples of heterocyclyl groups are shown in the following illustrative examples:

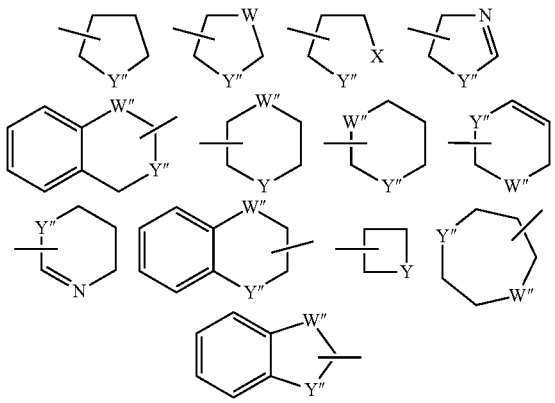

wherein each W" is selected from $CR^{67}$, $C(R^{67})_2$, $NR^{67}$, O, and S; and each Y" is selected from $NR^{67}$, O, and S; and $R^{67}$ is independently hydrogen, $C_1$-$C_8$ alkyl, $C_3$-$C_{10}$ cycloalkyl, 4-10 membered heterocyclyl, $C_6$-$C_{10}$ aryl, and 5-10-membered heteroaryl. These heterocyclyl rings may be optionally substituted with one or more groups selected from the group consisting of acyl, acylamino, acyloxy, alkoxy, alkoxycarbonyl, alkoxycarbonylamino, amino, substituted amino, aminocarbonyl (e.g., amido), aminocarbonylamino, aminosulfonyl, sulfonylamino, aryl, aryloxy, azido, carboxyl, cyano, cycloalkyl, halogen, hydroxy, keto, nitro, thiol, —S-alkyl, —S-aryl, —S(O)-alkyl, —S(O)-aryl, —S(O)$_2$-alkyl, and —S(O)$_2$-aryl. Substituting groups include carbonyl or thiocarbonyl which provide, for example, lactam and urea derivatives.

"Nitrogen-containing heterocyclyl" group means a 4- to 7-membered non-aromatic cyclic group containing at least one nitrogen atom, for example, but without limitation, morpholine, piperidine (e.g. 2-piperidinyl, 3-piperidinyl and 4-piperidinyl), pyrrolidine (e.g. 2-pyrrolidinyl and 3-pyrrolidinyl), azetidine, pyrrolidone, imidazoline, imidazolidinone, 2-pyrazoline, pyrazolidine, piperazine, and N-alkyl piperazines such as N-methyl piperazine. Particular examples include azetidine, piperidone and piperazone.

"Amino" refers to the radical —$NR^{70}R^{71}$, wherein $R^{70}$ and $R^{71}$ are each independently hydrogen, $C_1$-$C_8$ alkyl, $C_3$-$C_{10}$ cycloalkyl, 4-10 membered heterocyclyl, $C_6$-$C_{10}$ aryl, and 5-10-membered heteroaryl. In some embodiments, amino refers to $NH_2$.

"Cyano" refers to the radical —CN.

"Hydroxy" refers to the radical —OH.

Alkyl, alkenyl, alkynyl, cycloalkyl, heterocyclyl, aryl, and heteroaryl groups, as defined herein, are optionally substituted (e.g., "substituted" or "unsubstituted" alkyl, "substituted" or "unsubstituted" alkenyl, "substituted" or "unsubstituted" alkynyl, "substituted" or "unsubstituted" cycloalkyl, "substituted" or "unsubstituted" heterocyclyl, "substituted" or "unsubstituted" aryl or "substituted" or "unsubstituted" heteroaryl group). In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, such as any of the substituents described herein that result in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

A "counterion" or "anionic counterion" is a negatively charged group associated with a cationic quaternary amino group in order to maintain electronic neutrality. Exemplary counterions include halide ions (e.g., $F^-$, $Cl^-$, $Br^-$, $I^-$), $NO_3^-$, $ClO_4^-$, $OH^-$, $H_2PO_4^-$, $HSO_4^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), and carboxylate ions (e.g., acetate, ethanoate, propanoate, benzoate, glycerate, lactate, tartrate, glycolate, and the like).

The term "pharmaceutically acceptable salts" is meant to include salts of the active compounds that are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, e.g., Berge et al, *Journal of Pharmaceutical Science* 66: 1-19 (1977)). Certain specific compounds of the present invention contain both basic and acidic functionalities that allow the compounds to be converted into either base or acid addition salts. Other pharmaceutically acceptable carriers known to those of skill in the art are suitable for the present invention. Salts tend to be more soluble in aqueous or other protonic solvents that are the corresponding free base forms. In other cases, the preparation may be a lyophilized powder in a first buffer, e.g., in 1 mM-50 mM histidine, 0.1%-2% sucrose, 2%-7% mannitol at a pH range of 4.5 to 5.5, that is combined with a second buffer prior to use.

Thus, the compounds of the present invention may exist as salts, such as with pharmaceutically acceptable acids. The present invention includes such salts. Examples of such salts include hydrochlorides, hydrobromides, sulfates, methanesulfonates, nitrates, maleates, acetates, citrates, fumarates, tartrates (e.g., (+)-tartrates, (−)-tartrates, or mixtures thereof including racemic mixtures), succinates, benzoates, and salts with amino acids such as glutamic acid. These salts may be prepared by methods known to those skilled in the art.

The neutral forms of the compounds are preferably regenerated by contacting the salt with a base or acid and isolating the parent compound in the conventional manner. The parent form of the compound differs from the various salt forms in certain physical properties, such as solubility in polar solvents.

In addition to salt forms, the present invention provides compounds, which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

As used herein, the term "salt" refers to acid or base salts of the compounds used in the methods of the present invention. Illustrative examples of acceptable salts are mineral acid (hydrochloric acid, hydrobromic acid, phosphoric acid, and the like) salts, organic acid (acetic acid, propionic acid, glutamic acid, citric acid and the like) salts, quaternary ammonium (methyl iodide, ethyl iodide, and the like) salts.

Certain compounds of the present invention possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present invention. The compounds of the present invention do not include those which are known in art to be too unstable to synthesize and/or isolate. The present invention is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another.

It will be apparent to one skilled in the art that certain compounds of this invention may exist in tautomeric forms, all such tautomeric forms of the compounds being within the scope of the invention.

The terms "treating" or "treatment" refers to any indicia of success in the treatment or amelioration of an injury, disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation. For example, certain methods herein treat cancer (e.g. pancreatic cancer, breast cancer, multiple myeloma, cancers of secretory cells), neurodegenerative diseases (e.g. Alzheimer's disease, Parkinsons disease, frontotemporal dementia), leukodystrophies (e.g., vanishing white matter disease, childhood ataxia with CNS hypo-myelination), postsurgical cognitive dysfunction, traumatic brain injury, intellectual disability syndromes, inflammatory diseases, musculoskeletal diseases, metabolic diseases, or diseases or disorders associated with impaired function of eIF2B or components in a signal transduction or signaling pathway including the ISR and decreased eIF2 pathway activity). For example certain methods herein treat cancer by decreasing or reducing or preventing the occurrence, growth, metastasis, or progression of cancer or decreasing a symptom of cancer; treat neurodegeneration by improving mental wellbeing, increasing mental function, slowing the decrease of mental function, decreasing dementia, delaying the onset of dementia, improving cognitive skills, decreasing the loss of cognitive skills, improving memory, decreasing the degradation of memory, decreasing a symptom of neurodegeneration or extending survival; treat vanishing white matter disease by reducing a symptom of vanishing white matter disease or reducing the loss of white matter or reducing the loss of myelin or increasing the amount of myelin or increasing the amount of white matter; treat childhood ataxia with CNS hypo-myelination by decreasing a symptom of childhood ataxia with CNS hypo-myelination or increasing the level of myelin or decreasing the loss of myelin; treat an intellectual disability syndrome by decreasing a symptom of an intellectual disability syndrome, treat an inflammatory disease by treating a symptom of the inflammatory disease; treat a musculoskeletal disease by treating a symptom of the musculoskeletal disease; or treat a metabolic disease by treating a symptom of the metabolic disease. Symptoms of a disease, disorder, or condition described herein (e.g., cancer a neurodegenerative disease, a leukodystrophy, an inflammatory disease, a musculoskeletal disease, a metabolic disease, or a condition or disease associated with impaired function of eIF2B or components in a signal transduction pathway including the eIF2 pathway, eIF2α phosphorylation. or ISR pathway) would be known or may be determined by a person of ordinary skill in the art. The term "treating" and conjugations thereof, include prevention of an injury, pathology, condition, or disease (e.g. preventing the development of one or more symptoms of a disease, disorder, or condition described herein).

An "effective amount" is an amount sufficient to accomplish a stated purpose (e.g. achieve the effect for which it is administered, treat a disease, reduce enzyme activity, increase enzyme activity, or reduce one or more symptoms of a disease or condition). An example of an "effective amount" is an amount sufficient to contribute to the treatment, prevention, or reduction of a symptom or symptoms of a disease, which could also be referred to as a "therapeutically effective amount." A "prophylactically effective amount" of a drug is an amount of a drug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. The exact amounts will depend on the purpose of the treatment, and will be ascertainable by one skilled in the art using known techniques (see, e.g., Lieberman, Pharmaceutical Dosage Forms (vols. 1-3, 1992); Lloyd, The Art, Science and Technology of Pharmaceutical Compounding (1999); Pickar, Dosage Calculations (1999); and Remington: The Science and Practice of Pharmacy, 20th Edition, 2003, Gennaro, Ed., Lippincott, Williams & Wilkins).

A "reduction" of a symptom or symptoms (and grammatical equivalents of this phrase) means decreasing of the severity or frequency of the symptom(s), or elimination of the symptom(s).

The term "associated" or "associated with" in the context of a substance or substance activity or function associated with a disease (e.g., a disease or disorder described herein, e.g., cancer, a neurodegenerative disease, a leukodystrophy, an inflammatory disease, a musculoskeletal disease, a metabolic disease, or a disease or disorder associated with impaired function of eIF2B or components in a signal transduction pathway including the eIF2 pathway, eIF2α phosphorylation. or ISR pathway) means that the disease is caused by (in whole or in part), or a symptom of the disease is caused by (in whole or in part) the substance or substance activity or function. For example, a symptom of a disease or condition associated with an impaired function of the eIF2B may be a symptom that results (entirely or partially) from a decrease in eIF2B activity (e.g. decrease in eIF2B activity or levels, increase in eIF2α phosphorylation or activity of phosphorylated eIF2α or reduced eIF2 activity or increase in activity of phosphorylated eIF2α signal transduction or the ISR signalling pathway). As used herein, what is described as being associated with a disease, if a causative agent, could be a target for treatment of the disease. For example, a disease associated with decreased eIF2 activity or eIF2 pathway activity, may be treated with an agent (e.g., compound as described herein) effective for increasing the level or activity of eIF2 or eIF2 pathway or a decrease in phosphorylated eIF2α activity or the ISR pathway. For example, a disease associated with phosphorylated eIF2α may be treated with an agent (e.g., compound as described herein) effective for decreasing the level of activity of phosphorylated eIF2α or a downstream component or effector of phosphorylated eIF2α. For example, a disease associated with eIF2α, may be treated with an agent (e.g., compound as described herein) effective for increasing the level of activity of eIF2 or a downstream component or effector of eIF2.

"Control" or "control experiment" is used in accordance with its plain ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects.

"Contacting" is used in accordance with its plain ordinary meaning and refers to the process of allowing at least two distinct species (e.g. chemical compounds including biomolecules, or cells) to become sufficiently proximal to react, interact or physically touch. It should be appreciated, however, that the resulting reaction product can be produced directly from a reaction between the added reagents or from an intermediate from one or more of the added reagents which can be produced in the reaction mixture. The term "contacting" may include allowing two species to react, interact, or physically touch, wherein the two species may be a compound as described herein and a protein or enzyme (e.g. eIF2B, eIF2α, or a component of the eIF2 pathway or ISR pathway). In some embodiments contacting includes allowing a compound described herein to interact with a protein or enzyme that is involved in a signaling pathway (e.g. eIF2B, eIF2α, or a component of the eIF2 pathway or ISR pathway).

As defined herein, the term "inhibition", "inhibit", "inhibiting" and the like in reference to a protein-inhibitor (e.g., antagonist) interaction means negatively affecting (e.g., decreasing) the activity or function of the protein relative to the activity or function of the protein in the absence of the inhibitor. In some embodiments, inhibition refers to reduction of a disease or symptoms of disease. In some embodiments, inhibition refers to a reduction in the activity of a signal transduction pathway or signaling pathway. Thus, inhibition includes, at least in part, partially or totally blocking stimulation, decreasing, preventing, or delaying activation, or inactivating, desensitizing, or down-regulating signal transduction or enzymatic activity or the amount of a protein. In some embodiments, inhibition refers to a decrease in the activity of a signal transduction pathway or signaling pathway (e.g., eIF2B, eIF2α, or a component of the eIF2 pathway, pathway activated by eIF2α phosphorylation, or ISR pathway). Thus, inhibition may include, at least in part, partially or totally decreasing stimulation, decreasing or reducing activation, or inactivating, desensitizing, or down-regulating signal transduction or enzymatic activity or the amount of a protein increased in a disease (e.g. eIF2B, eIF2α, or a component of the eIF2 pathway or ISR pathway, wherein each is associated with cancer, a neurodegenerative disease, a leukodystrophy, an inflammatory disease, a musculoskeletal disease, or a metabolic disease). Inhibition may include, at least in part, partially or totally decreasing stimulation, decreasing or reducing activation, or deactivating, desensitizing, or down-regulating signal transduction or enzymatic activity or the amount of a protein (e.g. eIF2B, eIF2α, or component of the eIF2 pathway or ISR pathway) that may modulate the level of another protein or increase cell survival (e.g., decrease in phosphorylated eIF2α pathway activity may increase cell survival in cells that may or may not have an increase in phosphorylated eIF2α pathway activity relative to a non-disease control or decrease in eIF2α pathway activity may increase cell survival in cells that may or may not have an increase in eIF2α pathway activity relative to a non-disease control).

As defined herein, the term "activation", "activate", "activating" and the like in reference to a protein-activator (e.g. agonist) interaction means positively affecting (e.g. increasing) the activity or function of the protein (e.g. eIF2B, eIF2α, or component of the eIF2 pathway or ISR pathway) relative to the activity or function of the protein in the absence of the activator (e.g. compound described herein). In some embodiments, activation refers to an increase in the activity of a signal transduction pathway or signaling pathway (e.g. eIF2B, eIF2α, or component of the eIF2 pathway or ISR pathway). Thus, activation may include, at least in part, partially or totally increasing stimulation, increasing or enabling activation, or activating, sensitizing, or up-regulating signal transduction or enzymatic activity or the amount of a protein decreased in a disease (e.g. level of eIF2B, eIF2α, or component of the eIF2 pathway or ISR pathway associated with cancer, a neurodegenerative disease, a leukodystrophy, an inflammatory disease, a musculoskeletal disease, or a metabolic disease). Activation may include, at least in part, partially or totally increasing stimulation, increasing or enabling activation, or activating, sensitizing, or up-regulating signal transduction or enzymatic activity or the amount of a protein (e.g., eIF2B, eIF2α, or component of the eIF2 pathway or ISR pathway) that may modulate the level of another protein or increase cell survival (e.g., increase in eIF2α activity may increase cell survival in cells that may or may not have a reduction in eIF2α activity relative to a non-disease control).

The term "modulation" refers to an increase or decrease in the level of a target molecule or the function of a target molecule. In some embodiments, modulation of eIF2B, eIF2α, or a component of the eIF2 pathway or ISR pathway may result in reduction of the severity of one or more symptoms of a disease associated with eIF2B, eIF2α, or a component of the eIF2 pathway or ISR pathway (e.g., cancer, a neurodegenerative disease, a leukodystrophy, an inflammatory disease, a musculoskeletal disease, or a metabolic disease) or a disease that is not caused by eIF2B, eIF2α, or a component of the eIF2 pathway or ISR pathway but may benefit from modulation of eIF2B, eIF2α, or a component of the eIF2 pathway or ISR pathway (e.g., decreasing in level or level of activity of eIF2B, eIF2α or a component of the eIF2 pathway).

The term "modulator" as used herein refers to modulation of (e.g., an increase or decrease in) the level of a target molecule or the function of a target molecule. In embodiments, a modulator of eIF2B, eIF2α, or component of the eIF2 pathway or ISR pathway is an anti-cancer agent. In embodiments, a modulator of eIF2B, eIF2α, or component of the eIF2 pathway or ISR pathway is a neuroprotectant. In embodiments, a modulator of eIF2B, eIF2α, or component of the eIF2 pathway or ISR pathway is a memory enhancing agent. In embodiments, a modulator of eIF2B, eIF2α, or component of the eIF2 pathway or ISR pathway is a memory enhancing agent (e.g., a long term memory enhancing agent). In embodiments, a modulator of eIF2B, eIF2α, or component of the eIF2 pathway or ISR pathway is an anti-inflammatory agent. In some embodiments, a modulator of eIF2B, eIF2α, or component of the eIF2 pathway or ISR pathway is a pain-relieving agent.

"Patient" or "subject in need thereof" refers to a living organism suffering from or prone to a disease or condition that can be treated by administration of a compound or pharmaceutical composition, as provided herein. Non-limiting examples include humans, other mammals, bovines, rats, mice, dogs, monkeys, goat, sheep, cows, deer, and other non-mammalian animals. In some embodiments, a patient is human. In some embodiments, a patient is a domesticated animal. In some embodiments, a patient is a dog. In some embodiments, a patient is a parrot. In some embodiments, a patient is livestock animal. In some embodiments, a patient is a mammal. In some embodiments, a patient is a cat. In some embodiments, a patient is a horse. In some embodiments, a patient is bovine. In some embodiments, a patient is a canine. In some embodiments, a patient is a feline. In some embodiments, a patient is an ape. In some embodiments, a patient is a monkey. In some embodiments, a patient is a mouse. In some embodiments, a patient is an experimental animal. In some embodiments, a patient is a rat. In some embodiments, a patient is a hamster. In some embodiments, a patient is a test animal. In some embodiments, a patient is a newborn animal. In some embodiments, a patient is a newborn human. In some embodiments, a patient is a newborn mammal. In some embodiments, a patient is an elderly animal. In some embodiments, a patient is an elderly human. In some embodiments, a patient is an elderly mammal. In some embodiments, a patient is a geriatric patient.

"Disease", "disorder" or "condition" refers to a state of being or health status of a patient or subject capable of being treated with a compound, pharmaceutical composition, or method provided herein. In some embodiments, the compounds and methods described herein comprise reduction or elimination of one or more symptoms of the disease, disorder, or condition, e.g., through administration of a compound of Formula (I) or a pharmaceutically acceptable salt thereof.

The term "signaling pathway" as used herein refers to a series of interactions between cellular and optionally extracellular components (e.g. proteins, nucleic acids, small molecules, ions, lipids) that conveys a change in one component to one or more other components, which in turn may convey a change to additional components, which is optionally propagated to other signaling pathway components.

"Pharmaceutically acceptable excipient" and "pharmaceutically acceptable carrier" refer to a substance that aids the administration of an active agent to and absorption by a subject and can be included in the compositions of the present invention without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethylcellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention. One of skill in the art will recognize that other pharmaceutical excipients are useful in the present invention.

The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

As used herein, the term "administering" means oral administration, administration as a suppository, topical contact, intravenous, parenteral, intraperitoneal, intramuscular, intralesional, intrathecal, intracranial, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arterial, intradermal, subcutaneous, intraperitoneal, intraventricular, and intracranial. Other modes of delivery include, but are not limited to, the use of liposomal formulations, intravenous infusion, transdermal patches, etc. By "co-administer" it is meant that a composition described herein is administered at the same time, just prior to, or just after the administration of one or more additional therapies (e.g., anti-cancer agent, chemotherapeutic, or treatment for a neurodegenerative disease). The compound of the invention can be administered alone or can be coadministered to the patient. Coadministration is meant to include simultaneous or sequential administration of the compound individually or in combination (more than one compound or agent). Thus, the preparations can also be combined, when desired, with other active substances (e.g. to reduce metabolic degradation).

The term "eIF2B" as used herein refers to the heteropentameric eukaryotic translation initiation factor 2B. eIF2B is composed of five subunits: eIF2B1, eIF2B2, eIF2B3, eIF2B4 and eIF2B5. eIF2B1 refers to the protein associated with Entrez gene 1967, OMIM 606686, Uniprot Q14232, and/or RefSeq (protein) NP_001405. eIF2B2 refers to the protein associated with Entrez gene 8892, OMIM 606454, Uniprot P49770, and/or RefSeq (protein) NP_055054. eIF2B3 refers to the protein associated with Entrez gene 8891, OMIM 606273, Uniprot Q9NR50, and/or RefSeq (protein) NP_065098. eIF2B4 refers to the protein associated with Entrez gene 8890, OMIM 606687, Uniprot Q9UI10, and/or RefSeq (protein) NP_751945. eIF2B5 refers to the protein associated with Entrez gene 8893, OMIM 603945, Uniprot Q13144, and/or RefSeq (protein) NP_003898.

The terms "eIF2alpha", "eIF2a" or "eIF2α" are interchangeable and refer to the protein "eukaryotic translation initiation factor 2 alpha subunit eIF2S1". In embodiments, "eIF2alpha", "eIF2a" or "eIF2α" refer to the human protein. Included in the terms eIF2alpha", "eIF2a" or "eIF2α" are the wildtype and mutant forms of the protein. In embodiments, "eIF2alpha", "eIF2a" or "eIF2α" refer to the protein associated with Entrez Gene 1965, OMIM 603907, UniProt P05198, and/or RefSeq (protein) NP_004085. In embodiments, the reference numbers immediately above refer to the protein and associated nucleic acids known as of the date of filing of this application.

Compounds

In one aspect, the present invention features a compound of Formula (I):

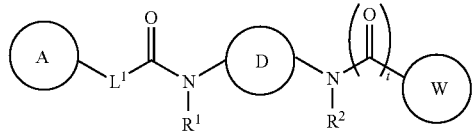

Formula (I)

or a pharmaceutically acceptable salt, solvate, hydrate, tautomer, or stereoisomer thereof, wherein D is a bridged monocyclic cycloalkyl, bridged monocyclic heterocyclyl, or cubanyl, wherein each bridged monocyclic cycloalkyl, bridged monocyclic heterocyclyl, or cubanyl is optionally substituted with 1-4 $R^X$; $L^1$ is $C_1$-$C_6$ alkylene, $C_1$-$C_6$ alkenylene, or 2-7-membered heteroalkylene, wherein each $C_1$-$C_6$ alkylene $C_1$-$C_6$ alkenylene, or 2-7-membered heteroalkylene is optionally substituted with 1-5 $R^X$; $R^1$ and $R^2$ are each independently hydrogen, $C_1$-$C_6$ alkyl, $C_1$-$C_6$ alkoxy-$C_1$-$C_6$ alkyl, hydroxy-$C_1$-$C_6$ alkyl, or silyloxy-$C_1$-$C_6$ alkyl; Q is C(O) or S(O)$_2$; A and W are each independently phenyl or 5-6-membered heteroaryl, wherein each phenyl or 5-6-membered heteroaryl is optionally substituted with 1-5 $R^Y$; each $R^X$ is independently selected from the group consisting of $C_1$-$C_6$ alkyl, hydroxy-$C_1$-$C_6$ alkyl, halo-$C_1$-$C_6$ alkyl, amino-$C_1$-$C_6$ alkyl, cyano-$C_1$-$C_6$ alkyl, oxo, halo, cyano, —$OR^A$, —$NR^BR^C$, —$NR^BC(O)R^D$, —$C(O)NR^BR^C$, —$C(O)R^D$, —C(O)OH, —$C(O)OR^D$, —$SR^E$, —$S(O)R^D$, —$S(O)_2R^D$, and $G^2$; each $R^Y$ is independently selected from the group consisting of hydrogen, $C_1$-$C_6$ alkyl, $C_1$-$C_6$ alkenyl, hydroxy-$C_1$-$C_6$ alkyl, hydroxy-$C_1$-$C_6$ alkenyl, halo-$C_1$-$C_6$ alkyl, halo-$C_1$-$C_6$ alkoxy, amino-$C_1$-$C_6$ alkyl, amido-$C_1$-$C_6$ alkyl, cyano-$C_1$-$C_6$ alkyl, siloxy-$C_1$-$C_6$ alkoxy, hydroxyl-$C_1$-$C_6$ alkoxy, $C_1$-$C_6$ alkoxy-$C_1$-$C_6$ alkyl, $C_1$-$C_6$ alkoxy-$C_1$-$C_6$ alkenyl, $C_1$-$C_6$ alkoxy-$C_1$-$C_6$ alkoxy, oxo, halo, cyano, —$OR^A$, —$NR^BR^C$, —$NR^BC(O)R^D$, —$C(O)NR^BR^C$, —$C(O)R^D$, —C(O)OH, —$C(O)OR^D$, —$S(R^F)_m$, —$S(O)R^D$, —$S(O)_2R^D$, $S(O)NR^BR^C$, —$NR^BS(O)_2R^D$, —$OS(O)R^D$, —$OS(O)_2R^D$, $R^FS$—$C_1$-$C_6$ alkyl, $R^BC(O)NR^B$—$C_1$-$C_6$ alkyl, $(R^B)(R^C)N$—$C_1$-$C_6$ alkoxy, $R^DOC(O)NR^B$—$C_1$-$C_6$ alkyl, $G^1$, $G^1$-$C_1$-$C_6$ alkyl, $G^1$-$N(R^B)$, $G^1$-$C_1$-$C_6$ alkenyl, $G^1$-O—, $G^1C(O)NR^B$—$C_1$-$C_6$ alkyl, and $G^1$-$NR^BC(O)$; or 2 $R^Y$ groups on adjacent atoms, together with the atoms to which they are attached form a fused phenyl, a 3-7-membered fused cycloalkyl ring, a 3-7-membered fused heterocyclyl ring, or a 5-6-membered fused heteroaryl ring, each optionally substituted with 1-5 $R^X$; each $G^1$ or $G^2$ is independently 3-7 membered cycloalkyl, 4-7-membered heterocyclyl, aryl, or 5-6-membered heteroaryl, wherein each 3-7 membered cycloalkyl, 4-7-membered heterocyclyl, aryl, or 5-6-membered heteroaryl is optionally substituted with 1-6$R^Z$; each $R^Z$ is independently selected from the group consisting of $C_1$-$C_6$ alkyl, hydroxy-$C_1$-$C_6$ alkyl, halo-$C_1$-$C_6$ alkyl, halo, cyano, oxo, —$OR^A$, —$NR^BR^C$, —$NR^BC(O)R^D$, —$C(O)NR^BR^C$, —$C(O)R^D$, —C(O)OH, —$C(O)OR^D$, and —$S(O)_2R^D$; $R^A$ is, at each occurrence, independently hydrogen, $C_1$-$C_6$ alkyl, halo-$C_1$-$C_6$ alkyl, —$OR^A$, —$C(O)NR^BR^C$, —$C(O)R^D$, —C(O)OH, or —$C(O)OR^D$; each of $R^B$ and $R^C$ is independently hydrogen, $C_1$-$C_6$ alkyl, hydroxy-$C_1$-$C_6$ alkyl, $G^1$-$C_1$-$C_6$ alkyl, 3-7 membered cycloalkyl, or 4-7-membered heterocyclyl, wherein each alkyl, cycloalkyl, or heterocyclyl is optionally substituted with 1-6 $R^Z$; or $R^B$ and $R^C$ together with the atom to which they are attached form a 3-7-membered cycloalkyl or heterocyclyl ring optionally substituted with 1-6 $R^Z$; $R^D$ is, at each occurrence, independently $C_1$-$C_6$ alkyl, $C_1$-$C_6$ alkoxy-$C_1$-$C_6$ alkyl, or halo-$C_1$-$C_6$ alkyl; each $R^E$ is independently hydrogen $C_1$-$C_6$ alkyl, or halo-$C_1$-$C_6$ alkyl; each $R^F$ is independently hydrogen, $C_1$-$C_6$ alkyl, or halo; each $RA^1$ is hydrogen, $C_1$-$C_6$ alkyl, halo-$C_1$-$C_6$ alkyl, 3-7 membered cycloalkyl, or 4-7-membered heterocyclyl; m is 1, 3, or 5; and t is 0 or 1.

In some embodiments, D is a bridged monocyclic cycloalkyl optionally substituted with 1-4 $R^X$. In some embodiments, D is a bridged 4-6 membered cycloalkyl optionally substituted with 1-4 $R^X$. In some embodiments, D is selected from bicyclo[1.1.1]pentane, bicyclo[2.2.1]heptane, bicyclo[2.2.2]octane, or bicyclo[2.1.1]hexane, each of which is optionally substituted with 1-4 $R^X$. In some embodiments, D is selected from bicyclo[1.1.1]pentane, bicyclo[2.2.2]octane, or bicyclo[2.1.1]hexane, each of which is optionally substituted with 1-4 $R^X$. In some embodiments, D is selected from:

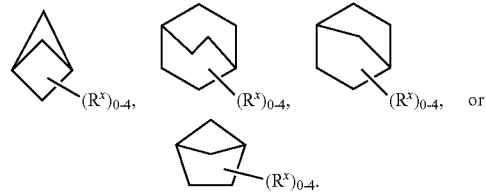

In some embodiments, D is selected from:

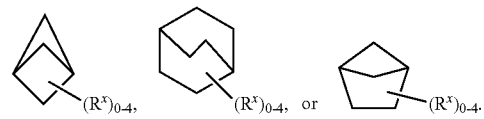

In some embodiments, D is selected from:

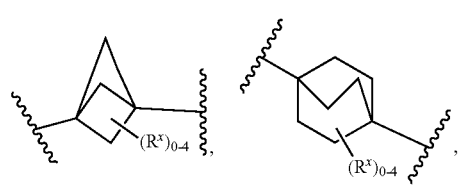

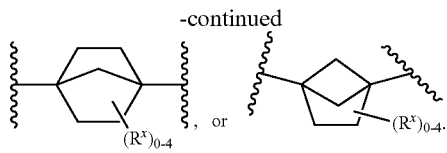

In some embodiments, D is selected from:

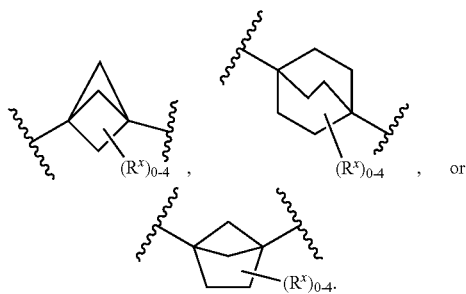

In some embodiments, D is substituted with 1 $R^X$. In some embodiments, D is substituted with one $R^X$, and $R^X$ is halo or —$OR^A$ (e.g., fluoro, OH). In some embodiments, D is substituted with 0 $R^X$. In some embodiments, D is

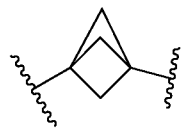

In some embodiments, $L^1$ is 2-7-membered heteroalkylene optionally substituted by 1-5 $R^X$. In some embodiments, $L^1$ is 2-7-membered heteroalkylene substituted by 0 $R^X$. In some embodiments, $L^1$ is $CH_2OCH_2$—*, $CH_2O$—*, wherein "—*" indicates the attachment point to A. In some embodiments, $L^1$ is $CH_2O$—*, wherein "—*" indicates the attachment point to A.

In some embodiments, Q is C(O). In some embodiments, Q is $S(O)_2$.

In some embodiments, t is 1. In some embodiments, t is 0.

In some embodiments, each of $R^1$ and $R^2$ is independently hydrogen or $C_1$-$C_6$ alkyl (e.g., $CH_3$). In some embodiments, each of $R^1$ and $R^2$ is independently hydrogen. In some embodiments, one of $R^1$ and $R^2$ is independently hydrogen and the other of $R^1$ and $R^2$ is independently is $C_1$-$C_6$ alkyl (e.g., $CH_3$).

In some embodiments, A is phenyl and W is independently phenyl or 5-6-membered heteroaryl. In some embodiments, each A and W is independently phenyl. In some embodiments, A is phenyl and W is 5-6-membered heteroaryl.

In some embodiments, W is a monocyclic 5-6-membered heteroaryl. In some embodiments, 2 $R^Y$ groups on adjacent atoms of W, together with the atoms to which they are attached form a 3-7-membered fused cycloalkyl or heterocyclyl optionally substituted with 1-5 $R^X$ forming a bicyclic heteroaryl. In some embodiments, W is a 10-membered heteroaryl, a 9-membered heteroaryl, a 6-membered heteroaryl, or a 5-membered heteroaryl. In some embodiments, W is a heteroaryl containing nitrogen, oxygen or sulfur as allowed by valence.

In some embodiments, each A and W is independently a phenyl or 5-6-membered heteroaryl optionally substituted with 1-5 $R^Y$, and each $R^Y$ is independently $C_1$-$C_6$ alkyl, hydroxy-$C_1$-$C_6$ alkyl, halo-$C_1$-$C_6$ alkyl, halo-$C_1$-$C_6$ alkoxy, $C_1$-$C_6$ alkoxy-$C_1$-$C_6$ alkyl, silyloxy-$C_1$-$C_6$ alkyl, halo, —$OR^A$, cycloalkyl, heterocyclyl, —C(O)OH, —C(O)$OR^D$, or $G^1$. In some embodiments, each of A and W is independently phenyl, pyridyl, pyrimidinyl, pyrazinyl, pyridazinyl, oxazolyl, isoxazolyl, furanyl, or pyrazolyl, each of which is optionally substituted with 1-5 $R^Y$ groups.

In some embodiments, each A and W is selected from:

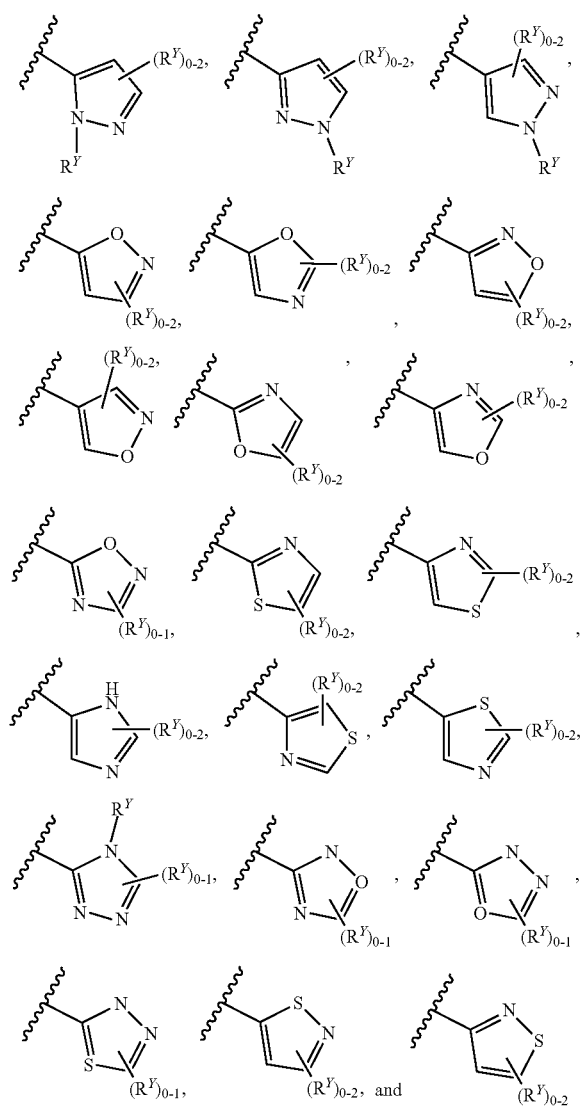
In some embodiments, each of A and W is selected from:
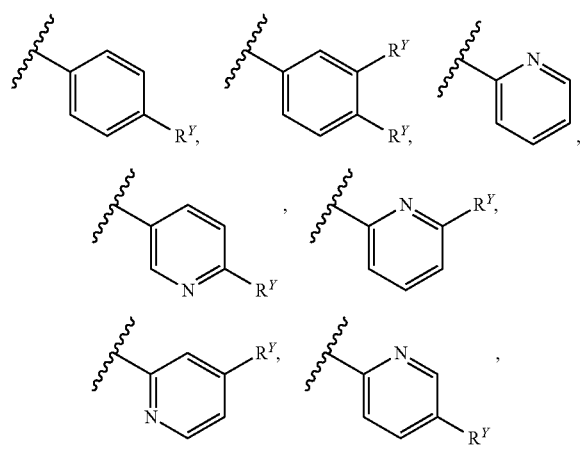
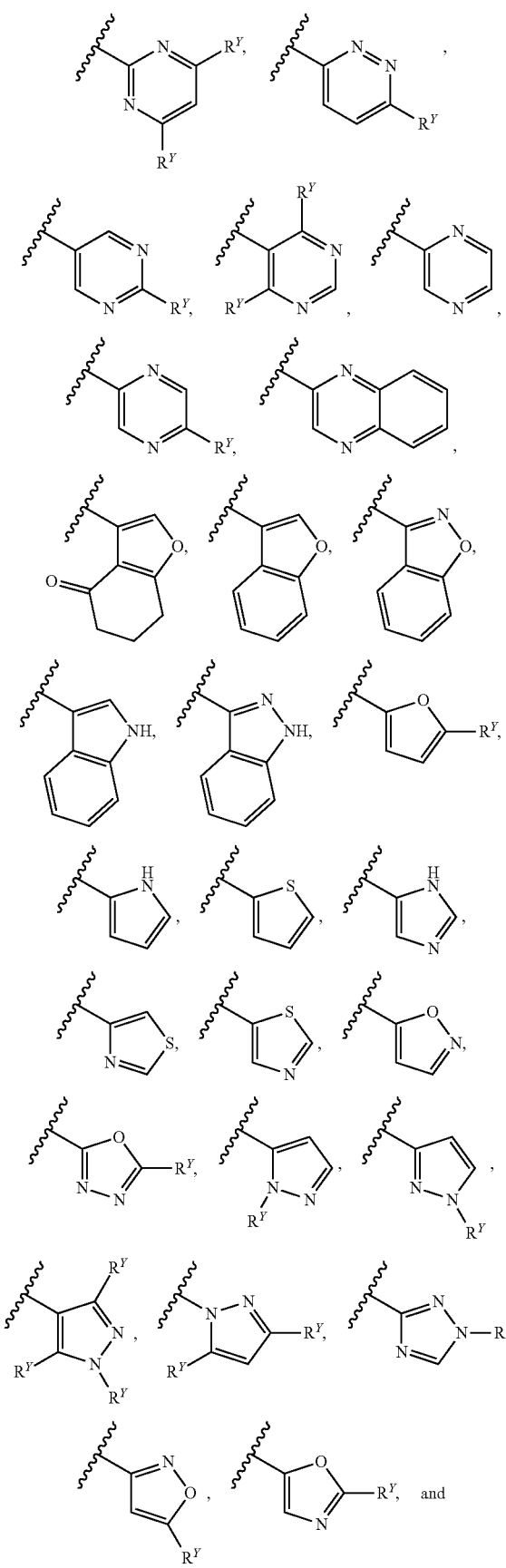

-continued

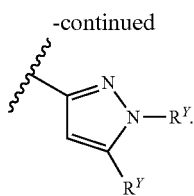

In some embodiments, each of A and W is selected from:

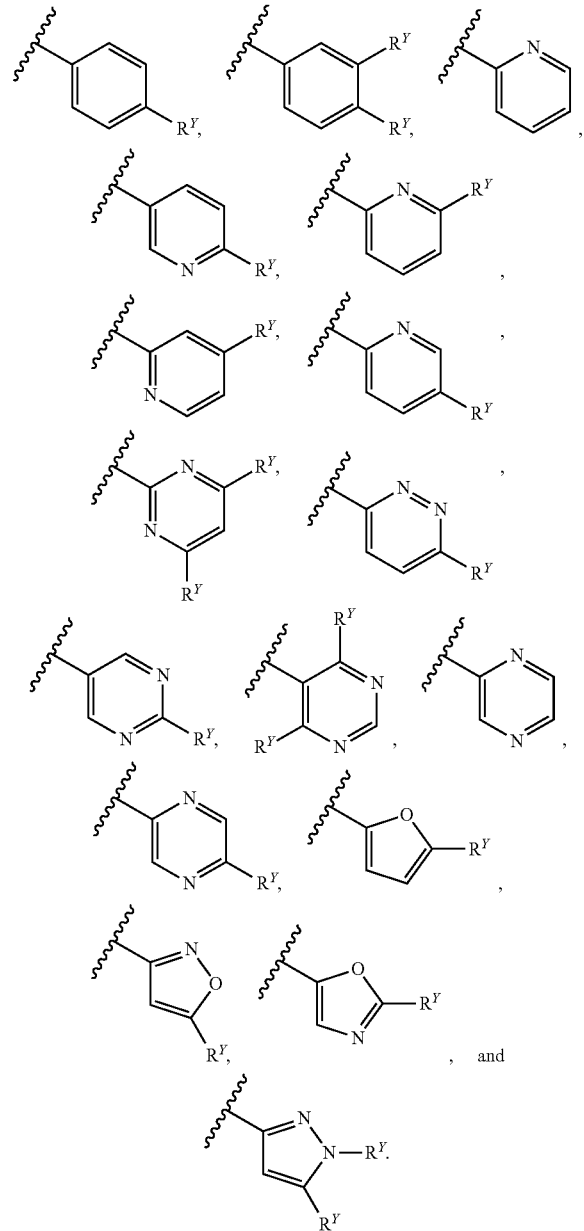

In some embodiments, A is phenyl or pyridyl and W is phenyl or 5-6-membered heteroaryl, each of A and W is optionally substituted with 1-5 $R^Y$, and each $R^Y$ is independently $C_1$-$C_6$ alkyl, hydroxy-$C_1$-$C_6$ alkyl, halo-$C_1$-$C_6$ alkyl, halo-$C_1$-$C_6$ alkoxy, siloxy-$C_1$-$C_6$ alkoxy, hydroxy $C_1$-$C_6$ alkoxy, halo, —$OR^A$, —C(O)OH, —C(O)$OR^D$, or $G^1$. In some embodiments, A is phenyl or pyridyl and W is phenyl, pyridyl, pyrimidinyl, pyrazinyl, pyridazinyl, oxazolyl, isoxazolyl, furanyl, or pyrazolyl, wherein A and W are each optionally substituted with 1-5 $R^Y$.

In some embodiments, A is,

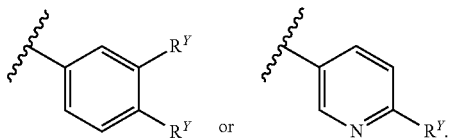

In some embodiments, A is

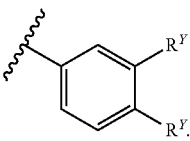

In some embodiments, W is selected from:

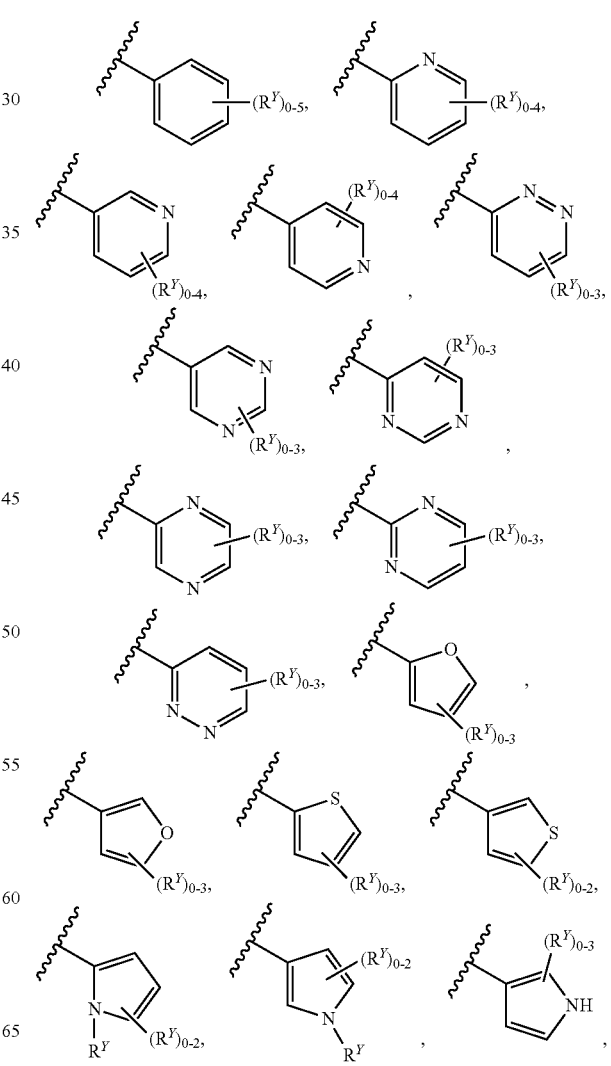

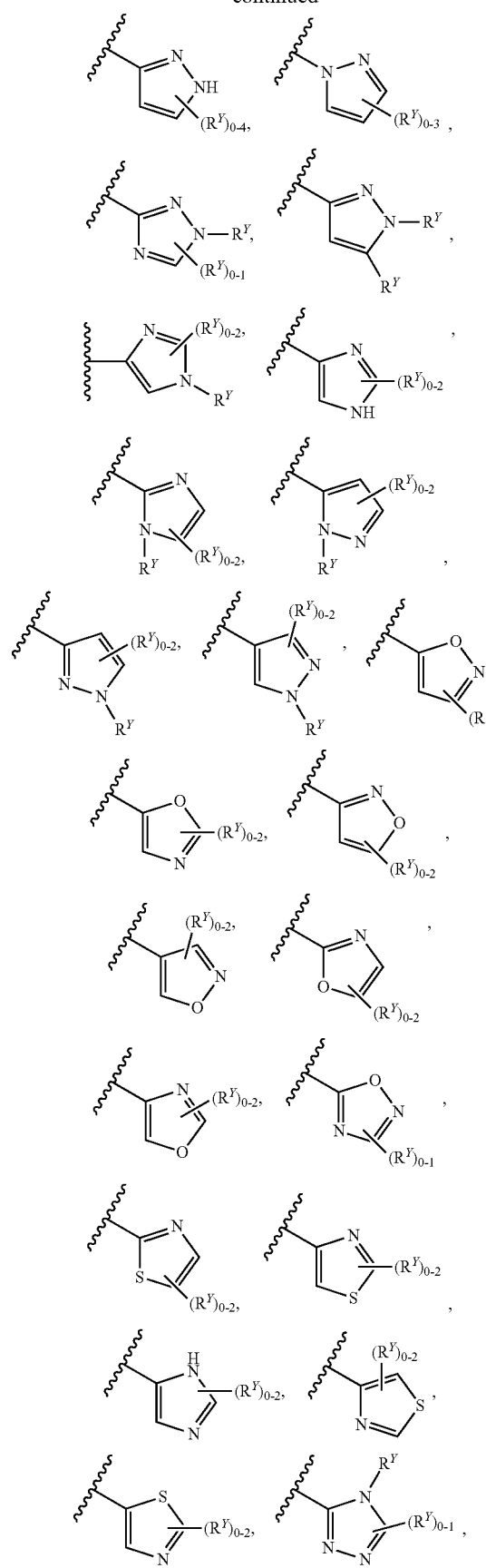
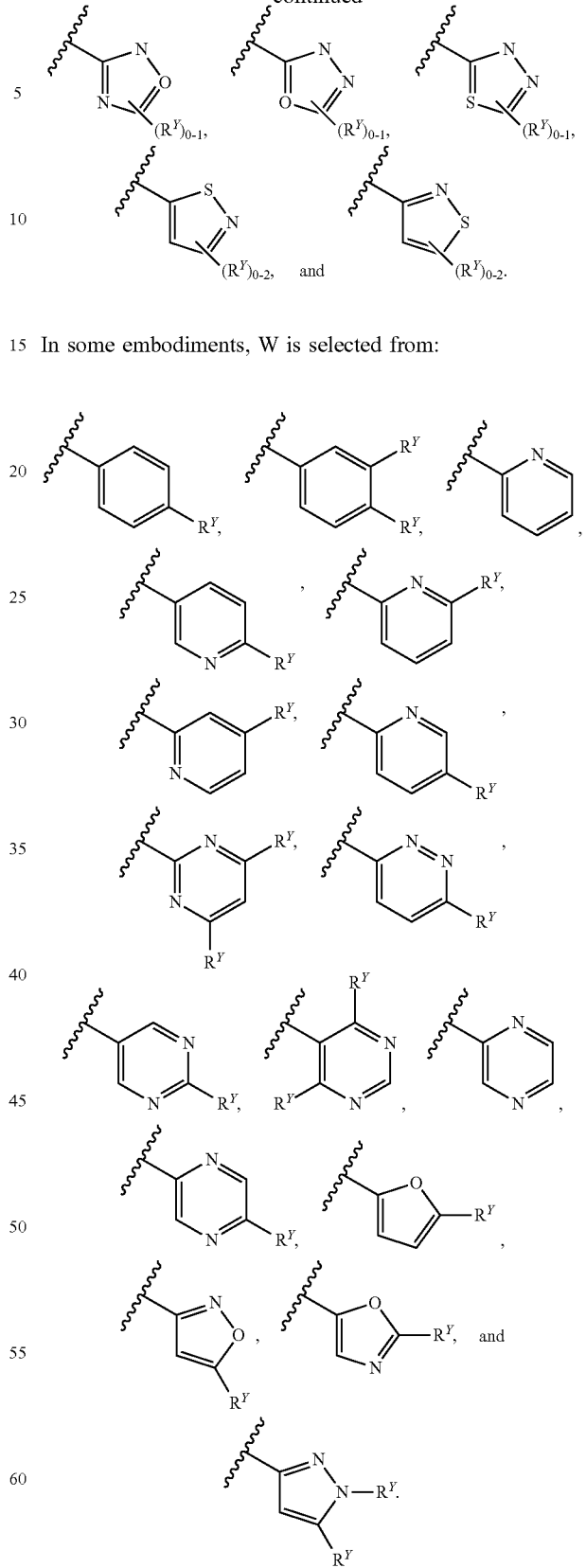
In some embodiments, W is selected from:
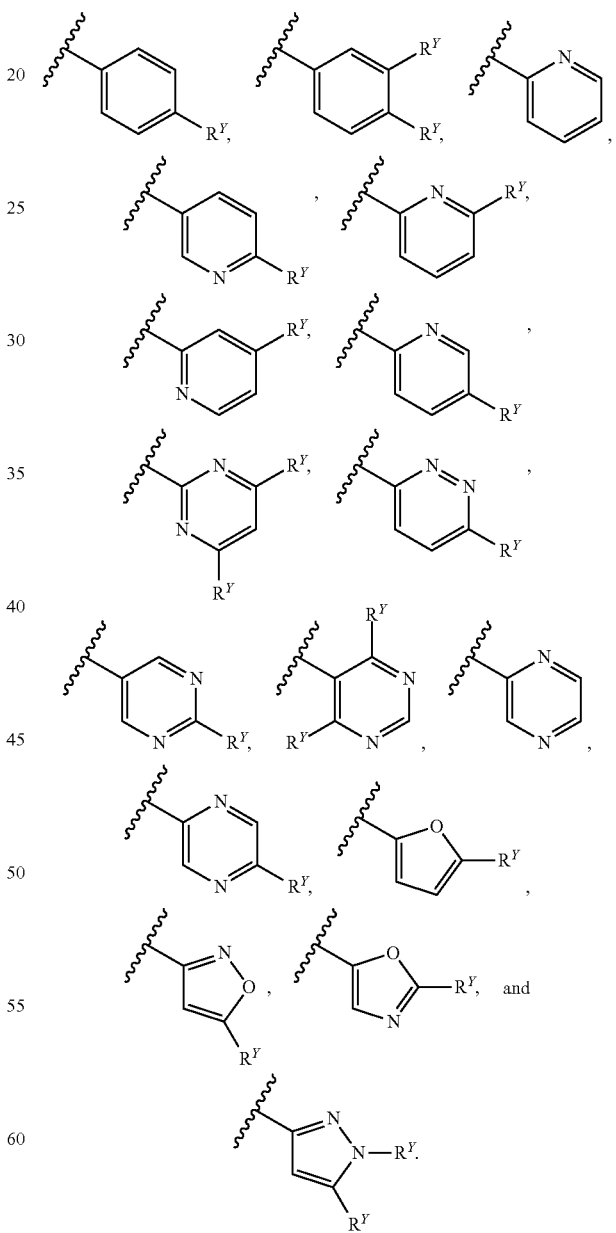
In some embodiments, each $R^Y$ is independently selected from chloro, fluoro, oxo, CN, OH, $CF_3$, $CHF_2$, $CH_3$, CH$_2$CH$_3$, CH$_2$CH$_2$CH$_2$CH$_3$, CH═CHCH$_2$OH, CH$_2$CH$_2$OH, CH$_2$NH$_2$, NHCH$_3$, CH$_2$NHC(O)CH$_3$, N(CH$_2$CH$_3$)$_2$, CH2N(CH$_3$)$_2$, C(CH$_3$)$_2$OH, CH(CH$_3$)$_2$, CH$_2$CH$_2$CH$_3$, C(CH$_3$)$_3$, CH$_2$CH(CH$_3$)$_2$, CH$_2$CH$_2$OCH$_3$, CH(OH)CH$_3$, CH$_2$CF$_3$, CH$_2$C(CH$_3$)$_2$OH, CH$_2$SCH$_3$, CH$_2$CN, CH$_2$CH$_2$CN, CH$_2$CH$_2$C(CH$_3$)$_2$OH, CH$_2$NHC(O)CH$_3$, OCH$_3$, OCH$_2$CH$_3$, OCH$_2$CH$_2$CH$_3$, OCH$_2$CH$_2$OCH$_3$, OCH(CH$_3$)$_2$, OCF$_3$, OCH$_2$CF$_3$, OCH$_2$CH$_2$N(CH$_3$)$_2$, CH$_2$OH, CH$_2$OCH$_3$, OCH$_2$CH$_2$OH, OCHF$_2$, OCF$_3$, OCH$_3$, CH$_2$OH, C(O)OH, C(O)CH$_3$, C(O)OCH$_3$, C(O)NH$_2$, C(O)NHCH$_2$CH$_2$CH$_2$OH, CH$_2$CN, C(O)OCH$_2$CH$_3$, C(O)NHCH$_2$CH$_3$, OCH$_2$CH$_2$OSi(CH$_3$)$_2$C(CH$_3$)$_3$, CH$_2$N(CH$_3$)$_2$, CH$_2$NHC(O)CH$_3$, CH$_2$NHC(O)OC(CH$_3$)$_3$, CH═CHCH$_2$OCH$_3$, CH═CHC(CH$_3$)$_2$OH, N(CH$_3$)$_2$, N(CH$_2$CH$_3$)$_2$, NHCH$_2$CH$_3$, NHC(O)CH$_3$, NHC(O)CH$_2$OCH$_3$, NHS(O)$_2$CH$_3$, SCH$_3$, SCH$_2$CH$_3$, SO$_2$NH$_2$, S(O)CH$_3$, S(O)$_2$CH$_3$, G$^1$, C(O)NHG$^1$, N(CH$_3$)CH$_2$G$^1$, NHG$^1$, OG$^1$, CH$_2$G$^1$, CH$_2$CH$_2$G$^1$, CH$_2$NHC(O)G$^1$, or CH═CHG$^1$. In some embodiments, each R$^Y$ is independently chloro, fluoro, CN, OH, CF$_3$, CHF$_2$, CH$_3$, CH$_2$CH$_3$, CH$_2$CH$_2$CH$_2$CH$_3$, CH═CHCH$_2$OH, CH$_2$CH$_2$OH, CH$_2$NH$_2$, NHCH$_3$, CH$_2$NHC(O)CH$_3$, N(CH$_2$CH$_3$)$_2$, CH$_2$N(CH$_3$)$_2$, C(CH$_3$)$_2$OH, OCH$_3$, CH$_2$OH, CH$_2$OCH$_3$, OCH$_2$CH$_2$OH, OCHF$_2$, OCF$_3$, OCH$_3$, CH$_2$OH, C(O)OH, CH$_2$CN, C(O)OCH$_2$CH$_3$, C(O)NHCH$_2$CH$_3$, OCH$_2$CH$_2$OSi(CH$_3$)$_2$C(CH$_3$)$_3$, or G$^1$.

In some embodiments, each of A and W is independently substituted with 2 R$^Y$ on adjacent atoms, and the 2 R$^Y$, together with the atoms to which they are attached, form a 3-7-membered fused heterocyclyl ring or 5-6-membered heteroaryl ring, each optionally substituted with 1-5 R$^X$. In some embodiments, the 2 R$^Y$ together with the atoms to which they are attached form a dioxolanyl, hexahydropyrimidinyl, pyridyl, or pyrimidinyl ring, each of which is optionally substituted with 1-5 R$^X$. In some embodiments, each R$^X$ is independently C$_1$-C$_6$ alkyl, fluoro, chloro, oxo, OCH$_3$, C(O)OCH$_3$, or G$^2$.

In some embodiments, G$^1$ or G$^2$ is pyrrolidinyl, azetidinyl, cyclopropyl, cyclohexyl, cyclohexenyl, tetrahydropyranyl, dihydropyranyl, tetrahydropyridinyl, piperidinyl, phenyl, pyridyl, pyrimidinyl, pyridazinyl, pyrazolyl, morpholino, furanyl, triazolyl, oxetanyl, or pyrazinyl, each of which is optionally substituted with 1-5 R$^Z$. In some embodiments, G$^1$ is pyrrolidinyl, cyclopropyl, cyclohexyl, cyclohexenyl, tetrahydropyranyl, dihydropyranyl, tetrahydropyridinyl, piperidinyl, phenyl, pyridyl, pyrimidinyl, pyridazinyl, or pyrazinyl, each of which is optionally substituted with 1-5 R$^Z$.

In some embodiments, G$^1$ is pyrrolidinyl, azetidinyl, cyclopropyl, cyclohexyl, cyclohexenyl, tetrahydropyranyl, dihydropyranyl, tetrahydropyridinyl, piperidinyl, phenyl, pyridyl, pyrimidinyl, pyridazinyl, pyrazolyl, morpholino, furanyl, triazolyl, oxetanyl, or pyrazinyl, each of which is optionally substituted with 1-5 R$^Z$. In some embodiments, G$^1$ is pyrrolidinyl, cyclopropyl, cyclohexyl, cyclohexenyl, tetrahydropyranyl, dihydropyranyl, tetrahydropyridinyl, piperidinyl, phenyl, pyridyl, pyrimidinyl, pyridazinyl, or pyrazinyl, each of which is optionally substituted with 1-5 R$^Z$.

In some embodiments, each R$^Z$ is independently OR$^A$, C(O)R$^D$, halo, halo C$_1$-C$_6$ alkyl, C$_1$-C$_6$ alkyl, C(O)R$^D$, or C(O)OR$^D$ (e.g., fluoro, chloro, OH, OCH$_3$, oxo, CH$_3$, CHF$_2$, CF$_3$, C(O)CH$_3$ or C(O)OC(CH$_3$)$_3$). In some embodiments, each R$^Z$ is independently OR$^A$, C(O)R$^D$, halo, halo C$_1$-C$_6$ alkyl, C$_1$-C$_6$ alkyl, or C(O)OR$^D$ (e.g., OH, C(O)CH$_3$ or C(O)OC(CH$_3$)$_3$).

In one aspect, the present invention features a compound of Formula (I-a):

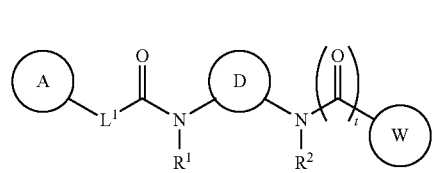

Formula (I-a)

or a pharmaceutically acceptable salt, solvate, hydrate, tautomer, or stereoisomer thereof, wherein D is a bridged monocyclic cycloalkyl, bridged monocyclic heterocyclyl, or cubanyl, wherein each bridged monocyclic cycloalkyl, bridged monocyclic heterocyclyl, or cubanyl is optionally substituted with 1-4 R$^X$; L$^1$ is C$_1$-C$_6$ alkylene or 2-7-membered heteroalkylene, wherein each C$_1$-C$_6$ alkylene or 2-7-membered heteroalkylene is optionally substituted with 1-5 R$^X$; R$^1$ and R$^2$ are each independently hydrogen, C$_1$-C$_6$ alkyl, C$_1$-C$_6$ alkoxy-C$_1$-C$_6$ alkyl, hydroxy-C$_1$-C$_6$ alkyl, or silyloxy-C$_1$-C$_6$ alkyl; A and W are each independently phenyl or 5-6-membered heteroaryl, wherein each phenyl or 5-6-membered heteroaryl is optionally substituted with 1-5 R$^Y$; each R$^X$ is independently selected from the group consisting of C$_1$-C$_6$ alkyl, hydroxy-C$_1$-C$_6$ alkyl, halo-C$_1$-C$_6$ alkyl, amino-C$_1$-C$_6$ alkyl, cyano-C$_1$-C$_6$ alkyl, oxo, halo, cyano, —OR$^A$, —NR$^B$R$^C$, —NR$^B$C(O)R$^D$, —C(O)NR$^B$R$^C$, —C(O)R$^D$, —C(O)OH, —C(O)OR$^D$, —SR$^E$, —S(O)R$^D$, and —S(O)$_2$R$^D$; each R$^Y$ is independently selected from the group consisting of hydrogen, C$_1$-C$_6$ alkyl, hydroxy-C$_1$-C$_6$ alkyl, halo-C$_1$-C$_6$ alkyl, halo-C$_1$-C$_6$ alkoxy, amino-C$_1$-C$_6$ alkyl, cyano-C$_1$-C$_6$ alkyl, siloxy-C$_1$-C$_6$ alkoxy, hydroxyl-C$_1$-C$_6$ alkoxy, oxo, halo, cyano, —OR$^A$, —NR$^B$R$^C$, —NR$^B$C(O)R$^D$, —C(O)NR$^B$R$^C$, —C(O)R$^D$, —C(O)OH, —C(O)OR$^D$, —S(R$^F$)$_m$, —S(O)R$^D$, —S(O)$_2$R$^D$, and G$^1$; or 2 R$^Y$ groups on adjacent atoms, together with the atoms to which they are attached form a 3-7-membered fused cycloalkyl ring, a 3-7-membered fused heterocyclyl ring, or a 5-6-membered fused heteroaryl ring, each optionally substituted with 1-5 R$^X$; each G$^1$ is independently 3-7 membered cycloalkyl, 4-7-membered heterocyclyl, aryl, or 5-6-membered heteroaryl, wherein each 3-7 membered cycloalkyl, 4-7-membered heterocyclyl, aryl, or 5-6-membered heteroaryl is optionally substituted with 1-3 R$^Z$; each R$^Z$ is independently selected from the group consisting of C$_1$-C$_6$ alkyl, hydroxy-C$_1$-C$_6$ alkyl, halo-C$_1$-C$_6$ alkyl, halo, cyano, —OR$^A$, —NR$^B$R$^C$, —NR$^B$C(O)R$^D$, —C(O)NR$^B$R$^C$, —C(O)R$^D$, —C(O)OH, —C(O)OR$^D$, and —S(O)$_2$R$^D$; R$^A$ is, at each occurrence, independently hydrogen, C$_1$-C$_6$ alkyl, halo-C$_1$-C$_6$ alkyl, —C(O)NR$^B$R$^C$, —C(O)R$^D$, —C(O)OH, or —C(O)OR$^D$; each of R$^B$ and R$^C$ is independently hydrogen or C$_1$-C$_6$ alkyl; or R$^B$ and R$^C$ together with the atom to which they are attached form a 3-7-membered cycloalkyl or heterocyclyl ring optionally substituted with 1-3 R$^Z$; R$^D$ is, at each occurrence, independently C$_1$-C$_6$ alkyl or halo-C$_1$-C$_6$ alkyl; each R$^E$ is independently hydrogen C$_1$-C$_6$ alkyl, or halo-C$_1$-C$_6$ alkyl; each R$^F$ is independently hydrogen, C$_1$-C$_6$ alkyl, or halo; m is 1, 3, or 5; and t is 0 or 1.

In some embodiments, D is a bridged monocyclic cycloalkyl optionally substituted with 1-4 R$^X$. In some embodiments, D is a bridged 4-6 membered cycloalkyl optionally substituted with 1-4 R$^X$. In some embodiments, D is selected from bicyclo[1.1.1]pentane, bicyclo[2.2.2]octane, or bicyclo[2.1.1]hexane, each of which is optionally substituted with 1-4 R$^X$. In some embodiments, D is selected from:

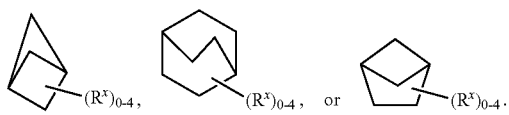

In some embodiments, D is selected from:

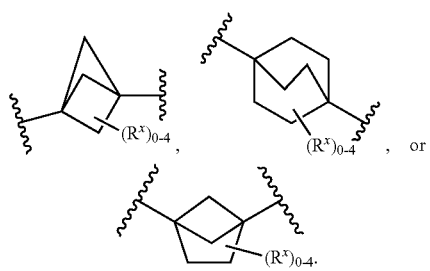

In some embodiments, D is substituted with 1 $R^X$. In some embodiments, D is substituted with one $R^X$, and $R^X$ is —$OR^A$ (e.g., OH). In some embodiments, D is substituted with 0 $R^X$. In some embodiments, D is

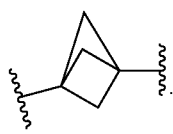 [SMILES: *C12CC(*)(C1)C2]

In some embodiments, $L^1$ is 2-7-membered heteroalkylene optionally substituted by 1-5 $R^X$. In some embodiments, $L^1$ is 2-7-membered heteroalkylene substituted by 0 $R^X$. In some embodiments, $L^1$ is CH$_2$O—*, wherein "—*" indicates the attachment point to A.

In some embodiments, t is 1. In some embodiments, t is 0.

In some embodiments, each of $R^1$ and $R^2$ is independently hydrogen.

In some embodiments, each A and W is independently a phenyl or 5-6-membered heteroaryl optionally substituted with 1-5 $R^Y$, and each $R^Y$ is independently $C_1$-$C_6$ alkyl, hydroxy-$C_1$-$C_6$ alkyl, halo-$C_1$-$C_6$ alkyl, halo-$C_1$-$C_6$ alkoxy, $C_1$-$C_6$ alkoxy-$C_1$-$C_6$ alkyl, silyloxy-$C_1$-$C_6$ alkyl, halo, —$OR^A$, cycloalkyl, heterocyclyl, —C(O)OH, —C(O)$OR^D$, or $G^1$. In some embodiments, each of A and W is independently phenyl, pyridyl, pyrimidinyl, pyrazinyl, pyridazinyl, oxazolyl, isoxazolyl, furanyl, or pyrazolyl, each of which is optionally substituted with 1-5 $R^Y$ groups. In some embodiments, each of A and W is selected from:

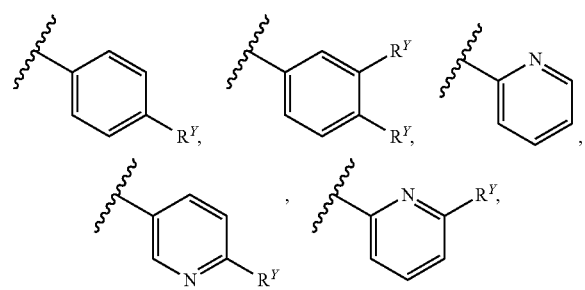

-continued

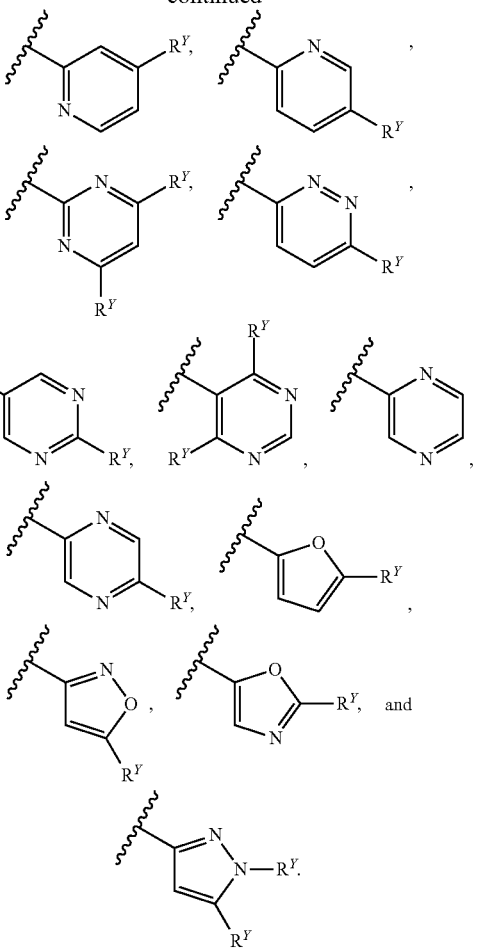

In some embodiments, A is phenyl or pyridyl and W is phenyl or 5-6-membered heteroaryl, each of A and W is optionally substituted with 1-5 $R^Y$, and each $R^Y$ is independently $C_1$-$C_6$ alkyl, hydroxy-$C_1$-$C_6$ alkyl, halo-$C_1$-$C_6$ alkyl, halo-$C_1$-$C_6$ alkoxy, siloxy-$C_1$-$C_6$ alkyl, hydroxy $C_1$-$C_6$ alkoxy, halo, —$OR^A$, —C(O)OH, —C(O)$OR^D$, or $G^1$. In some embodiments, A is phenyl or pyridyl and W is phenyl, pyridyl, pyrimidinyl, pyrazinyl, pyridazinyl, oxazolyl, isoxazolyl, furanyl, or pyrazolyl, wherein A and W are each optionally substituted with 1-5 $R^Y$.

In some embodiments, A is

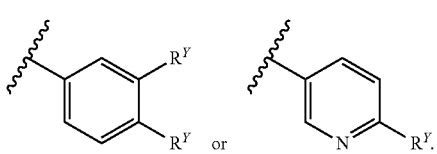

In some embodiments, W is selected from:

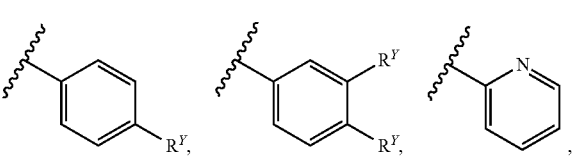

-continued

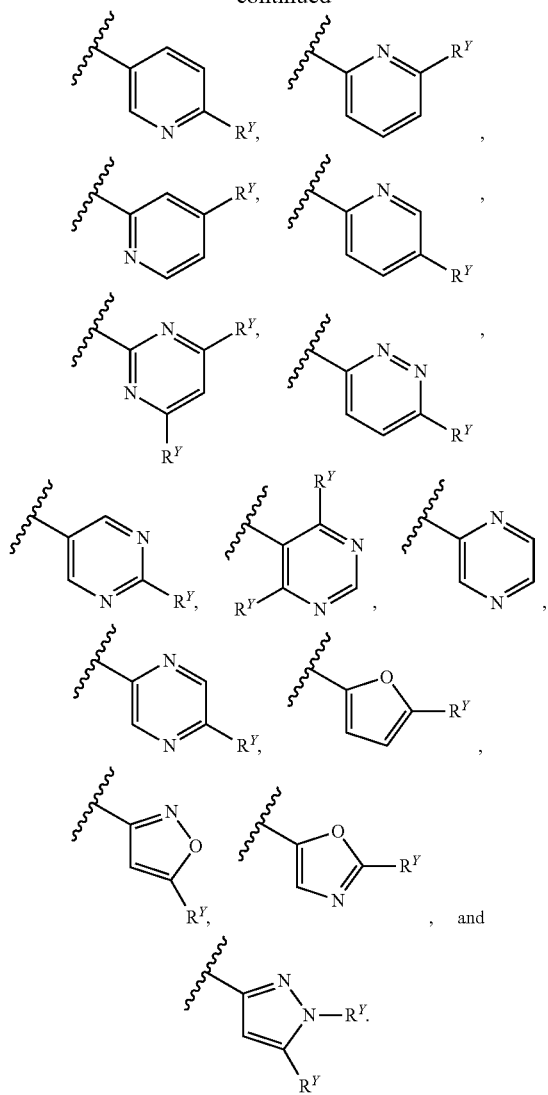

In some embodiments, each $R^Y$ is independently chloro, fluoro, $CF_3$, $CHF_2$, $CH_3$, $CH_2CH_3$, $CH_2CH_2CH_2CH_3$, $OCH_3$, $CH_2OH$, $OCH_2CH_2OH$, $OCHF_2$, $OCF_3$, $C(O)OH$, $OCH_2CH_2OSi(CH_3)_2C(CH_3)_3$, or $G^1$.

In some embodiments, each of A and W is independently substituted with 2 $R^Y$ on adjacent atoms, and the 2 $R^Y$, together with the atoms to which they are attached, form a 3-7-membered fused heterocyclyl ring or 5-6-membered heteroaryl ring, each optionally substituted with 1-5 $R^X$. In some embodiments, the 2 $R^Y$ together with the atoms to which they are attached form a dioxolanyl, hexahydropyrimidinyl, pyridyl, or pyrimidinyl ring, each of which is optionally substituted with 1-5 $R^X$. In some embodiments, each $R^X$ is independently fluoro.

In some embodiments, $G^1$ is pyrrolidinyl, cyclopropyl, cyclohexyl, cyclohexenyl, tetrahydropyranyl, dihydropyranyl, tetrahydropyridinyl, piperidinyl, phenyl, pyridyl, pyrimidinyl, pyridazinyl, or pyrazinyl, each of which is optionally substituted with 1-5 $R^Z$. In some embodiments, each $R^Z$ is independently $OR^A$, $C(O)R^D$, halo, halo $C_1$-$C_6$ alkyl, $C_1$-$C_6$ alkyl, or $C(O)OR^D$ (e.g., OH, $C(O)CH_3$ or $C(O)OC(CH_3)_3$).

In some embodiments, the compound of Formula (I) is a compound of Formula (I-b):

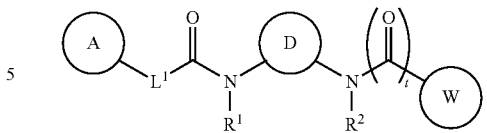

Formula (I-b)

or a pharmaceutically acceptable salt, solvate, hydrate, tautomer, or stereoisomer thereof, wherein D is bicyclo[1.1.1]pentane, bicyclo[2.2.1]heptane, bicyclo[2.2.2]octane, or bicyclo[2.1.1]hexane, each of which is optionally substituted with 1-4 $R^X$; $L^1$ $CH_2O$—*, wherein "—*" indicates the attachment point to A; $R^1$ and $R^2$ are each independently hydrogen or $C_1$-$C_6$ alkyl; A is phenyl optionally substituted with 1-2 $R^Y$; W is phenyl or 5-6 membered heteroaryl, wherein each phenyl or 5-6-membered heteroaryl is optionally substituted with 1-5 $R^Y$; each $R^X$ is independently $C_1$-$C_6$ alkyl, fluoro, chloro, oxo, $OCH_3$, $C(O)OCH_3$, or $G^2$; each $R^Y$ is independently chloro, fluoro, oxo, CN, OH, $CF_3$, $CHF_2$, $CH_3$, $CH_2CH_3$, $CH_2CH_2CH_2CH_3$, $CH=CHCH_2OH$, $CH_2CH_2OH$, $CH_2NH_2$, $NHCH_3$, $CH_2NHC(O)CH_3$, $N(CH_2CH_3)_2$, $CH_2N(CH_3)_2$, $C(CH_3)_2OH$, $CH(CH_3)_2$, $CH_2CH_2CH_3$, $C(CH_3)_3$, $CH_2CH(CH_3)_2$, $CH_2CH_2OH$, $CH(OH)CH_3$, $CH_2CH_2CH_2OCH_3$, $CH_2CF_3$, $CH_2C(CH_3)_2OH$, $CH_2SCH_3$, $CH_2CN$, $CH_2CH_2CN$, $CH_2CH_2C(CH_3)_2OH$, $CH_2NHC(O)CH_3$, $OCH_3$, $OCH_2CH_3$, $OCH_2CH_2CH_3$, $OCH_2CH_2OCH_3$, $OCH(CH_3)_2$, $OCF_3$, $OCH_2CF_3$, $OCH_2CH_2N(CH_3)_2$, $CH_2OH$, $CH_2OCH_3$, $OCH_2CH_2OH$, $OCHF_2$, $OCF_3$, $OCH_3$, $CH_2OH$, $C(O)OH$, $C(O)CH_3$, $C(O)OCH_3$, $C(O)NH_2$, $C(O)NHCH_2CH_2OH$, $CH_2CN$, $C(O)OCH_2CH_3$, $C(O)NHCH_2CH_3$, $OCH_2CH_2OSi(CH_3)_2C(CH_3)_3$, $CH_2N(CH_3)_2$, $CH_2NHC(O)CH_3$, $CH_2NHC(O)OC(CH_3)_3$, $CH=CHCH_2OCH_3$, $CH=CHC(CH_3)_2OH$, $N(CH_3)_2$, $N(CH_2CH_3)_2$, $NHCH_2CH_3$, $NHC(O)CH_3$, $NHC(O)CH_2OCH_3$, $NHS(O)_2CH_3$, $SCH_3$, $SCH_2CH_3$, $SO_2NH_2$, $S(O)CH_3$, $S(O)_2CH_3$, $G^1$, $C(O)NHG^1$, $N(CH_3)CH_2G^1$, $NHG^1$, $OG^1$, $CH_2G^1$, $CH_2CH_2G^1$, $CH_2NHC(O)G^1$, or $CH=CHG^1$; or 2 $R^Y$ groups on adjacent atoms, together with the atoms to which they are attached form a 5-7-membered fused heterocyclyl ring, 5-6-membered fused heteroaryl, a 5-6-membered fused cycloalkyl, or a fused phenyl, each optionally substituted with 1-5 $R^X$; and $G^1$ and $G^2$ are each independently pyrrolidinyl, azetidinyl, cyclopropyl, cyclohexyl, cyclohexenyl, tetrahydropyranyl, dihydropyranyl, tetrahydropyridinyl, piperidinyl, phenyl, pyridyl, pyrimidinyl, pyridazinyl, pyrazolyl, morpholino, furanyl, triazolyl, oxetanyl, or pyrazinyl, each of which is optionally substituted with 1-5 $R^Z$; each $R^Z$ is independently fluoro, chloro, OH, $OCH_3$, oxo, $CH_3$, $CHF_2$, $CF_3$, $C(O)CH_3$ or $C(O)OC(CH_3)_3$; and t is 0 or 1.

In some embodiments, the compound of Formula (I) is a compound of Formula (I-c):

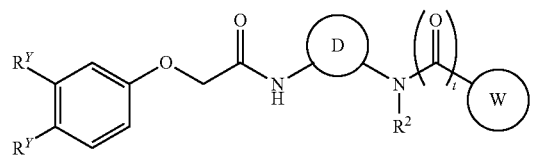

Formula (I-c)

or a pharmaceutically acceptable salt, solvate, hydrate, tautomer, or stereoisomer thereof, wherein each of W, D, $R^Y$, and t is defined as for Formula (I).

In some embodiments, D is a bridged monocyclic cycloalkyl optionally substituted with 1-4 $R^X$. In some embodiments, D is a bridged 4-6 membered cycloalkyl optionally substituted with 1-4 $R^X$. In some embodiments, D is selected from bicyclo[1.1.1]pentane, bicyclo[2.2.1]heptane, bicyclo[2.2.2]octane, or bicyclo[2.1.1]hexane, each of which is optionally substituted with 1-4 $R^X$. In some embodiments, D is selected from bicyclo[1.1.1]pentane, bicyclo[2.2.2]octane, or bicyclo[2.1.1]hexane, each of which is optionally substituted with 1-4 $R^X$. In some embodiments, D is selected from:

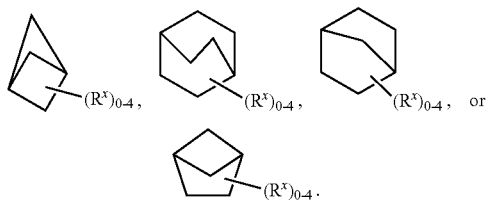

In some embodiments, D is selected from:

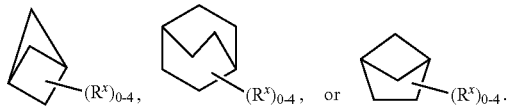

In some embodiments, D is selected from:

In some embodiments, D is selected from:

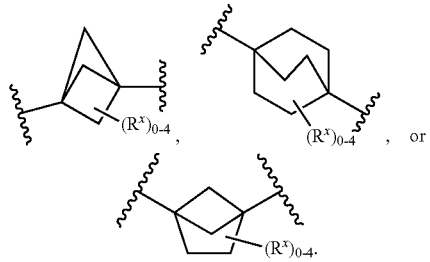

In some embodiments, D is substituted with 1 $R^X$. In some embodiments, D is substituted with one $R^X$, and $R^X$ is halo or —$OR^A$ (e.g., fluoro, OH). In some embodiments, D is substituted with 0 $R^X$. In some embodiments, D is

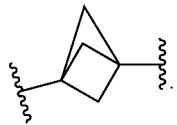 [SMILES: *C12CC(*)(C1)C2]

In some embodiments, t is 1. In some embodiments, t is 0.

In some embodiments, W is phenyl or 5-6-membered heteroaryl. In some embodiments, W is phenyl. In some embodiments, W is 5-6-membered heteroaryl.

In some embodiments, W is a monocyclic 5-6-membered heteroaryl. In some embodiments, 2 $R^Y$ groups on adjacent atoms of W, together with the atoms to which they are attached form a 3-7-membered fused cycloalkyl or heterocyclyl optionally substituted with 1-5 $R^X$ forming a bicyclic heteroaryl. In some embodiments, W is a 10-membered heteroaryl, a 9-membered heteroaryl, a 6-membered heteroaryl, or a 5-membered heteroaryl. In some embodiments, W is a heteroaryl containing nitrogen, oxygen or sulfur as allowed by valence.

In some embodiments, W is independently a phenyl or 5-6-membered heteroaryl optionally substituted with 1-5 $R^Y$, and each $R^Y$ is independently $C_1$-$C_6$ alkyl, hydroxy-$C_1$-$C_6$ alkyl, halo-$C_1$-$C_6$ alkyl, halo-$C_1$-$C_6$ alkoxy, $C_1$-$C_6$ alkoxy-$C_1$-$C_6$ alkyl, silyloxy-$C_1$-$C_6$ alkyl, halo, —$OR^A$, cycloalkyl, heterocyclyl, —C(O)OH, —C(O)$OR^D$, or $G^1$. In some embodiments, W is phenyl, pyridyl, pyrimidinyl, pyrazinyl, pyridazinyl, oxazolyl, isoxazolyl, furanyl, or pyrazolyl, each of which is optionally substituted with 1-5 $R^Y$ groups.

In some embodiments, W is selected from:

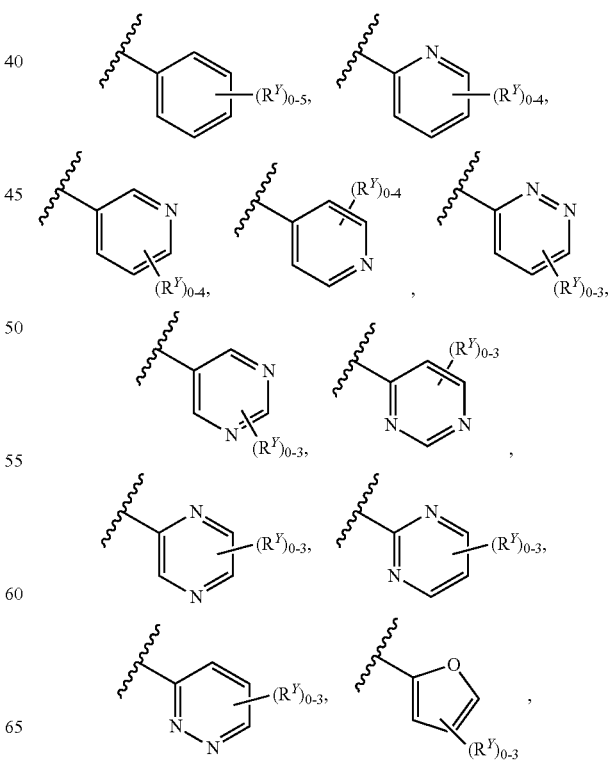

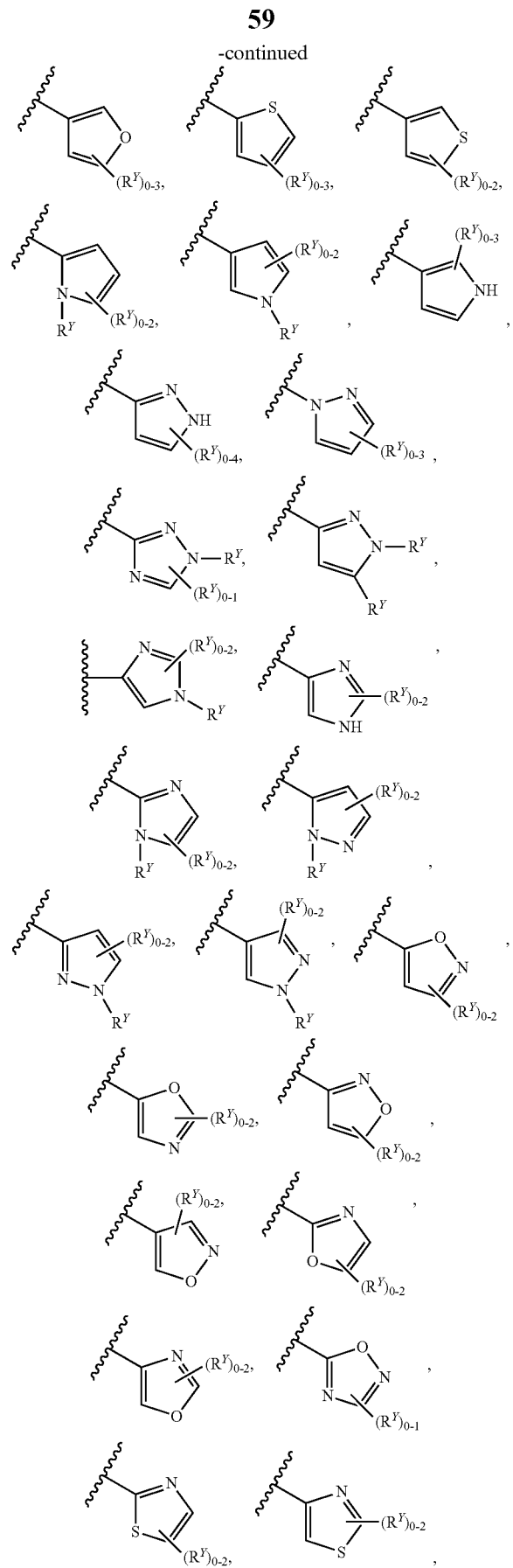

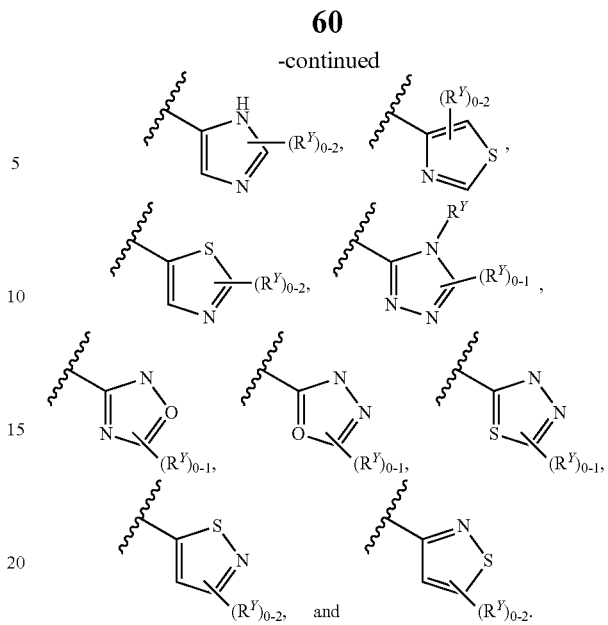

In some embodiments, each $R^Y$ is independently selected from chloro, fluoro, oxo, CN, OH, $CF_3$, $CHF_2$, $CH_3$, $CH_2CH_3$, $CH_2CH_2CH_2CH_3$, $CH=CHCH_2OH$, $CH_2CH_2OH$, $CH_2NH_2$, $NHCH_3$, $CH_2NHC(O)CH_3$, $N(CH_2CH_3)_2$, $CH2N(CH_3)_2$, $C(CH_3)_2OH$, $CH(CH_3)_2$, $CH_2CH_2CH_3$, $C(CH_3)_3$, $CH_2CH(CH_3)_2$, $CH_2CH_2OH$, $CH(OH)CH_3$, $CH_2CH_2CH_2OCH_3$, $CH_2CF_3$, $CH_2C(CH_3)_2OH$, $CH_2SCH_3$, $CH_2CN$, $CH_2CH_2CN$, $CH_2CH_2C(CH_3)_2OH$, $CH_2NHC(O)CH_3$, $OCH_3$, $OCH_2CH_3$, $OCH_2CH_2CH_3$, $OCH_2CH_2OCH_3$, $OCH(CH_3)_2$, $OCF_3$, $OCH_2CF_3$, $OCH_2CH_2N(CH_3)_2$, $CH_2OH$, $CH_2OCH_3$, $OCH_2CH_2OH$, $OCHF_2$, $OCF_3$, $OCH_3$, $CH_2OH$, $C(O)OH$, $C(O)CH_3$, $C(O)OCH_3$, $C(O)NH_2$, $C(O)NHCH_2CH_2CH_2OH$, $CH_2CN$, $C(O)OCH_2CH_3$, $C(O)NHCH_2CH_3$, $OCH_2CH_2OSi(CH_3)_2C(CH_3)_3$, $CH_2N(CH_3)_2$, $CH_2NHC(O)CH_3$, $CH_2NHC(O)OC(CH_3)_3$, $CH=CHCH_2OCH_3$, $CH=CHC(CH_3)_2OH$, $N(CH_3)_2$, $N(CH_2CH_3)_2$, $NHCH_2CH_3$, $NHC(O)CH_3$, $NHC(O)CH_2OCH_3$, $NHS(O)_2CH_3$, $SCH_3$, $SCH_2CH_3$, $SO_2NH_2$, $S(O)CH_3$, $S(O)_2CH_3$, $G^1$, $C(O)NHG^1$, $N(CH_3)CH_2G^1$, $NHG^1$, $OG^1$, $CH_2G^1$, $CH_2CH_2G^1$, $CH_2NHC(O)G^1$, or $CH=CHG^1$.

In some embodiments, each $R^Y$ is independently chloro, fluoro, CN, OH, $CF_3$, $CHF_2$, $CH_3$, $CH_2CH_3$, $CH_2CH_2CH_2CH_3$, $CH=CHCH_2OH$, $CH_2CH_2OH$, $CH_2NH_2$, $NHCH_3$, $CH_2NHC(O)CH_3$, $N(CH_2CH_3)_2$, $CH_2N(CH_3)_2$, $C(CH_3)_2OH$, $OCH_3$, $CH_2OH$, $CH_2OCH_3$, $OCH_2CH_2OH$, $OCHF_2$, $OCF_3$, $OCH_3$, $CH_2OH$, $C(O)OH$, $CH_2CN$, $C(O)OCH_2CH_3$, $C(O)NHCH_2CH_3$, $OCH_2CH_2OSi(CH_3)_2C(CH_3)_3$, or $G^1$.

In some embodiments, each $R^Y$ is independently chloro, fluoro, $CF_3$, $CHF_2$, $CH_3$, $CH_2CH_3$, $CH_2CH_2CH_2CH_3$, $OCH_3$, $CH_2OH$, $OCH_2CH_2OH$, $OCHF_2$, $OCF_3$, $C(O)OH$, $OCH_2CH_2OSi(CH_3)_2C(CH_3)_3$, or $G^1$.

In some embodiments, W is substituted with 2 $R^Y$ on adjacent atoms, and the 2 $R^Y$, together with the atoms to which they are attached, form a 3-7-membered fused heterocyclyl ring or 5-6-membered heteroaryl ring, each optionally substituted with 1-5 $R^X$. In some embodiments, the 2 $R^Y$ together with the atoms to which they are attached form a dioxolanyl, hexahydropyrimidinyl, pyridyl, or pyrimidinyl ring, each of which is optionally substituted with 1-5 $R^X$. In some embodiments, each $R^X$ is independently fluoro.

In some embodiments, $G^1$ or $G^2$ is pyrrolidinyl, azetidinyl, cyclopropyl, cyclohexyl, cyclohexenyl, tetrahydropyranyl, dihydropyranyl, tetrahydropyridinyl, piperidinyl, phenyl, pyridyl, pyrimidinyl, pyridazinyl, pyrazolyl, morphilino, furanyl, triazolyl, oxetanyl, or pyrazinyl, each of which is optionally substituted with 1-5 $R^Z$. In some embodiments, $G^1$ is pyrrolidinyl, cyclopropyl, cyclohexyl, cyclohexenyl, tetrahydropyranyl, dihydropyranyl, tetrahydropyridinyl, piperidinyl, phenyl, pyridyl, pyrimidinyl, pyridazinyl, or pyrazinyl, each of which is optionally substituted with 1-5 $R^Z$.

In some embodiments, $G^1$ is pyrrolidinyl, azetidinyl, cyclopropyl, cyclohexyl, cyclohexenyl, tetrahydropyranyl, dihydropyranyl, tetrahydropyridinyl, piperidinyl, phenyl, pyridyl, pyrimidinyl, pyridazinyl, pyrazolyl, morphilino, furanyl, triazolyl, oxetanyl, or pyrazinyl, each of which is optionally substituted with 1-5 $R^Z$. In some embodiments, $G^1$ is pyrrolidinyl, cyclopropyl, cyclohexyl, cyclohexenyl, tetrahydropyranyl, dihydropyranyl, tetrahydropyridinyl, piperidinyl, phenyl, pyridyl, pyrimidinyl, pyridazinyl, or pyrazinyl, each of which is optionally substituted with 1-5 $R^Z$.

In some embodiments, each $R^Z$ is independently $OR^A$, $C(O)R^D$, halo, halo $C_1$-$C_6$ alkyl, $C_1$-$C_6$ alkyl, $C(O)R^D$, or $C(O)OR^D$ (e.g., fluoro, chloro, OH, $OCH_3$, oxo, $CH_3$, $CHF_2$, $CF_3$, $C(O)CH_3$ or $C(O)OC(CH_3)_3$). In some embodiments, each $R^Z$ is independently $OR^A$, $C(O)R^D$, halo, halo $C_1$-$C_6$ alkyl, $C_1$-$C_6$ alkyl, or $C(O)OR^D$ (e.g., OH, $C(O)CH_3$ or $C(O)OC(CH_3)_3$).

In some embodiments, the compound of Formula (I) is a compound of Formula (I-d):

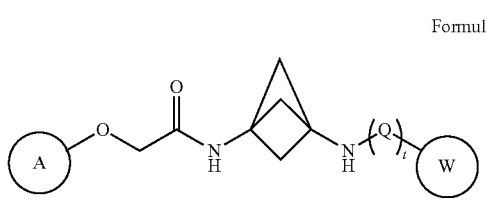

Formula (I-d)

or a pharmaceutically acceptable salt, solvate, hydrate, tautomer, or stereoisomer thereof, wherein each of A, W, Q, and t is defined as for Formula (I).

In some embodiments, Q is C(O). In some embodiments, Q is $S(O)_2$.

In some embodiments, t is 1. In some embodiments, t is 0.

In some embodiments, A is phenyl and W is independently phenyl or 5-6-membered heteroaryl. In some embodiments, each A and W is independently phenyl. In some embodiments, A is phenyl and W is 5-6-membered heteroaryl.

In some embodiments, W is a monocyclic 5-6-membered heteroaryl. In some embodiments, 2 $R^Y$ groups on adjacent atoms of W, together with the atoms to which they are attached form a 3-7-membered fused cycloalkyl or heterocyclyl optionally substituted with 1-5 $R^X$ forming a bicyclic heteroaryl. In some embodiments, W is a 10-membered heteroaryl, a 9-membered heteroaryl, a 6-membered heteroaryl, or a 5-membered heteroaryl. In some embodiments, W is a heteroaryl containing nitrogen, oxygen or sulfur as allowed by valence.

In some embodiments, each A and W is independently a phenyl or 5-6-membered heteroaryl optionally substituted with 1-5 $R^Y$, and each $R^Y$ is independently $C_1$-$C_6$ alkyl, hydroxy-$C_1$-$C_6$ alkyl, halo-$C_1$-$C_6$ alkyl, halo-$C_1$-$C_6$ alkoxy, $C_1$-$C_6$ alkoxy-$C_1$-$C_6$ alkyl, silyloxy-$C_1$-$C_6$ alkyl, halo, —$OR^A$, cycloalkyl, heterocyclyl, —C(O)OH, —$C(O)OR^D$, or $G^1$. In some embodiments, each of A and W is independently phenyl, pyridyl, pyrimidinyl, pyrazinyl, pyridazinyl, oxazolyl, isoxazolyl, furanyl, or pyrazolyl, each of which is optionally substituted with 1-5 $R^Y$ groups.

In some embodiments, each A and W is selected from:

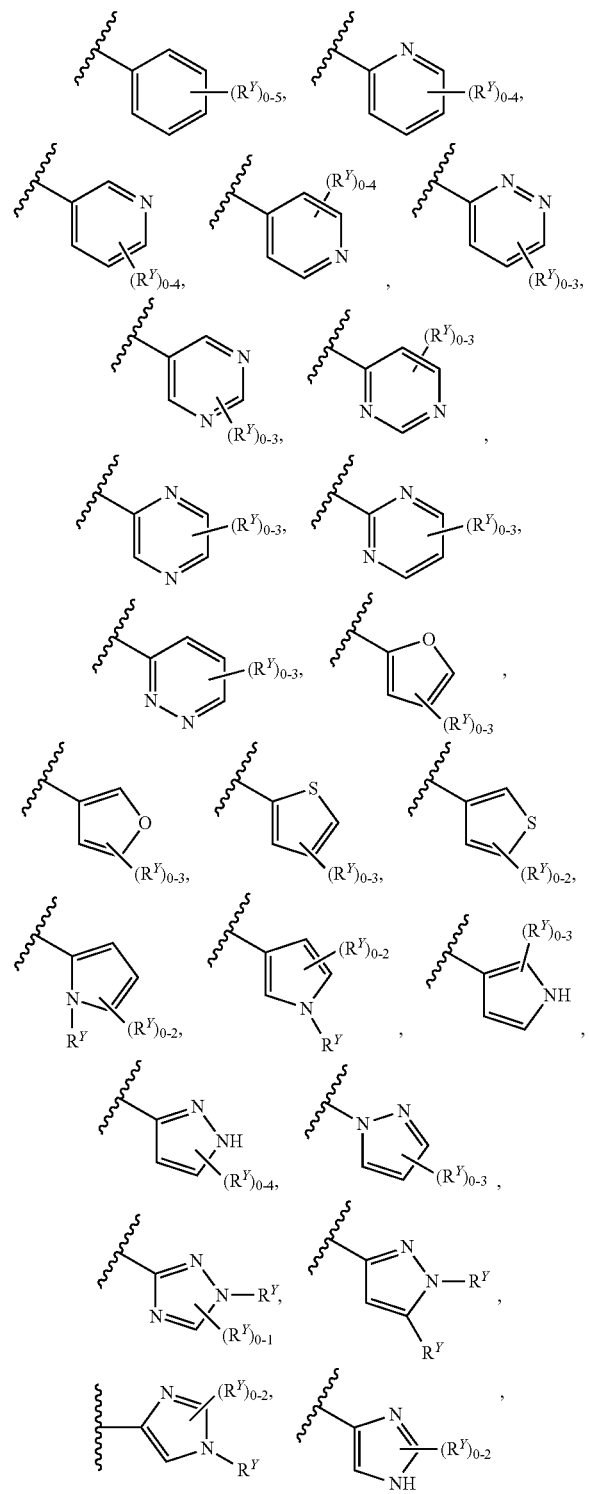

-continued
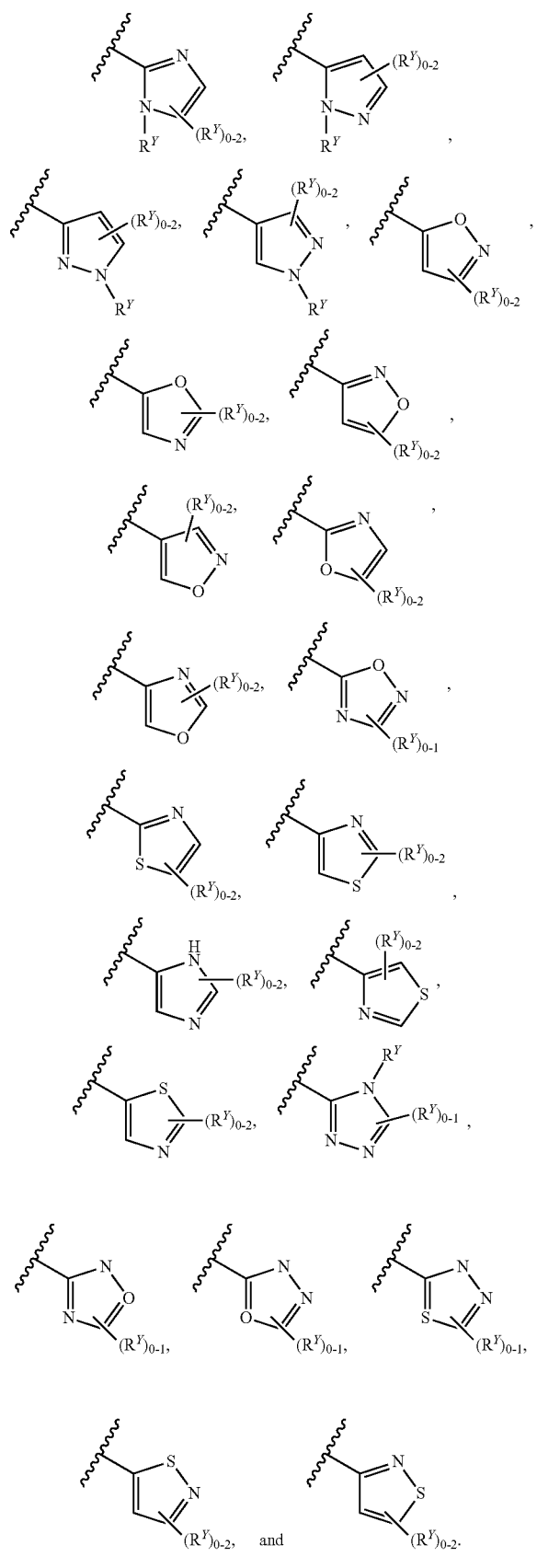
In some embodiments, each of A and W is selected from:
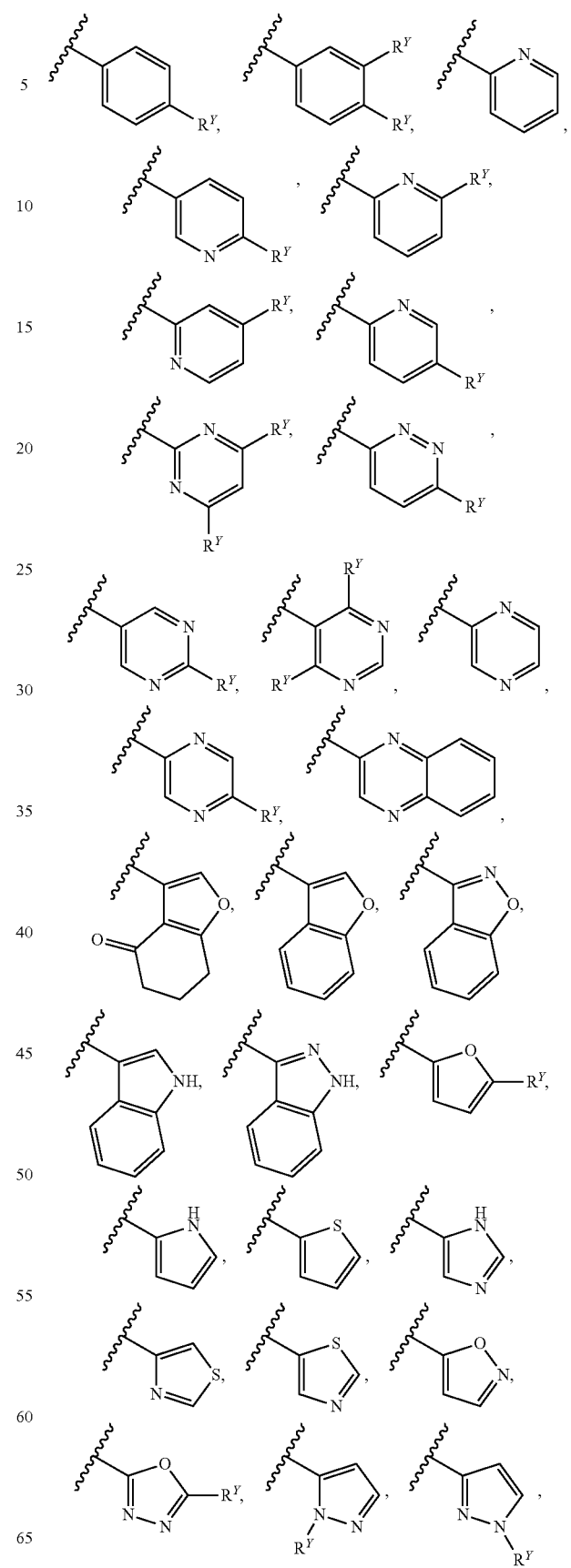

-continued

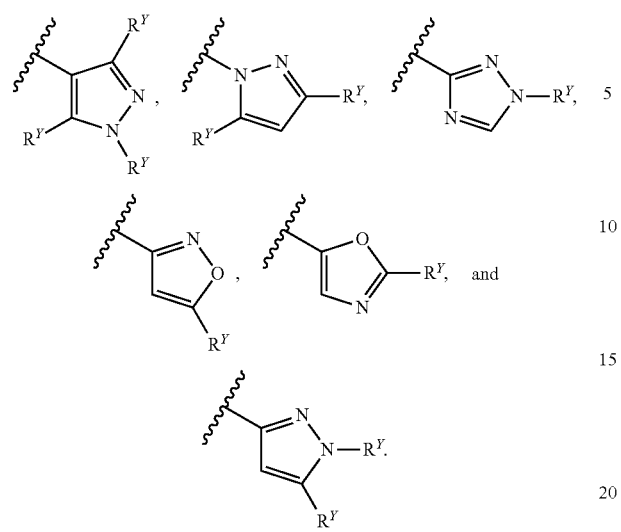

In some embodiments, each of A and W is selected from:

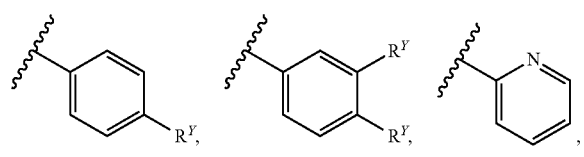

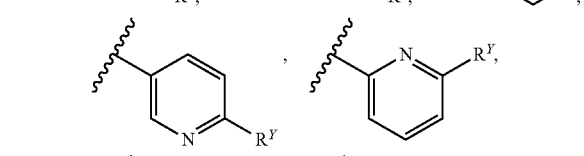

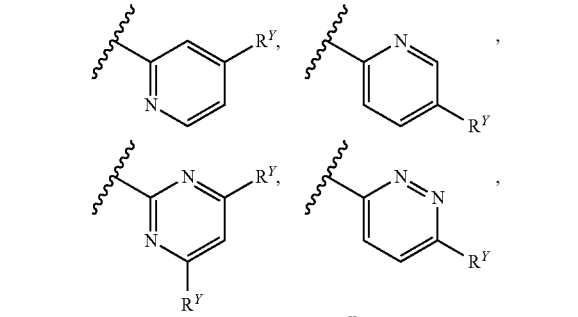

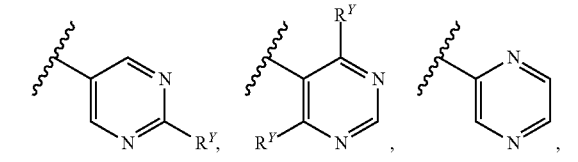

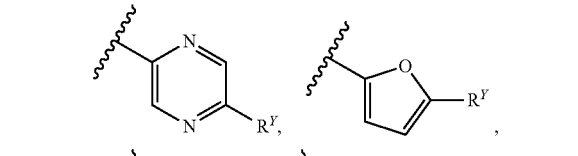

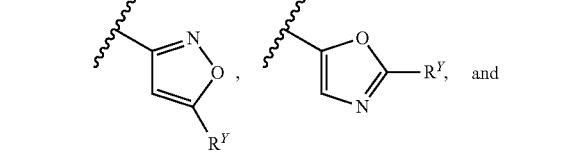

-continued

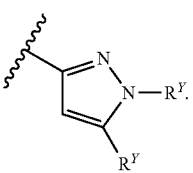

In some embodiments, A is phenyl or pyridyl and W is phenyl or 5-6-membered heteroaryl, each of A and W is optionally substituted with 1-5 $R^Y$, and each $R^Y$ is independently $C_1$-$C_6$ alkyl, hydroxy-$C_1$-$C_6$ alkyl, halo-$C_1$-$C_6$ alkyl, halo-$C_1$-$C_6$ alkoxy, siloxy-$C_1$-$C_6$ alkoxy, hydroxy $C_1$-$C_6$ alkoxy, halo, —$OR^A$, —C(O)OH, —C(O)$OR^D$, or $G^1$. In some embodiments, A is phenyl or pyridyl and W is phenyl, pyridyl, pyrimidinyl, pyrazinyl, pyridazinyl, oxazolyl, isoxazolyl, furanyl, or pyrazolyl, wherein A and W are each optionally substituted with 1-5 $R^Y$.

In some embodiments, A is

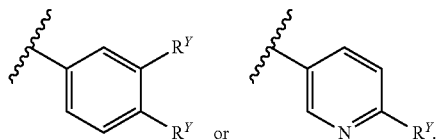

In some embodiments, A is

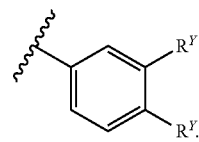

In some embodiments, W is selected from:

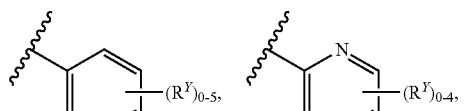

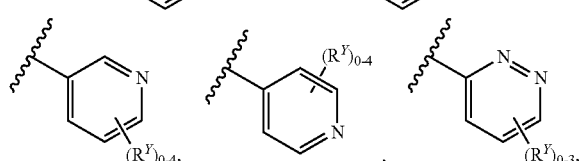

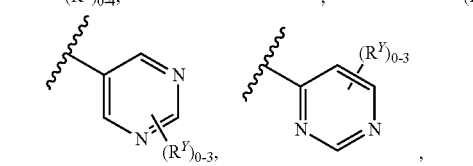

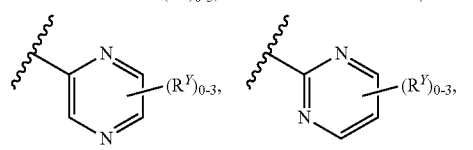

-continued
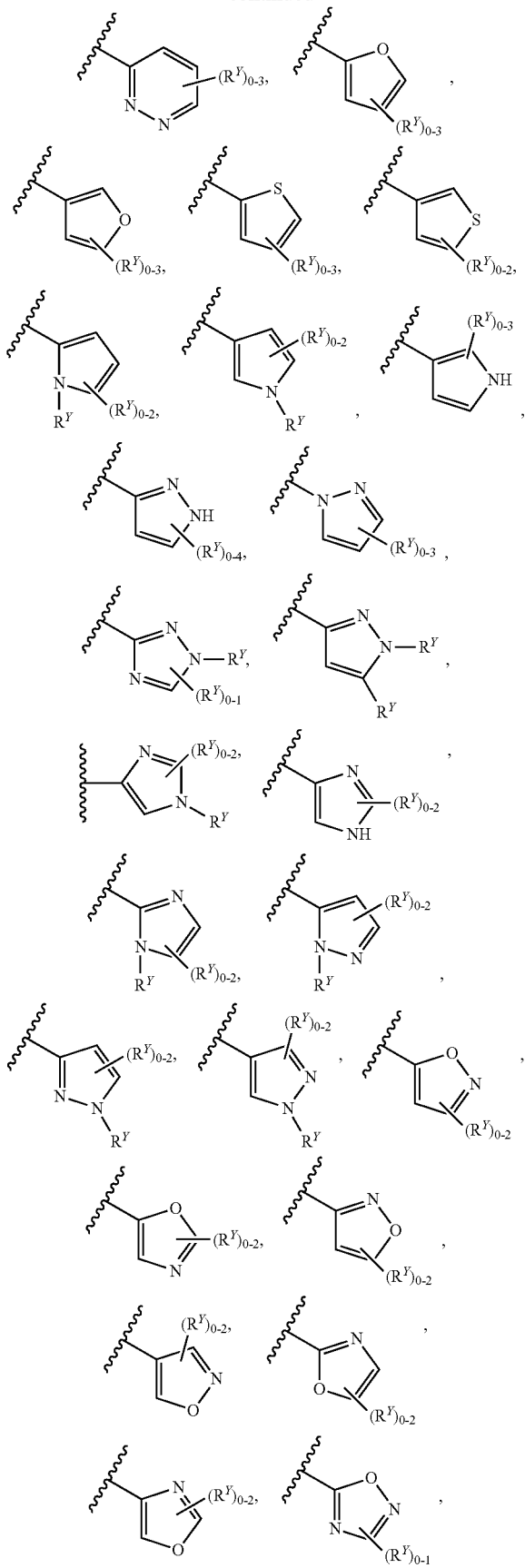
-continued
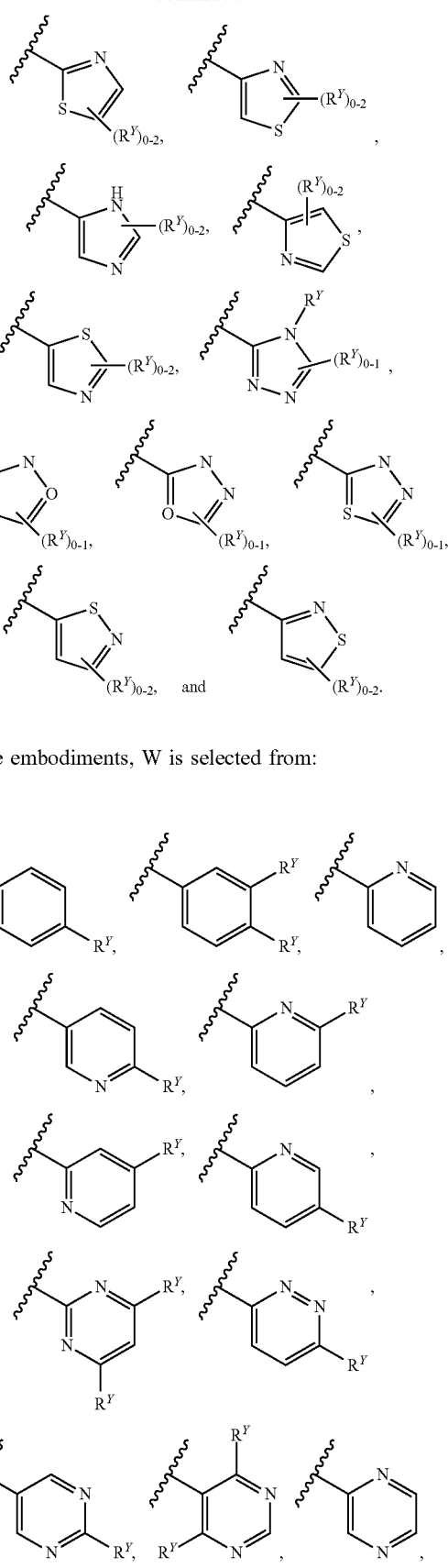
In some embodiments, W is selected from:

-continued

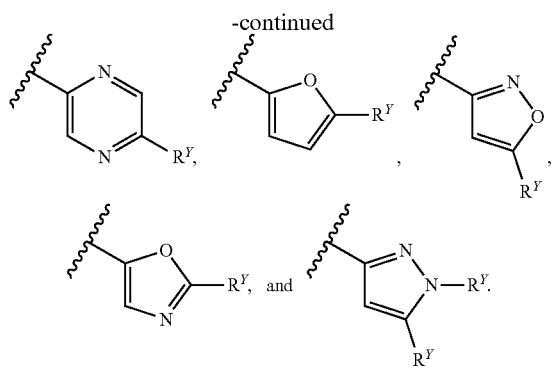

In some embodiments, each $R^Y$ is independently selected from chloro, fluoro, oxo, CN, OH, $CF_3$, $CHF_2$, $CH_3$, $CH_2CH_3$, $CH_2CH_2CH_2CH_3$, $CH=CHCH_2OH$, $CH_2CH_2OH$, $CH_2NH_2$, $NHCH_3$, $CH_2NHC(O)CH_3$, $N(CH_2CH_3)_2$, $CH2N(CH_3)_2$, $C(CH_3)_2OH$, $CH(CH_3)_2$, $CH_2CH_2CH_3$, $C(CH_3)_3$, $CH_2CH(CH_3)_2$, $CH_2CH_2OH$, $CH(OH)CH_3$, $CH_2CH_2CH_2OCH_3$, $CH_2CF_3$, $CH_2C(CH_3)_2OH$, $CH_2SCH_3$, $CH_2CN$, $CH_2CH_2CN$, $CH_2CH_2C(CH_3)_2OH$, $CH_2NHC(O)CH_3$, $OCH_3$, $OCH_2CH_3$, $OCH_2CH_2CH_3$, $OCH_2CH_2OCH_3$, $OCH(CH_3)_2$, $OCF_3$, $OCH_2CF_3$, $OCH_2CH_2N(CH_3)_2$, $CH_2OH$, $CH_2OCH_3$, $OCH_2CH_2OH$, $OCHF_2$, $OCF_3$, $OCH_3$, $CH_2OH$, $C(O)OH$, $C(O)CH_3$, $C(O)OCH_3$, $C(O)NH_2$, $C(O)NHCH_2CH_2CH_2OH$, $CH_2CN$, $C(O)OCH_2CH_3$, $C(O)NHCH_2CH_3$, $OCH_2CH_2OSi(CH_3)_2C(CH_3)_3$, $CH_2N(CH_3)_2$, $CH_2NHC(O)CH_3$, $CH_2NHC(O)OC(CH_3)_3$, $CH=CHCH_2OCH_3$, $CH=CHC(CH_3)_2OH$, $N(CH_3)_2$, $N(CH_2CH_3)_2$, $NHCH_2CH_3$, $NHC(O)CH_3$, $NHC(O)CH_2OCH_3$, $NHS(O)_2CH_3$, $SCH_3$, $SCH_2CH_3$, $SO_2NH_2$, $S(O)CH_3$, $S(O)_2CH_3$, $G^1$, $C(O)NHG^1$, $N(CH_3)CH_2G^1$, $NHG^1$, $OG^1$, $CH_2G^1$, $CH_2CH_2G^1$, $CH_2NHC(O)G^1$, or $CH=CHG^1$. In some embodiments, each $R^Y$ is independently chloro, fluoro, CN, OH, $CF_3$, $CHF_2$, $CH_3$, $CH_2CH_3$, $CH_2CH_2CH_2CH_3$, $CH=CHCH_2OH$, $CH_2CH_2OH$, $CH_2NH_2$, $NHCH_3$, $CH_2NHC(O)CH_3$, $N(CH_2CH_3)_2$, $CH_2N(CH_3)_2$, $C(CH_3)_2OH$, $OCH_3$, $CH_2OH$, $CH_2OCH_3$, $OCH_2CH_2OH$, $OCHF_2$, $OCF_3$, $OCH_3$, $CH_2OH$, $C(O)OH$, $CH_2CN$, $C(O)OCH_2CH_3$, $C(O)NHCH_2CH_3$, $OCH_2CH_2OSi(CH_3)_2C(CH_3)_3$, or $G^1$.

In some embodiments, each of A and W is independently substituted with 2 $R^Y$ on adjacent atoms, and the 2 $R^Y$, together with the atoms to which they are attached, form a 3-7-membered fused heterocyclyl ring or 5-6-membered heteroaryl ring, each optionally substituted with 1-5 $R^X$. In some embodiments, the 2 $R^Y$ together with the atoms to which they are attached form a dioxolanyl, hexahydropyrimidinyl, pyridyl, or pyrimidinyl ring, each of which is optionally substituted with 1-5 $R^X$. In some embodiments, each $R^X$ is independently $C_1$-$C_6$ alkyl, fluoro, chloro, oxo, $OCH_3$, $C(O)OCH_3$, or $G^2$.

In some embodiments, $G^1$ or $G^2$ is pyrrolidinyl, azetidinyl, cyclopropyl, cyclohexyl, cyclohexenyl, tetrahydropyranyl, dihydropyranyl, tetrahydropyridinyl, piperidinyl, phenyl, pyridyl, pyrimidinyl, pyridazinyl, pyrazolyl, morphilino, furanyl, triazolyl, oxetanyl, or pyrazinyl, each of which is optionally substituted with 1-5 $R^Z$. In some embodiments, $G^1$ is pyrrolidinyl, cyclopropyl, cyclohexyl, cyclohexenyl, tetrahydropyranyl, dihydropyranyl, tetrahydropyridinyl, piperidinyl, phenyl, pyridyl, pyrimidinyl, pyridazinyl, or pyrazinyl, each of which is optionally substituted with 1-5 $R^Z$.

In some embodiments, $G^1$ is pyrrolidinyl, azetidinyl, cyclopropyl, cyclohexyl, cyclohexenyl, tetrahydropyranyl, dihydropyranyl, tetrahydropyridinyl, piperidinyl, phenyl, pyridyl, pyrimidinyl, pyridazinyl, pyrazolyl, morphilino, furanyl, triazolyl, oxetanyl, or pyrazinyl, each of which is optionally substituted with 1-5 $R^Z$. In some embodiments, $G^1$ is pyrrolidinyl, cyclopropyl, cyclohexyl, cyclohexenyl, tetrahydropyranyl, dihydropyranyl, tetrahydropyridinyl, piperidinyl, phenyl, pyridyl, pyrimidinyl, pyridazinyl, or pyrazinyl, each of which is optionally substituted with 1-5 $R^Z$.

In some embodiments, each $R^Z$ is independently $OR^A$, $C(O)R^D$, halo, halo $C_1$-$C_6$ alkyl, $C_1$-$C_6$ alkyl, $C(O)R^D$, or $C(O)OR^D$ (e.g., fluoro, chloro, OH, $OCH_3$, oxo, $CH_3$, $CHF_2$, $CF_3$, $C(O)CH_3$ or $C(O)OC(CH_3)_3$). In some embodiments, each $R^Z$ is independently $OR^A$, $C(O)R^D$, halo, halo $C_1$-$C_6$ alkyl, $C_1$-$C_6$ alkyl, or $C(O)OR^D$ (e.g., OH, $C(O)CH_3$ or $C(O)OC(CH_3)_3$).

In some embodiments, the compound of Formula (I) is a compound of Formula (I-e):

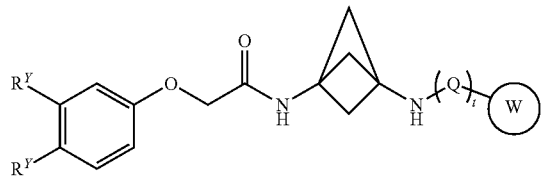

Formula (I-e)

or a pharmaceutically acceptable salt, solvate, hydrate, tautomer, or stereoisomer thereof, wherein each of W, Q, $R^Y$, and t is defined as for Formula (I).

In some embodiments, W is phenyl or 5-6-membered heteroaryl. In some embodiments, W is phenyl. In some embodiments, W is 5-6-membered heteroaryl.

In some embodiments, 2 $R^Y$ groups on adjacent atoms of W, together with the atoms to which they are attached form a 3-7-membered fused cycloalkyl or heterocyclyl optionally substituted with 1-5 $R^X$ forming a bicyclic heteroaryl. In some embodiments, W is a 10-membered heteroaryl, a 9-membered heteroaryl, a 6-membered heteroaryl, or a 5-membered heteroaryl. In some embodiments, W is a heteroaryl containing nitrogen, oxygen or sulfur as allowed by valence.

In some embodiments, W is a phenyl or 5-6-membered heteroaryl optionally substituted with 1-5 $R^Y$, and each $R^Y$ is independently $C_1$-$C_6$ alkyl, hydroxy-$C_1$-$C_6$ alkyl, halo-$C_1$-$C_6$ alkyl, halo-$C_1$-$C_6$ alkoxy, $C_1$-$C_6$ alkoxy-$C_1$-$C_6$ alkyl, silyloxy-$C_1$-$C_6$ alkyl, halo, —$OR^A$, cycloalkyl, heterocyclyl, —$C(O)OH$, —$C(O)OR^D$, or $G^1$. In some embodiments, W is phenyl, pyridyl, pyrimidinyl, pyrazinyl, pyridazinyl, oxazolyl, isoxazolyl, furanyl, or pyrazolyl, each of which is optionally substituted with 1-5 $R^Y$ groups.

In some embodiments, W is selected from:

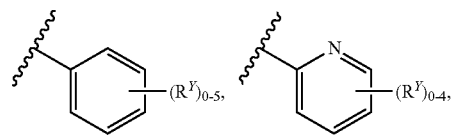

-continued

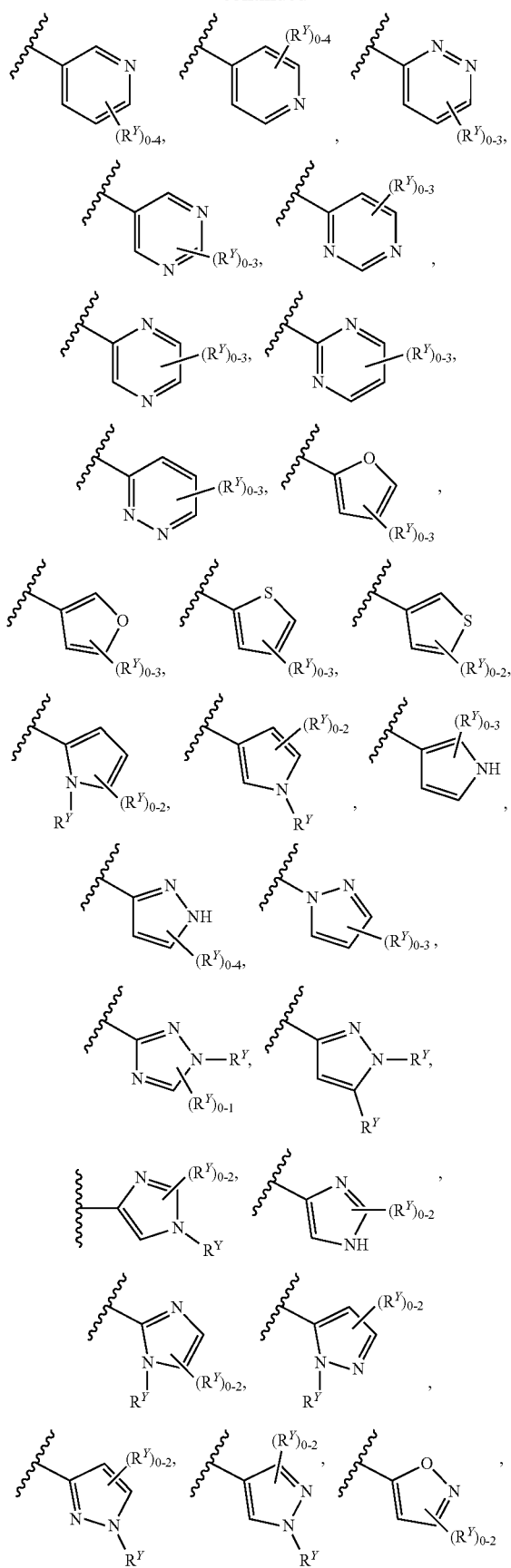

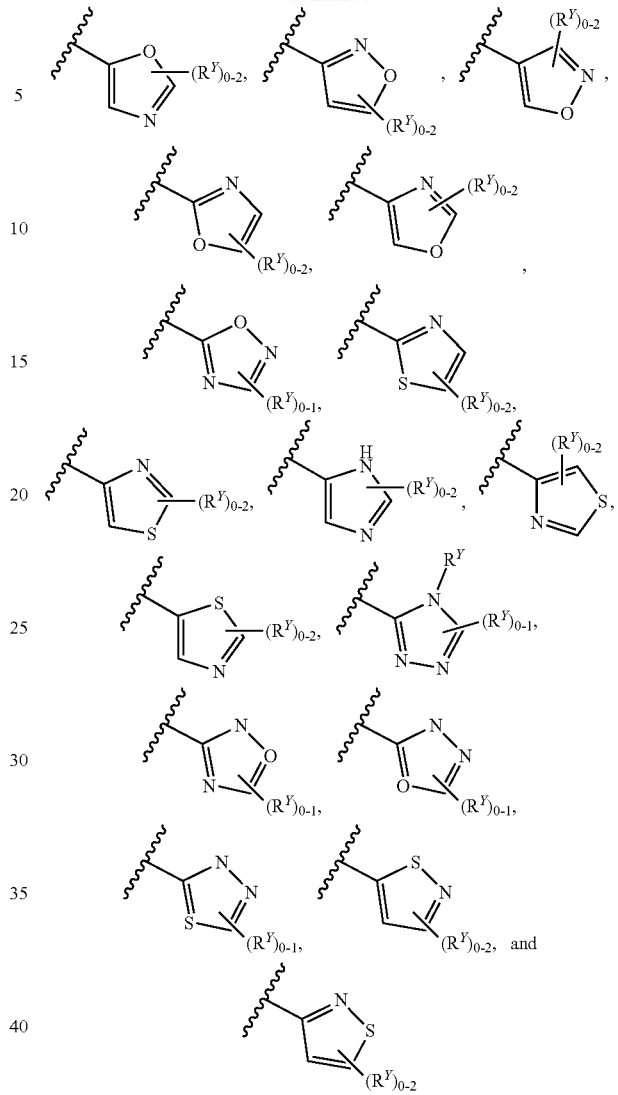

In some embodiments, W is phenyl or 5-6-membered heteroaryl, and is optionally substituted with 1-5 $R^Y$, wherein each $R^Y$ is independently $C_1$-$C_6$ alkyl, hydroxy-$C_1$-$C_6$ alkyl, halo-$C_1$-$C_6$ alkyl, halo-$C_1$-$C_6$ alkoxy, siloxy-$C_1$-$C_6$ alkoxy, hydroxy $C_1$-$C_6$ alkoxy, halo, —$OR^A$, —C(O)OH, —C(O)$OR^D$, or $G^1$. In some embodiments, W is phenyl, pyridyl, pyrimidinyl, pyrazinyl, pyridazinyl, oxazolyl, isoxazolyl, furanyl, or pyrazolyl, optionally substituted with 1-5 $R^Y$.

In some embodiments, W is selected from:

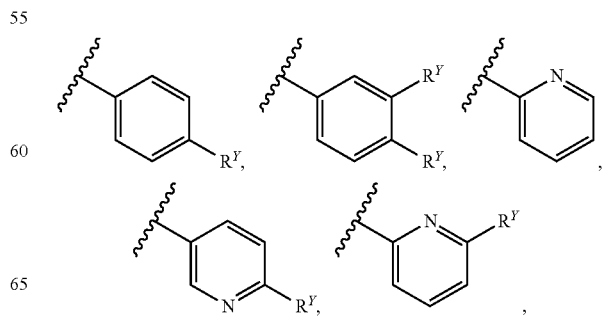

-continued

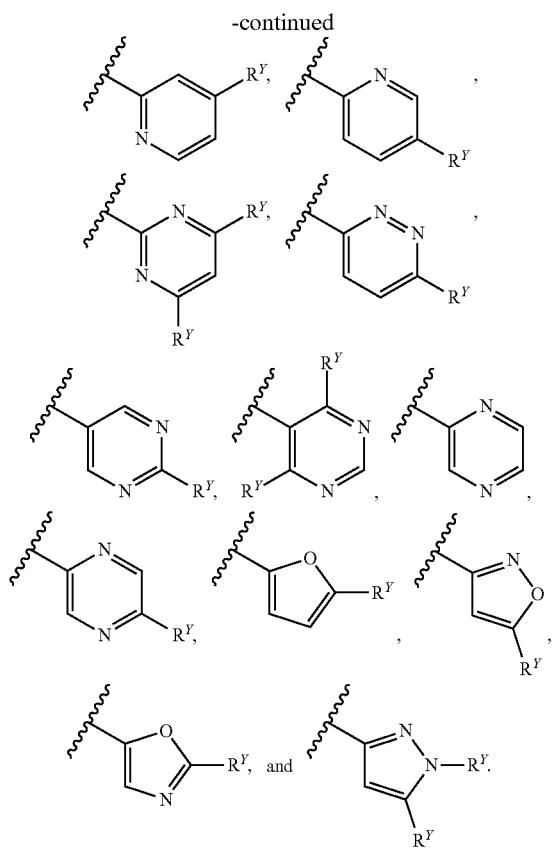

In some embodiments, each $R^Y$ is independently selected from chloro, fluoro, oxo, CN, OH, $CF_3$, $CHF_2$, $CH_3$, $CH_2CH_3$, $CH_2CH_2CH_2CH_3$, $CH=CHCH_2OH$, $CH_2CH_2OH$, $CH_2NH_2$, $NHCH_3$, $CH_2NHC(O)CH_3$, $N(CH_2CH_3)_2$, $CH2N(CH_3)_2$, $C(CH_3)_2OH$, $CH(CH_3)_2$, $CH_2CH_2CH_3$, $C(CH_3)_3$, $CH_2CH(CH_3)_2$, $CH_2CH_2OH$, $CH(OH)CH_3$, $CH_2CH_2CH_2OCH_3$, $CH_2CF_3$, $CH_2C(CH_3)_2OH$, $CH_2SCH_3$, $CH_2CN$, $CH_2CH_2CN$, $CH_2CH_2C(CH_3)_2OH$, $CH_2NHC(O)CH_3$, $OCH_3$, $OCH_2CH_3$, $OCH_2CH_2CH_3$, $OCH_2CH_2OCH_3$, $OCH(CH_3)_2$, $OCF_3$, $OCH_2CF_3$, $OCH_2CH_2N(CH_3)_2$, $CH_2OH$, $CH_2OCH_3$, $OCH_2CH_2OH$, $OCHF_2$, $OCF_3$, $OCH_3$, $CH_2OH$, $C(O)OH$, $C(O)CH_3$, $C(O)OCH_3$, $C(O)NH_2$, $C(O)NHCH_2CH_2OH$, $CH_2CN$, $C(O)OCH_2CH_3$, $C(O)NHCH_2CH_3$, $OCH_2CH_2OSi(CH_3)_2C(CH_3)_3$, $CH_2N(CH_3)_2$, $CH_2NHC(O)CH_3$, $CH_2NHC(O)OC(CH_3)_3$, $CH=CHCH_2OCH_3$, $CH=CHC(CH_3)_2OH$, $N(CH_3)_2$, $N(CH_2CH_3)_2$, $NHCH_2CH_3$, $NHC(O)CH_3$, $NHC(O)CH_2OCH_3$, $NHS(O)_2CH_3$, $SCH_3$, $SCH_2CH_3$, $SO_2NH_2$, $S(O)CH_3$, $S(O)_2CH_3$, $G^1$, $C(O)NHG^1$, $N(CH_3)CH_2G^1$, $NHG^1$, $OG^1$, $CH_2G^1$, $CH_2CH_2G^1$, $CH_2NHC(O)G^1$, or $CH=CHG^1$. In some embodiments, each $R^Y$ is independently chloro, fluoro, CN, OH, $CF_3$, $CHF_2$, $CH_3$, $CH_2CH_3$, $CH_2CH_2CH_2CH_3$, $CH=CHCH_2OH$, $CH_2CH_2OH$, $CH_2NH_2$, $NHCH_3$, $CH_2NHC(O)CH_3$, $N(CH_2CH_3)_2$, $CH_2N(CH_3)_2$, $C(CH_3)_2OH$, $OCH_3$, $CH_2OH$, $CH_2OCH_3$, $OCH_2CH_2OH$, $OCHF_2$, $OCF_3$, $OCH_3$, $CH_2OH$, $C(O)OH$, $CH_2CN$, $C(O)OCH_2CH_3$, $C(O)NHCH_2CH_3$, $OCH_2CH_2OSi(CH_3)_2C(CH_3)_3$, or $G^1$.

In some embodiments, W is substituted with 2 $R^Y$ on adjacent atoms, and the 2 $R^Y$, together with the atoms to which they are attached, form a 3-7-membered fused heterocyclyl ring or 5-6-membered heteroaryl ring, each optionally substituted with 1-5 $R^X$. In some embodiments, the 2 $R^Y$ together with the atoms to which they are attached form a dioxolanyl, hexahydropyrimidinyl, pyridyl, or pyrimidinyl ring, each of which is optionally substituted with 1-5 $R^X$. In some embodiments, each $R^X$ is independently $C_1$-$C_6$ alkyl, fluoro, chloro, oxo, $OCH_3$, $C(O)OCH_3$, or $G^2$.

In some embodiments, $G^1$ or $G^2$ is pyrrolidinyl, azetidinyl, cyclopropyl, cyclohexyl, cyclohexenyl, tetrahydropyranyl, dihydropyranyl, tetrahydropyridinyl, piperidinyl, phenyl, pyridyl, pyrimidinyl, pyridazinyl, pyrazolyl, morphilino, furanyl, triazolyl, oxetanyl, or pyrazinyl, each of which is optionally substituted with 1-5 $R^Z$. In some embodiments, $G^1$ is pyrrolidinyl, cyclopropyl, cyclohexyl, cyclohexenyl, tetrahydropyranyl, dihydropyranyl, tetrahydropyridinyl, piperidinyl, phenyl, pyridyl, pyrimidinyl, pyridazinyl, or pyrazinyl, each of which is optionally substituted with 1-5 $R^Z$.

In some embodiments, $G^1$ is pyrrolidinyl, azetidinyl, cyclopropyl, cyclohexyl, cyclohexenyl, tetrahydropyranyl, dihydropyranyl, tetrahydropyridinyl, piperidinyl, phenyl, pyridyl, pyrimidinyl, pyridazinyl, pyrazolyl, morphilino, furanyl, triazolyl, oxetanyl, or pyrazinyl, each of which is optionally substituted with 1-5 $R^Z$. In some embodiments, $G^1$ is pyrrolidinyl, cyclopropyl, cyclohexyl, cyclohexenyl, tetrahydropyranyl, dihydropyranyl, tetrahydropyridinyl, piperidinyl, phenyl, pyridyl, pyrimidinyl, pyridazinyl, or pyrazinyl, each of which is optionally substituted with 1-5 $R^Z$.

In some embodiments, each $R^Z$ is independently $OR^A$, $C(O)R^D$, halo, halo $C_1$-$C_6$ alkyl, $C_1$-$C_6$ alkyl, $C(O)R^D$, or $C(O)OR^D$ (e.g., fluoro, chloro, OH, $OCH_3$, oxo, $CH_3$, $CHF_2$, $CF_3$, $C(O)CH_3$ or $C(O)OC(CH_3)_3$). In some embodiments, each $R^Z$ is independently $OR^A$, $C(O)R^D$, halo, halo $C_1$-$C_6$ alkyl, $C_1$-$C_6$ alkyl, or $C(O)OR^D$ (e.g., OH, $C(O)CH_3$ or $C(O)OC(CH_3)_3$).

In some embodiments, the compound of Formula (I) is a compound of Formula (I-f):

Formula (I-f)

or a pharmaceutically acceptable salt, solvate, hydrate, tautomer, or stereoisomer thereof, wherein each of A and W is defined as for Formula (I).

In some embodiments, A is phenyl and W is independently phenyl or 5-6-membered heteroaryl. In some embodiments, each A and W is independently phenyl. In some embodiments, A is phenyl and W is 5-6-membered heteroaryl.

In some embodiments, W is a monocyclic 5-6-membered heteroaryl. In some embodiments, 2 $R^Y$ groups on adjacent atoms of W, together with the atoms to which they are attached form a 3-7-membered fused cycloalkyl or heterocyclyl optionally substituted with 1-5 $R^X$ forming a bicyclic heteroaryl. In some embodiments, W is a 10-membered heteroaryl, a 9-membered heteroaryl, a 6-membered heteroaryl, or a 5-membered heteroaryl. In some embodiments, W is a heteroaryl containing nitrogen, oxygen or sulfur as allowed by valence.

In some embodiments, each A and W is independently a phenyl or 5-6-membered heteroaryl optionally substituted with 1-5 $R^Y$, and each $R^Y$ is independently $C_1$-$C_6$ alkyl, hydroxy-$C_1$-$C_6$ alkyl, halo-$C_1$-$C_6$ alkyl, halo-$C_1$-$C_6$ alkoxy, $C_1$-$C_6$ alkoxy-$C_1$-$C_6$ alkyl, silyloxy-$C_1$-$C_6$ alkyl, halo, —$OR^A$, cycloalkyl, heterocyclyl, —C(O)OH, —C(O)$OR^D$, or $G^1$. In some embodiments, each of A and W is independently phenyl, pyridyl, pyrimidinyl, pyrazinyl, pyridazinyl, oxazolyl, isoxazolyl, furanyl, or pyrazolyl, each of which is optionally substituted with 1-5 $R^Y$ groups.

In some embodiments, each A and W is selected from:

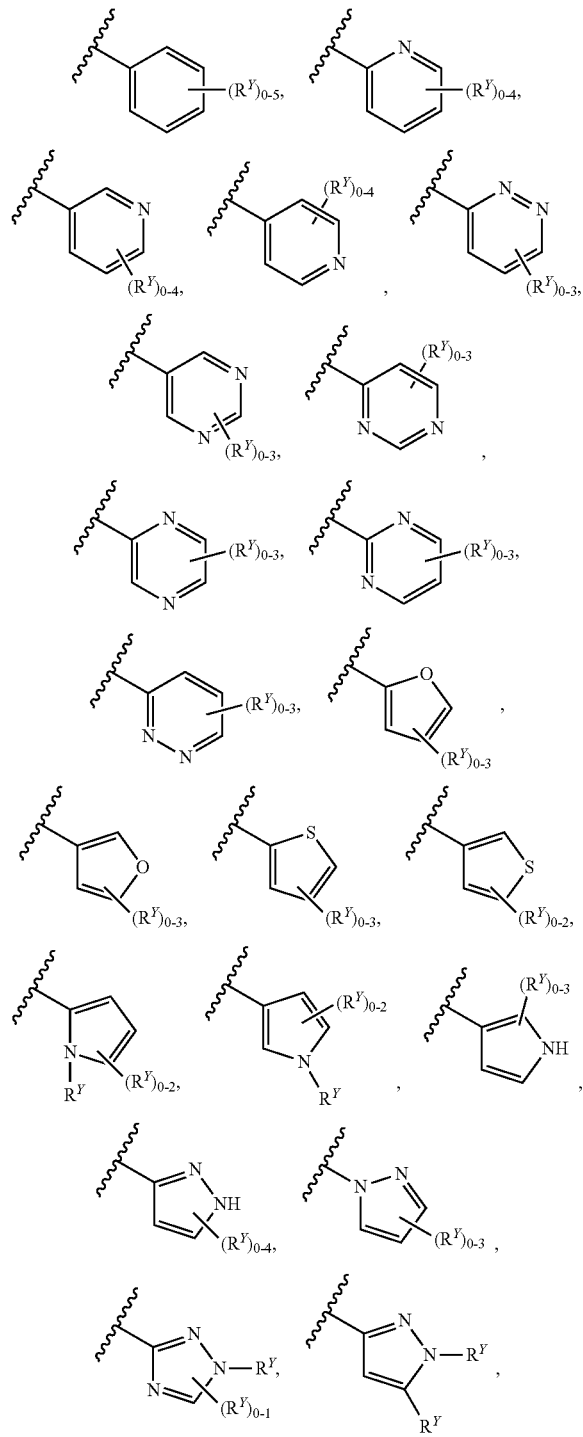

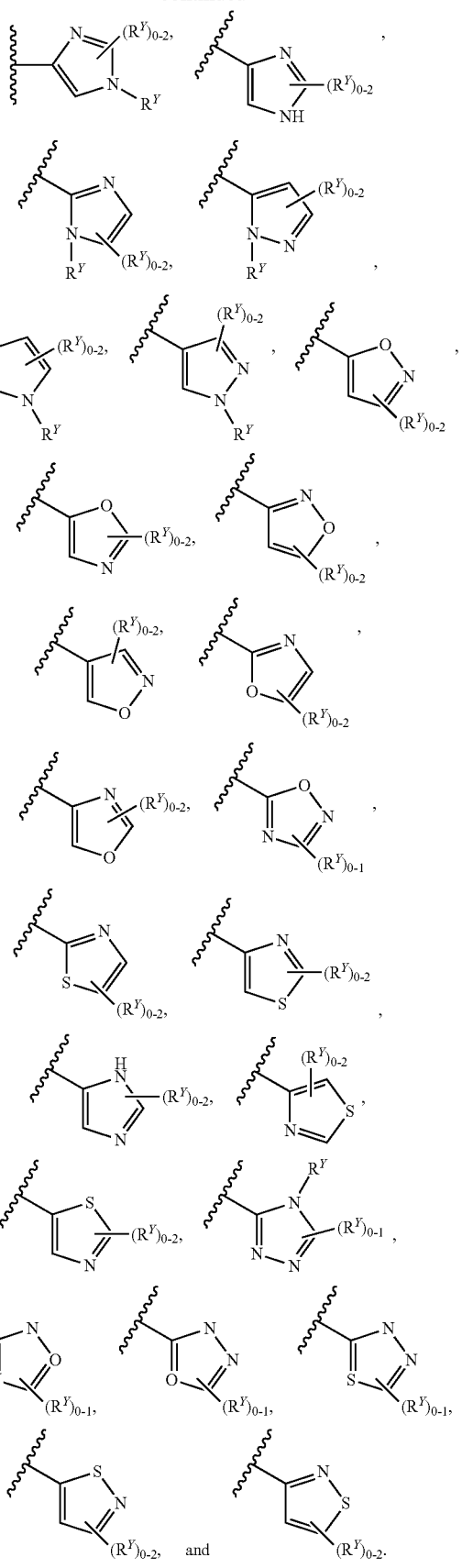

In some embodiments, each of A and W is selected from:
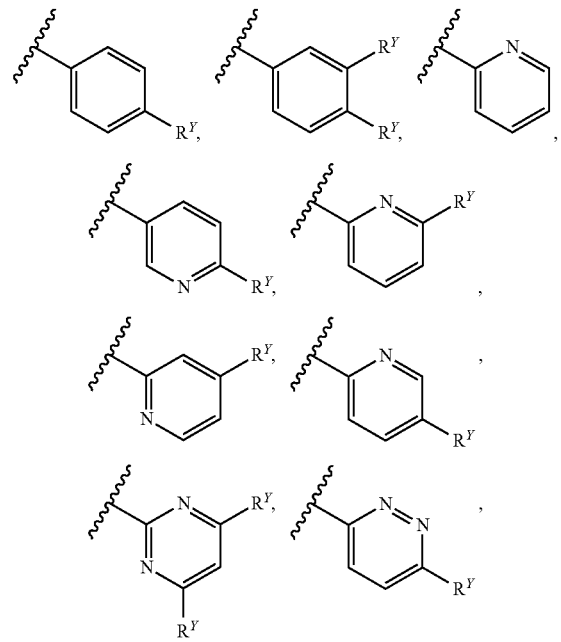
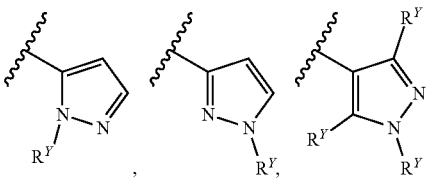
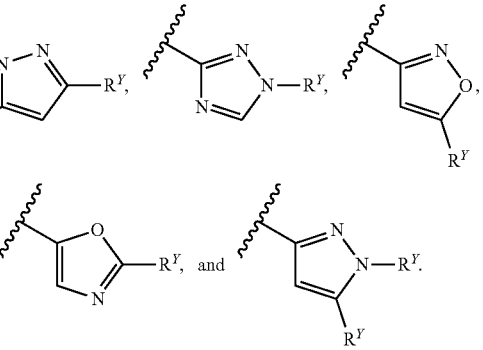
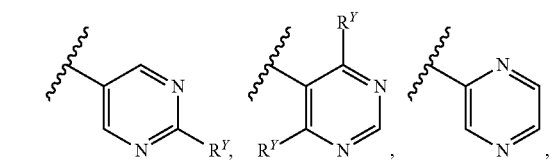
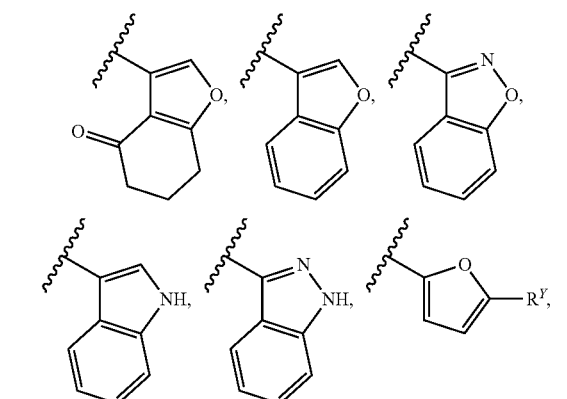
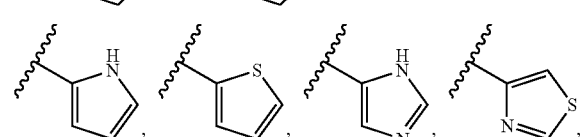
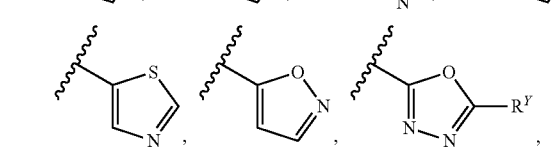
In some embodiments, each of A and W is selected from:
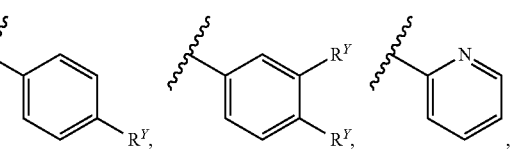
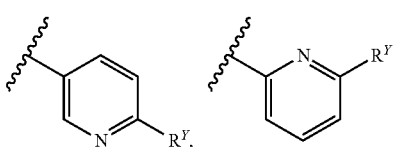
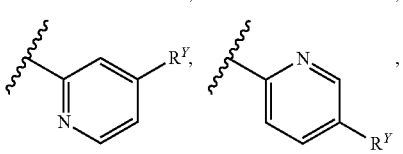
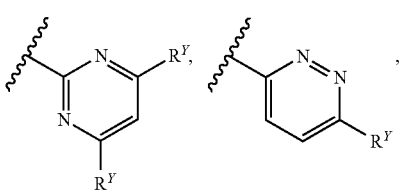
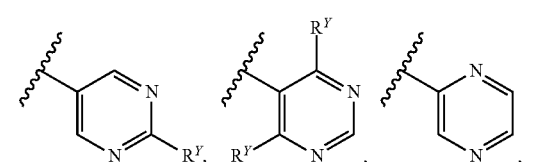
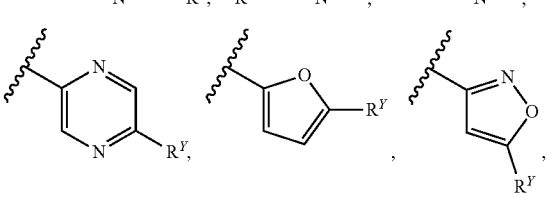

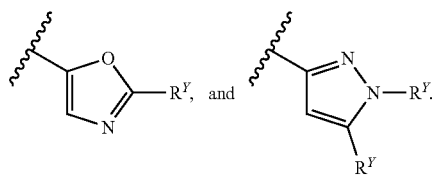

In some embodiments, A is phenyl or pyridyl and W is phenyl or 5-6-membered heteroaryl, each of A and W is optionally substituted with 1-5 $R^Y$, and each $R^Y$ is independently $C_1$-$C_6$ alkyl, hydroxy-$C_1$-$C_6$ alkyl, halo-$C_1$-$C_6$ alkyl, halo-$C_1$-$C_6$ alkoxy, siloxy-$C_1$-$C_6$ alkyl, hydroxy $C_1$-$C_6$ alkoxy, halo, —$OR^A$, —C(O)OH, —C(O)$OR^D$, or $G^1$. In some embodiments, A is phenyl or pyridyl and W is phenyl, pyridyl, pyrimidinyl, pyrazinyl, pyridazinyl, oxazolyl, isoxazolyl, furanyl, or pyrazolyl, wherein A and W are each optionally substituted with 1-5 $R^Y$.

In some embodiments, A is

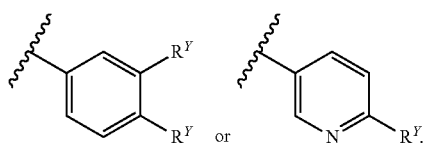

In some embodiments, A is

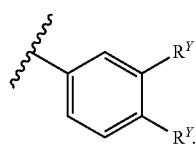

In some embodiments, W is selected from:

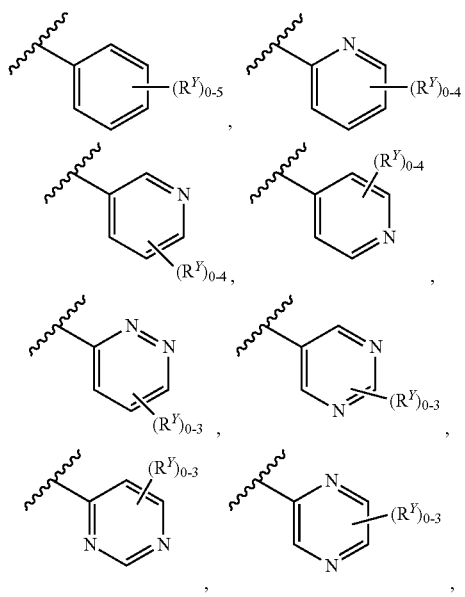

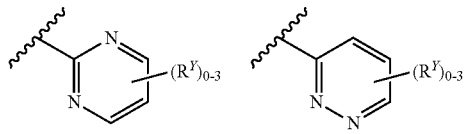

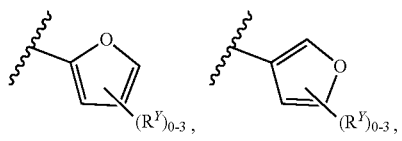

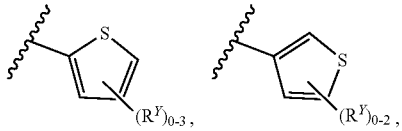

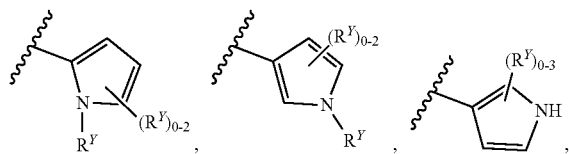

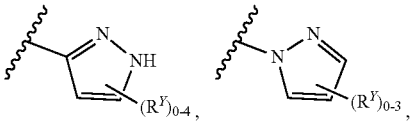

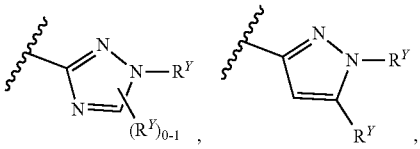

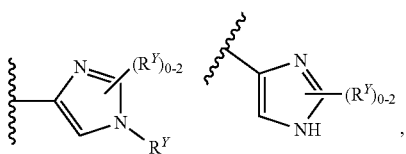

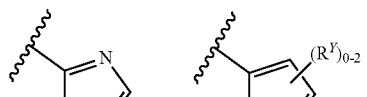

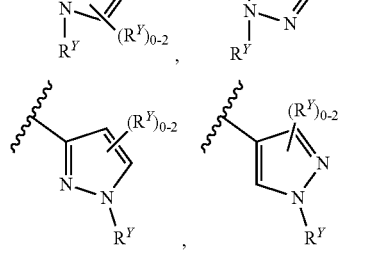

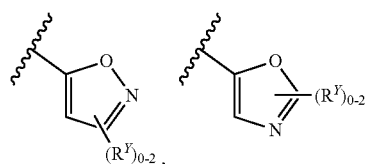

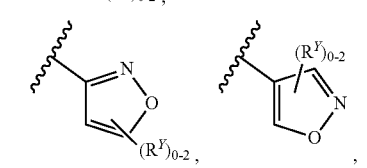

-continued

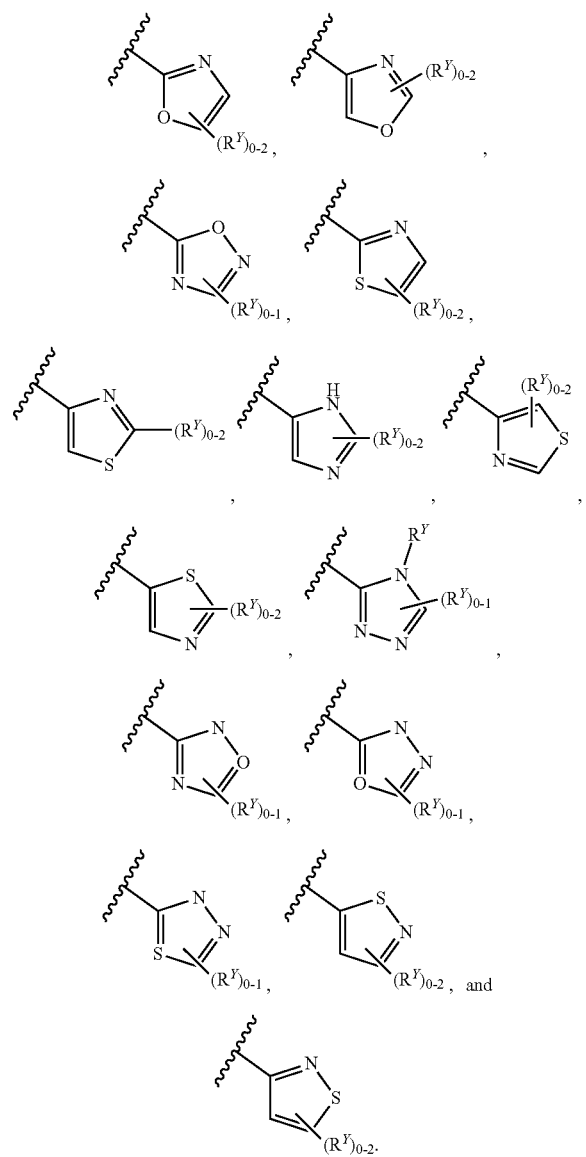

In some embodiments, W is selected from:

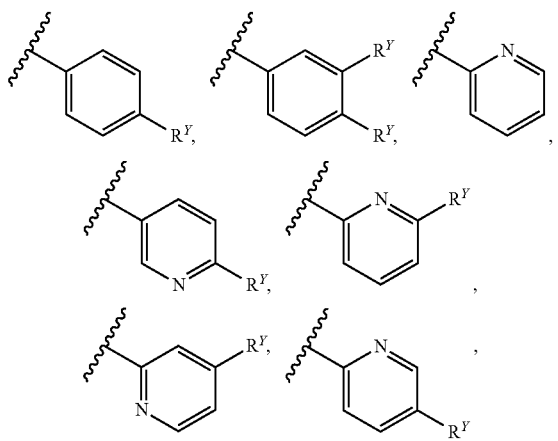

-continued

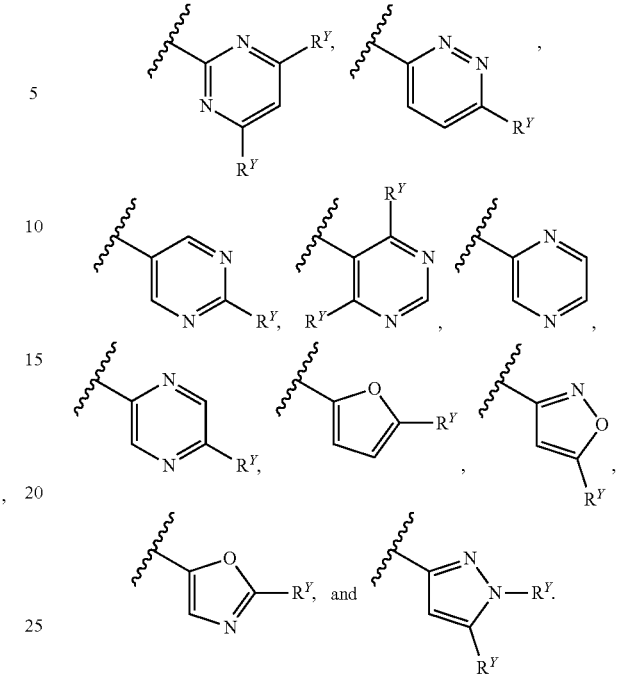

In some embodiments, each $R^Y$ is independently selected from chloro, fluoro, oxo, CN, OH, $CF_3$, $CHF_2$, $CH_3$, $CH_2CH_3$, $CH_2CH_2CH_2CH_3$, $CH=CHCH_2OH$, $CH_2CH_2OH$, $CH_2NH_2$, $NHCH_3$, $CH_2NHC(O)CH_3$, $N(CH_2CH_3)_2$, $CH2N(CH_3)_2$, $C(CH_3)_2OH$, $CH(CH_3)_2$, $CH_2CH_2CH_3$, $C(CH_3)_3$, $CH_2CH(CH_3)_2$, $CH_2CH_2OH$, $CH(OH)CH_3$, $CH_2CH_2CH_2OCH_3$, $CH_2CF_3$, $CH_2C(CH_3)_2OH$, $CH_2SCH_3$, $CH_2CN$, $CH_2CH_2CN$, $CH_2CH_2C(CH_3)_2OH$, $CH_2NHC(O)CH_3$, $OCH_3$, $OCH_2CH_3$, $OCH_2CH_2CH_3$, $OCH_2CH_2OCH_3$, $OCH(CH_3)_2$, $OCF_3$, $OCH_2CF_3$, $OCH_2CH_2N(CH_3)_2$, $CH_2OH$, $CH_2OCH_3$, $OCH_2CH_2OH$, $OCHF_2$, $OCF_3$, $OCH_3$, $CH_2OH$, $C(O)OH$, $C(O)CH_3$, $C(O)OCH_3$, $C(O)NH_2$, $C(O)NHCH_2CH_2CH_2OH$, $CH_2CN$, $C(O)OCH_2CH_3$, $C(O)NHCH_2CH_3$, $OCH_2CH_2OSi(CH_3)_2C(CH_3)_3$, $CH_2N(CH_3)_2$, $CH_2NHC(O)CH_3$, $CH_2NHC(O)OC(CH_3)_3$, $CH=CHCH_2OCH_3$, $CH=CHC(CH_3)_2OH$, $N(CH_3)_2$, $N(CH_2CH_3)_2$, $NHCH_2CH_3$, $NHC(O)CH_3$, $NHC(O)CH_2OCH_3$, $NHS(O)_2CH_3$, $SCH_3$, $SCH_2CH_3$, $SO_2NH_2$, $S(O)CH_3$, $S(O)_2CH_3$, $G^1$, $C(O)NHG^1$, $N(CH_3)CH_2G^1$, $NHG^1$, $OG^1$, $CH_2G^1$, $CH_2CH_2G^1$, $CH_2NHC(O)G^1$, or $CH=CHG^1$.
In some embodiments, each $R^Y$ is independently chloro, fluoro, CN, OH, $CF_3$, $CHF_2$, $CH_3$, $CH_2CH_3$, $CH_2CH_2CH_2CH_3$, $CH=CHCH_2OH$, $CH_2CH_2OH$, $CH_2NH_2$, $NHCH_3$, $CH_2NHC(O)CH_3$, $N(CH_2CH_3)_2$, $CH_2N(CH_3)_2$, $C(CH_3)_2OH$, $OCH_3$, $CH_2OH$, $CH_2OCH_3$, $OCH_2CH_2OH$, $OCHF_2$, $OCF_3$, $OCH_3$, $CH_2OH$, $C(O)OH$, $CH_2CN$, $C(O)OCH_2CH_3$, $C(O)NHCH_2CH_3$, $OCH_2CH_2OSi(CH_3)_2C(CH_3)_3$, or $G^1$.

In some embodiments, each of A and W is independently substituted with 2 $R^Y$ on adjacent atoms, and the 2 $R^Y$, together with the atoms to which they are attached, form a 3-7-membered fused heterocyclyl ring or 5-6-membered heteroaryl ring, each optionally substituted with 1-5 $R^X$. In some embodiments, the 2 $R^Y$ together with the atoms to which they are attached form a dioxolanyl, hexahydropyrimidinyl, pyridyl, or pyrimidinyl ring, each of which is optionally substituted with 1-5 $R^X$. In some embodiments, each $R^X$ is independently $C_1$-$C_6$ alkyl, fluoro, chloro, oxo, $OCH_3$, $C(O)OCH_3$, or $G^2$.

In some embodiments, $G^1$ or $G^2$ is pyrrolidinyl, azetidinyl, cyclopropyl, cyclohexyl, cyclohexenyl, tetrahydropyranyl, dihydropyranyl, tetrahydropyridinyl, piperidinyl, phenyl, pyridyl, pyrimidinyl, pyridazinyl, pyrazolyl, morphilino, furanyl, triazolyl, oxetanyl, or pyrazinyl, each of which is optionally substituted with 1-5 $R^Z$. In some embodiments, $G^1$ is pyrrolidinyl, cyclopropyl, cyclohexyl, cyclohexenyl, tetrahydropyranyl, dihydropyranyl, tetrahydropyridinyl, piperidinyl, phenyl, pyridyl, pyrimidinyl, pyridazinyl, or pyrazinyl, each of which is optionally substituted with 1-5 $R^Z$.

In some embodiments, $G^1$ is pyrrolidinyl, azetidinyl, cyclopropyl, cyclohexyl, cyclohexenyl, tetrahydropyranyl, dihydropyranyl, tetrahydropyridinyl, piperidinyl, phenyl, pyridyl, pyrimidinyl, pyridazinyl, pyrazolyl, morphilino, furanyl, triazolyl, oxetanyl, or pyrazinyl, each of which is optionally substituted with 1-5 $R^Z$. In some embodiments, $G^1$ is pyrrolidinyl, cyclopropyl, cyclohexyl, cyclohexenyl, tetrahydropyranyl, dihydropyranyl, tetrahydropyridinyl, piperidinyl, phenyl, pyridyl, pyrimidinyl, pyridazinyl, or pyrazinyl, each of which is optionally substituted with 1-5 $R^Z$.

In some embodiments, each $R^Z$ is independently $OR^A$, $C(O)R^D$, halo, halo $C_1$-$C_6$ alkyl, $C_1$-$C_6$ alkyl, $C(O)R^D$, or $C(O)OR^D$ (e.g., fluoro, chloro, OH, $OCH_3$, oxo, $CH_3$, $CHF_2$, $CF_3$, $C(O)CH_3$ or $C(O)OC(CH_3)_3$). In some embodiments, each $R^Z$ is independently $OR^A$, $C(O)R^D$, halo, halo $C_1$-$C_6$ alkyl, $C_1$-$C_6$ alkyl, or $C(O)OR^D$ (e.g., OH, $C(O)CH_3$ or $C(O)OC(CH_3)_3$).

In some embodiments, the compound of Formula (I) is a compound of Formula (I-g):

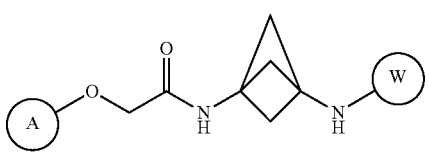

Formula (I-g)

or a pharmaceutically acceptable salt, solvate, hydrate, tautomer, or stereoisomer thereof, wherein each of A and W is defined as for Formula (I).

In some embodiments, A is phenyl and W is independently phenyl or 5-6-membered heteroaryl. In some embodiments, each A and W is independently phenyl. In some embodiments, A is phenyl and W is 5-6-membered heteroaryl.

In some embodiments, W is a monocyclic 5-6-membered heteroaryl. In some embodiments, 2 $R^Y$ groups on adjacent atoms of W, together with the atoms to which they are attached form a 3-7-membered fused cycloalkyl or heterocyclyl optionally substituted with 1-5 $R^X$ forming a bicyclic heteroaryl. In some embodiments, W is a 10-membered heteroaryl, a 9-membered heteroaryl, a 6-membered heteroaryl, or a 5-membered heteroaryl. In some embodiments, W is a heteroaryl containing nitrogen, oxygen or sulfur as allowed by valence.

In some embodiments, each A and W is independently a phenyl or 5-6-membered heteroaryl optionally substituted with 1-5 $R^Y$, and each $R^Y$ is independently $C_1$-$C_6$ alkyl, hydroxy-$C_1$-$C_6$ alkyl, halo-$C_1$-$C_6$ alkyl, halo-$C_1$-$C_6$ alkoxy, $C_1$-$C_6$ alkoxy-$C_1$-$C_6$ alkyl, silyloxy-$C_1$-$C_6$ alkyl, halo, —$OR^A$, cycloalkyl, heterocyclyl, —$C(O)OH$, —$C(O)OR^D$, or $G^1$. In some embodiments, each of A and W is independently phenyl, pyridyl, pyrimidinyl, pyrazinyl, pyridazinyl, oxazolyl, isoxazolyl, furanyl, or pyrazolyl, each of which is optionally substituted with 1-5 $R^Y$ groups.

In some embodiments, each A and W is selected from:

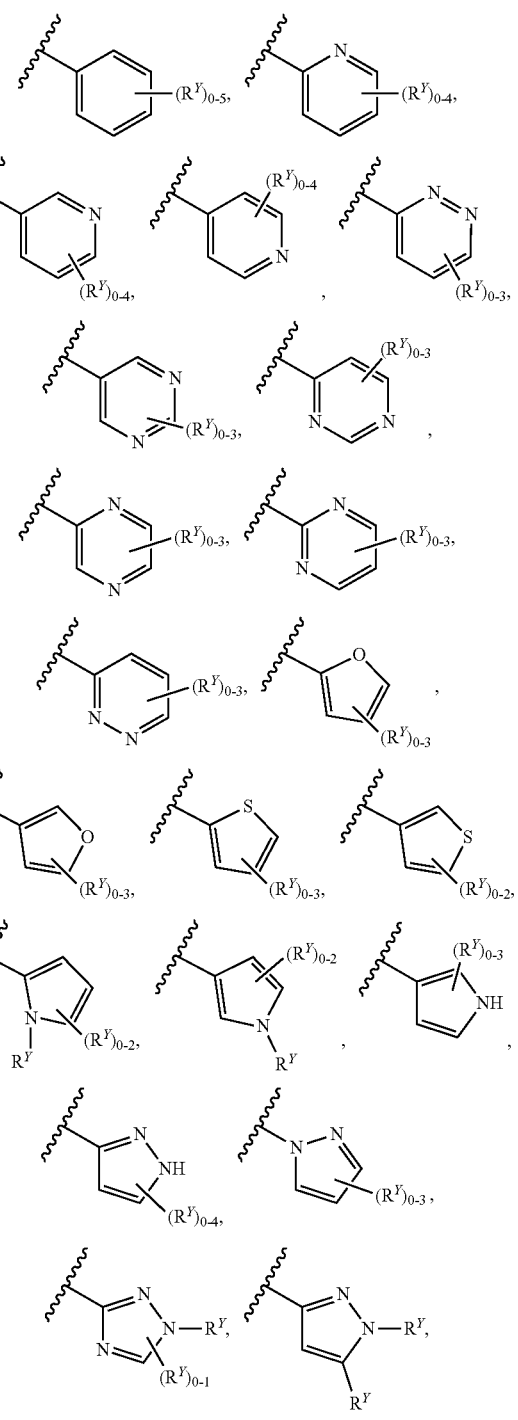

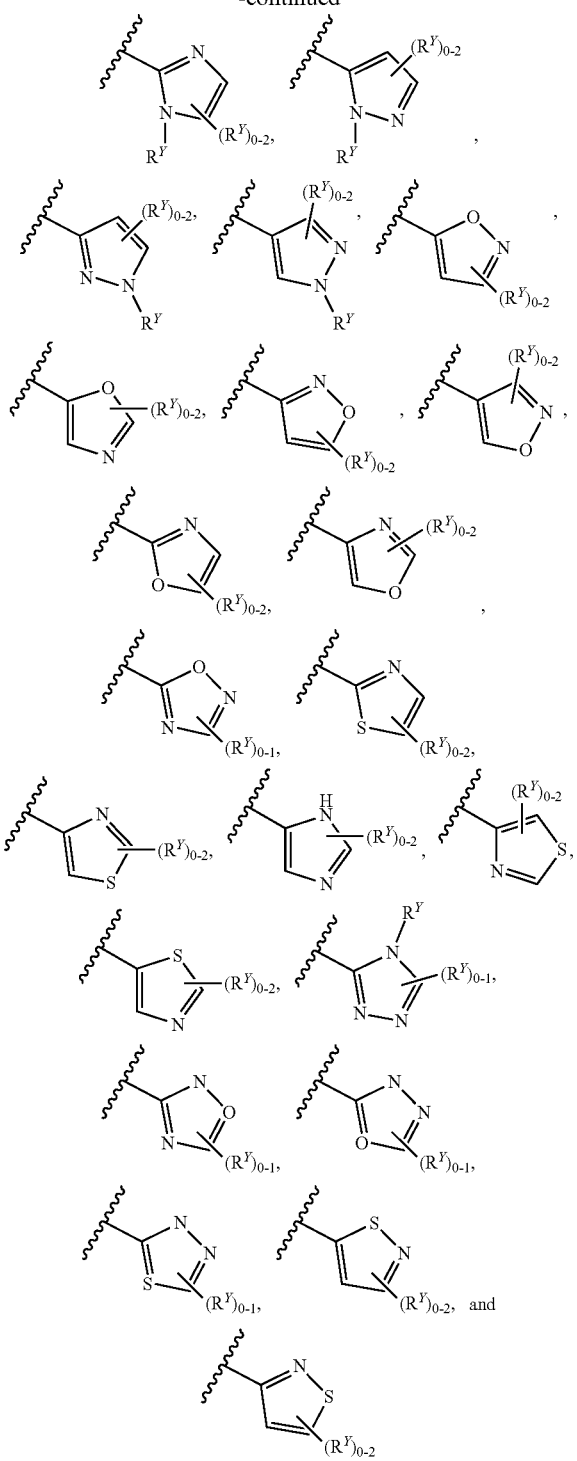
In some embodiments, each of A and W is selected from:
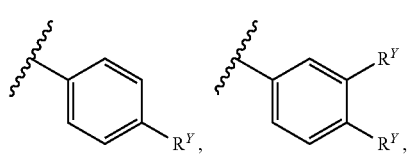
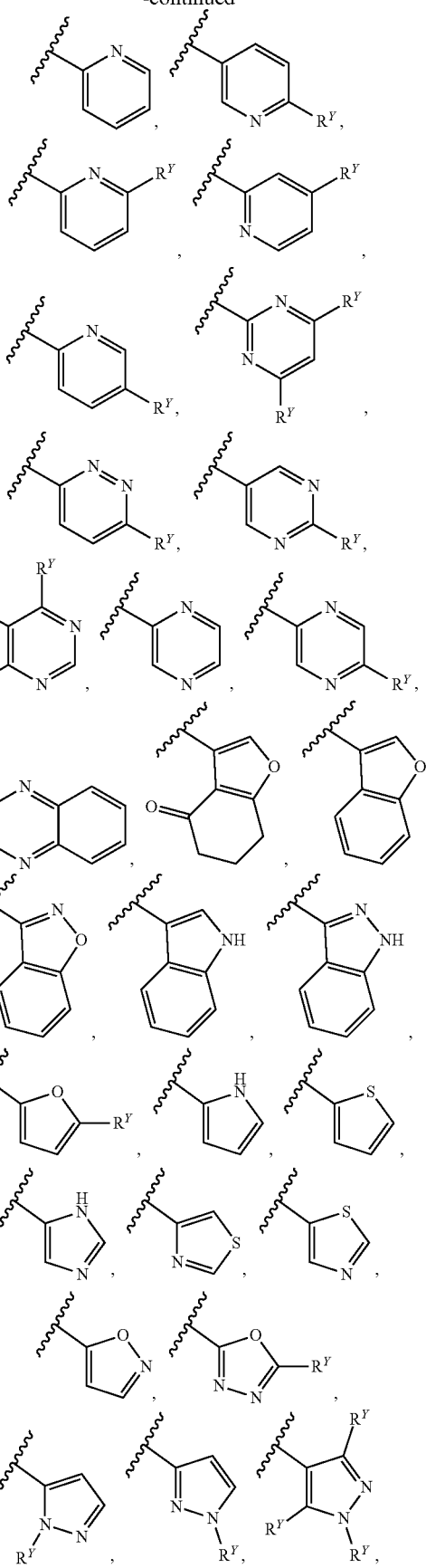

-continued

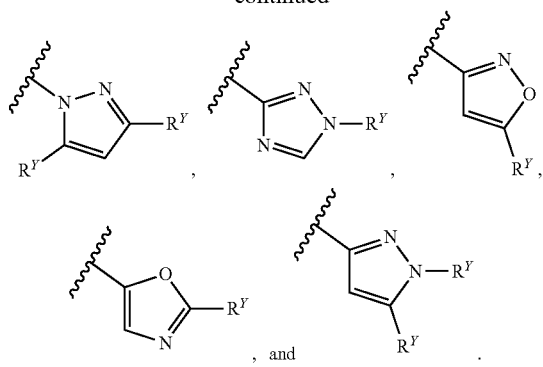

In some embodiments, each of A and W is selected from:

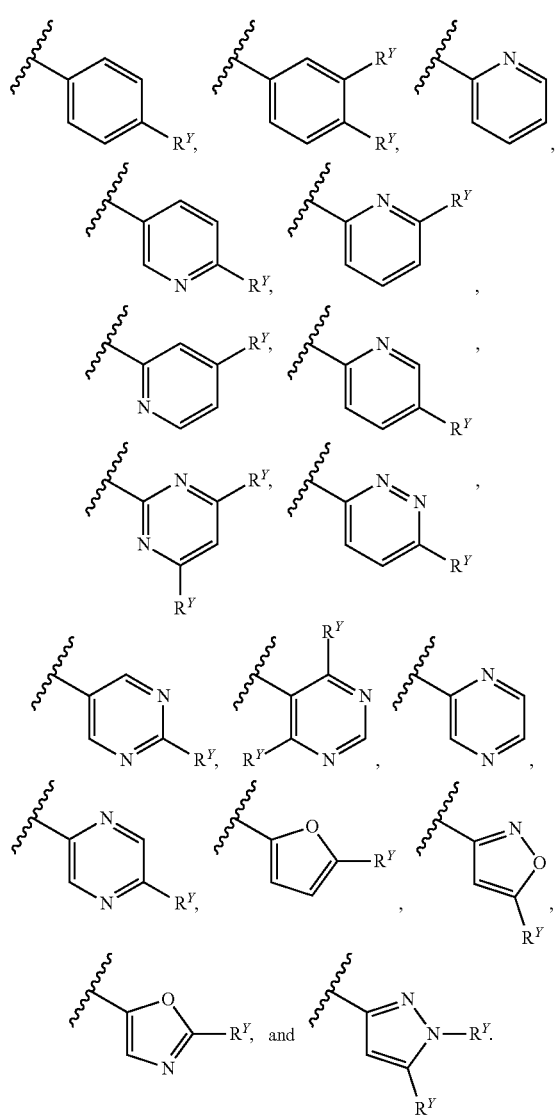

In some embodiments, A is phenyl or pyridyl and W is phenyl or 5-6-membered heteroaryl, each of A and W is optionally substituted with 1-5 $R^Y$, and each $R^Y$ is independently $C_1$-$C_6$ alkyl, hydroxy-$C_1$-$C_6$ alkyl, halo-$C_1$-$C_6$ alkyl, halo-$C_1$-$C_6$ alkoxy, siloxy-$C_1$-$C_6$ alkoxy, hydroxy $C_1$-$C_6$ alkoxy, halo, —$OR^A$, —C(O)OH, —C(O)$OR^D$, or $G^1$. In some embodiments, A is phenyl or pyridyl and W is phenyl, pyridyl, pyrimidinyl, pyrazinyl, pyridazinyl, oxazolyl, isoxazolyl, furanyl, or pyrazolyl, wherein A and W are each optionally substituted with 1-5 $R^Y$.

In some embodiments, A is

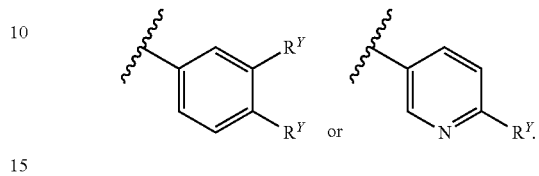

In some embodiments, A is

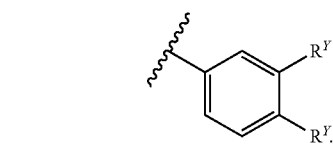

In some embodiments, W is selected from:

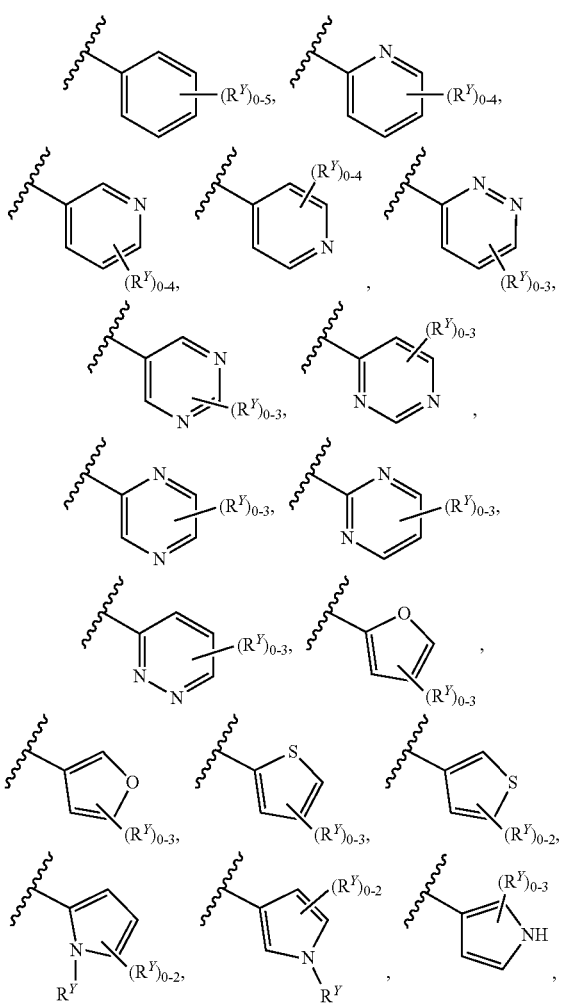

-continued

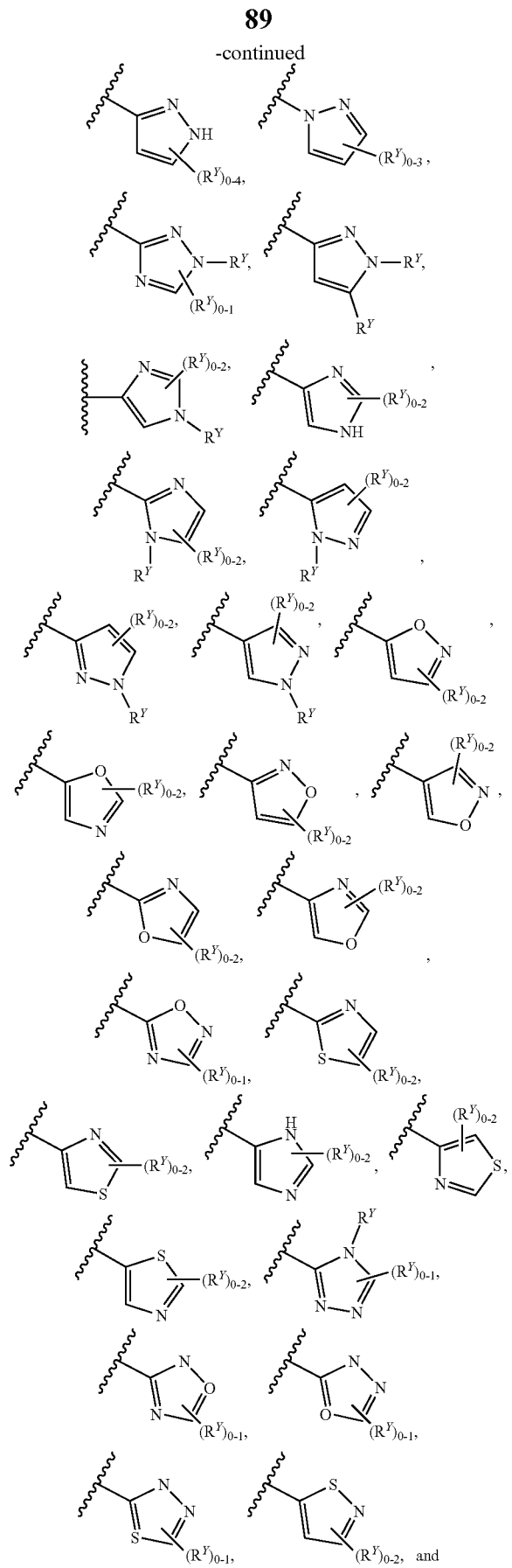

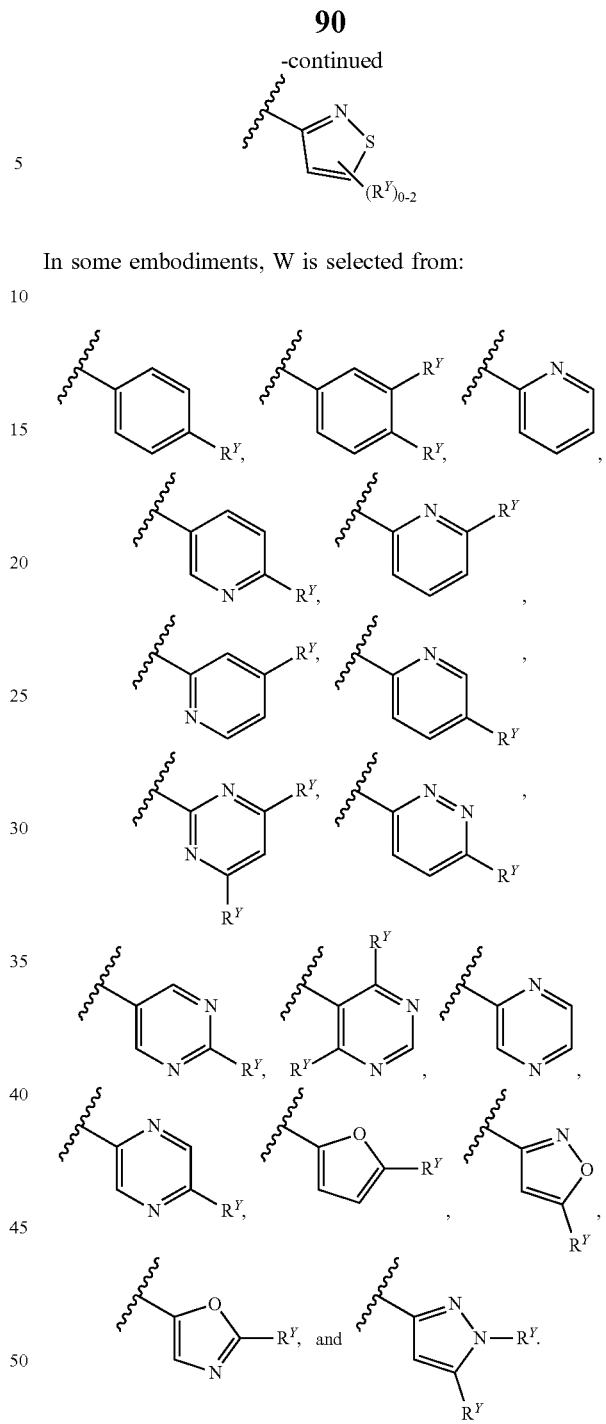

In some embodiments, W is selected from:

In some embodiments, each $R^Y$ is independently selected from chloro, fluoro, oxo, CN, OH, $CF_3$, $CHF_2$, $CH_3$, $CH_2CH_3$, $CH_2CH_2CH_2CH_3$, $CH=CHCH_2OH$, $CH_2CH_2OH$, $CH_2NH_2$, $NHCH_3$, $CH_2NHC(O)CH_3$, $N(CH_2CH_3)_2$, $CH2N(CH_3)_2$, $C(CH_3)_2OH$, $CH(CH_3)_2$, $CH_2CH_2CH_3$, $C(CH_3)_3$, $CH_2CH(CH_3)_2$, $CH_2CH_2OH$, $CH(OH)CH_3$, $CH_2CH_2CH_2OCH_3$, $CH_2CF_3$, $CH_2C(CH_3)_2OH$, $CH_2SCH_3$, $CH_2CN$, $CH_2CH_2CN$, $CH_2CH_2C(CH_3)_2OH$, $CH_2NHC(O)CH_3$, $OCH_3$, $OCH_2CH_3$, $OCH_2CH_3$, $OCH_2CH_2OCH_3$, $OCH(CH_3)_2$, $OCF_3$, $OCH_2CF_3$, $OCH_2CH_2N(CH_3)_2$, $CH_2OH$, $CH_2OCH_3$, $OCH_2CH_2OH$, $OCHF_2$, $OCF_3$, $OCH_3$, $CH_2OH$, $C(O)OH$, $C(O)CH_3$, $C(O)OCH_3$, $C(O)NH_2$, $C(O)NHCH_2CH_2CH_2OH$, $CH_2CN$, $C(O)$ OCH$_2$CH$_3$, C(O)NHCH$_2$CH$_3$, OCH$_2$CH$_2$OSi(CH$_3$)$_2$C (CH$_3$)$_3$, CH$_2$N(CH$_3$)$_2$, CH$_2$NHC(O)CH$_3$, CH$_2$NHC(O)OC (CH$_3$)$_3$, CH=CHCH$_2$OCH$_3$, CH=CHC(CH$_3$)$_2$OH, N(CH$_3$)$_2$, N(CH$_2$CH$_3$)$_2$, NHCH$_2$CH$_3$, NHC(O)CH$_3$, NHC(O)CH$_2$OCH$_3$, NHS(O)$_2$CH$_3$, SCH$_3$, SCH$_2$CH$_3$, SO$_2$NH$_2$, S(O)CH$_3$, S(O)$_2$CH$_3$, G$^1$, C(O)NHG$^1$, N(CH$_3$)CH$_2$G$^1$, NHG$^1$, OG$^1$, CH$_2$G$^1$, CH$_2$CH$_2$G$^1$, CH$_2$NHC(O)G$^1$, or CH=CHG$^1$. In some embodiments, each R$^Y$ is independently chloro, fluoro, CN, OH, CF$_3$, CHF$_2$, CH$_3$, CH$_2$CH$_3$, CH$_2$CH$_2$CH$_2$CH$_3$, CH=CHCH$_2$OH, CH$_2$CH$_2$OH, CH$_2$NH$_2$, NHCH$_3$, CH$_2$NHC(O)CH$_3$, N(CH$_2$CH$_3$)$_2$, CH$_2$N (CH$_3$)$_2$, C(CH$_3$)$_2$OH, OCH$_3$, CH$_2$OH, CH$_2$OCH$_3$, OCH$_2$CH$_2$OH, OCHF$_2$, OCF$_3$, OCH$_3$, CH$_2$OH, C(O)OH, CH$_2$CN, C(O)OCH$_2$CH$_3$, C(O)NHCH$_2$CH$_3$, OCH$_2$CH$_2$OSi (CH$_3$)$_2$C(CH$_3$)$_3$, or G$^1$.

In some embodiments, each of A and W is independently substituted with 2 R$^Y$ on adjacent atoms, and the 2 R$^Y$, together with the atoms to which they are attached, form a 3-7-membered fused heterocyclyl ring or 5-6-membered heteroaryl ring, each optionally substituted with 1-5 R$^X$. In some embodiments, the 2 R$^Y$ together with the atoms to which they are attached form a dioxolanyl, hexahydropyrimidinyl, pyridyl, or pyrimidinyl ring, each of which is optionally substituted with 1-5 R$^X$. In some embodiments, each R$^X$ is independently C$_1$-C$_6$ alkyl, fluoro, chloro, oxo, OCH$_3$, C(O)OCH$_3$, or G$^2$.

In some embodiments, G$^1$ or G$^2$ is pyrrolidinyl, azetidinyl, cyclopropyl, cyclohexyl, cyclohexenyl, tetrahydropyranyl, dihydropyranyl, tetrahydropyridinyl, piperidinyl, phenyl, pyridyl, pyrimidinyl, pyridazinyl, pyrazolyl, morpholino, furanyl, triazolyl, oxetanyl, or pyrazinyl, each of which is optionally substituted with 1-5 R$^Z$. In some embodiments, G$^1$ is pyrrolidinyl, cyclopropyl, cyclohexyl, cyclohexenyl, tetrahydropyranyl, dihydropyranyl, tetrahydropyridinyl, piperidinyl, phenyl, pyridyl, pyrimidinyl, pyridazinyl, or pyrazinyl, each of which is optionally substituted with 1-5 R$^Z$.

In some embodiments, G$^1$ is pyrrolidinyl, azetidinyl, cyclopropyl, cyclohexyl, cyclohexenyl, tetrahydropyranyl, dihydropyranyl, tetrahydropyridinyl, piperidinyl, phenyl, pyridyl, pyrimidinyl, pyridazinyl, pyrazolyl, morpholino, furanyl, triazolyl, oxetanyl, or pyrazinyl, each of which is optionally substituted with 1-5 R$^Z$. In some embodiments, G$^1$ is pyrrolidinyl, cyclopropyl, cyclohexyl, cyclohexenyl, tetrahydropyranyl, dihydropyranyl, tetrahydropyridinyl, piperidinyl, phenyl, pyridyl, pyrimidinyl, pyridazinyl, or pyrazinyl, each of which is optionally substituted with 1-5 R$^Z$.

In some embodiments, each R$^Z$ is independently OR$^A$, C(O)R$^D$, halo, halo C$_1$-C$_6$ alkyl, C$_1$-C$_6$ alkyl, C(O)R$^D$, or C(O)OR$^D$ (e.g., fluoro, chloro, OH, OCH$_3$, oxo, CH$_3$, CHF$_2$, CF$_3$, C(O)CH$_3$ or C(O)OC(CH$_3$)$_3$). In some embodiments, each R$^Z$ is independently OR$^A$, C(O)R$^D$, halo, halo C$_1$-C$_6$ alkyl, C$_1$-C$_6$ alkyl, or C(O)OR$^D$ (e.g., OH, C(O)CH$_3$ or C(O)OC(CH$_3$)$_3$).

In some embodiments, the compound of Formula (I) is a compound of Formula (I-h):

Formula (I-h)

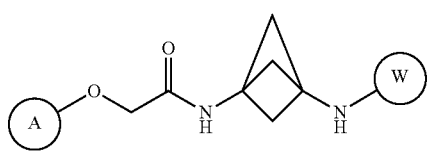

or a pharmaceutically acceptable salt, solvate, hydrate, tautomer, or stereoisomer thereof, wherein each of A and W is defined as for Formula (I).

In some embodiments, A is phenyl and W is independently phenyl or 5-6-membered heteroaryl. In some embodiments, each A and W is independently phenyl. In some embodiments, A is phenyl and W is 5-6-membered heteroaryl.

In some embodiments, W is a monocyclic 5-6-membered heteroaryl. In some embodiments, 2 R$^Y$ groups on adjacent atoms of W, together with the atoms to which they are attached form a 3-7-membered fused cycloalkyl or heterocyclyl optionally substituted with 1-5 R$^X$ forming a bicyclic heteroaryl. In some embodiments, W is a 10-membered heteroaryl, a 9-membered heteroaryl, a 6-membered heteroaryl, or a 5-membered heteroaryl. In some embodiments, W is a heteroaryl containing nitrogen, oxygen or sulfur as allowed by valence.

In some embodiments, each A and W is independently a phenyl or 5-6-membered heteroaryl optionally substituted with 1-5 R$^Y$, and each R$^Y$ is independently C$_1$-C$_6$ alkyl, hydroxy-C$_1$-C$_6$ alkyl, halo-C$_1$-C$_6$ alkyl, halo-C$_1$-C$_6$ alkoxy, C$_1$-C$_6$ alkoxy-C$_1$-C$_6$ alkyl, silyloxy-C$_1$-C$_6$ alkyl, halo, —OR$^A$, cycloalkyl, heterocyclyl, —C(O)OH, —C(O)OR$^D$, or G$^1$. In some embodiments, each of A and W is independently phenyl, pyridyl, pyrimidinyl, pyrazinyl, pyridazinyl, oxazolyl, isoxazolyl, furanyl, or pyrazolyl, each of which is optionally substituted with 1-5 R$^Y$ groups.

In some embodiments, each A and W is selected from:

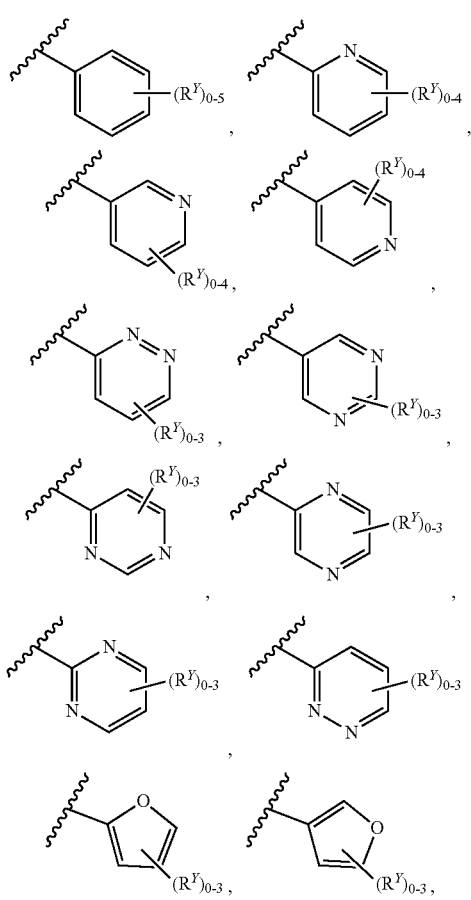

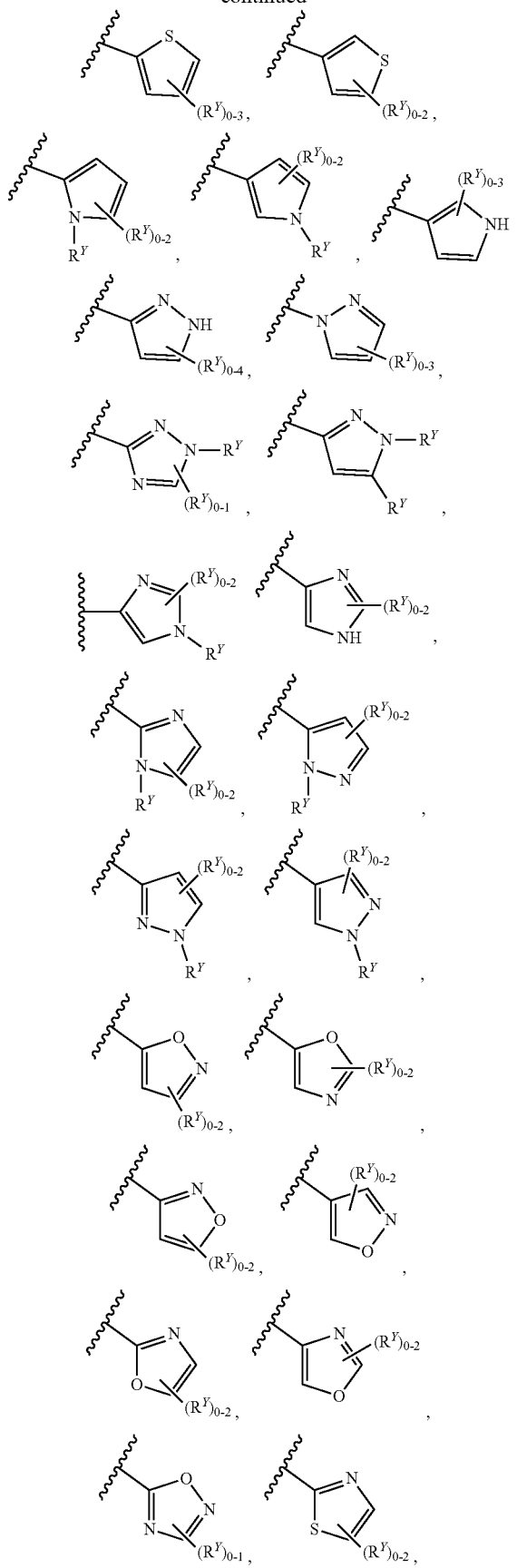
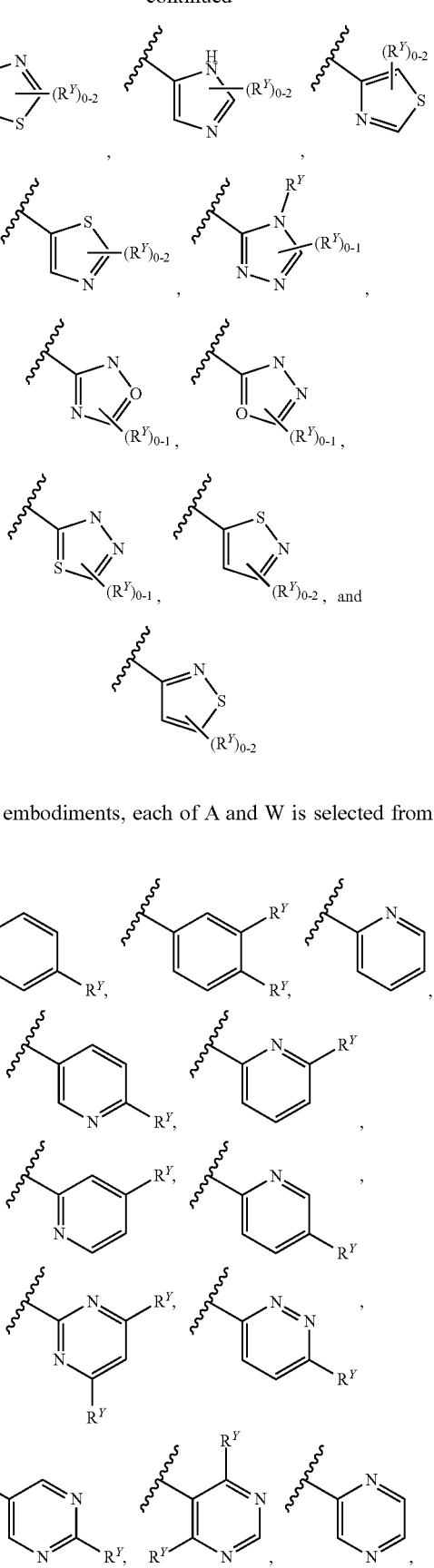
In some embodiments, each of A and W is selected from:

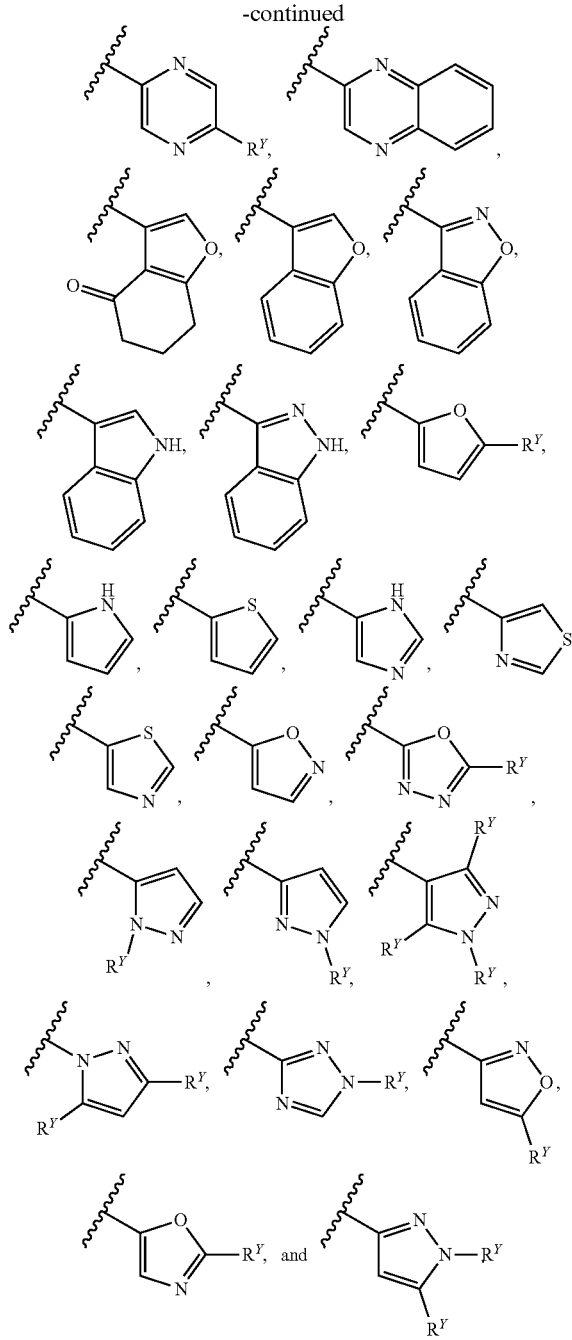

In some embodiments, each of A and W is selected from:

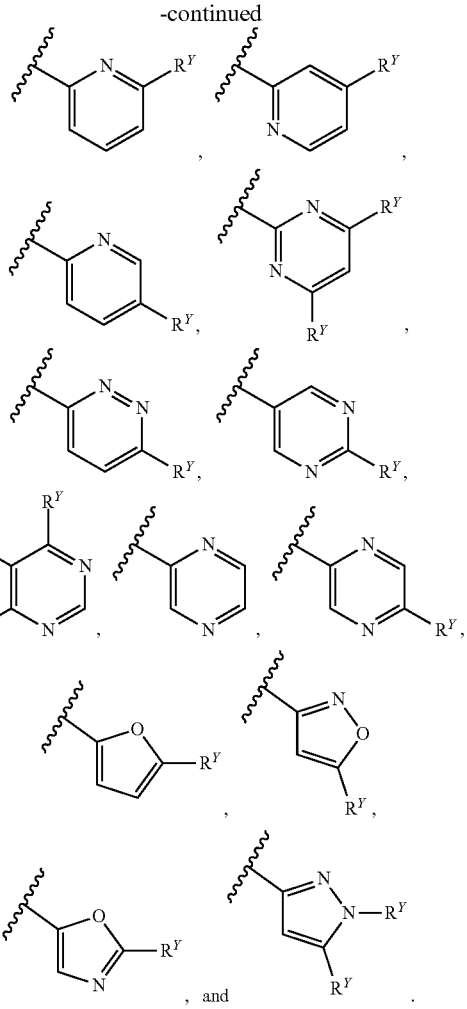

In some embodiments, A is phenyl or pyridyl and W is phenyl or 5-6-membered heteroaryl, each of A and W is optionally substituted with 1-5 $R^Y$, and each $R^Y$ is independently $C_1$-$C_6$ alkyl, hydroxy-$C_1$-$C_6$ alkyl, halo-$C_1$-$C_6$ alkyl, halo-$C_1$-$C_6$ alkoxy, siloxy-$C_1$-$C_6$ alkoxy, hydroxy $C_1$-$C_6$ alkoxy, halo, —$OR^A$, —C(O)OH, —C(O)$OR^D$, or $G^1$. In some embodiments, A is phenyl or pyridyl and W is phenyl, pyridyl, pyrimidinyl, pyrazinyl, pyridazinyl, oxazolyl, isoxazolyl, furanyl, or pyrazolyl, wherein A and W are each optionally substitute with 1-5 $R^Y$.

In some embodiments, A is

In some embodiments, A is

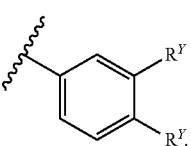

In some embodiments, W is selected from:
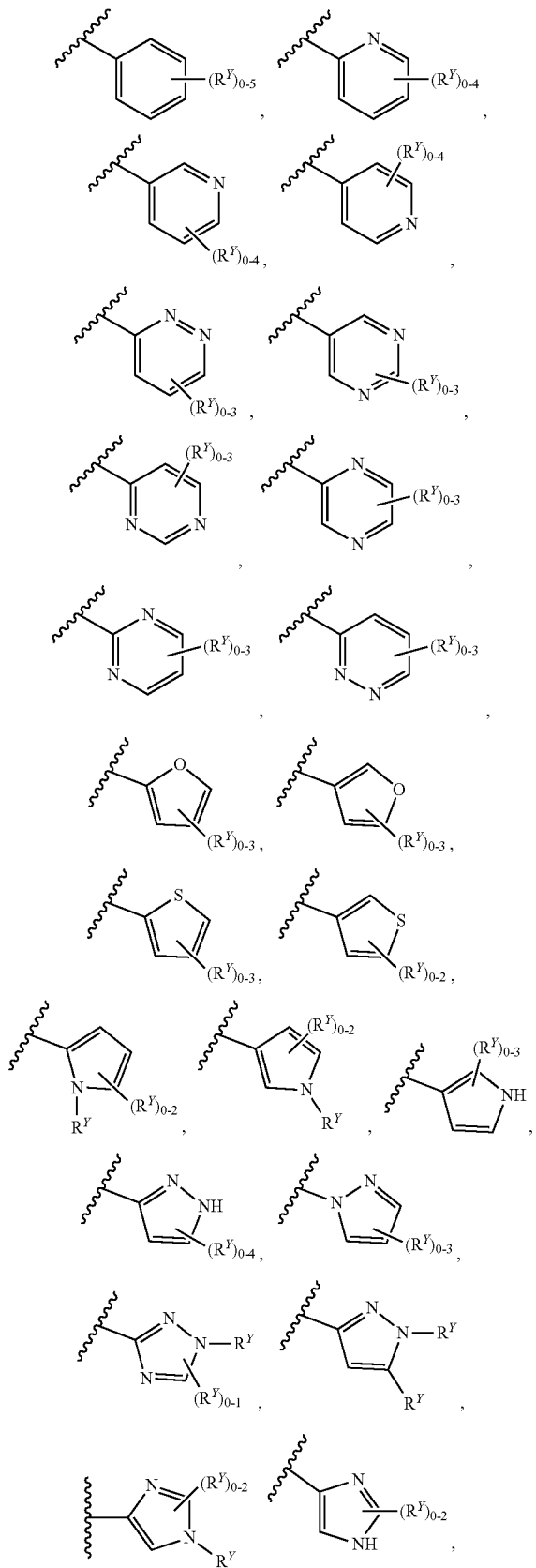
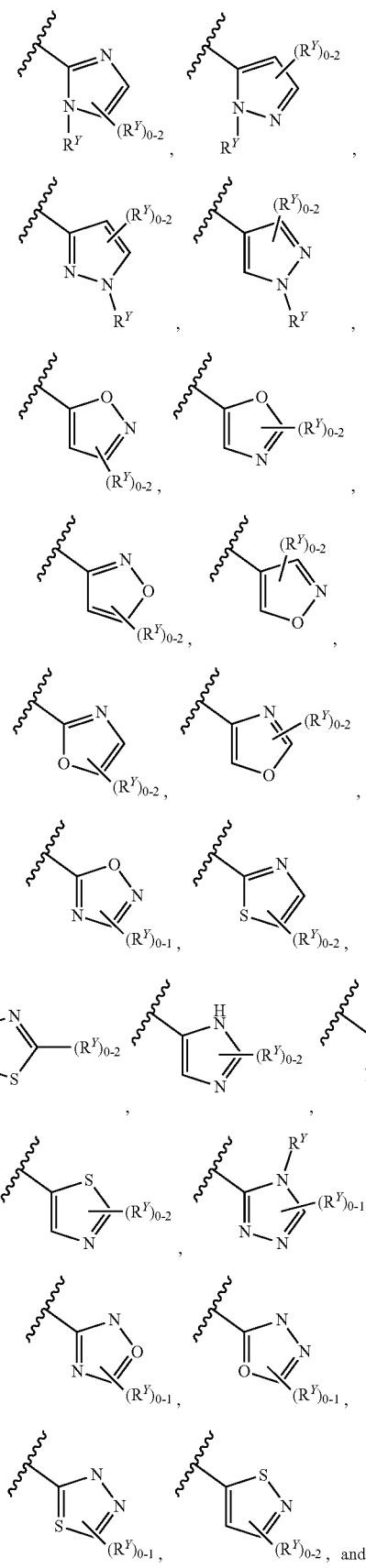

-continued

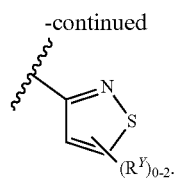

In some embodiments, W is selected from:

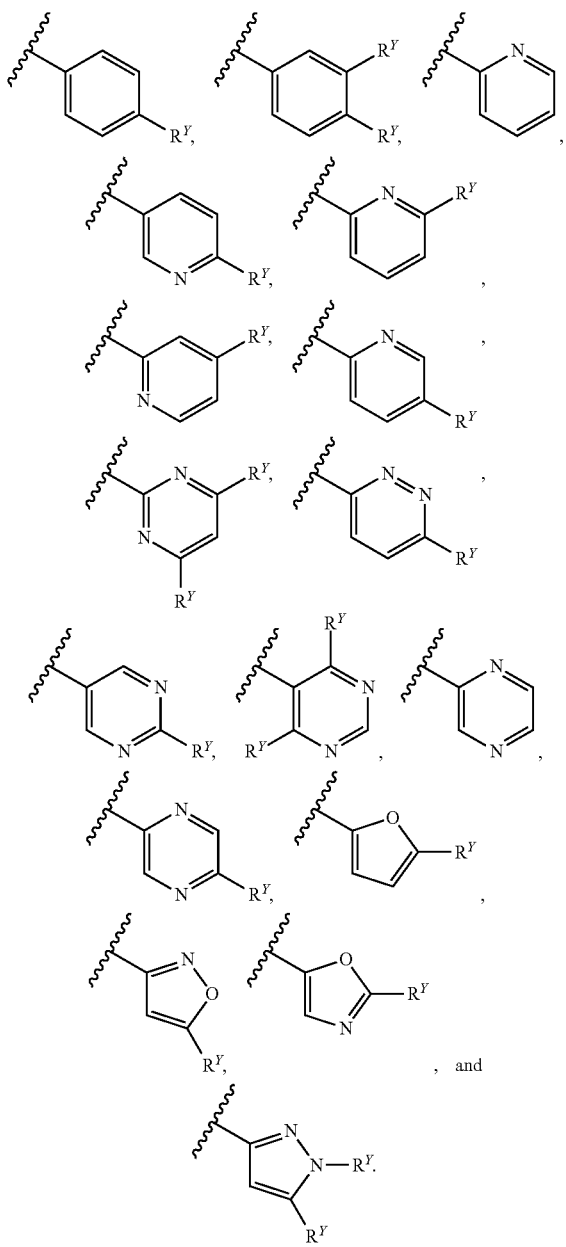

In some embodiments, each $R^Y$ is independently selected from chloro, fluoro, oxo, CN, OH, $CF_3$, $CHF_2$, $CH_3$, $CH_2CH_3$, $CH_2CH_2CH_2CH_3$, $CH=CHCH_2OH$, $CH_2CH_2OH$, $CH_2NH_2$, $NHCH_3$, $CH_2NHC(O)CH_3$, $N(CH_2CH_3)_2$, $CH2N(CH_3)_2$, $C(CH_3)_2OH$, $CH(CH_3)_2$, $CH_2CH_2CH_3$, $C(CH_3)_3$, $CH_2CH(CH_3)_2$, $CH_2CH_2OH$, $CH(OH)CH_3$, $CH_2CH_2CH_2OCH_3$, $CH_2CF_3$, $CH_2C(CH_3)_2OH$, $CH_2SCH_3$, $CH_2CN$, $CH_2CH_2CN$, $CH_2CH_2C(CH_3)_2OH$, $CH_2NHC(O)CH_3$, $OCH_3$, $OCH_2CH_3$, $OCH_2CH_2CH_3$, $OCH_2CH_2OCH_3$, $OCH(CH_3)_2$, $OCF_3$, $OCH_2CF_3$, $OCH_2CH_2N(CH_3)_2$, $CH_2OH$, $CH_2OCH_3$, $OCH_2CH_2OH$, $OCHF_2$, $OCF_3$, $OCH_3$, $CH_2OH$, $C(O)OH$, $C(O)CH_3$, $C(O)OCH_3$, $C(O)NH_2$, $C(O)NHCH_2CH_2CH_2OH$, $CH_2CN$, $C(O)OCH_2CH_3$, $C(O)NHCH_2CH_3$, $OCH_2CH_2OSi(CH_3)_2C(CH_3)_3$, $CH_2N(CH_3)_2$, $CH_2NHC(O)CH_3$, $CH_2NHC(O)OC(CH_3)_3$, $CH=CHCH_2OCH_3$, $CH=CHC(CH_3)_2OH$, $N(CH_3)_2$, $N(CH_2CH_3)_2$, $NHCH_2CH_3$, $NHC(O)CH_3$, $NHC(O)CH_2OCH_3$, $NHS(O)_2CH_3$, $SCH_3$, $SCH_2CH_3$, $SO_2NH_2$, $S(O)CH_3$, $S(O)_2CH_3$, $G^1$, $C(O)NHG^1$, $N(CH_3)CH_2G^1$, $NHG^1$, $OG^1$, $CH_2G^1$, $CH_2CH_2G^1$, $CH_2NHC(O)G^1$, or $CH=CHG^1$.

In some embodiments, each $R^Y$ is independently chloro, fluoro, CN, OH, $CF_3$, $CHF_2$, $CH_3$, $CH_2CH_3$, $CH_2CH_2CH_2CH_3$, $CH=CHCH_2OH$, $CH_2CH_2OH$, $CH_2NH_2$, $NHCH_3$, $CH_2NHC(O)CH_3$, $N(CH_2CH_3)_2$, $CH_2N(CH_3)_2$, $C(CH_3)_2OH$, $OCH_3$, $CH_2OH$, $CH_2OCH_3$, $OCH_2CH_2OH$, $OCHF_2$, $OCF_3$, $OCH_3$, $CH_2OH$, $C(O)OH$, $CH_2CN$, $C(O)OCH_2CH_3$, $C(O)NHCH_2CH_3$, $OCH_2CH_2OSi(CH_3)_2C(CH_3)_3$, or $G^1$.

In some embodiments, each of A and W is independently substituted with 2 $R^Y$ on adjacent atoms, and the 2 $R^Y$, together with the atoms to which they are attached, form a 3-7-membered fused heterocyclyl ring or 5-6-membered heteroaryl ring, each optionally substituted with 1-5 $R^X$. In some embodiments, the 2 $R^Y$ together with the atoms to which they are attached form a dioxolanyl, hexahydropyrimidinyl, pyridyl, or pyrimidinyl ring, each of which is optionally substituted with 1-5 $R^X$. In some embodiments, each $R^X$ is independently $C_1$-$C_6$ alkyl, fluoro, chloro, oxo, $OCH_3$, $C(O)OCH_3$, or $G^2$.

In some embodiments, $G^1$ or $G^2$ is pyrrolidinyl, azetidinyl, cyclopropyl, cyclohexyl, cyclohexenyl, tetrahydropyranyl, dihydropyranyl, tetrahydropyridinyl, piperidinyl, phenyl, pyridyl, pyrimidinyl, pyridazinyl, pyrazolyl, morphilino, furanyl, triazolyl, oxetanyl, or pyrazinyl, each of which is optionally substituted with 1-5 $R^Z$. In some embodiments, $G^1$ is pyrrolidinyl, cyclopropyl, cyclohexyl, cyclohexenyl, tetrahydropyranyl, dihydropyranyl, tetrahydropyridinyl, piperidinyl, phenyl, pyridyl, pyrimidinyl, pyridazinyl, or pyrazinyl, each of which is optionally substituted with 1-5 $R^Z$.

In some embodiments, $G^1$ is pyrrolidinyl, azetidinyl, cyclopropyl, cyclohexyl, cyclohexenyl, tetrahydropyranyl, dihydropyranyl, tetrahydropyridinyl, piperidinyl, phenyl, pyridyl, pyrimidinyl, pyridazinyl, pyrazolyl, morphilino, furanyl, triazolyl, oxetanyl, or pyrazinyl, each of which is optionally substituted with 1-5 $R^Z$. In some embodiments, $G^1$ is pyrrolidinyl, cyclopropyl, cyclohexyl, cyclohexenyl, tetrahydropyranyl, dihydropyranyl, tetrahydropyridinyl, piperidinyl, phenyl, pyridyl, pyrimidinyl, pyridazinyl, or pyrazinyl, each of which is optionally substituted with 1-5 $R^Z$.

In some embodiments, each $R^Z$ is independently $OR^A$, $C(O)R^D$, halo, halo $C_1$-$C_6$ alkyl, $C_1$-$C_6$ alkyl, $C(O)R^D$, or $C(O)OR^D$ (e.g., fluoro, chloro, OH, $OCH_3$, oxo, $CH_3$, $CHF_2$, $CF_3$, $C(O)CH_3$ or $C(O)OC(CH_3)_3$). In some embodiments, each $R^Z$ is independently $OR^A$, $C(O)R^D$, halo, halo $C_1$-$C_6$ alkyl, $C_1$-$C_6$ alkyl, or $C(O)OR^D$ (e.g., OH, $C(O)CH_3$ or $C(O)OC(CH_3)_3$).

In some embodiments, the compound of Formula (I) is a compound of Formula (I-i):

Formula (I-i)

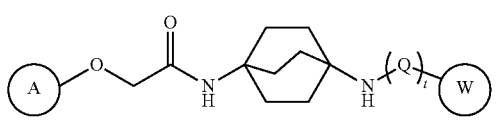

or a pharmaceutically acceptable salt, solvate, hydrate, tautomer, or stereoisomer thereof, wherein each of A, W, Q, and t is defined as for Formula (I).

In some embodiments, Q is C(O). In some embodiments, Q is $S(O)_2$.

In some embodiments, t is 1. In some embodiments, t is 0.

In some embodiments, A is phenyl and W is independently phenyl or 5-6-membered heteroaryl. In some embodiments, each A and W is independently phenyl. In some embodiments, A is phenyl and W is 5-6-membered heteroaryl.

In some embodiments, W is a monocyclic 5-6-membered heteroaryl. In some embodiments, 2 $R^Y$ groups on adjacent atoms of W, together with the atoms to which they are attached form a 3-7-membered fused cycloalkyl or heterocyclyl optionally substituted with 1-5 $R^X$ forming a bicyclic heteroaryl. In some embodiments, W is a 10-membered heteroaryl, a 9-membered heteroaryl, a 6-membered heteroaryl, or a 5-membered heteroaryl. In some embodiments, W is a heteroaryl containing nitrogen, oxygen or sulfur as allowed by valence.

In some embodiments, each A and W is independently a phenyl or 5-6-membered heteroaryl optionally substituted with 1-5 $R^Y$, and each $R^Y$ is independently $C_1$-$C_6$ alkyl, hydroxy-$C_1$-$C_6$ alkyl, halo-$C_1$-$C_6$ alkyl, halo-$C_1$-$C_6$ alkoxy, $C_1$-$C_6$ alkoxy-$C_1$-$C_6$ alkyl, silyloxy-$C_1$-$C_6$ alkyl, halo, —$OR^A$, cycloalkyl, heterocyclyl, —C(O)OH, —C(O)$OR^D$, or $G^1$. In some embodiments, each of A and W is independently phenyl, pyridyl, pyrimidinyl, pyrazinyl, pyridazinyl, oxazolyl, isoxazolyl, furanyl, or pyrazolyl, each of which is optionally substituted with 1-5 $R^Y$ groups.

In some embodiments, each A and W is selected from:

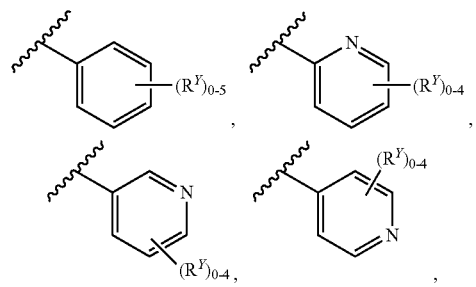

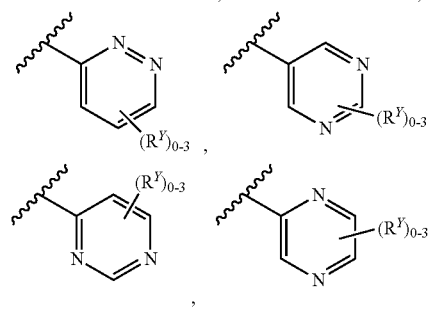

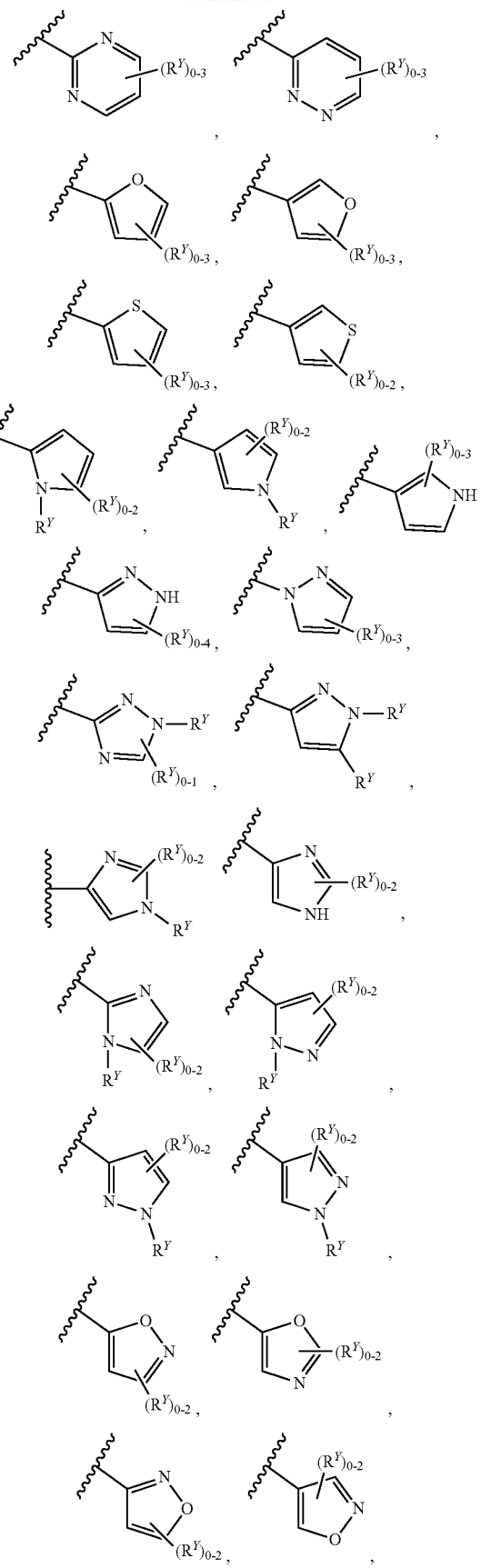

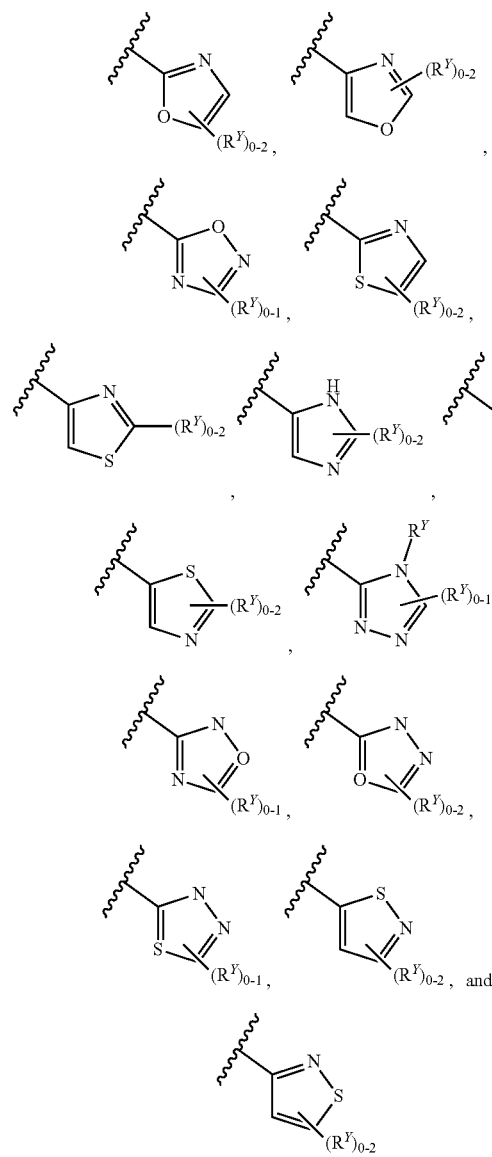
In some embodiments, each of A and W is selected from:
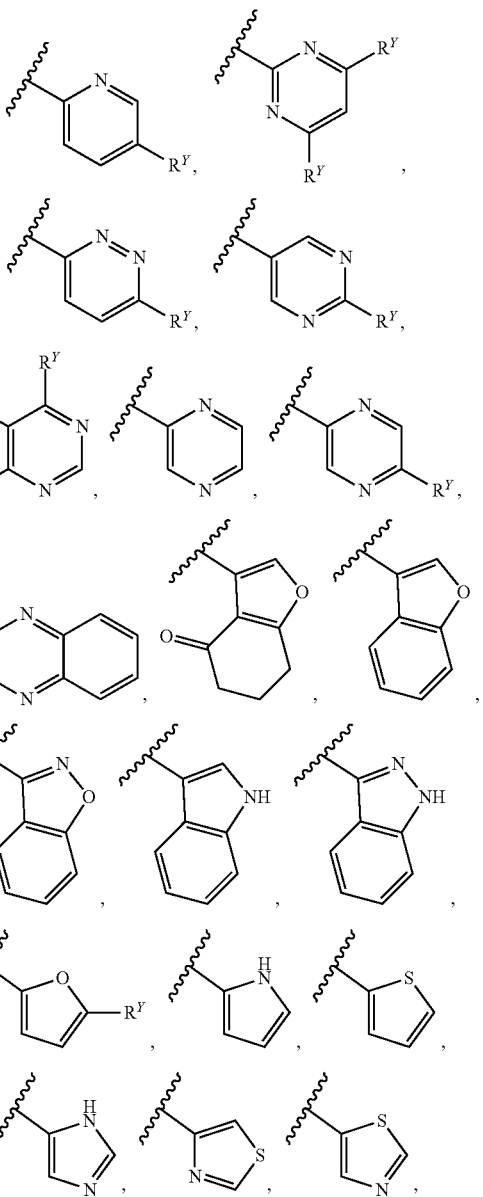
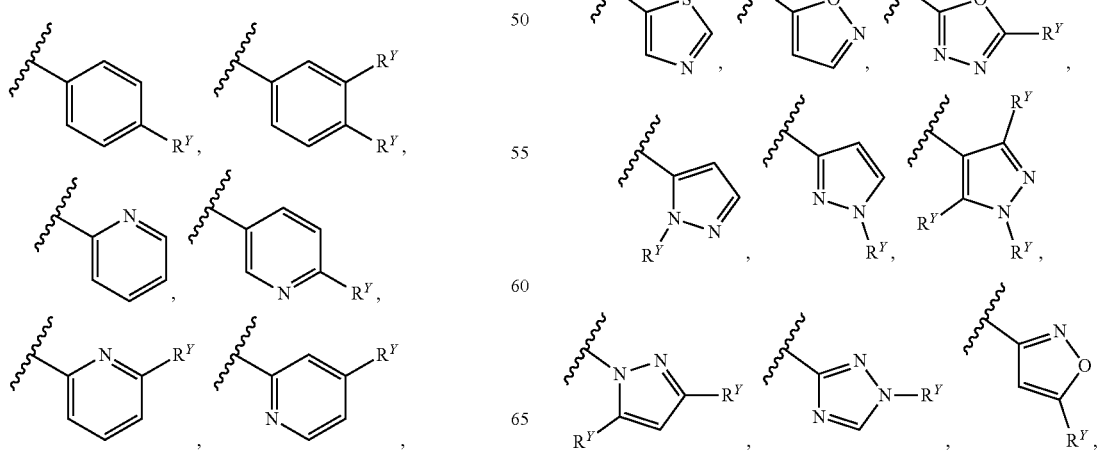

-continued

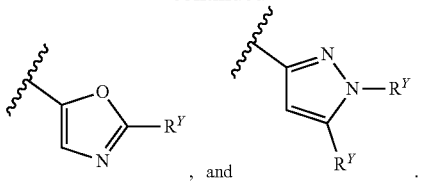

In some embodiments, each of A and W is selected from:

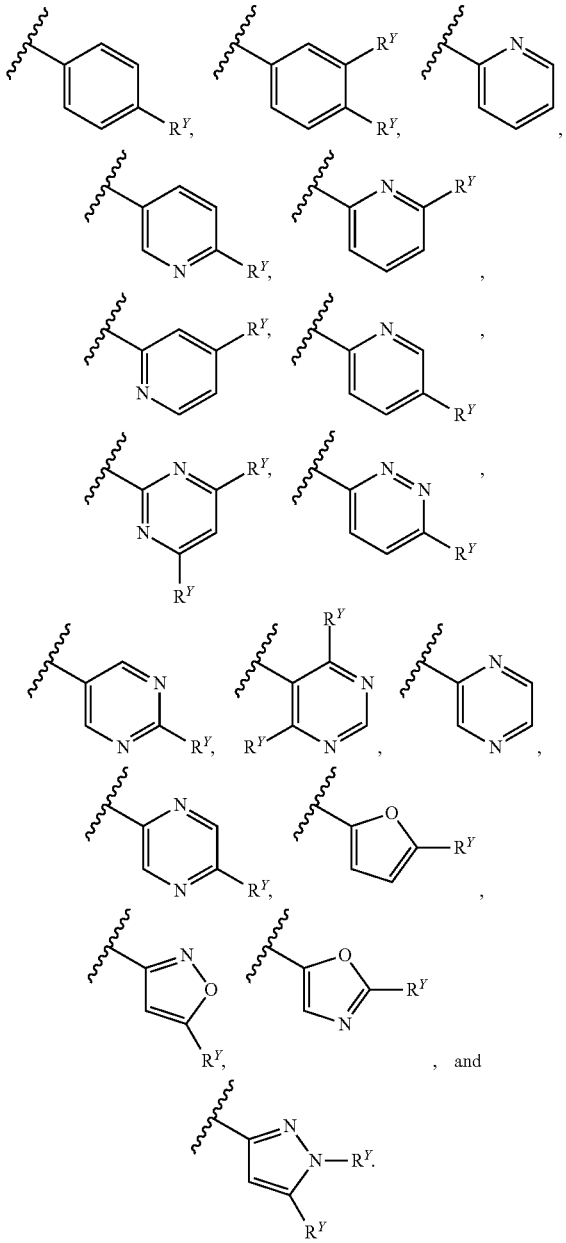

In some embodiments, A is phenyl or pyridyl and W is phenyl or 5-6-membered heteroaryl, each of A and W is optionally substituted with 1-5 $R^Y$, and each $R^Y$ is independently $C_1$-$C_6$ alkyl, hydroxy-$C_1$-$C_6$ alkyl, halo-$C_1$-$C_6$ alkyl, halo-$C_1$-$C_6$ alkoxy, siloxy-$C_1$-$C_6$ alkoxy, hydroxy $C_1$-$C_6$ alkoxy, halo, —$OR^A$, —C(O)OH, —C(O)$OR^D$, or $G^1$. In some embodiments, A is phenyl or pyridyl and W is phenyl, pyridyl, pyrimidinyl, pyrazinyl, pyridazinyl, oxazolyl, isoxazolyl, furanyl, or pyrazolyl, wherein A and W are each optionally substituted with 1-5 $R^Y$.

In some embodiments, A is

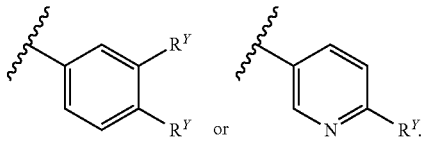

In some embodiments, A is

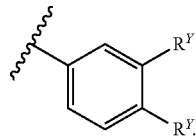

In some embodiments, W is selected from:

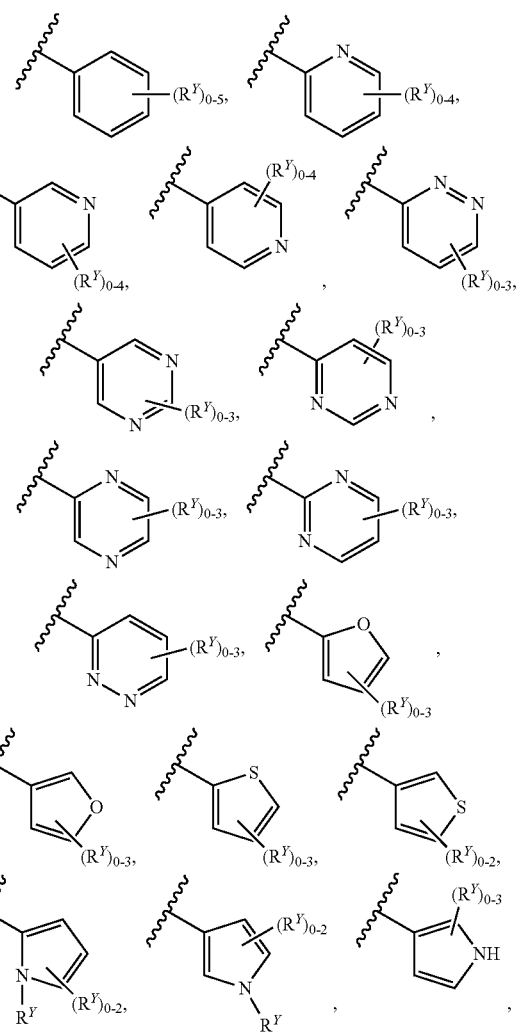

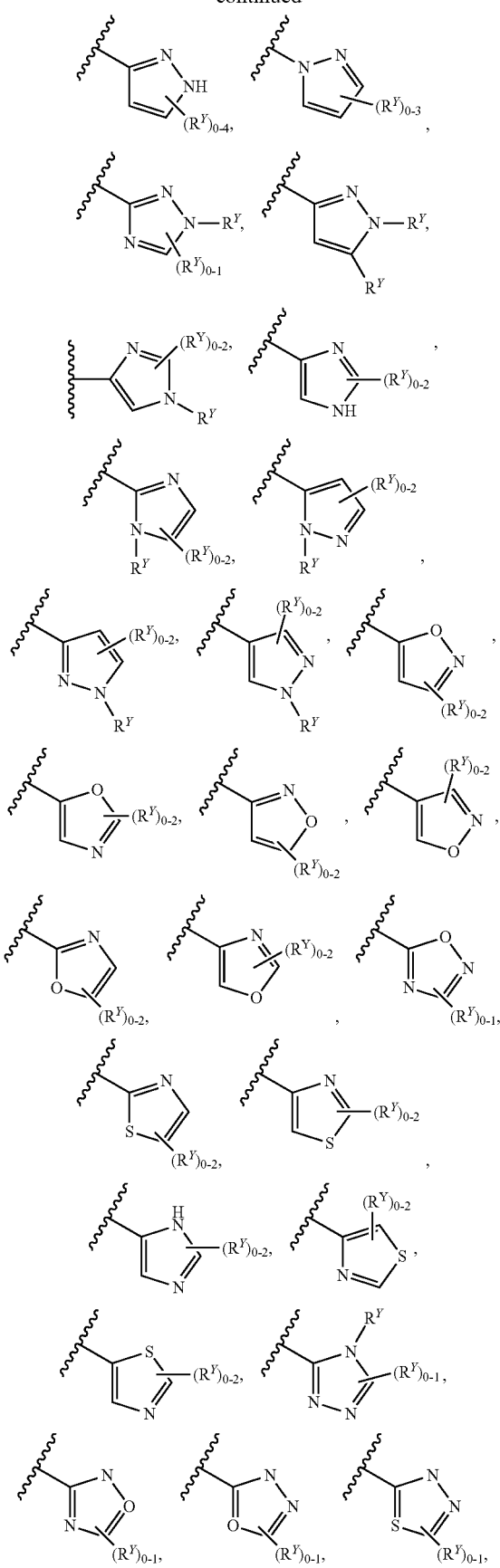
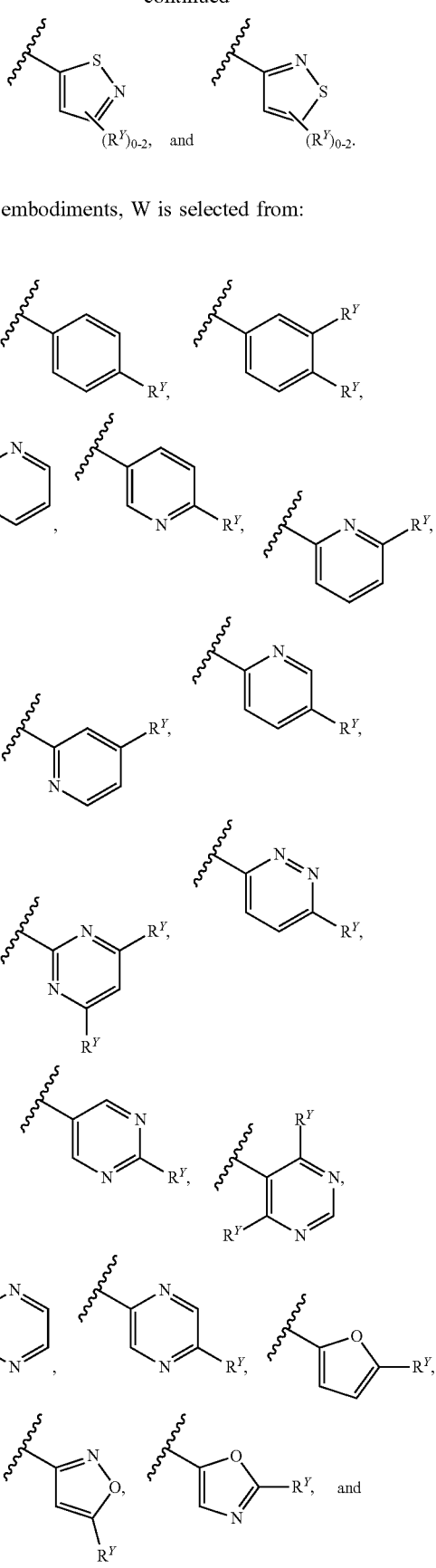
In some embodiments, W is selected from:

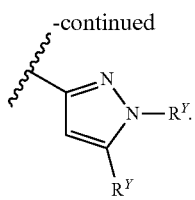

In some embodiments, each $R^Y$ is independently selected from chloro, fluoro, oxo, CN, OH, $CF_3$, $CHF_2$, $CH_3$, $CH_2CH_3$, $CH_2CH_2CH_2CH_3$, $CH=CHCH_2OH$, $CH_2CH_2OH$, $CH_2NH_2$, $NHCH_3$, $CH_2NHC(O)CH_3$, $N(CH_2CH_3)_2$, $CH2N(CH_3)_2$, $C(CH_3)_2OH$, $CH(CH_3)_2$, $CH_2CH_2CH_3$, $C(CH_3)_3$, $CH_2CH(CH_3)_2$, $CH_2CH_2OH$, $CH(OH)CH_3$, $CH_2CH_2CH_2OCH_3$, $CH_2CF_3$, $CH_2C(CH_3)_2OH$, $CH_2SCH_3$, $CH_2CN$, $CH_2CH_2CN$, $CH_2CH_2C(CH_3)_2OH$, $CH_2NHC(O)CH_3$, $OCH_3$, $OCH_2CH_3$, $OCH_2CH_2CH_3$, $OCH_2CH_2OCH_3$, $OCH(CH_3)_2$, $OCF_3$, $OCH_2CF_3$, $OCH_2CH_2N(CH_3)_2$, $CH_2OH$, $CH_2OCH_3$, $OCH_2CH_2OH$, $OCHF_2$, $OCF_3$, $OCH_3$, $CH_2OH$, $C(O)OH$, $C(O)CH_3$, $C(O)OCH_3$, $C(O)NH_2$, $C(O)NHCH_2CH_2OH$, $CH_2CN$, $C(O)OCH_2CH_3$, $C(O)NHCH_2CH_3$, $OCH_2CH_2OSi(CH_3)_2C(CH_3)_3$, $CH_2N(CH_3)_2$, $CH_2NHC(O)CH_3$, $CH_2NHC(O)OC(CH_3)_3$, $CH=CHCH_2OCH_3$, $CH=CHC(CH_3)_2OH$, $N(CH_3)_2$, $N(CH_2CH_3)_2$, $NHCH_2CH_3$, $NHC(O)CH_3$, $NHC(O)CH_2OCH_3$, $NHS(O)_2CH_3$, $SCH_3$, $SCH_2CH_3$, $SO_2NH_2$, $S(O)CH_3$, $S(O)_2CH_3$, $G^1$, $C(O)NHG^1$, $N(CH_3)CH_2G^1$, $NHG^1$, $OG^1$, $CH_2G^1$, $CH_2CH_2G^1$, $CH_2NHC(O)G^1$, or $CH=CHG^1$. In some embodiments, each $R^Y$ is independently chloro, fluoro, CN, OH, $CF_3$, $CHF_2$, $CH_3$, $CH_2CH_3$, $CH_2CH_2CH_2CH_3$, $CH=CHCH_2OH$, $CH_2CH_2OH$, $CH_2NH_2$, $NHCH_3$, $CH_2NHC(O)CH_3$, $N(CH_2CH_3)_2$, $CH2N(CH_3)_2$, $C(CH_3)_2OH$, $OCH_3$, $CH_2OH$, $CH_2OCH_3$, $OCH_2CH_2OH$, $OCHF_2$, $OCF_3$, $OCH_3$, $CH_2OH$, $C(O)OH$, $CH_2CN$, $C(O)OCH_2CH_3$, $C(O)NHCH_2CH_3$, $OCH_2CH_2OSi(CH_3)_2C(CH_3)_3$, or $G^1$.

In some embodiments, each of A and W is independently substituted with 2 $R^Y$ on adjacent atoms, and the 2 $R^Y$, together with the atoms to which they are attached, form a 3-7-membered fused heterocyclyl ring or 5-6-membered heteroaryl ring, each optionally substituted with 1-5 $R^X$. In some embodiments, the 2 $R^Y$ together with the atoms to which they are attached form a dioxolanyl, hexahydropyrimidinyl, pyridyl, or pyrimidinyl ring, each of which is optionally substituted with 1-5 $R^X$. In some embodiments, each $R^X$ is independently $C_1$-$C_6$ alkyl, fluoro, chloro, oxo, $OCH_3$, $C(O)OCH_3$, or $G^2$.

In some embodiments, $G^1$ or $G^2$ is pyrrolidinyl, azetidinyl, cyclopropyl, cyclohexyl, cyclohexenyl, tetrahydropyranyl, dihydropyranyl, tetrahydropyridinyl, piperidinyl, phenyl, pyridyl, pyrimidinyl, pyridazinyl, pyrazolyl, morphilino, furanyl, triazolyl, oxetanyl, or pyrazinyl, each of which is optionally substituted with 1-5 $R^Z$. In some embodiments, $G^1$ is pyrrolidinyl, cyclopropyl, cyclohexyl, cyclohexenyl, tetrahydropyranyl, dihydropyranyl, tetrahydropyridinyl, piperidinyl, phenyl, pyridyl, pyrimidinyl, pyridazinyl, or pyrazinyl, each of which is optionally substituted with 1-5 $R^Z$.

In some embodiments, $G^1$ is pyrrolidinyl, azetidinyl, cyclopropyl, cyclohexyl, cyclohexenyl, tetrahydropyranyl, dihydropyranyl, tetrahydropyridinyl, piperidinyl, phenyl, pyridyl, pyrimidinyl, pyridazinyl, pyrazolyl, morpholino, furanyl, triazolyl, oxetanyl, or pyrazinyl, each of which is optionally substituted with 1-5 $R^Z$. In some embodiments, $G^1$ is pyrrolidinyl, cyclopropyl, cyclohexyl, cyclohexenyl, tetrahydropyranyl, dihydropyranyl, tetrahydropyridinyl, piperidinyl, phenyl, pyridyl, pyrimidinyl, pyridazinyl, or pyrazinyl, each of which is optionally substituted with 1-5 $R^Z$.

In some embodiments, each $R^Z$ is independently $OR^A$, $C(O)R^D$, halo, halo $C_1$-$C_6$ alkyl, $C_1$-$C_6$ alkyl, $C(O)R^D$, or $C(O)OR^D$ (e.g., fluoro, chloro, OH, $OCH_3$, oxo, $CH_3$, $CHF_2$, $CF_3$, $C(O)CH_3$ or $C(O)OC(CH_3)_3$). In some embodiments, each $R^Z$ is independently $OR^A$, $C(O)R^D$, halo, halo $C_1$-$C_6$ alkyl, $C_1$-$C_6$ alkyl, or $C(O)OR^D$ (e.g., OH, $C(O)CH_3$ or $C(O)OC(CH_3)_3$).

In some embodiments, the compound of Formula (I) is a compound of Formula (I-j):

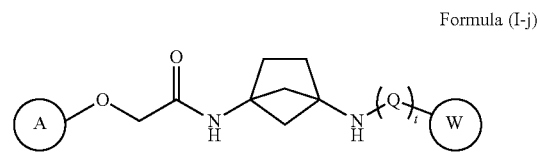

Formula (I-j)

or a pharmaceutically acceptable salt, solvate, hydrate, tautomer, or stereoisomer thereof, wherein each of A, W, Q, and t is defined as for Formula (I).

In some embodiments, Q is C(O). In some embodiments, Q is $S(O)_2$.

In some embodiments, t is 1. In some embodiments, t is 0.

In some embodiments, A is phenyl and W is independently phenyl or 5-6-membered heteroaryl. In some embodiments, each A and W is independently phenyl. In some embodiments, A is phenyl and W is 5-6-membered heteroaryl.

In some embodiments, W is a monocyclic 5-6-membered heteroaryl. In some embodiments, 2 $R^Y$ groups on adjacent atoms of W, together with the atoms to which they are attached form a 3-7-membered fused cycloalkyl or heterocyclyl optionally substituted with 1-5 $R^X$ forming a bicyclic heteroaryl. In some embodiments, W is a 10-membered heteroaryl, a 9-membered heteroaryl, a 6-membered heteroaryl, or a 5-membered heteroaryl. In some embodiments, W is a heteroaryl containing nitrogen, oxygen or sulfur as allowed by valence.

In some embodiments, each A and W is independently a phenyl or 5-6-membered heteroaryl optionally substituted with 1-5 $R^Y$, and each $R^Y$ is independently $C_1$-$C_6$ alkyl, hydroxy-$C_1$-$C_6$ alkyl, halo-$C_1$-$C_6$ alkyl, halo-$C_1$-$C_6$ alkoxy, $C_1$-$C_6$ alkoxy-$C_1$-$C_6$ alkyl, silyloxy-$C_1$-$C_6$ alkyl, halo, $-OR^A$, cycloalkyl, heterocyclyl, $-C(O)OH$, $-C(O)OR^D$, or $G^1$. In some embodiments, each of A and W is independently phenyl, pyridyl, pyrimidinyl, pyrazinyl, pyridazinyl, oxazolyl, isoxazolyl, furanyl, or pyrazolyl, each of which is optionally substituted with 1-5 $R^Y$ groups.

In some embodiments, each A and W is selected from:

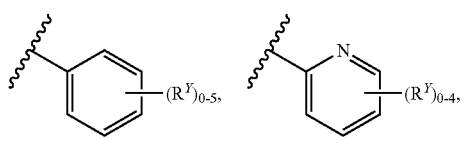

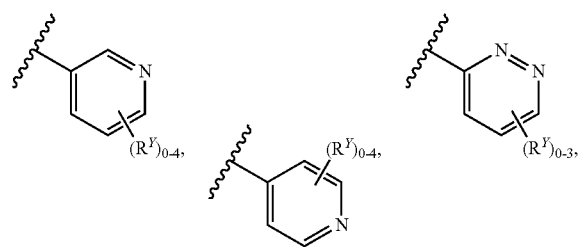
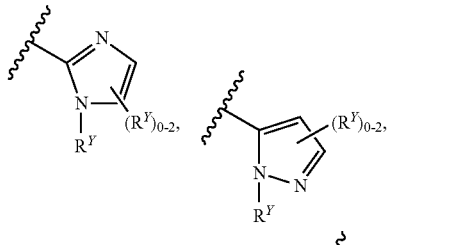
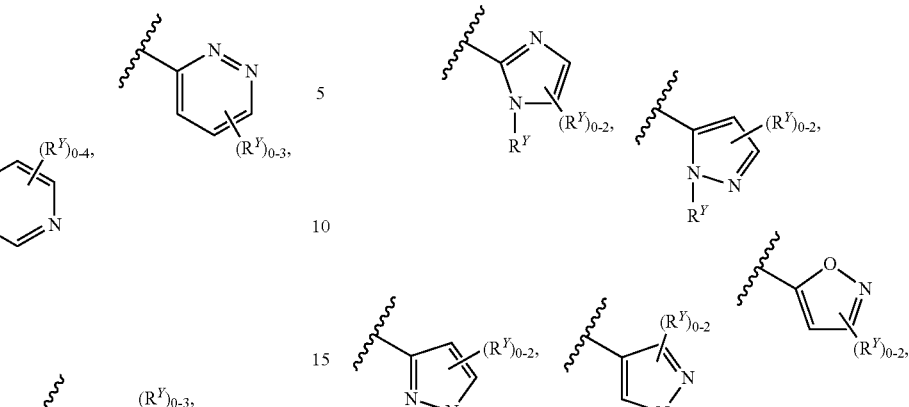
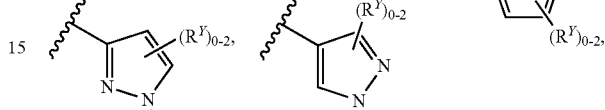
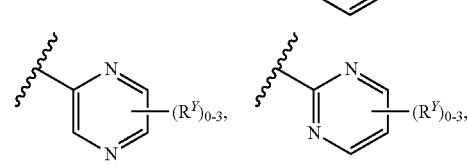
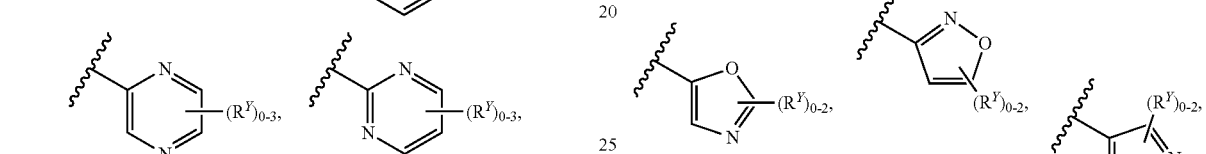
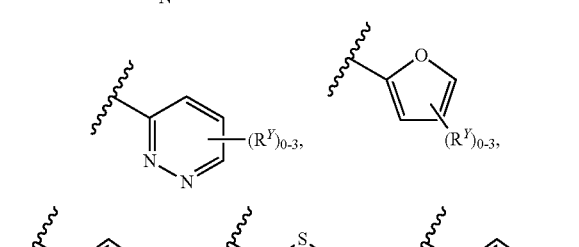
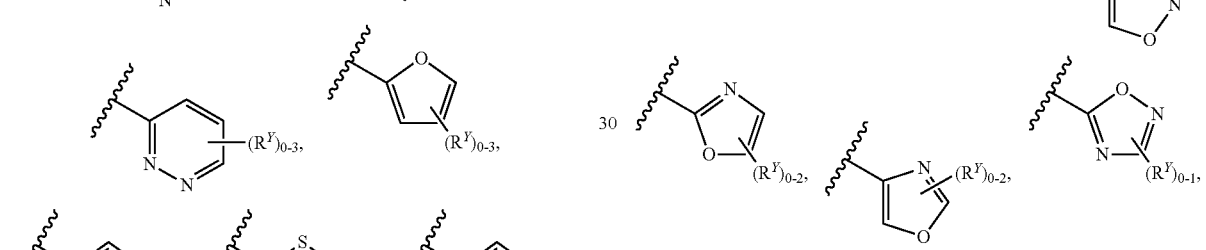
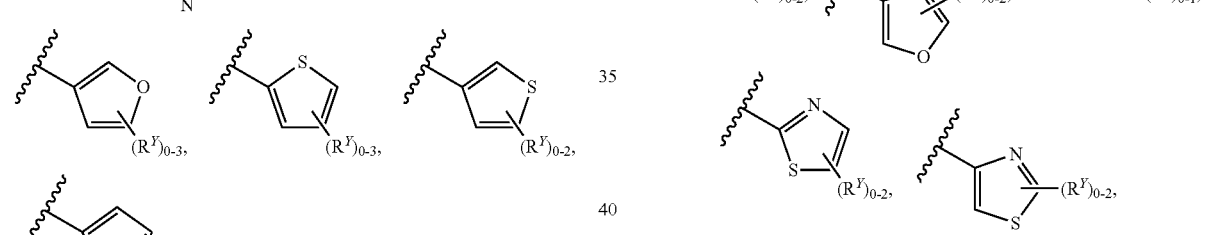
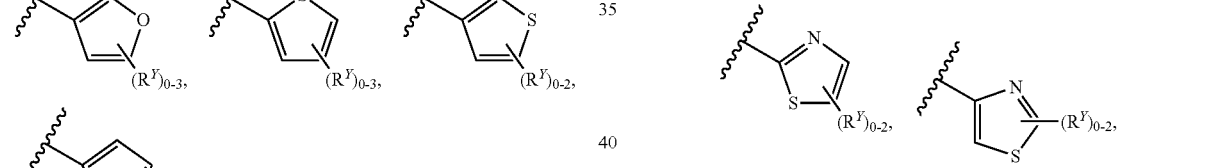
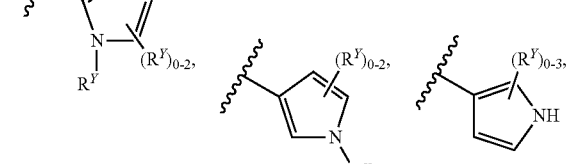
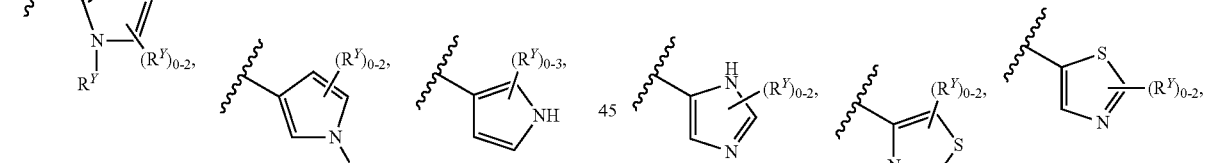
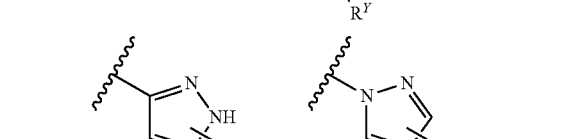
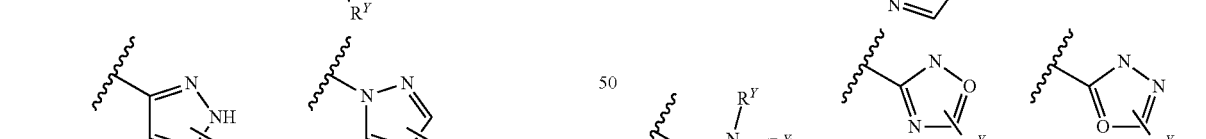
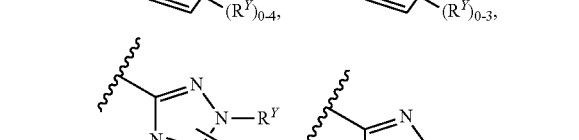
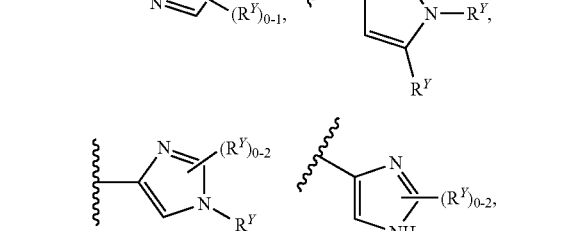
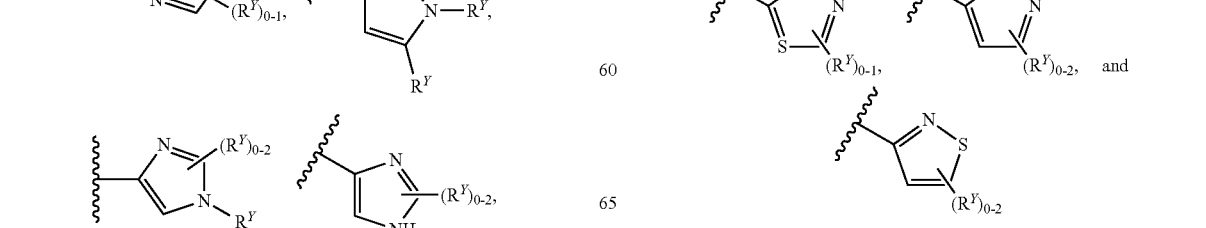

In some embodiments, each of A and W is selected from:
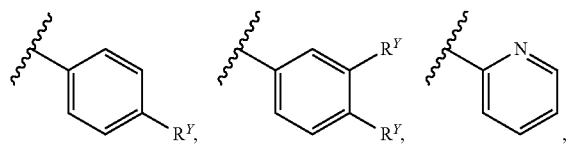
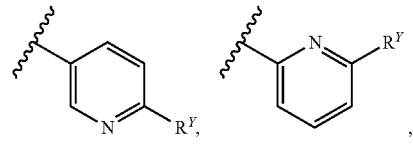
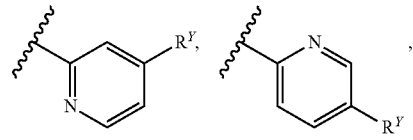
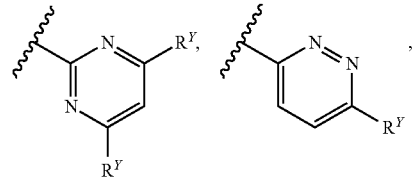
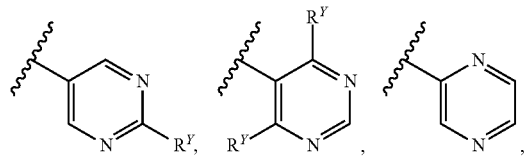
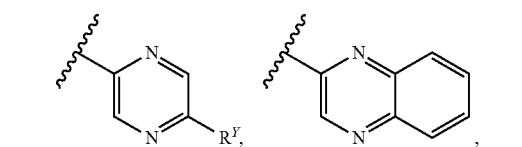
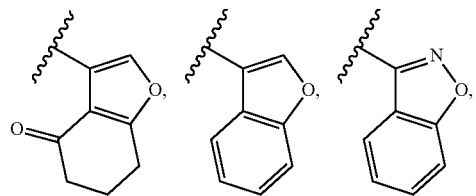
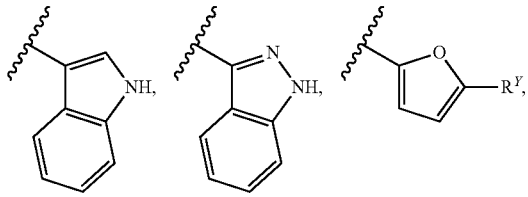
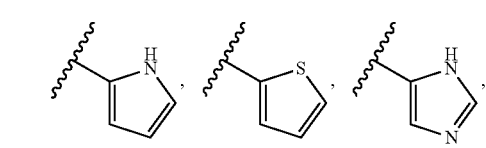
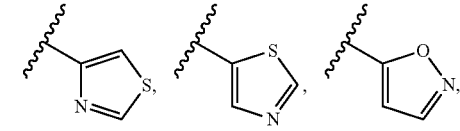
-continued
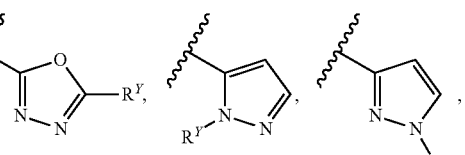
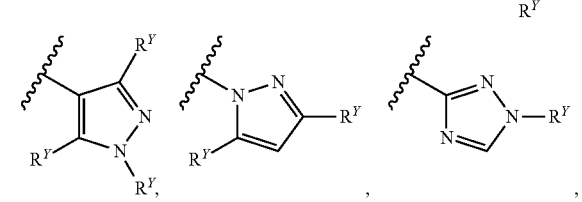
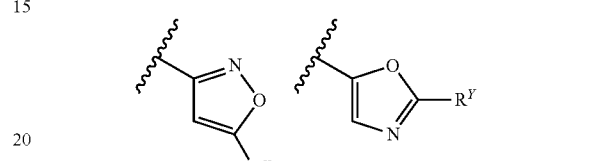
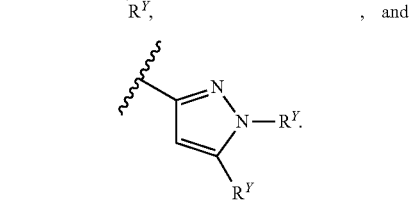
, and
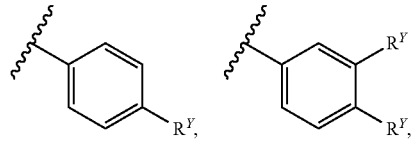
In some embodiments, each of A and W is selected from:
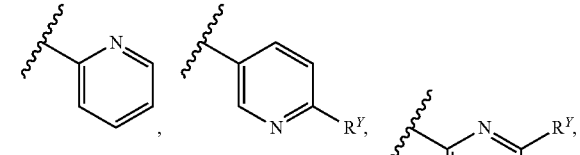
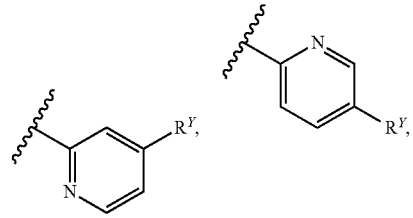
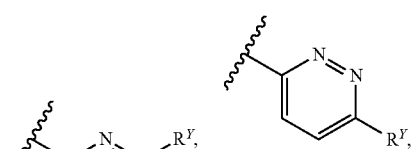
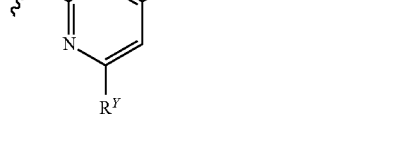

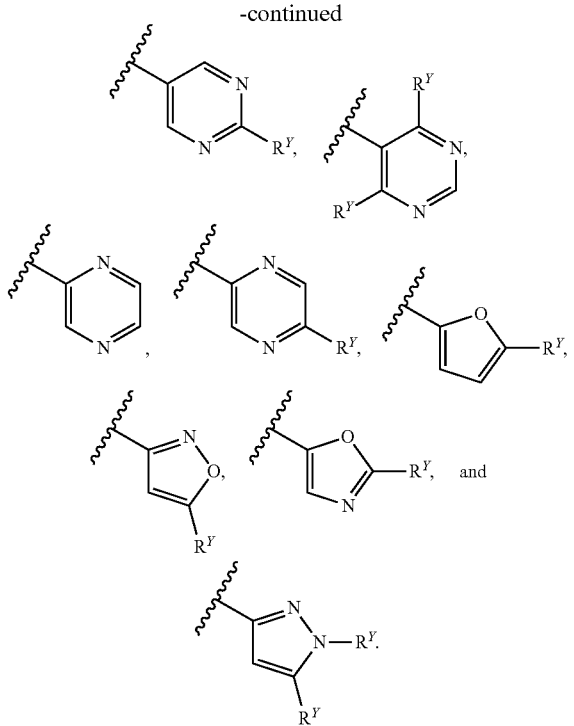

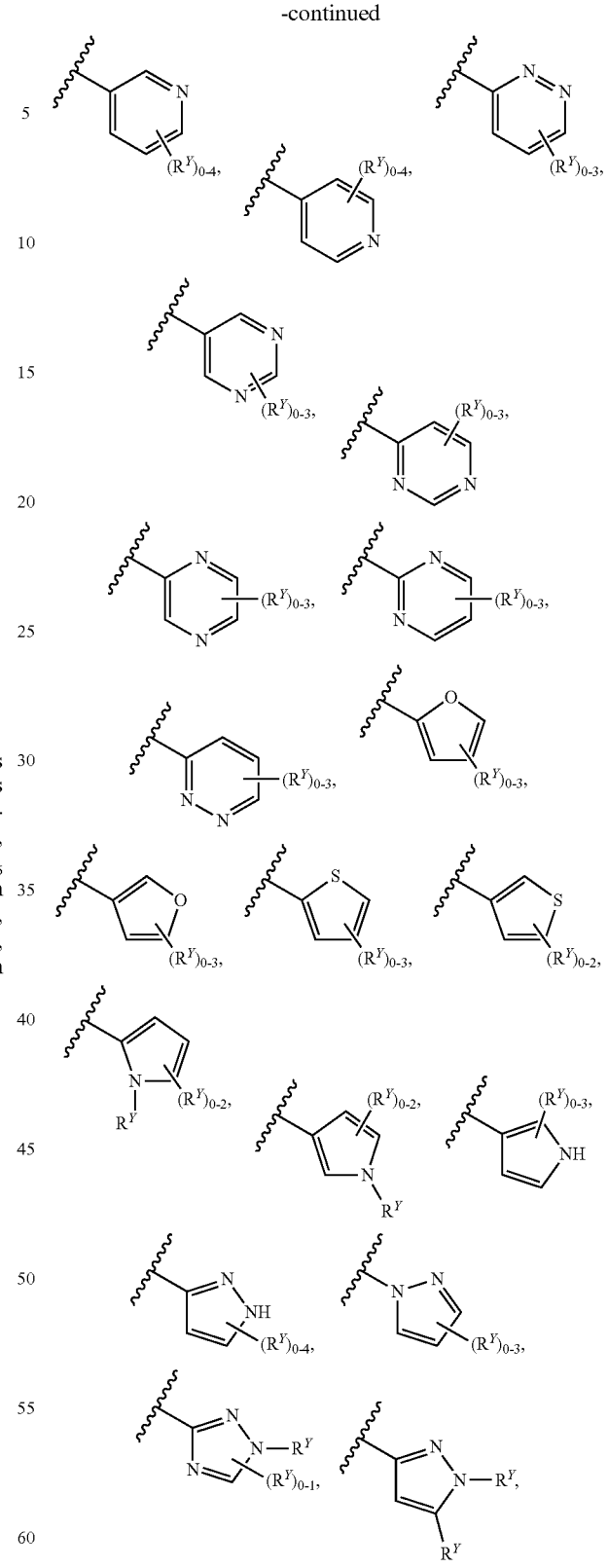

In some embodiments, A is phenyl or pyridyl and W is phenyl or 5-6-membered heteroaryl, each of A and W is optionally substituted with 1-5 $R^Y$, and each $R^Y$ is independently $C_1$-$C_6$ alkyl, hydroxy-$C_1$-$C_6$ alkyl, halo-$C_1$-$C_6$ alkyl, halo-$C_1$-$C_6$ alkoxy, siloxy-$C_1$-$C_6$ alkoxy, hydroxy $C_1$-$C_6$ alkoxy, halo, —$OR^A$, —C(O)OH, —C(O)$OR^D$, or $G^1$. In some embodiments, A is phenyl or pyridyl and W is phenyl, pyridyl, pyrimidinyl, pyrazinyl, pyridazinyl, oxazolyl, isoxazolyl, furanyl, or pyrazolyl, wherein A and W are each optionally substituted with 1-5 $R^Y$.

In some embodiments, A is

In some embodiments, A is

In some embodiments, W is selected from:

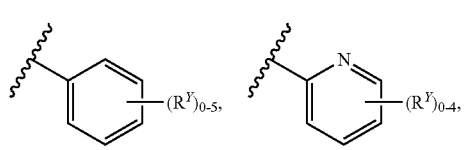

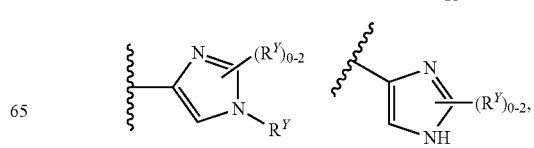

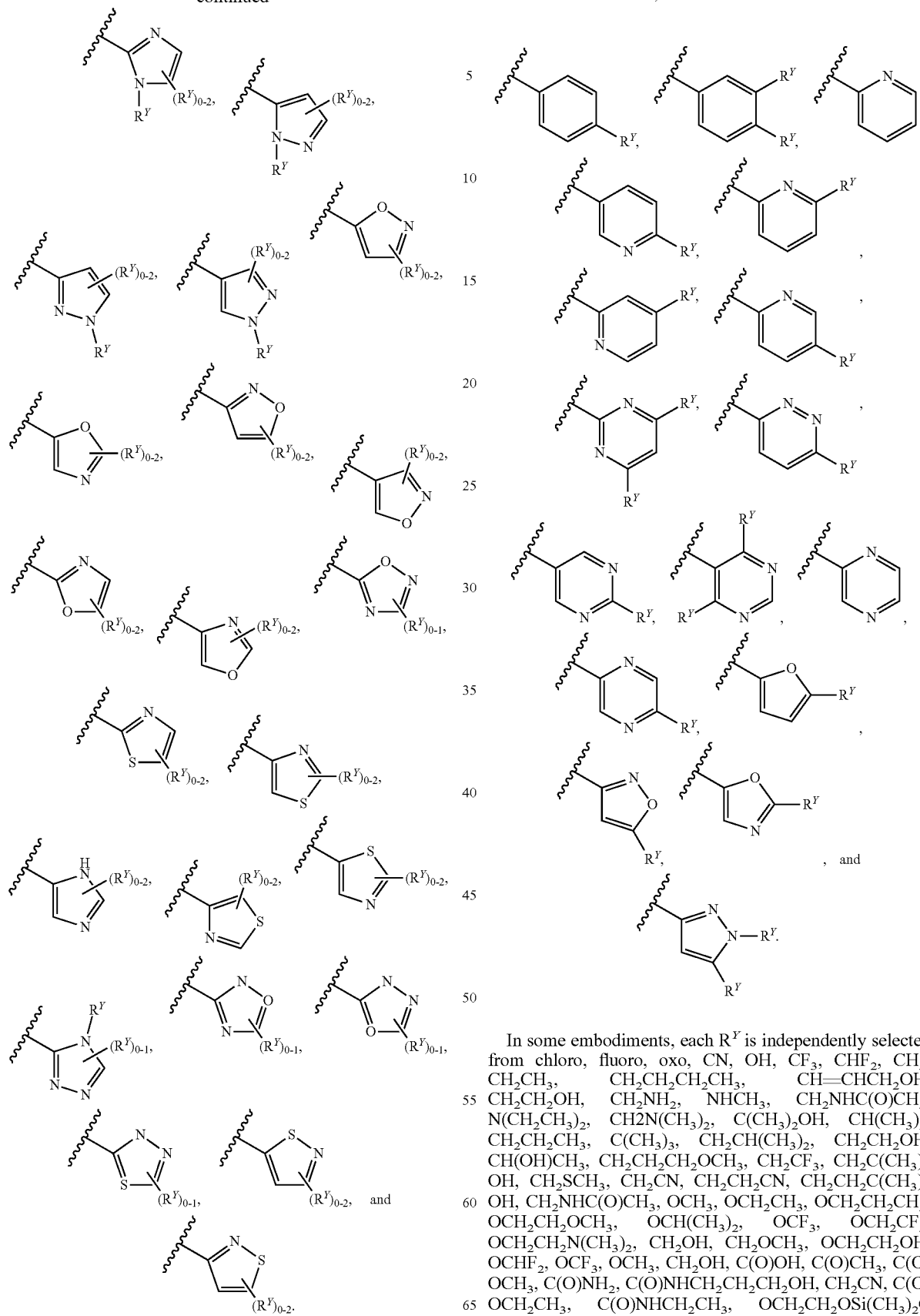

In some embodiments, W is selected from:

In some embodiments, each $R^Y$ is independently selected from chloro, fluoro, oxo, CN, OH, $CF_3$, $CHF_2$, $CH_3$, $CH_2CH_3$, $CH_2CH_2CH_2CH_3$, $CH=CHCH_2OH$, $CH_2CH_2OH$, $CH_2NH_2$, $NHCH_3$, $CH_2NHC(O)CH_3$, $N(CH_2CH_3)_2$, $CH2N(CH_3)_2$, $C(CH_3)_2OH$, $CH(CH_3)_2$, $CH_2CH_2CH_3$, $C(CH_3)_3$, $CH_2CH(CH_3)_2$, $CH_2CH_2OH$, $CH(OH)CH_3$, $CH_2CH_2CH_2OCH_3$, $CH_2CF_3$, $CH_2C(CH_3)_2OH$, $CH_2SCH_3$, $CH_2CN$, $CH_2CH_2CN$, $CH_2CH_2C(CH_3)_2OH$, $CH_2NHC(O)CH_3$, $OCH_3$, $OCH_2CH_3$, $OCH_2CH_2CH_3$, $OCH_2CH_2OCH_3$, $OCH(CH_3)_2$, $OCF_3$, $OCH_2CF_3$, $OCH_2CH_2N(CH_3)_2$, $CH_2OH$, $CH_2OCH_3$, $OCH_2CH_2OH$, $OCHF_2$, $OCF_3$, $OCH_3$, $CH_2OH$, $C(O)OH$, $C(O)CH_3$, $C(O)OCH_3$, $C(O)NH_2$, $C(O)NHCH_2CH_2CH_2OH$, $CH_2CN$, $C(O)OCH_2CH_3$, $C(O)NHCH_2CH_3$, $OCH_2CH_2OSi(CH_3)_2C(CH_3)_3$, $CH_2N(CH_3)_2$, $CH_2NHC(O)CH_3$, $CH_2NHC(O)OC(CH_3)_3$, $CH=CHCH_2OCH_3$, $CH=CHC(CH_3)_2OH$, N(CH$_3$)$_2$, N(CH$_2$CH$_3$)$_2$, NHCH$_2$CH$_3$, NHC(O)CH$_3$, NHC(O)CH$_2$OCH$_3$, NHS(O)$_2$CH$_3$, SCH$_3$, SCH$_2$CH$_3$, SO$_2$NH$_2$, S(O)CH$_3$, S(O)$_2$CH$_3$, G$^1$, C(O)NHG$^1$, N(CH$_3$)CH$_2$G$^1$, NHG$^1$, OG$^1$, CH$_2$G$^1$, CH$_2$CH$_2$G$^1$, CH$_2$NHC(O)G$^1$, or CH=CHG$^1$. In some embodiments, each R$^Y$ is independently chloro, fluoro, CN, OH, CF$_3$, CHF$_2$, CH$_3$, CH$_2$CH$_3$, CH$_2$CH$_2$CH$_2$CH$_3$, CH=CHCH$_2$OH, CH$_2$CH$_2$OH, CH$_2$NH$_2$, NHCH$_3$, CH$_2$NHC(O)CH$_3$, N(CH$_2$CH$_3$)$_2$, CH$_2$N(CH$_3$)$_2$, C(CH$_3$)$_2$OH, OCH$_3$, CH$_2$OH, CH$_2$OCH$_3$, OCH$_2$CH$_2$OH, OCHF$_2$, OCF$_3$, OCH$_3$, CH$_2$OH, C(O)OH, CH$_2$CN, C(O)OCH$_2$CH$_3$, C(O)NHCH$_2$CH$_3$, OCH$_2$CH$_2$OSi(CH$_3$)$_2$C(CH$_3$)$_3$, or G$^1$.

In some embodiments, each of A and W is independently substituted with 2 R$^Y$ on adjacent atoms, and the 2 R$^Y$, together with the atoms to which they are attached, form a 3-7-membered fused heterocyclyl ring or 5-6-membered heteroaryl ring, each optionally substituted with 1-5 R$^X$. In some embodiments, the 2 R$^Y$ together with the atoms to which they are attached form a dioxolanyl, hexahydropyrimidinyl, pyridyl, or pyrimidinyl ring, each of which is optionally substituted with 1-5 R$^X$. In some embodiments, each R$^X$ is independently C$_1$-C$_6$ alkyl, fluoro, chloro, oxo, OCH$_3$, C(O)OCH$_3$, or G$^2$.

In some embodiments, G$^1$ or G$^2$ is pyrrolidinyl, azetidinyl, cyclopropyl, cyclohexyl, cyclohexenyl, tetrahydropyranyl, dihydropyranyl, tetrahydropyridinyl, piperidinyl, phenyl, pyridyl, pyrimidinyl, pyridazinyl, pyrazolyl, morphilino, furanyl, triazolyl, oxetanyl, or pyrazinyl, each of which is optionally substituted with 1-5 R$^Z$. In some embodiments, G$^1$ is pyrrolidinyl, cyclopropyl, cyclohexyl, cyclohexenyl, tetrahydropyranyl, dihydropyranyl, tetrahydropyridinyl, piperidinyl, phenyl, pyridyl, pyrimidinyl, pyridazinyl, or pyrazinyl, each of which is optionally substituted with 1-5 R$^Z$.

In some embodiments, G$^1$ is pyrrolidinyl, azetidinyl, cyclopropyl, cyclohexyl, cyclohexenyl, tetrahydropyranyl, dihydropyranyl, tetrahydropyridinyl, piperidinyl, phenyl, pyridyl, pyrimidinyl, pyridazinyl, pyrazolyl, morphilino, furanyl, triazolyl, oxetanyl, or pyrazinyl, each of which is optionally substituted with 1-5 R$^Z$. In some embodiments, G$^1$ is pyrrolidinyl, cyclopropyl, cyclohexyl, cyclohexenyl, tetrahydropyranyl, dihydropyranyl, tetrahydropyridinyl, piperidinyl, phenyl, pyridyl, pyrimidinyl, pyridazinyl, or pyrazinyl, each of which is optionally substituted with 1-5 R$^Z$.

In some embodiments, each R$^Z$ is independently OR$^A$, C(O)R$^D$, halo, halo C$_1$-C$_6$ alkyl, C$_1$-C$_6$ alkyl, C(O)R$^D$, or C(O)OR$^D$ (e.g., fluoro, chloro, OH, OCH$_3$, oxo, CH$_3$, CHF$_2$, CF$_3$, C(O)CH$_3$ or C(O)OC(CH$_3$)$_3$). In some embodiments, each R$^Z$ is independently OR$^A$, C(O)R$^D$, halo, halo C$_1$-C$_6$ alkyl, C$_1$-C$_6$ alkyl, or C(O)OR$^D$ (e.g., OH, C(O)CH$_3$ or C(O)OC(CH$_3$)$_3$).

In some embodiments, the compound of Formula (I) (e.g., a compound of Formula (I-a), (I-b), (I-c), (I-d), (I-e), (I-f), (I-g), (I-h), or (I-i)) or a pharmaceutically acceptable salt thereof is formulated as a pharmaceutically acceptable composition comprising a compound of any one of the preceding claims and a pharmaceutically acceptable carrier In some embodiments, the compound is selected from any compound set forth in Table 1 or a pharmaceutically acceptable salt, solvate, hydrate, tautomer, or stereoisomer thereof.

TABLE 1

Exemplary compounds of the invention

| Compound No. | Structure |
| --- | --- |
| 100 | 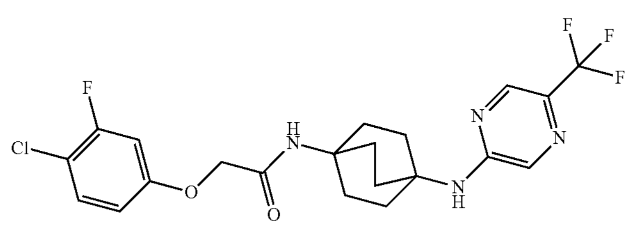 [SMILES: O=C(COc1ccc(Cl)c(F)c1)NC12CCC(Nc3cnc(C(F)(F)F)cn3)(CC1)CC2] |
| 101 | 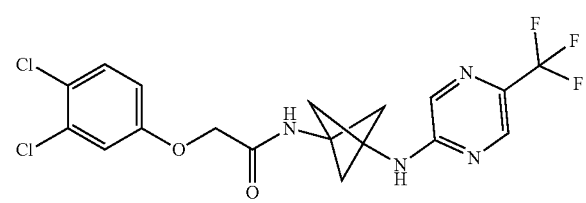 [SMILES: O=C(COc1ccc(Cl)c(Cl)c1)NC12CC(Nc3cnc(C(F)(F)F)cn3)(C1)C2] |
| 102 | 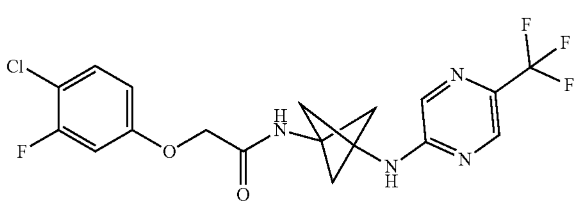 [SMILES: O=C(COc1ccc(Cl)c(F)c1)NC12CC(Nc3cnc(C(F)(F)F)cn3)(C1)C2] |

TABLE 1-continued

| Compound No. | Exemplary compounds of the invention Structure |
|---|---|
| 103 | (structure) |
| 104 | (structure) |
| 105 | (structure) |
| 106 | (structure) |
| 107 | (structure) |
| 108 | (structure) |
| 109 | (structure) |
| 110 | (structure) |

TABLE 1-continued

Exemplary compounds of the invention

| Compound No. | Structure |
| --- | --- |
| 111 | |
| 112 | |
| 113 | |
| 114 | |
| 115 | |
| 116 | |
| 117 | |

TABLE 1-continued

| Compound No. | Exemplary compounds of the invention Structure |
|---|---|
| 118 | (structure) |
| 119 | (structure) |
| 120 | (structure) |
| 121 | (structure) |
| 122 | (structure) |
| 123 | (structure) |
| 124 | (structure) |
| 125 | (structure) |
| 126 | (structure) |

TABLE 1-continued

Exemplary compounds of the invention

| Compound No. | Structure |
|---|---|
| 127 | |
| 128 | |
| 129 | |
| 130 | |
| 131 | |
| 132 | |
| 133 | |
| 134 | |
| 135 | |

TABLE 1-continued

Exemplary compounds of the invention

| Compound No. | Structure |
|---|---|
| 136 | (structure) |
| 137 | (structure) |
| 138 | (structure) |
| 139 | (structure) |
| 140 | (structure) |
| 141 | (structure) |
| 142 | (structure) |
| 143 | (structure) |
| 144 | (structure) |
| 145 | (structure) |

TABLE 1-continued

| Compound No. | Exemplary compounds of the invention Structure |
|---|---|
| 146 | |
| 147 | |
| 148 | |
| 149 | |
| 150 | |
| 151 | |
| 152 | |
| 153 | |
| 154 | |

TABLE 1-continued

| Compound No. | Exemplary compounds of the invention Structure |
|---|---|
| 155 | |
| 156 | |
| 157 | |
| 158 | |
| 159 | |
| 160 | |
| 161 | |
| 162 | |
| 163 | |
| 164 | |

TABLE 1-continued

Exemplary compounds of the invention

| Compound No. | Structure |
| --- | --- |
| 165 | |
| 166 | |
| 167 | |
| 168 | |
| 169 | |
| 170 | |

TABLE 1-continued
Exemplary compounds of the invention
| Compound No. | Structure |
|---|---|
| 171 | 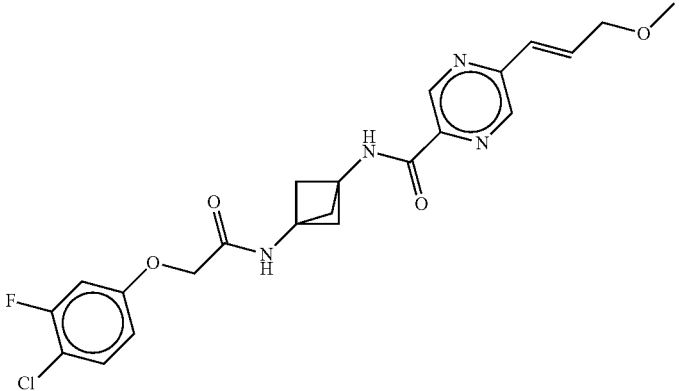 |
| 172 | 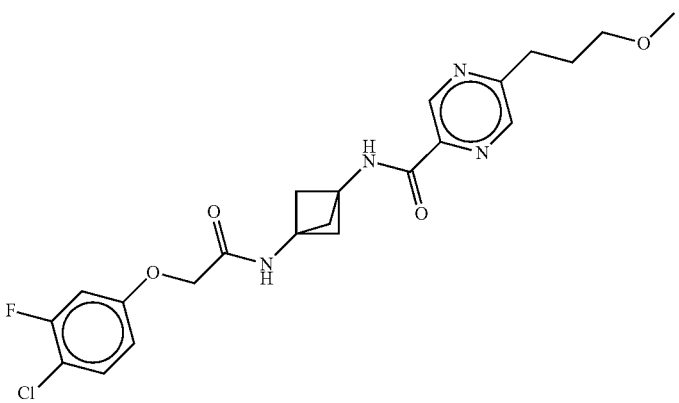 |
| 173 | 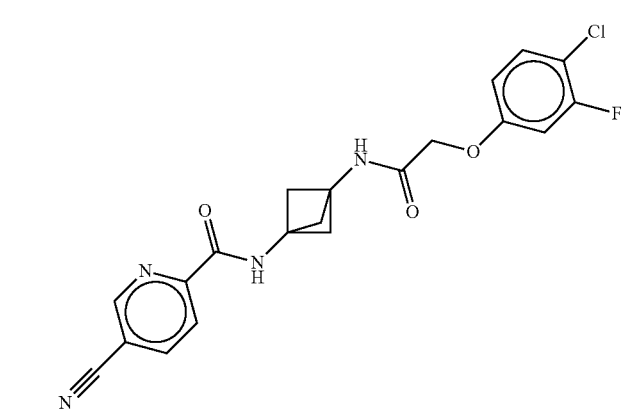 |
| 174 | 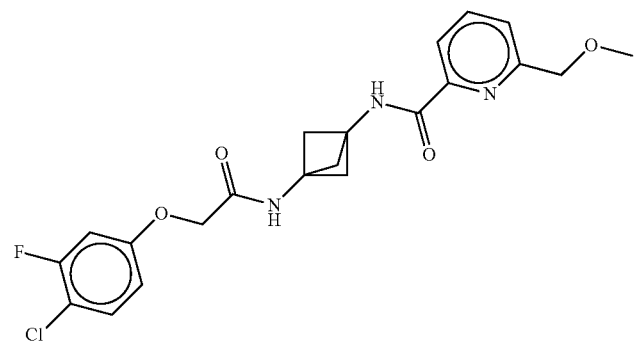 |

TABLE 1-continued
Exemplary compounds of the invention
| Compound No. | Structure |
| --- | --- |
| 175 | 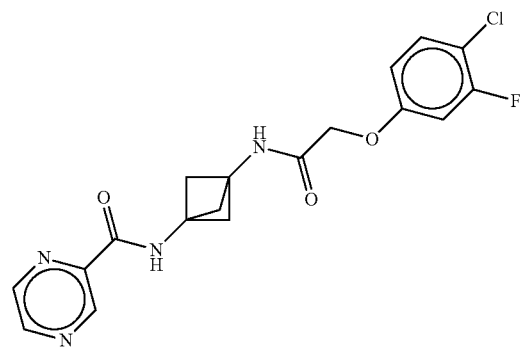 |
| 176 | 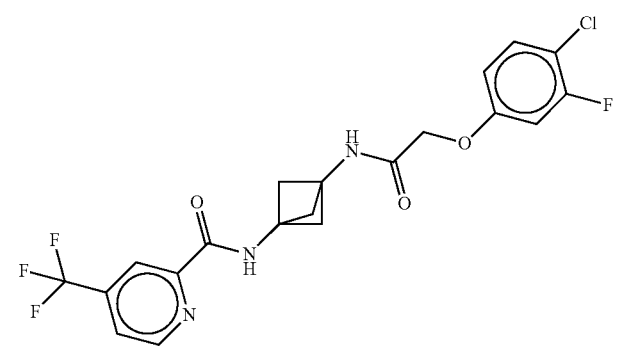 |
| 177 | 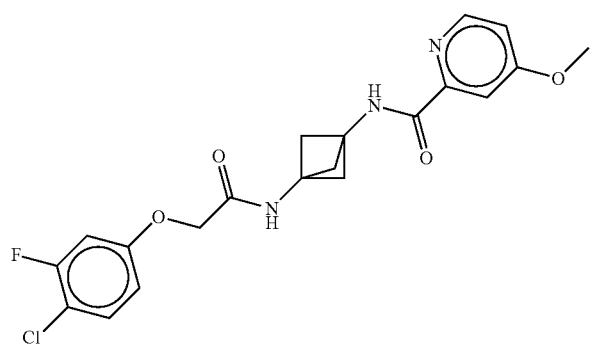 |
| 178 | 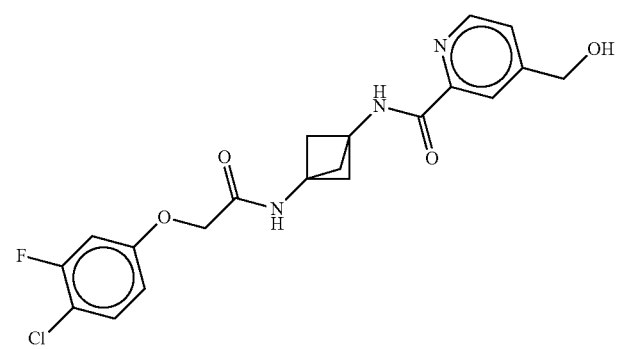 |

TABLE 1-continued

Exemplary compounds of the invention

| Compound No. | Structure |
|---|---|
| 179 | |
| 180 | |
| 181 | |
| 182 | |

TABLE 1-continued
Exemplary compounds of the invention
| Compound No. | Structure |
|---|---|
| 183 | 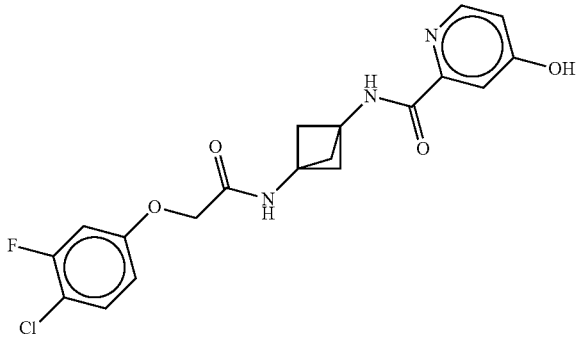 |
| 184 | 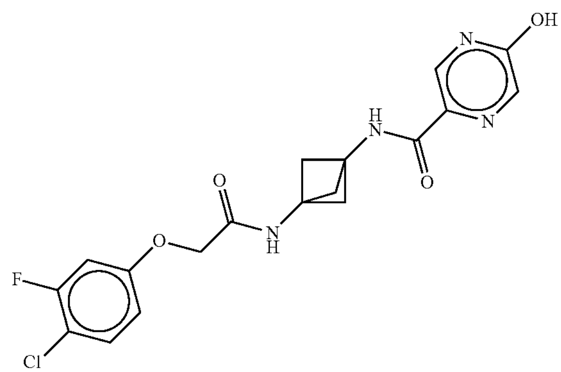 |
| 185 | 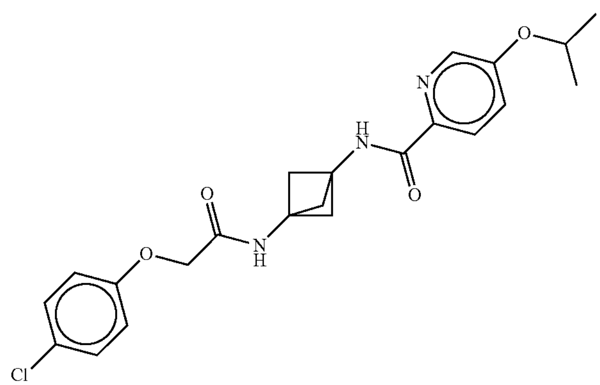 |
| 186 | 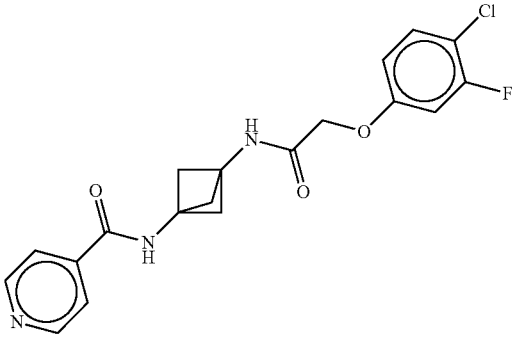 |

TABLE 1-continued
Exemplary compounds of the invention
| Compound No. | Structure |
|---|---|
| 187 | 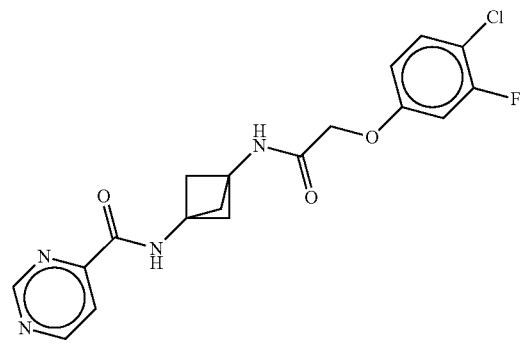 |
| 188 | 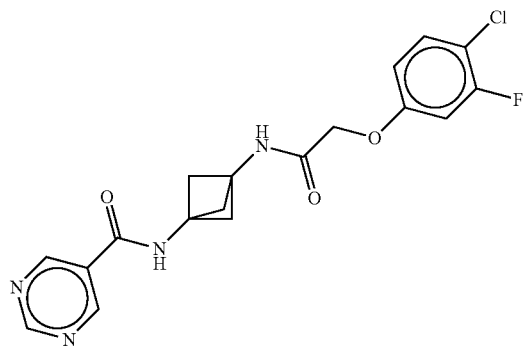 |
| 189 | 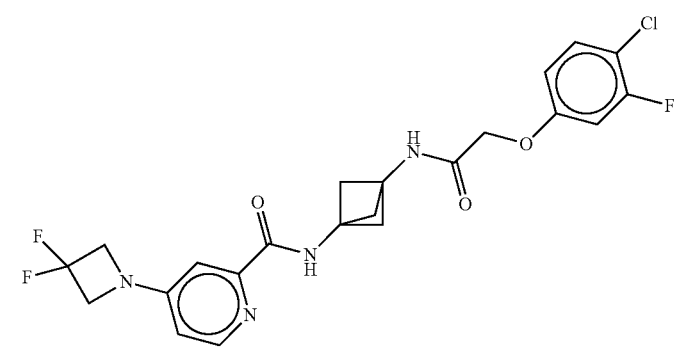 |
| 190 | 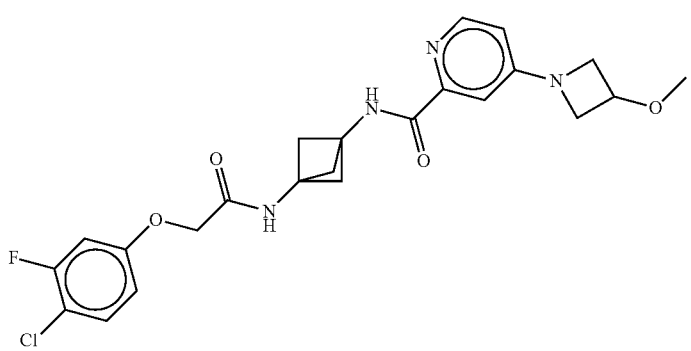 |

TABLE 1-continued
Exemplary compounds of the invention
| Compound No. | Structure |
|---|---|
| 191 | 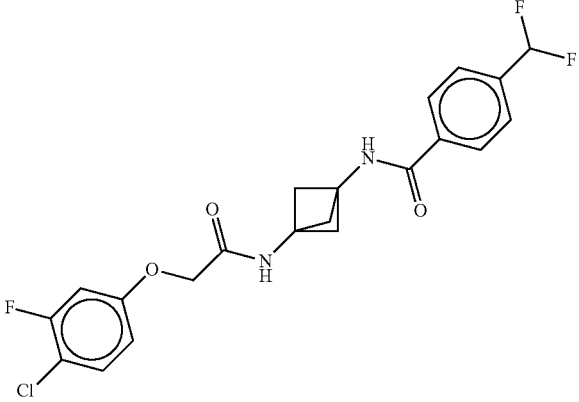 |
| 192 | 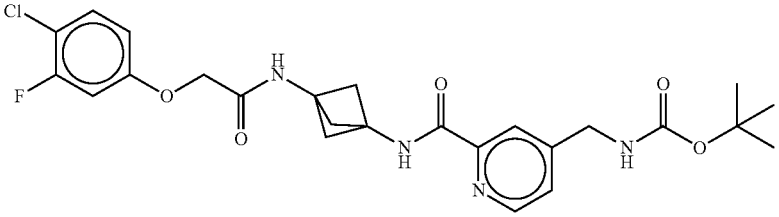 |
| 193 | 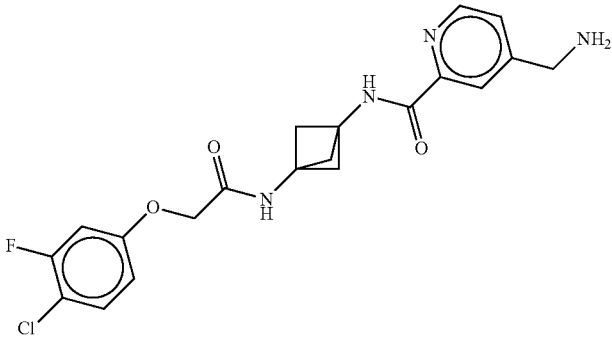 |
| 194 | 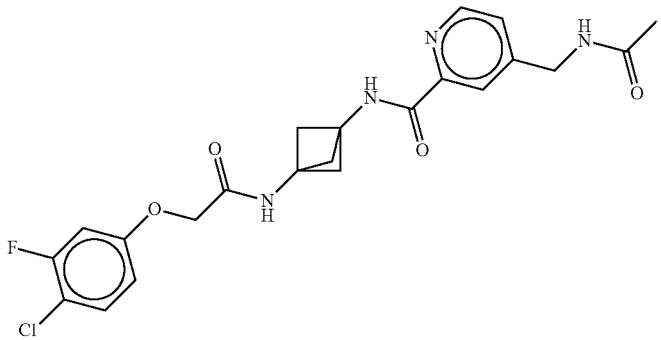 |

TABLE 1-continued
Exemplary compounds of the invention
| Compound No. | Structure |
|---|---|
| 195 | 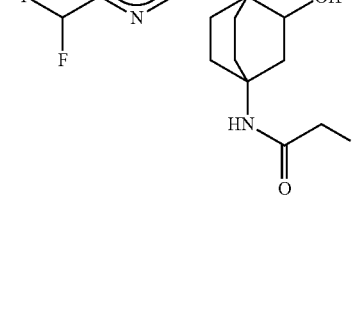 |
| 196 | 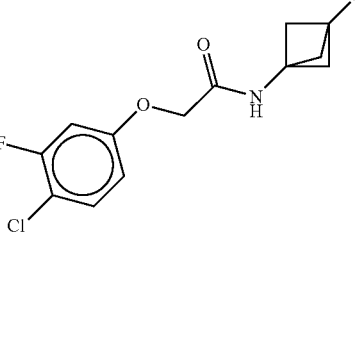 |
| 197 | 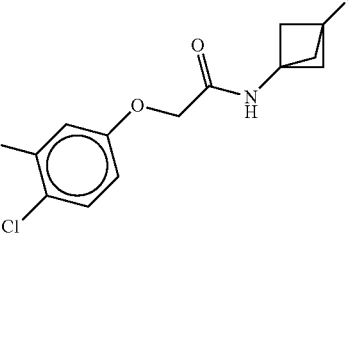 |
| 198 | 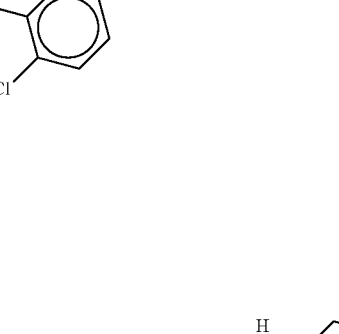 |

TABLE 1-continued

Exemplary compounds of the invention

| Compound No. | Structure |
|---|---|
| 199 | (structure) |
| 200 | (structure) |
| 201 | (structure) |
| 202 | (structure) |

TABLE 1-continued
Exemplary compounds of the invention
| Compound No. | Structure |
|---|---|
| 203 | 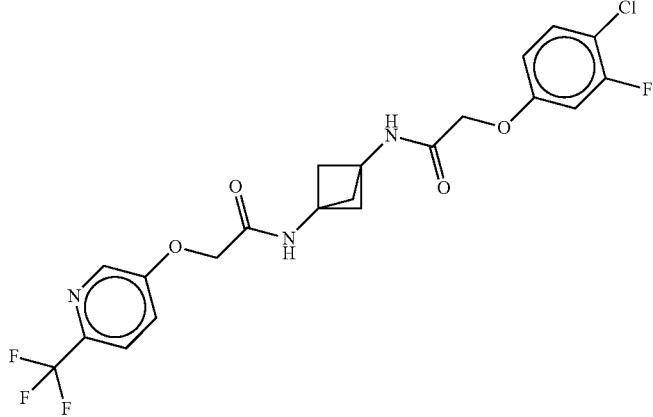 |
| 204 | 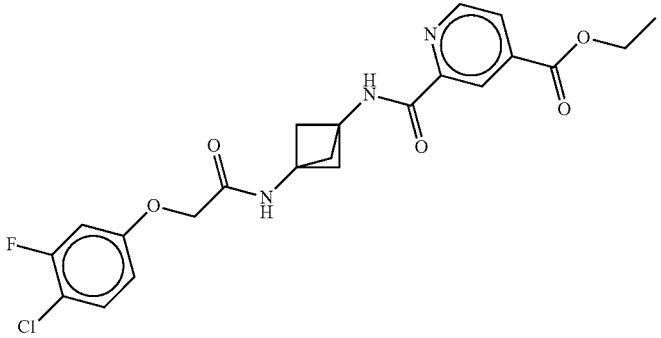 |
| 205 | 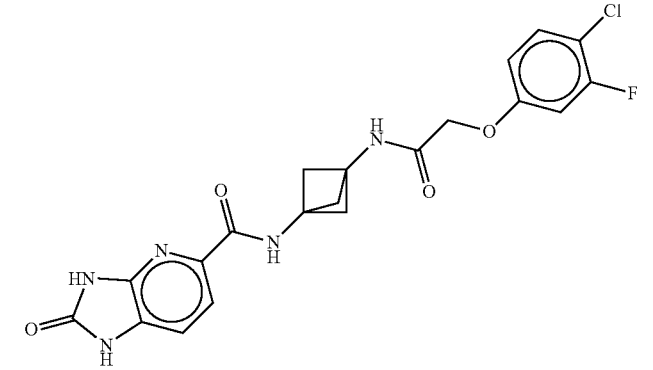 |
| 206 | 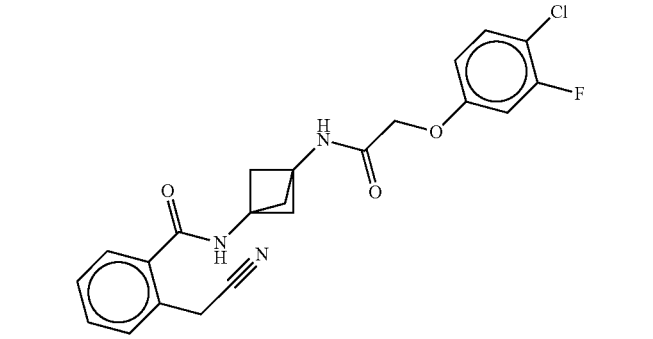 |

TABLE 1-continued

Exemplary compounds of the invention

| Compound No. | Structure |
|---|---|
| 207 | |
| 208 | |
| 209 | |
| 210 | |

TABLE 1-continued
Exemplary compounds of the invention
| Compound No. | Structure |
|---|---|
| 211 | 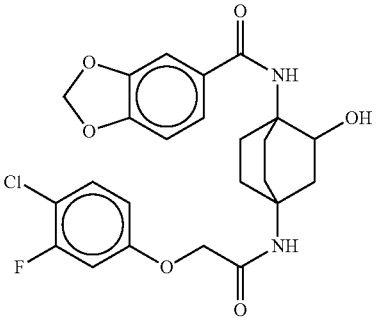 |
| 212 | 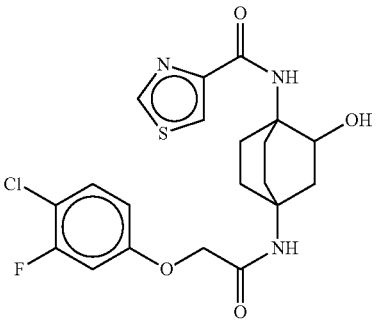 |
| 213 | 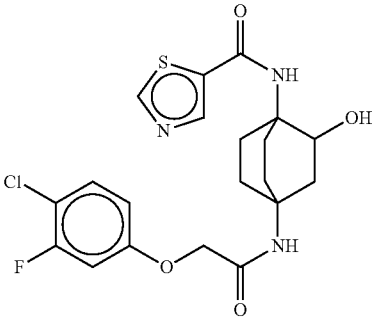 |
| 214 | 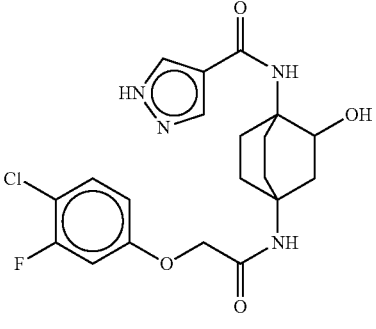 |

TABLE 1-continued
Exemplary compounds of the invention
| Compound No. | Structure |
|---|---|
| 215 | 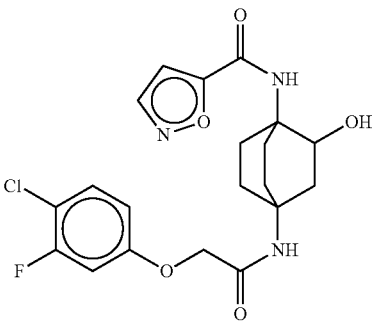 |
| 216 | 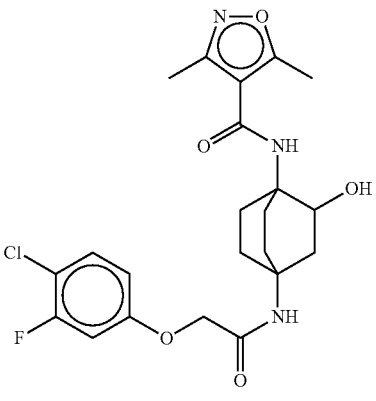 |
| 217 | 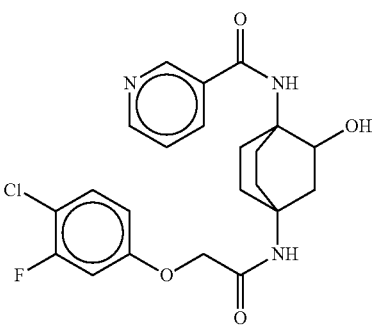 |
| 218 | 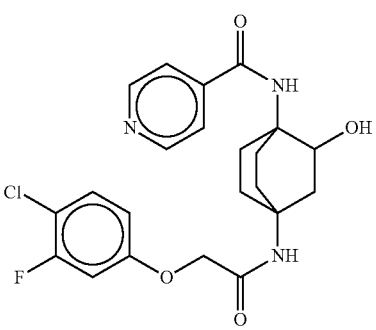 |

TABLE 1-continued
Exemplary compounds of the invention
| Compound No. | Structure |
|---|---|
| 219 | 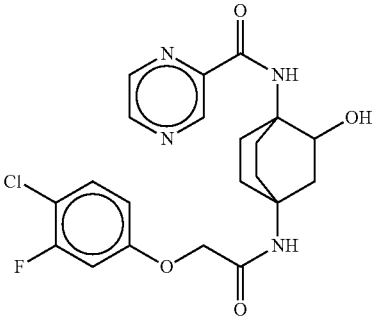 |
| 220 | 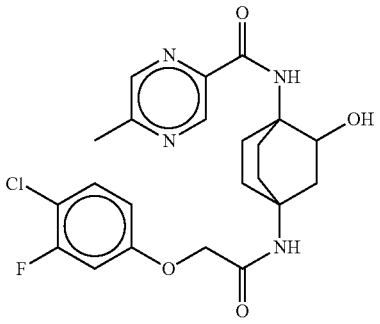 |
| 221 | 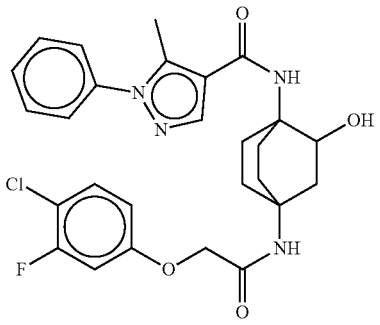 |
| 222 | 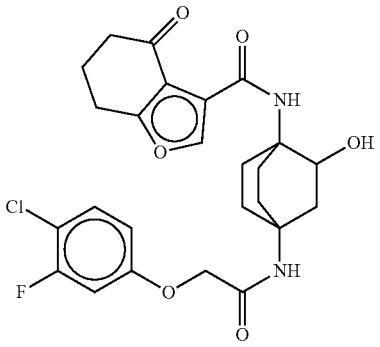 |

TABLE 1-continued
Exemplary compounds of the invention
| Compound No. | Structure |
|---|---|
| 223 | 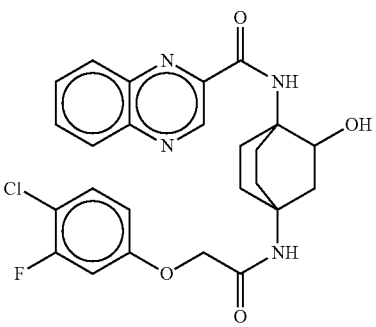 |
| 224 | 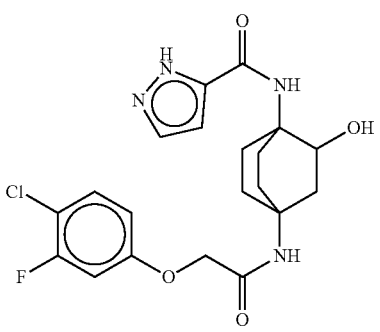 |
| 225 |  |
| 226 | 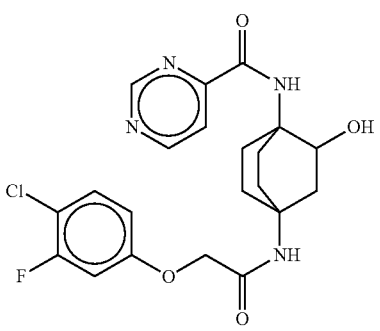 |

TABLE 1-continued
Exemplary compounds of the invention
| Compound No. | Structure |
|---|---|
| 227 | 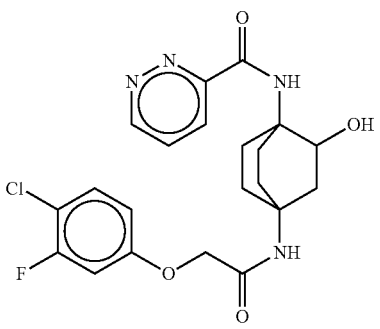 |
| 228 | 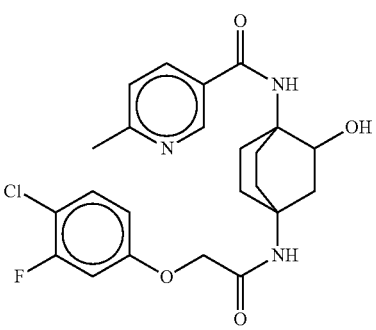 |
| 229 | 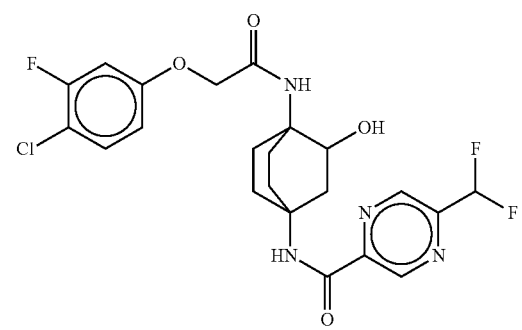 |
| 230 | 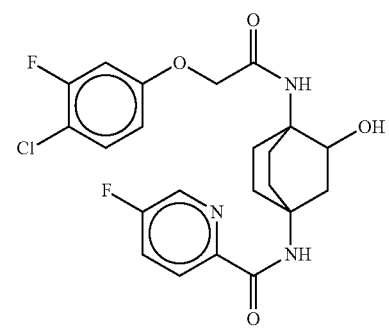 |

TABLE 1-continued

Exemplary compounds of the invention

| Compound No. | Structure |
| --- | --- |
| 231 | |
| 232 | |
| 233 | |
| 234 | |

TABLE 1-continued
Exemplary compounds of the invention
| Compound No. | Structure |
|---|---|
| 235 | 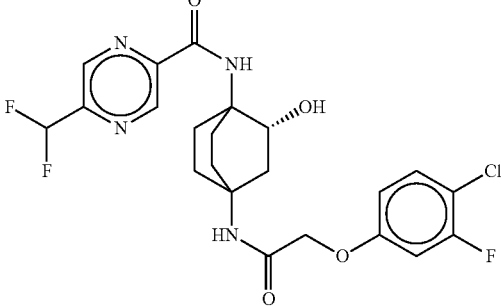 |
| 236 | 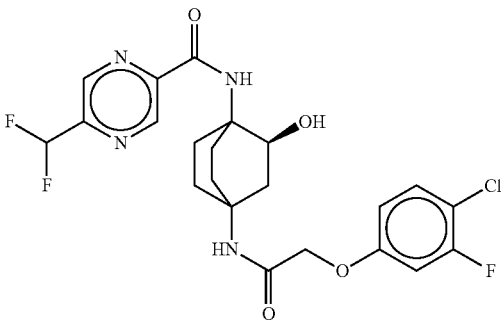 |
| 237 | 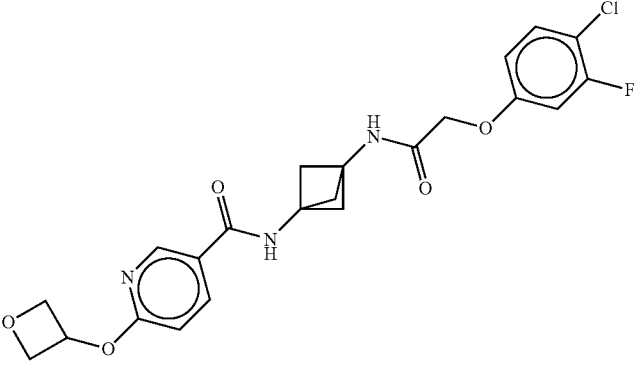 |
| 238 | 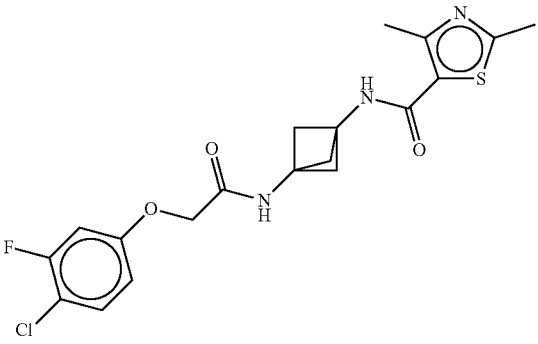 |

TABLE 1-continued

Exemplary compounds of the invention

| Compound No. | Structure |
|---|---|
| 239 | |
| 240 | |
| 241 | |
| 242 | |

TABLE 1-continued

Exemplary compounds of the invention

| Compound No. | Structure |
|---|---|
| 243 | |
| 244 | |
| 245 | |
| 246 | |

TABLE 1-continued
Exemplary compounds of the invention
| Compound No. | Structure |
|---|---|
| 247 | 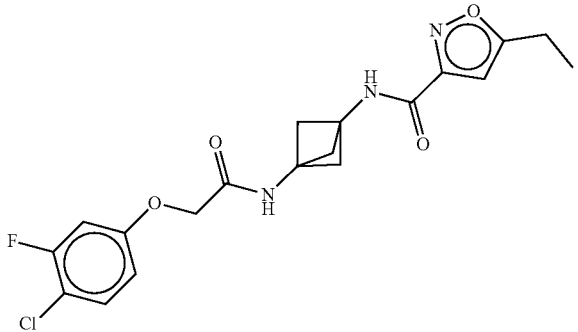 |
| 248 | 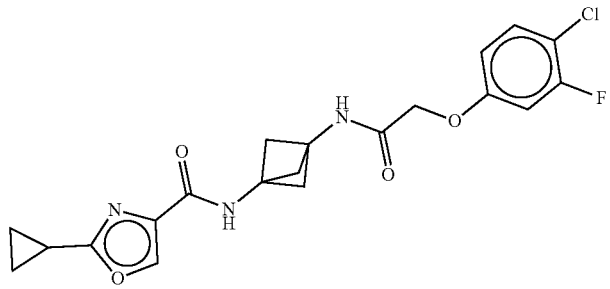 |
| 249 | 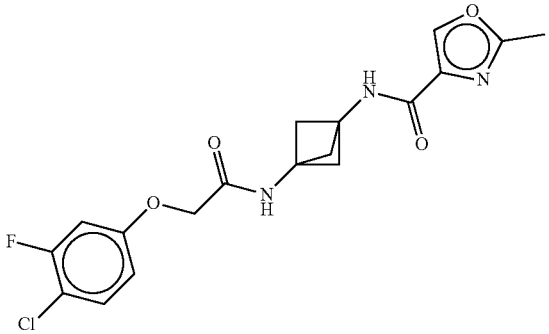 |
| 250 | 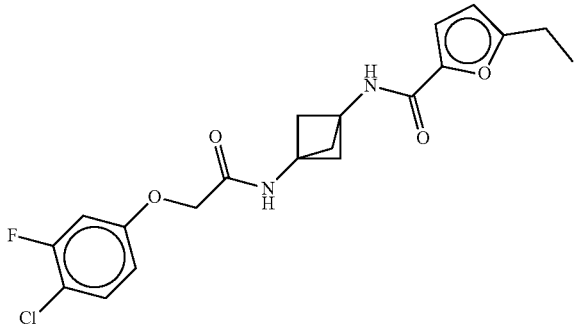 |

TABLE 1-continued
Exemplary compounds of the invention
| Compound No. | Structure |
|---|---|
| 251 | 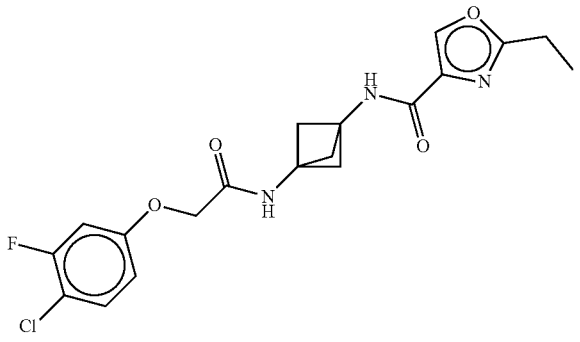 |
| 252 | 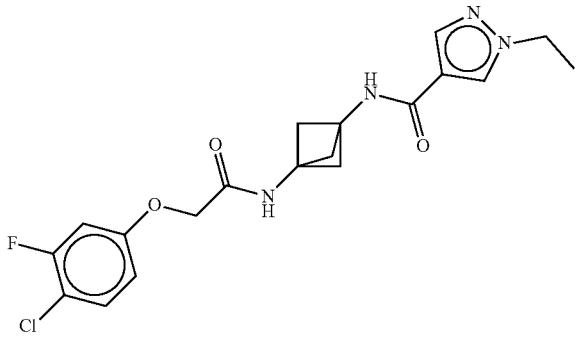 |
| 253 | 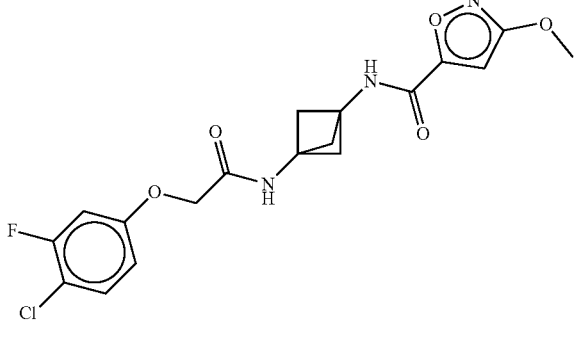 |
| 254 | 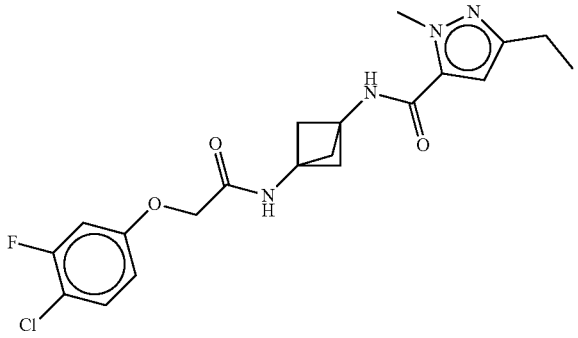 |

TABLE 1-continued

Exemplary compounds of the invention

| Compound No. | Structure |
|---|---|
| 255 | |
| 256 | |
| 257 | |
| 258 | |

TABLE 1-continued
Exemplary compounds of the invention
| Compound No. | Structure |
|---|---|
| 259 | 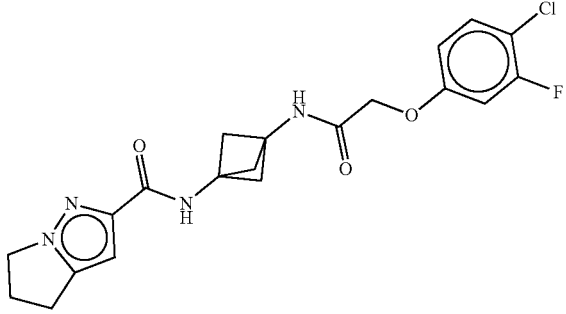 |
| 260 | 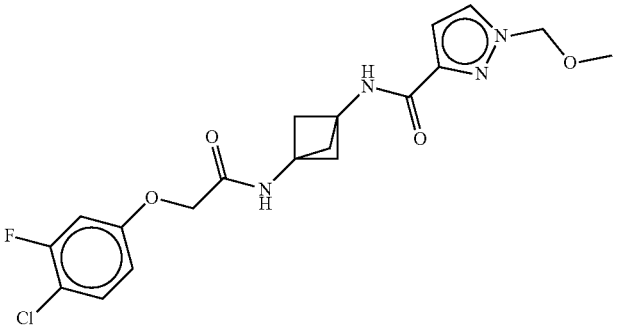 |
| 261 | 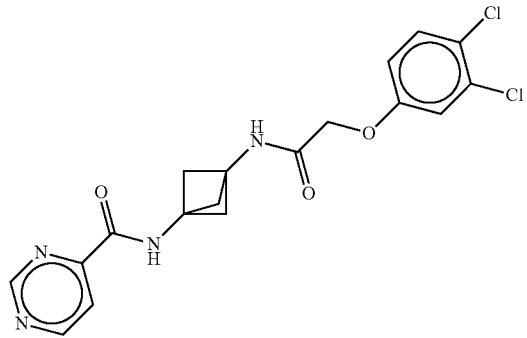 |
| 262 | 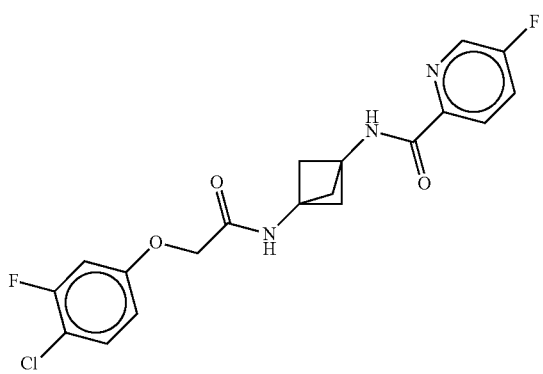 |

TABLE 1-continued
Exemplary compounds of the invention
| Compound No. | Structure |
|---|---|
| 263 | 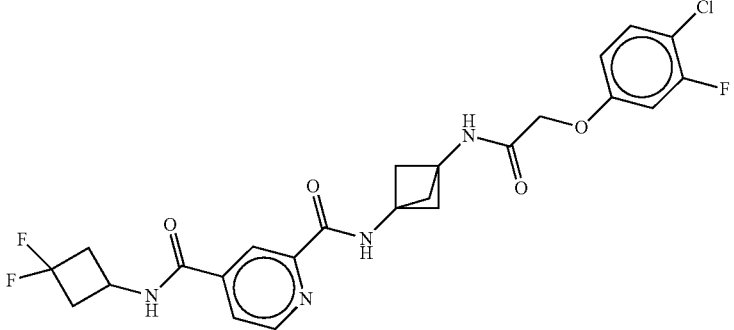 |
| 264 | 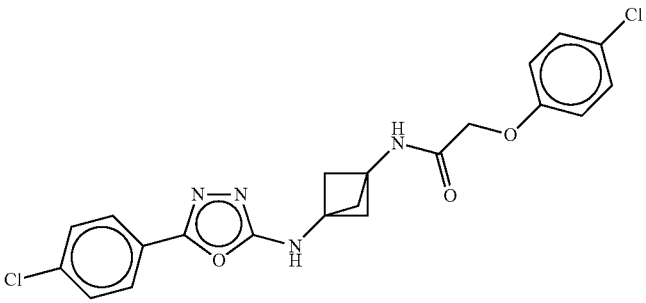 |
| 265 | 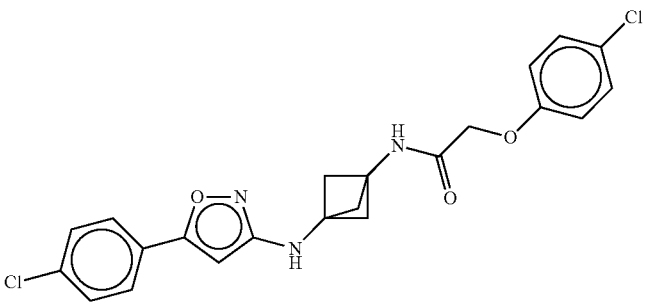 |
| 266 | 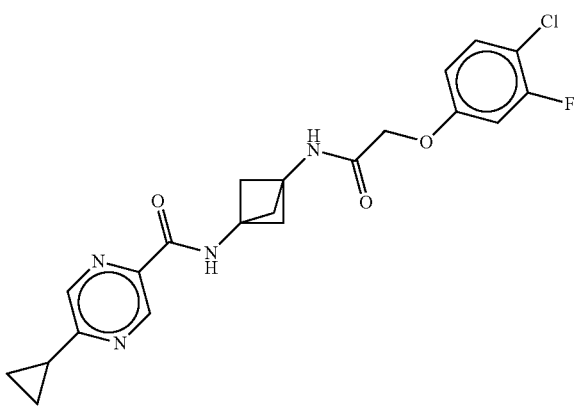 |

TABLE 1-continued

| Compound No. | Exemplary compounds of the invention Structure |
|---|---|
| 267 | |
| 268 | |
| 269 | |
| 270 | |

TABLE 1-continued

Exemplary compounds of the invention

| Compound No. | Structure |
|---|---|
| 271 | |
| 272 | |
| 273 | |
| 274 | |

TABLE 1-continued
Exemplary compounds of the invention
| Compound No. | Structure |
|---|---|
| 275 | 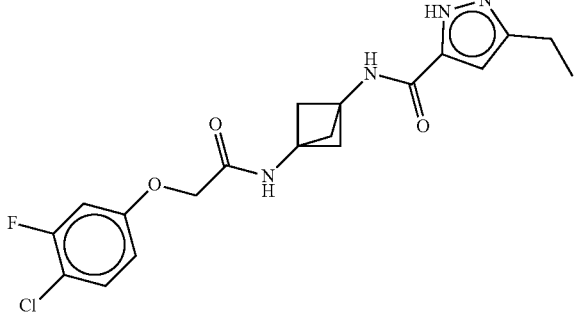 |
| 276 | 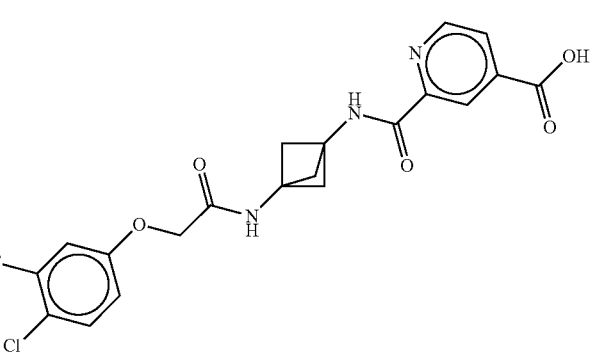 |
| 277 | 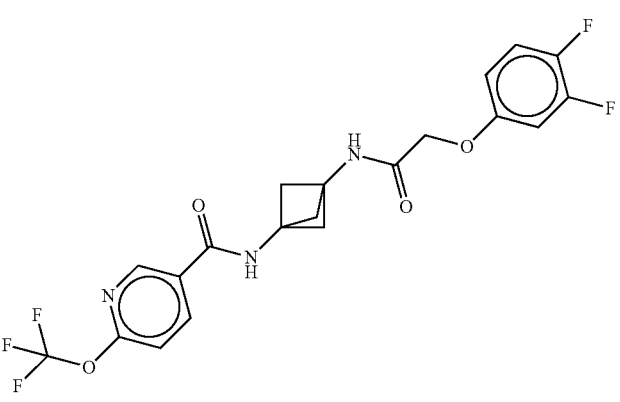 |
| 278 | 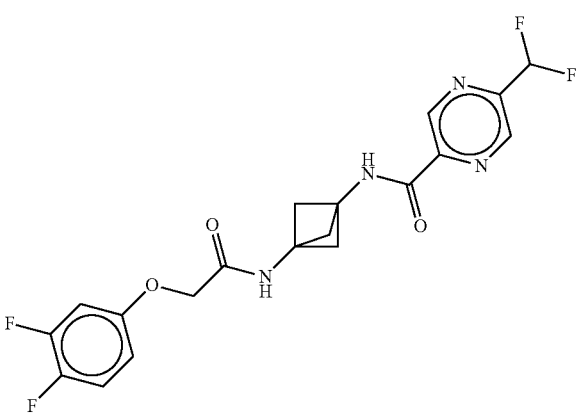 |

TABLE 1-continued
Exemplary compounds of the invention
| Compound No. | Structure |
|---|---|
| 279 | 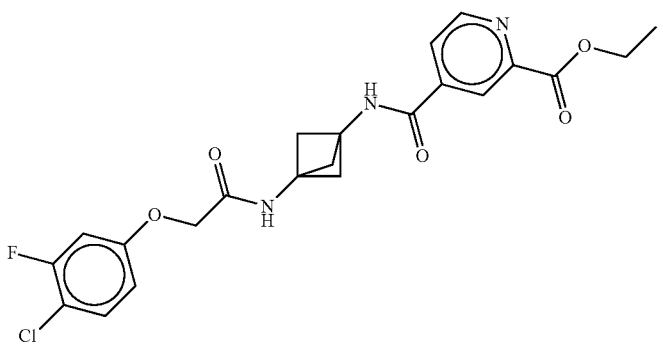 |
| 280 | 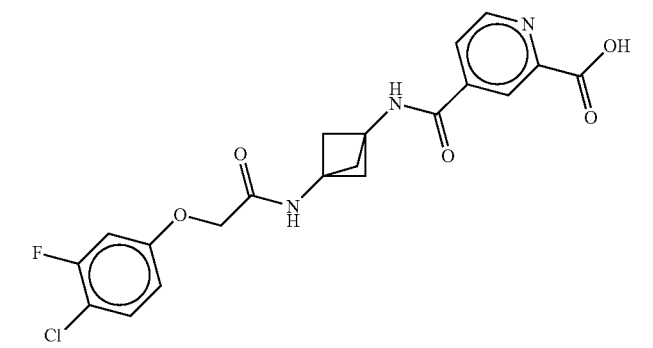 |
| 281 | 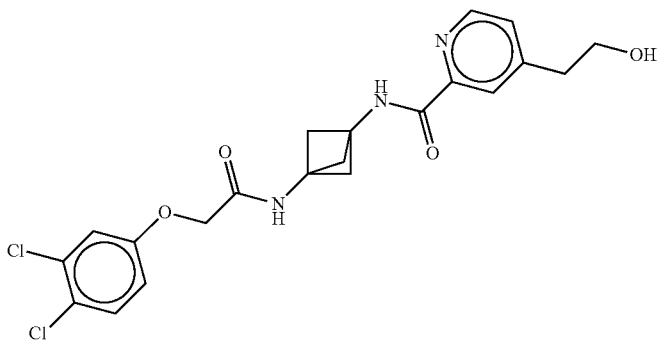 |
| 282 | 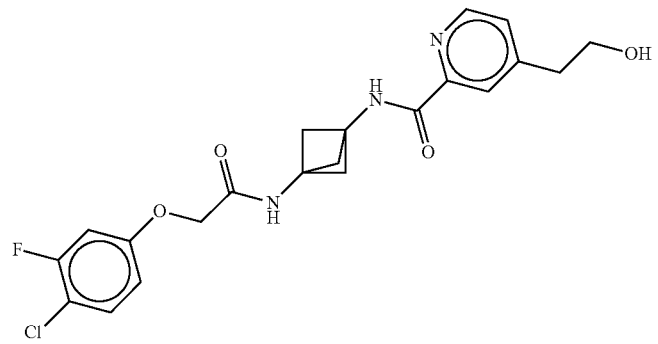 |

TABLE 1-continued
Exemplary compounds of the invention
| Compound No. | Structure |
| --- | --- |
| 283 | 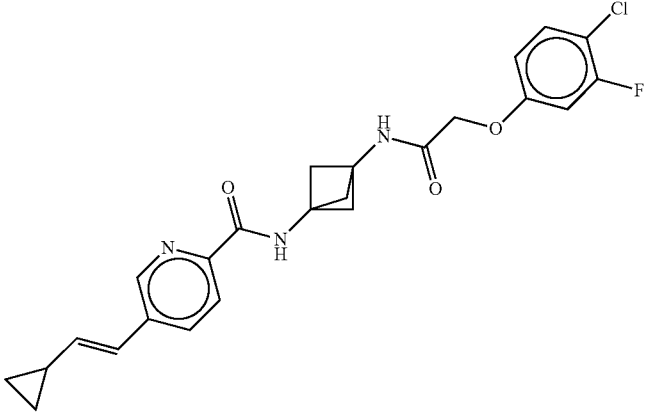 |
| 284 | 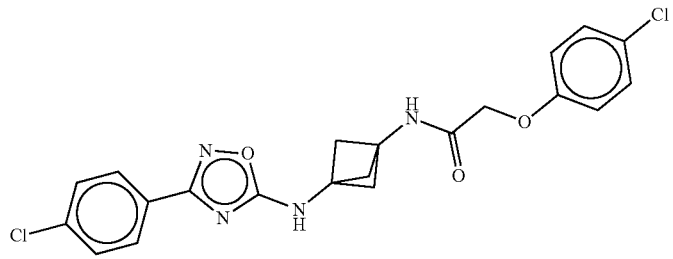 |
| 285 | 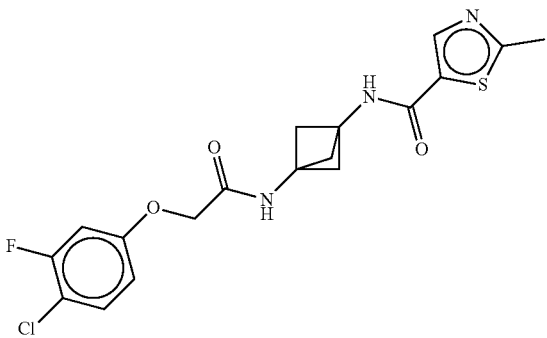 |
| 286 | 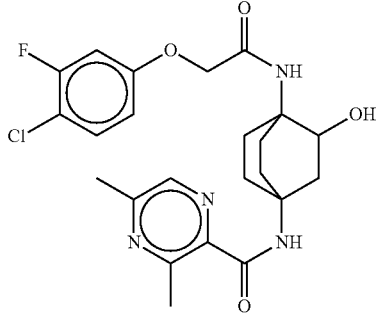 |

TABLE 1-continued
Exemplary compounds of the invention
| Compound No. | Structure |
|---|---|
| 287 | 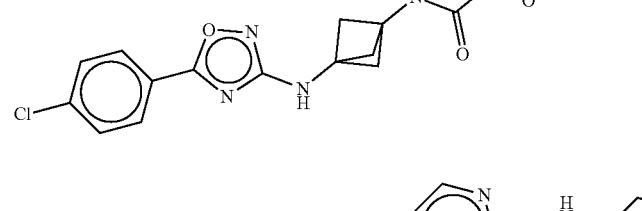 |
| 288 | 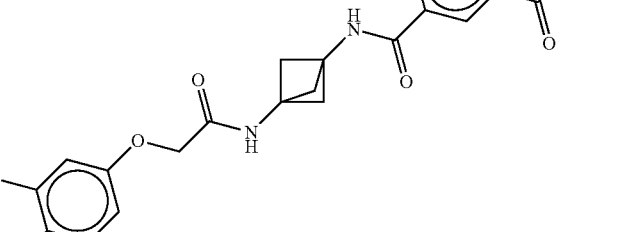 |
| 289 |  |
| 290 | 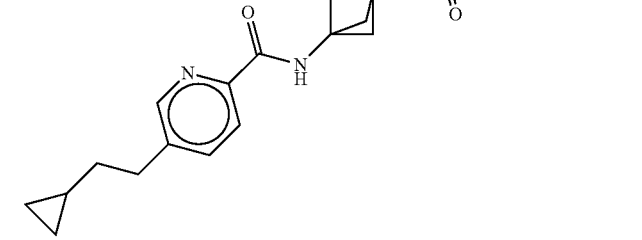 |

TABLE 1-continued

Exemplary compounds of the invention

| Compound No. | Structure |
|---|---|
| 291 | |
| 292 | |
| 293 | |
| 294 | |

TABLE 1-continued

| Compound No. | Exemplary compounds of the invention Structure |
|---|---|
| 295 | |
| 296 | |
| 297 | |
| 298 | |

TABLE 1-continued
Exemplary compounds of the invention
| Compound No. | Structure |
|---|---|
| 299 | 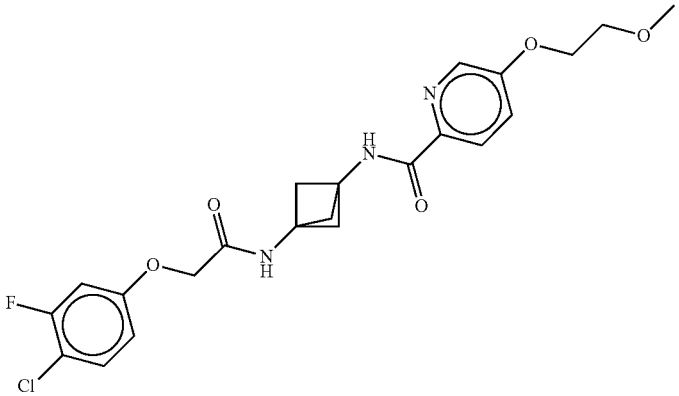 |
| 300 | 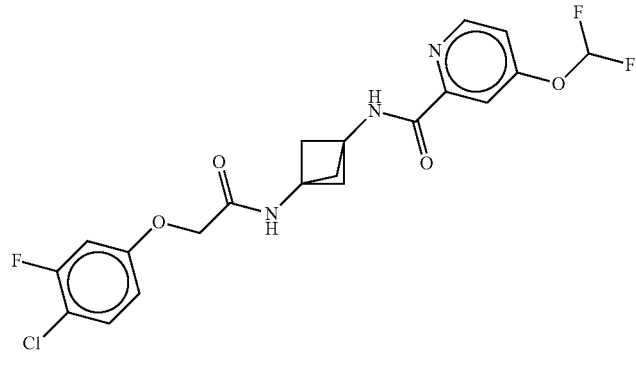 |
| 301 | 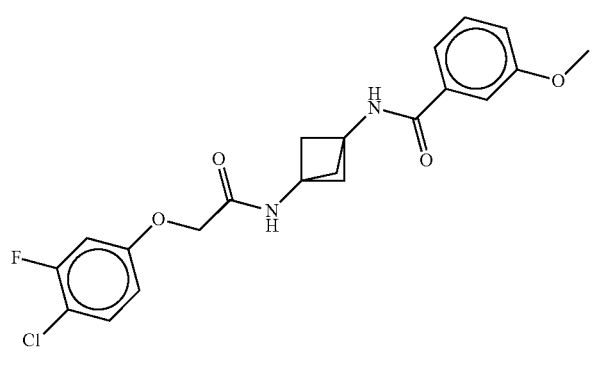 |
| 302 | 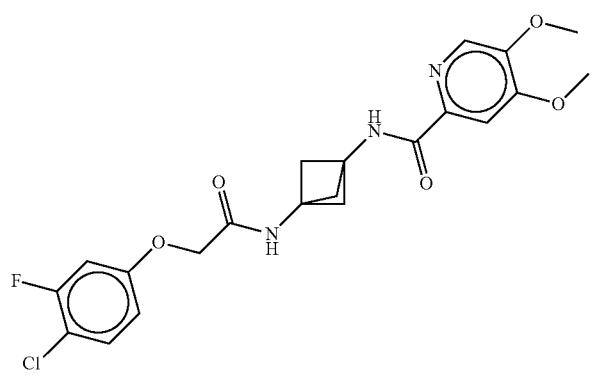 |

TABLE 1-continued
Exemplary compounds of the invention
| Compound No. | Structure |
| --- | --- |
| 303 | 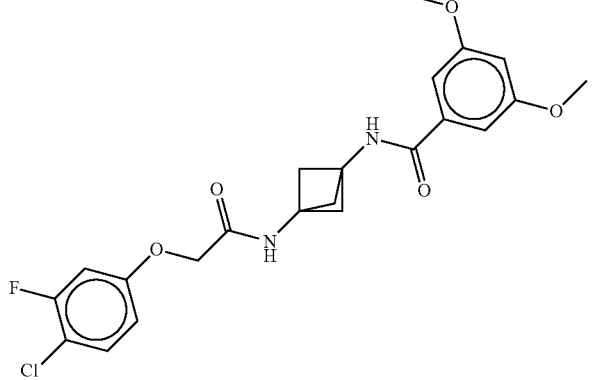 |
| 304 | 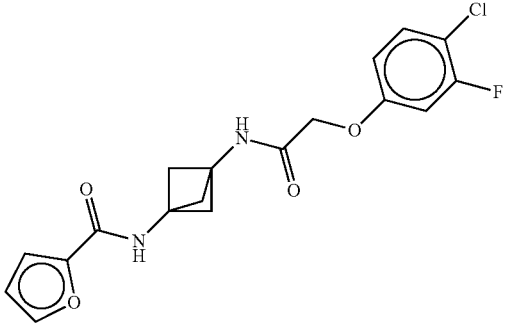 |
| 305 | 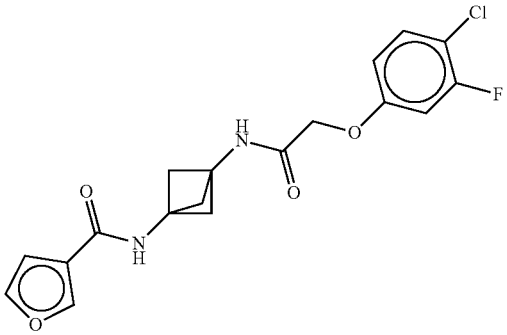 |
| 306 | 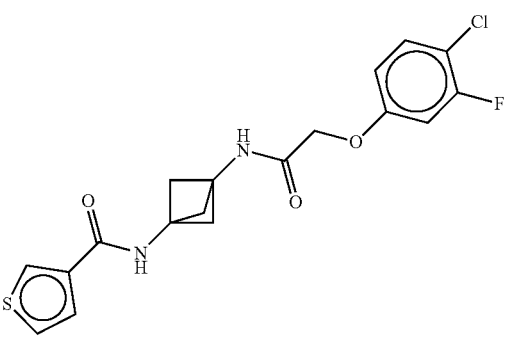 |

TABLE 1-continued
Exemplary compounds of the invention
| Compound No. | Structure |
|---|---|
| 307 | 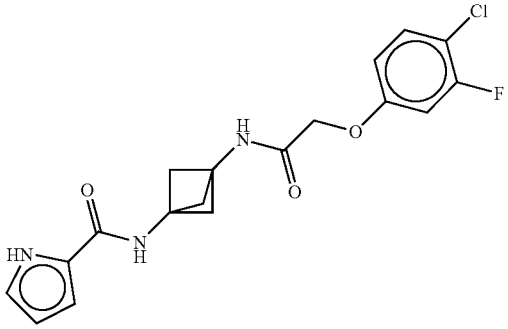 |
| 308 | 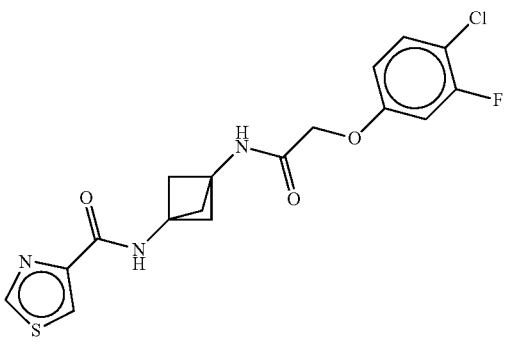 |
| 309 | 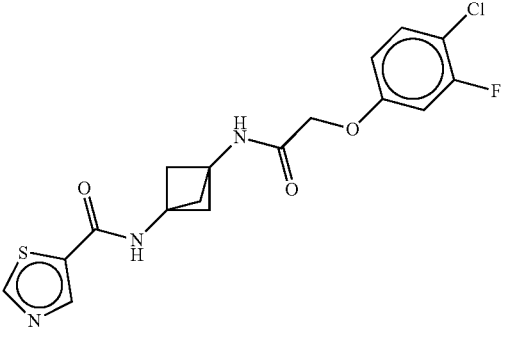 |
| 310 | 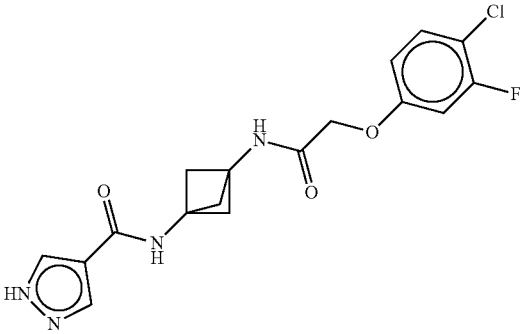 |

TABLE 1-continued

Exemplary compounds of the invention

| Compound No. | Structure |
|---|---|
| 311 | |
| 312 | |
| 313 | |
| 314 | |

TABLE 1-continued
Exemplary compounds of the invention
| Compound No. | Structure |
|---|---|
| 315 | 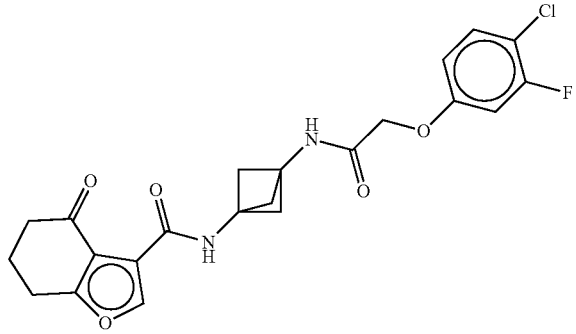 |
| 316 | 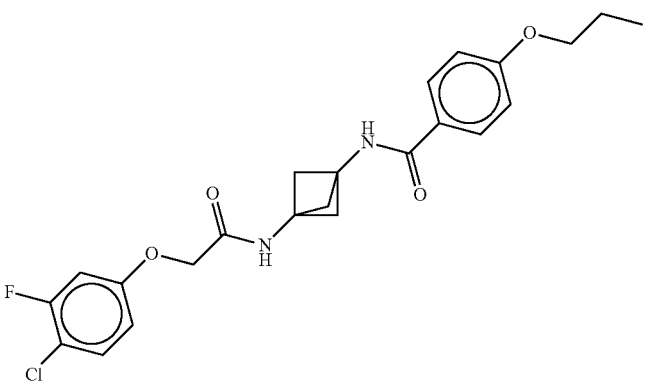 |
| 317 | 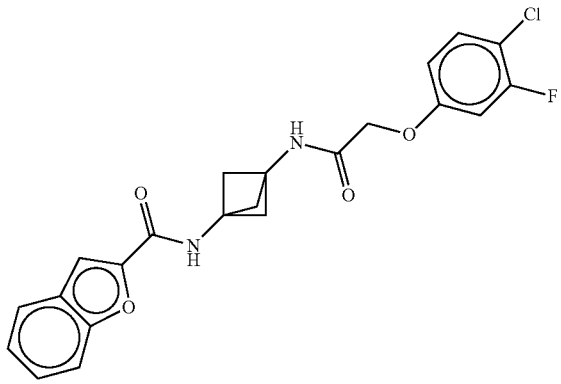 |
| 318 | 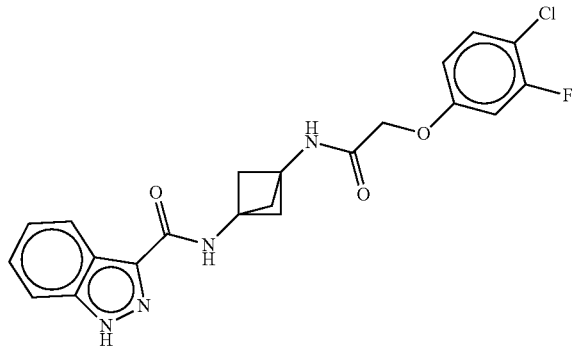 |

TABLE 1-continued

Exemplary compounds of the invention

| Compound No. | Structure |
|---|---|
| 319 | |
| 320 | |
| 321 | |
| 322 | |

TABLE 1-continued

Exemplary compounds of the invention

| Compound No. | Structure |
|---|---|
| 323 | |
| 324 | |
| 325 | |
| 326 | |

TABLE 1-continued

Exemplary compounds of the invention

| Compound No. | Structure |
|---|---|
| 327 | |
| 328 | |
| 329 | |
| 330 | |

TABLE 1-continued
Exemplary compounds of the invention
| Compound No. | Structure |
|---|---|
| 331 | 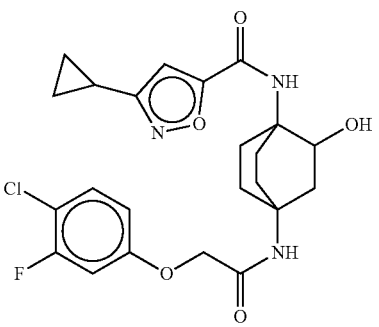 |
| 332 | 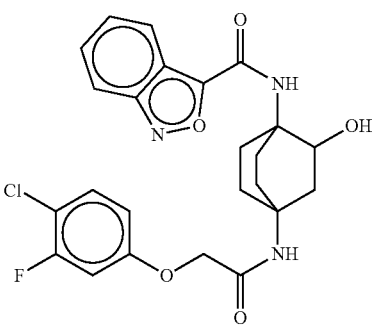 |
| 333 | 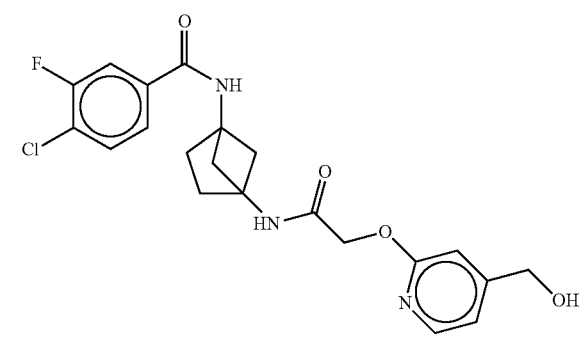 |
| 334 | 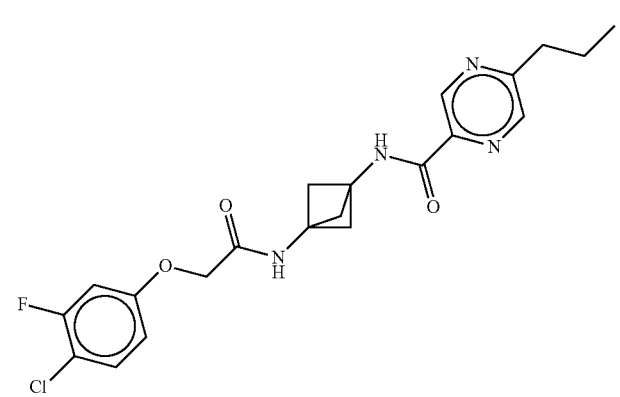 |

TABLE 1-continued

Exemplary compounds of the invention

| Compound No. | Structure |
|---|---|
| 335 | |
| 336 | |
| 337 | |
| 338 | |

TABLE 1-continued

| Compound No. | Exemplary compounds of the invention Structure |
|---|---|
| 339 | |
| 340 | |
| 341 | |
| 342 | |
| 343 | |

TABLE 1-continued
Exemplary compounds of the invention
| Compound No. | Structure |
|---|---|
| 344 | 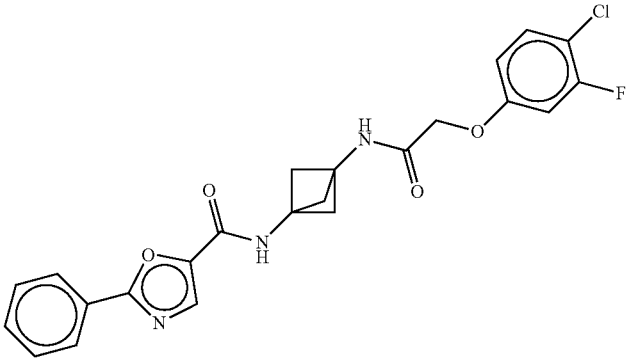 |
| 345 | 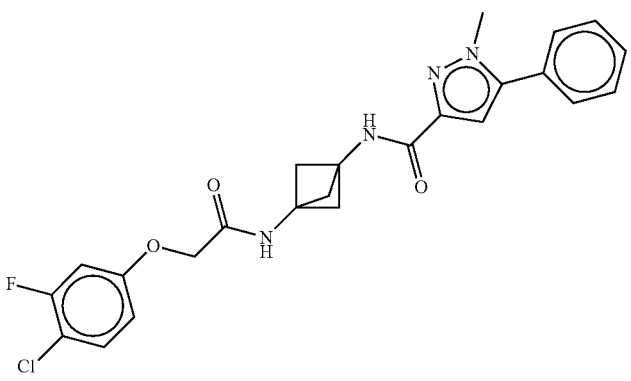 |
| 346 | 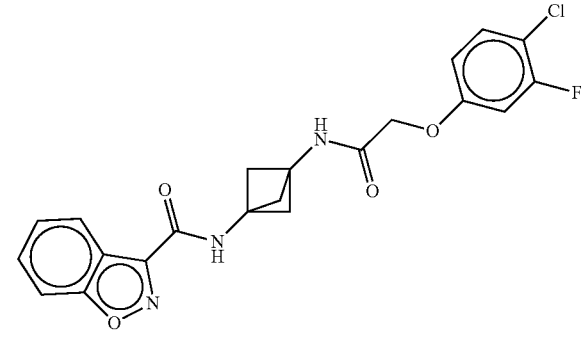 |
| 347 | 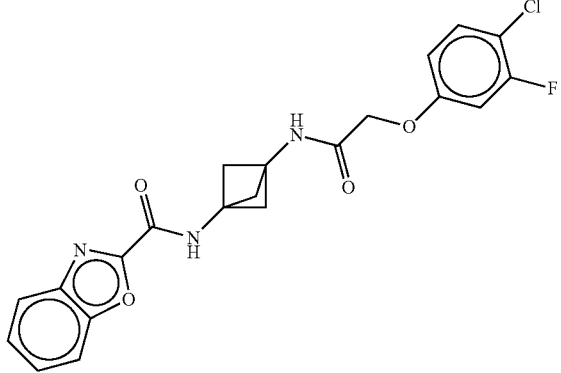 |

TABLE 1-continued

Exemplary compounds of the invention

| Compound No. | Structure |
| --- | --- |
| 348 | |
| 349 | |
| 350 | |
| 351 | |

TABLE 1-continued

Exemplary compounds of the invention

| Compound No. | Structure |
| --- | --- |
| 352 | |
| 353 | |
| 354 | |
| 355 | |

TABLE 1-continued

Exemplary compounds of the invention

| Compound No. | Structure |
|---|---|
| 356 | |
| 357 | |
| 358 | |
| 359 | |

TABLE 1-continued

Exemplary compounds of the invention

| Compound No. | Structure |
|---|---|
| 360 | |
| 361 | |
| 362 | |
| 363 | |

TABLE 1-continued
Exemplary compounds of the invention
| Compound No. | Structure |
|---|---|
| 364 | 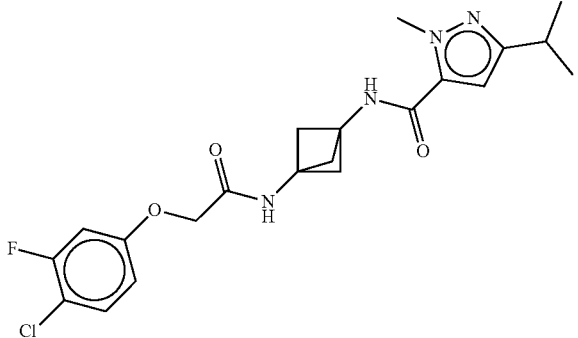 |
| 365 | 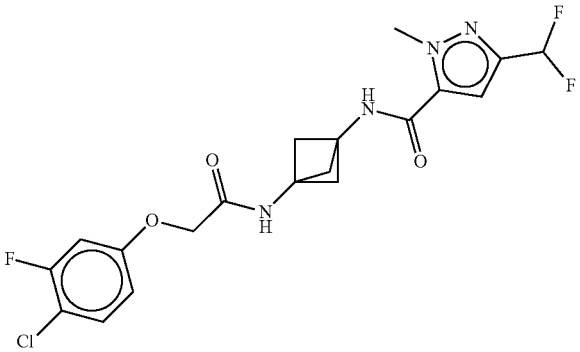 |
| 366 | 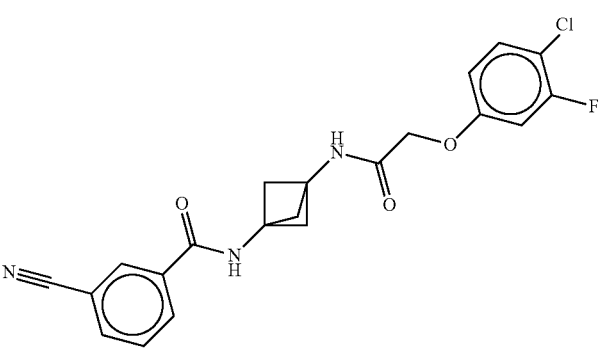 |
| 367 | 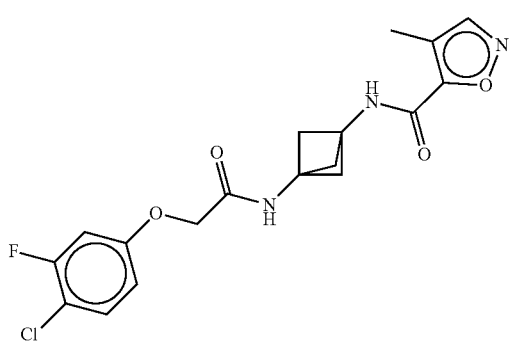 |

TABLE 1-continued
Exemplary compounds of the invention
| Compound No. | Structure |
|---|---|
| 368 | 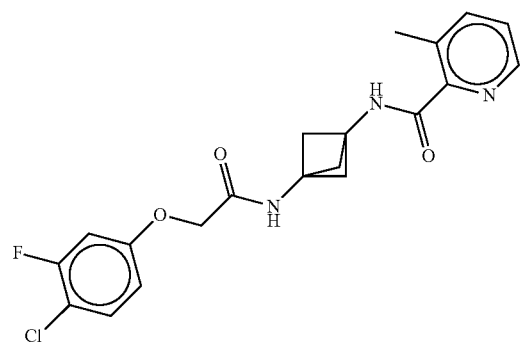 |
| 369 | 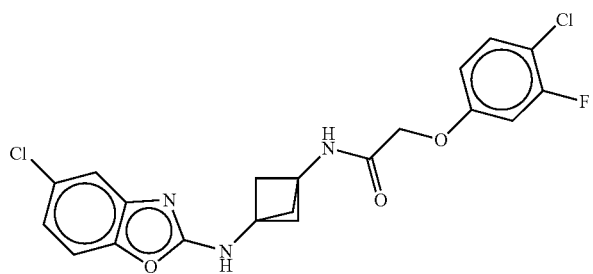 |
| 370 | 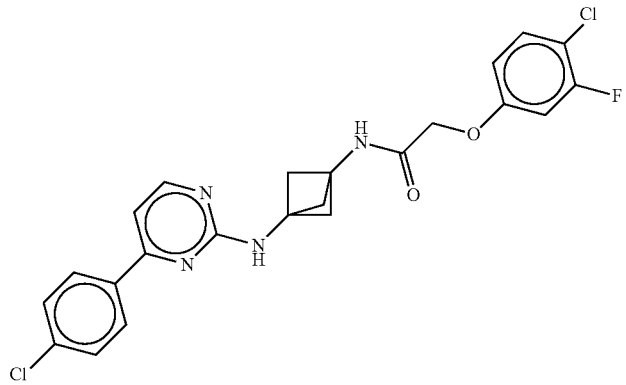 |
| 371 | 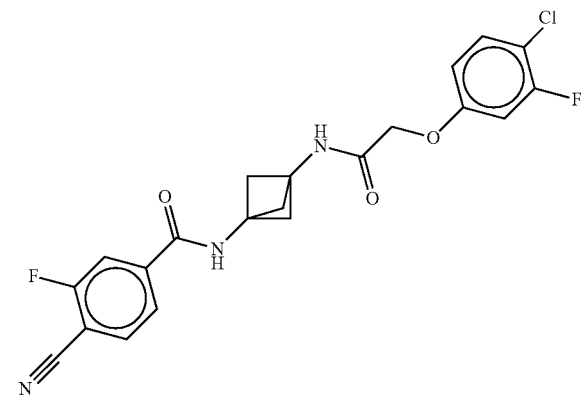 |

TABLE 1-continued

Exemplary compounds of the invention

| Compound No. | Structure |
| --- | --- |
| 372 | |
| 373 | |
| 374 | |
| 375 | |

TABLE 1-continued
Exemplary compounds of the invention
| Compound No. | Structure |
|---|---|
| 376 | 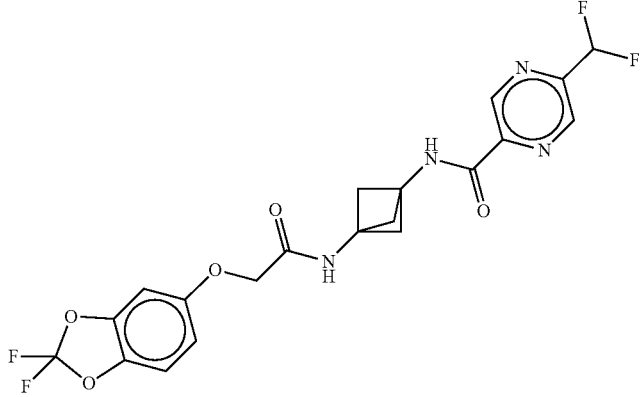 |
| 377 | 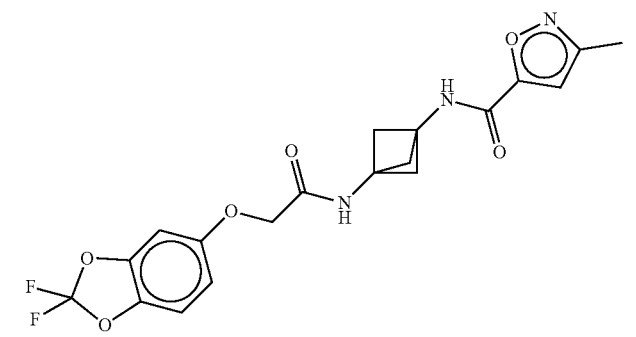 |
| 378 | 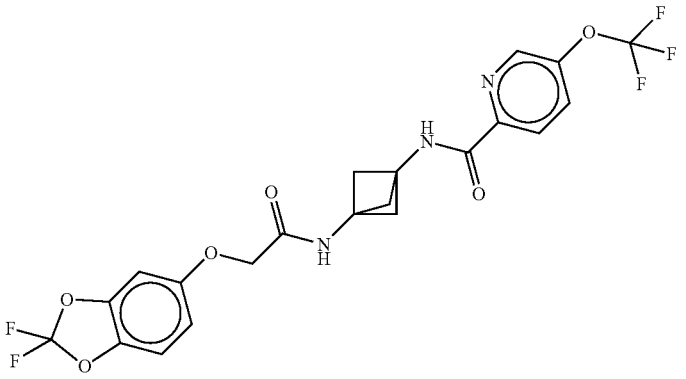 |
| 379 | 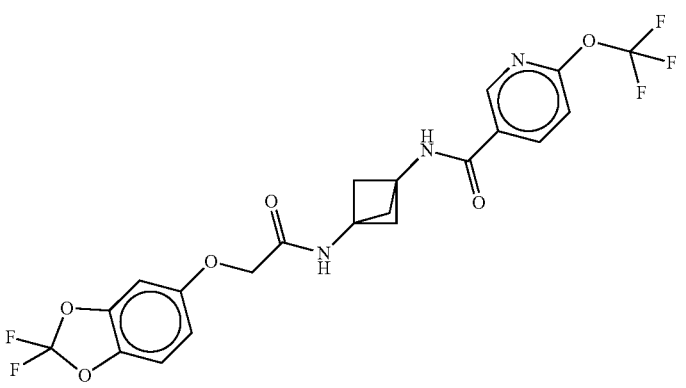 |

TABLE 1-continued

Exemplary compounds of the invention

| Compound No. | Structure |
|---|---|
| 380 | |
| 381 | |
| 382 | |
| 383 | |

TABLE 1-continued
Exemplary compounds of the invention
| Compound No. | Structure |
|---|---|
| 384 | 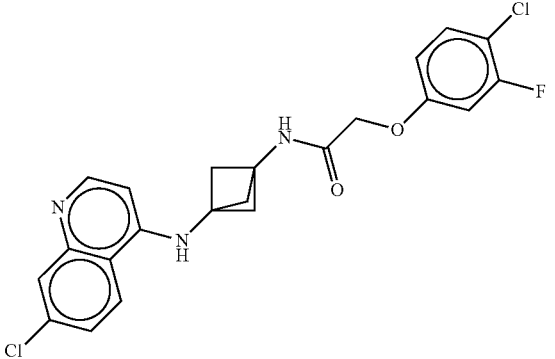 |
| 385 | 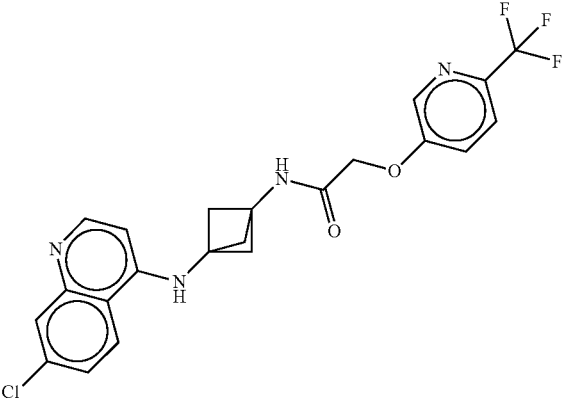 |
| 386 | 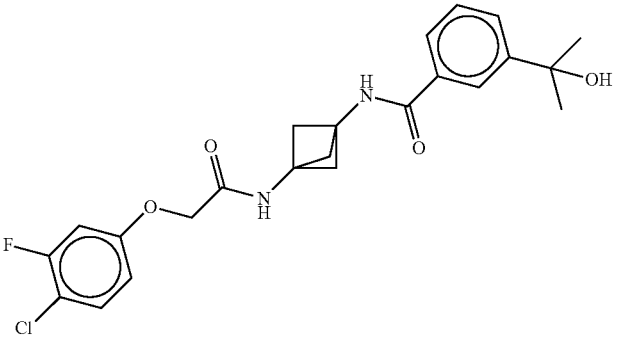 |
| 387 | 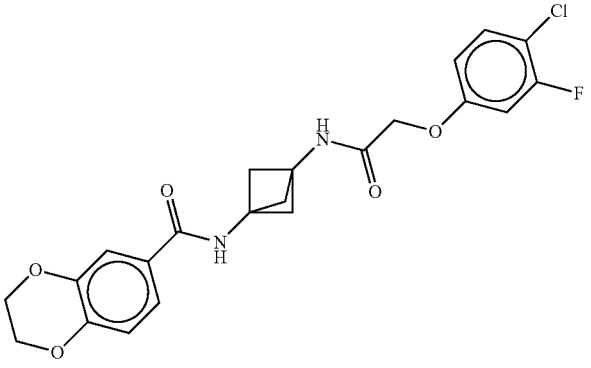 |

TABLE 1-continued

Exemplary compounds of the invention

| Compound No. | Structure |
|---|---|
| 388 | |
| 389 | |
| 390 | |
| 391 | |

TABLE 1-continued

Exemplary compounds of the invention

| Compound No. | Structure |
| --- | --- |
| 392 | |
| 393 | |
| 394 | |
| 395 | |

TABLE 1-continued

Exemplary compounds of the invention

| Compound No. | Structure |
|---|---|
| 396 | |
| 397 | |
| 398 | |
| 399 | |

TABLE 1-continued
Exemplary compounds of the invention
| Compound No. | Structure |
|---|---|
| 400 | 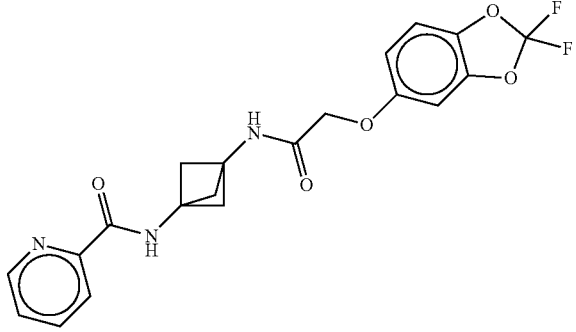 |
| 401 | 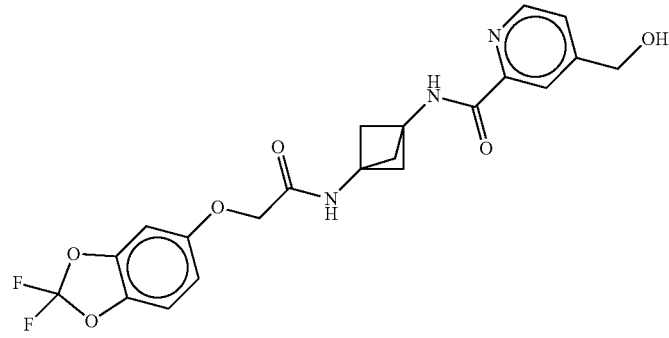 |
| 402 | 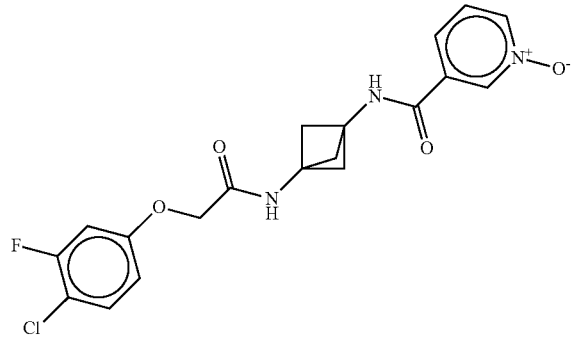 |
| 403 | 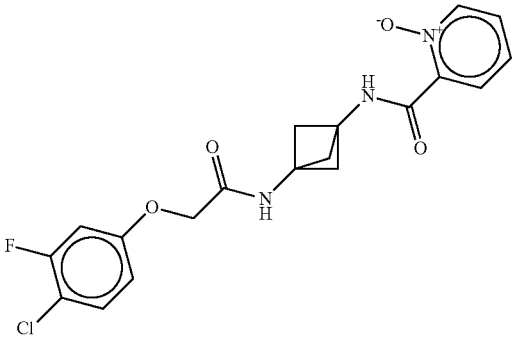 |

TABLE 1-continued

Exemplary compounds of the invention

| Compound No. | Structure |
| --- | --- |
| 404 | |
| 405 | |
| 406 | |
| 407 | |

TABLE 1-continued

Exemplary compounds of the invention

| Compound No. | Structure |
|---|---|
| 408 | |
| 409 | |
| 410 | |
| 411 | |

TABLE 1-continued

| Compound No. | Exemplary compounds of the invention Structure |
|---|---|
| 412 | |
| 413 | |
| 414 | |
| 415 | |
| 416 | |

TABLE 1-continued

Exemplary compounds of the invention

| Compound No. | Structure |
|---|---|
| 417 | |
| 418 | |
| 419 | |
| 420 | |

TABLE 1-continued
Exemplary compounds of the invention
| Compound No. | Structure |
|---|---|
| 421 | 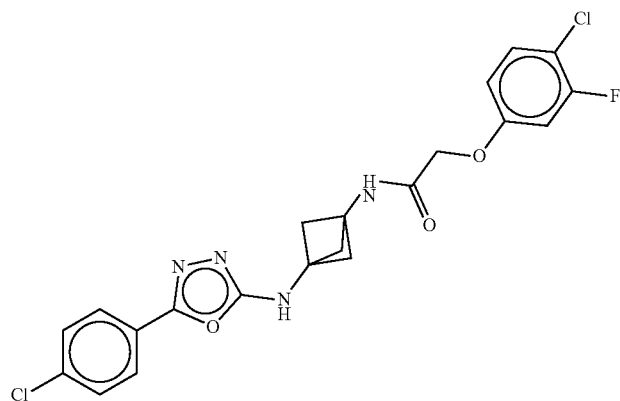 |
| 422 | 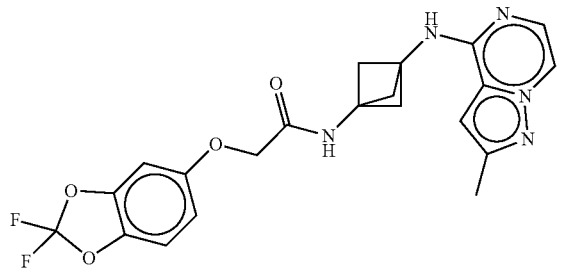 |
| 423 | 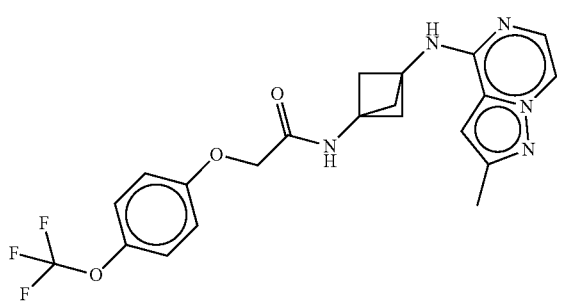 |
| 424 | 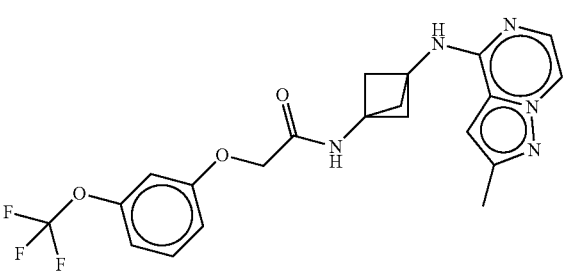 |

TABLE 1-continued

Exemplary compounds of the invention

| Compound No. | Structure |
|---|---|
| 425 | |
| 426 | |
| 427 | |
| 428 | |

TABLE 1-continued
Exemplary compounds of the invention
| Compound No. | Structure |
|---|---|
| 429 | 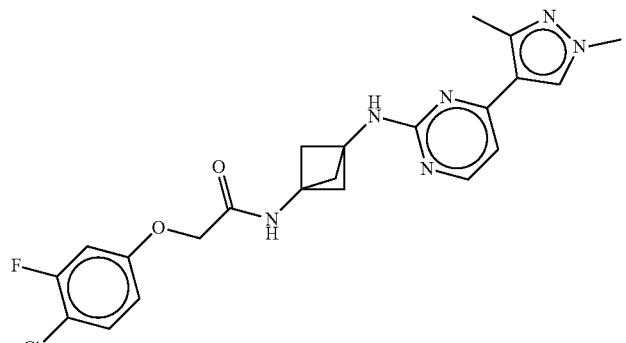 |
| 430 | 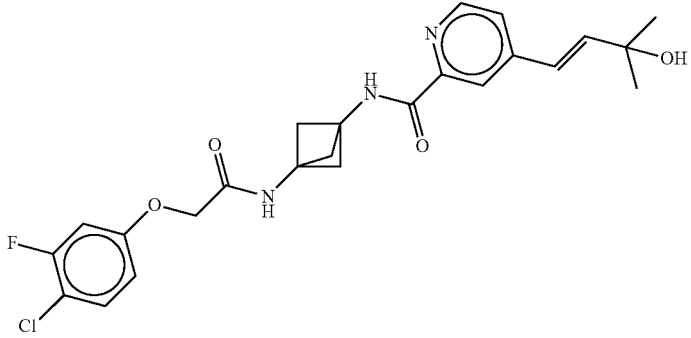 |
| 431 | 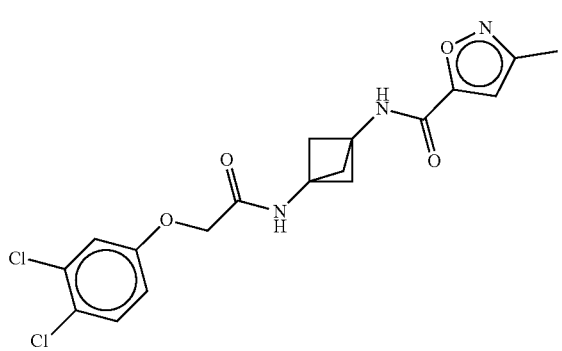 |
| 432 | 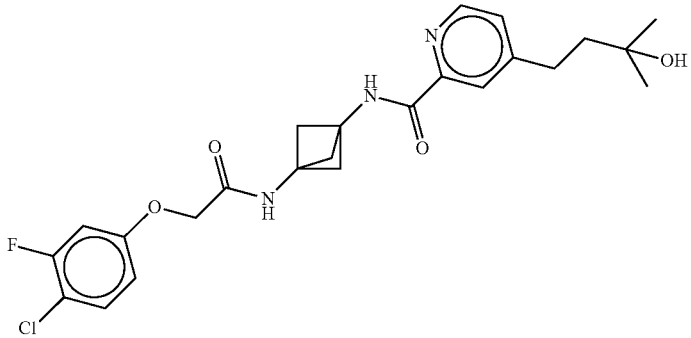 |

TABLE 1-continued
| Compound No. | Exemplary compounds of the invention Structure |
|---|---|
| 433 | 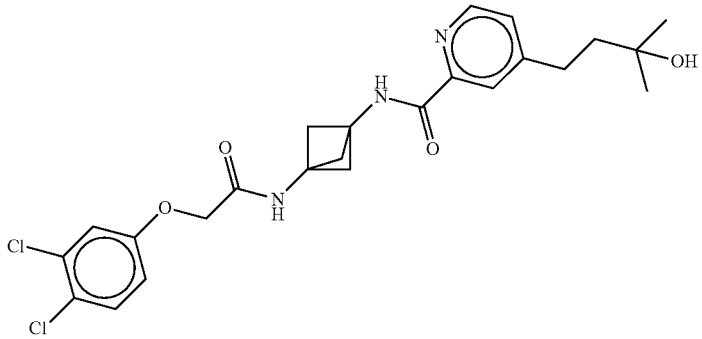 |
| 434 | 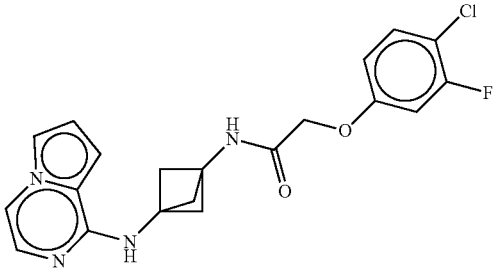 |
| 435 | 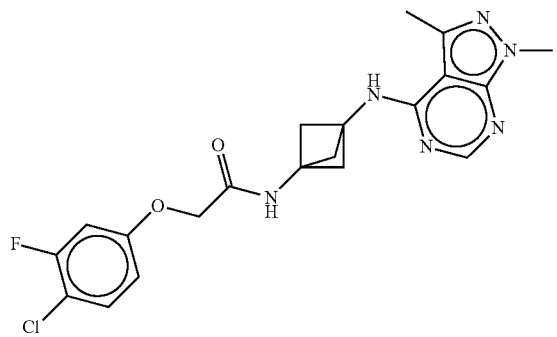 |
| 436 | 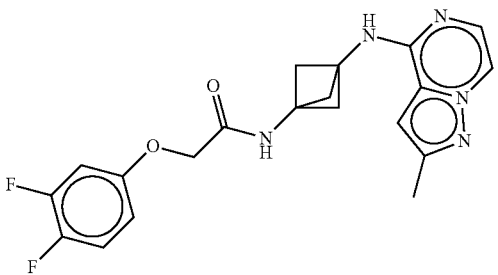 |
| 437 | 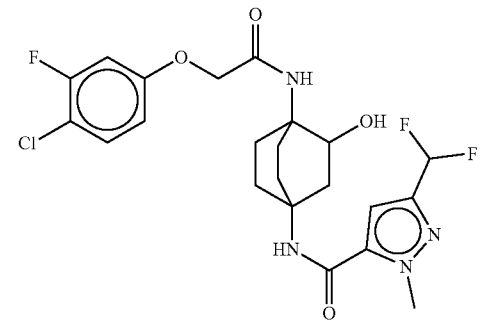 |

TABLE 1-continued
Exemplary compounds of the invention
| Compound No. | Structure |
|---|---|
| 438 | 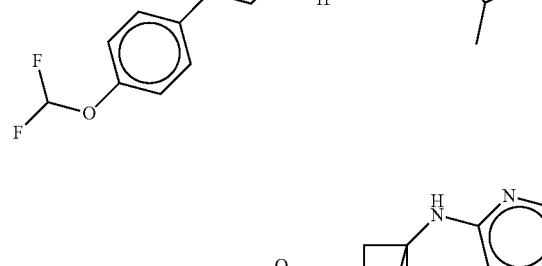 |
| 439 | 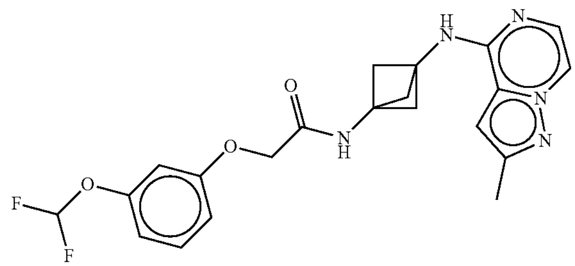 |
| 440 | 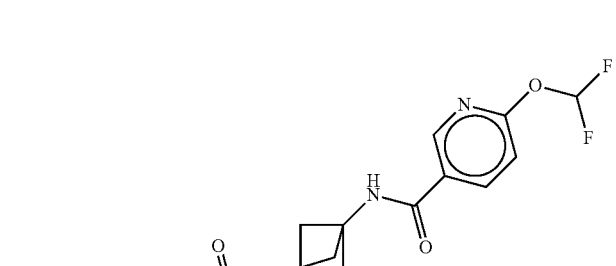 |
| 441 | 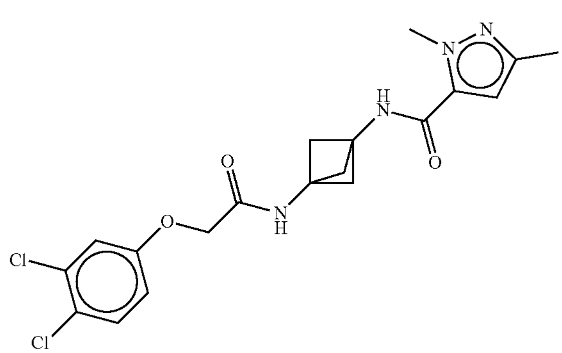 |

TABLE 1-continued
Exemplary compounds of the invention
| Compound No. | Structure |
|---|---|
| 442 | 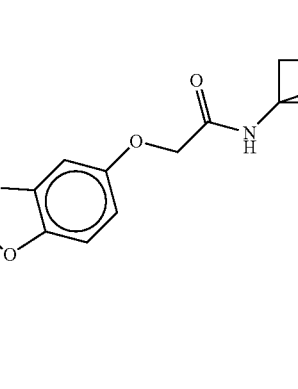 |
| 443 | 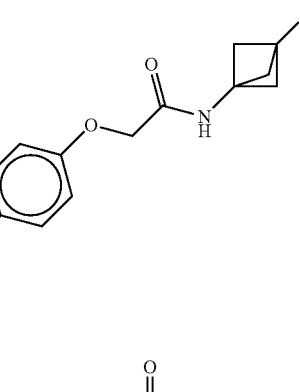 |
| 444 | 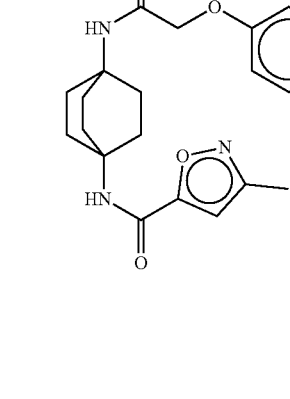 |
| 445 | 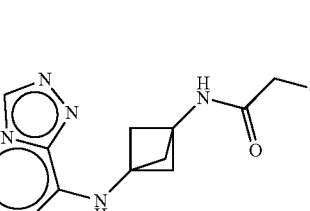 |

TABLE 1-continued

| Compound No. | Exemplary compounds of the invention Structure |
|---|---|
| 446 | (structure) |
| 447 | (structure) |
| 448 | (structure) |
| 449 | (structure) |
| 450 | (structure) |

TABLE 1-continued
Exemplary compounds of the invention
| Compound No. | Structure |
|---|---|
| 451 | 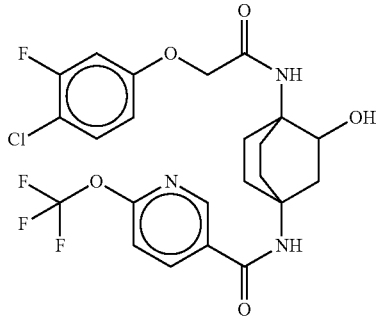 |
| 452 | 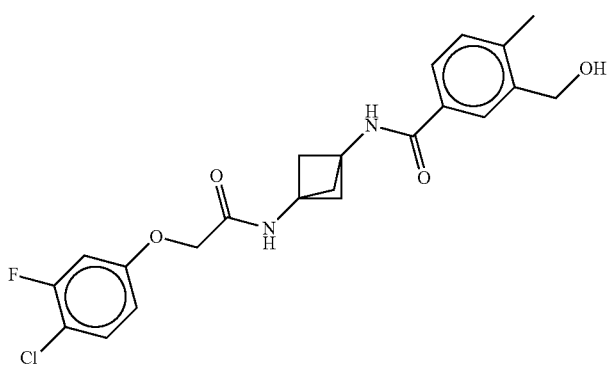 |
| 453 | 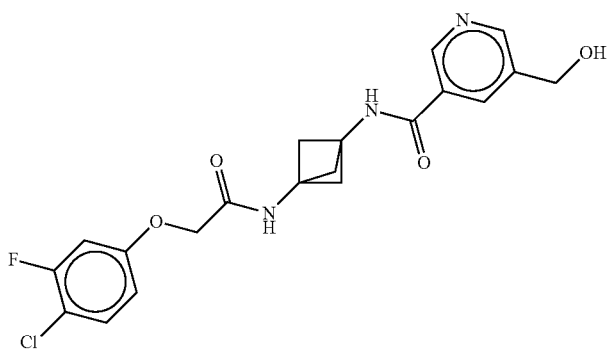 |
| 454 | 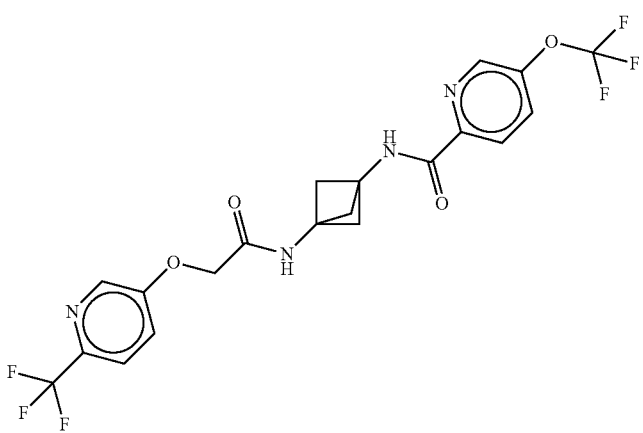 |

TABLE 1-continued
Exemplary compounds of the invention
| Compound No. | Structure |
|---|---|
| 455 | 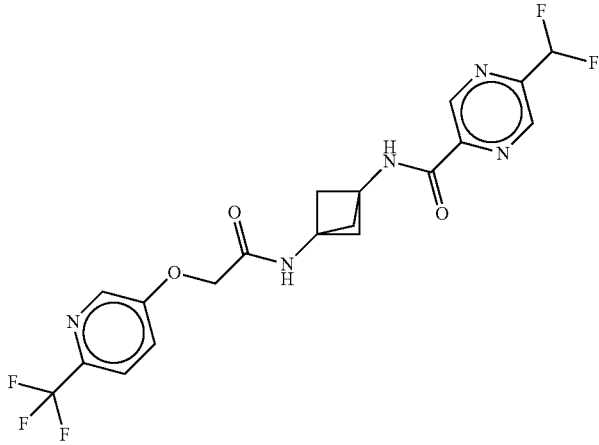 |
| 456 | 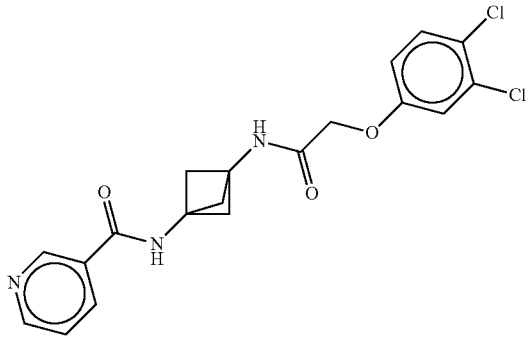 |
| 457 | 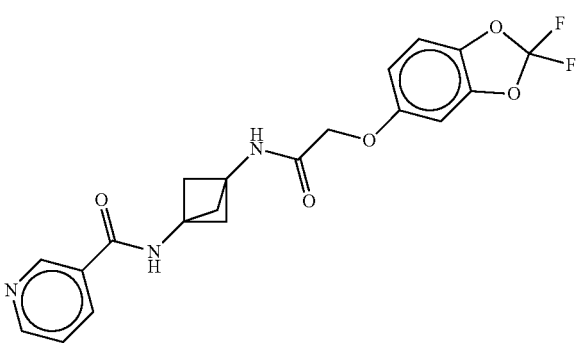 |
| 458 | 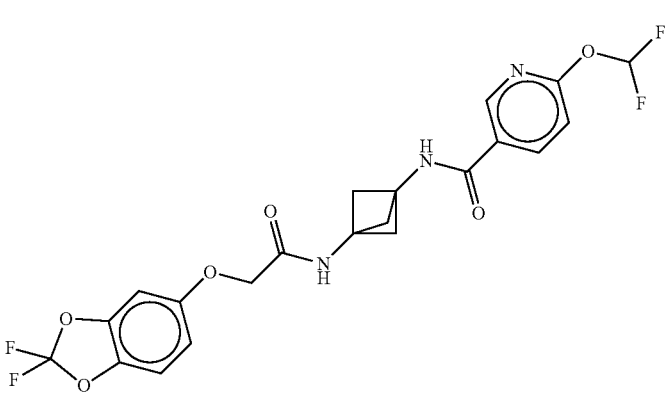 |

TABLE 1-continued
Exemplary compounds of the invention
| Compound No. | Structure |
|---|---|
| 459 | 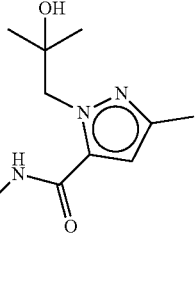 |
| 460 | 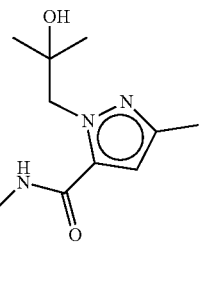 |
| 461 | 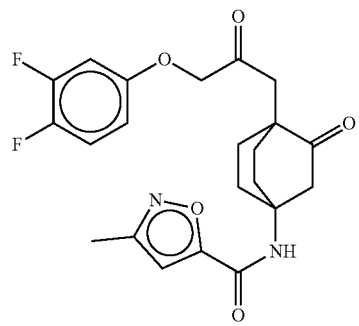 |
| 462 | 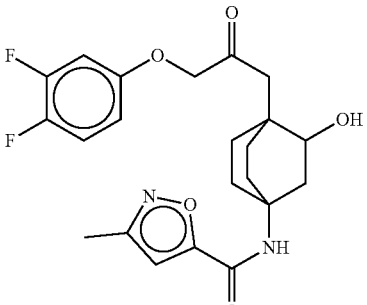 |

TABLE 1-continued

Exemplary compounds of the invention

| Compound No. | Structure |
|---|---|
| 463 | |
| 464 | |
| 465 | |
| 466 | |

TABLE 1-continued
Exemplary compounds of the invention
| Compound No. | Structure |
|---|---|
| 467 | 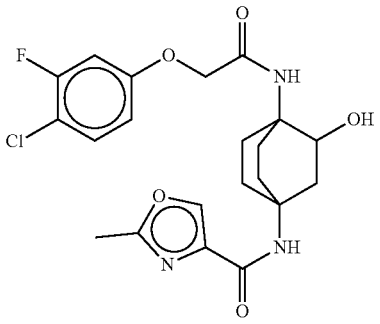 |
| 468 | 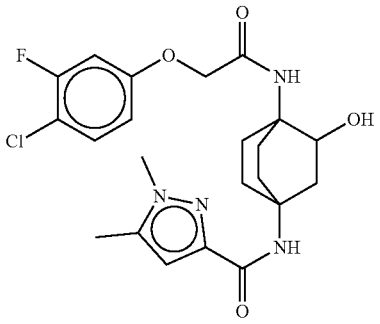 |
| 469 | 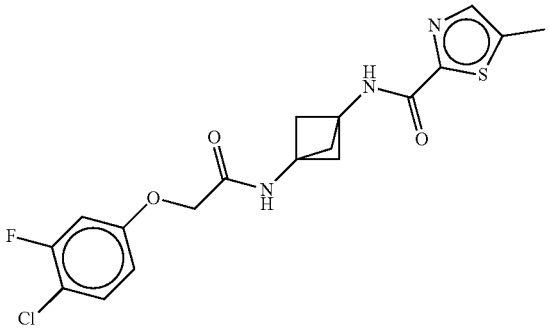 |
| 470 | 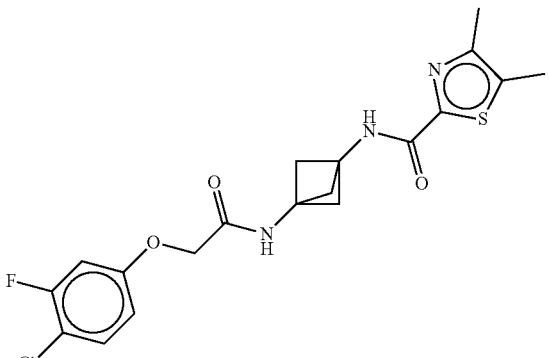 |

TABLE 1-continued

Exemplary compounds of the invention

| Compound No. | Structure |
|---|---|
| 471 | |
| 472 | |
| 473 | |
| 474 | |

TABLE 1-continued
Exemplary compounds of the invention
| Compound No. | Structure |
|---|---|
| 475 | 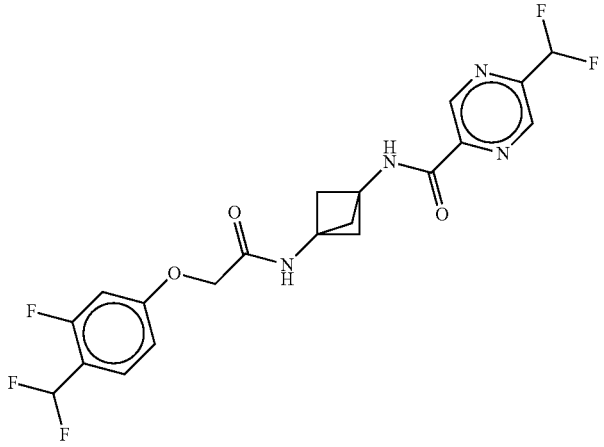 |
| 476 | 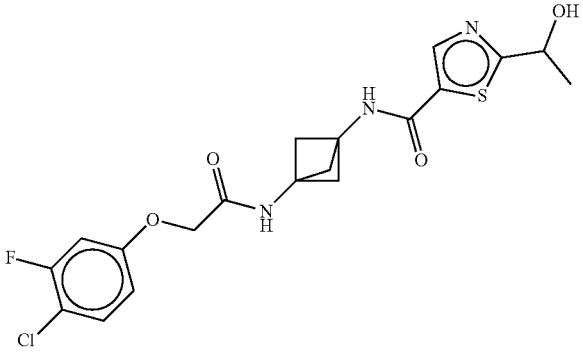 |
| 477 | 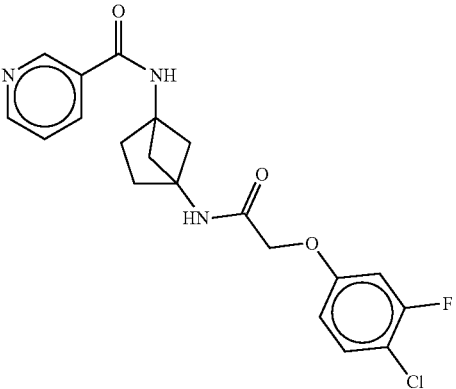 |
| 478 | 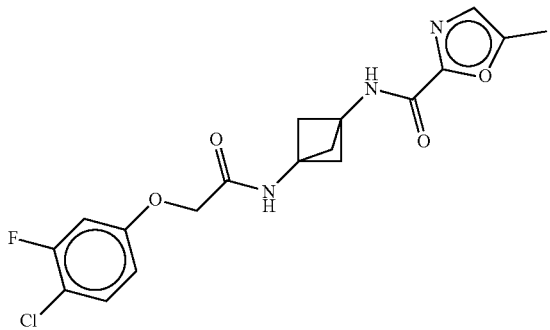 |

TABLE 1-continued
Exemplary compounds of the invention
| Compound No. | Structure |
|---|---|
| 479 | 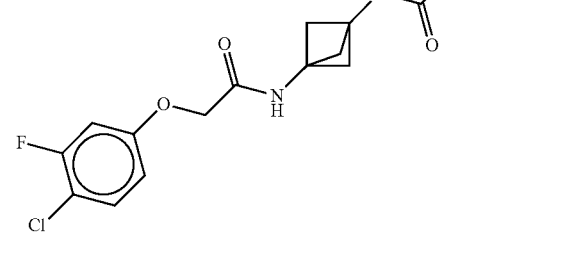 |
| 480 | 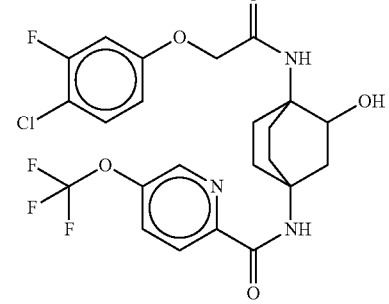 |
| 481 | 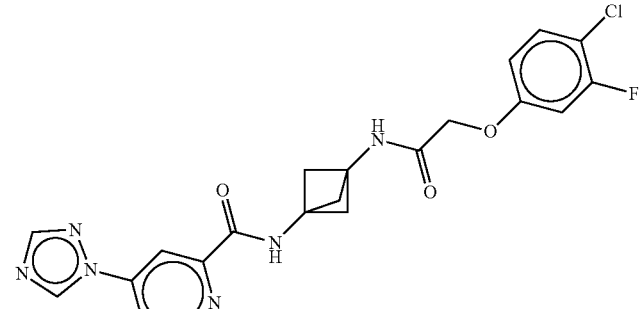 |
| 482 | 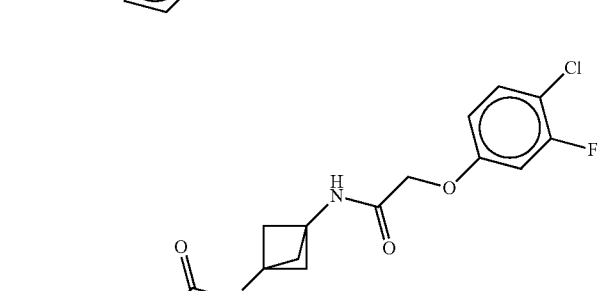 |

TABLE 1-continued
Exemplary compounds of the invention
| Compound No. | Structure |
|---|---|
| 483 |  |
| 484 | 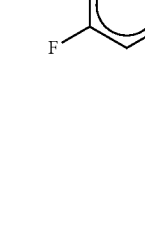 |
| 485 | 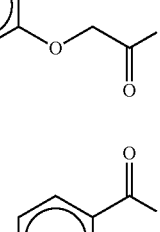 |
| 486 |  |

TABLE 1-continued
| Compound No. | Exemplary compounds of the invention Structure |
|---|---|
| 487 | 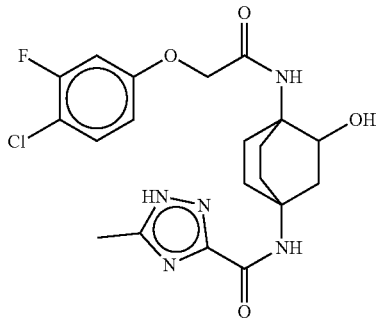 |
| 488 | 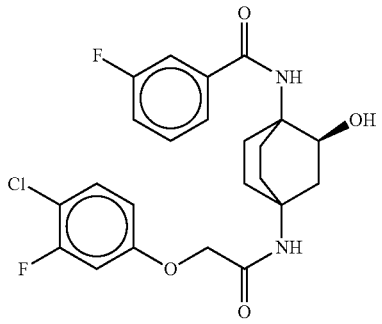 |
| 489 | 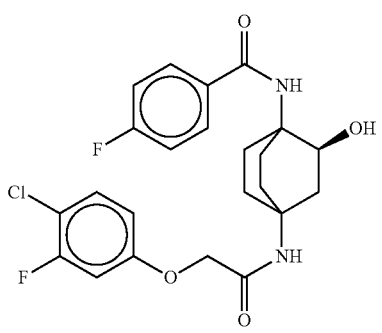 |
| 490 | 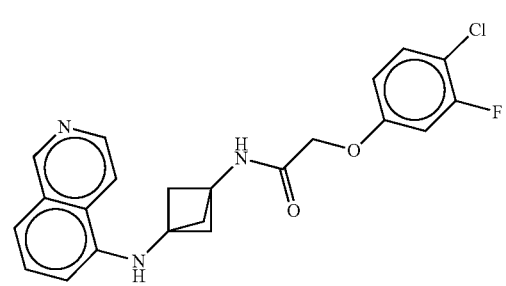 |
| 491 | 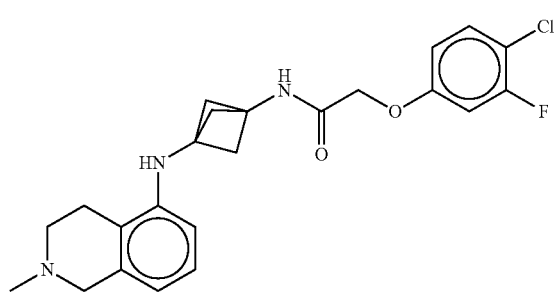 |

TABLE 1-continued

| Compound No. | Exemplary compounds of the invention Structure |
|---|---|
| 492 | |
| 493 | |
| 494 | |
| 495 | |
| 496 | |

TABLE 1-continued
Exemplary compounds of the invention
| Compound No. | Structure |
|---|---|
| 497 | 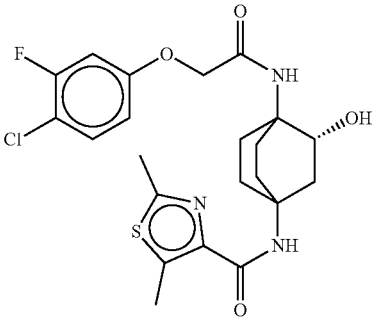 |
| 498 | 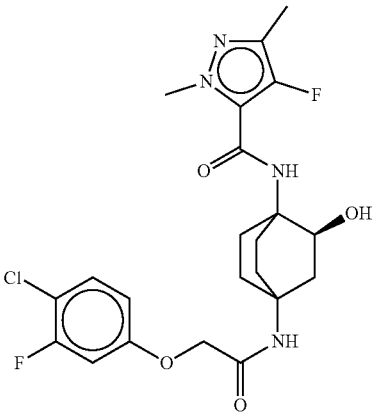 |
| 499 | 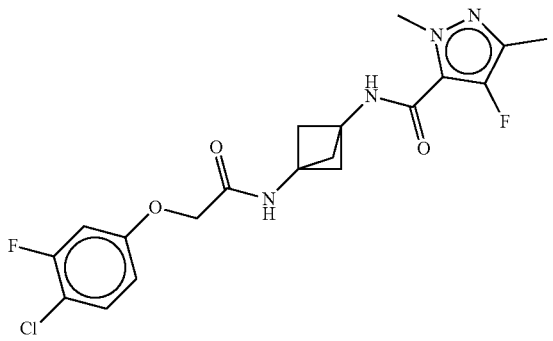 |
| 500 | 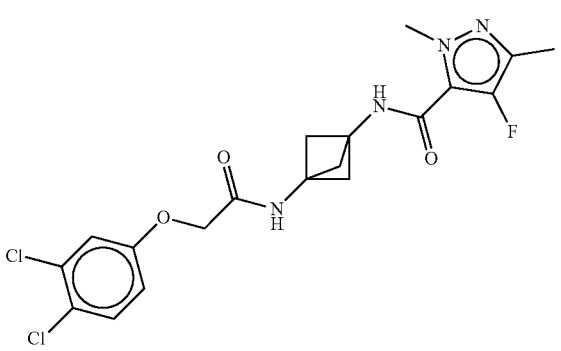 |

TABLE 1-continued

Exemplary compounds of the invention

| Compound No. | Structure |
| --- | --- |
| 501 | |
| 502 | |
| 503 | |
| 504 | |

TABLE 1-continued

Exemplary compounds of the invention

| Compound No. | Structure |
|---|---|
| 505 | |
| 506 | |
| 507 | |
| 508 | |

TABLE 1-continued
Exemplary compounds of the invention
| Compound No. | Structure |
|---|---|
| 509 | 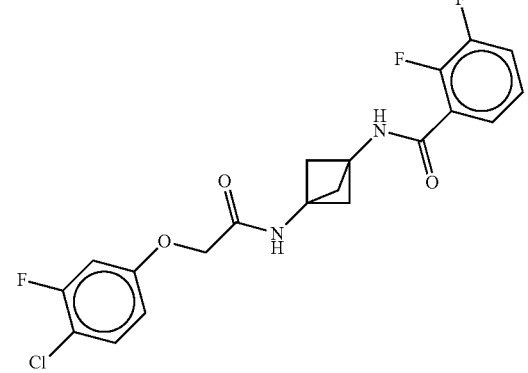 |
| 510 | 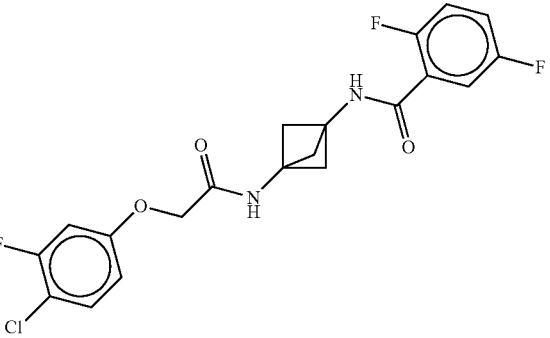 |
| 511 | 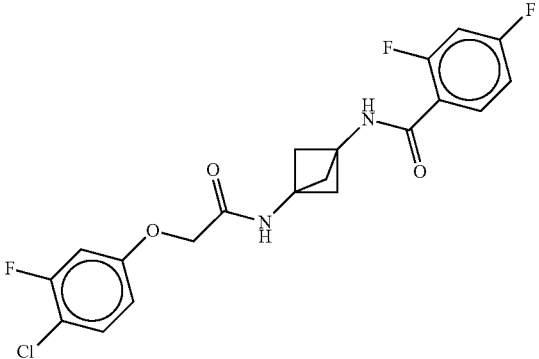 |
| 512 | 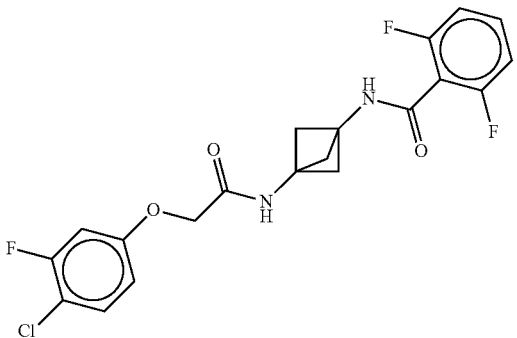 |

TABLE 1-continued

Exemplary compounds of the invention

| Compound No. | Structure |
| --- | --- |
| 513 | |
| 514 | |
| 515 | |
| 516 | |

TABLE 1-continued

Exemplary compounds of the invention

| Compound No. | Structure |
|---|---|
| 517 | |
| 518 | |
| 519 | |
| 520 | |

TABLE 1-continued
Exemplary compounds of the invention
| Compound No. | Structure |
|---|---|
| 521 | 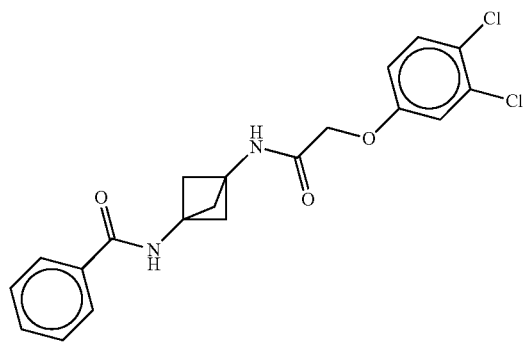 |
| 522 | 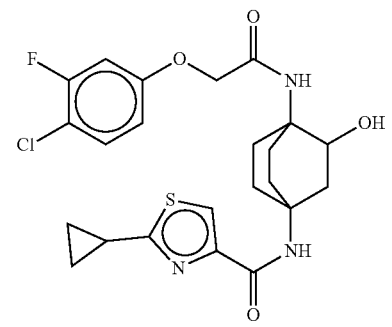 |
| 523 | 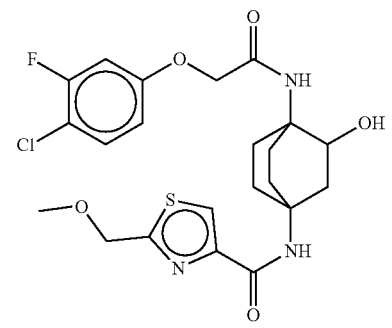 |
| 524 | 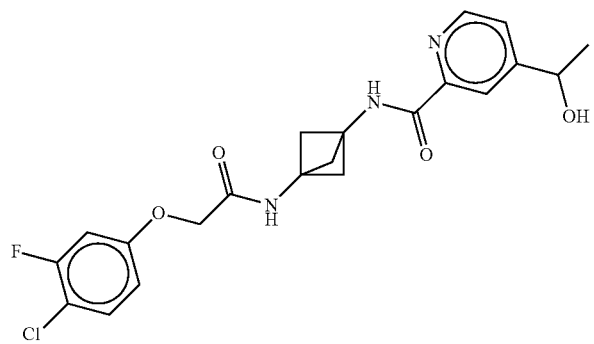 |

TABLE 1-continued

Exemplary compounds of the invention

| Compound No. | Structure |
|---|---|
| 525 | |
| 526 | |
| 527 | |
| 528 | |

TABLE 1-continued
Exemplary compounds of the invention
| Compound No. | Structure |
|---|---|
| 529 | 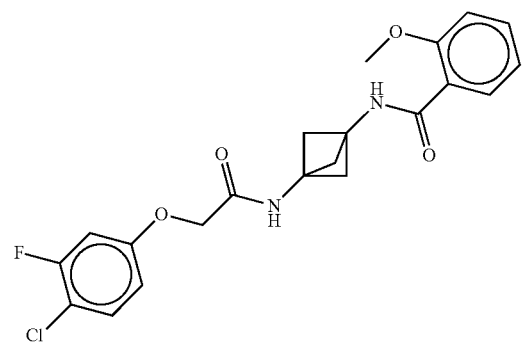 |
| 530 | 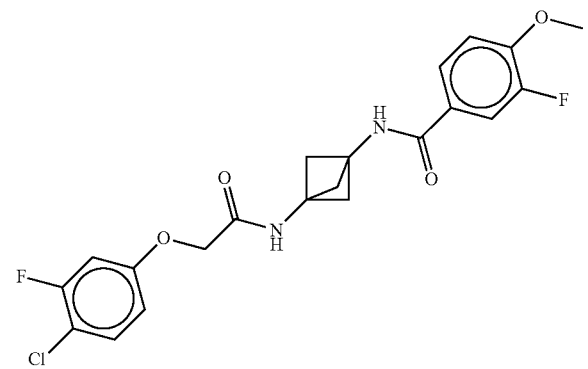 |
| 531 | 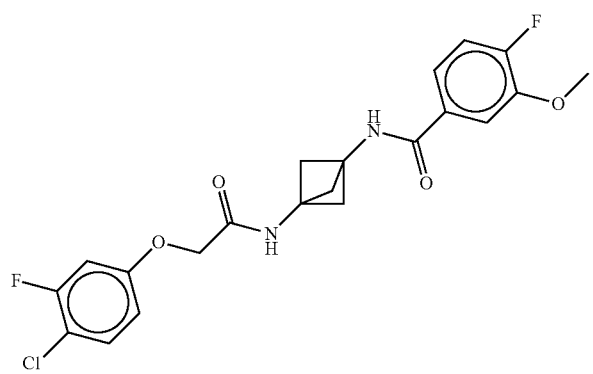 |
| 532 | 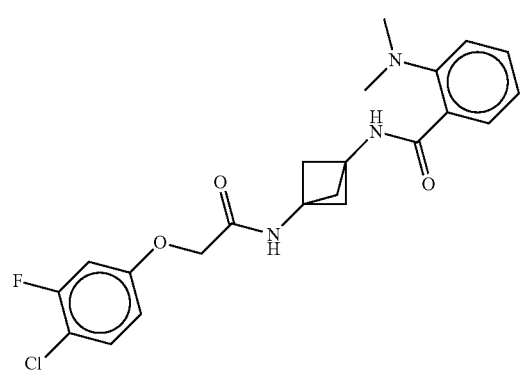 |

TABLE 1-continued
Exemplary compounds of the invention
| Compound No. | Structure |
|---|---|
| 533 | 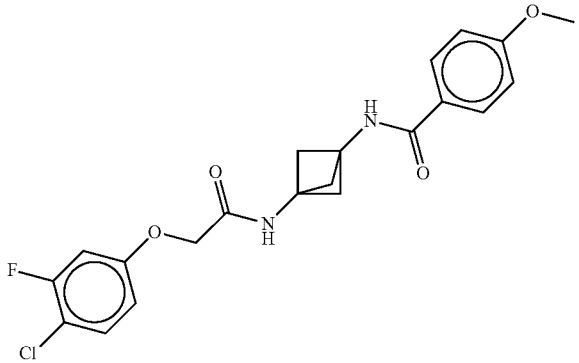 |
| 534 | 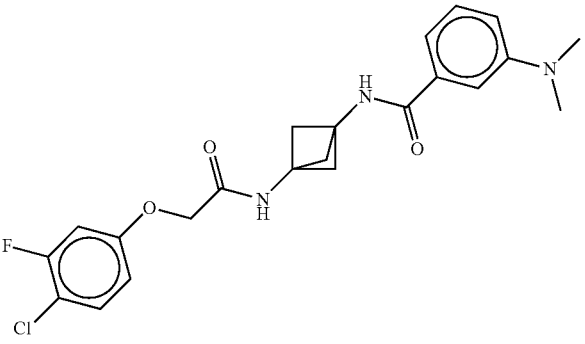 |
| 535 | 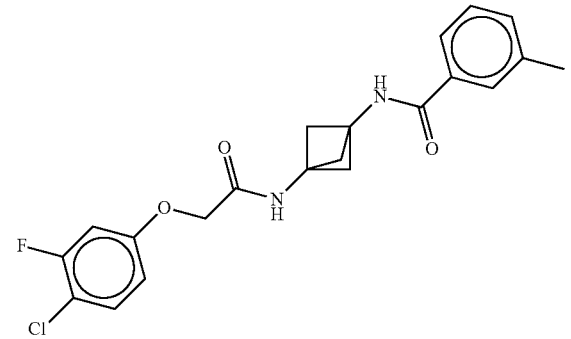 |
| 536 | 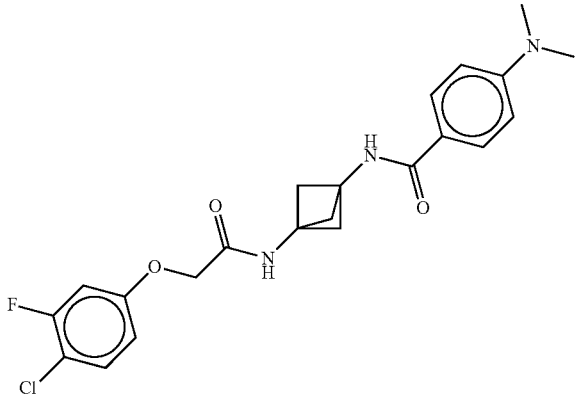 |

TABLE 1-continued

Exemplary compounds of the invention

| Compound No. | Structure |
|---|---|
| 537 | |
| 538 | |
| 539 | |
| 540 | |

TABLE 1-continued

Exemplary compounds of the invention

| Compound No. | Structure |
| --- | --- |
| 541 | |
| 542 | |
| 543 | |
| 544 | |

TABLE 1-continued
Exemplary compounds of the invention
| Compound No. | Structure |
|---|---|
| 545 | 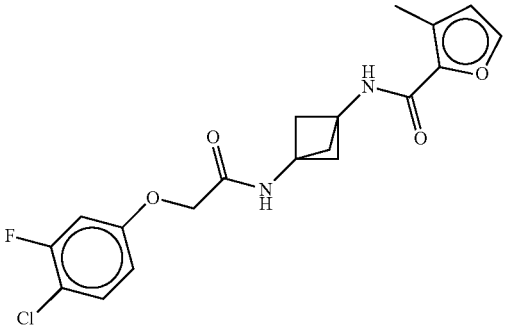 |
| 546 | 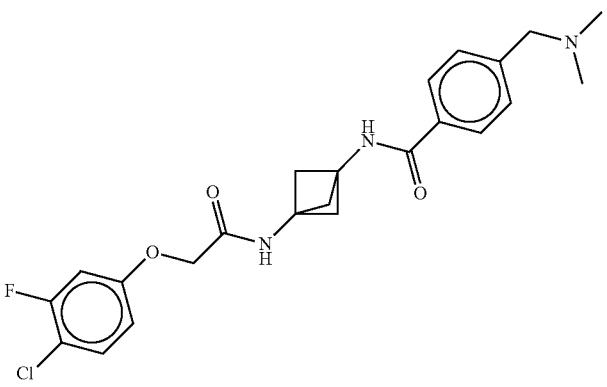 |
| 547 | 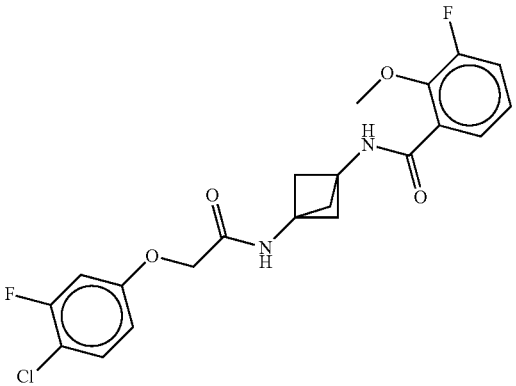 |
| 548 | 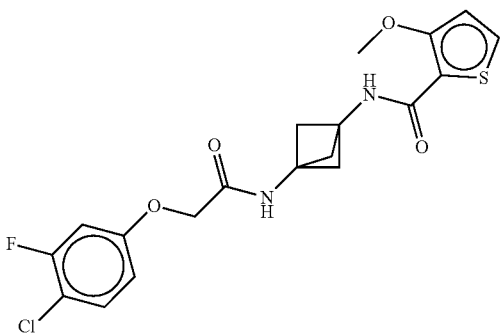 |

TABLE 1-continued
| Compound No. | Exemplary compounds of the invention Structure |
|---|---|
| 549 | 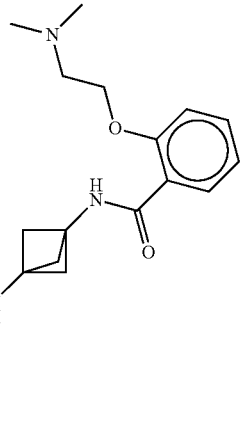 |
| 550 | 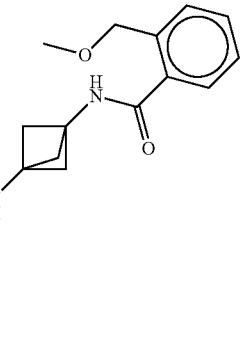 |
| 551 | 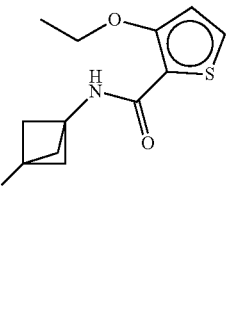 |
| 552 | 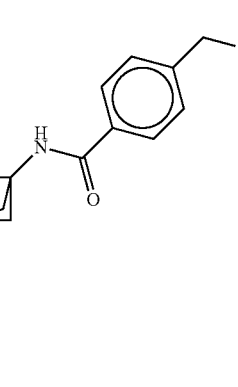 |

TABLE 1-continued
Exemplary compounds of the invention
| Compound No. | Structure |
|---|---|
| 553 | 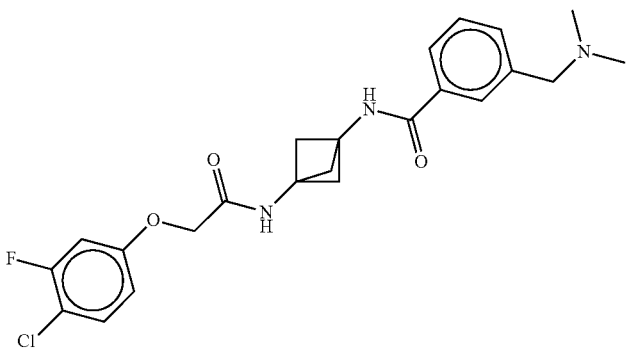 |
| 554 | 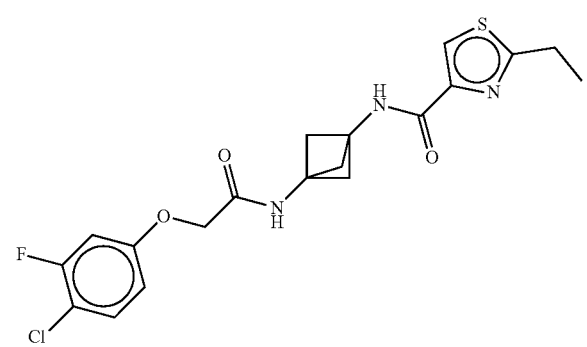 |
| 555 | 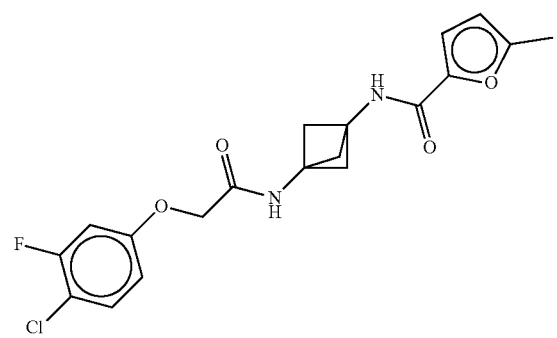 |
| 556 | 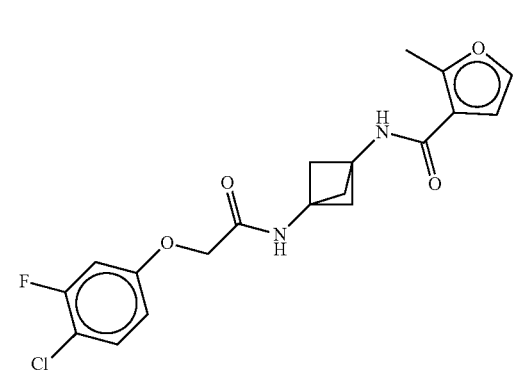 |

TABLE 1-continued
Exemplary compounds of the invention
| Compound No. | Structure |
|---|---|
| 557 | 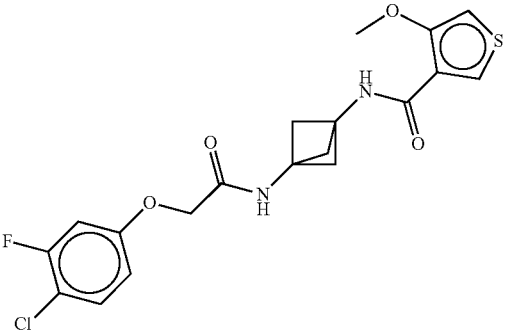 |
| 558 | 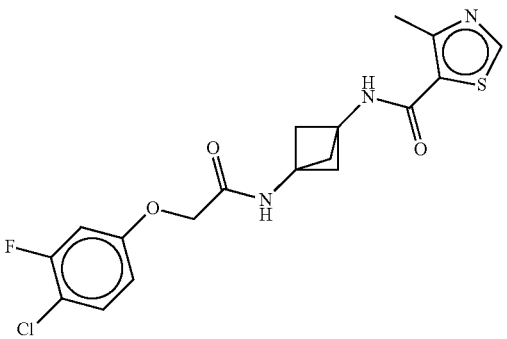 |
| 559 | 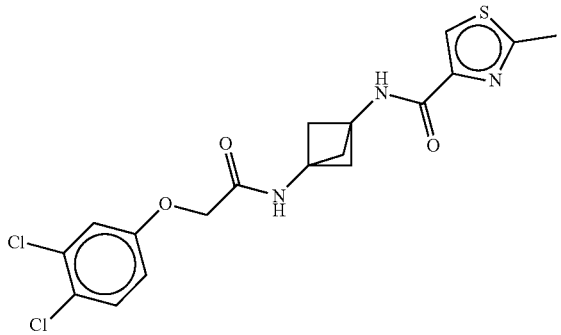 |
| 560 | 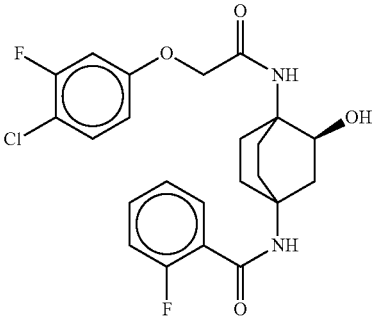 |

TABLE 1-continued
Exemplary compounds of the invention
| Compound No. | Structure |
| --- | --- |
| 561 | 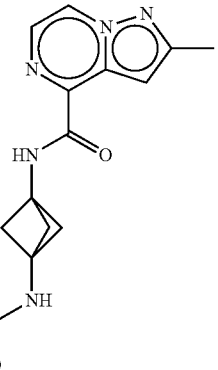 |
| 562 | 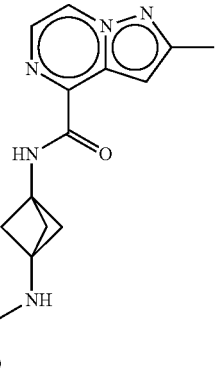 |
| 563 | 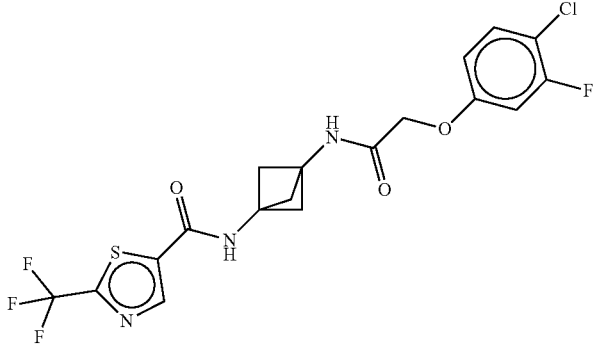 |
| 564 | 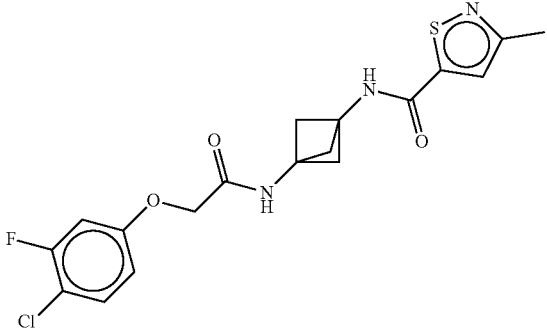 |

TABLE 1-continued
Exemplary compounds of the invention
| Compound No. | Structure |
|---|---|
| 565 | 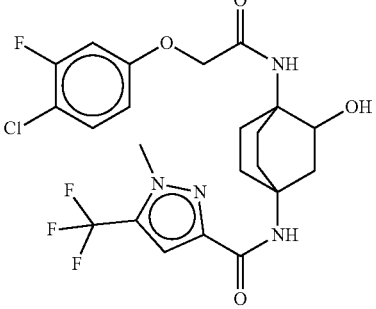 |
| 566 | 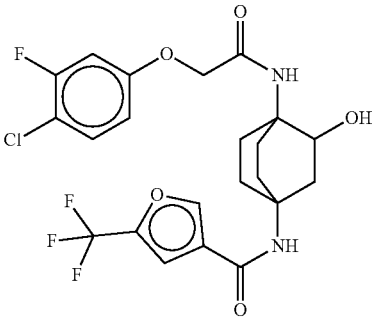 |
| 567 | 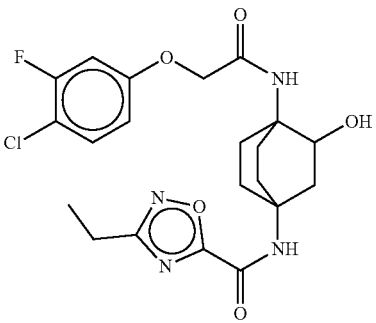 |
| 568 | 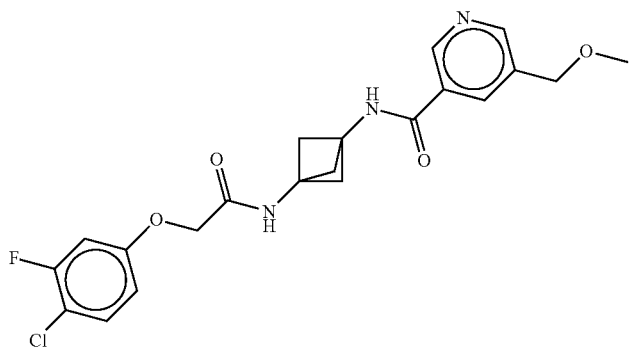 |

TABLE 1-continued
Exemplary compounds of the invention
| Compound No. | Structure |
|---|---|
| 569 | 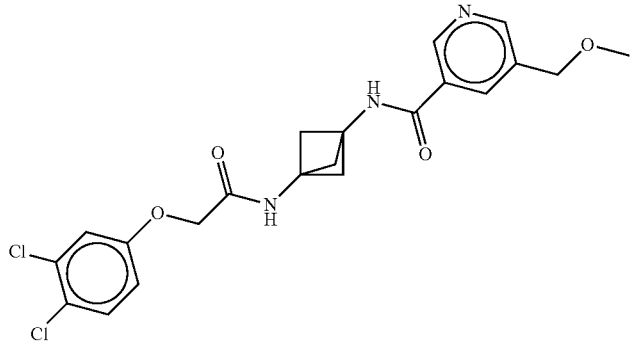 |
| 570 | 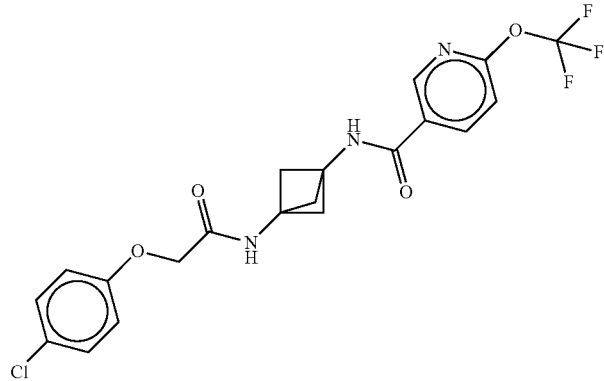 |
| 571 | 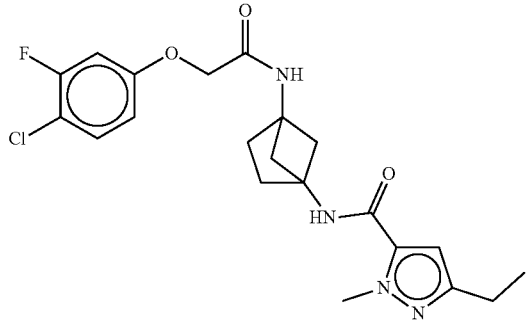 |
| 572 | 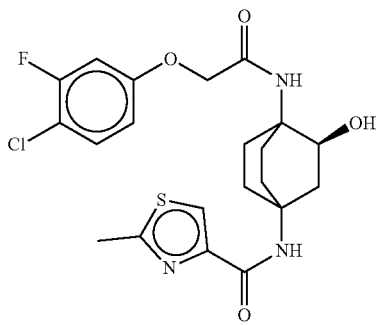 |

TABLE 1-continued
Exemplary compounds of the invention
| Compound No. | Structure |
|---|---|
| 573 | 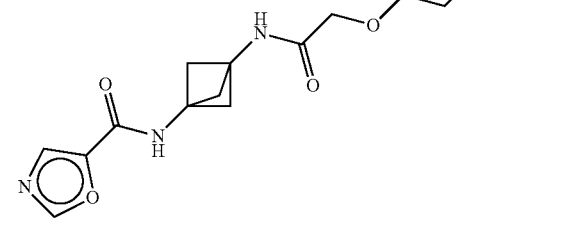 |
| 574 | 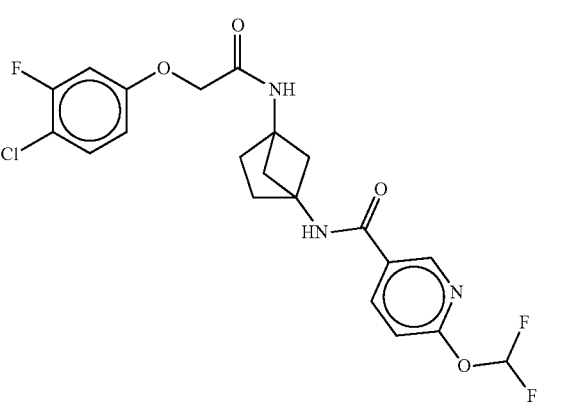 |
| 575 | 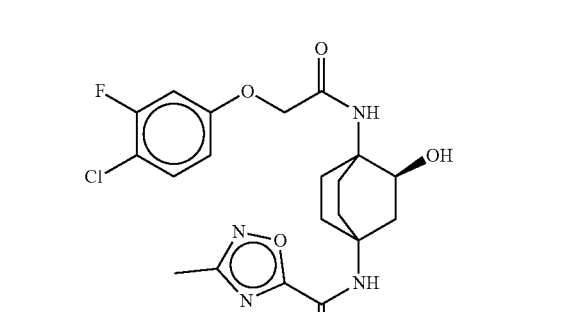 |
| 576 | 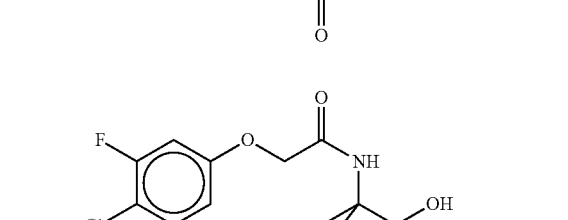 |

TABLE 1-continued

Exemplary compounds of the invention

| Compound No. | Structure |
|---|---|
| 577 | |
| 578 | |
| 579 | |
| 580 | |
| 581 | |

TABLE 1-continued

Exemplary compounds of the invention

| Compound No. | Structure |
|---|---|
| 582 | |
| 583 | |
| 584 | |
| 585 | |

TABLE 1-continued

Exemplary compounds of the invention

| Compound No. | Structure |
|---|---|
| 586 | |
| 587 | |
| 588 | |
| 589 | |

TABLE 1-continued
Exemplary compounds of the invention
| Compound No. | Structure |
|---|---|
| 590 | 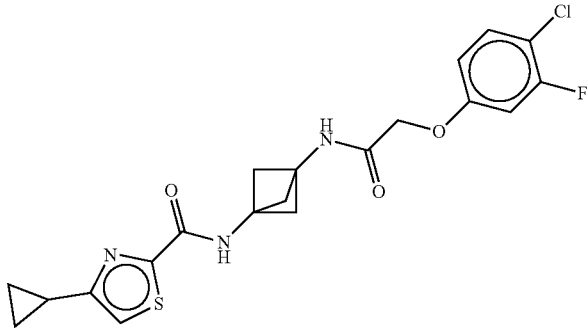 |
| 591 | 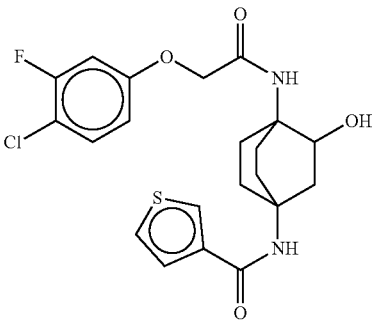 |
| 592 | 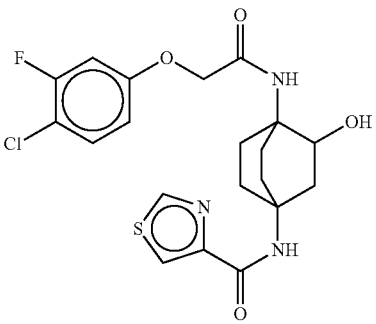 |
| 593 | 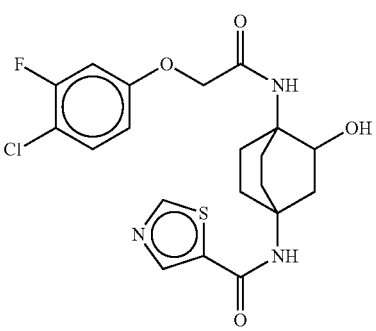 |

TABLE 1-continued

Exemplary compounds of the invention

| Compound No. | Structure |
| --- | --- |
| 594 | |
| 595 | |
| 596 | |
| 597 | |
| 598 | |

TABLE 1-continued
| Compound No. | Exemplary compounds of the invention Structure |
|---|---|
| 599 | 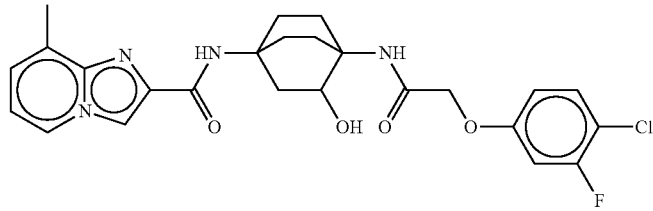 |
| 600 | 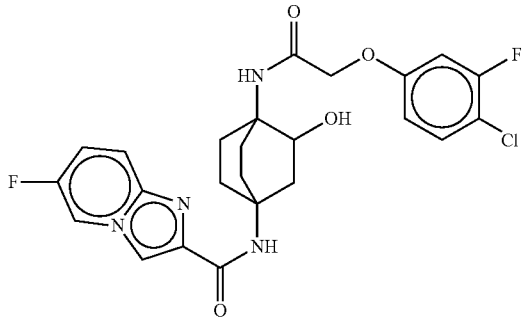 |
| 601 | 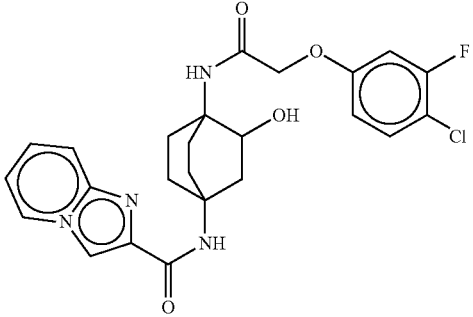 |
| 602 | 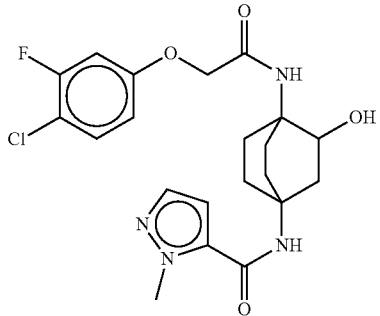 |
| 603 | 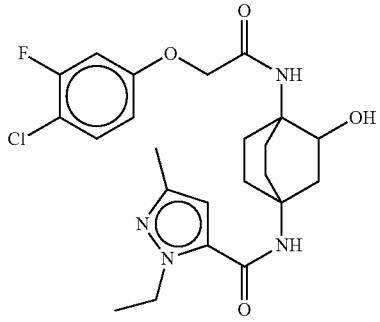 |

TABLE 1-continued

Exemplary compounds of the invention

| Compound No. | Structure |
| --- | --- |
| 604 | |
| 605 | |
| 606 | |
| 607 | |

TABLE 1-continued
Exemplary compounds of the invention
| Compound No. | Structure |
|---|---|
| 608 | 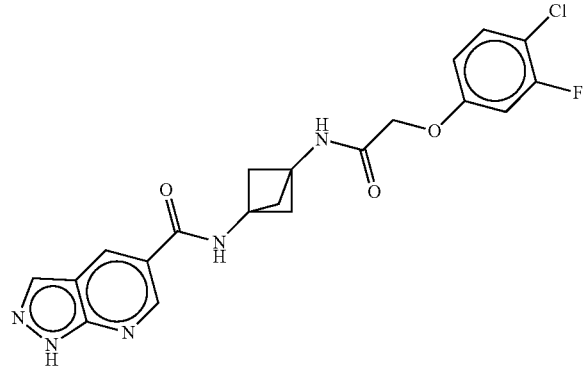 |
| 609 | 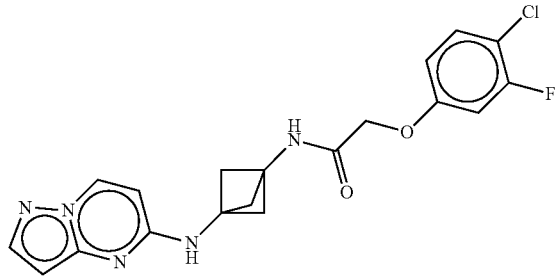 |
| 610 | 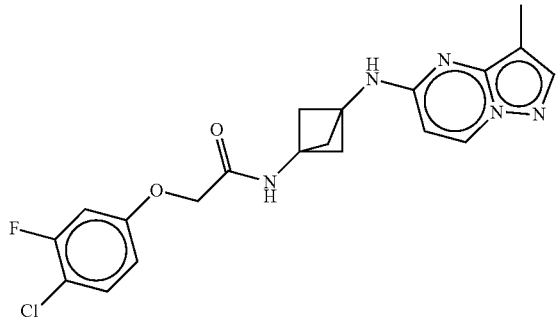 |
| 611 | 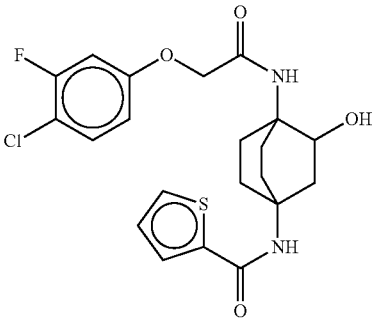 |

… 353 354
TABLE 1-continued
Exemplary compounds of the invention
| Compound No. | Structure |
|---|---|
| 612 | 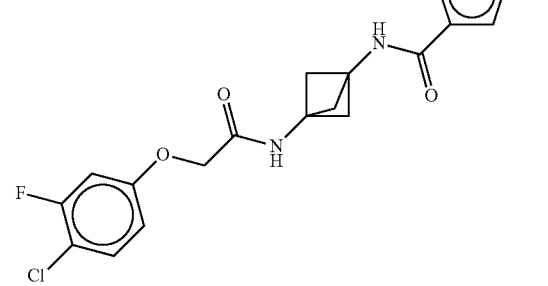 |
| 613 | 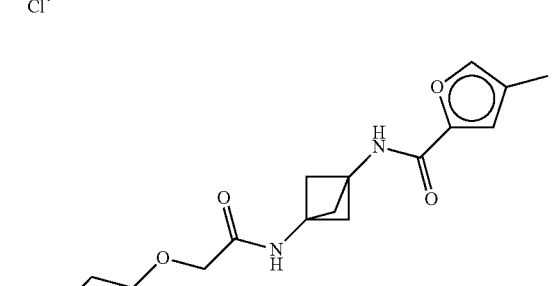 |
| 614 | 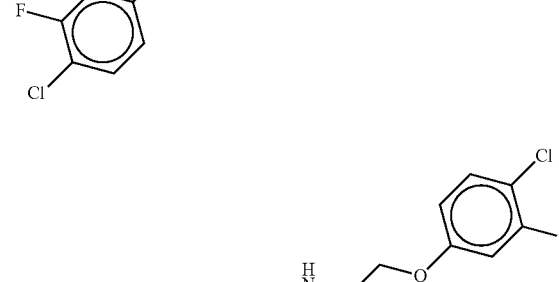 |
| 615 | 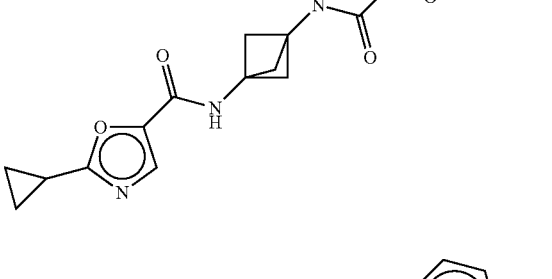 |

TABLE 1-continued

| Compound No. | Exemplary compounds of the invention Structure |
|---|---|
| 616 | |
| 617 | |
| 618 | |
| 619 | |
| 620 | |

TABLE 1-continued

Exemplary compounds of the invention

| Compound No. | Structure |
| --- | --- |
| 621 | |
| 622 | |
| 623 | |
| 624 | |

TABLE 1-continued

Exemplary compounds of the invention

| Compound No. | Structure |
|---|---|
| 625 | |
| 626 | |
| 627 | |
| 628 | |

TABLE 1-continued
Exemplary compounds of the invention
| Compound No. | Structure |
|---|---|
| 629 | 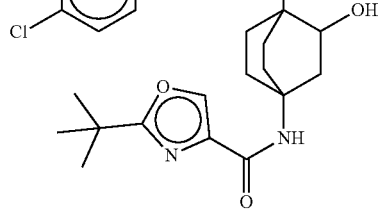 |
| 630 | 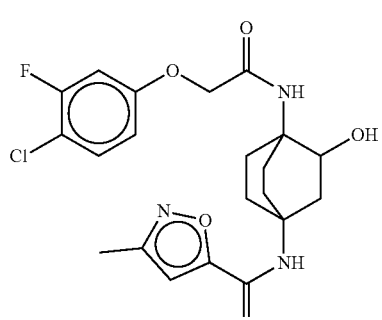 |
| 631 | 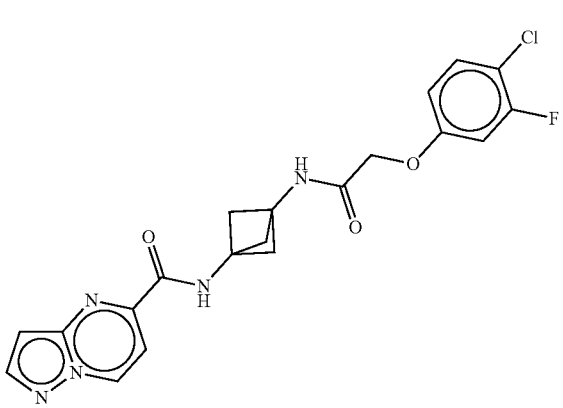 |
| 632 | 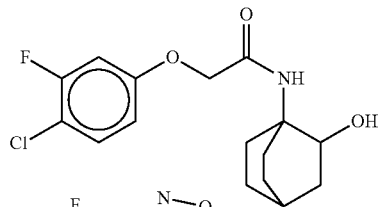 |

TABLE 1-continued
Exemplary compounds of the invention
| Compound No. | Structure |
|---|---|
| 633 | 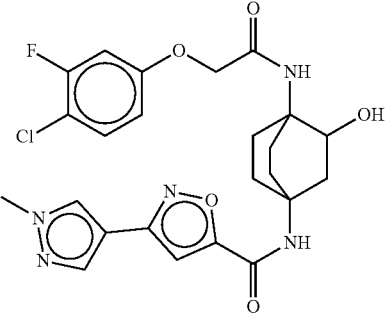 |
| 634 | 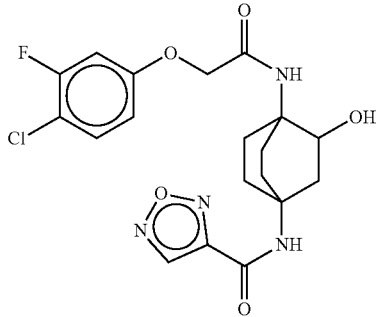 |
| 635 | 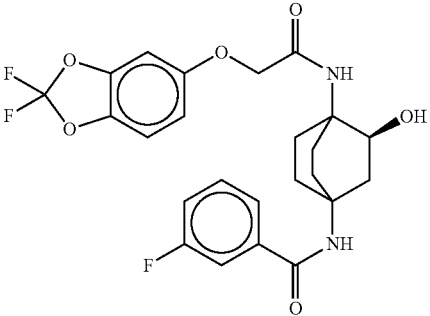 |
| 636 | 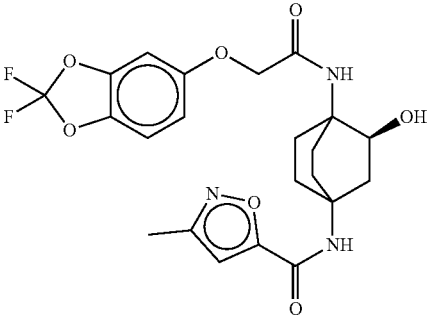 |

TABLE 1-continued
Exemplary compounds of the invention
| Compound No. | Structure |
|---|---|
| 637 | 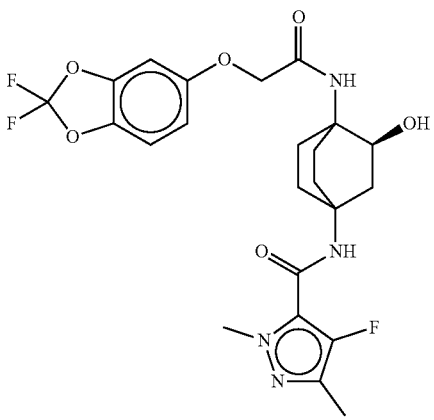 |
| 638 | 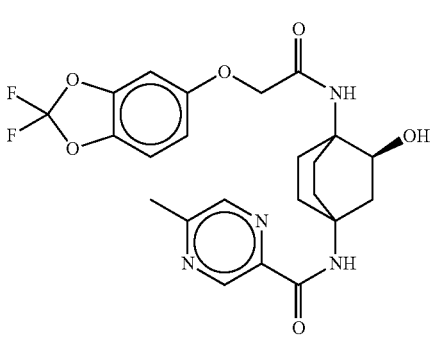 |
| 639 | 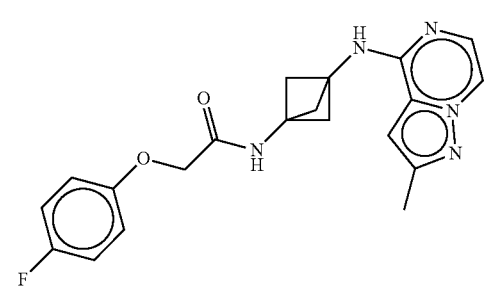 |
| 640 | 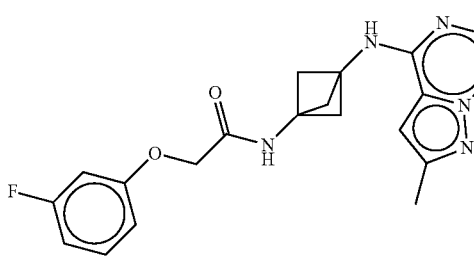 |

TABLE 1-continued
Exemplary compounds of the invention
| Compound No. | Structure |
|---|---|
| 641 | 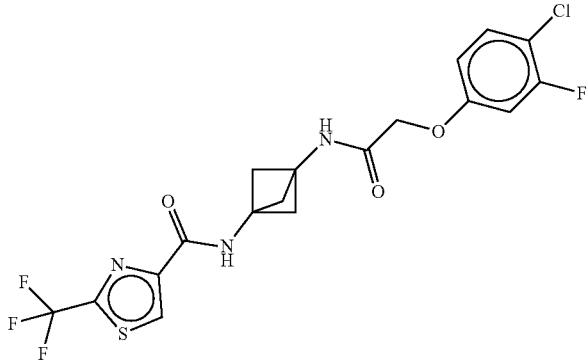 |
| 642 | 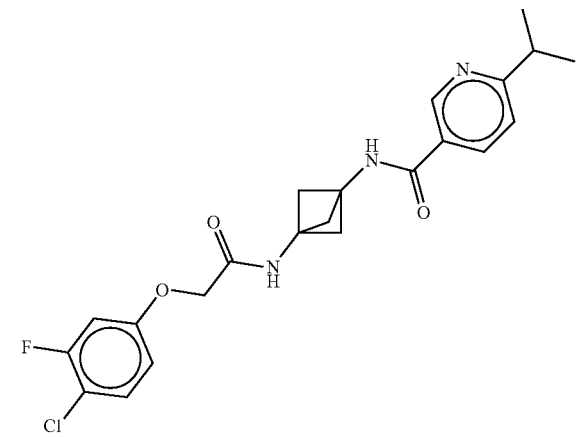 |
| 643 | 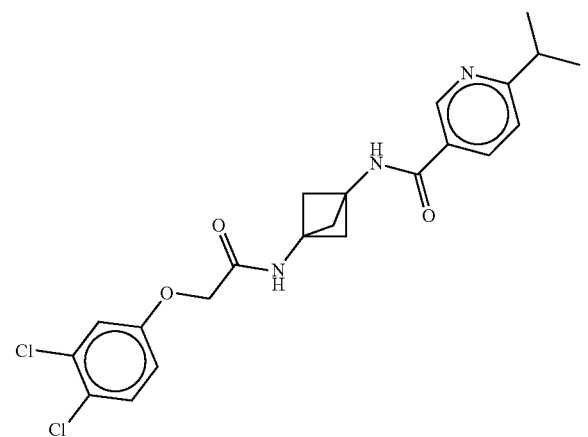 |

TABLE 1-continued
Exemplary compounds of the invention
| Compound No. | Structure |
|---|---|
| 644 | 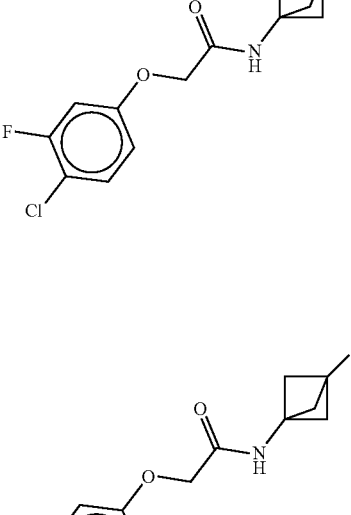 |
| 645 | 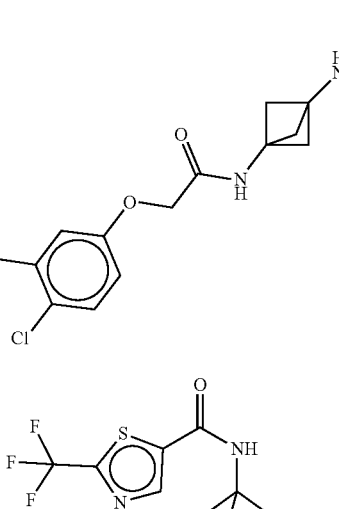 |
| 646 | 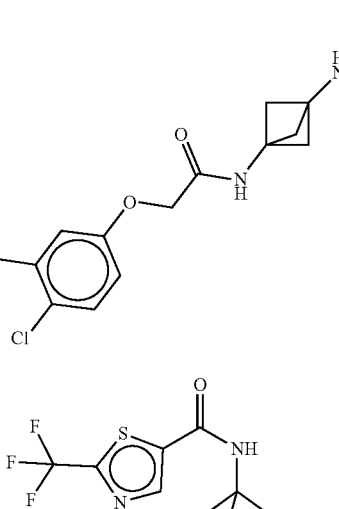 |
| 647 | 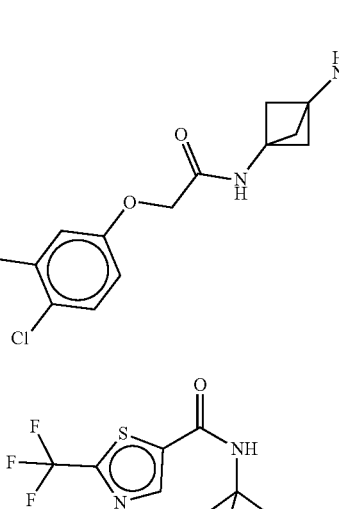 |

TABLE 1-continued
Exemplary compounds of the invention
| Compound No. | Structure |
|---|---|
| 648 | 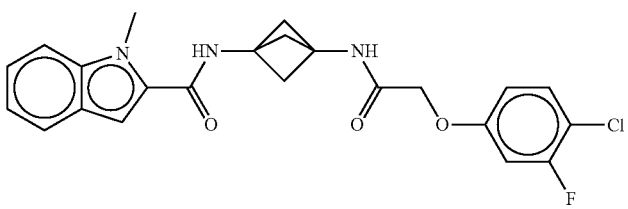 |
| 649 | 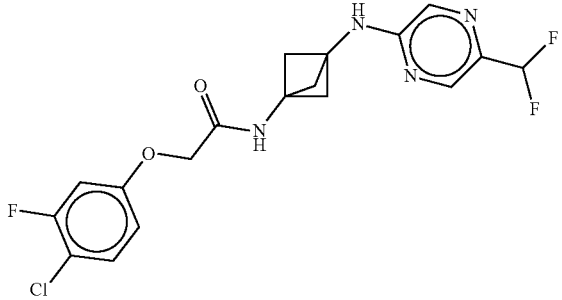 |
| 650 | 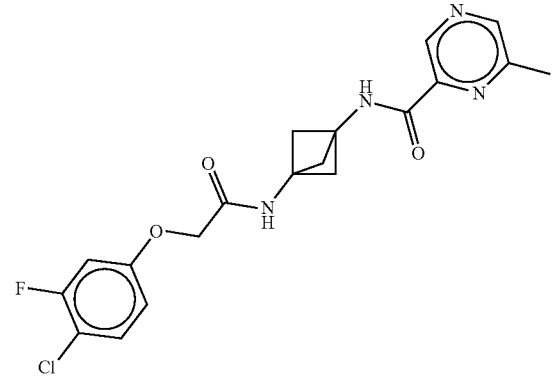 |
| 651 | 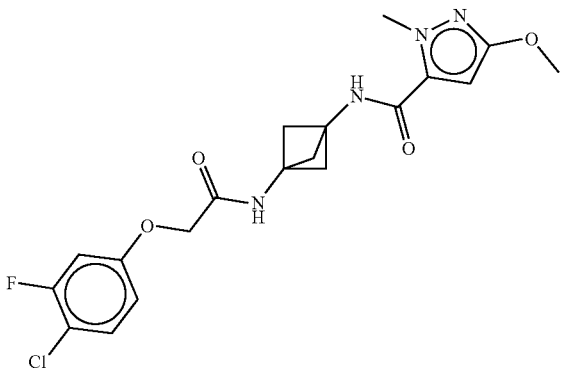 |

TABLE 1-continued
Exemplary compounds of the invention
| Compound No. | Structure |
|---|---|
| 652 | 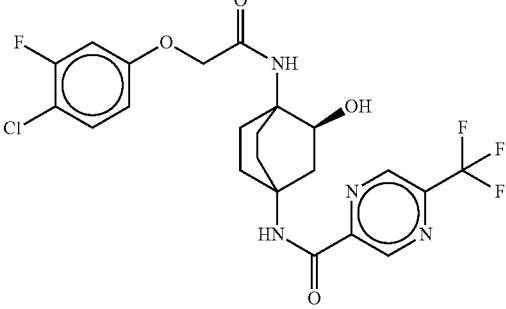 |
| 653 | 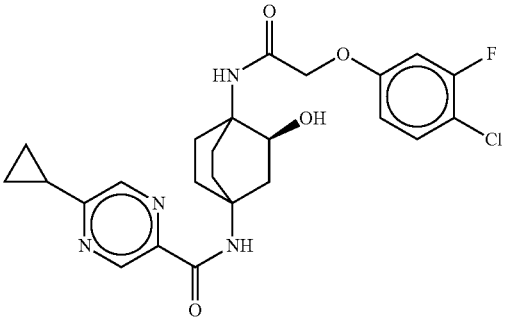 |
| 654 | 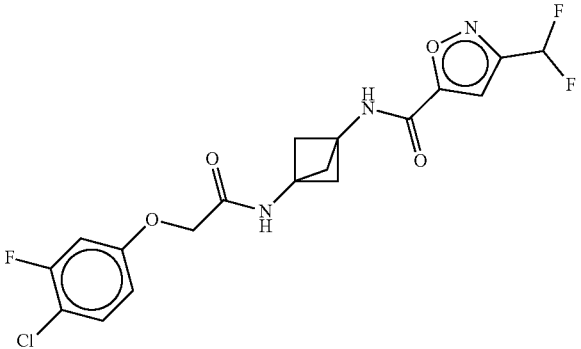 |
| 655 | 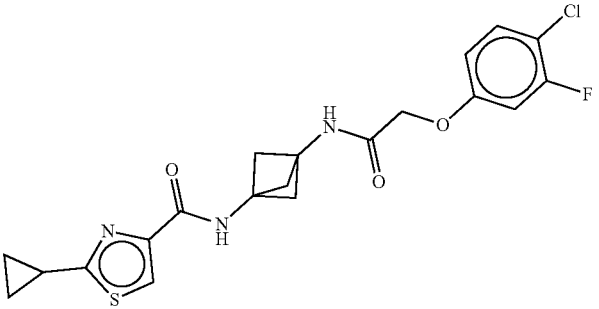 |

TABLE 1-continued

Exemplary compounds of the invention

| Compound No. | Structure |
|---|---|
| 656 | 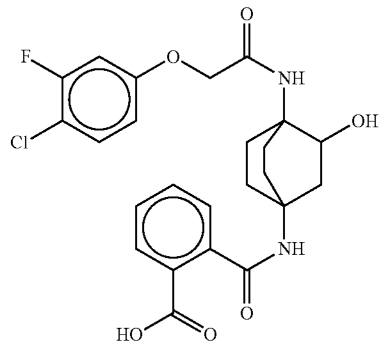 |
| 657 | 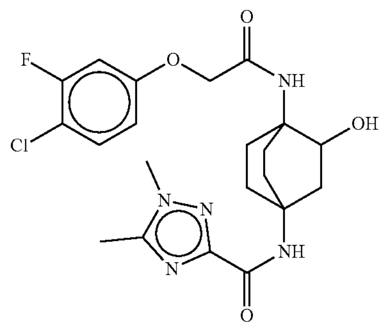 |
| 658 | 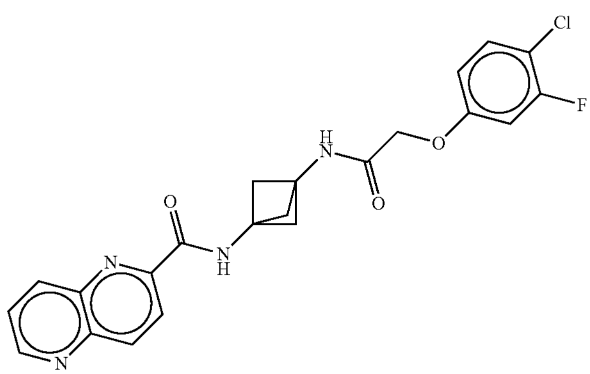 |
| 659 | 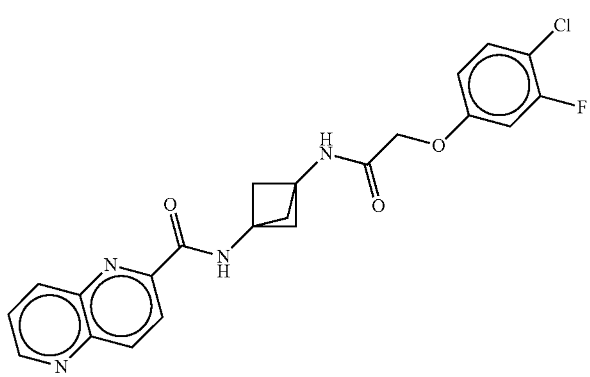 |

TABLE 1-continued
Exemplary compounds of the invention
| Compound No. | Structure |
|---|---|
| 660 | 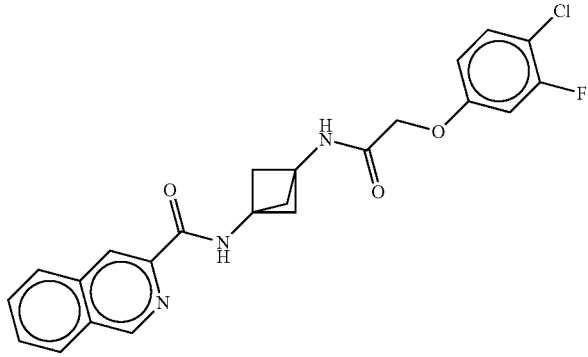 |
| 661 | 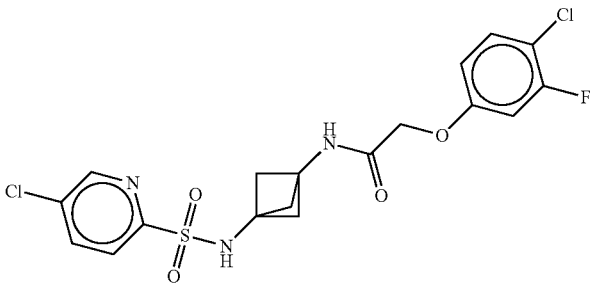 |
| 662 | 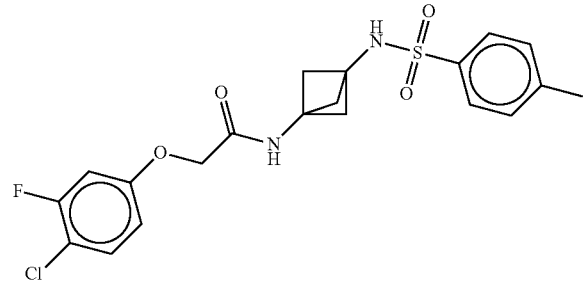 |
| 663 | 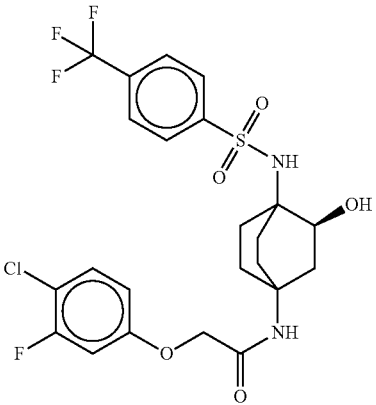 |

TABLE 1-continued
Exemplary compounds of the invention
| Compound No. | Structure |
|---|---|
| 664 | 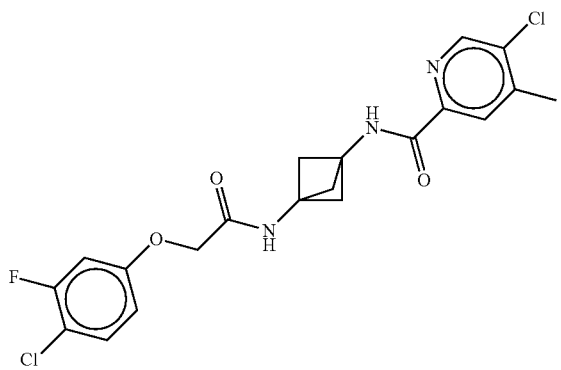 |
| 665 | 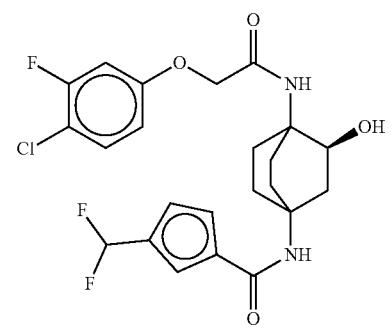 |
| 666 | 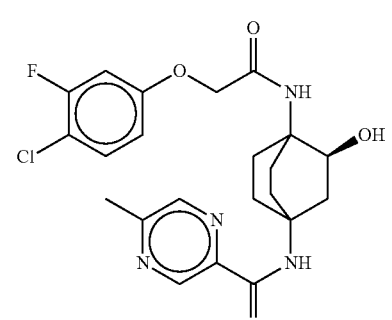 |
| 667 | 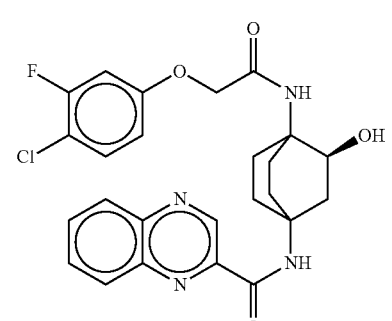 |

TABLE 1-continued

Exemplary compounds of the invention

| Compound No. | Structure |
|---|---|
| 668 | |
| 669 | |
| 670 | |
| 671 | |

TABLE 1-continued

Exemplary compounds of the invention

| Compound No. | Structure |
|---|---|
| 672 | |
| 673 | |
| 674 | |
| 675 | |

TABLE 1-continued

Exemplary compounds of the invention

| Compound No. | Structure |
|---|---|
| 676 | |
| 677 | |
| 678 | |
| 679 | |

TABLE 1-continued
Exemplary compounds of the invention
| Compound No. | Structure |
|---|---|
| 680 | 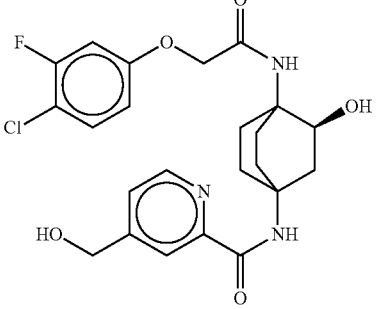 |
| 681 | 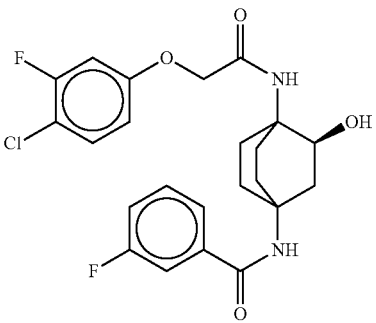 |
| 682 | 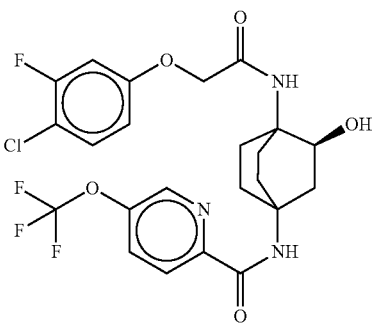 |
| 683 | 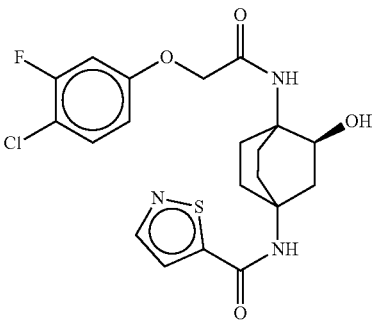 |

TABLE 1-continued
Exemplary compounds of the invention
| Compound No. | Structure |
|---|---|
| 684 | 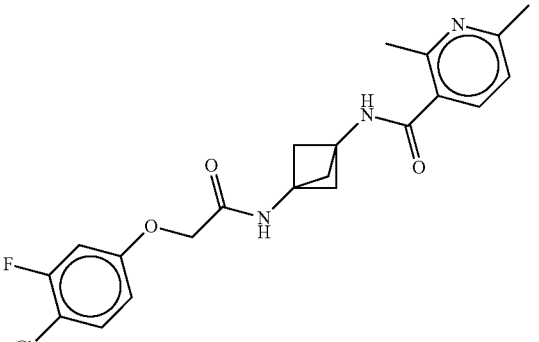 |
| 685 | 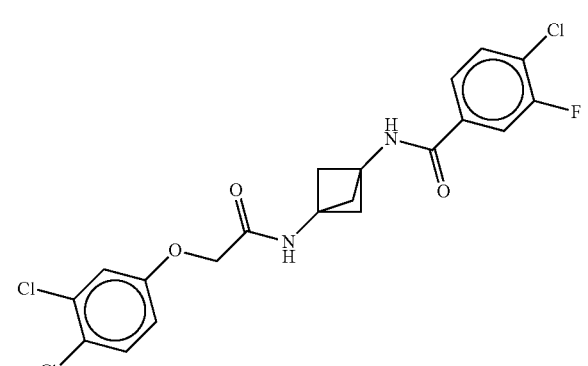 |
| 686 | 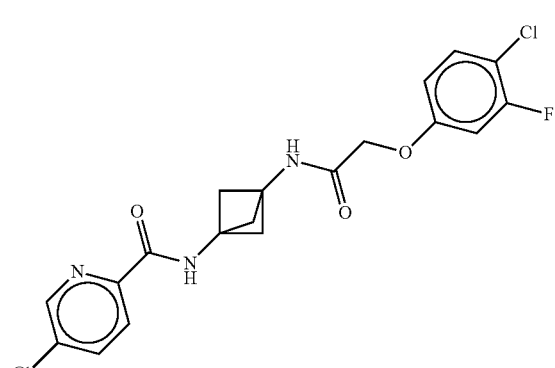 |
| 687 | 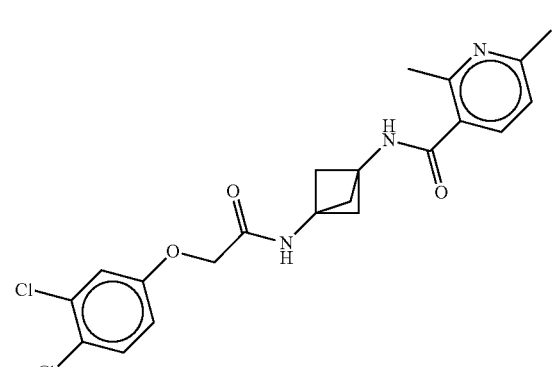 |

TABLE 1-continued
Exemplary compounds of the invention
| Compound No. | Structure |
|---|---|
| 688 | 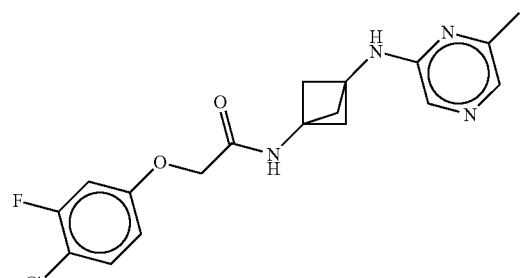 |
| 689 | 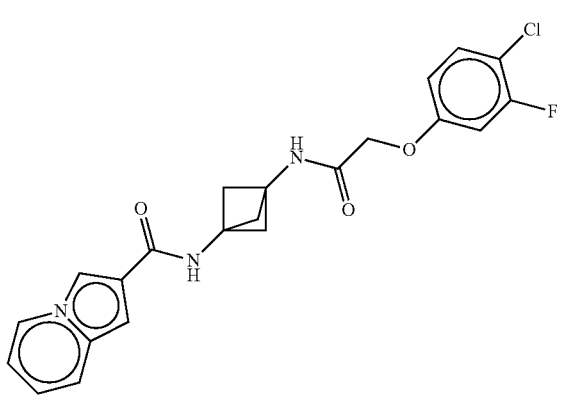 |
| 690 | 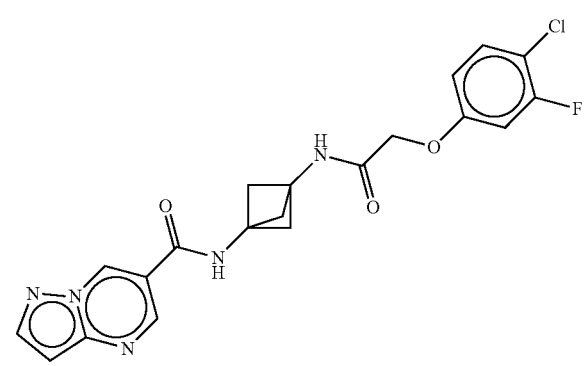 |
| 691 | 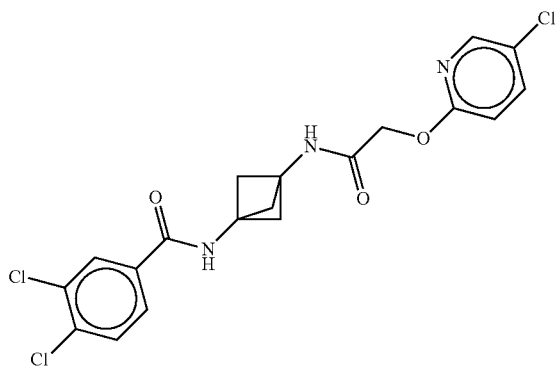 |

TABLE 1-continued

Exemplary compounds of the invention

| Compound No. | Structure |
|---|---|
| 692 | |
| 693 | |
| 694 | |
| 695 | |

TABLE 1-continued

Exemplary compounds of the invention

| Compound No. | Structure |
|---|---|
| 696 | 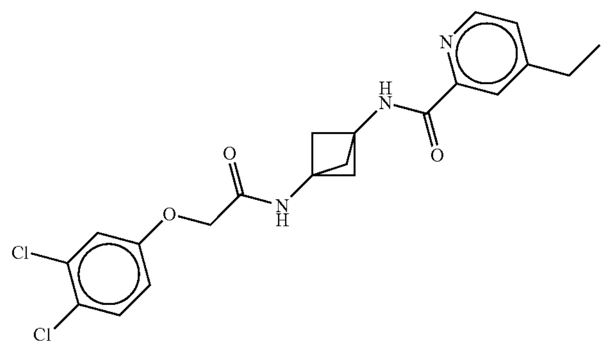 |
| 697 | 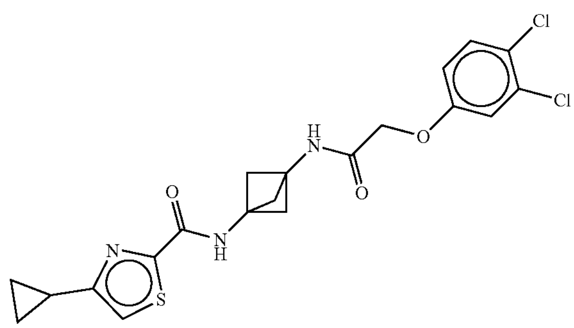 |
| 698 | 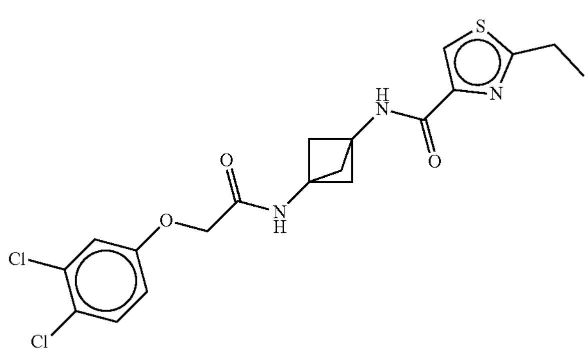 |
| 699 | 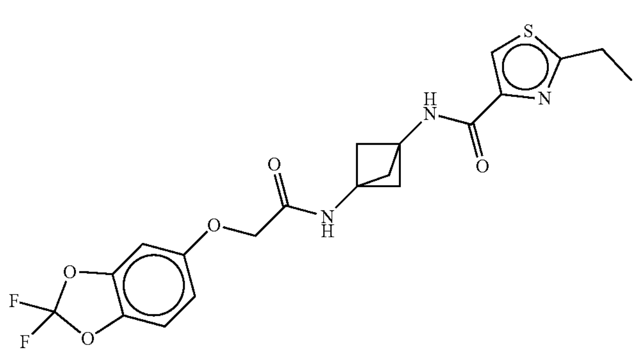 |

TABLE 1-continued

Exemplary compounds of the invention

| Compound No. | Structure |
|---|---|
| 700 | |
| 701 | |
| 702 | |
| 703 | |

TABLE 1-continued

Exemplary compounds of the invention

| Compound No. | Structure |
|---|---|
| 704 | |
| 705 | |
| 706 | |
| 707 | |

TABLE 1-continued

Exemplary compounds of the invention

| Compound No. | Structure |
|---|---|
| 708 | |
| 709 | |
| 710 | |
| 711 | |

TABLE 1-continued

Exemplary compounds of the invention

| Compound No. | Structure |
|---|---|
| 712 | |
| 713 | |
| 714 | |
| 715 | |

TABLE 1-continued
| Compound No. | Exemplary compounds of the invention Structure |
|---|---|
| 716 | 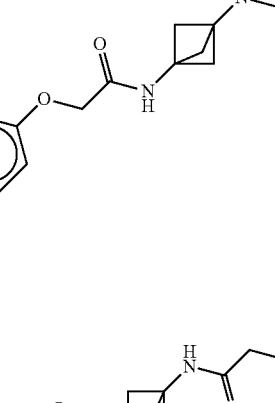 |
| 717 | 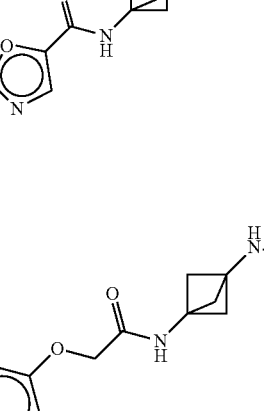 |
| 718 | 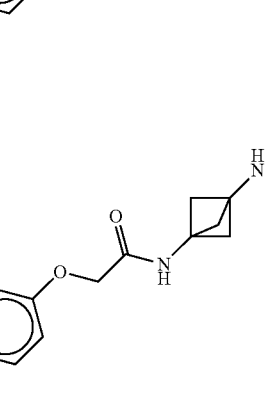 |
| 719 | 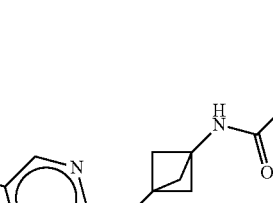 |
| 720 | |

TABLE 1-continued

| Compound No. | Exemplary compounds of the invention Structure |
|---|---|
| 721 | (structure) |
| 722 | (structure) |
| 723 | (structure) |
| 724 | (structure) |
| 725 | (structure) |

TABLE 1-continued

Exemplary compounds of the invention

| Compound No. | Structure |
|---|---|
| 726 | |
| 727 | |
| 728 | |
| 729 | |

TABLE 1-continued
| Compound No. | Exemplary compounds of the invention Structure |
|---|---|
| 730 | 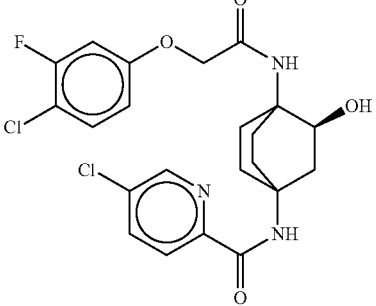 |
| 731 | 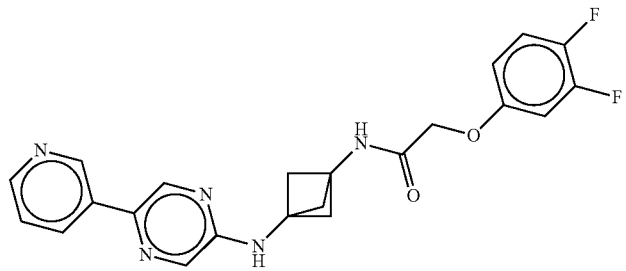 |
| 732 | 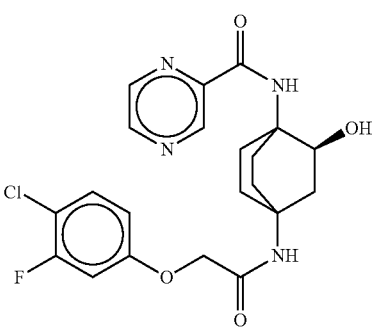 |
| 733 | 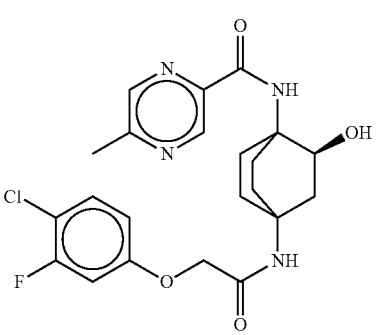 |
| 734 | 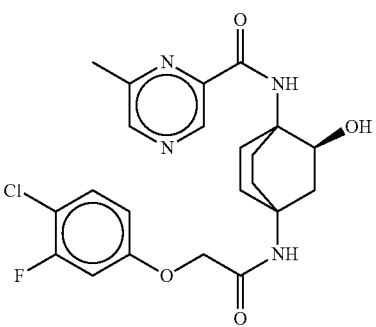 |

TABLE 1-continued
Exemplary compounds of the invention
| Compound No. | Structure |
|---|---|
| 735 | 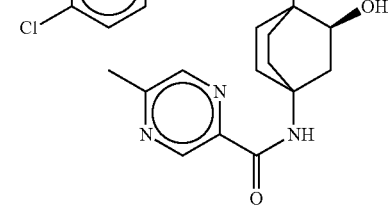 |
| 736 | 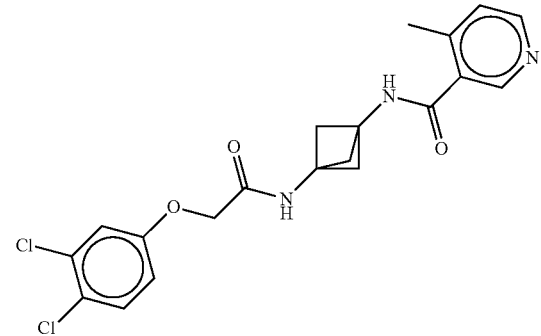 |
| 737 | 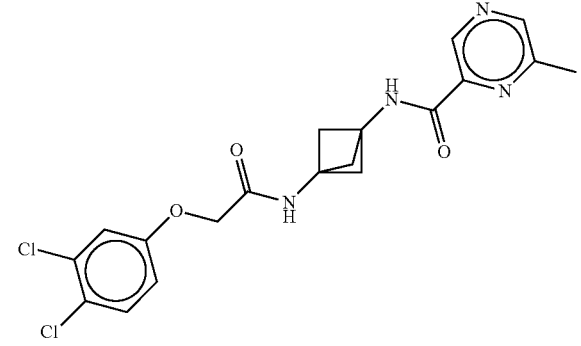 |
| 738 | 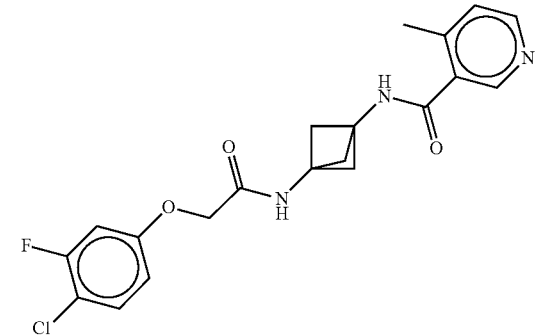 |

TABLE 1-continued
Exemplary compounds of the invention
| Compound No. | Structure |
|---|---|
| 739 | 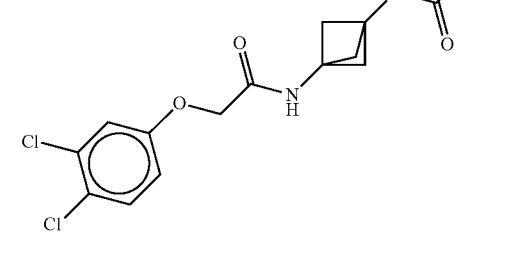 |
| 740 | 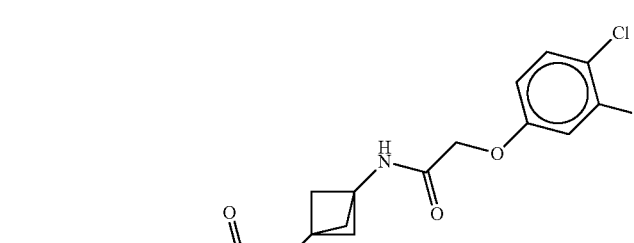 |
| 741 | 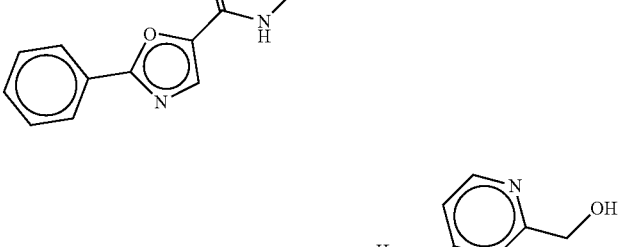 |
| 742 | 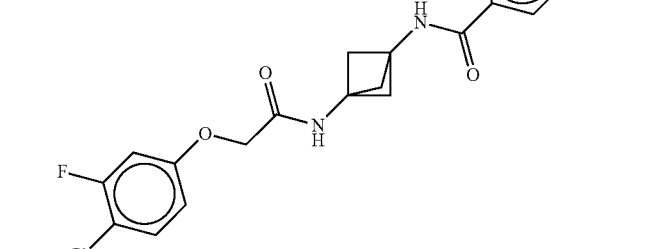 |

TABLE 1-continued
Exemplary compounds of the invention
| Compound No. | Structure |
|---|---|
| 743 | 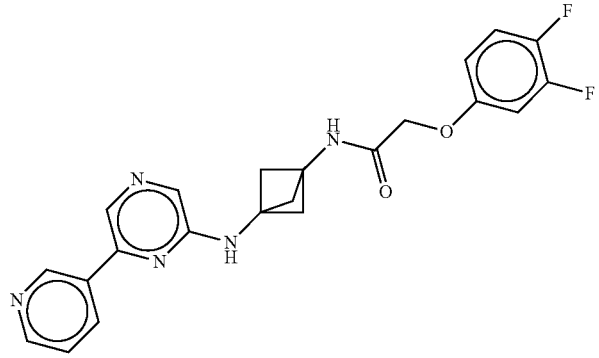 |
| 744 | 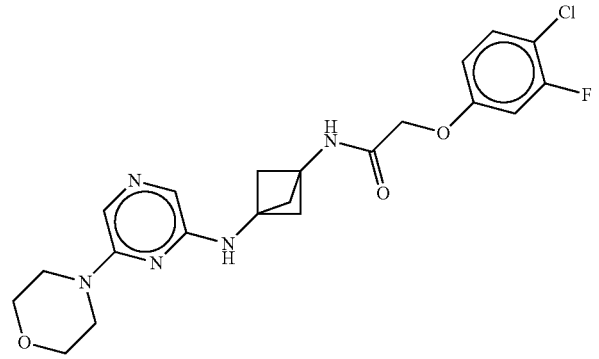 |
| 745 | 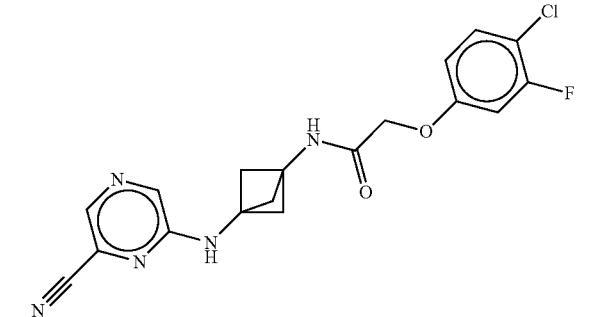 |
| 746 | 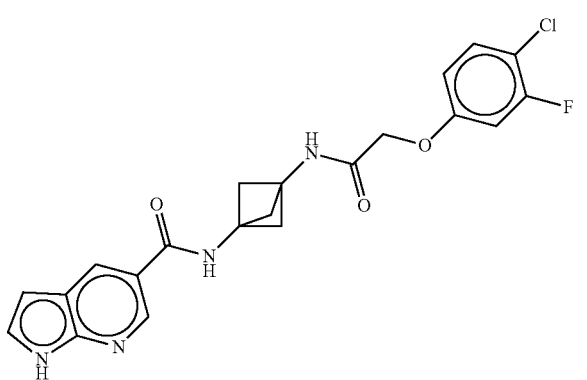 |

TABLE 1-continued

Exemplary compounds of the invention

| Compound No. | Structure |
|---|---|
| 747 | |
| 748 | |
| 749 | |
| 750 | |
| 751 | |

TABLE 1-continued

| Compound No. | Exemplary compounds of the invention Structure |
|---|---|
| 752 | |
| 753 | |
| 754 | |
| 755 | |
| 756 | |

TABLE 1-continued
Exemplary compounds of the invention
| Compound No. | Structure |
|---|---|
| 757 | 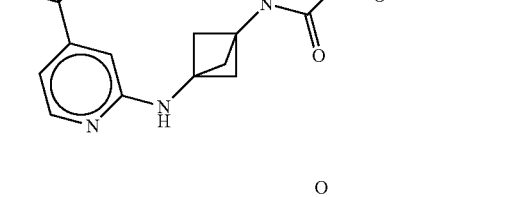 |
| 758 | 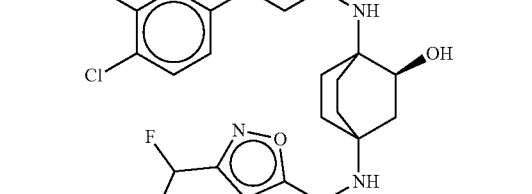 |
| 759 | 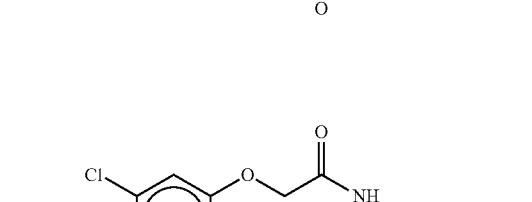 |
| 760 | 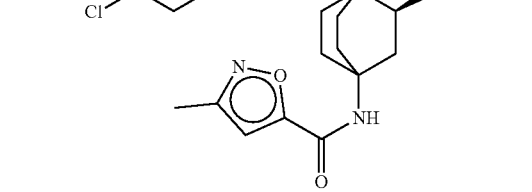 |

TABLE 1-continued
Exemplary compounds of the invention
| Compound No. | Structure |
|---|---|
| 761 | 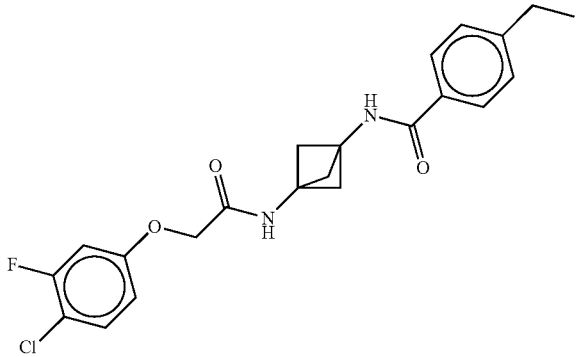 |
| 762 | 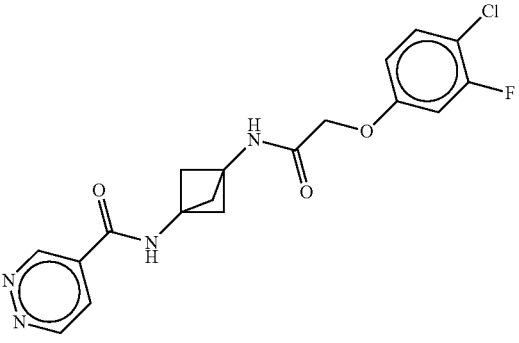 |
| 763 | 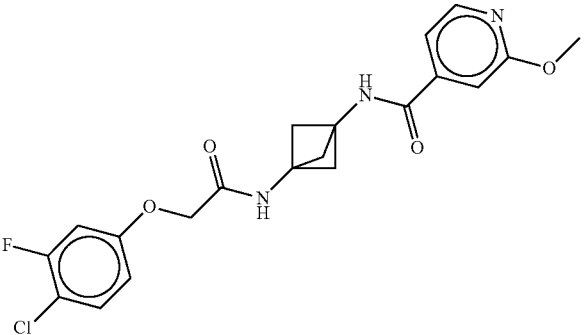 |
| 764 | 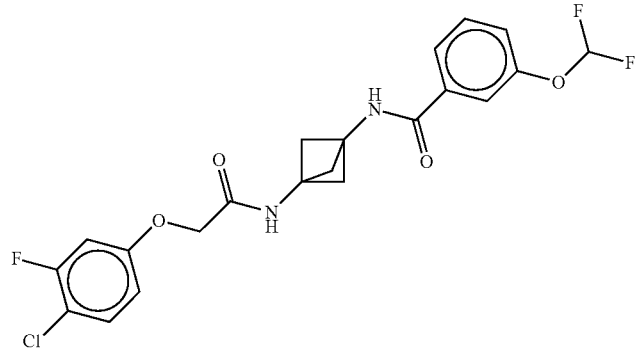 |

TABLE 1-continued
Exemplary compounds of the invention
| Compound No. | Structure |
| --- | --- |
| 765 | 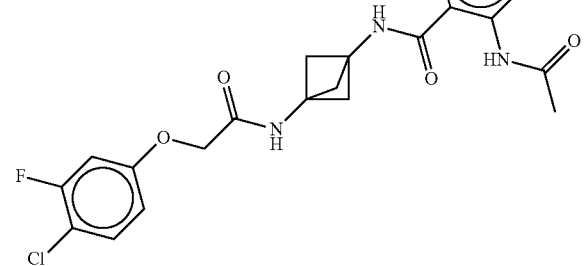 |
| 766 | 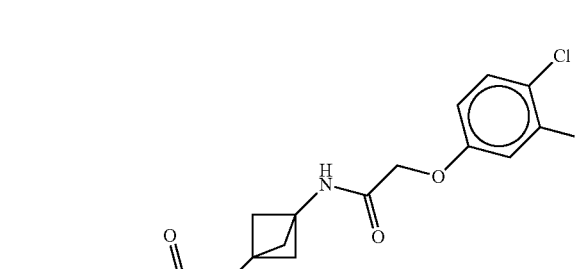 |
| 767 | 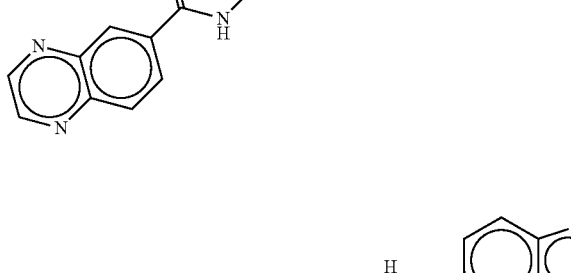 |
| 768 | 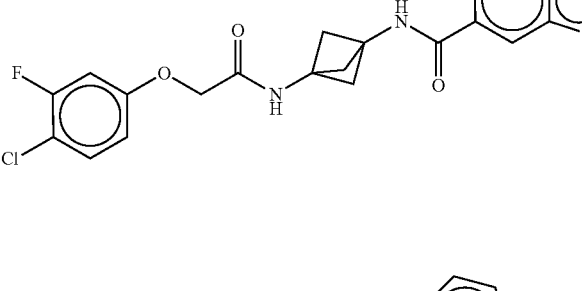 |

TABLE 1-continued
Exemplary compounds of the invention
| Compound No. | Structure |
|---|---|
| 769 | 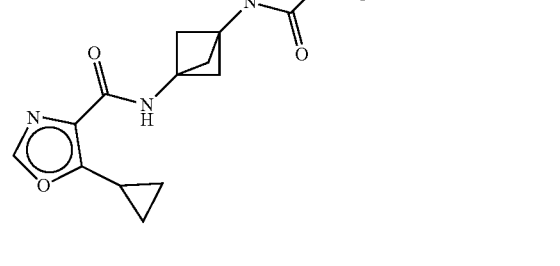 |
| 770 | 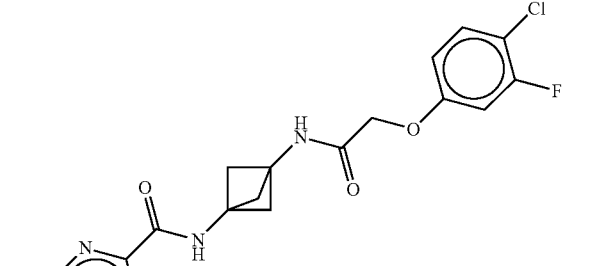 |
| 771 | 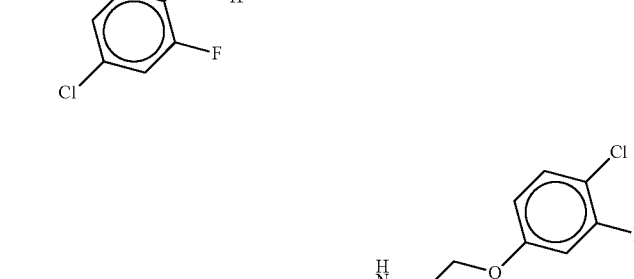 |
| 772 | 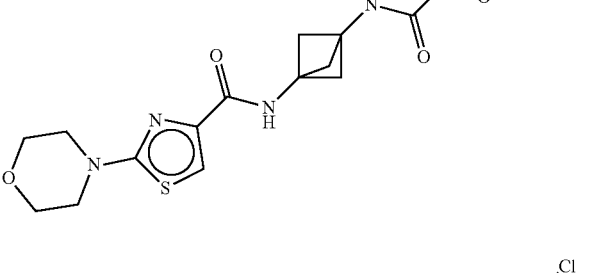 |

TABLE 1-continued

| Compound No. | Exemplary compounds of the invention Structure |
|---|---|
| 773 | |
| 774 | |
| 775 | |
| 776 | |
| 777 | |

TABLE 1-continued

Exemplary compounds of the invention

| Compound No. | Structure |
|---|---|
| 778 | |
| 779 | |
| 780 | |
| 781 | |

TABLE 1-continued

Exemplary compounds of the invention

| Compound No. | Structure |
|---|---|
| 782 | |
| 783 | |
| 784 | |
| 785 | |

TABLE 1-continued
Exemplary compounds of the invention
| Compound No. | Structure |
|---|---|
| 786 | 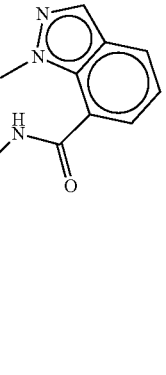 |
| 787 | 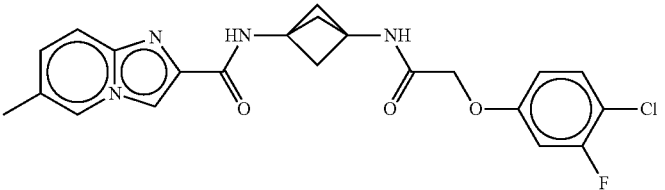 |
| 788 | 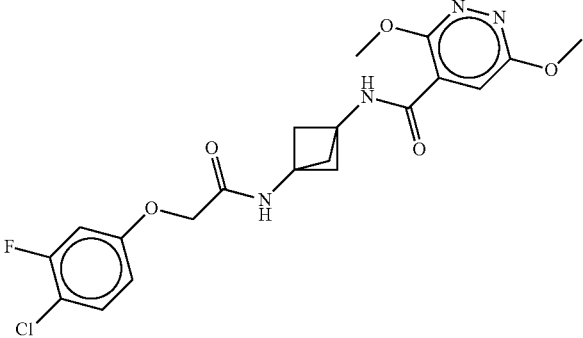 |
| 789 | 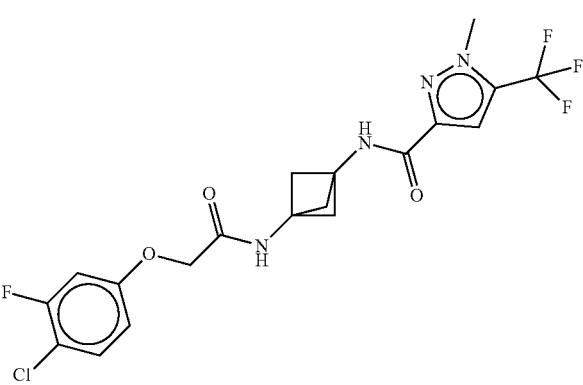 |

TABLE 1-continued
Exemplary compounds of the invention
| Compound No. | Structure |
|---|---|
| 790 | 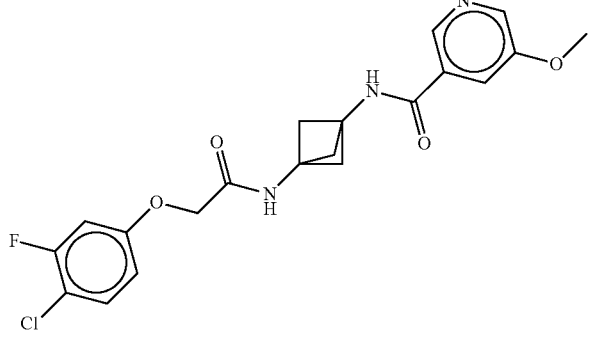 |
| 791 | 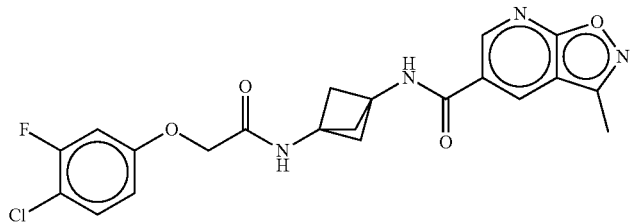 |
| 792 | 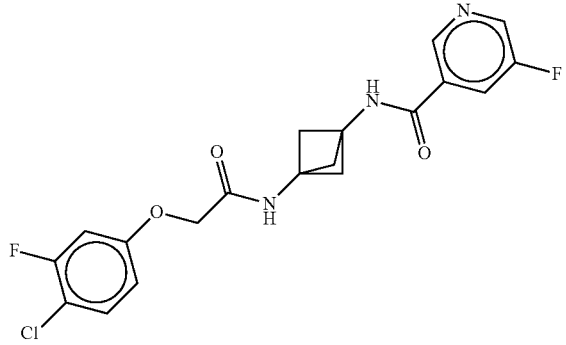 |
| 793 | 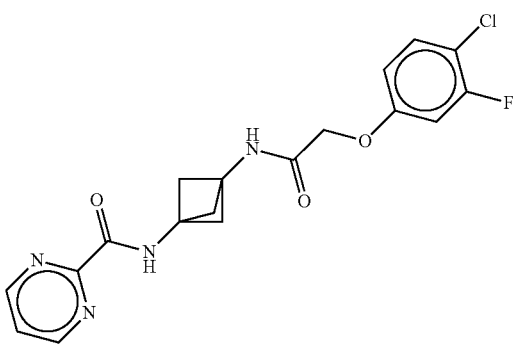 |

TABLE 1-continued

| Compound No. | Structure |
|---|---|
| 794 | |
| 795 | |
| 796 | |
| 797 | |

TABLE 1-continued

Exemplary compounds of the invention

| Compound No. | Structure |
|---|---|
| 798 | 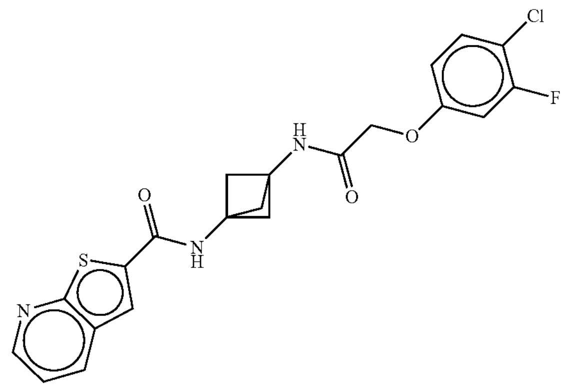 |
| 799 | 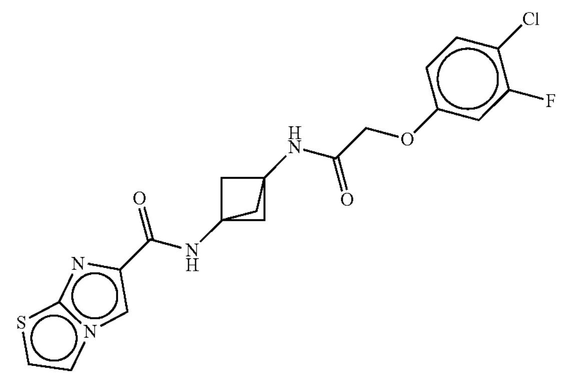 |
| 800 | 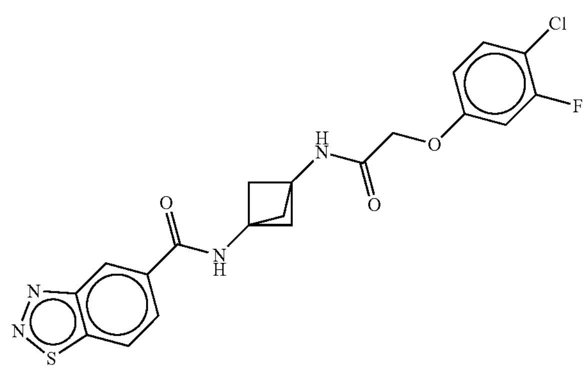 |
| 801 | 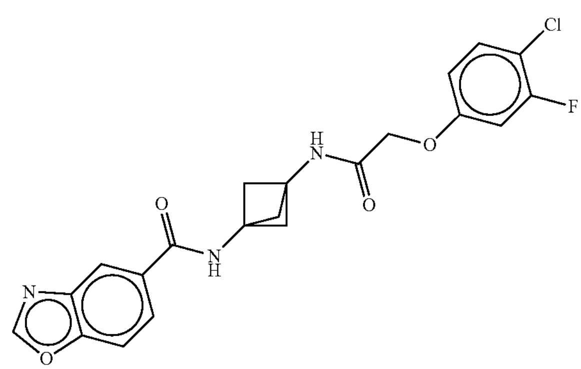 |

TABLE 1-continued
Exemplary compounds of the invention
| Compound No. | Structure |
|---|---|
| 802 | 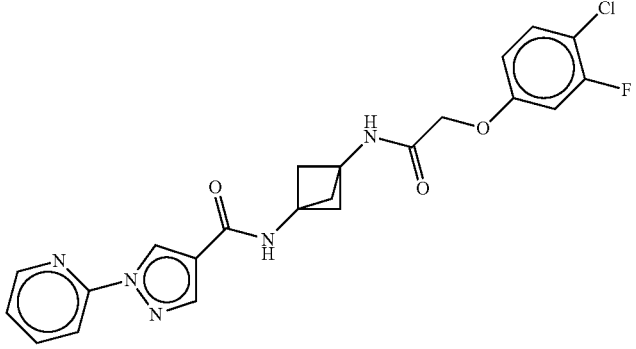 |
| 803 | 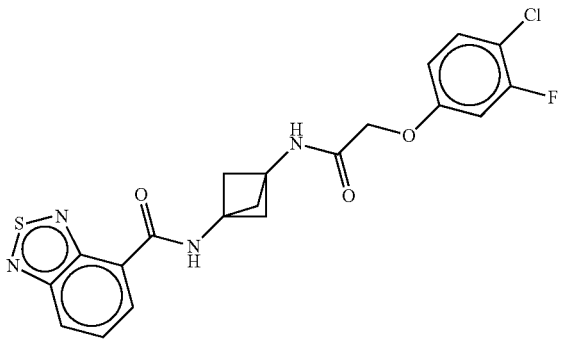 |
| 804 | 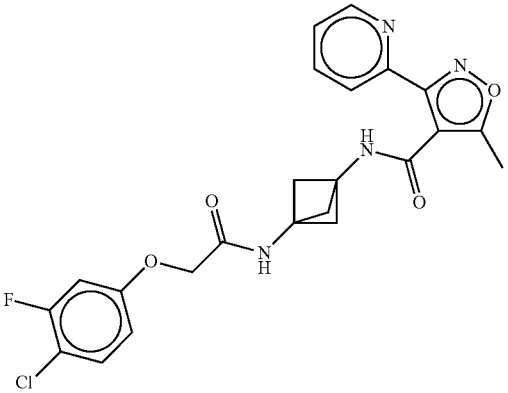 |
| 805 | 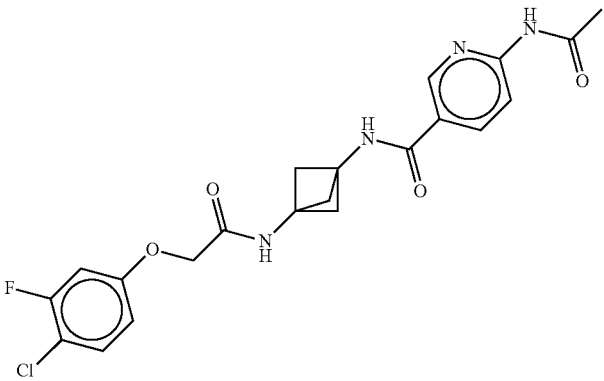 |

TABLE 1-continued

Exemplary compounds of the invention

| Compound No. | Structure |
| --- | --- |
| 806 | |
| 807 | |
| 808 | |
| 809 | |
| 810 | |

TABLE 1-continued

Exemplary compounds of the invention

| Compound No. | Structure |
|---|---|
| 811 | |
| 812 | |
| 813 | |
| 814 | |

TABLE 1-continued
Exemplary compounds of the invention
| Compound No. | Structure |
|---|---|
| 815 | 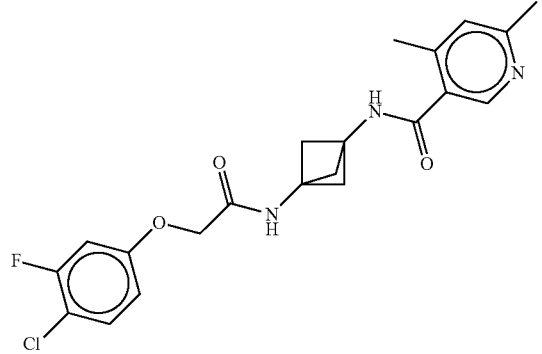 |
| 816 | 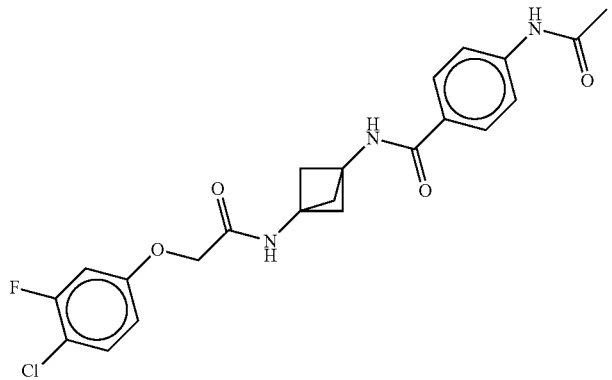 |
| 817 | 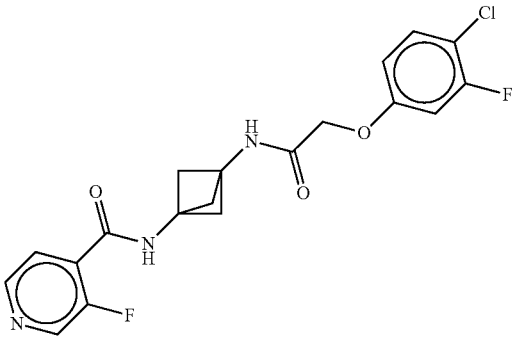 |
| 818 | 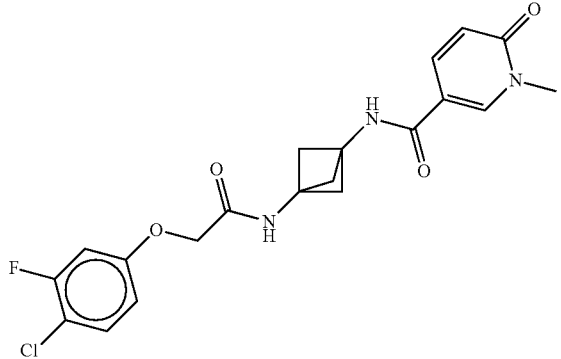 |

TABLE 1-continued
Exemplary compounds of the invention
| Compound No. | Structure |
|---|---|
| 819 | 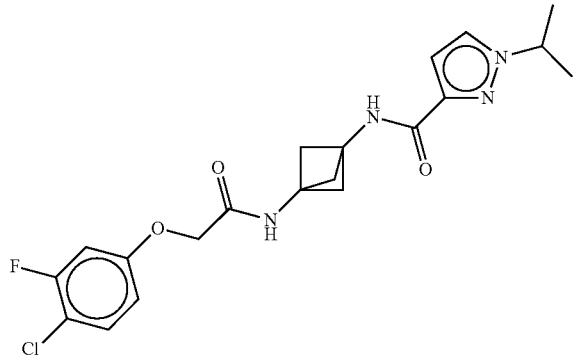 |
| 820 | 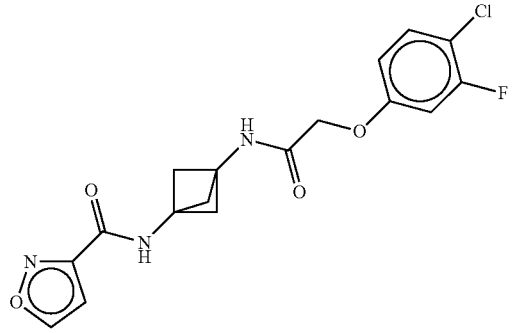 |
| 821 | 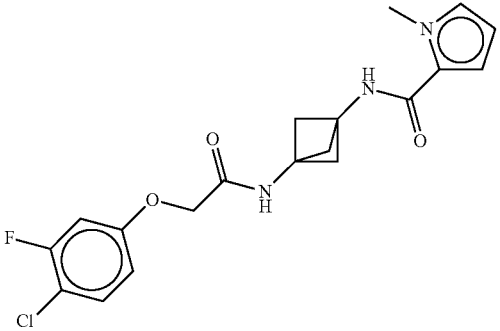 |
| 822 | 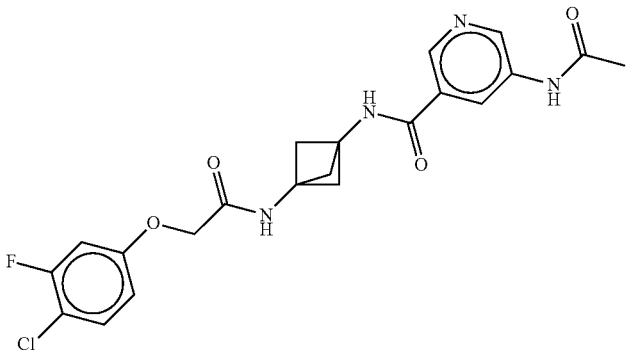 |

TABLE 1-continued

Exemplary compounds of the invention

| Compound No. | Structure |
|---|---|
| 823 | |
| 824 | |
| 825 | |
| 826 | |

TABLE 1-continued
Exemplary compounds of the invention
| Compound No. | Structure |
|---|---|
| 827 | 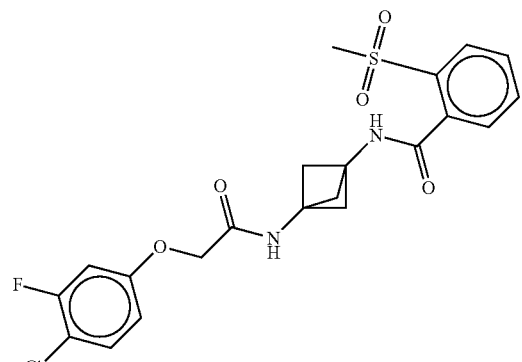 |
| 828 | 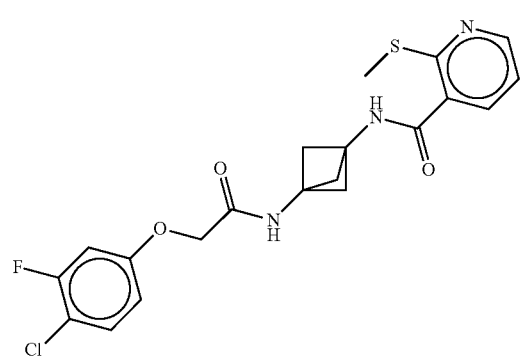 |
| 829 | 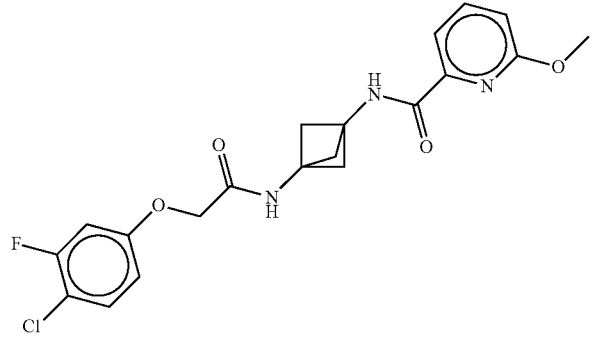 |
| 830 | 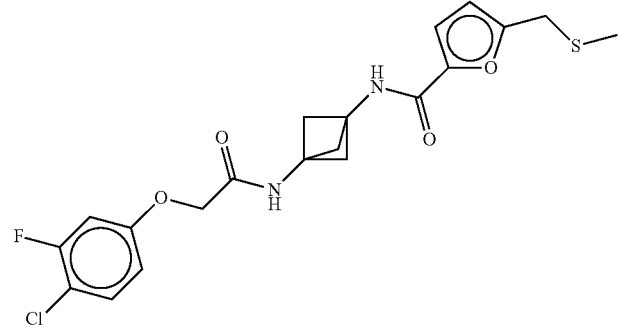 |

TABLE 1-continued

| Compound No. | Exemplary compounds of the invention Structure |
|---|---|
| 831 | |
| 832 | |
| 833 | |
| 834 | |
| 835 | |

461                                             462

TABLE 1-continued

Exemplary compounds of the invention

| Compound No. | Structure |
| --- | --- |
| 836 | |
| 837 | |
| 838 | |
| 839 | |

TABLE 1-continued

Exemplary compounds of the invention

| Compound No. | Structure |
|---|---|
| 840 | 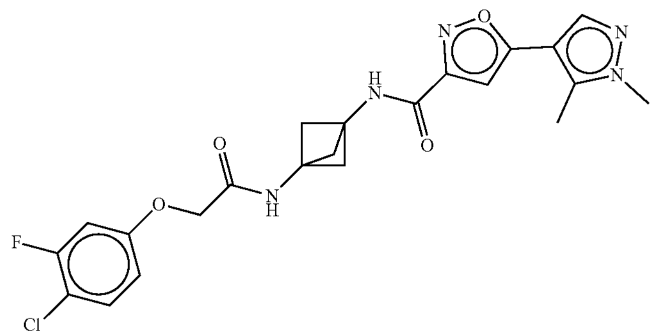 |
| 841 | 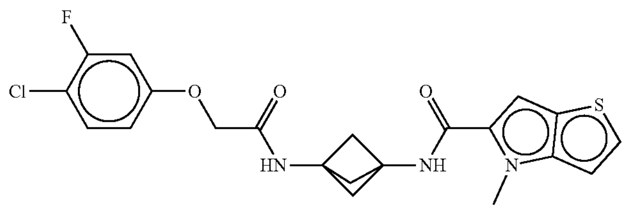 |
| 842 | 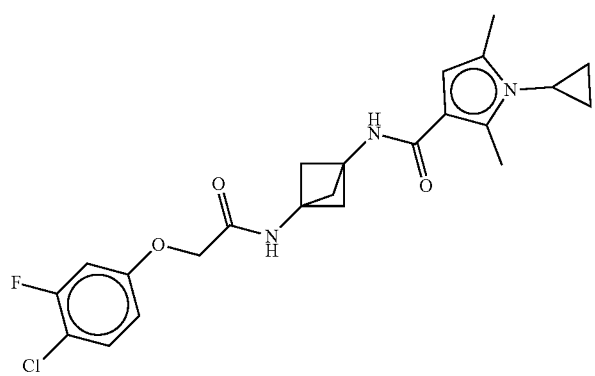 |
| 843 | 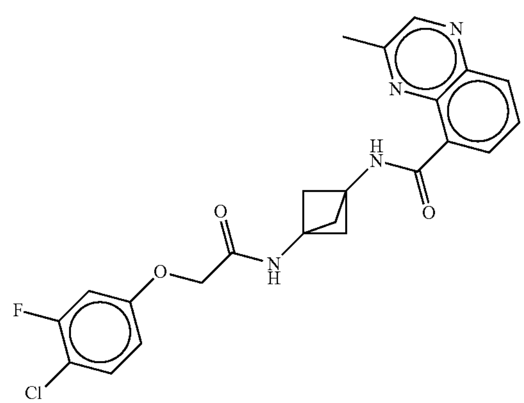 |

TABLE 1-continued
Exemplary compounds of the invention
| Compound No. | Structure |
|---|---|
| 844 | 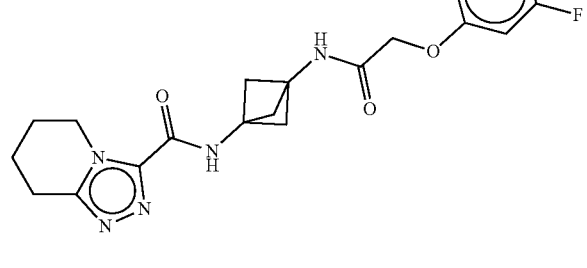 |
| 845 | 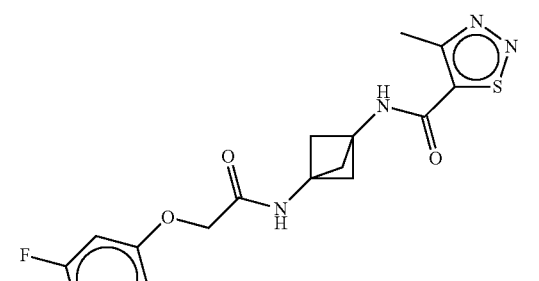 |
| 846 | 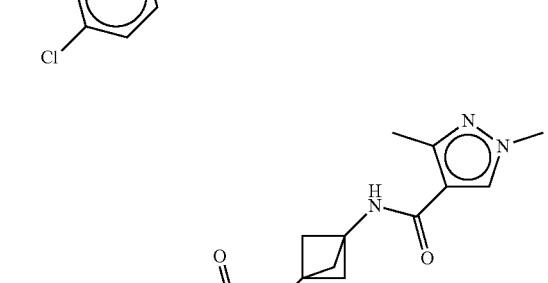 |
| 847 | 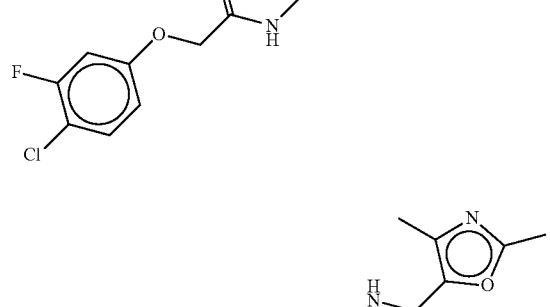 |

TABLE 1-continued

Exemplary compounds of the invention

| Compound No. | Structure |
|---|---|
| 848 | |
| 849 | |
| 850 | |
| 851 | |

TABLE 1-continued

Exemplary compounds of the invention

| Compound No. | Structure |
| --- | --- |
| 852 | |
| 853 | |
| 854 | |
| 855 | |

TABLE 1-continued

Exemplary compounds of the invention

| Compound No. | Structure |
|---|---|
| 856 | |
| 857 | |
| 858 | |
| 859 | |

TABLE 1-continued

Exemplary compounds of the invention

| Compound No. | Structure |
| --- | --- |
| 860 | 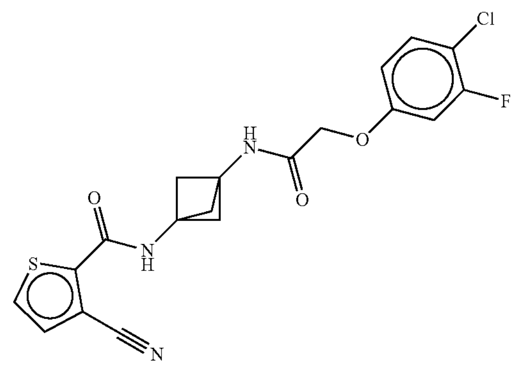 |
| 861 | 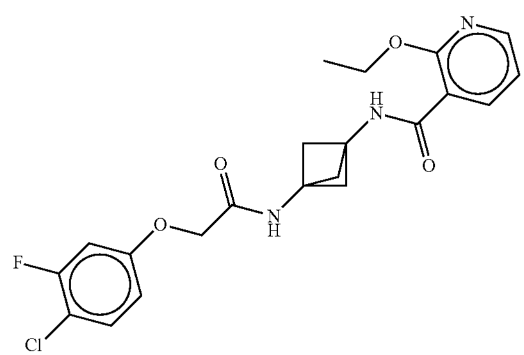 |
| 862 | 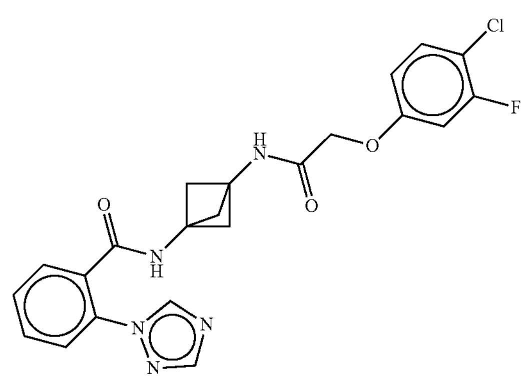 |
| 863 | 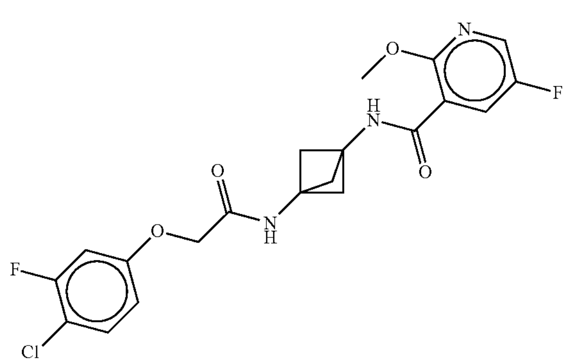 |

TABLE 1-continued
Exemplary compounds of the invention
| Compound No. | Structure |
| --- | --- |
| 864 | 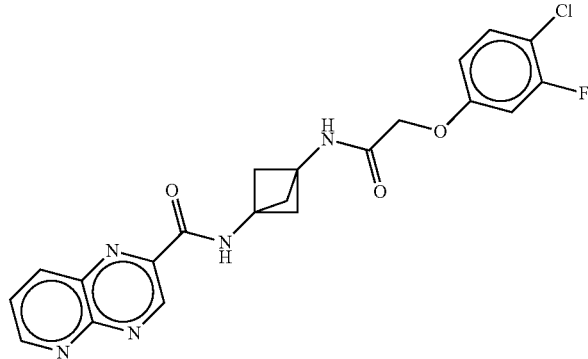 |
| 865 | 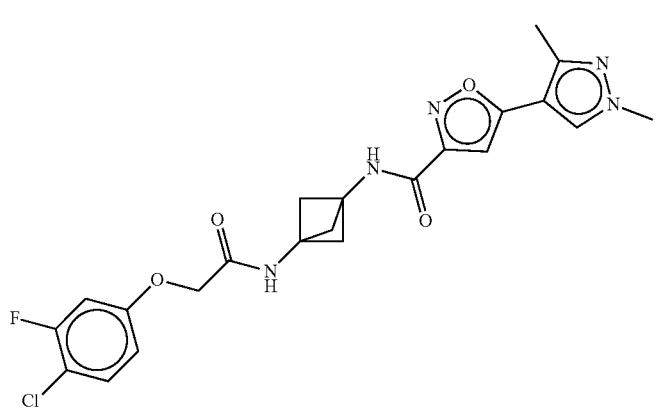 |
| 866 | 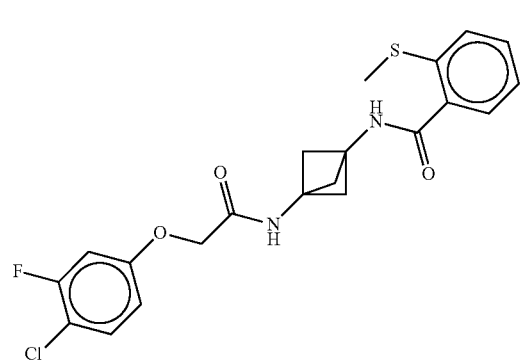 |
| 867 | 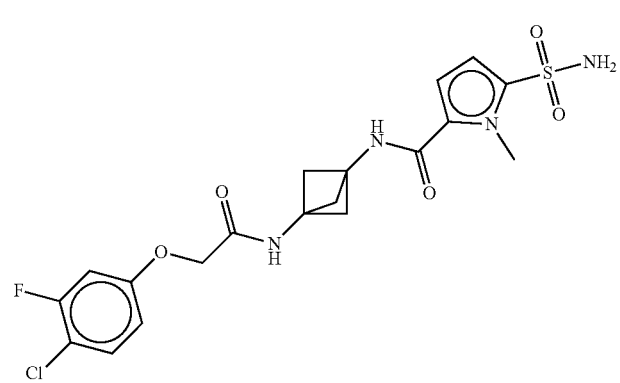 |

TABLE 1-continued

Exemplary compounds of the invention

| Compound No. | Structure |
| --- | --- |
| 868 | |
| 869 | |
| 870 | |
| 871 | |

TABLE 1-continued

Exemplary compounds of the invention

| Compound No. | Structure |
|---|---|
| 872 | |
| 873 | |
| 874 | |
| 875 | |

TABLE 1-continued

Exemplary compounds of the invention

| Compound No. | Structure |
|---|---|
| 876 | |
| 877 | |
| 878 | |
| 879 | |

TABLE 1-continued
Exemplary compounds of the invention
| Compound No. | Structure |
|---|---|
| 880 | 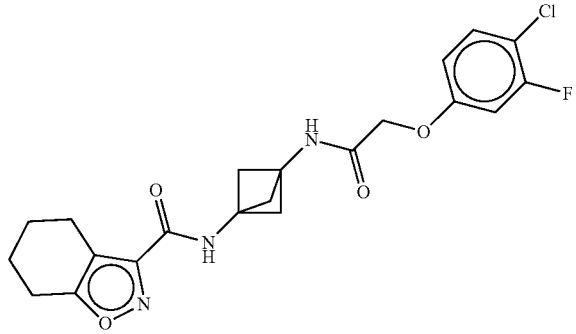 |
| 881 | 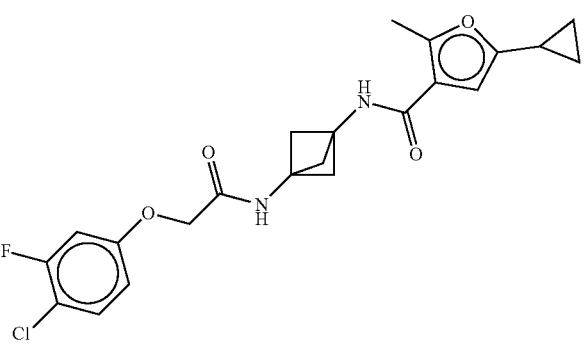 |
| 882 | 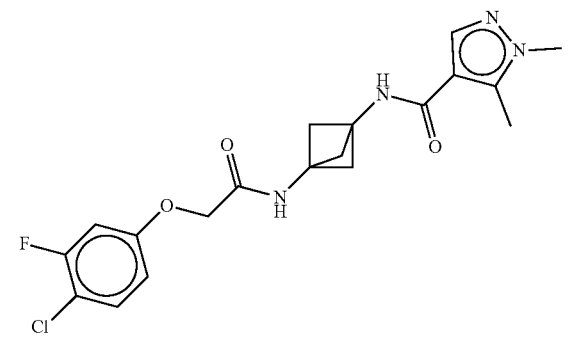 |
| 883 | 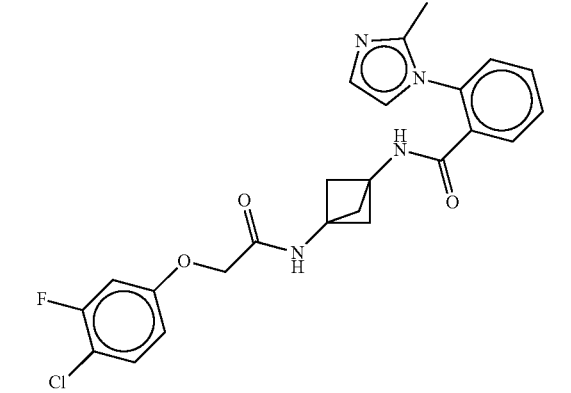 |

TABLE 1-continued

Exemplary compounds of the invention

| Compound No. | Structure |
|---|---|
| 884 | |
| 885 | |
| 886 | |
| 887 | |

TABLE 1-continued

| Compound No. | Exemplary compounds of the invention Structure |
|---|---|
| 888 | |
| 889 | |
| 890 | |
| 891 | |

TABLE 1-continued
Exemplary compounds of the invention
| Compound No. | Structure |
|---|---|
| 892 | 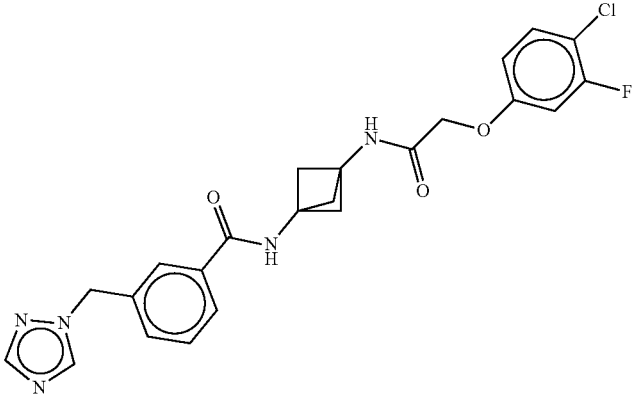 |
| 893 | 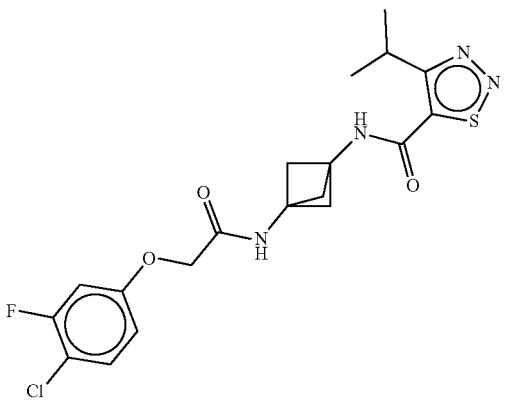 |
| 894 | 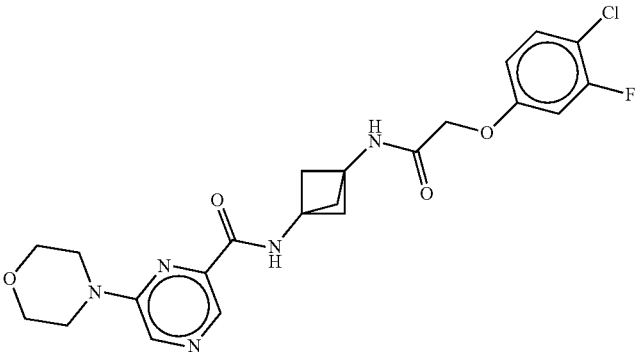 |
| 895 | 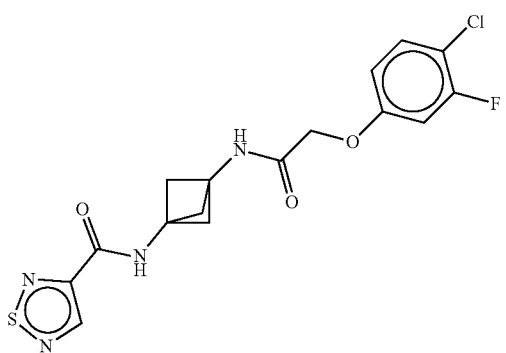 |

TABLE 1-continued

Exemplary compounds of the invention

| Compound No. | Structure |
| --- | --- |
| 896 | 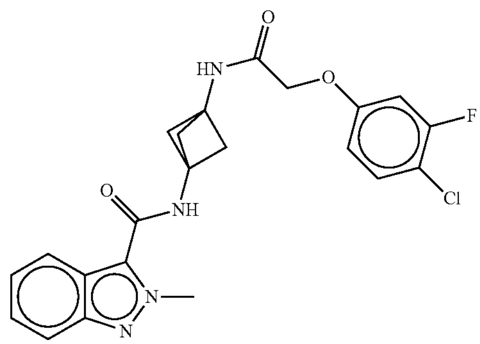 |
| 897 | 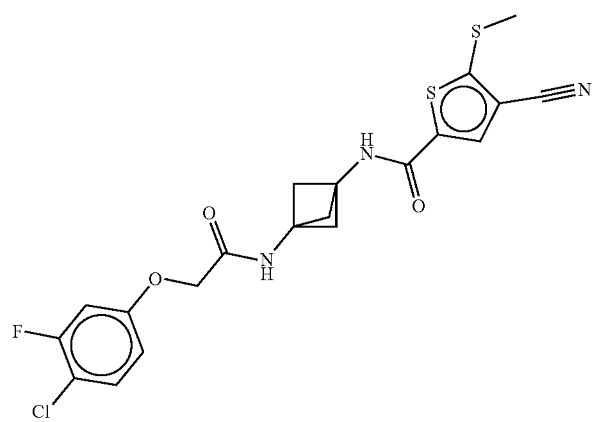 |
| 898 | 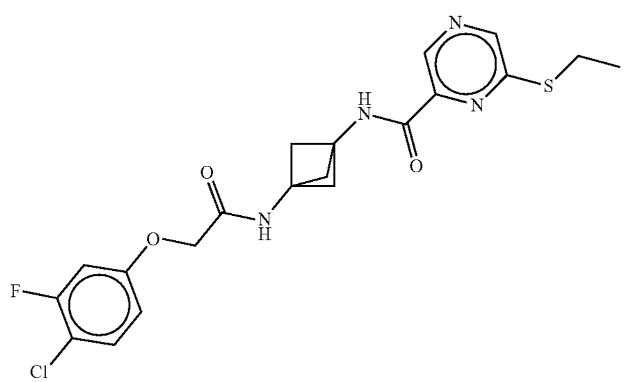 |
| 899 | 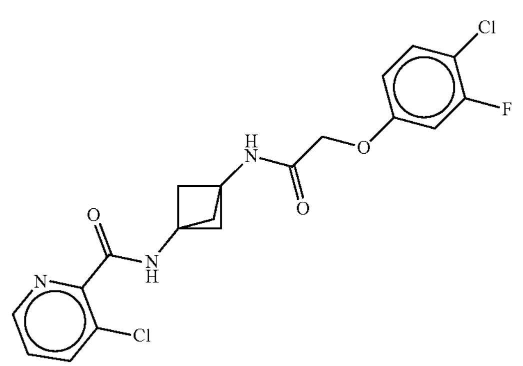 |

TABLE 1-continued
Exemplary compounds of the invention
| Compound No. | Structure |
|---|---|
| 900 | 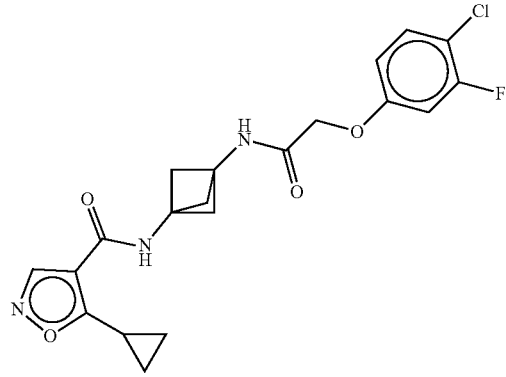 |
| 901 | 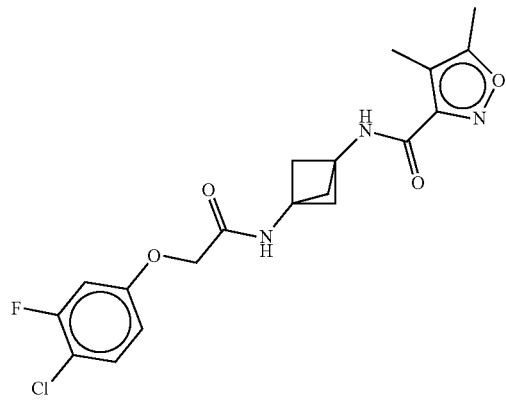 |
| 902 | 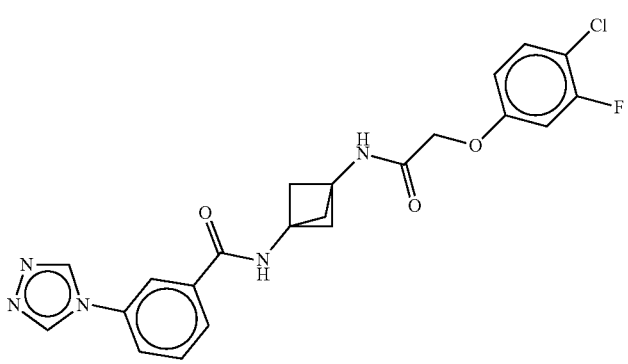 |
| 903 | 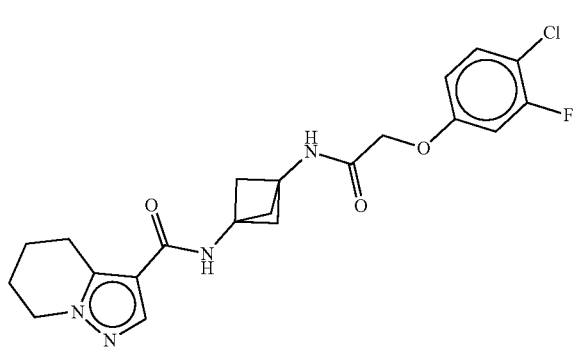 |

TABLE 1-continued

Exemplary compounds of the invention

| Compound No. | Structure |
|---|---|
| 904 | |
| 905 | |
| 906 | |
| 907 | |

TABLE 1-continued
Exemplary compounds of the invention
| Compound No. | Structure |
|---|---|
| 908 | 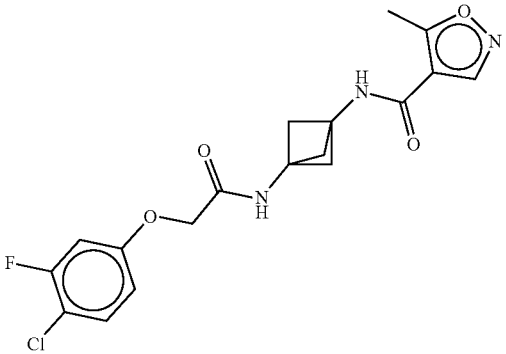 |
| 909 | 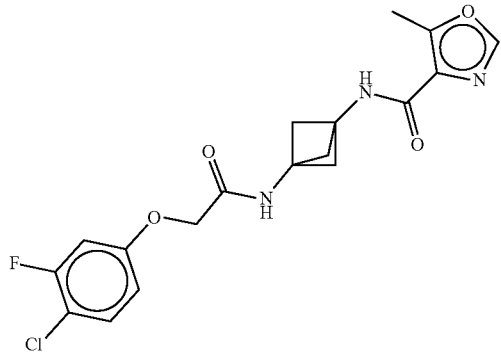 |
| 910 | 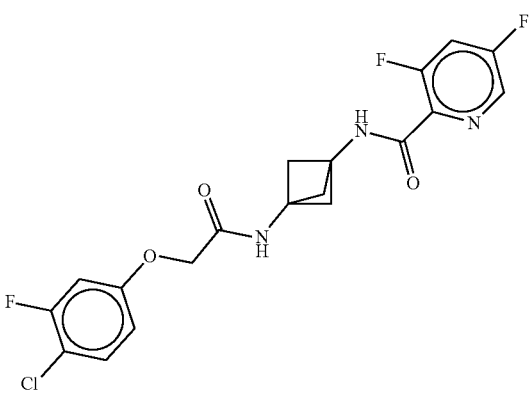 |
| 911 | 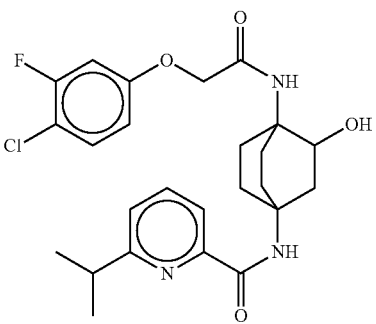 |

TABLE 1-continued
Exemplary compounds of the invention
| Compound No. | Structure |
| --- | --- |
| 912 | 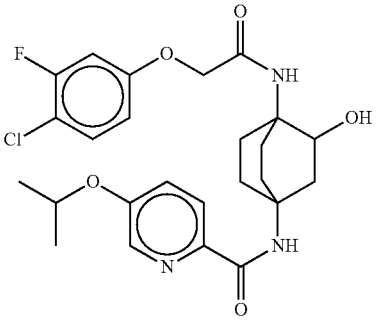 |
| 913 | 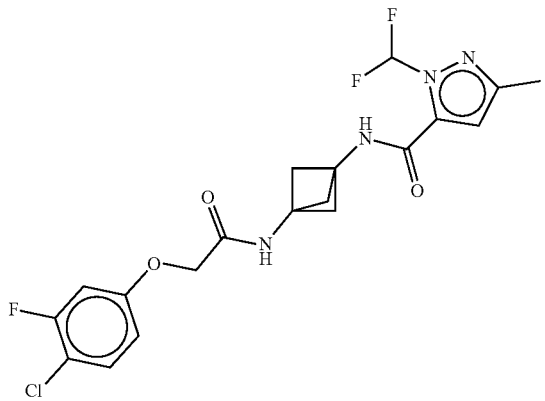 |
| 914 | 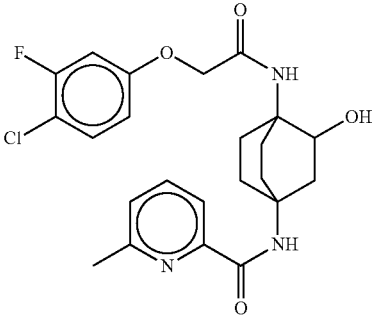 |
| 915 | 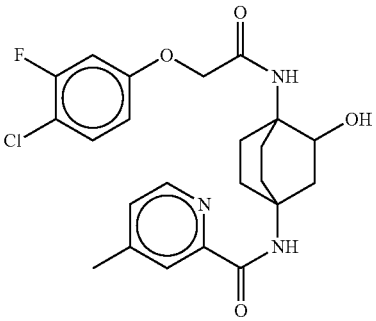 |

TABLE 1-continued

Exemplary compounds of the invention

| Compound No. | Structure |
|---|---|
| 916 | |
| 917 | |
| 918 | |
| 919 | |

TABLE 1-continued
Exemplary compounds of the invention
| Compound No. | Structure |
| --- | --- |
| 920 | 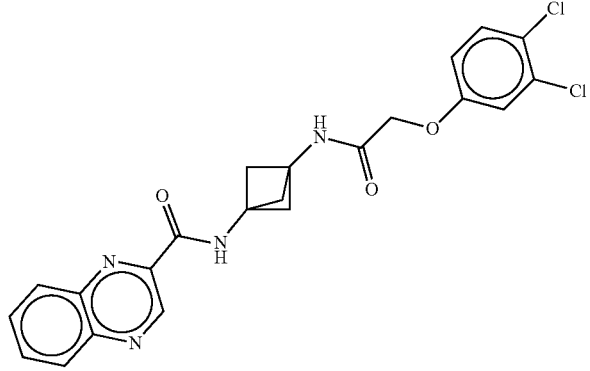 |
| 921 | 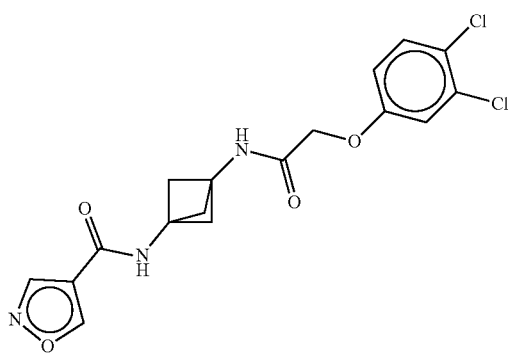 |
| 922 | 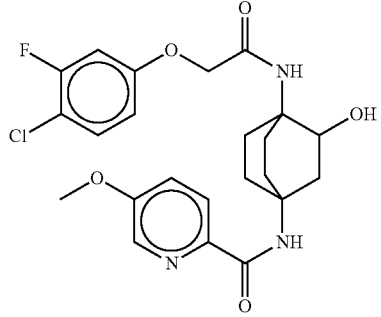 |
| 923 | 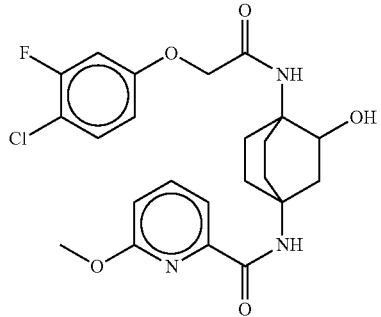 |

TABLE 1-continued

Exemplary compounds of the invention

| Compound No. | Structure |
|---|---|
| 924 | |
| 925 | |
| 926 | |
| 927 | |

TABLE 1-continued
Exemplary compounds of the invention
| Compound No. | Structure |
|---|---|
| 928 | 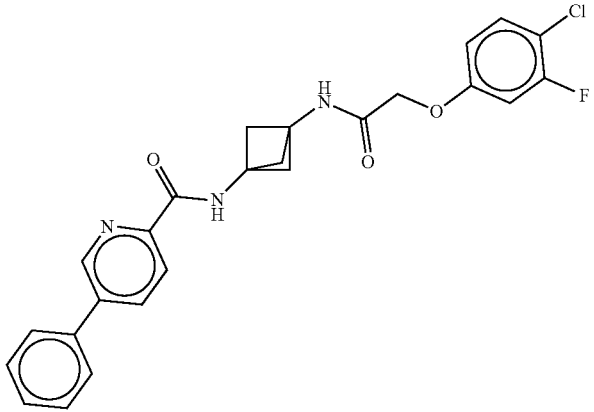 |
| 929 | 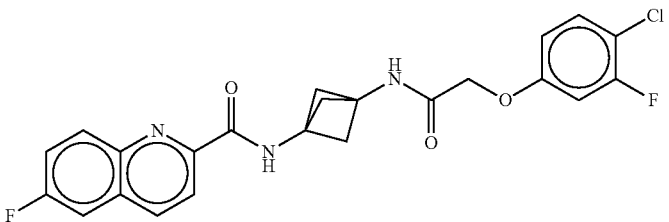 |
| 930 | 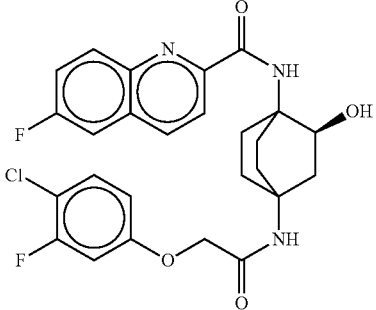 |
| 931 | 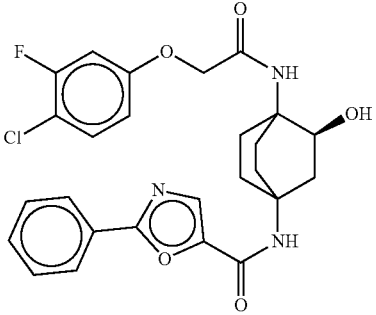 |

TABLE 1-continued
Exemplary compounds of the invention
| Compound No. | Structure |
|---|---|
| 932 | 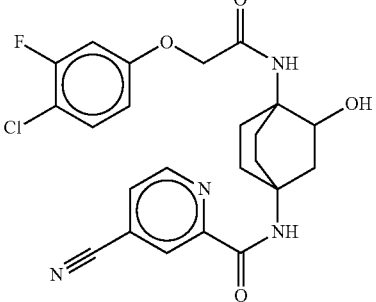 |
| 933 | 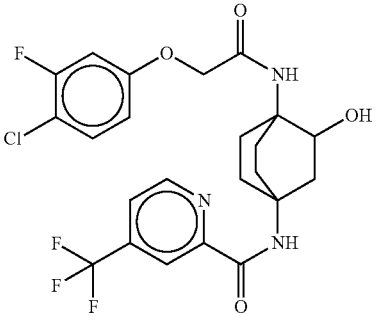 |
| 934 | 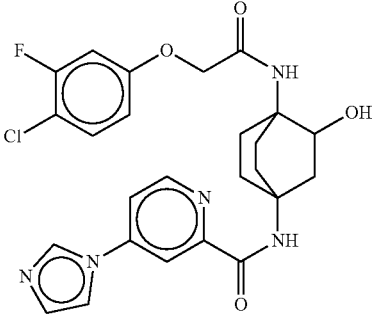 |
| 935 | 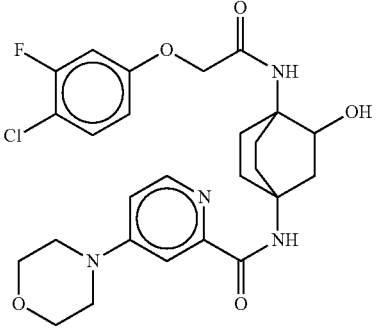 |

TABLE 1-continued

Exemplary compounds of the invention

| Compound No. | Structure |
|---|---|
| 936 | |
| 937 | |
| 938 | |
| 939 | |

TABLE 1-continued

Exemplary compounds of the invention

| Compound No. | Structure |
|---|---|
| 940 | |
| 941 | |
| 942 | |
| 943 | |

TABLE 1-continued
Exemplary compounds of the invention
| Compound No. | Structure |
|---|---|
| 944 | 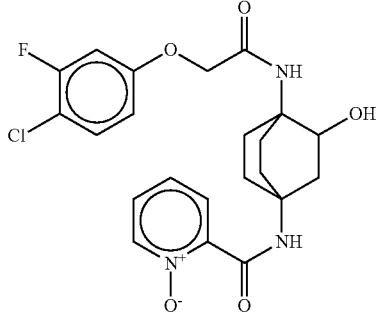 |
| 945 | 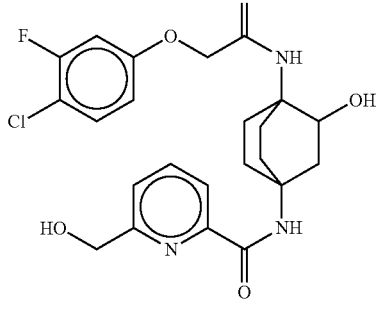 |
| 946 | 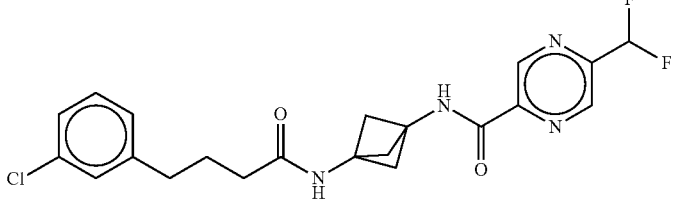 |
| 947 | 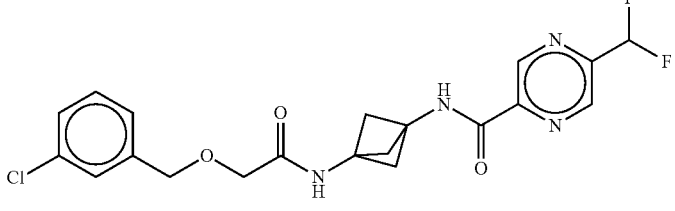 |
| 948 | 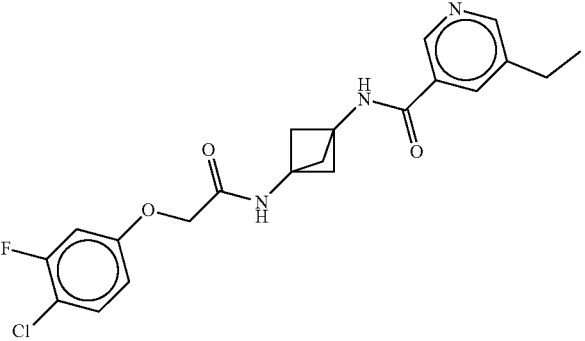 |

TABLE 1-continued

| Compound No. | Exemplary compounds of the invention Structure |
|---|---|
| 949 | |
| 950 | |
| 951 | |
| 952 | |
| 953 | |

TABLE 1-continued
Exemplary compounds of the invention
| Compound No. | Structure |
|---|---|
| 954 | 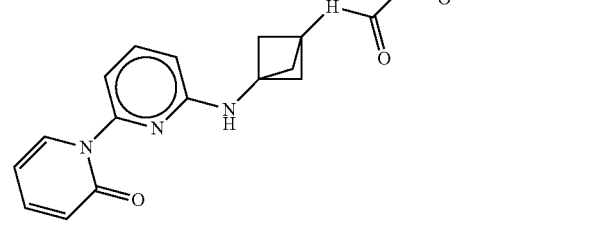 |
| 955 | 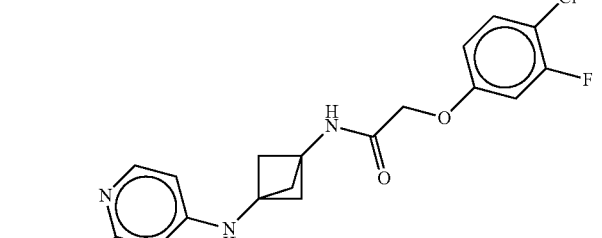 |
| 956 |  |
| 957 | 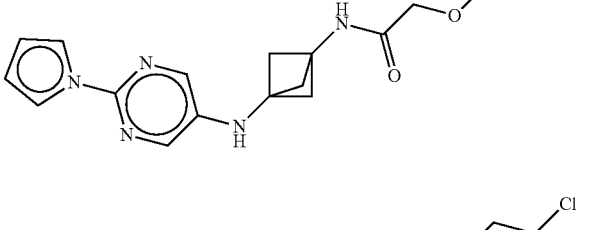 |

TABLE 1-continued

Exemplary compounds of the invention

| Compound No. | Structure |
|---|---|
| 958 | |
| 959 | |
| 960 | |
| 961 | |

TABLE 1-continued

| Compound No. | Exemplary compounds of the invention Structure |
|---|---|
| 962 | |
| 963 | |
| 964 | |
| 965 | |
| 966 | |

Methods of Making Exemplary Compounds

The compounds of the invention may be better understood in connection with the following synthetic schemes and methods which illustrate a means by which the compounds can be prepared. The compounds of this invention can be prepared by a variety of synthetic procedures. Representative synthetic procedures are shown in, but not limited to, Schemes 1-12. The variables A, D, W, $G^1$, $L^1$, $L^2$, $R^1$, and $R^2$ are defined as detailed herein, e.g., in the Summary.

Scheme 1: Representative scheme for synthesis of exemplary compounds of the invention.

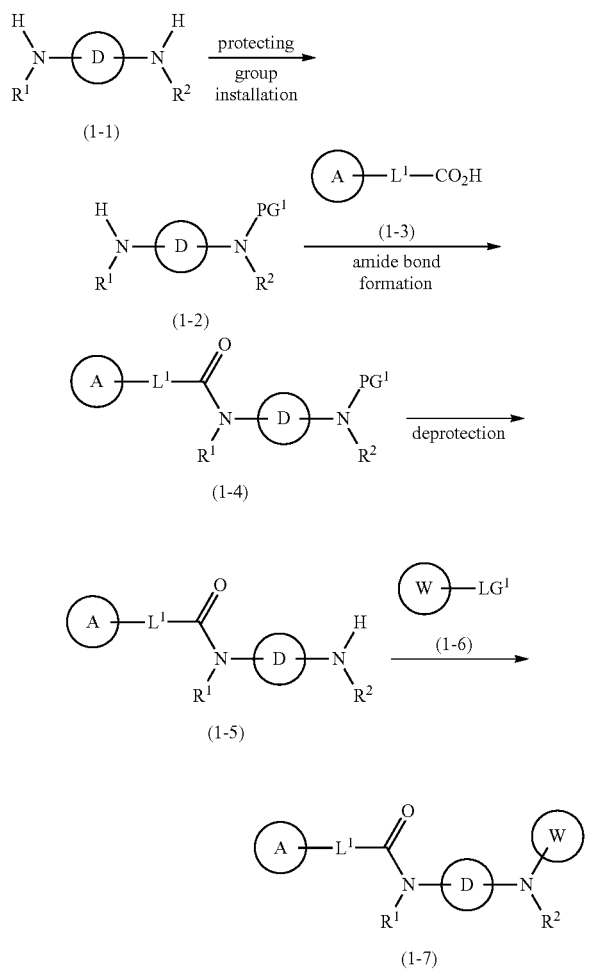

As shown in Scheme 1, compounds of formula (1-7) can be prepared from compounds of formula (1-1). Compounds of formula (1-1) can be converted to compounds of formula (1-2) by selective installation of a protecting group ($PG^1$, e.g. tert-butoxycarbonyl or benzyloxycarbonyl) using conditions known to one of skill in the art. Amines of formula (1-2) (also commercially available) can be coupled with carboxylic acids of formula (1-3) under amide bond forming conditions to give amides of formula (1-4). Examples of conditions known to generate amides from a mixture of a carboxylic acid and an amine include but are not limited to adding a coupling reagent such as N-(3-dimethylaminopropyl)-N'-ethylcarbodiimide or 1-(3-dimethylaminopropyl)-3-ethylcarbodiimide (EDC, EDAC or EDCI), 1,3-dicyclohexylcarbodiimide (DCC), bis(2-oxo-3-oxazolidinyl) phosphinic chloride (BOPCl), N-[(dimethylamino)-1H-1,2,3-triazolo-[4,5-b]pyridin-1-ylmethylene]-N-methylmethanaminium hexafluorophosphate N-oxide or 2-(7-azabenzotriazol-1-yl)-N,N,N',N'-tetramethyluronium hexafluorophosphate or 1-[bis(dimethylamino)methylene]-1H-1,2,3-triazolo[4,5-b]pyridinium 3-oxidhexafluorophosphate or 2-(3H-[1,2,3]triazolo[4,5-b]pyridin-3-yl)-1,1,3,3-tetramethylisouronium hexafluorophosphate(V) or 2-(7-aza-1H-benzotriazole-1-yl)-1,1,3,3-tetramethyluronium hexafluorophosphate (HATU), O-(benzotriazol-1-yl)-N,N,N',N'-tetramethyluronium tetrafluoroborate (TBTU), 2-(1H-benzo[d][1,2,3]triazol-1-yl)-1,1,3,3-tetramethylisouronium hexafluorophosphate(V) (HBTU), 2,4,6-tripropyl-1,3,5,2,4,6-trioxatriphosphinane 2,4,6-trioxide (T3P®), (1-cyano-2-ethoxy-2-oxoethylidenaminooxy)dimethylamino-morpholino-carbenium hexafluorophosphate (COMU®), and fluoro-N,N,N',N'-tetramethylformamidinium hexafluorophosphate. The coupling reagents may be added as a solid, a solution, or as the reagent bound to a solid support resin.

In addition to the coupling reagents, auxiliary-coupling reagents may facilitate the coupling reaction. Auxiliary coupling reagents that are often used in the coupling reactions include but are not limited to (dimethylamino)pyridine (DMAP), 1-hydroxy-7-azabenzotriazole (HOAT) and 1-hydroxybenzotriazole (HOBT). The reaction may be carried out optionally in the presence of a base such as triethylamine or diisopropylethylamine. The coupling reaction may be carried out in solvents such as but not limited to tetrahydrofuran, N,N-dimethylformamide, N,N-dimethylacetamide, dimethyl sulfoxide, dichloromethane, and ethyl acetate. Alternatively, carboxylic acids of formula (1-3) can be converted to the corresponding acid chlorides by reaction with thionyl chloride, $PCl_3$, $PCl_5$, cyanuric chloride, or oxalyl chloride. The reactions with thionyl chloride and oxalyl chloride can be catalyzed with N,N-dimethylformamide at ambient temperature in a solvent such as dichloromethane. The resultant acid chlorides can then reacted with amines of formula (1-2) optionally in the presence of a base such as a tertiary amine base such as triethylamine or diisopropylethylamine or an aromatic base such as pyridine, at room temperature in a solvent such as dichloromethane to give amides of formula (1-4).

Compounds of formula (1-4) can be deprotected using conditions known to one of skill in the art and dependent upon the protecting group ($PG^1$) used to give compounds of formula (1-5). Compounds of formula (1-5) can be reacted with compounds of formula (1-6), wherein $LG^1$ is a leaving group, e.g., halogen or sulfonate, under nuclear aromatic substitution reaction conditions to give compounds of formula (1-7). In a subset of compounds, wherein W of formula (1-6) is 6-membered nitrogen containing heteroaryl with a ring nitrogen adjacent to the carbon substituted with $LG^1$, compounds of formula (1-5) can be reacted with compounds of formula (1-6) in the presence of a base, such as potassium tert-butoxide at ambient temperature in a solvent such as tetrahydrofuran to also give compounds of formula (1-7). Alternatively, compounds of formula (1-5) can be reacted with compounds of formula (1-6) in the presence of a tertiary amine base, such as N,N-diisopropylethylamine at elevated temperature in a solvent such as N,N-dimethylformamide to also give compounds of formula (1-7). Compounds of formula (1-7) are representative of compounds of Formula (I).

Scheme 2: Representative scheme for synthesis of exemplary compounds of the invention

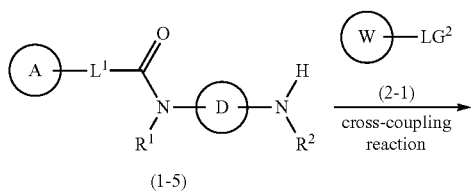

(1-5)

$\xrightarrow[\text{reaction}]{\text{(2-1)}}$
cross-coupling

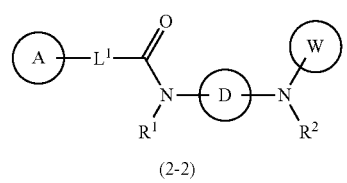

(2-2)

As shown in Scheme 2, compounds of formula (2-2) can be prepared from compounds of formula (1-5). Compounds of formula (1-5) can be reacted with compounds of formula (2-1), wherein $LG^2$ is a leaving group, e.g. chlorine, bromine, iodine, or a sulfonate, under palladium catalyzed cross-coupling reaction conditions to give compounds of formula (2-2). An example of palladium cross-coupling reaction conditions includes but is not limited to a palladium catalyst (e.g. tris(dibenzylideneacetone)dipalladium(0)), a ligand (e.g. Xantphos), and a base (e.g. potassium carbonate), heated in a solvent (e.g. dioxane) under an inert atmosphere.

Scheme 3: Representative scheme for synthesis of exemplary compounds of the invention

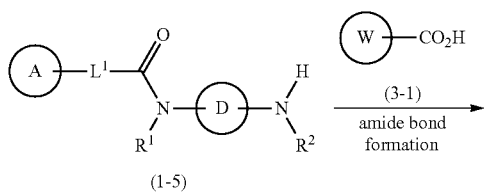

(1-5)

$\xrightarrow[\text{amide bond formation}]{\text{(3-1)}}$

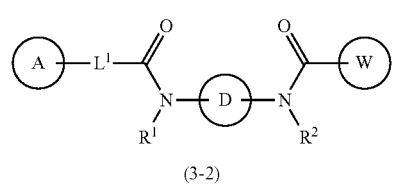

(3-2)

As shown in Scheme 3, compounds of formula (3-2) can be prepared from compounds of formula (1-5). Compounds of formula (1-5) can be reacted with compounds of formula (3-1) under the amide bond forming reaction conditions described in Scheme 1 to give compounds of formula (3-2). Compounds of formula (1-5) can also be reacted with the acid chlorides corresponding to carboxylic acids of formula (3-1) as described in Scheme 1. Compounds of formula (3-2) are representative of compounds of formula (I).

Scheme 4: Representative scheme for synthesis of exemplary compounds of the invention

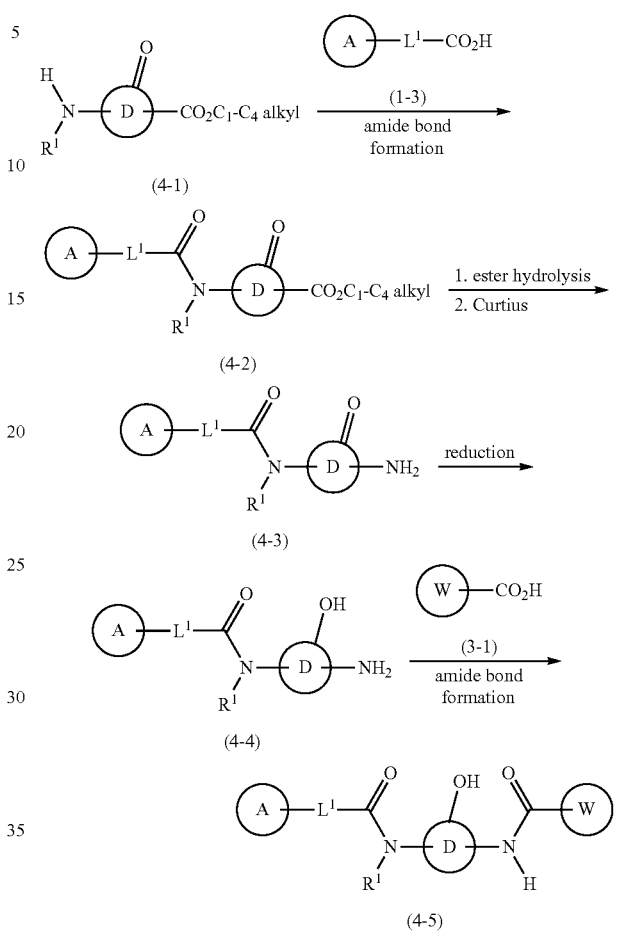

As shown in Scheme 4, compounds of formula (4-5) can be prepared from compounds of formula (4-1). Compounds of formula (4-1) can be reacted with compounds of formula (1-3) under the amide bond forming reaction conditions described in Scheme 1 to give compounds of formula (4-2). Compounds of formula (4-1) can also be reacted with the acid chlorides corresponding to carboxylic acids of formula (3-1) as described in Scheme 1 to give compound of formula (4-2). The ester moiety of compounds of formula (4-2) can be hydrolyzed under conditions known to one of skill in the art to give the corresponding carboxylic acids. The carboxylic acids can then be reacted under Curtius reaction conditions to give amines of formula (4-3). The ketone moiety in compounds of formula (4-3) can be reduced with a reductant such as sodium borohydride in solvents such as methanol or a mixture of dichloromethane and methanol to give compounds of formula (4-4). Compounds of formula (4-4) can be reacted with compounds of formula (3-1) under the amide bond forming reaction conditions described in Scheme 1 to give compounds of formula (4-5). Compounds of formula (4-5) are representative of compounds of formula (I).

Scheme 5: Representative scheme for synthesis of exemplary compounds of the invention

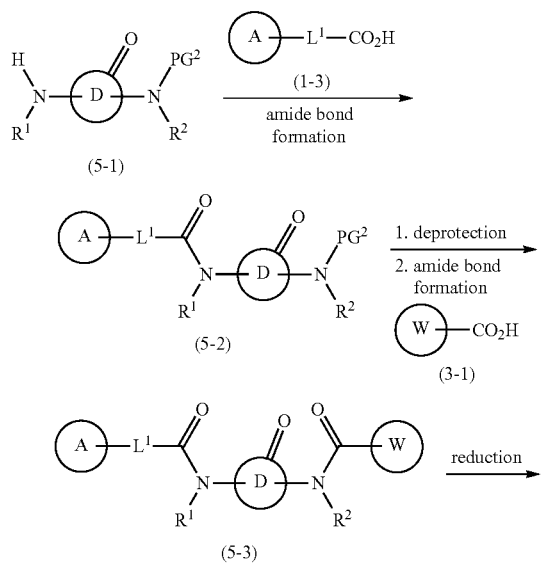

As shown in Scheme 5, compounds of formula (5-3) and formula (5-4) can be prepared from compounds of formula (5-1). Compounds of formula (5-1), wherein $PG^2$ is a suitable amine protecting group, can be reacted with compounds of formula (1-3) under the amide bond forming reaction conditions described in Scheme 1 to give compounds of formula (5-2). The protecting group in compounds of formula (5-2) can then be removed under conditions known to one of skill in the art followed by amide bond formation of the revealed amine with compounds of formula (3-1) under the amide bond forming reaction conditions described in Scheme 1 to give compounds of formula (5-3). Compounds of formula (5-3) can be reduced with a reductant such as sodium borohydride in solvents such as methanol or a mixture of dichloromethane and methanol to give compounds of formula (5-4). Compounds of formula (5-3) and compounds of formula (5-4) are representative of compounds of formula (I).

Scheme 6: Representative scheme for synthesis of exemplary compounds of the invention

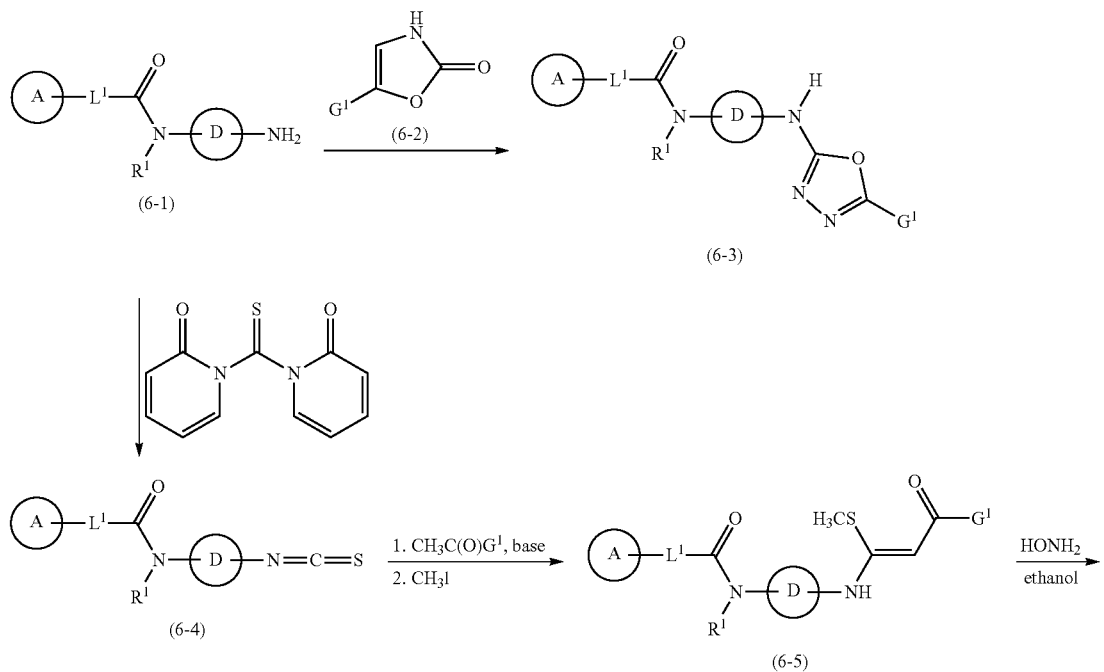

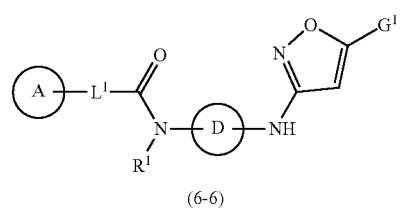

As shown in Scheme 6, compounds of formula (6-3) and compounds of formula (6-6) can be prepared from compounds of formula (6-1). Compounds of formula (6-1) can be reacted with compounds of formula (6-2) in the presence of a tertiary amine base such as N,N-diisopropylamine and ((1H-benzo[d][1,2,3]triazol-1-yl)oxy)tris(dimethylamino)phosphonium hexafluorophosphate(V) to give compounds of formula (6-3).

Compounds of formula (6-1) can also be reacted with 1,1'-thiocarbonylbis(pyridin-2(1H)-one) in the presence of a tertiary amine base such as N,N-diisopropylamine to give isothiocyanates of formula (6-4). Compounds of formula (6-4) can be reacted with the enolates of ketones, $CH_3C(O)G^1$, and then alkylated with iodomethane to give compounds of formula (6-5). Compounds of formula (6-5) can be reacted with aqueous hydroxylamine in heated ethanol to give compounds of formula (6-6).

Compounds of formula (6-3) and compounds of formula (6-6) are representative of compounds of formula (I).

Scheme 7: Representative scheme for synthesis of exemplary compounds of the invention

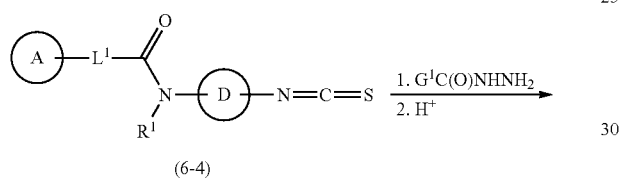

(6-4)

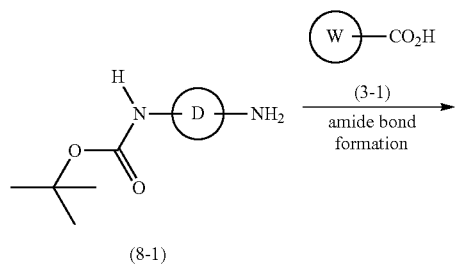

(7-1)

As shown in Scheme 7, compounds of formula (6-4) can be converted to compounds of formula (7-1). Compounds of formula (6-4) can be reacted with a hydrazide, $G^1C(O)NHNH_2$, in warmed dichloromethane and then an acid such as concentrated sulfuric acid at ambient temperature to give compounds of formula (7-1). Compounds of formula (7-1) are representative of compounds of formula (I).

Scheme 8: Representative scheme for synthesis of exemplary compounds of the invention

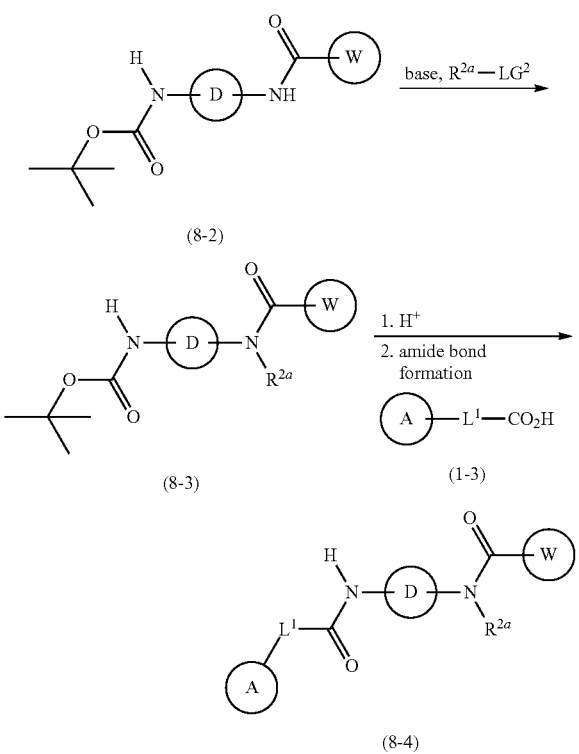

As shown in Scheme 8, compounds of formula (8-4) can be obtained from compounds of formula (8-1). Compounds of formula (8-1) can be reacted with compounds of formula (3-1) under the amide bond forming reaction conditions described in Scheme 1 to give compounds of formula (8-2). Compounds of formula (8-2) can alkylated with $R^{2a}$-$LG^2$, wherein $LG^2$ is a leaving group, e.g. chlorine, bromine, iodine, or a sulfonate and $R^{2a}$ is an optionally substituted $C_1$-$C_6$ alkyl, in the presence of a base such as sodium hydride at or near ambient temperature in a suitable solvent such as N,N-dimethylformamide to give compounds of formula (8-3). The tert-butoxycarbonyl protecting group of compounds of formula (8-3) can be removed under acidic conditions known to one of skill in the art, and the exposed amine can then be reacted in a second step with compounds of formula (1-3) under the amide bond forming reaction conditions described in Scheme 1 to give compounds of formula (8-4). Compounds of formula (8-4) are representative of compounds of formula (I).

Scheme 9: Representative scheme for synthesis of exemplary compounds of the invention.

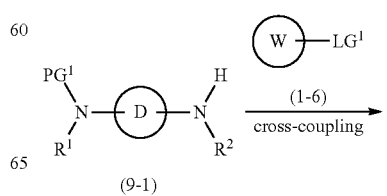

(9-1)

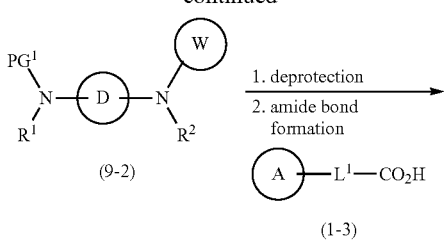

(9-2)

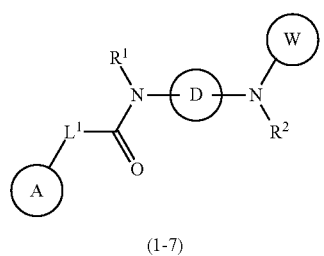

(1-7)

As shown in Scheme 9. Compounds of formula (1-7) can also be prepared from compounds of formula (9-1). Compounds of formula (9-1), wherein PG$^1$ is a suitable amine protecting group (PG$^1$, e.g. tert-butoxycarbonyl or benzyloxycarbonyl), can be reacted with compounds of formula (1-6), wherein LG$^1$ is a leaving group, e.g., halogen or sulfonate, under cross-coupling reaction conditions to give compounds of formula (9-2). Compounds of formula (9-2) can be deprotected using suitable conditions known to one of skill in the art to expose an amine that is subsequently coupled with compounds of formula (1-3) under the amide bond forming reaction conditions described in Scheme 1 to give compounds of formula (1-7). Compounds of formula (1-7) are representative of compounds of formula (I).

Scheme 10: Representative scheme for synthesis of exemplary compounds of the invention

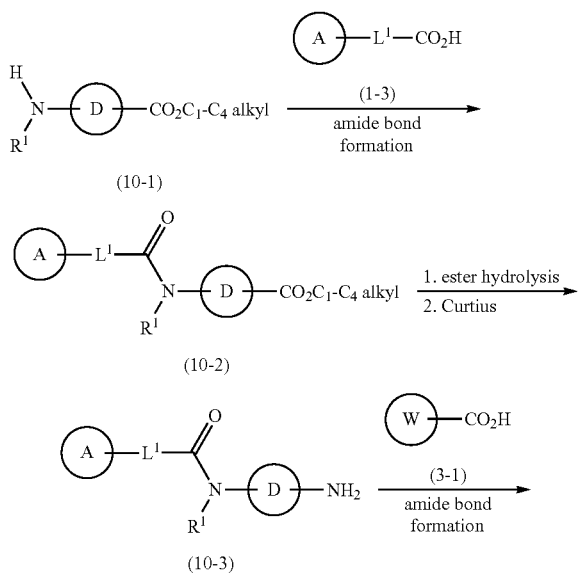

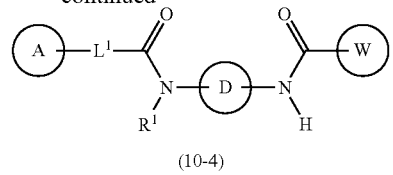

(10-4)

As shown in Scheme 10, compounds of formula (10-4) can be prepared from compounds of formula (10-1). Compounds of formula (10-1) can be coupled with compounds of formula (1-3) under the amide bond forming reaction conditions described in Scheme 1 to give compounds of formula (10-2). Compounds of formula (10-2) can be converted to compounds of formula (10-3) in a two-step process. In the first step, esters of formula (10-2) can be hydrolyzed to the corresponding carboxylic acids using conditions known to one of skill in the art. The carboxylic acids can be reacted under Curtius reaction conditions to give compounds of formula (10-3). Compounds of formula (10-3) can be reacted with compounds of formula (3-1) under the amide bond forming reaction conditions described in Scheme 1 to give compounds of formula (10-4). Compounds of formula (10-4) are representative of compounds of formula (I).

Scheme 11: Representative scheme for synthesis of exemplary compounds of the invention

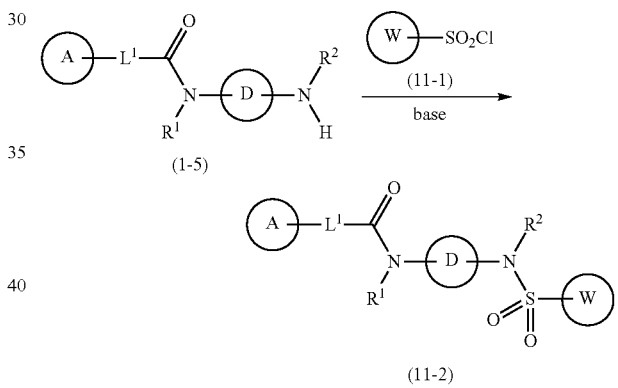

As shown in Scheme 11, sulfonamides of formula (11-2) can be prepared from compounds of formula (1-5). Compounds of formula (1-5) can be reacted with sulfonyl chlorides of formula (11-1) in the presence of a tertiary amine base such as triethylamine or N,N-diisopropylethylamine in a solvent such as N,N-dimethylformamide at ambient temperature to give compounds of formula (11-2). Compounds of formula (11-2) are representative of compounds of formula (I).

Scheme 12: Representative scheme for synthesis of exemplary compounds of the invention

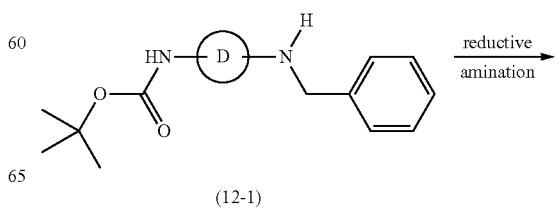

(12-1)

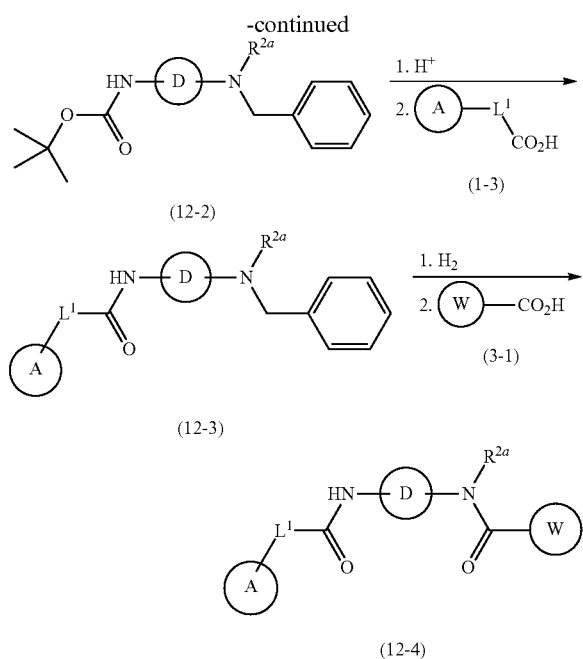

(12-2)

(12-3)

(12-4)

As shown in Scheme 12, compounds of formula (12-1) can be converted to compounds of formula (12-4). Compounds of formula (12-1) can be reductively aminated to compounds of formula (12-2), wherein $R^{2a}$ is optionally substituted $C_1$-$C_6$ alkyl. Compounds of formula (12-2) can be treated under acidic conditions known to one of skill in the art to selectively remove the tert-butoxy carbonyl protecting group and then couple the exposed amine with compounds of formula (1-3) using amide bond forming reaction conditions described in Scheme 1 to give compounds of formula (12-3). Alternatively, the corresponding acid chlorides of the carboxylic acids of formula (1-3) can be coupled with the amines also as described in Scheme 1. The benzyl protecting group of compounds of formula (12-3) can be removed under catalytic hydrogenation conditions, and then the revealed amine can be coupled with carboxylic acids of formula (3-1) to give compounds of formula (12-4). Compounds of formula (12-4) can also be obtained by reaction with the corresponding acid chloride with the previously mentioned revealed amine using conditions also described in Scheme 1. Compounds of formula (12-4) are representative of compounds of formula (I).

Pharmaceutical Compositions

The present invention features pharmaceutical compositions comprising a compound of Formula (I) or a pharmaceutically acceptable salt, solvate, hydrate, tautomer, or stereoisomer thereof. In some embodiments, the pharmaceutical composition further comprises a pharmaceutically acceptable excipient. In some embodiments, the compound of Formula (I) or a pharmaceutically acceptable salt, solvate, hydrate, tautomer, stereoisomer thereof is provided in an effective amount in the pharmaceutical composition. In some embodiments, the effective amount is a therapeutically effective amount. In certain embodiments, the effective amount is a prophylactically effective amount.

Pharmaceutical compositions described herein can be prepared by any method known in the art of pharmacology. In general, such preparatory methods include the steps of bringing the compound of Formula (I) (the "active ingredient") into association with a carrier and/or one or more other accessory ingredients, and then, if necessary and/or desirable, shaping and/or packaging the product into a desired single- or multi-dose unit. Pharmaceutical compositions can be prepared, packaged, and/or sold in bulk, as a single unit dose, and/or as a plurality of single unit doses. As used herein, a "unit dose" is a discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

Relative amounts of a compound of Formula (I), the pharmaceutically acceptable excipient, and/or any additional ingredients in a pharmaceutical composition of the invention will vary, depending upon the identity, size, and/or condition of the subject treated and further depending upon the route by which the composition is to be administered. By way of example, the composition may comprise between 0.1% and 100% (w/w) of a compound of Formula (I).

The term "pharmaceutically acceptable excipient" refers to a non-toxic carrier, adjuvant, diluent, or vehicle that does not destroy the pharmacological activity of the compound with which it is formulated. Pharmaceutically acceptable excipients useful in the manufacture of the pharmaceutical compositions of the invention are any of those that are well known in the art of pharmaceutical formulation and include inert diluents, dispersing and/or granulating agents, surface active agents and/or emulsifiers, disintegrating agents, binding agents, preservatives, buffering agents, lubricating agents, and/or oils. Pharmaceutically acceptable excipients useful in the manufacture of the pharmaceutical compositions of the invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

Compositions of the present invention may be administered orally, parenterally (including subcutaneous, intramuscular, intravenous and intradermal), by inhalation spray, topically, rectally, nasally, buccally, vaginally or via an implanted reservoir. In some embodiments, provided compounds or compositions are administrable intravenously and/or orally.

The term "parenteral" as used herein includes subcutaneous, intravenous, intramuscular, intraocular, intravitreal, intra-articular, intra-synovial, intrasternal, intrathecal, intrahepatic, intraperitoneal intralesional and intracranial injection or infusion techniques. Preferably, the compositions are administered orally, subcutaneously, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

Pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added. In some embodiments, a provided oral formulation is formulated for immediate release or sustained/delayed release. In some embodiments, the composition is suitable for buccal or sublingual administration, including tablets, lozenges and pastilles. A compound of Formula (I) may also be in micro-encapsulated form.

The compositions of the present invention can be delivered by transdermally, by a topical route, formulated as applicator sticks, solutions, suspensions, emulsions, gels, creams, ointments, pastes, jellies, paints, powders, and aerosols. Oral preparations include tablets, pills, powder, dragees, capsules, liquids, lozenges, cachets, gels, syrups, slurries, suspensions, etc., suitable for ingestion by the patient. Solid form preparations include powders, tablets, pills, capsules, cachets, suppositories, and dispersible granules. Liquid form preparations include solutions, suspensions, and emulsions, for example, water or water/propylene glycol solutions. The compositions of the present invention may additionally include components to provide sustained release and/or comfort. Such components include high molecular weight, anionic mucomimetic polymers, gelling polysaccharides and finely-divided drug carrier substrates. These components are discussed in greater detail in U.S. Pat. Nos. 4,911,920; 5,403,841; 5,212, 162; and 4,861,760. The entire contents of these patents are incorporated herein by reference in their entirety for all purposes. The compositions of the present invention can also be delivered as microspheres for slow release in the body. For example, microspheres can be administered via intradermal injection of drug-containing microspheres, which slowly release subcutaneously (see Rao, *J. Biomater Sci. Polym. Ed.* 7:623-645, 1995; as biodegradable and injectable gel formulations (see, e.g., *Gao Pharm. Res.* 12:857-863, 1995); or, as microspheres for oral administration (see, e.g., Eyles, J. *Pharm. Pharmacol.* 49:669-674, 1997). In another embodiment, the formulations of the compositions of the present invention can be delivered by the use of liposomes which fuse with the cellular membrane or are endocytosed, i.e., by employing receptor ligands attached to the liposome, that bind to surface membrane protein receptors of the cell resulting in endocytosis. By using liposomes, particularly where the liposome surface carries receptor ligands specific for target cells, or are otherwise preferentially directed to a specific organ, one can focus the delivery of the compositions of the present invention into the target cells in vivo. (See, e.g., Al-Muhammed, J. Microencapsul. 13:293-306, 1996; Chonn, *Curr. Opin. Biotechnol.* 6:698-708, 1995; Ostro, J. *Hosp. Pharm.* 46: 1576-1587, 1989). The compositions of the present invention can also be delivered as nanoparticles.

Alternatively, pharmaceutically acceptable compositions of this invention may be administered in the form of suppositories for rectal administration. Pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

In some embodiments, in order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation.

Compounds provided herein, e.g., a compound of Formula (I) or a pharmaceutically acceptable salt, solvate, hydrate, tautomer, or stereoisomer thereof are typically formulated in dosage unit form, e.g., single unit dosage form, for ease of administration and uniformity of dosage. It will be understood, however, that the total daily usage of the compositions of the present invention will be decided by the attending physician within the scope of sound medical judgment. The specific therapeutically effective dose level for any particular subject or organism will depend upon a variety of factors including the disease being treated and the severity of the disorder; the activity of the specific active ingredient employed; the specific composition employed; the age, body weight, general health, sex and diet of the subject; the time of administration, route of administration, and rate of excretion of the specific active ingredient employed; the duration of the treatment; drugs used in combination or coincidental with the specific active ingredient employed; and like factors well known in the medical arts.

The exact amount of a compound required to achieve an effective amount will vary from subject to subject, depending, for example, on species, age, and general condition of a subject, severity of the side effects or disorder, identity of the particular compound(s), mode of administration, and the like. The desired dosage can be delivered three times a day, two times a day, once a day, every other day, every third day, every week, every two weeks, every three weeks, or every four weeks. In certain embodiments, the desired dosage can be delivered using multiple administrations (e.g., two, three, four, five, six, seven, eight, nine, ten, eleven, twelve, thirteen, fourteen, or more administrations).

In certain embodiments, an effective amount of a compound of Formula (I) or a pharmaceutically acceptable salt, solvate, hydrate, tautomer, or stereoisomer thereof for administration one or more times a day may comprise about 0.0001 mg to about 5000 mg, e.g., from about 0.0001 mg to about 4000 mg, about 0.0001 mg to about 2000 mg, about 0.0001 mg to about 1000 mg, about 0.001 mg to about 1000 mg, about 0.01 mg to about 1000 mg, about 0.1 mg to about 1000 mg, about 1 mg to about 1000 mg, about 1 mg to about 100 mg, about 10 mg to about 1000 mg, or about 100 mg to about 1000 mg, of a compound per unit dosage form.

In certain embodiments, a compound of Formula (I) or a pharmaceutically acceptable salt, solvate, hydrate, tautomer, or stereoisomer thereof may be at dosage levels sufficient to deliver from about 0.001 mg/kg to about 1000 mg/kg, e.g., about 0.001 mg/kg to about 500 mg/kg, about 0.01 mg/kg to about 250 mg/kg, about 0.1 mg/kg to about 100 mg/kg, about 0.1 mg/kg to about 50 mg/kg, about 0.1 mg/kg to about 40 mg/kg, about 0.1 mg/kg to about 25 mg/kg, about 0.01 mg/kg to about 10 mg/kg, about 0.1 mg/kg to about 10 mg/kg, or about 1 mg/kg to about 50 mg/kg, of subject body weight per day, one or more times a day, to obtain the desired therapeutic effect.

It will be appreciated that dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult.

It will be also appreciated that a compound or composition, e.g., a compound of Formula (I) or a pharmaceutically acceptable salt, solvate, hydrate, tautomer, or stereoisomer thereof as described herein, can be administered in combination with one or more additional pharmaceutical agents. The compounds or compositions can be administered in combination with additional pharmaceutical agents that improve their bioavailability, reduce and/or modify their metabolism, inhibit their excretion, and/or modify their distribution within the body. It will also be appreciated that the therapy employed may achieve a desired effect for the same disorder, and/or it may achieve different effects.

The compound or composition can be administered concurrently with, prior to, or subsequent to, one or more additional pharmaceutical agents, which may be useful as, e.g., combination therapies. Pharmaceutical agents include therapeutically active agents. Pharmaceutical agents also include prophylactically active agents. Each additional pharmaceutical agent may be administered at a dose and/or on a time schedule determined for that pharmaceutical agent. The additional pharmaceutical agents may also be administered together with each other and/or with the compound or composition described herein in a single dose or administered separately in different doses. The particular combination to employ in a regimen will take into account compatibility of the inventive compound with the additional pharmaceutical agents and/or the desired therapeutic and/or prophylactic effect to be achieved. In general, it is expected that the additional pharmaceutical agents utilized in combination be utilized at levels that do not exceed the levels at which they are utilized individually. In some embodiments, the levels utilized in combination will be lower than those utilized individually.

Exemplary additional pharmaceutical agents include, but are not limited to, anti-proliferative agents, anti-cancer agents, anti-diabetic agents, anti-inflammatory agents, immunosuppressant agents, and a pain-relieving agents. Pharmaceutical agents include small organic molecules such as drug compounds (e.g., compounds approved by the U.S. Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins, and cells.

Pharmaceutical compositions provided by the present invention include compositions wherein the active ingredient (e.g., compounds described herein, including embodiments or examples) is contained in a therapeutically effective amount, i.e., in an amount effective to achieve its intended purpose. The actual amount effective for a particular application will depend, inter alia, on the condition being treated. When administered in methods to treat a disease, such compositions will contain an amount of active ingredient effective to achieve the desired result, e.g., modulating the activity of a target molecule (e.g. eIF2B, eIF2 or component of eIF2α signal transduction pathway or component of phosphorylated eIF2α pathway or the ISR pathway), and/or reducing, eliminating, or slowing the progression of disease symptoms (e.g. symptoms of cancer a neurodegenerative disease, a leukodystrophy, an inflammatory disease, a musculoskeletal disease, a metabolic disease, or a disease or disorder associated with impaired function of eIF2B, eIF2α or a component of the eIF2 pathway or ISR pathway). Determination of a therapeutically effective amount of a compound of the invention is well within the capabilities of those skilled in the art, especially in light of the detailed disclosure herein.

The dosage and frequency (single or multiple doses) administered to a mammal can vary depending upon a variety of factors, for example, whether the mammal suffers from another disease, and its route of administration; size, age, sex, health, body weight, body mass index, and diet of the recipient; nature and extent of symptoms of the disease being treated (e.g. a symptom of cancer, a neurodegenerative disease, a leukodystrophy, an inflammatory disease, a musculoskeletal disease, a metabolic disease, or a disease or disorder associated with impaired function of eIF2B, eIF2 α, or a component of the eIF2 pathway or ISR pathway), kind of concurrent treatment, complications from the disease being treated or other health-related problems. Other therapeutic regimens or agents can be used in conjunction with the methods and compounds of Applicants' invention. Adjustment and manipulation of established dosages (e.g., frequency and duration) are well within the ability of those skilled in the art.

For any compound described herein, the therapeutically effective amount can be initially determined from cell culture assays. Target concentrations will be those concentrations of active compound(s) that are capable of achieving the methods described herein, as measured using the methods described herein or known in the art.

As is well known in the art, therapeutically effective amounts for use in humans can also be determined from animal models. For example, a dose for humans can be formulated to achieve a concentration that has been found to be effective in animals. The dosage in humans can be adjusted by monitoring compounds effectiveness and adjusting the dosage upwards or downwards, as described above. Adjusting the dose to achieve maximal efficacy in humans based on the methods described above and other methods is well within the capabilities of the ordinarily skilled artisan.

Dosages may be varied depending upon the requirements of the patient and the compound being employed. The dose administered to a patient, in the context of the present invention should be sufficient to effect a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached. Dosage amounts and intervals can be adjusted individually to provide levels of the administered compound effective for the particular clinical indication being treated. This will provide a therapeutic regimen that is commensurate with the severity of the individual's disease state.

Utilizing the teachings provided herein, an effective prophylactic or therapeutic treatment regimen can be planned that does not cause substantial toxicity and yet is effective to treat the clinical symptoms demonstrated by the particular patient. This planning should involve the careful choice of active compound by considering factors such as compound potency, relative bioavailability, patient body weight, presence and severity of adverse side effects, preferred mode of administration and the toxicity profile of the selected agent.

Also encompassed by the invention are kits (e.g., pharmaceutical packs). The inventive kits may be useful for preventing and/or treating a disease (e.g., cancer, a neurodegenerative disease, a leukodystrophy, an inflammatory disease, a musculoskeletal disease, a metabolic disease, or other disease or condition described herein).

The kits provided may comprise an inventive pharmaceutical composition or compound and a container (e.g., a vial, ampule, bottle, syringe, and/or dispenser package, or other suitable container). In some embodiments, provided kits may optionally further include a second container comprising a pharmaceutical excipient for dilution or suspension of an inventive pharmaceutical composition or compound. In some embodiments, the inventive pharmaceutical composition or compound provided in the container and the second container are combined to form one unit dosage form.

Thus, in one aspect, provided are kits including a first container comprising a compound of Formula (I) or a pharmaceutically acceptable salt, solvate, hydrate, tautomer, or stereoisomer thereof, or a pharmaceutical composition thereof. In certain embodiments, the kits are useful in preventing and/or treating a proliferative disease in a subject. In certain embodiments, the kits further include instructions for administering a compound of Formula (I) or a pharmaceutically acceptable salt, solvate, hydrate, tautomer, or stereoisomer thereof, or a pharmaceutical composition thereof, to a subject to prevent and/or treat a disease described herein.

Methods of Treatment

The present invention features compounds, compositions, and methods comprising a compound of Formula (I) or a pharmaceutically acceptable salt, solvate, hydrate, tautomer, or stereoisomer thereof. In some embodiments, the compounds, compositions, and methods are used in the prevention or treatment of a disease, disorder, or condition. Exemplary diseases, disorders, or conditions include, but are not limited to a neurodegenerative disease, a leukodystrophy, cancer, an inflammatory disease, a musculoskeletal disease, or a metabolic disease.

In some embodiments, the disease, disorder, or condition is related to (e.g. caused by) modulation of (e.g., a decrease in) eIF2B activity or level, eIF2α activity or level, or a component of the eIF2 pathway or ISR pathway. In some embodiments, the disease, disorder, or condition is related to modulation of a signaling pathway related to a component of the eIF2 pathway or ISR pathway (e.g., phosphorylation of a component of the eIF2 pathway or ISR pathway). In some embodiments, the disease, disorder, or condition is related to (e.g. caused by) neurodegeneration. In some embodiments, the disease, disorder, or condition is related to (e.g. caused by) neural cell death or dysfunction. In some embodiments, the disease, disorder, or condition is related to (e.g. caused by) glial cell death or dysfunction. In some embodiments, the disease, disorder, or condition is related to (e.g. caused by) an increase in the level or activity of eIF2B, eIF2α, or a component of the eIF2 pathway or ISR pathway. In some embodiments, the disease, disorder, or condition is related to (e.g. caused by) a decrease in the level or activity of eIF2B, eIF2α, or a component of the eIF2 pathway or ISR pathway.

In some embodiments, the disease may be caused by a mutation to a gene or protein sequence related to a member of the eIF2 pathway (e.g., eIF2B, eIF2α, or other component). Exemplary mutations include an amino acid mutation in the eIF2B1, eIF2B2, eIF2B3, eIF2B4, eIF2B5 subunits. In some embodiments, an amino acid mutation (e.g., an amino acid substitution, addition, or deletion) in a particular protein that may result in a structural change, e.g., a conformational or steric change, that affects the function of the protein. For example, in some embodiments, amino acids in and around the active site or close to a binding site (e.g., a phosphorylation site, small molecule binding site, or protein-binding site) may be mutated such that the activity of the protein is impacted. In some instances, the amino acid mutation (e.g., an amino acid substitution, addition, or deletion) may be conservative and may not substantially impact the structure or function of a protein. For example, in certain cases, the substitution of a serine residue with a threonine residue may not significantly impact the function of a protein. In other cases, the amino acid mutation may be more dramatic, such as the substitution of a charged amino acid (e.g., aspartic acid or lysine) with a large, nonpolar amino acid (e.g., phenylalanine or tryptophan) and therefore may have a substantial impact on protein function. The nature of the mutations that affect the structure of function of a gene or protein may be readily identified using standard sequencing techniques, e.g., deep sequencing techniques, that are well known in the art. In some embodiments, a mutation in a member of the eIF2 pathway may affect binding or activity of a compound of Formula (I) or a pharmaceutically acceptable salt, solvate, hydrate, tautomer, or stereoisomer thereof and thereby modulate treatment of a particular disease, disorder, or condition, or a symptom thereof.

In some embodiments, an eIF2 protein may comprise an amino acid mutation (e.g., an amino acid substitution, addition, or deletion) at an alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, or valine residue. In some embodiments, an eIF2 protein may comprise an amino acid substitution at an alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, or valine residue. In some embodiments, an eIF2 protein may comprise an amino acid addition at an alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, or valine residue. In some embodiments, an eIF2 protein may comprise an amino acid deletion at an alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, or valine residue.

In some embodiments, the eIF2 protein may comprise an amino acid mutation (e.g., an amino acid substitution, addition, or deletion) at an alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, or valine residue in the eIF2B1, eIF2B2, eIF2B3, eIF2B4, eIF2B5 subunits. In some embodiments, the eIF2 protein may comprise an amino acid substitution at an alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, or valine residue in the eIF2B1, eIF2B2, eIF2B3, eIF2B4, eIF2B5 subunits. In some embodiments, the eIF2 protein may comprise an amino acid addition at an alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, or valine residue in the eIF2B1, eIF2B2, eIF2B3, eIF2B4, eIF2B5 subunits. In some embodiments, the eIF2 protein may comprise an amino acid deletion at an alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, or valine residue in the eIF2B1, eIF2B2, eIF2B3, eIF2B4, eIF2B5 subunits. Exemplary mutations include V183F (eIF2B1 subunit), H341Q (eIF2B3), I346T (eIF2B3), R483W (eIF2B4), R113H (eIF2B5), and R195H (eIF2B5).

In some embodiments, an amino acid mutation (e.g., an amino acid substitution, addition, or deletion) in a member of the eIF2 pathway (e.g., an eIF2B protein subunit) may affect binding or activity of a compound of Formula (I) or a pharmaceutically acceptable salt, solvate, hydrate, tautomer, or stereoisomer thereof and thereby modulate treatment of a particular disease, disorder, or condition, or a symptom thereof.

Neurodegenerative Disease

In some embodiments, the compound of Formula (I) or a pharmaceutically acceptable salt, solvate, hydrate, tautomer, or stereoisomer thereof is used to treat a neurodegenerative disease. As used herein, the term "neurodegenerative disease" refers to a disease or condition in which the function of a subject's nervous system becomes impaired. Examples of a neurodegenerative disease that may be treated with a compound, pharmaceutical composition, or method described herein include Alexander's disease, Alper's disease, Alzheimer's disease, Amyotrophic lateral sclerosis, Ataxia telangiectasia, Batten disease (also known as Spielmeyer-Vogt-Sjogren-Batten disease), Bovine spongiform encephalopathy (BSE), Canavan disease, Cockayne syndrome, Corticobasal degeneration, Creutzfeldt-Jakob disease, Frontotemporal dementia, Gerstmann-Straussler-Scheinker syndrome, Huntington's disease, HIV-associated dementia, Kennedy's disease, Krabbe's disease, Kuru, Lewy body dementia, Machado-Joseph disease (Spinocerebellar ataxia type 3), Multiple system atrophy, Narcolepsy, Neuroborreliosis, Parkinson's disease, Pelizaeus-Merzbacher Disease, Pick's disease, Primary lateral sclerosis, Prion diseases, Refsum's disease, Sandhoffs disease, Schilder's disease, Subacute combined degeneration of spinal cord secondary to Pernicious Anaemia, Schizophrenia, Spinocerebellar ataxia (multiple types with varying characteristics), Spinal muscular atrophy, Steele-Richardson-Olszewski disease, or Tabes dorsalis.

In some embodiments, the neurodegenerative disease comprises vanishing white matter disease, childhood ataxia with CNS hypo-myelination, a leukodystrophy, a leukoencephalopathy, a hypomyelinating or demyelinating disease, an intellectual disability syndrome, Alzheimer's disease, amyotrophic lateral sclerosis, Creutzfeldt-Jakob disease, Frontotemporal dementia, Gerstmann-Straussler-Scheinker disease, Huntington's disease, dementia (e.g., HIV-associated dementia or Lewy body dementia), Kuru, multiple sclerosis, Parkinson's disease, or a prion disease.

In some embodiments, the neurodegenerative disease comprises vanishing white matter disease, childhood ataxia with CNS hypo-myelination, a leukodystrophy, a leukoencephalopathy, a hypomyelinating or demyelinating disease, or an intellectual disability syndrome.

In some embodiments, the neurodegenerative disease comprises a psychiatric disease such as agoraphobia, Alzheimer's disease, anorexia nervosa, amnesia, anxiety disorder, attention deficit disorder, bipolar disorder, body dysmorphic disorder, bulimia nervosa, claustrophobia, depression, delusions, Diogenes syndrome, dyspraxia, insomnia, Munchausen's syndrome, narcolepsy, narcissistic personality disorder, obsessive-compulsive disorder, psychosis, phobic disorder, schizophrenia, seasonal affective disorder, schizoid personality disorder, sleepwalking, social phobia, substance abuse, tardive dyskinesia, Tourette syndrome, or trichotillomania.

In some embodiments, the compound of Formula (I) or a pharmaceutically acceptable salt, solvate, hydrate, tautomer, or stereoisomer thereof is used to treat vanishing white matter disease. Exemplary methods of treating vanishing white matter disease include, but are not limited to, reducing or eliminating a symptom of vanishing white matter disease, reducing the loss of white matter, reducing the loss of myelin, increasing the amount of myelin, or increasing the amount of white matter in a subject.

In some embodiments, the compound of Formula (I) or a pharmaceutically acceptable salt, solvate, hydrate, tautomer, or stereoisomer thereof is used to treat childhood ataxia with CNS hypo-myelination. Exemplary methods of treating childhood ataxia with CNS hypo-myelination include, but are not limited to, reducing or eliminating a symptom of childhood ataxia with CNS hypo-myelination, increasing the level of myelin, or decreasing the loss of myelin in a subject.

In some embodiments, the compound of Formula (I) or a pharmaceutically acceptable salt, solvate, hydrate, tautomer, or stereoisomer thereof is used to treat an intellectual disability syndrome. Exemplary methods of treating an intellectual disability syndrome include, but are not limited to, reducing or eliminating a symptom of an intellectual disability syndrome.

In some embodiments, the compound of Formula (I) or a pharmaceutically acceptable salt, solvate, hydrate, tautomer, or stereoisomer thereof is used to treat neurodegeneration. Exemplary methods of treating neurodegeneration include, but are not limited to, improvement of mental wellbeing, increasing mental function, slowing the decrease of mental function, decreasing dementia, delaying the onset of dementia, improving cognitive skills, decreasing the loss of cognitive skills, improving memory, decreasing the degradation of memory, or extending survival.

In some embodiments, the compound of Formula (I) or a pharmaceutically acceptable salt, solvate, hydrate, tautomer, or stereoisomer thereof is used to treat a leukoencephalopathy or demyelinating disease. Exemplary leukoencephalopathies include, but are not limited to, progressive multifocal leukoencephalopathy, toxic leukoencephalopathy, leukoencephalopathy with vanishing white matter, leukoencephalopathy with neuroaxonal spheroids, reversible posterior leukoencephalopathy syndrome, hypertensive leukoencephalopathy, megalencephalic leukoencephalopathy with subcortical cysts, Charcot-Marie-Tooth disorder, and Devic's disease. A leukoencephalopathy may comprise a demyelinating disease, which may be inherited or acquired. In some embodiments, an acquired demyelinating disease may be an inflammatory demyelinating disease (e.g., an infectious inflammatory demyelinating disease or a non-infectious inflammatory demyelinating disease), a toxic demyelinating disease, a metabolic demyelinating disease, a hypoxic demyelinating disease, a traumatic demyelinating disease, or an ischemic demyelinating disease (e.g., Binswanger's disease). Exemplary methods of treating a leukoencephalopathy or demyelinating disease include, but are not limited to, reducing or eliminating a symptom of a leukoencephalopathy or demyelinating disease, reducing the loss of myelin, increasing the amount of myelin, reducing the loss of white matter in a subject, or increasing the amount of white matter in a subject.

In some embodiments, the compound of Formula (I) or a pharmaceutically acceptable salt, solvate, hydrate, tautomer, or stereoisomer thereof is used to treat a traumatic injury or a toxin-induced injury to the nervous system (e.g., the brain). Exemplary traumatic brain injuries include, but are not limited to, a brain abscess, concussion, ischemia, brain bleeding, cranial fracture, diffuse axonal injury, locked-in syndrome, or injury relating to a traumatic force or blow to the nervous system or brain that causes damage to an organ or tissue. Exemplary toxin-induced brain injuries include, but are not limited to, toxic encephalopathy, meningitis (e.g. bacterial meningitis or viral meningitis), meningoencephalitis, encephalitis (e.g., Japanese encephalitis, eastern equine encephalitis, West Nile encephalitis), Guillan-Barre syndrome, Sydenham's chorea, rabies, leprosy, neurosyphilis, a prion disease, or exposure to a chemical (e.g., arsenic, lead, toluene, ethanol, manganese, fluoride, dichlorodiphenyltrichloroethane (DDT), dichlorodiphenyldichloroethylene (DDE), tetrachloroethylene, a polybrominated diphenyl ether, a pesticide, a sodium channel inhibitor, a potassium channel inhibitor, a chloride channel inhibitor, a calcium channel inhibitor, or a blood brain barrier inhibitor).

In other embodiments, the compound of Formula (I) or a pharmaceutically acceptable salt, solvate, hydrate, tautomer, or stereoisomer thereof is used to improve memory in a subject. Induction of memory has been shown to be facilitated by decreased and impaired by increased eIF2α phosphorylation. Regulators of translation, such as compounds disclosed herein (e.g. a compound of Formula (I)), could serve as therapeutic agents that improve memory in human disorders associated with memory loss such as Alzheimer's disease and in other neurological disorders that activate the UPR or ISR in neurons and thus could have negative effects on memory consolidation such as Parkinson's disease, schizophrenia, amyotrophic lateral sclerosis and prion diseases. In addition, a mutation in eIF2γ that disrupts complex integrity linked intellectual disability (intellectual disability syndrome or ID) to impaired translation initiation in humans. Hence, two diseases with impaired eIF2 function, ID and VWM, display distinct phenotypes but both affect mainly the brain and impair learning. In some embodiments, the disease or condition is unsatisfactory memory (e.g., working memory, long term memory, short term memory, or memory consolidation)

In still other embodiments, the compound of Formula (I) or a pharmaceutically acceptable salt, solvate, hydrate, tautomer, or stereoisomer thereof aspect is used in a method to improve memory in a subject (e.g., working memory, long term memory, short term memory, or memory consolidation). In some embodiments, the subject is human. In some embodiments, the subject is a non-human mammal. In some embodiments, the subject is a domesticated animal. In some embodiments, the subject is a dog. In some embodiments, the subject is a bird. In some embodiments, the subject is a horse. In embodiments, the patient is a bovine. In some embodiments, the subject is a primate.

Cancer

In some embodiments, the compound of Formula (I) or a pharmaceutically acceptable salt, solvate, hydrate, tautomer, or stereoisomer thereof is used to treat cancer. As used herein, "cancer" refers to human cancers and carcinomas, sarcomas, adenocarcinomas, lymphomas, leukemias, melanomas, etc., including solid and lymphoid cancers, kidney, breast, lung, bladder, colon, ovarian, prostate, pancreas, stomach, brain, head and neck, skin, uterine, testicular, glioma, esophagus, liver cancer, including hepatocarcinoma, lymphoma, including B-acute lymphoblastic lymphoma, non-Hodgkin's lymphomas (e.g., Burkitt's, Small Cell, and Large Cell lymphomas), Hodgkin's lymphoma, leukemia (including AML, ALL, and CML), and/or multiple myeloma. In some further instances, "cancer" refers to lung cancer, breast cancer, ovarian cancer, leukemia, lymphoma, melanoma, pancreatic cancer, sarcoma, bladder cancer, bone cancer, brain cancer, cervical cancer, colon cancer, esophageal cancer, gastric cancer, liver cancer, head and neck cancer, kidney cancer, myeloma, thyroid cancer, prostate cancer, metastatic cancer, or carcinoma.

As used herein, the term "cancer" refers to all types of cancer, neoplasm or malignant tumors found in mammals, including leukemia, lymphoma, carcinomas and sarcomas. Exemplary cancers that may be treated with a compound, pharmaceutical composition, or method provided herein include lymphoma, sarcoma, bladder cancer, bone cancer, brain tumor, cervical cancer, colon cancer, esophageal cancer, gastric cancer, head and neck cancer, kidney cancer, myeloma, thyroid cancer, leukemia, prostate cancer, breast cancer (e.g., ER positive, ER negative, chemotherapy resistant, herceptin resistant, HER2 positive, doxorubicin resistant, tamoxifen resistant, ductal carcinoma, lobular carcinoma, primary, metastatic), ovarian cancer, pancreatic cancer, liver cancer (e.g., hepatocellular carcinoma), lung cancer (e.g., non-small cell lung carcinoma, squamous cell lung carcinoma, adenocarcinoma, large cell lung carcinoma, small cell lung carcinoma, carcinoid, sarcoma), glioblastoma multiforme, glioma, or melanoma. Additional examples include, cancer of the thyroid, endocrine system, brain, breast, cervix, colon, head & neck, liver, kidney, lung, non-small cell lung, melanoma, mesothelioma, ovary, sarcoma, stomach, uterus or Medulloblastoma, Hodgkin's Disease, Non-Hodgkin's Lymphoma, multiple myeloma, neuroblastoma, glioma, glioblastoma multiforme, ovarian cancer, rhabdomyosarcoma, primary thrombocytosis, primary macroglobulinemia, primary brain tumors, cancer, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, endometrial cancer, adrenal cortical cancer, neoplasms of the endocrine or exocrine pancreas, medullary thyroid cancer, medullary thyroid carcinoma, melanoma, colorectal cancer, papillary thyroid cancer, hepatocellular carcinoma, Paget's Disease of the Nipple, Phyllodes Tumors, Lobular Carcinoma, Ductal Carcinoma, cancer of the pancreatic stellate cells, cancer of the hepatic stellate cells, or prostate cancer.

The term "leukemia" refers broadly to progressive, malignant diseases of the blood-forming organs and is generally characterized by a distorted proliferation and development of leukocytes and their precursors in the blood and bone marrow. Leukemia is generally clinically classified on the basis of (1) the duration and character of the disease-acute or chronic; (2) the type of cell involved; myeloid (myelogenous), lymphoid (lymphogenous), or monocytic; and (3) the increase or non-increase in the number abnormal cells in the blood-leukemic or aleukemic (subleukemic). Exemplary leukemias that may be treated with a compound, pharmaceutical composition, or method provided herein include, for example, acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocyte leukemia, micromyeloblastic leukemia, monocytic leukemia, myeloblasts leukemia, myelocytic leukemia, myeloid granulocytic leukemia, myelomonocytic leukemia, Naegeli leukemia, plasma cell leukemia, multiple myeloma, plasmacytic leukemia, promyelocytic leukemia, Rieder cell leukemia, Schilling's leukemia, stem cell leukemia, subleukemic leukemia, or undifferentiated cell leukemia.

The term "sarcoma" generally refers to a tumor which is made up of a substance like the embryonic connective tissue and is generally composed of closely packed cells embedded in a fibrillar or homogeneous substance. Sarcomas that may be treated with a compound, pharmaceutical composition, or method provided herein include a chondrosarcoma, fibrosarcoma, lymphosarcoma, melanosarcoma, myxosarcoma, osteosarcoma, Abernethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, or telangiectaltic sarcoma.

The term "melanoma" is taken to mean a tumor arising from the melanocytic system of the skin and other organs. Melanomas that may be treated with a compound, pharmaceutical composition, or method provided herein include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma, subungal melanoma, or superficial spreading melanoma.

The term "carcinoma" refers to a malignant new growth made up of epithelial cells tending to infiltrate the surrounding tissues and give rise to metastases. Exemplary carcinomas that may be treated with a compound, pharmaceutical composition, or method provided herein include, for example, medullary thyroid carcinoma, familial medullary thyroid carcinoma, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, ductal carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatiniforni carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypernephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lobular carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tubular carcinoma, tuberous carcinoma, verrucous carcinoma, or carcinoma villosum.

In some embodiments, the compound of Formula (I) or a pharmaceutically acceptable salt, solvate, hydrate, tautomer, or stereoisomer thereof is used to treat pancreatic cancer, breast cancer, multiple myeloma, cancers of secretory cells. For example certain methods herein treat cancer by decreasing or reducing or preventing the occurrence, growth, metastasis, or progression of cancer. In some embodiments, the methods described herein may be used to treat cancer by decreasing or eliminating a symptom of cancer. In some embodiments, the compound of Formula (I) or a pharmaceutically acceptable salt, solvate, hydrate, tautomer, or stereoisomer thereof may be used as a single agent in a composition or in combination with another agent in a composition to treat a cancer described herein (e.g., pancreatic cancer, breast cancer, multiple myeloma, cancers of secretory cells).

Inflammatory Disease

In some embodiments, the compound of Formula (I) or a pharmaceutically acceptable salt, solvate, hydrate, tautomer, or stereoisomer thereof is used to treat an inflammatory disease. As used herein, the term "inflammatory disease"

refers to a disease or condition characterized by aberrant inflammation (e.g. an increased level of inflammation compared to a control such as a healthy person not suffering from a disease). Examples of inflammatory diseases include postoperative cognitive dysfunction, arthritis (e.g., rheumatoid arthritis, psoriatic arthritis, juvenile idiopathic arthritis), systemic lupus erythematosus (SLE), myasthenia gravis, juvenile onset diabetes, diabetes mellitus type 1, Guillain-Barre syndrome, Hashimoto's encephalitis, Hashimoto's thyroiditis, ankylosing spondylitis, psoriasis, Sjogren's syndrome, vasculitis, glomerulonephritis, auto-immune thyroiditis, Behcet's disease, Crohn's disease, ulcerative colitis, bullous pemphigoid, sarcoidosis, ichthyosis, Graves ophthalmopathy, inflammatory bowel disease, Addison's disease, Vitiligo, asthma (e.g., allergic asthma), acne vulgaris, celiac disease, chronic prostatitis, inflammatory bowel disease, pelvic inflammatory disease, reperfusion injury, sarcoidosis, transplant rejection, interstitial cystitis, atherosclerosis, and atopic dermatitis. Proteins associated with inflammation and inflammatory diseases (e.g. aberrant expression being a symptom or cause or marker of the disease) include interleukin-6 (IL-6), interleukin-8 (IL-8), interleukin-18 (IL-18), TNF-a (tumor necrosis factor-alpha), and C-reactive protein (CRP).

In some embodiments, the inflammatory disease comprises postoperative cognitive dysfunction, arthritis (e.g., rheumatoid arthritis, psoriatic arthritis, or juvenile idiopathic arthritis), systemic lupus erythematosus (SLE), myasthenia gravis, diabetes (e.g., juvenile onset diabetes or diabetes mellitus type 1), Guillain-Barre syndrome, Hashimoto's encephalitis, Hashimoto's thyroiditis, ankylosing spondylitis, psoriasis, Sjogren's syndrome, vasculitis, glomerulonephritis, auto-immune thyroiditis, Behcet's disease, Crohn's disease, ulcerative colitis, bullous pemphigoid, sarcoidosis, ichthyosis, Graves ophthalmopathy, inflammatory bowel disease, Addison's disease, vitiligo, asthma (e.g., allergic asthma), acne vulgaris, celiac disease, chronic prostatitis, pelvic inflammatory disease, reperfusion injury, sarcoidosis, transplant rejection, interstitial cystitis, atherosclerosis, or atopic dermatitis.

In some embodiments, the inflammatory disease comprises postoperative cognitive dysfunction, which refers to a decline in cognitive function (e.g. memory or executive function (e.g. working memory, reasoning, task flexibility, speed of processing, or problem solving)) following surgery.

In other embodiments, the method of treatment is a method of prevention. For example, a method of treating postsurgical cognitive dysfunction may include preventing postsurgical cognitive dysfunction or a symptom of postsurgical cognitive dysfunction or reducing the severity of a symptom of postsurgical cognitive dysfunction by administering a compound described herein prior to surgery.

In some embodiments, the compound of Formula (I) or a pharmaceutically acceptable salt, solvate, hydrate, tautomer, or stereoisomer thereof is used to treat an inflammatory disease (e.g., an inflammatory disease described herein) by decreasing or eliminating a symptom of the disease. In some embodiments, the compound of Formula (I) or a pharmaceutically acceptable salt, solvate, hydrate, tautomer, or stereoisomer thereof may be used as a single agent in a composition or in combination with another agent in a composition to treat an inflammatory disease (e.g., an inflammatory disease described herein).

Musculoskeletal Diseases

In some embodiments, the compound of Formula (I) or a pharmaceutically acceptable salt, solvate, hydrate, tautomer, or stereoisomer thereof is used to treat a musculoskeletal disease. As used herein, the term "musculoskeletal disease" refers to a disease or condition in which the function of a subject's musculoskeletal system (e.g., muscles, ligaments, tendons, cartilage, or bones) becomes impaired. Exemplary musculoskeletal diseases that may be treated with a compound of Formula (I) or a pharmaceutically acceptable salt, solvate, hydrate, tautomer, or stereoisomer thereof include muscular dystrophy (e.g., Duchenne muscular dystrophy, Becker muscular dystrophy, distal muscular dystrophy, congenital muscular dystrophy, Emery-Dreifuss muscular dystrophy, facioscapulohumeral muscular dystrophy, or myotonic muscular dystrophy), multiple sclerosis, amyotropic lateral sclerosis, primary lateral sclerosis, progressive muscular atrophy, progressive bulbar palsy, pseudobulbar palsy, spinal muscular atrophy, progressive spinobulbar muscular atrophy, spinal cord spasticity, spinal muscle atrophy, myasthenia gravis, neuralgia, fibromyalgia, Machado-Joseph disease, cramp fasciculation syndrome, Freidrich's ataxia, a muscle wasting disorder (e.g., muscle atrophy, sarcopenia, cachexia), an inclusion body myopathy, motor neuron disease, or paralysis.

In some embodiments, the compound of Formula (I) or a pharmaceutically acceptable salt, solvate, hydrate, tautomer, or stereoisomer thereof is used to treat a musculoskeletal disease (e.g., a musculoskeletal disease described herein) by decreasing or eliminating a symptom of the disease. In some embodiments, the method of treatment comprises treatment of muscle pain or muscle stiffness associated with a musculoskeletal disease. In some embodiments, the compound of Formula (I) or a pharmaceutically acceptable salt, solvate, hydrate, tautomer, or stereoisomer thereof may be used as a single agent in a composition or in combination with another agent in a composition to treat a musculoskeletal disease (e.g., a musculoskeletal disease described herein).

Metabolic Diseases

In some embodiments, the compound of Formula (I) or a pharmaceutically acceptable salt, solvate, hydrate, tautomer, or stereoisomer thereof is used to treat metabolic disease. As used herein, the term "metabolic disease" refers to a disease or condition affecting a metabolic process in a subject. Exemplary metabolic diseases that may be treated with a compound of Formula (I) or a pharmaceutically acceptable salt, solvate, hydrate, tautomer, or stereoisomer thereof include non-alcoholic steatohepatitis (NASH), non-alcoholic fatty liver disease (NAFLD), liver fibrosis, obesity, heart disease, atherosclerosis, arthritis, cystinosis, diabetes (e.g., Type I diabetes, Type II diabetes, or gestational diabetes), phenylketonuria, proliferative retinopathy, or Kearns-Sayre disease.

In some embodiments, the compound of Formula (I) or a pharmaceutically acceptable salt, solvate, hydrate, tautomer, or stereoisomer thereof is used to treat a metabolic disease (e.g., a metabolic disease described herein) by decreasing or eliminating a symptom of the disease. In some embodiments, the method of treatment comprises decreasing or eliminating a symptom comprising elevated blood pressure, elevated blood sugar level, weight gain, fatigue, blurred vision, abdominal pain, flatulence, constipation, diarrhea, jaundice, and the like. In some embodiments, the compound of Formula (I) or a pharmaceutically acceptable salt, solvate, hydrate, tautomer, or stereoisomer thereof may be used as a single agent in a composition or in combination with another agent in a composition to treat a metabolic disease (e.g., a musculoskeletal disease described herein).

Methods of Increasing Protein Production

In another aspect, the compound of Formula (I) or a pharmaceutically acceptable salt, solvate, hydrate, tautomer, or stereoisomer thereof may be useful in applications where increasing protein production output is desirable, such as in vitro cell free systems for protein production.

In some embodiments, the present invention features a method of increasing protein expression of a cell or in vitro expression system, the method including administering an effective amount of a compound to the cell or expression system, wherein the compound is a the compound of Formula (I) or a pharmaceutically acceptable salt, solvate, hydrate, tautomer, or stereoisomer thereof. In some embodiments, the method is a method of increasing protein expression by a cell and includes administering an effective amount of a compound described herein (e.g. the compound of Formula (I) or a pharmaceutically acceptable salt, solvate, hydrate, tautomer, or stereoisomer thereof) to the cell. In other embodiments, the method is a method of increasing protein expression by an in vitro protein expression system and includes administering an effective amount of a compound described herein (e.g. the compound of Formula (I) or a pharmaceutically acceptable salt, solvate, hydrate, tautomer, or stereoisomer thereof) to the in vitro (e.g. cell free) protein expression system.

In some embodiments, the present invention features a method of increasing protein expression in a disease, disorder, or condition characterized by aberrant or lowered levels of protein production (e.g., a leukodystrophy, a leukoencephalopathy, a hypomyelinating or demyelinating disease, muscle-wasting disease, or sarcopenia).

In some embodiments, the compounds set forth herein are provided as pharmaceutical compositions including a compound of Formula (I) or a pharmaceutically acceptable salt, solvate, hydrate, tautomer, or stereoisomer thereof and a pharmaceutically acceptable excipient. In embodiments of the method, a compound of Formula (I) or a pharmaceutically acceptable salt, solvate, hydrate, tautomer, or stereoisomer thereof, is co-administered with a second agent (e.g. therapeutic agent). In other embodiments of the method, a compound of Formula (I) or a pharmaceutically acceptable salt, solvate, hydrate, tautomer, or stereoisomer thereof, is co-administered with a second agent (e.g. therapeutic agent), which is administered in a therapeutically effective amount. In embodiments, the second agent is an agent for improving memory.

Combination Therapy

In one aspect, the present invention features a pharmaceutical composition comprising a compound of Formula (I) or a pharmaceutically acceptable salt, solvate, hydrate, tautomer, or stereoisomer thereof as well as a second agent (e.g. a second therapeutic agent). In some embodiments, the pharmaceutical composition includes a second agent (e.g. a second therapeutic agent) in a therapeutically effective amount. In some embodiments, the second agent is an agent for treating cancer, a neurodegenerative disease, a leukodystrophy, an inflammatory disease, a musculoskeletal disease, a metabolic disease, or a disease or disorder associated with impaired function of eIF2B, eIF2α, or a component of the eIF2 pathway or ISR pathway.

The compounds described herein can be used in combination with one another, with other active agents known to be useful in treating cancer, a neurodegenerative disease, an inflammatory disease, a musculoskeletal disease, a metabolic disease, or a disease or disorder associated with impaired function of eIF2B, eIF2α, or a component of the eIF2 pathway or ISR pathway or with adjunctive agents that may not be effective alone, but may contribute to the efficacy of the active agent.

In some embodiments, co-administration includes administering one active agent within 0.5, 1, 2, 4, 6, 8, 10, 12, 16, 20, or 24 hours of a second active agent. Co-administration includes administering two active agents simultaneously, approximately simultaneously (e.g., within about 1, 5, 10, 15, 20, or 30 minutes of each other), or sequentially in any order. In some embodiments, co-administration can be accomplished by co-formulation, i.e., preparing a single pharmaceutical composition including both active agents. In other embodiments, the active agents can be formulated separately. In another embodiment, the active and/or adjunctive agents may be linked or conjugated to one another. In some embodiments, the compounds described herein may be combined with treatments for a cancer, a neurodegenerative disease, a leukodystrophy, an inflammatory disease, a musculoskeletal disease, a metabolic disease, or a disease or disorder associated with impaired function of eIF2B, eIF2α, or a component of the eIF2 pathway or ISR pathway.

In embodiments, the second agent is an anti-cancer agent. In embodiments, the second agent is a chemotherapeutic. In embodiments, the second agent is an agent for improving memory. In embodiments, the second agent is an agent for treating a neurodegenerative disease. In embodiments, the second agent is an agent for treating a leukodystrophy. In embodiments, the second agent is an agent for treating vanishing white matter disease. In embodiments, the second agent is an agent for treating childhood ataxia with CNS hypo-myelination. In embodiments, the second agent is an agent for treating an intellectual disability syndrome. In embodiments, the second agent is an agent for treating pancreatic cancer. In embodiments, the second agent is an agent for treating breast cancer. In embodiments, the second agent is an agent for treating multiple myeloma. In embodiments, the second agent is an agent for treating myeloma. In embodiments, the second agent is an agent for treating a cancer of a secretory cell. In embodiments, the second agent is an agent for reducing eIF2α phosphorylation. In embodiments, the second agent is an agent for inhibiting a pathway activated by eIF2α phosphorylation. In embodiments, the second agent is an agent for inhibiting a pathway activated by eIF2α. In embodiments, the second agent is an agent for inhibiting the integrated stress response. In embodiments, the second agent is an anti-inflammatory agent. In embodiments, the second agent is an agent for treating postsurgical cognitive dysfunction. In embodiments, the second agent is an agent for treating traumatic brain injury. In embodiments, the second agent is an agent for treating a musculoskeletal disease. In embodiments, the second agent is an agent for treating a metabolic disease. In embodiments, the second agent is an anti-diabetic agent.

Anti-Cancer Agents

"Anti-cancer agent" is used in accordance with its plain ordinary meaning and refers to a composition (e.g. compound, drug, antagonist, inhibitor, modulator) having antineoplastic properties or the ability to inhibit the growth or proliferation of cells. In some embodiments, an anti-cancer agent is a chemotherapeutic. In some embodiments, an anti-cancer agent is an agent identified herein having utility in methods of treating cancer. In some embodiments, an anticancer agent is an agent approved by the FDA or similar regulatory agency of a country other than the USA, for treating cancer. Examples of anti-cancer agents include, but are not limited to, MEK (e.g. MEK1, MEK2, or MEK1 and MEK2) inhibitors (e.g. XL518, CI-1040, PD035901, selumetinib/AZD6244, GSK1120212/trametinib, GDC-0973, ARRY-162, ARRY-300, AZD8330, PD0325901, U0126, PD98059, TAK-733, PD318088, AS703026, BAY 869766), alkylating agents (e.g., cyclophosphamide, ifosfamide, chlorambucil, busulfan, melphalan, mechlorethamine, uramustine, thiotepa, nitrosoureas, nitrogen mustards (e.g., mechloroethamine, cyclophosphamide, chlorambucil, meiphalan), ethylenimine and methylmelamines (e.g., hexamethlymelamine, thiotepa), alkyl sulfonates (e.g., busulfan), nitrosoureas (e.g., carmustine, lomusitne, semustine, streptozocin), triazenes (decarbazine), anti-metabolites (e.g., 5-azathioprine, leucovorin, capecitabine, fludarabine, gemcitabine, pemetrexed, raltitrexed, folic acid analog (e.g., methotrexate), or pyrimidine analogs (e.g., fluorouracil, floxouridine, Cytarabine), purine analogs (e.g., mercaptopurine, thioguanine, pentostatin), etc.), plant alkaloids (e.g., vincristine, vinblastine, vinorelbine, vindesine, podophyllotoxin, paclitaxel, docetaxel, etc.), topoisomerase inhibitors (e.g., irinotecan, topotecan, amsacrine, etoposide (VP 16), etoposide phosphate, teniposide, etc.), antitumor antibiotics (e.g., doxorubicin, adriamycin, daunorubicin, epirubicin, actinomycin, bleomycin, mitomycin, mitoxantrone, plicamycin, etc.), platinum-based compounds (e.g. cisplatin, oxaloplatin, carboplatin), anthracenedione (e.g., mitoxantrone), substituted urea (e.g., hydroxyurea), methyl hydrazine derivative (e.g., procarbazine), adrenocortical suppressant (e.g., mitotane, aminoglutethimide), epipodophyllotoxins (e.g., etoposide), antibiotics (e.g., daunorubicin, doxorubicin, bleomycin), enzymes (e.g., L-asparaginase), inhibitors of mitogen-activated protein kinase signaling (e.g. U0126, PD98059, PD184352, PD0325901, ARRY-142886, SB239063, SP600125, BAY 43-9006, wortmannin, or LY294002, Syk inhibitors, mTOR inhibitors, antibodies (e.g., rituxan), gossyphol, genasense, polyphenol E, Chlorofusin, all trans-retinoic acid (ATRA), bryostatin, tumor necrosis factor-related apoptosis-inducing ligand (TRAIL), 5-aza-2'-deoxycytidine, all trans retinoic acid, doxorubicin, vincristine, etoposide, gemcitabine, imatinib (Gleevec®), geldanamycin, 17-N-Allylamino-17-Demethoxygeldanamycin (17-AAG), flavopiridol, LY294002, bortezomib, trastuzumab, BAY 1 1-7082, PKC412, PD184352, 20-epi-1, 25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; 9-dioxamycin; diphenyl spiromustine; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; 06-benzylguanine; octreotide; okicenone; oligonucleotides; onapristone; ondansetron; ondansetron; oracin; oral cytokine inducer; ormaplatin; osaterone; oxaliplatin; oxaunomycin; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylerie conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone Bl; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen-binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; zinostatin stimalamer, Adriamycin, Dactinomycin, Bleomycin, Vinblastine, Cisplatin, acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cladribine; crisnatol mesylate; cyclophosphamide; cytarabine; dacarbazine; daunorubicin hydrochloride; decitabine; dexormaplatin; dezaguanine; dezaguanine mesylate; diaziquone; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; iimofosine; interleukin II (including recombinant interleukin II, or rIL.sub.2), interferon alfa-2a; interferon alfa-2b; interferon alfa-n1; interferon alfa-n3; interferon beta-1a; interferon gamma-1b; iprop latin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazoie; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride, agents that arrest cells in the G2-M phases and/or modulate the formation or stability of microtubules, (e.g. Taxol (i.e. paclitaxel), Taxotere, compounds comprising the taxane skeleton, Erbulozole (i.e. R-55104), Dolastatin 10 (i.e. DLS-10 and NSC-376128), Mivobulin isethionate (i.e. as CI-980), Vincristine, NSC-639829, Discodermolide (i.e. as NVP-XX-A-296), ABT-751 (Abbott, i.e. E-7010), Altorhyrtins (e.g. Altorhyrtin A and Altorhyrtin C), Spongistatins (e.g. Spongistatin 1, Spongistatin 2, Spongistatin 3, Spongistatin 4, Spongistatin 5, Spongistatin 6, Spongistatin 7, Spongistatin 8, and Spongistatin 9), Cemadotin hydrochloride (i.e. LU-103793 and SC-D-669356), Epothilones (e.g. Epothilone A, Epothilone B, Epothilone C (i.e. desoxyepothilone A or dEpoA), Epothilone D (i.e. KOS-862, dEpoB, and desoxyepothilone B), Epothilone E, Epothilone F, Epothilone B N-oxide, Epothilone A N-oxide, 16-aza-epothilone B, 21-aminoepothilone B (i.e. BMS-310705), 21-hydroxyepothilone D (i.e. Desoxyepothilone F and dEpoF), 26-fluoroepothilone, Auristatin PE (i.e. NSC-654663), Soblidotin (i.e. TZT-1027), LS-4559-P (Pharmacia, i.e. LS-4577), LS-4578 (Pharmacia, i.e. LS-477-P), LS-4477 (Pharmacia), LS-4559 (Pharmacia), RPR-1 12378 (Aventis), Vincristine sulfate, DZ-3358 (Daiichi), FR-182877 (Fujisawa, i.e. WS-9885B), GS-164 (Takeda), GS-198 (Takeda), KAR-2 (Hungarian Academy of Sciences), BSF-223651 (BASF, i.e. ILX-651 and LU-223651), SAH-49960 (Lilly/Novartis), SDZ-268970 (Lilly/Novartis), AM-97 (Armad/Kyowa Hakko), AM-132 (Armad), AM-138 (Armad/Kyowa Hakko), IDN-5005 (Indena), Cryptophycin 52 (i.e. LY-355703), AC-7739 (Ajinomoto, i.e. AVE-8063A and CS-39.HC1), AC-7700 (Ajinomoto, i.e. AVE-8062, AVE-8062A, CS-39-L-Ser.HC1, and RPR-258062A), Vitilevuamide, Tubulysin A, Canadensol, Centaureidin (i.e. NSC-106969), T-138067 (Tularik, i.e. T-67, TL-138067 and TI-138067), COBRA-1 (Parker Hughes Institute, i.e. DDE-261 and WHI-261), H10 (Kansas State University), H16 (Kansas State University), Oncocidin A 1 (i.e. BTO-956 and DIME), DDE-313 (Parker Hughes Institute), Fijianolide B, Laulimalide, SPA-2 (Parker Hughes Institute), SPA-1 (Parker Hughes Institute, i.e. SPIKET-P), 3-IAABU (Cytoskeleton/Mt. Sinai School of Medicine, i.e. MF-569), Narcosine (also known as NSC-5366), Nascapine, D-24851 (Asta Medica), A-105972 (Abbott), Hemiasterlin, 3-BAABU (Cytoskeleton/Mt. Sinai School of Medicine, i.e. MF-191), TMPN (Arizona State University), Vanadocene acetylacetonate, T-138026 (Tularik), Monsatrol, Inanocine (i.e. NSC-698666), 3-IAABE (Cytoskeleton/Mt. Sinai School of Medicine), A-204197 (Abbott), T-607 (Tularik, i.e. T-900607), RPR-115781 (Aventis), Eleutherobins (such as Desmethyleleutherobin, Desaetyleleutherobin, Isoeleutherobin A, and Z-Eleutherobin), Caribaeoside, Caribaeolin, Halichondrin B, D-64131 (Asta Medica), D-68144 (Asta Medica), Diazonamide A, A-293620 (Abbott), NPI-2350 (Nereus), Taccalonolide A, TUB-245 (Aventis), A-259754 (Abbott), Diozostatin, (−)-Phenylahistin (i.e. NSCL-96F037), D-68838 (Asta Medica), D-68836 (Asta Medica), Myoseverin B, D-43411 (Zentaris, i.e. D-81862), A-289099 (Abbott), A-318315 (Abbott), HTI-286 (i.e. SPA-1 10, trifluoroacetate salt) (Wyeth), D-82317 (Zentaris), D-82318 (Zentaris), SC-12983 (NCI), Resverastatin phosphate sodium, BPR-OY-007 (National Health Research Institutes), and SSR-25041 1 (Sanofi), steroids (e.g., dexamethasone), finasteride, aromatase inhibitors, gonadotropin-releasing hormone agonists (GnRH) such as goserelin or leuprolide, adrenocorticosteroids (e.g., prednisone), progestins (e.g., hydroxyprogesterone caproate, megestrol acetate, medroxyprogesterone acetate), estrogens (e.g., diethylstilbestrol, ethinyl estradiol), antiestrogen (e.g., tamoxifen), androgens (e.g., testosterone propionate, fluoxymesterone), antiandrogen (e.g., flutamide), immunostimulants (e.g., Bacillus Calmette-Guerin (BCG), levamisole, interleukin-2, alpha-interferon, etc.), monoclonal antibodies (e.g., anti-CD20, anti-HER2, anti-CD52, anti-HLA-DR, and anti-VEGF monoclonal antibodies), immunotoxins (e.g., anti-CD33 monoclonal antibody-calicheamicin conjugate, anti-CD22 monoclonal antibody-pseudomonas exotoxin conjugate, etc.), radioimmunotherapy (e.g., anti-CD20 monoclonal antibody conjugated to $^{111}$In, $^{90}$Y, or $^{131}$I, etc.), triptolide, homoharringtonine, dactinomycin, doxorubicin, epirubicin, topotecan, itraconazole, vindesine, cerivastatin, vincristine, deoxyadenosine, sertraline, pitavastatin, irinotecan, clofazimine, 5-nonyloxytryptamine, vemurafenib, dabrafenib, erlotinib, gefitinib, EGFR inhibitors, epidermal growth factor receptor (EGFR)-targeted therapy or therapeutic (e.g. gefitinib (Iressa™), erlotinib (Tarceva™), cetuximab (Erbitux™), lapatinib (Tykerb™), panitumumab (Vectibix™), vandetanib (Caprelsa™), afatinib/BIBW2992, CI-1033/canertinib, neratinib/HKI-272, CP-724714, TAK-285, AST-1306, ARRY334543, ARRY-380, AG-1478, dacomitinib/PF299804, OSI-420/desmethyl erlotinib, AZD8931, AEE788, pelitinib/EKB-569, CUDC-101, WZ8040, WZ4002, WZ3146, AG-490, XL647, PD153035, BMS-599626), sorafenib, imatinib, sunitinib, dasatinib, or the like.

"Chemotherapeutic" or "chemotherapeutic agent" is used in accordance with its plain ordinary meaning and refers to a chemical composition or compound having antineoplastic properties or the ability to inhibit the growth or proliferation of cells.

Additionally, the compounds described herein can be co-administered with conventional immunotherapeutic agents including, but not limited to, immunostimulants (e.g., Bacillus Calmette-Guerin (BCG), levamisole, interleukin-2, alpha-interferon, etc.), monoclonal antibodies (e.g., anti-CD20, anti-HER2, anti-CD52, anti-HLA-DR, and anti-VEGF monoclonal antibodies), immunotoxins (e.g., anti-CD33 monoclonal antibody-calicheamicin conjugate, anti-CD22 monoclonal antibody-pseudomonas exotoxin conjugate, etc.), and radioimmunotherapy (e.g., anti-CD20 monoclonal antibody conjugated to $^{m}$In, $^{90}$Y, or $^{131}$I, etc.).

In a further embodiment, the compounds described herein can be co-administered with conventional radiotherapeutic agents including, but not limited to, radionuclides such as $^{47}$Sc, $^{64}$Cu, $^{67}$Cu, $^{89}$Sr, $^{86}$Y, $^{87}$Y, $^{90}$Y, $^{105}$Rh, $^{m}$Ag, $^{m}$In, $^{117m}$Sn, $^{149}$Pm, $^{153}$Sm, $^{166}$Ho, $^{177}$Lu $^{186}$Re, $^{188}$Re, $^{211}$At, and $^{212}$Bi, optionally conjugated to antibodies directed against tumor antigens.

Additional Agents

In some embodiments, the second agent for use in combination with a compound (e.g., a compound of Formula (I)) or composition thereof described herein is an agent for use in treating a neurodegenerative disease, a leukodystrophy, an inflammatory disease, a musculoskeletal disease, or a metabolic disease. In some embodiments, a second agent for use in combination with a compound (e.g., a compound of Formula (I)) or composition thereof described herein is an agent approved by the FDA or similar regulatory agency of a country other than the USA, for treating a disease, disorder, or condition described herein.

In some embodiments, a second agent for use in treating a neurodegenerative disease, a leukodystrophy, an inflammatory disease, a musculoskeletal disease, or a metabolic disease includes, but is not limited to, an anti-psychotic drug, anti-depressive drug, anti-anxiety drug, analgesic, a stimulant, a sedative, a pain reliever, an anti-inflammatory agent, a benzodiazepine, a cholinesterase inhibitor, a non-steroidal anti-inflammatory drug (NSAID), a corticosteroid, a MAO inhibitor, a beta-blocker, a calcium channel blocker, an antacid, or other agent. Exemplary second agents may include donepezil, galantamine, rivastigmine, memantine, levodopa, dopamine, pramipexole, ropinirole, rotigotine, doxapram, oxazepam, quetiapine, selegiline, rasagiline, entacapone, benztropine, trihexyphenidyl, riluzole, diazepam, chlorodiazepoxide, lorazepam, alprazolam, buspirone, gepirone, ispapirone, hydroxyzine, propranolol, hydroxyzine, midazolam, trifluoperazine, methylphenidate, atomoxetine, methylphenidate, pemoline, perphenazine, divalproex, valproic acid, sertraline, fluoxetine, citalopram, escitalopram, paroxetine, fluvoxamine, trazodone, desvenlafaxine, duloxetine, venlafaxine, amitriptyline, amoxapine, clomipramine, desipramine, imipramine, nortriptyline, protriptyline, trimipramine, maprotiline, bupropion, nefazodone, vortioxetine, lithium, clozapine, fluphenazine, haloperidol, paliperidone, loxapine, thiothixene, pimozide, thioridazine, risperidone, aspirin, ibuprofen, naproxen, acetaminophen, azathioprine, methotrexate, mycophenolic acid, leflunomide, dibenzoylmethane, cilostazol, pentoxifylline, duloxetine, a cannabinoid (e.g., nabilone), simethicone, magaldrate, aluminum salts, calcium salts, sodium salts, magnesium salts, alginic acid, acarbose, albiglutide, alogliptin, metformin, insulin, lisinopril, atenolol, atorvastatin, fluvastatin, lovastatin, pitavastatin, simvastatin, rosuvastatin, and the like.

Naturally derived agents or supplements may also be used in conjunction with a compound of Formula (I) or a composition thereof to treat a neurodegenerative disease, an inflammatory disease, a musculoskeletal disease, or a metabolic disease. Exemplary naturally derived agents or supplements include omega-3 fatty acids, carnitine, citicoline, curcumin, gingko, vitamin E, vitamin B (e.g., vitamin B5, vitamin B6, or vitamin B12), huperzine A, phosphatidylserine, rosemary, caffeine, melatonin, chamomile, St. John's wort, tryptophan, and the like.

EXAMPLES

In order that the invention described herein may be more fully understood, the following examples are set forth. The synthetic and biological examples described in this application are offered to illustrate the compounds, pharmaceutical compositions, and methods provided herein and are not to be construed in any way as limiting their scope.

Synthetic Protocols

The compounds provided herein can be prepared from readily available starting materials using modifications to the specific synthesis protocols set forth below that would be well known to those of skill in the art. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvents used, but such conditions can be determined by those skilled in the art by routine optimization procedures. General schemes relating to methods of making exemplary compounds of the invention are additionally described in the section entitled Methods of Making Compounds.

Additionally, as will be apparent to those skilled in the art, conventional protecting groups may be necessary to prevent certain functional groups from undergoing undesired reactions. The choice of a suitable protecting group for a particular functional group as well as suitable conditions for protection and deprotection are well known in the art. For example, numerous protecting groups, and their introduction and removal, are described in Greene et al., *Protecting Groups in Organic Synthesis*, Second Edition, Wiley, New York, 1991, and references cited therein.

Abbreviations

APCI for atmospheric pressure chemical ionization; DMSO for dimethyl sulfoxide; ESI for electrospray ionization; HPLC for high performance liquid chromatography; MS for mass spectrum; and NMR for nuclear magnetic resonance.

Example 1: 2-(4-chloro-3-fluorophenoxy)-N-(4-{[5-(trifluoromethyl)pyrazin-2-yl]amino}bicyclo[2.2.2]octan-1-yl)acetamide (Compound 100)

Example 1A: tert-butyl (4-aminobicyclo[2.2.2]octan-1-yl)carbamate

Bicyclo[2.2.2]octane-1,4-diamine dihydrochloride (PharmaBlock, CAS #2277-93-2, 200 mg, 1.43 mmol) was dissolved in methanol (5 mL). The solution was basified with 50% aqueous sodium hydroxide. After stirring for 15 minutes (slight exotherm), the mixture was diluted with water and brine and extracted with dichloromethane (3×150 mL). The combined organic layers were dried ($Na_2SO_4$) and filtered. The filtrate was concentrated under reduced pressure to give the free base as a white solid. This free base, bicyclo[2.2.2]octane-1,4-diamine (176 mg, 1.255 mmol), di-tert-butyl dicarbonate (274 mg, 1.255 mmol), and tetrahydrofuran (100 mL) were stirred at ambient temperature for 17 hours. The reaction mixture was concentrated under reduced pressure, and the residue was partitioned between ethyl acetate and aqueous sodium carbonate. The organic layer was washed with brine, then dried ($MgSO_4$) and filtered. The filtrate was concentrated under reduced pressure to provide the title intermediate as an off-white solid (258 mg, 86% yield). $^1$H NMR (methanol-$d_4$) δ ppm 1.91-1.85 (m, 7H), 1.65-1.60 (m, 2H), 1.40 (s, 12H); MS (DCI-$NH_3$) m/z=241 $(M+H)^+$.

Example 1B: tert-butyl (4-(2-(4-chloro-3-fluorophenoxy)acetamido)bicyclo[2.2.2]octan-1-yl)carbamate A 50 mL round bottom flask, equipped with a magnetic stir bar, was charged with 2-(4-chloro-3-fluorophenoxy) acetic acid (234 mg, 1.144 mmol), tert-butyl (4-aminobicyclo[2.2.2]octan-1-yl)carbamate (Example 1A, 250 mg, 1.040 mmol), and COMU® (535 mg, 1.248 mmol). The flask contents were placed under a dry nitrogen atmosphere and N,N-dimethylformamide (4 mL) was introduced via syringe. The reaction mixture was then stirred at ambient temperature as N,N-diisopropylethylamine (0.545 mL, 3.12 mmol) was added dropwise via syringe. The reaction mixture was stirred at ambient temperature for 19 hours. The reaction mixture was diluted with water (pH=10). An insoluble beige solid was collected by filtration and rinsed thoroughly with water. The material was purified by column chromatography on an Analogix® IntelliFlash™-310 (Isco RediSep® 40 g silica gel cartridge, 70:30 to 0:100 heptane/ethyl acetate to give the title intermediate as a white solid (69.5 mg, 15.65% yield). $^1$H NMR ($CDCl_3$) δ ppm 7.31 (t, J=8.6 Hz, 1H), 6.73 (dd, J=10.3, 2.9 Hz, 1H), 6.64 (ddd, J=8.9, 2.9, 1.2 Hz, 1H), 6.07 (s, 1H), 4.32 (s, 1H), 4.31 (s, 2H), 2.05-1.91 (m, 12H), 1.42 (s, 9H); MS (+ESI) m/z=426 $(M+H)^+$, m/z=853 $(2M+H)^+$; MS (−ESI) m/z=425 $(M-H)^-$.

Example 1C: N-(4-aminobicyclo[2.2.2]octan-1-yl)-2-(4-chloro-3-fluorophenoxy)acetamide Hydrochloride A 4 mL vial, equipped with a magnetic stir bar, was charged with tert-butyl (4-(2-(4-chloro-3-fluorophenoxy)acetamido)bicyclo[2.2.2]octan-1-yl)carbamate (Example 1B, 69 mg, 0.162 mmol). Methanol (1 mL) was added, and the resulting solution was stirred at ambient temperature while 4 M HCl in dioxane (1.2 mL, 4.80 mmol) was added via syringe. The reaction mixture was stirred at ambient temperature for 89 hours. Volatiles were removed under reduced pressure to give the title intermediate as a white solid (58.3 mg, 99% yield). $^1$H NMR (methanol-$d_4$) δ ppm 7.36 (t, J=8.7 Hz, 1H), 6.89 (dd, J=11.0, 2.9 Hz, 1H), 6.79 (ddd, J=9.0, 2.9, 1.3 Hz, 1H), 4.43 (s, 2H), 2.15-2.08 (m, 6H), 1.94-1.87 (m, 6H); MS (+ESI) m/z=327 $(M+H)^+$; MS (−ESI) m/z=325 $(M-H)^-$.

Example 1D: 2-(4-chloro-3-fluorophenoxy)-N-(4-{[5-(trifluoromethyl)pyrazin-2-yl]amino}bicyclo[2.2.2]octan-1-yl)acetamide A 4 mL vial, equipped with a magnetic stir bar, was charged with N-(4-aminobicyclo[2.2.2]octan-1-yl)-2-(4-chloro-3-fluorophenoxy)acetamide hydrochloride (Example 1C, 28.2 mg, 0.078 mmol), 2-bromo-5-(trifluoromethyl) pyrazine (Anichem, CAS #1196152-38-1, 21.15 mg, 0.093 mmol), N,N-diisopropylethylamine (0.0542 mL, 0.310 mmol), and dimethylformamide (0.5 mL). The vial was sealed with a pressure relief septum cap, and the reaction mixture was stirred at 90° C. for 16.5 hours. The reaction mixture was allowed to cool to ambient temperature, and the septum cap was removed. The vial contents were partitioned between ethyl acetate and water. The aqueous layer was extracted once more with ethyl acetate. The combined organic layers were washed twice with brine, then dried ($MgSO_4$) and filtered. The filtrate was concentrated under reduced pressure to give a brown oil that was purified by column chromatography on an Analogix® IntelliFlash™-310 (Isco RediSep® 12 g silica gel cartridge, 100% heptane to 60:40 heptane/ethyl acetate). Fractions containing the title compound were combined and concentrated under reduced pressure to give the title compound as a white solid, but there was still contamination, so a second column was run (Practichem 2×4 g silica gel cartridges, 100% dichloromethane to 90:10 dichloromethane/ethyl acetate). Fractions containing the title compound were combined and concentrated under reduced pressure to give the title compound as a white solid that was dried overnight in a vacuum oven at 50° C. (3.5 mg, 9.5% yield). $^1$H NMR (CDCl$_3$) δ ppm 8.28 (s, 1H), 7.80 (d, J=1.4 Hz, 1H), 7.36-7.29 (m, 1H), 6.74 (dd, J=10.3, 2.8 Hz, 1H), 6.66 (ddd, J=8.9, 2.9, 1.3 Hz, 1H), 6.11 (s, 1H), 4.71 (s, 1H), 4.34 (s, 2H), 2.19-2.05 (m, 12H); MS (+ESI) m/z=473 (M+H)$^+$; (−ESI) m/z=471 (M−H)$^−$.

Example 2: 2-(3,4-dichlorophenoxy)-N-(3-{[5-(trifluoromethyl)pyrazin-2-yl]amino}bicyclo-[1.1.1]pentan-1-yl)acetamide (Compound 101)

Example 2A: tert-butyl (3-(2-(3,4-dichlorophenoxy)acetamido)bicyclo[1.1.1]pentan-1-yl)carbamate To a solution of 2-(3,4-dichlorophenoxy)acetic acid (3.53 g, 15.98 mmol) and tert-butyl (3-aminobicyclo[1.1.1]pentan-1-yl)carbamate (Pharmablock, 3.2 g, 14.53 mmol) in N,N-dimethylformamide (50 mL) was added N,N-diisopropylethylamine (12.69 mL, 72.6 mmol) and fluoro-N,N,N',N'-tetramethylformamidinium hexafluorophosphate (8.28 g, 21.79 mmol) at ambient temperature under nitrogen. The resulting mixture was stirred, diluted with water (300 mL) and extracted with ethyl acetate (3×200 mL). The combined organic layer was washed with brine (3×100 mL), dried (Na$_2$SO$_4$) and concentrated under reduced pressure. The residue was treated with methyl tert-butyl ether (15 mL) and dried under high vacuum to provide 4.2 g (72.3%) of the title compound as a yellow solid. MS (APCI) m/z 402 (M+H)$^+$.

Example 2B: N-(3-aminobicyclo[1.1.1]pentan-1-yl)-2-(3,4-dichlorophenoxy)acetamide hydrochloride To Example 2A (3.45 g, 15 mmol) in dichloromethane (10 mL)/methanol (1 mL) was added 4 N HCl in dioxane (53.8 mL, 215 mmol). The mixture was stirred at ambient temperature for 1 hour and then concentrated to give 2.91 g of the title compound (100% yield) as a white solid. $^1$H NMR (400 MHz, DMSO-d$_6$) δ ppm 8.90 (m, 4H), 7.55 (d, J=8, 1H), 7.22 (d, J=2, 1H), 6.98 (dd, J=8, 2, 1H), 4.50 (s, 2H), 2.23 (s, 6H). MS (ESI+) m/z 301 (M+H)$^+$.

Example 2C: 2-(3,4-dichlorophenoxy)-N-(3-{[5-(trifluoromethyl)pyrazin-2-yl]amino}bicyclo[1.1.1]pentan-1-yl)acetamide To a suspension of N-(3-aminobicyclo[1.1.1]pentan-1-yl)-2-(3,4-dichlorophenoxy)acetamide hydrochloride (0.08 g, 0.237 mmol, Example 2B) in N,N-dimethylformamide (0.5 mL, 6.46 mmol) was added N,N-diisopropylethylamine (0.166 mL, 0.948 mmol) followed by 2-bromo-5-(trifluoromethyl)pyrazine (0.065 g, 0.284 mmol). The reaction mixture was stirred overnight at 90° C. It was then concentrate under reduced pressure at 50° C. The residue was purified by flash column chromatography on silica gel (24 g) eluted with heptane and ethyl acetate (0 to 100%) to give 40 mg of the title compound (35.9% yield) as a white solid. $^1$H NMR (400 MHz, DMSO-d$_6$) δ ppm 8.78 (s, 1H), 8.59 (s, 1H), 8.44 (s, 1H), 7.99 (s, 1H), 7.55 (d, J=8.8 Hz, 1H), 7.27 (d, J=2.8 Hz, 1H), 6.99 (dd, J=9.0, 2.9 Hz, 1H), 4.51 (s, 2H), 2.37 (s, 6H). $^{19}$F NMR (376 MHz, DMSO-d$_6$) δ ppm −64.83; MS (ESI+) m/z 447 (M+H)$^+$.

Example 3: 2-(4-chloro-3-fluorophenoxy)-N-(3-{[5-(trifluoromethyl)pyrazin-2-yl]amino}bicyclo[1.1.1]pentan-1-yl)acetamide (Compound 102)

Example 3A: tert-butyl (3-(2-(4-chloro-3-fluorophenoxy)acetamido)bicyclo[1.1.1]pentan-1-yl)carbamate To a solution of 2-(4-chloro-3-fluorophenoxy)acetic acid (Aldlab Chemicals, 2.01 g, 9.84 mmol) in N,N-dimethylformamide (25 mL) was added N-ethyl-N-isopropylpropan-2-amine (3.96 mL, 22.7 mmol) followed by 2-(3H-[1,2,3]triazolo[4,5-b]pyridin-3-yl)-1,1,3,3-tetramethylisouronium hexafluorophosphate(V) (3.02 g, 7.94 mmol). This mixture was stirred at ambient temperature for 5 minutes, and then tert-butyl (3-aminobicyclo[1.1.1]pentan-1-yl)carbamate (PharmaBlock, 1.5 g, 7.57 mmol) was added. The mixture was allowed to stir at ambient temperature for 16 hours. The reaction mixture was quenched with saturated, aqueous NH$_4$Cl (20 mL) and then washed with CH$_2$Cl$_2$ (25 mL). The aqueous layer was extracted with CH$_2$Cl$_2$ (3×5 mL), and the combined organic fractions were dried over anhydrous Na$_2$SO$_4$, filtered, and concentrated under reduced pressure. The residue was purified by column chromatography (SiO$_2$, 10% ethyl acetate/heptanes to 80% ethyl acetate/heptanes) to give the title compound (2.65 g, 6.89 mmol, 91% yield). MS (ESI$^+$) m/z 402 (M+NH$_4$)$^+$.

Example 3B: N-(3-aminobicyclo[1.1.1]pentan-1-yl)-2-(4-chloro-3-fluorophenoxy)acetamide hydrochloride A mixture of Example 3A (1.20 g, 3.12 mmol) and 4 N HCl (in dioxane, 4.68 mL, 18.71 mmol) in dioxane (10 mL) was stirred overnight. The solids were filtered, washed with ethyl acetate, and vacuum oven-dried to give the title compound (0.985 g, 98%). MS (ESI$^+$) m/z 284.9 (M+H)$^+$.

Example 3C: 2-(4-chloro-3-fluorophenoxy)-N-(3-{[5-(trifluoromethyl)pyrazin-2-yl]amino}bicyclo[1.1.1]pentan-1-yl)acetamide To a suspension of Example 3B (0.08 g, 0.249 mmol) in N,N-dimethylformamide (0.5 mL, 6.46 mmol) were added N,N-diisopropylethylamine (0.174 mL, 0.996 mmol) and 2-bromo-5-(trifluoromethyl)-pyrazine (0.068 g, 0.299 mmol). The reaction mixture was stirred overnight at 90° C., and then it was concentrate under reduced pressure at 50° C. The residue was purified by flash column chromatography on silica gel (12 g) eluted with heptane and ethyl acetate (0 to 100%) to give 40 mg of the title compound (37.3% yield) as a white solid. $^1$H NMR (400 MHz, DMSO-d$_6$) δ ppm 8.78 (s, 1H), 8.59 (s, 1H), 8.44 (s, 1H), 7.99 (s, 1H), 7.55 (d, J=8.8 Hz, 1H), 7.27 (d, J=2.8 Hz, 1H), 6.99 (dd, J=9.0, 2.9 Hz, 1H), 4.51 (s, 2H), 2.37 (s, 6H); $^{19}$F NMR (376 MHz, DMSO-d$_6$) δ ppm −64.83, −114.06; MS (ESI$^+$) m/z 447 (M+H)$^+$.

Example 4: 2-(4-chloro-3-fluorophenoxy)-N-(3-{[5-(trifluoromethyl)pyridin-2-yl]amino}bicyclo[1.1.1]pentan-1-yl)acetamide (Compound 103)

Example 4A: N-(3-aminobicyclo[1.1.1]pentan-1-yl)-2-(4-chloro-3-fluorophenoxy)acetamide To solution of Example 3A (9 g, 23.39 mmol) in dichloromethane (100 mL) was added trifluoroacetic acid (30 mL, 389 mmol) at 0° C. The mixture was stirred at ambient temperature for 12 hours. The mixture was concentrated under reduced pressure, and the residue was diluted with water (300 mL). The aqueous phase was adjusted to pH=8 with NaHCO$_3$ and then extracted with dichloromethane (4×150 mL). The combined organic layer was dried (Na$_2$SO$_4$) and concentrated under reduced pressure to provide 6 g (90%) of the title compound as a white solid. MS (APCI) m/z 285 (M+H)$^+$ Example 4B: 2-(4-chloro-3-fluorophenoxy)-N-(3-{[5-(trifluoromethyl)pyridin-2-yl]amino}bicyclo[1.1.1]pentan-1-yl)acetamide To a solution of Example 4A (40 rag, 0.140 mmol) in dioxane (1 mL) were added tris(dibenzylideneacetone)dipalladium(0) (6.43 mg, 7.02 µmol, Pd$_2$(dba)$_3$), Xantphos (8.13 mg, 0.014 mmol) and 2-bromo-5-(trifluoromethyl) pyridine (34.9 mg, 0.155 mmol), followed by potassium carbonate (58.3 mg, 0.421 mmol). The reaction mixture was stirred overnight at 80° C. The reaction mixture was diluted with water and extracted with ethyl acetate (20 mL×3). The combined organic layers were dried with MgSO$_4$, filtered and concentrated under reduced pressure. The residue was purified by flash column chromatography on silica gel, (12 g) eluted with heptane and ethyl acetate (0 to 100%) to give 25 mg of the title compound (41.4% yield) as a white solid. $^1$H NMR (400 MHz, DMSO-d$_6$) δ ppm 8.74 (s, 1H), 8.37-8.31 (m, 1H), 7.97 (s, 1H), 7.67 (dd, J=8.9, 2.6 Hz, 1H), 7.50 (t, J=8.9 Hz, 1H), 7.08 (dd, J=11.4, 2.8 Hz, 1H), 6.86 (ddd, J=9.1, 2.9, 1.2 Hz, 1H), 6.61 (d, J=8.9 Hz, 1H), 4.49 (s, 2H), 2.34 (s, 6H); $^{19}$F NMR (376 MHz, DMSO-d$_6$) δ ppm −58.94, −113.65 (dd, J=11.3, 8.9 Hz); MS (ESI$^+$) m/z 430 (M+H)$^+$.

Example 5: 2-(4-chloro-3-fluorophenoxy)-N-(3-{[6-(trifluoromethyl)pyridin-3-yl]amino}bicyclo[1.1.1]pentan-1-yl)acetamide (Compound 104)

To a solution of Example 4A (40 mg, 0.140 mmol) in dioxane (1 mL) were added tris(dibenzylideneacetone)dipalladium(0) (6.43 mg, 7.02 µmol, Pd$_2$(dba)$_3$), Xantphos (8.13 mg, 0.014 mmol) and 5-bromo-2-(trifluoromethyl) pyridine (34.9 mg, 0.155 mmol), followed by potassium carbonate (58.3 mg, 0.421 mmol). The reaction mixture was stirred overnight at 80° C. The reaction mixture was diluted with water and extracted with ethyl acetate (20 mL×3). The combined organic layers was dried with MgSO$_4$, filtered and concentrated under reduced pressure. The residue was purified by flash column chromatography on silica gel, (12 g) eluted with heptane and ethyl acetate (0 to 100%) to give 5 mg of the title compound (8.28% yield) as a solid. $^1$H NMR (400 MHz, DMSO-d$_6$) δ ppm 8.81 (s, 1H), 8.11 (d, J=2.7 Hz, 1H), 7.55 (d, J=8.7 Hz, 1H), 7.50 (t, J=8.8 Hz, 1H), 7.42 (s, 1H), 7.17 (dd, J=8.8, 2.7 Hz, 1H), 7.08 (dd, J=11.4, 2.9 Hz, 1H), 6.86 (ddd, J=9.0, 2.9, 1.2 Hz, 1H), 4.51 (s, 2H), 2.35 (s, 6H); MS (ESI$^+$) m/z 430 (M+H)$^+$.

Example 6: N-{3-[2-(4-chloro-3-fluorophenoxy)acetamido]bicyclo[1.1.1]pentan-1-yl}-2-(4-chloro-3-fluorophenyl)-1,3-oxazole-5-carboxamide (Compound 105)

Example 6A: Ethyl 2-(4-chloro-3-fluorophenyl)oxazole-5-carboxylate

A mixture of ethyl 2-bromooxazole-5-carboxylate (ArkPharm Inc., 1 g, 4.55 mmol), (4-chloro-3-fluorophenyl) boronic acid (Combi-Blocks, 0.99 g, 5.68 mmol), (1S,3R,5R,7S)-1,3,5,7-tetramethyl-8-phenyl-2,4,6-trioxa-8-phosphaadamantane (Strem, 0.133 g, 0.455 mmol), bis(dibenzylideneacetone)palladium (0) (Strem, 0.13 g, 0.23 mmol) and potassium carbonate (1.57 g, 11.4 mmol) in a pressure tube was degassed three times with a nitrogen back flush each time. Tetrahydrofuran (15 mL) and water (3.0 mL) were added, and the mixture was again degassed three times with a nitrogen back flush each time. The reaction mixture was warmed to 65° C. and was allowed to stir for 12 hours. The mixture was allowed to cool to ambient temperature, anhydrous Na$_2$SO$_4$ was added, and the mixture was filtered through diatomaceous earth. The filtrate was concentrated under reduced pressure, and the residue was purified via column chromatography (SiO$_2$, 1-50% ethyl acetate/heptanes) to give the title compound (0.41 g, 1.52 mmol, 34% yield). MS (ESI$^+$) m/z 270 (M+H)$^+$.

Example 6B: 2-(4-chloro-3-fluorophenyl)oxazole-5-carboxylic acid

To a solution of the product of Example 6A (0.26 g, 0.96 mmol) in methanol (5 mL) and water (2.5 mL) was added sodium hydroxide (5 M, 1.93 mL, 9.64 mmol). This mixture was allowed to stir at ambient temperature for 16 hours. Then the mixture was concentrated under reduced pressure, and the residue was dissolved in water. The solution was acidified with concentrated HCl, and the resulting precipitate was isolated via filtration to give the title compound (0.21 g, 0.85 mmol, 88% yield). MS (ESI$^+$) m/z 240 (M−H)$^+$.

Example 6C: N-(3-aminobicyclo[1.1.1]pentan-1-yl)-2-(4-chloro-3-fluorophenoxy)acetamide trifluoroacetate To a solution of the product of Example 3A (0.79 g, 2.05 mmol) in CH$_2$Cl$_2$ (7 mL) at ambient temperature was added trifluoroacetic acid (3.16 mL, 41.1 mmol). This mixture was allowed to stir at ambient temperature for 3 hours. The mixture was concentrated under reduced pressure and azeotroped with toluene to give the title compound (1.06 g, 2.07 mmol, 100% yield) which was carried on without purification. MS (ESI$^+$) m/z 285 (M+H)$^+$.

Example 6D: N-{3-[2-(4-chloro-3-fluorophenoxy)acetamido]bicyclo[1.1.1]pentan-1-yl}-2-(4-chloro-3-fluorophenyl)-1,3-oxazole-5-carboxamide To a mixture of the product of Example 6C (0.11 g, 0.22 mmol) and the product of Example 6B (0.062 g, 0.26 mmol) in N,N-dimethylformamide (2 mL) was added N-ethyl-N-isopropylpropan-2-amine (0.15 mL, 0.86 mmol) followed by 2-(3H-[1,2,3]triazolo[4,5-b]pyridin-3-yl)-1,1,3,3-tetramethylisouronium hexafluorophosphate(V) (0.086 g, 0.23 mmol). This mixture was allowed to stir at ambient temperature for 16 hours and then was quenched with saturated, aqueous NaHCO$_3$ (10 mL) and diluted with CH$_2$Cl$_2$ (10 mL). The layers were separated, and the aqueous layer was extracted with CH$_2$Cl$_2$ (3×3 mL). The combined organic fractions were dried over anhydrous Na$_2$SO$_4$, filtered, and concentrated under reduced pressure. The residue was purified via column chromatography (SiO$_2$, 75% ethyl acetate/heptanes) to give the title compound (0.09 g, 0.18 mmol, 83% yield). $^1$H NMR (400 MHz, DMSO-d$_6$) δ ppm 9.29 (s, 1H), 8.76 (s, 1H), 8.11 (dd, J=9.9, 1.9 Hz, 1H), 7.98-7.92 (m, 1H), 7.87 (s, 1H), 7.82 (t, J=8.0 Hz, 1H), 7.49 (t, J=8.9 Hz, 1H), 7.07 (dd, J=11.3, 2.8 Hz, 1H), 6.89-6.81 (m, 1H), 4.48 (s, 2H), 2.35 (s, 6H); MS (ESI$^+$) m/z 508 (M+H)$^+$.

Example 7: N-{3-[2-(4-chloro-3-fluorophenoxy) acetamido]bicyclo[1.1.1]pentan-1-yl}-5-(4-chloro-3-fluorophenyl)furan-2-carboxamide (Compound 106)

Example 7A: Ethyl 5-(4-chloro-3-fluorophenyl)furan-2-carboxylate

A mixture of ethyl-5-bromofuran-2-carboxylate (Combi-Blocks, 1.0 g, 4.6 mmol), (4-chloro-3-fluorophenyl)boronic acid (Combi-Blocks, 1.0 g, 5.7 mmol), (1S,3R,5R,7S)-1,3,5,7-tetramethyl-8-phenyl-2,4,6-trioxa-8-phosphaadamantane (Strem, 0.133 g, 0.457 mmol), bis(dibenzylideneacetone)palladium (0) (Strem, 0.13 g, 0.23 mmol) and potassium carbonate (1.6 g, 11.4 mmol) in a pressure tube were degassed three times with a nitrogen back flush each time. Tetrahydrofuran (15 mL) and water (3.00 mL) were added, and the mixture was again degassed three times with a nitrogen back flush each time. The reaction mixture was warmed to 65° C. and was allowed to stir for 12 hours. The mixture was allowed to cool to ambient temperature, then anhydrous Na$_2$SO$_4$ was added, and the mixture was filtered through diatomaceous earth. The filtrate was concentrated under reduced pressure, and the residue was purified via column chromatography (SiO$_2$, 1-20% ethyl acetate/heptanes) to give the title compound (1.1 g, 4.1 mmol, 90% yield). MS (ESI$^+$) m/z 286 (M+NH$_4$)$^+$.

Example 7B: 5-(4-chloro-3-fluorophenyl)furan-2-carboxylic acid

To a solution of the product of Example 7A (1.1 g, 4.1 mmol) in methanol (15 mL) and water (7.50 mL) was added sodium hydroxide (8.2 mL, 40.9 mmol). This mixture was allowed to stir at ambient temperature for 16 hours, and then the mixture was concentrated under reduced pressure, and the residue was dissolved in water. The solution was acidified with concentrated HCl, and the resulting precipitate was isolated via filtration to give the title compound (0.98 g, 4.1 mmol, 99% yield). MS (ESI$^+$) m/z 258 (M+NH$_4$)$^+$.

Example 7C: N-{3-[2-(4-chloro-3-fluorophenoxy) acetamido]bicyclo[1.1.1]pentan-1-yl}-5-(4-chloro-3-fluorophenyl)furan-2-carboxamide To a mixture of the product of Example 6C (0.10 g, 0.25 mmol) and the product of Example 7B (0.094 g, 0.31 mmol) in N,N-dimethylformamide (3 mL) was added N-ethyl-N-isopropylpropan-2-amine (0.18 mL, 1.0 mmol) followed by 2-(3H-[1,2,3]triazolo[4,5-b]pyridin-3-yl)-1,1,3,3-tetramethylisouronium hexafluorophosphate(V) (0.10 g, 0.26 mmol). This mixture was allowed to stir at ambient temperature for 16 hours then was quenched with saturated, aqueous NaHCO$_3$ (10 mL) and diluted with CH$_2$Cl$_2$ (10 mL). The layers were separated, and the aqueous layer was extracted with CH$_2$Cl$_2$ (3×3 mL). The combined organic fractions were dried over anhydrous Na$_2$SO$_4$, filtered, and concentrated under reduced pressure. The residue was purified via HPLC (Waters XBridge™ C18 5 μm OBD™ column, 50×100 mm, flow rate 90 mL/minute, 20-100% gradient of methanol in buffer (0.025 M aqueous ammonium bicarbonate, adjusted to pH 10 with ammonium hydroxide)) to give the title compound (0.08 g, 0.16 mmol, 63% yield). $^1$H NMR (501 MHz, DMSO-d$_6$) δ ppm 9.09 (s, 1H), 8.74 (s, 1H), 8.03 (dd, J=10.7, 2.0 Hz, 1H), 7.78 (ddd, J=8.4, 2.0, 0.7 Hz, 1H), 7.68 (dd, J=8.4, 7.7 Hz, 1H), 7.48 (t, J=8.9 Hz, 1H), 7.21 (d, J=3.6 Hz, 1H), 7.14 (d, J=3.6 Hz, 1H), 7.07 (dd, J=11.4, 2.8 Hz, 1H), 6.85 (ddd, J=8.9, 2.9, 1.2 Hz, 1H), 4.48 (s, 2H), 2.34 (s, 6H); MS (ESI$^+$) m/z 507 (M−H)$^+$.

Example 8: N-{3-[2-(4-chloro-3-fluorophenoxy) acetamido]bicyclo[1.1.1]pentan-1-yl}-2-[6-(trifluoromethyl)pyridin-3-yl]-1,3-oxazole-5-carboxamide (Compound 107)

Example 8A: Ethyl 2-(6-(trifluoromethyl)pyridin-3-yl)oxazole-5-carboxylate

A mixture of ethyl-2-bromooxazole-5-carboxylate (0.50 g, 2.27 mmol), 5-(4,4,5,5-tetramethyl-1,3,2-dioxaborolan-2-yl)-2-(trifluoromethyl)pyridine (Combi-Blocks, 0.78 g, 2.84 mmol), (1S,3R,5R,7S)-1,3,5,7-tetramethyl-8-phenyl-2,4,6-trioxa-8-phosphaadamantane (Strem, 0.066 g, 0.23 mmol), bis(dibenzylideneacetone)palladium (0) (0.065 g, 0.114 mmol) and potassium carbonate (0.79 g, 5.68 mmol) in a pressure tube was degassed three times with a nitrogen back flush each time. Tetrahydrofuran (7.5 mL) and water (1.5 mL) were added, and the mixture was again degassed three times with a nitrogen back flush each time. The reaction mixture was warmed to 65° C. and was allowed to stir for 12 hours. The mixture was allowed to cool to ambient temperature, then anhydrous Na$_2$SO$_4$ was added, and the mixture was filtered through diatomaceous earth. The filtrate was concentrated under reduced pressure, and the residue was purified via column chromatography (SiO$_2$, 1-40% ethyl acetate/heptanes) to give the title compound (0.43 g, 1.50 mmol, 66% yield). MS (ESI$^+$) m/z 287 (M+H)$^+$.

Example 8B: 2-(6-(trifluoromethyl)pyridin-3-yl) oxazole-5-carboxylic acid

To a solution of the product of Example 8A (0.43 g, 1.50 mmol) in methanol (10 mL) and water (5.0 mL) was added NaOH (5 M, 3.00 mL, 15.0 mmol). This mixture was allowed to stir at ambient temperature for 16 hours then the mixture was concentrated under reduced pressure and dissolved in water. The solution was acidified with concentrated HCl and the resulting precipitate was isolated via filtration to give the title compound (0.40 g, 1.55 mmol, 100% yield). MS (ESI$^+$) m/z 257 (M−H)$^+$.

Example 8C: N-{3-[2-(4-chloro-3-fluorophenoxy) acetamido]bicyclo[1.1.1]pentan-1-yl}-2-[6-(trifluoromethyl)pyridin-3-yl]-1,3-oxazole-5-carboxamide To a mixture of the product of Example 6C (0.10 g, 0.195 mmol) and the product of Example 8B (0.060 g, 0.23 mmol) in N,N-dimethylformamide (2 mL) was added N-ethyl-N-isopropylpropan-2-amine (0.136 mL, 0.78 mmol) followed by 2-(3H-[1,2,3]triazolo[4,5-b]pyridin-3-yl)-1,1,3,3-tetramethylisouronium hexafluorophosphate(V) (0.078 g, 0.21 mmol). This mixture was allowed to stir at ambient temperature for 16 hours then was quenched with saturated, aqueous NaHCO$_3$ (10 mL) and diluted with ethyl acetate (10 mL). The layers were separated, and the aqueous layer was extracted with ethyl acetate (3×3 mL). The combined organic fractions were dried over anhydrous Na$_2$SO$_4$, filtered, and concentrated under reduced pressure. The residue was purified via column chromatography (SiO$_2$, 75% ethyl acetate/heptanes) to give the title compound (90 mg, 0.17 mmol, 88% yield). $^1$H NMR (400 MHz, DMSO-d$_6$) δ ppm 9.42 (d, J=1.9 Hz, 1H), 9.37 (s, 1H), 8.76 (s, 1H), 8.70 (dd, J=8.3, 2.0 Hz, 1H), 8.14 (d, J=8.2 Hz, 1H), 7.96 (s, 1H), 7.49 (t, J=8.9 Hz, 1H), 7.07 (dd, J=11.4, 2.8 Hz, 1H), 6.85 (ddd, J=9.0, 2.8, 1.2 Hz, 1H), 4.49 (s, 2H), 2.36 (s, 6H); MS (ESI$^+$) m/z 525 (M+H)$^+$.

Example 9 N-{3-[2-(4-chloro-3-fluorophenoxy)acetamido]bicyclo[1.1.1]pentan-1-yl}-2-(4-chloro-3-fluorophenyl)-1,3-oxazole-4-carboxamide (Compound 108)

Example 9A: Ethyl 2-(4-chloro-3-fluorophenyl)oxazole-4-carboxylate

A mixture of ethyl 2-bromooxazole-4-carboxylate (Combi-Blocks, 0.50 g, 2.27 mmol), (4-chloro-3-fluorophenyl)boronic acid (Combi-Blocks, 0.50 g, 2.84 mmol), (1S,3R,5R,7S)-1,3,5,7-tetramethyl-8-phenyl-2,4,6-trioxa-8-phosphaadamantane (Strem, 0.066 g, 0.227 mmol), bis(dibenzylideneacetone)palladium (0) (0.065 g, 0.114 mmol) and potassium carbonate (0.79 g, 5.68 mmol) in a pressure tube was degassed three times with a nitrogen back flush each time. Tetrahydrofuran (7.5 mL) and water (1.5 mL) were added, and the mixture was again degassed three times with a nitrogen back flush each time. The reaction mixture was warmed to 65° C. and was allowed to stir for 12 hours. The mixture was allowed to cool to ambient temperature, then anhydrous Na$_2$SO$_4$ was added, and the mixture was filtered through diatomaceous earth. The filtrate was concentrated under reduced pressure. The residue was purified via column chromatography (SiO$_2$, 1-40% ethyl acetate/heptanes) to give the title compound (0.61 g, 2.26 mmol, 100% yield). MS (ESI$^+$) m/z 270 (M+H)$^+$.

Example 9B: 2-(4-chloro-3-fluorophenyl)oxazole-4-carboxylic acid

To a solution of the product of Example 9A (0.64 g, 2.37 mmol) in methanol (10 mL) and water (5.00 mL) was added NaOH (5 M, 4.75 mL, 23.7 mmol). This mixture was allowed to stir at ambient temperature for 16 hours, and then the mixture was concentrated under reduced pressure. The residue was dissolved in water, and the solution was acidified with concentrated HCl to pH 1, and the resulting precipitate was isolated via filtration to give the title compound (0.60 g, 1.99 mmol, 84% yield). MS (ESI$^+$) m/z 240 (M–H)$^+$.

Example 9C: N-{3-[2-(4-chloro-3-fluorophenoxy)acetamido]bicyclo[1.1.1]pentan-1-yl}-2-(4-chloro-3-fluorophenyl)-1,3-oxazole-4-carboxamide To a mixture of the product of Example 6C (0.16 g, 0.312 mmol) and the product of Example 9B (0.113 g, 0.37 mmol) in N,N-dimethylformamide (2.5 mL) was added N-ethyl-N-isopropylpropan-2-amine (0.22 mL, 1.25 mmol) followed by 2-(3H-[1,2,3]triazolo[4,5-b]pyridin-3-yl)-1,1,3,3-tetramethylisouronium hexafluorophosphate(V) (0.13 g, 0.33 mmol). This mixture was allowed to stir at ambient temperature for 16 hours, then it was quenched with saturated, aqueous NaHCO$_3$ (10 mL) and diluted with ethyl acetate (10 mL). The layers were separated, and the aqueous layer was extracted with ethyl acetate (3×3 mL). The combined organic fractions were dried over anhydrous Na$_2$SO$_4$, filtered, and concentrated under reduced pressure. The residue was purified via column chromatography (SiO$_2$, 75% ethyl acetate/heptanes) to give the title compound (0.14 g, 0.28 mmol, 88% yield). $^1$H NMR (400 MHz, DMSO-d$_6$) δ ppm 8.90 (s, 1H), 8.72 (s, 1H), 8.71 (s, 1H), 7.95 (dd, J=9.9, 1.8 Hz, 1H), 7.90-7.76 (m, 2H), 7.48 (t, J=8.9 Hz, 1H), 7.06 (dd, J=11.4, 2.9 Hz, 1H), 6.84 (ddd, J=8.9, 2.8, 1.2 Hz, 1H), 4.48 (s, 2H), 2.33 (s, 6H); MS (ESI$^+$) m/z 508 (M+H)$^+$.

Example 10: N-{3-[2-(4-chloro-3-fluorophenoxy)acetamido]bicyclo[1.1.1]pentan-1-yl}-2-(2-methylpyrimidin-5-yl)-1,3-oxazole-5-carboxamide (Compound 109)

Example 10A: ethyl 2-(2-methylpyrimidin-5-yl)oxazole-5-carboxylate

A mixture of ethyl 2-bromooxazole-5-carboxylate (0.50 g, 2.3 mmol), 2-methylpyrimidine-5-boronic acid pinacol ester (0.625 g, 2.84 mmol), (1S,3R,5R,7S)-1,3,5,7-tetramethyl-8-phenyl-2,4,6-trioxa-8-phosphaadamantane (0.066 g, 0.23 mmol), bis(dibenzylideneacetone)palladium (0) (0.065 g, 0.11 mmol) and potassium carbonate (0.79 g, 5.7 mmol) in a pressure tube was degassed three times with a nitrogen back flush each time. Tetrahydrofuran (7.5 mL) and water (1.5 mL) were added, and the mixture was again degassed three times with a nitrogen back flush each time. The reaction mixture was warmed to 65° C. and stirred for 16 hours. The mixture was allowed to cool to ambient temperature, then anhydrous Na$_2$SO$_4$ was added, and the mixture was filtered through diatomaceous earth. The filtrate was then concentrated under reduced pressure. The residue was purified via column chromatography (SiO$_2$, 1-40% ethyl acetate/heptanes) to give the title compound (0.295 g, 1.27 mmol, 56% yield). MS (ESI$^+$) m/z 234 (M+H)$^+$.

Example 10B: 2-(2-methylpyrimidin-5-yl)oxazole-5-carboxylic acid

To a solution of the product of Example 10A (0.30 g, 1.27 mmol) in methanol (10 mL) and water (5.0 mL) was added NaOH (5 M, 2.53 mL, 12.7 mmol). This mixture was allowed to stir at ambient temperature for 16 hours, and then the mixture was concentrated under reduced pressure. The residue was dissolved in water, the solution was acidified with concentrated HCl to pH 1, and the resulting precipitate was isolated via filtration to give the title compound (0.10 g, 0.49 mmol, 39% yield). MS (ESI$^+$) m/z 206 (M+H)$^+$.

Example 10C: N-{3-[2-(4-chloro-3-fluorophenoxy)acetamido]bicyclo[1.1.1]pentan-1-yl}-2-(2-methylpyrimidin-5-yl)-1,3-oxazole-5-carboxamide To a mixture of the product of Example 6C (0.11 g, 0.22 mmol) and the product of Example 10B (0.053 g, 0.26 mmol) in N,N-dimethylformamide (2 mL) was added N-ethyl-N-isopropylpropan-2-amine (0.15 mL, 0.89 mmol) followed by 2-(3H-[1,2,3]triazolo[4,5-b]pyridin-3-yl)-1,1,3,3-tetramethylisouronium hexafluorophosphate(V) (0.086 g, 0.23 mmol). This mixture was allowed to stir at ambient temperature for 16 hours, then it was quenched with saturated, aqueous NaHCO$_3$ (10 mL) and diluted with ethyl acetate (10 mL). The layers were separated, and the aqueous layer was extracted with ethyl acetate (3×3 mL). The combined organic fractions were dried over anhydrous Na$_2$SO$_4$, filtered, and concentrated under reduced pressure. The residue was purified via column chromatography (SiO$_2$, 15% ethyl acetate/heptanes to 100% ethyl acetate to 10% methanol in ethyl acetate) to give the title compound (90 mg, 0.19 mmol, 89% yield). $^1$H NMR (400 MHz, DMSO-d$_6$) δ ppm 9.32 (s, 2H), 9.30 (s, 1H), 8.77 (s, 1H), 7.92 (s, 1H), 7.50 (t, J=8.9 Hz, 1H), 7.09 (dd, J=11.4, 2.8 Hz, 1H), 6.87 (ddd, J=9.0, 2.9, 1.2 Hz, 1H), 4.50 (s, 2H), 2.73 (s, 3H), 2.37 (s, 6H); MS (ESI$^+$) m/z 472 (M+H)$^+$.

Example 11: 2-(4-chloro-3-fluorophenyl)-N-{4-[2-(3,4-dichlorophenoxy)acetamido]bicyclo-[2.1.1]hexan-1-yl}-1,3-oxazole-5-carboxamide (Compound 110)

Example 11A: Benzyl {4-[2-(3,4-dichlorophenoxy)acetamido]bicyclo[2.1.1]hexan-1-yl}carbamate The title compound was prepared as described in Example 197A, substituting 2-(3,4-dichlorophenoxy)acetic acid (commercially available from Aldrich) for 2-(4-chloro-3-fluorophenoxy)acetic acid. $^1$H NMR (500 MHz, DMSO-d$_6$) δ ppm 8.47 (s, 1H), 7.79 (br s, 1H), 7.54 (d, J=8.9 Hz, 1H), 7.40-7.29 (m, 5H), 7.25 (d, J=2.9 Hz, 1H), 6.98 (dd, J=9.0, 2.9 Hz, 1H), 4.99 (s, 2H), 4.48 (s, 2H), 2.11-2.00 (m, 2H), 1.80-1.67 (m, 6H); MS (ESI$^-$) m/z 447 (M−H)$^-$.

Example 11B: N-(4-aminobicyclo[2.1.1]hexan-1-yl)-2-(3,4-dichlorophenoxy)acetamide The product of Example 11A (0.3 g, 0.668 mmol) was dissolved in trifluoroacetic acid (1.0 mL, 13.0 mmol) and stirred at 80° C. in a sealed tube for 1 hour. The reaction mixture was cooled to ambient temperature and then concentrated in vacuo. The resulting residue was taken up in methanol (3.0 mL), was filtered through a glass microfiber frit, and purified by preparative HPLC [Waters XBridge™ C18 5 µm OBD™ column, 30×100 mm, flow rate 40 mL/minute, 5-100% gradient of acetonitrile in buffer (0.025 M aqueous ammonium bicarbonate, adjusted to pH 10 with ammonium hydroxide)] to give the title compound (0.15 g, 0.48 mmol, 71% yield). MS (ESI$^+$) m/z 315 (M+H)$^+$.

Example 11C: 2-(4-chloro-3-fluorophenyl)-N-{4-[2-(3,4-dichlorophenoxy)acetamido]-bicyclo[2.1.1]hexan-1-yl}-1,3-oxazole-5-carboxamide The title compound was prepared as described in Example 197C substituting the product of Example 6B for 5-(difluoromethyl)pyrazine-2-carboxylic acid and the product of Example 11B for the product of Example 197B. $^1$H NMR (400 MHz, DMSO-d$_6$) δ ppm 9.05 (s, 1H), 8.55 (s, 1H), 8.13 (dd, J=9.9, 1.9 Hz, 1H), 7.98 (dd, J=8.4, 1.8 Hz, 1H), 7.88 (s, 1H), 7.84 (t, J=8.0 Hz, 1H), 7.55 (d, J=8.9 Hz, 1H), 7.27 (d, J=2.8 Hz, 1H), 7.00 (dd, J=8.9, 2.9 Hz, 1H), 4.51 (s, 2H), 2.19-2.12 (m, 2H), 1.99-1.82 (m, 6H); MS (ESI$^+$) m/z 538/540 (M+H)$^+$.

Example 12: 1-(4-chlorophenyl)-N-{4-[2-(3,4-dichlorophenoxy)acetamido]bicyclo[2.1.1]-hexan-1-yl}5-methyl-1H-pyrazole-3-carboxamide (Compound 111)

Example 12A: Ethyl 1-(4-chlorophenyl)-5-methyl-1H-pyrazole-3-carboxylate

4-Chlorophenylhydrazine sulfate (TCI Japan, 2.29 g, 5.98 mmol) was suspended in acetonitrile (50 mL), and triethylamine (0.83 mL, 5.98 mmol) was added followed by ethyl 2,4-dioxopentanoate (Aldrich, 0.84 mL, 5.98 mmol). The reaction mixture was stirred at ambient temperature for 18 hours. The resulting crude mixture was partitioned between dichloromethane (2×200 mL) and aqueous sodium carbonate (1.0 M, 200 mL). The organic layers were combined, dried over anhydrous sodium sulfate, and concentrated in vacuo. The residue was purified via flash chromatography (SiO$_2$, 3-25% ethyl acetate in heptane) to give the title compound (0.46 g, 1.74 mmol, 29% yield). MS (ESI$^+$) m/z 265 (M+H)$^+$.

Example 12B: 1-(4-chlorophenyl)-5-methyl-1H-pyrazole-3-carboxylic acid

The product of Example 12A (0.46 g, 1.738 mmol) was dissolved in ethanol (30 mL), aqueous sodium hydroxide (2.5 M, 10 mL) was added, and the resulting mixture was stirred at ambient temperature for 20 minutes. The mixture was partitioned between dichloromethane (2×100 mL) and aqueous citric acid (10 weight %, 100 mL). The organic layers were combined, dried over anhydrous sodium sulfate, and concentrated in vacuo to give the title compound (0.40 g, 1.70 mmol, 98% yield). MS (ESI$^+$) m/z 237 (M+H)$^+$.

Example 12C: 1-(4-chlorophenyl)-N-{4-[2-(3,4-dichlorophenoxy)acetamido]bicyclo[2.1.1]-hexan-1-yl}-5-methyl-1H-pyrazole-3-carboxamide The title compound was prepared as described in Example 197C, substituting the product of Example 12B for 5-(difluoromethyl)pyrazine-2-carboxylic acid and the product of Example 11B for the product of 197B. $^1$H NMR (500 MHz, DMSO-d$_6$) δ ppm 8.51 (s, 1H), 8.45 (s, 1H), 7.66-7.60 (m, 4H), 7.55 (d, J=8.9 Hz, 1H), 7.26 (d, J=2.9 Hz, 1H), 6.99 (dd, J=9.0, 2.9 Hz, 1H), 6.63 (d, J=0.9 Hz, 1H), 4.50 (s, 2H), 2.34-2.33 (m, 3H), 2.12-2.07 (m, 2H), 1.91-1.79 (m, 6H); MS (ESI$^+$) m/z 533/535 (M+H)$^+$.

Example 13: N-{3-[2-(4-chloro-3-fluorophenoxy)acetamido]bicyclo[1.1.1]pentan-1-yl}-1-(4-chlorophenyl)-5-methyl-1H-pyrazole-3-carboxamide (Compound 112)

N,N-Dimethylformamide (2 mL), triethylamine (0.05 mL, 0.34 mmol) and 1-[bis(dimethylamino)methylene]-1H-1,2,3-triazolo[4,5-b]pyridinium 3-oxidhexafluorophosphate (58 mg, 0.152 mmol, HATU) were added to a mixture of the product of Example 12B (29.3 mg, 0.124 mmol) and the product of Example 4A (32 mg, 0.112 mmol) in sequential order. The reaction mixture was then stirred at ambient temperature for 1 hour. The resulting solution was filtered through a glass microfiber frit and purified by preparative HPLC [Waters XBridge™ C18 5 µm OBD column, 30×100 mm, flow rate 40 mL/minute, 5-100% gradient of acetonitrile in buffer (0.025 M aqueous ammonium bicarbonate, adjusted to pH 10 with ammonium hydroxide)] to give the title compound (52 mg, 0.103 mmol, 92% yield). $^1$H NMR (500 MHz, DMSO-d$_6$) δ ppm 8.75 (s, 1H), 8.72 (s, 1H), 7.67-7.60 (m, 4H), 7.50 (t, J=8.9 Hz, 1H), 7.08 (dd, J=11.4, 2.8 Hz, 1H), 6.86 (ddd, J=8.9, 2.9, 1.2 Hz, 1H), 6.63 (d, J=0.9 Hz, 1H), 4.49 (s, 2H), 2.34 (d, J=0.8 Hz, 3H), 2.31 (br s, 6H); MS (ESI$^+$) m/z 503 (M+H)$^+$.

Example 14: N-{3-[2-(4-chloro-3-fluorophenoxy)acetamido]bicyclo[1.1.1]pentan-1-yl}-5-(4-chlorophenyl)-1,2-oxazole-3-carboxamide (Compound 113)

The title compound was prepared as described in Example 13 substituting 5-(4-chlorophenyl)isoxazole-3-carboxylic acid (commercially available from Enamine) for the product of Example 12B and the product of Example 6C for the product of Example 4A. $^1$H NMR (500 MHz, DMSO-d$_6$) δ ppm 9.44 (s, 1H), 8.76 (s, 1H), 7.97-7.93 (m, 2H), 7.66-7.61 (m, 2H), 7.50 (t, J=8.9 Hz, 1H), 7.37 (s, 1H), 7.08 (dd, J=11.3, 2.9 Hz, 1H), 6.86 (ddd, J=8.9, 2.8, 1.2 Hz, 1H), 4.50 (s, 2H), 2.35 (s, 6H); MS (ESI$^+$) m/z 490 (M+H)$^+$.

Example 15: N-{3-[2-(4-chloro-3-fluorophenoxy) acetamido]bicyclo[1.1.1]pentan-1-yl}-5-methylpyrazine-2-carboxamide (Compound 114)

The title compound was prepared as described in Example 13, substituting 5-methylpyrazine-2-carboxylic acid (commercially available from Alfa) for the product of Example 12B and the product of Example 6C for the product of Example 4A. $^1$H NMR (501 MHz, DMSO-d$_6$) δ ppm 9.36 (s, 1H), 9.01 (d, J=1.5 Hz, 1H), 8.74 (s, 1H), 8.59 (dd, J=1.4, 0.7 Hz, 1H), 7.50 (t, J=8.9 Hz, 1H), 7.08 (dd, J=11.4, 2.8 Hz, 1H), 6.86 (ddd, J=9.0, 2.9, 1.2 Hz, 1H), 4.49 (s, 2H), 2.59 (s, 3H), 2.35 (br s, 6H); MS (ESI$^+$) m/z 405 (M+H)$^+$.

Example 16: N-{3-[2-(4-chloro-3-fluorophenoxy) acetamido]bicyclo[1.1.1]pentan-1-yl}-5-(trifluoromethyl)pyrazine-2-carboxamide (Compound 115)

The title compound was prepared as described in Example 13 substituting 5-(trifluoromethyl)pyrazine-2-carboxylic acid (commercially available from Anichem) for the product of Example 12B and the product of Example 6C for the product of Example 4A. $^1$H NMR (400 MHz, DMSO-d$_6$) δ ppm 9.70 (s, 1H), 9.41-9.29 (m, 1H), 9.22 (dd, J=1.4, 0.6 Hz, 1H), 8.75 (s, 1H), 7.50 (t, J=8.9 Hz, 1H), 7.08 (dd, J=11.4, 2.8 Hz, 1H), 6.86 (ddd, J=9.0, 2.9, 1.2 Hz, 1H), 4.50 (s, 2H), 2.38 (br s, 6H); MS (ESI$^+$) m/z 459 (M+H)$^+$.

Example 17: N-{3-[2-(4-chloro-3-fluorophenoxy) acetamido]bicyclo[1.1.1]pentan-1-yl}-4,6-dimethoxypyrimidine-2-carboxamide (Compound 116)

The title compound was prepared as described in Example 13, substituting 4,6-dimethoxypyrimidine-2-carboxylic acid (commercially available from Ark Pharm) for the product of Example 12B and the product of Example 6C for the product of Example 4A. $^1$H NMR (400 MHz, DMSO-d$_6$) δ ppm 9.15 (s, 1H), 8.75 (s, 1H), 7.50 (t, J=8.9 Hz, 1H), 7.09 (dd, J=11.4, 2.8 Hz, 1H), 6.87 (ddd, J=8.9, 2.8, 1.2 Hz, 1H), 6.37 (s, 1H), 4.50 (s, 2H), 3.96 (s, 6H), 2.36 (br s, 6H); MS (ESI$^+$) m/z 451 (M+H)$^+$.

Example 18: N-{3-[2-(4-chloro-3-fluorophenoxy) acetamido]bicyclo[1.1.1]pentan-1-yl}-5-(trifluoromethoxy)pyridine-2-carboxamide (Compound 117)

The title compound was prepared as described in Example 13, substituting 5-(trifluoromethoxy)picolinic acid (commercially available from Oakwood Chemical) for the product of Example 12B and the product of Example 6C for the product of Example 4A. $^1$H NMR (400 MHz, DMSO-d$_6$) δ ppm 9.35 (s, 1H), 8.74 (s, 1H), 8.70 (d, J=2.6 Hz, 1H), 8.17-8.10 (m, 1H), 8.11-8.04 (m, 1H), 7.50 (t, J=8.8 Hz, 1H), 7.08 (dd, J=11.4, 2.9 Hz, 1H), 6.86 (dd, J=8.8, 2.5 Hz, 1H), 4.50 (s, 2H), 2.36 (br s, 6H); MS (ESI$^+$) m/z 474 (M+H)$^+$.

Example 19: N-{3-[2-(4-chloro-3-fluorophenoxy) acetamido]bicyclo[1.1.1]pentan-1-yl}-4,6-dimethoxypyrimidine-5-carboxamide (Compound 118)

The title compound was prepared as described in Example 13, substituting 4,6-dimethoxypyrimidine-5-carboxylic acid (commercially available from Pharmablock) for the product of Example 12B and the product of Example 6C for the product of Example 4A. $^1$H NMR (501 MHz, DMSO-d$_6$) δ ppm 8.83 (s, 1H), 8.74 (s, 1H), 8.50 (s, 1H), 7.50 (t, J=8.9 Hz, 1H), 7.08 (dd, J=11.4, 2.8 Hz, 1H), 6.86 (ddd, J=9.0, 2.9, 1.2 Hz, 1H), 4.49 (s, 2H), 3.91 (s, 6H), 2.28 (br s, 6H); MS (ESI$^+$) m/z 451 (M+H)$^+$.

Example 20: N-{3-[2-(4-chloro-3-fluorophenoxy) acetamido]bicyclo[1.1.1]pentan-1-yl}pyrazolo[1,5-a]pyridine-2-carboxamide (Compound 119)

The title compound was prepared as described in Example 13, substituting pyrazolo[1,5-a]pyridine-2-carboxylic acid (commercially available from Maybridge) for the product of Example 12B and the product of Example 6C for the product of Example 4A. $^1$H NMR (400 MHz, DMSO-d$_6$) δ ppm 8.98 (s, 1H), 8.74 (s, 1H), 8.65 (dq, J=7.1, 1.0 Hz, 1H), 7.77 (dt, J=9.0, 1.2 Hz, 1H), 7.50 (t, J=8.9 Hz, 1H), 7.29 (ddd, J=9.0, 6.7, 1.1 Hz, 1H), 7.09 (dd, J=11.4, 2.8 Hz, 1H), 7.03 (td, J=6.9, 1.4 Hz, 1H), 6.97 (d, J=0.9 Hz, 1H), 6.87 (ddd, J=9.0, 2.9, 1.2 Hz, 1H), 4.51 (s, 2H), 2.36 (br s, 6H); MS (ESI$^+$) m/z 429 (M+H)$^+$.

Example 21: N-{3-[2-(4-chloro-3-fluorophenoxy) acetamido]bicyclo[1.1.1]pentan-1-yl}-5-(trifluoromethyl)pyridine-2-carboxamide (Compound 120)

The title compound was prepared as described in Example 13, substituting 5-(trifluoromethyl)pyridine-2-carboxylic acid (commercially available from Ark Pharm) for the product of Example 12B and the product of Example 6C for the product of Example 4A. $^1$H NMR (400 MHz, DMSO-d$_6$) δ ppm 9.50 (s, 1H), 9.01 (d, J=2.1 Hz, 1H), 8.75 (s, 1H), 8.43 (dd, J=8.3, 2.3 Hz, 1H), 8.19 (d, J=8.2 Hz, 1H), 7.50 (t, J=8.9 Hz, 1H), 7.09 (dd, J=11.4, 2.8 Hz, 1H), 6.90-6.83 (m, 1H), 4.50 (s, 2H), 2.37 (br s, 6H); MS (ESI$^+$) m/z 458 (M+H)$^+$.

Example 22: N-{3-[2-(4-chloro-3-fluorophenoxy) acetamido]bicyclo[1.1.1]pentan-1-yl}-2-methylpyrimidine-5-carboxamide (Compound 121)

The title compound was prepared as described in Example 13, substituting 2-methylpyrimidine-5-carboxylic acid (commercially available from Combi-Blocks) for the product of Example 12B and the product of Example 6C for the product of Example 4A. $^1$H NMR (501 MHz, DMSO-d$_6$) δ ppm 9.32 (s, 1H), 9.03 (s, 2H), 8.76 (s, 1H), 7.50 (t, J=8.9 Hz, 1H), 7.09 (dd, J=11.4, 2.9 Hz, 1H), 6.87 (ddd, J=9.0, 2.9, 1.2 Hz, 1H), 4.50 (s, 2H), 2.67 (s, 3H), 2.36 (br s, 6H); MS (ESI$^+$) m/z 405 (M+H)$^+$.

Example 23: N-{3-[2-(4-chloro-3-fluorophenoxy) acetamido]bicyclo[1.1.1]pentan-1-yl}pyrazolo[1,5-a]pyrimidine-2-carboxamide (Compound 122)

The title compound was prepared as described in Example 13, substituting pyrazolo[1,5-a]pyrimidine-2-carboxylic acid (commercially available from Chem-Impex) for the product of Example 12B and the product of Example 6C for the product of Example 4A. $^1$H NMR (400 MHz, DMSO-d$_6$)

δ ppm 9.12 (s, 1H), 9.11-9.08 (m, 1H), 8.74 (s, 1H), 8.64 (dd, J=4.0, 1.7 Hz, 1H), 7.51 (t, J=8.9 Hz, 1H), 7.18 (dd, J=7.1, 4.0 Hz, 1H), 7.09 (dd, J=11.4, 2.8 Hz, 1H), 7.05 (s, 1H), 6.89-6.84 (m, 1H), 4.50 (s, 2H), 2.36 (br s, 6H); MS (ESI$^+$) m/z 430 (M+H)$^+$.

Example 24: N-{3-[2-(4-chloro-3-fluorophenoxy)acetamido]bicyclo[1.1.1]pentan-1-yl}-5-(pyrrolidin-1-yl)pyridine-2-carboxamide (Compound 123)

The title compound was prepared as described in Example 13, substituting 5-pyrrolidin-1-ylpyridine-2-carboxylic acid (commercially available from Ark Pharm) for the product of Example 12B and the product of Example 6C for the product of Example 4A. $^1$H NMR (400 MHz, DMSO-d$_6$) δ ppm 8.73 (s, 1H), 8.71 (s, 1H), 7.86 (d, J=2.8 Hz, 1H), 7.78 (d, J=8.7 Hz, 1H), 7.50 (t, J=8.9 Hz, 1H), 7.08 (dd, J=11.4, 2.8 Hz, 1H), 6.97 (dd, J=8.8, 2.8 Hz, 1H), 6.86 (ddd, J=9.1, 2.9, 1.2 Hz, 1H), 4.49 (s, 2H), 3.35-3.32 (m, 4H), 2.32 (br s, 6H), 2.03-1.93 (m, 4H); MS (ESI$^+$) m/z 459 (M+H)$^+$.

Example 25: N-{3-[2-(4-chloro-3-fluorophenoxy)acetamido]bicyclo[1.1.1]pentan-1-yl}-5-methoxy-pyrazine-2-carboxamide (Compound 124)

The title compound was prepared as described in Example 13, substituting 5-methoxypyrazine-2-carboxylic acid (commercially available from Ark Pharm) for the product of Example 12B and the product of Example 6C for the product of Example 4A. $^1$H NMR (501 MHz, DMSO-d$_6$) δ ppm 9.17 (s, 1H), 8.74 (d, J=1.4 Hz, 1H), 8.73 (s, 1H), 8.31 (d, J=1.4 Hz, 1H), 7.50 (t, J=8.9 Hz, 1H), 7.08 (dd, J=11.4, 2.8 Hz, 1H), 6.86 (ddd, J=9.0, 2.9, 1.2 Hz, 1H), 4.49 (s, 2H), 3.99 (s, 3H), 2.34 (br s, 6H); MS (ESI$^+$) m/z 421 (M+H)$^+$.

Example 26: N-{3-[2-(4-chloro-3-fluorophenoxy)acetamido]bicyclo[1.1.1]pentan-1-yl}-4,5,6,7-tetrahydropyrazolo[1,5-a]pyrimidine-2-carboxamide (Compound 125)

The product of Example 23 (54.5 mg, 0.127 mmol) and sodium cyanoborohydride (42 mg, 0.668 mmol) were combined with methanol (2.0 mL) and stirred at ambient temperature. Trifluoroacetic acid (50 μL, 0.649 mmol) was added in one portion. The resulting solution was stirred for 30 minutes and then concentrated in vacuo. The resulting residue was purified by preparative HPLC [Waters XBridge™ C18 5 μm OBD™ column, 50×100 mm, flow rate 90 mL/minute, 5-100% gradient of acetonitrile in buffer (0.025 M aqueous ammonium bicarbonate, adjusted to pH 10 with ammonium hydroxide)] to give the title compound (20 mg, 0.046 mmol, 36.4% yield). $^1$H NMR (400 MHz, DMSO-d$_6$) δ ppm 8.68 (s, 1H), 8.29 (s, 1H), 7.50 (t, J=8.9 Hz, 1H), 7.07 (dd, J=11.4, 2.8 Hz, 1H), 6.85 (ddd, J=9.0, 2.8, 1.2 Hz, 1H), 6.18-6.14 (m, 1H), 5.51 (s, 1H), 4.48 (s, 2H), 3.99 (t, J=6.1 Hz, 2H), 3.19-3.11 (m, 2H), 2.26 (br s, 6H), 2.03-1.95 (m, 2H); MS (ESI$^+$) m/z 434 (M+H)$^+$.

Example 27: N-{3-[2-(4-chloro-3-fluorophenoxy)acetamido]bicyclo[1.1.1]pentan-1-yl}-2-(4,4-difluorocyclohexyl)-1,3-oxazole-5-carboxamide (Compound 126)

Example 27A: Ethyl 2-(4,4-difluorocyclohex-1-en-1-yl)oxazole-5-carboxylate

A mixture of ethyl 2-bromooxazole-5-carboxylate (Ark Pharm, 0.26 g, 1.182 mmol), 2-(4,4-difluorocyclohex-1-en-1-yl)-4,4,5,5-tetramethyl-1,3,2-dioxaborolane (Emolecules, 0.288 g, 1.182 mmol), (1S,3R,5R,7S)-1,3,5,7-tetramethyl-8-phenyl-2,4,6-trioxa-8-phosphaadamantane (Aldrich, 0.035 g, 0.118 mmol), bis(dibenzylideneacetone)palladium (Strem, 0.034 g, 0.059 mmol) and potassium carbonate (0.408 g, 2.95 mmol) in a pressure tube were degassed three times with a nitrogen back flush each time. Then tetrahydrofuran (5.0 mL) and water (1.0 mL) were added, and the mixture was again degassed three times with a nitrogen back flush each time. The reaction mixture was sealed and stirred at 65° C. for 12 hours. The mixture was allowed to cool to ambient temperature, then anhydrous sodium sulfate was added, and the mixture was filtered through a pack of diatomaceous earth. The filtrate was concentrated under reduced pressure. The residue was purified via flash chromatography (SiO$_2$, 1-40% ethyl acetate in heptane) to give the title compound (0.255 g, 0.991 mmol, 84% yield). MS (ESI$^+$) m/z 258 (M+H)$^+$.

Example 27B: 2-(4,4-difluorocyclohexyl)oxazole-5-carboxylic acid

To a microwave vial (2 mL) was added the product of Example 27A (36 mg, 0.140 mmol), palladium on carbon (Aldrich, 10 weight % loading (dry basis) on wet support, (14.9 mg, 7.00 μmol)), ammonium formate (70.6 mg, 1.120 mmol) and ethanol (2 mL). The vial was sealed and heated in a Biotage® Initiator+microwave reactor and irradiated at 100° C. for 40 minutes. The vial was opened and more ammonium formate (40 mg, 0.63 mmol) and palladium on carbon (Aldrich, 10 weight % loading (dry), 11 mg, 10.34 μmol) were added, and the vial was sealed and irradiated again in the microwave reactor at 130° C. for 40 minutes. The resulting reaction mixture was filtered through a pack of diatomaceous earth, and the filtrate was washed with more methanol (5 mL). NaOH solution (2.5 M, 5 mL) was added to the filtrate, and the resulting solution was stirred at ambient temperature for 30 minutes and then partitioned between dichloromethane (2×30 mL) and aqueous citric acid (10%, 50 mL). The resulting organic layers were combined and dried over anhydrous sodium sulfate and concentrated in vacuo to give the title compound (27 mg, 0.117 mmol, 83% yield). MS (ESI$^-$) m/z 230 (M–H)$^-$.

Example 27C: N-{3-[2-(4-chloro-3-fluorophenoxy)acetamido]bicyclo[1.1.1]pentan-1-yl}-2-(4,4-difluorocyclohexyl)-1,3-oxazole-5-carboxamide The title compound was prepared as described in Example 13, substituting the product of Example 27B for the product of Example 12B and the product of Example 6C for the product of Example 4A. $^1$H NMR (400 MHz, DMSO-d$_6$) δ ppm 9.06 (s, 1H), 8.72 (s, 1H), 7.61 (s, 1H), 7.48 (t, J=8.9 Hz, 1H), 7.06 (dd, J=11.4, 2.8 Hz, 1H), 6.87-6.81 (m, 1H), 4.47 (s, 2H), 3.11-3.01 (m, 1H), 2.30 (br s, 6H), 2.13-1.85 (m, 6H), 1.85-1.70 (m, 2H); MS (ESI$^+$) m/z 498 (M+H)$^+$.

Example 28: 2-(4-chloro-3-fluorophenoxy)-N-(3-{[6-(trifluoromethyl)pyridazin-3-yl]amino}bicyclo[1.1.1]pentan-1-yl)acetamide (Compound 127)

To a mixture of Example 3B (0.1 g, 0.292 mmol) and 3-chloro-6-(trifluoromethyl)pyridazine (0.061 g, 0.336 mmol) in tetrahydrofuran (2.0 mL) at 0° C., potassium 2-methylpropan-2-olate (0.729 mL, 0.729 mmol, tetrahydrofuran) was added dropwise. The reaction mixture was stirred at ambient temperature for 16 hours and then concentrated. The residue was purified by HPLC (10~85% acetonitrile in 0.1% trifluoroacetic acid/water at 25 mL/minute on a Phenomenex® Luna® C18 5 μm 100 Å AXIA™ column (250 mm×21.2 mm)) to give 49 mg of the title compound as a yellow solid. $^1$H NMR (501 MHz, DMSO-$d_6$) δ ppm 8.77 (s, 1H), 8.31 (s, 1H), 7.67 (d, J=9.4 Hz, 1H), 7.48 (t, J=8.9 Hz, 1H), 7.07 (dd, J=11.3, 2.9 Hz, 1H), 6.95 (d, J=9.4 Hz, 1H), 6.85 (ddd, J=9.0, 2.9, 1.2 Hz, 1H), 4.49 (s, 2H), 2.38 (s, 6H); MS (ESI+) m/z 431.0 (M+H)$^+$.

Example 29: 4-[(3-{2-[(2,2-difluoro-2H-1,3-benzodioxol-5-yl)oxy]acetamido}bicyclo[1.1.1]-pentan-1-yl)carbamoyl]benzoic acid (Compound 128)

Example 29A: 2,2-difluorobenzo[d][1,3]dioxol-5-ol

To a cold solution of 5-bromo-2,2-difluorobenzo[d][1,3]dioxole (5.75 mL, 42.2 mmol) in tetrahydrofuran (80 mL) was added a 2.0 M solution of isopropylmagnesium chloride in tetrahydrofuran (28.1 mL, 56.1 mmol) within 5-10 minutes while maintaining the temperature in the range of 10-20° C. The reaction mixture was stirred at the same temperature for another 15 minutes and then allowed to attain room temperature with continued overnight stirring. The reaction mixture was cooled with an ice bath, triisopropyl borate (12.74 mL, 54.9 mmol) was added dropwise over 2 minutes, and stirring at room temperature was continued for 30 minutes. The reaction mixture was cooled to 10° C. and 10% $H_2SO_4$ solution (50 mL) was added slowly which resulted in a slight exotherm to 20° C. After stirring for 15 minutes, the mixture was partitioned between water and ethyl acetate, and the combined organic extracts were washed with saturated $NaHCO_3$ solution. The organic layer was separated, dried over magnesium sulfate, filtered, and concentrated. The residue was dissolved in 100 mL of tert-butyl methyl ether and cooled to 0° C. 30% Hydrogen peroxide solution in water (5.39 mL, 52.7 mmol) was added slowly, followed by water (60 mL), and the mixture was stirred overnight while warming up to ambient temperature. The reaction mixture was diluted with ethyl acetate and washed twice with sodium thiosulfate solution and brine. The organic layer was dried with magnesium sulfate and filtered. The filtrate was concentrated, and the residue was purified on silica gel (0~50% ethyl acetate in heptane) to give 6.43 g of the title compound as an amber oil. $^1$H NMR (400 MHz, DMSO-$d_6$) δ ppm 9.75 (s, 1H), 7.12 (d, J=8.7 Hz, 1H), 6.75 (d, J=2.4 Hz, 1H), 6.52 (dd, J=8.7, 2.5 Hz, 1H); MS (ESI-) m/z 173.1 (M-H)$^-$.

Example 29B: 2-((2,2-difluorobenzo[d][1,3]dioxol-5-yl)oxy)acetic acid

To a solution of Example 29A (3.0 g, 17.23 mmol) in N,N-dimethylformamide (30 mL) at ambient temperature was added potassium carbonate (4.76 g, 34.5 mmol) and tert-butyl bromoacetate (2.91 mL, 19.82 mmol). This mixture was warmed to 65° C. and was allowed to stir for 1.5 hours. The mixture was allowed to cool to ambient temperature and was then partitioned between ethyl acetate (50 mL) and $H_2O$ (50 mL). The layers were separated, and the aqueous layer was extracted with ethyl acetate (3×15 mL). The combined organic fractions were dried over anhydrous $Na_2SO_4$, filtered, and concentrated under reduced pressure to give 5.5 g of tert-butyl 2-((2,2-difluorobenzo[d][1,3]dioxol-5-yl)oxy)acetate, which was used without further purification. To a mixture of tert-butyl 2-((2,2-difluorobenzo[d][1,3]dioxol-5-yl)oxy)acetate (5.0 g, 17.35 mmol) in methanol (60 mL) and water (20.00 mL) was added NaOH (17.35 mL, 87 mmol, 5 M aqueous solution). This mixture was allowed to stir at ambient temperature for 2 hours, and then it was concentrated under reduced pressure. The residue was dissolved in water, and the pH was adjusted to ~1 with 1 N HCl. The resulting solid was collected by filtration to give the title compound (3.28 g, 14.13 mmol, 81% yield) as a white solid. $^1$H NMR (400 MHz, DMSO-$d_6$) δ ppm 13.10 (s, 1H), 7.30 (d, J=8.9 Hz, 1H), 7.13 (d, J=2.6 Hz, 1H), 6.73 (dd, J=8.9, 2.6 Hz, 1H), 4.69 (s, 2H).

Example 29C: N-(3-aminobicyclo[1.1.1]pentan-1-yl)-2-((2,2-difluorobenzo[d][1,3]dioxol-5-yl)oxy)acetamide hydrochloride The title compound was prepared using the procedures described in Examples 2A-2B, except substituting Example 29B for 2-(3,4-dichlorophenoxy)acetic acid. $^1$H NMR (400 MHz, DMSO-$d_6$) δ ppm (s, 3H), 8.88 (s, 1H), 7.29 (d, J=8.9 Hz, 1H), 7.11 (d, J=2.5 Hz, 1H), 6.73 (dd, J=8.9, 2.6 Hz, 1H), 4.44 (s, 2H), 2.21 (s, 6H).

Example 29D: 4-[(3-{2-[(2,2-difluoro-2H-1,3-benzodioxol-5-yl)oxy]acetamido}bicyclo[1.1.1]-pentan-1-yl)carbamoyl]benzoic acid The title compound was prepared as described in Example 6D, except substituting Example 29C for Example 6C and terephthalic acid for Example 6B. $^1$H NMR (400 MHz, DMSO-$d_6$) δ ppm 13.12 (s, 1H), 9.17 (s, 1H), 8.71 (s, 1H), 7.98 (d, J=8.5 Hz, 2H), 7.91 (d, J=8.5 Hz, 2H), 7.31 (d, J=8.8 Hz, 1H), 7.13 (d, J=2.5 Hz, 1H), 6.76 (dd, J=8.9, 2.6 Hz, 1H), 4.44 (s, 2H), 2.33 (s, 6H). MS (ESI+) m/z 460.9 (M+H)$^+$.

Example 30: N-{3-[2-(4-chloro-3-fluorophenoxy)acetamido]bicyclo[1.1.1]pentan-1-yl}pyridine-2-carboxamide (Compound 129)

The title compound was prepared using the methodologies described above. $^1$H NMR (400 MHz, DMSO-$d_6$) δ ppm 9.25 (s, 1H), 8.73 (s, 1H), 8.63 (dt, J=4.7, 1.3 Hz, 1H), 8.03-7.97 (m, 2H), 7.64-7.56 (m, 1H), 7.50 (t, J=8.9 Hz, 1H), 7.08 (dd, J=11.4, 2.8 Hz, 1H), 6.86 (ddd, J=8.9, 2.8, 1.2 Hz, 1H), 4.49 (s, 2H), 2.35 (br s, 6H); MS (ESI$^+$) m/z 390 (M+H)$^+$.

Example 31: N-{3-[2-(4-chloro-3-fluorophenoxy)acetamido]bicyclo[1.1.1]pentan-1-yl}pyridine-3-carboxamide (Compound 130)

The title compound was prepared using the methodologies described above. $^1$H NMR (501 MHz, DMSO-$d_6$) δ ppm 9.25 (s, 1H), 8.74 (s, 1H), 8.63 (dt, J=4.7, 1.4 Hz, 1H), 8.02-7.98 (m, 2H), 7.63-7.58 (m, 1H), 7.50 (t, J=8.9 Hz, 1H), 7.08 (dd, J=11.3, 2.9 Hz, 1H), 6.86 (ddd, J=9.0, 2.9, 1.2 Hz, 1H), 4.50 (s, 2H), 2.36 (br s, 6H); MS (ESI$^+$) m/z 390 (M+H)$^+$.

Example 32: N-{3-[2-(3,4-dichlorophenoxy)acetamido]bicyclo[1.1.1]pentan-1-yl}-5-methylpyrazine-2-carboxamide (Compound 131)

The title compound was prepared using the methodologies described above. $^1$H NMR (400 MHz, DMSO-$d_6$) δ ppm 9.37 (s, 1H), 9.02-9.00 (m, 1H), 8.73 (s, 1H), 8.61-8.58 (m, 1H), 7.55 (d, J=8.9 Hz, 1H), 7.27 (d, J=2.8 Hz, 1H), 7.00

(dd, J=8.9, 2.9 Hz, 1H), 4.51 (s, 2H), 2.59 (s, 3H), 2.35 (br s, 6H); MS (ESI⁺) m/z 421 (M+H)⁺.

Example 33: N-{3-[2-(4-chloro-3-fluorophenoxy)acetamido]bicyclo[1.1.1]pentan-1-yl}-6-(trifluoromethoxy)pyridine-3-carboxamide (Compound 132)

The title compound was prepared using the methodologies described above. ¹H NMR (501 MHz, DMSO-$d_6$) δ ppm 9.28 (s, 1H), 8.78-8.75 (m, 2H), 8.38 (dd, J=8.6, 2.5 Hz, 1H), 7.50 (t, J=8.9 Hz, 1H), 7.38 (dd, J=8.5, 0.7 Hz, 1H), 7.09 (dd, J=11.4, 2.9 Hz, 1H), 6.87 (ddd, J=9.1, 2.9, 1.2 Hz, 1H), 4.50 (s, 2H), 2.36 (br s, 6H); MS (ESI⁺) m/z 474 (M+H)⁺.

Example 34: N-{3-[2-(4-chloro-3-fluorophenoxy)acetamido]bicyclo[1.1.1]pentan-1-yl}-2-(trifluoromethyl)pyrimidine-5-carboxamide (Compound 133)

The title compound was prepared using the methodologies described above. ¹H NMR (501 MHz, DMSO-$d_6$) δ ppm 9.60 (s, 1H), 9.36 (s, 2H), 8.79 (s, 1H), 7.50 (t, J=8.9 Hz, 1H), 7.09 (dd, J=11.4, 2.8 Hz, 1H), 6.87 (ddd, J=9.0, 2.9, 1.2 Hz, 1H), 4.50 (s, 2H), 2.39 (br s, 6H); MS (ESI−) m/z 457 [M−H]⁻.

Example 35: N-{3-[2-(4-chloro-3-fluorophenoxy)acetamido]bicyclo[1.1.1]pentan-1-yl}-5-(difluoromethyl)pyrazine-2-carboxamide (Compound 134)

The title compound was prepared using the methodologies described above. ¹H NMR (500 MHz, DMSO-$d_6$) δ ppm 9.62 (s, 1H), 9.25 (d, J=1.4 Hz, 1H), 8.99 (d, J=1.2 Hz, 1H), 8.75 (s, 1H), 7.50 (t, J=8.9 Hz, 1H), 7.21 (t, J=54.0 Hz, 1H), 7.08 (dd, J=11.4, 2.8 Hz, 1H), 6.86 (ddd, J=9.0, 2.8, 1.1 Hz, 1H), 4.50 (s, 2H), 2.37 (br s, 6H); MS (ESI⁺) m/z 441 (M+H)⁺.

Example 36: 5-butyl-N-{3-[2-(4-chloro-3-fluorophenoxy)acetamido]bicyclo[1.1.1]pentan-1-yl}pyridine-2-carboxamide (Compound 135)

The title compound was prepared using the methodologies described above. ¹H NMR (500 MHz, DMSO-$d_6$) δ ppm 9.16 (s, 1H), 8.73 (s, 1H), 8.47-8.45 (m, 1H), 7.93-7.90 (m, 1H), 7.83-7.79 (m, 1H), 7.50 (t, J=8.9 Hz, 1H), 7.08 (dd, J=11.4, 2.9 Hz, 1H), 6.86 (dd, J=8.9, 2.8, 1.2 Hz, 1H), 4.49 (s, 2H), 2.67 (t, J=7.7 Hz, 2H), 2.35 (br s, 6H), 1.63-1.52 (m, 2H), 1.31 (h, J=7.3 Hz, 2H), 0.90 (t, J=7.3 Hz, 3H); MS (ESI⁺) m/z 446 (M+H)⁺.

Example 37: N-{3-[2-(4-chlorophenoxy)acetamido]bicyclo[1.1.1]pentan-1-yl}-5-methylpyrazine-2-carboxamide (Compound 136)

The title compound was prepared using the methodologies described above. ¹H NMR (400 MHz, DMSO-$d_6$) δ ppm 9.36 (s, 1H), 9.01 (d, J=1.4 Hz, 1H), 8.72 (s, 1H), 8.61-8.58 (m, 1H), 7.38-7.31 (m, 2H), 7.01-6.95 (m, 2H), 4.45 (s, 2H), 2.59 (s, 3H), 2.35 (br s, 6H); MS (ESI⁺) m/z 387 (M+H)⁺.

Example 38: N-{3-[2-(4-chloro-3-fluorophenoxy)acetamido]bicyclo[1.1.1]pentan-1-yl}-6-methylpyridazine-3-carboxamide (Compound 137)

The title compound was prepared using the methodologies described above. ¹H NMR (400 MHz, DMSO-$d_6$) δ ppm 9.70 (s, 1H), 8.74 (s, 1H), 8.05 (d, J=8.6 Hz, 1H), 7.76 (d, J=8.6 Hz, 1H), 7.50 (t, J=8.9 Hz, 1H), 7.09 (dd, J=11.4, 2.8 Hz, 1H), 6.87 (ddd, J=9.0, 2.9, 1.2 Hz, 1H), 4.50 (s, 2H), 2.71 (s, 3H), 2.37 (br s, 6H); MS (ESI⁺) m/z 405 (M+H)⁺.

Example 39: N-{3-[2-(4-chloro-3-fluorophenoxy)acetamido]bicyclo[1.1.1]pentan-1-yl}-2-(3,6-dihydro-2H-pyran-4-yl)-1,3-oxazole-5-carboxamide (Compound 138)

Example 39A: ethyl 2-(3,6-dihydro-2H-pyran-4-yl)oxazole-5-carboxylate

Dimethoxyethane (10 mL) and water (1 mL) were added to a mixture of ethyl 2-bromooxazole-5-carboxylate (Ark Pharm, 334 mg, 1.52 mmol), 3,6-dihydro-2H-pyran-4-boronic acid pinacol ester (Combi-Blocks, 319 mg, 1.52 mmol), [1,1'-bis(diphenylphosphino)ferrocene]dichloropalladium(II) (89 mg, 0.12 mmol) and potassium carbonate (525 mg, 3.80 mmol) in a microwave tube. The tube was sealed and degassed three times with a nitrogen back flush each time. The tube was heated in a Biotage® Initiator+ microwave reactor and irradiated at 115° C. for 35 minutes. The seal was opened, and the reaction mixture was combined with silica gel (15 g) and concentrated under reduced pressure to a free flowing powder. The powder was directly purified via flash chromatography (SiO₂, 15-100% ethyl acetate in heptane) to give the title compound (0.24 g, 1.08 mmol, 71% yield). MS (ESI⁺) m/z 224 (M+H)⁺.

Example 39B: 2-(3,6-dihydro-2H-pyran-4-yl)oxazole-5-carboxylic acid

The product of Example 39A (50 mg, 0.22 mmol) was dissolved in ethanol (2 mL). Aqueous sodium hydroxide (2.5 M, 1 mL) was added, and the resulting mixture was stirred at ambient temperature for 5 minutes. The mixture was partitioned between dichloromethane (4×30 mL), aqueous citric acid (10 weight %, 30 mL) and aqueous NaH₂PO₄ (0.5 M, 30 mL). The organic layers were combined, dried over anhydrous sodium sulfate, and concentrated in vacuo to give the title compound (31 mg, 0.16 mmol, 71% yield). MS (ESI⁺) m/z 196 (M+H)⁺.

Example 39C: N-{3-[2-(4-chloro-3-fluorophenoxy)acetamido]bicyclo[1.1.1]pentan-1-yl}-2-(3,6-dihydro-2H-pyran-4-yl)-1,3-oxazole-5-carboxamide The reaction and purification conditions described in Example 13 substituting the product of Example 39B for the product of Example 12B and the product of Example 6C for the product of Example 4A gave the title compound. ¹H NMR (400 MHz, DMSO-$d_6$) δ ppm 8.76-8.68 (m, 2H), 8.52 (s, 1H), 7.50 (t, J=8.9 Hz, 1H), 7.08 (dd, J=11.4, 2.8 Hz, 1H), 6.86 (ddd, J=9.1, 2.9, 1.2 Hz, 1H), 6.81-6.76 (m, 1H), 4.49 (s, 2H), 4.30-4.24 (m, 2H), 3.80 (t, J=5.4 Hz, 2H), 2.50 (d, J=4.0 Hz, 2H), 2.32 (br s, 6H); MS (ESI⁺) m/z 462 (M+H)⁺.

Example 40: N-{3-[2-(4-chloro-3-fluorophenoxy)acetamido]bicyclo[1.1.1]pentan-1-yl}-2-(oxan-4-yl)-1,3-oxazole-5-carboxamide (Compound 139)

Example 40A: 2-(tetrahydro-2H-pyran-4-yl)oxazole-5-carboxylic acid

The reaction and purification conditions described in Example 27B substituting the product of Example 39A for the product of Example 27A gave the title compound. MS (ESI$^+$) m/z 198 (M+H)$^+$.

Example 40B: N-{3-[2-(4-chloro-3-fluorophenoxy)acetamido]bicyclo[1.1.1]pentan-1-yl}-2-(oxan-4-yl)-1,3-oxazole-5-carboxamide The reaction and purification conditions described in Example 13 substituting the product of Example 40A for the product of Example 12B and the product of Example 6C for the product of Example 4A gave the title compound. $^1$H NMR (400 MHz, DMSO-d$_6$) δ ppm 8.71 (s, 1H), 8.66 (s, 1H), 8.47 (s, 1H), 7.50 (t, J=8.9 Hz, 1H), 7.08 (dd, J=11.4, 2.8 Hz, 1H), 6.86 (ddd, J=9.0, 2.9, 1.2 Hz, 1H), 4.49 (s, 2H), 3.88 (dt, J=11.6, 3.6 Hz, 2H), 3.45 (td, J=11.4, 2.3 Hz, 2H), 3.13 (tt, J=11.0, 4.1 Hz, 1H), 2.31 (br s, 6H), 1.95-1.87 (m, 2H), 1.80-1.67 (m, 2H); MS (ESI$^+$) m/z 464 (M+H)$^+$.

Example 41: N-{3-[2-(4-chloro-3-fluorophenoxy)acetamido]bicyclo[1.1.1]pentan-1-yl}-6-methylpyridine-3-carboxamide (Compound 140)

The title compound was prepared using the methodologies described above. $^1$H NMR (400 MHz, DMSO-d$_6$) δ ppm 9.13 (s, 1H), 8.86 (d, J=2.3 Hz, 1H), 8.75 (s, 1H), 8.06 (dd, J=8.1, 2.4 Hz, 1H), 7.50 (t, J=8.8 Hz, 1H), 7.34 (d, J=8.1 Hz, 1H), 7.09 (dd, J=11.4, 2.9 Hz, 1H), 6.87 (ddd, J=8.9, 2.9, 1.2 Hz, 1H), 4.49 (s, 2H), 2.50 (s, 3H), 2.34 (br s, 6H); MS (ESI$^+$) m/z 404 (M+H)$^+$.

Example 42: N-{3-[2-(4-chloro-3-fluorophenoxy)acetamido]bicyclo[1.1.1]pentan-1-yl}-5-methoxypyridine-2-carboxamide (Compound 141)

The title compound was prepared using the methodologies described above. $^1$H NMR (501 MHz, DMSO-d$_6$) δ ppm 9.04 (s, 1H), 8.73 (s, 1H), 8.27 (dd, J=2.9, 0.6 Hz, 1H), 7.97 (dd, J=8.7, 0.6 Hz, 1H), 7.54 (dd, J=8.8, 2.9 Hz, 1H), 7.50 (t, J=8.9 Hz, 1H), 7.08 (dd, J=11.4, 2.9 Hz, 1H), 6.86 (ddd, J=9.0, 2.9, 1.2 Hz, 1H), 4.49 (s, 2H), 3.90 (s, 3H), 2.34 (br s, 6H); MS (ESI$^+$) m/z 420 (M+H)$^+$.

Example 43: N-{4-[2-(3,4-dichlorophenoxy)acetamido]bicyclo[2.1.1]hexan-1-yl}-5-methylpyrazine-2-carboxamide (Compound 142)

The title compound was prepared using the methodologies described above. $^1$H NMR (400 MHz, DMSO-d$_6$) δ ppm 9.08 (s, 1H), 9.02 (d, J=1.5 Hz, 1H), 8.60-8.58 (m, 1H), 8.52 (s, 1H), 7.55 (d, J=9.0 Hz, 1H), 7.27 (d, J=2.9 Hz, 1H), 6.99 (dd, J=8.9, 2.9 Hz, 1H), 4.50 (s, 2H), 2.59 (s, 3H), 2.17-2.11 (m, 2H), 1.97-1.81 (m, 6H); MS (ESI$^+$) m/z 435 (M+H)$^+$.

Example 44: N-{3-[2-(4-chloro-3-fluorophenoxy)acetamido]bicyclo[1.1.1]pentan-1-yl}-5-cyclopropylpyridine-2-carboxamide (Compound 143)

The title compound was prepared using the methodologies described above. $^1$H NMR (400 MHz, DMSO-d$_6$) δ ppm 9.13 (s, 1H), 8.72 (s, 1H), 8.44 (dd, J=2.3, 0.8 Hz, 1H), 7.89-7.83 (m, 1H), 7.57 (dd, J=8.1, 2.3 Hz, 1H), 7.50 (t, J=8.9 Hz, 1H), 7.08 (dd, J=11.4, 2.8 Hz, 1H), 6.86 (ddd, J=8.9, 2.8, 1.2 Hz, 1H), 4.49 (s, 2H), 2.34 (br s, 6H), 2.06 (tt, J=8.4, 5.0 Hz, 1H), 1.13-1.03 (m, 2H), 0.84-0.78 (m, 2H); MS (ESI$^+$) m/z 430 (M+H)$^+$.

Example 45: N-{3-[2-(3,4-dichlorophenoxy)acetamido]bicyclo[1.1.1]pentan-1-yl}-5-(trifluoromethoxy)pyridine-2-carboxamide (Compound 144)

The title compound was prepared using the methodologies described above. $^1$H NMR (400 MHz, DMSO-d$_6$) δ ppm 9.35 (s, 1H), 8.74 (s, 1H), 8.71-8.68 (m, 1H), 8.16-8.12 (m, 1H), 8.10-8.05 (m, 1H), 7.55 (d, J=8.9 Hz, 1H), 7.27 (d, J=2.9 Hz, 1H), 7.00 (dd, J=8.9, 2.9 Hz, 1H), 4.51 (s, 2H), 2.35 (br s, 6H); MS (ESI$^+$) m/z 490 (M+H)$^+$.

Example 46: N-{3-[2-(4-chloro-3-fluorophenoxy)acetamido]bicyclo[1.1.1]pentan-1-yl}-5-ethylpyridine-2-carboxamide (Compound 145)

The title compound was prepared using the methodologies described above. $^1$H NMR (400 MHz, DMSO-d$_6$) δ ppm 9.17 (s, 1H), 8.73 (s, 1H), 8.48 (dd, J=2.3, 0.8 Hz, 1H), 7.95-7.90 (m, 1H), 7.86-7.81 (m, 1H), 7.50 (t, J=8.9 Hz, 1H), 7.08 (dd, J=11.4, 2.8 Hz, 1H), 6.86 (ddd, J=8.9, 2.8, 1.2 Hz, 1H), 4.50 (s, 2H), 2.71 (q, J=7.6 Hz, 2H), 2.35 (br s, 6H), 1.21 (t, J=7.6 Hz, 3H); MS (ESI$^+$) m/z 418 (M+H)$^+$.

Example 47: N-{3-[2-(4-chloro-3-fluorophenoxy)acetamido]bicyclo[1.1.1]pentan-1-yl}-5-methylpyridine-2-carboxamide (Compound 146)

The title compound was prepared using the methodologies described above. $^1$H NMR (400 MHz, DMSO-d$_6$) δ ppm 9.17 (s, 1H), 8.73 (s, 1H), 8.47-8.45 (m, 1H), 7.92-7.87 (m, 1H), 7.82-7.77 (m, 1H), 7.50 (t, J=8.9 Hz, 1H), 7.08 (dd, J=11.4, 2.8 Hz, 1H), 6.86 (ddd, J=9.0, 2.9, 1.2 Hz, 1H), 4.49 (s, 2H), 2.38 (s, 3H), 2.35 (br s, 6H); MS (ESI$^+$) m/z 404 (M+H)$^+$.

Example 48: N-{3-[2-(3,4-dichlorophenoxy)acetamido]bicyclo[1.1.1]pentan-1-yl}-6-(trifluoromethoxy)pyridine-3-carboxamide (Compound 147)

The title compound was prepared using the methodologies described above. $^1$H NMR (501 MHz, DMSO-d$_6$) δ ppm 9.29 (s, 1H), 8.77 (s, 1H), 8.76 (dd, J=2.5, 0.7 Hz, 1H), 8.38 (dd, J=8.6, 2.5 Hz, 1H), 7.56 (d, J=8.9 Hz, 1H), 7.39 (dd, J=8.5, 0.7 Hz, 1H), 7.28 (d, J=2.9 Hz, 1H), 7.00 (dd, J=9.0, 2.9 Hz, 1H), 4.51 (s, 2H), 2.36 (br s, 6H); MS (ESI$^+$) m/z 490 (M+H)$^+$.

Example 49: 2-(1-acetylpiperidin-4-yl)-N-{3-[2-(4-chloro-3-fluorophenoxy)acetamido]bicyclo[1.1.1]pentan-1-yl}-1,3-oxazole-5-carboxamide (Compound 148)

Example 49A: ethyl 2-(1-acetyl-1,2,3,6-tetrahydropyridin-4-yl)oxazole-5-carboxylate The reaction and purification conditions described in Example 39A substituting 1-(4-(4,4,5,5-tetramethyl-1,3,2-dioxaborolan-2-yl)-5,6-dihydropyridin-1(2H)-yl)ethanone (Ark Pharm) for 3,6-dihydro-2H-pyran-4-boronic acid pinacol ester gave the title compound. MS (ESI+) m/z 256 (M+H)+.

Example 49B: ethyl 2-(1-acetylpiperidin-4-yl)oxazole-5-carboxylate

To a microwave vial (5 mL) was added the product of Example 49A (36 mg, 0.140 mmol), palladium on carbon (Aldrich, 10 weight % loading, 9 mg, 8.5 μmol), ammonium formate (119 mg, 1.88 mmol) and ethanol (4.5 mL). The vial was sealed and heated in a Biotage® Initiator+microwave reactor and irradiated at 120° C. for 20 minutes. The resulting reaction mixture was filtered through a pack of diatomaceous earth. The filter cake was washed with more ethanol (5 mL), and the filtrate was concentrated in vacuo. The residue was purified by preparative HPLC [YMC Tri-Art™ C18 Hybrid 5 μm column, 50×100 mm, flow rate 90 mL/minute, 5-100% gradient of acetonitrile in buffer (0.025 M aqueous ammonium bicarbonate, adjusted to pH 10 with ammonium hydroxide)] to give the title compound (79 mg, 0.314 mmol, 94% yield). MS (ESI+) m/z 267 (M+H)+.

Example 49C: 2-(1-acetylpiperidin-4-yl)oxazole-5-carboxylic acid, 2 sodium hydroxide The product of Example 49B (78 mg, 0.29 mmol) was dissolved in ethanol (1 mL), aqueous sodium hydroxide (2.5 M, 0.23 mL) was added, and the resulting mixture was stirred at ambient temperature for 20 minutes. The reaction mixture was concentrated in vacuo to give the title compound (94 mg, 0.29 mmol, 100% yield). MS (ESI+) m/z 249 (M+H)+.

Example 49D: 2-(1-acetylpiperidin-4-yl)-N-[3-[2-(4-chloro-3-fluorophenoxy)acetamido]bicyclo[1.1.1]pentan-1-yl]-1,3-oxazole-5-carboxamide The reaction and purification conditions described in Example 13 substituting the product of Example 49C for the product of Example 12B and the product of Example 6C for the product of Example 4A gave the title compound. $^1$H NMR (400 MHz, DMSO-$d_6$) δ ppm 9.05 (s, 1H), 8.72 (s, 1H), 7.61 (s, 1H), 7.48 (t, J=8.9 Hz, 1H), 7.06 (dd, J=11.4, 2.8 Hz, 1H), 6.84 (ddd, J=9.0, 2.9, 1.2 Hz, 1H), 4.47 (s, 2H), 4.29-4.19 (m, 1H), 3.83-3.74 (m, 1H), 3.30-3.26 (m, 1H), 3.22-3.07 (m, 2H), 2.83-2.74 (m, 1H), 2.30 (br s, 6H), 2.03-1.90 (m, 4H), 1.72-1.60 (m, 1H), 1.54 (qd, J=11.4, 4.1 Hz, 1H); MS (ESI+) m/z 505 (M+H)+.

Example 50: 2-(1-acetylpiperidin-4-yl)-N-{3-[2-(3,4-dichlorophenoxy)acetamido]bicyclo[1.1.1]pentan-1-yl}-1,3-oxazole-5-carboxamide (Compound 149)

The reaction and purification conditions described in Example 13 substituting the product of Example 49C for the product of Example 12B and the product of Example 2B for the product of Example 4A gave the title compound. $^1$H NMR (400 MHz, DMSO-$d_6$) δ ppm 9.05 (s, 1H), 8.72 (s, 1H), 7.61 (s, 1H), 7.53 (d, J=9.0 Hz, 1H), 7.25 (d, J=2.9 Hz, 1H), 6.97 (dd, J=8.9, 3.0 Hz, 1H), 4.48 (s, 2H), 4.47-4.42 (m, 1H), 4.28-4.18 (m, 1H), 3.84-3.75 (m, 1H), 3.22-3.07 (m, 2H), 2.85-2.73 (m, 1H), 2.30 (br s, 6H), 2.04-1.91 (m, 4H), 1.76-1.59 (m, 1H), 1.60-1.47 (m, 1H); MS (ESI+) m/z 521 (M+H)+.

Example 51: tert-butyl 5-[5-({3-[2-(4-chloro-3-fluorophenoxy)acetamido]bicyclo[1.1.1]pentan-1-yl}carbamoyl)-1,3-oxazol-2-yl]-3,6-dihydropyridine-1(2H)-carboxylate (Compound 150)

Example 51A: ethyl 2-(1-(tert-butoxycarbonyl)-1,2,5,6-tetrahydropyridin-3-yl)oxazole-5-carboxylate The reaction and purification conditions described in Example 39A substituting tert-butyl 3-(4,4,5,5-tetramethyl-1,3,2-dioxaborolan-2-yl)-5,6-dihydropyridine-1(2H)-carboxylate (AstaTech) for 3,6-dihydro-2H-pyran-4-boronic acid pinacol ester gave the title compound. MS (ESI+) m/z 323 (M+H)+.

Example 51B: tert-butyl 5-[5-({3-[2-(4-chloro-3-fluorophenoxy)acetamido]bicyclo[1.1.1]pentan-1-yl}carbamoyl)-1,3-oxazol-2-yl]-3,6-dihydropyridine-1 (2H)-carboxylate The product of Example 51A (82 mg, 0.25 mmol) was dissolved in ethanol (1 mL), aqueous sodium hydroxide (2.5 M, 0.51 mL) was added, and the resulting mixture was stirred at ambient temperature for 3 minutes. The reaction mixture was concentrated in vacuo and to the resulting residue was added the product of Example 6C (130 mg, 0.25 mmol), triethylamine (0.18 mL, 1.27 mmol), 1-[bis(dimethylamino)methylene]-1H-1,2,3-triazolo[4,5-b]pyridinium 3-oxid hexafluorophosphate (126 mg, 0.33 mmol, HATU), and N,N-dimethylformamide (2.0 mL) in sequential order. The reaction mixture was then stirred at ambient temperature for 30 minutes. The resulting mixture was filtered through a glass microfiber frit, and the filtrate was purified by preparative HPLC [YMC TriArt™ C18 Hybrid 5 μm column, 50×100 mm, flow rate 70 mL/minute, 5-100% gradient of acetonitrile in buffer (0.025 M aqueous ammonium bicarbonate, adjusted to pH 10 with ammonium hydroxide)] to give the title compound (92 mg, 0.16 mmol, 64% yield). $^1$H NMR (400 MHz, DMSO-$d_6$) δ ppm 9.16 (s, 1H), 8.75 (s, 1H), 7.74 (s, 1H), 7.50 (t, J=8.9 Hz, 1H), 7.08 (dd, J=11.4, 2.8 Hz, 1H), 7.05-6.98 (m, 1H), 6.86 (ddd, J=8.9, 2.9, 1.2 Hz, 1H), 4.49 (s, 2H), 4.25-4.19 (m, 2H), 3.48 (t, J=5.6 Hz, 2H), 2.40-2.29 (m, 8H), 1.43 (s, 9H); MS (ESI−) m/z 559 [M−H]−.

Example 52: 2-(1-acetyl-1,2,3,6-tetrahydropyridin-4-yl)-N-{3-[2-(4-chloro-3-fluorophenoxy)acetamido]bicyclo[1.1.1]pentan-1-yl}-1,3-oxazole-5-carboxamide (Compound 151)

The product of Example 49A (28 mg, 0.11 mmol) was dissolved in ethanol (1 mL) and aqueous sodium hydroxide (2.5 M, 0.13 mL) was added. After the mixture was stirred at ambient temperature for 3 minutes, aqueous HCl (1.0 M, 0.48 mL) was added. The reaction mixture was concentrated in vacuo and to the resulting residue was added the product of Example 6C (54 mg, 0.11 mmol), triethylamine (0.09 mL, 0.64 mmol), 1-[bis(dimethylamino)methylene]-1H-1,2,3-triazolo[4,5-b]pyridinium 3-oxid hexafluorophosphate (52 mg, 0.14 mmol, HATU), and N,N-dimethylformamide (2.0 mL) in sequential order. The reaction mixture was then stirred at ambient temperature for 30 minutes. The resulting mixture was filtered through a glass microfiber frit, and the filtrate was purified by preparative HPLC [YMC TriArt™ C18 Hybrid 5 μm column, 50×100 mm, flow rate 70 mL/minute, 5-100% gradient of acetonitrile in buffer (0.025 M aqueous ammonium bicarbonate, adjusted to pH 10 with ammonium hydroxide)] to give the title compound (15 mg, 0.03 mmol, 28% yield). $^1$H NMR (400 MHz, DMSO-d$_6$, 120° C.) δ ppm 8.62 (s, 1H), 8.24 (s, 1H), 7.64 (s, 1H), 7.41 (t, J=8.8 Hz, 1H), 6.99 (dd, J=11.3, 2.8 Hz, 1H), 6.88-6.81 (m, 2H), 4.45 (s, 2H), 4.19 (q, J=3.0 Hz, 2H), 3.63 (t, J=5.8 Hz, 2H), 2.61-2.52 (m, 2H), 2.35 (br s, 6H), 2.04 (s, 3H); MS (ESI$^+$) m/z 503 (M+H)$^+$.

Example 53: N-{3-[2-(4-chloro-3-fluorophenoxy)acetamido]bicyclo[1.1.1]pentan-1-yl}-5-(difluoromethoxy)pyridine-2-carboxamide (Compound 152)

The title compound was prepared using the methodologies described above. $^1$H NMR (400 MHz, DMSO-d$_6$) δ ppm 9.25 (s, 1H), 8.73 (s, 1H), 8.50 (d, J=2.8 Hz, 1H), 8.07 (dd, J=8.7, 0.6 Hz, 1H), 7.91-7.79 (m, 1H), 7.50 (t, J=8.9 Hz, 1H), 7.44 (t, J=73.0 Hz, 1H), 7.08 (dd, J=11.4, 2.8 Hz, 1H), 6.86 (ddd, J=8.9, 2.8, 1.2 Hz, 1H), 4.49 (s, 2H), 2.35 (br s, 6H); MS (ESI$^+$) m/z 456 (M+H)$^+$.

Example 54: N-{3-[2-(3,4-dichlorophenoxy)acetamido]bicyclo[1.1.1]pentan-1-yl}-5-(difluoromethoxy)pyridine-2-carboxamide (Compound 153)

The title compound was prepared using the methodologies described above. $^1$H NMR (501 MHz, DMSO-d$_6$) δ ppm 9.26 (s, 1H), 8.74 (s, 1H), 8.50 (d, J=2.8 Hz, 1H), 8.07 (dd, J=8.6, 0.6 Hz, 1H), 7.83 (dd, J=8.6, 2.8 Hz, 1H), 7.55 (d, J=9.0 Hz, 1H), 7.44 (t, J=73.0 Hz, 1H), 7.27 (d, J=2.9 Hz, 1H), 7.00 (dd, J=8.9, 2.9 Hz, 1H), 4.50 (s, 2H), 2.35 (br s, 6H); MS (ESI$^+$) m/z 472 (M+H)$^+$.

Example 55: N-{3-[2-(4-chloro-3-fluorophenoxy)acetamido]bicyclo[1.1.1]pentan-1-yl}-6-methoxypyridine-3-carboxamide (Compound 154)

The title compound was prepared using the methodologies described above. $^1$H NMR (500 MHz, DMSO-d$_6$) δ ppm 9.04 (s, 1H), 8.77 (s, 1H), 8.64 (dd, J=2.5, 0.8 Hz, 1H), 8.11 (dd, J=8.7, 2.5 Hz, 1H), 7.51 (t, J=8.9 Hz, 1H), 7.09 (dd, J=11.3, 2.8 Hz, 1H), 6.90-6.84 (m, 2H), 4.50 (s, 2H), 3.90 (s, 3H), 2.34 (br s, 6H); MS (ESI$^+$) m/z 420 (M+H)$^+$.

Example 56: N-{3-[2-(4-chloro-3-fluorophenoxy)acetamido]bicyclo[1.1.1]pentan-1-yl}-6-(3,6-dihydro-2H-pyran-4-yl)pyridine-3-carboxamide (Compound 155)

Example 56A: tert-butyl 6-(3,6-dihydro-2H-pyran-4-yl)nicotinate

The reaction and purification conditions described in Example 39A substituting tert-butyl 6-bromonicotinate (Combi-Blocks) for ethyl 2-bromooxazole-5-carboxylate gave the title compound. MS (ESI$^+$) m/z 206 [M-(tert-butyl)]$^+$.

Example 56B: 6-(3,6-dihydro-2H-pyran-4-yl)nicotinic acid, trifluoroacetic acid The product of Example 56A (120 mg, 0.46 mmol) was dissolved in trifluoroacetic acid (3 mL, 39 mmol) and stirred at ambient temperature for 20 minutes and then at 40° C. for 1 hour. The resulting solution was concentrated under reduced pressure to give the title compound (0.15 g, 0.47 mmol, 100%). MS (ESI$^+$) m/z 206 (M+H)$^+$.

Example 56C: N-{3-[2-(4-chloro-3-fluorophenoxy)acetamido]bicyclo[1.1.1]pentan-1-yl}-6-(3,6-dihydro-2H-pyran-4-yl)pyridine-3-carboxamide The reaction and purification conditions described in Example 13 substituting the product of Example 56B for the product of Example 12B and the product of Example 6C for the product of Example 4A gave the title compound. $^1$H NMR (400 MHz, DMSO-d$_6$) δ ppm 9.16 (s, 1H), 8.92 (dd, J=2.4, 0.8 Hz, 1H), 8.74 (s, 1H), 8.14 (dd, J=8.4, 2.3 Hz, 1H), 7.66-7.58 (m, 1H), 7.48 (t, J=8.9 Hz, 1H), 7.07 (dd, J=11.4, 2.8 Hz, 1H), 6.90-6.87 (m, 1H), 6.85 (ddd, J=8.9, 2.8, 1.2 Hz, 1H), 4.48 (s, 2H), 4.29-4.24 (m, 2H), 3.81 (t, J=5.5 Hz, 2H), 2.63-2.50 (m, 2H), 2.33 (br s, 6H); MS (ESI$^+$) m/z 472 (M+H)$^+$.

Example 57: N-{3-[2-(3,4-dichlorophenoxy)acetamido]bicyclo[1.1.1]pentan-1-yl}pyridine-2-carboxamide (Compound 156)

The title compound was prepared using the methodologies described above. $^1$H NMR (400 MHz, DMSO-d$_6$) δ ppm 9.23 (s, 1H), 8.72 (s, 1H), 8.61 (dt, J=4.8, 1.4 Hz, 1H), 8.00-7.94 (m, 2H), 7.61-7.55 (m, 1H), 7.53 (d, J=9.0 Hz, 1H), 7.25 (d, J=2.9 Hz, 1H), 6.98 (dd, J=8.9, 2.9 Hz, 1H), 4.49 (s, 2H), 2.34 (br s, 6H); MS (ESI$^+$) m/z 406 (M+H)$^+$.

Example 58: 6-(2-{[tert-butyl(dimethyl)silyl]oxy}ethoxy)-N-{3-[2-(4-chloro-3-fluorophenoxy)acetamido]bicyclo[1.1.1]pentan-1-yl}pyridine-3-carboxamide (Compound 157)

Example 58A: methyl 6-(2-((tert-butyldimethylsilyl)oxy)ethoxy)nicotinate

To a tetrahydrofuran (5 mL) solution of 2-((tert-butyldimethylsilyl)oxy)ethanol (Ark Pharm, 200 mg, 1.134 mmol) stirred at ambient temperature was added sodium hydride (60% dispersion in mineral oil, 68 mg, 1.701 mmol) in one portion. After 5 minutes, methyl 6-fluoronicotinate (Combi-Blocks, 176 mg, 1.134 mmol) was added. After the reaction was stirred for 5 minutes, N,N-dimethylformamide (1 mL) was added. After 30 minutes, the reaction mixture was concentrated under reduced pressure and taken up in a solvent mixture of N,N-dimethylformamide (1.5 mL) and methanol (1.5 mL). The resulting suspension was filtered through a glass microfiber frit, and the filtrate was purified by preparative HPLC [YMC TriArt™ C18 Hybrid 20 µm column, 25×150 mm, flow rate 80 mL/minute, 20-100% gradient of acetonitrile in buffer (0.025 M aqueous ammonium bicarbonate, adjusted to pH 10 with ammonium hydroxide)] to give the title compound (0.11 g, 0.35 mmol, 31% yield). MS (ESI$^+$) m/z 312 (M+H)$^+$.

Example 58B: 6-(2-((tert-butyldimethylsilyl)oxy)ethoxy)nicotinic acid

The product of Example 58A (100 mg, 0.32 mmol) was dissolved in methanol (5 mL), and aqueous sodium hydroxide (2.5 M, 0.77 mL) was added. The resulting mixture was stirred at ambient temperature for 18 hours, filtered through a glass microfiber frit, and directly purified by preparative HPLC [YMC TriArt™ C18 Hybrid 20 µm column, 25×150 mm, flow rate 80 mL/minute, 0-100% gradient of acetonitrile in carbonic acid buffer (prepared by sparging carbon dioxide gas bubbled through deionized water for 15 minutes immediately before use)] to give the title compound (42 mg, 0.14 mmol, 44% yield). MS (ESI$^+$) m/z 298 (M+H)$^+$.

Example 58C: 6-(2-{[tert-butyl(dimethyl)silyl]oxy}ethoxy)-N-{3-[2-(4-chloro-3-fluorophenoxy)acetamido]bicyclo[1.1.1]pentan-1-yl}pyridine-3-carboxamide The reaction and purification conditions described in Example 13 substituting the product of Example 58B for the product of Example 12B and the product of Example 6C for the product of Example 4A gave the title compound. $^1$H NMR (400 MHz, DMSO-d$_6$) δ ppm 9.01 (s, 1H), 8.74 (s, 1H), 8.61 (d, J=2.4 Hz, 1H), 8.10 (dd, J=8.7, 2.5 Hz, 1H), 7.50 (t, J=8.8 Hz, 1H), 7.09 (dd, J=11.4, 2.8 Hz, 1H), 6.89-6.83 (m, 2H), 4.49 (s, 2H), 4.38-4.34 (m, 2H), 3.94-3.88 (m, 2H), 2.33 (s, 6H), 0.85 (s, 9H), 0.04 (s, 6H); MS (ESI$^+$) m/z 564 (M+H)$^+$.

Example 59: N-{3-[2-(3,4-dichlorophenoxy)acetamido]bicyclo[1.1.1]pentan-1-yl}-6-(2-hydroxyethoxy)pyridine-3-carboxamide (Compound 158)

Example 59A: 6-(2-hydroxyethoxy)nicotinic acid

The preparative HPLC purification in Example 58B also gave this title compound. MS (ESI$^+$) m/z 184 (M+H)$^+$.

Example 59B: N-{3-[2-(3,4-dichlorophenoxy)acetamido]bicyclo[1.1.1]pentan-1-yl}-6-(2-hydroxyethoxy)pyridine-3-carboxamide The reaction and purification conditions described in Example 13 substituting the product of Example 59A for the product of Example 12B and the product of Example 2B for the product of Example 4A gave the title compound. $^1$H NMR (400 MHz, DMSO-d$_6$) δ ppm 9.01 (s, 1H), 8.74 (s, 1H), 8.61 (d, J=2.4 Hz, 1H), 8.10 (dd, J=8.7, 2.5 Hz, 1H), 7.55 (d, J=8.9 Hz, 1H), 7.28 (d, J=2.9 Hz, 1H), 7.00 (dd, J=8.9, 2.9 Hz, 1H), 6.86 (d, J=8.7 Hz, 1H), 4.84 (br s, 1H), 4.51 (s, 2H), 4.34-4.29 (m, 2H), 3.74-3.68 (m, 2H), 2.33 (br s, 6H); MS (ESI$^+$) m/z 466 (M+H)$^+$.

Example 60: N-{3-[2-(4-chloro-3-fluorophenoxy)acetamido]bicyclo[1.1.1]pentan-1-yl}-5-(hydroxymethyl)pyridine-2-carboxamide (Compound 159)

The title compound was prepared using the methodologies described above. $^1$H NMR (400 MHz, DMSO-d$_6$) δ ppm 9.22 (s, 1H), 8.73 (s, 1H), 8.56 (dd, J=2.1, 0.9 Hz, 1H), 7.99-7.95 (m, 1H), 7.92-7.88 (m, 1H), 7.50 (t, J=8.9 Hz, 1H), 7.08 (dd, J=11.4, 2.9 Hz, 1H), 6.86 (ddd, J=9.0, 2.9, 1.2 Hz, 1H), 5.48-5.41 (m, 1H), 4.62 (d, J=3.8 Hz, 2H), 4.49 (s, 2H), 2.35 (s, 6H); MS (ESI$^+$) m/z 420 (M+H)$^+$.

Example 61: N-{3-[2-(3,4-dichlorophenoxy)acetamido]bicyclo[1.1.1]pentan-1-yl}-5-(hydroxymethyl)pyridine-2-carboxamide (Compound 160)

The title compound was prepared using the methodologies described above. $^1$H NMR (400 MHz, DMSO-d$_6$) δ ppm 9.22 (s, 1H), 8.73 (s, 1H), 8.56 (dd, J=2.1, 0.9 Hz, 1H), 7.98-7.95 (m, 1H), 7.92-7.87 (m, 1H), 7.55 (d, J=8.9 Hz, 1H), 7.27 (d, J=2.9 Hz, 1H), 6.99 (dd, J=8.9, 2.9 Hz, 1H), 5.46 (br s, 1H), 4.62 (s, 2H), 4.50 (s, 2H), 2.35 (br s, 6H); MS (ESI$^+$) m/z 436 (M+H)$^+$.

Example 62: N-{3-[2-(4-chloro-3-fluorophenoxy)acetamido]bicyclo[1.1.1]pentan-1-yl}-6-(2-hydroxyethoxy)pyridine-3-carboxamide (Compound 161)

The reaction and purification conditions described in Example 13 substituting the product of Example 59A for the product of Example 12B and the product of Example 6C for the product of Example 4A gave the title compound. $^1$H NMR (400 MHz, DMSO-d$_6$) δ ppm 9.01 (s, 1H), 8.74 (s, 1H), 8.61 (dd, J=2.6, 0.7 Hz, 1H), 8.09 (dd, J=8.7, 2.5 Hz, 1H), 7.50 (t, J=8.9 Hz, 1H), 7.08 (dd, J=11.4, 2.8 Hz, 1H), 6.89-6.84 (m, 2H), 4.89-4.78 (m, 1H), 4.49 (s, 2H), 4.32 (dd, J=5.8, 4.5 Hz, 2H), 3.74-3.68 (m, 2H), 2.33 (br s, 6H); MS (ESI$^+$) m/z 450 (M+H)$^+$.

Example 63: 5-methyl-N-[3-(2-{[6-(trifluoromethyl)pyridin-3-yl]oxy}acetamido)bicyclo[1.1.1]pentan-1-yl]pyrazine-2-carboxamide (Compound 162)

Example 63A: tert-butyl 2-((6-(trifluoromethyl)pyridin-3-yl)oxy)acetate

A mixture of 6-(trifluoromethyl)pyridin-3-ol (CombiBlocks, 10 g, 60.1 mmol), potassium carbonate (16.61 g, 120 mmol) and tert-butyl bromoacetate (9.25 mL, 63.1 mmol) in N,N-dimethylformamide (100 mL) was warmed to 65° C. and was allowed to stir for 16 hours. The mixture was cooled to ambient temperature and quenched with saturated, aqueous NaHCO$_3$ (40 mL) and diluted with ethyl acetate (40 mL) and water (20 mL). The layers were separated, and the aqueous layer was extracted with ethyl acetate (3×15 mL). The combined organic layers were dried over anhydrous sodium sulfate and concentrated under reduced pressure. The resulting residue was purified via column chromatography (SiO$_2$, 15-25% ethyl acetate/heptanes) to give the title compound (16.2 g, 58.4 mmol, 97% yield). MS (ESI$^+$) m/z 278 (M+H)$^+$.

Example 63B: 2-((6-(trifluoromethyl)pyridin-3-yl)oxy)acetic Acid

To a solution of the product of Example 63A (16.2 g, 58.4 mmol) in dichloromethane (100 mL) at ambient temperature was added trifluoroacetic acid (45.0 mL, 584 mmol). This mixture was allowed to stir at ambient temperature for 4 hours and then concentrated under reduced pressure and azeotroped with toluene to give solids which were precipitated from ethyl acetate/heptane to give the title compound (12.25 g, 55.4 mmol, 95% yield). MS (DCI) m/z 239 (M+NH$_4$)$^+$.

Example 63C: N-(3-aminobicyclo[1.1.1]pentan-1-yl)-5-methylpyrazine-2-carboxamide bis(2,2,2-trifluoroacetate)

N,N-Dimethylformamide (5.0 mL), pyridine (1.0 mL, 12.36 mmol), and 1-[bis(dimethylamino)methylene]-1H-1,2,3-triazolo[4,5-b]pyridinium 3-oxid hexafluorophosphate (945 mg, 2.48 mmol, HATU) were added to a mixture of 5-methylpyrazine-2-carboxylic acid (Alfa, 277 mg, 2.0 mmol) and tert-butyl (3-aminobicyclo[1.1.1]pentan-1-yl)carbamate (Pharmablock, 379 mg, 1.91 mmol) in sequential order. The reaction mixture was then stirred at ambient temperature for 1 hour and was then partitioned between dichloromethane (2×50 mL) and aqueous sodium carbonate (1.0 M, 100 mL). The combined organic layers were dried over anhydrous sodium sulfate and concentrated in vacuo. Trifluoroacetic acid (10 mL, 130 mmol) was added to the residue, and the resulting solution was stirred at ambient temperature for 1 hour and concentrated in vacuo. The residue was directly purified by preparative HPLC [Waters XBridge™ C18 5 µm OBD column, 50×100 mm, flow rate 90 mL/minute, 5-100% gradient of acetonitrile in buffer (0.1% trifluoroacetic acid)] to give the title compound ((0.71 g, 1.59 mmol, 83% yield). MS (ESI$^+$) m/z 219 (M+H)$^+$.

Example 63D: 5-methyl-N-[3-(2-{[6-(trifluoromethyl)pyridin-3-yl]oxy}acetamido)bicyclo[1.1.1]pentan-1-yl]pyrazine-2-carboxamide The reaction and purification conditions described in Example 13 substituting the product of Example 63B for the product of Example 12B and the product of Example 63C for the product of Example 4A gave the title compound. $^1$H NMR (500 MHz, DMSO-d$_6$) δ ppm 9.37 (s, 1H), 9.01 (d, J=1.4 Hz, 1H), 8.83 (s, 1H), 8.59 (d, J=1.4 Hz, 1H), 8.47 (d, J=2.8 Hz, 1H), 7.87 (d, J=8.7 Hz, 1H), 7.58 (dd, J=8.7, 2.9 Hz, 1H), 4.68 (s, 2H), 2.59 (s, 3H), 2.36 (br s, 6H); MS (ESI$^+$) m/z 422 (M+H)$^+$.

Example 64: N-{3-[2-(4-chloro-3-fluorophenoxy)acetamido]bicyclo[1.1.1]pentan-1-yl}-2-(4-hydroxycyclohex-1-en-1-yl)-1,3-oxazole-5-carboxamide (Compound 163)

Example 64A: ethyl 2-(4-hydroxycyclohex-1-en-1-yl)oxazole-5-carboxylate

The reaction and purification conditions described in Example 39A substituting 4-(4,4,5,5-tetramethyl-1,3,2-dioxaborolan-2-yl)cyclohex-3-enol(Aurum Pharmatech) for 3,6-dihydro-2H-pyran-4-boronic acid pinacol ester gave the title compound. MS (ESI$^+$) m/z 238 (M+H)$^+$.

Example 64B: N-{3-[2-(4-chloro-3-fluorophenoxy)acetamido]bicyclo[1.1.1]pentan-1-yl}-2-(4-hydroxycyclohex-1-en-1-yl)-1,3-oxazole-5-carboxamide The reaction and purification conditions described in Example 51B substituting the product of Example 64A for the product of Example 51A gave the title compound. $^1$H NMR (500 MHz, DMSO-d$_6$) δ ppm 9.08 (s, 1H), 8.74 (s, 1H), 7.68 (s, 1H), 7.50 (t, J=8.9 Hz, 1H), 7.08 (dd, J=11.4, 2.8 Hz, 1H), 6.86 (ddd, J=8.9, 2.9, 1.1 Hz, 1H), 6.84-6.80 (m, 1H), 4.76 (d, J=4.0 Hz, 1H), 4.49 (s, 2H), 3.85-3.78 (m, 1H), 2.61-2.53 (m, 1H), 2.47 (d, J=7.5 Hz, 1H), 2.43-2.34 (m, 1H), 2.32 (br s, 6H), 2.15-2.06 (m, 1H), 1.86-1.79 (m, 1H), 1.63-1.54 (m, 1H); MS (ESI$^+$) m/z 476 (M+H)$^+$.

Example 65: N-{3-[2-(3,4-dichlorophenoxy)acetamido]bicyclo[1.1.1]pentan-1-yl}pyrazine-2-carboxamide (Compound 164)

The title compound was prepared using the methodologies described above. $^1$H NMR (400 MHz, DMSO-d$_6$) δ ppm 9.46 (s, 1H), 9.15 (d, J=1.5 Hz, 1H), 8.86 (d, J=2.5 Hz, 1H), 8.74 (br s, 1H), 8.72-8.70 (m, 1H), 7.55 (d, J=8.9 Hz, 1H), 7.27 (d, J=2.9 Hz, 1H), 7.00 (dd, J=9.0, 2.9 Hz, 1H), 4.51 (s, 2H), 2.36 (br s, 6H); MS (ESI$^+$) m/z 407 (M+H)$^+$.

Example 66: N-{3-[2-(3,4-dichlorophenoxy)acetamido]bicyclo[1.1.1]pentan-1-yl}-6-(hydroxymethyl)pyridine-2-carboxamide (Compound 165)

The title compound was prepared using the methodologies described above. $^1$H NMR (400 MHz, DMSO-d$_6$) δ ppm 9.22 (s, 1H), 8.75 (s, 1H), 7.97 (t, J=7.7 Hz, 1H), 7.87-7.84 (m, 1H), 7.62-7.58 (m, 1H), 7.55 (d, J=8.9 Hz, 1H), 7.28 (d, J=2.9 Hz, 1H), 7.00 (dd, J=9.0, 2.9 Hz, 1H), 5.45 (t, J=5.7 Hz, 1H), 4.64 (d, J=5.3 Hz, 2H), 4.51 (s, 2H), 2.37 (br s, 6H); MS (ESI$^+$) m/z 436 (M+H)$^+$.

Example 67: N-{3-[2-(3,4-dichlorophenoxy)acetamido]bicyclo[1.1.1]pentan-1-yl}-4-(hydroxymethyl)pyridine-2-carboxamide (Compound 166)

The title compound was prepared using the methodologies described above. $^1$H NMR (400 MHz, DMSO-d$_6$) δ ppm 9.22 (s, 1H), 8.75 (s, 1H), 7.97 (t, J=7.7 Hz, 1H), 7.87-7.84 (m, 1H), 7.62-7.58 (m, 1H), 7.55 (d, J=8.9 Hz, 1H), 7.28 (d, J=2.9 Hz, 1H), 7.00 (dd, J=9.0, 2.9 Hz, 1H), 5.45 (t, J=5.7 Hz, 1H), 4.64 (d, J=5.3 Hz, 2H), 4.51 (s, 2H), 2.37 (br s, 6H); MS (ESI$^+$) m/z 436 (M+H)$^+$.

Example 68: N-{4-[2-(4-chloro-3-fluorophenoxy)acetamido]-2-hydroxybicyclo[2.2.2]octan-1-yl}pyridine-2-carboxamide (Compound 167)

Example 68A: ethyl 1,4-dioxaspiro[4.5]decane-8-carboxylate

A mixture of ethyl 4-oxocyclohexanecarboxylate (11.70 mL, 73.4 mmol), ethane-1,2-diol (12.29 mL, 220 mmol), and p-toluenesulfonic acid monohydrate (1.397 g, 7.34 mmol) in toluene (200 mL) was stirred at 120° C. with a Dean-Stark trap apparatus for 180 minutes. The reaction mixture was neutralized with N-ethyl-N-isopropylpropan-2-amine and then concentrated. The residue was purified on silica gel (0-30% ethyl acetate in heptane) to give 12.77 g of the title compound as a clear oil. $^1$H NMR (400 MHz, DMSO-d$_6$) δ ppm 4.01 (q, J=7.1 Hz, 2H), 3.81 (s, 4H), 2.32 (tt, J=10.4, 3.8 Hz, 1H), 1.83-1.71 (m, 2H), 1.66-1.57 (m, 1H), 1.62-1.38 (m, 5H), 1.13 (t, J=7.1 Hz, 3H).

Example 68B: ethyl 8-acetyl-1,4-dioxaspiro[4.5]decane-8-carboxylate

To a solution of diisopropylamine (5.19 mL, 36.4 mmol) in tetrahydrofuran (25 mL) at 0° C. was added n-butyllithium slowly below 5° C. After stirring for 30 minutes, the solution was cooled to −78° C. under nitrogen, and a solution of Example 68A (6.0 g, 28.0 mmol) in tetrahydrofuran (3 mL) was added slowly, and the resultant mixture was stirred for 30 minutes at the same temperature. Then acetyl chloride (2.59 mL, 36.4 mmol) was added slowly to maintain the temperature below −60° C., and the mixture was stirred at −70° C. for 2 hours. The reaction was quenched with saturated NH$_4$Cl solution, and the aqueous phase was extracted with ethyl acetate. The organic layer was washed with brine, dried over magnesium sulfate and filtered. The filtrate was concentrated, and the residue was purified on silica gel (0-70% ethyl acetate in heptane) to give 6.78 g of the title compound as a clear oil. $^1$H NMR (500 MHz, DMSO-d$_6$) δ ppm 4.19-4.11 (m, 2H), 3.85 (s, 4H), 2.13 (s, 3H), 2.10-2.01 (m, 2H), 1.90 (ddd, J=13.9, 9.6, 4.6 Hz, 2H), 1.54 (th, J=13.6, 4.7 Hz, 4H), 1.18 (dd, J=7.6, 6.5 Hz, 3H).

Example 68C: ethyl 1-acetyl-4-oxocyclohexane-1-carboxylate

A mixture of Example 68B (6.5 g, 25.4 mmol) and HCl (21.13 mL, 127 mmol) in acetone (60 mL) was stirred at ambient temperature overnight. Volatiles were removed under reduced pressure, and the residue was partitioned between water and dichloromethane. The organic layer was washed with brine, dried over magnesium sulfate and filtered. The filtrate was concentrated to give 5.46 g of the title compound as a clear oil, used without further purification. $^1$H NMR (400 MHz, DMSO-$d_6$) δ ppm 4.16 (q, J=7.1 Hz, 2H), 2.17 (s, 3H), 2.35-2.07 (m, 8H), 1.17 (t, J=7.1 Hz, 3H).

Example 68D: ethyl 4-(benzylamino)-2-oxobicyclo[2.2.2]octane-1-carboxylate, Hydrochloric Acid A mixture of Example 68C (9.7 g, 45.7 mmol), benzylamine (14.98 mL, 137 mmol), and p-toluenesulfonic acid monohydrate (0.087 g, 0.457 mmol) in toluene (100 mL) was stirred at 130° C. with Dean-Stark trap apparatus overnight. The mixture was concentrated, and the residue was stirred with a mixture of ethyl acetate (50 mL) and 3 N HCl (100 mL) for 30 minutes. The precipitate was collected by filtration, washed with mixture of ethyl acetate/heptane, air-dried to give 11.3 g of title compound as an HCl salt. The filtrate was neutralized with 6 N NaOH and extracted with ethyl acetate (100 mL×2). The organic layer was washed with brine, dried over magnesium sulfate and filtered. The residue was purified on silica gel (0-70% ethyl acetate in heptane) to give another 0.77 g of the title compound as yellow solid. $^1$H NMR (400 MHz, DMSO-$d_6$) δ ppm 9.73 (t, J=6.2 Hz, 2H), 7.87-7.12 (m, 5H), 4.09 (m, 4H), 2.88 (s, 2H), 2.08 (dt, J=20.7, 13.4 Hz, 6H), 1.16 (t, J=7.1 Hz, 3H); MS (ESI$^+$) m/z 302.1 (M+H)$^+$.

Example 68E: ethyl 4-amino-2-oxobicyclo[2.2.2]octane-1-carboxylate, Hydrochloric Acid To a mixture of Example 68D (11.2 g of HCl salt, 33.2 mmol) in tetrahydrofuran (110 mL) in a 50 mL pressure bottle was added 20% Pd(OH)$_2$/C, wet (2.2 g, 1.598 mmol), and the reaction was shaken at 50° C. under 50 psi of hydrogen for 22 hours. The reaction mixture was cooled to ambient temperature, solids were removed by filtration and washed with methanol (1 L). The filtrate and wash were concentrated to give 7.9 g of the title compound as a light yellow solid. $^1$H NMR (400 MHz, DMSO-$d_6$) δ ppm 8.46 (s, 3H), 4.07 (q, J=7.1 Hz, 2H), 2.62 (s, 2H), 2.17-2.05 (m, 2H), 2.04-1.78 (m, 6H), 1.14 (t, J=7.1 Hz, 3H).

Example 68F: ethyl 4-[2-(4-chloro-3-fluorophenoxy)acetamido]-2-oxobicyclo[2.2.2]octane-1-carboxylate To a suspension of Example 68E (7.8 g, 31.5 mmol), N-ethyl-N-isopropylpropan-2-amine (22.00 mL, 126 mmol) and 2-(4-chloro-3-fluorophenoxy)acetic acid (7.41 g, 36.2 mmol) in N,N-dimethylformamide (200 mL), 2-(3H-[1,2,3]triazolo[4,5-b]pyridin-3-yl)-1,1,3,3-tetramethylisouronium hexafluorophosphate(V) (14.97 g, 39.4 mmol) was added, and the resulting brown solution was stirred at ambient temperature for 16 hours. Water was added, and the mixture was stirred for 15 minutes. The precipitate was collected by filtration, washed with water, and air-dried to give 12.1 g of the title compound as an off-white solid. $^1$H NMR (400 MHz, DMSO-$d_6$) δ ppm 7.87 (s, 1H), 7.45 (t, J=8.9 Hz, 1H), 7.00 (dd, J=11.4, 2.9 Hz, 1H), 6.79 (ddd, J=8.9, 2.9, 1.2 Hz, 1H), 4.45 (s, 2H), 4.06 (q, J=7.1 Hz, 2H), 2.73 (s, 2H), 2.07 (m, 1H), 2.01-1.84 (m, 6H), 1.14 (t, J=7.1 Hz, 3H); MS (ESI$^+$) m/z 398.0 (M+H)$^+$.

Example 68G: 4-[2-(4-chloro-3-fluorophenoxy)acetamido]-2-oxobicyclo[2.2.2]octane-1-carboxylic acid A suspension of Example 68F (11.37 g, 28.6 mmol) and sodium hydroxide (7.15 mL, 57.2 mmol, 8 M solution) in methanol (100 mL) was stirred at ambient temperature for 16 hours. Volatiles were removed, and the residue was acidified with 1 N HCl. The precipitate was collected by filtration and dried in vacuum oven to give 9.9 g of the title compound as a white solid. $^1$H NMR (400 MHz, DMSO-$d_6$) δ ppm 12.49 (s, 1H), 7.86 (s, 1H), 7.45 (t, J=8.9 Hz, 1H), 7.00 (dd, J=11.4, 2.9 Hz, 1H), 6.83-6.74 (m, 1H), 4.45 (s, 2H), 2.71 (s, 2H), 2.01-1.81 (m, 7H); MS (ESI−) m/z 368.1 (M−H)$^−$.

Example 68H: N-(4-amino-3-oxobicyclo[2.2.2]octan-1-yl)-2-(4-chloro-3-fluorophenoxy)acetamide A mixture of Example 68G (3.24 g, 8.76 mmol), diphenylphosphoryl azide (2.84 mL, 13.14 mmol), and triethylamine (3.66 mL, 26.3 mmol) in toluene (100 mL) was heated at 110° C. for 2 hours. The solution was cooled to ambient temperature and poured into 150 mL of 3 N HCl solution. The mixture was stirred for 16 hours to give a suspension. The precipitate was filtered, washed with ethyl acetate, and air-dried to give the title compound (1.63 g) as an HCl salt as a white solid. The filtrate was then basified with solid sodium bicarbonate and extracted with ethyl acetate. The organic layer was washed with brine, dried over magnesium sulfate and filtered. The filtrate was concentrated and purified on silica gel (0-10% methanol/dichloromethane) to give the title compound (0.6 g) as the free base. $^1$H NMR (400 MHz, DMSO-$d_6$) δ ppm 8.49 (s, 3H), 8.08 (s, 1H), 7.45 (t, J=8.9 Hz, 1H), 7.01 (dd, J=11.4, 2.8 Hz, 1H), 6.79 (ddd, J=9.0, 2.9, 1.2 Hz, 1H), 4.48 (s, 2H), 2.90 (s, 2H), 2.12-1.79 (m, 8H).

Example 68I: N-(4-amino-3-hydroxybicyclo[2.2.2]octan-1-yl)-2-(4-chloro-3-fluorophenoxy)acetamide hydrochloride A mixture of Example 68H (2.5 g, 6.63 mmol) and sodium borohydride (1.254 g, 33.1 mmol) in a 1:1 mixture of methanol/dichloromethane (50 mL) was stirred for 24 hours. Volatiles were removed, and the residue was partitioned between water and dichloromethane. The organic fraction was separated, dried (MgSO$_4$), and concentrated. The residue was then treated with 4 N HCl in dioxane. The suspension was sonicated and concentrated. The residue was dried under vacuum to give 2.82 g of the title compound as a light yellow solid. $^1$H NMR (400 MHz, DMSO-$d_6$) δ ppm 7.97 (s, 3H), 7.72 (s, 1H), 7.40 (t, J=8.9 Hz, 1H), 6.95 (dd, J=11.4, 2.8 Hz, 1H), 6.74 (ddd, J=9.0, 2.9, 1.1 Hz, 1H), 5.64 (s, 1H), 4.41 (s, 2H), 3.83 (d, J=9.1 Hz, 1H), 2.24 (td, J=10.8, 9.9, 5.3 Hz, 1H), 1.96-1.51 (m, 9H); MS (ESI$^+$) m/z 343.0 (M+H)$^+$.

Example 68J: N-{4-[2-(4-chloro-3-fluorophenoxy)acetamido]-2-hydroxybicyclo[2.2.2]octan-1-yl}pyridine-2-carboxamide A mixture of Example 68I (0.05 g, 0.109 mmol), picolinic acid (0.015 g, 0.126 mmol) and N-ethyl-N-isopropylpropan- 2-amine (0.076 mL, 0.438 mmol) in N,N-dimethyl formamide (1.5 mL) was treated with 2-(3H-[1,2,3]triazolo[4,5-b]pyridin-3-yl)-1,1,3,3-tetramethylisouronium hexafluorophosphate(V) (0.062 g, 0.164 mmol), and the reaction mixture was stirred at ambient temperature overnight. Volatiles were removed under high vacuum, and the residue was purified by HPLC (performed on Phenomenex® Luna® C18(2) 5 am 100A AXIA™ column (250 mm×21.2 mm) with a linear gradient of 5-100% acetonitrile (A) and 0.1% trifluoroacetic acid in water (B) over about 15 minutes at a flow rate of 25 mL/minutes. Detection method was UV at wavelengths of 218 nM and 254 nM) to give 47 mg of product as a solid. $^1$H NMR (400 MHz, DMSO-$d_6$) δ ppm 8.56 (d, J=4.7 Hz, 1H), 8.24 (s, 1H), 8.01-7.89 (m, 2H), 7.59-7.50 (m, 1H), 7.54 (s, 1H), 7.43 (t, J=8.9 Hz, 1H), 6.97 (dd, J=11.4, 2.9 Hz, 1H), 6.77 (dd, J=9.0, 2.9 Hz, 1H), 4.40 (s, 2H), 3.97 (dt, J=9.3, 3.0 Hz, 1H), 2.51-2.44 (m, 1H), 2.32 (ddd, J=12.9, 9.5, 2.8 Hz, 1H), 2.07-1.67 (m, 8H); MS (ESI$^+$) m/z 448.1 (M+H)$^+$.

Example 69: N-{4-[2-(4-chloro-3-fluorophenoxy)acetamido]-2-hydroxybicyclo[2.2.2]octan-1-yl}-5-fluoropyridine-2-carboxamide (Compound 168)

The title compound was prepared using the methodologies described in Example 68 substituting 5-fluoropicolinic acid for picolinic acid. $^1$H NMR (400 MHz, DMSO-$d_6$) δ ppm 8.58 (d, J=2.8 Hz, 1H), 8.13-8.01 (m, 2H), 7.86 (td, J=8.7, 2.9 Hz, 1H), 7.51 (s, 1H), 7.45 (t, J=8.9 Hz, 1H), 7.00 (dd, J=11.4, 2.9 Hz, 1H), 6.78 (ddd, J=9.0, 2.9, 1.2 Hz, 1H), 5.29 (s, 1H), 4.41 (s, 2H), 4.00-3.91 (m, 1H), 2.57-2.47 (m, 1H), 2.31 (ddd, J=12.7, 9.4, 2.8 Hz, 1H), 2.11-1.99 (m, 1H), 2.00-1.74 (m, 6H), 1.79-1.63 (m, 1H); MS (ESI$^+$) m/z 466.0 (M+H)$^+$.

Example 70: N-{4-[2-(4-chloro-3-fluorophenoxy)acetamido]-2-hydroxybicyclo[2.2.2]octan-1-yl}-5-methylpyridine-2-carboxamide (Compound 169)

The title compound was prepared using the methodologies described in Example 68 substituting 5-methylpicolinic acid for picolinic acid $^1$H NMR (400 MHz, DMSO-$d_6$) δ ppm 8.40 (d, J=2.0 Hz, 1H), 8.17 (s, 1H), 7.87 (d, J=8.0 Hz, 1H), 7.75 (dd, J=8.0, 2.0 Hz, 1H), 7.53-7.40 (m, 2H), 7.00 (dd, J=11.4, 2.9 Hz, 1H), 6.78 (ddd, J=9.1, 2.9, 1.2 Hz, 1H), 4.41 (s, 2H), 3.95 (ddd, J=9.5, 3.7, 1.6 Hz, 1H), 2.57-2.46 (m, 1H), 2.33 (s, 3H), 2.37-2.25 (m, 1H), 2.10-1.99 (m, 1H), 2.01-1.85 (m, 2H), 1.80 (tt, J=9.5, 4.6 Hz, 5H), 1.69 (dtd, J=14.2, 8.0, 7.6, 4.1 Hz, 1H); MS (ESI$^+$) m/z 462.1 (M+H)$^+$.

Example 71: N-{4-[2-(4-chloro-3-fluorophenoxy)acetamido]-2-hydroxybicyclo[2.2.2]octan-1-yl}-5-cyanopyridine-2-carboxamide (Compound 170)

The title compound was prepared using the methodologies described in Example 68 substituting 5-cyanopicolinic acid for picolinic acid. $^1$H NMR (400 MHz, DMSO-$d_6$) δ ppm 9.04 (s, 1H), 8.47 (dd, J=8.2, 2.1 Hz, 1H), 8.23 (s, 1H), 8.11 (d, J=8.7 Hz, 1H), 7.52 (s, 1H), 7.45 (t, J=8.9 Hz, 1H), 6.99 (dd, J=11.4, 2.8 Hz, 1H), 6.78 (ddd, J=9.0, 2.9, 1.2 Hz, 1H), 4.42 (s, 2H), 3.98 (ddd, J=9.6, 3.9, 1.6 Hz, 1H), 2.46-2.54 (m, 1H), 2.32 (ddd, J=12.5, 9.3, 2.9 Hz, 1H), 2.11-2.00 (m, 1H), 2.01-1.86 (m, 2H), 1.88-1.75 (m, 4H), 1.80-1.65 (m, 1H); MS (ESI$^+$) m/z 472.9 (M+H)$^+$.

Example 72: N-{3-[2-(4-chloro-3-fluorophenoxy)acetamido]bicyclo[1.1.1]pentan-1-yl}-5-[(1E)-3-methoxyprop-1-en-1-yl]pyrazine-2-carboxamide (Compound 171)

Example 72A: (E)-methyl 5-(3-methoxyprop-1-en-1-yl)pyrazine-2-carboxylate

The reaction and purification conditions described in Example 39A substituting (E)-2-(3-methoxypropenyl)-4,4,5,5-tetramethyl-(1,3,2)-dioxaboroane (Aldrich) for 3,6-dihydro-2H-pyran-4-boronic acid pinacol ester, and methyl 5-bromopyrazine-2-carboxylate (Ark Pharm) for ethyl 2-bromooxazole-5-carboxylate gave the title compound. MS (ESI$^+$) m/z 209 (M+H)$^+$.

Example 72B: (E)-5-(3-methoxyprop-1-en-1-yl)pyrazine-2-carboxylic acid

The reaction and purification conditions described in Example 39B substituting the product of Example 72A for the product of Example 39A gave the title compound. MS (ESI$^+$) m/z 195 (M+H)$^+$.

Example 72C: N-{3-[2-(4-chloro-3-fluorophenoxy)acetamido]bicyclo[1.1.1]pentan-1-yl}-5-[(1E)-3-methoxyprop-1-en-1-yl]pyrazine-2-carboxamide The reaction and purification conditions described in Example 13 substituting the product of Example 72B for the product of Example 12B and the product of Example 6C for the product of Example 4A gave the title compound. $^1$H NMR (400 MHz, DMSO-$d_6$) δ ppm 9.38 (s, 1H), 9.06 (d, J=1.4 Hz, 1H), 8.76 (d, J=1.4 Hz, 1H), 8.74 (s, 1H), 7.50 (t, J=8.9 Hz, 1H), 7.11-7.03 (m, 2H), 6.89-6.81 (m, 2H), 4.49 (s, 2H), 4.17 (dd, J=4.8, 1.9 Hz, 2H), 3.35 (s, 3H), 2.36 (br s, 6H); MS (ESI$^+$) m/z 461 (M+H)$^+$.

Example 73: N-{3-[2-(4-chloro-3-fluorophenoxy)acetamido]bicyclo[1.1.1]pentan-1-yl}-5-(3-methoxypropyl)pyrazine-2-carboxamide (Compound 172)

Example 73A: 5-(3-methoxypropyl)pyrazine-2-carboxylic acid

To a microwave vial (2 mL) was added the product of Example 72A (76 mg, 0.365 mmol), PtO$_2$ (15 mg, 0.053 mmol), ammonium formate (161 mg, 2.56 mmol) and methanol (1 mL). The vial was sealed and heated in a Biotage® Initiator+microwave reactor and irradiated at 120° C. for 10 minutes and then at 100° C. for 1 hour. The resulting reaction mixture was filtered through a glass microfiber frit, and the filtrate was stirred with NaOH (2.5 M, 0.44 mL) for 10 minutes. The resulting solution was directly purified by preparative HPLC [YMC TriArt™ C18 Hybrid 20 μm column, 25×150 mm, flow rate 80 mL/minute, 0-100% gradient of acetonitrile in carbonic acid buffer (prepared by sparging carbon dioxide gas bubbled through deionized water for 15 minutes immediately before use)] to give the title compound (25 mg, 0.127 mmol, 35% yield). MS (ESI$^+$) m/z 197 (M+H)$^+$.

Example 73B: N-{3-[2-(4-chloro-3-fluorophenoxy) acetamido]bicyclo[1.1.1]pentan-1-yl}-5-(3-methoxypropyl)pyrazine-2-carboxamide The reaction and purification conditions described in Example 13 substituting the product of Example 73A for the product of Example 12B and the product of Example 6C for the product of Example 4A gave the title compound. $^1$H NMR (400 MHz, DMSO-d$_6$) δ ppm 9.37 (s, 1H), 9.04 (d, J=1.4 Hz, 1H), 8.74 (s, 1H), 8.60 (d, J=1.5 Hz, 1H), 7.50 (t, J=8.9 Hz, 1H), 7.08 (dd, J=11.4, 2.8 Hz, 1H), 6.86 (ddd, J=9.0, 2.9, 1.2 Hz, 1H), 4.49 (s, 2H), 3.36 (t, J=6.3 Hz, 2H), 3.22 (s, 3H), 2.94-2.89 (m, 2H), 2.35 (br s, 6H), 1.99-1.89 (m, 2H); MS (ESI$^+$) m/z 463 (M+H)$^+$.

Example 74: N-{3-[2-(4-chloro-3-fluorophenoxy) acetamido]bicyclo[1.1.1]pentan-1-yl}-5-cyanopyridine-2-carboxamide (Compound 173)

The title compound was prepared using the methodologies described above. $^1$H NMR (400 MHz, DMSO-d$_6$) δ ppm 9.52 (s, 1H), 9.10 (dd, J=2.0, 0.9 Hz, 1H), 8.74 (s, 1H), 8.51 (dd, J=8.2, 2.1 Hz, 1H), 8.14 (dd, J=8.2, 0.9 Hz, 1H), 7.50 (t, J=8.9 Hz, 1H), 7.08 (dd, J=11.4, 2.8 Hz, 1H), 6.86 (ddd, J=9.0, 2.9, 1.2 Hz, 1H), 4.49 (s, 2H), 2.36 (br s, 6H); MS (ESI$^+$) m/z 415 (M+H)$^+$.

Example 75: N-{3-[2-(4-chloro-3-fluorophenoxy) acetamido]bicyclo[1.1.1]pentan-1-yl}-6-(methoxyethyl)pyridine-2-carboxamide (Compound 174)

The title compound was prepared using the methodologies described above. $^1$H NMR (400 MHz, DMSO-d$_6$) δ ppm 9.06 (s, 1H), 8.74 (s, 1H), 8.00 (t, J=7.7 Hz, 1H), 7.92-7.88 (m, 1H), 7.62-7.58 (m, 1H), 7.50 (t, J=8.9 Hz, 1H), 7.09 (dd, J=11.4, 2.8 Hz, 1H), 6.86 (ddd, J=8.9, 2.8, 1.2 Hz, 1H), 4.57 (s, 2H), 4.50 (s, 2H), 3.39 (s, 3H), 2.37 (br s, 6H); MS (ESI$^+$) m/z 434 (M+H)$^+$.

Example 76: N-{3-[2-(4-chloro-3-fluorophenoxy) acetamido]bicyclo[1.1.1]pentan-1-yl}pyrazine-2-carboxamide (Compound 175)

The title compound was prepared using the methodologies described above. $^1$H NMR (400 MHz, DMSO-d$_6$) δ ppm 9.46 (s, 1H), 9.15 (d, J=1.5 Hz, 1H), 8.86 (d, J=2.5 Hz, 1H), 8.74 (s, 1H), 8.71 (dd, J=2.6, 1.5 Hz, 1H), 7.50 (t, J=8.9 Hz, 1H), 7.08 (dd, J=11.4, 2.8 Hz, 1H), 6.86 (ddd, J=9.0, 2.9, 1.2 Hz, 1H), 4.50 (s, 2H), 2.36 (br s, 6H); MS (ESI$^+$) m/z 391 (M+H)$^+$.

Example 77: N-{3-[2-(4-chloro-3-fluorophenoxy) acetamido]bicyclo[1.1.1]pentan-1-yl}-4-(trifluoromethyl)pyridine-2-carboxamide (Compound 176)

The title compound was prepared using the methodologies described above. $^1$H NMR (400 MHz, DMSO-d$_6$) δ ppm 9.51 (s, 1H), 8.93 (d, J=5.1 Hz, 1H), 8.75 (s, 1H), 8.22-8.19 (m, 1H), 8.04-8.00 (m, 1H), 7.50 (t, J=8.9 Hz, 1H), 7.08 (dd, J=11.4, 2.9 Hz, 1H), 6.86 (ddd, J=8.9, 2.9, 1.2 Hz, 1H), 4.50 (s, 2H), 2.37 (br s, 6H); MS (ESI$^+$) m/z 458 (M+H)$^+$.

Example 78: N-{3-[2-(4-chloro-3-fluorophenoxy) acetamido]bicyclo[1.1.1]pentan-1-yl}-4-methoxypyridine-2-carboxamide (Compound 177)

The title compound was prepared using the methodologies described above. $^1$H NMR (501 MHz, DMSO-d$_6$) δ ppm 9.21 (s, 1H), 8.73 (s, 1H), 8.43 (d, J=5.7 Hz, 1H), 7.53-7.47 (m, 2H), 7.15 (dd, J=5.7, 2.6 Hz, 1H), 7.08 (dd, J=11.4, 2.9 Hz, 1H), 6.86 (ddd, J=9.0, 2.9, 1.2 Hz, 1H), 4.49 (s, 2H), 3.89 (s, 3H), 2.35 (br s, 6H); MS (ESI$^+$) m/z 420 (M+H)$^+$.

Example 79: N-{3-[2-(4-chloro-3-fluorophenoxy) acetamido]bicyclo[1.1.1]pentan-1-yl}-4-(hydroxymethyl)pyridine-2-carboxamide (Compound 178)

The title compound was prepared using the methodologies described above. $^1$H NMR (501 MHz, DMSO-d$_6$) δ ppm 9.21 (s, 1H), 8.73 (s, 1H), 8.43 (d, J=5.7 Hz, 1H), 7.53-7.47 (m, 2H), 7.15 (dd, J=5.7, 2.6 Hz, 1H), 7.08 (dd, J=11.4, 2.9 Hz, 1H), 6.86 (ddd, J=9.0, 2.9, 1.2 Hz, 1H), 4.49 (s, 2H), 3.89 (s, 3H), 2.35 (br s, 6H); MS (ESI$^+$) m/z 420 (M+H)$^+$.

Example 80: N-{3-[2-(4-chloro-3-fluorophenoxy) acetamido]bicyclo[1.1.1]pentan-1-yl}-4-(3-hydroxyazetidin-1-yl)pyridine-2-carboxamide (Compound 179)

Example 80A: tert-butyl 4-(3-hydroxyazetidin-1-yl)picolinate

A sealed tube was charged with bis(tri-tert-butylphosphine)palladium(0) (Strem, 47.5 mg, 0.093 mmol), 3-hydroxyazetidine hydrochloride (AK Scientific, 204 mg, 1.86 mmol), cesium carbonate (909 mg, 2.79 mmol), tert-butyl 4-bromopyridine-2-carboxylate (CombiBlocks, 240 mg, 0.930 mmol) and dioxane (6.2 mL) in sequential order. The tube was sealed and degassed three times with a nitrogen back flush each time. The reaction mixture was stirred at 100° C. for 3 hours. The vial was cooled to ambient temperature, and the reaction mixture was combined with silica gel (15 g) and concentrated under reduced pressure to give a free flowing powder. The powder was directly purified via flash chromatography (SiO$_2$, 10-75% 2-propanol in heptane) to give the title compound (38 mg, 0.152 mmol, 16% yield).

Example 80B: N-{3-[2-(4-chloro-3-fluorophenoxy) acetamido]bicyclo[0.1.1]pentan-1-yl}-4-(3-hydroxyazetidin-1-yl)pyridine-2-carboxamide Trifluoroacetic acid (0.5 mL, 6.49 mmol) was added to the product of Example 80A (35 mg, 0.140 mmol), and the mixture was stirred at 40° C. for 1 hour. The resulting reaction mixture was concentrated under reduced pressure. To the resulting residue was added N,N-dimethylformamide (3 mL), triethylamine (0.117 mL, 0.84 mmol), the product of Example 6C (72 mg, 0.14 mmol), and 1-[bis(dimethylamino)methylene]-1H-1,2,3-triazolo[4,5-b]pyridinium 3-oxid hexafluorophosphate (64 mg, 0.168 mmol, HATU) in sequential order. The reaction mixture was then stirred at ambient temperature for 30 minutes. The resulting mixture was filtered through a glass microfiber frit, and the filtrate was purified by preparative HPLC [Waters XBridge™ C18 5 μm OBD™ column, 30×100 mm, flow rate 40 mL/minute, 5-100% gradient of acetonitrile in buffer (0.025 M aqueous ammonium bicarbonate, adjusted to pH 10 with ammonium hydroxide)] to give the title compound (48 mg, 0.104 mmol, 75% yield). $^1$H NMR (501 MHz, DMSO-d$_6$) δ ppm 9.04 (s, 1H), 8.71 (s, 1H), 8.12 (dd, J=5.5, 0.5 Hz, 1H), 7.50 (t, J=8.9 Hz, 1H), 7.08 (dd, J=11.4, 2.8 Hz, 1H), 6.94 (dd, J=2.5, 0.5 Hz, 1H), 6.86 (ddd, J=9.0, 2.9, 1.2 Hz, 1H), 6.47 (dd, J=5.6, 2.5 Hz, 1H), 5.77 (d, J=5.3 Hz, 1H), 4.65-4.58 (m, 1H), 4.49 (s, 2H), 4.21-4.16 (m, 2H), 3.68 (ddd, J=8.5, 4.5, 1.2 Hz, 2H), 2.33 (br s, 6H); MS (ESI$^+$) m/z 461 (M+H)$^+$.

Example 81: N-{3-[2-(4-chloro-3-fluorophenoxy)acetamido]bicyclo[1.1.1]pentan-1-yl}-4-(morpholin-4-yl)pyridine-2-carboxamide (Compound 180)

The title compound was prepared using the methodologies described above. $^1$H NMR (400 MHz, DMSO-d$_6$) δ ppm 9.08 (s, 1H), 8.72 (s, 1H), 8.21 (d, J=5.8 Hz, 1H), 7.50 (t, J=8.9 Hz, 1H), 7.42 (d, J=2.7 Hz, 1H), 7.08 (dd, J=11.4, 2.8 Hz, 1H), 6.99 (dd, J=5.9, 2.7 Hz, 1H), 6.86 (ddd, J=9.0, 2.9, 1.2 Hz, 1H), 4.49 (s, 2H), 3.74-3.70 (m, 4H), 3.36-3.32 (m, 4H), 2.33 (br s, 6H); MS (ESI$^+$) m/z 475 (M+H)$^+$.

Example 82: N-{3-[2-(4-chloro-3-fluorophenoxy)acetamido]bicyclo[1.1.1]pentan-1-yl}-4-(pyrrolidin-1-yl)pyridine-2-carboxamide (Compound 181)

The title compound was prepared using the methodologies described above. $^1$H NMR (501 MHz, DMSO-d$_6$) δ ppm 9.03 (s, 1H), 8.72 (s, 1H), 8.10 (d, J=5.8 Hz, 1H), 7.50 (t, J=8.9 Hz, 1H), 7.10-7.06 (m, 2H), 6.86 (ddd, J=9.0, 2.9, 1.2 Hz, 1H), 6.58 (dd, J=5.8, 2.6 Hz, 1H), 4.49 (s, 2H), 3.30 (d, J=6.7 Hz, 4H), 2.33 (br s, 6H), 2.00-1.94 (m, 4H); MS (ESI$^+$) m/z 459 (M+H)$^+$.

Example 83: N-{3-[2-(4-chloro-3-fluorophenoxy)acetamido]bicyclo[1.1.1]pentan-1-yl}-4-cyanopyridine-2-carboxamide (Compound 182)

The title compound was prepared using the methodologies described above. $^1$H NMR (400 MHz, DMSO-d$_6$) δ ppm 9.47 (s, 1H), 8.88 (dd, J=4.9, 0.9 Hz, 1H), 8.74 (s, 1H), 8.31 (dd, J=1.6, 0.9 Hz, 1H), 8.09 (dd, J=5.0, 1.6 Hz, 1H), 7.50 (t, J=8.9 Hz, 1H), 7.08 (dd, J=11.4, 2.9 Hz, 1H), 6.86 (ddd, J=9.0, 2.9, 1.2 Hz, 1H), 4.50 (s, 2H), 2.36 (br s, 6H); MS (ESI$^+$) m/z 415 (M+H)$^+$.

Example 84: N-{3-[2-(4-chloro-3-fluorophenoxy)acetamido]bicyclo[1.1.1]pentan-1-yl}-4-hydroxypyridine-2-carboxamide (Compound 183)

The title compound was prepared using the methodologies described above. $^1$H NMR (400 MHz, DMSO-d$_6$) δ ppm 11.05 (br s, 1H), 9.16-9.07 (m, 1H), 8.71 (s, 1H), 8.25 (br s, 1H), 7.48 (t, J=8.9 Hz, 1H), 7.35 (s, 1H), 7.06 (dd, J=11.4, 2.8 Hz, 1H), 6.94-6.80 (m, 2H), 4.47 (s, 2H), 2.32 (br s, 6H); MS (ESI$^+$) m/z 406 (M+H)$^+$.

Example 85: N-{3-[2-(4-chloro-3-fluorophenoxy)acetamido]bicyclo[1.1.1]pentan-1-yl}-5-hydroxypyrazine-2-carboxamide (Compound 184)

The title compound was prepared using the methodologies described above. $^1$H NMR (501 MHz, DMSO-d$_6$) δ ppm 12.71 (br s, 1H), 8.84 (s, 1H), 8.70 (s, 1H), 7.93 (d, J=1.2 Hz, 1H), 7.91 (br s, 1H), 7.50 (t, J=8.9 Hz, 1H), 7.08 (dd, J=11.4, 2.9 Hz, 1H), 6.85 (ddd, J=9.0, 2.9, 1.2 Hz, 1H), 4.48 (s, 2H), 2.31 (br s, 6H); MS (ESI$^+$) m/z 407 (M+H)$^+$.

Example 86: N-{3-[2-(4-chlorophenoxy)acetamido]bicyclo[1.1.1]pentan-1-yl}-5-[(propan-2-yl)oxy]pyridine-2-carboxamide (Compound 185)

The title compound was prepared using the methodologies described above. $^1$H NMR (400 MHz, DMSO-d$_6$) δ ppm 9.01 (s, 1H), 8.70 (s, 1H), 8.22 (dd, J=2.9, 0.6 Hz, 1H), 7.93 (dd, J=8.7, 0.6 Hz, 1H), 7.53 (dd, J=8.8, 2.9 Hz, 1H), 7.38-7.32 (m, 2H), 7.01-6.95 (m, 2H), 4.79 (hept, J=6.0 Hz, 1H), 4.44 (s, 2H), 2.33 (br s, 6H), 1.31 (d, J=6.0 Hz, 6H); MS (ESI$^+$) m/z 430 (M+H)$^+$.

Example 87: N-{3-[2-(4-chloro-3-fluorophenoxy)acetamido]bicyclo[1.1.1]pentan-1-yl}pyridine-4-carboxamide (Compound 186)

The title compound was prepared using the methodologies described above. $^1$H NMR (500 MHz, DMSO-d$_6$) δ ppm 9.33 (s, 1H), 8.78 (s, 1H), 8.73-8.70 (m, 2H), 7.75-7.72 (m, 2H), 7.51 (t, J=8.9 Hz, 1H), 7.09 (dd, J=11.4, 2.8 Hz, 1H), 6.87 (ddd, J=9.0, 2.9, 1.2 Hz, 1H), 4.50 (s, 2H), 2.35 (br s, 6H); MS (ESI$^+$) m/z 390 (M+H)$^+$.

Example 88: N-{3-[2-(4-chloro-3-fluorophenoxy)acetamido]bicyclo[1.1.1]pentan-1-yl}pyrimidine-4-carboxamide (Compound 187)

The title compound was prepared using the methodologies described above. $^1$H NMR (500 MHz, DMSO-d$_6$) δ ppm 9.59 (s, 1H), 9.32 (d, J=1.4 Hz, 1H), 9.07 (d, J=5.1 Hz, 1H), 8.76 (s, 1H), 7.99 (dd, J=5.0, 1.4 Hz, 1H), 7.50 (t, J=8.9 Hz, 1H), 7.09 (dd, J=11.4, 2.8 Hz, 1H), 6.86 (ddd, J=9.0, 2.9, 1.2 Hz, 1H), 4.50 (s, 2H), 2.36 (br s, 6H); MS (ESI$^+$) m/z 391 (M+H)$^+$.

Example 89: N-{3-[2-(4-chloro-3-fluorophenoxy)acetamido]bicyclo[1.1.1]pentan-1-yl}pyrimidine-5-carboxamide (Compound 188)

The title compound was prepared using the methodologies described above. $^1$H NMR (500 MHz, DMSO-d$_6$) δ ppm 9.42 (s, 1H), 9.31 (s, 1H), 9.14 (s, 2H), 8.79 (s, 1H), 7.51 (t, J=8.9 Hz, 1H), 7.09 (dd, J=11.4, 2.9 Hz, 1H), 6.87 (ddd, J=9.0, 2.9, 1.2 Hz, 1H), 4.50 (s, 2H), 2.37 (br s, 6H); MS (ESI$^+$) m/z 391 (M+H)$^+$.

Example 90: N-{3-[2-(4-chloro-3-fluorophenoxy)acetamido]bicyclo[1.1.1]pentan-1-yl}-4-(3,3-difluoroazetidin-1-yl)pyridine-2-carboxamide (Compound 189)

The title compound was prepared using the methodologies described above. $^1$H NMR (500 MHz, DMSO-d$_6$) δ ppm 9.10 (s, 1H), 8.72 (s, 1H), 8.25-8.23 (m, 1H), 7.50 (t, J=8.9 Hz, 1H), 7.12-7.05 (m, 2H), 6.86 (ddd, J=9.0, 2.9, 1.2 Hz, 1H), 6.65 (dd, J=5.6, 2.5 Hz, 1H), 4.51-4.41 (m, 6H), 2.33 (br s, 6H); MS (ESI$^+$) m/z 481 (M+H)$^+$.

Example 91: N-{3-[2-(4-chloro-3-fluorophenoxy)acetamido]bicyclo[1.1.1]pentan-1-yl}-4-(3-methoxyazetidin-1-yl)pyridine-2-carboxamide (Compound 190)

The title compound was prepared using the methodologies described above. $^1$H NMR (500 MHz, DMSO-d$_6$) δ ppm 9.06 (s, 1H), 8.73 (s, 1H), 8.14 (d, J=5.6 Hz, 1H), 7.50 (t, J=8.9 Hz, 1H), 7.08 (dd, J=11.4, 2.9 Hz, 1H), 6.95 (d, J=2.4 Hz, 1H), 6.86 (ddd, J=8.9, 2.8, 1.1 Hz, 1H), 6.49 (dd, J=5.6, 2.5 Hz, 1H), 4.49 (s, 2H), 4.36 (tt, J=6.2, 3.9 Hz, 1H), 4.16 (ddd, J=8.9, 6.3, 1.0 Hz, 2H), 3.81-3.76 (m, 2H), 3.26 (s, 3H), 2.32 (br s, 6H); MS (ESI$^+$) m/z 475 (M+H)$^+$.

Example 92: N-{3-[2-(4-chloro-3-fluorophenoxy)acetamido]bicyclo[1.1.1]pentan-1-yl}-4-(difluoromethyl)benzamide (Compound 191)

The title compound was prepared using the methodologies described above. ¹H NMR (501 MHz, DMSO-d₆) δ ppm 9.15 (s, 1H), 8.74 (s, 1H), 7.93 (d, J=8.1 Hz, 2H), 7.67-7.60 (m, 2H), 7.49 (t, J=8.9 Hz, 1H), 7.22-6.93 (m, 2H), 6.85 (ddd, J=9.0, 2.9, 1.2 Hz, 1H), 4.48 (s, 2H), 2.33 (s, 6H); MS (ESI⁺) m/z 439 (M+H)⁺.

Example 93: tert-butyl {[2-({3-[2-(4-chloro-3-fluorophenoxy)acetamido]bicyclo[1.1.1]pentan-1-yl}carbamoyl)pyridin-4-yl]methyl}carbamate (Compound 192)

The title compound was prepared using the methodologies described above. ¹H NMR (501 MHz, DMSO-d₆) δ ppm 9.24 (s, 1H), 8.74 (s, 1H), 8.54 (d, J=4.9 Hz, 1H), 7.90-7.86 (m, 1H), 7.57 (t, J=6.2 Hz, 1H), 7.50 (t, J=8.8 Hz, 1H), 7.43 (dd, J=5.0, 1.7 Hz, 1H), 7.08 (dd, J=11.4, 2.8 Hz, 1H), 6.86 (ddd, J=9.0, 2.9, 1.2 Hz, 1H), 4.49 (s, 2H), 4.22 (d, J=6.2 Hz, 2H), 2.35 (br s, 6H), 1.40 (s, 9H); MS (ESI⁺) m/z 519 (M+H)⁺.

Example 94: 4-(aminomethyl)-N-{3-[2-(4-chloro-3-fluorophenoxy)acetamido]bicyclo[1.1.1]pentan-1-yl}pyridine-2-carboxamide (Compound 193)

The product of Example 93 (85 mg, 0.164 mmol) was dissolved in trifluoroacetic acid (0.5 mL, 6.5 mmol) and stirred at ambient temperature for 30 minutes. The resulting solution was concentrated under reduced pressure, and the residue was purified by preparative HPLC [Waters XBridge™ C18 5 μm OBD™ column, 30×100 mm, flow rate 40 mL/minute, 5-100% gradient of acetonitrile in buffer (0.025 M aqueous ammonium bicarbonate, adjusted to pH 10 with ammonium hydroxide)] to give the title compound (59 mg, 0.14 mmol, 86% yield). ¹H NMR (500 MHz, methanol-d₄) δ ppm 8.54 (dd, J=5.0, 0.8 Hz, 1H), 8.04 (dd, J=1.7, 0.8 Hz, 1H), 7.52 (ddd, J=5.0, 1.7, 0.8 Hz, 1H), 7.38 (t, J=8.7 Hz, 1H), 6.94 (dd, J=10.9, 2.8 Hz, 1H), 6.83 (ddd, J=8.9, 2.9, 1.3 Hz, 1H), 4.49 (s, 2H), 3.90 (s, 2H), 2.50 (br s, 6H); MS (ESI⁺) m/z 419 (M+H)⁺.

Example 95: 4-(acetamidomethyl)-N-{3-[2-(4-chloro-3-fluorophenoxy)acetamido]bicyclo[1.1.1]pentan-1-yl}pyridine-2-carboxamide (Compound 194)

The reaction and purification conditions described in Example 13 substituting acetic acid for the product of Example 12B and the product of Example 94 for the product of Example 4A gave the title compound. ¹H NMR (501 MHz, DMSO-d₆) δ ppm 9.24 (s, 1H), 8.74 (s, 1H), 8.55-8.50 (m, 2H), 7.87 (dd, J=1.7, 0.9 Hz, 1H), 7.50 (t, J=8.9 Hz, 1H), 7.46-7.43 (m, 1H), 7.08 (dd, J=11.4, 2.8 Hz, 1H), 6.86 (ddd, J=8.9, 2.8, 1.2 Hz, 1H), 4.49 (s, 2H), 4.34 (d, J=6.0 Hz, 2H), 2.35 (br s, 6H), 1.92 (s, 3H); MS (ESI⁺) m/z 461 (M+H)⁺.

Example 96: N-{4-[2-(4-chloro-3-fluorophenoxy)acetamido]-2-hydroxybicyclo[2.2.2]octan-1-yl}-5-(difluoromethyl)pyrazine-2-carboxamide (Compound 195)

The title compound was prepared using the methodologies described in Example 68 substituting 5-(difluoromethyl)pyrazine-2-carboxylic acid for picolinic acid. ¹H NMR (501 MHz, DMSO-d₆) δ ppm 9.26 (d, J=1.4 Hz, 1H), 9.01 (d, J=1.4 Hz, 1H), 8.15 (s, 1H), 7.58 (s, 1H), 7.49 (t, J=8.9 Hz, 1H), 7.21 (t, J=55.1 Hz 1H), 7.04 (dd, J=11.4, 2.9 Hz, 1H), 6.82 (ddd, J=9.0, 2.9, 1.2 Hz, 1H), 5.33 (d, J=5.2 Hz, 1H), 4.46 (s, 2H), 4.06 (ddt, J=9.0, 5.2, 2.7 Hz, 1H), 2.54 (d, J=6.1 Hz, 1H), 2.36 (ddd, J=12.8, 9.5, 2.9 Hz, 1H), 2.14-2.05 (m, 1H), 2.04-1.93 (m, 2H), 1.96-1.76 (m, 5H); MS (ESI⁺) m/z 499.1 (M+H)⁺.

Example 97: N-{3-[2-(4-chloro-3-fluorophenoxy)acetamido]bicyclo[1.1.1]pentan-1-yl}-5,6-dimethylpyrazine-2-carboxamide (Compound 196)

The title compound was prepared using the methodologies described above. ¹H NMR (500 MHz, DMSO-d₆) δ ppm 9.19 (s, 1H), 8.81 (s, 1H), 8.76 (s, 1H), 7.51 (t, J=8.9 Hz, 1H), 7.09 (dd, J=11.3, 2.9 Hz, 1H), 6.87 (ddd, J=8.8, 2.8, 1.2 Hz, 1H), 4.50 (s, 2H), 2.56 (s, 6H), 2.37 (s, 6H); MS (ESI⁺) m/z 419 (M+H)⁺.

Example 98: N-{3-[2-(4-chloro-3-fluorophenoxy)acetamido]bicyclo[1.1.1]pentan-1-yl}-4-ethylpyridine-2-carboxamide (Compound 197)

The title compound was prepared using the methodologies described above. ¹H NMR (400 MHz, DMSO-d₆) δ ppm 9.18 (s, 1H), 8.71 (s, 1H), 8.48 (dd, J=4.9, 0.8 Hz, 1H), 7.84 (dd, J=1.8, 0.8 Hz, 1H), 7.48 (t, J=8.9 Hz, 1H), 7.43 (dd, J=4.9, 1.8 Hz, 1H), 7.06 (dd, J=11.4, 2.8 Hz, 1H), 6.84 (ddd, J=9.0, 2.9, 1.2 Hz, 1H), 4.47 (s, 2H), 2.69 (q, J=7.6 Hz, 2H), 2.33 (br s, 6H), 1.19 (t, J=7.6 Hz, 3H); MS (ESI⁺) m/z 418 (M+H)⁺.

Example 99: N-{3-[2-(4-chloro-3-fluorophenoxy)acetamido]bicyclo[1.1.1]pentan-1-yl}benzamide (Compound 198)

The title compound was prepared using the methodologies described above. ¹H NMR (400 MHz, DMSO-d₆) δ ppm 9.00 (s, 1H), 8.74 (s, 1H), 7.87-7.79 (m, 2H), 7.57-7.40 (m, 4H), 7.09 (dd, J=11.4, 2.9 Hz, 1H), 6.87 (ddd, J=9.0, 2.9, 1.2 Hz, 1H), 4.50 (s, 2H), 2.34 (br s, 6H); MS (ESI⁺) m/z 389 (M+H)⁺.

Example 100: 4-chloro-N-{3-[2-(4-chloro-3-fluorophenoxy)acetamido]bicyclo[1.1.1]pentan-1-yl}benzamide (Compound 199)

The title compound was prepared using the methodologies described above. ¹H NMR (400 MHz, DMSO-d₆) δ ppm 9.10 (s, 1H), 8.75 (s, 1H), 7.89-7.83 (m, 2H), 7.55-7.47 (m, 3H), 7.09 (dd, J=11.4, 2.8 Hz, 1H), 6.87 (ddd, J=9.0, 2.8, 1.2 Hz, 1H), 4.49 (s, 2H), 2.33 (br s, 6H); MS (ESI⁺) m/z 423 (M+H)⁺.

Example 101: N-{3-[2-(4-chloro-3-fluorophenoxy)acetamido]bicyclo[1.1.1]pentan-1-yl}-4-[(1E)-3-hydroxyprop-1-en-1-yl]pyridine-2-carboxamide (Compound 200)

Example 101A: (E)-tert-butyl 4-(3-hydroxyprop-1-en-1-yl)picolinate

The reaction and purification conditions described in Example 39A substituting (E)-3-(4,4,5,5-tetramethyl-1,3,2-dioxaborolan-2-yl)-2-propen-1-ol (AniChem) for 3,6-dihydro-2H-pyran-4-boronic acid pinacol ester, and tert-butyl 4-bromopyridine-2-carboxylate (Aldrich) for ethyl 2-bromooxazole-5-carboxylate gave the title compound. MS (ESI$^+$) m/z 236 (M+H)$^+$.

Example 101B: (E)-4-(3-hydroxyprop-1-en-1-yl) picolinic acid

The product of Example 101A (26 mg, 0.11 mmol) was dissolved in trifluoroacetic acid (2.0 mL, 26 mmol) and stirred at ambient temperature for 18 hours. The resulting solution was concentrated under reduced pressure, and the residue was purified by preparative HPLC [YMC TriArt™ C18 Hybrid 20 μm column, 25×150 mm, flow rate 80 mL/minute, 0-100% gradient of acetonitrile in carbonic acid buffer (prepared by sparging carbon dioxide gas bubbled through deionized water for 15 minutes immediately before use)] to give the title compound (15 mg, 0.084 mmol, 76% yield). MS (ESI$^+$) m/z 180 (M+H)$^+$.

Example 101C: N-{3-[2-(4-chloro-3-fluorophenoxy) acetamido]bicyclo[1.1.1]pentan-1-yl}-4-[(1E)-3-hydroxyprop-1-en-1-yl]pyridine-2-carboxamide The reaction and purification conditions described in Example 13 substituting the product of Example 101B for the product of Example 12B gave the title compound. $^1$H NMR (501 MHz, DMSO-d$_6$) δ ppm 8.56-8.52 (m, 1H), 8.09 (d, J=1.7 Hz, 1H), 7.58 (dd, J=5.2, 1.8 Hz, 1H), 7.38 (t, J=8.7 Hz, 1H), 6.94 (dd, J=11.0, 2.9 Hz, 1H), 6.85-6.69 (m, 3H), 4.50 (s, 2H), 4.31 (dd, J=4.6, 1.7 Hz, 2H), 2.51 (br s, 6H); MS (ESI$^+$) m/z 446 (M+H)$^+$.

Example 102: N-{3-[2-(3,4-dichlorophenoxy)acetamido]bicyclo[1.1.1]pentan-1-yl}-5-(difluoromethyl)pyrazine-2-carboxamide (Compound 201)

The title compound was prepared using the methodologies described above. $^1$H NMR (400 MHz, DMSO-d$_6$) δ ppm 9.63 (s, 1H), 9.26-9.24 (m, 1H), 9.01-8.98 (m, 1H), 8.76 (s, 1H), 7.56 (d, J=8.9 Hz, 1H), 7.28 (d, J=2.9 Hz, 1H), 7.21 (t, J=54.0 Hz, 1H), 7.00 (dd, J=9.0, 2.9 Hz, 1H), 4.51 (s, 2H), 2.37 (br s, 6H); MS (ESI$^+$) m/z 457 (M+H)$^+$.

Example 103: N-{3-[2-(4-chlorophenoxy)acetamido]bicyclo[1.1.1]pentan-1-yl}-5-(difluoromethyl)pyrazine-2-carboxamide (Compound 202)

The title compound was prepared using the methodologies described above. $^1$H NMR (501 MHz, DMSO-d$_6$) δ ppm 9.63 (s, 1H), 9.26-9.24 (m, 1H), 9.01-8.98 (m, 1H), 8.75 (s, 1H), 7.37-7.33 (m, 2H), 7.21 (t, J=54.0 Hz, 1H), 7.01-6.96 (m, 2H), 4.45 (s, 2H), 2.37 (br s, 6H); MS (ESI$^+$) m/z 423 (M+H)$^+$.

Example 104: N-{3-[2-(4-chloro-3-fluorophenoxy) acetamido]bicyclo[1.1.1]pentan-1-yl}-6-(trifluoromethyl)pyridine-3-carboxamide (Compound 203)

The title compound was prepared using the methodologies described above. $^1$H NMR (501 MHz, DMSO-d$_6$) δ ppm 9.47 (s, 1H), 9.13-9.12 (m, 1H), 8.78 (s, 1H), 8.46-8.43 (m, 1H), 8.04 (dd, J=8.3, 0.8 Hz, 1H), 7.51 (t, J=8.9 Hz, 1H), 7.09 (dd, J=11.4, 2.9 Hz, 1H), 6.87 (ddd, J=9.0, 2.9, 1.2 Hz, 1H), 4.50 (s, 2H), 2.37 (br s, 6H); MS (ESI$^+$) m/z 458 (M+H)$^+$.

Example 105: ethyl 2-({3-[2-(4-chloro-3-fluorophenoxy)acetamido]bicyclo[1.1.1]pentan-1-yl}carbamoyl)pyridine-4-carboxylate (Compound 204)

The title compound was prepared using the methodologies described above. $^1$H NMR (400 MHz, DMSO-d$_6$) δ ppm 9.43 (s, 1H), 8.84 (dd, J=4.9, 0.9 Hz, 1H), 8.75 (s, 1H), 8.38 (dd, J=1.8, 0.9 Hz, 1H), 8.03 (dd, J=5.0, 1.7 Hz, 1H), 7.50 (t, J=8.9 Hz, 1H), 7.08 (dd, J=11.4, 2.9 Hz, 1H), 6.86 (ddd, J=8.9, 2.8, 1.2 Hz, 1H), 4.49 (s, 2H), 4.39 (q, J=7.1 Hz, 2H), 2.36 (br s, 6H), 1.35 (t, J=7.1 Hz, 3H); MS (ESI$^+$) m/z 462 (M+H)$^+$.

Example 106: N-{3-[2-(4-chloro-3-fluorophenoxy) acetamido]bicyclo[1.1.1]pentan-1-yl}-2-oxo-2,3-dihydro-1H-imidazo[4,5-b]pyridine-5-carboxamide (Compound 205)

The title compound was prepared using the methodologies described above. $^1$H NMR (400 MHz, DMSO-d$_6$) δ ppm 11.44 (s, 1H), 11.18 (s, 1H), 8.73 (s, 1H), 8.63 (s, 1H), 7.63 (d, J=8.0 Hz, 1H), 7.49 (t, J=8.9 Hz, 1H), 7.32 (d, J=7.9 Hz, 1H), 7.07 (dd, J=11.4, 2.8 Hz, 1H), 6.84 (ddd, J=8.9, 2.9, 1.2 Hz, 1H), 4.47 (s, 2H), 2.32 (s, 6H); MS (ESI$^+$) m/z 446 (M+H)$^+$.

Example 107: N-{3-[2-(4-chloro-3-fluorophenoxy) acetamido]bicyclo[1.1.1]pentan-1-yl}-2-(cyanomethyl)benzamide (Compound 206)

The title compound was prepared using the methodologies described above. $^1$H NMR (400 MHz, DMSO-d$_6$) δ ppm 9.04 (s, 1H), 8.71 (s, 1H), 7.50-7.41 (m, 4H), 7.38 (td, J=7.1, 2.1 Hz, 1H), 7.05 (dd, J=11.4, 2.9 Hz, 1H), 6.83 (ddd, J=9.0, 2.8, 1.2 Hz, 1H), 4.46 (s, 2H), 4.07 (s, 2H), 2.30 (s, 6H); MS (ESI$^+$) m/z 428 (M+H)$^+$.

Example 108: N-{3-[2-(4-chloro-3-fluorophenoxy) acetamido]bicyclo[1.1.1]pentan-1-yl}-6-(difluoromethyl)pyridine-3-carboxamide (Compound 207)

The title compound was prepared using the methodologies described above. $^1$H NMR (400 MHz, DMSO-d$_6$) δ ppm 9.37 (s, 1H), 9.06-9.02 (m, 1H), 8.77 (s, 1H), 8.34 (dd, J=8.1, 2.2 Hz, 1H), 7.79 (d, J=8.2 Hz, 1H), 7.49 (t, J=8.9 Hz, 1H), 7.07 (dd, J=11.3, 2.9 Hz, 1H), 7.01 (s, 1H), 6.85 (ddd, J=9.0, 3.0, 1.3 Hz, 1H), 4.48 (s, 2H), 2.35 (s, 6H); MS (ESI$^+$) m/z 440 (M+H)$^+$.

Example 109: N-{3-[2-(4-chloro-3-fluorophenoxy) acetamido]bicyclo[1.1.1]pentan-1-yl}-4-(2-hydroxypropan-2-yl)benzamide (Compound 208)

The title compound was prepared using the methodologies described above. $^1$H NMR (400 MHz, DMSO-d$_6$) δ ppm 8.88 (s, 1H), 8.70 (s, 1H), 7.73 (d, J=8.5 Hz, 2H), 7.52-7.41 (m, 3H), 7.05 (dd, J=11.4, 2.8 Hz, 1H), 6.83 (ddd, J=8.9, 2.8, 1.2 Hz, 1H), 5.06 (s, 1H), 4.46 (s, 2H), 2.29 (s, 6H), 1.39 (s, 6H); MS (ESI$^+$) m/z 447 (M+H)$^+$.

Example 110: N-{4-[2-(4-chloro-3-fluorophenoxy) acetamido]-2-hydroxybicyclo[2.2.2]octan-1-yl}-3-cyanobenzamide (Compound 209)

A 4 mL vial was charged with a stir bar, a 500 μL solution of Example 68I (47.74 mg, 0.13 mmol) in N,N-dimethylacetamide, a 395.7 µL aliquot of a 0.35 mmol pre-weighed vial with a solution of 3-cyanobenzoic acid (20.58 mg, 0.14 mmol) in 1000 µL of N,N-dimethylacetamide, a 500 µL solution of 2-(3H-[1,2,3]triazolo[4,5-b]pyridin-3-yl)-1,1,3,3-tetramethylisouronium hexafluorophosphate(V) (57.4 mg, 0.15 mmol) in N,N-dimethylacetamide, and triethylamine (53.01 µL, 0.38 mmol). This was capped and placed to stir at room temperature for 1 hour. Upon completion, the mixture was concentrated to dryness and dissolved in 1.4 mL of dimethyl sulfoxide/methanol (1:1 v/v). The crude material was purified by HPLC purification (HPLC was performed on Phenomenex® Luna® C8(2) 5 m 100A AXIA™ column (30 mm×75 mm) with a gradient of 10-100% acetonitrile (A) in 0.1% trifluoroacetic acid in water (B) at a flow rate of 50 mL/minute) to give 17.1 mg of product as a solid. $^1$H NMR (400 MHz, DMSO-d$_6$) δ ppm 8.20 (t, J=1.6 Hz, 1H), 8.10-8.03 (m, 1H), 7.96 (dt, J=7.7, 1.4 Hz, 1H), 7.74-7.58 (m, 1H), 7.48 (t, J=8.9 Hz, 1H), 7.02 (dd, J=11.4, 2.9 Hz, 1H), 6.83 (ddd, J=9.0, 2.9, 1.2 Hz, 1H), 4.44 (s, 2H), 4.35-4.27 (m, 1H), 2.34 (ddd, J=12.7, 9.4, 2.7 Hz, 1H), 2.07 (ddt, J=31.7, 19.4, 8.6 Hz, 3H), 2.00-1.79 (m, 5H), 1.77 (dt, J=13.3, 2.8 Hz, 1H); MS (ESI$^+$) m/z 472.1 (M+H)$^+$.

Example 111: N-{4-[2-(4-chloro-3-fluorophenoxy)acetamido]-2-hydroxybicyclo[2.2.2]octan-1-yl}-4-cyanobenzamide (Compound 210)

The title compound was prepared using the methodologies described in Example 110 substituting 4-cyanobenzoic acid for 3-cyanobenzoic acid. $^1$H NMR (400 MHz, DMSO-d$_6$) δ ppm 7.91 (s, 4H), 7.73 (s, 1H), 7.60 (s, 1H), 7.48 (t, J=8.9 Hz, 1H), 7.02 (dd, J=11.4, 2.9 Hz, 1H), 6.83 (ddd, J=9.0, 2.9, 1.2 Hz, 1H), 4.44 (s, 2H), 4.33-4.25 (m, 1H), 2.34 (ddd, J=12.7, 9.4, 2.7 Hz, 1H), 2.16-1.72 (m, 9H); MS (ESI$^+$) m/z 472.1 (M+H)$^+$.

Example 112: N-{4-[2-(4-chloro-3-fluorophenoxy)acetamido]-2-hydroxybicyclo[2.2.2]octan-1-yl}-2H-1,3-benzodioxole-5-carboxamide (Compound 211)

The title compound was prepared using the methodologies described in Example 110 substituting 2H-1,3-benzodioxole-5-carboxylic acid for 3-cyanobenzoic acid. $^1$H NMR (400 MHz, DMSO-d$_6$) δ ppm 7.48 (t, J=8.9 Hz, 1H), 7.41-7.28 (m, 2H), 7.02 (dd, J=11.4, 2.9 Hz, 1H), 6.95 (d, J=8.1 Hz, 1H), 6.83 (ddd, J=9.0, 2.9, 1.2 Hz, 1H), 6.07 (s, 2H), 4.44 (s, 2H), 4.22-4.14 (m, 1H), 2.33 (ddd, J=12.6, 9.3, 2.8 Hz, 1H), 2.15-1.98 (m, 1H), 1.99-1.71 (m, 8H); MS (ESI$^+$) m/z 491.1 (M+H)$^+$.

Example 113: N-{4-[2-(4-chloro-3-fluorophenoxy)acetamido]-2-hydroxybicyclo[2.2.2]octan-1-yl}-1,3-thiazole-4-carboxamide (Compound 212)

The title compound was prepared using the methodologies described in Example 110 substituting 1,3-thiazole-4-carboxaylic acid for 3-cyanobenzoic acid. $^1$H NMR (400 MHz, DMSO-d$_6$) δ ppm 9.11 (d, J=2.0 Hz, 1H), 8.25 (d, J=2.0 Hz, 1H), 7.48 (t, J=8.9 Hz, 1H), 7.02 (dd, J=11.4, 2.9 Hz, 1H), 6.83 (ddd, J=8.9, 2.9, 1.2 Hz, 1H), 4.44 (s, 2H), 4.00 (ddd, J=9.5, 3.8, 1.5 Hz, 1H), 2.48 (dd, J=13.2, 7.2 Hz, 1H), 2.36 (ddd, J=12.5, 9.4, 2.7 Hz, 1H), 2.13-1.90 (m, 4H), 1.84 (dt, J=16.5, 6.1 Hz, 4H); MS (ESI$^+$) m/z 454.1 (M+H)$^+$.

Example 114: N-{4-[2-(4-chloro-3-fluorophenoxy)acetamido]-2-hydroxybicyclo[2.2.2]octan-1-yl}-1,3-thiazole-5-carboxamide (Compound 213)

The title compound was prepared using the methodologies described in Example 110 substituting 1,3-thiazole-5-carboxaylic acid for 3-cyanobenzoic acid. $^1$H NMR (400 MHz, DMSO-d$_6$) δ ppm 9.15 (d, J=0.6 Hz, 1H), 8.46 (d, J=0.7 Hz, 1H), 7.71 (s, 1H), 7.60 (s, 1H), 7.48 (t, J=8.9 Hz, 1H), 7.02 (dd, J=11.4, 2.9 Hz, 1H), 6.83 (ddd, J=8.9, 2.9, 1.2 Hz, 1H), 4.43 (s, 2H), 4.28 (d, J=7.6 Hz, 1H), 2.36-2.27 (m, 1H), 2.14-2.01 (m, 2H), 1.95 (td, J=12.1, 11.3, 5.6 Hz, 1H), 1.85 (s, 3H), 1.84-1.71 (m, 2H); MS (ESI$^+$) m/z 454.1 (M+H)$^+$.

Example 115: N-{4-[2-(4-chloro-3-fluorophenoxy)acetamido]-2-hydroxybicyclo[2.2.2]octan-1-yl}-1H-pyrazole-4-carboxamide (Compound 214)

The title compound was prepared using the methodologies described in Example 110 substituting 1H-pyrazole-4-carboxylic acid for 3-cyanobenzoic acid. $^1$H NMR (400 MHz, DMSO-d$_6$) δ ppm 8.03 (s, 2H), 7.48 (t, J=8.9 Hz, 1H), 7.02 (dd, J=11.4, 2.8 Hz, 1H), 6.83 (ddd, J=9.0, 2.9, 1.2 Hz, 1H), 4.43 (s, 2H), 4.19-4.11 (m, 1H), 2.36-2.26 (m, 1H), 2.13-2.03 (m, 1H), 2.05-1.93 (m, 2H), 1.91-1.70 (m, 6H); MS (ESI$^+$) m/z 437.1 (M+H)$^+$.

Example 116: N-{4-[2-(4-chloro-3-fluorophenoxy)acetamido]-2-hydroxybicyclo[2.2.2]octan-1-yl}-1,2-oxazole-5-carboxamide (Compound 215)

The title compound was prepared using the methodologies described in Example 110 substituting 1,2-oxazole-5-carboxylic acid for 3-cyanobenzoic acid. $^1$H NMR (400 MHz, DMSO-d$_6$) δ ppm 8.67 (d, J=1.9 Hz, 1H), 7.48 (t, J=8.9 Hz, 1H), 7.06-6.97 (m, 2H), 6.83 (ddd, J=9.0, 2.9, 1.2 Hz, 1H), 4.44 (s, 2H), 4.28-4.20 (m, 1H), 2.34 (ddd, J=12.8, 9.5, 2.9 Hz, 1H), 2.12-1.73 (m, 9H); MS (ESI$^+$) m/z 438.1 (M+H)$^+$.

Example 117: N-{4-[2-(4-chloro-3-fluorophenoxy)acetamido]-2-hydroxybicyclo[2.2.2]octan-1-yl}-3,5-dimethyl-1,2-oxazole-4-carboxamide (Compound 216)

The title compound was prepared using the methodologies described in Example 110 substituting 3,5-dimethyl-1,2-oxazole-4-carboxylic acid for 3-cyanobenzoic acid. $^1$H NMR (400 MHz, DMSO-d$_6$) δ 7.48 (t, J=8.9 Hz, 1H), 7.02 (dd, J=11.4, 2.8 Hz, 1H), 6.83 (ddd, J=9.0, 2.9, 1.2 Hz, 1H), 4.43 (s, 2H), 4.23-4.15 (m, 1H), 2.45 (s, 3H), 2.41-2.27 (m, 1H), 2.25 (s, 3H), 2.08-1.94 (m, 4H), 1.96-1.73 (m, 5H); MS (ESI$^+$) m/z 466.1 (M+H)$^+$.

Example 118: N-{4-[2-(4-chloro-3-fluorophenoxy)acetamido]-2-hydroxybicyclo[2.2.2]octan-1-yl}pyridine-3-carboxamide (Compound 217)

The title compound was prepared using the methodologies described in Example 110 substituting nicotinic acid for 3-cyanobenzoic acid. $^1$H NMR (400 MHz, DMSO-d$_6$) δ ppm 9.02 (d, J=2.0 Hz, 1H), 8.84-8.74 (m, 1H), 8.53-8.40 (m, 1H), 7.77 (ddd, J=8.1, 5.2, 0.8 Hz, 1H), 7.48 (t, J=8.8

Hz, 1H), 7.02 (dd, J=11.4, 2.8 Hz, 1H), 6.83 (ddd, J=9.0, 2.9, 1.2 Hz, 1H), 4.44 (s, 2H), 4.39-4.30 (m, 1H), 2.34 (ddd, J=13.0, 9.3, 2.5 Hz, 1H), 2.21-2.03 (m, 3H), 2.03-1.73 (m, 6H); MS (ESI$^+$) m/z 448.1 (M+H)$^+$.

Example 119: N-{4-[2-(4-chloro-3-fluorophenoxy) acetamido]-2-hydroxybicyclo[2.2.2]octan-1-yl}pyridine-4-carboxamide (Compound 218)

The title compound was prepared using the methodologies described in Example 110 substituting isonicotinic acid for 3-cyanobenzoic acid. $^1$H NMR (400 MHz, DMSO-d$_6$) δ 8.89-8.77 (m, 2H), 8.06-7.93 (m, 2H), 7.48 (t, J=8.9 Hz, 1H), 7.02 (dd, J=11.4, 2.9 Hz, 1H), 6.83 (ddd, J=9.0, 2.9, 1.2 Hz, 1H), 4.45 (d, J=7.9 Hz, 2H), 4.39-4.31 (m, 1H), 2.40-2.29 (m, 1H), 2.18-1.76 (m, 9H); MS (ESI$^+$) m/z 448.1 (M+H)$^+$.

Example 120: N-{4-[2-(4-chloro-3-fluorophenoxy) acetamido]-2-hydroxybicyclo[2.2.2]octan-1-yl}pyrazine-2-carboxamide (Compound 219)

The title compound was prepared using the methodologies described in Example 110 substituting pyrazine-2-carboxylic acid for 3-cyanobenzoic acid. $^1$H NMR (400 MHz, DMSO-d$_6$) δ ppm 9.16 (d, J=1.5 Hz, 1H), 8.86 (d, J=2.5 Hz, 1H), 8.70 (dd, J=2.5, 1.5 Hz, 1H), 7.48 (t, J=8.9 Hz, 1H), 7.02 (dd, J=11.4, 2.9 Hz, 1H), 6.83 (ddd, J=9.0, 2.9, 1.2 Hz, 1H), 4.44 (s, 2H), 4.11-4.03 (m, 1H), 2.53-2.38 (m, 1H), 2.37 (td, J=9.6, 9.2, 4.7 Hz, 1H), 2.13-2.03 (m, 1H), 2.08-1.92 (m, 2H), 1.86 (p, J=9.6, 8.4 Hz, 5H); MS (ESI$^+$) m/z 449.1 (M+H)$^+$.

Example 121: N-{4-[2-(4-chloro-3-fluorophenoxy) acetamido]-2-hydroxybicyclo[2.2.2]octan-1-yl}-5-methylpyrazine-2-carboxamide (Compound 220)

The title compound was prepared using the methodologies described in Example 110 substituting 5-methylpyrazine-2-carboxylic acid for 3-cyanobenzoic acid. $^1$H NMR (400 MHz, DMSO-d$_6$) δ ppm 9.01 (d, J=1.3 Hz, 1H), 8.57 (d, J=1.4 Hz, 1H), 7.48 (t, J=8.9 Hz, 1H), 7.02 (dd, J=11.4, 2.8 Hz, 1H), 6.87-6.80 (m, 1H), 4.44 (s, 2H), 4.05 (m, 1H), 2.58 (s, 3H), 2.36 (m, 1H), 2.07 (d, J=10.9 Hz, 1H), 1.96 (m, 2H), 1.86 (d, J=9.8 Hz, 6H); MS (ESI$^+$) m/z 463.1 (M+H)$^+$.

Example 122: N-{4-[2-(4-chloro-3-fluorophenoxy) acetamido]-2-hydroxybicyclo[2.2.2]octan-1-yl}-5-methyl-1-phenyl-1H-pyrazole-4-carboxamide (Compound 221)

The title compound was prepared using the methodologies described in Example 110 substituting 5-methyl-1-phenyl-1H-pyrazole-4-carboxylic acid for 3-cyanobenzoic acid. $^1$H NMR (400 MHz, DMSO-d$_6$) δ ppm 8.08 (s, 1H), 7.73-7.44 (m, 8H), 7.02 (dd, J=11.4, 2.8 Hz, 1H), 6.83 (ddd, J=9.0, 2.9, 1.2 Hz, 1H), 4.44 (s, 2H), 4.17 (d, J=7.8 Hz, 1H), 2.45 (s, 3H), 2.36-2.27 (m, 1H), 2.13-1.99 (m, 2H), 1.96 (d, J=16.1 Hz, 2H), 1.94-1.72 (m, 5H). MS (ESI$^+$) m/z 527.1 (M+H)$^+$.

Example 123: N-{4-[2-(4-chloro-3-fluorophenoxy) acetamido]-2-hydroxybicyclo[2.2.2]octan-1-yl}-4-oxo-4,5,6,7-tetrahydro-1-benzofuran-3-carboxamide (Compound 222)

The title compound was prepared using the methodologies described in Example 110 substituting 4-oxo-4,5,6,7-tetrahydro-1-benzofuran-3-carboxylic acid for 3-cyanobenzoic acid. $^1$H NMR (400 MHz, DMSO-d$_6$) δ ppm 9.56 (s, 1H), 8.12 (s, 1H), 7.60 (s, 1H), 7.48 (t, J=8.9 Hz, 1H), 7.02 (dd, J=11.4, 2.9 Hz, 1H), 6.83 (ddd, J=8.9, 2.8, 1.2 Hz, 1H), 4.44 (s, 2H), 4.24 (d, J=8.3 Hz, 1H), 2.93 (t, J=6.2 Hz, 2H), 2.60-2.53 (m, 4H), 2.37-2.26 (m, 1H), 2.11 (q, J=6.7 Hz, 4H), 1.91-1.71 (m, 5H); MS (ESI$^+$) m/z 505.1 (M+H)$^+$.

Example 124: N-{4-[2-(4-chloro-3-fluorophenoxy) acetamido]-2-hydroxybicyclo[2.2.2]octan-1-yl}quinoxaline-2-carboxamide (Compound 223)

The title compound was prepared using the methodologies described in Example 110 substituting quinoxaline-2-carboxylic acid for 3-cyanobenzoic acid. $^1$H NMR (400 MHz, DMSO-d$_6$) δ ppm 9.46 (s, 1H), 8.29-8.16 (m, 2H), 8.06-7.94 (m, 2H), 7.49 (t, J=8.9 Hz, 1H), 7.03 (dd, J=11.4, 2.8 Hz, 1H), 6.84 (ddd, J=8.9, 2.9, 1.2 Hz, 1H), 4.46 (s, 2H), 4.22-4.14 (m, 1H), 2.52-2.35 (m, 2H), 2.17-2.05 (m, 1H), 2.08-1.99 (m, 2H), 1.93 (dq, J=21.1, 12.9, 10.5 Hz, 5H); MS (ESI$^+$) m/z 499.1 (M+H)$^+$.

Example 125: N-{4-[2-(4-chloro-3-fluorophenoxy) acetamido]-2-hydroxybicyclo[2.2.2]octan-1-yl}-1H-pyrazole-5-carboxamide (Compound 224)

The title compound was prepared using the methodologies described in Example 110 substituting 1H-pyrazole-5-carboxylic acid for 3-cyanobenzoic acid. $^1$H NMR (400 MHz, DMSO-d$_6$) δ ppm 7.78 (s, 1H), 7.48 (t, J=8.9 Hz, 1H), 7.02 (dd, J=11.3, 2.9 Hz, 1H), 6.83 (ddd, J=9.0, 2.9, 1.2 Hz, 1H), 6.63 (s, 1H), 4.44 (s, 2H), 3.96 (m, 1H), 2.45 (s, 1H), 2.35 (td, J=11.7, 10.6, 5.3 Hz, 1H), 1.95-1.73 (m, 8H); MS (ESI$^+$) m/z 437.1 (M+H)$^+$.

Example 126: N-{4-[2-(4-chloro-3-fluorophenoxy) acetamido]-2-hydroxybicyclo[2.2.2]octan-1-yl}-4-(trifluoromethoxy)benzamide (Compound 225)

The title compound was prepared using the methodologies described in Example 110 substituting 4-(trifluoromethoxy)benzoic acid for 3-cyanobenzoic acid. $^1$H NMR (400 MHz, DMSO-d$_6$) δ ppm 7.92-7.84 (m, 2H), 7.59 (d, J=7.1 Hz, 1H), 7.48 (t, J=8.9 Hz, 1H), 7.46-7.38 (m, 2H), 7.02 (dd, J=11.4, 2.9 Hz, 1H), 6.83 (ddd, J=9.0, 2.9, 1.2 Hz, 1H), 4.44 (s, 2H), 4.26 (dd, J=8.6, 2.1 Hz, 1H), 2.34 (ddd, J=12.6, 9.3, 2.9 Hz, 1H), 2.09-1.99 (m, 5H), 2.00-1.72 (m, 4H); MS (ESI$^+$) m/z 531.0 (M+H)$^+$.

Example 127: N-{4-[2-(4-chloro-3-fluorophenoxy) acetamido]-2-hydroxybicyclo[2.2.2]octan-1-yl}pyrimidine-4-carboxamide (Compound 226)

The title compound was prepared using the methodologies described in Example 110 substituting pyrimidine-4-carboxylix acid for 3-cyanobenzoic acid. $^1$H NMR (400 MHz, DMSO-d$_6$) δ 9.29 (d, J=1.4 Hz, 1H), 9.06 (d, J=5.1 Hz, 1H), 8.30 (s, 1H), 8.01 (dd, J=5.1, 1.4 Hz, 1H), 7.63 (s, 1H), 7.48 (t, J=8.9 Hz, 1H), 7.02 (dd, J=11.4, 2.9 Hz, 1H), 6.83 (ddd, J=9.0, 2.9, 1.2 Hz, 1H), 4.44 (s, 2H), 4.06 (d, J=6.7 Hz, 1H), 2.52-2.33 (m, 2H), 2.13-2.03 (m, 1H), 2.05-1.91 (m, 2H), 1.90-1.75 (m, 6H); MS (ESI$^+$) m/z 449.1 (M+H)$^+$.

Example 128: N-{4-[2-(4-chloro-3-fluorophenoxy) acetamido]-2-hydroxybicyclo[2.2.2]octan-1-yl}pyridazine-3-carboxamide (Compound 227)

The title compound was prepared using the methodologies described in Example 110 substituting pyridazine-3- carboxylic acid for 3-cyanobenzoic acid. ¹H NMR (400 MHz, DMSO-d₆) δ ppm 9.38 (dd, J=5.0, 1.7 Hz, 1H), 8.20 (dd, J=8.4, 1.7 Hz, 1H), 7.91 (dd, J=8.5, 5.0 Hz, 1H), 7.48 (t, J=8.9 Hz, 1H), 7.03 (dd, J=11.4, 2.9 Hz, 1H), 6.84 (ddd, J=9.0, 2.9, 1.2 Hz, 1H), 4.45 (s, 2H), 4.15-4.06 (m, 1H), 2.53-2.44 (m, 1H), 2.39 (ddd, J=12.7, 9.5, 2.8 Hz, 1H), 2.11 (q, J=11.3, 10.4 Hz, 1H), 2.02 (dd, J=20.3, 8.6 Hz, 2H), 1.87 (t, J=8.1 Hz, 5H); MS (ESI⁺) m/z 449.1 (M+H)⁺.

Example 129: N-{4-[2-(4-chloro-3-fluorophenoxy) acetamido]-2-hydroxybicyclo[2.2.2]octan-1-yl}-6-methylpyridine-3-carboxamide (Compound 228)

The title compound was prepared using the methodologies described in Example 110 substituting 6-methylpyridine-3-carboxylic acid for 3-cyanobenzoic acid. ¹H NMR (400 MHz, DMSO-d₆) δ ppm 8.98-8.93 (m, 1H), 8.51 (dd, J=8.3, 2.2 Hz, 1H), 7.81-7.74 (m, 1H), 7.48 (t, J=8.9 Hz, 1H), 7.02 (dd, J=11.4, 2.8 Hz, 1H), 6.83 (ddd, J=9.0, 2.9, 1.2 Hz, 1H), 4.44 (s, 2H), 4.40-4.31 (m, 1H), 2.69 (s, 3H), 2.39-2.29 (m, 1H), 2.25-2.15 (m, 1H), 2.14-1.74 (m, 8H); MS (ESI⁺) m/z 462.1 (M+H)⁺.

Example 130: N-{4-[2-(4-chloro-3-fluorophenoxy) acetamido]-3-hydroxybicyclo[2.2.2]octan-1-yl}-5-(difluoromethyl)pyrazine-2-carboxamide (Compound 229)

Example 130A: 4-(benzylamino)-2-oxobicyclo [2.2.2]octane-1-carboxylic acid hydrochloride A mixture of 68D (20.7 g, 61.3 mmol) and 25% aqueous sodium hydroxide (49.0 mL, 306 mmol) in methanol (200 mL) and water (200 mL) was stirred for 24 hours at ambient temperature. The mixture was concentrated, and the residue was acidified with 1 N HCl. The precipitate was collected by filtration, washed with water, and air dried to give 16.4 g of the title compound as a yellow solid. ¹H NMR (400 MHz, DMSO-d₆) δ ppm 12.70 (s, 1H), 9.67 (s, 2H), 7.62 (dd, J=7.5, 2.0 Hz, 2H), 7.43 (d, J=6.6 Hz, 3H), 4.13 (s, 2H), 2.87 (s, 2H), 2.08 (tdq, J=14.4, 10.8, 5.8, 5.0 Hz, 8H).

Example 130B: 1-amino-4-(benzylamino)bicyclo [2.2.2]octan-2-one, Trifluoroacetic Acid To a mixture of Example 130A (5.0 g, 16.14 mmol) and oxalyl dichloride (24.21 mL, 48.4 mmol) in dichloromethane (100 mL) was added N,N-dimethylformamide (0.250 mL, 3.23 mmol), and the suspension was stirred at ambient temperature for 14 hours. The mixture was concentrated, and the residue was triturated with ether/heptane. The precipitate was collected by filtration and dried to give 4.99 g of crude product as a light yellow solid which was used in next step without further purification. To a mixture of sodium azide (0.832 g, 12.80 mmol) in dioxane (10 mL) and water (10 mL) at 0° C. was added a suspension of the crude 4-(benzylamino)-2-oxobicyclo[2.2.2]octane-1-carbonyl chloride (0.934 g, 3.2 mmol) in dioxane (30 mL), and the clear orange solution was stirred at ambient temperature for 30 minutes. Volatiles were removed to give the crude material as a pale white solid which was suspended with 50 mL of toluene and heated at 65° C. for 2 hours to convert to the isocyanate. Then 3 N HCl (40 mL) was added carefully, and the mixture was stirred at 100° C. for 3 hours. Volatiles were removed under vacuum, and the residue was stirred with methanol and the inorganic salts were removed by filtration. The filtrate was concentrated, and the residue was purified by HPLC (0-60% acetonitrile in 0.1% trifluoroacetic acid/water on Phenomenex® C18 10 μm (250 mm×50 mm) column at a flowrate of 50 mL/minute) to give 550 mg of title compound as a white solid. ¹H NMR (400 MHz, DMSO-d₆) δ ppm 9.47 (s, 2H), 8.59 (s, 3H), 7.55-7.39 (m, 5H), 4.18 (s, 2H), 3.01 (s, 2H), 2.28-2.09 (m, 6H), 1.96 (td, J=12.6, 12.0, 7.0 Hz, 2H); MS (ESI⁺) m/z 245.1 (M+H)⁺.

Example 130C: N-[4-(benzylamino)-2-oxobicyclo [2.2.2]octan-1-yl]-2-(4-chloro-3-fluorophenoxy) acetamide A mixture of Example 130B (0.66 g, 0.699 mmol), 2-(4-chloro-3-fluorophenoxy)acetic acid (0.179 g, 0.873 mmol) and N-ethyl-N-isopropylpropan-2-amine (0.610 mL, 3.49 mmol) in N,N-dimethylformamide (10 mL) was treated with 2-(3H-[1,2,3]triazolo[4,5-b]pyridin-3-yl)-1,1,3,3-tetramethylisouronium hexafluorophosphate(V) (0.398 g, 1.048 mmol), and the reaction mixture was stirred at ambient temperature for 15 minutes. The reaction mixture was partitioned between water and dichloromethane. The organic layer was concentrated, and the residue was purified by HPLC (15-100% acetonitrile in 0.1% trifluoroacetic acid/water on a Phenomenex® C18 10 μm (250 mm×50 mm) column at a flowrate of 50 mL/minute) to give 0.34 g of the title compound as a white solid. ¹H NMR (400 MHz, DMSO-d₆) δ ppm 9.23 (d, J=6.6 Hz, 2H), 7.84 (s, 1H), 7.55-7.39 (m, 6H), 7.09 (dd, J=11.4, 2.9 Hz, 1H), 6.86 (ddd, J=8.9, 2.8, 1.2 Hz, 1H), 4.59 (s, 2H), 4.17 (t, J=5.6 Hz, 2H), 2.90 (d, J=3.7 Hz, 2H), 2.50-2.36 (m, 2H), 2.23-2.09 (m, 2H), 2.13-1.95 (m, 4H); MS (ESI⁺) m/z 431.2 (M+H)⁺.

Example 130D: N-(4-amino-2-oxobicyclo[2.2.2] octan-1-yl)-2-(4-chloro-3-fluorophenoxy)acetamide, trifluoroacetic acid To a mixture of Pd(OH)₂ (2.7 g, 3.85 mmol) in tetrahydrofuran (500 mL) was added Example 130C (10 g, 22.05 mmol) under argon at ambient temperature, and the reaction mixture was stirred for 7.5 hours under H₂ at 50 psi. Methanol (1000 mL) was added, and the mixture was filtered through a pad of diatomaceous earth. The filter cake was washed with methanol (1000 mL), and the filtrate was concentrated under reduced pressure. The residue was purified by reversed phase HPLC (10-80% acetonitrile in 0.075% trifluoroacetic acid/water over 30 minutes on a 250 mm×80 mm Phenomenex® Luna®-C18 10 μm column at a flowrate of 80 mL/minute) to give the title compound as a white solid. ¹H NMR (400 MHz, DMSO-d₆) δ ppm 8.49 (s, 3H), 7.81 (s, 1H), 7.49 (t, J=8.8 Hz, 1H), 7.08 (dd, J=11.3, 2.6 Hz, 1H), 6.85 (dd, J=8.9, 2.6 Hz, 1H), 4.58 (s, 2H), 2.73 (s, 2H), 2.38 (t, J=9.1 Hz, 2H), 1.95 (d, J=8.3 Hz, 6H).

Example 130E: N-(4-amino-2-hydroxybicyclo [2.2.2]octan-1-yl)-2-(4-chloro-3-fluorophenoxy) acetamide, Trifluoroacetic Acid A suspension of Example 130D (2.7 g, 6.01 mmol) and sodium borohydride (0.455 g, 12.02 mmol) in methanol (40 mL) was stirred at ambient temperature for 48 hours. Solvent was removed, and the residue was purified by HPLC (20-100% acetonitrile in 0.1% trifluoroacetic acid/water on Phenomenex® C18 10 μm (250 mm×50 mm) column at a flowrate of 50 mL/minute) to give 1.75 g of the title compound as an off-white solid. ¹H NMR (400 MHz, DMSO-d₆) δ ppm 7.86 (s, 3H), 7.44 (t, J=8.9 Hz, 1H), 7.34 (s, 1H), 7.01 (dd, J=11.4, 2.9 Hz, 1H), 6.79 (ddd, J=9.0, 2.9, 1.2 Hz, 1H), 5.26 (s, 1H), 4.44 (s, 2H), 4.10 (d, J=9.2 Hz, 1H), 3.13 (s, 1H), 2.17-1.48 (m, 8H); MS (ESI$^+$) m/z 343.1 (M+H)$^+$.

Example 130F: N-{4-[2-(4-chloro-3-fluorophenoxy) acetamido]-3-hydroxybicyclo[2.2.2]octan-1-yl}-5-(difluoromethyl)pyrazine-2-carboxamide A mixture of Example 130E (0.05 g, 0.146 mmol), 5-(difluoromethyl)pyrazine-2-carboxylic acid (0.029 g, 0.168 mmol) and N-ethyl-N-isopropylpropan-2-amine (0.102 mL, 0.583 mmol) in N,N-dimethylformamide (1.5 mL) was treated with 2-(3H-[1,2,3]triazolo[4,5-b]pyridin-3-yl)-1,1,3,3-tetramethylisouronium hexafluorophosphate(V) (0.083 g, 0.219 mmol), and the reaction was stirred at ambient temperature for 30 minutes. Volatiles were removed under high vacuum, and the residue was purified by HPLC (10-95% acetonitrile in 0.1% trifluoroacetic acid/water on Phenomenex® C18 5 µm (250 mm×21.2 mm) column at a flowrate of 25 mL/minute) to give 43 mg of the title compound as a solid. $^1$H NMR (400 MHz, DMSO-d$_6$) δ ppm 9.19 (d, J=1.4 Hz, 1H), 8.94 (d, J=1.2 Hz, 1H), 8.03 (s, 1H), 7.45 (t, J=8.9 Hz, 1H), 7.28 (d, J=6.0 Hz, 1H), 7.16 (m, 1H), 7.07-6.98 (m, 1H), 6.80 (ddd, J=9.0, 2.9, 1.2 Hz, 1H), 5.13 (d, J=4.4 Hz, 1H), 4.44 (s, 2H), 4.08 (ddd, J=9.9, 5.4, 3.1 Hz, 1H), 2.39 (ddd, J=12.6, 9.5, 2.5 Hz, 1H), 2.13-2.01 (m, 2H), 1.95 (q, J=4.8, 2.6 Hz, 1H), 1.94-1.76 (m, 6H); MS (ESI$^+$) m/z 499.1 (M+H)$^+$.

Example 131: N-{4-[2-(4-chloro-3-fluorophenoxy) acetamido]-3-hydroxybicyclo[2.2.2]octan-1-yl}-5-fluoropyridine-2-carboxamide (Compound 230)

The title compound was prepared using the methodologies described in Example 130 substituting 5-fluoropicolinic acid for 5-(difluoromethyl)pyrazine-2-carboxylic acid. $^1$H NMR (400 MHz, DMSO-d$_6$) δ ppm 8.56 (d, J=2.8 Hz, 1H), 8.03 (dd, J=8.7, 4.7 Hz, 1H), 7.85 (td, J=8.7, 2.8 Hz, 1H), 7.82 (s, 1H), 7.45 (t, J=8.9 Hz, 1H), 7.27 (s, 1H), 7.02 (dd, J=11.4, 2.8 Hz, 1H), 6.80 (ddd, J=9.0, 2.9, 1.2 Hz, 1H), 5.11 (d, J=4.4 Hz, 1H), 4.44 (s, 2H), 4.13-4.02 (m, 1H), 2.37 (ddd, J=12.5, 9.5, 2.2 Hz, 1H), 2.14-1.77 (m, 9H); MS (ESI$^+$) m/z 466.0 (M+H)$^+$.

Example 132: N-{4-[2-(4-chloro-3-fluorophenoxy) acetamido]-3-hydroxybicyclo[2.2.2]octan-1-yl}-4-fluorobenzamide (Compound 231)

The title compound was prepared using the methodologies described in Example 130 substituting 4-fluorobenzoic acid for 5-(difluoromethyl)pyrazine-2-carboxylic acid. $^1$H NMR (400 MHz, DMSO-d$_6$) δ ppm 7.88-7.75 (m, 2H), 7.68 (s, 1H), 7.45 (t, J=8.9 Hz, 1H), 7.27-7.14 (m, 3H), 7.02 (dd, J=11.4, 2.9 Hz, 1H), 6.80 (ddd, J=9.0, 2.9, 1.2 Hz, 1H), 5.07 (d, J=4.4 Hz, 1H), 4.44 (s, 2H), 4.12-3.99 (m, 1H), 2.34 (ddd, J=12.6, 9.5, 2.3 Hz, 1H), 2.03-1.73 (m, 9H); MS (ESI$^+$) m/z 465.1 (M+H)$^+$.

Example 133: N-{3-[2-(4-chloro-3-fluorophenoxy) acetamido]bicyclo[1.1.1]pentan-1-yl}-4-[(propan-2-yl)oxy]benzamide (Compound 232)

The title compound was prepared using the methodologies described above. $^1$H NMR (400 MHz, DMSO-d$_6$) δ ppm 8.81 (s, 1H), 8.72 (s, 1H), 7.76 (d, J=8.9 Hz, 2H), 7.49 (t, J=8.9 Hz, 1H), 7.07 (dd, J=11.4, 2.8 Hz, 1H), 6.92 (d, J=8.9 Hz, 2H), 6.84 (ddd, J=8.9, 2.9, 1.2 Hz, 1H), 4.67 (p, J=6.0 Hz, 1H), 4.47 (s, 2H), 2.29 (s, 6H), 1.25 (d, J=6.0 Hz, 6H); MS (ESI$^+$) m/z 447 (M+H)$^+$.

Example 134: N-{3-[2-(4-chloro-3-fluorophenoxy) acetamido]bicyclo[1.1.1]pentan-1-yl}-5-(difluoromethyl)pyridine-2-carboxamide (Compound 233)

The title compound was prepared using the methodologies described above. $^1$H NMR (400 MHz, DMSO-d$_6$) δ ppm 9.39 (s, 1H), 8.86-8.79 (m, 1H), 8.72 (s, 1H), 8.23-8.08 (m, 2H), 7.48 (t, J=8.9 Hz, 1H), 7.38-7.09 (m, 1H), 7.11-7.02 (m, 1H), 6.84 (ddd, J=9.0, 2.9, 1.2 Hz, 1H), 4.48 (s, 2H), 2.34 (s, 6H); MS (ESI$^+$) m/z 440 (M+H)$^+$.

Example 135: N-{3-[2-(4-chloro-3-fluorophenoxy) acetamido]bicyclo[1.1.1]pentan-1-yl}-2,2-difluoro-2H-1,3-benzodioxole-5-carboxamide (Compound 234)

The title compound was prepared using the methodologies described above. $^1$H NMR (400 MHz, DMSO-d$_6$) δ ppm 9.05 (s, 1H), 8.72 (s, 1H), 7.79 (d, J=1.6 Hz, 1H), 7.72 (dd, J=8.5, 1.7 Hz, 1H), 7.47 (dt, J=8.9, 4.6 Hz, 2H), 7.05 (dd, J=11.4, 2.8 Hz, 1H), 6.83 (ddd, J=9.0, 2.9, 1.2 Hz, 1H), 4.46 (s, 2H), 2.30 (s, 6H); MS (ESI$^+$) m/z 469 (M+H)$^+$.

Example 136: N-{(2R)-4-[2-(4-chloro-3-fluorophenoxy)acetamido]-2-hydroxybicyclo[2.2.2]octan-1-yl}-5-(difluoromethyl)pyrazine-2-carboxamide (Compound 235)

The title compound was isolated by chiral preparative SFC (Supercritical Fluid Chromatography) of Example 96 as the first peak eluted off the column. Preparative SFC was performed on a THAR/Waters SFC 80 system running under SuperChrom™ software control. The preparative SFC system was equipped with a 8-way preparative column switcher, CO$_2$ pump, modifier pump, automated back pressure regulator (ABPR), UV detector, and 6-position fraction collector. The mobile phase comprised of supercritical CO$_2$ supplied by a Dewar of bone-dry non-certified CO$_2$ pressurized to 350 psi with a modifier of methanol at a flow rate of 70 g/minute. The column was at ambient temperature and the backpressure regulator was set to maintain 100 bar. The sample was dissolved in a mixture of methanol/dichloromethane (1:1) at a concentration of 15 mg/mL. The sample was loaded into the modifier stream in 2 mL (30 mg) injections. The mobile phase was held isocratically at 35% methanol:CO$_2$. Fraction collection was time triggered. The instrument was fitted with a Chiralcel® OJ-H column with dimensions 21 mm i.d.×250 mm length with 5 µm particles. $^1$H NMR (501 MHz, DMSO-d$_6$) δ ppm 9.24 (d, J=1.4 Hz, 1H), 8.98 (d, J=1.3 Hz, 1H), 8.12 (s, 1H), 7.55 (s, 1H), 7.47 (t, J=8.9 Hz, 1H), 7.18 (m, 1H), 7.01 (dd, J=11.4, 2.9 Hz, 1H), 6.80 (ddd, J=8.9, 2.9, 1.1 Hz, 1H), 5.30 (d, J=5.1 Hz, 1H), 4.43 (s, 2H), 4.06-4.00 (m, 1H), 2.34 (ddd, J=12.9, 9.4, 2.9 Hz, 1H), 2.11-2.03 (m, 1H), 2.02-1.89 (m, 2H), 1.83-1.74 (m, 5H); MS (ESI$^+$) m/z 499.1 (M+H)$^+$. X-ray crystallography confirmed the assigned stereochemistry.

Example 137: N-{(2S)-4-[2-(4-chloro-3-fluorophenoxy)acetamido]-2-hydroxybicyclo[2.2.2]octan-1-yl}-5-(difluoromethyl)pyrazine-2-carboxamide (Compound 236)

The title compound was isolated by chiral preparative SFC of Example 96 as the second peak eluted off the column using the methodologies described in Example 136. $^1$H NMR (501 MHz, DMSO-$d_6$) δ ppm 9.24 (d, J=1.4 Hz, 1H), 8.98 (d, J=1.3 Hz, 1H), 8.12 (s, 1H), 7.55 (s, 1H), 7.47 (t, J=8.9 Hz, 1H), 7.18 (m, 1H), 7.01 (dd, J=11.4, 2.8 Hz, 1H), 6.80 (ddd, J=8.9, 2.9, 1.1 Hz, 1H), 5.30 (d, J=5.2 Hz, 1H), 4.43 (s, 2H), 4.06-4.00 (m, 1H), 2.34 (ddd, J=12.9, 9.5, 2.9 Hz, 1H), 2.11-2.03 (m, 1H), 2.02-1.91 (m, 2H), 1.89-1.74 (m, 5H); MS (ESI$^+$) m/z 499.1 (M+H)$^+$.

Example 138: N-{3-[2-(4-chloro-3-fluorophenoxy)acetamido]bicyclo[1.1.1]pentan-1-yl}-6-[(oxetan-3-yl)oxy]pyridine-3-carboxamide (Compound 237)

Example 138A: methyl 6-(oxetan-3-yloxy)nicotinate

To a solution of 6-fluoronicotinic acid methyl ester (Combi-Blocks, 0.5 g, 3.22 mmol) and oxetan-3-ol (Combi-Blocks, 0.23 mL, 3.6 mmol) in tetrahydrofuran (20 mL) at 0° C. was added potassium bis(trimethylsilyl)amide (6.45 mL, 6.45 mmol) (1 M in tetrahydrofuran) dropwise via syringe pump over 15 minutes. The material was allowed to warm to ambient temperature and was allowed to stir for 3 hours. The material was quenched with saturated, aqueous NaHCO$_3$ (5 mL) and diluted with ethyl acetate (5 mL). The layers were separated, and the aqueous layer was extracted with ethyl acetate (3×3 mL). The combined organics were dried over anhydrous Na$_2$SO$_4$, filtered, and concentrated under reduced pressure. The residue was purified via column chromatography (SiO$_2$, 2% ethyl acetate/heptanes to 40% ethyl acetate/heptanes) to give the title compound (0.15 g, 0.72 mmol, 22% yield). MS (ESI$^+$) m/z 210 (M+H)$^+$.

Example 138B: 6-(oxetan-3-yloxy)nicotinic Acid

To a solution of the product of Example 138A (0.148 g, 0.71 mmol) in methanol (4.0 mL) and water (2.0 mL) was added NaOH (0.48 g, 6.0 mmol). This mixture was allowed to stir at ambient temperature for 30 minutes then the mixture was concentrated under reduced pressure and dissolved in water. The solution was acidified with concentrated HCl to pH-6 and then the organics were extracted with CH$_2$Cl$_2$ (3×5 mL). The combined organics were dried over anhydrous Na$_2$SO$_4$, filtered and concentrated under reduced pressure to give the title compound (75 mg, 0.38 mmol, 54% yield). MS (ESI$^+$) m/z 196 (M+H)$^+$.

Example 138C: N-{3-[2-(4-chloro-3-fluorophenoxy)acetamido]bicyclo[1.1.1]pentan-1-yl}-6-[(oxetan-3-yl)oxy]pyridine-3-carboxamide To a mixture of the product of Example 6C (0.14 g, 0.35 mmol) and the product of Example 138B (0.072 g, 0.37 mmol) in N,N-dimethylformamide (3 mL) was added N-ethyl-N-isopropylpropan-2-amine (0.25 mL, 1.40 mmol) followed by 2-(3H-[1,2,3]triazolo[4,5-b]pyridin-3-yl)-1,1,3,3-tetramethylisouronium hexafluorophosphate(V) (HATU, 0.15 g, 0.39 mmol). This mixture was allowed to stir at ambient temperature for 2 hours, then was quenched with saturated aqueous NaHCO$_3$ (10 mL) and diluted with ethyl acetate (10 mL). The layers were separated, and the aqueous layer was extracted with ethyl acetate (3×3 mL). The combined organics were dried over anhydrous Na$_2$SO$_4$, filtered, and concentrated under reduced pressure. The residue was purified via column chromatography (SiO$_2$, 75% ethyl acetate/heptanes) to give the title compound (0.12 g, 0.26 mmol, 74% yield). $^1$H NMR (400 MHz, DMSO-$d_6$) δ ppm 9.00 (s, 1H), 8.71 (s, 1H), 8.53 (dd, J=2.4, 0.8 Hz, 1H), 8.10 (dd, J=8.7, 2.5 Hz, 1H), 7.47 (t, J=8.9 Hz, 1H), 7.05 (dd, J=11.4, 2.9 Hz, 1H), 6.93 (dd, J=8.7, 0.7 Hz, 1H), 6.83 (ddd, J=9.0, 2.9, 1.2 Hz, 1H), 5.58 (tt, J=6.2, 5.1 Hz, 1H), 4.86 (ddd, J=7.2, 6.2, 1.0 Hz, 2H), 4.52 (ddd, J=7.5, 5.0, 0.9 Hz, 2H), 4.45 (s, 2H), 2.29 (s, 6H); MS (ESI$^+$) m/z 462 (M+H)$^+$.

Example 139: N-{3-[2-(4-chloro-3-fluorophenoxy)acetamido]bicyclo[1.1.1]pentan-1-yl}-2,4-dimethyl-1,3-thiazole-5-carboxamide (Compound 238)

2,4-Dimethylthiazole-5-carboxylic acid (17 mg, 0.11 mmol) and 1-[bis(dimethylamino)methylene]-1H-1,2,3-triazolo[4,5-b]pyridinium 3-oxid hexafluorophosphate (HATU, 93 mg, 0.25 mmol) were mixed in 0.5 mL of N,N-dimethylacetamide. The product of Example 4A (28 mg, 0.10 mmol) and N,N-diisopropylethylamine (69 μL, 0.39 mmol) were added. The reaction was stirred at ambient temperature for 16 hours before being purified by reverse phase chromatography: Phenomenex® Luna® C8(2) 5 μm 100A AXIA™ column (50 mm×30 mm). A gradient of CH$_3$CN (A) and 0.1% trifluoroacetic acid in H$_2$O (B) was used at a flow rate of 40 mL/minute (0-0.5 minute 5% A, 0.5-6.5 minute linear gradient 5-100% A, 6.5-8.5 minutes 100% A, 8.5-9.0 minutes linear gradient 100-5% A, 9.0-10.0 minutes 5% A) to yield the title compound (19 mg, 45%). $^1$H NMR (501 MHz, DMSO-$d_6$) δ ppm 7.49 (t, J=8.9 Hz, 1H), 7.07 (dd, J=11.3, 2.8 Hz, 1H), 6.87 (ddd, J=9.0, 2.9, 1.2 Hz, 11-), 4.48 (s, 2H), 2.61 (s, 3H), 2.49 (s, 311), 2.32 (s, 61H); MS (ESI$^+$) n/z 424 (M+H)$^+$.

Example 140: N-{3-[2-(4-chloro-3-fluorophenoxy)acetamido]bicyclo[1.1.1]pentan-1-yl}-2H-1,3-benzodioxole-5-carboxamide (Compound 239)

The title compound was prepared using the methodologies described above. $^1$H NMR (501 MHz, DMSO-$d_6$) δ ppm 7.50 (t, J=8.9 Hz, 1H), 7.42 (dd, J=8.2, 1.8 Hz, 1H), 7.35 (d, J=1.8 Hz, 1H), 7.07 (dd, J=11.3, 2.8 Hz, 1H), 6.97 (d, J=8.2 Hz, 1H), 6.87 (ddd, J=9.0, 2.9, 1.2 Hz, 1H), 6.08 (s, 2H), 4.49 (s, 2H), 2.33 (s, 6H); MS (ESI$^+$) m/z 433 (M+H)$^+$.

Example 141: N-{3-[2-(4-chloro-3-fluorophenoxy)acetamido]bicyclo[1.1.1]pentan-1-yl}-2H-1,3-benzodioxole-4-carboxamide (Compound 240)

The title compound was prepared using the methodologies described above. $^1$H NMR (501 MHz, DMSO-$d_6$) δ ppm 7.50 (t, J=8.9 Hz, 1H), 7.18 (dd, J=8.1, 1.2 Hz, 1H), 7.12-7.02 (m, 2H), 6.93 (t, J=7.9 Hz, 1H), 6.88 (ddd, J=9.0, 2.9, 1.2 Hz, 1H), 6.10 (s, 2H), 4.49 (s, 2H), 2.35 (s, 6H); MS (ESI$^+$) m/z 433 (M+H)$^+$.

Example 142: N-{3-[2-(4-chloro-3-fluorophenoxy)acetamido]bicyclo[1.1.1]pentan-1-yl}-1,3-dimethyl-1H-pyrazole-5-carboxamide (Compound 241)

The title compound was prepared using the methodologies described above. $^1$H NMR (501 MHz, DMSO-$d_6$) δ ppm 7.49 (t, J=8.9 Hz, 1H), 7.07 (dd, J=11.3, 2.8 Hz, 1H), 6.87 (ddd, J=9.1, 2.9, 1.2 Hz, 1H), 6.59 (d, J=0.7 Hz, 1H), 4.48 (s, 2H), 3.94 (s, 3H), 2.33 (s, 6H), 2.14 (s, 3H); MS (ESI$^+$) m/z 407 (M+H)$^+$.

Example 143: N-{3-[2-(4-chloro-3-fluorophenoxy)acetamido]bicyclo[1.1.1]pentan-1-yl}-5-(methoxymethyl)furan-2-carboxamide (Compound 242)

The title compound was prepared using the methodologies described above. ¹H NMR (501 MHz, DMSO-$d_6$) δ ppm 7.49 (t, J=8.9 Hz, 1H), 7.14-7.01 (m, 2H), 6.87 (ddd, J=8.9, 2.9, 1.2 Hz, 1H), 6.57 (d, J=3.4 Hz, 1H), 4.48 (s, 2H), 4.39 (s, 2H), 3.26 (s, 3H), 2.32 (s, 6H); MS (ESI⁺) m/z 423 (M+H).

Example 144: N-{3-[2-(4-chloro-3-fluorophenoxy)acetamido]bicyclo[1.1.1]pentan-1-yl}-1-benzofuran-3-carboxamide (Compound 243)

The title compound was prepared using the methodologies described above. ¹H NMR (501 MHz, DMSO-$d_6$) δ ppm 8.49 (s, 1H), 8.11-8.00 (m, 1H), 7.65 (dt, J=8.3, 0.9 Hz, 1H), 7.50 (t, J=8.9 Hz, 1H), 7.42-7.29 (m, 2H), 7.08 (dd, J=11.3, 2.8 Hz, 1H), 6.88 (ddd, J=9.0, 2.9, 1.2 Hz, 11-H), 4.50 (s, 21-), 2.37 (s, 6H); MS (ESI⁺) m/z 429 (M+H)⁺.

Example 145: N-{3-[2-(4-chloro-3-fluorophenoxy)acetamido]bicyclo[1.1.1]pentan-1-yl}-3-cyclopropyl-1,2-oxazole-5-carboxamide (Compound 244)

The title compound was prepared using the methodologies described above. ¹H NMR (501 MHz, DMSO-$d_6$) δ ppm 7.59-7.39 (m, 1H), 7.06 (dd, J=11.3, 2.9 Hz, 1H), 6.87 (ddd, J=9.0, 3.0, 1.2 Hz, 1H), 6.75 (s, 1H), 4.48 (s, 2H), 3.72 (s, 2H), 2.33 (s, 6H), 2.13-2.00 (m, 1H), 1.11-1.02 (m, 2H), 0.85-0.73 (m, 2H); MS (ESI⁺) m/z 420 (M+H)⁺.

Example 146: N-{3-[2-(4-chloro-3-fluorophenoxy)acetamido]bicyclo[1.1.1]pentan-1-yl}-2-(propan-2-yl)-1,3-oxazole-4-carboxamide (Compound 245)

The title compound was prepared using the methodologies described above. ¹H NMR (501 MHz, DMSO-$d_6$) δ ppm 8.40 (s, 1H), 7.49 (t, J=8.9 Hz, 11), 7.07 (dd, J=11.3, 2.9 Hz, 1H), 6.87 (ddd, J=8.9, 2.8, 1.1 Hz, 1H), 4.48 (s, 2H), 3.11 (hept, J=6.9 Hz, 1H), 2.32 (s, 6H), 1.28 (d, J=7.0 Hz, 61-1); MS (ESI⁺) m/z 422 (M+H)⁺.

Example 147: N-{3-[2-(4-chloro-3-fluorophenoxy)acetamido]bicyclo[1.1.1]pentan-1-yl}-1-methyl-1H-pyrazole-4-carboxamide (Compound 246)

The title compound was prepared using the methodologies described above. ¹H NMR (501 MHz, DMSO-$d_6$) δ ppm 8.06 (d, J=0.7 Hz, 1H), 7.81 (d, J=0.7 Hz, 1H), 7.49 (t, J=8.9 Hz, 1H), 7.07 (dd, J=11.3, 2.9 Hz, 1H), 6.87 (ddd, J=9.0, 2.9, 1.2 Hz, 11H), 4.48 (s, 2H), 3.84 (s, 3H), 2.30 (s, 6H); MS (ESI⁺) m/z 393 (M+H)⁺.

Example 148: N-{3-[2-(4-chloro-3-fluorophenoxy)acetamido]bicyclo[1.1.1]pentan-1-yl}-5-ethyl-1,2-oxazole-3-carboxamide (Compound 247)

The title compound was prepared using the methodologies described above. ¹H NMR (501 MHz, DMSO-$d_6$) δ ppm 7.49 (t, J=8.9 Hz, 1H), 7.07 (dd, J=11.3, 2.8 Hz, 1H), 6.87 (ddd, J=9.0, 2.9, 1.2 Hz, 1H), 6.52 (t, J=1.0 Hz, 1H), 4.48 (s, 2H), 2.80 (qd, J=7.6, 0.9 Hz, 2H), 2.34 (s, 6H), 1.23 (t, J=7.6 Hz, 3H); MS (ESI⁺) m/z 408 (M+H)⁺.

Example 149: N-{3-[2-(4-chloro-3-fluorophenoxy)acetamido]bicyclo[1.1.1]pentan-1-yl}-2-cyclopropyl-1,3-oxazole-4-carboxamide (Compound 248)

The title compound was prepared using the methodologies described above. ¹H NMR (501 MHz, DMSO-$d_6$) δ ppm 8.32 (s, 1H), 7.49 (t, J=8.9 Hz, 1H), 7.06 (dd, J=11.3, 2.9 Hz, 1H), 6.87 (ddd, J=9.0, 2.9, 1.1 Hz, 1H), 4.48 (s, 2H), 2.31 (s, 6H), 2.13 (tt, J=8.4, 4.9 Hz, 1H), 1.24-1.01 (m, 2H), 1.01-0.91 (m, 2H); MS (ESI⁺) m/z 420 (M+H)⁺.

Example 150: N-{3-[2-(4-chloro-3-fluorophenoxy)acetamido]bicyclo[1.1.1]pentan-1-yl}-2-methyl-1,3-oxazole-4-carboxamide (Compound 249)

The title compound was prepared using the methodologies described above. ¹H NMR (501 MHz, DMSO-$d_6$) δ ppm 8.37 (s, 1H), 7.49 (i, J=8.9 Hz, 11H), 7.06 (dd, J=11.3, 2.8 Hz, 1H), 6.87 (ddd, J=9.0, 2.9, 1.2 Hz, 1H), 4.48 (s, 2H), 2.44 (s, 3H), 2.31 (s, 6H); MS (ESI−) m/z 394 (M+H)⁺.

Example 151: N-{3-[2-(4-chloro-3-fluorophenoxy)acetamido]bicyclo[1.1.1]pentan-1-yl}-5-ethylfuran-2-carboxamide (Compound 250)

The title compound was prepared using the methodologies described above. ¹H NMR (501 MHz, DMSO-$d_6$) δ ppm 7.49 (t, J=8.9 Hz, 1H), 7.07 (dd, J=11.3, 2.9 Hz, 1H), 6.99 (d, J=3.4 Hz, 1H), 6.87 (ddd, J=9.0, 2.9, 1.2 Hz, 1H), 6.24 (dt, J=3.4, 1.0 Hz, 11H), 4.48 (s, 2H), 2.73-2.60 (m, 2H), 2.31 (s, 6H), 1.20 (t, J=7.6 Hz, 3H); MS (ESI) m/z 407 (M+H)⁺.

Example 152: N-{3-[2-(4-chloro-3-fluorophenoxy)acetamido]bicyclo[1.1.1]pentan-1-yl}-2-ethyl-1,3-oxazole-4-carboxamide (Compound 251)

The title compound was prepared using the methodologies described above. ¹H NMR (501 MHz, DMSO-$d_6$) δ ppm 8.39 (s, 1H), 7.49 (t, J=8.9 Hz, 1H), 7.06 (dd, J=11.3, 2.9 Hz, 1H), 6.87 (ddd, J=9.0, 2.9, 1.2 Hz, 1H), 4.48 (s, 2H), 2.79 (q, J=7.6 Hz, 2H), 2.32 (s, 6H), 1.25 (t, J=7.6 Hz, 3H); MS (ESI⁺) m/z 408 (M+H)⁺.

Example 153: N-{3-[2-(4-chloro-3-fluorophenoxy)acetamido]bicyclo[1.1.1]pentan-1-yl}-1-ethyl-1H-pyrazole-4-carboxamide (Compound 252)

The title compound was prepared using the methodologies described above. ¹H NMR (501 MHz, DMSO-$d_6$) δ ppm 8.11 (d, J=0.7 Hz, 1H), 7.82 (d, J=0.8 Hz, 1H), 7.49 (t, J=8.9 Hz, 1H), 7.07 (dd, J=11.3, 2.9 Hz, 1H), 6.87 (ddd, J=9.0, 2.9, 1.2 Hz, 1H), 4.48 is, 2H), 4.13 (q, J=7.3 Hz, 2H), 2.30 (s, 6H), 1.36 (t, J=7.3 Hz, 3H); MS (ESI⁺) m/z 407 (M+H)⁺.

Example 154: N-{3-[2-(4-chloro-3-fluorophenoxy)acetamido]bicyclo[1.1.1]pentan-1-yl}-3-methoxy-1,2-oxazole-5-carboxamide (Compound 253)

The title compound was prepared using the methodologies described above. ¹H NMR (501 MHz, DMSO-$d_6$) δ ppm 7.49 (t, J=8.9 Hz, 1H), 7.07 (dd, J=11.3, 2.9 Hz, 1H), 6.87 (ddd, J=9.0, 2.9, 1.2 Hz, 1H), 6.75 (s, 1H), 4.48 (s, 2H), 3.94 (s, 3H), 2.34 (s, 6H); MS (ESI⁺) m/Z 410 (M+H)⁺.

Example 155: N-{3-[2-(4-chloro-3-fluorophenoxy) acetamido]bicyclo[1.1.1]pentan-1-yl}-3-ethyl-1-methyl-1H-pyrazole-5-carboxamide (Compound 254)

The title compound was prepared using the methodologies described above. 1H NMR (501 MHz, DMSO-$d_6$) δ ppm 7.49 (t, J=8.9 Hz, 1H), 7.07 (dd, J=11.3, 2.8 Hz, 1H), 6.87 (ddd, J=9.0, 2.9, 1.2 Hz, 1H), 6.65 (s, 1H), 4.49 (s, 2H), 3.95 (s, 2H), 2.33 (s, 6H), 1.15 (t, J=7.6 Hz, 3H); MS (ESI$^+$) m/z 421 (M+H)$^+$.

Example 156: N-{3-[2-(4-chloro-3-fluorophenoxy) acetamido]bicyclo[1.1.1]pentan-1-yl}-5-(propan-2-yl)-1,2-oxazole-3-carboxamide (Compound 255)

The title compound was prepared using the methodologies described above. $^1$H NMR (501 MHz, DMSO-$d_6$) δ ppm 7.49 (t, J=8.9 Hz, 1H), 7.07 (dd, J=11.3, 2.9 Hz, 1H), 6.87 (ddd, J=8.9, 2.8, 1.2 Hz, 1H), 6.51 (d, J=0.9 Hz, 11H), 4.48 (s, 21H), 3.12 (qd, J=6.9, 0.9 Hz, 1H), 2.33 (s, 6H), 1.26 (d, J=6.9 Hz, 6H); MS (ESI$^+$) m/z 422 (M+H)$^+$.

Example 157: N-{3-[2-(4-chloro-3-fluorophenoxy) acetamido]bicyclo[1.1.1]pentan-1-yl}-5-cyclopropyl-1,2-oxazole-3-carboxamide (Compound 256)

The title compound was prepared using the methodologies described above. $^1$H NMR (501 MHz, DMSO-d) δ ppm 7.49 (t, J=8.9 Hz, 1H), 7.06 (dd, J=11.3, 2.9 Hz, 1H), 6.87 (ddd, J=9.0, 2.9, 1.2 Hz, 1H), 6.43 (s, 1), (s, 1-H, 4.48 (s, 2H), 2.33 (s, 6H), 2.19 (it, J=8.4, 5.0 Hz, 1H), 1.18-1.03 (m, 2H), 0.96-0.78 (m, 2H); MS (ESI$^+$) m/z 420 (M+H)$^+$.

Example 158: N-{3-[2-(4-chloro-3-fluorophenoxy) acetamido]bicyclo[1.1.1]pentan-1-yl}-2-methyl-1,3-oxazole-5-carboxamide (Compound 257)

The title compound was prepared using the methodologies described above. $^1$H NMR (501 MHz, DMSO-$d_6$) δ ppm 8.37 (s, 1H), 7.49 (t, J=8.9 Hz, 1H), 7.06 (dd, J=11.3, 2.9 Hz, 1H), 6.87 (ddd, J=9.0, 2.9, 1.2 Hz, 1H), 4.48 (s, 2H), 2.44 (s, 3H), 2.31 (s, 6H); MS (ESI$^+$) m/z 394 (M+H)$^+$.

Example 159: N-{3-[2-(4-chloro-3-fluorophenoxy) acetamido]bicyclo[1.1.1]pentan-1-yl}imidazo[1,2-a] pyridine-3-carboxamide (Compound 258)

The title compound was prepared using the methodologies described above. $^1$H NMR (501 MHz, DMSO-$d_6$) δ ppm 9.54 (dt, J=6.9, 1.2 Hz, 1H), 8.45 (s, 1H), 7.88-7.80 (m, 1H), 7.73 (t, J=8.0 Hz, 1H), 7.50 (t, J=8.9 Hz, 1H), 7.38-7.24 (m, 1H), 7.08 (dd, J=11.3, 2.9 Hz, 1H), 6.88 (ddd, J=9.0, 2.9, 1.2 Hz, 1H), 4.50 (s, 2H), 2.40 (s, 6H); MS (ESI$^+$) m/z 429 (M+H)$^+$.

Example 160: N-{3-[2-(4-chloro-3-fluorophenoxy) acetamido]bicyclo[1.1.1]pentan-1-yl}-5,6-dihydro-4H-pyrrolo[1,2-b]pyrazole-2-carboxamide (Compound 259)

The title compound was prepared using the methodologies described above. $^1$H NMR (501 MHz, DMSO-$d_6$) δ ppm 7.49 (t, J=8.9 Hz, 1H), 7.07 (dd, J=11.3, 2.9 Hz, 1H), 6.87 (ddd, J=9.0, 2.8, 1.2 Hz, 1H), 6.36 (d, J=0.9 Hz, 1H), 4.48 (s, 2H), 4.20-3.96 (min, 21-), 2.85 (t, J=7.3 Hz, 2H), 2.59-2.54 (m, 2H), 2.30 (s, 6H); MS (ESI$^+$) m/z 419 (M+H)$^+$.

Example 161: N-{3-[2-(4-chloro-3-fluorophenoxy) acetamido]bicyclo[1.1.1]pentan-1-yl}-1-(methoxymethyl)-1H-pyrazole-3-carboxamide (Compound 260)

The title compound was prepared using the methodologies described above. $^1$H NMR (500 MHz, DMSO-$d_6$) δ ppm 8.74-8.70 (m, 2H), 7.97 (d, J=2.4 Hz, 1H), 7.50 (t, J=8.9 Hz, 1H), 7.08 (dd, J=11.4, 2.9 Hz, 1H), 6.86 (ddd, J=9.0, 2.9, 1.2 Hz, 1H), 6.67 (d, J=2.4 Hz, 1H), 5.41 (s, 2H), 4.49 (s, 2H), 3.24 (s, 3H), 2.31 (br s, 6H); MS (ESI$^+$) m/z 423 (M+H)$^+$.

Example 162: N-{3-[2-(3,4-dichlorophenoxy)acetamido]bicyclo[1.1.1]pentan-1-yl}pyrimidine-4-carboxamide (Compound 261)

The title compound was prepared using the methodologies described above. $^1$H NMR (501 MHz, DMSO-$d_6$) δ ppm 9.58 (s, 1H), 9.31 (d, J=1.4 Hz, 1H), 9.06 (d, J=5.1 Hz, 1H), 8.76 (s, 1H), 7.99 (dd, J=5.0, 1.4 Hz, 1H), 7.55 (d, J=8.9 Hz, 1H), 7.27 (d, J=2.9 Hz, 1H), 7.00 (dd, J=9.0, 2.9 Hz, 1H), 4.51 (s, 2H), 2.36 (br s, 6H); MS (ESI$^+$) m/z 407 (M+H)$^+$.

Example 163: N-{3-[2-(4-chloro-3-fluorophenoxy) acetamido]bicyclo[1.1.1]pentan-1-yl}-5-fluoropyridine-2-carboxamide (Compound 262)

The title compound was prepared using the methodologies described above. $^1$H NMR (501 MHz, DMSO-$d_6$) δ ppm 9.25 (s, 1H), 8.74 (s, 1H), 8.62 (dd, J=2.9, 0.6 Hz, 1H), 8.08 (ddd, J=8.7, 4.7, 0.6 Hz, 1H), 7.90 (td, J=8.7, 2.8 Hz, 1H), 7.50 (t, J=8.9 Hz, 1H), 7.08 (dd, J=11.4, 2.8 Hz, 1H), 6.86 (ddd, J=9.0, 2.9, 1.2 Hz, 1H), 4.49 (s, 2H), 2.35 (br s, 6H); MS (ESI$^+$) m/z 408 (M+H)$^+$.

Example 164: N$^2$-{3-[2-(4-chloro-3-fluorophenoxy) acetamido]bicyclo[1.1.1]pentan-1-yl}-N$^4$-(3,3-difluorocyclobutyl)pyridine-2,4-dicarboxamide (Compound 263)

Example 164A: 2-((3-(2-(4-chloro-3-fluorophenoxy) acetamido)bicyclo[1.1.1]pentan-1-yl)carbamoyl) isonicotinic Acid The reaction conditions described in Example 39B substituting the product of Example 105 for the product of Example 39A gave the title compound. $^1$H NMR (501 MHz, DMSO-$d_6$) δ ppm 9.39 (s, 1H), 8.81 (d, J=4.9 Hz, 1H), 8.75 (s, 1H), 8.37 (d, J=1.2 Hz, 1H), 8.00 (dd, J=4.9, 1.7 Hz, 1H), 7.50 (t, J=8.9 Hz, 1H), 7.08 (dd, J=11.3, 2.8 Hz, 1H), 6.87 (dd, J=8.7, 2.7 Hz, 1H), 4.50 (s, 2H), 2.36 (s, 6H); MS (ESI$^+$) m/z 434 (M+H)$^+$.

Example 164B: N$^2$-{3-[2-(4-chloro-3-fluorophenoxy)acetamido]bicyclo[1.1.1]pentan-1-yl}-N$^4$-(3,3-difluorocyclobutyl)pyridine-2,4-dicarboxamide The reaction and purification conditions described in Example 13 substituting the product of Example 164A for the product of Example 12B and 3,3-difluorocyclobutanamine hydrochloride (PharmaBlock) for the product of Example 4A gave the title compound. $^1$H NMR (501 MHz, DMSO-d$_6$) δ ppm 9.36 (s, 1H), 9.29 (d, J=6.6 Hz, 1H), 8.76 (dd, J=5.0, 0.8 Hz, 1H), 8.73 (s, 1H), 8.41 (dd, J=1.8, 0.9 Hz, 1H), 7.93 (dd, J=5.0, 1.8 Hz, 1H), 7.48 (t, J=8.9 Hz, 1H), 7.06 (dd, J=11.4, 2.9 Hz, 1H), 6.84 (ddd, J=9.0, 2.8, 1.2 Hz, 1H), 4.47 (s, 2H), 4.31-4.22 (m, 1H), 3.01-2.89 (m, 2H), 2.83-2.69 (m, 2H), 2.35 (br s, 6H); MS (ESI$^+$) m/z 523 (M+H)$^+$.

Example 165: 2-(4-chlorophenoxy)-N-(3-{[5-(4-chlorophenyl)-1,3,4-oxadiazol-2-yl]amino}bicyclo[1.1.1]pentan-1-yl)acetamide (Compound 264)

Example 165A: tert-butyl {3-[2-(4-chlorophenoxy)acetamido]bicyclo[1.1.1]pentan-1-yl}carbamate To a solution of tert-butyl (3-aminobicyclo[1.1.1]pentan-1-yl)carbamate (PharmaBlock, 1.1 g, 5.55 mmol) in tetrahydrofuran (40 mL) was added triethylamine (2.320 mL, 16.64 mmol) followed by 4-chlorophenoxyacetyl chloride (0.87 mL, 5.6 mmol). The mixture was allowed to stir at ambient temperature for 4 hours. The resulting solids were isolated via filtration to give the title compound (2.0 g, 5.45 mmol, 98% yield). $^1$H NMR (501 MHz, DMSO-d$_6$) δ ppm 8.64 (s, 1H), 7.51 (s, 1H), 7.37-7.30 (m, 2H), 7.00-6.93 (m, 2H), 4.42 (s, 2H), 2.13 (s, 6H), 1.37 (s, 9H), 1.17 (t, J=7.3 Hz, 1H); MS (ESI$^+$) m/z 367 (M+H)$^+$.

Example 165B: N-(3-aminobicyclo[1.1.1]pentan-1-yl)-2-(4-chlorophenoxy)acetamide trifluoroacetate To a solution of the product of Example 165A (2 g, 5.45 mmol) in dichloromethane (25 mL) at ambient temperature was added trifluoroacetic acid (8.40 mL, 109 mmol). This mixture was allowed to stir at ambient temperature for 2 hours then was concentrated under reduced pressure and azeotroped with toluene to give the title compound (1.5 g, 3.9 mmol, 72% yield). $^1$H NMR (500 MHz, DMSO-d$_6$) δ ppm 8.84 (s, 1H), 8.66 (s, 3H), 7.38-7.31 (m, 2H), 7.01-6.94 (m, 2H), 4.45 (s, 2H), 2.24 (s, 6H); MS (ESI$^+$) m/z 267 (M+H)$^+$.

Example 165C: 2-(4-chlorophenoxy)-N-(3-{[5-(4-chlorophenyl)-1,3,4-oxadiazol-2-yl]amino}bicyclo[1.1.1]pentan-1-yl)acetamide The product of Example 165B (100 mg, 0.26 mmol), 5-(4-chlorophenyl)-1,3,4-oxadiazol-2(3H)-one (CombiBlocks, 25.8 mg, 0.131 mmol) and N-ethyl-N-isopropylpropan-2-amine (0.092 mL, 0.525 mmol) were treated with ((1H-benzo[d][1,2,3]triazol-1-yl)oxy)tris(dimethylamino)phosphonium hexafluorophosphate(V) (69.7 mg, 0.158 mmol). The reaction mixture was stirred at ambient temperature for 4 hours and then was concentrated under reduced pressure. The residue was purified via HPLC (Phenomenex® Luna® C18(2) 5 μm 100 Å AXIA™ column 250 mm×21.2 mm, flow rate 25 mL/minute, 10-90% gradient of acetonitrile in buffer (0.1% trifluoroacetic acid in water)) to give the title compound (17 mg, 0.038 mmol, 15% yield). $^1$H NMR (400 MHz, DMSO-d$_6$) δ ppm 8.77 (d, J=8.0 Hz, 2H), 7.88-7.77 (m, 3H), 7.66-7.58 (m, 2H), 7.40-7.31 (m, 2H), 7.03-6.94 (m, 2H), 4.46 (s, 2H), 2.33 (s, 6H); MS (APCI$^+$) m/z 446 (M+H)$^+$.

Example 166: 2-(4-chlorophenoxy)-N-(3-{[5-(4-chlorophenyl)-1,2-oxazol-3-yl]amino}bicyclo[1.1.1]pentan-1-yl)acetamide (Compound 265)

Example 166A: 2-(4-chlorophenoxy)-N-(3-isothiocyanatobicyclo[1.1.1]pentan-1-yl)acetamide The product of Example 165B (200 mg, 0.53 mmol) and N-ethyl-N-isopropylpropan-2-amine (0.092 mL, 0.525 mmol) in dichloromethane (0.5 mL) were treated dropwise with a dichloromethane (2.5 mL) solution of 1,1'-thiocarbonylbis(pyridin-2(1H)-one) (122 mg, 0.525 mmol), stirred at ambient temperature for 2 hours and then was concentrated under reduced pressure. Purification by flash chromatography (silica gel, 30% ethyl acetate/hexanes) afforded the title compound (158 mg, 0.51 mmol, 97% yield). MS (APCI$^+$) m/z 309 (M+H)$^+$.

Example 166B: 2-(4-chlorophenoxy)-N-(3-{[(1Z)-3-(4-chlorophenyl)-1-(methylsulfanyl)-3-oxoprop-1-en-1-yl]amino}bicyclo[1.1.1]pentan-1-yl)acetamide To 1-(4-chlorophenyl)ethanone (0.033 mL, 0.256 mmol) in N,N-dimethylformamide (0.5 mL) was added sodium hydride (10.2 mg, 0.26 mmol), and the mixture was stirred for 30 minutes at ambient temperature. A solution of the product of Example 166A (0.079 g, 0.26 mmol) in N,N-dimethylformamide (0.50 mL) was added dropwise, and the reaction mixture was stirred at ambient temperature for 2 hours. Iodomethane (0.28 mmol, 0.018 mL) was added, and the reaction mixture was allowed to stir for 2 hours at ambient temperature. The mixture was concentrated under reduced pressure to give the title compound (0.12 g, 0.25 mmol, 98% yield) which was carried on without purification or characterization.

Example 166C: 2-(4-chlorophenoxy)-N-(3-{[5-(4-chlorophenyl)-1,2-oxazol-3-yl]amino}bicyclo[1.1.1]pentan-1-yl)acetamide The product of Example 166B (0.12 g, 0.25 mmol) in ethanol (1 mL) and treated with 50% aqueous solution of hydroxylamine (0.066 mL, 1.0 mmol). The reaction was stirred at 100° C. for 2 hours and then was concentrated under reduced pressure. The residue was purified by HPLC (Phenomenex® Luna® C18(2) 5 μm 100 Å AXIA™ column 250 mm×21.2 mm, flow rate 25 mL/minute, 10-90% gradient of acetonitrile in buffer (0.1% trifluoroacetic acid in water)) to give the title compound (22 mg, 0.050 mmol, 20% yield). $^1$H NMR (400 MHz, DMSO-d$_6$) δ ppm 8.69 (s, 1H), 7.85-7.75 (m, 2H), 7.58-7.47 (m, 2H), 7.37-7.28 (m, 2H), 7.11 (s, 1H), 7.01-6.92 (m, 2H), 6.42 (s, 1H), 4.43 (s, 2H), 2.25 (s, 6H); MS (APCI$^+$) m/z 445 (M+H)$^+$.

Example 167: N-{3-[2-(4-chloro-3-fluorophenoxy)acetamido]bicyclo[1.1.1]pentan-1-yl}-5-cyclopropylpyrazine-2-carboxamide (Compound 266)

5-Cyclopropylpyrazine-2-carboxylic acid (AniChem, 20 mg, 0.122 mmol) was stirred with dichloromethane (1 mL) and oxalyl chloride (2.0 M solution in dichloromethane, 0.61 mL) was added followed by one drop of N,N-dimethylformamide. After stirring at ambient temperature for 5 minutes, the reaction mixture was concentrated under reduced pressure and to the resulting residue was added a pyridine (1 mL) solution of the product of Example 4A (35 mg, 0.12 mmol). The resulting mixture was stirred at ambient temperature for 30 minutes and concentrated under reduced pressure. The residue was taken up in N,N-dimethylformamide (2 mL), filtered through a glass microfiber frit, and then purified by preparative HPLC [Waters XBridge™ C18 5 μm OBD™ column, 30×100 mm, flow rate 40 mL/minute, 5-100% gradient of acetonitrile in buffer (0.025 M aqueous ammonium bicarbonate, adjusted to pH 10 with ammonium hydroxide)] to give the title compound (16 mg, 0.037 mmol, 31% yield). $^1$H NMR (400 MHz, DMSO-d$_6$) δ ppm 9.32 (s, 1H), 8.94 (d, J=1.4 Hz, 1H), 8.74 (s, 1H), 8.66 (d, J=1.4 Hz, 1H), 7.50 (t, J=8.9 Hz, 1H), 7.08 (dd, J=11.4, 2.9 Hz, 1H), 6.86 (ddd, J=8.9, 2.9, 1.2 Hz, 1H), 4.49 (s, 2H), 2.38-2.29 (m, 7H), 1.17-1.09 (m, 2H), 1.07-1.00 (m, 2H); MS (ESI$^+$) m/z 431 (M+H)$^+$.

Example 168: N-{3-[2-(4-chloro-3-fluorophenoxy)acetamido]bicyclo[1.1.1]pentan-1-yl}-5-(furan-2-yl)pyridine-2-carboxamide (Compound 267)

The title compound was prepared using the methodologies described above. $^1$H NMR (400 MHz, DMSO-d$_6$) δ ppm 9.25 (s, 1H), 8.94 (dd, J=2.3, 0.8 Hz, 1H), 8.74 (s, 1H), 8.24 (dd, J=8.2, 2.3 Hz, 1H), 8.03 (dd, J=8.2, 0.8 Hz, 1H), 7.91-7.89 (m, 1H), 7.50 (t, J=8.9 Hz, 1H), 7.28 (d, J=3.4 Hz, 1H), 7.08 (dd, J=11.5, 2.9 Hz, 1H), 6.86 (ddd, J=9.0, 2.9, 1.2 Hz, 1H), 6.70 (dd, J=3.5, 1.8 Hz, 1H), 4.49 (s, 2H), 2.36 (br s, 6H); MS (ESI$^+$) m/z 456 (M+H)$^+$.

Example 169: N-{3-[2-(4-chloro-3-fluorophenoxy)acetamido]bicyclo[1.1.1]pentan-1-yl}-5-methylpyrimidine-2-carboxamide (Compound 268)

The title compound was prepared using the methodologies described above. $^1$H NMR (400 MHz, DMSO-d$_6$) δ ppm 9.34 (s, 1H), 8.79-8.77 (m, 2H), 8.75 (s, 1H), 7.50 (t, J=8.9 Hz, 1H), 7.08 (dd, J=11.4, 2.9 Hz, 1H), 6.86 (ddd, J=9.0, 2.9, 1.2 Hz, 1H), 4.49 (s, 2H), 2.38-2.32 (m, 9H); MS (ESI$^+$) m/z 405 (M+H)$^+$.

Example 170: N-{3-[2-(4-chloro-3-fluorophenoxy)acetamido]bicyclo[1.1.1]pentan-1-yl}-5-(ethylamino)pyridine-2-carboxamide (Compound 269)

Example 170A: ethyl 5-(ethylamino)picolinate

Ethylamine (2.0 M in tetrahydrofuran, 6 mL) and ethyl 5-fluoropyridine-2-carboxylate (FluoroChem, 150 mg, 0.887 mmol) were combined in a 20 mL microwave tube. The tube was heated in a Biotage® Initiator+ microwave reactor and irradiated at 120° C. for 30 minutes, then at 180° C. for one hour and at 200° C. for 30 minutes. The resulting reaction mixture was concentrated under reduced pressure. The residue was taken up in N,N-dimethylformamide (3 mL), filtered through a glass microfiber frit and purified by preparative HPLC [YMC TriArt™ C$_{18}$ Hybrid 20 μm column, 25×150 mm, flow rate 80 mL/minute, 3-100% gradient of acetonitrile in buffer (0.1% trimethylamine)] to give the title compound (86 mg, 0.443 mmol, 50% yield). MS (ESI$^+$) m/z 217 (M+Na)$^+$.

Example 170B: 5-(ethylamino)picolinic Acid, Trifluoroacetic Acid

The reaction conditions described in Example 49C substituting the product of Example 170A for the product of Example 49B provided the sodium salt of the title compound which was further purified by preparative HPLC [YMC TriArt™ C18 Hybrid 20 μm column, 25×150 mm, flow rate 80 mL/minute, 3-100% gradient of acetonitrile in buffer (0.1% trifluoroacetic acid)] to give the title compound. MS (DCI) m/z 184 (M+NH$_4$)$^+$.

Example 170C: N-{3-[2-(4-chloro-3-fluorophenoxy)acetamido]bicyclo[1.1.1]pentan-1-yl}-5-(ethylamino)pyridine-2-carboxamide The reaction and purification conditions described in Example 13 substituting the product of Example 170B for the product of Example 12B and the product of Example 6C for the product of Example 4A gave the title compound. $^1$H NMR (400 MHz, DMSO-d$_6$) δ ppm 8.72 (s, 1H), 8.71 (s, 1H), 7.91 (dd, J=2.8, 0.6 Hz, 1H), 7.72 (d, J=8.6 Hz, 1H), 7.50 (t, J=8.9 Hz, 1H), 7.08 (dd, J=11.4, 2.8 Hz, 1H), 6.95 (dd, J=8.7, 2.7 Hz, 1H), 6.86 (ddd, J=9.0, 2.9, 1.2 Hz, 1H), 6.48 (t, J=5.3 Hz, 1H), 4.49 (s, 2H), 3.11 (qd, J=7.1, 5.2 Hz, 2H), 2.31 (br s, 6H), 1.18 (t, J=7.1 Hz, 3H); MS (ESI$^+$) m/z 433 (M+H)$^+$.

Example 171: N$^2$-{3-[2-(4-chloro-3-fluorophenoxy)acetamido]bicyclo[1.1.1]pentan-1-yl}-N$^5$-ethylpyridine-2,5-dicarboxamide (Compound 270)

Example 171A: methyl 5-(ethylcarbamoyl)picolinate

The reaction and purification conditions described in Example 167 substituting 6-(methoxycarbonyl)nicotinic acid (Combi-Blocks) for 5-cyclopropylpyrazine-2-carboxylic acid, and ethylamine for the product of Example 4A gave the title compound. MS (ESI$^+$) m/z 209 (M+H)$^+$.

Example 171B: N$^2$-{3-[2-(4-chloro-3-fluorophenoxy)acetamido]bicyclo[1.1.1]pentan-1-yl}-N$^5$-ethylpyridine-2,5-dicarboxamide The reaction and purification conditions described in Example 52 substituting the product of Example 171A for the product of Example 49A gave the title compound. $^1$H NMR (400 MHz, DMSO-d$_6$, 120° C.) δ ppm 9.36 (s, 1H), 8.97 (dd, J=2.2, 0.8 Hz, 1H), 8.79 (t, J=5.5 Hz, 1H), 8.72 (s, 1H), 8.33 (dd, J=8.1, 2.2 Hz, 1H), 8.05 (dd, J=8.2, 0.8 Hz, 1H), 7.48 (t, J=8.9 Hz, 1H), 7.06 (dd, J=11.3, 2.9 Hz, 1H), 6.84 (ddd, J=9.0, 2.8, 1.1 Hz, 1H), 4.48 (s, 2H), 3.37-3.23 (m, 2H), 2.34 (br s, 6H), 1.13 (t, J=7.2 Hz, 3H); MS (ESI$^+$) m/z 461 (M+H)$^+$.

Example 172: 2-(4-chlorophenoxy)-N-(3-{[5-(4-chlorophenyl)-1,3,4-thiadiazol-2-yl]amino}bicyclo[1.1.1]pentan-1-yl)acetamide (Compound 271)

A solution of 4-chlorobenzohydrazide (0.038 g, 0.220 mmol) and the product of Example 166A, (0.068 g, 0.220 mmol) in dichloromethane (1 mL) were stirred at 50° C. for 3 hours and concentrated sulfuric acid (0.24 mL, 4.40 mmol) was added dropwise. The reaction mixture was stirred at ambient temperature for 16 hours, then was quenched with saturated, aqueous sodium bicarbonate solution (5 mL), and was extracted with dichloromethane (2×5 mL). The organic layer was dried over diatomaceous earth, filtered and concentrated under reduced pressure. Purification of the residue by HPLC(Phenomenex® Luna® C18(2) 5 μm 100 Å AXIA™ column 250 mm×21.2 mm, flow rate 25 mL/minute, 20-100% gradient of acetonitrile in buffer (0.1% trifluoroacetic acid in water)) afforded the title compound (60 mg, 0.13 mmol, 59% yield). $^1$H NMR (500 MHz, DMSO-d$_6$) δ ppm 8.84 (s, 1H), 8.79 (s, 1H), 7.83-7.77 (m, 2H), 7.57-7.50 (m, 2H), 7.38-7.30 (m, 2H), 7.02-6.93 (m, 2H), 4.46 (s, 2H), 2.35 (s, 6H); MS (APCI$^+$) m/z 461 (M+H)$^+$.

Example 173: N-{4-[2-(4-chloro-3-fluorophenoxy)acetamido]-3-hydroxybicyclo[2.2.2]octan-1-yl}-5-methyl-1,2-oxazole-3-carboxamide (Compound 272)

The title compound was prepared using the methodologies described in Example 130 substituting 5-methylisoxazole-3-carboxylic acid for 5-(difluoromethyl)pyrazine-2-carboxylic acid. $^1$H NMR (400 MHz, DMSO-d$_6$) δ ppm 7.82 (s, 1H), 7.45 (t, J=8.9 Hz, 1H), 7.25 (s, 1H), 7.02 (dd, J=11.4, 2.8 Hz, 1H), 6.80 (dd, J=9.1, 2.7 Hz, 1H), 6.43 (s, 1H), 5.08 (d, J=4.3 Hz, 1H), 4.44 (s, 2H), 4.03 (dd, J=8.9, 4.3 Hz, 1H), 2.40 (s, 3H), 2.32 (ddd, J=12.3, 9.5, 2.2 Hz, 1H), 2.12-1.74 (m, 9H); MS (ESI$^+$) m/z 452.1 (M+H)$^+$.

Example 174: N-{3-[2-(4-chloro-3-fluorophenoxy)acetamido]bicyclo[1.1.1]pentan-1-yl}-5-methyl-1,2-oxazole-3-carboxamide (Compound 273)

The title compound was prepared using the methodologies described above. $^1$H NMR (400 MHz, DMSO-d$_6$) δ ppm 9.24 (s, 1H), 8.70 (s, 1H), 7.46 (t, J=8.9 Hz, 1H), 7.04 (dd, J=11.4, 2.9 Hz, 1H), 6.82 (ddd, J=8.9, 2.8, 1.2 Hz, 1H), 6.46 (d, J=0.9 Hz, 1H), 4.45 (s, 2H), 2.41 (d, J=0.9 Hz, 3H), 2.28 (s, 6H); MS (ESI$^+$) m/z 394 (M+H)$^+$.

Example 175: N-{4-[2-(4-chloro-3-fluorophenoxy)acetamido]-3-hydroxybicyclo[2.2.2]octan-1-yl}-3-methoxypyrazine-2-carboxamide (Compound 274)

The title compound was prepared using the methodologies described in Example 130 substituting 3-methoxypyrazine-2-carboxylic acid for 5-(difluoromethyl)pyrazine-2-carboxylic acid. $^1$H NMR (400 MHz, DMSO-d$_6$) δ ppm 8.25 (d, J=2.7 Hz, 1H), 8.13 (d, J=2.7 Hz, 1H), 7.93 (s, 1H), 7.45 (t, J=8.9 Hz, 1H), 7.25 (s, 1H), 7.03 (dd, J=11.4, 2.8 Hz, 1H), 6.80 (ddd, J=8.9, 2.9, 1.2 Hz, 1H), 5.07 (s, 1H), 4.44 (s, 2H), 4.09-4.00 (m, 1H), 3.88 (s, 3H), 3.13 (s, 1H), 2.51 (s, 1H), 2.32 (ddd, J=13.2, 9.5, 2.2 Hz, 1H), 2.14-1.99 (m, 1H), 2.03-1.90 (m, 1H), 1.85 (dddd, J=19.0, 11.6, 7.5, 3.1 Hz, 6H); MS (ESI$^+$) m/z 479.2 (M+H)$^+$.

Example 176: N-{3-[2-(4-chloro-3-fluorophenoxy)acetamido]bicyclo[1.1.1]pentan-1-yl}-3-ethyl-1H-pyrazole-5-carboxamide (Compound 275)

The title compound was prepared using the methodologies described above. $^1$H NMR (400 MHz, DMSO-d$_6$) δ ppm 12.87 (s, 1H), 8.68 (s, 1H), 8.48 (s, 1H), 7.48 (t, J=8.9 Hz, 1H), 7.06 (dd, J=11.4, 2.9 Hz, 1H), 6.84 (ddd, J=8.9, 2.9, 1.2 Hz, 1H), 6.34 (s, 1H), 4.46 (s, 2H), 2.60 (q, J=7.6 Hz, 2H), 2.27 (s, 6H), 1.16 (td, J=7.4, 3.1 Hz, 3H); MS (ESI$^+$) m/z 407 (M+H)$^+$.

Example 177: 2-({3-[2-(4-chloro-3-fluorophenoxy)acetamido]bicyclo[1.1.1]pentan-1-yl}carbamoyl)pyridine-4-carboxylic acid (Compound 276)

The reaction conditions described in Example 39B substituting the product of Example 105 for the product of Example 39A provided the sodium salt of the title compound which was further purified by HPLC [YMC TriArt™ C18 Hybrid 20 µm column, 25×150 mm, flow rate 80 mL/minute, 5-100% gradient of acetonitrile in buffer (0.1% trifluoroacetic acid)] to give the title compound. $^1$H NMR (501 MHz, DMSO-d$_6$) δ ppm 9.39 (s, 1H), 8.81 (d, J=4.9 Hz, 1H), 8.75 (s, 1H), 8.37 (d, J=1.2 Hz, 1H), 8.00 (dd, J=4.9, 1.7 Hz, 1H), 7.50 (t, J=8.9 Hz, 1H), 7.08 (dd, J=11.3, 2.8 Hz, 1H), 6.87 (dd, J=8.7, 2.7 Hz, 1H), 4.50 (s, 2H), 2.36 (s, 6H); MS (ESI$^+$) m/z 434 (M+H)$^+$.

Example 178: N-{3-[2-(3,4-difluorophenoxy)acetamido]bicyclo[1.1.1]pentan-1-yl}-6-(trifluoromethoxy)pyridine-3-carboxamide (Compound 277)

Example 178A: N-(3-aminobicyclo[1.1.1]pentan-1-yl)-2-(3,4-difluorophenoxy)acetamide The reaction and purification conditions described in Example 63C substituting (3,4-difluorophenoxy)acetic acid (Combi-Blocks) for 5-methylpyrazine-2-carboxylic acid, and previously described pH 10 buffer for the 0.1% trifluoroacetic acid buffer for preparative HPLC gave the title compound. MS (ESI$^+$) m/z 269 (M+H)$^+$.

Example 178B: N-{3-[2-(3,4-difluorophenoxy)acetamido]bicyclo[1.1.1]pentan-1-yl}-6-(trifluoromethoxy)pyridine-3-carboxamide The reaction and purification conditions described in Example 13 substituting 6-(trifluoromethoxy)nicotinic acid (Oakwood) for the product of Example 12B and the product of Example 178A for the product of Example 4A gave the title compound. $^1$H NMR (400 MHz, DMSO-d$_6$) δ ppm 9.28 (s, 1H), 8.77-8.75 (m, 1H), 8.74 (s, 1H), 8.38 (dd, J=8.6, 2.5 Hz, 1H), 7.43-7.33 (m, 2H), 7.10 (ddd, J=12.6, 6.7, 3.1 Hz, 1H), 6.84-6.77 (m, 1H), 4.46 (s, 2H), 2.36 (br s, 6H); MS (ESI$^+$) m/z 458 (M+H)$^+$.

Example 179: 5-(difluoromethyl)-N-{3-[2-(3,4-difluorophenoxy)acetamido]bicyclo[1.1.1]pentan-1-yl}pyrazine-2-carboxamide (Compound 278)

The title compound was prepared using the methodologies described above. $^1$H NMR (400 MHz, DMSO-d$_6$) δ ppm 9.62 (s, 1H), 9.26-9.23 (m, 1H), 9.01-8.98 (m, 1H), 8.73 (s, 1H), 7.43-7.33 (m, 1H), 7.21 (t, J=54.0 Hz, 1H), 7.14-7.07 (m, 1H), 6.84-6.78 (m, 1H), 4.46 (s, 2H), 2.38 (br s, 6H); MS (ESI$^+$) m/z 425 (M+H)$^+$.

Example 180: ethyl 4-({3-[2-(4-chloro-3-fluorophenoxy)acetamido]bicyclo[1.1.1]pentan-1-yl}carbamoyl)pyridine-2-carboxylate (Compound 279)

The title compound was prepared using the methodologies described above. $^1$H NMR (400 MHz, DMSO-d$_6$) δ ppm 9.54 (s, 1H), 8.86 (dd, J=5.0, 0.8 Hz, 1H), 8.77 (s, 1H), 8.41 (dd, J=1.8, 0.8 Hz, 1H), 7.98 (dd, J=5.0, 1.7 Hz, 1H), 7.50 (t, J=8.9 Hz, 1H), 7.09 (dd, J=11.4, 2.8 Hz, 1H), 6.87 (ddd, J=9.0, 2.9, 1.2 Hz, 1H), 4.50 (s, 2H), 4.38 (q, J=7.1 Hz, 2H), 2.37 (br s, 6H), 1.35 (t, J=7.1 Hz, 3H); MS (ESI$^+$) m/z 462 (M+H)$^+$.

Example 181: 4-({3-[2-(4-chloro-3-fluorophenoxy)acetamido]bicyclo[1.1.1]pentan-1-yl}carbamoyl)pyridine-2-carboxylic acid (Compound 280)

The product of Example 180 (84 mg, 0.18 mmol) was dissolved in methanol (2 mL). Aqueous sodium hydroxide (2.5 M, 0.29 mL) was added, and the resulting mixture was stirred at ambient temperature for 10 minutes. To the resulting suspension was added an HCl solution (3.0 M in dioxane, 0.273 mL), and the resulting clear solution was filter through a microfiber frit and purified by preparative HPLC [YMC TriArt™ C18 Hybrid 20 µm column, 25×150 mm, flow rate 80 mL/minute, 5-100% gradient of acetonitrile in buffer (0.1% trifluoroacetic acid)] to give the title compound. $^1$H NMR (501 MHz, DMSO-$d_6$) δ ppm 9.54 (s, 1H), 8.84 (d, J=4.9 Hz, 1H), 8.77 (s, 1H), 8.44-8.42 (m, 1H), 7.96 (dd, J=5.0, 1.7 Hz, 1H), 7.50 (t, J=8.9 Hz, 1H), 7.09 (dd, J=11.3, 2.9 Hz, 1H), 6.87 (ddd, J=8.9, 2.9, 1.2 Hz, 1H), 4.50 (s, 2H), 2.36 (br s, 6H); MS (ESI$^+$) m/z 434 (M+H)$^+$.

Example 182: N-{3-[2-(3,4-dichlorophenoxy)acetamido]bicyclo[1.1.1]pentan-1-yl}-4-(2-hydroxyethyl)pyridine-2-carboxamide (Compound 281)

The title compound was prepared using the methodologies described above. $^1$H NMR (400 MHz, DMSO-$d_6$) δ ppm 9.20 (s, 1H), 8.74 (s, 1H), 8.49 (dd, J=4.9, 0.8 Hz, 1H), 7.90-7.86 (m, 1H), 7.55 (d, J=8.9 Hz, 1H), 7.46 (dd, J=4.9, 1.7 Hz, 1H), 7.27 (d, J=2.9 Hz, 1H), 7.00 (dd, J=9.0, 2.9 Hz, 1H), 4.73 (t, J=5.1 Hz, 1H), 4.51 (s, 2H), 3.70-3.63 (m, 2H), 2.82 (t, J=6.4 Hz, 2H), 2.35 (s, 6H); MS (ESI$^+$) m/z 450 (M+H)$^+$.

Example 183: N-{3-[2-(4-chloro-3-fluorophenoxy)acetamido]bicyclo[1.1.1]pentan-1-yl}-4-(2-hydroxyethyl)pyridine-2-carboxamide (Compound 282)

The title compound was prepared using the methodologies described above. $^1$H NMR (400 MHz, DMSO-$d_6$) δ ppm 9.21 (s, 1H), 8.73 (s, 1H), 8.49 (d, J=5.0 Hz, 1H), 7.90-7.86 (m, 1H), 7.50 (t, J=8.9 Hz, 1H), 7.46 (dd, J=5.0, 1.8 Hz, 1H), 7.08 (dd, J=11.3, 2.9 Hz, 1H), 6.86 (ddd, J=9.0, 2.9, 1.2 Hz, 1H), 4.49 (s, 2H), 3.67 (t, J=6.4 Hz, 2H), 2.82 (t, J=6.4 Hz, 2H), 2.35 (br s, 6H); MS (ESI$^+$) m/z 434 (M+H)$^+$.

Example 184: N-{3-[2-(4-chloro-3-fluorophenoxy)acetamido]bicyclo[1.1.1]pentan-1-yl}-5-[(E)-2-cyclopropylethenyl]pyridine-2-carboxamide (Compound 283)

Example 184A: (E)-tert-butyl 5-(2-cyclopropylvinyl)picolinate

The reaction and purification conditions described in Example 39A substituting (E)-2-cyclopropylvinylboronic acid pinacol ester (Aldrich) for 3,6-dihydro-2H-pyran-4-boronic acid pinacol ester, and tert-butyl 5-bromopicolinate (Combi-Blocks) for 2-bromooxazole-5-carboxylate gave the title compound. MS (ESI$^+$) m/z 268 (M+Na)$^+$.

Example 184B: N-{3-[2-(4-chloro-3-fluorophenoxy)acetamido]bicyclo[1.1.1]pentan-1-yl}-5-[(E)-2-cyclopropylethenyl]pyridine-2-carboxamide The product of Example 184A (20 mg, 0.082 mmol) was dissolved in trifluoroacetic acid (1 mL, 13 mmol) and stirred at ambient temperature for 10 minutes. The reaction mixture was concentrated in vacuo and to the resulting residue was added the product of Example 6C (42 mg, 0.08 mmol), triethylamine (0.068 mL, 0.49 mmol), N,N-dimethylformamide (2.0 mL), and 1-[bis(dimethylamino)methylene]-1H-1,2,3-triazolo[4,5-b]pyridinium 3-oxid hexafluorophosphate (33 mg, 0.09 mmol, HATU) in sequential order. The mixture was stirred at ambient temperature for 30 minutes. The resulting solution was filtered through a glass microfiber frit and purified by preparative HPLC [Waters XBridge™ C18 5 μm OBD™ column, 30×100 mm, flow rate 40 mL/minute, 5-100% gradient of acetonitrile in buffer (0.025 M aqueous ammonium bicarbonate, adjusted to pH 10 with ammonium hydroxide)] to give the title compound (23 mg, 0.05 mmol, 62% yield). $^1$H NMR (500 MHz, DMSO-$d_6$) δ ppm 9.16 (s, 1H), 8.74 (s, 1H), 8.55 (d, J=2.2 Hz, 1H), 7.97-7.93 (m, 1H), 7.91-7.88 (m, 1H), 7.50 (t, J=8.9 Hz, 1H), 7.08 (dd, J=11.4, 2.8 Hz, 1H), 6.86 (ddd, J=9.0, 2.9, 1.1 Hz, 1H), 6.58 (d, J=15.9 Hz, 1H), 6.14 (dd, J=15.9, 9.3 Hz, 1H), 4.49 (s, 2H), 2.34 (br s, 6H), 1.68-1.60 (m, 1H), 0.91-0.81 (m, 2H), 0.63-0.55 (m, 2H); MS (ESI$^+$) m/z 456 (M+H)$^+$.

Example 185: 2-(4-chlorophenoxy)-N-(3-{[3-(4-chlorophenyl)-1,2,4-oxadiazol-5-yl]amino}bicyclo[1.1.1]pentan-1-yl)acetamide (Compound 284)

A N,N-dimethylformamide (0.50 mL) solution of the product of Example 165B (50 mg, 0.13 mmol), 5-chloro-3-(4-chlorophenyl)-1,2,4-oxadiazole (29.7 mg, 0.14 mmol) and N-ethyl-N-isopropylpropan-2-amine (0.069 mL, 0.39 mmol) was stirred at 90° C. for 2 hours and was concentrated under reduced pressure. Purification of the residue by HPLC (Phenomenex® Luna® C18(2) 5 m 100 Å AXIA™ column 250 mm×21.2 mm, flow rate 25 mL/minute, 10-80% gradient of acetonitrile in buffer (0.1% trifluoroacetic acid in water)) afforded the title compound (23 mg, 0.052 mmol, 40% yield). $^1$H NMR (400 MHz, DMSO-$d_6$) δ ppm 9.39 (s, 1H), 8.80 (s, 1H), 7.95-7.86 (m, 2H), 7.63-7.55 (m, 2H), 7.40-7.25 (m, 2H), 7.03-6.94 (m, 2H), 4.46 (s, 2H), 2.36 (s, 6H); MS (APCI$^+$) m/z 446 (M+H)$^+$.

Example 186: N-{3-[2-(4-chloro-3-fluorophenoxy)acetamido]bicyclo[1.1.1]pentan-1-yl}-2-methyl-1,3-thiazole-5-carboxamide (Compound 285)

The title compound was prepared using the methodologies described above. $^1$H NMR (400 MHz, DMSO-$d_6$) δ ppm 9.11 (s, 1H), 8.72 (s, 1H), 8.12 (s, 1H), 7.46 (t, J=8.9 Hz, 1H), 7.04 (dd, J=11.4, 2.8 Hz, 1H), 6.82 (ddd, J=9.0, 2.9, 1.2 Hz, 1H), 4.45 (s, 2H), 2.61 (s, 3H), 2.28 (s, 6H); MS (ESI$^+$) m/z 410 (M+H)$^+$.

Example 187: N-{4-[2-(4-chloro-3-fluorophenoxy)acetamido]-3-hydroxybicyclo[2.2.2]octan-1-yl}-3,5-dimethylpyrazine-2-carboxamide (Compound 286)

The title compound was prepared using the methodologies described in Example 130 substituting 3,5-dimethylpyrazine-2-carboxylic acid for 5-(difluoromethyl)pyrazine-2-carboxylic acid. $^1$H NMR (400 MHz, DMSO-$d_6$) δ ppm 8.35 (s, 1H), 7.95 (s, 1H), 7.49 (t, J=8.9 Hz, 1H), 7.29 (s, 1H), 7.07 (dd, J=11.4, 2.9 Hz, 1H), 6.84 (ddd, J=8.9, 2.9, 1.2 Hz, 1H), 5.12 (d, J=4.4 Hz, 1H), 4.48 (s, 2H), 4.09 (dq, J=9.5, 3.3 Hz, 1H), 2.62 (s, 3H), 2.49 (s, 3H), 2.39 (ddd, J=12.1, 9.4, 2.2 Hz, 1H), 2.18-2.07 (m, 1H), 2.09-1.99 (m, 1H), 2.01-1.80 (m, 7H); MS (ESI$^+$) m/z 477.1 (M+H)$^+$.

Example 188: 2-(4-chlorophenoxy)-N-(3-{[5-(4-chlorophenyl)-1,2,4-oxadiazol-3-yl]amino}bicyclo[1.1.1]pentan-1-yl)acetamide (Compound 287)

Example 188A: 3-chloro-5-(4-chlorophenyl)-1,2,4-oxadiazole

A solution of 5-(4-chlorophenyl)-1,2,4-oxadiazol-3-amine (0.25 g, 1.29 mmol) in concentrated hydrogen chloride (2.0 mL, 64.4 mmol) was cooled in an ice bath and treated with a solution of sodium nitrite (0.18 g, 2.6 mmol) in water (0.5 mL). The reaction was stirred for 1 hour in the bath, and then 2 hours at ambient temperature. The reaction mixture was extracted with ethyl acetate (10 mL) and washed with water (2×10 mL). The organic layer was dried over diatomaceous earth, filtered and concentrated under reduced pressure to provide the title compound (30 mg, 0.14 mmol, 11% yield). MS (APCI$^+$) m/z 216 (M+H)$^+$.

Example 188B: 2-(4-chlorophenoxy)-N-(3-{[5-(4-chlorophenyl)-1,2,4-oxadiazol-3-yl]amino}bicyclo[1.1.1]pentan-1-yl)acetamide trifluoroacetate A N,N-dimethylformamide (0.50 mL) solution of the product of Example 165B (50 mg, 0.13 mmol), the product of Example 188A (30 mg, 0.14 mmol) and N-ethyl-N-isopropylpropan-2-amine (0.069 mL, 0.39 mmol) was stirred at 100° C. for 24 hours and then was allowed to cool to ambient temperature and was concentrated under reduced pressure. Purification of the residue by HPLC (Phenomenex® Luna® C18(2) 5 μm 100 Å AXIA™ column 250 mm×21.2 mm, flow rate 25 mL/minute, 10-90% gradient of acetonitrile in buffer (0.1% trifluoroacetic acid in water)) afforded the title compound (12 mg, 0.21 mmol, 16% yield). $^1$H NMR (501 MHz, DMSO-d$_6$) δ ppm 8.86 (s, 1H), 7.98 (s, 2H), 7.65 (s, 2H), 7.39-7.32 (m, 2H), 7.02-6.95 (m, 2H), 4.47 (s, 2H), 2.48-2.44 (m, 6H); MS (APCI$^+$) m/z 446 (M+H)$^+$.

Example 189: N$^4$-{3-[2-(4-chloro-3-fluorophenoxy)acetamido]bicyclo[1.1.1]pentan-1-yl}-N$^2$-(2-hydroxyethyl)pyridine-2,4-dicarboxamide (Compound 288)

The reaction and purification conditions described in Example 167 substituting the product of Example 181 for 5-cyclopropylpyrazine-2-carboxylic acid, and ethanolamine for the product of Example 4A gave the title compound. $^1$H NMR (400 MHz, DMSO-d$_6$) δ ppm 9.56 (s, 1H), 8.81-8.69 (m, 3H), 8.43 (dd, J=1.8, 0.9 Hz, 1H), 7.94 (dd, J=5.0, 1.8 Hz, 1H), 7.50 (t, J=8.9 Hz, 1H), 7.09 (dd, J=11.4, 2.9 Hz, 1H), 6.87 (ddd, J=9.0, 2.9, 1.2 Hz, 1H), 4.81 (br s, 1H), 4.50 (s, 2H), 3.54 (t, J=6.1 Hz, 2H), 3.40 (q, J=6.1 Hz, 2H), 2.36 (br s, 6H); MS (ESI$^+$) m/z 477 (M+H)$^+$.

Example 190: N-{3-[2-(4-chloro-3-fluorophenoxy)acetamido]bicyclo[1.1.1]pentan-1-yl}-5-(2-cyclopropylethyl)pyridine-2-carboxamide (Compound 289)

Example 190A: tert-butyl 5-(2-cyclopropylethyl)picolinate: (E)-tert-butyl 5-(2-cyclopropylvinyl)picolinate (3:1)

A sealed tube (5 mL) was charged with the product of Example 184A (50 mg, 0.204 mmol), palladium on carbon (Aldrich, 10 weight %—wet support, 1 mg, 0.47 μmol), ammonium formate (90 mg, 1.43 mmol) and ethanol (4.0 mL). The tube was sealed and stirred at 45° C. for 1 hour, and then at 100° C. for 1 hour and at 90° C. for 8 hours. The reaction mixture was cooled to ambient temperature, filtered through a microfiber frit, concentrated under reduced pressure, and the resulting residue was purified via flash chromatography (SiO$_2$, 10-30% ethyl acetate in heptane) to give the title compound (32 mg, 3:1 mixture, 0.13 mmol, 64% yield). MS (ESI$^+$) m/z 190, 192 (M-(tert-butyl))$^+$.

Example 190B: 5-(2-cyclopropylethyl)picolinic acid, 0.15 trimethylamine

The product of Example 190A (32 mg, 0.13 mmol) was dissolved in trifluoroacetic acid (1 mL, 13 mmol) and stirred at 50° C. for 30 minutes. The reaction mixture was concentrated in vacuo, taken up in N,N-dimethylformamide (1 mL), filtered through a glass microfiber frit and purified by preparative HPLC [YMC TriArt™ C18 Hybrid 5 μm column, 50×100 mm, flow rate 90 mL/minute, 5-100% gradient of acetonitrile in buffer (0.1% trimethylamine)] to give the title compound (16 mg, 0.08 mmol, 61% yield). $^1$H NMR (501 MHz, DMSO-d$_6$) δ ppm 8.47 (d, J=2.1 Hz, 1H), 7.88 (d, J=7.9 Hz, 1H), 7.71 (dd, J=8.0, 2.2 Hz, 1H), 2.76-2.69 (m, 2H), 2.62 (q, J=7.1 Hz, 0.9H, triethylamine), 1.54-1.44 (m, 2H), 1.00 (t, J=7.2 Hz, 1.3H, triethylamine), 0.73-0.62 (m, 1H), 0.43-0.32 (m, 2H), 0.06--0.02 (m, 2H); MS (ESI$^+$) m/z 192 (M+H)$^+$.

Example 190C: N-{3-[2-(4-chloro-3-fluorophenoxy)acetamido]bicyclo[1.1.1]pentan-1-yl}-5-(2-cyclopropylethyl)pyridine-2-carboxamide The reaction and purification conditions described in Example 13 substituting the product of Example 190B for the product of Example 12B and the product of Example 6C for the product of Example 4A gave the title compound. $^1$H NMR (400 MHz, DMSO-d$_6$) δ ppm 9.17 (s, 1H), 8.73 (s, 1H), 8.47 (dd, J=2.2, 0.8 Hz, 1H), 7.91 (dd, J=7.9, 0.8 Hz, 1H), 7.82 (dd, J=8.0, 2.2 Hz, 1H), 7.50 (t, J=8.9 Hz, 1H), 7.08 (dd, J=11.4, 2.8 Hz, 1H), 6.86 (ddd, J=9.0, 2.9, 1.2 Hz, 1H), 4.49 (s, 2H), 2.79-2.72 (m, 2H), 2.34 (br s, 6H), 1.50 (q, J=7.2 Hz, 2H), 0.72-0.61 (m, 1H), 0.41-0.34 (m, 2H), 0.06--0.01 (m, 2H); MS (ESI$^+$) m/z 458 (M+H)$^+$.

Example 191: N-{3-[2-(4-chloro-3-fluorophenoxy)acetamido]bicyclo[1.1.1]pentan-1-yl}-2-ethyl-1,3-oxazole-5-carboxamide (Compound 290)

The title compound was prepared using the methodologies described above. $^1$H NMR (400 MHz, CDCl$_3$) δ ppm 7.61 (s, 1H), 7.34 (t, J=8.6 Hz, 1H), 6.92 (s, 1H), 6.78 (dd, J=10.3, 2.8 Hz, 1H), 6.70 (ddd, J=9.0, 2.9, 1.3 Hz, 1H), 6.58 (s, 1H), 4.43 (s, 2H), 2.86 (q, J=7.6 Hz, 2H), 2.58 (s, 6H), 1.39 (t, J=7.6 Hz, 3H); MS (ESI$^+$) m/z 408 (M+H)$^+$.

Example 192: 5-(2-cyclopropylethyl)-N-{3-[2-(3,4-difluorophenoxy)acetamido]bicyclo[1.1.1]pentan-1-yl}pyridine-2-carboxamide (Compound 291)

The reaction and purification conditions described in Example 13 substituting the product of Example 190B for the product of Example 12B and the product of Example 178A for the product of Example 4A gave the title compound. $^1$H NMR (400 MHz, DMSO-d$_6$) δ ppm 9.16 (s, 1H), 8.70 (s, 1H), 8.49-8.45 (m, 1H), 7.93-7.88 (m, 1H), 7.84-7.79 (m, 1H), 7.41-7.31 (m, 1H), 7.09 (ddd, J=12.5, 6.7, 2.9 Hz, 1H), 6.83-6.77 (m, 1H), 4.45 (s, 2H), 2.76 (t, J=7.6 Hz, 2H), 2.34 (br s, 6H), 1.50 (q, J=7.3 Hz, 2H), 0.72-0.61 (m, 1H), 0.41-0.34 (m, 2H), 0.05--0.02 (m, 2H); MS (ESI$^+$) m/z 442 (M+H)$^+$.

Example 193: N-{3-[2-(4-chloro-3-fluorophenoxy)acetamido]bicyclo[1.1.1]pentan-1-yl}-2-ethyl-1,3-thiazole-5-carboxamide (Compound 292)

The title compound was prepared using the methodologies described above. $^1$H NMR (400 MHz, DMSO-d$_6$) δ ppm 9.15 (s, 1H), 8.75 (s, 1H), 8.20 (s, 1H), 7.50 (t, J=8.9 Hz, 1H), 7.08 (dd, J=11.4, 2.8 Hz, 1H), 6.86 (ddd, J=9.0, 2.9, 1.2 Hz, 1H), 4.49 (s, 2H), 2.98 (q, J=7.5 Hz, 2H), 2.32 (s, 6H), 1.29 (t, J=7.5 Hz, 3H); MS (ESI$^+$) m/z 424 (M+H)$^+$.

Example 194: N-{3-[2-(4-chloro-3-fluorophenoxy) acetamido]bicyclo[1.1.1]pentan-1-yl}-2-propyl-1,3-thiazole-5-carboxamide (Compound 293)

The title compound was prepared using the methodologies described above. $^1$H NMR (400 MHz, DMSO-d$_6$) δ ppm 9.15 (s, 1H), 8.75 (s, 1H), 8.20 (s, 1H), 7.50 (t, J=8.9 Hz, 1H), 7.08 (dd, J=11.4, 2.9 Hz, 1H), 6.86 (ddd, J=8.9, 2.9, 1.2 Hz, 1H), 4.49 (s, 2H), 2.93 (t, J=7.4 Hz, 2H), 2.32 (s, 6H), 1.73 (h, J=7.3 Hz, 2H), 0.93 (t, J=7.3 Hz, 3H); MS (ESI$^+$) m/z 438 (M+H)$^+$.

Example 195: N-{3-[2-(4-chloro-3-fluorophenoxy) acetamido]bicyclo[1.1.1]pentan-1-yl}-2-ethyl-4-methyl-1,3-thiazole-5-carboxamide (Compound 294)

The title compound was prepared using the methodologies described above. $^1$H NMR (400 MHz, DMSO-d$_6$) δ ppm 8.73 (s, 1H), 8.69 (s, 1H), 7.50 (t, J=8.9 Hz, 1H), 7.08 (dd, J=11.4, 2.9 Hz, 1H), 6.86 (ddd, J=9.0, 2.8, 1.2 Hz, 1H), 4.48 (s, 2H), 2.93 (q, J=7.5 Hz, 2H), 2.50 (s, 3H), 2.30 (s, 6H), 1.27 (t, J=7.5 Hz, 3H); MS (ESI$^+$) m/z 438 (M+H)$^+$.

Example 196: N-{3-[2-(4-chloro-3-fluorophenoxy) acetamido]bicyclo[1.1.1]pentan-1-yl}-3-methyl-1,2-oxazole-5-carboxamide (Compound 295)

The title compound was prepared using the methodologies described above. $^1$H NMR (400 MHz, DMSO-d$_6$) δ ppm 9.46 (s, 1H), 8.75 (s, 1H), 7.50 (t, J=8.9 Hz, 1H), 7.08 (dd, J=11.4, 2.8 Hz, 1H), 6.88 (s, 1H), 6.86 (ddd, J=9.0, 2.9, 1.2 Hz, 1H), 4.49 (s, 2H), 2.32 (s, 6H), 2.28 (s, 3H); MS (ESI$^+$) m/z 394 (M+H)$^+$.

Example 197: N-{4-[2-(4-chloro-3-fluorophenoxy) acetamido]bicyclo[2.1.1]hexan-1-yl}-5-(difluoromethyl)pyrazine-2-carboxamide (Compound 296)

Example 197A: benzyl {4-[2-(4-chloro-3-fluorophenoxy)acetamido]bicyclo[2.1.1]hexan-1-yl}carbamate N,N-Dimethylformamide (9.9 mL), triethylamine (0.97 mL, 6.93 mmol) and 1-[bis(dimethylamino)methylene]-1H-1,2,3-triazolo[4,5-b]pyridinium 3-oxid hexafluorophosphate (0.489 g, 1.29 mmol, HATU) were added to a mixture of benzyl (4-aminobicyclo[2.1.1]hexan-1-yl)carbamate hydrochloride (MacroChem, 0.28 g, 0.99 mmol) and 2-(4-chloro-3-fluorophenoxy)acetic acid (Aldlab Chemicals, 0.223 g, 1.09 mmol) in sequential order. The reaction mixture was then stirred at ambient temperature for 1 hour. The resulting solution was filtered through a glass microfiber frit and purified by preparative HPLC [Waters XBridge™ C18 5 µm OBD column, 30×100 mm, flow rate 40 mL/minute, 20-100% gradient of acetonitrile in buffer (0.025 M aqueous ammonium bicarbonate, adjusted to pH 10 with ammonium hydroxide)] to give the title compound (0.36 g, 0.83 mmol, 84% yield). $^1$H NMR (400 MHz, DMSO-d$_6$) δ ppm 8.45 (s, 1H), 7.77 (s, 1H), 7.49 (t, J=8.9 Hz, 1H), 7.39-7.28 (m, 5H), 7.06 (dd, J=11.4, 2.8 Hz, 1H), 6.84 (ddd, J=9.0, 2.9, 1.2 Hz, 1H), 4.99 (s, 2H), 4.47 (s, 2H), 2.14-1.95 (m, 2H), 1.83-1.65 (m, 6H); MS (DCI) m/z 450 (M+NH$_4$)$^+$.

Example 197B: N-(4-aminobicyclo[2.1.1]hexan-1-yl)-2-(4-chloro-3-fluorophenoxy)acetamide trifluoroacetate The product of Example 197A (110 mg, 0.254 mmol) was dissolved in trifluoroacetic acid (2.0 mL, 26.0 mmol) and stirred at 80° C. in a sealed tube for 3 hours. The reaction mixture was cooled to ambient temperature and then concentrated in vacuo. The resulting residue was taken up in methanol (3.0 mL), was filtered through a glass microfiber frit, and was purified by preparative HPLC [YMC TriArt™ C18 Hybrid 20 µm column, 50×150 mm, flow rate 130 mL/minute, 3-100% gradient of acetonitrile in buffer (0.1% trifluoroacetic acid)] to give the title compound (95 mg, 0.230 mmol, 91% yield). MS (ESI$^+$) m/z 299 (M+H)$^+$.

Example 197C: N-{4-[2-(4-chloro-3-fluorophenoxy) acetamido]bicyclo[2.1.1]hexan-1-yl}-5-(difluoromethyl)pyrazine-2-carboxamide N,N-Dimethylformamide (2 mL), triethylamine (0.081 mL, 0.58 mmol) and 1-[bis(dimethylamino)methylene]-1H-1,2,3-triazolo[4,5-b]pyridinium 3-oxid hexafluorophosphate (48 mg, 0.126 mmol, HATU) were added to a mixture of the product of Example 197B (40 mg, 0.097 mmol) and 5-(difluoromethyl)pyrazine-2-carboxylic acid (Manchester, 16.9 mg, 0.097 mmol) in sequential order. The reaction mixture was then stirred at ambient temperature for 0.5 hour. The resulting solution was filtered through a glass microfiber frit and purified by preparative HPLC [Waters XBridge™ C18 5 µm OBD column, 30×100 mm, flow rate 40 mL/minute, 5-100% gradient of acetonitrile in buffer (0.025 M aqueous ammonium bicarbonate, adjusted to pH 10 with ammonium hydroxide)] to give the title compound (39 mg, 0.086 mmol, 88% yield). $^1$H NMR (500 MHz, DMSO-d$_6$) δ ppm 9.34 (s, 1H), 9.31-9.22 (m, 1H), 8.99 (s, 1H), 8.53 (s, 1H), 7.50 (t, J=8.9 Hz, 1H), 7.21 (t, J=54.0 Hz, 1H), 7.08 (dd, J=11.4, 2.8 Hz, 1H), 6.86 (ddd, J=9.0, 3.0, 1.1 Hz, 1H), 4.49 (s, 2H), 2.18-2.12 (m, 2H), 1.99-1.80 (m, 6H); MS (ESI$^+$) m/z 455 (M+H)$^+$.

Example 198: N-{4-[2-(4-chloro-3-fluorophenoxy) acetamido]bicyclo[2.1.1]hexan-1-yl}-5-(trifluoromethoxy)pyridine-2-carboxamide (Compound 297)

The title compound was prepared using the methodologies described above. $^1$H NMR (400 MHz, DMSO-d$_6$) δ ppm 9.05 (s, 1H), 8.68 (dt, J=2.8, 0.7 Hz, 1H), 8.50 (s, 1H), 8.14-8.10 (m, 1H), 8.08-8.02 (m, 1H), 7.48 (t, J=8.9 Hz, 1H), 7.06 (dd, J=11.4, 2.8 Hz, 1H), 6.84 (ddd, J=8.8, 2.8, 1.2 Hz, 1H), 4.47 (s, 2H), 2.17-2.07 (m, 2H), 1.97-1.77 (m, 6H); MS (ESI$^+$) m/z 488 (M+H)$^+$.

Example 199: N-{4-[2-(4-chloro-3-fluorophenoxy) acetamido]bicyclo[2.1.1]hexan-1-yl}-6-(trifluoromethoxy)pyridine-3-carboxamide (Compound 298)

The title compound was prepared using the methodologies described above. $^1$H NMR (400 MHz, DMSO-d$_6$) δ ppm 9.03 (s, 1H), 8.77 (dd, J=2.6, 0.7 Hz, 1H), 8.52 (s, 1H), 8.39 (dd, J=8.5, 2.5 Hz, 1H), 7.50 (t, J=8.9 Hz, 1H), 7.38 (dd, J=8.5, 0.7 Hz, 1H), 7.08 (dd, J=11.4, 2.8 Hz, 1H), 6.86 (ddd, J=9.0, 2.9, 1.2 Hz, 1H), 4.50 (s, 2H), 2.20-2.11 (m, 2H), 1.97-1.81 (m, 6H); MS (ESI$^+$) m/z 488 (M+H)$^+$.

Example 200: N-{3-[2-(4-chloro-3-fluorophenoxy)acetamido]bicyclo[1.1.1]pentan-1-yl}-5-(2-methoxyethoxy)pyridine-2-carboxamide (Compound 299)

The title compound was prepared using the methodologies described above. $^1$H NMR (400 MHz, DMSO-$d_6$) δ ppm 9.05 (s, 1H), 8.73 (s, 1H), 8.29 (d, J=2.8 Hz, 1H), 7.95 (d, J=8.6 Hz, 1H), 7.55 (dd, J=8.8, 2.9 Hz, 1H), 7.50 (t, J=8.9 Hz, 1H), 7.08 (dd, J=11.3, 2.8 Hz, 1H), 6.86 (ddd, J=8.9, 2.8, 1.1 Hz, 1H), 4.49 (s, 2H), 4.27-4.22 (m, 2H), 3.72-3.66 (m, 2H), 3.31 (s, 3H), 2.34 (br s, 6H); MS (ESI$^+$) m/z 464 (M+H)$^+$.

Example 201: N-{3-[2-(4-chloro-3-fluorophenoxy)acetamido]bicyclo[1.1.1]pentan-1-yl}-4-(difluoromethoxy)pyridine-2-carboxamide (Compound 300)

The title compound was prepared using the methodologies described above. $^1$H NMR (400 MHz, DMSO-$d_6$) δ ppm 9.32 (s, 1H), 8.70 (s, 1H), 8.59 (d, J=5.6 Hz, 1H), 7.69 (d, J=2.5 Hz, 1H), 7.55 (t, J=72.5 Hz, 1H), 7.47 (t, J=8.9 Hz, 1H), 7.41-7.34 (m, 1H), 7.05 (dd, J=11.3, 2.8 Hz, 1H), 6.83 (ddd, J=9.0, 2.9, 1.1 Hz, 1H), 4.46 (s, 2H), 2.32 (s, 6H); MS (ESI$^+$) m/z 456 (M+H)$^+$.

Example 202: N-{3-[2-(4-chloro-3-fluorophenoxy)acetamido]bicyclo[1.1.1]pentan-1-yl}-3-methoxybenzamide (Compound 301)

The title compound was prepared using the methodologies described above. $^1$H NMR (400 MHz, DMSO-$d_6$/$D_2$O) δ ppm 8.84 (s, OH), 7.50 (t, J=8.9 Hz, 1H), 7.44-7.34 (m, 3H), 7.15-7.04 (m, 2H), 6.88 (ddd, J=8.9, 2.9, 1.1 Hz, 1H), 4.49 (s, 2H), 3.80 (s, 3H), 2.36 (s, 6H); MS (ESI$^+$) m/z 419 (M+H)$^+$.

Example 203: N-{3-[2-(4-chloro-3-fluorophenoxy)acetamido]bicyclo[1.1.1]pentan-1-yl}-3,4-dimethoxybenzamide (Compound 302)

The title compound was prepared using the methodologies described above. $^1$H NMR (400 MHz, DMSO-$d_6$/$D_2$O) δ ppm 8.95 (s, 1H), 7.57-7.36 (m, 3H), 7.07 (dd, J=11.3, 2.9 Hz, 1H), 7.01 (d, J=8.5 Hz, 1H), 6.88 (dt, J=8.9, 1.8 Hz, 1H), 4.49 (s, 2H), 3.80 (d, J=2.5 Hz, 6H), 2.35 (s, 6H); MS (ESI$^+$) m/z 449 (M+H)$^+$.

Example 204: N-{3-[2-(4-chloro-3-fluorophenoxy)acetamido]bicyclo[1.1.1]pentan-1-yl}-3,5-dimethoxybenzamide (Compound 303)

The title compound was prepared using the methodologies described above. $^1$H NMR (400 MHz, DMSO-$d_6$/$D_2$O) δ ppm 7.50 (t, J=8.8 Hz, 1H), 7.07 (dd, J=11.3, 2.8 Hz, 1H), 6.99 (d, J=2.2 Hz, 2H), 6.92-6.83 (m, 1H), 6.64 (t, J=2.3 Hz, 1H), 4.49 (s, 2H), 3.78 (s, 6H), 2.35 (s, 6H); MS (ESI$^+$) m/z 449 (M+H)$^+$.

Example 205: N-{3-[2-(4-chloro-3-fluorophenoxy)acetamido]bicyclo[1.1.1]pentan-1-yl}furan-2-carboxamide (Compound 304)

The title compound was prepared using the methodologies described above. $^1$H NMR (400 MHz, DMSO-$d_6$/$D_2$O) δ ppm 7.78 (dd, J=1.7, 0.8 Hz, 1H), 7.49 (t, J=8.8 Hz, 1H), 7.10 (d, J=3.5 Hz, 1H), 7.07 (dd, J=11.3, 2.8 Hz, 1H), 6.91-6.84 (m, 1H), 6.62 (dd, J=3.5, 1.8 Hz, 1H), 4.49 (s, 2H), 2.33 (s, 6H); MS (ESI$^+$) m/z 379 (M+H)$^+$.

Example 206: N-{3-[2-(4-chloro-3-fluorophenoxy)acetamido]bicyclo[1.1.1]pentan-1-yl}furan-3-carboxamide (Compound 305)

The title compound was prepared using the methodologies described above. $^1$H NMR (400 MHz, DMSO-$d_6$/$D_2$O) δ ppm 8.13 (dd, J=1.6, 0.8 Hz, 1H), 7.70 (t, J=1.8 Hz, 1H), 7.49 (t, J=8.8 Hz, 1H), 7.07 (dd, J=11.3, 2.8 Hz, 1H), 6.87 (ddd, J=9.1, 3.0, 1.1 Hz, 1H), 6.81 (dd, J=1.8, 0.9 Hz, 1H), 4.49 (s, 2H), 2.32 (s, 6H); MS (ESI$^+$) m/z 379 (M+H)$^+$.

Example 207: N-{3-[2-(4-chloro-3-fluorophenoxy)acetamido]bicyclo[1.1.1]pentan-1-yl}thiophene-3-carboxamide (Compound 306)

The title compound was prepared using the methodologies described above. $^1$H NMR (400 MHz, DMSO-$d_6$/$D_2$O) δ ppm 8.14-8.04 (m, 1H), 7.57 (dd, J=5.1, 2.9 Hz, 1H), 7.53-7.43 (m, 2H), 7.07 (dd, J=11.3, 2.8 Hz, 1H), 6.88 (dt, J=9.0, 1.8 Hz, 1H), 4.49 (s, 2H), 2.34 (s, 6H); MS (ESI$^+$) m/z 395 (M+H)$^+$.

Example 208: N-{3-[2-(4-chloro-3-fluorophenoxy)acetamido]bicyclo[1.1.1]pentan-1-yl}-1H-pyrrole-2-carboxamide (Compound 307)

The title compound was prepared using the methodologies described above. $^1$H NMR (400 MHz, DMSO-$d_6$/$D_2$O) δ ppm 7.48 (t, J=8.9 Hz, 1H), 7.05 (dd, J=11.3, 2.8 Hz, 1H), 6.90-6.82 (m, 2H), 6.79-6.71 (m, 1H), 6.08 (dd, J=3.6, 2.6 Hz, 1H), 4.47 (s, 2H), 2.30 (s, 6H); MS (ESI$^+$) m/z 395 (M+NH$_4$)$^+$.

Example 209: N-{3-[2-(4-chloro-3-fluorophenoxy)acetamido]bicyclo[1.1.1]pentan-1-yl}-1,3-thiazole-4-carboxamide (Compound 308)

The title compound was prepared using the methodologies described above. $^1$H NMR (400 MHz, DMSO-$d_6$/$D_2$O) δ ppm 9.13 (d, J=2.0 Hz, 1H), 8.28 (d, J=2.0 Hz, 1H), 7.50 (t, J=8.9 Hz, 1H), 7.07 (dd, J=11.3, 2.9 Hz, 1H), 6.87 (ddd, J=9.0, 2.9, 1.1 Hz, 1H), 4.49 (s, 2H), 2.35 (s, 6H); MS (ESI$^+$) m/z 396 (M+H)$^+$.

Example 210: N-{3-[2-(4-chloro-3-fluorophenoxy)acetamido]bicyclo[1.1.1]pentan-1-yl}-1,3-thiazole-5-carboxamide (Compound 309)

The title compound was prepared using the methodologies described above. $^1$H NMR (400 MHz, DMSO-$d_6$/$D_2$O) δ ppm 9.20 (s, 1H), 8.42 (s, 1H), 7.50 (t, J=8.8 Hz, 1H), 7.07 (dd, J=11.3, 2.8 Hz, 1H), 6.87 (dd, J=9.0, 2.8 Hz, 1H), 4.49 (s, 2H), 2.35 (s, 6H); MS (ESI$^+$) m/z 396 (M+H)$^+$.

Example 211: N-{3-[2-(4-chloro-3-fluorophenoxy)acetamido]bicyclo[1.1.1]pentan-1-yl}-1H-pyrazole-4-carboxamide (Compound 310)

The title compound was prepared using the methodologies described above. $^1$H NMR (400 MHz, DMSO-$d_6$/$D_2$O) δ ppm 8.01 (s, 2H), 7.49 (t, J=8.9 Hz, 1H), 7.07 (dd, J=11.3, 2.8 Hz, 1H), 6.87 (ddd, J=9.0, 2.9, 1.1 Hz, 1H), 4.48 (s, 2H), 2.32 (s, 6H); MS (ESI$^+$) m/z 379 (M+H)$^+$.

Example 212: N-{3-[2-(4-chloro-3-fluorophenoxy) acetamido]bicyclo[1.1.1]pentan-1-yl}-1,2-oxazole-5-carboxamide (Compound 311)

The title compound was prepared using the methodologies described above. $^1$H NMR (400 MHz, DMSO-d$_6$/D$_2$O) δ ppm 8.70 (d, J=1.8 Hz, 1H), 7.50 (t, J=8.9 Hz, 1H), 7.07 (dd, J=11.3, 2.9 Hz, 1H), 7.03 (d, J=1.9 Hz, 1H), 6.87 (ddd, J=8.8, 3.0, 1.1 Hz, 1H), 4.49 (s, 2H), 2.36 (s, 6H); MS (ESI$^+$) m/z 380 (M+H)$^+$.

Example 213: N-{3-[2-(4-chloro-3-fluorophenoxy) acetamido]bicyclo[1.1.1]pentan-1-yl}-3,5-dimethyl-1,2-oxazole-4-carboxamide (Compound 312)

The title compound was prepared using the methodologies described above. $^1$H NMR (400 MHz, DMSO-d$_6$/D$_2$O) δ ppm 8.75 (s, 1H), 8.53 (s, 1H), 7.50 (t, J=8.9 Hz, 1H), 7.09 (dd, J=11.3, 2.8 Hz, 1H), 6.86 (ddd, J=9.0, 2.9, 1.2 Hz, 1H), 4.49 (s, 2H), 2.47 (s, 3H), 2.31 (s, 6H), 2.26 (s, 3H); MS (ESI$^+$) m/z 408 (M+H)$^+$.

Example 214: N-{3-[2-(4-chloro-3-fluorophenoxy) acetamido]bicyclo[1.1.1]pentan-1-yl}-1H-indole-3-carboxamide (Compound 313)

The title compound was prepared using the methodologies described above. $^1$H NMR (400 MHz, DMSO-d$_6$/D$_2$O) δ ppm 7.62 (d, J=8.0 Hz, 1H), 7.50 (t, J=8.9 Hz, 1H), 7.46 (d, J=8.1 Hz, 1H), 7.21 (ddd, J=8.2, 6.9, 1.1 Hz, 1H), 7.14-6.99 (m, 3H), 6.88 (ddd, J=9.0, 3.0, 1.1 Hz, 1H), 4.50 (s, 2H), 2.38 (s, 6H); MS (ESI$^+$) m/z 428 (M+H)$^+$.

Example 215: N-{3-[2-(4-chloro-3-fluorophenoxy) acetamido]bicyclo[1.1.1]pentan-1-yl}-8-methyl-4-oxo-4H-pyrido[1,2-a]pyrimidine-3-carboxamide (Compound 314)

The title compound was prepared using the methodologies described above. $^1$H NMR (400 MHz, DMSO-d$_6$/D$_2$O) δ ppm 9.08 (d, J=7.2 Hz, 1H), 8.96 (s, 1H), 7.73 (s, 1H), 7.56-7.45 (m, 2H), 7.08 (dd, J=11.3, 2.9 Hz, 1H), 6.88 (dd, J=8.9, 2.9 Hz, 1H), 4.50 (s, 2H), 2.56 (s, 3H), 2.39 (s, 6H); MS (ESI$^+$) m/z 471 (M+H)$^+$.

Example 216: N-{3-[2-(4-chloro-3-fluorophenoxy) acetamido]bicyclo[1.1.1]pentan-1-yl}-4-oxo-4,5,6,7-tetrahydro-1-benzofuran-3-carboxamide (Compound 315)

The title compound was prepared using the methodologies described above. $^1$H NMR (400 MHz, DMSO-d$_6$/D$_2$O) δ ppm 10.24 (s, 1H), 8.19 (s, 1H), 7.49 (t, J=8.9 Hz, 1H), 7.07 (dd, J=11.3, 2.8 Hz, 1H), 6.87 (dt, J=8.8, 1.7 Hz, 1H), 4.49 (s, 2H), 2.94 (t, J=6.2 Hz, 2H), 2.57 (t, J=6.5 Hz, 2H), 2.35 (s, 6H), 2.14-2.03 (m, 2H); MS (ESI$^+$) m/z 447 (M+H)$^+$.

Example 217: N-{3-[2-(4-chloro-3-fluorophenoxy) acetamido]bicyclo[1.1.1]pentan-1-yl}-4-propoxy-benzamide (Compound 316)

The title compound was prepared using the methodologies described above. $^1$H NMR (400 MHz, DMSO-d$_6$/D$_2$O) δ ppm 8.83 (s, 1H), 7.79 (d, J=8.8 Hz, 2H), 7.50 (t, J=8.9 Hz, 1H), 7.07 (dd, J=11.3, 2.9 Hz, 1H), 6.97 (d, J=8.9 Hz, 2H), 6.88 (ddd, J=8.9, 2.9, 1.2 Hz, 1H), 4.49 (s, 2H), 3.98 (t, J=6.5 Hz, 2H), 2.33 (s, 6H), 1.74 (h, J=7.1 Hz, 2H), 0.98 (t, J=7.4 Hz, 3H); MS (ESI$^+$) m/z 447 (M+H)$^+$.

Example 218: N-{3-[2-(4-chloro-3-fluorophenoxy) acetamido]bicyclo[1.1.1]pentan-1-yl}-1-benzofuran-2-carboxamide (Compound 317)

The title compound was prepared using the methodologies described above. $^1$H NMR (400 MHz, DMSO-d$_6$/D$_2$O) δ ppm 7.78 (d, J=7.7 Hz, 1H), 7.66 (d, J=8.4 Hz, 1H), 7.56-7.45 (m, 3H), 7.35 (t, J=7.5 Hz, 1H), 7.08 (dd, J=11.3, 2.8 Hz, 1H), 6.88 (dd, J=8.9, 2.8 Hz, 1H), 4.50 (s, 2H), 2.37 (s, 6H); MS (ESI$^+$) m/z 429 (M+H)$^+$.

Example 219: N-{3-[2-(4-chloro-3-fluorophenoxy) acetamido]bicyclo[1.1.1]pentan-1-yl}-1H-indazole-3-carboxamide (Compound 318)

The title compound was prepared using the methodologies described above. $^1$H NMR (400 MHz, DMSO-d$_6$/D$_2$O) δ ppm 8.22-8.10 (m, 1H), 7.63 (d, J=8.5 Hz, 1H), 7.50 (t, J=8.9 Hz, 1H), 7.44 (ddd, J=8.3, 6.8, 1.1 Hz, 1H), 7.27 (dd, J=8.1, 7.0 Hz, 1H), 7.08 (dd, J=11.3, 2.9 Hz, 1H), 6.88 (ddd, J=8.9, 2.9, 1.1 Hz, 1H), 4.50 (s, 2H), 2.39 (s, 6H); MS (ESI$^+$) m/z 429 (M+H)$^+$.

Example 220: N-{3-[2-(4-chloro-3-fluorophenoxy) acetamido]bicyclo[1.1.1]pentan-1-yl}-5-methoxy-1-benzofuran-2-carboxamide (Compound 319)

The title compound was prepared using the methodologies described above. $^1$H NMR (400 MHz, DMSO-d$_6$/D$_2$O) δ ppm 9.36 (s, 1H), 8.86 (s, 1H), 7.56 (d, J=9.1 Hz, 1H), 7.50 (t, J=8.9 Hz, 1H), 7.47-7.45 (m, 1H), 7.27 (d, J=2.6 Hz, 1H), 7.08 (t, J=3.3 Hz, 1H), 7.06 (dd, J=2.7, 1.6 Hz, 1H), 6.93-6.83 (m, 1H), 4.49 (s, 2H), 3.80 (s, 3H), 2.36 (s, 6H); MS (ESI$^+$) m/z 459 (M+H)$^+$.

Example 221: N-{3-[2-(4-chloro-3-fluorophenoxy) acetamido]bicyclo[1.1.1]pentan-1-yl}-1H-pyrazole-5-carboxamide (Compound 320)

The title compound was prepared using the methodologies described above. $^1$H NMR (400 MHz, DMSO-d$_6$/D$_2$O) δ ppm 7.74 (d, J=2.3 Hz, 1H), 7.50 (t, J=8.9 Hz, 1H), 7.07 (dd, J=11.3, 2.8 Hz, 1H), 6.87 (dd, J=9.0, 2.9 Hz, 1H), 6.68 (d, J=2.3 Hz, 1H), 4.48 (s, 2H), 2.33 (s, 6H); MS (ESI$^+$) m/z 379 (M+H)$^+$.

Example 222: N-{3-[2-(4-chloro-3-fluorophenoxy) acetamido]bicyclo[1.1.1]pentan-1-yl}-4-(trifluoromethoxy)benzamide (Compound 321)

The title compound was prepared using the methodologies described above. $^1$H NMR (400 MHz, DMSO-d$_6$/D$_2$O) δ ppm 7.98-7.90 (m, 2H), 7.50 (t, J=8.9 Hz, 1H), 7.45 (d, J=8.4 Hz, 2H), 7.07 (dd, J=11.3, 2.8 Hz, 1H), 6.88 (dt, J=9.0, 1.8 Hz, 1H), 4.49 (s, 2H), 2.36 (s, 6H); MS (ESI$^+$) m/z 473 (M+H)$^+$.

Example 223: N-{3-[2-(4-chloro-3-fluorophenoxy) acetamido]bicyclo[1.1.1]pentan-1-yl}-6-hydroxy-pyridine-3-carboxamide (Compound 322)

The title compound was prepared using the methodologies described above. $^1$H NMR (400 MHz, DMSO-d$_6$/D$_2$O) δ ppm 7.99 (d, J=2.7 Hz, 1H), 7.86 (dd, J=9.6, 2.8 Hz, 1H), 7.49 (t, J=8.8 Hz, 1H), 7.07 (dd, J=11.4, 2.9 Hz, 1H), 6.87 (d, J=9.8 Hz, 1H), 6.39 (d, J=9.6 Hz, 1H), 4.48 (s, 2H), 2.31 (s, 6H); MS (ESI$^+$) m/z 406 (M+H)$^+$.

Example 224: N-{3-[2-(4-chloro-3-fluorophenoxy)acetamido]bicyclo[1.1.1]pentan-1-yl}-3-ethyl-1,2-oxazole-5-carboxamide (Compound 323)

The title compound was prepared using the methodologies described above. $^1$H NMR (400 MHz, DMSO-d$_6$) δ ppm 9.42 (s, 1H), 8.72 (s, 1H), 7.47 (t, J=8.8 Hz, 1H), 7.04 (dd, J=11.4, 2.8 Hz, 1H), 6.92 (s, 1H), 6.82 (dt, J=8.9, 1.8 Hz, 1H), 4.46 (s, 2H), 2.64 (q, J=7.6 Hz, 2H), 2.29 (s, 6H), 1.17 (t, J=7.6 Hz, 3H); MS (ESI$^+$) m/z 408 (M+H)$^+$.

Example 225: N-{4-[2-(4-chloro-3-fluorophenoxy)acetamido]bicyclo[2.1.1]hexan-1-yl}-3-methyl-1,2-oxazole-5-carboxamide (Compound 324)

The title compound was prepared using the methodologies described above. $^1$H NMR (400 MHz, DMSO-d$_6$) δ ppm 9.20 (s, 1H), 8.50 (s, 1H), 7.47 (t, J=8.9 Hz, 1H), 7.05 (dd, J=11.4, 2.9 Hz, 1H), 6.87 (s, 1H), 6.84 (ddd, J=9.0, 2.9, 1.2 Hz, 1H), 4.46 (s, 2H), 2.26 (s, 3H), 2.13-2.03 (m, 2H), 1.91-1.76 (m, 6H); MS (ESI$^+$) m/z 408 (M+H)$^+$.

Example 226: N-{3-[2-(4-chloro-3-fluorophenoxy)acetamido]bicyclo[1.1.1]pentan-1-yl}-6-sulfamoylpyridine-3-carboxamide (Compound 325)

The title compound was prepared using the methodologies described above. $^1$H NMR (400 MHz, DMSO-d$_6$) δ ppm 9.43 (s, 1H), 9.06 (dd, J=2.2, 0.9 Hz, 1H), 8.78 (s, 1H), 8.40 (dd, J=8.2, 2.2 Hz, 1H), 8.01 (dd, J=8.1, 0.8 Hz, 1H), 7.57 (br s, 2H), 7.50 (t, J=8.9 Hz, 1H), 7.09 (dd, J=11.3, 2.8 Hz, 1H), 6.87 (ddd, J=9.0, 2.9, 1.2 Hz, 1H), 4.50 (s, 2H), 2.37 (s, 6H); MS (ESI$^+$) m/z 469 (M+H)$^+$.

Example 227: N-{4-[2-(4-chloro-3-fluorophenoxy)acetamido]-3-hydroxybicyclo[2.2.2]octan-1-yl}-3-methyl-1,2-oxazole-5-carboxamide (Compound 326)

The title compound was prepared using the methodologies described in Example 130 substituting 3-methyl-1,2-oxazole-5-carboxylic acid for 5-(difluoromethyl)pyrazine-2-carboxylic acid. $^1$H NMR (400 MHz, DMSO-d$_6$) δ ppm 8.06 (s, 1H), 7.47 (t, J=8.9 Hz, 1H), 7.26 (s, 1H), 7.04 (dd, J=11.4, 2.8 Hz, 1H), 6.89-6.77 (m, 2H), 5.09 (d, J=4.4 Hz, 1H), 4.45 (s, 2H), 4.09-4.01 (m, 1H), 2.33 (s, 1H), 2.25 (s, 3H), 2.07 (dd, J=11.9, 8.7 Hz, 1H), 2.03-1.92 (m, 1H), 1.95-1.76 (m, 7H); MS (ESI$^+$) m/z 452.1 (M+H)$^+$.

Example 228: N-{4-[2-(4-chloro-3-fluorophenoxy)acetamido]-3-hydroxybicyclo[2.2.2]octan-1-yl}-3-cyclopropyl-1,2-oxazole-5-carboxamide (Compound 327)

The title compound was prepared using the methodologies described in Example 130 substituting 3-cyclopropyl-1,2-oxazole-5-carboxylic acid for 5-(difluoromethyl)pyrazine-2-carboxylic acid. $^1$H NMR (400 MHz, DMSO-d$_6$) δ ppm 8.02 (s, 1H), 7.46 (t, J=8.9 Hz, 1H), 7.26 (s, 1H), 7.04 (dd, J=11.4, 2.8 Hz, 1H), 6.81 (ddd, J=9.0, 2.9, 1.2 Hz, 1H), 6.74 (s, 1H), 5.09 (d, J=4.4 Hz, 1H), 4.45 (s, 2H), 4.05 (dt, J=9.0, 4.0 Hz, 1H), 2.32 (td, J=11.2, 10.4, 5.1 Hz, 1H), 2.13-1.96 (m, 3H), 1.87 (dq, J=18.7, 7.6, 6.2 Hz, 7H), 1.06-0.95 (m, 2H), 0.81-0.72 (m, 2H); MS (ESI$^+$) m/z 478.1 (M+H)$^+$.

Example 229: N-{4-[2-(4-chloro-3-fluorophenoxy)acetamido]-3-hydroxybicyclo[2.2.2]octan-1-yl}-2,1-benzoxazole-3-carboxamide (Compound 328)

The title compound was prepared using the methodologies described in Example 130 substituting 2,1-benzoxazole-3-carboxylic acid for 5-(difluoromethyl)pyrazine-2-carboxylic acid. $^1$H NMR (400 MHz, DMSO-d$_6$) δ ppm 8.48 (s, 1H), 7.86 (d, J=8.8 Hz, 1H), 7.70 (d, J=9.1 Hz, 1H), 7.50-7.39 (m, 2H), 7.30-7.16 (m, 2H), 7.03 (dd, J=11.4, 2.9 Hz, 1H), 6.85-6.76 (m, 1H), 5.11 (s, 1H), 4.45 (s, 2H), 4.12-4.03 (m, 1H), 2.40 (ddd, J=12.5, 9.4, 2.6 Hz, 1H), 2.13-1.76 (m, 9H); MS (ESI$^+$) m/z 488.1 (M+H)$^+$.

Example 230: N-{3-[2-(4-chloro-3-fluorophenoxy)acetamido]bicyclo[1.1.1]pentan-1-yl}-3-cyclopropyl-1-methyl-1H-pyrazole-5-carboxamide (Compound 329)

The title compound was prepared using the methodologies described above. $^1$H NMR (500 MHz, DMSO-d$_6$) δ ppm 8.87 (s, 1H), 8.76 (s, 1H), 7.51 (t, J=8.9 Hz, 1H), 7.09 (dd, J=11.4, 2.8 Hz, 1H), 6.87 (ddd, J=9.0, 2.9, 1.2 Hz, 1H), 6.53 (s, 1H), 4.49 (s, 2H), 3.94 (s, 3H), 2.31 (s, 6H), 1.84 (tt, J=8.4, 5.0 Hz, 1H), 0.93-0.81 (m, 2H), 0.65-0.55 (m, 2H); MS (ESI$^+$) m/z 433 (M+H)$^+$.

Example 231: N-{4-[2-(4-chloro-3-fluorophenoxy)acetamido]-2-hydroxybicyclo[2.2.2]octan-1-yl}-3-methyl-1,2-oxazole-5-carboxamide (Compound 330)

The title compound was prepared using the methodologies described in Example 68 substituting 3-methyl-1,2-oxazole-5-carboxylic acid for picolinic acid. $^1$H NMR (400 MHz, DMSO-d$_6$) δ ppm 7.64 (s, 1H), 7.53-7.39 (m, 2H), 6.99 (dd, J=11.4, 2.8 Hz, 1H), 6.84 (s, 1H), 6.78 (dt, J=8.9, 1.8 Hz, 1H), 5.08 (d, J=4.5 Hz, 1H), 4.40 (s, 2H), 4.19-4.05 (m, 1H), 2.28 (td, J=9.7, 4.7 Hz, 1H), 2.24 (s, 3H), 2.06 (ddd, J=12.6, 10.5, 5.2 Hz, 1H), 2.00-1.69 (m, 8H); MS (ESI$^+$) m/z 452.1 (M+H)$^+$.

Example 232: N-{4-[2-(4-chloro-3-fluorophenoxy)acetamido]-2-hydroxybicyclo[2.2.2]octan-1-yl}-3-cyclopropyl-1,2-oxazole-5-carboxamide (Compound 331)

The title compound was prepared using the methodologies described in Example 68 substituting 3-cyclopropyl-1,2-oxazole-5-carboxylic acid for picolinic acid. $^1$H NMR (400 MHz, DMSO-d$_6$) δ ppm 7.60 (s, 1H), 7.53-7.39 (m, 2H), 6.98 (dd, J=11.4, 2.8 Hz, 1H), 6.77 (ddd, J=9.0, 2.9, 1.1 Hz, 1H), 6.73 (s, 1H), 5.06 (d, J=4.6 Hz, 1H), 4.40 (s, 2H), 4.14 (dt, J=8.6, 3.9 Hz, 1H), 2.26 (ddd, J=12.7, 9.5, 2.9 Hz, 1H), 2.10-1.69 (m, 9H), 1.05-0.94 (m, 2H), 0.79-0.68 (m, 2H); MS (ESI$^+$) m/z 478.1 (M+H)$^+$.

Example 233: N-{4-[2-(4-chloro-3-fluorophenoxy)acetamido]-2-hydroxybicyclo[2.2.2]octan-1-yl}-2,1-benzoxazole-3-carboxamide (Compound 332)

The title compound was prepared using the methodologies described in Example 68 substituting 2,1-benzoxazole- 3-carboxylic acid for picolinic acid. $^1$H NMR (400 MHz, DMSO-$d_6$) δ ppm 8.02 (s, 1H), 7.87 (d, J=8.8 Hz, 1H), 7.69 (d, J=9.0 Hz, 1H), 7.53 (s, 1H), 7.44 (t, J=8.4 Hz, 2H), 7.21 (dd, J=8.9, 6.4 Hz, 1H), 6.99 (dd, J=11.4, 2.8 Hz, 1H), 6.78 (dd, J=9.0, 2.7 Hz, 1H), 4.41 (s, 2H), 4.24 (dd, J=9.7, 3.1 Hz, 1H), 2.32 (dd, J=22.7, 2.8 Hz, 1H), 2.17 (ddd, J=12.7, 10.3, 5.4 Hz, 1H), 2.08-1.88 (m, 4H), 1.90-1.73 (m, 4H); MS (ESI$^+$) m/z 488.1 (M+H)$^+$.

Example 234: N-{4-[2-(4-chloro-3-fluorophenoxy)acetamido]bicyclo[2.1.1]hexan-1-yl}-4-(hydroxymethyl)pyridine-2-carboxamide (Compound 333)

The title compound was prepared using the methodologies described above. $^1$H NMR (400 MHz, DMSO-$d_6$) δ ppm 8.92 (s, 1H), 8.51 (d, J=5.0 Hz, 1H), 8.48 (s, 1H), 7.94 (d, J=1.6 Hz, 1H), 7.50-7.43 (m, 2H), 7.05 (dd, J=11.4, 2.8 Hz, 1H), 6.85-6.80 (m, 1H), 5.50 (t, J=5.6 Hz, 1H), 4.58 (d, J=5.3 Hz, 2H), 4.46 (s, 2H), 2.16-2.08 (m, 2H), 1.93-1.75 (m, 6H); MS (ESI$^+$) m/z 434 (M+H)$^+$.

Example 235: N-{3-[2-(4-chloro-3-fluorophenoxy)acetamido]bicyclo[1.1.1]pentan-1-yl}-5-propylpyrazine-2-carboxamide (Compound 334)

Example 235A: methyl 5-propylpyrazine-2-carboxylate

A 20 mL sealed tube was charged with methyl 5-bromopyrazine-2-carboxylate (Ark Pharm, 0.4.0 g, 1.84 mmol), tris(dibenzylideneacetone)dipalladium(0) (0.025 g, 0.028 mmol), tri(2-furyl)phosphine (0.026 g, 0.111 mmol), and N,N-dimethylformamide (4.6 mL). The tube was purged with a nitrogen stream for 2 minutes, sealed and stirred at ambient temperature. Propylzinc(II) bromide (0.5 M in tetrahydrofuran, 5.16 mL) was added dropwise over 2 minutes via a cannula needle. The reaction mixture was stirred at ambient temperature for 1 hour and then quenched with water (0.5 mL). The resulting mixture was concentrated under reduced pressure briefly to remove most of the tetrahydrofuran solvent. The resulting solution was filtered through a glass microfiber frit and directly purified by reverse-phase flash chromatography [150 g Redisep® Gold $C_{18}$ column, flow rate 110 mL/minute, 5-100% gradient of acetonitrile in buffer (0.1% trifluoroacetic acid)] to give the title compound (0.33 g, 1.83 mmol, 99% yield) as a light yellow syrup. MS (ESI$^+$) m/z 181 (M+H)$^+$.

Example 235B: N-{3-[2-(4-chloro-3-fluorophenoxy)acetamido]bicyclo[1.1.1]pentan-1-yl}-5-propylpyrazine-2-carboxamide The reaction and purification conditions described in Example 52 substituting the product of Example 235A for the product of Example 49A gave the title compound. $^1$H NMR (400 MHz, DMSO-$d_6$) δ ppm 9.37 (s, 1H), 9.06-9.04 (m, 1H), 8.74 (s, 1H), 8.61-8.58 (m, 1H), 7.50 (t, J=8.9 Hz, 1H), 7.08 (dd, J=11.3, 2.9 Hz, 1H), 6.90-6.82 (m, 1H), 4.49 (s, 2H), 2.85 (t, J=7.5 Hz, 2H), 2.35 (s, 6H), 1.74 (h, J=7.4 Hz, 2H), 0.91 (t, J=7.3 Hz, 3H); MS (ESI$^+$) m/z 433 (M+H)$^+$.

Example 236: N-{3-[2-(4-chloro-3-fluorophenoxy)acetamido]bicyclo[1.1.1]pentan-1-yl}-5-(2-cyanoethyl)pyridine-2-carboxamide (Compound 335)

Example 236A: tert-butyl 5-(2-cyanoethyl)picolinate

A 20 mL sealed tube was charged with tris(dibenzylideneacetone)dipalladium(0) (0.049 g, 0.053 mmol), tri-tert-butylphosphonium tetrafluoroborate (Strem, 0.037 g, 0.127 mmol), tert-butyl 5-bromopicolinate (Combi-Blocks, 0.456 g, 1.767 mmol), and N,N-dimethylformamide (8.8 mL). The tube was purged with a nitrogen stream for 2 minutes, sealed and stirred at ambient temperature. 2-cyanoethylzinc bromide (0.5 M in tetrahydrofuran, 4.77 mL) was added dropwise over 2 minutes via a cannula needle. The reaction mixture was stirred at ambient temperature for 6 hours and then at 75° C. for 18 hours. The reaction was cooled to ambient temperature and quenched with water (0.5 mL), and the resulting mixture was concentrated under reduced pressure briefly to remove most of the tetrahydrofuran solvent. The resulting solution was filtered through a glass microfiber frit and directly purified by reverse-phase flash chromatography [150 g Redisep® Gold C18 column, flow rate 110 mL/minute, 5-100% gradient of acetonitrile in buffer (0.1% trifluoroacetic acid)] to give the title compound (0.15 g, 0.65 mmol, 37% yield). MS (ESI$^+$) m/z 233 (M+H)$^+$.

Example 236B: 5-(2-cyanoethyl)picolinic acid

The reaction and purification conditions described in Example 190B substituting the product of Example 236A for the product of Example 190A, and 0.1% trifluoroacetic acid buffer for the 0.1% trimethylamine buffer for preparative HPLC gave the title compound. MS (ESI$^+$) m/z 177 (M+H)$^+$.

Example 236C: N-{3-[2-(4-chloro-3-fluorophenoxy)acetamido]bicyclo[0.1.1]pentan-1-yl}-5-(2-cyanoethyl)pyridine-2-carboxamide The reaction and purification conditions described in Example 13 substituting the product of Example 236B for the product of Example 12B and the product of Example 6C for the product of Example 4A gave the title compound. $^1$H NMR (501 MHz, DMSO-$d_6$) δ ppm 9.22 (s, 1H), 8.71 (s, 1H), 8.55 (dd, J=2.2, 0.8 Hz, 1H), 7.97-7.93 (m, 1H), 7.93-7.88 (m, 1H), 7.48 (t, J=8.9 Hz, 1H), 7.06 (dd, J=11.4, 2.8 Hz, 1H), 6.84 (ddd, J=9.0, 2.9, 1.2 Hz, 1H), 4.47 (s, 2H), 3.01-2.96 (m, 2H), 2.90-2.85 (m, 2H), 2.33 (s, 6H); MS (ESI$^+$) m/z 443 (M+H)$^+$.

Example 237: N-{4-[2-(4-chloro-3-fluorophenoxy)acetamido]bicyclo[2.1.1]hexan-1-yl}-5-(2-cyanoethyl)pyridine-2-carboxamide (Compound 336)

The reaction and purification conditions described in Example 197C substituting the product of Example 236B for 5-(difluoromethyl)pyrazine-2-carboxylic acid gave the title compound. $^1$H NMR (400 MHz, DMSO-$d_6$) δ ppm 9.83 (s, 1H), 8.75 (s, 1H), 7.48 (t, J=8.9 Hz, 1H), 7.06 (dd, J=11.4, 2.8 Hz, 1H), 6.84 (ddd, J=8.9, 2.9, 1.2 Hz, 1H), 4.47 (s, 2H), 2.54 (s, 3H), 2.31 (s, 6H); MS (ESI$^+$) m/z 395 (M+H)$^+$.

Example 238: N-{4-[2-(4-chloro-3-fluorophenoxy)acetamido]bicyclo[2.1.1]hexan-1-yl}-5-(difluoromethoxy)pyridine-2-carboxamide (Compound 337)

The title compound was prepared using the methodologies described above. $^1$H NMR (400 MHz, DMSO-$d_6$) δ ppm 8.99 (s, 1H), 8.54 (s, 1H), 8.50 (d, J=2.8 Hz, 1H), 8.11-8.04 (m, 1H), 7.83 (dd, J=8.7, 2.9 Hz, 1H), 7.50 (t, J=8.9 Hz, 1H), 7.44 (t, J=73.0 Hz, 1H), 7.08 (dd, J=11.4, 2.9

Hz, 1H), 6.86 (ddd, J=8.9, 2.8, 1.2 Hz, 1H), 4.49 (s, 2H), 2.17-2.07 (m, 2H), 1.96-1.78 (m, 6H); MS (ESI$^+$) m/z 470 (M+H)$^+$.

Example 239: 3-tert-butyl-N-{3-[2-(4-chloro-3-fluorophenoxy)acetamido]bicyclo[1.1.1]pentan-1-yl}-1-methyl-1H-pyrazole-5-carboxamide (Compound 338)

The title compound was prepared using the methodologies described above. $^1$H NMR (500 MHz, DMSO-d$_6$/D$_2$O) δ ppm 7.50 (t, J=8.9 Hz, 1H), 7.07 (dd, J=11.3, 2.8 Hz, 1H), 6.88 (ddd, J=9.0, 2.9, 1.2 Hz, 1H), 6.73 (s, 1H), 4.49 (s, 2H), 3.96 (s, 3H), 2.33 (s, 6H), 1.23 (s, 9H); MS (ESI$^+$) m/z 449 (M+H)$^+$.

Example 240: N-{3-[2-(4-chloro-3-fluorophenoxy)acetamido]bicyclo[1.1.1]pentan-1-yl}-2-phenyl-1,3-thiazole-4-carboxamide (Compound 339)

The title compound was prepared using the methodologies described above. $^1$H NMR (500 MHz, DMSO-d$_6$/D$_2$O) δ ppm 8.26 (s, 1H), 8.13-8.03 (m, 2H), 7.58-7.53 (m, 3H), 7.50 (t, J=8.9 Hz, 1H), 7.08 (dd, J=11.3, 2.8 Hz, 1H), 6.88 (ddd, J=8.9, 2.8, 1.2 Hz, 1H), 4.50 (s, 2H), 2.40 (s, 6H); MS (ESI$^+$) m/z 472 (M+H)$^+$.

Example 241: N-{3-[2-(4-chloro-3-fluorophenoxy)acetamido]bicyclo[1.1.1]pentan-1-yl}-1-methyl-3-phenyl-1H-pyrazole-5-carboxamide (Compound 340)

The title compound was prepared using the methodologies described above. $^1$H NMR (500 MHz, DMSO-d$_6$/D$_2$O) δ ppm 7.81-7.72 (m, 2H), 7.50 (t, J=8.8 Hz, 1H), 7.45 (dd, J=8.4, 7.1 Hz, 2H), 7.39-7.32 (m, 1H), 7.24 (s, 1H), 7.08 (dd, J=11.3, 2.8 Hz, 1H), 6.88 (ddd, J=9.0, 2.8, 1.1 Hz, 1H), 4.50 (s, 2H), 4.09 (s, 3H), 2.37 (s, 6H); MS (ESI$^+$) m/z 469 (M+H)$^+$.

Example 242: N-{3-[2-(4-chloro-3-fluorophenoxy)acetamido]bicyclo[1.1.1]pentan-1-yl}-2-methyl-1,3-benzoxazole-6-carboxamide (Compound 341)

The title compound was prepared using the methodologies described above. $^1$H NMR (500 MHz, DMSO-d$_6$/D$_2$O) δ ppm 7.89 (d, J=8.4 Hz, 1H), 7.50 (t, J=8.9 Hz, 1H), 7.33 (d, J=2.1 Hz, 1H), 7.27 (dd, J=8.4, 2.0 Hz, 1H), 7.07 (dd, J=11.3, 2.8 Hz, 1H), 6.88 (ddd, J=9.0, 2.9, 1.1 Hz, 1H), 4.49 (s, 2H), 2.33 (s, 6H), 2.13 (s, 3H); MS (ESI$^+$) m/z 444 (M+H)$^+$.

Example 243: N-{3-[2-(4-chloro-3-fluorophenoxy)acetamido]bicyclo[1.1.1]pentan-1-yl}-3-methyl-4-oxo-3,4-dihydroquinazoline-7-carboxamide (Compound 342)

The title compound was prepared using the methodologies described above. $^1$H NMR (500 MHz, DMSO-d$_6$/D$_2$O) δ ppm 9.43 (s, 1H), 8.88 (s, 1H), 8.40 (s, 1H), 8.23 (d, J=8.3 Hz, 1H), 8.11 (d, J=1.8 Hz, 1H), 7.93 (dd, J=8.4, 1.7 Hz, 1H), 7.50 (t, J=8.9 Hz, 1H), 7.08 (dd, J=11.3, 2.9 Hz, 1H), 6.88 (ddd, J=9.0, 2.8, 1.1 Hz, 1H), 4.50 (s, 2H), 3.52 (s, 3H), 2.38 (s, 6H); MS (ESI$^+$) m/z 470 (M+H)$^+$.

Example 244: N-{3-[2-(4-chloro-3-fluorophenoxy)acetamido]bicyclo[1.1.1]pentan-1-yl}-1-propyl-1H-pyrazole-3-carboxamide (Compound 343)

The title compound was prepared using the methodologies described above. $^1$H NMR (500 MHz, DMSO-d$_6$/D$_2$O) δ ppm 7.77 (d, J=2.3 Hz, 1H), 7.50 (t, J=8.9 Hz, 1H), 7.07 (dd, J=11.3, 2.9 Hz, 1H), 6.87 (ddd, J=9.0, 2.8, 1.2 Hz, 1H), 6.62 (d, J=2.3 Hz, 1H), 4.49 (s, 2H), 4.10 (t, J=6.9 Hz, 2H), 2.33 (s, 6H), 1.80 (h, J=7.2 Hz, 2H), 0.81 (t, J=7.4 Hz, 3H); MS (ESI$^+$) m/z 421 (M+H)$^+$.

Example 245: N-{3-[2-(4-chloro-3-fluorophenoxy)acetamido]bicyclo[1.1.1]pentan-1-yl}-2-phenyl-1,3-oxazole-5-carboxamide (Compound 344)

The title compound was prepared using the methodologies described above. $^1$H NMR (500 MHz, DMSO-d$_6$/D$_2$O) δ ppm 8.18-8.08 (m, 2H), 7.86 (s, 1H), 7.67-7.56 (m, 3H), 7.50 (t, J=8.9 Hz, 1H), 7.08 (dd, J=11.3, 2.9 Hz, 1H), 6.88 (ddd, J=8.9, 2.9, 1.2 Hz, 1H), 4.50 (s, 2H), 2.38 (s, 6H); MS (ESI$^+$) m/z 456 (M+H)$^+$.

Example 246: N-{3-[2-(4-chloro-3-fluorophenoxy)acetamido]bicyclo[1.1.1]pentan-1-yl}-1-methyl-5-phenyl-1H-pyrazole-3-carboxamide (Compound 345)

The title compound was prepared using the methodologies described above. $^1$H NMR (500 MHz, DMSO-d$_6$/D$_2$O) δ ppm 7.62-7.45 (m, 6H), 7.08 (dd, J=11.3, 2.8 Hz, 1H), 6.88 (ddd, J=8.9, 2.8, 1.2 Hz, 1H), 6.77 (s, 1H), 4.49 (s, 2H), 3.90 (s, 3H), 2.34 (s, 6H); MS (ESI$^+$) m/z 469 (M+H)$^+$.

Example 247: N-{3-[2-(4-chloro-3-fluorophenoxy)acetamido]bicyclo[1.1.1]pentan-1-yl}-1,2-benzoxazole-3-carboxamide (Compound 346)

The title compound was prepared using the methodologies described above. $^1$H NMR (500 MHz, DMSO-d$_6$/D$_2$O) δ ppm 8.10 (dt, J=8.0, 1.1 Hz, 1H), 7.86 (dt, J=8.5, 0.8 Hz, 1H), 7.75 (ddd, J=8.5, 7.1, 1.2 Hz, 1H), 7.56-7.46 (m, 2H), 7.08 (dd, J=11.3, 2.9 Hz, 1H), 6.88 (ddd, J=9.0, 2.9, 1.2 Hz, 1H), 4.50 (s, 2H), 2.41 (s, 6H); MS (ESI$^+$) m/z 430 (M+H)$^+$.

Example 248: N-{3-[2-(4-chloro-3-fluorophenoxy)acetamido]bicyclo[1.1.1]pentan-1-yl}-1,3-benzoxazole-2-carboxamide (Compound 347)

The title compound was prepared using the methodologies described above. $^1$H NMR (500 MHz, DMSO-d$_6$/D$_2$O) δ ppm 8.05-7.92 (m, 1H), 7.92-7.81 (m, 1H), 7.61-7.55 (m, 1H), 7.55-7.47 (m, 2H), 7.08 (dd, J=11.3, 2.9 Hz, 1H), 6.88 (ddd, J=9.0, 2.9, 1.2 Hz, 1H), 4.50 (s, 2H), 2.39 (s, 6H); MS (ESI$^+$) m/z 430 (M+H)$^+$.

Example 249: N-{3-[2-(4-chloro-3-fluorophenoxy)acetamido]bicyclo[1.1.1]pentan-1-yl}-3-(2-methylpropyl)-1,2-oxazole-5-carboxamide (Compound 348)

The title compound was prepared using the methodologies described above. $^1$H NMR (500 MHz, DMSO-d$_6$/D$_2$O) δ ppm 7.50 (t, J=8.9 Hz, 1H), 7.07 (dd, J=11.3, 2.9 Hz, 1H), 6.92 (s, 1H), 6.87 (ddd, J=9.1, 3.0, 1.2 Hz, 1H), 4.49 (s, 2H), 2.34 (s, 6H), 1.94 (dp, J=13.5, 7.1, 6.6 Hz, 1H), 1.23 (dd, J=6.7, 5.7 Hz, 2H), 0.90 (dd, J=6.6, 3.7 Hz, 6H); MS (ESI+) m/z 436 (M+H)+.

Example 250: N-{4-[2-(3,4-difluorophenoxy)acetamido]-2-hydroxybicyclo[2.2.2]octan-1-yl}-5-(trifluoromethyl)pyridine-2-carboxamide (Compound 349)

Example 250A: N-(4-amino-3-hydroxybicyclo[2.2.2]octan-1-yl)-2-(3,4-difluorophenoxy)acetamide hydrochloride The title compound was prepared using the methodologies described in Example 68F-68I substituting 2-(3,4-difluorophenoxy)acetic acid for 2-(4-chloro-3-fluorophenoxy)acetic acid. $^1$H NMR (500 MHz, DMSO-$d_6$) δ ppm 8.00 (s, 3H), 7.74 (s, 1H), 7.35 (dt, J=10.6, 9.3 Hz, 1H), 7.04 (ddd, J=12.7, 6.7, 3.1 Hz, 1H), 6.75 (dtd, J=8.5, 3.3, 1.6 Hz, 1H), 5.62 (s, 1H), 4.43 (s, 2H), 3.85 (dt, J=9.3, 2.4 Hz, 1H), 2.32 (ddd, J=12.9, 9.5, 3.0 Hz, 1H), 2.08-1.92 (m, 2H), 1.85 (tt, J=13.6, 6.9 Hz, 5H), 1.68 (ddt, J=11.5, 7.2, 3.5 Hz, 1H), 1.59 (ddt, J=14.4, 10.3, 2.2 Hz, 1H); MS (ESI+) m/z 327.3 (M+H)+.

Example 250B: N-{4-[2-(3,4-difluorophenoxy)acetamido]-2-hydroxybicyclo[2.2.2]octan-1-yl}-5-(trifluoromethyl)pyridine-2-carboxamide The title compound was prepared using the methodologies described in Example 68 substituting Example 250A for Example 68I and 5-(trifluoromethyl)pyridine-2-carboxylic acid for picolinic acid. $^1$H NMR (400 MHz, DMSO-$d_6$) δ ppm 9.02-8.96 (m, 1H), 8.38 (dd, J=8.3, 2.2 Hz, 1H), 8.25 (s, 1H), 8.17 (d, J=8.2 Hz, 1H), 7.49 (s, 1H), 7.32 (dt, J=10.6, 9.3 Hz, 1H), 7.01 (ddd, J=12.7, 6.7, 3.0 Hz, 1H), 6.73 (dtd, J=8.6, 3.3, 1.7 Hz, 1H), 5.22 (s, 1H), 4.38 (s, 2H), 3.99 (ddd, J=9.6, 3.8, 1.5 Hz, 1H), 2.57-2.47 (m, 1H), 2.32 (ddd, J=12.8, 9.4, 2.8 Hz, 1H), 2.12-2.01 (m, 1H), 2.02-1.67 (m, 7H); MS (ESI+) m/z 500.1 (M+H)+.

Example 251: N-{3-[2-(4-chloro-3-fluorophenoxy)acetamido]bicyclo[1.1.1]pentan-1-yl}-3-(propan-2-yl)-1,2-oxazole-5-carboxamide (Compound 350)

The title compound was prepared using the methodologies described above. $^1$H NMR (501 MHz, DMSO-$d_6$) δ ppm 9.42 (s, 1H), 8.73 (s, 1H), 7.48 (t, J=8.9 Hz, 1H), 7.06 (dd, J=11.4, 2.8 Hz, 1H), 6.99 (s, 1H), 6.84 (ddd, J=9.0, 2.9, 1.2 Hz, 1H), 4.47 (s, 2H), 3.03 (p, J=6.9 Hz, 1H), 2.30 (s, 6H), 1.21 (d, J=6.9 Hz, 6H); MS (ESI+) m/z 422 (M+H)+.

Example 252: N-{3-[2-(4-chloro-3-fluorophenoxy)acetamido]bicyclo[1.1.1]pentan-1-yl}-4-ethoxybenzamide (Compound 351)

The title compound was prepared using the methodologies described above. $^1$H NMR (400 MHz, DMSO-$d_6$/D$_2$O) δ ppm 8.88 (s, 1H), 8.79 (s, 1H), 7.79 (d, J=8.9 Hz, 2H), 7.50 (t, J=8.9 Hz, 1H), 7.08 (dd, J=11.3, 2.9 Hz, 1H), 6.96 (d, J=8.9 Hz, 2H), 6.87 (ddd, J=9.0, 2.9, 1.2 Hz, 1H), 4.49 (s, 2H), 4.08 (q, J=7.0 Hz, 2H), 2.33 (s, 6H), 1.34 (t, J=7.0 Hz, 3H); MS (ESI+) m/z 433 (M+H)+.

Example 253: N-{3-[2-(4-chloro-3-fluorophenoxy)acetamido]bicyclo[1.1.1]pentan-1-yl}-5-(difluoromethyl)-N-methylpyrazine-2-carboxamide (Compound 352)

Example 253A: tert-butyl (3-{[5-(difluoromethyl)pyrazine-2-carbonyl]amino}bicyclo[1.1.1]pentan-1-yl)carbamate The reaction and purification conditions described in Example 13 substituting 5-(difluoromethyl)pyrazine-2-carboxylic acid (Ark Pharm) for the product of Example 12B and tert-butyl (3-aminobicyclo[1.1.1]pentan-1-yl)carbamate (PharmaBlock) for the product of Example 4A gave the title compound. MS (ESI+) m/z 299 (M-(tert-butyl))+.

Example 253B: tert-butyl (3-{[5-(difluoromethyl)pyrazine-2-carbonyl](methyl)amino}bicyclo[1.1.1]pentan-1-yl)carbamate To the product of Example 253A (103 mg, 0.291 mmol) in N,N-dimethylacetamide (3 mL) was added sodium hydride (60% dispersion in mineral oil, 15.4 mg, 0.385 mmol) in one portion followed by tetrahydrofuran (2 mL). After stirring at ambient temperature for 5 minutes, methyl iodide (0.029 mL, 0.465 mmol) was added in one portion. After 1 hour, the reaction was quenched with water (1 mL), and the resulting solution was concentrated briefly under reduced pressure until less than 4 mL of volume was left. The mixture was then filtered through a glass microfiber frit and purified by preparative HPLC [Waters XBridge™ C18 5 μm OBD™ column, 30×100 mm, flow rate 40 mL/minute, 5-100% gradient of acetonitrile in buffer (0.025 M aqueous ammonium bicarbonate, adjusted to pH 10 with ammonium hydroxide)] to give the title compound (64 mg, 0.17 mmol, 60% yield). MS (ESI+) m/z 369 (M+H)+.

Example 253C: N-{3-[2-(4-chloro-3-fluorophenoxy)acetamido]bicyclo[1.1.1]pentan-1-yl}-5-(difluoromethyl)-N-methylpyrazine-2-carboxamide The reaction and purification conditions described in Example 184B substituting the product of Example 253B for the product of example 184A, and 2-(4-chloro-3-fluorophenoxy)acetic acid (Aldlab Chemicals) for the product of Example 6C gave the title compound. $^1$H NMR (501 MHz, DMSO-$d_6$, 120° C.) δ ppm 8.91-8.90 (m, 1H), 8.85 (d, J=1.4 Hz, 1H), 8.20 (s, 1H), 7.39 (t, J=8.8 Hz, 1H), 7.05 (t, J=54.2 Hz, 1H), 6.95 (dd, J=11.2, 2.8 Hz, 1H), 6.80 (ddd, J=9.0, 2.8, 1.2 Hz, 1H), 4.41 (s, 2H), 2.99 (s, 3H), 2.16 (br s, 6H); MS (ESI+) m/z 455 (M+H)+.

Example 254: 3-tert-butyl-N-{4-[2-(4-chloro-3-fluorophenoxy)acetamido]-3-hydroxybicyclo[2.2.2]octan-1-yl}-1,2-oxazole-5-carboxamide (Compound 353)

The title compound was prepared using the methodologies described in Example 130 substituting 3-tert-butyl-1,2-oxazole-5-carboxylic acid for 5-(difluoromethyl)pyrazine-2-carboxylic acid. $^1$H NMR (400 MHz, DMSO-$d_6$) δ ppm 8.03 (s, 1H), 7.45 (t, J=8.9 Hz, 1H), 7.26 (s, 1H), 7.04 (s, 1H), 7.02 (dd, J=11.4, 2.9 Hz, 1H), 6.80 (ddd, J=8.9, 2.8, 1.2 Hz, 1H), 5.09 (d, J=4.4 Hz, 1H), 4.44 (s, 2H), 4.10-3.99

(m, 1H), 2.31 (ddd, J=12.4, 9.1, 1.8 Hz, 1H), 2.05-1.82 (m, 9H), 1.24 (s, 9H); MS (ESI$^+$) m/z 494.2 (M+H)$^+$.

Example 255: N-{3-[2-(4-chloro-3-fluorophenoxy)acetamido]bicyclo[1.1.1]pentan-1-yl}-5-methyl-1,3,4-oxadiazole-2-carboxamide (Compound 354)

The title compound was prepared using the methodologies described above. $^1$H NMR (400 MHz, Methanol-d$_4$) δ ppm 7.61 (s, 1H), 7.34 (t, J=8.6 Hz, 1H), 6.92 (s, 1H), 6.78 (dd, J=10.3, 2.8 Hz, 1H), 6.70 (ddd, J=9.0, 2.9, 1.3 Hz, 1H), 6.58 (s, 1H), 4.43 (s, 2H), 2.86 (q, J=7.6 Hz, 2H), 2.58 (s, 6H), 1.39 (t, J=7.6 Hz, 3H); MS (ESI$^+$) m/z 408 (M+H)$^+$.

Example 256: N-{3-[2-(4-chloro-3-fluorophenoxy)acetamido]bicyclo[1.1.1]pentan-1-yl}-N,3-dimethyl-1,2-oxazole-5-carboxamide (Compound 355)

Example 256A: tert-butyl {3-[(3-methyl-1,2-oxazole-5-carbonyl)amino]bicyclo[1.1.1]pentan-1-yl}carbamate The reaction and purification conditions described in Example 13 substituting 3-methylisoxazole-5-carboxylic acid (Alfa Aesar) for the product of Example 12B and tert-butyl (3-aminobicyclo[1.1.1]pentan-1-yl)carbamate (PharmaBlock) for the product of Example 4A gave the title compound. MS (ESI$^+$) m/z 330 (M+Na)$^+$.

Example 256B: tert-butyl {3-[(3-methyl-1,2-oxazole-5-carbonyl)amino]bicyclo[1.1.1]pentan-1-yl}carbamate The reaction and purification conditions described in Example 253B substituting the product of Example 256A for the product of Example 253A gave the title compound. MS (ESI$^+$) m/z 344 (M+Na)$^+$.

Example 256C: N-{3-[2-(4-chloro-3-fluorophenoxy)acetamido]bicyclo[1.1.1]pentan-1-yl}-N, 3-dimethyl-1,2-oxazole-5-carboxamide The reaction and purification conditions described in Example 184B substituting the product of Example 256B for the product of example 184A, and 2-(4-chloro-3-fluorophenoxy)acetic acid (Aldlab Chemicals) for the product of Example 6C gave the title compound. $^1$H NMR (400 MHz, DMSO-d$_6$, 90° C.) δ ppm 8.41 (s, 1H), 7.43 (t, J=8.8 Hz, 1H), 7.00 (dd, J=11.3, 2.8 Hz, 1H), 6.83 (ddd, J=8.9, 2.9, 1.2 Hz, 1H), 6.64 (s, 1H), 4.44 (s, 2H), 2.98 (s, 3H), 2.28 (s, 3H), 2.26 (br s, 6H); MS (ESI$^+$) m/z 408 (M+H)$^+$.

Example 257: N-{4-[2-(4-chloro-3-fluorophenoxy)acetamido]bicyclo[2.1.1]hexan-1-yl}pyridine-2-carboxamide (Compound 356)

The title compound was prepared using the methodologies described above. $^1$H NMR (400 MHz, DMSO-d$_6$) δ ppm 8.98 (s, 1H), 8.63 (dt, J=4.7, 1.4 Hz, 1H), 8.52 (s, 1H), 8.04-7.95 (m, 2H), 7.60 (ddd, J=6.8, 4.7, 2.4 Hz, 1H), 7.50 (t, J=8.9 Hz, 1H), 7.08 (dd, J=11.4, 2.8 Hz, 1H), 6.86 (ddd, J=9.0, 2.9, 1.2 Hz, 1H), 4.49 (s, 2H), 2.21-2.08 (m, 2H), 1.98-1.81 (m, 6H); MS (ESI$^+$) m/z 404 (M+H)$^+$.

Example 258: N-{(3R)-4-[2-(4-chloro-3-fluorophenoxy)acetamido]-3-hydroxybicyclo[2.2.2]octan-1-yl}-3-methyl-1,2-oxazole-5-carboxamide (Compound 357)

The title compound was isolated by chiral preparative SFC of Example 227 as the first peak eluted off the column using the methodologies described in Example 136. $^1$H NMR (400 MHz, DMSO-d$_6$) δ ppm 8.06 (s, 1H), 7.47 (t, J=8.9 Hz, 1H), 7.26 (s, 1H), 7.04 (dd, J=11.4, 2.9 Hz, 1H), 6.89-6.77 (m, 2H), 5.10 (d, J=4.4 Hz, 1H), 4.45 (s, 2H), 4.09-4.01 (m, 1H), 3.30 (d, J=1.4 Hz, 2H), 2.33 (t, J=11.3 Hz, 1H), 2.25 (s, 3H), 2.13-1.90 (m, 2H), 1.94-1.76 (m, 4H); MS (ESI$^+$) m/z 452.1 (M+H)$^+$.

Example 259: N-{(3S)-4-[2-(4-chloro-3-fluorophenoxy)acetamido]-3-hydroxybicyclo[2.2.2]octan-1-yl}-3-methyl-1,2-oxazole-5-carboxamide (Compound 358)

The title compound was isolated by chiral preparative SFC of Example 227 as the second peak eluted off the column using the methodologies described in Example 136. $^1$H NMR (400 MHz, DMSO-d$_6$) δ ppm 8.06 (s, 1H), 7.47 (t, J=8.9 Hz, 1H), 7.26 (s, 1H), 7.04 (dd, J=11.4, 2.9 Hz, 1H), 6.89-6.77 (m, 2H), 5.10 (d, J=4.4 Hz, 1H), 4.45 (s, 2H), 4.05 (dd, J=9.3, 4.5 Hz, 1H), 2.32 (dd, J=12.7, 9.6 Hz, 1H), 2.25 (s, 3H), 2.13-1.83 (m, 5H), 1.88-1.76 (m, 2H); MS (ESI$^+$) m/z 452.1 (M+H)$^+$.

Example 260: N-{3-[2-(4-chloro-3-fluorophenoxy)acetamido]bicyclo[1.1.1]pentan-1-yl}-1-ethyl-3-methyl-1H-pyrazole-5-carboxamide (Compound 359)

The title compound was prepared using the methodologies described above. $^1$H NMR (400 MHz, DMSO-d$_6$) δ ppm 8.85 (s, 1H), 8.73 (s, 1H), 7.48 (t, J=8.9 Hz, 1H), 7.06 (dd, J=11.4, 2.8 Hz, 1H), 6.84 (ddd, J=9.0, 2.9, 1.2 Hz, 1H), 6.57 (s, 1H), 4.47 (s, 2H), 4.36 (q, J=7.1 Hz, 2H), 2.29 (s, 6H), 2.13 (s, 3H), 1.24 (t, J=7.1 Hz, 3H); MS (ESI$^+$) m/z 421 (M+H)$^+$.

Example 261: N-{3-[(1,3-benzoxazol-2-yl)amino]bicyclo[1.1.1]pentan-1-yl}-2-(4-chloro-3-fluorophenoxy)acetamide (Compound 360)

The reaction and purification conditions described in Example 264 substituting 2-chlorobenzo[d]oxazole for 2-chloro-4-phenylpyrimidine gave the title compound. $^1$H NMR (501 MHz, DMSO-d$_6$) δ ppm 8.79 (s, 1H), 8.76 (s, 1H), 7.51 (t, J=8 Hz, 1H), 7.38 (d, J=8 Hz, 1H), 7.31 (d, J=8 Hz, 1H), 7.14 (ddd, J=8, 7, 1 Hz, 1H), 7.09 (dd, J=9, 3 Hz, 1H), 7.02 (ddd, J=8, 7, 1 Hz, 1H), 6.87 (br d, J=8 Hz, 1H), 4.52 (s, 2H), 2.36 (s, 6H); MS (ESI$^+$) m/z 402 (M+H)$^+$.

Example 262: N-{4-[2-(4-chloro-3-fluorophenoxy)acetamido]-3-hydroxybicyclo[2.2.2]octan-1-yl}-1-methyl-1H-pyrazole-3-carboxamide (Compound 361)

The title compound was prepared using the methodologies described in Example 130 substituting 1-methyl-1H-pyrazole-3-carboxylic acid for 5-(difluoromethyl)pyrazine-2-carboxylic acid. $^1$H NMR (400 MHz, DMSO-d$_6$) δ ppm 7.68 (d, J=2.3 Hz, 1H), 7.44 (t, J=8.9 Hz, 1H), 7.25 (s, 1H), 7.15-6.97 (m, 2H), 6.83-6.73 (m, 1H), 6.52 (d, J=2.3 Hz, 1H), 4.43 (s, 2H), 4.04 (dd, J=9.6, 3.0 Hz, 1H), 3.82 (s, 3H), 2.33 (ddd, J=12.4, 9.5, 2.3 Hz, 1H), 2.04-1.77 (m, 9H); MS (ESI+) m/z 451.1 (M+H)+.

Example 263: N-(3-{[(4-chloro-3-fluorophenoxy)acetyl](methyl)amino}bicyclo[1.1.1]pentan-1-yl)-5-(difluoromethyl)-N-methylpyrazine-2-carboxamide (Compound 362)

Example 263A: tert-butyl (3-(5-(difluoromethyl)-N-methylpyrazine-2-carboxamido)bicyclo[1.1.1]pentan-1-yl)(methyl)carbamate The preparative HPLC purification in Example 253B also gave this title compound. MS (ESI+) m/z 405 (M+Na)+.

Example 263B: N-(3-(2-(4-chloro-3-fluorophenoxy)-N-methylacetamido)bicyclo[1.1.1]pentan-1-yl)-5-(difluoromethyl)-N-methylpyrazine-2-carboxamide The reaction and purification conditions described in Example 184B substituting the product of Example 263A for the product of example 184A, and 2-(4-chloro-3-fluorophenoxy)acetic acid (Aldlab Chemicals) for the product of Example 6C gave the title compound. $^1$H NMR (400 MHz, DMSO-$d_6$, 120° C.) δ ppm 8.91-8.89 (m, 1H), 8.86-8.85 (m, 1H), 7.37 (t, J=8.8 Hz, 1H), 7.11 (d, J=54.2 Hz, 1H), 6.92 (dd, J=11.5, 2.6 Hz, 1H), 6.77 (ddd, J=9.0, 2.9, 1.3 Hz, 1H), 4.72 (s, 2H), 2.99 (s, 3H), 2.84 (s, 3H), 2.30 (s, 6H); MS (ESI+) m/z 469 (M+H)+.

Example 264: 2-(4-chloro-3-fluorophenoxy)-N-{3-[(4-phenylpyrimidin-2-yl)amino]bicyclo[1.1.1]pentan-1-yl}acetamide (Compound 363)

A mixture of the product of Example 6C (40 mg, 0.100 mmol), 2-chloro-4-phenylpyrimidine (23 mg, 0.120 mmol) and N-ethyl-N-isopropylpropan-2-amine (49.3 mg, 0.381 mmol) in dimethyl sulfoxide (0.5 mL) was heated at 70° C. for 3 days. The resulting solution was filtered through a glass microfiber frit and purified by preparative HPLC [Waters XBridge™ C18 5 μm OBD™ column, 30×100 mm, flow rate 40 mL/minute, 5-100% gradient of acetonitrile in buffer (0.1% trifluoroacetic acid)] to give the title compound (0.01 g, 0.023 mmol, 23% yield). $^1$H NMR (501 MHz, DMSO-$d_6$) δ ppm 8.76 (s, 1H), 8.38 (d, J=7 Hz, 1H), 8.12 (m, 2H), 7.98 (br s, 1H), 7.54 (m, 3H), 7.50 (t, J=8 Hz, 1H), 7.24 (d, J=7 Hz, 1H), 7.10 (dd, J=9, 3 Hz, 1H), 6.88 (br d, J=8 Hz, 1H), 4.51 (s, 2H), 2.39 (s, 6H); MS (ESI+) m/z 439 (M+H)+.

Example 265: N-{3-[2-(4-chloro-3-fluorophenoxy)acetamido]bicyclo[1.1.1]pentan-1-yl}-1-methyl-3-(propan-2-yl)-1H-pyrazole-5-carboxamide (Compound 364)

The title compound was prepared using the methodologies described above. $^1$H NMR (500 MHz, DMSO-$d_6$) δ ppm 8.90 (s, 1H), 8.76 (s, 1H), 7.50 (t, J=8.9 Hz, 1H), 7.09 (dd, J=11.4, 2.8 Hz, 1H), 6.87 (ddd, J=9.0, 2.9, 1.2 Hz, 1H), 6.70 (d, J=0.5 Hz, 1H), 4.49 (s, 2H), 3.97 (s, 3H), 2.85 (p, J=6.9 Hz, 1H), 2.31 (s, 6H), 1.23-1.13 (m, 6H); MS (ESI+) m/z 435 (M+H)+.

Example 266: N-{3-[2-(4-chloro-3-fluorophenoxy)acetamido]bicyclo[1.1.1]pentan-1-yl}-3-(difluoromethyl)-1-methyl-1H-pyrazole-5-carboxamide (Compound 365)

Example 266A: methyl 3-(difluoromethyl)-1-methyl-1H-pyrazole-5-carboxylate

To a solution of methyl 3-formyl-1-methyl-1H-pyrazole-5-carboxylate (Bellen Chem; 1 g, 5.95 mmol) in $CH_2Cl_2$ (30 mL) at 0° C. was added bis-(2-methoxyethyl)aminosulfur-trifluoride (3.29 mL, 17.8 mmol) in $CH_2Cl_2$ (5 mL) dropwise via syringe pump over 40 minutes. The mixture was allowed to stir at 0° C. for 20 minutes, then the ice-bath was removed, and the mixture was allowed to warm to ambient temperature. The mixture was then allowed to stir for an additional 90 minutes and was quenched by slow addition of saturated, aqueous $NaHCO_3$ (25 mL) added via syringe pump over 1 hour. The mixture was diluted with $CH_2Cl_2$ (15 mL), then the layers were separated, and the aqueous layer was extracted with $CH_2Cl_2$ (3×7 mL). The combined organic fractions were dried over anhydrous $Na_2SO_4$, filtered, and concentrated under reduced pressure. The residue was purified via column chromatography ($SiO_2$, 50% ethyl acetate/heptanes) to give the title compound (1.01 g, 5.31 mmol, 89% yield). MS (ESI+) m/z 191 (M+H)+.

Example 266B: 3-(difluoromethyl)-1-methyl-1H-pyrazole-5-carboxylic Acid

To a solution of the product of Example 266A (1 g, 5.26 mmol) in methanol (20 mL) and water (10.0 mL) was added NaOH (2.52 g, 31.6 mmol). This mixture was allowed to stir at ambient temperature for 90 minutes, and then the mixture was concentrated under reduced pressure and dissolved in water. The solution was acidified with concentrated HCl to pH-3, and the resulting precipitate was isolated via filtration to give the title compound (0.61 g, 3.5 mmol, 66% yield). $^1$H NMR (400 MHz, DMSO-$d_6$) δ ppm 7.28-6.64 (m, 2H), 4.08 (s, 3H), 3.31 (s, 1H).

Example 266C: N-{3-[2-(4-chloro-3-fluorophenoxy)acetamido]bicyclo[1.1.1]pentan-1-yl}-3-(difluoromethyl)-1-methyl-1H-pyrazole-5-carboxamide To a mixture of the product of Example 4A (0.145 g, 0.509 mmol) and the product of Example 266B (0.099 g, 0.56 mmol) in N,N-dimethylformamide (2.5 mL) was added triethylamine (0.28 mL, 2.04 mmol) followed by 2-(3H-[1,2,3]triazolo[4,5-b]pyridin-3-yl)-1,1,3,3-tetramethylisouronium hexafluorophosphate(V) (HATU, 0.213 g, 0.560 mmol). This mixture was allowed to stir at ambient temperature for 14 hours then was quenched with saturated, aqueous $NaHCO_3$ (10 mL) and diluted with ethyl acetate (10 mL). The layers were separated, and the aqueous layer was extracted with ethyl acetate (3×3 mL). The combined organic fractions were dried over anhydrous $Na_2SO_4$, filtered, and concentrated under reduced pressure. The residue was purified via column chromatography ($SiO_2$, 75% ethyl acetate/heptanes) to give the title compound (0.18 g, 0.41 mmol, 80% yield). $^1$H NMR (500 MHz, DMSO-$d_6$) δ ppm 9.14 (s, 1H), 8.76 (s, 1H), 7.50 (t, J=8.9 Hz, 1H), 7.17-6.82 (m, 4H), 4.49 (s, 2H), 4.08 (d, J=0.9 Hz, 3H), 2.33 (s, 6H); MS (ESI+) m/z 443 (M+H)+.

Example 267: N-{3-[2-(4-chloro-3-fluorophenoxy)acetamido]bicyclo[1.1.1]pentan-1-yl}-3-cyanobenzamide (Compound 366)

The title compound was prepared using the methodologies described above. $^1$H NMR (501 MHz, DMSO-$d_6$) δ ppm 9.23 (s, 1H), 8.75 (s, 1H), 8.23 (td, J=1.6, 0.5 Hz, 1H), 8.12 (ddd, J=8.0, 1.8, 1.2 Hz, 1H), 7.98 (dt, J=7.7, 1.4 Hz, 1H), 7.67 (td, J=7.8, 0.6 Hz, 1H), 7.48 (t, J=8.9 Hz, 1H), 7.06 (dd, J=11.4, 2.8 Hz, 1H), 6.85 (ddd, J=9.0, 2.8, 1.2 Hz, 1H), 4.48 (s, 2H), 2.33 (s, 6H); MS (ESI+) m/z 414 (M+H)+.

Example 268: N-{3-[2-(4-chloro-3-fluorophenoxy) acetamido]bicyclo[1.1.1]pentan-1-yl}-4-methyl-1,2-oxazole-5-carboxamide (Compound 367)

The title compound was prepared using the methodologies described above. $^1$H NMR (400 MHz, DMSO-$d_6$) δ ppm 8.55 (s, 1H), 7.47 (t, J=8.9 Hz, 1H), 7.05 (dd, J=11.3, 2.9 Hz, 1H), 6.85 (ddd, J=8.9, 2.9, 1.2 Hz, 1H), 4.47 (s, 2H), 2.33 (s, 6H), 2.20 (s, 3H); MS (ESI+) m/z 394 (M+H)+.

Example 269: N-{3-[2-(4-chloro-3-fluorophenoxy) acetamido]bicyclo[1.1.1]pentan-1-yl}-3-methylpyridine-2-carboxamide (Compound 368)

The title compound was prepared using the methodologies described above. $^1$H NMR (400 MHz, DMSO-$d_6$) δ ppm 9.08 (s, 1H), 8.74 (s, 1H), 8.44-8.40 (m, 1H), 7.73 (ddd, J=7.8, 1.7, 0.8 Hz, 1H), 7.50 (t, J=8.8 Hz, 1H), 7.44 (dd, J=7.8, 4.6 Hz, 1H), 7.08 (dd, J=11.4, 2.8 Hz, 1H), 6.86 (ddd, J=8.9, 2.8, 1.2 Hz, 1H), 4.49 (s, 2H), 2.52 (s, 3H), 2.34 (s, 6H); MS (DCI) m/z 404 (M+H)+.

Example 270: N-{3-[(5-chloro-1,3-benzoxazol-2-yl) amino]bicyclo[1.1.1]pentan-1-yl}-2-(4-chloro-3-fluorophenoxy)acetamide (Compound 369)

The reaction and purification conditions described in Example 264 substituting 2,5-dichlorobenzooxazole for 2-chloro-4-phenylpyrimidine gave the title compound. $^1$H NMR (501 MHz, DMSO-$d_6$) δ ppm 8.97 (s, 1H), 8.82 (s, 1H), 7.51 (t, J=8, 1H), 7.39 (d, J=8 Hz, 1H), 7.35 (d, J=3 Hz, 1H), 7.08 (dd, J=9, 3 Hz, 1H), 7.04 (dd, J=8, 3 Hz, 1H), 6.87 (br d, J=8 Hz, 1H), 4.52 (s, 2H), 2.36 (s, 6H); MS (ESI+) m/z 436 (M+H)+.

Example 271: 2-(4-chloro-3-fluorophenoxy)-N-(3-{ [4-(4-chlorophenyl)pyrimidin-2-yl]amino}bicyclo [1.1.1]pentan-1-yl)acetamide (Compound 370)

The reaction and purification conditions described in Example 264 substituting 2-chloro-4-(4-chlorophenyl)pyrimidine for 2-chloro-4-phenylpyrimidine gave the title compound. $^1$H NMR (501 MHz, DMSO-$d_6$) δ ppm 8.77 (s, 1H), 8.40 (d, J=7 Hz, 1H), 8.13 (d, J=8 Hz, 2H), 7.97 (s, 1H), 7.60 (d, J=8 Hz, 2H), 7.51 (t, J=8 Hz, 1H), 7.23 (d, J=7 Hz, 1H), 7.10 (dd, J=9, 3 Hz, 1H), 6.88 (br d, J=8 Hz, 1H), 4.51 (s, 2H), 2.37 (s, 6H); MS (ESI+) m/z 473 (M+H)+.

Example 272: N-{3-[2-(4-chloro-3-fluorophenoxy) acetamido]bicyclo[1.1.1]pentan-1-yl}-4-cyano-3-fluorobenzamide (Compound 371)

The title compound was prepared using the methodologies described above. $^1$H NMR (501 MHz, DMSO-$d_6$) δ ppm 9.34 (s, 1H), 8.75 (s, 1H), 8.04 (dd, J=8.1, 6.6 Hz, 1H), 7.87 (dd, J=10.2, 1.5 Hz, 1H), 7.81 (dd, J=8.1, 1.5 Hz, 1H), 7.48 (t, J=8.9 Hz, 1H), 7.06 (dd, J=11.4, 2.9 Hz, 1H), 6.84 (ddd, J=8.9, 2.9, 1.2 Hz, 1H), 4.48 (s, 2H), 2.33 (s, 6H); MS (ESI+) m/z 432 (M+H)+.

Example 273: N-{4-[2-(4-chloro-3-fluorophenoxy) acetamido]-2-fluorobicyclo[2.2.2]octan-1-yl}-6-(trifluoromethyl)pyridine-3-carboxamide (Compound 372)

Example 273A: ethyl 4-[2-(4-chloro-3-fluorophenoxy)acetamido]-2-hydroxybicyclo[2.2.2]octane-1-carboxylate To a solution of the product of Example 68F (350 mg, 0.88 mmol) in $CH_2Cl_2$ (5 mL) and methanol (5 mL) was added sodium tetrahydroborate (36.6 mg, 0.97 mmol). The reaction mixture was stirred for 1.5 hours. The solution was treated with brine and saturated, aqueous $NaHCO_3$ and was extracted with $CH_2Cl_2$ (2×). The combined organic layers were dried over anhydrous $MgSO_4$, filtered, and concentrated under reduced pressure. The residue was purified on a 12 g silica gel column using a Biotage® Isolera™ One flash system eluting with heptanes/ethyl acetate (5:5 to 4:6) to provide the title compound (0.223 g, 0.56 mmol, 63% yield). MS (ESI+) m/z 399.9 (M+H)+.

Example 273B: ethyl 4-[2-(4-chloro-3-fluorophenoxy)acetamido]-2-fluorobicyclo[2.2.2]octane-1-carboxylate To a solution of the product of Example 273A (185.0 mg, 0.463 mmol) in $CH_2Cl_2$ (10 mL) at 0° C. was added diethylaminosulfur trifluoride (DAST, 0.122 mL, 0.925 mmol). After 1 hour, the reaction mixture was warmed to room temperature and stirred for 5 hours. The reaction mixture was quenched with saturated, aqueous $NaHCO_3$ and extracted with $CH_2Cl_2$ (2×). The combined organic layers were dried over anhydrous $MgSO_4$, filtered, and concentrated under reduced pressure. The residue was purified on a 12 g column using the Biotage® Isolera™ One flash system eluting with heptanes/ethyl acetate (6:4) to provide the title compound (0.124 g, 0.31 mmol, 67% yield). MS (ESI+) m/z 402.2 (M+H)+.

Example 273C: 4-[2-(4-chloro-3-fluorophenoxy) acetamido]-2-fluorobicyclo[2.2.2]octane-1-carboxylic acid To a solution of the product of Example 273B (0.120 g, 0.30 mmol) in methanol (1.5 mL) and tetrahydrofuran (1.5 mL) was added a solution of lithium hydroxide (0.021 g, 0.90 mmol) in water (0.5 mL). The mixture was stirred for 16 hours. Most of the volatiles were evaporated. The remaining solution was diluted with 1 mL of water and treated with 2.5 N HCl until a white suspension appeared. The suspension was collected by filtration, washed with water, and vacuum oven-dried to provide the title compound (88.9 mg, 0.24 mmol, 80% yield). MS (ESI+) m/z 374.1 (M+H)+.

Example 273D: N-(4-amino-3-fluorobicyclo[2.2.2] octan-1-yl)-2-(4-chloro-3-fluorophenoxy)acetamide To a suspension of the product of Example 273C (1.00 g, 2.68 mmol) in toluene (40 mL) were added triethylamine (0.93 mL, 6.69 mmol) and diphenylphosphoryl azide (0.87 mL, 4.01 mmol). The mixture was heated at 110° C. for 1 hour. After cooling, the reaction mixture was treated with 3 N HCl (40 mL) and was stirred for 16 hours. The suspension in the organic layer was collected by filtration and then washed with water and ether. The solids were suspended in saturated, aqueous $NaHCO_3$ and extracted with ethyl acetate (2×). The combined organic layers were washed with brine, dried over anhydrous MgSO₄, and concentrated to provide the crude title compound (0.393 g, 1.14 mmol, 43% yield). The crude title compound was carried into the next step without further purification. MS (ESI⁺) m/z 345.2 (M+H)⁺.

Example 273E: N-{4-[2-(4-chloro-3-fluorophenoxy)acetamido]-2-fluorobicyclo[2.2.2]octan-1-yl}-6-(trifluoromethyl)pyridine-3-carboxamide A mixture of the product of Example 273D (50.0 mg, 0.16 mmol), 6-(trifluoromethyl)nicotinic acid (30.5 mg, 0.16 mmol), N-[(dimethylamino)-1H-1,2,3-triazolo-[4,5-b]pyridin-1-ylmethylene]-N-methylmethanaminium hexafluorophosphate N-oxide (HATU, 66.2 mg, 0.17 mmol), and triethylamine (0.030 mL, 0.22 mmol) in tetrahydrofuran (1.5 mL) was stirred for 16 hours. The reaction mixture was treated with saturated, aqueous NaHCO₃ and brine and extracted with ethyl acetate (2×). The combined organic layers were dried over anhydrous MgSO₄, filtered, and concentrated under reduced pressure. The residue was purified by reverse-phase HPLC performed on a Zorbax Rx-C18 column (250×21.2 mm, 7 µm particle size) using a gradient of 10% to 95% acetonitrile:0.1% aqueous trifluoroacetic acid over 30 minutes at a flow rate of 18 mL/minute to provide the title compound (23.5 mg, 0.045 mmol, 28% yield). ¹H NMR (400 MHz, DMSO-d₆) δ ppm 9.12-8.99 (m, 1H), 8.41 (d, J=7.9 Hz, 2H), 8.01 (d, J=8.2 Hz, 1H), 7.84 (s, 1H), 7.49 (t, J=8.9 Hz, 1H), 7.04 (dd, J=11.5, 2.9 Hz, 1H), 6.83 (ddd, J=9.0, 2.7, 1.1 Hz, 1H), 5.51 (dd, J=54.1, 8.7 Hz, 1H), 4.49 (s, 2H), 2.44-1.73 (m, 10H); MS (ESI⁺) m/z 518.2 (M+H)⁺.

Example 274: N-{4-[2-(4-chloro-3-fluorophenoxy)acetamido]-2-fluorobicyclo[2.2.2]octan-1-yl}-5-(difluoromethyl)pyrazine-2-carboxamide (Compound 373)

The reaction described in Example 273E substituting 5-(difluoromethyl)pyrazine-2-carboxylic acid for 6-(trifluoromethyl)nicotinic acid gave the title compound. ¹H NMR (400 MHz, DMSO-d₆) δ ppm 9.25 (d, J=1.4 Hz, 1H), 9.01 (d, J=1.3 Hz, 1H), 8.21 (s, 1H), 7.72 (s, 1H), 7.49 (t, J=8.9 Hz, 1H), 7.21 (t, J=54.0 Hz, 1H), 7.04 (dd, J=11.4, 2.9 Hz, 1H), 6.82 (ddd, J=9.0, 2.9, 1.2 Hz, 1H), 5.47 (dd, J=54.4, 8.9 Hz, 1H), 4.47 (s, 2H), 2.46-1.71 (m, 10H); MS (ESI⁺) m/z 501.1 (M+H)⁺.

Example 275: N-{4-[2-(4-chloro-3-fluorophenoxy)acetamido]-2-fluorobicyclo[2.2.2]octan-1-yl}-3-methyl-1,2-oxazole-5-carboxamide (Compound 374)

The reaction described in Example 273E substituting 3-methylisoxazole-5-carboxylic acid for 6-(trifluoromethyl)nicotinic acid gave the title compound. ¹H NMR (400 MHz, DMSO-d₆) δ ppm 8.27 (s, 1H), 7.69 (s, 1H), 7.48 (t, J=8.9 Hz, 1H), 7.03 (dd, J=11.4, 2.9 Hz, 1H), 6.93 (s, 1H), 6.82 (dt, J=9.1, 1.9 Hz, 1H), 5.44 (dd, J=54.1, 8.6 Hz, 1H), 4.46 (s, 2H), 2.47-2.32 (m, 1H), 2.28 (s, 3H), 2.25-1.54 (m, 9H); MS (ESI⁺) m/z 454.1 (M+H)⁺.

Example 276: N-{3-[2-(4-chloro-3-fluorophenoxy)acetamido]bicyclo[1.1.1]pentan-1-yl}-3-methyl-1,2,4-oxadiazole-5-carboxamide (Compound 375)

The title compound was prepared using the methodologies described above. ¹H NMR (400 MHz, DMSO-d₆) δ ppm 10.01 (s, 1H), 8.77 (s, 1H), 7.50 (t, J=8.9 Hz, 1H), 7.08 (dd, J=11.4, 2.8 Hz, 1H), 6.86 (ddd, J=9.0, 2.9, 1.2 Hz, 1H), 4.49 (s, 2H), 2.42 (s, 3H), 2.34 (s, 6H); MS (ESI⁺) m/z 395 (M+H)⁺.

Example 277: N-(3-{2-[(2,2-difluoro-2H-1,3-benzodioxol-5-yl)oxy]acetamido}bicyclo[1.1.1]pentan-1-yl)-5-(difluoromethyl)pyrazine-2-carboxamide (Compound 376)

The title compound was prepared using the methodologies described above. ¹H NMR (400 MHz, DMSO-d₆) δ ppm 9.62 (s, 1H), 9.25 (d, J=1.4 Hz, 1H), 9.01-8.99 (m, 1H), 8.74 (s, 1H), 7.37-7.05 (m, 3H), 6.78 (dd, J=8.9, 2.6 Hz, 1H), 4.46 (s, 2H), 2.38 (s, 6H); MS (ESI⁺) m/z 469 (M+H)⁺.

Example 278: N-(3-{2-[(2,2-difluoro-2H-1,3-benzodioxol-5-yl)oxy]acetamido}bicyclo[1.1.1]pentan-1-yl)-3-methyl-1,2-oxazole-5-carboxamide (Compound 377)

The title compound was prepared using the methodologies described above. ¹H NMR (501 MHz, DMSO-d₆) δ ppm 9.47 (s, 1H), 8.74 (s, 1H), 7.33 (d, J=8.9 Hz, 1H), 7.14 (d, J=2.5 Hz, 1H), 6.89 (s, 1H), 6.78 (dd, J=8.9, 2.6 Hz, 1H), 4.45 (s, 2H), 2.33 (s, 6H), 2.29 (s, 3H); MS (ESI⁺) m/z 422 (M+H)⁺.

Example 279: N-(3-{2-[(2,2-difluoro-2H-1,3-benzodioxol-5-yl)oxy]acetamido}bicyclo[1.1.1]pentan-1-yl)-5-(trifluoromethoxy)pyridine-2-carboxamide (Compound 378)

The title compound was prepared using the methodologies described above. ¹H NMR (400 MHz, DMSO-d₆) δ ppm 9.33 (s, 1H), 8.70 (s, 1H), 8.68 (d, J=2.6 Hz, 1H), 8.15-8.09 (m, 1H), 8.09-8.03 (m, 1H), 7.31 (d, J=8.9 Hz, 1H), 7.13 (d, J=2.6 Hz, 1H), 6.76 (dd, J=8.9, 2.6 Hz, 1H), 4.44 (s, 2H), 2.34 (s, 6H); MS (ESI⁺) m/z 502 (M+H)⁺.

Example 280: N-(3-{2-[(2,2-difluoro-2H-1,3-benzodioxol-5-yl)oxy]acetamido}bicyclo[1.1.1]pentan-1-yl)-6-(trifluoromethoxy)pyridine-3-carboxamide (Compound 379)

The title compound was prepared using the methodologies described above. ¹H NMR (501 MHz, DMSO-d₆) δ ppm 9.27 (s, 1H), 8.74-8.72 (m, 2H), 8.35 (dd, J=8.6, 2.5 Hz, 1H), 7.36 (dd, J=8.6, 0.7 Hz, 1H), 7.31 (d, J=8.8 Hz, 1H), 7.13 (d, J=2.6 Hz, 1H), 6.76 (dd, J=8.9, 2.6 Hz, 1H), 4.44 (s, 2H), 2.34 (s, 6H); MS (ESI⁺) m/z 502 (M+H)⁺.

Example 281: N-{3-[2-(4-chloro-3-fluorophenoxy)acetamido]bicyclo[1.1.1]pentan-1-yl}-3-(trifluoromethyl)-1,2-oxazole-5-carboxamide (Compound 380)

Example 281A: (E)-2,2,2-trifluoroacetaldehyde oxime

To a solution of hydroxylamine hydrochloride (3.70 g, 53.3 mmol) and 2,2,2-trifluoro-1-methoxyethanol (6.3 g, 48.4 mmol) in water (20 mL) and methanol (25 mL) was added aqueous NaOH (50 weight %, 9 mL, 48.4 mmol) at 0° C. The reaction mixture was then allowed to warm to 20° C. with stirring over 16 hours. Heptane (50 mL) was added, and the layers were separated. The aqueous layer was then acidified by addition of hydrochloric acid (6 M aqueous solution, 30 mL) and then was extracted with diethyl ether (2×100 mL). The organic extracts were combined and dried over anhydrous $Na_2SO_4$, filtered and concentrated at atmospheric pressure to afford the title compound (20 g, 91% yield, 25% purity) which was used in the next step without further purification. $^1$H NMR (400 MHz, $CDCl_3$) δ ppm 7.42 (q, J=4.28 Hz, 1H), 11.18 (br s, 1H).

Example 281B:
(Z)-2,2,2-trifluoro-N-hydroxyacetimidoyl Bromide

To a solution of Example 281A (16 g, 35.4 mmol, 25% purity) in N,N-dimethylformamide (DMF) (150 mL) was added 1-bromopyrrolidine-2,5-dione (9.45 g, 53.1 mmol) in portions at 0° C. The reaction mixture was then allowed to warm to 20° C. with stirring over 16 hours. The reaction mixture was diluted with water (1000 mL) and extracted with methyl tert-butyl ether (3×350 mL). The combined organic extracts were washed with brine (3×200 mL), dried over anhydrous $Na_2SO_4$, filtered and concentrated under reduced pressure to give the title compound (9.5 g, 80% yield, 57% purity). $^1$H NMR (400 MHz, $CDCl_3$) δ ppm 10.78 (br s, 1H).

Example 281C:
(3-(trifluoromethyl)isoxazol-5-yl)methanol

Example 281B (7.5 g, 22.3 mmol, 57% purity) and prop-2-yn-1-ol (3.75 g, 66.8 mmol) were combined in toluene (50 mL). A solution of $Na_2CO_3$ (4.72 g, 44.5 mmol) in water (75 mL) was added dropwise to the stirred reaction mixture via syringe pump over 16 hours at 20° C. Hexane (100 mL) was added, and the reaction mixture was extracted with methyl tert-butyl ether (3×150 mL). The organic layer was washed with brine (100 mL), dried over anhydrous $Na_2SO_4$ and concentrated under reduced pressure to give the title compound (16 g, 65% yield, 15% purity) which was used to next step without further purification. $^1$H NMR (400 MHz, $CDCl_3$) δ ppm 4.82 (d, J=6.14 Hz, 2H), 6.53 (s, 1H).

Example 281D:
3-(trifluoromethyl)isoxazole-5-carboxylic acid

To a solution of Example 281C (16 g, 14.36 mmol) in acetone (120 mL) was added Jone's reagent (55 mL, 14.4 mmol) dropwise at 0° C. The mixture was stirred at 20° C. for additional 12 hours. Then methanol (50 mL) was added to the mixture, and the mixture was stirred for 1 hour. The mixture was diluted with water (500 mL) and extracted with ethyl acetate (5×100 mL). The combined organic layers were extracted with saturated, aqueous $NaHCO_3$ (3×100 mL). Then the aqueous layer was acidified with HCl (2 N) to pH=1 and extracted with ethyl acetate (5×100 mL). The combined organic layers were dried over anhydrous $Na_2SO_4$ and concentrated under reduced pressure to give the crude product. This material was purified by reverse phase flash column chromatography (Biotage® Snap C18 column, 400 g, flowrate 70 mL/minute, 0-100% gradient of acetonitrile in buffer (0.05% trifluoroacetic acid)). The resulting solution (2.5 L) was concentrated under reduced pressure until most of the acetonitrile was evaporated. The remaining mostly aqueous mixture was extracted with ethyl acetate (4×200 mL). The combined organic layers were dried over anhydrous $Na_2SO_4$ and filtered. The filtrate was concentrated under reduced pressure to give the title compound (920 mg, 4.93 mmol, 34% yield, 97% purity). $^1$H NMR (400 MHz, $CDCl_3$) δ ppm 7.31 (s, 1H), 10.03 (br s, 1H).

Example 281E: N-{3-[2-(4-chloro-3-fluorophenoxy) acetamido]bicyclo[1.1.1]pentan-1-yl}-3-(trifluoromethyl)-1,2-oxazole-5-carboxamide The title compound was prepared using the methodologies described above. $^1$H NMR (501 MHz, DMSO-$d_6$) δ ppm 9.77 (s, 1H), 8.76 (s, 1H), 7.63 (s, 1H), 7.48 (t, J=8.9 Hz, 1H), 7.06 (dd, J=11.3, 2.9 Hz, 1H), 6.84 (ddd, J=9.0, 2.9, 1.2 Hz, 1H), 4.48 (s, 2H), 2.34 (s, 6H); MS (ESI$^+$) m/z 448 (M+H)$^+$.

Example 282: 2-(4-chloro-3-fluorophenoxy)-N-(3-{[4-(1-methyl-1H-pyrazol-4-yl)pyrimidin-2-yl]amino}bicyclo[1.1.1]pentan-1-yl)acetamide (Compound 381)

Example 282A:
2-chloro-4-(1-methyl-1H-pyrazol-4-yl)pyrimidine

A mixture of 2,4-dichloropyrimidine (149 mg, 1 mmol), 1-methyl-4-(4,4,5,5-tetramethyl-1,3,2-dioxaborolan-2-yl)-1H-pyrazole (208 mg, 1.000 mmol), tetrakis(triphenylphosphine)palladium(0) (57.8 mg, 0.050 mmol) in 1,4-dioxane (2.5 mL) and water (0.25 mL) was heated at 100° C. for 18 hours. After cooling to ambient temperature, the mixture was diluted with ethyl acetate (100 mL), washed with water (40 mL) and brine (20 mL), dried over anhydrous $Na_2SO_4$ and concentrated under reduced pressure. The residue was purified on silica gel (40 g), eluting with 10% to 100% ethyl acetate in heptane, to give the title compound (120 mg, 0.617 mmol, 62% yield). $^1$H NMR (501 MHz, DMSO-$d_6$) δ ppm 8.64 (d, J=8 Hz, 1H), 8.55 (s, 1H), 8.18 (s, 1H), 7.75 (d, J=8 Hz, 1H), 3.92 (s, 3H); MS (ESI$^+$) m/z 195 (M+H)$^+$.

Example 282B: 2-(4-chloro-3-fluorophenoxy)-N-(3-{[4-(1-methyl-1H-pyrazol-4-yl)pyrimidin-2-yl]amino}bicyclo[1.1.1]pentan-1-yl)acetamide The reaction and purification conditions described in Example 264 substituting the product of Example 282A for 2-chloro-4-phenylpyrimidine gave the title compound (0.016 g, 0.036 mmol, 16% yield). $^1$H NMR (501 MHz, DMSO-$d_6$) δ ppm 8.75 (s, 1H), 8.36 (s, 1H), 8.24 (d, J=7 Hz, 1H), 8.04 (s, 2H), 7.50 (t, J=8 Hz, 1H), 7.09 (dd, J=9, 3 Hz, 1H), 6.96 (d, J=7 Hz, 1H), 6.88 (br d, J=8 Hz, 1H), 4.50 (s, 2H), 3.91 (s, 3H), 2.37 (s, 6H); MS (ESI$^+$) m/z 443 (M+H)$^+$.

Example 283: 2-(4-chloro-3-fluorophenoxy)-N-[3-({4-[1-(difluoromethyl)-1H-pyrazol-4-yl]pyrimidin-2-yl}amino)bicyclo[1.1.1]pentan-1-yl]acetamide (Compound 382)

Example 283A: 2-chloro-4-(1-(difluoromethyl)-1H-pyrazol-4-yl)pyrimidine

The reaction and purification conditions described in Example 282A substituting 1-(difluoromethyl)-4-(4,4,5,5-tetramethyl-1,3,2-dioxaborolan-2-yl)-1H-pyrazole for 1-methyl-4-(4,4,5,5-tetramethyl-1,3,2-dioxaborolan-2-yl)-1H-pyrazole gave the title compound. $^1$H NMR (501 MHz, DMSO-$d_6$) δ ppm 9.12 (s, 1H), 8.76 (d, J=8 Hz, 1H), 8.50 (s, 1H), 7.94 (d, J=8 Hz, 1H), 7. (t, J=60 Hz, 1H); MS (ESI$^+$) m/z 231 (M+H)$^+$.

Example 283B: 2-(4-chloro-3-fluorophenoxy)-N-[3-([4-[1-(difluoromethyl)-1H-pyrazol-4-yl]pyrimidin-2-yl]amino)bicyclo[1.1.1]pentan-1-yl]acetamide The reaction and purification conditions described in Example 264 substituting Example 283A for 2-chloro-4-phenylpyrimidine gave the title compound. $^1$H NMR (501 MHz, DMSO-$d_6$) δ ppm 8.86 (s, 1H), 8.75 (s, 1H), 8.35 (s, 1H), 8.32 (d, J=7 Hz, 1H), 8.00 (br s, 1H), 7.0 (t, J=60 Hz, 1H), 7.50 (t, J=8 Hz, 1H), 7.08 (dd, J=9, 3 Hz, 1H), 7.06 (d, J=7 Hz, 1H), 6.88 (br d, J=8 Hz, 1H), 4.50 (s, 2H), 2.37 (s, 6H); MS (ESI$^+$) m/z 479 (M+H)$^+$.

Example 284: 2-(4-chloro-3-fluorophenoxy)-N-{3-[(4-ethoxy-6-methylpyrimidin-2-yl)amino]bicyclo[1.1.1]pentan-1-yl}acetamide (Compound 383)

The reaction and purification conditions described in Example 264 substituting 2-chloro-4-ethoxy-6-methyl-pyrimidine for 2-chloro-4-phenylpyrimidine gave the title compound. $^1$H NMR (501 MHz, DMSO-$d_6$) δ ppm 8.94 (brs, 1H), 8.80 (s, 1H), 7.50 (t, J=8 Hz, 1H), 7.08 (dd, J=9, 3 Hz, 1H), 6.87 (br d, J=8 Hz, 1H), 6.24 (br s, 1H), 4.50 (s, 2H), 4.42 (m, 2H), 3.91 (s, 3H), 2.38 (s, 6H), 2.27 (s, 3H), 1.34 (t, J=8 Hz, 3H); MS (ESI$^+$) m/z 421 (M+H)$^+$.

Example 285: 2-(4-chloro-3-fluorophenoxy)-N-{3-[(7-chloroquinolin-4-yl)amino]bicyclo[1.1.1]pentan-1-yl}acetamide (Compound 384)

Example 285A: tert-butyl {3-[(7-chloroquinolin-4-yl)amino]bicyclo[1.1.1]pentan-1-yl}carbamate A mixture of tert-butyl (3-aminobicyclo[1.1.1]pentan-1-yl)carbamate (PharmaBlock, 800.0 mg, 4.04 mmol), 4-bromo-7-chloroquinoline (979 mg, 4.04 mmol), (R)-(+)-(1,1'-binaphthalene-2,2'-diyl)bis(diphenylphosphine) ((R)-BINAP, 201 mg, 0.323 mmol), palladium(II) acetate (Pd(OAc)$_2$, 36.2 mg, 0.161 mmol) and K$_3$PO$_4$ (2141 mg, 10.09 mmol) in 1,4-dioxane (25 mL) was degassed and heated at 85° C. for 16 hours. The reaction mixture was treated with water and brine and extracted with ethyl acetate (2×). The combined organic layers were dried over anhydrous MgSO$_4$, filtered, and concentrated under reduced pressure. The residue was purified on a 120 g silica gel column using the Biotage® Isolera™ One flash system eluting with heptanes/ethyl acetate (2:8 to 1:9) to provide the title compound (0.640 g, 1.78 mmol, 44% yield). MS (ESI$^+$) m/z 360.2 (M+H)$^+$.

Example 285B: N$^1$-(7-chloroquinolin-4-yl)bicyclo[1.1.1]pentane-1,3-diamine hydrochloride A mixture of the product of Example 285A (0.63 g, 1.75 mmol) and trifluoroacetic acid (1.35 mL, 17.5 mmol) in CH$_2$Cl$_2$ (6 mL) was stirred for 3 hours. The reaction mixture was concentrated. The concentrate was dissolved in 5 mL of methanol and treated with 2 N HCl in ether (5 mL). The resulting suspension was diluted with ether and stirred for 15 minutes. The solids were filtered, washed with ether, and vacuum oven-dried to provide the title compound (0.521 g, 1.56 mmol, 89% yield). MS (ESI$^+$) m/z 260.2 (M+H)$^+$.

Example 285C: 2-(4-chloro-3-fluorophenoxy)-N-{3-[(7-chloroquinolin-4-yl)amino]bicyclo[1.1.1]pentan-1-yl}acetamide A mixture of the product of Example 285B (45.0 mg, 0.135 mmol), 2-(4-chloro-3-fluorophenoxy)acetic acid (30.4 mg, 0.15 mmol), N-[(dimethylamino)-1H-1,2,3-triazolo-[4,5-b]pyridin-1-ylmethylene]-N-methylmethanaminium hexafluorophosphate N-oxide (HATU, 61.7 mg, 0.162 mmol), and triethylamine (0.075 mL, 0.54 mmol) in tetrahydrofuran (1.5 mL) was stirred for 4 hours. The reaction mixture was treated with water and brine and extracted with ethyl acetate (2×). The combined organic layers were concentrated and purified by reverse-phase HPLC (see protocol in Example 273E) to provide the title compound as a trifluoroacetic acid salt (52.4 mg, 0.096 mmol, 69% yield). $^1$H NMR (400 MHz, DMSO-$d_6$) δ ppm 9.75 (s, 1H), 8.96 (s, 1H), 8.59 (t, J=8.2 Hz, 2H), 8.00 (d, J=2.1 Hz, 1H), 7.83 (dd, J=9.2, 2.1 Hz, 1H), 7.51 (t, J=8.9 Hz, 1H), 7.16-7.03 (m, 2H), 6.88 (dd, J=8.9, 2.7 Hz, 1H), 4.55 (s, 2H), 2.59 (s, 6H); MS (ESI$^+$) m/z 446.2 (M+H)$^+$.

Example 286: N-{3-[(7-chloroquinolin-4-yl)amino]bicyclo[1.1.1]pentan-1-yl}-2-{[6-(trifluoromethyl)pyridin-3-yl]oxy}acetamide (Compound 385)

The reaction described in Example 285C substituting 2-((6-(trifluoromethyl)pyridin-3-yl)oxy)acetic acid for 2-(4-chloro-3-fluorophenoxy)acetic acid gave the title compound. $^1$H NMR (400 MHz, DMSO-$d_6$) δ ppm 9.76 (s, 1H), 9.05 (s, 1H), 8.59 (t, J=8.1 Hz, 2H), 8.49 (d, J=2.8 Hz, 1H), 8.00 (d, J=2.1 Hz, 1H), 7.94-7.77 (m, 2H), 7.61 (dd, J=8.7, 2.9 Hz, 1H), 7.11 (d, J=7.1 Hz, 1H), 4.74 (s, 2H), 2.60 (s, 6H); MS (ESI$^+$) m/z 463.1 (M+H)$^+$.

Example 287: N-{3-[2-(4-chloro-3-fluorophenoxy)acetamido]bicyclo[1.1.1]pentan-1-yl}-3-(2-hydroxypropan-2-yl)benzamide (Compound 386)

The title compound was prepared using the methodologies described above. $^1$H NMR (500 MHz, DMSO-$d_6$) δ ppm 8.99 (s, 1H), 8.75 (s, 1H), 7.92 (t, J=1.9 Hz, 1H), 7.66 (ddd, J=7.7, 1.8, 1.2 Hz, 1H), 7.62 (ddd, J=7.8, 1.9, 1.1 Hz, 1H), 7.51 (t, J=8.9 Hz, 1H), 7.37 (t, J=7.7 Hz, 1H), 7.09 (dd, J=11.4, 2.8 Hz, 1H), 6.87 (ddd, J=9.0, 2.9, 1.2 Hz, 1H), 5.09 (s, 1H), 4.50 (s, 2H), 2.34 (s, 6H), 1.45 (s, 6H); MS (ESI$^+$) m/z 432 (M+H)$^+$.

Example 288: N-{3-[2-(4-chloro-3-fluorophenoxy)acetamido]bicyclo[1.1.1]pentan-1-yl}-2,3-dihydro-1,4-benzodioxine-6-carboxamide (Compound 387)

The title compound was prepared using the methodologies described above. $^1$H NMR (400 MHz, DMSO-$d_6$) δ ppm 8.80 (s, 1H), 8.70 (s, 1H), 7.48 (t, J=8.9 Hz, 1H), 7.37-7.30 (m, 2H), 7.06 (dd, J=11.4, 2.8 Hz, 1H), 6.88 (d, J=8.3 Hz, 1H), 6.84 (ddd, J=9.0, 2.9, 1.2 Hz, 1H), 4.47 (s, 2H), 4.25 (td, J=5.2, 3.7 Hz, 4H), 2.29 (s, 6H); MS (ESI$^+$) m/z 447 (M+H)$^+$.

Example 289: N-{3-[2-(4-chloro-3-fluorophenoxy)acetamido]bicyclo[1.1.1]pentan-1-yl}-1-methyl-1H-pyrazole-5-carboxamide (Compound 388)

The title compound was prepared using the methodologies described above. $^1$H NMR (400 MHz, DMSO-$d_6$) δ ppm 8.98 (s, 1H), 8.76 (s, 1H), 7.50 (t, J=8.9 Hz, 1H), 7.43 (d, J=2.1 Hz, 1H), 7.08 (dd, J=11.4, 2.8 Hz, 1H), 6.88-6.84 (m, 2H), 4.49 (s, 2H), 4.03 (s, 3H), 2.33 (s, 6H); MS (ESI$^+$) m/z 393 (M+H)$^+$.

Example 290: N-{3-[2-(4-chloro-3-fluorophenoxy) acetamido]bicyclo[1.1.1]pentan-1-yl}-1-methyl-1H-pyrazole-3-carboxamide (Compound 389)

The title compound was prepared using the methodologies described above. $^1$H NMR (400 MHz, DMSO-$d_6$) δ ppm 8.71 (s, 1H), 8.59 (s, 1H), 7.75 (d, J=2.3 Hz, 1H), 7.50 (t, J=8.9 Hz, 1H), 7.08 (dd, J=11.4, 2.8 Hz, 1H), 6.86 (ddd, J=9.1, 2.9, 1.2 Hz, 1H), 6.58 (d, J=2.3 Hz, 1H), 4.48 (s, 2H), 3.88 (s, 3H), 2.29 (s, 6H); MS (ESI$^+$) m/z 393 (M+H)$^+$.

Example 291: N-{3-[2-(4-chloro-3-fluorophenoxy) acetamido]bicyclo[1.1.1]pentan-1-yl}-4-(cyclopropylamino)pyridine-2-carboxamide (Compound 390)

The title compound was prepared using the methodologies described above. $^1$H NMR (400 MHz, DMSO-$d_6$) δ ppm 9.00 (s, 1H), 8.73 (s, 1H), 8.08 (d, J=5.6 Hz, 1H), 7.50 (t, J=8.9 Hz, 1H), 7.30 (d, J=2.4 Hz, 1H), 7.22 (d, J=2.0 Hz, 1H), 7.08 (dd, J=11.4, 2.8 Hz, 1H), 6.86 (ddd, J=9.0, 2.9, 1.2 Hz, 1H), 6.73 (dd, J=5.7, 2.4 Hz, 1H), 4.49 (s, 2H), 2.46-2.39 (m, 1H), 2.33 (s, 6H), 0.79-0.71 (m, 2H), 0.46-0.38 (m, 2H); MS (ESI$^+$) m/z 445 (M+H)$^+$.

Example 292: N-{3-[2-(4-chloro-3-fluorophenoxy) acetamido]bicyclo[1.1.1]pentan-1-yl}-4-{[(cyclopropanecarbonyl)amino]methyl}pyridine-2-carboxamide (Compound 391)

The reaction and purification conditions described in Example 13 substituting cyclopropanecarboxylic acid for the product of 12B and the product of Example 94 for the product of Example 4A gave the title compound. $^1$H NMR (400 MHz, DMSO-$d_6$) δ ppm 9.21 (s, 1H), 8.73-8.68 (m, 2H), 8.52 (dd, J=4.9, 0.8 Hz, 1H), 7.88-7.84 (m, 1H), 7.48 (t, J=8.9 Hz, 1H), 7.42 (dd, J=5.0, 1.7 Hz, 1H), 7.06 (dd, J=11.4, 2.8 Hz, 1H), 6.84 (ddd, J=8.9, 2.8, 1.2 Hz, 1H), 4.47 (s, 2H), 4.36 (d, J=6.0 Hz, 2H), 2.33 (s, 6H), 1.63 (p, J=6.2 Hz, 1H), 0.71-0.67 (m, 4H); MS (ESI$^+$) m/z 487 (M+H)$^+$.

Example 293: N-{3-[2-(4-chloro-3-fluorophenoxy) acetamido]bicyclo[1.1.1]pentan-1-yl}-3-(4-chlorophenyl)-1,2-oxazole-5-carboxamide (Compound 392)

The title compound was prepared using the methodologies described above. $^1$H NMR (400 MHz, DMSO-$d_6$) δ ppm 9.59 (s, 1H), 8.74 (s, 1H), 7.95-7.86 (m, 2H), 7.62-7.54 (m, 3H), 7.47 (t, J=8.9 Hz, 1H), 7.05 (dd, J=11.4, 2.8 Hz, 1H), 6.83 (ddd, J=9.0, 2.9, 1.2 Hz, 1H), 4.46 (s, 2H), 2.32 (s, 6H); MS (ESI$^+$) m/z 490 (M+H)$^+$.

Example 294: 2-(4-chloro-3-fluorophenoxy)-N-{3-[(5-methyl-1,3,4-oxadiazol-2-yl)amino]bicyclo[1.1.1]pentan-1-yl}acetamide (Compound 393)

To a solution of Example 4A (60 mg, 0.21 mmol) in N,N-dimethylformamide (1 mL) was added N,N-diisopropylethylamine (0.18 mL, 1.05 mmol) and 2-bromo-5-methyl-1,3,4-oxadiazole (37.8 mg, 0.22 mmol). The reaction mixture was stirred for 72 hours at 80° C. The mixture was then purified with preparative HPLC [Waters XBridge™ C18 5 µm OBD™ column, 30×100 mm, flow rate 40 mL/minute, 5-100% gradient of acetonitrile in buffer (0.1% trifluoroacetic acid)] to give the title compound (36 mg, 0.098 mmol, 47% yield). $^1$H NMR (400 MHz, DMSO-$d_6$) δ ppm 8.73 (s, 1H), 8.26 (s, 1H), 7.47 (t, J=8.9 Hz, 1H), 7.05 (dd, J=11.4, 2.8 Hz, 1H), 6.84 (ddd, J=9.0, 2.8, 1.2 Hz, 1H), 4.47 (s, 2H), 2.28 (s, 3H), 2.24 (s, 6H); MS (ESI$^+$) m/z 367 (M+H)$^+$.

Example 295: 2-(4-chloro-3-fluorophenoxy)-N-{3-[(2-methylpyrazolo[1,5-a]pyrazin-4-yl)amino]bicyclo[1.1.1]pentan-1-yl}acetamide (Compound 394)

The reaction and purification conditions described in Example 264 substituting 4-chloro-2-methylpyrazolo[1,5-a]pyrazine for 2-chloro-4-phenylpyrimidine gave the title compound. $^1$H NMR (501 MHz, DMSO-$d_6$) δ ppm 8.77 (s, 1H), 8.00 (s, 1H), 7.83 (d, J=6 Hz, 1H), 7.51 (t, J=8 Hz, 1H), 7.24 (d, J=6 Hz, 1H), 7.08 (dd, J=9, 3 Hz, 1H), 6.87 (br d, J=8 Hz, 1H), 6.70 (s, 1H), 4.51 (s, 2H), 2.41 (s, 6H), 2.35 (s, 3H); MS (ESI$^+$) m/z 416 (M+H)$^+$.

Example 296: 2-(4-chloro-3-fluorophenoxy)-N-(3-{[6-(4-chlorophenyl)pyrazin-2-yl]amino}bicyclo [1.1.1]pentan-1-yl)acetamide (Compound 395)

Example 296A: N-{3-[(6-bromopyrazin-2-yl)amino] bicyclo[1.1.1]pentan-1-yl}-2-(4-chloro-3-fluorophenoxy)acetamide To a solution of the product of Example 4A (100 mg, 0.35 mmol) in dioxane (1 mL) was added 2,6-dibromopyrazine (251 mg, 1.05 mmol), Pd$_2$(dba)$_3$ (16.1 mg, 0.018 mmol), xantphos (20.3 mg, 0.035 mmol), and potassium carbonate (146 mg, 1.05 mmol). The reaction mixture was heated at 80° C. for 18 hours and then was diluted with ethyl acetate (10 mL) and water. The separated organic layer was concentrated under reduced pressure, and the residue was purified by flash column chromatography (SiO$_2$, heptane:ethyl acetate 0-100%) to give the title compound (80 mg, 0.18 mmol, 52% yield). $^1$H NMR (501 MHz, DMSO-$d_6$) δ ppm 8.74 (s, 1H), 8.21 (s, 1H), 7.86 (s, 1H), 7.83 (s, 1H), 7.48 (t, J=8.8 Hz, 1H), 7.06 (dd, J=11.4, 2.9 Hz, 1H), 6.84 (ddd, J=9.0, 2.9, 1.2 Hz, 1H), 4.48 (s, 2H), 2.31 (s, 6H); MS (ESI$^+$) m/z 442 (M+H)$^+$.

Example 296B: 2-(4-chloro-3-fluorophenoxy)-N-(3-{[6-(4-chlorophenyl)pyrazin-2-yl]amino}bicyclo [1.1.1]pentan-1-yl)acetamide To a solution of the product of Example 296A (70 mg, 0.16 mmol) in 1,4-dioxane (1 mL) was added (4-chlorophenyl)boronic acid (24.8 mg, 0.16 mmol), Pd(Ph$_3$P)$_4$ (18.3 mg, 0.016 mmol), potassium carbonate (65.7 mg, 0.475 mmol) and water (0.2 mL). The reaction mixture was stirred 4 hours at 80° C. The reaction mixture was diluted with ethyl acetate (10 mL) and water. The separated organic layer was concentrated under reduced pressure, and the residue was purified by flash column chromatography (SiO$_2$, heptane:ethyl acetate 0-100%) followed by preparative HPLC [Waters XBridge™ C18 5 µm OBD™ column, 30×100 mm, flow rate 40 mL/minute, 5-100% gradient of acetonitrile in buffer (0.1% trifluoroacetic acid)] to give the title compound (45 mg, 0.095 mmol, 60% yield). $^1$H NMR (400 MHz, DMSO-$d_6$) δ ppm 8.77 (s, 1H), 8.34 (s, 1H), 8.07-8.00 (m, 2H), 7.91 (s, 1H), 7.85 (s, 1H), 7.55-7.51 (m, 2H), 7.47 (t, J=8.9 Hz, 1H), 4.47 (s, 2H), 2.37 (s, 6H); MS (ESI$^+$) m/z 473 (M+H)$^+$.

Example 297: N-{3-[2-(4-chloro-3-fluorophenoxy) acetamido]bicyclo[1.1.1]pentan-1-yl}-2-oxo-2H-1-benzopyran-6-carboxamide (Compound 396)

The title compound was prepared using the methodologies described above. $^1$H NMR (400 MHz, DMSO-$d_6$) δ ppm 9.17 (s, 1H), 8.77 (s, 1H), 8.20 (d, J=2.2 Hz, 1H), 8.10 (d, J=9.6 Hz, 1H), 8.04 (dd, J=8.7, 2.1 Hz, 1H), 7.55-7.42 (m, 2H), 7.09 (dd, J=11.3, 2.8 Hz, 1H), 6.87 (ddd, J=9.0, 2.9, 1.2 Hz, 1H), 6.56 (d, J=9.6 Hz, 1H), 4.50 (s, 2H), 2.35 (s, 6H); MS (ESI$^+$) m/z 457 (M+H)$^+$.

Example 298: N-{4-[2-(4-chloro-3-fluorophenoxy)acetamido]-3-hydroxybicyclo[2.2.2]octan-1-yl}-3-(2-methoxyphenyl)-1,2-oxazole-5-carboxamide (Compound 397)

The title compound was prepared using the methodologies described in Example 130 substituting 3-(2-methoxyphenyl)-1,2-oxazole-5-carboxylic acid for 5-(difluoromethyl)pyrazine-2-carboxylic acid. $^1$H NMR (400 MHz, DMSO-d$_6$) δ ppm 8.20 (s, 1H), 7.71 (dd, J=7.6, 1.8 Hz, 1H), 7.52-7.40 (m, 2H), 7.36 (s, 1H), 7.28 (s, 1H), 7.17 (d, J=8.3 Hz, 1H), 7.08-6.98 (m, 2H), 6.80 (ddd, J=8.9, 2.9, 1.1 Hz, 1H), 5.14 (d, J=4.4 Hz, 1H), 4.44 (s, 2H), 4.10-4.02 (m, 1H), 3.85 (s, 3H), 2.35 (ddd, J=11.9, 9.3, 2.1 Hz, 1H), 2.12-1.97 (m, 2H), 1.98-1.74 (m, 7H); MS (ESI$^+$) m/z 544.2 (M+H)$^+$.

Example 299: 2-(4-chloro-3-fluorophenoxy)-N-(3-{[6-(4-chlorophenyl)pyridin-2-yl]amino}bicyclo[1.1.1]pentan-1-yl)acetamide (Compound 398)

Example 299A: N-{3-[(6-bromopyridin-2-yl)amino]bicyclo[1.1.1]pentan-1-yl}-2-(4-chloro-3-fluorophenoxy)acetamide The reaction and purification conditions described in Example 296A substituting 2,6-dibromopyridine for 2,6-dibromopyrazine gave the title compound. MS (ESI$^+$) m/z 397 (M+H)$^+$.

Example 299B: 2-(4-chloro-3-fluorophenoxy)-N-(3-{[6-(4-chlorophenyl)pyridin-2-yl]amino}bicyclo[1.1.1]pentan-1-yl)acetamide The reaction and purification conditions described in Example 296B substituting the product of Example 299A for the product of Example 296A gave the title compound. $^1$H NMR (501 MHz, DMSO-d$_6$) δ ppm 8.75 (s, 1H), 8.00 (d, J=8.6 Hz, 2H), 7.53-7.45 (m, 4H), 7.13 (d, J=7.4 Hz, 1H), 7.07 (dd, J=11.4, 2.8 Hz, 1H), 6.85 (ddd, J=8.9, 2.9, 1.2 Hz, 1H), 6.51 (d, J=8.3 Hz, 1H), 4.49 (s, 2H), 2.37 (s, 6H); MS (ESI$^+$) m/z 472 (M+H)$^+$.

Example 300: N-(3-{2-[(2,2-difluoro-2H-1,3-benzodioxol-5-yl)oxy]acetamido}bicyclo[1.1.1]pentan-1-yl)-3-ethyl-1-methyl-1H-pyrazole-5-carboxamide (Compound 399)

The title compound was prepared using the methodologies described above. $^1$H NMR (501 MHz, DMSO-d$_6$) δ ppm 8.89 (s, 1H), 8.72 (s, 1H), 7.33 (d, J=8.9 Hz, 1H), 7.15 (d, J=2.5 Hz, 1H), 6.78 (dd, J=8.9, 2.6 Hz, 1H), 6.67 (s, 1H), 4.45 (s, 2H), 3.96 (s, 3H), 2.55-2.51 (m, 2H), 2.31 (s, 6H), 1.15 (t, J=7.6 Hz, 3H); MS (ESI$^+$) m/z 449 (M+H)$^+$.

Example 301: N-(3-{2-[(2,2-difluoro-2H-1,3-benzodioxol-5-yl)oxy]acetamido}bicyclo[1.1.1]pentan-1-yl)pyridine-2-carboxamide (Compound 400)

The title compound was prepared using the methodologies described above. $^1$H NMR (400 MHz, DMSO-d$_6$) δ ppm 9.25 (s, 1H), 8.71 (s, 1H), 8.63 (dt, J=4.7, 1.4 Hz, 1H), 8.03-7.97 (m, 2H), 7.63-7.57 (m, 1H), 7.33 (d, J=9.0 Hz, 1H), 7.15 (d, J=2.6 Hz, 1H), 6.78 (dd, J=8.9, 2.5 Hz, 1H), 4.46 (s, 2H), 2.36 (s, 6H); MS (ESI$^+$) m/z 418 (M+H)$^+$.

Example 302: N-(3-{2-[(2,2-difluoro-2H-1,3-benzodioxol-5-yl)oxy]acetamido}bicyclo[1.1.1]pentan-1-yl)-4-(hydroxymethyl)pyridine-2-carboxamide (Compound 401)

The title compound was prepared using the methodologies described above. $^1$H NMR (400 MHz, DMSO-d$_6$) δ ppm 9.22 (s, 1H), 8.71 (s, 1H), 8.54 (dd, J=4.9, 0.8 Hz, 1H), 7.97 (dd, J=1.7, 0.9 Hz, 1H), 7.53-7.50 (m, 1H), 7.33 (d, J=8.9 Hz, 1H), 7.15 (d, J=2.6 Hz, 1H), 6.78 (dd, J=8.9, 2.6 Hz, 1H), 5.54 (t, J=5.7 Hz, 1H), 4.62 (d, J=5.5 Hz, 2H), 4.46 (s, 2H), 2.36 (s, 6H); MS (ESI$^+$) m/z 448 (M+H)$^+$.

Example 303: N-{3-[2-(4-chloro-3-fluorophenoxy)acetamido]bicyclo[1.1.1]pentan-1-yl}-1-oxo-1λ$^5$-pyridine-3-carboxamide (Compound 402)

The title compound was prepared using the methodologies described above. $^1$H NMR (400 MHz, DMSO-d$_6$) δ ppm 9.33 (s, 1H), 8.78 (s, 1H), 8.56 (t, J=1.7 Hz, 1H), 8.34 (ddd, J=6.4, 1.8, 0.9 Hz, 1H), 7.71 (dt, J=8.0, 1.2 Hz, 1H), 7.54-7.48 (m, 2H), 7.09 (dd, J=11.4, 2.8 Hz, 1H), 6.86 (ddd, J=9.0, 2.8, 1.1 Hz, 1H), 4.50 (s, 2H), 2.34 (s, 6H); MS (ESI$^+$) m/z 406 (M+H)$^+$.

Example 304: N-{3-[2-(4-chloro-3-fluorophenoxy)acetamido]bicyclo[1.1.1]pentan-1-yl}-1-oxo-1λ$^5$-pyridine-2-carboxamide (Compound 403)

The title compound was prepared using the methodologies described above. $^1$H NMR (400 MHz, DMSO-d$_6$) δ ppm 11.63 (s, 1H), 8.77 (s, 1H), 8.44-8.38 (m, 1H), 8.20-8.14 (m, 1H), 7.64-7.55 (m, 2H), 7.47 (t, J=8.9 Hz, 1H), 7.05 (dd, J=11.4, 2.8 Hz, 1H), 6.83 (ddd, J=8.9, 2.9, 1.2 Hz, 1H), 4.46 (s, 2H), 2.34 (s, 6H); MS (ESI$^+$) m/z 406 (M+H)$^+$.

Example 305: 2-(4-chloro-3-fluorophenoxy)-N-{3-[(5-phenyl-1,3,4-oxadiazol-2-yl)amino]bicyclo[1.1.1]pentan-1-yl}acetamide (Compound 404)

The reaction and purification conditions described in Example 294 substituting 2-bromo-5-phenyl-1,3,4-oxadiazole for 2-bromo-5-methyl-1,3,4-oxadiazole gave the titled compound. $^1$H NMR (400 MHz, DMSO-d$_6$) δ ppm 8.77 (s, 1H), 8.68 (s, 1H), 7.83-7.73 (m, 2H), 7.56-7.42 (m, 4H), 7.05 (dd, J=11.4, 2.9 Hz, 1H), 6.83 (ddd, J=9.0, 2.8, 1.2 Hz, 1H), 4.47 (s, 2H), 2.30 (s, 6H); MS (ESI$^+$) m/z 429 (M+H)$^+$.

Example 306: N-{3-[2-(4-chloro-3-fluorophenoxy)acetamido]bicyclo[1.1.1]pentan-1-yl}-1-ethyl-2-oxo-1,2-dihydropyridine-4-carboxamide (Compound 405)

The title compound was prepared using the methodologies described above. $^1$H NMR (400 MHz, DMSO-d$_6$) δ ppm 9.12 (s, 1H), 8.72 (s, 1H), 7.76 (d, J=7.0 Hz, 1H), 7.48 (t, J=8.9 Hz, 1H), 7.06 (dd, J=11.4, 2.8 Hz, 1H), 6.84 (ddd, J=8.9, 2.9, 1.1 Hz, 1H), 6.75 (d, J=1.9 Hz, 1H), 6.49 (dd, J=7.0, 2.0 Hz, 1H), 4.47 (s, 2H), 3.89 (q, J=7.1 Hz, 2H), 2.29 (s, 6H), 1.19 (t, J=7.1 Hz, 3H); MS (ESI$^+$) m/z 434 (M+H)$^+$.

Example 307: N-{3-[2-(4-chloro-3-fluorophenoxy) acetamido]bicyclo[1.1.1]pentan-1-yl}-4-(propan-2-yl)-1,3-thiazole-2-carboxamide (Compound 406)

The title compound was prepared using the methodologies described above. $^1$H NMR (400 MHz, DMSO-d$_6$) δ ppm 9.21 (s, 1H), 8.73 (s, 1H), 7.54 (s, 1H), 7.46 (t, J=8.9 Hz, 1H), 7.04 (dd, J=11.4, 2.9 Hz, 1H), 6.82 (ddd, J=8.9, 3.1, 1.1 Hz, 1H), 4.45 (s, 2H), 3.04 (p, J=6.9 Hz, 1H), 2.30 (s, 6H), 1.24 (d, J=6.9 Hz, 6H); MS (ESI$^+$) m/z 438 (M+H)$^+$.

Example 308: N-{(2S)-4-[2-(4-chloro-3-fluorophenoxy)acetamido]-2-hydroxybicyclo[2.2.2]octan-1-yl}-2-oxo-2H-1-benzopyran-6-carboxamide (Compound 407)

Example 308A: N-[(3S)-4-amino-3-hydroxybicyclo [2.2.2]octan-1-yl]-2-(4-chloro-3-fluorophenoxy) acetamide trifluoroacetate The title compound was isolated by chiral preparative SFC of Example 68I as the second peak eluted off the column, followed by reverse phase HPLC purification to give the title compound as a trifluoroacetic acid salt. The preparative SFC (Supercritical Fluid Chromatography) was performed on a Thar 200 preparative SFC (SFC-5) system using a Chiralpak® IC, 300×50 mm I.D., 10 µm column. The column was heated at 38° C., and the backpressure regulator was set to maintain 100 bar. The mobile phase A was CO$_2$ and B was isopropanol (0.1% NH$_4$OH). The eluent was held isocratically at 45% of mobile phase B at a flowrate of 200 mL/minute. Fraction collection was time triggered with UV monitor wavelength set at 220 nm. Preparative HPLC was performed on a Gilson 281 semi-preparative HPLC system using a Phenomenex® Luna® C18(2) 10 µm 100 Å AXIA™ column (250 mm×80 mm) column. A gradient of acetonitrile (A) and 0.075% trifluoroacetic acid in water (B) was used at a flow rate of 80 mL/minute. A linear gradient was used from about 30% of A to about 100% of A over about 30 minutes. Detection method was UV at wave length of 220 nM and 254 nM. $^1$H NMR (400 MHz, methanol-d$_4$) δ ppm 7.36 (t, J=8.77 Hz, 1H), 6.89 (dd, J=10.74, 2.85 Hz, 1H), 6.79 (br d, J=9.21 Hz, 1H), 4.43 (s, 2H), 3.94 (br d, J=8.33 Hz, 1H), 2.55 (br t, J=12.50 Hz, 1H), 2.35-1.84 (m, 8H), 1.83-1.58 (m, 2H); MS (ESI$^+$) m/z 343.0 (M+H)$^+$.

Example 308B: N-[(2S)-4-[2-(4-chloro-3-fluorophenoxy)acetamido]-2-hydroxybicyclo[2.2.2]octan-1-yl]-2-oxo-2H-1-benzopyran-6-carboxamide A mixture of Example 308A (75 mg, 0.164 mmol), 2-oxo-2H-chromene-6-carboxylic acid (37.5 mg, 0.197 mmol) and N-ethyl-N-isopropylpropan-2-amine (0.143 mL, 0.821 mmol) in N,N-dimethylformamide (1.5 mL) was treated with 2-(3H-[1,2,3]triazolo[4,5-b]pyridin-3-yl)-1,1,3,3-tetramethylisouronium hexafluorophosphate(V) (94 mg, 0.246 mmol), and the reaction mixture was stirred at ambient temperature for 16 hours. The reaction mixture was concentrate, and the residue was purified by HPLC (20-100% acetonitrile in 0.1% trifluoroacetic acid/water on Phenomenex® C18 10 m (250 mm×50 mm) column at a flowrate of 50 mL/minute) to give 52 mg of the title compound as a white solid. $^1$H NMR (400 MHz, DMSO-d$_6$) δ ppm 8.14-8.03 (m, 2H), 7.96 (dd, J=8.7, 2.1 Hz, 1H), 7.65 (d, J=25.1 Hz, 1H), 7.56 (s, 1H), 7.53-7.38 (m, 3H), 7.00 (dd, J=11.4, 2.9 Hz, 1H), 6.78 (dd, J=9.2, 2.9 Hz, 1H), 6.52 (d, J=9.6 Hz, 1H), 5.09 (s, 1H), 4.41 (s, 2H), 4.22 (dd, J=9.7, 2.8 Hz, 1H), 2.28 (ddd, J=12.6, 9.3, 2.9 Hz, 1H), 2.10-1.70 (m, 9H); MS (ESI$^+$) m/z 515.1 (M+H)$^+$.

Example 309: N-{4-[2-(4-chloro-3-fluorophenoxy) acetamido]-3-hydroxybicyclo[2.2.2]octan-1-yl}-3-cyclohexyl-1,2-oxazole-5-carboxamide (Compound 408)

The title compound was prepared using the methodologies described in Example 130 substituting 3-cyclohexyl-1,2-oxazole-5-carboxylic acid for 5-(difluoromethyl)pyrazine-2-carboxylic. $^1$H NMR (400 MHz, DMSO-d$_6$) δ ppm 8.04 (s, 1H), 7.45 (t, J=8.9 Hz, 1H), 7.26 (s, 1H), 7.02 (dd, J=11.4, 2.9 Hz, 1H), 6.95 (s, 1H), 6.80 (ddd, J=9.0, 2.9, 1.1 Hz, 1H), 5.09 (d, J=4.4 Hz, 1H), 4.44 (s, 2H), 4.04 (dt, J=8.7, 3.8 Hz, 1H), 2.76-2.64 (m, 1H), 2.31 (ddd, J=12.5, 9.8, 1.9 Hz, 1H), 2.11-1.59 (m, 13H), 1.45-1.15 (m, 5H); MS (ESI$^+$) m/z 520.2 (M+H)$^+$.

Example 310: N-{4-[2-(4-chloro-3-fluorophenoxy) acetamido]-3-hydroxybicyclo[2.2.2]octan-1-yl}-3-(2,6-difluorophenyl)-1,2-oxazole-5-carboxamide (Compound 409)

The title compound was prepared using the methodologies described in Example 130 substituting 3-(2,6-difluorophenyl)-1,2-oxazole-5-carboxylic acid for 5-(difluoromethyl)pyrazine-2-carboxylic. $^1$H NMR (400 MHz, DMSO-d$_6$) δ ppm 8.31 (s, 1H), 7.63 (tt, J=8.5, 6.5 Hz, 1H), 7.45 (t, J=8.9 Hz, 1H), 7.38-7.25 (m, 4H), 7.03 (dd, J=11.4, 2.9 Hz, 1H), 6.80 (ddd, J=9.0, 2.9, 1.2 Hz, 1H), 5.11 (d, J=4.4 Hz, 1H), 4.45 (s, 2H), 4.11-4.02 (m, 1H), 2.35 (ddd, J=12.4, 9.6, 2.0 Hz, 1H), 2.14-1.75 (m, 9H); MS (ESI$^+$) m/z 550.1 (M+H)$^+$.

Example 311: N-{4-[2-(4-chloro-3-fluorophenoxy) acetamido]-3-hydroxybicyclo[2.2.2]octan-1-yl}-3-[(4-chlorophenyl)methyl]-1,2-oxazole-5-carboxamide (Compound 410)

The title compound was prepared using the methodologies described in Example 130 substituting 3-[(4-chlorophenyl)methyl]-1,2-oxazole-5-carboxylic acid for 5-(difluoromethyl)pyrazine-2-carboxylic. $^1$H NMR (400 MHz, DMSO-d$_6$) δ ppm 8.07 (s, 1H), 7.45 (t, J=8.9 Hz, 1H), 7.40-7.32 (m, 2H), 7.31-7.22 (m, 3H), 7.02 (dd, J=11.4, 2.9 Hz, 1H), 6.87-6.75 (m, 2H), 5.08 (d, J=4.4 Hz, 1H), 4.43 (s, 2H), 4.05 (dt, J=14.4, 5.2 Hz, 1H), 4.00 (s, 2H), 2.28 (ddd, J=12.4, 9.6, 2.2 Hz, 1H), 2.10-1.97 (m, 1H), 1.99-1.86 (m, 1H), 1.90-1.73 (m, 7H); MS (ESI$^+$) m/z 562.2 (M+H)$^+$.

Example 312: N-{4-[2-(4-chloro-3-fluorophenoxy) acetamido]-3-hydroxybicyclo[2.2.2]octan-1-yl}-3-hydroxy-1,2-oxazole-5-carboxamide (Compound 411)

The title compound was prepared using the methodologies described in Example 130 substituting 3-hydroxy-1,2-oxazole-5-carboxylic acid for 5-(difluoromethyl)pyrazine-2-carboxylic. $^1$H NMR (400 MHz, DMSO-d$_6$) δ ppm 11.58 (s, 1H), 7.98 (s, 1H), 7.45 (t, J=8.9 Hz, 1H), 7.25 (s, 1H), 7.02 (dd, J=11.4, 2.9 Hz, 1H), 6.80 (dd, J=8.8, 2.8 Hz, 1H), 6.51 (s, 1H), 5.08 (s, 1H), 4.44 (s, 2H), 4.03 (dd, J=9.6, 3.0 Hz, 1H), 2.30 (ddd, J=12.0, 9.5, 2.1 Hz, 1H), 2.11-1.73 (m, 9H); MS (ESI$^+$) m/z 454.2 (M+H)$^+$.

Example 313: N-{4-[2-(4-chloro-3-fluorophenoxy) acetamido]-3-hydroxybicyclo[2.2.2]octan-1-yl}-4-methyl-4H-imidazo[4,5-c][1,2]oxazole-3-carboxamide (Compound 412)

The title compound was prepared using the methodologies described in Example 130 substituting 4-methyl-4H-imidazo[4,5-c][1,2]oxazole-3-carboxylic acid for 5-(difluoromethyl)pyrazine-2-carboxylic. $^1$H NMR (400 MHz, DMSO-$d_6$) δ ppm 8.34 (s, 2H), 8.21 (s, 2H), 7.45 (t, J=8.9 Hz, 2H), 7.26 (s, 2H), 7.03 (dd, J=11.4, 2.8 Hz, 2H), 6.80 (ddd, J=9.0, 2.9, 1.2 Hz, 2H), 5.72 (s, 1H), 5.09 (s, 2H), 4.44 (s, 4H), 4.05 (dd, J=9.5, 3.2 Hz, 2H), 3.87 (s, 3H), 3.76 (s, 5H), 3.13 (s, 2H), 2.35 (ddd, J=12.6, 9.5, 2.6 Hz, 2H), 2.05 (ddd, J=13.4, 11.1, 5.4 Hz, 4H), 2.00-1.87 (m, 6H), 1.91-1.74 (m, 8H); MS (ESI$^+$) m/z 492.2 (M+H)$^+$.

Example 314: N-{(2S)-4-[2-(4-chloro-3-fluorophenoxy)acetamido]-2-hydroxybicyclo[2.2.2]octan-1-yl}-3-(difluoromethyl)-1-methyl-1H-pyrazole-5-carboxamide (Compound 413)

The title compound was prepared using the methodologies described in Example 308 substituting 3-(difluoromethyl)-1-methyl-1H-pyrazole-5-carboxylic acid for 2-oxo-2H-chromene-6-carboxylic acid. $^1$H NMR (400 MHz, DMSO-$d_6$) δ ppm 7.57-7.40 (m, 2H), 7.09 (d, J=5.5 Hz, 1H), 7.04-6.93 (m, 1H), 6.97 (t, J=54.0 Hz, 1H), 6.85-6.74 (m, 1H), 4.41 (s, 2H), 4.25 (dd, J=9.7, 2.8 Hz, 1H), 3.99 (s, 3H), 2.26 (ddd, J=12.6, 9.5, 2.6 Hz, 1H), 2.14-1.68 (m, 9H); MS (ESI$^+$) m/z 501.1 (M+H)$^+$.

Example 315: 3-chloro-N-{4-[2-(4-chloro-3-fluorophenoxy)acetamido]-3-hydroxybicyclo[2.2.2]octan-1-yl}-1,2-oxazole-5-carboxamide (Compound 414)

The title compound was prepared using the methodologies described in Example 130 substituting 3-chloro-1,2-oxazole-5-carboxylic acid for 5-(difluoromethyl)pyrazine-2-carboxylic. $^1$H NMR (400 MHz, DMSO-$d_6$) δ ppm 8.28 (s, 1H), 7.45 (t, J=8.9 Hz, 1H), 7.32 (s, 1H), 7.26 (s, 1H), 7.02 (dd, J=11.4, 2.9 Hz, 1H), 6.80 (ddd, J=9.0, 2.9, 1.2 Hz, 1H), 5.10 (s, 1H), 4.44 (s, 2H), 4.05 (dd, J=9.7, 3.0 Hz, 1H), 2.31 (ddd, J=12.0, 9.3, 2.2 Hz, 1H), 2.09-1.77 (m, 9H); MS (ESI$^+$) m/z 472.1 (M+H)$^+$.

Example 316: 2-(4-chloro-3-fluorophenoxy)-N-(3-{[4-(4-chlorophenyl)pyridin-2-yl]amino}bicyclo[1.1.1]pentan-1-yl)acetamide (Compound 415)

Example 316A: N-{3-[(4-bromopyridin-2-yl)amino]bicyclo[1.1.1]pentan-1-yl}-2-(4-chloro-3-fluorophenoxy)acetamide The reaction and purification conditions described in Example 296A substituting 2,4-dibromopyridine for 2,6-dibromopyrazine gave the title compound. $^1$H NMR (500 MHz, DMSO-$d_6$) δ ppm 8.75 (s, 1H), 7.90 (d, J=5.5 Hz, 2H), 7.52-7.47 (m, 2H), 7.08 (dd, J=11.4, 2.8 Hz, 1H), 6.86 (ddd, J=9.0, 2.8, 1.2 Hz, 1H), 6.74 (dd, J=5.4, 1.7 Hz, 1H), 6.67 (d, J=1.7 Hz, 1H), 4.49 (s, 2H), 2.30 (s, 6H); MS (ESI$^+$) m/z 441 (M+H)$^+$.

Example 316B: 2-(4-chloro-3-fluorophenoxy)-N-(3-{[4-(4-chlorophenyl)pyridin-2-yl]amino}bicyclo[1.1.1]pentan-1-yl)acetamide The reaction and purification conditions described in Example 296B substituting the product of Example 316A for the product of Example 296A gave the title compound. $^1$H NMR (400 MHz, DMSO-$d_6$) δ ppm 8.80 (s, 1H), 8.06 (d, J=6.0 Hz, 1H), 7.72 (d, J=8.5 Hz, 2H), 7.57 (d, J=8.6 Hz, 2H), 7.47 (t, J=8.9 Hz, 1H), 7.05 (dd, J=11.5, 2.9 Hz, 2H), 6.90 (s, 1H), 6.83 (dd, J=9.0, 2.8 Hz, 1H), 4.48 (s, 2H), 2.39 (s, 6H); $^{19}$F NMR (376 MHz, DMSO-$d_6$) δ ppm −74.08, −114.08; MS (ESI$^+$) m/z 472 (M+H)$^+$.

Example 317: 2-(4-chloro-3-fluorophenoxy)-N-(3-{[5-chloro-6-oxo-1-(2,2,2-trifluoroethyl)-1,6-dihydropyridazin-4-yl]amino}bicyclo[1.1.1]pentan-1-yl) acetamide (Compound 416)

The reaction and purification conditions described in Example 264 substituting 4,5-dichloro-2-(2,2,2-trifluoroethyl)pyridazin-3(2H)-one for 2-chloro-4-phenylpyrimidine gave the title compound as the major product (first fraction). $^1$H NMR (501 MHz, DMSO-$d_6$) δ ppm 8.82 (s, 1H), 8.11 (s, 1H), 7.59 (s, 1H), 7.50 (t, J=8 Hz, 1H), 7.08 (dd, J=9, 3 Hz, 1H), 6.86 (br d, J=8 Hz, 1H), 4.89 (q, J=8 Hz, 2H), 4.50 (s, 2H), 2.44 (s, 6H); MS (ESI$^+$) m/z 495 (M+H)$^+$.

Example 318: 2-(4-chloro-3-fluorophenoxy)-N-(3-{[5-chloro-3-oxo-2-(2,2,2-trifluoroethyl)-2,3-dihydropyridazin-4-yl]amino}bicyclo[1.1.1]pentan-1-yl) acetamide (Compound 417)

The reaction and purification conditions described in Example 264 substituting 4,5-dichloro-2-(2,2,2-trifluoroethyl)pyridazin-3(2H)-one for 2-chloro-4-phenylpyrimidine gave the title compound as the minor product (second fraction). $^1$H NMR (501 MHz, DMSO-$d_6$) δ ppm 8.73 (s, 1H), 7.84 (s, 1H), 7.50 (t, J=8 Hz, 1H), 7.11 (s, 1H), 7.08 (dd, J=9, 3 Hz, 1H), 6.85 (br d, J=8 Hz, 1H), 4.89 (q, J=8 Hz, 2H), 4.48 (s, 2H), 2.42 (s, 6H); MS (ESI$^+$) m/z 495 (M+H)$^+$.

Example 319: N-(3-{2-[(2,2-difluoro-2H-1,3-benzodioxol-5-yl)oxy]acetamido}bicyclo[1.1.1]pentan-1-yl)pyridine-4-carboxamide (Compound 418)

The title compound was prepared using the methodologies described above. $^1$H NMR (400 MHz, DMSO-$d_6$) δ ppm 9.32 (s, 1H), 8.75-8.70 (m, 3H), 7.75-7.72 (m, 2H), 7.33 (d, J=8.9 Hz, 1H), 7.15 (d, J=2.6 Hz, 1H), 6.78 (dd, J=8.9, 2.6 Hz, 1H), 4.46 (s, 2H), 2.35 (s, 6H); MS (ESI$^+$) m/z 418 (M+H)$^+$.

Example 320: N-{3-[2-(4-chloro-3-fluorophenoxy) acetamido]bicyclo[1.1.1]pentan-1-yl}-3-(hydroxymethyl)benzamide (Compound 419)

The title compound was prepared using the methodologies described above. $^1$H NMR (400 MHz, DMSO-$d_6$) δ ppm 8.97 (s, 1H), 8.71 (s, 1H), 7.77-7.74 (m, 1H), 7.65 (dt, J=7.6, 1.6 Hz, 1H), 7.47 (t, J=8.9 Hz, 1H), 7.44-7.40 (m, 1H), 7.38-7.33 (m, 1H), 7.05 (dd, J=11.4, 2.8 Hz, 1H), 6.83 (ddd, J=9.0, 2.9, 1.2 Hz, 1H), 5.24 (t, J=4.3 Hz, 1H), 4.50 (d, J=3.7 Hz, 2H), 4.46 (s, 2H), 2.29 (s, 6H); MS (ESI$^+$) m/z 419 (M+H)$^+$.

Example 321: N-{3-[2-(4-chloro-3-fluorophenoxy) acetamido]bicyclo[1.1.1]pentan-1-yl}-5-[(cyclobutylmethyl)(methyl)amino]pyrazine-2-carboxamide (Compound 420)

Example 321A: methyl 5-((cyclobutylmethyl)(methyl)amino)pyrazine-2-carboxylate Dioxane (10 mL) was added to a mixture of methyl 5-bromopyrazine-2-carboxylate (Ark Pharm, 400 mg, 1.84 mmol), (cyclobutylmethyl)methylamine hydrochloride (ChemBridge, 238 mg, 2.4 mmol), bis(tri-tert-butylphosphine)palladium(0) (Strem, 94 mg, 0.184 mmol) and cesium carbonate (1.2 g, 3.69 mmol) in a sealed tube. The tube was sealed and degassed three times with a nitrogen back flush each time. The reaction mixture was stirred at 95° C. for 18 hours, cooled to ambient temperature, and filtered through a pack of diatomaceous earth. The filter cake was further rinsed with more N,N-dimethylformamide (3 mL), and the resulting filtrate was filtered through a glass microfiber frit and purified by preparative HPLC [YMC TriArt™ Hybrid C18 20 μm column, 50×150 mm, flow rate 100 mL/minute, 5-100% gradient of acetonitrile in buffer (0.025 M aqueous ammonium bicarbonate, adjusted to pH 10 with ammonium hydroxide)] to give the title compound (78 mg, 0.33 mmol, 18% yield). $^1$H NMR (501 MHz, DMSO-$d_6$) δ ppm 8.61 (d, J=1.4 Hz, 1H), 8.17 (d, J=1.4 Hz, 1H), 3.78 (s, 3H), 3.66 (d, J=7.3 Hz, 2H), 3.11 (s, 3H), 2.68-2.57 (m, 1H), 2.01-1.89 (m, 2H), 1.86-1.66 (m, 4H).

Example 321B: 5-((cyclobutylmethyl)(methyl) amino)pyrazine-2-carboxylic Acid

The reaction and purification conditions described in Example 181 substituting the product of Example 321A for the product of Example 180 gave the title compound. MS (ESI$^+$) m/z 244 (M+Na)$^+$.

Example 321C: N-{3-[2-(4-chloro-3-fluorophenoxy) acetamido]bicyclo[1.1.1]pentan-1-yl}-5-[(cyclobutylmethyl)(methyl)amino]pyrazine-2-carboxamide The reaction and purification conditions described in Example 13 substituting the product of Example 321B for the product of Example 12B and the product of Example 6C for the product of Example 4A gave the title compound. $^1$H NMR (501 MHz, DMSO-$d_6$) δ ppm 8.74 (s, 1H), 8.70 (s, 1H), 8.53 (d, J=1.3 Hz, 1H), 8.01 (d, J=1.5 Hz, 1H), 7.47 (t, J=8.9 Hz, 1H), 7.05 (dd, J=11.4, 2.9 Hz, 1H), 6.84 (ddd, J=9.0, 2.9, 1.2 Hz, 1H), 4.46 (s, 2H), 3.64 (d, J=7.2 Hz, 2H), 3.09 (s, 3H), 2.62 (hept, J=7.6 Hz, 1H), 2.30 (s, 6H), 1.99-1.89 (m, 2H), 1.86-1.67 (m, 4H); MS (ESI$^+$) m/z 488 (M+H)$^+$.

Example 322: 2-(4-chloro-3-fluorophenoxy)-N-(3-{[5-(4-chlorophenyl)-1,3,4-oxadiazol-2-yl] amino}bicyclo[1.1.1]pentan-1-yl)acetamide (Compound 421)

The reaction and purification conditions described in Example 294 substituting 2-bromo-5-(4-chlorophenyl)-1,3,4-oxadiazole for 2-bromo-5-methyl-1,3,4-oxadiazole gave the title compound. $^1$H NMR (400 MHz, DMSO-$d_6$) δ ppm 8.76 (s, 1H), 8.73 (s, 1H), 7.77 (d, J=8.6 Hz, 2H), 7.57 (d, J=8.6 Hz, 2H), 7.46 (t, J=8.9 Hz, 1H), 7.05 (dd, J=11.4, 2.8 Hz, 1H), 6.83 (ddd, J=8.9, 2.9, 1.2 Hz, 1H), 4.47 (s, 2H), 2.30 (s, 6H); MS (ESI$^+$) m/z 464 (M+H)$^+$.

Example 323: 2-[(2,2-difluoro-2H-1,3-benzodioxol-5-yl)oxy]-N-{3-[(2-methylpyrazolo[1,5-a]pyrazin-4-yl)amino]bicyclo[1.1.1]pentan-1-yl}acetamide (Compound 422)

Example 323A: tert-butyl {3-[(2-methylpyrazolo[1,5-a]pyrazin-4-yl)amino]bicyclo[1.1.1]pentan-1-yl}carbamate A mixture of 4-chloro-2-methylpyrazolo[1,5-a]pyrazine (141 mg, 0.84 mmol), tert-butyl (3-aminobicyclo[1.1.1] pentan-1-yl)carbamate (283 mg, 1.428 mmol) and N-ethyl-N-isopropylpropan-2-amine (244 mg, 1.890 mmol) in dimethyl sulfoxide (0.5 mL) was stirred at 65° C. for 6 days. The resulting solution was filtered through a glass microfiber frit and purified by preparative HPLC [Waters XBridge™ C18 5 μm OBD™ column, 50×100 mm, flow rate 90 mL/minute, 5-100% gradient of acetonitrile in buffer (0.025 M aqueous ammonium bicarbonate, adjusted to pH 10 with ammonium hydroxide)] to give the title compound (0.161 g, 0.489 mmol, 58% yield). $^1$H NMR (501 MHz, DMSO-$d_6$) δ ppm 7.94 (s, 1H), 7.82 (d, J=6 Hz, 1H), 7.55 (br s, 1H), 7.22 (d, J=6 Hz, 1H), 6.68 (s, 1H), 2.35 (s, 3H), 2.28 (s, 6H), 1.40 (s, 9H); MS (ESI$^+$) m/z 330 (M+H)$^+$.

Example 323B: N$^1$-(2-methylpyrazolo[1,5-a] pyrazin-4-yl)bicyclo[1.1.1]pentane-1,3-diamine, Trifluoroacetic Acid A mixture of the product of Example 323A (144 mg, 0.437 mmol) and trifluoroacetic acid (997 mg, 8.74 mmol) in dichloromethane (3 mL) was stirred at ambient temperature for 1 hour. The mixture was concentrated under reduced pressure to give the title compound (0.25 g, 0.438 mmol, 100% yield). $^1$H NMR (501 MHz, DMSO-$d_6$) δ ppm 8.76 (br s, 3H), 8.31 (br s, 1H), 7.89 (d, J=6 Hz, 1H), 7.24 (d, J=6 Hz, 1H), 6.73 (s, 1H), 2.41 (s, 6H), 2.37 (s, 3H); MS (ESI$^+$) m/z 230 (M+H)$^+$.

Example 323C: 2-[(2,2-difluoro-2H-1,3-benzodioxol-5-yl)oxy]-N-{3-[(2-methylpyrazolo[1,5-a] pyrazin-4-yl)amino]bicyclo[1.1.1]pentan-1-yl}acetamide To a mixture of the product of Example 323B (0.036 g, 0.063 mmol), the product of Example 29B (0.015 g, 0.063 mmol) and N-ethyl-N-isopropylpropan-2-amine (0.073 g, 0.568 mmol) in N,N-dimethylformamide (1 mL) was added 1-[bis(dimethylamino)methylene]-1H-1,2,3-triazolo[4,5-b] pyridinium 3-oxid hexafluorophosphate (0.031 g, 0.082 mmol, HATU). The mixture was stirred at ambient temperature for 0.5 hour. The resulting solution was filtered through a glass microfiber frit and purified by preparative HPLC [Waters XBridge™ C18 5 μm OBD™ column, 30×100 mm, flow rate 40 mL/minute, 5-100% gradient of acetonitrile in buffer (0.1% trifluoroacetic acid)] to give the title compound (0.031 g, 0.056 mmol, 88% yield). $^1$H NMR (501 MHz, DMSO-$d_6$) δ ppm 8.80 (s, 1H), 8.70 (br s, 1H), 7.92 (d, J=6 Hz, 1H), 7.34 (d, J=8 Hz, 1H), 7.23 (d, J=6 Hz, 1H), 7.16 (d, J=3 Hz, 1H), 6.86 (br s, 1H), 6.78 (dd, J=8, 3 Hz, 1H), 4.48 (s, 2H), 2.48 (s, 6H), 2.38 (s, 3H); MS (ESI$^+$) m/z 444 (M+H)$^+$.

Example 324: N-{3-[(2-methylpyrazolo[1,5-a] pyrazin-4-yl)amino]bicyclo[1.1.1]pentan-1-yl}-2-[4-(trifluoromethoxy)phenoxy]acetamide (Compound 423)

The reaction and purification conditions described in Example 323 substituting 2-(4-(trifluoromethoxy)phenoxy) acetic acid for 2-((2,2-difluorobenzo[d][1,3]dioxol-5-yl) oxy)acetic acid gave the title compound. $^1$H NMR (501 MHz, DMSO-$d_6$) δ ppm 8.85 (s, 1H), 8.82 (br s, 1H), 7.94 (d, J=6 Hz, 1H), 7.35 (d, J=8 Hz, 2H), 7.25 (d, J=6 Hz, 1H), 7.08 (br d, J=8 Hz, 2H), 6.90 (s, 1H), 4.52 (s, 2H), 2.49 (s, 6H), 2.40 (s, 3H); MS (ESI$^+$) m/z 448 (M+H)$^+$.

Example 325: N-{3-[(2-methylpyrazolo[1,5-a]pyrazin-4-yl)amino]bicyclo[1.1.1]pentan-1-yl}-2-[3-(trifluoromethoxy)phenoxy]acetamide (Compound 424)

The reaction and purification conditions described in Example 323 substituting 2-(3-(trifluoromethoxy)phenoxy)acetic acid for 2-((2,2-difluorobenzo[d][1,3]dioxol-5-yl)oxy)acetic acid gave the title compound. $^1$H NMR (501 MHz, DMSO-$d_6$) δ ppm 8.87 (s, 1H), 8.77 (br s, 1H), 7.94 (d, J=6 Hz, 1H), 7.46 (t, J=8 Hz, 1H), 7.25 (d, J=6 Hz, 1H), 7.03 (m, 3H), 6.88 (s, 1H), 4.55 (s, 2H), 2.49 (s, 6H), 2.40 (s, 3H); MS (ESI$^+$) m/z 448 (M+H)$^+$.

Example 326: N-{3-[2-(4-chloro-3-fluorophenoxy)acetamido]bicyclo[1.1.1]pentan-1-yl}-5-(difluoromethyl)-1,3-thiazole-2-carboxamide (Compound 425)

Example 326A: ethyl 5-(difluoromethyl)thiazole-2-carboxylate

Diethylaminosulfur trifluoride (DAST, 13.7 mL, 104 mmol) in CH$_2$Cl$_2$ (54 mL) was added to a solution of 2-ethylthiazole-5-carbaldehyde (Enamine, 9 g, 52.0 mmol) in CH$_2$Cl$_2$ (91 mL), and the mixture was stirred at 17° C. for 3 hours. The reaction mixture was slowly quenched with saturated, aqueous NaHCO$_3$ (100 mL) and extracted with ethyl acetate (3×200 mL). The combined organic fractions were dried over anhydrous Na$_2$SO$_4$, filtered and concentrated under reduced pressure to give the title compound (19.8 g, 50.7 mmol, 49% yield) which was carried on with purification or characterization.

Example 326B: Potassium 5-(difluoromethyl)thiazole-2-carboxylate

To a solution of the product of Example 326A (0.4 g, 2.05 mmol) in tetrahydrofuran (15 mL) at 0° C. was added potassium trimethylsilanolate (0.28 g, 2.15 mmol) in portions, and the mixture was allowed to stir at 20° C. for 4 hours. The mixture was then concentrated under reduced pressure to give the title compound (0.47 g, 2.03 mmol, 80% yield). MS (ESI$^+$) m/z 180 (M+H)$^+$.

Example 326C: N-{3-[2-(4-chloro-3-fluorophenoxy)acetamido]bicyclo[1.1.1]pentan-1-yl}-5-(difluoromethyl)-1,3-thiazole-2-carboxamide To a mixture of the product of Example 4A (0.13 g, 0.46 mmol) and the product of Example 326B (0.105 g, 0.48 mmol) in N,N-dimethylformamide (3 mL) was added triethylamine (0.48 mL, 3.42 mmol) followed by 2-(3H-[1,2,3]triazolo[4,5-b]pyridin-3-yl)-1,1,3,3-tetramethylisouronium hexafluorophosphate(V) (HATU, 0.19 g, 0.50 mmol). This mixture was allowed to stir at ambient temperature for 16 hours and then was partitioned between saturated aqueous NaHCO$_3$ (20 mL) and ethyl acetate (20 mL). The layers were separated, and the aqueous layer was extracted with ethyl acetate (3×10 mL). The combined organic fractions were dried over anhydrous Na$_2$SO$_4$, filtered, concentrated under reduced pressure. The residue was purified via column chromatography (SiO$_2$, 75% ethyl acetate/heptanes) to give the title compound (0.11 g, 0.26 mmol, 54% yield). $^1$H NMR (400 MHz, DMSO-$d_6$) δ ppm 9.66 (s, 1H), 8.73 (s, 1H), 8.30 (t, J=2.1 Hz, 1H), 7.60-7.24 (m, 2H), 7.05 (dd, J=11.4, 2.8 Hz, 1H), 6.82 (ddd, J=9.0, 2.9, 1.2 Hz, 1H), 4.46 (s, 2H), 2.31 (s, 6H); MS (ESI$^+$) m/z 446 (M+H)$^+$.

Example 327: 2-(4-chloro-3-fluorophenoxy)-N-{3-[(1,3-dimethyl-1H-pyrazolo[4,3-d]pyrimidin-7-yl)amino]bicyclo[1.1.1]pentan-1-yl}acetamide (Compound 426)

The reaction and purification conditions described in Example 264 substituting 7-chloro-1,3-dimethyl-1H-pyrazolo[4,3-d]pyrimidine for 2-chloro-4-phenylpyrimidine gave the title compound. $^1$H NMR (501 MHz, DMSO-$d_6$) δ ppm 8.82 (s, 1H), 8.57 (br s, 1H), 8.53 (s, 1H), 7.47 (t, J=8 Hz, 1H), 7.06 (dd, J=9, 3 Hz, 1H), 6.84 (br d, J=8 Hz, 1H), 4.48 (s, 2H), 4.18 (s, 3H), 2.47 (s, 6H), 2.38 (s, 3H); MS (ESI$^+$) m/z 431 (M+H)$^+$.

Example 328: 2-(4-chloro-3-fluorophenoxy)-N-(3-{[2-(4-chlorophenyl)pyrimidin-4-yl]amino}bicyclo[1.1.1]pentan-1-yl)acetamide (Compound 427)

Example 328A: N-{3-[(2-bromopyrimidin-4-yl)amino]bicyclo[1.1.1]pentan-1-yl}-2-(4-chloro-3-fluorophenoxy)acetamide The reaction and purification conditions described in Example 296A substituting 2,4-dibromopyrimidine for 2,6-dibromopyrazine gave the title compound. MS (ESI$^+$) m/z 442 (M+H)$^+$.

Example 328B: 2-(4-chloro-3-fluorophenoxy)-N-(3-{[2-(4-chlorophenyl)pyrimidin-4-yl]amino}bicyclo[1.1.1]pentan-1-yl)acetamide The reaction and purification conditions described in Example 296B substituting the product of Example 328A for the product of Example 296A gave the title compound. $^1$H NMR (501 MHz, DMSO-$d_6$) δ ppm 8.91 (s, 1H), 8.82 (s, 1H), 8.30-8.17 (m, 3H), 7.63 (d, J=8.6 Hz, 2H), 7.50 (t, J=8.9 Hz, 1H), 7.11-7.05 (m, 1H), 6.86 (ddd, J=9.0, 2.8, 1.2 Hz, 1H), 6.56 (s, 1H), 4.50 (s, 2H), 2.44 (s, 6H); $^{19}$F NMR (376 MHz, DMSO-$d_6$) δ ppm −74.33, −114.08; MS (ESI$^+$) m/z 473 (M+H)$^+$.

Example 329: 2-(4-chloro-3-fluorophenoxy)-N-{3-[(7-chloroimidazo[1,2-c]pyrimidin-5-yl)amino]bicyclo[1.1.1]pentan-1-yl}acetamide (Compound 428)

The reaction and purification conditions described in Example 294 substituting 5,7-dichloroimidazo[1,2-c]pyrimidine for 2-bromo-5-methyl-1,3,4-oxadiazole gave the title compound. $^1$H NMR (400 MHz, DMSO-$d_6$) δ ppm 9.41 (s, 1H), 8.82 (s, 1H), 8.11 (d, J=2.0 Hz, 1H), 7.83 (d, J=2.0 Hz, 1H), 7.47 (t, J=8.9 Hz, 1H), 7.17 (s, 1H), 7.06 (dd, J=11.4, 2.9 Hz, 1H), 6.84 (ddd, J=9.0, 2.9, 1.2 Hz, 1H), 4.49 (s, 2H), 2.44 (s, 6H); $^{19}$F NMR (376 MHz, DMSO-$d_6$) δ ppm −74.32, −114.09; MS (ESI$^+$) m/z 436 (M+H)$^+$.

Example 330: 2-(4-chloro-3-fluorophenoxy)-N-(3-{[4-(1,3-dimethyl-1H-pyrazol-4-yl)pyrimidin-2-yl]amino}bicyclo[1.1.1]pentan-1-yl)acetamide (Compound 429)

Example 330A: 2-chloro-4-(1,3-dimethyl-1H-pyrazol-4-yl)pyrimidine

The reaction and purification conditions described in Example 282A substituting 1,3-dimethyl-4-(4,4,5,5-tetramethyl-1,3,2-dioxaborolan-2-yl)-1H-pyrazole for 1-methyl-4-(4,4,5,5-tetramethyl-1,3,2-dioxaborolan-2-yl)-1H-pyrazole gave the title compound. $^1$H NMR (501 MHz, DMSO-d$_6$) δ ppm 8.64 (d, J=6 Hz, 1H), 8.53 (s, 1H), 7.67 (d, J=6 Hz, 1H), 3.86 (s, 3H), 2.48 (s, 3H); MS (ESI$^+$) m/z 209 (M+H)$^+$.

Example 330B: 2-(4-chloro-3-fluorophenoxy)-N-(3-{[4-(1,3-dimethyl-1H-pyrazol-4-yl)pyrimidin-2-yl]amino}bicyclo[1.1.1]pentan-1-yl)acetamide The reaction and purification conditions described in Example 264 substituting Example 330A for 2-chloro-4-phenylpyrimidine gave the title compound. $^1$H NMR (501 MHz, DMSO-d$_6$) δ ppm 8.78 (s, 1H), 8.34 (s, 1H), 8.23 (br s, 1H), 8.22 (d, J=6 Hz, 1H), 7.51 (t, J=8, 1H), 7.08 (dd, J=9, 3 Hz, 1H), 6.92 (d, J=6 Hz, 1H), 6.88 (br d, J=8 Hz, 1H), 4.51 (s, 2H), 3.82 (s, 3H), 2.48 (s, 3H), 2.37 (s, 6H); MS (ESI$^+$) m/z 457 (M+H)$^+$ Example 331: N-{3-[2-(4-chloro-3-fluorophenoxy)acetamido]bicyclo[1.1.1]pentan-1-yl}-4-[(1E)-3-hydroxy-3-methylbut-1-en-1-yl]pyridine-2-carboxamide (Compound 430)

Example 331A: (E)-methyl 4-(3-hydroxy-3-methylbut-1-en-1-yl)picolinate

The reaction and purification conditions described in Example 39A substituting (E)-2-methyl-4-(4,4,5,5-tetramethyl-1,3,2-dioxaborolan-2-yl)but-3-en-2-ol (Ark Pharm) for 3,6-dihydro-2H-pyran-4-boronic acid pinacol ester, tris(dibenzylideneacetone)dipalladium(0) (Aldrich, 0.1 eq) and 1,3,5,7-tetramethyl-6-phenyl-2,4,8-trioxa-6-phosphaadamantane (Aldrich, 0.2 eq) for [1,1'-bis(diphenylphosphino)ferrocene]dichloropalladium(II), and methyl 4-bromopicolinate (Combi-Blocks) for ethyl 2-bromooxazole-5-carboxylate gave the title compound. MS (ESI$^+$) m/z 222 (M+H)$^+$.

Example 331B: N-{3-[2-(4-chloro-3-fluorophenoxy)acetamido]bicyclo[1.1.1]pentan-1-yl}-4-[(1E)-3-hydroxy-3-methylbut-1-en-1-yl]pyridine-2-carboxamide The reaction and purification conditions described in Example 51B substituting the product of Example 331A for the product of Example 51A gave the title compound. $^1$H NMR (400 MHz, DMSO-d$_6$) δ ppm 9.23 (s, 1H), 8.74 (s, 1H), 8.52 (d, J=5.1 Hz, 1H), 7.97 (d, J=1.7 Hz, 1H), 7.60 (dd, J=5.1, 1.8 Hz, 1H), 7.50 (t, J=8.9 Hz, 1H), 7.08 (dd, J=11.4, 2.9 Hz, 1H), 6.86 (ddd, J=8.9, 2.9, 1.2 Hz, 1H), 6.80 (d, J=16.0 Hz, 1H), 6.60 (d, J=16.0 Hz, 1H), 4.88 (s, 1H), 4.49 (s, 2H), 2.35 (s, 6H), 1.29 (s, 6H); MS (ESI$^+$) m/z 474 (M+H)$^+$.

Example 332: N-{3-[2-(3,4-dichlorophenoxy)acetamido]bicyclo[1.1.1]pentan-1-yl}-3-methyl-1,2-oxazole-5-carboxamide (Compound 431)

The title compound was prepared using the methodologies described above. $^1$H NMR (500 MHz, DMSO-d$_6$) δ ppm 9.47 (s, 1H), 8.76 (s, 1H), 7.56 (d, J=8.9 Hz, 1H), 7.27 (d, J=2.9 Hz, 1H), 7.00 (dd, J=8.9, 2.9 Hz, 1H), 6.89 (s, 1H), 4.51 (s, 2H), 2.33 (s, 6H), 2.29 (s, 3H); MS (ESI$^+$) m/z 410 (M+H)$^+$.

Example 333: N-{3-[2-(4-chloro-3-fluorophenoxy)acetamido]bicyclo[1.1.1]pentan-1-yl}-4-(3-hydroxy-3-methylbutyl)pyridine-2-carboxamide (Compound 432)

Example 333A: methyl 4-(3-hydroxy-3-methylbutyl)picolinate, Formic Acid

A microwave tube (20 mL) was charged with the product of Example 331A (66 mg, 0.30 mmol), palladium on carbon (Aldrich, 10 wt. % wet support, 20 mg, 9.4 iµmol)), ammonium formate (90 mg, 1.43 mmol) and methanol (8.0 mL). The tube was sealed and heated in a Biotage® Initiator+ microwave reactor and irradiated at 110° C. for 30 minutes. The reaction mixture was cooled to ambient temperature, filtered through a microfiber frit, and concentrated in vacuo to give the title compound (85 mg, 0.31 mmol, quantitative). MS (ESI$^+$) m/z 222 (M+H)$^+$.

Example 333B: N-{3-[2-(4-chloro-3-fluorophenoxy)acetamido]bicyclo[1.1.1]pentan-1-yl}-4-(3-hydroxy-3-methylbutyl)pyridine-2-carboxamide The reaction and purification conditions described in Example 51B substituting the product of Example 333A for the product of Example 51A gave the title compound. $^1$H NMR (501 MHz, DMSO-d$_6$) δ ppm 9.18 (s, 1H), 8.71 (s, 1H), 8.46 (dd, J=5.0, 0.8 Hz, 1H), 7.83 (dd, J=1.7, 0.8 Hz, 1H), 7.48 (t, J=8.9 Hz, 1H), 7.42 (dd, J=4.9, 1.7 Hz, 1H), 7.06 (dd, J=11.4, 2.8 Hz, 1H), 6.84 (ddd, J=9.0, 2.9, 1.2 Hz, 1H), 4.48 (s, 2H), 4.31 (s, 1H), 2.75-2.66 (m, 2H), 2.33 (s, 6H), 1.68-1.58 (m, 2H), 1.13 (s, 6H); MS (ESI$^+$) m/z 476 (M+H)$^+$.

Example 334: N-{3-[2-(3,4-dichlorophenoxy)acetamido]bicyclo[1.1.1]pentan-1-yl}-4-(3-hydroxy-3-methylbutyl)pyridine-2-carboxamide (Compound 433)

The reaction and purification conditions described in Example 51B substituting the product of Example 333A for the product of Example 51A, and the product of Example 2B for the product of Example 6C gave the title compound. $^1$H NMR (501 MHz, DMSO-d$_6$) δ ppm 9.20 (s, 1H), 8.73 (s, 1H), 8.48 (dd, J=4.9, 0.8 Hz, 1H), 7.85 (dd, J=1.8, 0.8 Hz, 1H), 7.55 (d, J=8.9 Hz, 1H), 7.44 (dd, J=4.9, 1.8 Hz, 1H), 7.27 (d, J=2.9 Hz, 1H), 7.00 (dd, J=8.9, 2.9 Hz, 1H), 4.51 (s, 2H), 4.32 (s, 1H), 2.76-2.67 (m, 2H), 2.35 (s, 6H), 1.69-1.61 (m, 2H), 1.14 (s, 6H); MS (ESI$^+$) m/z 492 (M+H)$^+$.

Example 335: 2-(4-chloro-3-fluorophenoxy)-N-{3-[(pyrrolo[1,2-a]pyrazin-1-yl)amino]bicyclo[1.1.1]pentan-1-yl}acetamide (Compound 434)

To a solution of the product of Example 4A in dioxane (1 mL) were added 1-chloropyrrolo[1,2-a]pyrazine (64.3 mg, 0.421 mmol), palladium(II) acetate (7.89 mg, 0.035 mmol), xantphos (20.3 mg, 0.035 mmol), and potassium carbonate (146 mg, 1.05 mmol). The reaction mixture was heated at 80° C. for 18 hours. The reaction mixture was concentrated under reduced pressure, and the residue was purified with flash column chromatography (SiO$_2$, heptane:ethyl acetate 0-100%) followed by preparative HPLC [Waters XBridge™ C18 5 µm OBD™ column, 30×100 mm, flow rate 40 mL/minute, 5-100% gradient of acetonitrile in buffer (0.1% trifluoroacetic acid)] to give the title compound (8 mg, 0.020 mmol, 6% yield). $^1$H NMR (400 MHz, DMSO-d$_6$) δ ppm 8.92 (s, 1H), 7.88 (d, J=5.7 Hz, 1H), 7.86-7.82 (m, 1H), 7.52 (d, J=4.3 Hz, 1H), 7.47 (t, J=8.8 Hz, 1H), 7.05 (dd, J=11.3, 2.9 Hz, 1H), 7.00 (d, J=5.7 Hz, 1H), 6.87-6.81 (m, 2H), 4.51 (s, 2H), 2.57 (s, 6H); MS (ESI+) m/z 401 (M+H)+.

Example 336: 2-(4-chloro-3-fluorophenoxy)-N-{3-[(1,3-dimethyl-1H-pyrazolo[3,4-d]pyrimidin-4-yl)amino]bicyclo[1.1.1]pentan-1-yl}acetamide (Compound 435)

The reaction and purification conditions described in Example 264 substituting 4-chloro-1,3-dimethyl-1H-pyrazolo[3,4-d]pyrimidine for 2-chloro-4-phenylpyrimidine gave the title compound. $^1$H NMR (501 MHz, DMSO-d$_6$) δ ppm 8.78 (s, 1H), 8.30 (s, 1H), 7.68 (s, 1H), 7.50 (t, J=8 Hz, 1H), 7.09 (dd, J=9, 3 Hz, 1H), 6.87 (br d, J=8 Hz, 1H), 4.51 (s, 2H), 3.81 (s, 3H), 2.55 (s, 3H), 2.47 (s, 6H); MS (ESI+) m/z 431 (M+H)+.

Example 337: 2-(3,4-difluorophenoxy)-N-{3-[(2-methylpyrazolo[1,5-a]pyrazin-4-yl)amino]bicyclo[1.1.1]pentan-1-yl}acetamide (Compound 436)

The reaction and purification conditions described in Example 323 substituting 2-(3,4-difluorophenoxy)acetic acid for 2-((2,2-difluorobenzo[d][1,3]dioxol-5-yl)oxy)acetic acid gave the title compound. $^1$H NMR (501 MHz, DMSO-d$_6$) δ ppm 8.80 (s, 1H), 8.74 (br s, 1H), 7.93 (d, J=6 Hz, 1H), 7.38 (q, J=8 Hz, 1H), 7.23 (d, J=6 Hz, 1H), 7.11 (m, 1H), 6.88 (br s, 1H), 6.82 (m, 1H), 4.48 (s, 2H), 2.47 (s, 6H), 2.38 (s, 3H); MS (ESI+) m/z 400 (M+H)+.

Example 338: N-{4-[2-(4-chloro-3-fluorophenoxy)acetamido]-3-hydroxybicyclo[2.2.2]octan-1-yl}-3-(difluoromethyl)-1-methyl-1H-pyrazole-5-carboxamide (Compound 437)

The title compound was prepared using the methodologies described in Example 130F substituting 3-(difluoromethyl)-1-methyl-1H-pyrazole-5-carboxylic acid for 5-(difluoromethyl)pyrazine-2-carboxylic. $^1$H NMR (400 MHz, DMSO-d$_6$) δ ppm 7.84 (s, 1H), 7.45 (t, J=8.9 Hz, 1H), 7.25 (s, 1H), 7.11-6.98 (m, 2H), 6.95 (s, 1H), 6.84-6.76 (m, 1H), 5.08 (d, J=4.3 Hz, 1H), 4.44 (s, 2H), 4.08-3.96 (m, 1H), 3.99 (s, 3H), 2.32 (ddd, J=12.3, 9.1, 2.0 Hz, 1H), 2.10-1.75 (m, 9H); MS (ESI+) m/z 501.1 (M+H)+.

Example 339: 2-[4-(difluoromethoxy)phenoxy]-N-{3-[(2-methylpyrazolo[1,5-a]pyrazin-4-yl)amino]bicyclo[1.1.1]pentan-1-yl}acetamide (Compound 438)

The reaction and purification conditions described in Example 323 substituting 2-(4-(difluoromethoxy)phenoxy)acetic acid for 2-((2,2-difluorobenzo[d][1,3]dioxol-5-yl)oxy)acetic acid gave the title compound. $^1$H NMR (501 MHz, DMSO-d$_6$) δ ppm 8.81 (s, 1H), 8.77 (br s, 1H), 7.93 (d, J=6 Hz, 1H), 7.23 (d, J=6 Hz, 1H), 7.15 (d, J=8 Hz, 2H), 7.10 (t, J=74 Hz, 1H), 7.01 (d, J=8 Hz, 2H), 6.88 (s, 1H), 4.46 (s, 2H), 2.47 (s, 6H), 2.38 (s, 3H); MS (ESI+) m/z 430 (M+H)+.

Example 340: 2-[3-(difluoromethoxy)phenoxy]-N-{3-[(2-methylpyrazolo[1,5-a]pyrazin-4-yl)amino]bicyclo[1.1.1]pentan-1-yl}acetamide (Compound 439)

The reaction and purification conditions described in Example 323 substituting 2-(3-(difluoromethoxy)phenoxy) acetic acid for 2-((2,2-difluorobenzo[d][1,3]dioxol-5-yl)oxy)acetic acid gave the title compound. $^1$H NMR (501 MHz, DMSO-d$_6$) δ ppm 8.82 (s, 1H), 8.70 (br s, 1H), 7.93 (d, J=6 Hz, 1H), 7.35 (t, J=8 Hz, 1H), 7.24 (t, J=74 Hz, 1H), 7.23 (d, J=6 Hz, 1H), 6.82 (m, 4H), 4.49 (s, 2H), 2.48 (s, 6H), 2.38 (s, 3H); MS (ESI+) m/z 430 (M+H)+.

Example 341: N-{3-[2-(4-chloro-3-fluorophenoxy)acetamido]bicyclo[1.1.1]pentan-1-yl}-6-(difluoromethoxy)pyridine-3-carboxamide (Compound 440)

The title compound was prepared using the methodologies described above. $^1$H NMR (400 MHz, DMSO-d$_6$) δ ppm 9.21 (s, 1H), 8.77 (s, 1H), 8.68 (d, J=2.4 Hz, 1H), 8.29 (dd, J=8.6, 2.4 Hz, 1H), 7.77 (t, J=72.4 Hz, 1H), 7.50 (t, J=8.9 Hz, 1H), 7.17 (d, J=8.5 Hz, 1H), 7.08 (dd, J=11.3, 2.8 Hz, 1H), 6.87 (ddd, J=9.0, 2.9, 1.2 Hz, 1H), 4.49 (s, 2H), 2.35 (s, 6H); MS (ESI+) m/z 456 (M+H)+.

Example 342: N-{3-[2-(3,4-dichlorophenoxy)acetamido]bicyclo[1.1.1]pentan-1-yl}-1,3-dimethyl-1H-pyrazole-5-carboxamide (Compound 441)

The title compound was prepared using the methodologies described above. $^1$H NMR (400 MHz, DMSO-d$_6$) δ ppm 8.85 (s, 1H), 8.71 (s, 1H), 7.52 (d, J=8.9 Hz, 1H), 7.24 (d, J=2.9 Hz, 1H), 6.96 (dd, J=9.0, 2.9 Hz, 1H), 6.57 (s, 1H), 4.47 (s, 2H), 3.91 (s, 3H), 2.28 (s, 6H), 2.10 (s, 3H); MS (ESI+) m/z 423 (M+H)+.

Example 343: N-(3-{2-[(2,2-difluoro-2H-1,3-benzodioxol-5-yl)oxy]acetamido}bicyclo[1.1.1]pentan-1-yl)-1,3-dimethyl-1H-pyrazole-5-carboxamide (Compound 442)

The title compound was prepared using the methodologies described above. $^1$H NMR (400 MHz, DMSO-d$_6$) δ ppm 8.85 (s, 1H), 8.69 (s, 1H), 7.29 (d, J=8.9 Hz, 1H), 7.11 (d, J=2.5 Hz, 1H), 6.74 (dd, J=8.9, 2.5 Hz, 1H), 6.57 (s, 1H), 4.42 (s, 2H), 3.91 (s, 3H), 2.28 (s, 6H), 2.10 (s, 3H); MS (ESI+) m/z 435 (M+H)+.

Example 344: N-{3-[2-(4-chloro-3-fluorophenoxy)acetamido]bicyclo[1.1.1]pentan-1-yl}-2-(difluoromethyl)-1,3-thiazole-5-carboxamide (Compound 443)

Example 344A: methyl 2-(difluoromethyl)thiazole-5-carboxylate

To a solution of methyl 2-formylthiazole-5-carboxylate (Pharmablock, 0.50 g, 2.92 mmol) in dichloromethane (11.7 mL) at −10° C. was added a solution of bis(2-methoxyethyl)aminosulfur trifluoride (Aldrich, 1.62 mL, 8.76 mmol) in dichloromethane (5 mL) via a syringe pump over 30 minutes. The internal temperature was maintained between −5° C. and 0° C. during the addition. The mixture was then allowed to warm to ambient temperature over a period of 30 minutes and was allowed to stir for an additional 2 hours at ambient temperature. The reaction was quenched by addition of saturated, aqueous sodium bicarbonate solution (15 mL) via a syringe pump over 1 hour. The resulting mixture was combined with dichloromethane (5 mL). The layers were separated, and the organic layer was concentrated under reduced pressure. The residue was purified via column chromatography (SiO$_2$, 10-50% ethyl acetate in heptane) to give the title compound (0.11 g, 0.569 mmol, 20% yield). MS (ESI$^+$) m/z 194 (M+H)$^+$.

Example 344B: N-{3-[2-(4-chloro-3-fluorophenoxy)acetamido]bicyclo[1.1.1]pentan-1-yl}-2-(difluoromethyl)-1,3-thiazole-5-carboxamide The reaction and purification conditions described in Example 52 substituting the product of Example 344A for the product of Example 49A gave the title compound. $^1$H NMR (400 MHz, DMSO-d$_6$) δ ppm 9.48 (s, 1H), 8.77 (s, 1H), 8.50-8.48 (m, 1H), 7.50 (t, J=8.9 Hz, 1H), 7.34 (t, J=54.0 Hz, 1H), 7.08 (dd, J=11.4, 2.8 Hz, 1H), 6.86 (ddd, J=8.9, 2.9, 1.1 Hz, 1H), 4.50 (s, 2H), 2.35 (s, 6H); MS (ESI$^+$) m/z 446 (M+H)$^+$.

Example 345: N-{4-[2-(4-chloro-3-fluorophenoxy)acetamido]bicyclo[2.2.2]octan-1-yl}-3-methyl-1,2-oxazole-5-carboxamide (Compound 444)

Example 345A: methyl 4-[2-(4-chloro-3-fluorophenoxy)acetamido]bicyclo[2.2.2]octane-carboxylate A mixture of methyl 4-aminobicyclo[2.2.2]octane-1-carboxylate hydrochloride (Prime Organics, 0.25 g, 1.14 mmol), 2-(4-chloro-3-fluorophenoxy)acetic acid (0.28 g, 1.36 mmol), (1-cyano-2-ethoxy-2-oxoethylidenaminooxy)dimethylamino-morpholino-carbenium hexafluorophosphate (COMU, 0.63 g, 1.48 mmol), and triethylamine (0.48 mL, 3.44 mmol) in N,N-dimethyl formamide (2.5 mL) was stirred for 18 hours. The mixture was diluted with ethyl acetate (7 mL), washed with water (5 mL) and brine (5 mL), dried over anhydrous Na$_2$SO$_4$ and purified via column chromatography (SiO$_2$, 20-60% ethyl acetate/heptanes) to give the title compound (0.33 g, 0.90 mmol, 79% yield). MS (APCI$^+$) m/z 370 (M+H)$^+$.

Example 345B: 4-[2-(4-chloro-3-fluorophenoxy)acetamido]bicyclo[2.2.2]octane-1-carboxylic acid A mixture of the product of Example 345A, (0.33 g, 0.90 mmol), and 1 M aqueous sodium hydroxide (1.0 mL, 1.00 mmol) in tetrahydrofuran (2 mL) and methanol (1 mL) was stirred for 1 hour, and then additional 1 M aqueous sodium hydroxide (0.5 mL, 0.50 mmol) was added. The mixture was stirred at 40° C. for 2 hours, and then was concentrated under reduced pressure. The residue was diluted with water (5 mL). This mixture was washed with dichloromethane, and then the aqueous layer was acidified with 1 N HCl (1.7 mL). The aqueous fraction was extracted with ethyl acetate (2×5 mL), and the combined organic fractions were washed with brine (5 mL), dried over anhydrous Na$_2$SO$_4$, and concentrated under reduced pressure to give the title compound (0.30 g, 0.85 mmol, 95% yield). MS (APCI$^+$) m/z 356 (M+H)$^+$.

Example 345C: N-(4-aminobicyclo[2.2.2]octan-1-yl)-2-(4-chloro-3-fluorophenoxy)acetamide To a mixture of the product of Example 345B (0.30 g, 0.85 mmol) and triethylamine (0.35 mL, 2.51 mmol) in toluene (3.0 mL) at ambient temperature was added diphenyl phosphorazidate (0.28 mL, 1.3 mmol). The mixture was then slowly heated to 105° C. and was stirred for 1 hour and then cooled to ambient temperature. 2 M Hydrochloric acid (3 mL) was added. The mixture was stirred for 16 hours, then was diluted with ethyl acetate (5 mL) and neutralized with saturated, aqueous 1 N NaOH (4 mL). The layers were separated, and the organic layer was washed with brine (5 mL) and concentrated under reduced pressure to give a white solid which was collected by filtration and washed with methyl t-butyl ether. The material contained ~1:1 title compound:diphenyl hydrogen phosphate, so the solids were acidified with a mixture of 1 N HCl (2 mL) and diluted with water (5 mL). This material was washed with methyl tert-butyl ether (5 mL) and then basified with 1 N NaOH (3 mL). The aqueous layer was extracted with ethyl acetate (2×5 mL), and the combined organic fractions were washed with water (5 mL) and brine (5 mL) and concentrated under reduced pressure to give the title compound (0.12 g, 0.36 mmol, 43% yield). MS (APCI$^+$) m/z 327 (M+H)$^+$.

Example 345D: N-{4-[2-(4-chloro-3-fluorophenoxy)acetamido]bicyclo[2.2.2]octan-1-yl}-3-methyl-1,2-oxazole-5-carboxamide A solution of the product of Example 345C (0.12 g, 0.36 mmol), 3-methylisoxazole-5-carboxylic acid (0.060 g, 0.47 mmol), (1-cyano-2-ethoxy-2-oxoethylidenaminooxy)dimethylamino-morpholino-carbenium (COMU®, 0.202 g, 0.47 mmol), and triethylamine (0.075 mL, 0.54 mmol) in N,N-dimethyl formamide (1.1 mL) was stirred for 20 hours. The reaction mixture was diluted with ethyl acetate (10 mL), and the organic layer was washed with water (5 mL) and brine (5 mL) and then was concentrated under reduced pressure. The residue was adsorbed onto silica and purified via column chromatography (SiO$_2$, 5% CH$_3$OH/CH$_2$Cl$_2$) to give material which was triturated with methyl tert-butyl ether and purified via column chromatography (SiO$_2$, 15% ethyl acetate/CH$_2$Cl$_2$ to 3% CH$_3$OH/CH$_2$Cl$_2$). The still impure material was diluted with ethyl acetate (5 mL), washed with 1 N NaOH (3 mL) and brine (3 mL), dried over anhydrous Na$_2$SO$_4$, and purified via column chromatography (SiO$_2$, 3% CH$_3$OH/CH$_2$Cl$_2$). The resulting material was triturated with methyl tert-butyl ether to give the title compound (0.032 g, 0.072 mmol, 20% yield). $^1$H NMR (501 MHz, DMSO-d$_6$) δ ppm 8.05 (s, 1H), 7.52-7.44 (m, 2H), 7.02 (dd, J=11.4, 2.8 Hz, 1H), 6.87 (s, 1H), 6.81 (ddd, J=9.0, 2.9, 1.2 Hz, 1H), 4.44 (s, 2H), 2.26 (s, 3H), 2.03-1.96 (m, 6H), 1.96-1.88 (m, 6H); MS (ESI$^+$) m/z 436 (M+H)$^+$.

Example 346: 2-(4-chloro-3-fluorophenoxy)-N-{3-[([1,2,4]triazolo[4,3-a]pyrazin-8-yl)amino]bicyclo[1.1.1]pentan-1-yl}acetamide (Compound 445)

The reaction and purification conditions described in Example 294 substituting 8-chloro-[1,2,4]triazolo[4,3-a]pyrazine for 2-bromo-5-methyl-1,3,4-oxadiazole gave the title compound. $^1$H NMR (400 MHz, DMSO-d$_6$) δ ppm 9.18 (s, 1H), 8.74 (s, 1H), 8.72 (s, 1H), 7.78 (d, J=4.7 Hz, 1H), 7.49 (t, J=8.9 Hz, 1H), 7.30 (d, J=4.7 Hz, 1H), 7.07 (dd, J=11.4, 2.8 Hz, 1H), 6.85 (ddd, J=9.0, 2.9, 1.2 Hz, 1H), 4.49 (s, 2H), 2.40 (s, 6H); MS (ESI$^+$) m/z 420 (M+H)$^+$.

Example 347: N-{4-[2-(4-chloro-3-fluorophenoxy)acetamido]-3-hydroxybicyclo[2.2.2]octan-1-yl}-2,4-dimethyl-1,3-thiazole-5-carboxamide (Compound 446)

The title compound was prepared using the methodologies described in Example 130 substituting 2,4-dimethyl-1,3-thiazole-5-carboxylic acid for 5-(difluoromethyl)pyrazine-2-carboxylic. $^1$H NMR (400 MHz, DMSO-d$_6$) δ ppm 7.55 (s, 1H), 7.50-7.40 (m, 2H), 7.23 (s, 1H), 7.02 (dd, J=11.4, 2.9 Hz, 1H), 6.80 (dd, J=8.9, 2.6 Hz, 1H), 4.43 (s, 2H), 4.02 (dd, J=9.6, 3.1 Hz, 1H), 2.53 (s, 3H), 2.38 (s, 3H), 2.30-2.27 (m, 1H), 2.11-1.73 (m, 9H); MS (ESI$^+$) m/z 482.2 (M+H)$^+$.

Example 348: N-{4-[2-(4-chloro-3-fluorophenoxy)acetamido]-3-hydroxybicyclo[2.2.2]octan-1-yl}-1,3-dimethyl-1H-pyrazole-5-carboxamide (Compound 447)

The title compound was prepared using the methodologies described in Example 130 substituting 1,3-dimethyl-1H-pyrazole-5-carboxylic acid for 5-(difluoromethyl)pyrazine-2-carboxylic. $^1$H NMR (400 MHz, DMSO-d$_6$) δ ppm 7.55 (s, 1H), 7.45 (t, J=8.9 Hz, 1H), 7.24 (s, 1H), 7.02 (dd, J=11.4, 2.8 Hz, 1H), 6.80 (ddd, J=9.0, 2.9, 1.2 Hz, 1H), 6.54 (s, 1H), 4.44 (s, 2H), 4.02 (dd, J=9.6, 3.2 Hz, 1H), 3.85 (s, 3H), 3.13 (s, 1H), 2.30 (ddd, J=12.2, 9.4, 2.2 Hz, 1H), 2.11 (s, 3H), 2.07-1.73 (m, 9H); MS (ESI$^+$) m/z 465.2 (M+H)$^+$.

Example 349: 2-(4-chloro-3-fluorophenoxy)-N-{3-[([1,2,4]triazolo[1,5-a]pyrazin-8-yl)amino]bicyclo[1.1.1]pentan-1-yl}acetamide (Compound 448)

The reaction and purification conditions described in Example 264 substituting 8-chloro-[1,2,4]triazolo[1,5-a]pyrazine for 2-chloro-4-phenylpyrimidine gave the title compound. $^1$H NMR (501 MHz, DMSO-d$_6$) δ ppm 8.74 (s, 1H), 8.57 (s, 1H), 8.48 (s, 1H), 8.19 (d, J=6 Hz, 1H), 7.60 (d, J=6 Hz, 1H), 7.50 (t, J=8 Hz, 1H), 7.09 (dd, J=9, 3 Hz, 1H), 6.87 (br d, J=8 Hz, 1H), 4.51 (s, 2H), 2.47 (s, 6H); MS (ESI$^+$) m/z 403 (M+H)$^+$.

Example 350: N-{3-[2-(4-chloro-3-fluorophenoxy)acetamido]bicyclo[1.1.1]pentan-1-yl}-2-(pyrrolidin-1-yl)-1,3-thiazole-5-carboxamide (Compound 449)

The title compound was prepared using the methodologies described above. $^1$H NMR (400 MHz, DMSO-d$_6$) δ ppm 8.68 (s, 1H), 8.65 (s, 1H), 7.75 (s, 1H), 7.46 (t, J=8.9 Hz, 1H), 7.04 (dd, J=11.4, 2.8 Hz, 1H), 6.82 (ddd, J=9.0, 2.8, 1.2 Hz, 1H), 4.45 (s, 2H), 3.38-3.31 (m, 4H), 2.25 (s, 6H), 1.98-1.91 (m, 4H); MS (ESI$^+$) m/z 465 (M+H)$^+$.

Example 351: N-{3-[2-(4-chloro-3-fluorophenoxy)acetamido]bicyclo[1.1.1]pentan-1-yl}-4-methyl-1,3-thiazole-2-carboxamide (Compound 450)

The title compound was prepared using the methodologies described above. $^1$H NMR (400 MHz, DMSO-d$_6$) δ ppm 9.33 (s, 1H), 8.73 (s, 1H), 7.60-7.57 (m, 1H), 7.50 (t, J=8.9 Hz, 1H), 7.08 (dd, J=11.4, 2.8 Hz, 1H), 6.86 (ddd, J=9.0, 2.9, 1.2 Hz, 1H), 4.49 (s, 2H), 2.43 (d, J=0.9 Hz, 3H), 2.32 (s, 6H); MS (ESI$^+$) m/z 410 (M+H)$^+$.

Example 352: N-{4-[2-(4-chloro-3-fluorophenoxy)acetamido]-3-hydroxybicyclo[2.2.2]octan-1-yl}-6-(trifluoromethoxy)pyridine-3-carboxamide (Compound 451)

The title compound was prepared using the methodologies described in Example 130 substituting 6-(trifluoromethoxy)pyridine-3-carboxylic acid for 5-(difluoromethyl)pyrazine-2-carboxylic. $^1$H NMR (400 MHz, DMSO-d$_6$) δ ppm 8.69 (d, J=2.4 Hz, 1H), 8.31 (dd, J=8.5, 2.5 Hz, 1H), 7.99 (s, 1H), 7.49 (t, J=8.9 Hz, 1H), 7.34 (d, J=8.5 Hz, 1H), 7.29 (s, 1H), 7.06 (dd, J=11.4, 2.8 Hz, 1H), 6.84 (dt, J=8.9, 1.9 Hz, 1H), 4.48 (s, 2H), 4.09 (dd, J=9.9, 3.1 Hz, 1H), 2.38 (ddd, J=13.8, 10.1, 3.0 Hz, 1H), 2.17-2.00 (m, 2H), 2.01-1.80 (m, 7H); MS (ESI$^+$) m/z 532.1 (M+H)$^+$.

Example 353: N-{3-[2-(4-chloro-3-fluorophenoxy)acetamido]bicyclo[1.1.1]pentan-1-yl}-3-(hydroxymethyl)-4-methylbenzamide (Compound 452)

The title compound was prepared using the methodologies described above. $^1$H NMR (400 MHz, DMSO-d$_6$) δ ppm 8.93 (s, 1H), 8.73 (s, 1H), 7.86 (d, J=1.9 Hz, 1H), 7.61 (dd, J=7.8, 2.0 Hz, 1H), 7.50 (t, J=8.9 Hz, 1H), 7.19 (d, J=7.9 Hz, 1H), 7.09 (dd, J=11.4, 2.8 Hz, 1H), 6.86 (ddd, J=9.0, 2.9, 1.2 Hz, 1H), 5.14 (t, J=4.8 Hz, 1H), 4.51 (d, J=4.1 Hz, 2H), 4.49 (s, 2H), 2.32 (s, 6H), 2.27 (s, 3H); MS (ESI$^+$) m/z 433 (M+H)$^+$.

Example 354: N-{3-[2-(4-chloro-3-fluorophenoxy)acetamido]bicyclo[1.1.1]pentan-1-yl}-5-(hydroxymethyl)pyridine-3-carboxamide (Compound 453)

The reaction and purification conditions described in Example 52 substituting ethyl 5-(hydroxymethyl)nicotinate (Ark Pharm) for the product of Example 49A gave the title compound. $^1$H NMR (400 MHz, DMSO-d$_6$) δ ppm 9.24 (s, 1H), 8.86 (d, J=2.1 Hz, 1H), 8.76 (s, 1H), 8.63 (d, J=2.0 Hz, 1H), 8.13 (t, J=2.2 Hz, 1H), 7.50 (t, J=8.9 Hz, 1H), 7.09 (dd, J=11.4, 2.8 Hz, 1H), 6.87 (ddd, J=9.0, 2.9, 1.2 Hz, 1H), 5.43 (br s, 1H), 4.58 (br s, 2H), 4.50 (s, 2H), 2.35 (s, 6H); MS (ESI$^+$) m/z 420 (M+H)$^+$.

Example 355: 5-(trifluoromethoxy)-N-[3-(2-{[6-(trifluoromethyl)pyridin-3-yl]oxy}acetamido)bicyclo[1.1.1]pentan-1-yl]pyridine-2-carboxamide (Compound 454)

Example 355A: 2-((6-(trifluoromethyl)pyridin-3-yl)oxy)acetic acid

The reaction and purification conditions described in Example 29B substituting 6-(trifluoromethyl)pyridin-3-ol for the product of Example 29A gave the title compound. MS (DCI) m/z 239 (M+NH$_4$)$^+$.

Example 355B: tert-butyl[3-(2-{[6-(trifluoromethyl)pyridin-3-yl]oxy}acetamido)bicyclo[1.1.1]pentan-1-yl]carbamate The reaction and purification conditions described in Example 13 substituting the product of Example 355A for the product of Example 12B and tert-butyl (3-aminobicyclo[1.1.1]pentan-1-yl)carbamate (Pharmablock) for the product of Example 4A gave the title compound. MS (ESI$^+$) m/z 402 (M+H)$^+$.

Example 355C: 5-(trifluoromethoxy)-N-[3-(2-{[6-(trifluoromethyl)pyridin-3-yl]oxy}acetamido)bicyclo[1.1.1]pentan-1-yl]pyridine-2-carboxamide The reaction and purification conditions described in Example 184B substituting the product of Example 355B for the product of Example 184A, and 5-(trifluoromethoxy)picolinic acid (Ark Pharm) for the product of Example 6C gave the title compound. $^1$H NMR (400 MHz, DMSO-d$_6$) δ ppm 9.36 (s, 1H), 8.83 (s, 1H), 8.71-8.68 (m, 1H), 8.48 (d, J=2.8 Hz, 1H), 8.16-8.11 (m, 1H), 8.10-8.05 (m, 1H), 7.87

(d, J=8.6 Hz, 1H), 7.62-7.54 (m, 1H), 4.68 (s, 2H), 2.36 (s, 6H); MS (ESI$^+$) m/z 491 (M+H)$^+$.

Example 356: 5-(difluoromethyl)-N-[3-(2-{[6-(trifluoromethyl)pyridin-3-yl]oxy}acetamido)bicyclo[1.1.1]pentan-1-yl]pyrazine-2-carboxamide (Compound 455)

The reaction and purification conditions described in Example 184B substituting the product of Example 355B for the product of Example 184A, and 5-(difluoromethyl)pyrazine-2-carboxylic acid (Ark Pharm) for the product of Example 6C gave the title compound. $^1$H NMR (400 MHz, DMSO-d$_6$) δ ppm 9.62 (s, 1H), 9.27-9.23 (m, 1H), 9.01-8.99 (m, 1H), 8.85 (s, 1H), 8.48 (d, J=2.8 Hz, 1H), 7.87 (d, J=8.7 Hz, 1H), 7.60-7.55 (m, 1H), 7.21 (t, J=53.9 Hz, 1H), 4.68 (s, 2H), 2.38 (s, 6H); MS (ESI$^+$) m/z 458 (M+H)$^+$.

Example 357: N-{3-[2-(3,4-dichlorophenoxy)acetamido]bicyclo[1.1.1]pentan-1-yl}pyridine-3-carboxamide (Compound 456)

The title compound was prepared using the methodologies described above. $^1$H NMR (400 MHz, DMSO-d$_6$) δ ppm 9.22 (s, 1H), 8.99-8.96 (m, 1H), 8.76 (s, 1H), 8.70 (dd, J=4.8, 1.7 Hz, 1H), 8.17 (dt, J=8.1, 1.9 Hz, 1H), 7.55 (d, J=8.9 Hz, 1H), 7.49 (ddd, J=8.0, 4.9, 0.9 Hz, 1H), 7.28 (d, J=2.9 Hz, 1H), 7.00 (dd, J=8.9, 2.9 Hz, 1H), 4.51 (s, 2H), 2.35 (s, 6H); MS (ESI$^+$) m/z 406 (M+H)$^+$.

Example 358: N-(3-{2-[(2,2-difluoro-2H-1,3-benzodioxol-5-yl)oxy]acetamido}bicyclo[1.1.1]pentan-1-yl)pyridine-3-carboxamide (Compound 457)

The title compound was prepared using the methodologies described above. $^1$H NMR (400 MHz, DMSO-d$_6$) δ ppm 9.23 (s, 1H), 8.99 (dd, J=2.3, 0.9 Hz, 1H), 8.74 (s, 1H), 8.70 (dd, J=4.8, 1.7 Hz, 1H), 8.17 (ddd, J=8.0, 2.3, 1.7 Hz, 1H), 7.50 (ddd, J=7.9, 4.8, 0.9 Hz, 1H), 7.33 (d, J=8.8 Hz, 1H), 7.16 (d, J=2.5 Hz, 1H), 6.79 (dd, J=8.9, 2.6 Hz, 1H), 4.46 (s, 2H), 2.36 (s, 6H); MS (ESI$^+$) m/z 418 (M+H)$^+$.

Example 359: N-(3-{2-[(2,2-difluoro-2H-1,3-benzodioxol-5-yl)oxy]acetamido}bicyclo[1.1.1]pentan-1-yl)-6-(difluoromethoxy)pyridine-3-carboxamide (Compound 458)

The title compound was prepared using the methodologies described above. $^1$H NMR (500 MHz, DMSO-d$_6$) δ ppm 9.20 (s, 1H), 8.74 (s, 1H), 8.69 (dd, J=2.5, 0.7 Hz, 1H), 8.30 (dd, J=8.6, 2.5 Hz, 1H), 7.77 (t, J=72.4 Hz, 1H), 7.33 (d, J=8.9 Hz, 1H), 7.17 (dd, J=8.7, 0.7 Hz, 1H), 7.15 (d, J=2.5 Hz, 1H), 6.78 (dd, J=8.8, 2.6 Hz, 1H), 4.46 (s, 2H), 2.35 (s, 6H); MS (ESI$^+$) m/z 484 (M+H)$^+$.

Example 360: N-{3-[2-(4-chloro-3-fluorophenoxy)acetamido]bicyclo[1.1.1]pentan-1-yl}-1-(2-hydroxy-2-methylpropyl)-3-methyl-1H-pyrazole-5-carboxamide (Compound 459)

Example 360A: ethyl 1-(2-hydroxy-2-methylpropyl)-3-methyl-1H-pyrazole-5-carboxylate 1-Hydrazinyl-2-methylpropan-2-ol (ChemBridge, 0.48 g, 4.61 mmol) was dissolved in acetonitrile (50 mL) and triethylamine (0.64 mL, 4.61 mmol) was added followed by ethyl 2,4-dioxopentanoate (Aldrich, 0.647 mL, 4.61 mmol). The reaction mixture was stirred at ambient temperature for 18 hours and then concentrated under reduced pressure. The resulting residue was dissolved in N,N-dimethylformamide (10 mL), filtered through a glass microfiber frit and purified by preparative HPLC [YMC TriArt™ C18 Hybrid 20 μm column, 25×250 mm, flow rate 70 mL/minute, 5-100% gradient of acetonitrile in buffer (0.025 M aqueous ammonium bicarbonate, adjusted to pH 10 with ammonium hydroxide)] to give the title compound (0.23 g, 1.02 mmol, 22% yield). MS (ESI$^+$) m/z 227 (M+H)$^+$.

Example 360B: 1-(2-hydroxy-2-methylpropyl)-3-methyl-1H-pyrazole-5-carboxylic acid•4sodium hydroxide The product of Example 360A (29 mg, 0.13 mmol) was dissolved in ethanol (3 mL). Aqueous sodium hydroxide (2.5 M, 0.205 mL) was added, and the resulting mixture was stirred at 55° C. for 1 hour and was allowed to stir at ambient temperature for 18 hours. The mixture was concentrated in vacuo to provide the title compound (48 mg, 0.13 mmol, 100% yield). MS (DCI) m/z 199 (M+H)$^+$.

Example 360C: N-{3-[2-(4-chloro-3-fluorophenoxy)acetamido]bicyclo[1.1.1]pentan-1-yl}-1-(2-hydroxy-2-methylpropyl)-3-methyl-1H-pyrazole-5-carboxamide The reaction and purification conditions described in Example 13 substituting the product of Example 360B for the product of Example 12B gave the title compound. $^1$H NMR (400 MHz, DMSO-d$_6$) δ ppm 8.71 (s, 1H), 8.45 (s, 1H), 7.50 (t, J=8.9 Hz, 1H), 7.08 (dd, J=11.4, 2.8 Hz, 1H), 6.86 (ddd, J=8.9, 2.8, 1.2 Hz, 1H), 6.38-6.37 (m, 1H), 4.66 (s, 1H), 4.48 (s, 2H), 3.95 (s, 2H), 2.30 (s, 6H), 2.29-2.29 (m, 3H), 1.10 (s, 6H); MS (ESI$^+$) m/z 465 (M+H)$^+$.

Example 361: N-{3-[2-(3,4-dichlorophenoxy)acetamido]bicyclo[1.1.1]pentan-1-yl}-1-(2-hydroxy-2-methylpropyl)-3-methyl-1H-pyrazole-5-carboxamide (Compound 460)

The reaction and purification conditions described in Example 13 substituting the product of Example 360B for the product of Example 12B and the product of Example 2B for the product of Example 4A gave the title compound. $^1$H NMR (400 MHz, DMSO-d$_6$) δ ppm 8.71 (s, 1H), 8.46 (s, 1H), 7.55 (d, J=8.9 Hz, 1H), 7.27 (d, J=2.9 Hz, 1H), 6.99 (dd, J=8.9, 2.9 Hz, 1H), 6.38 (d, J=0.9 Hz, 1H), 4.67 (s, 1H), 4.49 (s, 2H), 3.95 (s, 2H), 2.30 (s, 6H), 2.30-2.29 (m, 3H), 1.10 (s, 6H); MS (ESI$^+$) m/z 481 (M+H)$^+$.

Example 362: N-{4-[2-(3,4-difluorophenoxy)acetamido]-3-oxobicyclo[2.2.2]octan-1-yl}-3-methyl-1,2-oxazole-5-carboxamide (Compound 461)

Example 362A: 1-amino-4-(benzylamino)bicyclo[2.2.2]octan-2-one, hydrochloric acid To a suspension of the product of Example 130A (10.01 g, 32.3 mmol) in toluene (100 mL) was added a 50% ethyl acetate solution of 2,4,6-tripropyl-1,3,5,2,4,6-trioxatriphosphinane 2,4,6-trioxide (22 mL, 37.0 mmol), trimethylsilyl azide (5.0 mL, 37.7 mmol), and triethylamine (11.5 mL, 83 mmol). The mixture was stirred for 30 minutes at ambient temperature, then was heated for 2 hours at 85° C. and 3 N aqueous hydrogen chloride (86 mL, 258 mmol) was added.

The mixture was stirred at 85° C. for an additional 90 minutes and was concentrated under reduced pressure. The resulting material was stirred with acetonitrile (150 mL) to precipitate a white solid, which was collected by filtration, washed with acetonitrile (30 mL) and $CH_2Cl_2$ (25 mL), and vacuum-dried to provide the title compound as an HCl salt (6.24 g, 19.7 mmol, 61% yield). MS (APCI$^+$) m/z 245.0 (M+H)$^+$.

Example 362B: N-[4-(benzylamino)-2-oxobicyclo[2.2.2]octan-1-yl]-2-(3,4-difluorophenoxy)acetamide A mixture of the product of Example 362A (0.250 g, 0.788 mmol), 2-(3,4-difluorophenoxy)acetic acid (0.156 g, 0.827 mmol), N-[(dimethylamino)-1H-1,2,3-triazolo-[4,5-b]pyridin-1-ylmethylene]-N-methylmethanaminium hexafluorophosphate N-oxide (HATU, 0.449 g, 1.182 mmol), and triethylamine (0.549 mL, 3.94 mmol) in dimethyl formamide (4 mL) was stirred for 1 hour. Water was added to the reaction mixture. The resulting suspension was stirred for 30 minutes, rinsed with water and ether, and purified on a 12 g silica gel column using a Biotage® Isolera™ One flash system eluting with heptanes/ethyl acetate (4:6 to 2:8) to provide the title compound (0.18 g, 0.435 mmol, 55% yield). MS (ESI$^+$) m/z 415.2 (M+H)$^+$.

Example 362C: N-(4-amino-2-oxobicyclo[2.2.2]octan-1-yl)-2-(3,4-difluorophenoxy)acetamide, trifluoroacetic acid To a mixture of the product of Example 362B (0.175 g, 0.422 mmol) in tetrahydrofuran (4 mL) was added 20% Pd(OH)$_2$/C (0.105 mg, 0.381 μmol, 51% in water) in a 20 mL Barnstead Hastelloy® C reactor. The mixture was stirred for 17.7 hours at 25° C. with 50 psi of hydrogen. The reaction mixture was filtered. The filtrate was concentrated, and the residue was purified by HPLC performed on a Phenomenex® Luna® C18 (2) AXIA™ column (250×50 mm, 10 μm particle size) using a gradient of 5% to 100% acetonitrile:0.1% aqueous trifluoroacetic acid over 15 minutes at a flow rate of 50 mL/minute to provide the title compound (98.5 mg, 0.23 mmol, 55% yield). MS (ESI$^+$) m/z 325.1 (M+H)$^+$.

Example 362D: N-{4-[2-(3,4-difluorophenoxy)acetamido]-3-oxobicyclo[2.2.2]octan-1-yl}-3-methyl-1,2-oxazole-5-carboxamide A mixture of the product of Example 362C (95.0 mg, 0.217 mmol), 3-methylisoxazole-5-carboxylic acid (33.1 mg, 0.260 mmol), N-[(dimethylamino)-1H-1,2,3-triazolo-[4,5-b]pyridin-1-ylmethylene]-N-methylmethanaminium hexafluorophosphate N-oxide (HATU, 124 mg, 0.325 mmol), and triethylamine (0.106 mL, 0.759 mmol) in tetrahydrofuran (4 mL) was stirred for 3 hours. The reaction mixture was quenched with brine and extracted with ethyl acetate (2×). The combined organic layers were dried over anhydrous MgSO$_4$, filtered, and concentrated under reduced pressure. The residue was purified by reverse-phase HPLC (see protocol in Example 273E) to provide the title compound (60.3 mg, 0.14 mmol, 64% yield). $^1$H NMR (400 MHz, DMSO-d$_6$) δ ppm 8.51 (s, 1H), 7.71 (s, 1H), 7.37 (dt, J=10.6, 9.3 Hz, 1H), 7.10 (ddd, J=12.6, 6.7, 3.1 Hz, 1H), 6.93 (s, 1H), 6.81 (dtd, J=8.6, 3.3, 1.7 Hz, 1H), 4.54 (s, 2H), 2.95 (s, 2H), 2.49-2.37 (m, 2H), 2.28 (s, 3H), 2.14 (t, J=8.3 Hz, 4H), 1.87 (dt, J=12.9, 8.2 Hz, 2H); MS (ESI$^+$) m/z 434.2 (M+H)$^+$.

Example 363: N-{4-[2-(3,4-difluorophenoxy)acetamido]-3-hydroxybicyclo[2.2.2]octan-1-yl}-3-methyl-1,2-oxazole-5-carboxamide (Compound 462)

A mixture of the product of Example 362D (55.1 mg, 0.127 mmol) and sodium borohydride (7.21 mg, 0.191 mmol) in $CH_2Cl_2$ (1.5 mL) and methanol (1.5 mL) was stirred for 2 hours. The reaction mixture was concentrated and purified by reverse-phase HPLC (see protocol in Example 273E) to provide the title compound (38.2 mg, 0.088 mmol, 69% yield). $^1$H NMR (400 MHz, DMSO-d$_6$) δ ppm 8.08 (s, 1H), 7.36 (dt, J=10.5, 9.3 Hz, 1H), 7.25 (s, 1H), 7.08 (ddd, J=12.7, 6.7, 3.1 Hz, 1H), 6.88 (s, 1H), 6.78 (dtd, J=9.1, 3.2, 1.7 Hz, 1H), 5.13 (d, J=4.4 Hz, 1H), 4.44 (s, 2H), 4.11-4.00 (m, 1H), 2.35 (ddd, J=11.8, 9.5, 1.9 Hz, 1H), 2.27 (s, 3H), 2.16-1.79 (m, 9H); MS (ESI$^+$) m/z 436.1 (M+H)$^+$.

Example 364: 2-(4-chloro-3-fluorophenoxy)-N-{3-[(2-methylimidazo[1,2-a]pyrazin-8-yl)amino]bicyclo[1.1.1]pentan-1-yl}acetamide (Compound 463)

The reaction and purification conditions described in Example 264 substituting 8-chloro-2-methylimidazo[1,2-a]pyrazine for 2-chloro-4-phenylpyrimidine gave the title compound. $^1$H NMR (501 MHz, DMSO-d$_6$) δ ppm 8.82 (s, 1H), 7.88 (d, J=6 Hz, 1H), 7.79 (s, 1H), 7.51 (t, J=8 Hz, 1H), 7.32 (d, J=6 Hz, 1H), 7.08 (dd, J=9, 3 Hz, 1H), 6.87 (br d, J=8 Hz, 1H), 4.52 (s, 2H), 2.46 (s, 6H), 2.38 (s, 3H); MS (ESI$^+$) m/z 416 (M+H)$^+$.

Example 365: 2-(4-chloro-3-fluorophenoxy)-N-{(3R)-3-hydroxy-4-[([1,2,4]triazolo[4,3-a]pyrazin-8-yl)amino]bicyclo[2.2.2]octan-1-yl}acetamide (Compound 464)

Example 365A: N-[(3R)-4-amino-3-hydroxybicyclo[2.2.2]octan-1-yl]-2-(4-chloro-3-fluorophenoxy)acetamide, trifluoroacetic acid The title compound was isolated by chiral preparative SFC of Example 68I as the first peak eluted off the column using the methodologies described in Example 308A. $^1$H NMR (400 MHz, methanol-d$_4$) δ ppm 7.36 (t, J=8.77 Hz, 1H), 6.89 (dd, J=10.74, 2.85 Hz, 1H), 6.83-6.74 (m, 1H), 4.43 (s, 2H), 3.94 (br d, J=8.33 Hz, 1H), 2.55 (br t, J=12.50 Hz, 1H), 2.32-1.86 (m, 8H), 1.82-1.58 (m, 2H); MS (ESI$^+$) m/z 343.0 (M+H)$^+$ Example 365B: 2-(4-chloro-3-fluorophenoxy)-N-{(3R)-3-hydroxy-4-[([1,2,4]triazolo[4,3-a]pyrazin-8-yl)amino]bicyclo[2.2.2]octan-1-yl}acetamide To a solution of the product of Example 365A (70 mg, 0.153 mmol) in N,N-dimethylformamide (1 mL) was added 8-chloro-[1,2,4]triazolo[4,3-a]pyrazine (35.5 mg, 0.230 mmol) and N,N-diisopropylethylamine (0.080 mL, 0.460 mmol). The reaction mixture was stirred for 4 days at 70° C. and then was purified by preparative HPLC [Waters XBridge™ C18 5 μm OBD™ column, 30×100 mm, flow rate 40 mL/minute, 5-100% gradient of acetonitrile in buffer (0.1% trifluoroacetic acid)] to give the title compound (15 mg, 0.026 mmol, 17% yield). $^1$H NMR (400 MHz, DMSO-d$_6$) δ ppm 9.17 (s, 1H), 7.75 (d, J=4.8 Hz, 1H), 7.54 (s, 1H), 7.45 (t, J=8.9 Hz, 1H), 7.23 (d, J=4.9 Hz, 1H), 7.00 (dd, J=11.4, 2.9 Hz, 2H), 6.79 (ddd, J=9.0, 2.9, 1.2 Hz, 1H), 4.42 (s, 2H), 4.17-4.14 (m, 2H), 2.64-2.50 (m, 1H), 2.35 (ddd, J=12.8, 9.4, 2.9 Hz, 1H), 2.27-2.13 (m, 1H), 2.04-1.77 (m, 8H); $^{19}$F NMR (376 MHz, DMSO-d$_6$) δ ppm −75.00, −114.17; MS (ESI$^+$) m/z 461 (M+H)$^+$.

Example 366: 2-(4-chloro-3-fluorophenoxy)-N-{3-[(3-methyl[1,2,4]triazolo[4,3-a]pyrazin-8-yl)amino]bicyclo[1.1.1]pentan-1-yl}acetamide (Compound 465)

The reaction and purification conditions described in Example 264 substituting 8-chloro-3-methyl-[1,2,4]triazolo[4,3-a]pyrazine for 2-chloro-4-phenylpyrimidine gave the title compound. $^1$H NMR (501 MHz, DMSO-d$_6$) δ ppm 8.74 (s, 1H), 8.63 (s, 1H), 7.65 (d, J=6 Hz, 1H), 7.50 (t, J=8 Hz, 1H), 7.32 (d, J=6 Hz, 1H), 7.09 (dd, J=9, 3 Hz, 1H), 6.87 (br d, J=8 Hz, 1H), 4.51 (s, 2H), 2.63 (s, 3H), 2.41 (s, 6H); MS (ESI$^+$) m/z 417 (M+H)$^+$.

Example 367: N-{4-[2-(4-chloro-3-fluorophenoxy)acetamido]-3-hydroxybicyclo[2.2.2]octan-1-yl}-2-(trifluoromethyl)-1,3-thiazole-4-carboxamide (Compound 466)

The title compound was prepared using the methodologies described in Example 130 substituting 2-(trifluoromethyl)-1,3-thiazole-4-carboxylic acid for 5-(difluoromethyl)pyrazine-2-carboxylic. $^1$H NMR (400 MHz, DMSO-d$_6$) δ ppm 8.62 (s, 1H), 7.58 (s, 1H), 7.49 (t, J=8.9 Hz, 1H), 7.29 (s, 1H), 7.06 (dd, J=11.4, 2.9 Hz, 1H), 6.84 (ddd, J=9.0, 2.9, 1.2 Hz, 1H), 5.08 (s, 1H), 4.48 (s, 2H), 4.13-4.05 (m, 1H), 2.40 (ddd, J=12.4, 9.5, 2.3 Hz, 1H), 2.18-2.03 (m, 2H), 2.05-1.78 (m, 7H); MS (ESI$^+$) m/z 521.9 (M+H)$^+$.

Example 368: N-{4-[2-(4-chloro-3-fluorophenoxy)acetamido]-3-hydroxybicyclo[2.2.2]octan-1-yl}-2-methyl-1,3-oxazole-4-carboxamide (Compound 467)

The title compound was prepared using the methodologies described in Example 130 substituting 2-methyl-1,3-oxazole-4-carboxylic acid for 5-(difluoromethyl)pyrazine-2-carboxylic. $^1$H NMR (400 MHz, DMSO-d$_6$) δ ppm 8.40 (s, 1H), 7.54 (t, J=8.9 Hz, 1H), 7.40 (s, 1H), 7.26 (s, 1H), 7.10 (dd, J=11.4, 2.8 Hz, 1H), 6.95-6.87 (m, 1H), 6.01 (s, 1H), 4.53 (s, 2H), 4.18 (m, 1H), 2.49 (s, 3H), 2.43 (d, J=2.3 Hz, 1H), 2.18-2.02 (m, 2H), 2.05-1.97 (m, 1H), 1.93 (ddd, J=19.6, 8.9, 2.5 Hz, 5H); MS (ESI$^+$) m/z 452.0 (M+H)$^+$.

Example 369: N-{4-[2-(4-chloro-3-fluorophenoxy)acetamido]-3-hydroxybicyclo[2.2.2]octan-1-yl}-1,5-dimethyl-1H-pyrazole-3-carboxamide (Compound 468)

The title compound was prepared using the methodologies described in Example 130 substituting 1,5-dimethyl-1H-pyrazole-3-carboxylic acid for 5-(difluoromethyl)pyrazine-2-carboxylic. $^1$H NMR (400 MHz, DMSO-d$_6$) δ ppm 7.49 (t, J=8.9 Hz, 1H), 7.26 (s, 1H), 7.06 (dd, J=11.4, 2.8 Hz, 1H), 6.91 (s, 1H), 6.83 (ddd, J=9.0, 2.9, 1.2 Hz, 1H), 6.35 (s, 1H), 4.47 (s, 2H), 4.06 (dd, J=9.7, 3.1 Hz, 1H), 3.74 (s, 3H), 2.36 (ddd, J=12.3, 9.4, 2.1 Hz, 1H), 2.24 (s, 3H), 2.15-2.02 (m, 1H), 2.05-1.80 (m, 8H); MS (ESI$^+$) m/z 465.1 (M+H)$^+$.

Example 370: N-{3-[2-(4-chloro-3-fluorophenoxy)acetamido]bicyclo[1.1.1]pentan-1-yl}-5-methyl-1,3-thiazole-2-carboxamide (Compound 469)

The title compound was prepared using the methodologies described above. $^1$H NMR (501 MHz, DMSO-d$_6$) δ ppm 9.28 (s, 1H), 8.71 (s, 1H), 7.67 (d, J=1.2 Hz, 1H), 7.48 (t, J=8.9 Hz, 1H), 7.06 (dd, J=11.4, 2.8 Hz, 1H), 6.84 (ddd, J=9.0, 2.9, 1.2 Hz, 1H), 4.47 (s, 2H), 2.48 (s, 3H), 2.30 (s, 6H); MS (ESI$^+$) m/z 410 (M+H)$^+$.

Example 371: N-{3-[2-(4-chloro-3-fluorophenoxy)acetamido]bicyclo[1.1.1]pentan-1-yl}-4,5-dimethyl-1,3-thiazole-2-carboxamide (Compound 470)

The title compound was prepared using the methodologies described above. $^1$H NMR (501 MHz, DMSO-d$_6$) δ ppm 9.19 (s, 1H), 8.72 (s, 1H), 7.50 (t, J=8.9 Hz, 1H), 7.08 (dd, J=11.4, 2.8 Hz, 1H), 6.86 (ddd, J=9.0, 2.9, 1.2 Hz, 1H), 4.48 (s, 2H), 2.39 (d, J=0.8 Hz, 3H), 2.31 (d, J=0.9 Hz, 3H), 2.31 (s, 6H); MS (ESI$^+$) m/z 424 (M+H)$^+$.

Example 372: N-{4-[2-(4-chloro-3-fluorophenoxy)acetamido]-3-hydroxybicyclo[2.2.2]octan-1-yl}-2-methyl-1,3-thiazole-5-carboxamide (Compound 471)

The title compound was prepared using the methodologies described in Example 130 substituting 2-methyl-1,3-thiazole-5-carboxylic acid for 5-(difluoromethyl)pyrazine-2-carboxylic. $^1$H NMR (400 MHz, DMSO-d$_6$) δ ppm 8.20 (s, 1H), 7.80 (s, 1H), 7.49 (t, J=8.9 Hz, 1H), 7.27 (s, 1H), 7.06 (dd, J=11.4, 2.9 Hz, 1H), 6.83 (ddd, J=9.0, 2.9, 1.2 Hz, 1H), 4.48 (s, 2H), 4.10-4.02 (m, 1H), 2.63 (s, 3H), 2.34 (ddd, J=12.6, 9.4, 2.2 Hz, 1H), 2.16-2.01 (m, 1H), 2.04-1.78 (m, 8H); MS (ESI$^+$) m/z 468.0 (M+H)$^+$.

Example 373: N-{4-[2-(4-chloro-3-fluorophenoxy)acetamido]-3-hydroxybicyclo[2.2.2]octan-1-yl}-2,5-dimethyl-1,3-oxazole-4-carboxamide (Compound 472)

The title compound was prepared using the methodologies described in Example 130 substituting 2,5-dimethyl-1,3-oxazole-4-carboxylic acid for 5-(difluoromethyl)pyrazine-2-carboxylic. $^1$H NMR (501 MHz, DMSO-d$_6$) δ ppm 7.49 (t, J=8.9 Hz, 1H), 7.27 (s, 1H), 7.06 (dd, J=11.4, 2.9 Hz, 1H), 6.94 (s, 1H), 6.83 (ddd, J=9.0, 2.9, 1.2 Hz, 1H), 4.47 (s, 2H), 4.07 (ddd, J=9.6, 3.2, 1.2 Hz, 1H), 2.48 (s, 3H), 2.36 (s, 3H), 2.40-2.31 (m, 1H), 2.13-1.96 (m, 2H), 1.99-1.90 (m, 1H), 1.86 (dtdd, J=17.6, 14.6, 8.5, 6.2 Hz, 6H); MS (ESI$^+$) m/z 466.0 (M+H)$^+$.

Example 374: N-{4-[2-(4-chloro-3-fluorophenoxy)acetamido]-3-hydroxybicyclo[2.2.2]octan-1-yl}-2-methyl-1,3-thiazole-4-carboxamide (Compound 473)

The title compound was prepared using the methodologies described in Example 130 substituting 2-methyl-1,3-thiazole-4-carboxylic acid for 5-(difluoromethyl)pyrazine-2-carboxylic. $^1$H NMR (400 MHz, DMSO-d$_6$) δ ppm 8.02 (s, 1H), 7.49 (t, J=8.9 Hz, 1H), 7.29 (d, J=10.5 Hz, 2H), 7.06 (dd, J=11.4, 2.8 Hz, 1H), 6.84 (dd, J=9.0, 2.9, 1.2 Hz, 1H), 4.48 (s, 2H), 4.13-4.04 (m, 1H), 2.68 (s, 3H), 2.39 (ddd, J=12.7, 9.6, 2.2 Hz, 1H), 2.16-2.06 (m, 1H), 2.08-1.99 (m, 1H), 2.01-1.86 (m, 4H), 1.90-1.79 (m, 3H); MS (ESI$^+$) m/z 467.9 (M+H)$^+$.

Example 375: N-{4-[2-(4-chloro-3-fluorophenoxy)acetamido]-3-hydroxybicyclo[2.2.2]octan-1-yl}-4,5-dimethylfuran-2-carboxamide (Compound 474)

The title compound was prepared using the methodologies described in Example 130 substituting 4,5-dimethylfuran-2-carboxylic acid for 5-(difluoromethyl)pyrazine-2-carboxylic. $^1$H NMR (501 MHz, DMSO-d$_6$) δ ppm 7.49 (t, J=8.9 Hz, 1H), 7.26 (s, 1H), 7.17 (s, 1H), 7.06 (dd, J=11.4, 2.9 Hz, 1H), 6.87-6.80 (m, 2H), 5.05 (s, 1H), 4.47 (s, 2H), 4.08-4.02 (m, 1H), 2.34 (ddd, J=12.6, 9.3, 2.3 Hz, 1H), 2.21 (s, 3H), 2.14-2.05 (m, 1H), 2.05-1.98 (m, 1H), 2.01-1.76 (m, 11H); MS (ESI$^+$) m/z 465.0 (M+H)$^+$.

Example 376: 5-(difluoromethyl)-N-(3-{2-[4-(difluoromethyl)-3-fluorophenoxy]acetamido}bicyclo[1.1.1]pentan-1-yl)pyrazine-2-carboxamide (Compound 475)

Example 376A: tert-butyl 2-(4-(difluoromethyl)-3-fluorophenoxy)acetate

To a solution of 2-fluoro-4-hydroxybenzaldehyde (Combi-Blocks, 0.96 g, 6.85 mmol) in dichloromethane (27.4 mL) at −10° C. in a recovery flask (200 mL) was added bis(2-methoxyethyl)aminosulfur trifluoride (Aldrich, 3.79 mL, 20.56 mmol) in dichloromethane (5 mL) via a syringe pump over 30 minutes. The internal temperature was maintained between −5° C. and 0° C. over the course of the addition. The mixture was allowed to warm up to ambient temperature over a period of 1 hour and was allowed to stir at ambient temperature for 18 hours. The reaction was quenched by slow addition of saturated, aqueous sodium bicarbonate (25 mL) via a syringe pump over 1 hour. The resulting mixture was left stirring at ambient temperature. After 18 hours of stirring, the layers were separated, and the organic layer was dried over sodium sulfate, concentrated in vacuo and directly purified via column chromatography (SiO$_2$, 10-50% ethyl acetate in heptane) to give the crude phenol intermediate. Fractions containing the crude phenol intermediate were concentrated, and the residue was combined with N,N-dimethylformamide (10 mL), heptane (10 mL) and ethyl acetate (20 mL) and stirred at ambient temperature. Potassium carbonate (0.947 g, 6.85 mmol) and tert-butyl bromoacetate (0.506 mL, 3.43 mmol) were added sequentially, and the resulting mixture was stirred at ambient temperature for 18 hours. The reaction mixture was then concentrated in vacuo, and the residue was partitioned between dichloromethane (2×50 mL) and water (100 mL). The combined organic layers were dried over anhydrous sodium sulfate and concentrated in vacuo. The residue was purified by preparative HPLC [YMC TriArt™ C18 Hybrid 20 μm column, 25×250 mm, flow rate 70 mL/minute, 5-100% gradient of acetonitrile in buffer (0.025 M aqueous ammonium bicarbonate, adjusted to pH 10 with ammonium hydroxide)] to give the title compound (12 mg, 0.043 mmol, 0.6% yield). MS (DCI) m/z 294 (M+H)$^+$.

Example 376B: tert-butyl (3-{[5-(difluoromethyl)pyrazine-2-carbonyl]amino}bicyclo[1.1.1]pentan-1-yl)carbamate The reaction and purification conditions described in Example 13 substituting 5-(difluoromethyl)pyrazine-2-carboxylic acid (Manchester) for the product of Example 12B and tert-butyl (3-aminobicyclo[1.1.1]pentan-1-yl)carbamate (Pharmablock) for the product of Example 4A gave the title compound. MS (ESI$^+$) m/z 299 (M+H)$^+$.

Example 376C: 5-(difluoromethyl)-N-(3-{2-[4-(difluoromethyl)-3-fluorophenoxy]acetamido}bicyclo[1.1.1]pentan-1-yl)pyrazine-2-carboxamide 1-yl)pyridine-2-carboxamide Trifluoroacetic acid (1 mL, 13.0 mmol) was added to a mixture of the product of Example 376A (11 mg, 0.04 mmol) and the product of Example 376B (17 mg, 0.048 mmol), and the mixture was stirred at ambient temperature for 30 minutes. The resulting reaction mixture was concentrated under reduced pressure. To the resulting residue was added N, N-dimethylformamide (2 mL), triethylamine (0.055 mL, 0.40 mmol), and 1-[bis(dimethylamino)methylene]-1H-1,2,3-triazolo[4,5-b]pyridinium 3-oxid hexafluorophosphate (16.4 mg, 0.043 mmol, HATU) in sequential order. The reaction mixture was then stirred at ambient temperature for 30 minutes, filtered through a glass microfiber frit, and purified by preparative HPLC [YMC TriArt™ C18 Hybrid 20 μm column, 25×150 mm, flow rate 80 mL/minute, 5-100% gradient of acetonitrile in buffer (0.025 M aqueous ammonium bicarbonate, adjusted to pH 10 with ammonium hydroxide)] to give the title compound (3.5 mg, 0.008 mmol, 19% yield). $^1$H NMR (400 MHz, CDCl$_3$) δ ppm 9.41-9.39 (m, 1H), 8.84 (d, J=1.4 Hz, 1H), 8.20 (s, 1H), 7.56 (t, J=8.3 Hz, 1H), 6.99-6.60 (m, 5H), 4.47 (s, 2H), 1.75-1.58 (m, 6H); MS (ESI$^+$) m/z 457 (M+H)$^+$.

Example 377: N-{3-[2-(4-chloro-3-fluorophenoxy)acetamido]bicyclo[1.1.1]pentan-1-yl}-2-(1-hydroxyethyl)-1,3-thiazole-5-carboxamide (Compound 476)

The title compound was prepared using the methodologies described above. $^1$H NMR (400 MHz, DMSO-d$_6$) δ ppm 9.13 (s, 1H), 8.75 (s, 1H), 8.22 (s, 1H), 7.50 (t, J=8.9 Hz, 1H), 7.08 (dd, J=11.4, 2.8 Hz, 1H), 6.86 (ddd, J=8.9, 2.8, 1.2 Hz, 1H), 6.24 (br s, 1H), 4.93-4.85 (m, 1H), 4.49 (s, 2H), 2.32 (s, 6H), 1.43 (d, J=6.5 Hz, 3H); MS (ESI$^+$) m/z 440 (M+H)$^+$.

Example 378: N-{4-[2-(4-chloro-3-fluorophenoxy)acetamido]bicyclo[2.1.1]hexan-1-yl}pyridine-3-carboxamide (Compound 477)

The title compound was prepared using the methodologies described above. $^1$H NMR (501 MHz, DMSO-d$_6$) δ ppm 8.99 (dd, J=2.3, 0.9 Hz, 1H), 8.97 (s, 1H), 8.69 (dd, J=4.8, 1.7 Hz, 1H), 8.52 (s, 1H), 8.17 (ddd, J=8.0, 2.3, 1.7 Hz, 1H), 7.53-7.46 (m, 2H), 7.08 (dd, J=11.4, 2.8 Hz, 1H), 6.86 (ddd, J=9.0, 2.9, 1.2 Hz, 1H), 4.49 (s, 2H), 2.19-2.10 (m, 2H), 1.94-1.82 (m, 6H); MS (ESI$^+$) m/z 404 (M+H)$^+$.

Example 379: N-{3-[2-(4-chloro-3-fluorophenoxy)acetamido]bicyclo[1.1.1]pentan-1-yl}-5-methyl-1,3-oxazole-2-carboxamide (Compound 478)

The title compound was prepared using the methodologies described above. $^1$H NMR (400 MHz, DMSO-d$_6$) δ ppm 9.36 (s, 1H), 8.73 (s, 1H), 7.50 (t, J=8.9 Hz, 1H), 7.14-7.01 (m, 2H), 6.86 (ddd, J=9.0, 2.9, 1.2 Hz, 1H), 4.49 (s, 2H), 2.36 (d, J=1.2 Hz, 3H), 2.31 (s, 6H); MS (ESI$^+$) m/z 394 (M+H)$^+$.

Example 380: N-{3-[2-(4-chloro-3-fluorophenoxy)acetamido]bicyclo[1.1.1]pentan-1-yl}-3-ethyl-1,2,4-oxadiazole-5-carboxamide (Compound 479)

The title compound was prepared using the methodologies described above. $^1$H NMR (400 MHz, DMSO-d$_6$) δ ppm 9.99 (s, 1H), 8.77 (s, 1H), 7.50 (t, J=8.9 Hz, 1H), 7.08 (dd, J=11.4, 2.8 Hz, 1H), 6.86 (ddd, J=9.0, 2.8, 1.2 Hz, 1H), 4.49 (s, 2H), 2.80 (q, J=7.6 Hz, 2H), 2.34 (s, 6H), 1.26 (t, J=7.5 Hz, 3H); MS (ESI$^+$) m/z 409 (M+H)$^+$.

Example 381: N-{4-[2-(4-chloro-3-fluorophenoxy)acetamido]-3-hydroxybicyclo[2.2.2]octan-1-yl}-5-(trifluoromethoxy)pyridine-2-carboxamide (Compound 480)

The title compound was prepared using the methodologies described in Example 130 substituting 5-(trifluoromethoxy)pyridine-2-carboxylic acid for 5-(difluoromethyl)pyrazine-2-carboxylic. $^1$H NMR (400 MHz, DMSO-$d_6$) δ ppm 8.69 (d, J=2.6 Hz, 1H), 8.13 (d, J=8.7 Hz, 1H), 8.06 (ddd, J=8.7, 2.6, 1.3 Hz, 1H), 7.92 (s, 1H), 7.49 (t, J=8.9 Hz, 1H), 7.30 (s, 1H), 7.07 (dd, J=11.4, 2.8 Hz, 1H), 6.84 (ddd, J=9.0, 2.9, 1.2 Hz, 1H), 5.13 (s, 1H), 4.48 (s, 2H), 4.15-4.07 (m, 1H), 2.47-2.36 (m, 1H), 2.19-2.04 (m, 2H), 1.99-1.81 (m, 7H); MS (ESI$^+$) m/z 532.0 (M+H)$^+$.

Example 382: N-{3-[2-(4-chloro-3-fluorophenoxy)acetamido]bicyclo[1.1.1]pentan-1-yl}-4-(1H-1,2,4-triazol-1-yl)pyridine-2-carboxamide (Compound 481)

Example 382A: 4-(1H-1,2,4-triazol-1-yl)picolinic acid, 2 sodium Chloride

Methyl 4-fluoropicolinate (Combi-Blocks, 210 mg, 1.354 mmol), 1,2,4-triazole (Aldrich, 112 mg, 1.624 mmol) and potassium carbonate (561 mg, 4.06 mmol) were combined with dimethyl sulfoxide (5.0 mL), and the mixture was stirred at 75° C. for 18 hours. The resulting reaction mixture was filtered through a glass microfiber frit and purified by preparative HPLC [YMC TriArt™ C18 Hybrid 20 μm column, 25×250 mm, flow rate 70 mL/minute, 5-100% gradient of acetonitrile in buffer (0.025 M aqueous ammonium bicarbonate, adjusted to pH 10 with ammonium hydroxide)]. Fractions containing the crude methyl ester were combined and concentrated under reduced pressure, and to the resulting residue was added methanol (5 mL) and aqueous NaOH (2.5 M, 0.54 mL). The resulting suspension was stirred at ambient temperature for 30 minutes and then concentrated in vacuo. To the resulting white power was added aqueous HCl (2.5 M, 2.71 mL) and the clear solution was concentrated in vacuo to give the title compound (0.25 g, 0.728 mmol, 54% yield). MS (ESI$^+$) m/z 191 (M+H)$^+$.

Example 382B: N-{3-[2-(4-chloro-3-fluorophenoxy)acetamido]bicyclo[1.1.1]pentan-1-yl}-4-(1H-1,2,4-triazol-1-yl)pyridine-2-carboxamide The reaction and purification conditions described in Example 13 substituting the product of Example 382A for the product of Example 12B, and the product of Example 6C for the product of Example 4A gave the title compound. $^1$H NMR (400 MHz, DMSO-$d_6$) δ ppm 9.65 (s, 1H), 9.41 (s, 1H), 8.78 (dd, J=5.4, 0.7 Hz, 1H), 8.75 (s, 1H), 8.50-8.47 (m, 1H), 8.38 (s, 1H), 8.11 (dd, J=5.4, 2.2 Hz, 1H), 7.50 (t, J=8.9 Hz, 1H), 7.09 (dd, J=11.4, 2.8 Hz, 1H), 6.87 (ddd, J=9.0, 2.9, 1.2 Hz, 1H), 4.50 (s, 2H), 2.38 (s, 6H); MS (ESI$^+$) m/z 457 (M+H)$^+$.

Example 383: N-{3-[2-(4-chloro-3-fluorophenoxy)acetamido]bicyclo[1.1.1]pentan-1-yl}quinoxaline-2-carboxamide (Compound 482)

To a solution of the product of Example 4A (25 mg, 0.088 mmol) in N,N-dimethylformamide (0.5 mL) was added quinoxaline-2-carboxylic acid (16.8 mg, 0.097 mmol), 1-[bis(dimethylamino)methylene]-1H-1,2,3-triazolo[4,5-b]pyridinium 3-oxid hexafluorophosphate (36.7 mg, 0.097 mmol, HATU), and N,N-diisopropylethylamine (0.046 mL, 0.26 mmol) at ambient temperature. The reaction mixture was stirred for 3 hours and then was purified by preparative HPLC [Waters XBridge™ C18 5 μm OBD™ column, 30×100 mm, flow rate 40 mL/minute, 5-100% gradient of acetonitrile in buffer (0.1% trifluoroacetic acid)] to give the title compound (30 mg, 0.068 mmol, 77% yield). $^1$H NMR (400 MHz, DMSO-$d_6$) δ ppm 9.57 (s, 1H), 9.40 (s, 1H), 8.74 (s, 1H), 8.21-8.10 (m, 2H), 7.96 (ddd, J=5.5, 4.6, 3.2 Hz, 2H), 7.47 (t, J=8.9 Hz, 1H), 7.05 (dd, J=11.4, 2.8 Hz, 1H), 6.84 (ddd, J=8.9, 2.9, 1.2 Hz, 1H), 4.47 (s, 2H), 2.38 (s, 6H); MS (ESI$^+$) m/z 440 (M+H)$^+$.

Example 384: N-{(2S)-4-[2-(4-chloro-3-fluorophenoxy)acetamido]-2-hydroxybicyclo[2.2.2]octan-1-yl}-2-fluorobenzamide (Compound 483)

To a mixture of the product of Example 308A (45.7 mg, 0.10 mmol), 1-[bis(dimethylamino)methylene]-1H-1,2,3-triazolo[4,5-b]pyridinium 3-oxid hexafluorophosphate (39.9 mg, 0.105 mmol, HATU) and 2-fluorobenzoic acid (14.01 mg, 0.100 mmol) was added N-ethyl-N-isopropylpropan-2-amine (78 mg, 0.600 mmol) in N,N-dimethylformamide (0.9 mL). The mixture was stirred at ambient temperature for 0.5 hour. The resulting solution was filtered through a glass microfiber frit and purified by preparative HPLC [Waters XBridge™ C18 5 μm OBD™ column, 30×100 mm, flow rate 40 mL/minute, 5-100% gradient of acetonitrile in buffer (0.1% trifluoroacetic acid)] to give the title compound (0.039 g, 0.084 mmol, 84% yield). $^1$H NMR (501 MHz, DMSO-$d_6$) δ ppm 7.62 (dt, J=2, 7 Hz, 1H), 7.52 (m, 3H), 7.49 (t, J=8 Hz, 1H), 7.27 (d, J=7 Hz, 1H), 7.24 (m, 1H), 7.04 (dd, J=9, 3 Hz, 1H), 6.82 (br d, J=8 Hz, 1H), 5.16 (br s, 1H), 4.45 (s, 2H), 4.08 (m, 1H), 2.23-2.36 (m, 2H), 1.78-2.02 (m, 8H); MS (ESI$^+$) m/z 465 (M+H)$^+$.

Example 385: N-{(2S)-4-[2-(4-chloro-3-fluorophenoxy)acetamido]-2-hydroxybicyclo[2.2.2]octan-1-yl}benzamide (Compound 484)

The reaction and purification conditions described in Example 384 substituting benzoic acid for 2-fluorobenzoic acid gave the title compound (0.030 g, 0.067 mmol, 67% yield). $^1$H NMR (501 MHz, DMSO-$d_6$) δ ppm 7.77 (dd, J=2, 7 Hz, 2H), 7.54 (s, 1H), 7.42-7.52 (m, 5H), 7.04 (dd, J=9, 3 Hz, 1H), 6.82 (br d, J=8 Hz, 1H), 4.45 (s, 2H), 4.19 (m, 1H), 2.32 (m, 1H), 2.14 (m, 1H), 1.76-2.06 (m, 8H); MS (ESI$^+$) m/z 447 (M+H)$^+$.

Example 386: N-{(3S)-4-[2-(4-chloro-3-fluorophenoxy)acetamido]-3-hydroxybicyclo[2.2.2]octan-1-yl}-1,3-dimethyl-1H-pyrazole-5-carboxamide (Compound 485)

The title compound was isolated by chiral preparative SFC of Example 348 as the second peak eluted off the column using the methodologies described in Example 136. $^1$H NMR (400 MHz, DMSO-$d_6$) δ ppm 7.57 (s, 1H), 7.42 (t, J=8.8 Hz, 1H), 7.26 (s, 1H), 6.99 (dd, J=11.4, 2.9 Hz, 1H), 6.78 (ddd, J=9.0, 2.9, 1.1 Hz, 1H), 6.50 (s, 1H), 5.16 (d, J=4.2 Hz, 1H), 4.41 (s, 2H), 3.83 (s, 3H), 2.31 (ddd, J=12.3, 9.5, 2.3 Hz, 1H), 2.07 (s, 3H), 2.05-1.89 (m, 2H), 1.92-1.71 (m, 7H); MS (ESI$^+$) m/z 465.2 (M+H)$^+$.

Example 387: N-{(3R)-4-[2-(4-chloro-3-fluorophenoxy)acetamido]-3-hydroxybicyclo[2.2.2]octan-1-yl}-1,3-dimethyl-1H-pyrazole-5-carboxamide (Compound 486)

The title compound was isolated by chiral preparative SFC of Example 348 as the first peak eluted off the column using the methodologies described in Example 136. $^1$H NMR (400 MHz, DMSO-d$_6$) δ ppm 7.57 (s, 1H), 7.42 (t, J=8.8 Hz, 1H), 7.26 (s, 1H), 6.99 (dd, J=11.4, 2.7 Hz, 1H), 6.78 (dd, J=9.0, 2.6 Hz, 1H), 6.50 (s, 1H), 5.15 (d, J=4.1 Hz, 1H), 4.41 (s, 2H), 4.03 (d, J=9.8 Hz, 1H), 3.83 (s, 3H), 2.36-2.25 (m, 1H), 2.07 (s, 3H), 1.93 (ddd, J=34.0, 14.0, 6.3 Hz, 4H), 1.87-1.76 (m, 5H); MS (ESI$^+$) m/z 465.2 (M+H)$^+$.

Example 388: N-{4-[2-(4-chloro-3-fluorophenoxy)acetamido]-3-hydroxybicyclo[2.2.2]octan-1-yl}-5-methyl-1H-1,2,4-triazole-3-carboxamide (Compound 487)

Example 388A: 5-methyl-1H-1,2,4-triazole-3-carboxylic acid, trifluoroacetic acid A mixture of ethyl 5-methyl-1H-1,2,4-triazole-3-carboxylate (1.0 g, 6.45 mmol) and sodium hydroxide (1.702 mL, 32.2 mmol) in tetrahydrofuran (30 mL) was stirred at ambient temperature for 16 hours. Volatiles were removed, and the residue was acidified with 1 N HCl solution. Water was removed under high vacuum, and the crude residue was purified by HPLC (0-70% acetonitrile in 0.1% trifluoroacetic acid/water on Phenomenex® C18 10 m (250 mm×50 mm) column at a flowrate of 50 mL/minute) to give 460 mg of the title compound as a white solid.

Example 388B: N-{4-[2-(4-chloro-3-fluorophenoxy)acetamido]-3-oxobicyclo[2.2.2]octan-1-yl}-5-methyl-1H-1,2,4-triazole-3-carboxamide A mixture of Example 130D (71 mg, 0.188 mmol), Example 388A (56.7 mg, 0.235 mmol) and N-ethyl-N-isopropylpropan-2-amine (0.164 mL, 0.941 mmol) in N,N-dimethylformamide (2.5 mL) was treated with 2-(3H-[1,2,3]triazolo[4,5-b]pyridin-3-yl)-1,1,3,3-tetramethylisouronium hexafluorophosphate(V) (107 mg, 0.282 mmol), and the reaction mixture was stirred at ambient temperature for 30 minutes. Volatiles were removed, and the residue was purified by HPLC (20-100% acetonitrile in 0.1% trifluoroacetic acid/water on Phenomenex® C18 10 m (250 mm×50 mm) column at a flowrate of 50 mL/minute) to give 40 mg of the title compound as a solid. $^1$H NMR (400 MHz, DMSO-d$_6$) δ ppm 7.88 (s, 1H), 7.69 (s, 1H), 7.46 (t, J=8.9 Hz, 1H), 7.05 (dd, J=11.4, 2.9 Hz, 1H), 6.82 (dd, J=8.9, 2.8 Hz, 1H), 4.54 (s, 2H), 2.92 (s, 2H), 2.46-2.33 (m, 2H), 2.32 (s, 3H), 2.11 (t, J=8.3 Hz, 4H), 1.84 (dt, J=11.5, 8.1 Hz, 2H); MS (ESI$^+$) m/z 450.1 (M+H)$^+$.

Example 388C: N-{4-[2-(4-chloro-3-fluorophenoxy)acetamido]-3-hydroxybicyclo[2.2.2]octan-1-yl}-5-methyl-1H-1,2,4-triazole-3-carboxamide, trifluoroacetic acid A mixture of Example 388B (0.038 g, 0.084 mmol) and sodium tetrahydroborate (9.59 mg, 0.253 mmol) in dichloromethane (1.0 mL) and methanol (1 mL) was stirred at ambient temperature for 2 hours. Volatiles were removed, and the residue was purified by HPLC (20-100% acetonitrile in 0.1% trifluoroacetic acid/water on Phenomenex® C18 10 μm (250 mm×50 mm) column at a flowrate of 50 mL/minute) to give 31 mg of product as a solid. $^1$H NMR (400 MHz, DMSO-d$_6$) δ ppm 7.53-7.44 (m, 2H), 7.29 (s, 1H), 7.06 (dd, J=11.3, 2.9 Hz, 1H), 6.84 (dd, J=8.9, 2.8 Hz, 1H), 4.48 (s, 2H), 4.08 (dd, J=9.6, 3.0 Hz, 1H), 2.57-2.47 (m, 4H), 2.40 (m, 1H), 2.35 (s, 3H), 2.15-2.05 (m, 1H), 2.07-1.95 (m, 1H), 1.98-1.78 (m, 7H); MS (ESI$^+$) m/z 452.1 (M+H)$^+$.

Example 389: N-{(2S)-4-[2-(4-chloro-3-fluorophenoxy)acetamido]-2-hydroxybicyclo[2.2.2]octan-1-yl}-3-fluorobenzamide (Compound 488)

The reaction and purification conditions described in Example 384 substituting 3-fluorobenzoic acid for 2-fluorobenzoic acid gave the title compound. $^1$H NMR (501 MHz, DMSO-d$_6$) δ ppm 7.56-7.66 (m, 2H), 7.50 (m, 4H), 7.35 (m, 1H), 7.04 (dd, J=9, 3 Hz, 1H), 6.82 (br d, J=8 Hz, 1H), 4.46 (s, 2H), 4.24 (m, 1H), 2.32 (m, 1H), 1.70-2.10 (m, 9H); MS (ESI$^+$) m/z 465 (M+H)$^+$.

Example 390: N-{(2S)-4-[2-(4-chloro-3-fluorophenoxy)acetamido]-2-hydroxybicyclo[2.2.2]octan-1-yl}-4-fluorobenzamide (Compound 489)

The reaction and purification conditions described in Example 384 substituting 4-fluorobenzoic acid for 2-fluorobenzoic acid gave the title compound. $^1$H NMR (501 MHz, DMSO-d$_6$) δ ppm 7.85 (dd, J=6, 8 Hz, 2H), 7.52 (s, 1H), 7.48 (t, J=8, 1H), 7.45 (s, 1H), 7.25 (t, J=8 Hz, 2H), 7.03 (dd, J=9, 3 Hz, 1H), 6.81 (br d, J=8 Hz, 1H), 4.44 (s, 2H), 4.20 (m, 1H), 2.30 (m, 1H), 1.72-2.12 (m, 9H); MS (ESI$^+$) m/z 465 (M+H)$^+$.

Example 391: 2-(4-chloro-3-fluorophenoxy)-N-{3-[(isoquinolin-5-yl)amino]bicyclo[1.1.1]pentan-1-yl}acetamide (Compound 490)

Example 391A: tert-butyl {3-[(isoquinolin-5-yl)amino]bicyclo[1.1.1]pentan-1-yl}carbamate A mixture of tert-butyl (3-aminobicyclo[1.1.1]pentan-1-yl)carbamate (PharmaBlock, 0.875 g, 4.41 mmol), 5-bromoisoquinoline (0.900 g, 4.33 mmol), and six HPMC catalyst capsules (115 mg loading per capsule with 1 weight % of Allyl Pd, 4 weight % of cBRIDP, and 95 weight % of KO$^t$Bu) in water (12 mL) was degassed and stirred at 50° C. for 2 hours. The reaction mixture was diluted with brine and saturated, aqueous Na$_2$SO$_4$ and extracted with ethyl acetate (2×). The combined organic layers were dried over anhydrous MgSO$_4$, filtered, and concentrated under reduced pressure. The residue was purified on an 80 g column using the Biotage® Isolera™ One flash system eluting with heptanes/ethyl acetate (4:6 to 3:7) to provide the title compound (0.262 g, 0.81 mmol, 19% yield). HPMC: (hydroxypropyl) methyl cellulose. cBRIDP: di-tert-butyl(2,2-diphenyl-1-methyl-1-cyclopropyl)phosphine. MS (ESI$^+$) m/z 326.2 (M+H)$^+$.

Example 391B: N'-(isoquinolin-5-yl)bicyclo[1.1.1]pentane-1,3-diamine, hydrochloric acid A mixture of the product of Example 391A (0.231 g, 0.710 mmol) and trifluoroacetic acid (0.547 mL, 7.10 mmol)

in CH$_2$Cl$_2$ (4 mL) was stirred for 4 hours. The reaction mixture was concentrated, and the residue was dissolved in 3 mL of methanol. The solution was treated with 3 mL of 2 M HCl in ether, diluted with 5 mL of ether, and stirred for 15 minutes. The solids were collected by filtration, washed with ether, and vacuum oven-dried to provide the title compound (0.172 g, 0.57 mmol, 81% yield). MS (ESI$^+$) m/z 226.1 (M+H)$^+$.

Example 391C: 2-(4-chloro-3-fluorophenoxy)-N-{3-[(isoquinolin-5-yl)amino]bicyclo[1.1.1]pentan-1-yl}acetamide A mixture of the product of Example 391B (0.171 g, 0.573 mmol), 2-(4-chloro-3-fluorophenoxy)acetic acid (0.135 g, 0.66 mmol), N-[(dimethylamino)-1H-1,2,3-triazolo-[4,5-b]pyridin-1-ylmethylene]-N-methylmethanaminium hexafluorophosphate N-oxide (HATU, 0.283 g, 0.745 mmol), and triethylamine (0.400 mL, 2.87 mmol) in dimethyl formamide (4 mL) was stirred for 2 hours. Water was added to the reaction mixture. The resulting suspension was diluted with brine and saturated, aqueous NaHCO$_3$, and extracted with ethyl acetate (2×). The combined organic layers were washed with brine, dried over anhydrous MgSO$_4$, filtered, and concentrated under reduced pressure. The residue was purified on a 12 g silica gel column using a Biotage® Isolera™ One flash system eluting with heptanes/ethyl acetate (1:9) to 100% ethyl acetate to provide the title compound (0.171 g, 0.42 mmol, 72% yield). $^1$H NMR (500 MHz, DMSO-d$_6$) δ ppm 9.13 (d, J=0.9 Hz, 1H), 8.81 (s, 1H), 8.39 (d, J=6.0 Hz, 1H), 8.07 (dt, J=6.2, 0.9 Hz, 1H), 7.58-7.42 (m, 2H), 7.32 (dt, J=8.2, 0.9 Hz, 1H), 7.10 (dd, J=11.3, 2.9 Hz, 1H), 7.05-6.95 (m, 2H), 6.88 (ddd, J=8.9, 2.8, 1.2 Hz, 1H), 4.53 (s, 2H), 2.43 (s, 6H); MS (ESI$^+$) m/z 412.2 (M+H)$^+$.

Example 392: 2-(4-chloro-3-fluorophenoxy)-N-{3-[(2-methyl-1,2,3,4-tetrahydroisoquinolin-5-yl)amino]bicyclo[1.1.1]pentan-1-yl}acetamide (Compound 491)

To a suspension of the product of Example 391C (30.0 mg, 0.073 mmol) in methanol (1 mL) was added methyl iodide (0.027 mL, 0.44 mmol). The reaction mixture was stirred for 3 hours, and CH$_2$Cl$_2$ (0.5 mL) was added to turn the suspension into a solution. The solution was stirred for 16 hours. Additional methyl iodide (0.1 mL) was added, and the mixture was heated to 40° C. for 6 hours. The reaction mixture was concentrated under reduced pressure. The concentrate was suspended in methanol (1.5 mL) and treated with sodium borohydride (8.27 mg, 0.22 mmol). The solution was stirred overnight. The reaction mixture was concentrated, and the residue was purified by reverse-phase HPLC (see protocol in Example 273E) to provide the title compound as a trifluoroacetic acid salt (13.2 mg, 0.025 mmol, 34% yield). $^1$H NMR (400 MHz, DMSO-d$_6$) δ ppm 9.85 (s, 1H), 8.74 (s, 1H), 7.47 (t, J=8.9 Hz, 1H), 7.13-6.98 (m, 2H), 6.88-6.69 (m, 2H), 6.43 (d, J=7.6 Hz, 1H), 4.46 (s, 2H), 4.37-4.30 (m, 1H), 4.21-4.12 (m, 1H), 3.73-3.62 (m, 1H), 3.30-3.21 (m, 1H), 2.88 (s, 3H), 2.74-2.61 (m, 2H), 2.29 (s, 6H); MS (ESI$^+$) m/z 430.2 (M+H)$^+$.

Example 393: 2-(4-chloro-3-fluorophenoxy)-N-{3-[(2-methyl-2H-pyrazolo[4,3-c]pyridin-4-yl)amino]bicyclo[1.1.1]pentan-1-yl}acetamide (Compound 492)

The reaction and purification conditions described in Example 264 substituting 4-chloro-2-methyl-2H-pyrazolo[4,3-c]pyridine for 2-chloro-4-phenylpyrimidine gave the title compound. $^1$H NMR (501 MHz, DMSO-d$_6$) δ ppm 11.05 (br s, 1H), 10.52 (br s, 1H), 8.97 (s, 1H), 8.83 (s, 1H), 7.52 (d, J=6 Hz, 1H), 7.51 (t, J=8 Hz, 1H), 7.12 (d, J=6 Hz, 1H), 7.09 (dd, J=9, 3 Hz, 1H), 6.87 (br d, J=8 Hz, 1H), 4.56 (s, 2H), 4.18 (s, 3H), 2.63 (s, 6H); MS (ESI$^+$) m/z 416 (M+H)$^+$.

Example 394: 2-(4-chloro-3-fluorophenoxy)-N-{3-[(2-methyl-2H-pyrazolo[3,4-c]pyridin-7-yl)amino]bicyclo[1.1.1]pentan-1-yl}acetamide (Compound 493)

The reaction and purification conditions described in Example 264 substituting 7-chloro-2-methyl-2H-pyrazolo[3,4-c]pyridine for 2-chloro-4-phenylpyrimidine gave the title compound. $^1$H NMR (501 MHz, DMSO-d$_6$) δ ppm 11.36 (br s, 1H), 10.70 (br s, 1H), 8.94 (s, 1H), 8.52 (s, 1H), 7.51 (t, J=8 Hz, 1H), 7.35 (d, J=6 Hz, 1H), 7.19 (d, J=6 Hz, 1H), 7.09 (dd, J=9, 3 Hz, 1H), 6.87 (br d, J=8 Hz, 1H), 4.55 (s, 2H), 4.25 (s, 3H), 2.60 (s, 6H); MS (ESI$^+$) m/z 416 (M+H)$^+$.

Example 395: 2-(3,4-dichlorophenoxy)-N-{3-[(2-methylpyrazolo[1,5-a]pyrazin-4-yl)amino]bicyclo[1.1.1]pentan-1-yl}acetamide (Compound 494)

To a solution of the product of Example 323B (30 mg, 0.087 mmol) in N,N-dimethylformamide (0.5 mL) was added 2-(3,4-dichlorophenoxy)acetic acid (21.3 mg, 0.096 mmol), N-[(dimethylamino)-1H-1,2,3-triazolo-[4,5-b]pyridin-1-ylmethylene]-N-methylmethanaminium hexafluorophosphate N-oxide (36.5 mg, 0.096 mmol, HATU) and N,N-diisopropylethylamine (0.076 mL, 0.437 mmol) at ambient temperature. The reaction mixture was stirred for 1 hour and then was purified by preparative HPLC [Waters XBridge™ C18 5 μm OBD™ column, 30×100 mm, flow rate 40 mL/minute, 5-100% gradient of acetonitrile in buffer (0.1% trifluoroacetic acid)] to give the title compound (25 mg, 0.046 mmol, 52% yield). $^1$H NMR (400 MHz, DMSO-d$_6$) δ ppm 8.80 (s, 1H), 7.90 (d, J=5.0 Hz, 1H), 7.56 (d, J=8.9 Hz, 1H), 7.28 (d, J=2.9 Hz, 1H), 7.23 (d, J=4.9 Hz, 1H), 7.00 (dd, J=8.9, 2.9 Hz, 1H), 6.83 (s, 1H), 4.52 (s, 2H), 2.45 (s, 6H), 2.38 (s, 3H); $^{19}$F NMR (376 MHz, DMSO-d$_6$) δ ppm −74.55; MS (ESI$^+$) m/z 432 (M+H)$^+$.

Example 396: N-{3-[(2-methylpyrazolo[1,5-a]pyrazin-4-yl)amino]bicyclo[1.1.1]pentan-1-yl}-2-(3,4,5-trifluorophenoxy)acetamide (Compound 495)

The reaction and purification conditions described in Example 395 substituting 2-(3,4,5-trifluorophenoxy)acetic acid for 2-(3,4-dichlorophenoxy)acetic acid gave the title compound. $^1$H NMR (501 MHz, DMSO-d$_6$) δ ppm 8.79 (s, 1H), 7.91 (d, J=5.0 Hz, 1H), 7.23 (d, J=5.0 Hz, 1H), 7.04-6.97 (m, 2H), 6.85 (s, 1H), 4.51 (s, 2H), 2.46 (s, 6H), 2.38 (s, 3H); $^{19}$F NMR (376 MHz, DMSO-d$_6$) δ ppm −74.62, −134.63 (dd, J=22.5, 9.9 Hz), −171.61 (tt, J=22.6, 5.9 Hz); MS (ESI$^+$) m/z 432 (M+H)$^+$.

Example 397: 2-[3-fluoro-4-(trifluoromethoxy)phenoxy]-N-{3-[(2-methylpyrazolo[1,5-a]pyrazin-4-yl)amino]bicyclo[1.1.1]pentan-1-yl}acetamide (Compound 496)

The reaction and purification conditions described in Example 395 substituting 2-(3-fluoro-4-(trifluoromethoxy)

phenoxy)acetic acid for 2-(3,4-dichlorophenoxy)acetic acid gave the title compound. ¹H NMR (400 MHz, DMSO-d₆) δ ppm 9.06 (s, 1H), 8.83 (s, 1H), 7.92 (d, J=5.2 Hz, 1H), 7.46 (t, J=9.0 Hz, 1H), 7.19 (d, J=5.2 Hz, 1H), 7.10 (dd, J=12.3, 2.9 Hz, 1H), 6.91 (s, 1H), 6.87 (dd, J=8.8, 2.9 Hz, 1H), 4.51 (s, 2H), 2.46 (s, 6H), 2.35 (s, 3H); ¹⁹F NMR (376 MHz, DMSO-d₆) δ ppm −58.49 (d, J=5.1 Hz), −74.69, −127.56, −127.71 (m); MS (ESI⁺) m/z 466 (M+H)⁺.

Example 398: N-{(3R)-4-[2-(4-chloro-3-fluorophenoxy)acetamido]-3-hydroxybicyclo[2.2.2]octan-1-yl}-2,5-dimethyl-1,3-thiazole-4-carboxamide (Compound 497)

Example 398A: N-[(2R)-4-amino-2-hydroxybicyclo[2.2.2]octan-1-yl]-2-(4-chloro-3-fluorophenoxy)acetamide, Hydrochloric Acid The title compound was isolated by chiral preparative SFC of Example 130E as the second peak eluted off the column, followed by reverse phase HPLC purification to give the product as a hydrochloride salt. The preparative SFC (Supercritical Fluid Chromatography) was performed on a Thar 200 preparative SFC (SFC-5) system using a Chiralpak® IC-H, 250×30 mm I.D., 5 μm column. The column was at 38° C., and the backpressure regulator was set to maintain 100 bar. The mobile phase A is CO₂ and B is isopropanol (0.1% ammonium hydroxide). The eluent is held isocratically at 40% of mobile phase B at a flowrate of 75 mL/minute. Fraction collection was time triggered with UV monitor wavelength set at 220 nm. Preparative HPLC was performed on a Gilson 281 semi-preparative HPLC system using a SNAP® C18 column. A gradient of acetonitrile (A) and 0.05% hydrochloric acid in water (B) is used, at a flow rate of 50 mL/minute. A linear gradient is used from about 30% of A to about 100% of A over about 50 minutes. Detection method is UV at wavelengths of 220 nM and 254 nM. ¹H NMR (400 MHz, methanol-d₄) δ ppm 7.37 (t, J=8.55 Hz, 1H), 6.93 (dd, J=10.96, 2.63 Hz, 1H), 6.82 (dd, J=8.99, 1.53 Hz, 1H), 4.37 (br d, J=8.77 Hz, 1H), 4.48 (s, 2H), 2.40-2.26 (m, 1H), 2.25-2.08 (m, 3H), 2.06-1.63 (m, 7H); MS (ESI⁺) m/z 343.1 (M+H)⁺. X-ray crystallography confirmed the assigned stereochemistry.

Example 398B: N-{(3R)-4-[2-(4-chloro-3-fluorophenoxy)acetamido]-3-hydroxybicyclo[2.2.2]octan-1-yl}-2,5-dimethyl-1,3-thiazole-4-carboxamide A mixture of Example 398A (32 mg, 0.070 mmol), 2,5-dimethylthiazole-4-carboxylic acid (13.76 mg, 0.088 mmol) and N-ethyl-N-isopropylpropan-2-amine (0.061 mL, 0.350 mmol) in N,N-dimethylformamide (1.5 mL) was treated with 2-(3H-[1,2,3]triazolo[4,5-b]pyridin-3-yl)-1,1,3,3-tetramethylisouronium hexafluorophosphate(V) (40.0 mg, 0.105 mmol), and the reaction mixture was stirred at ambient temperature for 30 minutes. Volatiles were removed, and the residue was purified by HPLC (20-100% acetonitrile in 0.1% trifluoroacetic acid/water on Phenomenex® C18 10 μm (250 mm×50 mm) column at a flowrate of 50 mL/minute) to give 21 mg of the title compound as a solid. ¹H NMR (400 MHz, DMSO-d₆) δ ppm 7.49 (t, J=8.9 Hz, 1H), 7.28 (d, J=7.7 Hz, 2H), 7.06 (dd, J=11.4, 2.8 Hz, 1H), 6.84 (ddd, J=9.0, 2.9, 1.2 Hz, 1H), 4.48 (s, 2H), 4.08 (dd, J=9.6, 3.0 Hz, 1H), 2.64 (s, 3H), 2.57 (s, 3H), 2.37 (ddd, J=12.5, 9.7, 1.8 Hz, 1H), 2.16-2.00 (m, 2H), 2.02-1.90 (m, 1H), 1.86 (dd, J=15.8, 6.0 Hz, 6H); MS (ESI⁺) m/z 482.0 (M+H)⁺.

Example 399: N-{(2S)-4-[2-(4-chloro-3-fluorophenoxy)acetamido]-2-hydroxybicyclo[2.2.2]octan-1-yl}-4-fluoro-1,3-dimethyl-1H-pyrazole-5-carboxamide (Compound 498)

Example 399A: methyl 4-fluoro-5-methyl-1H-pyrazole-3-carboxylate

A mixture of 4-fluoro-5-methyl-1H-pyrazole-3-carboxylic acid hydrochloride (0.54 g, 3 mmol) and sulfuric acid (0.35 g, 3.60 mmol) in methanol (3 mL) was stirred at 60° C. for 18 hours. Then aqueous 0.3 N NaOH (23 mL) was added. The mixture was extracted with ethyl acetate (100 mL). The organic phase was washed with brine (20 mL), then dried over Na₂SO₄, filtered and concentrated under reduced pressure. The resulting solid was purified by flash column chromatography on silica gel (40 g) eluted with 70 to 100% ethyl acetate in heptane to give the title compound (0.48 g, 3 mmol, 100% yield). ¹H NMR (501 MHz, DMSO-d₆) δ ppm 13.4 (br s, 1H), 3.85 (s, 3H), 2.19 (s, 3H); MS (ESI⁺) m/z 159 (M+H)⁺.

Example 399B: methyl 4-fluoro-1,3-dimethyl-1H-pyrazole-5-carboxylate

A mixture of Example 399A (237 mg, 1.5 mmol) and dimethyl sulfate (212 mg, 1.680 mmol) in toluene (1 mL) was stirred at 80° C. for 4 hours. The mixture was concentrated under reduced pressure, and the resulting product was purified by flash column chromatography on silica gel (40 g) eluted with 20 to 50% ethyl acetate in heptane to give the title compound (0.103 g, 0.598 mmol, 40% yield). ¹H NMR (400 MHz, CDCl₃) δ ppm 4.04 (s, 3H), 3.92 (s, 3H), 2.23 (s, 3H); MS (ESI⁺) m/z 173 (M+H)⁺.

Example 399C: 4-fluoro-1,3-dimethyl-1H-pyrazole-5-carboxylic acid

To a mixture of Example 399B (240 mg, 1.394 mmol) in methanol (8 mL) was added 3 N NaOH solution (2.32 mL). The mixture was stirred at ambient temperature for 18 hours. Then the mixture was cooled to ambient temperature, and 2 N HCl aqueous solution (3.5 mL) was added. The mixture was concentrated under reduced pressure, and then ethyl acetate (80 mL) was added to the resulting solids. The material was filtered, and the filtrate was concentrated under reduced pressure to give the title compound (0.218 g, 1.379 mmol, 99% yield). ¹H NMR (400 MHz, CDCl₃) δ ppm 4.07 (s, 3H), 2.25 (s, 3H); MS (ESI⁺) m/z 159 (M+H)⁺.

Example 399D: N-{(2S)-4-[2-(4-chloro-3-fluorophenoxy)acetamido]-2-hydroxybicyclo[2.2.2]octan-1-yl}-4-fluoro-1,3-dimethyl-1H-pyrazole-5-carboxamide The reaction and purification conditions described in Example 384 substituting Example 399C for 2-fluorobenzoic acid gave the title compound (0.047 g, 0.097 mmol, 81% yield). ¹H NMR (501 MHz, DMSO-d₆) δ ppm 7.55 (s, 1H), 7.48 (t, J=8 Hz, 1H), 7.11 (d, J=5 Hz, 1H), 7.03 (dd, J=9, 3 Hz, 1H), 6.81 (br d, J=8 Hz, 1H), 5.20 (br s, 1H), 4.45 (s, 2H), 4.04 (m, 1H), 3.86 (s, 3H), 2.33 (m, 2H), 2.12 (s, 3H), 1.80-1.98 (m, 8H); MS (ESI⁺) m/z 483 (M+H)⁺.

Example 400: N-{3-[2-(4-chloro-3-fluorophenoxy) acetamido]bicyclo[1.1.1]pentan-1-yl}-4-fluoro-1,3-dimethyl-1H-pyrazole-5-carboxamide (Compound 499)

The reaction and purification conditions described in Example 383 substituting the product of Example 399C for quinoxaline-2-carboxylic acid gave the title compound. $^1$H NMR (400 MHz, DMSO-$d_6$) δ ppm 8.75 (s, 1H), 8.69 (s, 1H), 7.50 (t, J=8.9 Hz, 1H), 7.08 (dd, J=11.4, 2.8 Hz, 1H), 6.86 (ddd, J=9.0, 2.9, 1.2 Hz, 1H), 4.49 (s, 2H), 3.84 (s, 3H), 2.32 (s, 6H), 2.13 (s, 3H); $^{19}$F NMR (376 MHz, DMSO-$d_6$) δ ppm −114.07, −169.72; MS (ESI$^+$) m/z 442 (M+H)$^+$.

Example 401: N-{3-[2-(3,4-dichlorophenoxy)acetamido]bicyclo[1.1.1]pentan-1-yl}-4-fluoro-1,3-dimethyl-1H-pyrazole-5-carboxamide (Compound 500)

To a solution of the product of Example 2B (25 mg, 0.088 mmol) in N,N-dimethylformamide (0.5 mL) was added Example 399C (14.44 mg, 0.091 mmol), N-[(dimethyl-amino)-1H-1,2,3-triazolo-[4,5-b]pyridin-1-ylmethylene]-N-methylmethanaminium hexafluorophosphate N-oxide (34.7 mg, 0.091 mmol, HATU) and N,N-diisopropylethylamine (0.043 mL, 0.249 mmol) at ambient temperature. The reaction mixture was stirred for 3 hours and then was purified by preparative HPLC [Waters XBridge™ C18 5 μm OBD™ column, 30×100 mm, flow rate 40 mL/minute, 5-100% gradient of acetonitrile in buffer (0.1% trifluoroacetic acid)] to give the title compound (27 mg, 0.061 mmol, 74% yield). $^1$H NMR (400 MHz, DMSO-$d_6$) δ ppm 8.71 (s, 1H), 8.65 (s, 1H), 7.51 (d, J=8.9 Hz, 1H), 7.24 (d, J=2.9 Hz, 1H), 6.96 (dd, J=8.9, 2.9 Hz, 1H), 4.46 (s, 2H), 3.81 (s, 3H), 2.29 (s, 6H), 2.09 (s, 3H); MS (ESI$^+$) m/z 482 (M+CH$_3$CN)$^+$.

Example 402: 4-acetyl-N-{3-[2-(4-chloro-3-fluorophenoxy)acetamido]bicyclo[1.1.1]pentan-1-yl}pyridine-2-carboxamide (Compound 501)

The reaction and purification conditions described in Example 52 substituting ethyl 4-acetylpicolinate (J&W Pharmlab) for the product of Example 49A gave the title compound. $^1$H NMR (400 MHz, DMSO-$d_6$) δ ppm 9.39 (s, 1H), 8.85 (dd, J=5.0, 0.9 Hz, 1H), 8.74 (s, 1H), 8.35 (dd, J=1.8, 0.8 Hz, 1H), 8.01 (dd, J=5.0, 1.7 Hz, 1H), 7.50 (t, J=8.9 Hz, 1H), 7.08 (dd, J=11.3, 2.9 Hz, 1H), 6.86 (ddd, J=8.9, 2.8, 1.2 Hz, 1H), 4.49 (s, 2H), 2.67 (s, 3H), 2.37 (s, 6H); MS (ESI$^+$) m/z 432 (M+H)$^+$.

Example 403: N-{4-[2-(4-chloro-3-fluorophenoxy) acetamido]-3-hydroxybicyclo[2.2.2]octan-1-yl}-2-propyl-1,3-thiazole-4-carboxamide (Compound 502)

The title compound was prepared using the methodologies described in Example 130 substituting 2-propyl-1,3-thiazole-4-carboxylic acid for 5-(difluoromethyl)pyrazine-2-carboxylic. $^1$H NMR (400 MHz, DMSO-$d_6$) δ ppm 8.06 (s, 1H), 7.49 (t, J=8.9 Hz, 1H), 7.28 (d, J=1.6 Hz, 2H), 7.06 (dd, J=11.4, 2.9 Hz, 1H), 6.93-6.80 (m, 1H), 4.48 (s, 2H), 4.08 (dd, J=9.7, 3.0 Hz, 1H), 2.96 (t, J=7.6 Hz, 2H), 2.39 (ddd, J=12.6, 9.5, 2.2 Hz, 1H), 2.16-2.03 (m, 2H), 2.07-1.88 (m, 3H), 1.93-1.84 (m, 4H), 1.74 (h, J=7.4 Hz, 2H), 0.95 (t, J=7.3 Hz, 3H); MS (ESI$^+$) m/z 496.1 (M+H)$^+$.

Example 404: N-{4-[2-(4-chloro-3-fluorophenoxy) acetamido]-3-hydroxybicyclo[2.2.2]octan-1-yl}-3-methyl-1,2,4-oxadiazole-5-carboxamide (Compound 503)

The title compound was prepared using the methodologies described in Example 130 substituting 3-methyl-1,2,4-oxadiazole-5-carboxylic acid for 5-(difluoromethyl)pyrazine-2-carboxylic. $^1$H NMR (400 MHz, DMSO-$d_6$) δ ppm 8.65 (s, 1H), 7.49 (t, J=8.9 Hz, 1H), 7.29 (s, 1H), 7.06 (dd, J=11.4, 2.8 Hz, 1H), 6.83 (ddd, J=9.0, 2.9, 1.2 Hz, 1H), 5.14 (d, J=4.4 Hz, 1H), 4.47 (s, 2H), 4.08 (dt, J=8.5, 3.6 Hz, 1H), 2.41 (m, 4H), 2.09 (dd, J=12.1, 8.7 Hz, 1H), 2.06-1.95 (m, 1H), 1.89 (dddd, J=20.7, 12.6, 9.9, 4.0 Hz, 7H); MS (ESI$^+$) m/z 453.1 (M+H)$^+$.

Example 405: N-{4-[2-(4-chloro-3-fluorophenoxy) acetamido]-3-hydroxybicyclo[2.2.2]octan-1-yl}-2-methyl-4-(trifluoromethyl)-1,3-thiazole-5-carboxamide (Compound 504)

The title compound was prepared using the methodologies described in Example 130 substituting 2-methyl-4-(trifluoromethyl)-1,3-thiazole-5-carboxylic acid for 5-(difluoromethyl)pyrazine-2-carboxylic. $^1$H NMR (400 MHz, DMSO-$d_6$) δ ppm 8.08 (s, 1H), 7.49 (t, J=8.9 Hz, 1H), 7.28 (s, 1H), 7.06 (dd, J=11.4, 2.9 Hz, 1H), 6.83 (ddd, J=9.1, 2.9, 1.2 Hz, 1H), 5.13 (s, 1H), 4.48 (s, 2H), 4.12-4.04 (m, 1H), 2.54 (s, 3H), 2.42-2.30 (m, 1H), 2.16-1.79 (m, 9H); MS (ESI$^+$) m/z 536.0 (M+H)$^+$.

Example 406: 4-acetamido-N-{4-[2-(4-chloro-3-fluorophenoxy)acetamido]-3-hydroxybicyclo[2.2.2] octan-1-yl}-1,3-dimethyl-1H-pyrazole-5-carboxamide (Compound 505)

The title compound was prepared using the methodologies described in Example 130 substituting 4-acetamido-1,3-dimethyl-1H-pyrazole-5-carboxylic acid for 5-(difluoromethyl)pyrazine-2-carboxylic. $^1$H NMR (400 MHz, DMSO-$d_6$) δ ppm 9.42 (s, 1H), 7.53-7.44 (m, 2H), 7.28 (s, 1H), 7.06 (dd, J=11.4, 2.9 Hz, 1H), 6.83 (ddd, J=8.9, 2.8, 1.2 Hz, 1H), 4.47 (s, 2H), 4.07 (dd, J=9.7, 3.0 Hz, 1H), 3.79 (s, 3H), 2.29 (td, J=10.0, 9.4, 4.9 Hz, 1H), 2.09 (ddd, J=12.2, 10.5, 4.8 Hz, 1H), 2.04 (s, 3H), 2.00 (s, 3H), 1.99-1.91 (m, 3H), 1.94-1.79 (m, 3H), 1.83-1.70 (m, 2H); MS (ESI$^+$) m/z 522.1 (M+H)$^+$.

Example 407: N-{(2S)-4-[2-(4-chloro-3-fluorophenoxy)acetamido]-2-hydroxybicyclo[2.2.2]octan-1-yl}-1,3-dimethyl-1H-pyrazole-5-carboxamide (Compound 506)

The reaction and purification conditions described in Example 384 substituting 1,3-dimethyl-1H-pyrazole-5-carboxylic acid for 2-fluorobenzoic acid gave the title compound. $^1$H NMR (501 MHz, DMSO-$d_6$) δ ppm 7.52 (s, 1H), 7.48 (t, J=8 Hz, 1H), 7.27 (s, 1H), 7.03 (dd, J=9, 3 Hz, 1H), 6.81 (br d, J=8 Hz, 1H), 6.56 (s, 1H), 4.45 (s, 2H), 4.18 (m, 1H), 3.90 (s, 3H), 2.30 (m, 1H), 2.13 (s, 3H), 1.75-2.10 (m, 9H); MS (ESI$^+$) m/z 465 (M+H)$^+$.

Example 408: N-{3-[2-(4-chloro-3-fluorophenoxy) acetamido]bicyclo[1.1.1]pentan-1-yl}-2-fluorobenzamide (Compound 507)

The reaction and purification conditions described in Example 6D substituting 2-fluorobenzoic acid for Example 6B gave the title compound. $^1$H NMR (501 MHz, DMSO-$d_6$) δ ppm 8.80 (s, 1H), 8.75 (s, 1H), 7.50 (m, 2H), 7.49 (t, J=8 Hz, 1H), 7.25 (m, 2H), 7.07 (dd, J=9, 3 Hz, 1H), 6.85 (br d, J=8 Hz, 1H), 4.47 (s, 2H), 2.25 (s, 6H); MS (ESI$^+$) m/z 407 (M+H)$^+$.

Example 409: N-{3-[2-(4-chloro-3-fluorophenoxy) acetamido]bicyclo[1.1.1]pentan-1-yl}-3-fluorobenzamide (Compound 508)

The reaction and purification conditions described in Example 6D substituting 3-fluorobenzoic acid for Example 6B gave the title compound. $^1$H NMR (501 MHz, DMSO-$d_6$) δ ppm 9.10 (s, 1H), 8.70 (s, 1H), 7.70 (br d, J=6 Hz, 1H), 7.62 (br d, J=8 Hz, 1H), 7.50 (m, 1H), 7.49 (t, J=8 Hz, 1H), 7.32 (m, 1H), 7.07 (dd, J=9, 3 Hz, 1H), 6.84 (br d, J=8 Hz, 1H), 4.47 (s, 2H), 2.26 (s, 6H); MS (ESI$^+$) m/z 407 (M+H)$^+$.

Example 410: N-{3-[2-(4-chloro-3-fluorophenoxy) acetamido]bicyclo[1.1.1]pentan-1-yl}-2,3-difluorobenzamide (Compound 509)

The reaction and purification conditions described in Example 6D substituting 2,3-difluorobenzoic acid for Example 6B gave the title compound. $^1$H NMR (501 MHz, DMSO-$d_6$) δ ppm 9.08 (s, 1H), 8.75 (s, 1H), 7.55 (m, 1H), 7.50 (t, J=8 Hz, 1H), 7.36 (m, 1H), 7.26 (m, 1H), 7.08 (dd, J=9, 3 Hz, 1H), 6.86 (br d, J=8 Hz, 1H), 4.50 (s, 2H), 2.35 (s, 6H); MS (ESI$^+$) m/z 425 (M+H)$^+$.

Example 411: N-{3-[2-(4-chloro-3-fluorophenoxy) acetamido]bicyclo[1.1.1]pentan-1-yl}-2,5-difluorobenzamide (Compound 510)

The reaction and purification conditions described in Example 6D substituting 2,5-difluorobenzoic acid for Example 6B gave the title compound. $^1$H NMR (501 MHz, DMSO-$d_6$) δ ppm 9.00 (s, 1H), 8.75 (s, 1H), 7.50 (t, J=8 Hz, 1H), 7.38 (m, 3H), 7.08 (dd, J=9, 3 Hz, 1H), 6.86 (br d, J=8 Hz, 1H), 4.50 (s, 2H), 2.23 (s, 6H); MS (ESI$^+$) m/z 425 (M+H)$^+$.

Example 412: N-{3-[2-(4-chloro-3-fluorophenoxy) acetamido]bicyclo[1.1.1]pentan-1-yl}-2,4-difluorobenzamide (Compound 511)

The reaction and purification conditions described in Example 6D substituting 2,4-difluorobenzoic acid for Example 6B gave the title compound. $^1$H NMR (501 MHz, DMSO-$d_6$) δ ppm 8.91 (s, 1H), 8.75 (s, 1H), 7.65 (m, 1H), 7.50 (t, J=8 Hz, 1H), 7.33 (dt, J=8, 3 Hz, 1H), 7.15 (dt, J=8, 3 Hz, 1H), 7.08 (dd, J=9, 3 Hz, 1H), 6.86 (br d, J=8 Hz, 1H), 4.50 (s, 2H), 2.33 (s, 6H); MS (ESI$^+$) m/z 425 (M+H)$^+$.

Example 413: N-{3-[2-(4-chloro-3-fluorophenoxy) acetamido]bicyclo[1.1.1]pentan-1-yl}-2,6-difluorobenzamide (Compound 512)

The reaction and purification conditions described in Example 6D substituting 2,6-difluorobenzoic acid for Example 6B gave the title compound. $^1$H NMR (501 MHz, DMSO-$d_6$) δ ppm 9.28 (s, 1H), 8.75 (s, 1H), 7.51 (m, 1H), 7.50 (t, J=8 Hz, 1H), 7.16 (m, 2H), 7.08 (dd, J=9, 3 Hz, 1H), 6.86 (br d, J=8 Hz, 1H), 4.50 (s, 2H), 2.35 (s, 6H); MS (ESI$^+$) m/z 425 (M+H)$^+$.

Example 414: N-{3-[2-(4-chloro-3-fluorophenoxy) acetamido]bicyclo[1.1.1]pentan-1-yl}-3,5-difluorobenzamide (Compound 513)

The reaction and purification conditions described in Example 6D substituting 3,5-difluorobenzoic acid for Example 6B gave the title compound. $^1$H NMR (501 MHz, DMSO-$d_6$) δ ppm 9.20 (s, 1H), 8.75 (s, 1H), 7.55 (m, 2H), 7.50 (t, J=8 Hz, 1H), 7.46 (m, 1H), 7.08 (dd, J=9, 3 Hz, 1H), 6.86 (br d, J=8 Hz, 1H), 4.50 (s, 2H), 2.35 (s, 6H); MS (ESI$^+$) m/z 425 (M+H)$^+$.

Example 415: N-{3-[2-(4-chloro-3-fluorophenoxy) acetamido]bicyclo[1.1.1]pentan-1-yl}-3,4-difluorobenzamide (Compound 514)

The reaction and purification conditions described in Example 6D substituting 3,4-difluorobenzoic acid for Example 6B gave the title compound. $^1$H NMR (501 MHz, DMSO-$d_6$) δ ppm 9.13 (s, 1H), 8.75 (s, 1H), 7.78 (ddd, J=7, 9, 3 Hz, 1H), 7.75 (m, 1H), 7.55 (m, 1H), 7.50 (t, J=8 Hz, 1H), 7.08 (dd, J=9, 3 Hz, 1H), 6.86 (br d, J=8 Hz, 1H), 4.50 (s, 2H), 2.35 (s, 6H), 2.35 (s, 6H); MS (ESI$^+$) m/z 425 (M+H)$^+$.

Example 416: N-{4-[2-(4-chloro-3-fluorophenoxy) acetamido]-3-hydroxybicyclo[2.2.2]octan-1-yl}-3-ethyl-1,2-oxazole-5-carboxamide (Compound 515)

The title compound was prepared using the methodologies described in Example 130 substituting 3-ethyl-1,2-oxazole-5-carboxylic acid for 5-(difluoromethyl)pyrazine-2-carboxylic. $^1$H NMR (400 MHz, DMSO-$d_6$) δ ppm 8.08 (s, 1H), 7.49 (t, J=8.9 Hz, 1H), 7.28 (s, 1H), 7.06 (dd, J=11.4, 2.8 Hz, 1H), 6.96 (s, 1H), 6.83 (ddd, J=8.9, 2.8, 1.2 Hz, 1H), 5.11 (s, 1H), 4.48 (s, 2H), 4.07 (dd, J=9.8, 3.1 Hz, 1H), 2.66 (q, J=7.6 Hz, 2H), 2.35 (ddd, J=12.5, 9.4, 2.2 Hz, 1H), 2.14-2.01 (m, 1H), 2.05-1.88 (m, 3H), 1.86 (tq, J=9.3, 3.7 Hz, 4H), 1.19 (t, J=7.6 Hz, 3H); MS (ESI$^+$) m/z 466.1 (M+H)$^+$.

Example 417: N-{4-[2-(4-chloro-3-fluorophenoxy) acetamido]-3-hydroxybicyclo[2.2.2]octan-1-yl}-5-methyl-1,3,4-oxadiazole-2-carboxamide (Compound 516)

The title compound was prepared using the methodologies described in Example 130 substituting 5-methyl-1,3,4-oxadiazole-2-carboxylic acid for 5-(difluoromethyl)pyrazine-2-carboxylic. $^1$H NMR (501 MHz, DMSO-$d_6$) δ ppm 8.49 (s, 1H), 7.49 (t, J=8.9 Hz, 1H), 7.29 (s, 1H), 7.06 (dd, J=11.4, 2.9 Hz, 1H), 6.83 (ddd, J=8.9, 2.9, 1.2 Hz, 1H), 4.48 (d, J=0.8 Hz, 2H), 4.08 (ddd, J=9.4, 3.3, 1.4 Hz, 1H), 2.55 (s, 3H), 2.40-2.31 (m, 1H), 2.14-1.79 (m, 9H); MS (ESI$^+$) m/z 453.1 (M+H)$^+$.

Example 418: N-{4-[2-(4-chloro-3-fluorophenoxy) acetamido]-3-hydroxybicyclo[2.2.2]octan-1-yl}-4-fluoro-1,3-dimethyl-1H-pyrazole-5-carboxamide (Compound 517)

The title compound was prepared using the methodologies described in Example 130 substituting Example 399C for 5-(difluoromethyl)pyrazine-2-carboxylic. $^1$H NMR (501 MHz, DMSO-$d_6$) δ ppm 7.55 (d, J=1.6 Hz, 1H), 7.49 (t, J=8.9 Hz, 1H), 7.28 (s, 1H), 7.06 (dd, J=11.4, 2.9 Hz, 1H), 6.83 (ddd, J=9.0, 2.9, 1.2 Hz, 1H), 4.47 (s, 2H), 4.08 (ddd, J=9.5, 3.3, 1.2 Hz, 1H), 3.79 (s, 3H), 2.34 (ddd, J=13.0, 9.5, 2.3 Hz, 1H), 2.14 (d, J=6.3 Hz, 1H), 2.11 (s, 3H), 2.11-2.04 (m, 1H), 2.06-1.95 (m, 1H), 1.98-1.78 (m, 6H); MS (ESI$^+$) m/z 483.1 (M+H)$^+$.

Example 419: N-{3-[2-(4-chloro-3-fluorophenoxy)acetamido]bicyclo[1.1.1]pentan-1-yl}-2-fluoro-4-methoxybenzamide (Compound 185)

The reaction and purification conditions described in Example 6D substituting 2-fluoro-4-methoxybenzoic acid for Example 6B gave the title compound. $^1$H NMR (501 MHz, DMSO-d$_6$) δ ppm 8.74 (s, 1H), 8.62 (d, J=3 Hz, 1H), 7.58 (t, J=8 Hz, 1H), 7.50 (t, J=8 Hz, 1H), 7.08 (dd, J=9, 3 Hz, 1H), 6.82-6.90 (m, 3H), 4.50 (s, 2H), 3.82 (s, 3), 2.32 (s, 6H); MS (ESI$^+$) m/z 437 (M+H)$^+$.

Example 420: N-{3-[2-(4-chloro-3-fluorophenoxy)acetamido]bicyclo[1.1.1]pentan-1-yl}-2-fluoro-3-methoxybenzamide (Compound 519)

The reaction and purification conditions described in Example 6D substituting 2-fluoro-3-methoxybenzoic acid for Example 6B gave the title compound. $^1$H NMR (501 MHz, DMSO-d$_6$) δ ppm 8.91 (s, 1H), 8.75 (s, 1H), 7.50 (t, J=8 Hz, 1H), 1H7.25 (dt, J=2, 8 Hz, 1H), 7.15 (dt, J=2, 8 Hz, 1H), 7.08 (dd, J=9, 3 Hz, 1H), 7.04 (m, 1H), 6.86 (br d, J=8 Hz, 1H), 4.50 (s, 2H), 3.85 (s, 3H), 2.32 (s, 6H); MS (ESI$^+$) m/z 437 (M+H)$^+$.

Example 421: N-{3-[2-(4-chloro-3-fluorophenoxy)acetamido]bicyclo[1.1.1]pentan-1-yl}-2-fluoro-5-methoxybenzamide (Compound 520)

The reaction and purification conditions described in Example 6D substituting 2-fluoro-5-methoxybenzoic acid for Example 6B gave the title compound. $^1$H NMR (501 MHz, DMSO-d$_6$) δ ppm 8.86 (s, 1H), 8.74 (s, 1H), 7.50 (t, J=8 Hz, 1H), 7.19 (t, J=8 Hz, 1H), 7.02-7.10 (m, 3H), 6.86 (br d, J=8 Hz, 1H), 4.50 (s, 2H), 3.76 (s, 3H), 2.33 (s, 6H); MS (ESI$^+$) m/z 437 (M+H)$^+$.

Example 422: N-{3-[2-(3,4-dichlorophenoxy)acetamido]bicyclo[1.1.1]pentan-1-yl}benzamide (Compound 521)

The reaction and purification conditions described in Example 6D substituting benzoic acid for Example 6B and Example 2B for Example 6C gave the title compound. $^1$H NMR (501 MHz, DMSO-d$_6$) δ ppm 9.01 (s, 1H), 8.75 (s, 1H), 7.84 (d, J=8 Hz, 2H), 7.43-7.58 (m, 4H), 7.27 (d, J=3 Hz, 1H), 6.99 (dd, J=8, 3 Hz, 1H), 4.50 (s, 2H), 2.35 (s, 6H); MS (ESI$^+$) m/z 405 (M+H)$^+$.

Example 423: N-{4-[2-(4-chloro-3-fluorophenoxy)acetamido]-3-hydroxybicyclo[2.2.2]octan-1-yl}-2-cyclopropyl-1,3-thiazole-4-carboxamide (Compound 522)

The title compound was prepared using the methodologies described in Example 130 substituting 2-cyclopropyl-1,3-thiazole-4-carboxylic acid for 5-(difluoromethyl)pyrazine-2-carboxylic. $^1$H NMR (501 MHz, DMSO-d$_6$) δ ppm 7.94 (s, 1H), 7.49 (t, J=8.9 Hz, 1H), 7.26 (d, J=18.0 Hz, 2H), 7.06 (dd, J=11.4, 2.9 Hz, 1H), 6.84 (ddd, J=8.9, 2.9, 1.2 Hz, 1H), 5.08 (s, 1H), 4.48 (s, 2H), 4.08 (dd, J=9.5, 3.0 Hz, 1H), 2.40 (dddd, J=20.9, 15.7, 8.8, 3.6 Hz, 2H), 2.14-2.05 (m, 1H), 2.07-1.94 (m, 1H), 1.98-1.80 (m, 7H), 1.17-1.08 (m, 2H), 1.02-0.93 (m, 2H); MS (ESI$^+$) m/z 494.2 (M+H)$^+$.

Example 424: N-{4-[2-(4-chloro-3-fluorophenoxy)acetamido]-3-hydroxybicyclo[2.2.2]octan-1-yl}-2-(methoxymethyl)-1,3-thiazole-4-carboxamide (Compound 523)

The title compound was prepared using the methodologies described in Example 130 substituting 2-(methoxymethyl)-1,3-thiazole-4-carboxylic acid for 5-(difluoromethyl)pyrazine-2-carboxylic. $^1$H NMR (400 MHz, DMSO-d$_6$) δ ppm 8.20 (s, 1H), 7.49 (t, J=8.9 Hz, 1H), 7.34 (s, 1H), 7.28 (s, 1H), 7.06 (dd, J=11.4, 2.9 Hz, 1H), 6.84 (ddd, J=9.0, 2.9, 1.2 Hz, 1H), 4.72 (s, 2H), 4.48 (s, 2H), 4.13-4.04 (m, 1H), 3.41 (s, 3H), 2.39 (ddd, J=12.3, 9.4, 2.2 Hz, 1H), 2.18-2.02 (m, 2H), 2.04-1.79 (m, 7H); MS (ESI$^+$) m/z 498.1 (M+H)$^+$.

Example 425: N-{3-[2-(4-chloro-3-fluorophenoxy)acetamido]bicyclo[1.1.1]pentan-1-yl}-4-(1-hydroxyethyl)pyridine-2-carboxamide (Compound 524)

To a 4 mL vial was added sodium tert-butoxide (0.401 mg, 4.17 μmol), toluene (2 mL), the product of Example 402 (36 mg, 0.083 mmol) and pinacolborane (0.013 mL, 0.092 mmol) in sequential order. The reaction mixture was stirred at ambient temperature for 4 hours. Water (1 mL) and methanol (1 mL) were added to the reaction mixture, and the resulting mixture was concentrated in vacuo. The residue was then taken up in a solvent mix of water (0.5 mL), methanol (1 mL) and N,N-dimethylformamide (1 mL). The resulting solution was filtered through a glass microfiber frit and purified by preparative HPLC [YMC TriArt™ C18 Hybrid 20 μm column, 25×250 mm, flow rate 70 mL/minute, 5-100% gradient of acetonitrile in buffer (0.025 M aqueous ammonium bicarbonate, adjusted to pH 10 with ammonium hydroxide)] to give the title compound (25 mg, 0.058 mmol, 69% yield). $^1$H NMR (400 MHz, DMSO-d$_6$) δ ppm 9.21 (s, 1H), 8.73 (s, 1H), 8.54 (dd, J=5.0, 0.8 Hz, 1H), 8.01-7.97 (m, 1H), 7.56-7.53 (m, 1H), 7.50 (t, J=8.9 Hz, 1H), 7.08 (dd, J=11.4, 2.9 Hz, 1H), 6.86 (ddd, J=9.0, 2.9, 1.2 Hz, 1H), 5.51 (br s, 1H), 4.81 (q, J=7.1 Hz, 1H), 4.49 (s, 2H), 2.35 (s, 6H), 1.33 (d, J=6.5 Hz, 3H); MS (ESI$^+$) m/z 434 (M+H)$^+$.

Example 426: N-{3-[2-(4-chloro-3-fluorophenoxy)acetamido]bicyclo[1.1.1]pentan-1-yl}-4-methylpyridine-2-carboxamide (Compound 525)

The title compound was prepared using the methodologies described above. $^1$H NMR (400 MHz, DMSO-d$_6$) δ ppm 9.19 (s, 1H), 8.73 (s, 1H), 8.47 (dd, J=4.9, 0.7 Hz, 1H), 7.85-7.82 (m, 1H), 7.50 (t, J=8.9 Hz, 1H), 7.42 (ddd, J=4.9, 1.8, 0.8 Hz, 1H), 7.08 (dd, J=11.4, 2.8 Hz, 1H), 6.86 (ddd, J=8.9, 2.9, 1.2 Hz, 1H), 4.49 (s, 2H), 2.40 (d, J=0.8 Hz, 3H), 2.35 (s, 6H); MS (ESI$^+$) m/z 404 (M+H)$^+$.

Example 427: N-{3-[2-(3,4-dichlorophenoxy)acetamido]bicyclo[1.1.1]pentan-1-yl}-4-methylpyridine-2-carboxamide (Compound 526)

The title compound was prepared using the methodologies described above. $^1$H NMR (400 MHz, DMSO-d$_6$) δ ppm 9.19 (s, 1H), 8.73 (s, 1H), 8.47 (d, J=4.9 Hz, 1H), 7.85-7.81 (m, 1H), 7.55 (d, J=8.9 Hz, 1H), 7.45-7.40 (m, 1H), 7.27 (d, J=2.9 Hz, 1H), 6.99 (dd, J=9.0, 2.9 Hz, 1H), 4.50 (s, 2H), 2.40 (s, 3H), 2.34 (s, 6H); MS (ESI$^+$) m/z 420 (M+H)$^+$.

Example 428: N-{3-[2-(4-chloro-3-fluorophenoxy)acetamido]bicyclo[1.1.1]pentan-1-yl}-4-fluoro-2-methoxybenzamide (Compound 5227)

The reaction and purification conditions described in Example 6D substituting 4-fluoro-2-methoxybenzoic acid for Example 6B gave the title compound. $^1$H NMR (501 MHz, DMSO-d$_6$) δ ppm 8.75 (s, 1H), 8.49 (s, 1H), 7.75 (dd, J=9, 8 Hz, 1H), 7.50 (t, J=8 Hz, 1H), 7.08 (dd, J=9, 3 Hz, 1H), 7.04 (dd, J=9, 3 Hz, 1H), 6.90 (m, 2H), 4.50 (s, 2H), 3.90 (s, 3H), 2.35 (s, 6H); MS (ESI$^+$) m/z 437 (M+H)$^+$.

Example 429: N-{3-[2-(4-chloro-3-fluorophenoxy)acetamido]bicyclo[1.1.1]pentan-1-yl}-2-fluoro-6-methoxybenzamide (Compound 528)

The reaction and purification conditions described in Example 6D substituting 2-fluoro-6-methoxybenzoic acid for Example 6B gave the title compound. $^1$H NMR (501 MHz, DMSO-d$_6$) δ ppm 8.92 (s, 1H), 8.75 (s, 1H), 7.50 (t, J=8 Hz, 1H), 7.36 (m, 1H), 7.08 (dd, J=9, 3 Hz, 1H), 6.85-6.95 (m, 3H), 4.50 (s, 2H), 3.86 (s, 3H), 2.35 (s, 6H); MS (ESI$^+$) m/z 437 (M+H)$^+$.

Example 430: N-{3-[2-(4-chloro-3-fluorophenoxy)acetamido]bicyclo[1.1.1]pentan-1-yl}-2-methoxybenzamide (Compound 529)

The reaction and purification conditions described in Example 6D substituting 2-methoxybenzoic acid for Example 6B gave the title compound. $^1$H NMR (501 MHz, DMSO-d$_6$) δ ppm 8.75 (s, 1H), 8.53 (s, 1H), 7.67 (dd, J=8, 2 Hz, 1H), 7.50 (t, J=8 Hz, 1H), 7.45 (m, 1H), 7.12 (t, J=8 Hz, 1H), 7.08 (dd, J=9, 3 Hz, 1H), 7.00 (t, J=8 Hz, 1H), 6.87 (br d, J=8 Hz, 1H), 4.50 (s, 2H), 3.87 (s, 3H), 2.35 (s, 6H); MS (ESI$^+$) m/z 419 (M+H)$^+$.

Example 431: N-{3-[2-(4-chloro-3-fluorophenoxy)acetamido]bicyclo[1.1.1]pentan-1-yl}-3-fluoro-4-methoxybenzamide (Compound 530)

The reaction and purification conditions described in Example 6D substituting 3-fluoro-4-methoxybenzoic acid for Example 6B gave the title compound. $^1$H NMR (501 MHz, DMSO-d$_6$) δ ppm 8.95 (s, 1H), 8.75 (s, 1H), 7.69 (m, 2H), 7.50 (t, J=8 Hz, 1H), 7.22 (t, J=8 Hz, 1H), 7.08 (dd, J=9, 3 Hz, 1H), 6.87 (br d, J=8 Hz, 1H), 4.50 (s, 2H), 3.87 (s, 3H), 2.35 (s, 6H); MS (ESI$^+$) m/z 437 (M+H)$^+$.

Example 432: N-{3-[2-(4-chloro-3-fluorophenoxy)acetamido]bicyclo[1.1.1]pentan-1-yl}-4-fluoro-3-methoxybenzamide (Compound 531)

The reaction and purification conditions described in Example 6D substituting 4-fluoro-3-methoxybenzoic acid for Example 6B gave the title compound. $^1$H NMR (501 MHz, DMSO-d$_6$) δ ppm 9.05 (s, 1H), 8.75 (s, 1H), 7.60 (dd, J=8, 2 Hz, 1H), 7.50 (t, J=8, 1H), 7.46 (m, 1H), 7.28 (dd, J=8, 9 Hz, 1H), 7.08 (dd, J=9, 3 Hz, 1H), 6.86 (br d, J=8 Hz, 1H), 4.50 (s, 2H), 3.88 (s, 3H), 2.35 (s, 6H); MS (ESI$^+$) m/z 437 (M+H)$^+$.

Example 433: N-{3-[2-(4-chloro-3-fluorophenoxy)acetamido]bicyclo[1.1.1]pentan-1-yl}-2-(dimethylamino)benzamide (Compound 532)

The reaction and purification conditions described in Example 6D substituting 2-(dimethylamino)benzoic acid for Example 6B gave the title compound. $^1$H NMR (501 MHz, DMSO-d$_6$) δ ppm 9.58 (s, 1H), 8.78 (s, 1H), 6.78 (br d, J=8 Hz, 1H), 7.58 (m, 2H), 7.50 (t, J=8 Hz, 1H), 7.31 (m, 1H), 7.08 (dd, J=9, 3 Hz, 1H), 6.87 (br d, J=8 Hz, 1H), 4.50 (s, 2H), 2.96 (s, 6H), 2.37 (s, 6H); MS (ESI$^+$) m/z 432 (M+H)$^+$.

Example 434: N-{3-[2-(4-chloro-3-fluorophenoxy)acetamido]bicyclo[1.1.1]pentan-1-yl}-4-methoxybenzamide (Compound 533)

The reaction and purification conditions described in Example 6D substituting 4-methoxybenzoic acid for Example 6B gave the title compound. $^1$H NMR (501 MHz, DMSO-d$_6$) δ ppm 8.87 (s, 1H), 8.75 (s, 1H), 7.82 (d, J=8 Hz, 2H), 7.50 (t, J=8 Hz, 1H), 7.08 (dd, J=9, 3 Hz, 1H), 7.00 (d, J=8 Hz, 2H), 6.87 (br d, J=8 Hz, 1H), 4.50 (s, 2H), 3.82 (s, 3H), 2.35 (s, 6H); MS (ESI$^+$) m/z 419 (M+H)$^+$.

Example 435: N-{3-[2-(4-chloro-3-fluorophenoxy)acetamido]bicyclo[1.1.1]pentan-1-yl}-3-(dimethylamino)benzamide (Compound 534)

The reaction and purification conditions described in Example 6D substituting 3-(dimethylamino)benzoic acid for Example 6B gave the title compound. $^1$H NMR (501 MHz, DMSO-d$_6$) δ ppm 8.88 (s, 1H), 8.73 (s, 1H), 7.50 (t, J=8 Hz, 1H), 7.24 (t, J=8 Hz, 1H), 7.05-7.15 (m, 3H), 6.86 (m, 2H), 4.50 (s, 2H), 2.94 (s, 6H), 2.37 (s, 6H); MS (ESI$^+$) m/z 432 (M+H)$^+$.

Example 436: N-{3-[2-(4-chloro-3-fluorophenoxy)acetamido]bicyclo[1.1.1]pentan-1-yl}-3-methylbenzamide (Compound 535)

3-Methylbenzoic acid (27 mg, 0.20 mmol) and 1-[bis(dimethylamino)methylene]-1H-1,2,3-triazolo[4,5-b]pyridinium 3-oxid hexafluorophosphate (HATU, 84 mg, 0.22 mmol) were mixed in 0.5 mL of N,N-dimethylacetamide. The product of Example 4A (38 mg, 0.13 mmol) in 0.5 mL N,N-dimethylacetamide and N,N-diisopropylethylamine (70 μL, 0.40 mmol) were added. The reaction was stirred at room temperature for 16 hours before being purified by reverse phase chromatography: Phenomenex® Luna® C8(2) 5 m 100 Å AXIA™ column (50 mm×30 mm). A gradient of acetonitrile (A) and 0.1% trifluoroacetic acid in H$_2$O (B) was used at a flow rate of 40 mL/minute (0-0.5 minute 5% A, 0.5-6.5 minutes linear gradient 5-100% A, 6.5-8.5 minutes 100% A, 8.5-9.0 minutes linear gradient 100-5% A, 9.0-10.0 minutes 5% A) to yield the title compound (43 mg, 81%). $^1$H NMR (400 MHz, DMSO-d$_6$) δ ppm 7.65-7.53 (m, 2H), 7.48 (t, J=8.9 Hz, 1H), 7.37-7.30 (m, 2H), 7.06 (dd, J=1 1.3, 2.9 Hz, 1H), 6.86 (ddd, J=9.1, 2.9, 1.2 Hz, 1H), 4.47 (s, 2H), 2.36-2.29 (m, 9H); MS (ESI$^+$) m/z 403 (M+H)$^+$.

Example 437: N-{3-[2-(4-chloro-3-fluorophenoxy)acetamido]bicyclo[1.1.1]pentan-1-yl}-4-(dimethylamino)benzamide (Compound 536)

The title compound was prepared using the methodologies described above. J-j NMR (400 MHz, DMSO-d$_6$) δ ppm 7.73-7.61 (m, 2H), 7.50 (t, J=8.9 Hz, 1H), 7.07 (dd, J=11.3, 2.9 Hz, 1H), 6.87 (ddd, J=9.0, 2.9, 1.2 Hz, 1H), 6.73-6.65 (m, 2H), 4.48 (s, 2H), 2.97 (s, 6H), 2.32 (s, 61H); MS (ESI$^+$) m/z 432 (M+H)$^+$.

Example 438: N-{3-[2-(4-chloro-3-fluorophenoxy)acetamido]bicyclo[1.1.1]pentan-1-yl}-2,5-dimethylfuran-3-carboxamide (Compound 537)

The title compound was prepared using the methodologies described above. $^1$H NMR (400 MHz, DMSO-d) 53 ppm 7.49 (t, J=8.9 Hz, 1H), 7.07 (dd, J=11.3, 2.8 Hz, 1H), 6.87 (ddd, J=9.0, 2.9, 1.2 Hz, 1H), 6.38 (d, J=1.2 Hz, 1H), 4.48 (s, 2H), 2.43 (s, 3H), 2.30 (s, 6H), 2.20 (s, 3I); MS (ESI) m/z 407 (M+H)$^+$.

Example 439: N-{3-[2-(4-chloro-3-fluorophenoxy)acetamido]bicyclo[1.1.1]pentan-1-yl}-2-ethoxybenzamide (Compound 538)

The title compound was prepared using the methodologies described above. $^1$H NMR (400 MHz, DMSO-d$_6$) δ ppm 7.71 (dd, J=7.7, 1.8 Hz, 1H), 7.56-7.34 (m, 2H), 7.18-6.97 (m, 3H), 6.88 (ddd, J=8.9, 2.8, 1.2 Hz, 1H), 4.49 (s, 2H), 4.15 (q, J=6.9 Hz, 2H), 2.34 (s, 6H), 1.38 (t, J=6.9 Hz, 3H); MS (ESI$^+$) m/z 433 (M+H)$^+$.

Example 440: N-{3-[2-(4-chloro-3-fluorophenoxy)acetamido]bicyclo[1.1.1]pentan-1-yl}-2-methyl-1,3-thiazole-4-carboxamide (Compound 539)

The title compound was prepared using the methodologies described above. $^1$H NMR (400 MHz, DMSO-d$_6$) δ ppm 8.05 (s, 1H), 7.49 (i, J=8.9 Hz, 1H), 7.07 (dd, J=11.3, 2.8 Hz, 1H), 6.87 (ddd, J=9.0, 2.9, 1.2 Hz, 1H), 4.48 (s, 2H), 2.69 (s, 3H), 2.34 (s, 6H); MS (ESI$^+$) m/z. 410 (M+H)$^+$.

Example 441: N-{3-[2-(4-chloro-3-fluorophenoxy)acetamido]bicyclo[1.1.1]pentan-1-yl}-5-fluoro-2-methoxybenzamide (Compound 540)

The title compound was prepared using the methodologies described above. $^1$H NMR (400 MHz, DMSO-d) δ ppm 7.49 (t, J=8.9 Hz, 1H), 7.44 (dd, J=8.9, 3.1 Hz, 1H), 7.32 (ddd, J=9.1, 7.9, 3.3 Hz, 1H), 7.16 (dd, J=9.2, 4.3 Hz, 1H), 7.07 (dd, J=11.3, 2.8 Hz, 1H), 6.88 (ddd, J=9.0, 2.9, 1.2 Hz, 1H), 4.49 (s, 2H), 3.86 (s, 3H), 2.35 (s, 6H); MS (ESI$^+$) m/z 437 (M+H)$^+$.

Example 442: N-{3-[2-(4-chloro-3-fluorophenoxy)acetamido]bicyclo[1.1.1]pentan-1-yl}-5-methyl-1,3-thiazole-4-carboxamide (Compound 541)

The title compound was prepared using the methodologies described above. $^1$H NMR (400 MHz, DMSO-d$_6$) δ ppm 8.85 (s, 1H), 7.49 (t, J=8.9 Hz, 1H), 7.07 (dd, J=11.3, 2.8 Hz, 1H), 6.87 (ddd, J=9.0, 2.9, 1.2 Hz, 1H), 4.48 (s, 2H), 2.73 (s, 3H), 2.34 (s, 6H); MS (ESI$^+$) m/z 410 (M+H)$^+$.

Example 443: N-{3-[2-(4-chloro-3-fluorophenoxy)acetamido]bicyclo[1.1.1]pentan-1-yl}-2-[(dimethylamino)methyl]benzamide (Compound 542)

The title compound was prepared using the methodologies described above. $^1$H NMR (400 MHz, DMSO-d$_6$) δ ppm 7.73 (dd, J=7.4, 1.7 Hz, 1H), 7.67-7.56 (m, 3H), 7.50 (t, J=8.9 Hz, 1H), 7.07 (dd, J=11.3, 2.9 Hz, 1H), 6.88 (ddd, J=9.0, 2.9, 1.2 Hz, 1H), 4.50 (s, 2H), 4.28 (s, 2H), 2.77 (s, 6H), 2.40 (s, 6H): MS (ESI$^+$) m/z 446 (M+H)$^+$.

Example 444: N-{3-[2-(4-chloro-3-fluorophenoxy)acetamido]bicyclo[1.1.1]pentan-1-yl}-3-(diethylamino)benzamide (Compound 543)

The title compound was prepared using the methodologies described above. $^1$H NMR (400 MHz, DMSO-d$_6$) δ ppm 7.80-7.67 (m, 2H), 7.59 (t, J=7.9 Hz, 1H), 7.50 (t, J=8.9 Hz, 2H), 7.07 (dd, J=11.3, 2.9 Hz, 1H), 6.88 (ddd, J=9.0, 2.9, 1.2 Hz, 1H), 4.50 (s, 2H), 3.56 (q, J=7.1 Hz, 4I-), 2.37 (s, 6H), 1.03 (t, J=7.1 Hz, 6H); MS (ESI$^+$) m/z 460 (M+H)$^+$.

Example 445: N-{3-[2-(4-chloro-3-fluorophenoxy)acetamido]bicyclo[1.1.1]pentan-1-yl}-5-(trifluoromethyl)furan-3-carboxamide (Compound 544)

The title compound was prepared using the methodologies described above. $^1$H NMR (400 MHz, DMSO-d$_6$) δ ppm 8.41 (d, J=0.8 Hz, 1H), 7.56-7.40 (m, 2H), 7.07 (dd, J=11.3, 2.8 Hz, 1H), 6.87 (ddd, J=9.0, 2.9, 1.2 Hz, 1H), 4.49 (s, 2H), 2.33 (s, 6H); MS (ESI$^+$) m/z 447 (M+H)$^+$.

Example 446: N-{3-[2-(4-chloro-3-fluorophenoxy)acetamido]bicyclo[1.1.1]pentan-1-yl}-3-methylfuran-2-carboxamide (Compound 545)

The title compound was prepared using the methodologies described above. 1H NMR (400 MHz, DMSO-d$_6$) δ ppm 7.61 (d, J=1.7 Hz, 1H), 7.49 (t, J=8.8 Hz, 1H), 7.07 (dd, J=11.3, 2.9 Hz, 1H), 6.87 (ddd, J=9.0, 2.9, 1.2 Hz, 1H), 6.49 (d, J=1.7 Hz, 1H), 4.48 (s, 2H), 2.31 (s, 6H), 2.26 (s, 3H); MS (ESI$^+$) m/z 393 (M+H)$^+$.

Example 447: N-{3-[2-(4-chloro-3-fluorophenoxy)acetamido]bicyclo[1.1.1]pentan-1-yl}-4-[(dimethylamino)methyl]benzamide (Compound 546)

The title compound was prepared using the methodologies described above. $^1$H NMR (400 MHz, DMSO-d$_6$) δ ppm 9.18 (s, 1H), 8.84 (s, 1H), 7.90 (d, J=8.2 Hz, 2H), 7.57 (d, J=8.1 Hz, 2H), 7.50 (t, J=8.9 Hz, 1H), 7.07 (dd, J=11.3, 2.8 Hz, 1H), 6.93-6.77 (m, 1H), 4.49 (s, 2H), 4.28 (s, 2H), 2.71 (s, 6H), 2.36 (s, 6H); MS (ESI$^+$) m/z 446 (M+H)$^+$.

Example 448: N-{3-[2-(4-chloro-3-fluorophenoxy)acetamido]bicyclo[1.1.1]pentan-1-yl}-3-fluoro-2-methoxybenzamide (Compound 547)

The title compound was prepared using the methodologies described above. $^1$H NMR (400 MHz, DMSO-d$_6$) δ ppm 7.50 (L, J=8.8 Hz, 1H), 7.37 (ddd, J=11.6, 8.2, 1.7 Hz, 1H), 7.29 (dt, J=7.8, 1.4 Hz, 1H), 7.20-7.14 (m, 1H), 7.07 (dd, J=11.3, 2.8 Hz, 1H), 6.88 (ddd, J=9.0, 2.9, 1.2 Hz, 1H), 4.49 (s, 2H), 3.87 (d, J=1.4 Hz, 3H), 2.34 (s, 6H); MS (ESI$^+$) m/z 437 (M+H)$^+$.

Example 449: N-{3-[2-(4-chloro-3-fluorophenoxy)acetamido]bicyclo[1.1.1]pentan-1-yl}-3-methoxythiophene-2-carboxamide (Compound 548)

The title compound was prepared using the methodologies described above. $^1$H NMR (400 MHz, DMSO-d$_6$) δ ppm 7.70 (d, J=5.5 Hz, 1H), 7.49 (t, J=8.9 Hz, 1H), 7.18-6.98 (m, 2H), 6.87 (dd, J=8.9, 2.9, 1.2 Hz, 1H), 4.48 (s, 21H), 3.96 (s, 31H), 2.34 (s, 6H): MS (ESI) n/z 425 (M+H)$^+$.

Example 450: N-{3-[2-(4-chloro-3-fluorophenoxy)acetamido]bicyclo[1.1.1]pentan-1-yl}-2-[2-(dimethylamino)ethoxy]benzamide (Compound 549)

The title compound was prepared using the methodologies described above. $^1$H NMR (400 MHz, DMSO-d$_6$) δ ppm 7.57-7.40 (m, 3H), 7.16 (dd, J=8.8, 1.0 Hz, 1H), 7.12-7.00 (m, 2H), 6.87 (ddd, J=8.9, 2.8, 1.2 Hz, 1H), 4.49

(s, 2H), 4.40 (dd, J=5.6, 4.0 Hz, 2H), 3.60-3.45 (m, 2H), 2.91 (s, 6H), 2.34 (s, 6H); MS (ESI$^+$) E/V 476 (M+H)$^+$.

Example 451: N-{3-[2-(4-chloro-3-fluorophenoxy)acetamido]bicyclo[1.1.1]pentan-1-yl}-2-(methoxymethyl)benzamide (Compound 550)

The title compound was prepared using the methodologies described above. $^1$H NMR (400 MHz, DMSO-d$_6$) δ ppm 7.57-7.23 (m, 5H), 7.07 (dd, J=11.3, 2.8 Hz, 1H), 6.88 (ddd, J=9.0, 2.9, 1.2 Hz, 11-), 4.52 (s, 2H), 4.49 (s, 2H), 3.29 (s, 3H), 2.34 (s, 6H); MS (ESI$^+$) m/z 433 (M+H)$^+$.

Example 452: N-{3-[2-(4-chloro-3-fluorophenoxy)acetamido]bicyclo[1.1.1]pentan-1-yl}-3-ethoxythiophene-2-carboxamide (Compound 551)

The title compound was prepared using the methodologies described above. $^1$H NMR (400 MHz, DMSO-d$_6$) δ ppm 7.70 (d, J=5.5 Hz, 1H), 7.49 (t, J=8.9 Hz, 1H), 7.17-6.99 (m, 2H), 6.87 (ddd, J=9.0, 2.9, 1.2 Hz, 1H), 4.49 (s, 2H), 4.26 (q, J=7.0 Hz, 2H), 2.34 (s, 6H), 1.36 (t, J=7.0 Hz, 3H); MS (ESI$^+$) m/z 439 (M+H)$^+$.

Example 453: N-{3-[2-(4-chloro-3-fluorophenoxy)acetamido]bicyclo[1.1.1]pentan-1-yl}-4-(methoxymethyl)benzamide (Compound 552)

The title compound was prepared using the methodologies described above. $^1$H NMR (400 MHz, DMSO-d$_6$) δ ppm 7.86-7.72 (m, 2H), 7.50 (t, J=8.9 Hz, 1H), 7.43-7.32 (m, 2H), 7.07 (dd, J=1.3, 2.8 Hz, 1H), 6.88 (ddd, J=8.9, 2.9, 1.2 Hz, 11H), 4.49 (s, 2H), 4.46 (s, 2H), 3.31 (s, 3H), 2.35 (s, 6H); MS (ESI$^+$) m/z 433 (M+H)$^+$.

Example 454: N-{3-[2-(4-chloro-3-fluorophenoxy)acetamido]bicyclo[1.1.1]pentan-1-yl}-3-[(dimethylamino)methyl]benzamide (Compound 553)

The title compound was prepared using the methodologies described above. $^1$H NMR (400 MHz, DMSO-d$_6$) δ ppm 8.00-7.78 (m, 2H), 7.66 (dt, J=7.7, 1.5 Hz, 1H), 7.58 (t, J=7.6 Hz, 1H), 7.50 (t, J=8.9 Hz, 1H), 7.07 (dd, J=11.3, 2.8 Hz, 1H), 6.88 (ddd, J=8.9, 2.9, 1.2 Hz, 1H), 4.50 (s, 2H), 4.32 (s, 2H), 2.75 (s, 6H), 2.37 (s, 6H); MS (ESI$^+$) m/z 446 (M+H)$^+$.

Example 455: N-{3-[2-(4-chloro-3-fluorophenoxy)acetamido]bicyclo[1.1.1]pentan-1-yl}-2-ethyl-1,3-thiazole-4-carboxamide (Compound 554)

The title compound was prepared using the methodologies described above. 1H NMR (400 MHz, DMSO-d$_6$) δ ppm 8.07 (s, 1H), 7.49 (t, J=8.9 Hz, 1H), 7.07 (dd, J=11.3, 2.9 Hz, 1H), 6.87 (ddd, J=9.0, 2.9, 1.2 Hz, 1H), 4.49 (s, 2H), 3.01 (q, J=7.6 Hz, 2H), 2.35 (s, 6H), 1.32 (t, J=7.5 Hz, 3H); MS (ESI) m/z 424 (M+H)$^+$.

Example 456: N-{3-[2-(4-chloro-3-fluorophenoxy)acetamido]bicyclo[1.1.1]pentan-1-yl}-5-methylfuran-2-carboxamide (Compound 555)

The title compound was prepared using the methodologies described above. $^1$H NMR (400 MHz, DMSO-d$_6$) δ ppm 7.49 (t, J=8.8 Hz, 11H), 7.06 (dd, J=11.3, 2.8 Hz, 1H), 6.98 (d, J=3.4 Hz, 1H), 6.87 (ddd, J=9.0, 2.9, 1.2 Hz, 1H), 6.24 (dt, J=3.4, 1.0 Hz, 1H), 4.48 (s, 2H), 2.31 (d, J=2.1 Hz, 9H); MS (ESI$^+$) m/z 393 (M+H)$^+$.

Example 457: N-{3-[2-(4-chloro-3-fluorophenoxy)acetamido]bicyclo[1.1.1]pentan-1-yl}-2-methylfuran-3-carboxamide (Compound 556)

The title compound was prepared using the methodologies described above. $^1$H NMR (400 MHz, DMSO-d$_6$) δ ppm 7.55-7.35 (min, 2H), 7.07 (dd, J=11.3, 2.8 Hz, 1H), 6.87 (ddd, J=9.0, 2.9, 1.2 Hz, 1H), 6.80 (d, J=2.1 Hz, 1H), 4.48 (s, 2H), 2.53 (p, J=1.9 Hz, 3H), 2.32 (s, 6H); MS (ESI$^+$) m/z 393 (M+H)$^+$.

Example 458: N-{3-[2-(4-chloro-3-fluorophenoxy)acetamido]bicyclo[1.1.1]pentan-1-yl}-4-methoxythiophene-3-carboxamide (Compound 557)

The title compound was prepared using the methodologies described above. $^1$H NMR (400 MHz, DMSO-d$_6$) δ ppm 7.98 (d, J=3.6 Hz, 1H), 7.49 (t, J=8.9 Hz, 1H), 7.07 (dd, J=11.3, 2.8 Hz, 1H), 6.87 (ddd, J=8.8, 2.8, 1.1 Hz, 1H), 6.73 (d, J=3.6 Hz, 1H), 4.48 (s, 2H), 3.86 (s, 3H), 2.34 (s, 6H); MS (ESI$^+$) m/z 425 (M+H)$^+$.

Example 459: N-{3-[2-(4-chloro-3-fluorophenoxy)acetamido]bicyclo[1.1.1]pentan-1-yl}-4-methyl-1,3-thiazole-5-carboxamide (Compound 558)

The title compound was prepared using the methodologies described above. $^1$H NMR (400 MHz, DMSO-d$_6$) δ ppm 9.01 (s, 1H), 7.49 (t, J=8.9 Hz, 1H), 7.07 (dd, J=11.3, 2.8 Hz, 1H), 6.87 (ddd, J=8.9, 2.9, 1.2 Hz, 1H), 4.49 (s, 2H), 2.57 (s, 3H), 2.33 (s, 6H); MS (ESI$^+$) m/z 410 (M+H)$^+$.

Example 460: N-{3-[2-(3,4-dichlorophenoxy)acetamido]bicyclo[1.1.1]pentan-1-yl}-2-methyl-1,3-thiazole-4-carboxamide (Compound 559)

The title compound was prepared using the methodologies described above. $^1$H NMR (501 MHz, DMSO-d$_6$) δ ppm 8.81 (s, 1H), 8.72 (s, 1H), 8.05 (s, 1H), 7.55 (d, J=8.9 Hz, 1H), 7.27 (d, J=2.9 Hz, 1H), 6.99 (dd, J=8.9, 2.9 Hz, 1H), 4.50 (s, 2H), 2.69 (s, 3H), 2.32 (s, 6H); MS (ESI$^+$) m/z 426 (M+H)$^+$.

Example 461: N-{(3S)-4-[2-(4-chloro-3-fluorophenoxy)acetamido]-3-hydroxybicyclo[2.2.2]octan-1-yl}-2-fluorobenzamide (Compound 560)

To a solution of the product of Example 473A (20 mg, 0.053 mmol) in dimethylformamide (0.5 mL) was added 2-fluorobenzoic acid (8.1 mg, 0.058 mmol), 1-[bis(dimethylamino)methylene]-1H-1,2,3-triazolo[4,5-b]pyridinium 3-oxid hexafluorophosphate (HATU, 22.0 mg, 0.058 mmol), and N,N-diisopropylethylamine (0.037 mL, 0.211 mmol) at ambient temperature. The reaction mixture was stirred for 1 hour and then was purified by preparative HPLC [Waters XBridge™ C18 5 μm OBD™ column, 30×100 mm, flow rate 40 mL/minute, 5-100% gradient of acetonitrile in buffer (0.1% trifluoroacetic acid)] to give the title compound (20 mg, 0.043 mmol, 82% yield). $^1$H NMR (400 MHz, DMSO-d$_6$) δ ppm 7.79 (d, J=1.7 Hz, 1H), 7.53-7.43 (m, 3H), 7.30-7.17 (m, 3H), 7.06 (dd, J=11.4, 2.8 Hz, 1H), 6.84 (dd, J=8.9, 2.9 Hz, 1H), 4.48 (s, 2H), 4.07 (dd, J=9.6, 3.0 Hz, 1H), 2.36 (ddd, J=12.6, 9.6, 2.2 Hz, 1H), 2.14-1.79 (m, 9H); $^{19}$F NMR (376 MHz, DMSO-d$_6$) δ ppm −114.03, −115.07; MS (ESI$^+$) m/z 465 (M+H)$^+$.

Example 462: N-{3-[2-(4-chloro-3-fluorophenoxy)acetamido]bicyclo[1.1.1]pentan-1-yl}-2-methylpyrazolo[1,5-a]pyrazine-4-carboxamide (Compound 561)

Example 462A: ethyl 2-methylpyrazolo[1,5-a]pyrazine-4-carboxylate

To a mixture of 4-chloro-2-methylpyrazolo[1,5-a]pyrazine (200 mg, 1.19 mmol), 1,4-bis(diphenylphosphino)butane-palladium(II) chloride (Pd(dppb)Cl$_2$, 18.6 mg, 0.029 mmol), and triethylamine (0.16 mL, 1.17 mmol) in a 20 mL pressure tube was added ethanol (8 mL). The mixture was degassed with nitrogen followed by carbon monoxide. Under an atmosphere of carbon monoxide (60 psi), the mixture was warmed to 120° C. for 24.5 hours. The reaction mixture was allowed to cool to ambient temperature and was passed through diatomaceous earth. The filtrate was concentrated under reduced pressure to give the title compound (186 mg, 0.9 mmol, 76% yield). $^1$H NMR (501 MHz, DMSO-d$_6$) δ ppm 8.94 (dd, J=4.5, 1.0 Hz, 1H), 8.00 (d, J=4.5 Hz, 1H), 7.06 (d, J=0.8 Hz, 1H), 4.43 (q, J=7.1 Hz, 2H), 1.39 (t, J=7.1 Hz, 3H); MS (ESI$^+$) m/z 206 (M+H)$^+$.

Example 462B: 2-methylpyrazolo[1,5-a]pyrazine-4-carboxylic acid

To a solution of Example 462A (180 mg, 0.88 mmol) in tetrahydrofuran (3 mL) were added lithium hydroxide (84 mg, 3.51 mmol) and water (0.75 mL). The mixture was stirred at ambient temperature for 18 hours. The reaction mixture was diluted with water (10 mL) and then was acidified with 6 N HCl (aqueous) to pH=3. The solution was concentrated under reduced pressure, and the residue was purified by preparative HPLC [Waters XBridge™ C18 5 μm OBD™ column, 30×100 mm, flow rate 40 mL/minute, 5-100% gradient of acetonitrile in buffer (0.1% trifluoroacetic acid)] to give the title compound (60 mg, 0.34 mmol, 39% yield). $^1$H NMR (501 MHz, DMSO-d$_6$) δ ppm 8.90 (dd, J=4.6, 0.9 Hz, 1H), 7.98 (d, J=4.6 Hz, 1H), 7.06 (s, 1H), 2.50 (s, 3H).

Example 462C: N-{3-[2-(4-chloro-3-fluorophenoxy)acetamido]bicyclo[0.1.1]pentan-1-yl}-2-methylpyrazolo[1,5-a]pyrazine-4-carboxamide The reaction and purification conditions described in Example 383 substituting the product of Example 462B for quinoxaline-2-carboxylic acid gave the title compound. $^1$H NMR (400 MHz, DMSO-d$_6$) δ ppm 9.42 (s, 1H), 8.87 (dd, J=4.6, 1.0 Hz, 1H), 8.75 (s, 1H), 7.88 (d, J=4.6 Hz, 1H), 7.50 (t, J=8.9 Hz, 1H), 7.19 (s, 1H), 7.09 (dd, J=11.4, 2.8 Hz, 1H), 6.87 (ddd, J=8.9, 2.8, 1.2 Hz, 1H), 4.50 (s, 2H), 2.49 (s, 3H), 2.38 (s, 6H); MS (ESI$^+$) m/z 444 (M+H)$^+$.

Example 463: N-{3-[2-(3,4-dichlorophenoxy)acetamido]bicyclo[1.1.1]pentan-1-yl}-2-methylpyrazolo[1,5-a]pyrazine-4-carboxamide (Compound 562)

The reaction and purification conditions described in Example 401 substituting the product of Example 462B for the product of Example 399C gave the title compound. $^1$H NMR (400 MHz, DMSO-d$_6$) δ ppm 9.42 (s, 1H), 8.87 (dd, J=4.5, 1.0 Hz, 1H), 8.76 (s, 1H), 7.88 (d, J=4.6 Hz, 1H), 7.56 (d, J=8.9 Hz, 1H), 7.28 (d, J=2.9 Hz, 1H), 7.19 (s, 1H), 7.00 (dd, J=8.9, 2.9 Hz, 1H), 4.51 (s, 2H), 2.49 (s, 3H), 2.38 (s, 6H); MS (ESI$^+$) m/z 460 (M+H)$^+$.

Example 464: N-{3-[2-(4-chloro-3-fluorophenoxy)acetamido]bicyclo[1.1.1]pentan-1-yl}-2-(trifluoromethyl)-1,3-thiazole-5-carboxamide (Compound 563)

The title compound was prepared using the methodologies described above. $^1$H NMR (400 MHz, DMSO-d$_6$) δ ppm 9.59 (s, 1H), 8.75 (s, 1H), 8.56 (d, J=1.3 Hz, 1H), 7.47 (t, J=8.9 Hz, 1H), 7.05 (dd, J=11.3, 2.8 Hz, 1H), 6.83 (ddd, J=9.0, 2.9, 1.2 Hz, 1H), 4.46 (s, 2H), 2.32 (s, 6H); MS (ESI$^+$) m/z 464 (M+H)$^+$.

Example 465: N-{3-[2-(4-chloro-3-fluorophenoxy)acetamido]bicyclo[1.1.1]pentan-1-yl}-3-methyl-1,2-thiazole-5-carboxamide (Compound 564)

The title compound was prepared using the methodologies described above. $^1$H NMR (501 MHz, DMSO-d$_6$) δ ppm 9.35 (s, 1H), 8.75 (s, 1H), 7.63 (s, 1H), 7.49 (t, J=8.9 Hz, 1H), 7.07 (dd, J=11.4, 2.8 Hz, 1H), 6.85 (ddd, J=9.0, 2.8, 1.2 Hz, 1H), 4.48 (s, 2H), 2.43 (s, 3H), 2.32 (s, 6H); MS (ESI$^+$) m/z 410 (M+H)$^+$.

Example 466: N-{4-[2-(4-chloro-3-fluorophenoxy)acetamido]-3-hydroxybicyclo[2.2.2]octan-1-yl}-1-methyl-5-(trifluoromethyl)-1H-pyrazole-3-carboxamide (Compound 565)

The title compound was prepared using the methodologies described in Example 130 substituting 1-methyl-5-(trifluoromethyl)-1H-pyrazole-3-carboxylic acid for 5-(difluoromethyl)pyrazine-2-carboxylic. $^1$H NMR (501 MHz, DMSO-d$_6$) δ ppm 7.49 (t, J=8.9 Hz, 1H), 7.39 (s, 1H), 7.28 (s, 1H), 7.20 (s, 1H), 7.06 (dd, J=11.4, 2.9 Hz, 1H), 6.84 (ddd, J=9.0, 2.9, 1.2 Hz, 1H), 5.09 (s, 1H), 4.48 (s, 2H), 4.07 (ddd, J=9.5, 3.3, 1.3 Hz, 1H), 4.00 (d, J=0.9 Hz, 3H), 2.37 (ddd, J=12.5, 9.4, 2.5 Hz, 1H), 2.15-1.79 (m, 9H); MS (ESI$^+$) m/z 519.1 (M+H)$^+$.

Example 467: N-{4-[2-(4-chloro-3-fluorophenoxy)acetamido]-3-hydroxybicyclo[2.2.2]octan-1-yl}-5-(trifluoromethyl)furan-3-carboxamide (Compound 566)

The title compound was prepared using the methodologies described in Example 130 substituting 5-(trifluoromethyl)furan-3-carboxylic acid for 5-(difluoromethyl)pyrazine-2-carboxylic. $^1$H NMR (400 MHz, DMSO-d$_6$) δ ppm 8.35 (s, 1H), 7.56-7.48 (m, 2H), 7.39 (t, J=8.9 Hz, 1H), 7.18 (s, 1H), 6.97 (dd, J=11.4, 2.9 Hz, 1H), 6.74 (ddd, J=9.0, 2.9, 1.2 Hz, 1H), 4.39 (s, 2H), 3.98 (dd, J=9.6, 3.1 Hz, 1H), 2.26 (ddd, J=12.4, 9.5, 2.2 Hz, 1H), 2.07-1.93 (m, 1H), 1.98-1.86 (m, 1H), 1.90-1.82 (m, 1H), 1.86-1.68 (m, 6H); MS (ESI$^+$) m/z 505.0 (M+H)$^+$.

Example 468: N-{4-[2-(4-chloro-3-fluorophenoxy)acetamido]-3-hydroxybicyclo[2.2.2]octan-1-yl}-3-ethyl-1,2,4-oxadiazole-5-carboxamide (Compound 567)

The title compound was prepared using the methodologies described in Example 130 substituting 3-ethyl-1,2,4-oxadiazole-5-carboxylic acid for 5-(difluoromethyl)pyrazine-2-carboxylic. $^1$H NMR (400 MHz, DMSO-d$_6$) δ ppm 8.60 (s, 1H), 7.45 (t, J=8.9 Hz, 1H), 7.26 (s, 1H), 7.02 (dd, J=11.3, 2.8 Hz, 1H), 6.80 (ddd, J=9.0, 2.8, 1.2 Hz, 1H), 4.44 (s, 2H), 4.09-4.01 (m, 1H), 2.75 (q, J=7.5 Hz, 2H), 2.32 (ddd, J=12.7, 9.6, 1.8 Hz, 1H), 2.03 (ddd, J=18.3, 11.0, 7.9 Hz, 2H), 1.87 (dtd, J=23.3, 13.5, 12.2, 5.9 Hz, 7H), 1.22 (t, J=7.6 Hz, 3H); MS (ESI$^+$) m/z 467.0 (M+H)$^+$.

Example 469: N-{3-[2-(4-chloro-3-fluorophenoxy)acetamido]bicyclo[1.1.1]pentan-1-yl}-5-(methoxymethyl)pyridine-3-carboxamide (Compound 568)

The title compound was prepared using the methodologies described above. $^1$H NMR (400 MHz, DMSO-d$_6$) δ ppm 9.26 (s, 1H), 8.91 (d, J=2.2 Hz, 1H), 8.75 (s, 1H), 8.64 (d, J=2.1 Hz, 1H), 8.13 (t, J=2.2 Hz, 1H), 7.50 (t, J=8.9 Hz, 1H), 7.08 (dd, J=11.4, 2.9 Hz, 1H), 6.86 (ddd, J=9.0, 2.9, 1.2 Hz, 1H), 4.54-4.45 (m, 4H), 3.33 (s, 3H), 2.35 (s, 6H); MS (APCI) m/z 434 (M+H)$^+$.

Example 470: N-{3-[2-(3,4-dichlorophenoxy)acetamido]bicyclo[1.1.1]pentan-1-yl}-5-(methoxymethyl)pyridine-3-carboxamide (Compound 569)

The title compound was prepared using the methodologies described above. $^1$H NMR (501 MHz, DMSO-d$_6$) δ ppm 9.31 (s, 1H), 8.94 (d, J=2.2 Hz, 1H), 8.76 (s, 1H), 8.68 (d, J=2.0 Hz, 1H), 8.22 (t, J=2.1 Hz, 1H), 7.55 (d, J=8.9 Hz, 1H), 7.27 (d, J=2.9 Hz, 1H), 7.00 (dd, J=8.9, 2.9 Hz, 1H), 4.52 (s, 2H), 4.51 (s, 2H), 3.34 (s, 3H), 2.35 (s, 6H); MS (APCI) m/z 450 (M+H)$^+$.

Example 471: N-{3-[2-(4-chlorophenoxy)acetamido]bicyclo[1.1.1]pentan-1-yl}-6-(trifluoromethoxy)pyridine-3-carboxamide (Compound 570)

The title compound was prepared using the methodologies described above. $^1$H NMR (501 MHz, DMSO-d$_6$) δ ppm 9.28 (s, 1H), 8.76 (dd, J=2.6, 0.7 Hz, 1H), 8.75 (s, 1H), 8.38 (dd, J=8.6, 2.5 Hz, 1H), 7.38 (dd, J=8.5, 0.7 Hz, 1H), 7.37-7.33 (m, 2H), 7.01-6.96 (m, 2H), 4.45 (s, 2H), 2.35 (s, 6H); MS (ESI$^+$) m/z 456 (M+H)$^+$.

Example 472: N-{4-[2-(4-chloro-3-fluorophenoxy)acetamido]bicyclo[2.1.1]hexan-1-yl}-3-ethyl-1-methyl-1H-pyrazole-5-carboxamide (Compound 571)

The title compound was prepared using the methodologies described above. $^1$H NMR (400 MHz, DMSO-d$_6$) δ ppm 8.65 (s, 1H), 8.49 (s, 1H), 7.50 (t, J=8.9 Hz, 1H), 7.07 (dd, J=11.4, 2.9 Hz, 1H), 6.86 (ddd, J=8.9, 2.8, 1.2 Hz, 1H), 6.68 (s, 1H), 4.49 (s, 2H), 3.95 (s, 3H), 2.57-2.50 (m, 2H), 2.15-2.07 (m, 2H), 1.90-1.78 (m, 6H), 1.15 (t, J=7.6 Hz, 3H); MS (ESI$^+$) m/z 435 (M+H)$^+$.

Example 473: N-{(3S)-4-[2-(4-chloro-3-fluorophenoxy)acetamido]-3-hydroxybicyclo[2.2.2]octan-1-yl}-2-methyl-1,3-thiazole-4-carboxamide (Compound 572)

Example 473A: N-[(2S)-4-amino-2-hydroxybicyclo[2.2.2]octan-1-yl]-2-(4-chloro-3-fluorophenoxy)acetamide, hydrochloric acid The title compound was isolated by chiral preparative SFC of Example 130E as the first peak eluted off the column, followed by preparative HPLC to give the title compound using the methodologies described in Example 398A. $^1$H NMR (400 MHz, methanol-d$_4$) δ ppm 7.36 (t, J=8.71 Hz, 1H), 6.91 (dd, J=10.91, 2.76 Hz, 1H), 6.80 (dd, J=8.82, 1.32 Hz, 1H), 4.45 (s, 2H), 4.28 (br d, J=8.60 Hz, 1H), 2.22-1.98 (m, 4H), 1.90 (td, J=11.74, 4.30 Hz, 1H), 1.82-1.49 (m, 8H); MS (ESI$^+$) m/z 343.1 (M+H)$^+$.

Example 473B: N-{(3S)-4-[2-(4-chloro-3-fluorophenoxy)acetamido]-3-hydroxybicyclo[2.2.2]octan-1-yl}-2-methyl-1,3-thiazole-4-carboxamide A mixture of Example 473A (40.0 mg, 0.105 mmol), 2-methylthiazole-4-carboxylic acid (17.36 mg, 0.121 mmol) and N-ethyl-N-isopropylpropan-2-amine (0.064 mL, 0.369 mmol) in N,N-dimethylformamide (1.5 mL) was treated with 2-(3H-[1,2,3]triazolo[4,5-b]pyridin-3-yl)-1,1,3,3-tetramethylisouronium hexafluorophosphate(V) (50.1 mg, 0.132 mmol), and the reaction mixture was stirred at ambient temperature for 30 minutes. Volatiles were removed, and the residue was purified by HPLC (20-100% acetonitrile in 0.1% trifluoroacetic acid/water on Phenomenex® C18 10 μm (250 mm×50 mm) column at a flowrate of 50 mL/minute) to give 37 mg of product as a solid. $^1$H NMR (501 MHz, DMSO-d$_6$) δ ppm 8.03 (s, 1H), 7.49 (t, J=8.9 Hz, 1H), 7.30 (d, J=13.7 Hz, 2H), 7.06 (dd, J=11.4, 2.9 Hz, 1H), 6.84 (ddd, J=9.0, 2.9, 1.2 Hz, 1H), 4.48 (d, J=0.9 Hz, 2H), 4.08 (ddd, J=9.5, 3.3, 1.3 Hz, 1H), 2.68 (s, 3H), 2.39 (ddd, J=12.7, 9.4, 2.3 Hz, 1H), 2.17-2.00 (m, 2H), 2.00-1.92 (m, 1H), 1.95-1.80 (m, 6H); MS (ESI$^+$) m/z 468.0 (M+H)$^+$.

Example 474: N-{3-[2-(4-chloro-3-fluorophenoxy)acetamido]bicyclo[1.1.1]pentan-1-yl}-1,3-oxazole-5-carboxamide (Compound 573)

The title compound was prepared using the methodologies described above. $^1$H NMR (400 MHz, DMSO-d$_6$) δ ppm 9.16 (s, 1H), 8.71 (s, 1H), 8.50 (s, 1H), 7.71 (s, 1H), 7.46 (t, J=8.9 Hz, 1H), 7.04 (dd, J=11.4, 2.8 Hz, 1H), 6.82 (ddd, J=9.0, 2.9, 1.2 Hz, 1H), 4.45 (s, 2H), 2.28 (s, 6H); MS (APCI) m/z 380 (M+H)$^+$.

Example 475: N-{4-[2-(4-chloro-3-fluorophenoxy)acetamido]bicyclo[2.1.1]hexan-1-yl}-6-(difluoromethoxy)pyridine-3-carboxamide (Compound 574)

The title compound was prepared using the methodologies described above. $^1$H NMR (400 MHz, DMSO-d$_6$) δ ppm 8.94 (s, 1H), 8.69 (dd, J=2.5, 0.7 Hz, 1H), 8.51 (s, 1H), 8.30 (dd, J=8.6, 2.4 Hz, 1H), 7.77 (t, J=72.4 Hz, 1H), 7.50 (t, J=8.9 Hz, 1H), 7.16 (dd, J=8.6, 0.7 Hz, 1H), 7.08 (dd, J=11.4, 2.8 Hz, 1H), 6.86 (ddd, J=9.0, 2.9, 1.2 Hz, 1H), 4.49 (s, 2H), 2.21-2.08 (m, 2H), 1.93-1.81 (m, 6H); MS (ESI$^+$) m/z 470 (M+H)$^+$.

Example 476: N-{(3S)-4-[2-(4-chloro-3-fluorophenoxy)acetamido]-3-hydroxybicyclo[2.2.2]octan-1-yl}-3-methyl-1,2,4-oxadiazole-5-carboxamide (Compound 575)

The title compound was prepared using the methodologies described in Example 473 substituting 3-methyl-1,2,4-oxadiazole-5-carboxylic acid for 2-methylthiazole-4-carboxylic acid. $^1$H NMR (400 MHz, DMSO-d$_6$) δ ppm 8.61 (s, 1H), 7.45 (t, J=8.9 Hz, 1H), 7.26 (s, 1H), 7.02 (dd, J=11.4, 2.8 Hz, 1H), 6.80 (ddd, J=9.1, 2.9, 1.2 Hz, 1H), 5.10 (d, J=4.1 Hz, 1H), 4.44 (s, 2H), 4.05 (d, J=9.4 Hz, 1H), 2.37 (m, 4H), 2.12-1.75 (m, 7H); MS (ESI$^+$) m/z 453.1 (M+H)$^+$.

Example 477: N-{4-[2-(4-chloro-3-fluorophenoxy)acetamido]-3-hydroxybicyclo[2.2.2]octan-1-yl}-3-methoxy-1,2-oxazole-5-carboxamide (Compound 576)

The title compound was prepared using the methodologies described in Example 130 substituting 3-methoxy-1,2-oxazole-5-carboxylic acid for 5-(difluoromethyl)pyrazine-2-carboxylic. $^1$H NMR (400 MHz, DMSO-d$_6$) δ ppm 8.08 (s, 1H), 7.49 (t, J=8.8 Hz, 1H), 7.28 (s, 1H), 7.06 (dd, J=11.4, 2.8 Hz, 1H), 6.87-6.74 (m, 2H), 4.47 (s, 2H), 4.07 (dd, J=9.5, 3.1 Hz, 1H), 3.92 (s, 3H), 2.39-2.28 (m, 1H), 2.15-2.03 (m, 1H), 2.07-1.98 (m, 1H), 2.00-1.82 (m, 6H), 1.86-1.78 (m, 1H); MS (ESI$^+$) m/z 468.0 (M+H)$^+$.

Example 478: N-{4-[2-(4-chloro-3-fluorophenoxy)acetamido]-3-hydroxybicyclo[2.2.2]octan-1-yl}-3-(propan-2-yl)-1,2-oxazole-5-carboxamide (Compound 577)

The title compound was prepared using the methodologies described in Example 130 substituting 3-(propan-2-yl)-1,2-oxazole-5-carboxylic acid for 5-(difluoromethyl)pyrazine-2-carboxylic. $^1$H NMR (400 MHz, DMSO-d$_6$) δ ppm 8.07 (s, 1H), 7.49 (t, J=8.9 Hz, 1H), 7.28 (s, 1H), 7.10 6.98-(m, 2H), 6.83 (ddd, J=9.0, 2.8, 1.2 Hz, 1H), 5.10 (s, 1H), 4.48 (s, 2H), 4.07 (dd, J=9.6, 3.1 Hz, 1H), 3.03 (p, J=6.9 Hz, 1H), 2.35 (ddd, J=12.5, 9.5, 1.9 Hz, 1H), 2.16-1.95 (m, 2H), 2.00-1.93 (m, 2H), 1.87 (tdd, J=12.1, 7.2, 3.5 Hz, 5H), 1.22 (d, J=6.9 Hz, 6H); MS (ESI$^+$) m/z 480.1 (M+H)$^+$.

Example 479: N-{4-[2-(4-chloro-3-fluorophenoxy)acetamido]-3-hydroxybicyclo[2.2.2]octan-1-yl}-3-methyl-1,2-thiazole-5-carboxamide (Compound 578)

The title compound was prepared using the methodologies described in Example 130 substituting 3-methyl-1,2-thiazole-5-carboxylic acid for 5-(difluoromethyl)pyrazine-2-carboxylic. $^1$H NMR (400 MHz, DMSO-d$_6$) δ ppm 8.03 (s, 1H), 7.72 (s, 1H), 7.49 (t, J=8.9 Hz, 1H), 7.28 (s, 1H), 7.06 (dd, J=11.4, 2.9 Hz, 1H), 6.83 (ddd, J=9.0, 2.9, 1.2 Hz, 1H), 4.48 (s, 2H), 4.12-4.04 (m, 1H), 2.43 (s, 3H), 2.40-2.30 (m, 1H), 2.16-1.79 (m, 9H); MS (ESI$^+$) m/z 468.0 (M+H)$^+$.

Example 480: N-{4-[2-(4-chloro-3-fluorophenoxy)acetamido]-3-hydroxybicyclo[2.2.2]octan-1-yl}-6-(2,2,2-trifluoroethoxy)pyridine-3-carboxamide (Compound 579)

The title compound was prepared using the methodologies described in Example 130 substituting 6-(2,2,2-trifluoroethoxy)pyridine-3-carboxylic acid for 5-(difluoromethyl)pyrazine-2-carboxylic. $^1$H NMR (400 MHz, DMSO-d$_6$) δ ppm 8.59 (d, J=2.4 Hz, 1H), 8.15 (dd, J=8.7, 2.4 Hz, 1H), 7.81 (s, 1H), 7.49 (t, J=8.8 Hz, 1H), 7.28 (s, 1H), 7.11-6.99 (m, 2H), 6.84 (ddd, J=8.9, 2.9, 1.2 Hz, 1H), 5.05 (q, J=9.0 Hz, 2H), 4.48 (s, 2H), 4.12-4.04 (m, 1H), 2.38 (ddd, J=12.5, 9.4, 2.3 Hz, 1H), 2.18-1.77 (m, 9H); MS (ESI$^+$) m/z 546.2 (M+H)$^+$.

Example 481: tert-butyl {[2-({3-[2-(3,4-dichlorophenoxy)acetamido]bicyclo[1.1.1]pentan-1-yl}carbamoyl)pyridin-4-yl]methyl}carbamate (Compound 580)

The title compound was prepared using the methodologies described above. $^1$H NMR (400 MHz, DMSO-d$_6$) δ ppm 9.23 (s, 1H), 8.73 (s, 1H), 8.54 (d, J=4.9 Hz, 1H), 7.89 (s, 1H), 7.60-7.52 (m, 2H), 7.43 (dd, J=5.0, 1.7 Hz, 1H), 7.27 (d, J=2.9 Hz, 1H), 6.99 (dd, J=9.0, 2.9 Hz, 1H), 4.50 (s, 2H), 4.22 (d, J=6.2 Hz, 2H), 2.35 (s, 6H), 1.40 (s, 9H); MS (ESI$^+$) m/z 535 (M+H)$^+$.

Example 482: 3-tert-butyl-N-{(3S)-4-[2-(4-chloro-3-fluorophenoxy)acetamido]-3-hydroxybicyclo[2.2.2]octan-1-yl}-1,2-oxazole-5-carboxamide (Compound 581)

The title compound was prepared using the methodologies described in Example 473 substituting 3-tert-butyl-1,2-oxazole-5-carboxylic acid for 2-methylthiazole-4-carboxylic acid. $^1$H NMR (400 MHz, DMSO-d$_6$) δ ppm 8.07 (s, 1H), 7.49 (t, J=8.9 Hz, 1H), 7.30 (s, 1H), 7.06 (d, J=12.8 Hz, 2H), 6.83 (ddd, J=9.0, 2.9, 1.2 Hz, 1H), 4.48 (s, 2H), 4.11-4.03 (m, 1H), 2.40-2.29 (m, 1H), 2.16-2.03 (m, 1H), 2.02 (s, 2H), 1.89 (dq, J=24.1, 10.9, 9.1 Hz, 6H), 1.28 (s, 9H); MS (ESI$^+$) m/z 494.1 (M+H)$^+$.

Example 483: N-{3-[2-(4-chloro-3-fluorophenoxy)acetamido]bicyclo[1.1.1]pentan-1-yl}-1-methyl-3-(trifluoromethyl)-1H-pyrazole-5-carboxamide (Compound 582)

The title compound was prepared using the methodologies described above. $^1$H NMR (400 MHz, DMSO-d$_6$) δ ppm 9.21 (s, 1H), 8.77 (s, 1H), 7.50 (t, J=8.9 Hz, 1H), 7.31 (s, 1H), 7.08 (dd, J=11.4, 2.8 Hz, 1H), 6.86 (ddd, J=9.0, 2.9, 1.2 Hz, 1H), 4.49 (s, 2H), 4.12 (s, 3H), 2.34 (s, 6H); MS (ESI$^+$) m/z 461 (M+H)$^+$.

Example 484: N-{3-[2-(4-chloro-3-fluorophenoxy)acetamido]bicyclo[1.1.1]pentan-1-yl}-2-cyclopropyl-1,3-oxazole-5-carboxamide (Compound 583)

The title compound was prepared using the methodologies described above. $^1$H NMR (400 MHz, DMSO-d$_6$) δ ppm 8.98 (s, 1H), 8.74 (s, 1H), 7.55 (s, 1H), 7.50 (t, J=8.9 Hz, 1H), 7.08 (dd, J=11.4, 2.8 Hz, 1H), 6.86 (ddd, J=9.0, 2.9, 1.2 Hz, 1H), 4.49 (s, 2H), 2.31 (s, 6H), 2.18-2.08 (m, 1H), 1.12-0.99 (m, 4H); MS (ESI$^+$) m/z 420 (M+H)$^+$.

Example 485: N-{3-[2-(3,4-dichlorophenoxy)acetamido]bicyclo[1.1.1]pentan-1-yl}-3-ethyl-1-methyl-1H-pyrazole-5-carboxamide (Compound 584)

The title compound was prepared using the methodologies described above. $^1$H NMR (400 MHz, DMSO-d$_6$) δ ppm 8.89 (s, 1H), 8.74 (s, 1H), 7.55 (d, J=9.0 Hz, 1H), 7.27 (d, J=2.9 Hz, 1H), 7.00 (dd, J=9.0, 2.9 Hz, 1H), 6.67 (s, 1H), 4.50 (s, 2H), 3.96 (s, 3H), 2.55-2.49 (m, 2H), 2.31 (s, 6H), 1.15 (t, J=7.6 Hz, 3H); MS (ESI$^+$) m/z 437 (M+H)$^+$.

Example 486: N-{3-[2-(3,4-dichlorophenoxy)acetamido]bicyclo[1.1.1]pentan-1-yl}-2-methyl-1,3-thiazole-5-carboxamide (Compound 585)

The title compound was prepared using the methodologies described above. $^1$H NMR (400 MHz, DMSO-d$_6$) δ ppm 9.14 (s, 1H), 8.74 (s, 1H), 8.16 (s, 1H), 7.55 (d, J=8.9 Hz, 1H), 7.27 (d, J=2.9 Hz, 1H), 6.99 (dd, J=9.0, 2.9 Hz, 1H), 4.50 (s, 2H), 2.65 (s, 3H), 2.31 (s, 6H); MS (ESI$^+$) m/z 426 (M+H)$^+$.

Example 487: N-{3-[2-(4-chloro-3-fluorophenoxy)acetamido]bicyclo[1.1.1]pentan-1-yl}quinoline-2-carboxamide (Compound 586)

The reaction and purification conditions described in Example 383 substituting quinoline-2-carboxylic acid for quinoxaline-2-carboxylic acid gave the title compound. $^1$H NMR (400 MHz, DMSO-d$_6$) δ ppm 9.40 (s, 1H), 8.77 (s, 1H), 8.56 (d, J=8.5 Hz, 1H), 8.19-8.13 (m, 1H), 8.12 (d, J=8.5 Hz, 1H), 8.08 (dd, J=8.2, 1.4 Hz, 1H), 7.88 (ddd, J=8.5, 6.8, 1.5 Hz, 1H), 7.72 (ddd, J=8.0, 6.8, 1.2 Hz, 1H), 7.51 (t, J=8.9 Hz, 1H), 7.10 (dd, J=11.3, 2.8 Hz, 1H), 6.88 (ddd, J=9.0, 2.9, 1.2 Hz, 1H), 4.51 (s, 2H), 2.42 (s, 6H); $^{19}$F NMR (376 MHz, DMSO-d$_6$) δ ppm −114.07; MS (ESI$^+$) m/z 440 (M+H)$^+$.

Example 488: N-{3-[2-(4-chloro-3-fluorophenoxy)acetamido]bicyclo[1.1.1]pentan-1-yl}quinoline-3-carboxamide (Compound 587)

The reaction and purification conditions described in Example 383 substituting quinoline-3-carboxylic acid for quinoxaline-2-carboxylic acid gave the title compound. $^1$H NMR (400 MHz, DMSO-d$_6$) δ ppm 9.42 (s, 1H), 9.28 (d, J=2.2 Hz, 1H), 8.87 (d, J=2.2 Hz, 1H), 8.79 (s, 1H), 8.14-8.05 (m, 2H), 7.90 (ddd, J=8.5, 6.8, 1.4 Hz, 1H), 7.72 (ddd, J=8.0, 6.8, 1.2 Hz, 1H), 7.51 (t, J=8.8 Hz, 1H), 7.10 (dd, J=11.4, 2.8 Hz, 1H), 6.88 (ddd, J=9.0, 2.9, 1.2 Hz, 1H), 4.51 (s, 2H), 2.40 (s, 6H); 19F NMR (376 MHz, DMSO-d$_6$) δ ppm −74.90, −114.06; MS (ESI$^+$) m/z 440 (M+H)$^+$.

Example 489: N-{(2S)-4-[2-(4-chloro-3-fluorophenoxy)acetamido]-2-hydroxybicyclo[2.2.2]octan-1-yl}pyridine-2-carboxamide (Compound 588)

The reaction and purification conditions described in Example 384 substituting picolinic acid for 2-fluorobenzoic acid gave the title compound. $^1$H NMR (501 MHz, DMSO-d$_6$) δ ppm 8.60 (br d, J=7 Hz, 1H), 8.26 (s, 1H), 7.97 (m, 2H), 7.58 (m, 1H), 7.54 (s, 1H), 7.48 (t, J=8 Hz, 1H), 7.02 (dd, J=9, 3 Hz, 1H), 6.81 (br d, J=8 Hz, 1H), 5.32 (br s, 1H), 4.43 (s, 2H), 3.98 (m, 1H), 2.53 (m, 1H), 2.32 (m, 1H), 1.65-2.10 (m, 8H); MS (ESI$^+$) m/z 448 (M+H)$^+$.

Example 490: N-{(2S)-4-[2-(4-chloro-3-fluorophenoxy)acetamido]-2-hydroxybicyclo[2.2.2]octan-1-yl}-5-methylpyridine-2-carboxamide (Compound 589)

The reaction and purification conditions described in Example 384 substituting 5-methylpicolinic acid for 2-fluorobenzoic acid gave the title compound. $^1$H NMR (501 MHz, DMSO-d$_6$) δ ppm 8.41 (s, 1H), 8.21 (s, 1H), 7.90 (d, J=8 Hz, 1H), 7.76 (d, J=8 Hz, 1H), 7.53 (s, 1H), 7.48 (t, J=8 Hz, 1H), 7.02 (dd, J=9, 3 Hz, 1H), 6.81 (br d, J=8 Hz, 1H), 4.43 (s, 2H), 3.95 (m, 1H), 2.53 (m, 1H), 2.35 (s, 3H), 2.28 (m, 1H), 1.65-2.10 (m, 8H); MS (ESI$^+$) m/z 462 (M+H)$^+$.

Example 491: N-{3-[2-(4-chloro-3-fluorophenoxy)acetamido]bicyclo[1.1.1]pentan-1-yl}-4-cyclopropyl-1,3-thiazole-2-carboxamide (Compound 590)

The title compound was prepared using the methodologies described above. $^1$H NMR (501 MHz, DMSO-d$_6$) δ ppm 9.15 (s, 1H), 8.71 (s, 1H), 7.53 (s, 1H), 7.48 (t, J=8.9 Hz, 1H), 7.06 (dd, J=11.4, 2.8 Hz, 1H), 6.84 (ddd, J=9.0, 2.9, 1.2 Hz, 1H), 4.47 (s, 2H), 2.31 (s, 6H), 2.14-2.03 (m, 1H), 0.97-0.82 (m, 4H); MS (ESI$^+$) m/z 436 (M+H)$^+$.

Example 492: N-{4-[2-(4-chloro-3-fluorophenoxy)acetamido]-3-hydroxybicyclo[2.2.2]octan-1-yl}thiophene-3-carboxamide (Compound 591)

In 4 mL vial a solution thiophene-3-carboxylic acid (9 mg, 0.07 mmol) dissolved in N,N-dimethylacetamide (0.5 mL) was added, followed by a solution of 2-(3H-[1,2,3]triazolo[4,5-b]pyridin-3-yl)-1,1,3,3-tetramethylisouronium hexafluorophosphate(V) (35 mg, 0.09 mmol) dissolved in N,N-dimethylacetamide (0.5 mL), followed by 39 µL of neat N,N-diisopropylethylamine. Then a solution of Example 130E (21.7 mg, 0.06 mmol) dissolved in N,N-dimethylacetamide (0.5 mL) was added, and the reaction was shaken at room temperature for 30 minutes. The reaction mixture was then purified by reverse phase HPLC (trifluoroacetic acid method described below), to provide the title compound. $^1$H NMR (400 MHz, DMSO-d$_6$) δ ppm 8.08 (dd, J=3.0, 1.3 Hz, 1H), 7.57-7.42 (m, 3H), 7.05 (dd, J=11.3, 2.8 Hz, 1H), 6.85 (ddd, J=9.0, 2.9, 1.2 Hz, 1H), 4.47 (s, 2H), 4.10 (ddd, J=9.5, 3.2, 1.3 Hz, 1H), 2.46-2.35 (m, 1H), 2.14-1.81 (m, 9H); MS (ESI$^+$) m/z 453.0 (M+H)$^+$.

Reverse phase HPLC method: A gradient of acetonitrile (A) and 0.1% trifluoroacetic acid in water (B) was used, at a flow rate of 50 mL/minute (0-0.5 minute 5% A, 0.5-8.5 minutes linear gradient 05-100% A, 8.7-10.7 minutes 100% A, 10.7-11 minutes linear gradient 100-05% A). Samples were injected in 1.5 mL of dimethyl sulfoxide:methanol (1:1). An Agilent 1100 Series Purification system was used, consisting of the following modules: Agilent 1100 Series LC/MSD SL mass spectrometer with API-electrospray source; two Agilent 1100 Series preparative pumps; Agilent 1100 Series isocratic pump; Agilent 1100 Series diode array detector with preparative (0.3 mm) flow cell; Agilent active-splitter, IFC-PAL fraction collector/autosampler. The make-up pump for the mass spectrometer used 3:1 methanol:water with 0.1% formic acid at a flow rate of 1 mL/minute. Fraction collection was automatically triggered when the extracted ion chromatogram (EIC) for the target mass exceeded the threshold specified in the method. The system was controlled using Agilent Chemstation (Rev B.10.03), Agilent A2Prep, and Leap FractPal software, with custom Chemstation macros for data export.

Example 493: N-{4-[2-(4-chloro-3-fluorophenoxy)acetamido]-3-hydroxybicyclo[2.2.2]octan-1-yl}-1,3-thiazole-4-carboxamide (Compound 592)

The title compound was prepared using the methodologies described in Example 492 substituting 1,3-thiazole-4-carboxylic acid for thiophene-3-carboxylic acid. $^1$H NMR (400 MHz, DMSO-d$_6$) δ ppm 9.11 (d, J=2.0 Hz, 1H), 8.25 (d, J=2.0 Hz, 1H), 7.49 (t, J=8.8 Hz, 1H), 7.05 (dd, J=11.3, 2.8 Hz, 1H), 6.85 (ddd, J=9.0, 2.9, 1.2 Hz, 1H), 4.47 (s, 2H), 4.13 (ddd, J=9.3, 3.2, 1.2 Hz, 1H), 2.43 (ddd, J=12.4, 9.4, 2.3 Hz, 1H), 2.07 (tt, J=11.1, 6.2 Hz, 2H), 2.03-1.91 (m, 3H), 1.95-1.80 (m, 4H); MS (ESI$^+$) m/z 454.0 (M+H)$^+$.

Example 494: N-{4-[2-(4-chloro-3-fluorophenoxy)acetamido]-3-hydroxybicyclo[2.2.2]octan-1-yl}-1,3-thiazole-5-carboxamide (Compound 593)

The title compound was prepared using the methodologies described in Example 492 substituting 1,3-thiazole-5- carboxylic acid for thiophene-3-carboxylic acid. $^1$H NMR (400 MHz, DMSO-d$_6$) δ ppm 9.15 (s, 1H), 8.45 (s, 1H), 7.48 (t, J=8.8 Hz, 1H), 7.05 (dd, J=11.3, 2.8 Hz, 1H), 6.85 (ddd, J=9.1, 2.9, 1.1 Hz, 1H), 4.47 (s, 2H), 4.11 (ddd, J=9.5, 3.2, 1.3 Hz, 1H), 2.39 (ddd, J=12.3, 9.4, 2.4 Hz, 1H), 2.18-1.79 (m, 5H), 1.92 (s, 4H); MS (ESI$^+$) m/z 453.0 (M+H)$^+$.

Example 495: N-{4-[2-(4-chloro-3-fluorophenoxy)acetamido]-3-hydroxybicyclo[2.2.2]octan-1-yl}pyrazolo[1,5-a]pyridine-2-carboxamide (Compound 594)

The title compound was prepared using the methodologies described in Example 492 substituting pyrazolo[1,5-a]pyridine-2-carboxylic acid for thiophene-3-carboxylic acid. $^1$H NMR (400 MHz, DMSO-d$_6$) δ ppm 8.66 (dd, J=7.1, 1.2 Hz, 1H), 7.76 (dt, J=9.1, 1.2 Hz, 1H), 7.49 (t, J=8.9 Hz, 1H), 7.29 (ddd, J=9.0, 6.7, 1.0 Hz, 1H), 7.10-6.99 (m, 2H), 6.97 (d, J=0.8 Hz, 1H), 6.86 (ddd, J=8.9, 2.8, 1.2 Hz, 1H), 4.48 (s, 2H), 4.17-4.09 (m, 1H), 2.45 (ddd, J=12.5, 9.5, 2.4 Hz, 1H), 2.16-2.04 (m, 2H), 2.07-1.92 (m, 4H), 1.97-1.79 (m, 3H); MS (ESI$^+$) m/z 487.1 (M+H)$^+$.

Example 496: N-{4-[2-(4-chloro-3-fluorophenoxy)acetamido]-3-hydroxybicyclo[2.2.2]octan-1-yl}imidazo[1,2-a]pyridine-3-carboxamide (Compound 595)

The title compound was prepared using the methodologies described in Example 492 substituting imidazo[1,2-a]pyridine-3-carboxylic acid for thiophene-3-carboxylic acid. $^1$H NMR (400 MHz, DMSO-d$_6$) δ ppm 9.56 (dt, J=7.0, 1.1 Hz, 1H), 8.67 (s, 1H), 8.00-7.88 (m, 2H), 7.55-7.43 (m, 2H), 7.05 (dd, J=11.3, 2.8 Hz, 1H), 6.86 (ddd, J=9.0, 2.9, 1.2 Hz, 1H), 4.49 (s, 2H), 4.15 (ddd, J=9.5, 3.2, 1.4 Hz, 1H), 2.45 (ddd, J=12.6, 9.4, 2.6 Hz, 1H), 2.18-2.04 (m, 2H), 2.07-1.78 (m, 7H); MS (ESI$^+$) m/z 487.1 (M+H)$^+$.

Example 497: N-{4-[2-(4-chloro-3-fluorophenoxy)acetamido]-3-hydroxybicyclo[2.2.2]octan-1-yl}pyrazolo[1,5-a]pyridine-3-carboxamide (Compound 596)

The title compound was prepared using the methodologies described in Example 492 substituting 1-yl}pyrazolo[1,5-a]pyridine-3-carboxylic acid for thiophene-3-carboxylic acid. $^1$H NMR (400 MHz, DMSO-d$_6$) δ ppm 8.76-8.67 (m, 1H), 8.56 (s, 1H), 8.16 (dt, J=8.9, 1.3 Hz, 1H), 7.58-7.39 (m, 2H), 7.18-7.01 (m, 2H), 6.86 (ddd, J=9.0, 2.9, 1.2 Hz, 1H), 4.48 (s, 2H), 4.12 (ddd, J=9.5, 3.2, 1.4 Hz, 1H), 2.45 (ddd, J=12.6, 9.5, 2.6 Hz, 1H), 2.13-1.77 (m, 9H); MS (ESI$^+$) m/z 487.1 (M+H)$^+$.

Example 498: N-{4-[2-(4-chloro-3-fluorophenoxy)acetamido]-3-hydroxybicyclo[2.2.2]octan-1-yl}-6-methylimidazo[1,2-a]pyridine-2-carboxamide (Compound 597)

The title compound was prepared using the methodologies described in Example 492 substituting 6-methylimidazo[1,2-a]pyridine-2-carboxylic acid for thiophene-3-carboxylic acid. $^1$H NMR (400 MHz, DMSO-d$_6$) δ ppm 8.58 (q, J=1.4 Hz, 1H), 8.52 (s, 1H), 7.73-7.62 (m, 2H), 7.49 (t, J=8.9 Hz, 1H), 7.05 (dd, J=11.3, 2.9 Hz, 1H), 6.85 (ddd, J=9.0, 2.9, 1.2 Hz, 1H), 4.48 (s, 2H), 4.15 (ddd, J=9.5, 3.1, 1.3 Hz, 1H), 2.44 (td, J=10.3, 9.9, 4.8 Hz, 1H), 2.37 (d, J=1.2 Hz, 3H), 2.14-2.00 (m, 2H), 2.02-1.82 (m, 7H); MS (ESI$^+$) m/z 501.1 (M+H)$^+$.

Example 499: N-{4-[2-(4-chloro-3-fluorophenoxy)acetamido]-3-hydroxybicyclo[2.2.2]octan-1-yl}-7-methylimidazo[1,2-a]pyridine-2-carboxamide (Compound 598)

The title compound was prepared using the methodologies described in Example 492 substituting 7-methylimidazo[1,2-a]pyridine-2-carboxylic acid for thiophene-3-carboxylic acid. $^1$H NMR (400 MHz, DMSO-d$_6$) δ ppm 8.67 (d, J=7.0 Hz, 1H), 8.56 (s, 1H), 7.57 (s, 1H), 7.49 (t, J=8.8 Hz, 1H), 7.25 (dd, J=7.0, 1.5 Hz, 1H), 7.05 (dd, J=11.4, 2.8 Hz, 1H), 6.85 (ddd, J=9.0, 2.9, 1.2 Hz, 1H), 4.48 (s, 2H), 4.15 (ddd, J=9.5, 3.1, 1.3 Hz, 1H), 2.52-2.38 (m, 4H), 2.16-2.00 (m, 2H), 2.05-1.93 (m, 5H), 1.93 (dd, J=6.6, 4.0 Hz, 1H), 1.93-1.82 (m, 1H); MS (ESI$^+$) m/z 501.1 (M+H)$^+$.

Example 500: N-{4-[2-(4-chloro-3-fluorophenoxy)acetamido]-3-hydroxybicyclo[2.2.2]octan-1-yl}-8-methylimidazo[1,2-a]pyridine-2-carboxamide (Compound 599)

The title compound was prepared using the methodologies described in Example 492 substituting 8-methylimidazo[1,2-a]pyridine-2-carboxylic acid for thiophene-3-carboxylic acid. $^1$H NMR (400 MHz, DMSO-d$_6$) δ ppm 8.62-8.51 (m, 2H), 7.58-7.44 (m, 2H), 7.22 (t, J=6.9 Hz, 1H), 7.05 (dd, J=11.3, 2.8 Hz, 1H), 6.86 (ddd, J=8.9, 2.9, 1.1 Hz, 1H), 4.48 (s, 2H), 4.20-4.11 (m, 1H), 2.56 (s, 3H), 2.45 (ddd, J=12.6, 9.5, 2.5 Hz, 1H), 2.15-2.05 (m, 2H), 2.10-1.81 (m, 7H); MS (ESI$^+$) m/z 501.1 (M+H)$^+$.

Example 501: N-{4-[2-(4-chloro-3-fluorophenoxy)acetamido]-3-hydroxybicyclo[2.2.2]octan-1-yl}-6-fluoroimidazo[1,2-a]pyridine-2-carboxamide (Compound 600)

The title compound was prepared using the methodologies described in Example 492 substituting 6-fluoroimidazo[1,2-a]pyridine-2-carboxylic acid for thiophene-3-carboxylic acid. $^1$H NMR (400 MHz, DMSO-d$_6$) δ ppm 8.88 (t, J=3.3 Hz, 1H), 8.45 (d, J=7.2 Hz, 1H), 7.74 (dd, J=10.0, 5.1 Hz, 1H), 7.64 (ddd, J=10.2, 8.3, 2.4 Hz, 1H), 7.54-7.43 (m, 1H), 7.05 (dd, J=11.3, 2.8 Hz, 1H), 6.99-6.81 (m, 1H), 4.48 (s, 2H), 4.18-4.10 (m, 1H), 2.44 (dd, J=13.2, 10.0 Hz, 1H), 2.11-1.84 (m, 9H); MS (ESI$^+$) m/z 505.1 (M+H)$^+$.

Example 502: N-{4-[2-(4-chloro-3-fluorophenoxy)acetamido]-3-hydroxybicyclo[2.2.2]octan-1-yl}imidazo[1,2-a]pyridine-2-carboxamide (Compound 601)

The title compound was prepared using the methodologies described in Example 492 substituting imidazo[1,2-a]pyridine-2-carboxylic acid for thiophene-3-carboxylic acid. $^1$H NMR (400 MHz, DMSO-d$_6$) δ ppm 8.78 (dt, J=6.9, 1.2 Hz, 1H), 8.62 (s, 1H), 7.85-7.74 (m, 2H), 7.49 (t, J=8.9 Hz, 1H), 7.35 (ddd, J=6.8, 5.7, 2.3 Hz, 1H), 7.05 (dd, J=11.3, 2.9 Hz, 1H), 6.86 (ddd, J=9.0, 2.9, 1.2 Hz, 1H), 4.48 (s, 2H), 4.15 (ddd, J=9.5, 3.2, 1.3 Hz, 1H), 2.44 (ddd, J=12.6, 9.5, 2.4 Hz, 1H), 2.16-1.83 (m, 9H); MS (ESI$^+$) m/z 487.1 (M+H)$^+$.

Example 503: N-{4-[2-(4-chloro-3-fluorophenoxy)acetamido]-3-hydroxybicyclo[2.2.2]octan-1-yl}-1-methyl-1H-pyrazole-5-carboxamide (Compound 602)

The title compound was prepared using the methodologies described in Example 492 substituting 1-methyl-1H-pyrazole-5-carboxylic acid for thiophene-3-carboxylic acid. $^1$H NMR (400 MHz, DMSO-$d_6$) δ ppm 7.48 (t, J=8.9 Hz, 1H), 7.41 (d, J=2.1 Hz, 1H), 7.05 (dd, J=11.3, 2.9 Hz, 1H), 6.89-6.75 (m, 2H), 4.47 (s, 2H), 4.10 (ddd, J=9.4, 3.2, 1.3 Hz, 1H), 3.97 (s, 3H), 2.45-2.33 (m, 1H), 2.13-1.88 (m, 4H), 1.93-1.77 (m, 5H); MS (ESI$^+$) m/z 451.1 (M+H)$^+$.

Example 504: N-{4-[2-(4-chloro-3-fluorophenoxy)acetamido]-3-hydroxybicyclo[2.2.2]octan-1-yl}-1-ethyl-3-methyl-1H-pyrazole-5-carboxamide (Compound 603)

The title compound was prepared using the methodologies described in Example 492 substituting 1-ethyl-3-methyl-1H-pyrazole-5-carboxylic acid for thiophene-3-carboxylic acid. $^1$H NMR (400 MHz, DMSO-$d_6$) δ ppm 7.48 (t, J=8.9 Hz, 1H), 7.05 (dd, J=11.4, 2.8 Hz, 1H), 6.85 (ddd, J=9.0, 2.9, 1.2 Hz, 1H), 6.51 (d, J=0.6 Hz, 1H), 4.47 (s, 2H), 4.31 (q, J=7.1 Hz, 2H), 4.14-4.05 (m, 1H), 2.37 (ddd, J=13.1, 9.4, 2.2 Hz, 1H), 2.14 (s, 3H), 2.11-1.77 (m, 9H), 1.25 (t, J=7.1 Hz, 3H); MS (ESI$^+$) m/z 479.1 (M+H)$^+$.

Example 505: N-{4-[2-(4-chloro-3-fluorophenoxy)acetamido]-3-hydroxybicyclo[2.2.2]octan-1-yl}-5-methyl-1,2-oxazole-4-carboxamide (Compound 604)

The title compound was prepared using the methodologies described in Example 492 substituting 5-methyl-1,2-oxazole-4-carboxylic acid for thiophene-3-carboxylic acid. $^1$H NMR (400 MHz, DMSO-$d_6$) δ ppm 8.84 (d, J=0.8 Hz, 1H), 7.48 (t, J=8.9 Hz, 1H), 7.05 (dd, J=11.4, 2.9 Hz, 1H), 6.85 (ddd, J=8.9, 2.9, 1.2 Hz, 1H), 4.47 (s, 2H), 4.13-4.05 (m, 1H), 2.58 (s, 3H), 2.33 (m, 1H), 2.10-1.80 (m, 9H); MS (ESI$^+$) m/z 452.0 (M+H)$^+$.

Example 506: N-{4-[2-(4-chloro-3-fluorophenoxy)acetamido]-3-hydroxybicyclo[2.2.2]octan-1-yl}-3-methyl-1,2-oxazole-4-carboxamide (Compound 605)

The title compound was prepared using the methodologies described in Example 492 substituting 3-methyl-1,2-oxazole-4-carboxylic acid for thiophene-3-carboxylic acid. $^1$H NMR (400 MHz, DMSO-$d_6$) δ ppm 9.16 (d, J=0.7 Hz, 1H), 7.48 (t, J=8.9 Hz, 1H), 7.05 (dd, J=11.3, 2.9 Hz, 1H), 6.85 (ddd, J=8.9, 2.9, 1.2 Hz, 1H), 4.47 (s, 2H), 4.14-4.05 (m, 1H), 2.42-2.33 (m, 1H), 2.34 (s, 3H), 2.11-1.91 (m, 2H), 1.95-1.77 (m, 7H); MS (ESI$^+$) m/z 452.1 (M+H)$^+$.

Example 507: N-{4-[2-(4-chloro-3-fluorophenoxy)acetamido]-3-hydroxybicyclo[2.2.2]octan-1-yl}-5-ethyl-1,2-oxazole-3-carboxamide (Compound 606)

The title compound was prepared using the methodologies described in Example 492 substituting 5-ethyl-1,2-oxazole-3-carboxylic acid for thiophene-3-carboxylic acid. $^1$H NMR (400 MHz, DMSO-$d_6$) δ ppm 7.48 (t, J=8.9 Hz, 1H), 7.05 (dd, J=11.3, 2.8 Hz, 1H), 6.85 (ddd, J=9.0, 2.9, 1.2 Hz, 1H), 6.49 (d, J=0.9 Hz, 1H), 4.47 (s, 2H), 4.10 (ddd, J=9.7, 3.4, 1.3 Hz, 1H), 2.79 (qd, J=7.5, 0.9 Hz, 2H), 2.38 (ddd, J=12.2, 9.4, 2.1 Hz, 1H), 2.12-1.78 (m, 9H), 1.22 (t, J=7.6 Hz, 3H); MS (ESI$^+$) m/z 466.1 (M+H)$^+$.

Example 508: N-{4-[2-(4-chloro-3-fluorophenoxy)acetamido]-3-hydroxybicyclo[2.2.2]octan-1-yl}-2-(propan-2-yl)-1,3-oxazole-4-carboxamide (Compound 607)

The title compound was prepared using the methodologies described in Example 492 substituting 2-(propan-2-yl)-1,3-oxazole-4-carboxylic acid for thiophene-3-carboxylic acid. $^1$H NMR (400 MHz, DMSO-$d_6$) δ ppm 8.38 (s, 1H), 7.48 (t, J=8.9 Hz, 1H), 7.05 (dd, J=11.3, 2.9 Hz, 1H), 6.85 (ddd, J=9.0, 2.9, 1.2 Hz, 1H), 4.47 (s, 2H), 4.15-4.07 (m, 1H), 3.20-3.02 (m, 1H), 2.45-2.33 (m, 1H), 2.13-1.96 (m, 2H), 2.01-1.78 (m, 7H), 1.27 (d, J=6.9 Hz, 6H); MS (ESI$^+$) m/z 480.1 (M+H)$^+$.

Example 509: N-{3-[2-(4-chloro-3-fluorophenoxy)acetamido]bicyclo[1.1.1]pentan-1-yl}-1H-pyrazolo[3,4-b]pyridine-5-carboxamide (Compound 608)

The reaction and purification conditions described in Example 383 substituting 1H-pyrazolo[3,4-b]pyridine-5-carboxylic acid for quinoxaline-2-carboxylic acid gave the title compound. $^1$H NMR (501 MHz, DMSO-$d_6$) δ ppm 9.19 (s, 1H), 8.96 (d, J=2.1 Hz, 1H), 8.76 (s, 1H), 8.69 (d, J=2.1 Hz, 1H), 8.28 (s, 1H), 7.51 (t, J=8.9 Hz, 1H), 7.09 (dd, J=11.4, 2.9 Hz, 1H), 6.87 (ddd, J=8.9, 2.9, 1.2 Hz, 1H), 4.50 (s, 2H), 2.37 (s, 6H); MS (ESI$^+$) m/z 430 (M+H)$^+$.

Example 510: 2-(4-chloro-3-fluorophenoxy)-N-{3-[(pyrazolo[1,5-a]pyrimidin-5-yl)amino]bicyclo[1.1.1]pentan-1-yl}acetamide (Compound 609)

The reaction and purification conditions described in Example 294 substituting 5-chloropyrazolo[1,5-a]pyrimidine for 2-bromo-5-methyl-1,3,4-oxadiazole gave the title compound. $^1$H NMR (400 MHz, DMSO-$d_6$) δ ppm 8.74 (s, 1H), 8.48 (dd, J=7.5, 0.8 Hz, 1H), 8.02 (s, 1H), 7.79 (d, J=2.1 Hz, 1H), 7.50 (td, J=8.9, 3.7 Hz, 1H), 7.08 (dt, J=11.4, 2.8 Hz, 1H), 6.86 (dtd, J=9.0, 2.6, 1.2 Hz, 1H), 6.20 (d, J=7.6 Hz, 1H), 6.01 (dd, J=2.2, 0.8 Hz, 1H), 4.51 (s, 2H), 2.37 (s, 6H); MS (ESI$^+$) m/z 402 (M+H)$^+$.

Example 511: 2-(4-chloro-3-fluorophenoxy)-N-{3-[(3-methylpyrazolo[1,5-a]pyrimidin-5-yl)amino]bicyclo[1.1.1]pentan-1-yl}acetamide (Compound 610)

The reaction and purification conditions described in Example 294 substituting 5-chloro-3-methylpyrazolo[1,5-a]pyrimidine for 2-bromo-5-methyl-1,3,4-oxadiazole gave the title compound. $^1$H NMR (400 MHz, DMSO-$d_6$) δ ppm 8.75 (s, 1H), 8.40 (d, J=7.5 Hz, 1H), 7.94 (s, 1H), 7.66 (s, 1H), 7.50 (t, J=8.9 Hz, 1H), 7.09 (dd, J=11.4, 2.8 Hz, 1H), 6.87 (dd, J=8.5, 2.9 Hz, 1H), 6.13 (d, J=7.6 Hz, 1H), 4.50 (s, 2H), 2.40 (s, 6H), 2.09 (s, 3H); MS (ESI$^+$) m/z 416 (M+H)$^+$.

Example 512: N-{4-[2-(4-chloro-3-fluorophenoxy)acetamido]-3-hydroxybicyclo[2.2.2]octan-1-yl}thiophene-2-carboxamide (Compound 611)

The title compound was prepared using the methodologies described in Example 492 substituting thiophene-2-carboxylic acid for thiophene-3-carboxylic acid. $^1$H NMR (400 MHz, DMSO-d$_6$) δ ppm 7.78 (dd, J=3.8, 1.2 Hz, 1H), 7.72-7.66 (m, 2H), 7.49 (t, J=8.8 Hz, 1H), 7.29 (s, 1H), 7.13-7.03 (m, 2H), 6.84 (ddd, J=9.0, 3.0, 1.2 Hz, 1H), 5.11 (s, 1H), 4.48 (s, 2H), 4.08 (d, J=8.4 Hz, 1H), 2.37 (ddd, J=12.6, 9.5, 2.5 Hz, 1H), 2.10 (dd, J=11.9, 8.4 Hz, 1H), 2.08-1.99 (m, 1H), 2.00-1.79 (m, 7H); MS (ESI$^+$) m/z 452.9 (M+H)$^+$.

Example 513: N-{3-[2-(4-chloro-3-fluorophenoxy)acetamido]bicyclo[1.1.1]pentan-1-yl}-4,5-dimethylfuran-2-carboxamide (Compound 612)

The reaction and purification conditions described in Example 6D substituting 4,5-dimethylfuran-2-carboxylic acid for Example 6B gave the title compound. $^1$H NMR (501 MHz, DMSO-d$_6$) δ ppm 8.71 (s, 1H), 8.66 (s, 1H), 7.50 (t, J=8 Hz, 1H), 7.07 (dd, J=9, 3 Hz, 1H), 6.85 (m, 2H), 4.48 (s, 2H), 2.29 (s, 6H), 2.03 (s, 3H), 1.93 (s, 3H); MS (ESI$^+$) m/z 407 (M+H)$^+$.

Example 514: N-{3-[2-(4-chloro-3-fluorophenoxy)acetamido]bicyclo[1.1.1]pentan-1-yl}-4-methylfuran-2-carboxamide (Compound 613)

The reaction and purification conditions described in Example 6D substituting 4-methylfuran-2-carboxylic acid for Example 6B gave the title compound. $^1$H NMR (501 MHz, DMSO-d$_6$) δ ppm 8.83 (s, 1H), 8.72 (s, 1H), 7.55 (s, 1H), 7.50 (t, J=8 Hz, 1H), 7.08 (dd, J=9, 3 Hz, 1H), 6.95 (s, 1H), 6.85 (br d, J=8 Hz, 1H), 4.50 (s, 2H), 2.30 (s, 6H), 2.00 (s, 3H); MS (ESI$^+$) m/z 393 (M+H)$^+$.

Example 515: 2-cyclopropyl-N-{3-[2-(3,4-dichlorophenoxy)acetamido]bicyclo[1.1.1]pentan-1-yl}-1,3-oxazole-5-carboxamide (Compound 614)

The title compound was prepared using the methodologies described above. $^1$H NMR (501 MHz, DMSO-d$_6$) δ ppm 8.99 (s, 1H), 8.74 (s, 1H), 7.58-7.53 (m, 2H), 7.27 (d, J=2.9 Hz, 1H), 6.99 (dd, J=8.9, 2.9 Hz, 1H), 4.50 (s, 2H), 2.30 (s, 6H), 2.14 (tt, J=8.3, 4.9 Hz, 1H), 1.12-1.05 (m, 2H), 1.04-1.00 (m, 2H); MS (ESI$^+$) m/z 436 (M+H)$^+$.

Example 516: 4-(aminomethyl)-N-{3-[2-(3,4-dichlorophenoxy)acetamido]bicyclo[1.1.1]pentan-1-yl}pyridine-2-carboxamide (Compound 615)

The reaction and purification conditions described in Example 94 substituting the product of Example 481 for the product of Example 93 gave the title compound. $^1$H NMR (400 MHz, DMSO-d$_6$) δ ppm 9.19 (s, 1H), 8.73 (s, 1H), 8.51 (d, J=4.9 Hz, 1H), 7.99 (d, J=1.6 Hz, 1H), 7.59-7.51 (m, 2H), 7.27 (d, J=2.9 Hz, 1H), 6.99 (dd, J=8.9, 2.9 Hz, 1H), 4.50 (s, 2H), 3.81 (s, 2H), 2.35 (s, 6H); MS (ESI$^+$) m/z 435 (M+H)$^+$.

Example 517: N-{4-[2-(4-chloro-3-fluorophenoxy)acetamido]bicyclo[2.1.1]hexan-1-yl}-5-methyl-1,3-thiazole-2-carboxamide (Compound 616)

The title compound was prepared using the methodologies described above. $^1$H NMR (400 MHz, DMSO-d$_6$) δ ppm 9.02 (s, 1H), 8.50 (s, 1H), 7.72-7.65 (m, 1H), 7.49 (t, J=8.9 Hz, 1H), 7.07 (dd, J=11.4, 2.9 Hz, 1H), 6.85 (ddd, J=9.0, 2.9, 1.2 Hz, 1H), 4.48 (s, 2H), 2.54-2.45 (m, 3H), 2.18-2.04 (m, 2H), 1.93-1.78 (m, 6H); MS (ESI$^+$) m/z 425 (M+H)$^+$.

Example 518: N-{3-[2-(3,4-dichlorophenoxy)acetamido]bicyclo[1.1.1]pentan-1-yl}-3-methyl-1,2-thiazole-5-carboxamide (Compound 617)

The title compound was prepared using the methodologies described above. $^1$H NMR (400 MHz, DMSO-d$_6$) δ ppm 9.36 (s, 1H), 8.76 (s, 1H), 7.63 (s, 1H), 7.55 (d, J=8.9 Hz, 1H), 7.27 (d, J=2.9 Hz, 1H), 6.99 (dd, J=9.0, 2.9 Hz, 1H), 4.50 (s, 2H), 2.44 (s, 3H), 2.33 (s, 6H); MS (ESI$^+$) m/z 426 (M+H)$^+$.

Example 519: N-{(3S)-4-[2-(4-chloro-3-fluorophenoxy)acetamido]-3-hydroxybicyclo[2.2.2]octan-1-yl}-3-ethyl-1,2-oxazole-5-carboxamide (Compound 618)

The title compound was prepared using the methodologies described in Example 473 substituting 3-ethyl-1,2-oxazole-5-carboxylic acid for 2-methylthiazole-4-carboxylic acid. $^1$H NMR (400 MHz, DMSO-d$_6$) δ ppm 8.01 (s, 1H), 7.42 (t, J=8.9 Hz, 1H), 7.21 (s, 1H), 6.99 (dd, J=11.4, 2.9 Hz, 1H), 6.89 (s, 1H), 6.77 (ddd, J=9.0, 2.9, 1.1 Hz, 1H), 5.04 (s, 1H), 4.41 (s, 2H), 4.00 (dd, J=9.6, 3.1 Hz, 1H), 2.59 (q, J=7.6 Hz, 2H), 2.28 (ddd, J=12.4, 9.4, 2.2 Hz, 1H), 2.09-1.96 (m, 1H), 1.99-1.88 (m, 1H), 1.91-1.77 (m, 5H), 1.78 (d, J=8.8 Hz, 2H), 1.13 (t, J=7.6 Hz, 3H); MS (ESI$^+$) m/z 466.1 (M+H)$^+$.

Example 520: N-{(3S)-4-[2-(4-chloro-3-fluorophenoxy)acetamido]-3-hydroxybicyclo[2.2.2]octan-1-yl}-2-(methoxymethyl)-1,3-thiazole-4-carboxamide (Compound 619)

The title compound was prepared using the methodologies described in Example 473 substituting 2-(methoxymethyl)-1,3-thiazole-4-carboxylic acid for 2-methylthiazole-4-carboxylic acid. $^1$H NMR (400 MHz, DMSO-d$_6$) δ ppm 8.16 (s, 1H), 7.45 (t, J=8.8 Hz, 1H), 7.31 (s, 1H), 7.25 (s, 1H), 7.02 (dd, J=11.4, 2.9 Hz, 1H), 6.80 (ddd, J=9.0, 2.9, 1.2 Hz, 1H), 5.07 (s, 1H), 4.68 (s, 2H), 4.44 (s, 2H), 4.05 (dd, J=9.6, 3.0 Hz, 1H), 3.38 (s, 3H), 2.36 (ddd, J=12.5, 9.5, 2.2 Hz, 1H), 2.05 (ddt, J=18.3, 11.5, 6.3 Hz, 2H), 2.00-1.75 (m, 7H); MS (ESI$^+$) m/z 498.1 (M+H)$^+$.

Example 521: N-{3-[2-(4-chloro-3-fluorophenoxy)acetamido]bicyclo[1.1.1]pentan-1-yl}-1-methyl-1H-pyrazolo[3,4-b]pyridine-5-carboxamide (Compound 620)

To a solution of the product of Example 509 (25 mg, 0.058 mmol) in N,N-dimethylformamide (0.3 mL) was added methyl iodide (0.06 mL, 0.116 mmol) and K$_2$CO$_3$ (24.1 mg, 0.174 mmol). The reaction mixture was stirred for 3 hours at 60° C. then was purified with preparative HPLC [Waters XBridge™ C18 5 μm OBD™ column, 30×100 mm, flow rate 40 mL/minute, 5-100% gradient of acetonitrile in buffer (0.1% trifluoroacetic acid)] to give the title compound (20 mg, 0.045 mmol, 77% yield). $^1$H NMR (400 MHz, DMSO-d$_6$) δ ppm 9.23 (s, 1H), 9.00 (d, J=2.1 Hz, 1H), 8.77 (s, 1H), 8.70 (d, J=2.1 Hz, 1H), 8.29 (s, 1H), 7.51 (t, J=8.9 Hz, 1H), 7.13-7.06 (m, 1H), 6.90-6.83 (m, 1H), 4.50 (s, 2H), 4.09 (s, 3H), 2.37 (s, 6H); MS (ESI$^+$) m/z 444 (M+H)$^+$.

Example 522: N-{4-[2-(4-chloro-3-fluorophenoxy)acetamido]-3-hydroxybicyclo[2.2.2]octan-1-yl}-5-methylthiophene-2-carboxamide (Compound 621)

The title compound was prepared using the methodologies described in Example 492 substituting 5-methylthiophene-2-carboxylic acid for thiophene-3-carboxylic acid. $^1$H NMR (400 MHz, DMSO-d$_6$) δ ppm 7.57-7.44 (m, 2H), 7.05 (dd, J=11.3, 2.9 Hz, 1H), 6.89-6.76 (m, 2H), 4.47 (s, 2H), 4.13-4.05 (m, 1H), 2.43 (d, J=1.1 Hz, 3H), 2.41-2.32 (m, 1H), 2.10-1.82 (m, 9H); MS (ESI$^+$) m/z 467.1 (M+H)$^+$.

Example 523: N-{4-[2-(4-chloro-3-fluorophenoxy) acetamido]-3-hydroxybicyclo[2.2.2]octan-1-yl}-4-methylthiophene-2-carboxamide (Compound 622)

The title compound was prepared using the methodologies described in Example 492 substituting 4-methylthiophene-2-carboxylic acid for thiophene-3-carboxylic acid. $^1$H NMR (400 MHz, DMSO-d$_6$) δ ppm 7.57 (d, J=1.4 Hz, 1H), 7.48 (t, J=8.9 Hz, 1H), 7.27 (t, J=1.3 Hz, 1H), 7.05 (dd, J=11.4, 2.9 Hz, 1H), 6.85 (ddd, J=9.0, 2.9, 1.2 Hz, 1H), 4.47 (s, 2H), 4.14-4.05 (m, 1H), 2.38 (ddd, J=12.7, 9.5, 2.4 Hz, 1H), 2.20 (d, J=1.0 Hz, 3H), 2.11-1.99 (m, 2H), 2.02-1.93 (m, 1H), 1.95-1.83 (m, 5H), 1.83 (t, J=2.6 Hz, 1H); MS (ESI$^+$) m/z 467.0 (M+H)$^+$.

Example 524: N-{4-[2-(4-chloro-3-fluorophenoxy) acetamido]-3-hydroxybicyclo[2.2.2]octan-1-yl}-5-(difluoromethyl)thiophene-2-carboxamide (Compound 623)

The title compound was prepared using the methodologies described in Example 492 substituting 5-(difluoromethyl)thiophene-2-carboxylic acid for thiophene-3-carboxylic acid. $^1$H NMR (400 MHz, DMSO-d$_6$) δ ppm 7.75 (dt, J=3.7, 1.6 Hz, 1H), 7.53-7.36 (m, 2H), 7.25 (t, J=52.0 Hz, 1H), 7.05 (dd, J=11.3, 2.9 Hz, 1H), 6.85 (ddd, J=9.0, 2.9, 1.2 Hz, 1H), 4.47 (s, 2H), 4.19-4.07 (m, 1H), 2.45-2.36 (m, 1H), 2.11-1.79 (m, 9H); MS (ESI$^+$) m/z 503.1 (M+H)$^+$.

Example 525: N-{4-[2-(4-chloro-3-fluorophenoxy) acetamido]-3-hydroxybicyclo[2.2.2]octan-1-yl}-5-methylfuran-2-carboxamide (Compound 624)

The title compound was prepared using the methodologies described in Example 492 substituting 5-methylfuran-2-carboxylic acid for thiophene-3-carboxylic acid. $^1$H NMR (400 MHz, DMSO-d$_6$) δ ppm 7.48 (t, J=8.9 Hz, 1H), 7.05 (dd, J=11.4, 2.8 Hz, 1H), 6.96 (d, J=3.4 Hz, 1H), 6.85 (ddd, J=8.9, 2.9, 1.2 Hz, 1H), 6.20 (dd, J=3.4, 1.1 Hz, 1H), 4.47 (s, 2H), 4.13-4.05 (m, 1H), 3.74 (s, 1H), 2.43-2.28 (m, 4H), 2.11-1.93 (m, 2H), 1.93-1.77 (m, 7H); MS (ESI$^+$) m/z 451.1 (M+H)$^+$.

Example 526: N-{4-[2-(4-chloro-3-fluorophenoxy) acetamido]-3-hydroxybicyclo[2.2.2]octan-1-yl}-5-(trifluoromethyl)furan-2-carboxamide (Compound 625)

The title compound was prepared using the methodologies described in Example 492 substituting 5-(trifluoromethyl)furan-2-carboxylic acid for thiophene-3-carboxylic acid. $^1$H NMR (400 MHz, DMSO-d$_6$) δ ppm 7.48 (t, J=8.9 Hz, 1H), 7.32-7.23 (m, 2H), 7.05 (dd, J=11.3, 2.8 Hz, 1H), 6.85 (ddd, J=9.0, 2.9, 1.2 Hz, 1H), 4.47 (s, 2H), 4.11 (dt, J=9.6, 1.9 Hz, 1H), 3.74 (s, 1H), 3.18 (s, 1H), 2.44-2.35 (m, 1H), 2.11-1.78 (m, 9H); MS (ESI$^+$) m/z 505.0 (M+H)$^+$.

Example 527: N-{4-[2-(4-chloro-3-fluorophenoxy) acetamido]-3-hydroxybicyclo[2.2.2]octan-1-yl}-1-methyl-1H-pyrazole-4-carboxamide (Compound 626)

The title compound was prepared using the methodologies described in Example 492 substituting 1-methyl-1H-pyrazole-4-carboxylic acid for thiophene-3-carboxylic acid. $^1$H NMR (400 MHz, DMSO-d$_6$) δ ppm 8.08 (s, 1H), 7.79 (d, J=0.7 Hz, 1H), 7.49 (t, J=8.9 Hz, 1H), 7.30 (s, 1H), 7.21 (s, 1H), 7.06 (dd, J=11.4, 2.9 Hz, 1H), 6.91-6.79 (m, 1H), 5.14-5.08 (m, 1H), 4.48 (s, 2H), 4.04 (d, J=9.0 Hz, 1H), 3.81 (s, 3H), 2.34 (ddd, J=13.3, 9.5, 2.1 Hz, 1H), 2.16-2.02 (m, 1H), 2.05-1.86 (m, 2H), 1.89-1.77 (m, 7H); MS (ESI$^+$) m/z 451.2 (M+H)$^+$.

Example 528: N-{4-[2-(4-chloro-3-fluorophenoxy) acetamido]-3-hydroxybicyclo[2.2.2]octan-1-yl}thieno[2,3-b]pyrazine-6-carboxamide (Compound 627)

The title compound was prepared using the methodologies described in Example 492 substituting thieno[2,3-b]pyrazine-6-carboxylic acid for thiophene-3-carboxylic acid. $^1$H NMR (400 MHz, DMSO-d$_6$) δ ppm 8.81 (d, J=2.3 Hz, 1H), 8.69 (d, J=2.3 Hz, 1H), 8.33 (s, 1H), 7.49 (t, J=8.8 Hz, 1H), 7.05 (dd, J=11.3, 2.9 Hz, 1H), 6.85 (ddd, J=9.0, 2.9, 1.2 Hz, 1H), 4.48 (s, 2H), 4.18-4.10 (m, 1H), 2.44 (ddd, J=12.6, 9.3, 2.6 Hz, 1H), 2.10-1.88 (m, 9H); MS (ESI$^+$) m/z 505.1 (M+H)$^+$.

Example 529: N-{4-[2-(4-chloro-3-fluorophenoxy) acetamido]-3-hydroxybicyclo[2.2.2]octan-1-yl}-1,2-oxazole-5-carboxamide (Compound 628)

The title compound was prepared using the methodologies described in Example 492 substituting, 2-oxazole-5-carboxylic acid for thiophene-3-carboxylic acid. $^1$H NMR (400 MHz, DMSO-d$_6$) δ ppm 8.66 (d, J=1.9 Hz, 1H), 7.48 (t, J=8.9 Hz, 1H), 7.09-6.98 (m, 2H), 6.85 (ddd, J=9.0, 2.9, 1.2 Hz, 1H), 4.47 (s, 2H), 4.11 (ddd, J=9.4, 3.3, 1.3 Hz, 1H), 2.44-2.33 (m, 1H), 2.11-1.77 (m, 9H); MS (ESI$^+$) m/z 438.0 (M+H)$^+$.

Example 530: 2-tert-butyl-N-{4-[2-(4-chloro-3-fluorophenoxy)acetamido]-3-hydroxybicyclo[2.2.2]octan-1-yl}-1,3-oxazole-4-carboxamide (Compound 629)

The title compound was prepared using the methodologies described in Example 492 substituting 2-tert-butyl-1,3-oxazole-4-carboxylic acid for thiophene-3-carboxylic acid. $^1$H NMR (400 MHz, DMSO-d$_6$) δ ppm 8.39 (s, 1H), 7.48 (t, J=8.9 Hz, 1H), 7.05 (dd, J=11.3, 2.8 Hz, 1H), 6.85 (ddd, J=9.0, 2.9, 1.2 Hz, 1H), 4.47 (s, 2H), 4.15-4.07 (m, 1H), 2.44-2.34 (m, 1H), 2.13-1.89 (m, 5H), 1.92-1.75 (m, 4H), 1.33 (s, 9H); MS (ESI$^+$) m/z 494.1 (M+H)$^+$.

Example 531: N-{4-[2-(4-chloro-3-fluorophenoxy) acetamido]-3-oxobicyclo[2.2.2]octan-1-yl}-3-methyl-1,2-oxazole-5-carboxamide (Compound 630)

A suspension of Example 130D (0.14 g, 0.154 mmol), 3-methylisoxazole-5-carboxylic acid (0.024 g, 0.192 mmol) and N-ethyl-N-isopropylpropan-2-amine (0.094 mL, 0.539 mmol) in N,N-dimethylformamide (1.5 mL) was treated with 2-(3H-[1,2,3]triazolo[4,5-b]pyridin-3-yl)-1,1,3,3-tetramethylisouronium hexafluorophosphate(V) (0.088 g, 0.231 mmol), and the reaction mixture was stirred at ambient temperature for 16 hours. Volatiles were removed under high vacuum, and the residue was purified by HPLC (10-95% acetonitrile in 0.1% trifluoroacetic acid/water on Phenomenex® C18 5 m (250 mm×21.2 mm) column at a flowrate of 25 mL/minute) to give the title compound. $^1$H NMR (501 MHz, DMSO-d$_6$) δ ppm 8.51 (s, 1H), 7.73 (s, 1H), 7.50 (t, J=8.9 Hz, 1H), 7.09 (dd, J=11.3, 2.9 Hz, 1H), 6.93 (s, 1H), 6.86 (ddd, J=9.0, 2.9, 1.2 Hz, 1H), 4.58 (s, 2H), 2.95 (s, 2H), 2.44 (dt, J=13.1, 9.2 Hz, 2H), 2.28 (s, 3H), 2.14 (t, J=8.3 Hz, 4H), 1.93-1.83 (m, 2H); MS (ESI$^+$) m/z 450.1 (M+H)$^+$.

Example 532: N-{3-[2-(4-chloro-3-fluorophenoxy)acetamido]bicyclo[1.1.1]pentan-1-yl}pyrazolo[1,5-a]pyrimidine-5-carboxamide (Compound 631)

The reaction and purification conditions described in Example 383 substituting pyrazolo[1,5-a]pyrimidine-5-carboxylic acid for quinoxaline-2-carboxylic acid gave the title compound. $^1$H NMR (400 MHz, DMSO-d$_6$) δ ppm 9.50 (s, 1H), 9.26 (dd, J=7.2, 0.8 Hz, 1H), 8.75 (s, 1H), 8.37 (d, J=2.4 Hz, 1H), 7.56-7.46 (m, 2H), 7.09 (dd, J=11.4, 2.9 Hz, 1H), 6.89-6.85 (m, 2H), 4.50 (s, 2H), 2.37 (s, 6H); MS (ESI$^+$) m/z 430 (M+H)$^+$.

Example 533: N-{4-[2-(4-chloro-3-fluorophenoxy)acetamido]-3-hydroxybicyclo[2.2.2]octan-1-yl}-3-(difluoromethyl)-1,2-oxazole-5-carboxamide (Compound 632)

The title compound was prepared using the methodologies described in Example 130 substituting the product of Example 555F for 5-(difluoromethyl)pyrazine-2-carboxylic. $^1$H NMR (400 MHz, DMSO-d$_6$) δ ppm 8.34 (s, 1H), 7.53-7.44 (m, 1H), 7.40 (s, 1H), 7.33 (t, J=52 Hz, 1H), 7.30 (s, 1H), 7.06 (dd, J=11.4, 2.8 Hz, 1H), 6.84 (ddd, J=9.0, 3.0, 1.2 Hz, 1H), 5.08 (s, 1H), 4.48 (s, 2H), 4.10 (dd, J=9.6, 3.1 Hz, 1H), 2.37 (ddd, J=12.5, 9.5, 2.2 Hz, 1H), 2.08 (ddd, J=20.5, 11.1, 8.0 Hz, 2H), 1.98 (d, J=7.8 Hz, 1H), 1.89 (dtdd, J=13.2, 9.5, 7.1, 4.5 Hz, 6H); MS (ESI$^+$) m/z 488.1 (M+H)$^+$.

Example 534: N-{4-[2-(4-chloro-3-fluorophenoxy)acetamido]-3-hydroxybicyclo[2.2.2]octan-1-yl}-3-(1-methyl-1H-pyrazol-4-yl)-1,2-oxazole-5-carboxamide (Compound 633)

The title compound was prepared using the methodologies described in Example 130 substituting 3-(1-methyl-1H-pyrazol-4-yl)-1,2-oxazole-5-carboxylic acid for 5-(difluoromethyl)pyrazine-2-carboxylic. $^1$H NMR (501 MHz, DMSO-d$_6$) δ ppm 8.28 (s, 1H), 8.20 (s, 1H), 7.91 (d, J=0.8 Hz, 1H), 7.49 (t, J=8.9 Hz, 1H), 7.30 (d, J=5.8 Hz, 2H), 7.06 (dd, J=11.4, 2.9 Hz, 1H), 6.84 (ddd, J=9.1, 2.9, 1.2 Hz, 1H), 4.48 (s, 2H), 4.09 (ddd, J=9.5, 3.2, 1.4 Hz, 1H), 3.90 (s, 3H), 2.37 (ddd, J=12.5, 9.3, 2.5 Hz, 1H), 2.16-2.01 (m, 2H), 2.00-1.89 (m, 4H), 1.92-1.81 (m, 3H); MS (ESI$^+$) m/z 518.2 (M+H)$^+$.

Example 535: N-{4-[2-(4-chloro-3-fluorophenoxy)acetamido]-3-hydroxybicyclo[2.2.2]octan-1-yl}-1,2,5-oxadiazole-3-carboxamide (Compound 634)

The title compound was prepared using the methodologies described in Example 130 substituting 1,2,5-oxadiazole-3-carboxylic acid for 5-(difluoromethyl)pyrazine-2-carboxylic. $^1$H NMR (501 MHz, DMSO-d$_6$) δ ppm 14.33 (s, 1H), 7.71 (s, 1H), 7.48 (t, J=8.9 Hz, 1H), 7.28 (s, 1H), 7.05 (dd, J=11.4, 2.9 Hz, 1H), 6.83 (ddd, J=9.0, 2.9, 1.2 Hz, 1H), 4.47 (s, 2H), 4.10-4.03 (m, 1H), 2.30 (ddd, J=13.1, 9.4, 2.2 Hz, 1H), 2.07 (ddd, J=13.1, 11.1, 4.5 Hz, 1H), 2.02-1.94 (m, 1H), 1.97-1.89 (m, 1H), 1.90 (dt, J=5.7, 2.3 Hz, 1H), 1.90-1.76 (m, 5H); MS (ESI$^+$) m/z 439.1 (M+H)$^+$.

Example 536: N-[(3S)-4-{2-[(2,2-difluoro-2H-1,3-benzodioxol-5-yl)oxy]acetamido}-3-hydroxybicyclo[2.2.2]octan-1-yl]-3-fluorobenzamide (Compound 635)

Example 536A: (2S)-1-amino-4-(benzylamino)bicyclo[2.2.2]octan-2-ol, hydrochloric acid The product of Example 362A (0.56 g, 1.77 mmol), MgSO$_4$ (1 M, 90 μL), nicotinamide adenine dinucleotide phosphate (NADPH, 50 mg/mL, 224 μL) were mixed in 11 mL of potassium phosphate buffer (120 mM, pH=7.0) and 5.6 mL of isopropanol. To this solution was added Codexis KRED P02C2 enzyme (50.4 mg) dissolved in 5.4 mL of the same potassium phosphate buffer. The reaction was stirred at 30° C. overnight. The volatile components (isopropanol) and a portion of the water were removed in vacuo. The remaining aqueous fraction was adjusted to pH=10.5 with saturated, aqueous NaOH and lyophilized. The resulting powder was slurried with ethyl acetate (2×25 mL), filtered, and the solids were washed with ethyl acetate. The filtrate was concentrated under reduced pressure. The concentrate was dissolved in methanol (~10 mL) and treated with 3 N HCl in 1,4-dioxane (3 mL). The solution was stirred for 5 minutes and concentrated. The concentrate was slurried in acetone and filtered. The filtrate was concentrated under reduced pressure, and the resulting solids were dried in vacuum to provide the title product (0.46 g, 82% yield). MS (ESI$^+$) m/z 247.3 (M+H)$^+$.

Example 536B: N-[(2S)-4-(benzylamino)-2-hydroxybicyclo[2.2.2]octan-1-yl]-2-[(2,2-difluoro-2H-1,3-benzodioxol-5-yl)oxy]acetamide A solution of the product of Example 29B (0.62 g, 2.67 mmol), triethylamine (0.68 mL, 4.85 mmol), and N-[(dimethylamino)-1H-1,2,3-triazolo-[4,5-b]pyridin-1-ylmethylene]-N-methylmethanaminium hexafluorophosphate N-oxide (HATU, 1.014 g, 2.67 mmol) in N,N-dimethylformamide (6 mL) was stirred for 10 minutes and added to a suspension of the product of Example 536A (0.39 g, 1.21 mmol) in N,N-dimethylformamide (6 mL) dropwise. The reaction mixture was stirred for 1 hour and was treated with 2.5 M sodium hydroxide (2.91 mL, 7.27 mmol). The mixture was stirred for 3 hours, quenched with brine, and extracted with ethyl acetate (2×). The combined organic layers were washed with brine, dried over anhydrous MgSO$_4$, filtered, and concentrated under reduced pressure. The residue was purified on a 40 g silica gel column using the Biotage® Isolera™ One flash system eluting with CH$_2$Cl$_2$/CH$_3$OH/NH$_4$OH (18:1:0.1) to provide the title compound (0.48 g, 1.04 mmol, 86% yield). MS (ESI$^+$) m/z 461.2 (M+H)$^+$.

Example 536C: N-[(2S)-4-amino-2-hydroxybicyclo[2.2.2]octan-1-yl]-2-[(2,2-difluoro-2H-1,3-benzodioxol-5-yl)oxy]acetamide The product of Example 536B (400 mg, 0.87 mmol) in tetrahydrofuran (5.3 mL) was added to 20% Pd(OH)$_2$/C (83 mg, 0.060 mmol, 51% in water) in a 20 mL Barnstead Hastelloy® C reactor purged with argon. The mixture was stirred under 50 psi of hydrogen at 25° C. for 19 hours. The mixture was filtered and concentrated under reduced pressure. The concentrate was purified on a 12 g silica gel column using the Biotage® Isolera™ One flash system eluting with CH$_2$Cl$_2$/CH$_3$OH/NH$_4$OH (9:1:0.1) to provide the title compound (0.216 g, 0.58 mmol, 67% yield). MS (ESI$^+$) m/z 371.1 (M+H)$^+$.

Example 536D: N-[(3S)-4-{2-[(2,2-difluoro-2H-1,3-benzodioxol-5-yl)oxy]acetamido}-3-hydroxybicyclo [2.2.2]octan-1-yl]-3-fluorobenzamide To a mixture of the product of Example 536C (52.0 mg, 0.140 mmol) in N,N-dimethylformamide (1.5 mL) was added triethylamine (0.039 mL, 0.281 mmol), 3-fluorobenzoic acid (21.64 mg, 0.154 mmol) and N-[(dimethylamino)-1H-1,2,3-triazolo-[4,5-b]pyridin-1-ylmethylene]-N-methyl-methanaminium hexafluorophosphate N-oxide (HATU, 80 mg, 0.211 mmol). The mixture was stirred for 2 hours. The reaction mixture was quenched with brine and extracted with ethyl acetate (2×). The combined organic layers were concentrated under reduced pressure, and the residue was purified by reverse-phase HPLC (see protocol in Example 273E) to provide the title compound (33.2 mg, 0.067 mmol, 48% yield). $^1$H NMR (400 MHz, DMSO-d$_6$) δ ppm 7.74 (s, 1H), 7.63-7.49 (m, 2H), 7.44 (td, J=8.0, 5.8 Hz, 1H), 7.30 (dd, J=11.7, 8.7 Hz, 2H), 7.21 (s, 1H), 7.10 (d, J=2.5 Hz, 1H), 6.72 (dd, J=8.9, 2.6 Hz, 1H), 5.09 (s, brd, 1H), 4.41 (s, 2H), 4.03 (dd, J=9.8, 3.2 Hz, 1H), 2.35 (ddd, J=12.4, 9.6, 2.2 Hz, 1H), 2.17-1.72 (m, 9H); MS (ESI$^+$) m/z 493.0 (M+H)$^+$.

Example 537: N-[(3S)-4-{2-[(2,2-difluoro-2H-1,3-benzodioxol-5-yl)oxy]acetamido}-3-hydroxybicyclo [2.2.2]octan-1-yl]-3-methyl-1,2-oxazole-5-carboxamide (Compound 636)

The reaction described in Example 536D substituting 3-methylisoxazole-5-carboxylic acid for 3-fluorobenzoic acid gave the title compound. $^1$H NMR (400 MHz, DMSO-d$_6$) δ ppm 8.05 (s, 1H), 7.28 (d, J=8.9 Hz, 1H), 7.21 (s, 1H), 7.09 (d, J=2.6 Hz, 1H), 6.84 (s, 1H), 6.71 (dd, J=8.9, 2.6 Hz, 1H), 5.11 (d, J=4.5 Hz, 1H), 4.40 (s, 2H), 4.04 (dq, J=13.1, 4.5, 3.8 Hz, 1H), 2.32 (ddd, J=12.4, 9.7, 2.0 Hz, 1H), 2.23 (s, 3H), 2.13-1.76 (m, 9H); MS (ESI$^+$) m/z 480.1 (M+H)$^+$.

Example 538: N-[(3S)-4-{2-[(2,2-difluoro-2H-1,3-benzodioxol-5-yl)oxy]acetamido}-3-hydroxybicyclo [2.2.2]octan-1-yl]-4-fluoro-1,3-dimethyl-1H-pyrazole-5-carboxamide (Compound 637)

The reaction described in Example 536D substituting 4-fluoro-1,3-dimethyl-1H-pyrazole-5-carboxylic acid for 3-fluorobenzoic acid gave the title compound. $^1$H NMR (400 MHz, DMSO-d$_6$) δ ppm 7.52 (d, J=1.7 Hz, 1H), 7.28 (d, J=8.8 Hz, 1H), 7.21 (s, 1H), 7.09 (d, J=2.5 Hz, 1H), 6.71 (dd, J=8.9, 2.6 Hz, 1H), 4.40 (s, 2H), 4.03 (dd, J=9.7, 3.1 Hz, 1H), 3.76 (s, 3H), 2.31 (ddd, J=12.4, 9.6, 2.1 Hz, 1H), 2.07 (s, 3H), 2.11-1.76 (m, 9H); MS (ESI$^+$) m/z 511.2 (M+H)$^+$.

Example 539: N-[(3S)-4-{2-[(2,2-difluoro-2H-1,3-benzodioxol-5-yl)oxy]acetamido}-3-hydroxybicyclo [2.2.2]octan-1-yl]-5-methylpyrazine-2-carboxamide (Compound 638)

The reaction described in Example 536D substituting 5-methylpyrazine-2-carboxylic acid for 3-fluorobenzoic acid gave the title compound. $^1$H NMR (400 MHz, DMSO-d$_6$) δ ppm 8.96 (d, J=1.5 Hz, 1H), 8.53 (d, J=1.3 Hz, 1H), 7.82 (s, 1H), 7.28 (d, J=8.9 Hz, 1H), 7.23 (s, 1H), 7.10 (d, J=2.5 Hz, 1H), 6.72 (dd, J=8.9, 2.6 Hz, 1H), 5.12 (d, J=4.5 Hz, 1H), 4.41 (s, 2H), 4.11-3.92 (m, 1H), 2.54 (s, 3H), 2.38 (td, J=10.7, 10.0, 5.2 Hz, 1H), 2.18-1.75 (m, 9H); MS (ESI$^+$) m/z 491.1 (M+H)$^+$.

Example 540: 2-(4-fluorophenoxy)-N-{3-[(2-methylpyrazolo[1,5-a]pyrazin-4-yl)amino]bicyclo[1.1.1] pentan-1-yl}acetamide (Compound 639)

The reaction and purification conditions described in Example 323 substituting 2-(4-fluorophenoxy)acetic acid for 2-((2,2-difluorobenzo[d][1,3]dioxol-5-yl)oxy)acetic acid gave the title compound. $^1$H NMR (501 MHz, DMSO-d$_6$) δ ppm 8.78 (br s, 2H), 7.94 (d, J=6 Hz, 1H), 7.23 (d, J=6 Hz, 1H), 7.15 (m, 2H), 7.00 (m, 2H), 6.88 (br s, 1H), 4.45 (s, 2H), 2.47 (s, 6H), 2.38 (s, 3H); MS (ESI$^+$) m/z 382 (M+H)$^+$.

Example 541: 2-(3-fluorophenoxy)-N-{3-[(2-methylpyrazolo[1,5-a]pyrazin-4-yl)amino]bicyclo[1.1.1] pentan-1-yl}acetamide (Compound 640)

The reaction and purification conditions described in Example 323 substituting 2-(3-fluorophenoxy)acetic acid for 2-((2,2-difluorobenzo[d][1,3]dioxol-5-yl)oxy)acetic acid gave the title compound. $^1$H NMR (501 MHz, DMSO-d$_6$) δ ppm 8.80 (br s, 2H), 7.94 (d, J=6 Hz, 1H), 7.36 (q, J=8 Hz, 1H), 7.23 (d, J=6 Hz, 1H), 6.80-6.90 (m, 4H), 4.50 (s, 2H), 2.47 (s, 6H), 2.38 (s, 3H); MS (ESI$^+$) m/z 382 (M+H)$^+$.

Example 542: N-{3-[2-(4-chloro-3-fluorophenoxy) acetamido]bicyclo[1.1.1]pentan-1-yl}-2-(trifluoromethyl)-1,3-thiazole-4-carboxamide (Compound 641)

The title compound was prepared using the methodologies described above. $^1$H NMR (501 MHz, DMSO-d$_6$) δ ppm 9.20 (s, 1H), 8.74 (s, 1H), 8.65 (s, 1H), 7.50 (t, J=8.9 Hz, 1H), 7.08 (dd, J=11.4, 2.8 Hz, 1H), 6.86 (ddd, J=8.9, 2.8, 1.2 Hz, 1H), 4.49 (s, 2H), 2.34 (s, 6H); MS (ESI$^+$) m/z 464 (M+H)$^+$.

Example 543: N-{3-[2-(4-chloro-3-fluorophenoxy) acetamido]bicyclo[1.1.1]pentan-1-yl}-6-(propan-2-yl)pyridine-3-carboxamide (Compound 642)

The title compound was prepared using the methodologies described above. $^1$H NMR (400 MHz, DMSO-d$_6$) δ ppm 9.12 (s, 1H), 8.89 (d, J=2.2 Hz, 1H), 8.75 (s, 1H), 8.09 (dd, J=8.2, 2.4 Hz, 1H), 7.50 (t, J=8.9 Hz, 1H), 7.36 (d, J=8.1 Hz, 1H), 7.09 (dd, J=11.4, 2.8 Hz, 1H), 6.87 (ddd, J=8.9, 2.9, 1.1 Hz, 1H), 4.50 (s, 2H), 3.06 (hept, J=6.9 Hz, 1H), 2.35 (s, 6H), 1.24 (d, J=6.9 Hz, 6H); MS (ESI$^+$) m/z 432 (M+H)$^+$.

Example 544: N-{3-[2-(3,4-dichlorophenoxy)acetamido]bicyclo[1.1.1]pentan-1-yl}-6-(propan-2-yl) pyridine-3-carboxamide (Compound 643)

The title compound was prepared using the methodologies described above. $^1$H NMR (501 MHz, DMSO-d$_6$) δ ppm 9.12 (s, 1H), 8.89 (dd, J=2.3, 0.8 Hz, 1H), 8.75 (s, 1H), 8.09 (dd, J=8.2, 2.4 Hz, 1H), 7.55 (d, J=9.0 Hz, 1H), 7.36 (dd, J=8.2, 0.8 Hz, 1H), 7.28 (d, J=2.9 Hz, 1H), 7.00 (dd, J=9.0, 2.9 Hz, 1H), 4.51 (s, 2H), 3.06 (hept, J=7.0 Hz, 1H), 2.34 (s, 6H), 1.24 (d, J=6.9 Hz, 6H); MS (ESI$^+$) m/z 448 (M+H)$^+$.

Example 545: N-{3-[2-(4-chloro-3-fluorophenoxy)acetamido]bicyclo[1.1.1]pentan-1-yl}-5-methylpyridine-3-carboxamide (Compound 644)

The title compound was prepared using the methodologies described above. $^1$H NMR (501 MHz, DMSO-$d_6$) δ ppm 9.16 (s, 1H), 8.78 (d, J=2.1 Hz, 1H), 8.75 (s, 1H), 8.54 (dd, J=2.2, 0.8 Hz, 1H), 8.01-7.98 (m, 1H), 7.50 (t, J=8.9 Hz, 1H), 7.09 (dd, J=11.4, 2.8 Hz, 1H), 6.87 (ddd, J=9.0, 2.9, 1.2 Hz, 1H), 4.50 (s, 2H), 2.37-2.33 (m, 9H); MS (ESI$^+$) m/z 404 (M+H)$^+$.

Example 546: N-{3-[2-(3,4-dichlorophenoxy)acetamido]bicyclo[1.1.1]pentan-1-yl}-5-methylpyridine-3-carboxamide (Compound 645)

The title compound was prepared using the methodologies described above. $^1$H NMR (501 MHz, DMSO-$d_6$) δ ppm 9.16 (s, 1H), 8.78 (d, J=2.1 Hz, 1H), 8.75 (s, 1H), 8.55-8.53 (m, 1H), 8.01-7.97 (m, 1H), 7.55 (d, J=8.9 Hz, 1H), 7.28 (d, J=2.9 Hz, 1H), 7.00 (dd, J=9.0, 2.9 Hz, 1H), 4.51 (s, 2H), 2.36-2.32 (m, 9H); MS (ESI$^+$) m/z 420 (M+H)$^+$.

Example 547: N-{3-[2-(3,4-dichlorophenoxy)acetamido]bicyclo[1.1.1]pentan-1-yl}-2-(trifluoromethyl)-1,3-thiazole-5-carboxamide (Compound 646)

The title compound was prepared using the methodologies described above. $^1$H NMR (501 MHz, DMSO-$d_6$) δ ppm 9.62 (s, 1H), 8.78 (s, 1H), 8.62-8.58 (m, 1H), 7.55 (d, J=8.9 Hz, 1H), 7.27 (d, J=2.9 Hz, 1H), 7.00 (dd, J=8.9, 2.9 Hz, 1H), 4.51 (s, 2H), 2.36 (s, 6H); MS (ESI$^+$) m/z 497 (M+NH$_4$)$^+$.

Example 548: N-{4-[2-(4-chloro-3-fluorophenoxy)acetamido]bicyclo[2.1.1]hexan-1-yl}-2-(trifluoromethyl)-1,3-thiazole-5-carboxamide (Compound 647)

The title compound was prepared using the methodologies described above. $^1$H NMR (501 MHz, DMSO-$d_6$) δ ppm 9.37 (s, 1H), 8.66-8.61 (m, 1H), 8.54 (s, 1H), 7.50 (t, J=8.9 Hz, 1H), 7.08 (dd, J=11.4, 2.8 Hz, 1H), 6.86 (ddd, J=9.0, 2.9, 1.2 Hz, 1H), 4.50 (s, 2H), 2.21-2.13 (m, 2H), 1.96-1.83 (m, 6H); MS (ESI$^+$) m/z 495 (M+NH$_4$)$^+$.

Example 549: N-{3-[2-(4-chloro-3-fluorophenoxy)acetamido]bicyclo[1.1.1]pentan-1-yl}-1-methyl-1H-indole-2-carboxamide (Compound 648)

The reaction and purification conditions described in Example 383 substituting 1-methyl-1H-indole-2-carboxylic acid for quinoxaline-2-carboxylic acid gave the title compound. $^1$H NMR (400 MHz, DMSO-$d_6$) δ ppm 9.02 (s, 1H), 8.76 (s, 1H), 7.62 (d, J=7.9 Hz, 1H), 7.50 (t, J=8.8 Hz, 2H), 7.27 (ddd, J=8.3, 6.9, 1.2 Hz, 1H), 7.15-7.05 (m, 3H), 6.87 (ddd, J=9.0, 2.9, 1.2 Hz, 1H), 4.50 (s, 2H), 3.98 (s, 3H), 2.36 (s, 6H); MS (ESI$^+$) m/z 442 (M+H)$^+$.

Example 550: 2-(4-chloro-3-fluorophenoxy)-N-(3-{[5-(difluoromethyl)pyrazin-2-yl]amino}bicyclo[1.1.1]pentan-1-yl)acetamide (Compound 649)

Example 550A: 2-chloro-5-(difluoromethyl)pyrazine

To a solution of 5-chloropyrazine-2-carbaldehyde (500 mg, 3.51 mmol) in CH$_2$Cl$_2$ (10 mL) was added (diethylamino)difluorosulfonium tetrafluoroborate (2.0 g, 8.77 mmol) and triethylamine trihydrofluoride (0.57 mL, 3.51 mmol). The reaction mixture was stirred for 18 hours at ambient temperature. The reaction mixture was diluted with water and was extracted with CH$_2$Cl$_2$. The organic layer was dried over anhydrous MgSO$_4$, filtered and concentrated under reduced pressure. Purification of the residue via column chromatography (SiO$_2$, heptane:ethyl acetate 0-65%) gave the title (200 mg, 1.22 mmol, 35% yield). $^1$H NMR (500 MHz, DMSO-$d_6$) δ ppm 9.00-8.93 (m, 1H), 8.86 (q, J=1.1 Hz, 1H), 7.17 (t, J=54.0 Hz, 1H); MS (ESI$^+$) m/z 186 (M+Na)$^+$.

Example 550B: 2-(4-chloro-3-fluorophenoxy)-N-(3-{[5-(difluoromethyl)pyrazin-2-yl]amino}bicyclo[1.1.1]pentan-1-yl)acetamide The reaction and purification conditions described in Example 294 substituting the product of Example 550A for 2-bromo-5-methyl-1,3,4-oxadiazole gave the title compound. $^1$H NMR (400 MHz, DMSO-$d_6$) δ ppm 8.77 (s, 1H), 8.35-8.22 (m, 2H), 7.97 (d, J=1.5 Hz, 1H), 7.50 (t, J=8.9 Hz, 1H), 7.08 (dd, J=11.3, 2.9 Hz, 1H), 7.01-6.70 (m, 2H), 4.51 (s, 2H), 2.37 (s, 6H); MS (ESI$^+$) m/z 413 (M+H)$^+$.

Example 551: N-{3-[2-(4-chloro-3-fluorophenoxy)acetamido]bicyclo[1.1.1]pentan-1-yl}-6-methylpyrazine-2-carboxamide (Compound 650)

The title compound was prepared using the methodologies described above. $^1$H NMR (400 MHz, DMSO-$d_6$) δ ppm 9.27 (s, 1H), 8.93 (s, 1H), 8.74 (s, 2H), 7.50 (t, J=8.9 Hz, 1H), 7.08 (dd, J=11.4, 2.9 Hz, 1H), 6.86 (ddd, J=9.0, 2.8, 1.2 Hz, 1H), 4.49 (s, 2H), 2.58 (s, 3H), 2.37 (s, 6H); MS (ESI$^+$) m/z 405 (M+H)$^+$.

Example 552: N-{3-[2-(4-chloro-3-fluorophenoxy)acetamido]bicyclo[1.1.1]pentan-1-yl}-3-methoxy-1-methyl-1H-pyrazole-5-carboxamide (Compound 651)

The title compound was prepared using the methodologies described above. $^1$H NMR (400 MHz, DMSO-$d_6$) δ ppm 8.91 (s, 1H), 8.75 (s, 1H), 7.50 (t, J=8.9 Hz, 1H), 7.08 (dd, J=11.4, 2.8 Hz, 1H), 6.86 (ddd, J=8.9, 2.9, 1.2 Hz, 1H), 6.27 (s, 1H), 4.49 (s, 2H), 3.89 (s, 3H), 3.75 (s, 3H), 2.32 (s, 6H); MS (ESI$^+$) m/z 423 (M+H)$^+$.

Example 553: N-{(3S)-4-[2-(4-chloro-3-fluorophenoxy)acetamido]-3-hydroxybicyclo[2.2.2]octan-1-yl}-5-(trifluoromethyl)pyrazine-2-carboxamide (Compound 652)

The title compound was prepared using the methodologies described in Example 473 substituting 5-(trifluoromethyl)pyrazine-2-carboxylic acid for 2-methylthiazole-4-carboxylic acid. $^1$H NMR (400 MHz, DMSO-$d_6$) δ ppm 9.29 (d, J=1.3 Hz, 1H), 9.20 (d, J=1.2 Hz, 1H), 8.11 (s, 1H), 7.49 (t, J=8.9 Hz, 1H), 7.30 (s, 1H), 7.06 (dd, J=11.4, 2.9 Hz, 1H), 6.84 (ddd, J=9.0, 2.9, 1.2 Hz, 1H), 5.14 (d, J=4.4 Hz, 1H), 4.48 (s, 2H), 4.15-4.08 (m, 1H), 2.43 (td, J=9.9, 9.5, 4.8 Hz, 1H), 2.11 (td, J=13.7, 12.3, 8.3 Hz, 2H), 2.04-1.80 (m, 7H); MS (ESI⁺) m/z 517.1 (M+H)⁺.

Example 554: N-{(3S)-4-[2-(4-chloro-3-fluorophenoxy)acetamido]-3-hydroxybicyclo[2.2.2]octan-1-yl}-5-cyclopropylpyrazine-2-carboxamide (Compound 653)

The title compound was prepared using the methodologies described in Example 473 substituting 5-cyclopropylpyrazine-2-carboxylic acid for 2-methylthiazole-4-carboxylic acid. $^1$H NMR (501 MHz, DMSO-d$_6$) δ ppm 8.93 (d, J=1.4 Hz, 1H), 8.63 (d, J=1.4 Hz, 1H), 7.81 (s, 1H), 7.49 (t, J=8.9 Hz, 1H), 7.30 (s, 1H), 7.06 (dd, J=11.4, 2.9 Hz, 1H), 6.84 (ddd, J=9.0, 2.9, 1.2 Hz, 1H), 5.11 (s, 1H), 4.48 (s, 2H), 4.10 (ddd, J=9.6, 3.3, 1.4 Hz, 1H), 2.41 (ddd, J=12.6, 9.4, 2.6 Hz, 1H), 2.32 (tt, J=8.1, 4.7 Hz, 1H), 2.17-2.08 (m, 1H), 2.11-2.04 (m, 1H), 2.02-1.81 (m, 7H), 1.17-1.08 (m, 2H), 1.02 (dt, J=4.6, 3.1 Hz, 2H); MS (ESI⁺) m/z 489.2 (M+H)⁺.

Example 555: N-{3-[2-(4-chloro-3-fluorophenoxy)acetamido]bicyclo[1.1.1]pentan-1-yl}-3-(difluoromethyl)-1,2-oxazole-5-carboxamide (Compound 654)

Example 555A: 2,2-dimethoxyacetaldehyde Oxime

To a solution of hydroxylamine, hydrochloric acid (2.0 g, 28.8 mmol) in water (20 mL) was added a solution of NaHCO$_3$ (3.87 g, 46.1 mmol) in water (20 mL) at 20° C., then a solution of 2,2-dimethoxyacetaldehyde (5 g, 28.8 mmol) in 2-methoxy-2-methylpropane (30 mL) was added at 20° C., and the resulting solution was stirred for 12 hours at 20° C. The mixture was extracted with ethyl acetate (2×100 mL), and the combined organic fractions was dried over anhydrous Na$_2$SO$_4$, filtered and concentrated under reduced pressure to give the title compound (3.5 g, 26.4, 92% yield). $^1$H NMR (400 MHz, CDCl$_3$) δ ppm 8.71 (s, 1H), 7.37 (d, J=5.26 Hz, 1H), 4.86 (d, J=5.26 Hz, 1H), 3.37-3.44 (m, 6H).

Example 555B: N-hydroxy-2,2-dimethoxyacetimidoyl Chloride

To a solution of the product of Example 555A (3.5 g, 26.4 mmol) in N,N-dimethylformamide, (50 mL) was added N-chlorosuccinimide (NCS, 4.24 g, 31.7 mmol) at 0° C. The reaction mixture was then allowed to warm to 20° C. with stirring over 16 hours. The reaction mixture was diluted with water (150 mL) and extracted with CH$_2$Cl$_2$ (3×200 mL). The combined organic fractions were washed with brine (3×200 mL), filtered and concentrated under reduced pressure to give the title compound (3.3 g, 19.3 mmol, 73% yield). $^1$H NMR (400 MHz, CDCl$_3$) δ ppm 8.58 (s, 1H), 4.91 (s, 1H), 3.42 (s, 6H).

Example 555C: methyl 3-(dimethoxymethyl)isoxazole-5-carboxylate

To a solution of methyl propiolate (3.15 g, 37.5 mmol) in toluene (100 mL) at 5° C. was added the product of Example 555B (3.2 g, 18.75 mmol). Then N,N-diisopropylethylamine (3.60 mL, 20.6 mmol) was added dropwise at 5° C., and the mixture was allowed to warm to ambient temperature and was stirred for 12 hours. The reaction mixture was diluted with water (100 mL) and extracted with ethyl acetate (2×100 mL). The combined organic fractions were dried over anhydrous Na$_2$SO$_4$, filtered, and concentrated under reduced pressure. The residue was purified by column chromatography (SiO$_2$, petroleum ether and ethyl acetate (100:1 to 50:1)) to give the title compound (2.2 g, 10.4 mmol, 55% yield). $^1$H NMR (400 MHz, CDCl$_3$) δ ppm 7.01 (s, 1H), 5.53 (s, 1H), 3.98 (s, 3H), 3.43 (s, 6H).

Example 555D: methyl 3-formylisoxazole-5-carboxylate

A mixture of the product of Example 555C (2.1 g, 9.92 mmol) in trifluoroacetic acid (30 mL) and water (3 mL) was stirred for 12 hours at 20° C. The mixture was diluted with water (100 mL) and was extracted with CH$_2$Cl$_2$ (3×100 mL). The combined organic fractions were washed with saturated, aqueous NaHCO$_3$ (carefully), washed with brine (100 mL), dried over anhydrous Na$_2$SO$_4$. The mixture was filtered, and the filtrate was concentrated under reduced pressure to give the title compound. $^1$H NMR (400 MHz, CDCl$_3$) δ ppm 9.98-10.23 (m, 1H), 5.23 (s, 1H), 3.94 (s, 3H), 3.35 (s, 2H).

Example 555E: methyl 3-(difluoromethyl)isoxazole-5-carboxylate

To a solution of the product of Example 555D (1.05 g, 6.43 mmol) in CH$_2$Cl$_2$ (50 mL) at −40° C. under N$_2$ was added diethylaminosulfur trifluoride (DAST, 1.7 mL, 12.9 mmol), and the resulting solution was allowed to warm to 20° C. and was stirred for 12 hours. The reaction was quenched with saturated, aqueous NaHCO$_3$, and the layers were separated. The organic fraction was washed with brine (100 mL), dried over anhydrous Na$_2$SO$_4$ and concentrated under reduced pressure to give the title compound (1.0 g, 5.1 mmol, 79% yield). $^1$H NMR (400 MHz, CDCl$_3$) δ ppm 7.15 (s, 1H), 6.66-6.99 (m, 1H), 3.98-4.03 (m, 3H).

Example 555F: 3-(difluoromethyl)isoxazole-5-carboxylic Acid

To a solution of the product of Example 555E (0.95 g, 4.8 mmol) in tetrahydrofuran (20 mL), methanol (5 mL) and water (5 mL) was added LiOH (0.23 g, 9.7 mmol) at 0° C., and the resulting solution was stirred for 2 hours at 20° C. The material was concentrated under reduced pressure, and the residue was diluted with water (20 mL) and extracted with CH$_2$Cl$_2$ (50 mL). The aqueous layer was adjusted to pH=1 by addition of aqueous HCl (0.5 M), and the resulting mixture was extracted with ethyl acetate (2×50 mL). The ethyl acetate extracts were combined, dried over anhydrous Na$_2$SO$_4$ and concentrated under reduced pressure to the title compound (0.73 g, 4.4 mmol, 91% yield). $^1$H NMR (400 MHz, CDCl$_3$) δ ppm 7.50 (s, 1H), 7.18-7.47 (m, 1H).

Example 555G: N-{3-[2-(4-chloro-3-fluorophenoxy)acetamido]bicyclo[1.1.1.1]pentan-1-yl}-3-(difluoromethyl)-1,2-oxazole-5-carboxamide To a mixture of the product of Example 4A (0.1 g, 0.35 mmol) and the product of Example 555F (0.057 g, 0.35 mmol) in N,N-dimethylformamide (3 mL) was added triethylamine (0.20 mL, 1.41 mmol) followed by 2-(3H-[1,2,3]triazolo[4,5-b]pyridin-3-yl)-1,1,3,3-tetramethylisouronium hexafluorophosphate(V) (HATU, 0.147 g, 0.386 mmol). This mixture was allowed to stir at ambient temperature for 16 hours and then was diluted with saturated, aqueous NaHCO$_3$ (20 mL) and ethyl acetate (20 mL). The layers were separated, and the aqueous layer was extracted with ethyl acetate (3×10 mL). The combined organic fractions were dried over anhydrous Na$_2$SO$_4$, filtered, and concentrated under reduced pressure. The residue was purified via column chromatography (SiO$_2$, 75% ethyl acetate/heptanes) and then was purified by preparative HPLC [Waters XBridge™ C18 5 μm OBD™ column, 50×100 mm, flow rate 90 mL/minute, 5-100% gradient of acetonitrile in buffer (0.1% trifluoroacetic acid)] to give the title compound (0.07 g, 0.16 mmol, 46% yield). $^1$H NMR (400 MHz, DMSO-d$_6$) δ ppm 9.68 (s, 1H), 8.77 (s, 1H), 7.61-7.14 (m, 3H), 7.08 (dd, J=11.4, 2.8 Hz, 1H), 6.86 (ddd, J=8.9, 2.9, 1.2 Hz, 1H), 4.50 (s, 2H), 2.35 (s, 6H); MS (ESI$^+$) m/z 430 (M+H)$^+$.

Example 556: N-{3-[2-(4-chloro-3-fluorophenoxy)acetamido]bicyclo[1.1.1]pentan-1-yl}-2-cyclopropyl-1,3-thiazole-4-carboxamide (Compound 655)

The title compound was prepared using the methodologies described above. $^1$H NMR (400 MHz, DMSO-d$_6$) δ ppm 8.72 (s, 1H), 8.70 (s, 1H), 7.95 (s, 1H), 7.50 (t, J=8.9 Hz, 1H), 7.08 (dd, J=11.4, 2.8 Hz, 1H), 6.86 (ddd, J=9.0, 2.9, 1.2 Hz, 1H), 4.49 (s, 2H), 2.47-2.37 (m, 1H), 2.32 (s, 6H), 1.17-1.10 (m, 2H), 1.08-1.01 (m, 2H); MS (ESI$^+$) m/z 436 (M+H)$^+$.

Example 557: 2-({4-[2-(4-chloro-3-fluorophenoxy)acetamido]-3-hydroxybicyclo[2.2.2]octan-1-yl}carbamoyl)benzoic acid (Compound 656)

A mixture of Example 130E (200 mg, 0.527 mmol), N-carbethoxyphthalimide (139 mg, 0.633 mmol) and potassium carbonate (200 mg, 1.450 mmol) in water (3 mL) was stirred at ambient temperature for 16 hours. Acetonitrile (3 mL) and excess N-ethyl-N-isopropylpropan-2-amine were added, and the mixture was stirred at 50° C. for another 48 hours. Volatiles were removed, and the residue was purified by HPLC (20-100% acetonitrile in 0.1% trifluoroacetic acid/water on Phenomenex® C18 5 μm (250 mm×21.2 mm) column at a flowrate of 25 mL/minute) to give 30 mg of product as a white solid. $^1$H NMR (400 MHz, DMSO-d$_6$) δ ppm 12.83 (s, 1H), 7.78-7.71 (m, 1H), 7.59-7.41 (m, 3H), 7.40-7.24 (m, 4H), 7.06 (dd, J=11.4, 2.8 Hz, 1H), 6.84 (ddd, J=9.0, 2.9, 1.2 Hz, 1H), 5.07 (s, 1H), 4.47 (s, 2H), 4.08-4.00 (m, 1H), 2.36 (ddd, J=13.3, 9.4, 2.1 Hz, 1H), 2.17-2.00 (m, 1H), 2.03-1.89 (m, 1H), 1.93-1.77 (m, 7H); MS (ESI$^+$) m/z 491.2 (M+H)$^+$.

Example 558: N-{4-[2-(4-chloro-3-fluorophenoxy)acetamido]-3-hydroxybicyclo[2.2.2]octan-1-yl}-1,5-dimethyl-1H-1,2,4-triazole-3-carboxamide (Compound 657)

The title compound was prepared using the methodologies described in Example 130 substituting 1,5-dimethyl-1H-1,2,4-triazole-3-carboxylic acid for 5-(difluoromethyl)pyrazine-2-carboxylic. $^1$H NMR (500 MHz, DMSO-d$_6$) δ ppm 7.49 (t, J=8.9 Hz, 1H), 7.35 (s, 1H), 7.29 (s, 1H), 7.06 (dd, J=11.4, 2.8 Hz, 1H), 6.83 (ddd, J=9.0, 2.8, 1.1 Hz, 1H), 4.48 (s, 2H), 4.07 (dd, J=9.6, 3.1 Hz, 1H), 3.80 (s, 3H), 2.40 (s, 4H), 2.13-2.01 (m, 1H), 1.97-1.81 (m, 8H); MS (ESI$^+$) m/z 466.2 (M+H)$^+$.

Example 559: N-{3-[2-(4-chloro-3-fluorophenoxy)acetamido]bicyclo[1.1.1]pentan-1-yl}-1,5-naphthyridine-2-carboxamide (Compound 658)

The reaction and purification conditions described in Example 383 substituting 1,5-naphthyridine-2-carboxylic acid for quinoxaline-2-carboxylic acid gave the title compound. $^1$H NMR (400 MHz, DMSO-d$_6$) δ ppm 9.49 (s, 1H), 9.12 (dd, J=4.2, 1.7 Hz, 1H), 8.79 (s, 1H), 8.61 (d, J=8.7 Hz, 1H), 8.54 (dt, J=8.5, 1.2 Hz, 1H), 8.35 (d, J=8.7 Hz, 1H), 7.91 (dd, J=8.6, 4.2 Hz, 1H), 7.51 (t, J=8.9 Hz, 1H), 7.10 (dd, J=11.3, 2.9 Hz, 1H), 6.88 (ddd, J=9.0, 2.8, 1.2 Hz, 1H), 4.52 (s, 2H), 2.43 (s, 6H); MS (ESI$^+$) m/z 441 (M+H)$^+$.

Example 560: N-{3-[2-(4-chloro-3-fluorophenoxy)acetamido]bicyclo[1.1.1]pentan-1-yl}-1,6-naphthyridine-2-carboxamide (Compound 659)

The reaction and purification conditions described in Example 383 substituting 1,6-naphthyridine-2-carboxylic acid for quinoxaline-2-carboxylic acid gave the title compound. $^1$H NMR (400 MHz, DMSO-d$_6$) δ ppm 9.58 (d, J=2.6 Hz, 2H), 8.86 (d, J=6.0 Hz, 1H), 8.82 (d, J=8.5 Hz, 1H), 8.78 (s, 1H), 8.28 (d, J=8.5 Hz, 1H), 8.07 (d, J=6.0 Hz, 1H), 7.51 (t, J=8.9 Hz, 1H), 7.09 (dd, J=11.3, 2.8 Hz, 1H), 6.88 (dt, J=9.1, 1.8 Hz, 1H), 4.51 (s, 2H), 2.42 (s, 6H); $^{19}$F NMR (376 MHz, DMSO-d$_6$) δ ppm −74.91, −114.11 MS (ESI$^+$) m/z 442 (M+H)$^+$.

Example 561: N-{3-[2-(4-chloro-3-fluorophenoxy)acetamido]bicyclo[1.1.1]pentan-1-yl}isoquinoline-3-carboxamide (Compound 660)

The reaction and purification conditions described in Example 383 substituting isoquinoline-3-carboxylic acid for quinoxaline-2-carboxylic acid gave the title compound. $^1$H NMR (400 MHz, DMSO-d$_6$) δ ppm 9.58 (d, J=2.6 Hz, 2H), 8.86 (d, J=6.0 Hz, 1H), 8.82 (d, J=8.5 Hz, 1H), 8.78 (s, 1H), 8.28 (d, J=8.5 Hz, 1H), 8.07 (d, J=6.0 Hz, 1H), 7.51 (t, J=8.9 Hz, 1H), 7.09 (dd, J=11.3, 2.8 Hz, 1H), 6.88 (dt, J=9.1, 1.8 Hz, 1H), 4.51 (s, 2H), 2.42 (s, 6H); MS (ESI$^+$) m/z 440 (M+H)$^+$.

Example 562: 2-(4-chloro-3-fluorophenoxy)-N-{3-[(5-chloropyridine-2-sulfonyl)amino]bicyclo[1.1.1]pentan-1-yl}acetamide (Compound 661)

To a solution of Example 3B (60.0 mg, 0.187 mmol) and 5-chloropyridine-2-sulfonyl chloride (43.6 mg, 0.205 mmol) in N,N-dimethylformamide (1.5 mL) was added triethylamine (0.065 mL, 0.467 mmol). The mixture was stirred for 2 hours, quenched with saturated NaHCO$_3$ and brine, and extracted with ethyl acetate (2×). The combined organic layers were concentrated, and the residue was purified by reverse-phase HPLC (see protocol in Example 273E) to provide the title compound (26.7 mg, 31%). $^1$H NMR (500 MHz, DMSO-d$_6$) δ ppm 9.05 (s, 1H), 8.85 (dd, J=2.5, 0.7 Hz, 1H), 8.65 (s, 1H), 8.24 (dd, J=8.4, 2.4 Hz, 1H), 8.00 (dd, J=8.4, 0.7 Hz, 1H), 7.48 (t, J=8.8 Hz, 1H), 7.03 (dd, J=11.3, 2.9 Hz, 1H), 6.81 (ddd, J=9.0, 2.9, 1.2 Hz, 1H), 4.42 (s, 2H), 1.96 (s, 6H); MS (ESI$^+$) m/z 460.3 (M+H)$^+$.

Example 563: 2-(4-chloro-3-fluorophenoxy)-N-{3-[(4-methylbenzene-1-sulfonyl)amino]bicyclo[1.1.1]pentan-1-yl}acetamide (Compound 662)

The reaction described in Example 562 substituting p-toluenesulfonyl chloride for 5-chloropyridine-2-sulfonyl chloride gave the title compound. $^1$H NMR (400 MHz, DMSO-d$_6$) δ ppm 8.64 (s, 1H), 8.59 (s, 1H), 7.75-7.65 (m, 2H), 7.49 (t, J=8.9 Hz, 1H), 7.42 (d, J=8.1 Hz, 2H), 7.04 (dd, J=11.3, 2.8 Hz, 1H), 6.82 (dt, J=8.9, 1.8 Hz, 1H), 4.43 (s, 2H), 2.53 (p, J=1.9 Hz, 3H), 1.94 (s, 6H); MS (ESI$^+$) m/z 439.0 [M+H]$^+$.

Example 564: 2-(4-chloro-3-fluorophenoxy)-N-[(3S)-3-hydroxy-4-{[4-(trifluoromethyl)benzene-1-sulfonyl]amino}bicyclo[2.2.2]octan-1-yl]acetamide (Compound 663)

Example 564A: N-[(3S)-4-amino-3-hydroxybicyclo[2.2.2]octan-1-yl]-2-(4-chloro-3-fluorophenoxy)acetamide hydrochloride A mixture of Example 308A (4.5 g, 9.85 mmol) and hydrogen chloride (4 N in 1,4-dioxane, 10.0 mL, 40.0 mmol) in ether (100 mL) was stirred at room temperature for 16 hours. Volatiles were removed, and the residue was triturated with CH$_2$Cl$_2$/CH$_3$OH/hexane to give the title compound (3.2 g, 86%). MS (ESI$^+$) m/z 343.2 (M+H)$^+$.

Example 564B: 2-(4-chloro-3-fluorophenoxy)-N-[(3S)-3-hydroxy-4-{[4-(trifluoromethyl)benzene-1-sulfonyl]amino}bicyclo[2.2.2]octan-1-yl]acetamide To a solution of Example 564A (55.0 mg, 0.145 mmol) and 4-(trifluoromethyl)benzene-1-sulfonyl chloride (35.5 mg, 0.145 mmol) in N,N-dimethylformamide (2 mL) was added triethylamine (0.051 mL, 0.363 mmol). The mixture was stirred for 3 hours, treated with brine, and extracted with ethyl acetate (2×). The combined organic layers were dried over MgSO$_4$, filtered, and concentrated. The residue was purified by reverse-phase HPLC (see protocol in Example 273E) to provide the title compound (34.0 mg, 43%). $^1$H NMR (500 MHz, DMSO-d$_6$) δ ppm 8.04 (d, J=8.2 Hz, 2H), 7.94 (d, J=8.3 Hz, 2H), 7.47 (dd, J=17.9, 9.3 Hz, 3H), 6.99 (dd, J=11.4, 2.9 Hz, 1H), 6.78 (ddd, J=9.0, 2.9, 1.1 Hz, 1H), 4.39 (s, 2H), 3.78 (dt, J=9.3, 2.0 Hz, 1H), 2.22 (ddd, J=12.8, 9.4, 3.0 Hz, 1H), 1.89-1.50 (m, 9H); MS (ESI$^+$) m/z 567.9 (M+NH$_4$)$^+$.

Example 565: 5-chloro-N-{3-[2-(4-chloro-3-fluorophenoxy)acetamido]bicyclo[1.1.1]pentan-1-yl}-4-methylpyridine-2-carboxamide (Compound 664)

The title compound was prepared using the methodologies described above. $^1$H NMR (400 MHz, DMSO-d$_6$) δ ppm 9.18 (s, 1H), 8.64 (s, 1H), 8.50 (s, 1H), 7.90 (d, J=0.7 Hz, 1H), 7.42 (t, J=8.9 Hz, 1H), 7.00 (dd, J=11.4, 2.8 Hz, 1H), 6.78 (ddd, J=9.0, 2.9, 1.2 Hz, 1H), 4.41 (s, 2H), 2.35 (d, J=0.6 Hz, 3H), 2.26 (s, 6H); MS (ESI$^+$) m/z 438 (M+H)$^+$.

Example 566: N-{(3S)-4-[2-(4-chloro-3-fluorophenoxy)acetamido]-3-hydroxybicyclo[2.2.2]octan-1-yl}-4-(difluoromethyl)thiophene-2-carboxamide (Compound 665)

The title compound was prepared using the methodologies described in Example 473 substituting Example 567B for Example 473A and 4-(difluoromethyl)thiophene-2-carboxylic acid for 2-methylthiazole-4-carboxylic acid. $^1$H NMR (501 MHz, DMSO-d$_6$) δ ppm 7.91 (s, 1H), 7.78 (dd, J=3.8, 1.8 Hz, 1H), 7.55-7.40 (m, 2H), 7.28 (t, J=52.0 Hz, 1H), 7.28 (s, 1H), 7.15 (s, OH), 7.06 (dd, J=11.4, 2.9 Hz, 1H), 6.84 (ddd, J=9.0, 2.9, 1.2 Hz, 1H), 4.48 (s, 2H), 4.12-4.04 (m, 1H), 2.36 (ddd, J=12.3, 9.4, 2.2 Hz, 1H), 2.17-1.95 (m, 3H), 1.99-1.84 (m, 5H), 1.89-1.79 (m, 1H); MS (ESI$^+$) m/z 502.6 (M+H)$^+$.

Example 567: N-{(3S)-4-[2-(4-chloro-3-fluorophenoxy)acetamido]-3-hydroxybicyclo[2.2.2]octan-1-yl}-5-methylpyrazine-2-carboxamide (Compound 666)

Example 567A: N-(4-amino-2-hydroxybicyclo[2.2.2]octan-1-yl)-2-(4-chloro-3-fluorophenoxy)acetamide hydrochloride A mixture of Example 130D (7 g, 15.39 mmol) and NaBH$_4$ (0.582 g, 15.39 mmol) in a mixture of methanol (200 mL) and methylene chloride (200 mL) was stirred at 20° C. for 12 hours. The solution was concentrated, and the residue was purified by preparative HPLC (5~100% acetonitrile in water with 0.05% HCl on a SNAP C18 (20-35 μm, 800 g) column at a flow rate of 200 mL/minute) to provide the title compound (5.0 g, 83%). MS (ESI$^+$) m/z 343.1 (M+H)$^+$.

Example 567B: N-[(2S)-4-amino-2-hydroxybicyclo[2.2.2]octan-1-yl]-2-(4-chloro-3-fluorophenoxy)acetamide The title compound was isolated by chiral preparative SFC (see SFC protocol in Example 398A) as the first peak eluted off the column. MS (ESI$^+$) m/z 343.1 (M+H)$^+$.

Example 567C: N-{(3S)-4-[2-(4-chloro-3-fluorophenoxy)acetamido]-3-hydroxybicyclo[2.2.2]octan-1-yl}-5-methylpyrazine-2-carboxamide (Compound 666)

To a mixture of Example 567B (55.0 mg, 0.160 mmol) in N,N-dimethylformamide (1.5 mL) was added triethylamine (0.034 mL, 0.241 mmol), 5-methylpyrazine-2-carboxylic acid (24.38 mg, 0.176 mmol) and (1-cyano-2-ethoxy-2-oxoethylidenaminooxy)dimethylamino-morpholino-carbenium hexafluorophosphate (COMU, 82 mg, 0.193 mmol). The mixture was stirred for 4 hours. The reaction mixture was quenched with brine and saturated NaHCO$_3$ and extracted with ethyl acetate (2×). The combined organic layers were concentrated and purified by reverse-phase HPLC (see protocol in Example 273E) to provide the title compound (36.7 mg, 49%). $^1$H NMR (501 MHz, DMSO-d$_6$) δ ppm 8.98 (d, J=1.4 Hz, 1H), 8.54 (d, J=1.4 Hz, 1H), 7.83 (s, 1H), 7.47 (t, J=8.9 Hz, 1H), 7.28 (s, 1H), 7.04 (dd, J=11.3, 2.9 Hz, 1H), 6.82 (ddd, J=9.0, 2.9, 1.2 Hz, 1H), 4.46 (s, 2H), 4.08 (ddd, J=9.5, 3.3, 1.4 Hz, 1H), 2.56 (s, 3H), 2.40 (ddd, J=12.6, 9.5, 2.7 Hz, 1H), 2.15-1.76 (m, 9H); MS (ESI$^+$) m/z 463.1 (M+H)$^+$.

Example 568: N-{(3S)-4-[2-(4-chloro-3-fluorophenoxy)acetamido]-3-hydroxybicyclo[2.2.2]octan-1-yl}quinoxaline-2-carboxamide (Compound 667)

To a mixture of Example 567B (40.0 mg, 0.117 mmol), and N-ethyl-N-isopropylpropan-2-amine (0.102 mL, 0.583 mmol) in dichloromethane (1.5 mL) was added quinoxaline-2-carbonyl chloride (49.4 mg, 0.257 mmol), and the reaction was stirred at ambient temperature for 30 minutes. Volatiles were removed, and the residue was purified by HPLC (20-100% acetonitrile in 0.1% trifluoroacetic acid/water on a Phenomenex® C18 10 μm (250 mm×50 mm) column at a flow rate of 50 mL/minute) to give 35 mg of the title compound as a white solid. $^1$H NMR (400 MHz, DMSO-d$_6$)

δ ppm 9.42 (s, 1H), 8.26-8.13 (m, 2H), 8.12 (s, 1H), 7.98 (tt, J=5.9, 4.6 Hz, 2H), 7.50 (t, J=8.9 Hz, 1H), 7.32 (s, 1H), 7.07 (dd, J=11.4, 2.9 Hz, 1H), 6.85 (ddd, J=8.9, 2.9, 1.2 Hz, 1H), 5.16 (d, J=4.4 Hz, 1H), 4.50 (s, 2H), 4.19-4.04 (m, 2H), 3.17 (d, J=5.0 Hz, 1H), 2.51-2.43 (m, 1H), 2.16 (td, J=9.7, 9.2, 3.7 Hz, 2H), 2.07-1.94 (m, 6H), 1.98-1.83 (m, 1H); MS (ESI$^+$) m/z 498.6 (M+NH$_4$—H$_2$O)$^+$.

Example 569: N-{(3S)-4-[2-(4-chloro-3-fluorophenoxy)acetamido]-3-hydroxybicyclo[2.2.2]octan-1-yl}-5-ethyl-1,2-oxazole-3-carboxamide (Compound 668)

The title compound was prepared using the methodologies described in Example 473 substituting Example 567B for Example 473A and 5-ethylisoxazole-3-carboxylic acid for 2-methylthiazole-4-carboxylic acid. $^1$H NMR (400 MHz, DMSO-d$_6$) δ ppm 7.86 (s, 1H), 7.49 (t, J=8.9 Hz, 1H), 7.28 (s, 1H), 7.06 (dd, J=11.4, 2.8 Hz, 1H), 6.83 (ddd, J=9.0, 2.9, 1.2 Hz, 1H), 6.50 (s, 1H), 5.11 (s, 1H), 4.47 (s, 2H), 4.10-4.04 (m, 1H), 2.82-2.74 (m, 2H), 2.35 (ddd, J=12.6, 9.3, 2.5 Hz, 1H), 2.14-2.04 (m, 1H), 2.07-1.99 (m, 1H), 1.98-1.79 (m, 7H), 1.22 (t, J=7.6 Hz, 3H); MS (ESI$^+$) m/z 466.1 (M+H)$^+$.

Example 570: N-{3-[2-(4-chloro-3-fluorophenoxy)acetamido]bicyclo[1.1.1]pentan-1-yl}-1,8-naphthyridine-2-carboxamide (Compound 669)

The reaction and purification conditions described in Example 383 substituting 1,8-naphthyridine-2-carboxylic acid (20.19 mg, 0.116 mmol) for quinoxaline-2-carboxylic acid (16.82 mg, 0.097 mmol) gave the title compound. $^1$H NMR (500 MHz, DMSO-d$_6$) δ ppm 9.54 (s, 1H), 9.21 (dd, J=4.2, 2.0 Hz, 1H), 8.79 (s, 1H), 8.69 (d, J=8.4 Hz, 1H), 8.59 (dd, J=8.2, 2.0 Hz, 1H), 8.23 (d, J=8.3 Hz, 1H), 7.75 (dd, J=8.2, 4.2 Hz, 1H), 7.51 (t, J=8.9 Hz, 1H), 7.10 (dd, J=11.4, 2.9 Hz, 1H), 6.91-6.85 (m, 1H), 4.51 (s, 2H), 2.42 (s, 6H); $^{19}$F NMR (376 MHz, DMSO-d$_6$) δ ppm −74.70, −114.15; MS (ESI$^+$) m/z 441 (M+H)$^+$.

Example 571: N-{(3S)-4-[2-(4-chloro-3-fluorophenoxy)acetamido]-3-hydroxybicyclo[2.2.2]octan-1-yl}pyrazine-2-carboxamide (Compound 670)

The title compound was prepared using the methodologies described in Example 473 substituting Example 567B for Example 473A and pyrazine-2-carboxylic acid for 2-methylthiazole-4-carboxylic acid. $^1$H NMR (400 MHz, DMSO-d$_6$) δ ppm 9.14 (d, J=1.5 Hz, 1H), 8.86 (d, J=2.5 Hz, 1H), 8.72-8.67 (m, 1H), 7.95 (d, J=3.6 Hz, 1H), 7.49 (t, J=8.9 Hz, 1H), 7.30 (s, 1H), 7.10-7.03 (m, 1H), 6.87-6.79 (m, 1H), 5.14 (d, J=4.4 Hz, 1H), 4.48 (d, J=0.9 Hz, 2H), 4.15-4.07 (m, 1H), 2.42 (ddd, J=12.7, 9.5, 2.6 Hz, 1H), 2.17-2.05 (m, 2H), 2.02 1.82 (m, 7H); MS (ESI$^+$) m/z 449.0 (M+H)$^+$.

Example 572: N-{(3S)-4-[2-(4-chloro-3-fluorophenoxy)acetamido]-3-hydroxybicyclo[2.2.2]octan-1-yl}-3-(difluoromethyl)-1,2-oxazole-5-carboxamide (Compound 671)

The title compound was prepared using the methodologies described in Example 473 substituting Example 567B for Example 473A and Example 555F for 2-methylthiazole-4-carboxylic acid. $^1$H NMR (400 MHz, DMSO-d$_6$) δ ppm 8.33 (s, 1H), 7.53-7.44 (m, 1H), 7.40 (s, 1H), 7.33 (t, J=52.0 Hz, 1H), 7.32 (d, J=15.2 Hz, 1H), 7.06 (dd, J=11.4, 2.9 Hz, 1H), 6.83 (ddd, J=9.0, 2.9, 1.2 Hz, 1H), 5.09 (s, 1H), 4.48 (s, 2H), 4.09 (dd, J=9.6, 3.1 Hz, 1H), 2.36 (ddd, J=12.5, 9.7, 1.8 Hz, 1H), 2.10 (dd, J=12.0, 8.7 Hz, 1H), 2.03 (d, J=10.7 Hz, 1H), 2.01-1.79 (m, 7H); MS (ESI$^+$) m/z 488.1 (M+H)$^+$.

Example 573: N-{(3S)-4-[2-(4-chloro-3-fluorophenoxy)acetamido]-3-hydroxybicyclo[2.2.2]octan-1-yl}-5,6-dimethylpyrazine-2-carboxamide (Compound 672)

The title compound was prepared using the methodologies described in Example 473 substituting Example 567B for Example 473A and 5,6-dimethylpyrazine-2-carboxylic acid for 2-methylthiazole-4-carboxylic acid. $^1$H NMR (400 MHz, DMSO-d$_6$) δ ppm 8.80 (s, 1H), 7.76 (s, 1H), 7.49 (t, J=8.9 Hz, 1H), 7.30 (s, 1H), 7.06 (dd, J=11.4, 2.9 Hz, 1H), 6.84 (ddd, J=9.0, 2.9, 1.2 Hz, 1H), 4.48 (s, 2H), 4.15-4.06 (m, 1H), 2.55 (d, J=3.6 Hz, 6H), 2.41 (ddd, J=12.5, 9.5, 2.3 Hz, 1H), 2.19-2.01 (m, 2H), 2.03-1.81 (m, 7H); MS (ESI$^+$) m/z 477.2 (M+H)$^+$.

Example 574: N-{(3S)-4-[2-(4-chloro-3-fluorophenoxy)acetamido]-3-hydroxybicyclo[2.2.2]octan-1-yl}-5-methyl-1H-1,2,4-triazole-3-carboxamide (Compound 673)

The title compound was prepared using the methodologies described in Example 473 substituting Example 567B for Example 473A and Example 388A for 2-methylthiazole-4-carboxylic acid. $^1$H NMR (400 MHz, DMSO-d$_6$) δ ppm 7.53-7.43 (m, 2H), 7.28 (s, 1H), 7.06 (dd, J=11.4, 2.9 Hz, 1H), 6.84 (ddd, J=9.0, 2.9, 1.2 Hz, 1H), 4.48 (s, 2H), 4.12-4.04 (m, 1H), 2.43-2.32 (m, 1H), 2.35 (s, 3H), 2.17-1.98 (m, 2H), 2.00-1.78 (m, 7H); MS (ESI$^+$) m/z 452.2 (M+H)$^+$.

Example 575: N-{3-[2-(3,4-dichlorophenoxy)acetamido]bicyclo[1.1.1]pentan-1-yl}-2-ethyl-1,3-oxazole-5-carboxamide (Compound 674)

The title compound was prepared using the methodologies described above. $^1$H NMR (400 MHz, DMSO-d$_6$) δ ppm 9.05 (s, 1H), 8.74 (s, 1H), 7.61 (s, 1H), 7.55 (d, J=8.8 Hz, 1H), 7.27 (d, J=2.9 Hz, 1H), 6.99 (dd, J=8.9, 2.9 Hz, 1H), 4.50 (s, 2H), 2.79 (q, J=7.6 Hz, 2H), 2.31 (s, 6H), 1.25 (t, J=7.6 Hz, 3H); MS (ESI$^+$) m/z 424 (M+H)$^+$.

Example 576: N-{3-[2-(3,4-dichlorophenoxy)acetamido]bicyclo[1.1.1]pentan-1-yl}-2-methyl-1,3-oxazole-5-carboxamide (Compound 675)

The reaction and purification conditions described in Example 52 substituting methyl 2-methyloxazole-5-carboxylate (Combi-Blocks) for the product of Example 49A, methanol for ethanol, and the product of Example 2B for the product of Example 6C gave the title compound. $^1$H NMR (400 MHz, DMSO-d$_6$) δ ppm 1H NMR (400 MHz, DMSO-d$_6$) δ ppm 9.05 (s, 1H), 8.73 (s, 1H), 7.59 (s, 1H), 7.55 (d, J=8.9 Hz, 1H), 7.27 (d, J=2.9 Hz, 1H), 6.99 (dd, J=8.9, 2.9 Hz, 1H), 4.50 (s, 2H), 2.46 (s, 3H), 2.30 (s, 6H); MS (ESI$^+$) m/z 451 (M+H)$^+$.

Example 577: N-{3-[2-(3,4-dichlorophenoxy)acetamido]bicyclo[1.1.1]pentan-1-yl}-2-(trifluoromethyl)-1,3-thiazole-4-carboxamide (Compound 676)

The title compound was prepared using the methodologies described above. $^1$H NMR (400 MHz, DMSO-d$_6$) δ ppm 9.20 (s, 1H), 8.73 (s, 1H), 8.65 (s, 1H), 7.55 (d, J=9.0 Hz, 1H), 7.27 (d, J=2.9 Hz, 1H), 7.00 (dd, J=9.0, 2.9 Hz, 1H), 4.50 (s, 2H), 2.34 (s, 6H); MS (ESI$^+$) m/z 480 (M+H)$^+$.

Example 578: N-{3-[2-(4-chloro-3-fluorophenoxy)acetamido]bicyclo[1.1.1]pentan-1-yl}-5-methyl-1,2-thiazole-3-carboxamide (Compound 677)

The title compound was prepared using the methodologies described above. $^1$H NMR (400 MHz, DMSO-d$_6$) δ ppm 9.11 (s, 1H), 8.72 (s, 1H), 7.57-7.43 (m, 2H), 7.08 (dd, J=11.4, 2.9 Hz, 1H), 6.86 (ddd, J=9.0, 2.9, 1.3 Hz, 1H), 4.49 (s, 2H), 2.59 (d, J=1.0 Hz, 3H), 2.31 (s, 6H); MS (ESI$^+$) m/z 410 (M+H)$^+$.

Example 579: 2-(4-chloro-3-fluorophenoxy)-N-{3-[(3-methylpyrazin-2-yl)amino]bicyclo[1.1.1]pentan-1-yl}acetamide (Compound 678)

To a solution of Example 4A (50 mg, 0.176 mmol) in dioxane (0.8 mL) were added tris(dibenzylideneacetone)dipalladium(0) (Pd$_2$(dba)$_3$, 8.0 mg, 8.78 µmol), xantphos (10.2 mg, 0.018 mmol) and 2-chloro-3-methylpyrazine (24.8 mg, 0.193 mmol). Then potassium carbonate (72.8 mg, 0.527 mmol) was added. The reaction mixture was stirred overnight at 80° C. The reaction mixture was filtered, and the solids were washed with acetonitrile (3×2 mL). The filtrate and washes were concentrated under reduced pressure, and the residue was purified by preparative HPLC (Phenomenex® Luna® C8(2) 5 µm 100 Å AXIA™ column (30 mm×75 mm); a gradient of acetonitrile (A) and 0.1% trifluoroacetic acid in water (B) was used, at a flow rate of 50 mL/minute (0-1.0 minute 5% A, 1.0-8.5 minutes linear gradient 5-100% A, 8.5-11.5 minutes 100% A, 11.5-12.0 minutes linear gradient 95-5% A) to give the title compound (50 mg, 0.13 mmol, 76% yield). $^1$H NMR (501 MHz, DMSO-d$_6$) δ ppm 8.72 (s, 1H), 7.93 (dd, J=2.9, 0.8 Hz, 1H), 7.65 (d, J=2.9 Hz, 1H), 7.50 (t, J=8.9 Hz, 1H), 7.14 (s, 1H), 7.08 (dd, J=11.4, 2.8 Hz, 1H), 6.86 (ddd, J=9.0, 2.9, 1.2 Hz, 1H), 4.49 (s, 2H), 2.36 (s, 6H), 2.30 (s, 3H); MS (ESI$^+$) m/z 377 (M+H)$^+$.

Example 580: N-{(3S)-4-[2-(4-chloro-3-fluorophenoxy)acetamido]-3-hydroxybicyclo[2.2.2]octan-1-yl}-3-methyl-1,2-thiazole-5-carboxamide (Compound 679)

The title compound was prepared using the methodologies described in Example 473 substituting Example 567B for Example 473A and 3-methylisothiazole-5-carboxylic acid for 2-methylthiazole-4-carboxylic acid. $^1$H NMR (400 MHz, DMSO-d$_6$) δ ppm 8.03 (s, 1H), 7.72 (s, 1H), 7.49 (t, J=8.9 Hz, 1H), 7.28 (s, 1H), 7.06 (dd, J=11.4, 2.8 Hz, 1H), 6.83 (ddd, J=8.9, 2.9, 1.2 Hz, 1H), 5.11 (s, 1H), 4.48 (s, 2H), 4.12-4.04 (m, 1H), 2.43 (s, 3H), 2.35 (td, J=9.8, 4.7 Hz, 1H), 2.16-2.03 (m, 1H), 2.07-1.87 (m, 4H), 1.91-1.79 (m, 4H); MS (ESI$^+$) m/z 468.0 (M+H)$^+$.

Example 581: N-{(3S)-4-[2-(4-chloro-3-fluorophenoxy)acetamido]-3-hydroxybicyclo[2.2.2]octan-1-yl}-4-(hydroxymethyl)pyridine-2-carboxamide (Compound 680)

A mixture of Example 473A (55.0 mg, 0.145 mmol), triethylamine (0.051 mL, 0.363 mmol), 4-(hydroxymethyl)picolinic acid (28.9 mg, 0.189 mmol) and 1-[bis(dimethylamino)methylene]-1H-1,2,3-triazolo[4,5-b]pyridinium 3-oxid hexafluorophosphate, 71.7 mg, 0.189 mmol, HATU) in N,N-dimethylformamide (2 mL) was stirred for 2 hours. The reaction mixture was quenched with brine and saturated NaHCO$_3$ and extracted with ethyl acetate (2×). The combined organic layers were concentrated, and the residue was purified by reverse-phase HPLC (see protocol in Example 273E) to provide the title compound (36.7 mg, 49%). $^1$H NMR (400 MHz, CD$_3$OD) δ ppm 8.53 (d, J=5.1 Hz, 1H), 8.07 (dd, J=1.7, 0.9 Hz, 1H), 7.60-7.50 (m, 1H), 7.37 (t, J=8.8 Hz, 1H), 6.93 (dd, J=10.9, 2.8 Hz, 1H), 6.82 (ddd, J=8.9, 2.9, 1.3 Hz, 1H), 4.72 (t, J=0.9 Hz, 2H), 4.51-4.42 (m, 2H), 4.32 (ddd, J=9.4, 3.3, 1.5 Hz, 1H), 2.70-2.54 (m, 1H), 2.29-1.89 (m, 9H); MS (ESI$^+$) m/z 478.2 (M+H)$^+$.

Example 582: N-{(3S)-4-[2-(4-chloro-3-fluorophenoxy)acetamido]-3-hydroxybicyclo[2.2.2]octan-1-yl}-3-fluorobenzamide (Compound 681)

To a mixture of Example 567B (55.0 mg, 0.160 mmol) in N,N-dimethylformamide (2 mL) was added triethylamine (0.036 mL, 0.257 mmol), 3-fluorobenzoic acid (24.73 mg, 0.176 mmol) and 1-[bis(dimethylamino)methylene]-1H-1,2,3-triazolo[4,5-b]pyridinium 3-oxid hexafluorophosphate (HATU, 79 mg, 0.209 mmol). The mixture was stirred for 1 hour. The reaction mixture was quenched with brine and saturated NaHCO$_3$ and extracted with ethyl acetate (2×). The combined organic layers were concentrated, and the residue was purified by reverse-phase HPLC (see protocol in Example 273E) to provide the title compound (42.5 mg, 57%). $^1$H NMR (500 MHz, DMSO-d$_6$) δ ppm 7.78 (s, 1H), 7.62 (dt, J=7.9, 1.2 Hz, 1H), 7.57 (ddd, J=10.1, 2.6, 1.5 Hz, 1H), 7.52-7.44 (m, 2H), 7.34 (tdd, J=8.3, 2.7, 1.0 Hz, 1H), 7.28 (s, 1H), 7.06 (dd, J=11.4, 2.9 Hz, 1H), 6.84 (ddd, J=8.9, 2.8, 1.2 Hz, 1H), 5.10 (d, J=4.4 Hz, 1H), 4.52-4.43 (m, 2H), 4.08 (dt, J=11.0, 3.6 Hz, 1H), 2.38 (ddd, J=12.5, 9.4, 2.5 Hz, 1H), 2.16-2.00 (m, 2H), 2.00-1.79 (m, 7H); MS (ESI$^+$) m/z 465.1 (M+H)$^+$.

Example 583: N-{(3S)-4-[2-(4-chloro-3-fluorophenoxy)acetamido]-3-hydroxybicyclo[2.2.2]octan-1-yl}-5-(trifluoromethoxy)pyridine-2-carboxamide (Compound 682)

The reaction described in Example 582 substituting 5-(trifluoromethoxy)picolinic acid for 3-fluorobenzoic acid gave the title compound. $^1$H NMR (501 MHz, DMSO-d$_6$) δ ppm 8.70 (d, J=2.6 Hz, 1H), 8.17-8.10 (m, 1H), 8.06 (ddq, J=8.6, 2.3, 1.1 Hz, 1H), 7.92 (s, 1H), 7.49 (t, J=8.9 Hz, 1H), 7.30 (s, 1H), 7.07 (dd, J=11.4, 2.9 Hz, 1H), 6.84 (ddd, J=9.0, 2.9, 1.2 Hz, 1H), 5.13 (s, 1H), 4.49 (s, 2H), 4.17-4.05 (m, 1H), 2.42 (ddd, J=12.6, 9.5, 2.5 Hz, 1H), 2.18-2.04 (m, 2H), 2.03-1.79 (m, 7H); MS (ESI$^+$) m/z 532.3 (M+H)$^+$.

Example 584: N-{(3S)-4-[2-(4-chloro-3-fluorophenoxy)acetamido]-3-hydroxybicyclo[2.2.2]octan-1-yl}-1,2-thiazole-5-carboxamide (Compound 683)

The title compound was prepared using the methodologies described in Example 473 substituting Example 567B for Example 473A and isothiazole-5-carboxylic acid for 2-methylthiazole-4-carboxylic acid. $^1$H NMR (400 MHz, DMSO-d$_6$) δ ppm 8.61 (d, J=1.8 Hz, 1H), 8.12 (s, 1H), 7.94 (d, J=1.8 Hz, 1H), 7.49 (t, J=8.9 Hz, 1H), 7.29 (s, 1H), 7.06 (dd, J=11.4, 2.8 Hz, 1H), 6.84 (ddd, J=8.9, 2.9, 1.2 Hz, 1H), 4.48 (s, 2H), 4.08 (ddd, J=9.5, 3.3, 1.2 Hz, 1H), 2.37 (ddd, J=12.5, 9.4, 2.2 Hz, 1H), 2.17-2.05 (m, 1H), 2.08-2.00 (m, 1H), 2.01-1.87 (m, 5H), 1.86 (dt, J=11.4, 3.5 Hz, 2H); MS (ESI⁺) m/z 454.0 (M+H)⁺.

Example 585: N-{3-[2-(4-chloro-3-fluorophenoxy) acetamido]bicyclo[1.1.1]pentan-1-yl}-2,6-dimethylpyridine-3-carboxamide (Compound 684)

The title compound was prepared using the methodologies described above. ¹H NMR (500 MHz, DMSO-d₆) δ ppm 8.91 (s, 1H), 8.75 (s, 1H), 7.60 (d, J=7.8 Hz, 1H), 7.50 (t, J=8.9 Hz, 1H), 7.14-7.06 (m, 2H), 6.86 (ddd, J=9.0, 2.8, 1.2 Hz, 1H), 4.49 (s, 2H), 2.47 (s, 3H), 2.43 (s, 3H), 2.32 (s, 6H); MS (APCI⁺) m/z 418 (M+H)⁺.

Example 586: 4-chloro-N-{3-[2-(3,4-dichlorophenoxy)acetamido]bicyclo[1.1.1]pentan-1-yl}-3-fluorobenzamide (Compound 685)

The title compound was prepared using the methodologies described above. ¹H NMR (400 MHz, DMSO-d₆) δ ppm 9.18 (s, 1H), 8.75 (s, 1H), 7.89-7.79 (m, 1H), 7.74-7.68 (m, 2H), 7.55 (d, J=8.9 Hz, 1H), 7.27 (d, J=2.9 Hz, 1H), 7.00 (dd, J=8.9, 2.9 Hz, 1H), 4.51 (s, 2H), 2.34 (s, 6H); MS (ESI⁺) m/z 457/459 (M+H)⁺.

Example 587: 5-chloro-N-{3-[2-(4-chloro-3-fluorophenoxy)acetamido]bicyclo[1.1.1]pentan-1-yl}pyridine-2-carboxamide (Compound 686)

The title compound was prepared using the methodologies described above. ¹H NMR (500 MHz, DMSO-d₆) δ ppm 9.33 (s, 1H), 8.75 (s, 1H), 8.67 (dd, J=2.4, 0.7 Hz, 1H), 8.13 (dd, J=8.5, 2.4 Hz, 1H), 8.01 (dd, J=8.4, 0.7 Hz, 1H), 7.50 (t, J=8.9 Hz, 1H), 7.08 (dd, J=11.4, 2.8 Hz, 1H), 6.86 (ddd, J=8.9, 2.9, 1.2 Hz, 1H), 4.49 (s, 2H), 2.35 (s, 6H); MS (ESI⁺) m/z 424 (M+H)⁺.

Example 588: N-{3-[2-(3,4-dichlorophenoxy)acetamido]bicyclo[1.1.1]pentan-1-yl}-2,6-dimethylpyridine-3-carboxamide (Compound 687)

The title compound was prepared using the methodologies described above. ¹H NMR (501 MHz, DMSO-d₆) δ ppm 8.90 (s, 1H), 8.74 (s, 1H), 7.60 (d, J=7.8 Hz, 1H), 7.55 (d, J=8.9 Hz, 1H), 7.27 (d, J=2.9 Hz, 1H), 7.09 (d, J=7.8 Hz, 1H), 7.00 (dd, J=8.9, 2.9 Hz, 1H), 4.50 (s, 2H), 2.47 (s, 3H), 2.43 (s, 3H), 2.32 (s, 6H); MS (APCI⁺) m/z 434 (M+H)⁺.

Example 589: 2-(4-chloro-3-fluorophenoxy)-N-{3-[(6-methylpyrazin-2-yl)amino]bicyclo[1.1.1]pentan-1-yl}acetamide (Compound 688)

The reaction and purification conditions described in Example 579 substituting 2-bromo-6-methylpyrazine (33.4 mg, 0.193 mmol) for 2-chloro-3-methylpyrazine (24.8 mg, 0.193 mmol) gave the title compound. ¹H NMR (501 MHz, DMSO-d₆) δ ppm 8.73 (s, 1H), 7.72 (s, 1H), 7.63 (s, 1H), 7.60 (s, 1H), 7.50 (t, J=8.9 Hz, 1H), 7.08 (dd, J=11.4, 2.8 Hz, 1H), 6.86 (ddd, J=8.9, 2.9, 1.2 Hz, 1H), 4.50 (s, 2H), 2.33 (s, 6H), 2.27 (s, 3H); MS (ESI⁺) m/z 377 (M+H)⁺.

Example 590: N-{3-[2-(4-chloro-3-fluorophenoxy) acetamido]bicyclo[1.1.1]pentan-1-yl}indolizine-2-carboxamide (Compound 689)

The reaction and purification conditions described in Example 383 substituting indolizine-2-carboxylic acid (18.7 mg, 0.116 mmol) for quinoxaline-2-carboxylic acid (16.8 mg, 0.097 mmol) gave the title compound. ¹H NMR (501 MHz, DMSO-d₆) δ ppm 8.72 (d, J=11.1 Hz, 2H), 8.25 (dq, J=7.1, 1.1 Hz, 1H), 7.93 (dd, J=1.7, 0.7 Hz, 1H), 7.50 (t, J=8.8 Hz, 1H), 7.42 (dq, J=9.2, 1.1 Hz, 1H), 7.09 (dd, J=11.4, 2.8 Hz, 1H), 6.87 (ddd, J=9.0, 2.9, 1.2 Hz, 1H), 6.77 (t, J=1.3 Hz, 1H), 6.71 (ddd, J=9.1, 6.5, 1.1 Hz, 1H), 6.58 (td, J=6.8, 1.3 Hz, 1H), 4.50 (s, 2H), 2.33 (s, 6H); MS (ESI⁺) m/z 428 (M+H)⁺.

Example 591: N-{3-[2-(4-chloro-3-fluorophenoxy) acetamido]bicyclo[1.1.1]pentan-1-yl}pyrazolo[1,5-a]pyrimidine-6-carboxamide (Compound 690)

The reaction and purification conditions described in Example 383 substituting pyrazolo[1,5-a]pyrimidine-6-carboxylic acid (18.9 mg, 0.116 mmol) for quinoxaline-2-carboxylic acid (16.8 mg, 0.097 mmol) gave the title compound. ¹H NMR (500 MHz, DMSO-d₆) δ ppm 9.52 (dd, J=2.2, 0.9 Hz, 1H), 9.30 (s, 1H), 8.90 (d, J=2.2 Hz, 1H), 8.79 (s, 1H), 8.37 (d, J=2.3 Hz, 1H), 7.51 (t, J=8.9 Hz, 1H), 7.09 (dd, J=11.4, 2.9 Hz, 1H), 6.87 (ddd, J=9.0, 2.9, 1.2 Hz, 1H), 6.82 (d, J=2.3, 0.9 Hz, 1H), 4.51 (s, 2H), 2.37 (s, 6H); MS (ESI⁺) m/z 430 (M+H)⁺.

Example 592: 5-chloro-N-{3-[2-(3,4-dichlorophenoxy)acetamido]bicyclo[1.1.1]pentan-1-yl}pyridine-2-carboxamide (Compound 691)

The title compound was prepared using the methodologies described above. ¹H NMR (400 MHz, DMSO-d₆) δ ppm 9.32 (s, 1H), 8.73 (s, 1H), 8.67 (dd, J=2.4, 0.7 Hz, 1H), 8.12 (dd, J=8.4, 2.4 Hz, 1H), 8.00 (dd, J=8.4, 0.7 Hz, 1H), 7.55 (d, J=8.9 Hz, 1H), 7.27 (d, J=2.9 Hz, 1H), 6.99 (dd, J=9.0, 2.9 Hz, 1H), 4.50 (s, 2H), 2.35 (s, 6H); MS (APCI⁺) m/z 440/442 (M+H)⁺.

Example 593: 4-chloro-N-{3-[2-(4-chloro-3-fluorophenoxy)acetamido]bicyclo[1.1.1]pentan-1-yl}-3-fluorobenzamide (Compound 692)

The title compound was prepared using the methodologies described above. ¹H NMR (500 MHz, DMSO-d₆) δ ppm 9.20 (s, 1H), 8.77 (s, 1H), 7.83 (ddd, J=10.3, 1.6, 0.8 Hz, 1H), 7.74-7.69 (m, 2H), 7.50 (t, J=8.9 Hz, 1H), 7.09 (dd, J=11.4, 2.9 Hz, 1H), 6.86 (ddd, J=9.0, 2.9, 1.2 Hz, 1H), 4.49 (s, 2H), 2.34 (s, 6H); MS (APCI⁺) m/z 441 (M+H)⁺.

Example 594: N-{3-[2-(3,4-dichlorophenoxy)acetamido]bicyclo[1.1.1]pentan-1-yl}-5,6-dimethylpyridine-3-carboxamide (Compound 693)

The title compound was prepared using the methodologies described above. ¹H NMR (400 MHz, DMSO-d₆) δ ppm 9.07 (s, 1H), 8.74 (s, 1H), 8.67 (d, J=2.1 Hz, 1H), 7.93-7.88 (m, 1H), 7.55 (d, J=8.9 Hz, 1H), 7.28 (d, J=2.9 Hz, 1H), 7.00 (dd, J=9.0, 2.9 Hz, 1H), 4.50 (s, 2H), 2.46 (s, 3H), 2.34 (s, 6H), 2.28 (s, 3H); MS (ESI⁺) m/z 434 (M+H)⁺.

Example 595: N-{(3S)-4-[2-(3,4-dichlorophenoxy) acetamido]-3-hydroxybicyclo[2.2.2]octan-1-yl}-3-ethyl-1,2-oxazole-5-carboxamide (Compound 694)

Example 595A: N-[(2S)-4-(benzylamino)-2-hydroxybicyclo[2.2.2]octan-1-yl]-2-(3,4-dichlorophenoxy)acetamide To a suspension of Example 536A (1.159 g, 3.63 mmol), 1-[bis(dimethylamino)methylene]-1H-1,2,3-triazolo[4,5-b]

pyridinium 3-oxid hexafluorophosphate (1.519 g, 4.00 mmol, HATU), and triethylamine (1.70 mL, 12.20 mmol) in N,N-dimethylformamide (12 mL) at 0° C. was added 2-(3,4-dichlorophenoxy)acetic acid (0.8435 g, 3.82 mmol). The mixture was warmed to room temperature and stirred for 40 minutes. The reaction mixture was diluted with ethyl acetate, washed with 1 N NaOH and brine, dried over $Na_2SO_4$, and concentrated. The residue was chromatographed (10-20% $CH_3OH/CH_2Cl_2$ on a 40 g RediSep® silica column) to provide the title compound (1.341 g, 82%). MS (APCI$^+$) m/z 449.1 (M+H)$^+$.

Example 595B: N-[(2S)-4-amino-2-hydroxybicyclo[2.2.2]octan-1-yl]-2-(3,4-dichlorophenoxy)acetamide hydrochloride Example 595A (1.4695 g, 3.27 mmol) in tetrahydrofuran (40.9 mL) was added to 20% Pd(OH)$_2$/carbon (0.293 g, 1.063 mmol, 51% in water) and 4 M HCl in dioxane (0.981 mL, 3.92 mmol) in a 250 mL pressure bottle and shaken for 16 hours under 50 psi of hydrogen. The pressure bottle was vented and more 20% Pd(OH)$_2$/carbon (0.900 g, 3.27 mmol, 51% in water) was added. The reaction was shaken under 50 psi of hydrogen for 17 hours, vented, and filtered. The filtrate was concentrated. The concentrate was triturated with tert-butyl methyl ether (MTBE, 6 mL), and the solids were collected via filtration. This material was diluted with saturated $NaHCO_3$ and extracted with ~5% $CH_3OH$ in $CH_2Cl_2$. The organic layer was dried over $Na_2SO_4$, filtered and concentrated. The residue was chromatographed (5% $CH_3OH$ in $CH_2Cl_2$ with 2% triethylamine on a 24 g silica column) to give 0.54 g of impure material, which was further purified by preparative HPLC (see protocol in Example 273E). The trifluoroacetic acid salt of the title compound was treated with 2 M HCl in ether (2 mL) and ether (2 mL). The suspension was stirred for 15 minutes, collected by filtration, washed with ether, and vacuum oven-dried to provide the title compound. MS (ESI$^+$) m/z 359.2 (M+H)$^+$.

Example 595C: N-{(3S)-4-[2-(3,4-dichlorophenoxy)acetamido]-3-hydroxybicyclo[2.2.2]octan-1-yl}-3-ethyl-1,2-oxazole-5-carboxamide The title compound was prepared using the methodologies described in Example 473 substituting Example 595B for Example 473A and 3-ethylisoxazole-5-carboxylic acid for 2-methylthiazole-4-carboxylic acid. $^1$H NMR (400 MHz, DMSO-d$_6$) δ ppm 8.05 (s, 1H), 7.50 (d, J=8.9 Hz, 1H), 7.27-7.18 (m, 2H), 6.97-6.89 (m, 2H), 5.08 (d, J=4.4 Hz, 1H), 4.45 (s, 2H), 4.04 (dt, J=8.2, 4.3 Hz, 1H), 2.62 (q, J=7.6 Hz, 2H), 2.31 (ddd, J=12.2, 9.4, 2.0 Hz, 1H), 2.13-1.75 (m, 7H), 1.16 (t, J=7.6 Hz, 3H); MS (ESI$^+$) m/z 482.1 (M+H)$^+$.

Example 596: N-{(3S)-4-[2-(4-chloro-3-fluorophenoxy)acetamido]-3-hydroxybicyclo[2.2.2]octan-1-yl}-1,2-thiazole-3-carboxamide (Compound 685)

The title compound was prepared using the methodologies described in Example 473 substituting Example 567B for Example 473A and isothiazole-5-carboxylic acid for 2-methylthiazole-4-carboxylic acid. $^1$H NMR (400 MHz, DMSO-d$_6$) δ ppm 8.61 (d, J=1.8 Hz, 1H), 8.12 (s, 1H), 7.94 (d, J=1.8 Hz, 1H), 7.49 (t, J=8.9 Hz, 1H), 7.29 (s, 1H), 7.06 (dd, J=11.4, 2.8 Hz, 1H), 6.84 (ddd, J=8.9, 2.9, 1.2 Hz, 1H), 4.48 (s, 2H), 4.08 (ddd, J=9.5, 3.3, 1.2 Hz, 1H), 2.37 (ddd, J=12.5, 9.4, 2.2 Hz, 1H), 2.17-2.05 (m, 1H), 2.08-2.00 (m, 1H), 2.01-1.87 (m, 5H), 1.86 (dt, J=11.4, 3.5 Hz, 2H); MS (ESI$^+$) m/z 454.0 (M+H)$^+$.

Example 597: N-{3-[2-(3,4-dichlorophenoxy)acetamido]bicyclo[1.1.1]pentan-1-yl}-4-ethylpyridine-2-carboxamide (Compound 696)

The title compound was prepared using the methodologies described above. $^1$H NMR (400 MHz, DMSO-d$_6$) δ ppm 9.20 (s, 1H), 8.73 (s, 1H), 8.50 (dd, J=4.9, 0.7 Hz, 1H), 7.86 (dd, J=1.8, 0.8 Hz, 1H), 7.55 (d, J=8.9 Hz, 1H), 7.48-7.43 (m, 1H), 7.27 (d, J=2.9 Hz, 1H), 7.00 (dd, J=8.9, 2.9 Hz, 1H), 4.51 (s, 2H), 2.71 (q, J=7.6 Hz, 2H), 2.35 (s, 6H), 1.21 (t, J=7.6 Hz, 3H); MS (APCI$^+$) m/z 434 (M+H)$^+$.

Example 598: 4-cyclopropyl-N-{3-[2-(3,4-dichlorophenoxy)acetamido]bicyclo[1.1.1]pentan-1-yl}-1,3-thiazole-2-carboxamide (Compound 697)

The title compound was prepared using the methodologies described above. $^1$H NMR (501 MHz, DMSO-d$_6$) δ ppm 9.17 (s, 1H), 8.73 (s, 1H), 7.57-7.53 (m, 2H), 7.27 (d, J=2.9 Hz, 1H), 6.99 (dd, J=8.9, 2.9 Hz, 1H), 4.50 (s, 2H), 2.33 (s, 6H), 2.12 (tt, J=8.2, 5.0 Hz, 1H), 0.97-0.86 (m, 4H); MS (ESI$^+$) m/z 452 (M+H)$^+$.

Example 599: N-{3-[2-(3,4-dichlorophenoxy)acetamido]bicyclo[1.1.1]pentan-1-yl}-2-ethyl-1,3-thiazole-4-carboxamide (Compound 698)

The title compound was prepared using the methodologies described above. $^1$H NMR (500 MHz, DMSO-d$_6$) δ ppm 9.16 (s, 1H), 8.76 (s, 1H), 8.20 (s, 1H), 7.55 (d, J=8.9 Hz, 1H), 7.27 (d, J=2.9 Hz, 1H), 7.00 (dd, J=8.9, 2.9 Hz, 1H), 4.50 (s, 2H), 2.98 (q, J=7.5 Hz, 2H), 2.32 (s, 6H), 1.29 (t, J=7.5 Hz, 3H); MS (ESI$^+$) m/z 440 (M+H)$^+$.

Example 600: N-(3-{2-[(2,2-difluoro-2H-1,3-benzodioxol-5-yl)oxy]acetamido}bicyclo[1.1.1]pentan-1-yl)-2-ethyl-1,3-thiazole-4-carboxamide (Compound 699)

The title compound was prepared using the methodologies described above. $^1$H NMR (500 MHz, DMSO-d$_6$) δ ppm 8.79 (s, 1H), 8.71 (s, 1H), 8.08 (s, 1H), 7.33 (d, J=8.9 Hz, 1H), 7.15 (d, J=2.6 Hz, 1H), 6.78 (dd, J=8.9, 2.6 Hz, 1H), 4.45 (s, 2H), 3.01 (q, J=7.5 Hz, 2H), 2.33 (s, 6H), 1.32 (t, J=7.5 Hz, 3H); MS (ESI$^+$) m/z 452 (M+H)$^+$.

Example 601: N-{3-[2-(3,4-dichlorophenoxy)acetamido]bicyclo[1.1.1]pentan-1-yl}-5-ethylpyridine-2-carboxamide (Compound 700)

The title compound was prepared using the methodologies described above. $^1$H NMR (500 MHz, DMSO-d$_6$) δ ppm 9.19 (s, 1H), 8.74 (s, 1H), 8.51-8.43 (m, 1H), 7.94-7.90 (m, 1H), 7.85-7.82 (m, 1H), 7.56 (d, J=8.9 Hz, 1H), 7.28 (d, J=2.9 Hz, 1H), 7.00 (dd, J=9.0, 2.9 Hz, 1H), 4.51 (s, 2H), 2.71 (q, J=7.6 Hz, 2H), 2.35 (s, 6H), 1.21 (t, J=7.6 Hz, 3H); MS (ESI$^+$) m/z 434 (M+H)$^+$.

Example 602: N-{(3S)-4-[2-(3,4-dichlorophenoxy)acetamido]-3-hydroxybicyclo[2.2.2]octan-1-yl}-2-methyl-1,3-thiazole-4-carboxamide (Compound 701)

The title compound was prepared using the methodologies described in Example 473 substituting Example 595B for Example 473A. $^1$H NMR (400 MHz, DMSO-$d_6$) δ ppm 8.03 (s, 1H), 7.54 (d, J=9.0 Hz, 1H), 7.31 (d, J=9.8 Hz, 2H), 7.24 (d, J=2.9 Hz, 1H), 6.97 (dd, J=8.9, 2.9 Hz, 1H), 5.12 (s, 1H), 4.49 (s, 2H), 4.12-4.05 (m, 1H), 2.68 (s, 3H), 2.39 (ddd, J=12.2, 9.4, 2.3 Hz, 1H), 2.14-1.98 (m, 2H), 1.95 (dd, J=15.3, 5.0 Hz, 1H), 1.94-1.80 (m, 6H); MS (ESI$^+$) m/z 484.1 (M+H)$^+$.

Example 603: N-{(3S)-4-[2-(3,4-dichlorophenoxy) acetamido]-3-hydroxybicyclo[2.2.2]octan-1-yl}-5-methyl-1H-1,2,4-triazole-3-carboxamide (Compound 702)

The title compound was prepared using the methodologies described in Example 473 substituting Example 595B for Example 473A and Example 388A for 2-methylthiazole-4-carboxylic acid. $^1$H NMR (500 MHz, DMSO-$d_6$) δ ppm 7.58-7.48 (m, 2H), 7.29 (s, 1H), 7.24 (d, J=2.9 Hz, 1H), 6.97 (dd, J=8.9, 2.9 Hz, 1H), 4.49 (s, 2H), 4.11-4.04 (m, 1H), 2.42-2.35 (m, 1H), 2.35 (s, 3H), 2.15-1.93 (m, 2H), 1.97-1.80 (m, 7H); MS (ESI$^+$) m/z 468.2 (M+H)$^+$.

Example 604: N-{(3S)-4-[2-(3,4-dichlorophenoxy) acetamido]-3-hydroxybicyclo[2.2.2]octan-1-yl}-5-(difluoromethyl)pyrazine-2-carboxamide (Compound 703)

The title compound was prepared using the methodologies described in Example 473 substituting Example 595B for Example 473A and 5-(difluoromethyl)pyrazine-2-carboxylic acid for 2-methylthiazole-4-carboxylic acid. $^1$H NMR (500 MHz, DMSO-$d_6$) δ ppm 9.23 (d, J=1.4 Hz, 1H), 8.98 (d, J=1.3 Hz, 1H), 8.07 (s, 1H), 7.54 (d, J=8.9 Hz, 1H), 7.32 (d, J=2.5 Hz, 1H), 7.27-7.19 (m, 1H), 7.21 (t, J=52.0 Hz, 1H), 6.98 (dd, J=8.9, 2.9 Hz, 1H), 5.15 (d, J=4.4 Hz, 1H), 4.50 (s, 2H), 4.15-4.07 (m, 1H), 2.43 (ddd, J=12.5, 9.4, 2.6 Hz, 1H), 2.11 (td, J=13.9, 12.5, 8.6 Hz, 2H), 2.02-1.83 (m, 7H); MS (ESI$^+$) m/z 515.2 (M+H)$^+$.

Example 605: N-{(3S)-4-[2-(4-chloro-3-fluorophenoxy)acetamido]-3-hydroxybicyclo[2.2.2]octan-1-yl}-3-(trifluoromethyl)-1,2-oxazole-5-carboxamide (Compound 704)

The title compound was prepared using the methodologies described in Example 473 substituting Example 567B for Example 473A and Example 281D for 2-methylthiazole-4-carboxylic acid. $^1$H NMR (400 MHz, DMSO-$d_6$) δ ppm 8.40 (s, 1H), 7.65 (s, 1H), 7.45 (t, J=8.9 Hz, 1H), 7.26 (s, 1H), 7.02 (dd, J=11.4, 2.9 Hz, 1H), 6.80 (ddd, J=8.9, 2.9, 1.2 Hz, 1H), 5.11 (d, J=4.3 Hz, 1H), 4.44 (s, 2H), 4.06 (d, J=9.3 Hz, 1H), 2.38-2.27 (m, 1H), 2.04 (ddd, J=19.9, 10.7, 7.7 Hz, 2H), 1.97-1.85 (m, 3H), 1.89-1.76 (m, 4H); MS (ESI$^+$) m/z 506.0 (M+H)$^+$.

Example 606: 5-tert-butyl-N-{(3S)-4-[2-(4-chloro-3-fluorophenoxy)acetamido]-3-hydroxybicyclo[2.2.2]octan-1-yl}pyrazine-2-carboxamide (Compound 705)

The title compound was prepared using the methodologies described in Example 473 substituting Example 567B for Example 473A and 5-(tert-butyl)pyrazine-2-carboxylic acid for 2-methylthiazole-4-carboxylic acid. $^1$H NMR (400 MHz, DMSO-$d_6$) δ ppm 9.00 (d, J=1.4 Hz, 1H), 8.72 (d, J=1.4 Hz, 1H), 7.81 (s, 1H), 7.45 (t, J=8.9 Hz, 1H), 7.26 (s, 1H), 7.03 (dd, J=11.4, 2.8 Hz, 1H), 6.80 (ddd, J=9.0, 2.9, 1.2 Hz, 1H), 5.11 (d, J=4.2 Hz, 1H), 4.45 (s, 2H), 4.11-4.03 (m, 1H), 2.44-2.33 (m, 1H), 2.15-1.99 (m, 2H), 1.99-1.77 (m, 7H), 1.33 (s, 9H); MS (ESI$^+$) m/z 505.2 (M+H)$^+$.

Example 607: N-{(3S)-4-[2-(4-chloro-3-fluorophenoxy)acetamido]-3-hydroxybicyclo[2.2.2]octan-1-yl}-N,3-dimethyl-1,2-oxazole-5-carboxamide (Compound 706)

Example 607A: tert-butyl (S)-(4-(benzylamino)-2-hydroxybicyclo[2.2.2]octan-1-yl)carbamate Example 362A (2.50 g), MgSO$_4$ (1 M, 200 μL), nicotinamide adenine dinucleotide phosphate (NADPH, 50 mg) were mixed in 50 mL of potassium phosphate buffer (120 mM, pH=7.0) and 25 mL of isopropanol. To this solution was added Codexis KRED P02C2 enzyme (200 mg) dissolved in 25 mL of the same potassium phosphate buffer. The reaction was stirred overnight. The cloudy, aqueous solution was adjusted to pH >11 with 50% weight/weight aqueous sodium hydroxide. To this mixture was added 2.58 g (11.58 mmol, 1.5 equivalent) of di-tert-butyl dicarbonate in 100 mL of ethyl acetate. The biphasic solution was stirred for two hours and monitored as the reaction proceeded. The aqueous layer was routinely checked to maintain pH >10. At 2 hours, an additional 0.42 mg (0.25 eq) di-tert-butyl dicarbonate was added, and the reaction was let go for an additional hour. The two layers were separated. The aqueous layer was extracted with ethyl acetate (50 mL×2). The organic layers were combined, washed with brine (30 mL), and concentrated in vacuo. The residue was precipitated in ethyl acetate/hexanes to provide the title compound (1.30 g, 48%). MS (APCI$^+$) m/z 347.4 (M+H)$^+$.

Example 607B: (S)-tert-butyl (4-(benzyl(methyl)amino)-2-hydroxybicyclo[2.2.2]octan-1-yl)carbamate To a mixture of the product of Example 607A (1.00 g, 2.89 mmol) in CH$_2$Cl$_2$ (25 mL) was added acetic acid (0.496 mL, 8.66 mmol), formaldehyde (37% in water) (0.901 mL, 11.55 mmol), and macroporous cyanoborohydride resin (2.32 g, 5.77 mmol, reagent on solid support from Biotage®, 2.49 mmol/g). The reaction mixture was stirred for 3 hours and filtered. The filtrate was concentrated, treated with ethyl acetate, and washed with saturated NaHCO$_3$ and brine. The organic layer was dried over MgSO$_4$, filtered, concentrated, and purified on a 40 g column using the Biotage® Isolera™ One flash system eluting with CH$_2$Cl$_2$/CH$_3$OH (95:5) to provide the title compound (0.599 g, 58%). MS (ESI$^+$) m/z 361.3 (M+H)$^+$.

Example 607C: (S)-1-amino-4-(benzyl(methyl)amino)bicyclo[2.2.2]octan-2-ol, 2 hydrochloric Acid A mixture of Example 607B (0.520 g, 1.442 mmol) and trifluoroacetic acid (1.11 mL, 14.42 mmol) in CH$_2$Cl$_2$ (8 mL) was stirred for 6 hours. The reaction mixture was concentrated, and the residue was dissolved in CH$_3$OH (5 mL). To the resulting solution was added 2 N HCl in ether (4 mL), and the mixture was stirred for 15 minutes and concentrated. The concentrate was suspended in ether, and the mixture was stirred for 15 minutes. The solid was collected by filtration, washed with ether, and vacuum oven-dried to provide title compound (0.415 g, 86%). MS (ESI$^+$) m/z 261.3 (M+H)$^+$.

Example 607D: N-{(2S)-4-[benzyl(methyl)amino]-2-hydroxybicyclo[2.2]octan-1-yl}-2-(4-chloro-3-fluorophenoxy)acetamide A mixture of Example 607C (0.409 g, 1.227 mmol), 1-[bis(dimethylamino)methylene]-1H-1,2,3-triazolo[4,5-b]pyridinium 3-oxid hexafluorophosphate (0.980 g, 2.58 mmol, HATU), 2-(4-chloro-3-fluorophenoxy)acetic acid (0.527 g, 2.58 mmol), and triethylamine (0.684 mL, 4.91 mmol) in N,N-dimethylformamide (6 mL) was stirred for 4 hours. The reaction mixture was quenched with brine and extracted with ethyl acetate (2×). The combined organic layers were dried over MgSO$_4$, filtered and concentrated. The concentrate was dissolved in CH$_3$OH (2 mL) and tetrahydrofuran (2 mL) and treated with 2.5 M sodium hydroxide (1.96 mL, 4.91 mmol). The mixture was stirred for 2 hours, quenched with brine, and extracted with ethyl acetate (2×). The combined organic layers were washed with water, dried over MgSO$_4$, filtered, and concentrated. The residue was purified on a 12 g silica column using the Biotage® Isolera™ One flash system eluting with heptanes/ethyl acetate (1:9) to provide the title compound (0.205 g, 37%). MS (ESI$^+$) m/z 447.2 (M+H)$^+$.

Example 607E: 2-(4-chloro-3-fluorophenoxy)-N-[(2S)-2-hydroxy-4-(methylamino)bicyclo[2.2.2]octan-1-yl]acetamide, hydrochloric acid To the product of Example 607D (150 mg, 0.336 mmol) in methanol (3 mL) and 4 M HCl in dioxane (0.252 mL, 1.007 mmol) in a 20 mL Barnstead Hastelloy® C reactor was added 20% Pd(OH)$_2$/carbon (65 mg, 0.047 mmol, 51% in water). The reactor was purged with argon.

The mixture was stirred at 1600 RPM under 50 psi of hydrogen at 25° C. The reactor was vented after 1.6 hours. The reaction mixture was filtered, and the filtrate was concentrated to provide the title compound (0.125 g, 95%) that was used in the nest step without further purifications. MS (ESI$^+$) m/z 357.2 (M+H)$^+$.

Example 607F: N-{(3S)-4-[2-(4-chloro-3-fluorophenoxy)acetamido]-3-hydroxybicyclo[2.2.2]octan-1-yl}-N, 3-dimethyl-1,2-oxazole-5-carboxamide A mixture of Example 607E (30.0 mg, 0.076 mmol), 1-[bis(dimethylamino)methylene]-1H-1,2,3-triazolo[4,5-b]pyridinium 3-oxid hexafluorophosphate (HATU, 34.8 mg, 0.092 mmol), 3-methylisoxazole-5-carboxylic acid (11.63 mg, 0.092 mmol), and triethylamine (0.032 mL, 0.229 mmol) in N,N-dimethylformamide (2 mL) was stirred for 2 hours. The reaction was quenched with brine and extracted with ethyl acetate (2×). The combined organic layers were dried over MgSO$_4$, filtered, concentrated. The residue was purified by reverse-phase HPLC (see protocol in Example 273E) to provide the title compound (8.5 mg, 24%). $^1$H NMR (501 MHz, DMSO-d$_6$) δ ppm 7.49 (t, J=8.9 Hz, 1H), 7.31 (s, 1H), 7.06 (dd, J=11.4, 2.9 Hz, 1H), 6.84 (ddd, J=9.0, 2.9, 1.2 Hz, 1H), 6.66 (s, 1H), 5.16 (s, 1H), 4.48 (s, 2H), 4.13-4.04 (m, 1H), 2.84 (s, 3H), 2.49-2.44 (m, 1H), 2.26 (s, 3H), 2.21-1.76 (m, 9H); MS (ESI$^+$) m/z 466.1 (M+H)$^+$.

Example 608: N-{4-[2-(4-chloro-3-fluorophenoxy)acetamido]bicyclo[2.1.1]hexan-1-yl}-3-methoxy-1, 2-oxazole-5-carboxamide (Compound 707)

The title compound was prepared using the methodologies described above. $^1$H NMR (400 MHz, DMSO-d$_6$) δ ppm 9.22 (s, 1H), 8.52 (s, 1H), 7.50 (t, J=8.9 Hz, 1H), 7.07 (dd, J=11.4, 2.9 Hz, 1H), 6.86 (ddd, J=9.0, 2.8, 1.2 Hz, 1H), 6.78 (s, 1H), 4.49 (s, 2H), 3.93 (s, 3H), 2.17-2.07 (m, 2H), 1.94-1.79 (m, 6H); MS (APCI$^+$) m/z 424 (M+H)$^+$.

Example 609: N-{3-[2-(4-chloro-3-fluorophenoxy)acetamido]bicyclo[1.1.1]pentan-1-yl}-5-ethylpyrazine-2-carboxamide (Compound 708)

Example 609A: methyl 5-ethylpyrazine-2-carboxylate

Zinc dust (964 mg, 14.75 mmol) was charged to a nitrogen filled sealed tube (4 mL). N,N-dimethylformamide (1.0 mL) and trimethylchlorosilane (0.306 mL, 2.40 mmol) were added sequentially, and the mixture was stirred vigorously for 30 minutes at ambient temperature and then concentrated on a 70° C. heating block under reduced pressure for 30 minutes. The vial was cooled to ambient temperature, and a solution of iodoethane (0.194 mL, 2.40 mmol) in N,N-dimethylformamide (1.17 mL) was added to the activated zinc. The reaction mixture was stirred at ambient temperature for 15 minutes and then was directly transferred with a pipet to a plastic syringe and filtered through a glass microfiber syringe filter into a sealed tube (20 mL) containing tris(dibenzylideneacetone)dipalladium (0) (25.3 mg, 0.028 mmol), tri(2-furyl)phosphine (25.7 mg, 0.111 mmol), and methyl 5-bromopyrazine-2-carboxylate (400 mg, 1.843 mmol) in N,N-dimethylformamide (0.88 mL). The resulting mixture was stirred at ambient temperature for 2 hours. The tube was opened, and the reaction mixture was combined with methanol (3 mL) and silica gel (15 g). The mixture was concentrated under reduced pressure to give a free flowing powder. The powder was directly purified via flash chromatography (SiO$_2$, 10-35% ethyl acetate in heptane) to give the title compound (156 mg, 0.94 mmol, 51% yield). MS (ESI$^+$) m/z 167 (M+H)$^+$.

Example 609B: N-{3-[2-(4-chloro-3-fluorophenoxy)acetamido]bicyclo[1.1.1]pentan-1-yl}-5-ethylpyrazine-2-carboxamide (Compound 708)

The reaction and purification conditions described in Example 52 substituting the product of Example 609A for the product of Example 49A, and methanol for ethanol gave the title compound. $^1$H NMR (400 MHz, DMSO-d$_6$) δ ppm 9.36 (s, 1H), 9.04 (d, J=1.4 Hz, 1H), 8.74 (s, 1H), 8.61 (d, J=1.5 Hz, 1H), 7.50 (t, J=8.9 Hz, 1H), 7.08 (dd, J=11.4, 2.8 Hz, 1H), 6.86 (ddd, J=9.0, 2.9, 1.2 Hz, 1H), 4.49 (s, 2H), 2.90 (q, J=7.6 Hz, 2H), 2.36 (s, 6H), 1.27 (t, J=7.6 Hz, 3H); MS (ESI$^+$) m/z 419 (M+H)$^+$.

Example 610: N-{3-[2-(3,4-dichlorophenoxy)acetamido]bicyclo[1.1.1]pentan-1-yl}-3-methoxy-1,2-oxazole-5-carboxamide (Compound 709)

The title compound was prepared using the methodologies described above. $^1$H NMR (501 MHz, DMSO-d$_6$) δ ppm 9.47 (s, 1H), 8.75 (s, 1H), 7.55 (d, J=8.9 Hz, 1H), 7.27 (d, J=2.9 Hz, 1H), 6.99 (dd, J=8.9, 2.9 Hz, 1H), 6.77 (s, 1H), 4.50 (s, 2H), 3.93 (s, 3H), 2.32 (s, 6H); MS (APCI$^+$) m/z 467 (M+CH$_3$CN+H)$^+$.

Example 611: N-{4-[2-(4-chloro-3-fluorophenoxy)acetamido]bicyclo[2.1.1]hexan-1-yl}-3-methyl-1,2-thiazole-5-carboxamide (Compound 710)

The title compound was prepared using the methodologies described above. $^1$H NMR (400 MHz, DMSO-d$_6$) δ ppm 9.10 (s, 1H), 8.52 (s, 1H), 7.68 (s, 1H), 7.50 (t, J=8.9 Hz, 1H), 7.08 (dd, J=11.4, 2.8 Hz, 1H), 6.86 (ddd, J=9.0, 2.9, 1.2 Hz, 1H), 4.49 (s, 2H), 2.44 (s, 3H), 2.16-2.10 (m, 2H), 1.91-1.80 (m, 6H); MS (ESI$^+$) m/z 424 (M+H)$^+$.

Example 612: N-{3-[2-(3,4-dichlorophenoxy)acetamido]bicyclo[1.1.1]pentan-1-yl}-5-ethylpyrazine-2-carboxamide (Compound 711)

The reaction and purification conditions described in Example 52 substituting the product of Example 609A for the product of Example 49A, the product of Example 2B for the product of Example 6C, and methanol for ethanol gave the title compound. $^1$H NMR (400 MHz, DMSO-d$_6$) δ ppm 9.36 (s, 1H), 9.04 (d, J=1.5 Hz, 1H), 8.74 (s, 1H), 8.61 (d, J=1.5 Hz, 1H), 7.55 (d, J=8.9 Hz, 1H), 7.27 (d, J=2.9 Hz, 1H), 7.00 (dd, J=8.9, 2.9 Hz, 1H), 4.51 (s, 2H), 2.90 (q, J=7.5 Hz, 2H), 2.36 (s, 6H), 1.27 (t, J=7.5 Hz, 3H); MS (ESI$^+$) m/z 435 (M+H)$^+$.

Example 613: N-{4-[2-(4-chloro-3-fluorophenoxy)acetamido]bicyclo[2.1.1]hexan-1-yl}-5-ethylpyrazine-2-carboxamide (Compound 712)

The reaction and purification conditions described in Example 52 substituting the product of Example 609A for the product of Example 49A, the product of Example 197B for the product of Example 6C, and methanol for ethanol gave the title compound. $^1$H NMR (400 MHz, DMSO-d$_6$) δ ppm 9.08 (s, 1H), 9.05 (d, J=1.4 Hz, 1H), 8.60 (d, J=1.4 Hz, 1H), 8.52 (s, 1H), 7.50 (t, J=8.9 Hz, 1H), 7.08 (dd, J=11.4, 2.9 Hz, 1H), 6.86 (ddd, J=9.0, 2.9, 1.2 Hz, 1H), 4.49 (s, 2H), 2.90 (q, J=7.6 Hz, 2H), 2.18-2.05 (m, 2H), 1.98-1.77 (m, 6H), 1.27 (t, J=7.6 Hz, 3H); MS (ESI$^+$) m/z 433 (M+H)$^+$.

Example 614: N-{3-[2-(3,4-dichlorophenoxy)acetamido]bicyclo[1.1.1]pentan-1-yl}-1-methyl-1H-pyrazole-3-carboxamide (Compound 713)

The title compound was prepared using the methodologies described above. $^1$H NMR (501 MHz, DMSO-d$_6$) δ ppm 8.70 (s, 1H), 8.57 (s, 1H), 7.74 (d, J=2.3 Hz, 1H), 7.55 (d, J=8.9 Hz, 1H), 7.27 (d, J=2.9 Hz, 1H), 6.99 (dd, J=9.0, 2.9 Hz, 1H), 6.58 (d, J=2.3 Hz, 1H), 4.49 (s, 2H), 3.88 (s, 3H), 2.29 (s, 6H); MS (ESI$^+$) m/z 409 (M+H)$^+$.

Example 615: 2-(4-chloro-3-fluorophenoxy)-N-{3-[(6-cyclopropylpyrazin-2-yl)amino]bicyclo[1.1.1]pentan-1-yl}acetamide (Compound 714)

The reaction and purification conditions described in Example 579 substituting 2-bromo-6-cyclopropylpyrazine (52.4 mg, 0.263 mmol) for 2-chloro-3-methylpyrazine (24.8 mg, 0.193 mmol) gave the title compound. $^1$H NMR (500 MHz, DMSO-d$_6$) δ ppm 8.73 (s, 1H), 7.72 (s, 1H), 7.62 (s, 1H), 7.61 (s, 1H), 7.50 (t, J=8.9 Hz, 1H), 7.09 (dd, J=11.4, 2.9 Hz, 1H), 6.86 (ddd, J=9.0, 2.9, 1.2 Hz, 1H), 4.49 (s, 2H), 2.28 (s, 6H), 1.95 (tt, J=8.0, 4.7 Hz, 1H), 0.94-0.90 (m, 2H), 0.86 (dt, J=4.4, 2.8 Hz, 2H); MS (ESI$^+$) m/z 403 (M+H)$^+$.

Example 616: N-{3-[2-(3,4-dichlorophenoxy)acetamido]bicyclo[1.1.1]pentan-1-yl}-2-(hydroxymethyl)pyridine-4-carboxamide (Compound 715)

The title compound was prepared using the methodologies described above. $^1$H NMR (501 MHz, methanol-d$_4$) δ ppm 8.69 (d, J=5.6 Hz, 1H), 8.06 (s, 1H), 7.91-7.82 (m, 1H), 7.43 (d, J=8.9 Hz, 1H), 7.19 (d, J=2.9 Hz, 1H), 7.03-6.90 (m, 1H), 4.87 (s, 2H), 4.50 (s, 2H), 2.50 (d, J=0.6 Hz, 6H); MS (ESI$^+$) m/z 436 (M+H)$^+$.

Example 617: N-{3-[2-(3,4-dichlorophenoxy)acetamido]bicyclo[1.1.1]pentan-1-yl}-4-(difluoromethoxy)pyridine-2-carboxamide (Compound 716)

The title compound was prepared using the methodologies described above. $^1$H NMR (400 MHz, DMSO-d$_6$) δ ppm 9.35 (s, 1H), 8.73 (s, 1H), 8.63 (dd, J=5.6, 0.5 Hz, 1H), 7.79-7.38 (m, 4H), 7.27 (d, J=2.9 Hz, 1H), 7.00 (dd, J=9.0, 2.9 Hz, 1H), 4.51 (s, 2H), 2.36 (s, 6H); MS (ESI$^+$) m/z 472 (M+H)$^+$.

Example 618: 2-cyclopropyl-N-(3-{2-[(2,2-difluoro-2H-1,3-benzodioxol-5-yl)oxy]acetamido}bicyclo[1.1.1]pentan-1-yl)-1,3-oxazole-5-carboxamide (Compound 717)

The title compound was prepared using the methodologies described above. $^1$H NMR (500 MHz, DMSO-d$_6$) δ ppm 8.99 (s, 1H), 8.72 (s, 1H), 7.55 (s, 1H), 7.33 (d, J=8.9 Hz, 1H), 7.14 (d, J=2.6 Hz, 1H), 6.77 (dd, J=8.9, 2.6 Hz, 1H), 4.45 (s, 2H), 2.31 (s, 6H), 2.14 (tt, J=8.3, 4.9 Hz, 1H), 1.12-0.98 (m, 4H); MS (ESI$^+$) m/z 448 (M+H)$^+$.

Example 619: N-{3-[2-(4-chloro-3-fluorophenoxy)acetamido]bicyclo[1.1.1]pentan-1-yl}-6-(hydroxymethyl)pyridine-3-carboxamide (Compound 718)

The title compound was prepared using the methodologies described above. $^1$H NMR (500 MHz, DMSO-d$_6$) δ ppm 9.21 (s, 1H), 8.93-8.89 (m, 1H), 8.77 (s, 1H), 8.22 (dd, J=8.2, 2.3 Hz, 1H), 7.58 (dd, J=8.2, 0.8 Hz, 1H), 7.51 (t, J=8.9 Hz, 1H), 7.23-6.97 (m, 2H), 6.87 (ddd, J=8.9, 2.8, 1.2 Hz, 1H), 4.62 (s, 2H), 4.50 (s, 2H), 2.35 (s, 6H); MS (ESI$^+$) m/z 420 (M+H)$^+$.

Example 620: N-{3-[2-(3,4-dichlorophenoxy)acetamido]bicyclo[1.1.1]pentan-1-yl}-6-(hydroxymethyl)pyridine-3-carboxamide (Compound 719)

The title compound was prepared using the methodologies described above. $^1$H NMR (400 MHz, DMSO-d$_6$) δ ppm 9.21 (s, 1H), 8.91 (d, J=2.1 Hz, 1H), 8.75 (s, 1H), 8.24 (dd, J=8.2, 2.3 Hz, 1H), 7.59 (d, J=8.2 Hz, 1H), 7.55 (d, J=8.9 Hz, 1H), 7.28 (d, J=2.9 Hz, 1H), 7.00 (dd, J=9.0, 2.9 Hz, 1H), 4.63 (s, 2H), 4.51 (s, 2H), 2.35 (s, 6H); MS (ESI$^+$) m/z 436 (M+H)$^+$.

Example 621: 2-(4-chloro-3-fluorophenoxy)-N-{3-[(5-cyanopyrazin-2-yl)amino]bicyclo[1.1.1]pentan-1-yl}acetamide (Compound 720)

To a solution of Example 4A (30 mg, 0.105 mmol) in N,N-dimethylformamide (DMF) (0.5 mL) were added 5-bromopyrazine-2-carbonitrile (23.26 mg, 0.126 mmol) and N,N-diisopropylethylamine (0.055 mL, 0.316 mmol). The reaction mixture was stirred overnight at 80° C., and then the mixture was allowed to cool to ambient temperature. The mixture was directly purified by preparative HPLC (Phenomenex® Luna® C8(2) 5 μm 100 Å AXIA™ column (30 mm×75 mm); a gradient of acetonitrile (A) and 0.1% trifluoroacetic acid in water (B) was used, at a flow rate of 50 mL/minute (0-1.0 minute 5% A, 1.0-8.5 minutes linear gradient 5-100% A, 8.5-11.5 minutes 100% A, 11.5-12.0 minutes linear gradient 95-5% A) to give the title compound (25 mg, 0.064 mmol, 61% yield). $^1$H NMR (501 MHz, DMSO-$d_6$) δ ppm 8.86 (s, 1H), 8.79 (s, 1H), 8.53 (d, J=1.4 Hz, 1H), 7.96 (s, 1H), 7.50 (t, J=8.9 Hz, 1H), 7.08 (dd, J=11.4, 2.9 Hz, 1H), 6.86 (ddd, J=8.9, 2.9, 1.2 Hz, 1H), 4.50 (s, 2H), 2.37 (s, 6H); MS (ESI+) m/z 388 (M+H)$^+$.

Example 622: 2-(4-chloro-3-fluorophenoxy)-N-(3-{[2-(morpholin-4-yl)pyrimidin-4-yl]amino}bicyclo[1.1.1]pentan-1-yl)acetamide (Compound 721)

To a solution of Example 296A (50 mg, 0.113 mmol) and morpholine (0.015 mL, 0.170 mmol) in dioxane (0.5 mL) were added xantphos (6.6 mg, 0.011 mmol) and tris(dibenzylideneacetone)dipalladium(0) (Pd$_2$(dba)$_3$, 5.2 mg, 5.66 μmol). Potassium carbonate (46.9 mg, 0.340 mmol) was added, and the reaction mixture was stirred overnight at 80° C. The mixture was allowed to cool to ambient temperature and ethyl acetate (10 mL) and water (2 mL) were added. The layers were separated, and the organic layer was dried over anhydrous MgSO$_4$. The mixture was filtered, and the filtrate was concentrated under reduced pressure. The residue was purified by preparative HPLC [Waters XBridge™ C18 5 μm OBD™ column, 30×100 mm, flow rate 40 mL/minute, 5-100% gradient of acetonitrile in aqueous buffer (0.1% trifluoroacetic acid)] to give the title compound (27 mg, 0.060 mmol, 53% yield). $^1$H NMR (400 MHz, DMSO-$d_6$) δ ppm 9.49 (s, 1H), 8.83 (s, 1H), 7.80-7.74 (m, 1H), 7.50 (t, J=8.8 Hz, 1H), 7.08 (dd, J=11.4, 2.8 Hz, 1H), 6.86 (ddd, J=9.0, 2.9, 1.2 Hz, 1H), 6.12 (d, J=7.1 Hz, 1H), 4.50 (s, 2H), 3.71 (dd, J=16.0, 5.1 Hz, 8H), 2.40 (s, 6H); MS (ESI$^+$) m/z 448 (M+H)$^+$.

Example 623: 2-(4-chloro-3-fluorophenoxy)-N-{3-[(pyrazolo[1,5-a]pyrazin-4-yl)amino]bicyclo[1.1.1]pentan-1-yl}acetamide (Compound 722)

The reaction and purification conditions described in Example 579 substituting 4-chloropyrazolo[1,5-a]pyrazine (27.0 mg, 0.176 mmol) for 2-chloro-3-methylpyrazine (24.83 mg, 0.193 mmol) gave the title compound. $^1$H NMR (500 MHz, DMSO-$d_6$) δ ppm 8.81 (s, 1H), 8.01 (d, J=4.9 Hz, 1H), 7.98-7.92 (m, 1H), 7.51 (t, J=8.9 Hz, 1H), 7.31 (d, J=4.9 Hz, 1H), 7.12-7.02 (m, 2H), 6.87 (ddd, J=9.0, 2.8, 1.2 Hz, 1H), 4.52 (s, 2H), 2.46 (s, 6H); MS (ESI$^+$) m/z 402 (M+H)$^+$.

Example 624: N-{3-[2-(4-chloro-3-fluorophenoxy)acetamido]bicyclo[1.1.1]pentan-1-yl}thieno[2,3-b]pyridine-5-carboxamide (Compound 723)

The reaction and purification conditions described in Example 383 substituting thieno[2,3-b]pyridine-5-carboxylic acid (20.8 mg, 0.116 mmol) for quinoxaline-2-carboxylic acid (16.8 mg, 0.097 mmol) gave the title compound. $^1$H NMR (400 MHz, DMSO-$d_6$) δ ppm 9.30 (s, 1H), 8.97 (d, J=2.1 Hz, 1H), 8.77 (s, 1H), 8.68 (d, J=2.1 Hz, 1H), 7.98 (d, J=6.0 Hz, 1H), 7.55 (d, J=6.0 Hz, 1H), 7.51 (t, J=8.9 Hz, 1H), 7.09 (dd, J=11.3, 2.9 Hz, 1H), 6.87 (ddd, J=9.0, 2.9, 1.2 Hz, 1H), 4.51 (s, 2H), 2.38 (s, 6H); MS (ESI$^+$) m/z 446 (M+H)$^+$.

Example 625: N-{3-[2-(4-chloro-3-fluorophenoxy)acetamido]bicyclo[1.1.1]pentan-1-yl}-1-(difluoromethyl)-1H-pyrazole-4-carboxamide (Compound 724)

The reaction and purification conditions described in Example 383 substituting 1-(difluoromethyl)-1H-pyrazole-4-carboxylic acid (17.1 mg, 0.105 mmol) for quinoxaline-2-carboxylic acid (16.8 mg, 0.097 mmol) gave the title compound. $^1$H NMR (501 MHz, DMSO-$d_6$) δ ppm 8.98 (s, 1H), 8.72 (s, 1H), 8.31 (d, J=2.6 Hz, 1H), 7.84 (t, J=58.8 Hz, 1H), 7.50 (t, J=8.9 Hz, 1H), 7.08 (dd, J=11.4, 2.8 Hz, 1H), 6.86 (ddd, J=8.9, 2.9, 1.2 Hz, 1H), 6.84 (d, J=2.6 Hz, 1H), 4.49 (s, 2H), 2.32 (s, 6H); MS (ESI$^+$) m/z 429 (M+H)$^+$.

Example 626: 2-(4-chloro-3-fluorophenoxy)-N-{3-[(pyrazin-2-yl)amino]bicyclo[1.1.1]pentan-1-yl}acetamide (Compound 725)

The reaction and purification conditions described in Example 579 substituting 2-chloropyrazine (0.017 mL, 0.193 mmol) for 2-chloro-3-methylpyrazine (24.83 mg, 0.193 mmol) gave the title compound. $^1$H NMR (500 MHz, DMSO-$d_6$) δ ppm 8.77 (s, 1H), 8.00 (dd, J=2.8, 1.5 Hz, 1H), 7.92 (d, J=1.5 Hz, 1H), 7.78 (s, 1H), 7.74 (d, J=2.8 Hz, 1H), 7.50 (t, J=8.8 Hz, 1H), 7.09 (dd, J=11.4, 2.9 Hz, 1H), 6.87 (ddd, J=8.9, 2.9, 1.2 Hz, 1H), 4.50 (s, 2H), 2.34 (s, 6H); MS (ESI$^+$) m/z 363 (M+H)$^+$ Example 627: N-{3-[2-(4-chloro-3-fluorophenoxy)acetamido]bicyclo[1.1.1]pentan-1-yl}-4-methyl-1H-pyrrole-2-carboxamide (Compound 726)

The reaction and purification conditions described in Example 383 substituting 4-methyl-1H-pyrrole-2-carboxylic acid (24.2 mg, 0.193 mmol) for quinoxaline-2-carboxylic acid (16.8 mg, 0.097 mmol) gave the title compound. $^1$H NMR (501 MHz, DMSO-$d_6$) δ ppm 11.00 (t, J=2.8 Hz, 1H), 8.72 (s, 1H), 8.38 (s, 1H), 7.50 (t, J=8.9 Hz, 1H), 7.08 (dd, J=11.4, 2.8 Hz, 1H), 6.86 (ddd, J=9.0, 2.8, 1.1 Hz, 1H), 6.62 (p, J=1.1 Hz, 1H), 6.56 (t, J=2.1 Hz, 1H), 4.49 (s, 2H), 2.29 (s, 6H), 2.00 (s, 3H); MS (ESI$^+$) m/z 392 (M+H)$^+$.

Example 628: N-{(3S)-4-[2-(4-chloro-3-fluorophenoxy)acetamido]-3-hydroxybicyclo[2.2.2]octan-1-yl}pyridine-2-carboxamide (Compound 727)

The reaction described in Example 582 substituting picolinic acid for 3-fluorobenzoic acid gave the title compound. $^1$H NMR (500 MHz, DMSO-$d_6$) δ ppm 8.61 (dt, J=4.8, 1.4 Hz, 1H), 8.05-7.93 (m, 3H), 7.59 (ddd, J=6.9, 4.8, 2.1 Hz, 1H), 7.49 (t, J=8.9 Hz, 1H), 7.30 (s, 1H), 7.07 (dd, J=11.3, 2.9 Hz, 1H), 6.84 (ddd, J=8.9, 2.9, 1.2 Hz, 1H), 5.13 (s, 1H, brd), 4.49 (s, 2H), 4.16-4.02 (m, 1H), 2.42 (ddd, J=12.6, 9.5, 2.5 Hz, 1H), 2.17-2.05 (m, 2H), 2.03-1.85 (m, 7H); MS (ESI$^+$) m/z 447.9 (M+H)$^+$.

Example 629: N-{(3S)-4-[2-(4-chloro-3-fluorophenoxy)acetamido]-3-hydroxybicyclo[2.2.2]octan-1-yl}-5-(trifluoromethyl)pyridine-2-carboxamide (Compound 728)

The reaction described in Example 582 substituting 5-(trifluoromethyl)picolinic acid for 3-fluorobenzoic acid gave the title compound. $^1$H NMR (400 MHz, DMSO-$d_6$) δ ppm 9.04-8.94 (m, 1H), 8.41 (dd, J=8.3, 2.3 Hz, 1H), 8.20 (t, J=7.4 Hz, 1H), 8.04 (s, 1H), 7.49 (t, J=8.9 Hz, 1H), 7.31 (s, 1H), 7.07 (dd, J=11.4, 2.9 Hz, 1H), 6.84 (ddd, J=9.0, 2.9, 1.2 Hz, 1H), 5.15 (s, 1H, brd), 4.49 (s, 2H), 4.12 (dd, J=9.6, 3.1 Hz, 1H), 2.43 (ddd, J=12.4, 9.5, 2.2 Hz, 1H), 2.19-1.82 (m, 9H); MS (ESI$^+$) m/z 516.2 (M+H)$^+$.

Example 630: N-{(3S)-4-[2-(4-chloro-3-fluorophenoxy)acetamido]-3-hydroxybicyclo[2.2.2]octan-1-yl}-5-methylpyridine-2-carboxamide (Compound 729)

The reaction described in Example 582 substituting 5-methylpicolinic acid for 3-fluorobenzoic acid gave the title compound. $^1$H NMR (400 MHz, DMSO-$d_6$) δ ppm 8.49-8.31 (m, 1H), 7.95-7.84 (m, 2H), 7.79 (dd, J=8.2, 2.1 Hz, 1H), 7.49 (t, J=8.9 Hz, 1H), 7.29 (s, 1H), 7.07 (dd, J=11.4, 2.8 Hz, 1H), 6.84 (ddd, J=9.0, 2.9, 1.2 Hz, 1H), 4.48 (s, 2H), 4.16-4.04 (m, 1H), 2.47-2.28 (m, 4H), 2.18-1.76 (m, 9H); MS (ESI$^+$) m/z 462.2 (M+H)$^+$.

Example 631: 5-chloro-N-{(3S)-4-[2-(4-chloro-3-fluorophenoxy)acetamido]-3-hydroxybicyclo[2.2.2]octan-1-yl}pyridine-2-carboxamide (Compound 730)

The reaction described in Example 582 substituting 5-chloropicolinic acid for 3-fluorobenzoic acid gave the title compound. $^1$H NMR (501 MHz, DMSO-$d_6$) δ ppm 8.96 (d, J=1.4 Hz, 1H), 8.82 (d, J=1.4 Hz, 1H), 7.94 (s, 1H), 7.49 (t, J=8.9 Hz, 1H), 7.30 (s, 1H), 7.06 (dd, J=11.4, 2.8 Hz, 1H), 6.84 (ddd, J=8.9, 2.9, 1.2 Hz, 1H), 5.14 (d, J=4.4 Hz, 1H), 4.53-4.48 (s, 2H), 4.16-4.01 (m, 1H), 2.42 (ddd, J=12.5, 9.4, 2.6 Hz, 1H), 2.17-2.04 (m, 2H), 2.03-1.80 (m, 7H); MS (ESI$^+$) m/z 483.1 (M+H)$^+$.

Example 632: 2-(3,4-difluorophenoxy)-N-(3-{[5-(pyridin-3-yl)pyrazin-2-yl]amino}bicyclo[1.1.1]pentan-1-yl)acetamide (Compound 731)

Example 632A: tert-butyl (3-{[5-(pyridin-3-yl)pyrazin-2-yl]amino}bicyclo[1.1.1]pentan-1-yl)carbamate, trifluoroacetic acid The reaction and purification conditions described in Example 323A substituting 2-bromo-5-(pyridin-3-yl)pyrazine for 4-chloro-2-methylpyrazolo[1,5-a]pyrazine gave the title compound (0.221 g, 0.473 mmol, 41% yield). $^1$H NMR (400 MHz, DMSO-$d_6$) δ ppm 9.25 (br s, 1H), 8.79 (s, 1H), 8.67 (m, 2H), 8.18 (s, 1H), 8.04 (s, 1H), 7.79 (dd, J=8, 6 Hz, 1H), 7.59 (br s, 1H), 2.26 (s, 6H), 1.38 (s, 9H), 1.40 (s, 9H); MS (ESI$^+$) m/z 354 (M+H)$^+$.

Example 632B: N$^1$-[5-(pyridin-3-yl)pyrazin-2-yl]bicyclo[1.1.1]pentane-1,3-diamine, trifluoroacetic acid The reaction and purification conditions described in Example 323B substituting Example 632A for Example 323A gave the title compound (0.268 g, 0.45 mmol, 100% yield). $^1$H NMR (400 MHz, DMSO-$d_6$) δ ppm 9.34 (s, 1H), 8.89 (m, 1H), 8.88 (d, J=2 Hz, 1H), 8.84 (br s, 2H), 8.80 (br d, J=6 Hz, 1H), 8.46 (br s, 1H), 8.11 (d, J=2 Hz, 1H), 7.98 (dd, J=8, 6 Hz, 1H), 2.35 (s, 6H); MS (ESI$^+$) m/z 254 (M+H)$^+$.

Example 632C: 2-(3,4-difluorophenoxy)-N-(3-{[5-(pyridin-3-yl)pyrazin-2-yl]amino}bicyclo[1.1.1]pentan-1-yl)acetamide, trifluoroacetic acid The reaction and purification conditions described in Example 323C substituting 2-(3,4-difluorophenoxy)acetic acid for Example 29B and Example 632B for Example 323B gave the title compound (0.040 g, 0.086 mmol, 80% yield). $^1$H NMR (400 MHz, DMSO-$d_6$) (9.27 (s, 1H), 8.82 (d, J=2 Hz, 1H), 8.76 (s, 1H), 8.70 (m, 2H), 8.25 (s, 1H), 8.07 (d, J=2 Hz, 1H), 7.82 (dd, J=8 Hz, 6, 1H), 7.37 (q, J=8 Hz, 1H), 7.09 (m, 1H), 6.82 (m, 1H), 4.47 (s, 2H), 2.40 (s, 6H); MS (ESI$^+$) m/z 424 (M+H)$^+$.

Example 633: N-{(2S)-4-[2-(4-chloro-3-fluorophenoxy)acetamido]-2-hydroxybicyclo[2.2.2]octan-1-yl}pyrazine-2-carboxamide (Compound 732)

The reaction and purification conditions described in Example 384 substituting pyrazine-2-carboxylic acid for 2-fluorobenzoic acid gave the title compound (0.035 g, 0.078 mmol, 78% yield). $^1$H NMR (400 MHz, DMSO-$d_6$) δ ppm 9.17 (d, J=2 Hz, 1H), 8.87 (d, J=3 Hz, 1H), 8.68 (dd, J=3, 2 Hz, 1H), 8.11 (s, 1H), 7.55 (s, 1H), 7.47 (t, J=8 Hz, 1H), 7.02 (dd, J=9, 3 Hz, 1H), 6.81 (br d, J=8 Hz, 1H), 5.32 (m, 1H), 4.43 (s, 2H), 4.02 (m, 1H), 2.53 (m, 1H), 2.35 (m, 1H), 1.72-2.10 (m, 8H); MS (ESI$^+$) m/z 449 (M+H)$^+$.

Example 634: N-{(2S)-4-[2-(4-chloro-3-fluorophenoxy)acetamido]-2-hydroxybicyclo[2.2.2]octan-1-yl}-5-methylpyrazine-2-carboxamide (Compound 733)

The reaction and purification conditions described in Example 384 substituting 5-methylpyrazine-2-carboxylic acid for 2-fluorobenzoic acid gave the title compound (0.040 g, 0.086 mmol, 86% yield). $^1$H NMR (400 MHz, DMSO-$d_6$) δ ppm 9.02 (d, J=2 Hz, 1H), 8.57 (m, 1H), 8.06 (s, 1H), 7.56 (s, 1H), 7.48 (t, J=8 Hz, 1H), 7.03 (dd, J=9, 3 Hz, 1H), 6.82 (br d, J=8 Hz, 1H), 5.34 (d, J=6 Hz, 1H), 4.45 (s, 2H), 4.02 (m, 1H), 2.58 (s, 3H), 2.53 (m, 1H), 2.35 (m, 1H), 1.72-2.12 (m, 8H); MS (ESI$^+$) m/z 463 (M+H)$^+$.

Example 635: N-{(2S)-4-[2-(4-chloro-3-fluorophenoxy)acetamido]-2-hydroxybicyclo[2.2.2]octan-1-yl}-6-methylpyrazine-2-carboxamide (Compound 734)

The reaction and purification conditions described in Example 384 substituting 6-methylpyrazine-2-carboxylic acid for 2-fluorobenzoic acid gave the title compound (0.040 g, 0.086 mmol, 80% yield). $^1$H NMR (400 MHz, DMSO-$d_6$) δ ppm 8.96 (s, 1H), 8.75 (s, 1H), 8.08 (s, 1H), 7.58 (s, 1H), 7.49 (t, J=8 Hz, 1H), 7.03 (dd, J=9, 3 Hz, 1H), 6.82 (br d, J=8 Hz, 1H), 4.45 (s, 2H), 4.03 (m, 1H), 2.57 (s, 3H), 2.53 (m, 1H), 2.35 (m, 1H), 1.75-2.12 (m, 8H); MS (ESI$^+$) m/z 463 (M+H)$^+$.

Example 636: N-{(3S)-4-[2-(3,4-dichlorophenoxy)acetamido]-3-hydroxybicyclo[2.2.2]octan-1-yl}-5-methylpyrazine-2-carboxamide (Compound 735)

The title compound was prepared using the methodologies described in Example 473 substituting Example 595B for Example 473A and 5-methylpyrazine-2-carboxylic acid for 2-methylthiazole-4-carboxylic acid. $^1$H NMR (400 MHz, DMSO-$d_6$) δ ppm 8.96 (d, J=1.4 Hz, 1H), 8.53 (d, J=1.4 Hz, 1H), 7.82 (s, 1H), 7.50 (d, J=9.0 Hz, 1H), 7.26 (s, 1H), 7.21 (d, J=2.9 Hz, 1H), 6.94 (dd, J=9.0, 2.9 Hz, 1H), 5.09 (s, 1H), 4.46 (s, 2H), 4.06 (dd, J=9.7, 2.9 Hz, 1H), 2.54 (s, 3H), 2.38 (ddd, J=12.3, 9.5, 2.3 Hz, 1H), 2.07 (td, J=10.9, 7.4 Hz, 2H), 1.99 1.86 (m, 5H), 1.90-1.78 (m, 2H); MS (ESI$^+$) m/z 479.1 (M+H)$^+$.

Example 637: N-{3-[2-(3,4-dichlorophenoxy)acetamido]bicyclo[1.1.1]pentan-1-yl}-4-methylpyridine-3-carboxamide (Compound 736)

The title compound was prepared using the methodologies described above. $^1$H NMR (500 MHz, DMSO-$d_6$) δ ppm 9.05 (s, 1H), 8.76 (s, 1H), 8.49-8.43 (m, 2H), 7.56 (d, J=8.9 Hz, 1H), 7.30-7.26 (m, 2H), 7.00 (dd, J=9.0, 2.9 Hz, 1H), 4.51 (s, 2H), 2.36-2.34 (m, 3H), 2.33 (s, 6H); MS (APCI$^+$) m/z 420 (M+H)$^+$.

Example 638: N-{3-[2-(3,4-dichlorophenoxy)acetamido]bicyclo[1.1.1]pentan-1-yl}-6-methylpyrazine-2-carboxamide (Compound 737)

The title compound was prepared using the methodologies described above. $^1$H NMR (500 MHz, DMSO-$d_6$) δ ppm 9.29 (s, 1H), 9.00-8.91 (m, 1H), 8.77-8.74 (m, 2H), 7.56 (d, J=8.9 Hz, 1H), 7.28 (d, J=2.9 Hz, 1H), 7.00 (dd, J=8.9, 2.9 Hz, 1H), 4.51 (s, 2H), 2.58 (d, J=0.6 Hz, 3H), 2.37 (s, 6H); MS (ESI$^+$) m/z 421 (M+H)$^+$.

Example 639: N-{3-[2-(4-chloro-3-fluorophenoxy)acetamido]bicyclo[1.1.1]pentan-1-yl}-4-methylpyridine-3-carboxamide (Compound 738)

The title compound was prepared using the methodologies described above. $^1$H NMR (501 MHz, DMSO-$d_6$) δ ppm 9.04 (s, 1H), 8.75 (s, 1H), 8.49-8.43 (m, 2H), 7.50 (t, J=8.9 Hz, 1H), 7.28 (dt, J=5.0, 0.8 Hz, 1H), 7.09 (dd, J=11.4, 2.8 Hz, 1H), 6.87 (ddd, J=8.9, 2.8, 1.2 Hz, 1H), 4.49 (s, 2H), 2.35 (s, 3H), 2.33 (s, 6H); MS (APCI$^+$) m/z 404 (M+H)$^+$.

Example 640: N-{3-[2-(3,4-dichlorophenoxy)acetamido]bicyclo[1.1.1]pentan-1-yl}-3-methylpyridine-2-carboxamide (Compound 739)

The title compound was prepared using the methodologies described above. $^1$H NMR (501 MHz, DMSO-$d_6$) δ ppm 8.99 (s, 1H), 8.75 (s, 1H), 8.48 (dd, J=4.9, 1.8 Hz, 1H), 7.69 (dd, J=7.7, 1.8 Hz, 1H), 7.55 (d, J=8.9 Hz, 1H), 7.28 (d, J=2.9 Hz, 1H), 7.25 (ddd, J=7.6, 4.9, 0.6 Hz, 1H), 7.00 (dd, J=9.0, 2.9 Hz, 1H), 4.51 (s, 2H), 2.50 (s, 3H), 2.33 (s, 6H); MS (APCI$^+$) m/z 420 (M+H)$^+$.

Example 641: N-{3-[2-(3,4-dichlorophenoxy)acetamido]bicyclo[1.1.1]pentan-1-yl}-2-phenyl-1,3-oxazole-5-carboxamide (Compound 740)

The title compound was prepared using the methodologies described above. $^1$H NMR (400 MHz, DMSO-$d_6$) δ ppm 9.27 (s, 1H), 8.77 (s, 1H), 8.17-8.08 (m, 2H), 7.85 (s, 1H), 7.62-7.53 (m, 4H), 7.28 (d, J=2.9 Hz, 1H), 7.00 (dd, J=8.9, 2.9 Hz, 1H), 4.51 (s, 2H), 2.36 (s, 6H); MS (APCI$^+$) m/z 472 (M+H)$^+$.

Example 642: N-{3-[2-(4-chloro-3-fluorophenoxy)acetamido]bicyclo[1.1.1]pentan-1-yl}-2-(hydroxymethyl)pyridine-4-carboxamide (Compound 741)

The title compound was prepared using the methodologies described above. $^1$H NMR (500 MHz, methanol-$d_4$) δ ppm 9.46 (s, 1H), 8.81 (s, 1H), 8.70 (d, J=5.6 Hz, 1H), 8.07 (s, 1H), 7.88 (d, J=5.6 Hz, 1H), 7.38 (t, J=8.7 Hz, 1H), 6.94 (dd, J=11.0, 2.8 Hz, 1H), 6.83 (ddd, J=8.9, 2.8, 1.3 Hz, 1H), 4.88 (s, 2H), 4.49 (s, 2H), 2.50 (s, 6H); MS (ESI$^+$) m/z 420 (M+H)$^+$.

Example 643: N-(3-{2-[(2,2-difluoro-2H-1,3-benzodioxol-5-yl)oxy]acetamido}bicyclo[1.1.1]pentan-1-yl)-2-phenyl-1,3-oxazole-5-carboxamide (Compound 742)

The title compound was prepared using the methodologies described above. $^1$H NMR (501 MHz, DMSO-$d_6$) δ ppm 9.27 (s, 1H), 8.75 (s, 1H), 8.15-8.10 (m, 2H), 7.86 (s, 1H), 7.62-7.56 (m, 3H), 7.34 (d, J=8.9 Hz, 1H), 7.16 (d, J=2.6 Hz, 1H), 6.79 (dd, J=8.9, 2.6 Hz, 1H), 4.47 (s, 2H), 2.37 (s, 6H); MS (ESI$^+$) m/z 484 (M+H)$^+$.

Example 644: 2-(3,4-difluorophenoxy)-N-(3-{[6-(pyridin-3-yl)pyrazin-2-yl]amino}bicyclo[1.1.1]pentan-1-yl)acetamide (Compound 743)

The reaction and purification conditions described in Example 632 substituting 2-bromo-6-(pyridin-3-yl)pyrazine for 2-bromo-5-(pyridin-3-yl)pyrazine gave the title compound (0.035 g, 0.065 mmol, 81% yield). $^1$H NMR (400 MHz, DMSO-$d_6$) δ ppm 9.32 (br s, 1H), 8.78 (m, 2H), 8.67 (br d, J=8 Hz, 1H), 8.50 (s, 1H), 8.08 (br s, 1H), 7.97 (s, 1H), 7.79 (dd, J=8, 6 Hz, 1H), 7.37 (q, J=8 Hz, 1H), 7.12 (m, 1H), 6.82 (m, 1H), 4.50 (s, 2H), 2.43 (s, 6H); MS (ESI$^+$) m/z 424 (M+H)$^+$.

Example 645: 2-(4-chloro-3-fluorophenoxy)-N-(3-{[6-(morpholin-4-yl)pyrazin-2-yl]amino}bicyclo[1.1.1]pentan-1-yl)acetamide (Compound 744)

The reaction and purification conditions described in Example 579 substituting 4-(6-bromopyrazin-2-yl)morpholine (51.4 mg, 0.211 mmol) for 2-chloro-3-methylpyrazine (24.8 mg, 0.193 mmol) gave the title compound. $^1$H NMR (400 MHz, DMSO-$d_6$) δ ppm 8.75 (s, 1H), 7.84 (s, 1H), 7.50 (t, J=8.9 Hz, 1H), 7.44 (s, 1H), 7.21 (s, 1H), 7.08 (dd, J=11.4, 2.9 Hz, 1H), 6.86 (ddd, J=8.9, 2.9, 1.2 Hz, 1H), 5.75 (s, 1H), 3.71 (dd, J=5.8, 4.0 Hz, 4H), 3.47 (t, J=4.9 Hz, 4H), 2.32 (s, 6H); MS (ESI$^+$) m/z 447 (M+H)$^+$.

Example 646: 2-(4-chloro-3-fluorophenoxy)-N-{3-[(6-cyanopyrazin-2-yl)amino]bicyclo[1.1.1]pentan-1-yl}acetamide (Compound 745)

The reaction and purification conditions described in Example 579 substituting 6-bromopyrazine-2-carbonitrile (38.8 mg, 0.211 mmol) for 2-chloro-3-methylpyrazine (24.8 mg, 0.193 mmol) gave the title compound. $^1$H NMR (501 MHz, DMSO-$d_6$) δ ppm 8.77 (s, 1H), 8.49 (s, 1H), 8.25 (s, 1H), 8.16 (s, 1H), 7.50 (t, J=8.9 Hz, 1H), 7.08 (dd, J=11.4, 2.8 Hz, 1H), 6.86 (ddd, J=9.0, 2.9, 1.2 Hz, 1H), 4.50 (s, 2H), 2.35 (s, 6H); MS (ESI$^+$) m/z 388 (M+H)$^+$.

Example 647: N-{3-[2-(4-chloro-3-fluorophenoxy)acetamido]bicyclo[1.1.1]pentan-1-yl}-1H-pyrrolo[2,3-b]pyridine-5-carboxamide (Compound 746)

The reaction and purification conditions described in Example 383 substituting 1H-pyrrolo[2,3-b]pyridine-5-carboxylic acid (31.3 mg, 0.193 mmol) for quinoxaline-2-carboxylic acid (16.82 mg, 0.097 mmol) gave the title compound. $^1$H NMR (501 MHz, DMSO-$d_6$) δ ppm 1H NMR (400 MHz, DMSO-$d_6$) δ ppm 11.88 (s, 1H), 9.02 (s, 1H), 8.75 (s, 1H), 8.70 (d, J=2.1 Hz, 1H), 8.42 (d, J=2.2, 0.7 Hz, 1H), 7.55 (dd, J=3.5, 2.5 Hz, 1H), 7.51 (t, J=8.9 Hz, 1H), 7.09 (dd, J=11.4, 2.8 Hz, 1H), 6.87 (ddd, J=9.0, 2.9, 1.2

Hz, 1H), 6.55 (dd, J=3.5, 1.8 Hz, 1H), 4.50 (s, 2H), 2.35 (s, 6H); MS (ESI+) m/z 429 (M+H)+.

Example 648: 2-(4-chloro-3-fluorophenoxy)-N-(3-{[6-(trifluoromethyl)pyrazin-2-yl]amino}bicyclo[1.1.1]pentan-1-yl)acetamide (Compound 747)

The reaction and purification conditions described in Example 621 substituting 2-chloro-6-(trifluoromethyl)pyrazine (24.0 mg, 0.132 mmol) for 5-bromopyrazine-2-carbonitrile (23.3 mg, 0.126 mmol) gave the title compound. $^1$H NMR (500 MHz, DMSO-$d_6$) δ ppm 8.78 (s, 1H), 8.46 (s, 1H), 8.19-8.15 (m, 2H), 7.50 (t, J=8.9 Hz, 1H), 7.08 (dd, J=11.4, 2.9 Hz, 1H), 6.86 (ddd, J=8.9, 2.9, 1.2 Hz, 1H), 4.50 (s, 2H), 2.36 (s, 6H); MS (ESI+) m/z 431 (M+H)+.

Example 649: N-{3-[2-(4-chloro-3-fluorophenoxy)acetamido]bicyclo[1.1.1]pentan-1-yl}-2-methylpyrazolo[1,5-a]pyrimidine-6-carboxamide (Compound 748)

The reaction and purification conditions described in Example 383 substituting 2-methylpyrazolo[1,5-a]pyrimidine-6-carboxylic acid (15.56 mg, 0.088 mmol) for quinoxaline-2-carboxylic acid (16.82 mg, 0.097 mmol) gave the title compound. $^1$H NMR (400 MHz, DMSO-$d_6$) δ ppm 9.36 (dd, J=2.2, 0.9 Hz, 1H), 9.24 (s, 1H), 8.83 (d, J=2.2 Hz, 1H), 8.77 (s, 1H), 7.50 (t, J=8.9 Hz, 1H), 7.09 (dd, J=11.4, 2.9 Hz, 1H), 6.87 (ddd, J=8.9, 2.9, 1.2 Hz, 1H), 6.61 (t, J=0.7 Hz, 1H), 4.50 (s, 2H), 2.45 (s, 3H), 2.37 (s, 6H); MS (ESI+) m/z 444 (M+H)+.

Example 650: N-{3-[2-(4-chloro-3-fluorophenoxy)acetamido]bicyclo[1.1.1]pentan-1-yl}quinazoline-2-carboxamide (Compound 749)

The reaction and purification conditions described in Example 383 substituting quinazoline-2-carboxylic acid (16.8 mg, 0.097 mmol) for quinoxaline-2-carboxylic acid (16.8 mg, 0.097 mmol) gave the title compound. $^1$H NMR (500 MHz, DMSO-$d_6$) δ ppm 9.75 (s, 1H), 9.54 (s, 1H), 8.79 (s, 1H), 8.28 (dt, J=8.1, 1.1 Hz, 1H), 8.18-8.10 (m, 2H), 7.89 (ddd, J=8.1, 6.1, 1.9 Hz, 1H), 7.51 (t, J=8.9 Hz, 1H), 7.10 (dd, J=11.3, 2.8 Hz, 1H), 6.88 (ddd, J=9.0, 2.9, 1.2 Hz, 1H), 4.52 (s, 2H), 2.41 (s, 6H); MS (ESI+) m/z 441 (M+H)+.

Example 651: N-{(3S)-4-[2-(4-chloro-3-fluorophenoxy)acetamido]-3-hydroxybicyclo[2.2.2]octan-1-yl}-5,7-dimethyl[1,2,4]triazolo[1,5-a]pyrimidine-2-carboxamide (Compound 750)

The title compound was prepared using the methodologies described in Example 473 substituting Example 567B for Example 473A and 5,7-dimethyl-[1,2,4]triazolo[1,5-a]pyrimidine-2-carboxylic acid for 2-methylthiazole-4-carboxylic acid. $^1$H NMR (400 MHz, DMSO-$d_6$) δ ppm 7.79 (s, 1H), 7.45 (t, J=8.9 Hz, 1H), 7.29-7.21 (m, 2H), 7.03 (dd, J=11.4, 2.9 Hz, 1H), 6.81 (ddd, J=9.0, 2.9, 1.2 Hz, 1H), 4.45 (s, 2H), 4.07 (ddd, J=9.5, 3.3, 1.4 Hz, 1H), 2.72 (d, J=0.9 Hz, 3H), 2.57 (s, 3H), 2.39 (ddd, J=12.2, 9.4, 2.4 Hz, 1H), 2.15-2.02 (m, 2H), 2.00-1.77 (m, 7H); MS (ESI+) m/z 517.2 (M+H)+.

Example 652: N-{(3S)-4-[2-(4-chloro-3-fluorophenoxy)acetamido]-3-hydroxybicyclo[2.2.2]octan-1-yl}-2-cyclopropyl-1,3-thiazole-4-carboxamide (Compound 751)

The title compound was prepared using the methodologies described in Example 473 substituting Example 567B for Example 473A and 2-cyclopropylthiazole-4-carboxylic acid for 2-methylthiazole-4-carboxylic acid. $^1$H NMR (400 MHz, DMSO-$d_6$) δ ppm 7.63-7.44 (m, 3H), 7.29 (s, 1H), 7.06 (dd, J=11.4, 2.9 Hz, 1H), 6.84 (ddd, J=9.0, 2.9, 1.2 Hz, 1H), 5.10 (s, 1H), 4.48 (s, 2H), 4.13-4.05 (m, 1H), 2.39 (ddd, J=12.5, 9.5, 2.2 Hz, 1H), 2.17-2.08 (m, 1H), 2.12-2.04 (m, 1H), 2.09-1.89 (m, 4H), 1.93-1.79 (m, 4H), 0.97-0.78 (m, 4H); MS (ESI+) m/z 494.1 (M+H)+.

Example 653: N-{(3S)-4-[2-(4-chloro-3-fluorophenoxy)acetamido]-3-hydroxybicyclo[2.2.2]octan-1-yl}-5-(difluoromethyl)pyridine-2-carboxamide (Compound 752)

The reaction described in Example 582 substituting 5-(difluoromethyl)picolinic acid for 3-fluorobenzoic acid gave the title compound. $^1$H NMR (501 MHz, DMSO-$d_6$) δ ppm 8.82 (dq, J=2.2, 1.2 Hz, 1H), 8.20 (ddt, J=8.0, 2.0, 1.0 Hz, 1H), 8.13 (dd, J=8.2, 0.9 Hz, 1H), 8.01 (s, 1H), 7.48 (q, J=8.7 Hz, 1H), 7.38-7.11 (m, 2H), 7.07 (dd, J=11.3, 2.9 Hz, 1H), 6.84 (ddd, J 25=9.0, 2.9, 1.2 Hz, 1H), 4.51-4.47 (m, 2H), 4.11 (ddd, J=9.5, 3.2, 1.4 Hz, 1H), 2.43 (ddd, J=12.6, 9.4, 2.6 Hz, 1H), 2.12 (dqd, J=12.9, 6.5, 5.8, 3.7 Hz, 2H), 2.03-1.81 (m, 7H); MS (ESI+) m/z 498.2 (M+H)+.

Example 654: N-{(3S)-4-[2-(4-chloro-3-fluorophenoxy)acetamido]-3-hydroxybicyclo[2.2.2]octan-1-yl}-5-(hydroxymethyl)pyridine-2-carboxamide (Compound 753)

The reaction described in Example 582 substituting 5-(hydroxymethyl)picolinic acid for 3-fluorobenzoic acid gave the title compound. $^1$H NMR (500 MHz, DMSO-$d_6$) δ ppm 8.53 (dd, J=2.1, 0.9 Hz, 1H), 7.97 (dd, J=8.0, 0.8 Hz, 1H), 7.95-7.87 (m, 2H), 7.48 (q, J=8.8 Hz, 1H), 7.30 (s, 1H), 7.07 (dd, J=11.4, 2.9 Hz, 1H), 6.84 (ddd, J=9.0, 2.9, 1.2 Hz, 1H), 4.61 (s, 2H), 4.49 (s, 2H), 4.15-4.07 (m, 1H), 2.42 (ddd, J=12.6, 9.5, 2.5 Hz, 1H), 2.17-2.04 (m, 2H), 2.03-1.82 (m, 7H); MS (ESI+) m/z 478.2 (M+H)+.

Example 655: N-{(3S)-4-[2-(4-chloro-3-fluorophenoxy)acetamido]-3-hydroxybicyclo[2.2.2]octan-1-yl}-5-ethylpyridine-2-carboxamide (Compound 754)

The reaction described in Example 582 substituting 5-ethylpicolinic acid for 3-fluorobenzoic acid gave the title compound. $^1$H NMR (500 MHz, DMSO-$d_6$) δ ppm 8.47 (dd, J=2.2, 0.8 Hz, 1H), 7.97-7.87 (m, 2H), 7.86-7.79 (m, 1H), 7.48 (q, J=8.8 Hz, 1H), 7.30 (s, 1H), 7.07 (dd, J=11.4, 2.9 Hz, 1H), 6.84 (ddd, J=8.9, 2.8, 1.2 Hz, 1H), 4.49 (s, 2H), 4.10 (ddd, J=9.5, 3.2, 1.3 Hz, 1H), 2.69 (q, J=7.6 Hz, 2H), 2.41 (ddd, J=12.5, 9.4, 2.4 Hz, 1H), 2.16-2.04 (m, 2H), 2.02-1.82 (m, 7H), 1.20 (t, J=7.6 Hz, 3H); MS (ESI+) m/z 476.3 (M+H)+.

Example 656: 2-(4-chloro-3-fluorophenoxy)-N-(3-{[2-(trifluoromethyl)pyrimidin-5-yl]amino}bicyclo[1.1.1]pentan-1-yl)acetamide (Compound 755)

The reaction and purification conditions described in Example 579 substituting 5-bromo-2-(trifluoromethyl)pyrimidine (39.9 mg, 0.176 mmol) for 2-chloro-3-methylpyrazine (24.8 mg, 0.193 mmol) gave the title compound. $^1$H NMR (501 MHz, DMSO-$d_6$) δ ppm 8.84 (s, 1H), 8.35 (s, 2H), 7.71 (s, 1H), 7.50 (t, J=8.8 Hz, 1H), 7.09 (dd, J=11.3, 2.9 Hz, 1H), 6.87 (ddd, J=9.0, 2.9, 1.2 Hz, 1H), 4.52 (s, 2H), 2.39 (s, 6H); $^{19}$F NMR (376 MHz, DMSO-d$_6$) δ ppm −67.28, −114.09; MS (ESI$^+$) m/z 431 (M+H)$^+$.

Example 657: 2-(4-chloro-3-fluorophenoxy)-N-{3-[(6-methoxypyrazin-2-yl)amino]bicyclo[1.1.1]pentan-1-yl}acetamide (Compound 756)

The reaction and purification conditions described in Example 579 substituting 2-bromo-6-methoxypyrazine (49.8 mg, 0.263 mmol) for 2-chloro-3-methylpyrazine (24.8 mg, 0.193 mmol) gave the title compound. $^1$H NMR (400 MHz, DMSO-d$_6$) δ ppm 8.74 (s, 1H), 7.75 (s, 1H), 7.50 (t, J=8.9 Hz, 1H), 7.46 (s, 1H), 7.37 (s, 1H), 7.08 (dd, J=11.4, 2.8 Hz, 1H), 6.86 (ddd, J=9.0, 2.9, 1.2 Hz, 1H), 4.49 (s, 2H), 3.82 (s, 3H), 2.35 (s, 6H); MS (ESI$^+$) m/z 393 (M+H)$^+$.

Example 658: 2-(4-chloro-3-fluorophenoxy)-N-(3-{[4-(trifluoromethyl)pyridin-2-yl]amino}bicyclo[1.1.1]pentan-1-yl)acetamide (Compound 757)

The reaction and purification conditions described in Example 579 substituting 2-chloro-4-(trifluoromethyl)pyridine (0.027 mL, 0.211 mmol) for 2-chloro-3-methylpyrazine (24.8 mg, 0.193 mmol) gave the title compound. 1H NMR (501 MHz, DMSO-d$_6$) δ ppm 8.75 (s, 1H), 8.28-8.21 (m, 1H), 7.50 (t, J=8.9 Hz, 1H), 7.08 (dd, J=11.4, 2.9 Hz, 1H), 6.86 (ddd, J=9.0, 2.9, 1.2 Hz, 1H), 6.80 (dd, J=5.3, 1.5 Hz, 1H), 6.74 (dt, J=1.7, 0.8 Hz, 1H), 4.50 (s, 2H), 2.34 (s, 6H); MS (ESI$^+$) m/z 430 (M+H)$^+$.

Example 659: N-{(3S)-4-[2-(3,4-dichlorophenoxy)acetamido]-3-hydroxybicyclo[2.2.2]octan-1-yl}-3-(difluoromethyl)-1,2-oxazole-5-carboxamide (Compound 758)

The title compound was prepared using the methodologies described in Example 473 substituting Example 595B for Example 473A and Example 555F for 2-methylthiazole-4-carboxylic acid. $^1$H NMR (400 MHz, DMSO-d$_6$) δ ppm 8.29 (s, 1H), 7.50 (d, J=8.9 Hz, 1H), 7.37 (s, 1H), 7.29 (t, J=52.0 Hz, 1H), 7.20 (d, J=4.4 Hz, 1H), 6.93 (dd, J=9.0, 2.9 Hz, 1H), 5.10 (d, J=4.4 Hz, 1H), 4.45 (s, 2H), 4.05 (dq, J=6.6, 2.9, 1.9 Hz, 1H), 2.32 (ddd, J=12.1, 9.6, 1.9 Hz, 1H), 2.13-1.76 (m, 9H); MS (ESI$^+$) m/z 504.0 (M+H)$^+$.

Example 660: N-{(3S)-4-[2-(3,4-dichlorophenoxy)acetamido]-3-hydroxybicyclo[2.2.2]octan-1-yl}-3-methyl-1,2-oxazole-5-carboxamide (Compound 759)

The title compound was prepared using the methodologies described in Example 473 substituting Example 595B for Example 473A and 3-methylisoxazole-5-carboxylic acid for 2-methylthiazole-4-carboxylic acid. $^1$H NMR (400 MHz, DMSO-d$_6$) δ ppm 8.05 (s, 1H), 7.50 (d, J=9.0 Hz, 1H), 7.27-7.18 (m, 2H), 6.93 (dd, J=9.0, 2.9 Hz, 1H), 6.84 (s, 1H), 5.08 (s, 1H), 4.45 (s, 2H), 4.03 (d, J=8.0 Hz, 1H), 2.31 (ddd, J=12.4, 9.5, 2.1 Hz, 1H), 2.23 (s, 3H), 2.12 1.75 (m, 9H); MS (ESI$^+$) m/z 468.1 (M+H)$^+$.

The compounds in the following table were prepared using the methodologies described above.

| Example | Name (Compound Number) | NMR | MS |
|---|---|---|---|
| Example 661 | N-{3-[2-(4-chloro-3-fluorophenoxy)acetamido]bicyclo[1.1.1]pentan-1-yl}imidazo[1,2-b]pyridazine-3-carboxamide (Compound 760) | $^1$H NMR (400 MHz, DMSO-d$_6$_D$_2$O) δ ppm 8.78 (dd, J = 4.6, 1.6 Hz, 1H), 8.44-8.21 (m, 2H), 7.57-7.39 (m, 2H), 7.08 (dd, J = 11.3, 2.8 Hz, 1H), 6.88 (ddd, J = 9.0, 2.9, 1.2 Hz, 1H), 4.50 (s, 2H), 2.43 (s, 6H) | MS (APCI$^+$) m/z 430 (M + H)$^+$ |
| Example 662 | N-{3-[2-(4-chloro-3-fluorophenoxy)acetamido]bicyclo[1.1.1]pentan-1-yl}-4-ethylbenzamide (Compound 761) | | MS (APCI$^+$) m/z 417 (M + H)$^+$ |
| Example 663 | N-{3-[2-(4-chloro-3-fluorophenoxy)acetamido]bicyclo[1.1.1]pentan-1-yl}pyridazine-4-carboxamide (Compound 762) | | MS (APCI$^+$) m/z 391 (M + H)$^+$ |
| Example 664 | N-{3-[2-(4-chloro-3-fluorophenoxy)acetamido]bicyclo[1.1.1]pentan-1-yl}-2-methoxypyridine-4-carboxamide (Compound 763) | | MS (APCI$^+$) m/z 420 (M + H)$^+$ |
| Example 665 | N-{3-[2-(4-chloro-3-fluorophenoxy)acetamido]bicyclo[1.1.1]pentan-1-yl}-3-(difluoromethoxy)benzamide (Compound 764) | | MS (APCI$^+$) m/z 455 (M + H)$^+$ |
| Example 666 | 2-acetamido-N-{3-[2-(4-chloro-3-fluorophenoxy)acetamido]bicyclo[1.1.1]pentan-1-yl}-5-fluorobenzamide (Compound 765) | $^1$H NMR (400 MHz, DMSO-d$_6$_D$_2$O) δ ppm 8.22 (dd, J = 9.1, 5.2 Hz, 1H), 7.53-7.46 (m, 2H), 7.36 (ddd, J = 9.2, 8.0, 3.0 Hz, 1H), 7.07 (dd, J = 11.3, 2.8 Hz, 1H), 6.88 (ddd, J = 9.0, 2.9, 1.2 Hz, 1H), 4.49 (s, 2H), 2.36 (s, 6H), 2.08 (s, 3H) | MS (APCI$^+$) m/z 464 (M + H)$^+$ |

-continued

| Example | Name (Compound Number) | NMR | MS |
|---|---|---|---|
| Example 667 | N-{3-[2-(4-chloro-3-fluorophenoxy)acetamido]bicyclo[1.1.1]pentan-1-yl}quinoxaline-6-carboxamide (Compound 766) | $^1$H NMR (400 MHz, DMSO-$d_6$_$D_2O$) δ ppm 9.03 (d, J = 2.6 Hz, 2H), 8.59 (d, J = 1.9 Hz, 1H), 8.26 (dd, J = 8.8, 2.0 Hz, 1H), 8.19 (d, J = 8.7 Hz, 1H), 7.50 (t, J = 8.9 Hz, 1H), 7.08 (dd, J = 11.3, 2.9 Hz, 1H), 6.89 (ddd, J = 9.0, 2.9, 1.2 Hz, 1H), 4.51 (s, 2H), 2.42 (s, 6H) | MS (APCI$^+$) m/z 441 (M + H)$^+$ |
| Example 668 | N-{3-[2-(4-chloro-3-fluorophenoxy)acetamido]bicyclo[1.1.1]pentan-1-yl}-1-methyl-1H-benzimidazole-5-carboxamide (Compound 767) | $^1$H NMR (400 MHz, DMSO-$d_6$_$D_2O$) δ ppm 9.29 (s, 1H), 8.28 (d, J = 1.4 Hz, 1H), 8.03 (dd, J = 8.7, 1.6 Hz, 1H), 7.95 (d, J = 8.7 Hz, 1H), 7.50 (t, J = 8.9 Hz, 1H), 7.08 (dd, J = 11.3, 2.9 Hz, 1H), 6.88 (ddd, J = 9.0, 2.9, 1.2 Hz, 1H), 4.50 (s, 2H), 4.04 (s, 3H), 2.39 (s, 6H) | MS (APCI$^+$) m/z 443 (M + H)$^+$ |
| Example 669 | N-{3-[2-(4-chloro-3-fluorophenoxy)acetamido]bicyclo[1.1.1]pentan-1-yl}-3-sulfamoylbenzamide (Compound 768) | $^1$H NMR (400 MHz, DMSO-$d_6$_$D_2O$) δ ppm 8.27 (t, J = 1.9 Hz, 1H), 8.10-7.93 (m, 2H), 7.68 (t, J = 7.8 Hz, 1H), 7.50 (t, J = 8.9 Hz, 1H), 7.07 (dd, J = 11.3, 2.9 Hz, 1H), 6.88 (ddd, J = 9.0, 2.9, 1.2 Hz, 1H), 4.49 (s, 2H), 2.37 (s, 6H) | MS (APCI$^+$) m/z 468 (M + H)$^+$ |
| Example 670 | N-{3-[2-(4-chloro-3-fluorophenoxy)acetamido]bicyclo[1.1.1]pentan-1-yl}-5-cyclopropyl-1,3-oxazole-4-carboxamide (Compound 769) | $^1$H NMR (400 MHz, DMSO-$d_6$_$D_2O$) δ ppm 8.13 (d, J = 0.5 Hz, 1H), 7.49 (t, J = 8.9 Hz, 1H), 7.07 (dd, J = 11.3, 2.8 Hz, 1H), 6.87 (ddd, J = 9.0, 2.9, 1.2 Hz, 1H), 4.48 (s, 2H), 2.75 (tt, J = 8.5, 5.1 Hz, 1H), 2.33 (s, 6H), 1.15-1.07 (m, 2H), 1.02-0.92 (m, 2H) | MS (APCI$^+$) m/z 420 (M + H)$^+$ |
| Example 671 | 5-chloro-N-{3-[2-(4-chloro-3-fluorophenoxy)acetamido]bicyclo[1.1.1]pentan-1-yl}-3-fluoropyridine-2-carboxamide (Compound 770) | $^1$H NMR (400 MHz, DMSO-$d_6$_$D_2O$) δ ppm 8.53 (dd, J = 1.9, 0.8 Hz, 1H), 8.16 (dd, J = 10.3, 1.9 Hz, 1H), 7.49 (t, J = 8.9 Hz, 1H), 7.07 (dd, J = 11.3, 2.9 Hz, 1H), 6.87 (ddd, J = 9.0, 2.8, 1.2 Hz, 1H), 4.49 (s, 2H), 2.36 (s, 6H) | MS (APCI$^+$) m/z 442 (M + H)$^+$ |
| Example 672 | N-{3-[2-(4-chloro-3-fluorophenoxy)acetamido]bicyclo[1.1.1]pentan-1-yl}-2-(morpholin-4-yl)-1,3-thiazole-4-carboxamide (Compound 771) | $^1$H NMR (400 MHz, DMSO-$d_6$_$D_2O$) δ ppm 8.82 (s, 1H), 8.62 (s, 1H), 7.49 (t, J = 8.9 Hz, 1H), 7.42 (s, 1H), 7.06 (dd, J = 11.3, 2.8 Hz, 1H), 6.87 (ddd, J = 9.0, 2.9, 1.2 Hz, 1H), 4.48 (s, 2H), 3.73 (s, 4H), 3.51-3.38 (m, 4H), 2.33 (s, 6H) | MS (APCI$^+$) m/z 481 (M + H)$^+$ |
| Example 673 | N-{3-[2-(4-chloro-3-fluorophenoxy)acetamido]bicyclo[1.1.1]pentan-1-yl}imidazo[1,2-a]pyrimidine-2-carboxamide (Compound 772) | $^1$H NMR (400 MHz, DMSO-$d_6$_$D_2O$) δ ppm 9.76 (dd, J = 7.0, 2.0 Hz, 1H), 8.76 (dd, J = 4.2, 2.0 Hz, 1H), 8.48 (s, 1H), 7.50 (t, J = 8.9 Hz, 1H), 7.33 (dd, J = 7.0, 4.2 Hz, 1H), 7.08 (dd, J = 11.3, 2.8 Hz, 1H), 6.88 (ddd, J = 8.9, 2.8, 1.1 Hz, 1H), 4.50 (s, 2H), 2.39 (s, 6H) | MS (APCI$^+$) m/z 430 (M + H)$^+$ |
| Example 674 | N-{3-[2-(4-chloro-3-fluorophenoxy)acetamido]bicyclo[1.1.1]pentan-1-yl}-1,3-benzothiazole-6-carboxamide (Compound 773) | $^1$H NMR (400 MHz, DMSO-$d_6$_$D_2O$) δ ppm 9.51 (s, 1H), 9.27 (s, 1H), 8.86 (s, 1H), 8.61 (d, J = 1.7 Hz, 1H), 8.15 (d, J = 8.6 Hz, 1H), 7.99 (dd, J = 8.6, 1.8 Hz, 1H), 7.50 (t, J = 8.9 Hz, 1H), 7.08 (dd, J = 11.3, 2.8 Hz, 1H), 6.88 (ddd, J = 9.0, 2.9, 1.2 Hz, 1H), 4.50 (s, 2H), 2.38 (s, 6H) | MS (APCI$^+$) m/z 446 (M+H)$^+$ |

| Example | Name (Compound Number) | NMR | MS |
|---|---|---|---|
| Example 675 | N-{3-[2-(4-chloro-3-fluorophenoxy)acetamido]bicyclo[1.1.1]pentan-1-yl}-2-methyl-1,3-benzothiazole-6-carboxamide (Compound 774) | $^1$H NMR (400 MHz, DMSO-$d_6$_$D_2O$) δ ppm 8.47 (dd, J = 1.7, 0.7 Hz, 1H), 7.99-7.90 (m, 2H), 7.50 (s, 1H), 7.08 (dd, J = 11.3, 2.9 Hz, 1H), 6.93-6.84 (m, 1H), 4.50 (s, 2H), 2.83 (s, 3H), 2.37 (s, 6H) | MS (APCI$^+$) m/z 460 (M + H)$^+$ |
| Example 676 | N-{3-[2-(4-chloro-3-fluorophenoxy)acetamido]bicyclo[1.1.1]pentan-1-yl}-1-ethyl-1H-imidazole-5-carboxamide (Compound 775) | $^1$H NMR (400 MHz, DMSO-$d_6$_$D_2O$) δ ppm 9.08 (d, J = 1.5 Hz, 1H), 8.07 (d, J = 1.5 Hz, 1H), 7.50 (t, J = 8.8 Hz, 1H), 7.07 (dd, J = 11.3, 2.9 Hz, 1H), 6.87 (ddd, J = 9.0, 2.9, 1.2 Hz, 1H), 4.49 (s, 2H), 4.48 (s, 2H), 2.36 (s, 6H), 1.40 (t, J = 7.2 Hz, 3H) | MS (APCI$^+$) m/z 407 (M + H)$^+$ |
| Example 677 | N-{3-[2-(4-chloro-3-fluorophenoxy)acetamido]bicyclo[1.1.1]pentan-1-yl}-1,3-dimethyl-2-oxo-2,3-dihydro-1H-benzimidazole-5-carboxamide (Compound 776) | $^1$H NMR (400 MHz, DMSO-$d_6$_$D_2O$) δ ppm 7.69-7.60 (m, 2H), 7.50 (t, J = 8.9 Hz, 1H), 7.21 (dd, J = 7.9, 0.9 Hz, 1H), 7.07 (dd, J = 11.3, 2.9 Hz, 1H), 6.88 (ddd, J = 9.0, 2.9, 1.2 Hz, 1H), 4.50 (s, 2H), 3.37 (d, J = 2.9 Hz, 6H), 2.37 (s, 6H) | MS (APCI$^+$) m/z 473 (M + H)$^+$ |
| Example 678 | 5-chloro-N-{3-[2-(4-chloro-3-fluorophenoxy)acetamido]bicyclo[1.1.1]pentan-1-yl}-3-methylpyridine-2-carboxamide (Compound 777) | $^1$H NMR (400 MHz, DMSO-$d_6$_$D_2O$) δ ppm 8.84 (s, 1H), 8.46 (dd, J = 2.3, 0.7 Hz, 1H), 7.91 (dd, J = 2.3, 0.8 Hz, 1H), 7.49 (t, J = 8.9 Hz, 1H), 7.07 (dd, J = 11.3, 2.8 Hz, 1H), 6.88 (ddd, J = 9.0, 2.9, 1.2 Hz, 1H), 4.49 (s, 2H), 2.51 (s, 3H), 2.35 (s, 6H) | MS (APCI$^+$) m/z 438 (M + H)$^+$ |
| Example 679 | 5-(acetamidomethyl)-N-{3-[2-(4-chloro-3-fluorophenoxy)acetamido]bicyclo[1.1.1]pentan-1-yl}furan-2-carboxamide (Compound 778) | $^1$H NMR (400 MHz, DMSO-$d_6$_$D_2O$) δ ppm 7.49 (t, J = 8.9 Hz, 1H), 7.06 (dd, J = 11.3, 2.9 Hz, 1H), 7.02 (d, J = 3.4 Hz, 1H), 6.87 (ddd, J = 9.0, 2.9, 1.2 Hz, 1H), 6.37 (d, J = 3.5 Hz, 1H), 4.48 (s, 2H), 4.28 (s, 2H), 2.32 (s, 7H), 1.88 (s, 3H) | MS (APCI$^+$) m/z 450 (M + H)$^+$ |
| Example 680 | N-{3-[2-(4-chloro-3-fluorophenoxy)acetamido]bicyclo[1.1.1]pentan-1-yl}-2,3-dimethylquinoxaline-6-carboxamide (Compound 779) | $^1$H NMR (400 MHz, DMSO-$d_6$_$D_2O$) δ ppm 8.53 (d, J = 1.2 Hz, 1H), 8.03 (dd, J = 8.8, 1.5 Hz, 1H), 7.90 (dd, J = 8.7, 0.8 Hz, 1H), 7.50 (t, J = 8.9 Hz, 1H), 7.08 (dd, J = 11.3, 2.9 Hz, 1H), 6.88 (ddd, J = 9.1, 2.9, 1.2 Hz, 1H), 4.50 (s, 2H), 4.33 (s, 3H), 2.39 (s, 6H) | MS (APCI$^+$) m/z 469 (M + H)$^+$ |
| Example 681 | 4-chloro-N-{3-[2-(4-chloro-3-fluorophenoxy)acetamido]bicyclo[1.1.1]pentan-1-yl}-1,5-dimethyl-1H-pyrazole-3-carboxamide (Compound 780) | $^1$H NMR (400 MHz, DMSO-$d_6$_$D_2O$) δ ppm 7.49 (t, J = 8.9 Hz, 1H), 7.07 (dd, J = 11.3, 2.9 Hz, 1H), 6.87 (ddd, J = 9.0, 2.9, 1.2 Hz, 1H), 4.48 (s, 2H), 3.79 (s, 3H), 2.31 (s, 6H), 2.23 (s, 3H) | MS (APCI$^+$) m/z 441 (M + H)$^+$ |
| Example 682 | N-{3-[2-(4-chloro-3-fluorophenoxy)acetamido]bicyclo[1.1.1]pentan-1-yl}-6-(trifluoromethyl)pyridine-2-carboxamide (Compound 781) | $^1$H NMR (400 MHz, DMSO-$d_6$_$D_2O$) δ ppm 8.35-8.24 (m, 2H), 8.10 (dd, J = 6.9, 2.0 Hz, 1H), 7.50 (t, J = 8.9 Hz, 1H), 7.08 (dd, J = 11.3, 2.8 Hz, 1H), 6.88 (ddd, J = 9.0, 2.9, 1.2 Hz, 1H), 4.50 (s, 2H), 2.41 (s, 6H) | MS (APCI$^+$) m/z 458 (M + H)$^+$ |
| Example 683 | N-{3-[2-(4-chloro-3-fluorophenoxy)acetamido]bicyclo[1.1.1]pentan-1-yl}imidazo[1,5-a]pyridine-1-carboxamide (Compound 782) | $^1$H NMR (400 MHz, DMSO-$d_6$_$D_2O$) δ ppm 8.49-8.38 (m, 2H), 8.06 (dd, J = 9.1, 0.9 Hz, 1H), 7.50 (t, J = 8.9 Hz, 1H), 7.15 (ddd, J = 9.2, 6.5, 1.0 Hz, 1H), 7.07 (dd, J = 11.3, 2.9 Hz, 1H), 6.93-6.84 (m, 2H), 4.49 (s, 2H), 2.36 (s, 6H) | MS (APCI$^+$) m/z 429 (M + H)$^+$ |
| Example 684 | N-{3-[2-(4-chloro-3-fluorophenoxy)acetamido]bicyclo[1.1.1]pentan-1-yl}-4-(1H-1,2,4-triazol-1- | $^1$H NMR (400 MHz, DMSO-$d_6$_$D_2O$) δ ppm 9.35 (s, 1H), 8.29 (s, 1H), 8.06-7.88 (m, 4H), 7.50 (t, J = 8.9 Hz, 1H), | MS (APCI$^+$) m/z 456 (M + H)$^+$ |

| Example | Name (Compound Number) | NMR | MS |
|---|---|---|---|
| | yl)benzamide (Compound 783) | 7.08 (dd, J = 11.3, 2.8 Hz, 1H), 6.88 (ddd, J = 9.0, 2.9, 1.2 Hz, 1H), 4.50 (s, 2H), 2.37 (s, 6H) | |
| Example 685 | N-{3-[2-(4-chloro-3-fluorophenoxy)acetamido]bicyclo[1.1.1]pentan-1-yl}-2,4-dimethylpyrimidine-5-carboxamide (Compound 784) | $^1$H NMR (400 MHz, DMSO-$d_6$_$D_2O$) δ ppm 9.23 (s, 1H), 8.86 (s, 1H), 8.57 (s, 1H), 7.50 (t, J = 8.9 Hz, 1H), 7.07 (dd, J = 11.3, 2.9 Hz, 1H), 6.88 (ddd, J = 9.0, 2.9, 1.2 Hz, 1H), 4.49 (s, 2H), 2.60 (s, 3H), 2.49 (s, 3H), 2.35 (s, 6H) | MS (APCI$^+$) m/z 419 (M + H)$^+$ |
| Example 686 | N-{3-[2-(4-chloro-3-fluorophenoxy)acetamido]bicyclo[1.1.1]pentan-1-yl}-1-methyl-1H-benzotriazole-5-carboxamide (Compound 785) | $^1$H NMR (400 MHz, DMSO-$d_6$_$D_2O$) δ ppm 8.53 (d, J = 1.2 Hz, 1H), 8.03 (dd, J = 8.8, 1.5 Hz, 1H), 7.90 (dd, J = 8.7, 0.8 Hz, 1H), 7.50 (t, J = 8.9 Hz, 1H), 7.08 (dd, J = 11.3, 2.9 Hz, 1H), 6.88 (ddd, J = 9.1, 2.9, 1.2 Hz, 1H), 4.50 (s, 2H), 4.33 (s, 3H), 2.39 (s, 6H) | MS (APCI$^+$) m/z 444 (M + H)$^+$ |
| Example 687 | N-{3-[2-(4-chloro-3-fluorophenoxy)acetamido]bicyclo[1.1.1]pentan-1-yl}-1-methyl-1H-indazole-7-carboxamide (Compound 786) | $^1$H NMR (400 MHz, DMSO-$d_6$_$D_2O$) δ ppm 9.29 (s, 1H), 8.28 (d, J = 1.4 Hz, 1H), 8.03 (dd, J = 8.7, 1.6 Hz, 1H), 7.95 (d, J = 8.7 Hz, 1H), 7.50 (t, J = 8.9 Hz, 1H), 7.08 (dd, J = 11.3, 2.9 Hz, 1H), 6.88 (ddd, J = 9.0, 2.9, 1.2 Hz, 1H), 4.50 (s, 2H), 4.04 (s, 3H), 2.39 (s, 6H) | MS (APCI$^+$) m/z 443 (M + H)$^+$ |
| Example 688 | N-{3-[2-(4-chloro-3-fluorophenoxy)acetamido]bicyclo[1.1.1]pentan-1-yl}-6-methylimidazo[1,2-a]pyridine-2-carboxamide (Compound 787) | $^1$H NMR (400 MHz, DMSO-$d_6$_$D_2O$) δ ppm 8.60 (d, J = 1.3 Hz, 1H), 8.46 (s, 1H), 7.73-7.58 (m, 2H), 7.50 (t, J = 8.9 Hz, 1H), 7.07 (dd, J = 11.3, 2.8 Hz, 1H), 6.88 (ddd, J = 8.9, 2.9, 1.2 Hz, 1H), 4.50 (s, 2H), 2.39 (s, 6H), 2.37 (d, J = 1.1 Hz, 3H) | MS (APCI$^+$) m/z 443 (M + H)$^+$ |
| Example 689 | N-{3-[2-(4-chloro-3-fluorophenoxy)acetamido]bicyclo[1.1.1]pentan-1-yl}-3,6-dimethoxypyridazine-4-carboxamide (Compound 788) | $^1$H NMR (400 MHz, DMSO-$d_6$_$D_2O$) δ ppm 7.49 (t, J = 8.9 Hz, 1H), 7.26 (s, 1H), 7.07 (dd, J = 11.3, 2.9 Hz, 1H), 6.87 (ddd, J = 9.0, 2.9, 1.2 Hz, 1H), 4.49 (s, 2H), 4.00 (s, 3H), 3.97 (s, 3H), 2.35 (s, 6H) | MS (APCI$^+$) m/z 451 (M + H)$^+$ |
| Example 690 | N-{3-[2-(4-chloro-3-fluorophenoxy)acetamido]bicyclo[1.1.1]pentan-1-yl}-1-methyl-5-(trifluoromethyl)-1H-pyrazole-3-carboxamide (Compound 789) | $^1$H NMR (400 MHz, DMSO-$d_6$_$D_2O$) δ ppm 9.04 (s, 1H), 8.83 (s, 1H), 7.49 (t, J = 8.8 Hz, 1H), 7.20 (t, J = 0.8 Hz, 1H), 7.07 (dd, J = 11.3, 2.8 Hz, 1H), 6.87 (ddd, J = 9.0, 2.9, 1.2 Hz, 1H), 4.48 (s, 2H), 4.08-3.89 (m, 3H), 2.33 (s, 6H) | MS (APCI$^+$) m/z 461 (M + H)$^+$ |
| Example 691 | N-{3-[2-(4-chloro-3-fluorophenoxy)acetamido]bicyclo[1.1.1]pentan-1-yl}-5-methoxypyridine-3-carboxamide (Compound 790) | $^1$H NMR (400 MHz, DMSO-$d_6$_$D_2O$) δ ppm 8.61 (d, J = 1.8 Hz, 1H), 8.47 (d, J = 2.9 Hz, 1H), 7.83 (dd, J = 2.8, 1.7 Hz, 1H), 7.50 (t, J = 8.9 Hz, 1H), 7.07 (dd, J = 11.3, 2.9 Hz, 1H), 6.88 (ddd, J = 9.0, 2.9, 1.2 Hz, 1H), 4.50 (s, 2H), 3.90 (s, 3H), 2.38 (s, 6H) | MS (APCI$^+$) m/z 420 (M + H)$^+$ |
| Example 692 | N-{3-[2-(4-chloro-3-fluorophenoxy)acetamido]bicyclo[1.1.1]pentan-1-yl}-3-methyl[1,2]oxazolo[5,4-b]pyridine-5-carboxamide (Compound 791) | $^1$H NMR (400 MHz, DMSO-$d_6$_$D_2O$) δ ppm 9.42 (s, 1H), 9.04 (d, J = 2.1 Hz, 1H), 8.87 (s, 1H), 8.78 (d, J = 2.1 Hz, 1H), 7.50 (t, J = 8.9 Hz, 1H), 7.08 (dd, J = 11.3, 2.9 Hz, 1H), 6.88 (ddd, J = 8.9, 2.9, 1.2 Hz, 1H), 4.50 (s, 2H), 2.61 (s, 3H), 2.40 (s, 6H) | MS (APCI$^+$) m/z 445 (M + H)$^+$ |
| Example 693 | N-{3-[2-(4-chloro-3-fluorophenoxy)acetamido]bicyclo[1.1.1]pentan-1-yl}-5-fluoropyridine-3-carboxamide | $^1$H NMR (400 MHz, DMSO-$d_6$_$D_2O$) δ ppm 8.85 (t, J = 1.7 Hz, 1H), 8.73 (d, J = 2.7 Hz, 1H), 8.04 (ddd, J = 9.5, 2.8, 1.7 Hz, 1H), 7.50 (t, J = 8.9 | MS (APCI$^+$) m/z 408 (M + H)$^+$ |

-continued

| Example | Name (Compound Number) | NMR | MS |
|---|---|---|---|
| | (Compound 792) | Hz, 1H), 7.07 (dd, J = 11.3, 2.8 Hz, 1H), 6.88 (ddd, J = 9.0, 2.9, 1.2 Hz, 1H), 4.49 (s, 2H), 2.37 (s, 6H) | |
| Example 694 | N-{3-[2-(4-chloro-3-fluorophenoxy)acetamido]bi-cyclo[1.1.1]pentan-1-yl}pyrimidine-2-carboxamide (Compound 793) | $^1$H NMR (400 MHz, DMSO-$d_6$_$D_2O$) δ ppm 8.94 (d, J = 4.9 Hz, 2H), 7.67 (t, J = 4.9 Hz, 1H), 7.50 (t, J = 8.9 Hz, 1H), 7.07 (dd, J = 11.3, 2.8 Hz, 1H), 6.89-6.78 (m, 1H), 4.50 (s, 2H), 2.38 (s, 6H) | MS (APCI$^+$) m/z 391 (M + H)$^+$ |
| Example 695 | N-{3-[2-(4-chloro-3-fluorophenoxy)acetamido]bi-cyclo[1.1.1]pentan-1-yl}-3-oxo-3,4-dihydro-2H-1,4-benzoxazine-7-carboxamide (Compound 794) | $^1$H NMR (400 MHz, DMSO-$d_6$_$D_2O$) δ ppm 7.55-7.39 (m, 3H), 7.07 (dd, J = 11.3, 2.8 Hz, 1H), 6.95 (d, J = 8.2 Hz, 1H), 6.87 (ddd, J = 8.9, 2.8, 1.2 Hz, 1H), 4.62 (s, 2H), 4.49 (s, 2H), 2.33 (s, 6H) | MS (APCI$^+$) m/z 460 (M + H)$^+$ |
| Example 696 | N-{3-[2-(4-chloro-3-fluorophenoxy)acetamido]bi-cyclo[1.1.1]pentan-1-yl}-2,5-dimethyl-1,3-oxazole-4-carboxamide (Compound 795) | $^1$H NMR (400 MHz, DMSO-$d_6$_$D_2O$) δ ppm 8.80 (s, 1H), 7.49 (t, J = 8.9 Hz, 1H), 7.06 (dd, J = 11.3, 2.9 Hz, 1H), 6.87 (ddd, J = 9.0, 2.9, 1.2 Hz, 1H), 4.48 (s, 2H), 2.49 (s, 3H), 2.38 (s, 3H), 2.31 (s, 6H) | MS (APCI$^+$) m/z 408 (M + H)$^+$ |
| Example 697 | N-{3-[2-(4-chloro-3-fluorophenoxy)acetamido]bi-cyclo[1.1.1]pentan-1-yl}-3-fluorothiophene-2-carboxamide (Compound 796) | $^1$H NMR (400 MHz, DMSO-$d_6$_$D_2O$) δ ppm 7.74 (dd, J = 5.5, 4.0 Hz, 1H), 7.49 (t, J = 8.9 Hz, 1H), 7.11-7.02 (m, 2H), 6.87 (ddd, J = 8.9, 2.9, 1.2 Hz, 1H), 4.48 (s, 2H), 2.33 (s, 6H) | MS (APCI$^+$) m/z 413 (M + H)$^+$ |
| Example 698 | N-{3-[2-(4-chloro-3-fluorophenoxy)acetamido]bi-cyclo[1.1.1]pentan-1-yl}-2,1,3-benzothiadiazole-5-carboxamide (Compound 797) | $^1$H NMR (400 MHz, DMSO-$d_6$_$D_2O$) δ ppm 8.55 (dd, J = 1.7, 0.9 Hz, 1H), 8.16 (dd, J = 9.2, 0.9 Hz, 1H), 8.10 (dd, J = 9.2, 1.7 Hz, 1H), 7.50 (t, J = 8.9 Hz, 1H), 7.08 (dd, J = 11.3, 2.8 Hz, 1H), 6.89 (ddd, J = 9.0, 2.9, 1.2 Hz, 1H), 4.50 (s, 2H), 2.40 (s, 6H) | MS (APCI$^+$) m/z 447 (M + H)$^+$ |
| Example 699 | N-{3-[2-(4-chloro-3-fluorophenoxy)acetamido]bi-cyclo[1.1.1]pentan-1-yl}thieno[2,3-b]pyridine-2-carboxamide (Compound 798) | $^1$H NMR (400 MHz, DMSO-$d_6$_$D_2O$) δ ppm 8.66 (dd, J = 4.6, 1.6 Hz, 1H), 8.36 (dd, J = 8.2, 1.6 Hz, 1H), 8.03 (s, 1H), 7.55-7.40 (m, 2H), 7.08 (dd, J = 11.3, 2.8 Hz, 1H), 6.88 (ddd, J = 9.0, 2.9, 1.2 Hz, 1H), 4.50 (s, 2H), 2.38 (s, 6H) | MS (APCI$^+$) m/z 446 (M + H)$^+$ |
| Example 700 | N-{3-[2-(4-chloro-3-fluorophenoxy)acetamido]bi-cyclo[1.1.1]pentan-1-yl}imidazo[2,1-b][1,3]thiazole-6-carboxamide (Compound 799) | $^1$H NMR (400 MHz, DMSO-$d_6$_$D_2O$) δ ppm 8.20 (s, 1H), 7.93 (d, J = 4.5 Hz, 1H), 7.49 (t, J = 8.9 Hz, 1H), 7.35 (d, J = 4.5 Hz, 1H), 7.07 (dd, J = 11.3, 2.9 Hz, 1H), 6.87 (ddd, J = 8.9, 2.9, 1.2 Hz, 1H), 4.49 (s, 2H), 2.34 (s, 6H) | MS (APCI$^+$) m/z 435 (M + H)$^+$ |
| Example 701 | N-{3-[2-(4-chloro-3-fluorophenoxy)acetamido]bi-cyclo[1.1.1]pentan-1-yl}-1,2,3-benzothiadiazole-5-carboxamide (Compound 800) | $^1$H NMR (400 MHz, DMSO-$d_6$_$D_2O$) δ ppm 9.51 (s, 1H), 9.14 (dd, J = 1.6, 0.7 Hz, 1H), 8.88 (s, 1H), 8.47 (dd, J = 8.6, 0.7 Hz, 1H), 8.22 (dd, J = 8.6, 1.6 Hz, 1H), 7.50 (t, J = 8.8 Hz, 1H), 7.08 (dd, J = 11.3, 2.8 Hz, 1H), 6.89 (ddd, J = 9.0, 2.9, 1.2 Hz, 1H), 4.51 (s, 2H), 2.42 (s, 6H) | MS (APCI$^+$) m/z 447 (M + H)$^+$ |
| Example 702 | N-{3-[2-(4-chloro-3-fluorophenoxy)acetamido]bi-cyclo[1.1.1]pentan-1-yl}-1,3-benzoxazole-5-carboxamide (Compound 801) | $^1$H NMR (400 MHz, DMSO-$d_6$_$D_2O$) δ ppm 8.46 (d, J = 2.2 Hz, 1H), 8.30 (s, 1H), 7.49 (t, J = 8.9 Hz, 2H), 7.46-7.42 (m, 1H), 7.07 (dd, J = 11.3, 2.8 Hz, 2H), 6.95-6.82 (m, 2H), 4.49 (s, 2H), 2.33 (s, 6H) | MS (APCI$^+$) m/z 430 (M + H)$^+$ |
| Example 703 | N-{3-[2-(4-chloro-3-fluorophenoxy)acetamido]bi- | $^1$H NMR (400 MHz, DMSO-$d_6$_$D_2O$) δ ppm 9.11 (d, J = 0.8 | MS (APCI$^+$) |

| Example | Name (Compound Number) | NMR | MS |
|---|---|---|---|
| | cyclo[1.1.1]pentan-1-yl}-1-(pyridin-2-yl)-1H-pyrazole-4-carboxamide (Compound 802) | Hz, 1H), 8.52 (ddd, J = 4.9, 1.9, 0.9 Hz, 1H), 8.15 (d, J = 0.8 Hz, 1H), 8.05 (ddd, J = 8.3, 7.3, 1.8 Hz, 1H), 7.96 (dt, J = 8.3, 1.0 Hz, 1H), 7.50 (t, J = 8.9 Hz, 1H), 7.44 (ddd, J = 7.4, 4.9, 1.1 Hz, 1H), 7.07 (dd, J = 11.3, 2.8 Hz, 1H), 6.88 (ddd, J = 9.0, 2.9, 1.2 Hz, 1H), 4.49 (s, 2H), 2.34 (s, 6H) | m/z 456 (M + H)$^+$ |
| Example 704 | N-{3-[2-(4-chloro-3-fluorophenoxy)acetamido]bicyclo[1.1.1]pentan-1-yl}-2,1,3-benzothiadiazole-4-carboxamide (Compound 803) | $^1$H NMR (400 MHz, DMSO-d$_6$_D$_2$O) δ ppm 8.36-8.20 (m, 2H), 7.86 (dd, J = 8.8, 7.0 Hz, 1H), 7.50 (t, J = 8.8 Hz, 1H), 7.08 (dd, J = 11.3, 2.9 Hz, 1H), 6.89 (ddd, J = 9.0, 2.9, 1.2 Hz, 1H), 4.51 (s, 2H), 2.45 (s, 6H) | MS (APCI$^+$) m/z 447 (M + H)$^+$ |
| Example 705 | N-{3-[2-(4-chloro-3-fluorophenoxy)acetamido]bicyclo[1.1.1]pentan-1-yl}-5-methyl-3-(pyridin-2-yl)-1,2-oxazole-4-carboxamide (Compound 804) | $^1$H NMR (400 MHz, DMSO-d$_6$_D$_2$O) δ ppm 8.73 (ddd, J = 4.9, 1.7, 1.0 Hz, 1H), 8.14-7.97 (m, 2H), 7.65 (ddd, J = 6.9, 4.9, 1.8 Hz, 1H), 7.49 (t, J = 8.9 Hz, 1H), 7.07 (dd, J = 11.3, 2.9 Hz, 1H), 6.87 (ddd, J = 9.0, 2.9, 1.2 Hz, 1H), 4.49 (s, 2H), 2.67 (s, 3H), 2.34 (s, 6H) | MS (APCI$^+$) m/z 471 (M + H)$^+$ |
| Example 706 | 6-acetamido-N-{3-[2-(4-chloro-3-fluorophenoxy)acetamido]bicyclo[1.1.1]pentan-1-yl}pyridine-3-carboxamide (Compound 805) | $^1$H NMR (400 MHz, DMSO-d$_6$_D$_2$O) δ ppm 8.73 (dd, J = 2.3, 0.9 Hz, 1H), 8.16 (dd, J = 8.8, 2.4 Hz, 1H), 8.10 (dd, J = 8.7, 0.9 Hz, 1H), 7.50 (t, J = 8.9 Hz, 1H), 7.07 (dd, J = 11.3, 2.9 Hz, 1H), 6.88 (ddd, J = 9.0, 2.9, 1.2 Hz, 1H), 4.49 (s, 2H), 2.36 (s, 6H), 2.13 (s, 3H) | MS (APCI$^+$) m/z 447 (M + H)$^+$ |
| Example 707 | N-{3-[2-(4-chloro-3-fluorophenoxy)acetamido]bicyclo[1.1.1]pentan-1-yl}-6-methylpyrazolo[1,5-a]pyrimidine-3-carboxamide (Compound 806) | $^1$H NMR (400 MHz, DMSO-d$_6$_D$_2$O) δ ppm 9.09 (dd, J = 2.1, 1.2 Hz, 1H), 8.72 (d, J = 2.1 Hz, 1H), 8.48 (s, 1H), 7.50 (t, J = 8.9 Hz, 1H), 7.08 (dd, J = 11.4, 2.8 Hz, 1H), 6.88 (ddd, J = 9.0, 2.9, 1.2 Hz, 1H), 4.50 (s, 2H), 3.73 (s, 3H), 2.40 (s, 6H) | MS (APCI$^+$) m/z 444 (M + H)$^+$ |
| Example 708 | N-{3-[2-(4-chloro-3-fluorophenoxy)acetamido]bicyclo[1.1.1]pentan-1-yl}-2-(1H-pyrazol-1-yl)pyridine-3-carboxamide (Compound 807) | $^1$H NMR (400 MHz, DMSO-d$_6$_D$_2$O) δ ppm 8.52 (dd, J = 4.8, 1.8 Hz, 1H), 8.41 (dd, J = 2.6, 0.7 Hz, 1H), 7.88 (dd, J = 7.6, 1.8 Hz, 1H), 7.74-7.66 (m, 1H), 7.55-7.36 (m, 2H), 7.07 (dd, J = 11.3, 2.9 Hz, 1H), 6.87 (ddd, J = 9.0, 2.9, 1.2 Hz, 1H), 6.54 (dd, J = 2.6, 1.7 Hz, 1H), 4.48 (s, 2H), 2.28 (s, 6H) | MS (APCI$^+$) m/z 456 (M + H)$^+$ |
| Example 709 | N-{3-[2-(4-chloro-3-fluorophenoxy)acetamido]bicyclo[1.1.1]pentan-1-yl}-7-methylimidazo[1,2-a]pyridine-2-carboxamide (Compound 808) | $^1$H NMR (400 MHz, DMSO-d$_6$_D$_2$O) δ ppm 8.68 (d, J = 7.0 Hz, 1H), 8.48 (d, J = 0.8 Hz, 1H), 7.56 (d, J = 1.7 Hz, 1H), 7.50 (t, J = 8.9 Hz, 1H), 7.23 (dd, J = 7.1, 1.5 Hz, 1H), 7.07 (dd, J = 11.3, 2.9 Hz, 1H), 6.88 (ddd, J = 9.0, 2.9, 1.2 Hz, 1H), 4.50 (s, 2H), 2.49 (d, J = 1.1 Hz, 3H), 2.39 (s, 6H) | MS (APCI$^+$) m/z 443 (M + H)$^+$ |
| Example 710 | N-{3-[2-(4-chloro-3-fluorophenoxy)acetamido]bicyclo[1.1.1]pentan-1-yl}-2-methoxypyridine-3-carboxamide (Compound 809) | $^1$H NMR (400 MHz, DMSO-d$_6$_D$_2$O) δ ppm 8.29 (dd, J = 4.9, 2.0 Hz, 1H), 8.06 (dd, J = 7.4, 2.0 Hz, 1H), 7.50 (t, J = 8.8 Hz, 1H), 7.12 (dd, J = 7.5, 4.9 Hz, 1H), 7.07 (dd, J = 11.3, 2.8 Hz, 1H), 6.88 (ddd, J = 8.9, 2.8, 1.2 Hz, 1H), 4.49 (s, 2H), 3.96 (s, 3H), 2.36 (s, 6H) | MS (APCI$^+$) m/z 420 (M + H)$^+$ |
| Example 711 | N-{3-[2-(4-chloro-3-fluorophenoxy)acetamido]bicyclo[1.1.1]pentan-1-yl}- | $^1$H NMR (400 MHz, DMSO-d$_6$_D$_2$O) δ ppm 8.21 (d, J = 1.5 Hz, 1H), 8.09-7.91 (m, 2H), | MS (APCI$^+$) m/z 457 |

-continued

| Example | Name (Compound Number) | NMR | MS |
|---|---|---|---|
| | 1,2-dimethyl-1H-benzimidazole-5-carboxamide (Compound 810) | 7.50 (t, J = 8.9 Hz, 1H), 7.08 (dd, J = 11.3, 2.8 Hz, 1H), 6.88 (ddd, J = 9.0, 2.8, 1.2 Hz, 1H), 4.50 (s, 2H), 3.93 (s, 3H), 2.82 (s, 3H), 2.39 (s, 6H) | (M + H)$^+$ |
| Example 712 | N-{3-[2-(4-chloro-3-fluorophenoxy)acetamido]bicyclo[1.1.1]pentan-1-yl}imidazo[1,2-a]pyridine-6-carboxamide (Compound 811) | $^1$H NMR (400 MHz, DMSO-d$_6$_D$_2$O) δ ppm 9.32 (t, J = 1.3 Hz, 1H), 8.37 (d, J = 2.1 Hz, 1H), 8.25 (dd, J = 9.4, 1.7 Hz, 1H), 8.19 (d, J = 2.1 Hz, 1H), 8.00 (d, J = 9.4 Hz, 1H), 7.50 (t, J = 8.9 Hz, 1H), 7.08 (dd, J = 11.3, 2.9 Hz, 1H), 6.88 (ddd, J = 9.0, 2.9, 1.2 Hz, 1H), 4.50 (s, 2H), 2.40 (s, 6H) | MS (APCI$^+$) m/z 429 (M + H)$^+$ |
| Example 713 | N-{3-[2-(4-chloro-3-fluorophenoxy)acetamido]bicyclo[1.1.1]pentan-1-yl}-2-hydroxy-1H-imidazole-5-carboxamide (Compound 812) | $^1$H NMR (501 MHz, DMSO-d$_6$_D$_2$O) δ ppm 7.50 (td, J = 8.9, 1.0 Hz, 1H), 7.07 (ddd, J = 11.4, 2.9, 1.3 Hz, 1H), 7.03 (s, 1H), 6.87 (ddd, J = 8.9, 2.8, 1.2 Hz, 1H), 4.48 (s, 2H), 2.32-2.28 (m, 6H) | MS (APCI$^+$) m/z 395 (M + H)$^+$ |
| Example 714 | N-{3-[2-(4-chloro-3-fluorophenoxy)acetamido]bicyclo[1.1.1]pentan-1-yl}-3-(methanesulfonyl)benzamide (Compound 813) | | MS (APCI$^+$) m/z 467 (M + H)$^+$ |
| Example 715 | N-{3-[2-(4-chloro-3-fluorophenoxy)acetamido]bicyclo[1.1.1]pentan-1-yl}-3-methylpyridine-4-carboxamide (Compound 814) | | MS (APCI$^+$) m/z 404 (M + H)$^+$ |
| Example 716 | N-{3-[2-(4-chloro-3-fluorophenoxy)acetamido]bicyclo[1.1.1]pentan-1-yl}-4,6-dimethylpyridine-3-carboxamide (Compound 815) | | MS (APCI$^+$) m/z 418 (M + H)$^+$ |
| Example 717 | 4-acetamido-N-{3-[2-(4-chloro-3-fluorophenoxy)acetamido]bicyclo[1.1.1]pentan-1-yl}benzamide (Compound 816) | | MS (APCI$^+$) m/z 446 (M + H)$^+$ |
| Example 718 | N-{3-[2-(4-chloro-3-fluorophenoxy)acetamido]bicyclo[1.1.1]pentan-1-yl}-3-fluoropyridine-4-carboxamide (Compound 817) | | MS (APCI$^+$) m/z 408 (M + H)$^+$ |
| Example 719 | N-{3-[2-(4-chloro-3-fluorophenoxy)acetamido]bicyclo[1.1.1]pentan-1-yl}-1-methyl-6-oxo-1,6-dihydropyridine-3-carboxamide (Compound 818) | | MS (APCI$^+$) m/z 420 (M + H)$^+$ |
| Example 720 | N-{3-[2-(4-chloro-3-fluorophenoxy)acetamido]bicyclo[1.1.1]pentan-1-yl}-1-(propan-2-yl)-1H-pyrazole-3-carboxamide (Compound 819) | $^1$H NMR (501 MHz, DMSO-d$_6$_D$_2$O) δ ppm 7.80 (d, J = 2.4 Hz, 1H), 7.49 (t, J = 8.9 Hz, 1H), 7.07 (dd, J = 11.3, 2.8 Hz, 1H), 6.87 (ddd, J = 9.0, 2.9, 1.2 Hz, 1H), 6.62 (d, J = 2.4 Hz, 1H), 4.54 (p, J = 6.7 Hz, 1H), 4.49 (s, 2H), 2.33 (s, 6H), 1.43 (d, J = 6.7 Hz, 6H) | MS (APCI$^+$) m/z 421 (M + H)$^+$ |
| Example 721 | N-{3-[2-(4-chloro-3-fluorophenoxy)acetamido]bicyclo[1.1.1]pentan-1-yl}-1,2-oxazole-3-carboxamide (Compound 820) | | MS (APCI$^+$) m/z 380 (M + H)$^+$ |
| Example 722 | N-{3-[2-(4-chloro-3-fluorophenoxy)acetamido]bicyclo[1.1.1]pentan-1-yl}-1-methyl-1H-pyrrole-2- | | MS (APCI$^+$) m/z 392 (M + H)$^+$ |

| Example | Name (Compound Number) | NMR | MS |
|---|---|---|---|
| | carboxamide (Compound 821) | | |
| Example 723 | 5-acetamido-N-{3-[2-(4-chloro-3-fluorophenoxy)acetamido]bicyclo[1.1.1]pentan-1-yl}pyridine-3-carboxamide (Compound 822) | | MS (APCI$^+$) m/z 447 (M + H)$^+$ |
| Example 724 | N-{3-[2-(4-chloro-3-fluorophenoxy)acetamido]bicyclo[1.1.1]pentan-1-yl}-1-methyl-1H-indazole-3-carboxamide (Compound 823) | $^1$H NMR (501 MHz, DMSO-d$_6$_D$_2$O) δ ppm 8.22-8.09 (m, 1H), 7.71 (d, J = 8.5 Hz, 1H), 7.56-7.43 (m, 2H), 7.30 (ddd, J = 7.8, 6.9, 0.8 Hz, 1H), 7.08 (dd, J = 11.3, 2.8 Hz, 1H), 6.88 (ddd, J = 8.9, 2.9, 1.2 Hz, 1H), 4.50 (s, 2H), 4.11 (s, 3H), 2.38 (s, 6H) | MS (APCI$^+$) m/z 443 (M + H)$^+$ |
| Example 725 | N-{3-[2-(4-chloro-3-fluorophenoxy)acetamido]bicyclo[1.1.1]pentan-1-yl}-3-ethyl-5-methyl-1,2-oxazole-4-carboxamide (Compound 824) | $^1$H NMR (501 MHz, DMSO-d$_6$_D$_2$O) δ ppm 7.49 (t, J = 8.9 Hz, 1H), 7.07 (dd, J = 11.3, 2.9 Hz, 1H), 6.87 (ddd, J = 8.9, 2.9, 1.2 Hz, 1H), 4.48 (s, 2H), 2.70 (q, J = 7.5 Hz, 2H), 2.45 (s, 3H), 2.32 (s, 6H), 1.14 (t, J = 7.5 Hz, 3H) | MS (APCI$^+$) m/z 422 (M + H)$^+$ |
| Example 726 | N-{3-[2-(4-chloro-3-fluorophenoxy)acetamido]bicyclo[1.1.1]pentan-1-yl}-1-ethyl-3-methyl-1H-pyrazole-4-carboxamide (Compound 825) | $^1$H NMR (400 MHz, DMSO-d$_6$_D$_2$O) δ ppm 8.81 (s, 1H), 8.43 (s, 1H), 8.05 (s, 1H), 7.49 (t, J = 8.9 Hz, 1H), 7.07 (dd, J = 11.3, 2.9 Hz, 1H), 6.87 (ddd, J = 9.0, 2.9, 1.2 Hz, 1H), 4.48 (s, 2H), 4.03 (q, J = 7.2 Hz, 2H), 2.29 (s, 9H), 1.34 (t, J = 7.3 Hz, 3H) | MS (APCI$^+$) m/z 421 (M + H)$^+$ |
| Example 727 | N$^3$-{3-[2-(4-chloro-3-fluorophenoxy)acetamido]bicyclo[1.1.1]pentan-1-yl}pyridine-3,4-dicarboxamide (Compound 826) | $^1$H NMR (501 MHz, DMSO-d$_6$_D$_2$O) δ ppm 8.71 (d, J = 5.0 Hz, 1H), 8.67 (d, J = 0.7 Hz, 1H), 7.55-7.44 (m, 2H), 7.07 (dd, J = 11.3, 2.9 Hz, 1H), 6.88 (ddd, J = 9.0, 2.9, 1.2 Hz, 1H), 4.49 (s, 2H), 2.33 (s, 6H) | MS (APCI$^+$) m/z 433 (M + H)$^+$ |
| Example 728 | N-{3-[2-(4-chloro-3-fluorophenoxy)acetamido]bicyclo[1.1.1]pentan-1-yl}-2-(methanesulfonyl)benzamide (Compound 827) | $^1$H NMR (501 MHz, DMSO-d$_6$_D$_2$O) δ ppm 7.97 (dd, J = 7.8, 1.3 Hz, 1H), 7.77 (td, J = 7.5, 1.3 Hz, 1H), 7.70 (td, J = 7.7, 1.4 Hz, 1H), 7.56-7.45 (m, 2H), 7.07 (dd, J = 11.3, 2.9 Hz, 1H), 6.88 (ddd, J = 9.0, 2.9, 1.2 Hz, 1H), 4.49 (s, 2H), 3.33 (s, 3H), 2.34 (s, 6H) | MS (APCI$^+$) m/z 467 (M + H)$^+$ |
| Example 729 | N-{3-[2-(4-chloro-3-fluorophenoxy)acetamido]bicyclo[1.1.1]pentan-1-yl}-2-(methylsulfanyl)pyridine-3-carboxamide (Compound 828) | $^1$H NMR (501 MHz, DMSO-d$_6$_D$_2$O) δ ppm 8.53 (dd, J = 4.8, 1.8 Hz, 1H), 7.75 (dd, J = 7.6, 1.8 Hz, 1H), 7.50 (t, J = 8.8 Hz, 1H), 7.18 (dd, J = 7.6, 4.9 Hz, 1H), 7.07 (dd, J = 11.3, 2.9 Hz, 1H), 6.88 (ddd, J = 9.0, 2.9, 1.2 Hz, 1H), 4.49 (s, 2H), 2.43 (s, 3H), 2.34 (s, 6H) | MS (APCI$^+$) m/z 436 (M + H)$^+$ |
| Example 730 | N-{3-[2-(4-chloro-3-fluorophenoxy)acetamido]bicyclo[1.1.1]pentan-1-yl}-6-methoxypyridine-2-carboxamide (Compound 829) | $^1$H NMR (400 MHz, DMSO-d$_6$_D$_2$O) δ ppm 7.87 (dd, J = 8.3, 7.3 Hz, 1H), 7.60 (dd, J = 7.3, 0.9 Hz, 1H), 7.50 (t, J = 8.8 Hz, 1H), 7.07 (dd, J = 11.3, 2.9 Hz, 1H), 7.01 (dd, J = 8.3, 0.8 Hz, 1H), 6.88 (ddd, J = 9.0, 2.9, 1.2 Hz, 1H), 4.50 (s, 2H), 3.97 (s, 3H), 2.40 (s, 6H) | MS (APCI$^+$) m/z 420 (M + H)$^+$ |
| Example 731 | N-{3-[2-(4-chloro-3-fluorophenoxy)acetamido]bicyclo[1.1.1]pentan-1-yl}-5-[(methylsulfanyl)methyl]furan-2-carboxamide (Compound 830) | $^1$H NMR (400 MHz, DMSO-d$_6$_D$_2$O) δ ppm 7.49 (t, J = 8.9 Hz, 1H), 7.07 (dd, J = 11.3, 2.9 Hz, 1H), 7.03 (d, J = 3.4 Hz, 1H), 6.87 (ddd, J = 9.0, 2.9, 1.2 Hz, 1H), 6.43 (d, J = 3.4 Hz, 1H), 4.48 (s, 2H), 3.76 (s, 2H), 2.32 (s, 6H), 2.04 (s, 3H) | MS (APCI$^+$) m/z 439 (M + H)$^+$ |

| Example | Name (Compound Number) | NMR | MS |
|---|---|---|---|
| Example 732 | N-{3-[2-(4-chloro-3-fluorophenoxy)acetamido]bicyclo[1.1.1]pentan-1-yl}-6-methylimidazo[2,1-b][1,3]thiazole-5-carboxamide (Compound 831) | $^1$H NMR (400 MHz, DMSO-$d_6$_$D_2$O) δ ppm 8.07 (d, J = 4.4 Hz, 1H), 7.50 (t, J = 8.9 Hz, 1H), 7.35 (d, J = 4.4 Hz, 1H), 7.07 (dd, J = 11.3, 2.9 Hz, 1H), 6.88 (ddd, J = 9.0, 2.9, 1.2 Hz, 1H), 4.49 (s, 2H), 2.48 (s, 3H), 2.37 (s, 6H) | MS (APCI$^+$) m/z 449 (M + H)$^+$ |
| Example 733 | N-{3-[2-(4-chloro-3-fluorophenoxy)acetamido]bicyclo[1.1.1]pentan-1-yl}-3-fluoro-6-methylpyridine-2-carboxamide (Compound 832) | $^1$H NMR (501 MHz, DMSO-$d_6$_$D_2$O) δ ppm 7.69 (dd, J = 10.6, 8.6 Hz, 1H), 7.57-7.39 (m, 2H), 7.07 (dd, J = 11.3, 2.9 Hz, 1H), 6.88 (ddd, J = 9.0, 2.9, 1.2 Hz, 1H), 4.49 (s, 2H), 2.50 (d, J = 0.8 Hz, 3H), 2.37 (s, 6H) | MS (APCI$^+$) m/z 422 (M + H)$^+$ |
| Example 734 | N-{3-[2-(4-chloro-3-fluorophenoxy)acetamido]bicyclo[1.1.1]pentan-1-yl}-6-methylpyrazolo[1,5-a]pyrimidine-2-carboxamide (Compound 833) | $^1$H NMR (501 MHz, DMSO-$d_6$_$D_2$O) δ ppm 8.89 (dd, J = 2.1, 1.1 Hz, 1H), 8.54 (d, J = 2.1 Hz, 1H), 7.50 (t, J = 8.9 Hz, 1H), 7.07 (dd, J = 11.3, 2.9 Hz, 1H), 7.02 (d, J = 0.9 Hz, 1H), 6.88 (ddd, J = 9.0, 2.9, 1.2 Hz, 1H), 4.49 (s, 2H), 2.37 (s, 6H), 2.37 (d, J = 1.2 Hz, 3H) | MS (APCI$^+$) m/z 444 (M + H)$^+$ |
| Example 735 | N-{3-[2-(4-chloro-3-fluorophenoxy)acetamido]bicyclo[1.1.1]pentan-1-yl}-1,3-benzoxazole-6-carboxamide (Compound 834) | $^1$H NMR (501 MHz, DMSO-$d_6$_$D_2$O) δ ppm 8.33 (s, 1H), 8.14 (d, J = 8.4 Hz, 1H), 7.50 (t, J = 8.9 Hz, 1H), 7.35 (d, J = 2.0 Hz, 1H), 7.33-7.26 (m, 1H), 7.07 (ddd, J = 11.3, 2.9, 1.0 Hz, 1H), 6.88 (ddd, J = 9.0, 2.9, 1.2 Hz, 1H), 4.49 (s, 2H), 2.34 (s, 6H) | MS (APCI$^+$) m/z 430 (M + H)$^+$ |
| Example 736 | N-{3-[2-(4-chloro-3-fluorophenoxy)acetamido]bicyclo[1.1.1]pentan-1-yl}-3-(1-methyl-1H-pyrazol-4-yl)-1,2-oxazole-5-carboxamide (Compound 835) | $^1$H NMR (501 MHz, DMSO-$d_6$_$D_2$O) δ ppm 8.27 (s, 1H), 7.93 (d, J = 0.8 Hz, 1H), 7.50 (t, J = 8.9 Hz, 1H), 7.29 (s, 1H), 7.07 (dd, J = 11.3, 2.9 Hz, 1H), 6.88 (ddd, J = 8.9, 2.9, 1.1 Hz, 1H), 4.49 (s, 2H), 3.91 (s, 3H), 2.36 (s, 6H) | MS (APCI$^+$) m/z 460 (M + H)$^+$ |
| Example 737 | N-{3-[2-(4-chloro-3-fluorophenoxy)acetamido]bicyclo[1.1.1]pentan-1-yl}-1-ethyl-5-methyl-1H-pyrazole-3-carboxamide (Compound 836) | $^1$H NMR (400 MHz, DMSO-$d_6$_$D_2$O) δ ppm 8.80 (s, 1H), 8.53 (s, 1H), 7.49 (t, J = 8.9 Hz, 1H), 7.06 (dd, J = 11.3, 2.8 Hz, 1H), 6.87 (ddd, J = 9.0, 2.8, 1.2 Hz, 1H), 6.40 (d, J = 0.9 Hz, 1H), 4.48 (s, 2H), 4.08 (q, J = 7.2 Hz, 2H), 2.31 (s, 6H), 2.27 (d, J = 0.8 Hz, 3H), 1.31 (t, J = 7.2 Hz, 3H) | MS (APCI$^+$) m/z 421 (M + H)$^+$ |
| Example 738 | N-{3-[2-(4-chloro-3-fluorophenoxy)acetamido]bicyclo[1.1.1]pentan-1-yl}-2-methyl-4-(trifluoromethyl)-1,3-thiazole-5-carboxamide (Compound 837) | $^1$H NMR (400 MHz, DMSO-$d_6$_$D_2$O) δ ppm 7.49 (t, J = 8.9 Hz, 1H), 7.07 (dd, J = 11.3, 2.8 Hz, 1H), 6.87 (ddd, J = 9.0, 2.9, 1.2 Hz, 1H), 4.48 (s, 2H), 2.71 (s, 3H), 2.32 (s, 6H) | MS (APCI$^+$) m/z 478 (M + H)$^+$ |
| Example 739 | N-{3-[2-(4-chloro-3-fluorophenoxy)acetamido]bicyclo[1.1.1]pentan-1-yl}-2-(methylsulfanyl)pyrimidine-4-carboxamide (Compound 838) | $^1$H NMR (501 MHz, DMSO-$d_6$_$D_2$O) δ ppm 8.85 (d, J = 4.9 Hz, 1H), 7.62 (d, J = 5.0 Hz, 1H), 7.50 (t, J = 8.9 Hz, 1H), 7.07 (dd, J = 11.3, 2.9 Hz, 1H), 6.88 (ddd, J = 9.0, 2.9, 1.2 Hz, 1H), 4.49 (s, 2H), 2.61 (s, 3H), 2.39 (s, 6H) | MS (APCI$^+$) m/z 437 (M + H)$^+$ |
| Example 740 | N-{3-[2-(4-chloro-3-fluorophenoxy)acetamido]bicyclo[1.1.1]pentan-1-yl}-2-(1H-pyrazol-1-yl)benzamide (Compound 839) | $^1$H NMR (501 MHz, DMSO-$d_6$_$D_2$O) δ ppm 7.94 (dd, J = 2.4, 0.6 Hz, 1H), 7.68 (d, J = 1.9, 0.6 Hz, 1H), 7.61-7.55 (m, 2H), 7.52-7.43 (m, 3H), 7.06 (dd, J = 11.3, 2.8 Hz, 1H), 6.86 (ddd, J = 9.0, 2.9, 1.2 Hz, 1H), 6.49 (dd, J = 2.5, 1.8 Hz, 1H), 4.47 (s, 2H), 2.22 (s, 6H) | MS (APCI$^+$) m/z 455 (M + H)$^+$ |

-continued

| Example | Name (Compound Number) | NMR | MS |
|---|---|---|---|
| Example 741 | N-{3-[2-(4-chloro-3-fluorophenoxy)acetamido]bicyclo[1.1.1]pentan-1-yl}-5-(1,5-dimethyl-1H-pyrazol-4-yl)-1,2-oxazole-3-carboxamide (Compound 840) | $^1$H NMR (501 MHz, DMSO-$d_6$_$D_2O$) δ ppm 7.87 (s, 1H), 7.50 (t, J = 8.9 Hz, 1H), 7.07 (dd, J = 11.3, 2.8 Hz, 1H), 6.88 (ddd, J = 9.0, 2.9, 1.2 Hz, 1H), 6.82 (s, 1H), 4.49 (s, 2H), 3.81 (s, 3H), 2.49 (s, 3H), 2.37 (s, 6H) | MS (APCI$^+$) m/z 474 (M + H)$^+$ |
| Example 742 | N-{3-[2-(4-chloro-3-fluorophenoxy)acetamido]bicyclo[1.1.1]pentan-1-yl}-4-methyl-4H-thieno[3,2-b]pyrrole-5-carboxamide (Compound 841) | $^1$H NMR (400 MHz, DMSO-$d_6$_$D_2O$) δ ppm 7.50 (t, J = 8.9 Hz, 1H), 7.45 (d, J = 5.3 Hz, 1H), 7.18 (dd, J = 5.4, 0.7 Hz, 1H), 7.10-7.04 (m, 2H), 6.88 (ddd, J = 8.9, 3.0, 1.2 Hz, 1H), 4.49 (s, 2H), 3.96 (s, 3H), 2.34 (s, 6H) | |
| Example 743 | N-{3-[2-(4-chloro-3-fluorophenoxy)acetamido]bicyclo[1.1.1]pentan-1-yl}-1-cyclopropyl-2,5-dimethyl-1H-pyrrole-3-carboxamide (Compound 842) | $^1$H NMR (400 MHz, DMSO-$d_6$_$D_2O$) δ ppm 7.49 (t, J = 8.9 Hz, 1H), 7.06 (dd, J = 11.3, 2.9 Hz, 1H), 6.87 (ddd, J = 9.0, 2.9, 1.2 Hz, 1H), 6.11 (d, J = 1.1 Hz, 1H), 4.47 (s, 2H), 3.01-2.87 (m, 1H), 2.47 (s, 3H), 2.26 (s, 6H), 2.19 (d, J = 0.9 Hz, 3H), 1.12-0.98 (m, 2H), 0.84-0.74 (m, 2H) | MS (APCI$^+$) m/z 446 (M + H)$^+$ |
| Example 744 | N-{3-[2-(4-chloro-3-fluorophenoxy)acetamido]bicyclo[1.1.1]pentan-1-yl}-3-methylquinoxaline-5-carboxamide (Compound 843) | $^1$H NMR (400 MHz, DMSO-$d_6$_$D_2O$) δ ppm 8.68 (s, 1H), 8.02 (s, 1H), 7.80 (d, J = 8.3 Hz, 2H), 7.49 (t, J = 8.9 Hz, 1H), 7.34 (d, J = 8.4 Hz, 2H), 7.07 (dd, J = 11.3, 2.9 Hz, 1H), 6.87 (ddd, J = 9.0, 2.9, 1.2 Hz, 1H), 5.48 (s, 2H), 4.49 (s, 2H), 2.34 (s, 6H) | MS (APCI$^+$) m/z 470 (M + H)$^+$ |
| Example 745 | N-{3-[2-(4-chloro-3-fluorophenoxy)acetamido]bicyclo[1.1.1]pentan-1-yl}-5,6,7,8-tetrahydro[1,2,4]triazolo[4,3-a]pyridine-3-carboxamide (Compound 844) | $^1$H NMR (501 MHz, DMSO-$d_6$_$D_2O$) δ ppm 7.49 (t, J = 8.9 Hz, 1H), 7.07 (dd, J = 11.3, 2.9 Hz, 1H), 6.87 (ddd, J = 9.0, 2.9, 1.2 Hz, 1H), 4.48 (s, 2H), 4.24 (t, J = 6.0 Hz, 2H), 2.90 (t, J = 6.3 Hz, 2H), 2.35 (s, 6H), 1.91 (dd, J = 10.7, 6.0 Hz, 2H), 1.87-1.79 (m, 2H) | MS (APCI$^+$) m/z 434 (M + H)$^+$ |
| Example 746 | N-{3-[2-(4-chloro-3-fluorophenoxy)acetamido]bicyclo[1.1.1]pentan-1-yl}-4-methyl-1,2,3-thiadiazole-5-carboxamide (Compound 845) | $^1$H NMR (501 MHz, DMSO-$d_6$_$D_2O$) δ ppm 8.87 (s, 1H), 7.49 (t, J = 8.9 Hz, 1H), 7.07 (dd, J = 11.3, 2.8 Hz, 1H), 6.95-6.80 (m, 1H), 4.49 (s, 2H), 2.77 (s, 3H), 2.36 (s, 6H) | MS (APCI$^+$) m/z 411 (M + H)$^+$ |
| Example 747 | N-{3-[2-(4-chloro-3-fluorophenoxy)acetamido]bicyclo[1.1.1]pentan-1-yl}-1,3-dimethyl-1H-pyrazole-4-carboxamide (Compound 846) | $^1$H NMR (501 MHz, DMSO-$d_6$_$D_2O$) δ ppm 8.81 (s, 1H), 8.45 (s, 1H), 7.99 (s, 1H), 7.49 (t, J = 8.9 Hz, 1H), 7.07 (dd, J = 11.3, 2.8 Hz, 1H), 6.87 (ddd, J = 9.0, 2.9, 1.2 Hz, 1H), 4.48 (s, 2H), 3.75 (s, 3H), 2.29 (s, 6H), 2.29 (s, 3H) | MS (APCI$^+$) m/z 407 (M + H)$^+$ |
| Example 748 | N-{3-[2-(4-chloro-3-fluorophenoxy)acetamido]bicyclo[1.1.1]pentan-1-yl}-2,4-dimethyl-1,3-oxazole-5-carboxamide (Compound 847) | $^1$H NMR (400 MHz, DMSO-$d_6$_$D_2O$) δ ppm 8.93 (s, 1H), 8.82 (s, 1H), 7.49 (t, J = 8.9 Hz, 1H), 7.06 (dd, J = 11.3, 2.8 Hz, 1H), 6.87 (ddd, J = 9.0, 2.9, 1.2 Hz, 1H), 4.48 (s, 2H), 2.41 (s, 3H), 2.32 (s, 6H), 2.29 (s, 3H) | MS (APCI$^+$) m/z 408 (M + H)$^+$ |
| Example 749 | N-{3-[2-(4-chloro-3-fluorophenoxy)acetamido]bicyclo[1.1.1]pentan-1-yl}-1,5-dimethyl-1H-pyrazole-3-carboxamide (Compound 848) | $^1$H NMR (400 MHz, DMSO-$d_6$_$D_2O$) δ ppm 7.49 (t, J = 8.9 Hz, 1H), 7.07 (dd, J = 11.3, 2.8 Hz, 1H), 6.87 (ddd, J = 9.0, 2.9, 1.2 Hz, 1H), 6.59 (d, J = 0.6 Hz, 1H), 4.49 (s, 2H), 3.94 (s, 3H), 2.33 (s, 6H), 2.15 (s, 3H) | MS (APCI$^+$) m/z 407 (M + H)$^+$ |
| Example 750 | N-{3-[2-(4-chloro-3-fluorophenoxy)acetamido]bi- | $^1$H NMR (400 MHz, DMSO-$d_6$_$D_2O$) δ ppm 8.68 (s, 1H), | MS (APCI$^+$) |

| Example | Name (Compound Number) | NMR | MS |
|---|---|---|---|
| | cyclo[1.1.1]pentan-1-yl}-4-[(1H-1,2,4-triazol-1-yl)methyl]benzamide (Compound 849) | 8.02 (s, 1H), 7.80 (d, J = 8.3 Hz, 2H), 7.49 (t, J = 8.9 Hz, 1H), 7.34 (d, J = 8.4 Hz, 2H), 7.07 (dd, J = 11.3, 2.9 Hz, 1H), 6.87 (ddd, J = 9.0, 2.9, 1.2 Hz, 1H), 5.48 (s, 2H), 4.49 (s, 2H), 2.34 (s, 6H) | m/z 470 (M + H)$^+$ |
| Example 751 | N-{3-[2-(4-chloro-3-fluorophenoxy)acetamido]bicyclo[1.1.1]pentan-1-yl}-1-ethyl-1H-pyrazole-3-carboxamide (Compound 850) | $^1$H NMR (400 MHz, DMSO-d$_6$_D$_2$O) δ ppm 7.78 (d, J = 2.3 Hz, 1H), 7.49 (t, J = 8.9 Hz, 1H), 7.07 (dd, J = 11.3, 2.8 Hz, 1H), 6.87 (ddd, J = 9.0, 2.9, 1.2 Hz, 1H), 6.62 (d, J = 2.3 Hz, 1H), 4.48 (s, 2H), 4.17 (q, J = 7.3 Hz, 2H), 2.32 (s, 6H), 1.39 (t, J = 7.3 Hz, 3H) | MS (APCI$^+$) m/z 407 (M + H)$^+$ |
| Example 752 | N-{3-[2-(4-chloro-3-fluorophenoxy)acetamido]bicyclo[1.1.1]pentan-1-yl}-3-[(methanesulfonyl)amino]benzamide (Compound 851) | $^1$H NMR (501 MHz, DMSO-d$_6$_D$_2$O) δ ppm 7.63 (t, J = 2.0 Hz, 1H), 7.58-7.54 (m, 1H), 7.50 (t, J = 8.9 Hz, 1H), 7.44 (t, J = 7.9 Hz, 1H), 7.36 (ddd, J = 8.0, 2.3, 1.1 Hz, 1H), 7.07 (dd, J = 11.3, 2.8 Hz, 1H), 6.88 (ddd, J = 9.0, 2.9, 1.2 Hz, 1H), 4.49 (s, 2H), 3.00 (s, 3H), 2.35 (s, 6H) | MS (APCI$^+$) m/z 482 (M + H)$^+$ |
| Example 753 | N-{3-[2-(4-chloro-3-fluorophenoxy)acetamido]bicyclo[1.1.1]pentan-1-yl}-1,3-oxazole-4-carboxamide (Compound 852) | $^1$H NMR (501 MHz, DMSO-d$_6$_D$_2$O) δ ppm 8.55 (d, J = 1.0 Hz, 1H), 8.44 (d, J = 1.0 Hz, 1H), 7.49 (t, J = 8.9 Hz, 1H), 7.07 (dd, J = 11.3, 2.9 Hz, 1H), 6.87 (ddd, J = 9.0, 2.9, 1.2 Hz, 1H), 4.48 (s, 2H), 2.33 (s, 6H) | MS (APCI$^+$) m/z 380 (M + H)$^+$ |
| Example 754 | N-2-{3-[2-(4-chloro-3-fluorophenoxy)acetamido]bicyclo[1.1.1]pentan-1-yl}pyrazine-2,3-dicarboxamide (Compound 853) | $^1$H NMR (501 MHz, DMSO-d$_6$_D$_2$O) δ ppm 8.76-8.73 (m, 2H), 7.50 (t, J = 8.9 Hz, 1H), 7.07 (dd, J = 11.3, 2.9 Hz, 1H), 6.88 (ddd, J = 9.0, 2.9, 1.2 Hz, 1H), 4.49 (s, 2H), 2.35 (s, 6H) | MS (APCI$^+$) m/z 434 (M + H)$^+$ |
| Example 755 | N-{3-[2-(4-chloro-3-fluorophenoxy)acetamido]bicyclo[1.1.1]pentan-1-yl}-4,5,6,7-tetrahydro-2,1-benzoxazole-3-carboxamide (Compound 854) | $^1$H NMR (400 MHz, DMSO-d$_6$_D$_2$O) δ ppm 9.37 (s, 1H), 8.84 (s, 1H), 7.49 (t, J = 8.9 Hz, 1H), 7.07 (dd, J = 11.3, 2.9 Hz, 1H), 6.87 (ddd, J = 9.0, 2.9, 1.2 Hz, 1H), 4.48 (s, 2H), 2.81-2.64 (m, 3H), 2.33 (s, 6H), 1.81-1.58 (m, 4H) | MS (APCI$^+$) m/z 434 (M + H)$^+$ |
| Example 756 | N-{3-[2-(4-chloro-3-fluorophenoxy)acetamido]bicyclo[1.1.1]pentan-1-yl}-5-(propan-2-yl)-1,2-oxazole-4-carboxamide (Compound 855) | $^1$H NMR (400 MHz, DMSO-d$_6$_D$_2$O) δ ppm 8.93 (s, 1H), 8.84 (s, 1H), 8.80 (d, J = 0.6 Hz, 1H), 7.49 (t, J = 8.9 Hz, 1H), 7.07 (dd, J = 11.3, 2.9 Hz, 1H), 6.87 (ddd, J = 9.0, 2.9, 1.2 Hz, 1H), 4.49 (s, 2H), 3.88-3.76 (m, 1H), 2.33 (s, 6H), 1.25 (d, J = 7.0 Hz, 6H) | MS (APCI$^+$) m/z 422 (M + H)$^+$ |
| Example 757 | N-{3-[2-(4-chloro-3-fluorophenoxy)acetamido]bicyclo[1.1.1]pentan-1-yl}-5,6-dimethylpyridine-3-carboxamide (Compound 856) | $^1$H NMR (501 MHz, , DMSO-d$_6$_D$_2$O) δ ppm 8.85 (d, J = 2.0 Hz, 1H), 8.49 (dd, J = 2.1, 0.9 Hz, 1H), 7.50 (t, J = 8.9 Hz, 1H), 7.07 (dd, J = 11.3, 2.8 Hz, 1H), 6.88 (ddd, J = 9.0, 2.9, 1.2 Hz, 1H), 4.50 (s, 2H), 2.65 (s, 3H), 2.43 (s, 3H), 2.38 (s, 6H) | MS (APCI$^+$) m/z 418 (M + H)$^+$ |
| Example 758 | N-{3-[2-(4-chloro-3-fluorophenoxy)acetamido]bicyclo[1.1.1]pentan-1-yl}-4-methoxythiophene-2-carboxamide (Compound 857) | $^1$H NMR (501 MHz, DMSO-d$_6$_D$_2$O) δ ppm 9.08 (s, 1H), 8.84 (s, 1H), 7.49 (t, J = 8.9 Hz, 1H), 7.44-7.38 (m, 1H), 7.07 (dd, J = 11.3, 2.8 Hz, 1H), 6.87 (ddd, J = 9.0, 2.9, 1.2 Hz, 1H), 6.83 (d, J = 1.7 Hz, 1H), 4.48 (s, 2H), 3.75 (s, 3H), 2.33 (s, 6H) | MS (APCI$^+$) m/z 425 (M + H)$^+$ |
| Example 759 | N-{3-[2-(4-chloro-3-fluorophenoxy)acetamido]bi- | $^1$H NMR (400 MHz, DMSO-d$_6$_D$_2$O) δ ppm 8.16-8.06 (m, | MS (APCI$^+$) |

| Example | Name (Compound Number) | NMR | MS |
|---|---|---|---|
| | cyclo[1.1.1]pentan-1-yl}-2-(methanesulfinyl)benzamide (Compound 858) | 1H), 7.89-7.80 (m, 2H), 7.70-7.60 (m, 1H), 7.50 (t, J = 8.9 Hz, 1H), 7.07 (dd, J = 11.3, 2.8 Hz, 1H), 6.88 (ddd, J = 9.0, 2.9, 1.2 Hz, 1H), 4.49 (s, 2H), 2.79 (s, 3H), 2.36 (s, 6H) | m/z 451 (M + H)+ |
| Example 760 | N-{3-[2-(4-chloro-3-fluorophenoxy)acetamido]bicyclo[1.1.1]pentan-1-yl}-5-ethyl-1,3-oxazole-4-carboxamide (Compound 859) | 1H NMR (501 MHz, DMSO-$d_6$_$D_2O$) δ ppm 8.26 (s, 1H), 7.49 (t, J = 8.9 Hz, 1H), 7.07 (dd, J = 11.3, 2.9 Hz, 1H), 6.87 (ddd, J = 8.9, 2.8, 1.2 Hz, 1H), 4.48 (s, 2H), 3.01 (q, J = 7.6 Hz, 2H), 2.33 (s, 6H), 1.18 (t, J = 7.6 Hz, 3H) | MS (APCI+) m/z 408 (M + H)+ |
| Example 761 | N-{3-[2-(4-chloro-3-fluorophenoxy)acetamido]bicyclo[1.1.1]pentan-1-yl}-3-cyanothiophene-2-carboxamide (Compound 860) | 1H NMR (501 MHz, DMSO-$d_6$_$D_2O$) δ ppm 7.91 (d, J = 5.1 Hz, 1H), 7.54 (d, J = 5.1 Hz, 1H), 7.50 (t, J = 8.9 Hz, 1H), 7.07 (dd, J = 11.3, 2.8 Hz, 1H), 6.88 (ddd, J = 9.0, 2.9, 1.2 Hz, 1H), 4.49 (s, 2H), 2.36 (s, 6H) | MS (APCI+) m/z 420 (M + H)+ |
| Example 762 | N-{3-[2-(4-chloro-3-fluorophenoxy)acetamido]bicyclo[1.1.1]pentan-1-yl}-2-ethoxypyridine-3-carboxamide (Compound 861) | 1H NMR (501 MHz, DMSO-$d_6$_$D_2O$) δ ppm 8.27 (dd, J = 4.9, 2.0 Hz, 1H), 8.07 (dd, J = 7.5, 2.0 Hz, 1H), 7.50 (t, J = 8.8 Hz, 1H), 7.11 (dd, J = 7.5, 4.9 Hz, 1H), 7.07 (dd, J = 11.3, 2.8 Hz, 1H), 6.88 (ddd, J = 9.0, 2.9, 1.2 Hz, 1H), 4.49 (s, 2H), 4.43 (q, J = 7.0 Hz, 2H), 2.36 (s, 6H), 1.37 (t, J = 7.0 Hz, 3H) | MS (APCI+) m/z 434 (M + H)+ |
| Example 763 | N-{3-[2-(4-chloro-3-fluorophenoxy)acetamido]bicyclo[1.1.1]pentan-1-yl}-2-(1H-1,2,4-triazol-1-yl)benzamide (Compound 862) | 1H NMR (400 MHz, DMSO-$d_6$_$D_2O$) δ ppm 8.87 (s, 1H), 8.80 (s, 1H), 8.72 (s, 1H), 8.16 (s, 1H), 7.73-7.53 (m, 4H), 7.49 (t, J = 8.9 Hz, 1H), 7.06 (dd, J = 11.3, 2.9 Hz, 1H), 6.86 (ddd, J = 9.0, 2.9, 1.2 Hz, 1H), 4.47 (s, 2H), 2.21 (s, 6H) | MS (APCI+) m/z 456 (M + H)+ |
| Example 764 | N-{3-[2-(4-chloro-3-fluorophenoxy)acetamido]bicyclo[1.1.1]pentan-1-yl}-5-fluoro-2-methoxypyridine-3-carboxamide (Compound 863) | 1H NMR (400 MHz, DMSO-$d_6$_$D_2O$) δ ppm 8.29 (d, J = 3.1 Hz, 1H), 7.93 (dd, J = 8.3, 3.1 Hz, 1H), 7.50 (t, J = 8.9 Hz, 1H), 7.07 (dd, J = 11.3, 2.8 Hz, 1H), 6.88 (ddd, J = 9.0, 2.9, 1.2 Hz, 1H), 4.49 (s, 2H), 3.95 (s, 3H), 2.36 (s, 6H) | MS (APCI+) m/z 438 (M + H)+ |
| Example 765 | N-{3-[2-(4-chloro-3-fluorophenoxy)acetamido]bicyclo[1.1.1]pentan-1-yl}pyrido[2,3-b]pyrazine-2-carboxamide (Compound 864) | 1H NMR (501 MHz, DMSO-$d_6$_$D_2O$) δ ppm 8.42 (s, 1H), 8.04 (dd, J = 6.7, 0.9 Hz, 1H), 7.50 (t, J = 8.9 Hz, 1H), 7.14-7.04 (m, 2H), 6.88 (ddd, J = 9.0, 2.9, 1.2 Hz, 1H), 6.73 (dd, J = 7.7, 0.9 Hz, 1H), 4.50 (s, 2H), 2.40 (s, 6H) | |
| Example 766 | N-{3-[2-(4-chloro-3-fluorophenoxy)acetamido]bicyclo[1.1.1]pentan-1-yl}-5-(1,3-dimethyl-1H-pyrazol-4-yl)-1,2-oxazole-3-carboxamide (Compound 865) | 1H NMR (501 MHz, DMSO-$d_6$_$D_2O$) δ ppm 8.23 (s, 1H), 7.50 (t, J = 8.9 Hz, 1H), 7.07 (dd, J = 11.3, 2.8 Hz, 1H), 6.87 (ddd, J = 9.0, 2.9, 1.1 Hz, 1H), 6.75 (s, 1H), 4.49 (s, 2H), 3.83 (s, 3H), 3.18 (s, 3H), 2.36 (d, J = 2.3 Hz, 6H) | MS (APCI+) m/z 474 (M + H)+ |
| Example 767 | N-{3-[2-(4-chloro-3-fluorophenoxy)acetamido]bicyclo[1.1.1]pentan-1-yl}-2-(methylsulfanyl)benzamide (Compound 866) | 1H NMR (501 MHz, DMSO-$d_6$_$D_2O$) δ ppm 7.50 (t, J = 8.9 Hz, 1H), 7.44 (ddd, J = 8.0, 7.3, 1.5 Hz, 1H), 7.38 (dd, J = 7.6, 1.5 Hz, 1H), 7.33 (dd, J = 8.2, 1.1 Hz, 1H), 7.18 (td, J = 7.5, 1.1 Hz, 1H), 7.07 (dd, J = 11.3, 2.8 Hz, 1H), 6.88 (ddd, J = 9.0, 2.9, 1.2 Hz, 1H), 4.49 (s, 2H), 2.39 (s, 3H), 2.33 (s, 6H) | MS (APCI+) m/z 435 (M + H)+ |
| Example 768 | N-{3-[2-(4-chloro-3-fluorophenoxy)acetamido]bi- | 1H NMR (400 MHz, DMSO-$d_6$_$D_2O$) δ ppm 7.49 (t, J = 8.9 | MS (APCI+) |

| Example | Name (Compound Number) | NMR | MS |
|---|---|---|---|
| | cyclo[1.1.1]pentan-1-yl}-1-methyl-5-sulfamoyl-1H-pyrrole-2-carboxamide (Compound 867) | Hz, 1H), 7.38 (d, J = 1.9 Hz, 1H), 7.13-7.00 (m, 2H), 6.87 (ddd, J = 8.9, 2.9, 1.2 Hz, 1H), 4.48 (s, 2H), 3.84 (s, 3H), 2.31 (s, 6H) | m/z 471 (M + H)+ |
| Example 769 | N-{3-[2-(4-chloro-3-fluorophenoxy)acetamido]bicyclo[1.1.1]pentan-1-yl}-1-methyl-3-(trifluoromethyl)-1H-pyrazole-4-carboxamide (Compound 868) | $^1$H NMR (400 MHz, DMSO-$d_6$_$D_2O$) δ ppm 8.23 (d, J = 1.1 Hz, 1H), 7.49 (t, J = 8.9 Hz, 1H), 7.07 (dd, J = 11.3, 2.9 Hz, 1H), 6.87 (ddd, J = 8.9, 2.9, 1.2 Hz, 1H), 4.48 (s, 2H), 3.91 (s, 3H), 2.31 (s, 6H) | MS (APCI+) m/z 461 (M + H)+ |
| Example 770 | N-{3-[2-(4-chloro-3-fluorophenoxy)acetamido]bicyclo[1.1.1]pentan-1-yl}-4-methyl-1,3-oxazole-5-carboxamide (Compound 869) | $^1$H NMR (400 MHz, DMSO-$d_6$_$D_2O$) δ ppm 8.32 (s, 1H), 7.49 (t, J = 8.9 Hz, 1H), 7.07 (dd, J = 11.3, 2.9 Hz, 1H), 6.87 (ddd, J = 8.9, 2.9, 1.2 Hz, 1H), 4.48 (s, 2H), 2.36 (s, 3H), 2.33 (s, 6H) | MS (APCI+) m/z 394 (M + H)+ |
| Example 771 | 2-acetamido-N-{3-[2-(4-chloro-3-fluorophenoxy)acetamido]bicyclo[1.1.1]pentan-1-yl}-1,3-thiazole-4-carboxamide (Compound 870) | $^1$H NMR (400 MHz, DMSO-$d_6$_$D_2O$) δ ppm 7.74 (s, 1H), 7.49 (t, J = 8.9 Hz, 1H), 7.07 (dd, J = 11.3, 2.9 Hz, 1H), 6.87 (ddd, J = 9.0, 2.9, 1.2 Hz, 1H), 4.49 (s, 2H), 2.35 (s, 6H), 2.18 (s, 3H) | MS (APCI+) m/z 453 (M + H)+ |
| Example 772 | 4-chloro-N-{3-[2-(4-chloro-3-fluorophenoxy)acetamido]bicyclo[1.1.1]pentan-1-yl}-1-methyl-1H-pyrazole-3-carboxamide (Compound 871) | $^1$H NMR (501 MHz, DMSO-$d_6$_$D_2O$) δ ppm 7.97 (s, 1H), 7.49 (t, J = 8.9 Hz, 1H), 7.07 (dd, J = 11.3, 2.9 Hz, 1H), 6.87 (ddd, J = 8.9, 2.9, 1.2 Hz, 1H), 4.48 (s, 2H), 3.86 (s, 3H), 2.32 (s, 6H) | MS (APCI+) m/z 427 (M + H)+ |
| Example 773 | N-{3-[2-(4-chloro-3-fluorophenoxy)acetamido]bicyclo[1.1.1]pentan-1-yl}-2-methoxy-4-methyl-1,3-thiazole-5-carboxamide (Compound 872) | $^1$H NMR (501 MHz, DMSO-$d_6$_$D_2O$) δ ppm 7.49 (t, J = 8.8 Hz, 1H), 7.06 (dd, J = 11.3, 2.9 Hz, 1H), 6.87 (ddd, J = 9.0, 2.9, 1.2 Hz, 1H), 4.48 (s, 2H), 4.02 (s, 3H), 2.42 (s, 3H), 2.31 (s, 6H) | MS (APCI+) m/z 440 (M + H)+ |
| Example 774 | N-{3-[2-(4-chloro-3-fluorophenoxy)acetamido]bicyclo[1.1.1]pentan-1-yl}-2,3-dihydrothieno[3,4-b][1,4]dioxine-5-carboxamide (Compound 873) | $^1$H NMR (501 MHz DMSO-$d_6$_$D_2O$) δ ppm 7.49 (t, J = 8.9 Hz, 1H), 7.07 (dd, J = 11.3, 2.8 Hz, 1H), 6.88 (s, 1H), 6.88-6.86 (m, 1H), 4.48 (s, 2H), 4.41-4.32 (m, 2H), 4.28-4.19 (m, 2H), 2.33 (s, 6H) | MS (APCI+) m/z 453 (M + H)+ |
| Example 775 | N-{3-[2-(4-chloro-3-fluorophenoxy)acetamido]bicyclo[1.1.1]pentan-1-yl}-1-methyl-5-(trifluoromethyl)-1H-pyrazole-4-carboxamide (Compound 874) | $^1$H NMR (501 MHz, DMSO-$d_6$_$D_2O$) δ ppm 7.85 (d, J = 0.8 Hz, 1H), 7.49 (t, J = 8.9 Hz, 1H), 7.07 (dd, J = 11.3, 2.8 Hz, 1H), 6.87 (ddd, J = 9.0, 2.9, 1.2 Hz, 1H), 4.48 (s, 2H), 4.00 (d, J = 1.6 Hz, 3H), 2.31 (s, 6H) | MS (APCI+) m/z 461 (M + H)+ |
| Example 776 | N-{3-[2-(4-chloro-3-fluorophenoxy)acetamido]bicyclo[1.1.1]pentan-1-yl}-4-methylthiophene-2-carboxamide (Compound 875) | $^1$H NMR (501 MHz, DMSO-$d_6$_$D_2O$) δ ppm 7.53 (d, J = 1.4 Hz, 1H), 7.49 (t, J = 8.9 Hz, 1H), 7.33 (t, J = 1.2 Hz, 1H), 7.07 (dd, J = 11.3, 2.8 Hz, 1H), 6.87 (ddd, J = 9.0, 2.9, 1.2 Hz, 1H), 4.48 (s, 2H), 2.32 (s, 6H), 2.21 (d, J = 1.2 Hz, 3H) | MS (APCI+) m/z 409 (M + H)+ |
| Example 777 | 2-acetamido-N-{3-[2-(4-chloro-3-fluorophenoxy)acetamido]bicyclo[1.1.1]pentan-1-yl}thiophene-3-carboxamide (Compound 876) | $^1$H NMR (400 MHz, DMSO-$d_6$_$D_2O$) δ ppm 8.92 (s, 1H), 8.85 (s, 1H), 7.50 (t, J = 8.9 Hz, 1H), 7.39 (d, J = 5.9 Hz, 1H), 7.07 (dd, J = 11.3, 2.8 Hz, 1H), 6.95 (d, J = 5.9 Hz, 1H), 6.88 (ddd, J = 9.0, 2.9, 1.2 Hz, 1H), 4.49 (s, 2H), 2.36 (s, 6H), 2.21 (s, 3H) | MS (APCI+) m/z 452 (M + H)+ |
| Example 778 | N-{3-[2-(4-chloro-3-fluorophenoxy)acetamido]bicyclo[1.1.1]pentan-1-yl}-1-methyl-1,4,5,6-tetrahydro- | $^1$H NMR (400 MHz, DMSO-$d_6$_$D_2O$) δ ppm 7.49 (t, J = 8.9 Hz, 1H), 7.06 (dd, J = 11.3, 2.9 Hz, 1H), 6.87 (ddd, J = 8.9, | MS (APCI+) m/z 433 (M + H)+ |

| Example | Name (Compound Number) | NMR | MS |
|---|---|---|---|
| | cyclopenta[c]pyrazole-3-carboxamide (Compound 877) | 2.9, 1.2 Hz, 1H), 4.48 (s, 2H), 3.73 (s, 3H), 2.66 (ddd, J = 14.1, 7.8, 6.4 Hz, 4H), 2.53-2.41 (m, 2H), 2.30 (s, 6H) | |
| Example 779 | N-{3-[2-(4-chloro-3-fluorophenoxy)acetamido]bicyclo[1.1.1]pentan-1-yl}-1,3-dimethyl-1H-thieno[2,3-c]pyrazole-5-carboxamide (Compound 878) | $^1$H NMR (400 MHz, DMSO-$d_6$_$D_2O$) δ ppm 7.71 (s, 1H), 7.50 (t, J = 8.9 Hz, 1H), 7.07 (dd, J = 11.3, 2.8 Hz, 1H), 6.88 (ddd, J = 9.0, 2.9, 1.2 Hz, 1H), 4.49 (s, 2H), 3.85 (s, 3H), 2.35 (s, 3H), 2.34 (s, 6H) | MS (APCI$^+$) m/z 463 (M + H)$^+$ |
| Example 780 | N-{3-[2-(4-chloro-3-fluorophenoxy)acetamido]bicyclo[1.1.1]pentan-1-yl}-3-methyl-1,2-oxazole-4-carboxamide (Compound 879) | $^1$H NMR (400 MHz, DMSO-$d_6$_$D_2O$) δ ppm 9.16 (t, J = 0.7 Hz, 1H), 9.00 (s, 1H), 8.84 (s, 1H), 7.49 (t, J = 8.9 Hz, 1H), 7.07 (dd, J = 11.3, 2.8 Hz, 1H), 6.87 (ddd, J = 9.0, 2.9, 1.2 Hz, 1H), 4.48 (s, 2H), 2.37 (d, J = 0.6 Hz, 3H), 2.32 (s, 6H) | MS (APCI$^+$) m/z 394 (M + H)$^+$ |
| Example 781 | N-{3-[2-(4-chloro-3-fluorophenoxy)acetamido]bicyclo[1.1.1]pentan-1-yl}-4,5,6,7-tetrahydro-1,2-benzoxazole-3-carboxamide (Compound 880) | $^1$H NMR (400 MHz, DMSO-$d_6$_$D_2O$) δ ppm 9.37 (s, 1H), 8.84 (s, 1H), 7.49 (t, J = 8.9 Hz, 1H), 7.06 (dd, J = 11.3, 2.8 Hz, 1H), 6.87 (ddd, J = 9.0, 2.9, 1.2 Hz, 1H), 4.48 (s, 2H), 2.75-2.64 (m, 4H), 2.33 (s, 6H), 1.81-1.60 (m, 4H) | MS (APCI$^+$) m/z 434 (M + H)$^+$ |
| Example 782 | N-{3-[2-(4-chloro-3-fluorophenoxy)acetamido]bicyclo[1.1.1]pentan-1-yl}-5-cyclopropyl-2-methylfuran-3-carboxamide (Compound 881) | $^1$H NMR (400 MHz, DMSO-$d_6$_$D_2O$) δ ppm 7.80-7.72 (m, 3H), 7.68 (d, J = 2.1 Hz, 1H), 7.67-7.63 (m, 1H), 7.61 (d, J = 2.1 Hz, 1H), 7.49 (t, J = 8.9 Hz, 1H), 7.09-7.03 (m, 1H), 6.86 (ddd, J = 8.8, 2.8, 1.2 Hz, 1H), 4.47 (s, 2H), 2.37 (s, 3H), 2.22 (s, 6H) | MS (APCI$^+$) m/z 469 (M + H)$^+$ |
| Example 783 | N-{3-[2-(4-chloro-3-fluorophenoxy)acetamido]bicyclo[1.1.1]pentan-1-yl}-1,5-dimethyl-1H-pyrazole-4-carboxamide (Compound 882) | $^1$H NMR (400 MHz, DMSO-$d_6$_$D_2O$) δ ppm 8.53 (s, 1H), 7.80 (s, 1H), 7.49 (t, J = 8.9 Hz, 1H), 7.07 (dd, J = 11.3, 2.8 Hz, 1H), 6.87 (ddd, J = 9.0, 2.9, 1.2 Hz, 1H), 4.48 (s, 2H), 3.74 (s, 3H), 3.71 (s, 3H), 2.30 (s, 6H) | MS (APCI$^+$) m/z 407 (M + H)$^+$ |
| Example 784 | N-{3-[2-(4-chloro-3-fluorophenoxy)acetamido]bicyclo[1.1.1]pentan-1-yl}-2-(2-methyl-1H-imidazol-1-yl)benzamide (Compound 883) | $^1$H NMR (400 MHz, DMSO-$d_6$_$D_2O$) δ ppm 7.80-7.72 (m, 3H), 7.68 (d, J = 2.1 Hz, 1H), 7.67-7.63 (m, 1H), 7.61 (d, J = 2.1 Hz, 1H), 7.49 (t, J = 8.9 Hz, 1H), 7.09-7.03 (m, 1H), 6.86 (ddd, J = 8.8, 2.8, 1.2 Hz, 1H), 4.47 (s, 3H), 2.93 (s, 2H), 2.42-2.30 (m, 3H), 2.22 (s, 5H) | MS (APCI$^+$) m/z 469 (M + H)$^+$ |
| Example 785 | 6-acetamido-N-{3-[2-(4-chloro-3-fluorophenoxy)acetamido]bicyclo[1.1.1]pentan-1-yl}pyridine-2-carboxamide (Compound 884) | $^1$H NMR (400 MHz, DMSO-$d_6$_$D_2O$) δ ppm 8.20 (d, J = 8.3 Hz, 1H), 7.97 (dd, J = 8.4, 7.5 Hz, 1H), 7.69 (dd, J = 7.5, 0.9 Hz, 1H), 7.50 (t, J = 8.9 Hz, 1H), 7.07 (dd, J = 11.3, 2.8 Hz, 1H), 6.88 (ddd, J = 8.9, 2.8, 1.2 Hz, 1H), 4.50 (s, 2H), 2.39 (s, 6H), 2.14 (s, 3H) | MS (APCI$^+$) m/z 447 (M + H)$^+$ |
| Example 786 | N-{3-[2-(4-chloro-3-fluorophenoxy)acetamido]bicyclo[1.1.1]pentan-1-yl}-5-cyanothiophene-2-carboxamide (Compound 885) | $^1$H NMR (400 MHz, DMSO-$d_6$_$D_2O$) δ ppm 7.94 (d, J = 4.0 Hz, 1H), 7.79 (d, J = 4.0 Hz, 1H), 7.49 (t, J = 8.9 Hz, 1H), 7.07 (dd, J = 11.3, 2.9 Hz, 1H), 6.87 (ddd, J = 9.0, 2.9, 1.2 Hz, 1H), 4.49 (s, 2H), 2.35 (s, 6H) | MS (APCI$^+$) m/z 461 (M + NH$_4$)$^+$ |
| Example 787 | N-{3-[2-(4-chloro-3-fluorophenoxy)acetamido]bicyclo[1.1.1]pentan-1-yl}thieno[2,3-b]pyrazine-6-carboxamide (Compound 886) | $^1$H NMR (400 MHz, DMSO-$d_6$_$D_2O$) δ ppm 8.83 (d, J = 2.4 Hz, 1H), 8.71 (d, J = 2.4 Hz, 1H), 8.23 (s, 1H), 7.50 (t, J = 8.9 Hz, 1H), 7.08 (dd, J = 11.3, 2.8 Hz, 1H), 6.88 (ddd, J = 9.0, | MS (APCI$^+$) m/z 447 (M + H)$^+$ |

-continued

| Example | Name (Compound Number) | NMR | MS |
|---|---|---|---|
| Example 788 | N-{3-[2-(4-chloro-3-fluorophenoxy)acetamido]bicyclo[1.1.1]pentan-1-yl}-2-(2-methoxyacetamido)benzamide (Compound 887) | ¹H NMR (400 MHz, DMSO-d₆_D₂O) δ ppm 11.58 (s, 1H), 9.29 (d, J = 1.9 Hz, 1H), 8.85 (s, 1H), 8.46 (dd, J = 8.3, 1.1 Hz, 1H), 7.69 (dt, J = 7.9, 1.3 Hz, 1H), 7.59-7.43 (m, 2H), 7.18 (td, J = 7.6, 1.2 Hz, 1H), 7.07 (dd, J = 11.3, 2.8 Hz, 1H), 6.88 (ddd, J = 9.0, 2.9, 1.2 Hz, 1H), 4.50 (s, 2H), 4.00 (s, 2H), 3.42 (s, 3H), 2.37 (s, 6H) [preceded by: 2.9, 1.2 Hz, 1H), 4.50 (s, 2H), 2.40 (s, 6H)] | MS (APCI⁺) m/z 476 (M + H)⁺ |
| Example 789 | N-{3-[2-(4-chloro-3-fluorophenoxy)acetamido]bicyclo[1.1.1]pentan-1-yl}-2-cyclopropylpyrimidine-5-carboxamide (Compound 888) | ¹H NMR (400 MHz, DMSO-d₆_D₂O) δ ppm 8.94 (s, 2H), 7.50 (t, J = 8.9 Hz, 1H), 7.07 (dd, J = 11.3, 2.9 Hz, 1H), 6.87 (ddd, J = 9.0, 2.9, 1.2 Hz, 1H), 4.49 (s, 2H), 2.36 (s, 6H), 2.32-2.21 (m, 1H), 1.21-1.11 (m, 2H), 1.10-1.02 (m, 2H) | MS (APCI⁺) m/z 431 (M + H)⁺ |
| Example 790 | N-{3-[2-(4-chloro-3-fluorophenoxy)acetamido]bicyclo[1.1.1]pentan-1-yl}-4,6-dimethylpyridine-2-carboxamide (Compound 889) | ¹H NMR (400 MHz, DMSO-d₆_D₂O) δ ppm 7.73-7.63 (m, 1H), 7.50 (t, J = 8.9 Hz, 1H), 7.34 (t, J = 1.0 Hz, 1H), 7.07 (dd, J = 11.3, 2.8 Hz, 1H), 6.88 (ddd, J = 9.0, 2.9, 1.2 Hz, 1H), 4.49 (s, 2H), 2.52 (s, 3H), 2.38 (s, 6H), 2.37 (s, 3H) | MS (APCI⁺) m/z 418 (M + H)⁺ |
| Example 791 | N-{3-[2-(4-chloro-3-fluorophenoxy)acetamido]bicyclo[1.1.1]pentan-1-yl}-2-[(1H-pyrazol-1-yl)methyl]benzamide (Compound 890) | ¹H NMR (400 MHz, DMSO-d₆_D₂O) δ ppm 9.14 (s, 1H), 8.84 (s, 1H), 7.73 (dd, J = 2.3, 0.7 Hz, 1H), 7.56-7.32 (m, 5H), 7.07 (dd, J = 11.3, 2.8 Hz, 1H), 7.01 (dd, J = 7.6, 1.4 Hz, 1H), 6.88 (ddd, J = 9.0, 2.9, 1.2 Hz, 1H), 6.28 (t, J = 2.1 Hz, 1H), 5.47 (s, 2H), 4.49 (s, 2H), 2.35 (s, 6H) | MS (APCI⁺) m/z 469 (M + H)⁺ |
| Example 792 | N-{3-[2-(4-chloro-3-fluorophenoxy)acetamido]bicyclo[1.1.1]pentan-1-yl}-6-methylpyridine-2-carboxamide (Compound 891) | ¹H NMR (400 MHz, DMSO-d₆_D₂O) δ ppm 8.94 (s, 2H), 7.50 (t, J = 8.9 Hz, 1H), 7.07 (dd, J = 11.3, 2.9 Hz, 1H), 6.87 (ddd, J = 9.0, 2.9, 1.2 Hz, 1H), 4.49 (s, 2H), 2.36 (s, 6H), 2.32-2.21 (m, 1H), 1.21-1.11 (m, 2H), 1.10-1.02 (m, 2H) | MS (APCI⁺) m/z 431 (M + H)⁺ |
| Example 793 | N-{3-[2-(4-chloro-3-fluorophenoxy)acetamido]bicyclo[1.1.1]pentan-1-yl}-3-[(1H-1,2,4-triazol-1-yl)methyl]benzamide (Compound 892) | ¹H NMR (400 MHz, DMSO-d₆) δ ppm 9.12 (s, 1H), 8.84 (s, 1H), 8.68 (s, 1H), 8.01 (s, 1H), 7.76 (ddd, J = 5.8, 3.3, 1.8 Hz, 1H), 7.75-7.71 (m, 1H), 7.53-7.42 (m, 3H), 7.07 (dd, J = 11.3, 2.9 Hz, 1H), 6.88 (ddd, J = 8.9, 2.9, 1.2 Hz, 1H), 5.46 (s, 2H), 4.49 (s, 2H), 2.35 (s, 6H) | MS (APCI⁺) m/z 470 (M + H)⁺ |
| Example 794 | N-{3-[2-(4-chloro-3-fluorophenoxy)acetamido]bicyclo[1.1.1]pentan-1-yl}-4-(propan-2-yl)-1,2,3-thiadiazole-5-carboxamide (Compound 893) | ¹H NMR (400 MHz, DMSO-d₆_D₂O) δ ppm 7.49 (t, J = 8.9 Hz, 1H), 7.07 (dd, J = 11.3, 2.8 Hz, 1H), 6.87 (ddd, J = 9.0, 2.9, 1.2 Hz, 1H), 4.49 (s, 2H), 3.68-3.58 (m, 1H), 2.36 (s, 6H), 1.38 (d, J = 6.9 Hz, 6H) | MS (APCI⁺) m/z 439 (M + H)⁺ |
| Example 795 | N-{3-[2-(4-chloro-3-fluorophenoxy)acetamido]bicyclo[1.1.1]pentan-1-yl}-6-(morpholin-4-yl)pyrazine-2-carboxamide (Compound 894) | ¹H NMR (501 MHz, DMSO-d₆_D₂O) δ ppm 8.44 (s, 1H), 8.35 (s, 1H), 7.50 (t, J = 8.9 Hz, 1H), 7.07 (dd, J = 11.3, 2.9 Hz, 1H), 6.88 (ddd, J = 9.0, 2.9, 1.2 Hz, 1H), 4.49 (s, 2H), 3.75-3.71 (m, 4H), 3.69-3.62 (m, 4H), 2.39 (s, 6H) | MS (APCI⁺) m/z 476 (M + H)⁺ |

| Example | Name (Compound Number) | NMR | MS |
|---|---|---|---|
| Example 796 | N-{3-[2-(4-chloro-3-fluorophenoxy)acetamido]bicyclo[1.1.1]pentan-1-yl}-1,2,5-thiadiazole-3-carboxamide (Compound 895) | $^1$H NMR (501 MHz, DMSO-$d_6$_$D_2O$) δ ppm 9.13 (s, 1H), 7.50 (t, J = 8.9 Hz, 1H), 7.07 (dd, J = 11.3, 2.9 Hz, 1H), 6.88 (ddd, J = 9.0, 2.9, 1.2 Hz, 1H), 4.49 (s, 2H), 2.38 (s, 6H) | MS (APCI$^+$) m/z 397 (M + H)$^+$ |
| Example 797 | N-{3-[2-(4-chloro-3-fluorophenoxy)acetamido]bicyclo[1.1.1]pentan-1-yl}-2-methyl-2H-indazole-3-carboxamide (Compound 896) | $^1$H NMR (501 MHz, DMSO-$d_6$_$D_2O$) δ ppm 8.15 (d, J = 8.1 Hz, 1H), 7.80-7.63 (m, 1H), 7.59-7.42 (m, 2H), 7.30 (ddd, J = 7.9, 6.9, 0.8 Hz, 1H), 7.08 (dd, J = 11.3, 2.8 Hz, 1H), 6.88 (ddd, J = 8.9, 2.9, 1.2 Hz, 1H), 4.50 (s, 2H), 4.11 (s, 3H), 2.38 (s, 6H) | MS (APCI$^+$) m/z 443 (M + H)$^+$ |
| Example 798 | N-{3-[2-(4-chloro-3-fluorophenoxy)acetamido]bicyclo[1.1.1]pentan-1-yl}-4-cyano-5-(methylsulfanyl)thiophene-2-carboxamide (Compound 897) | $^1$H NMR (400 MHz, DMSO-$d_6$_$D_2O$) δ ppm 7.88 (s, 1H), 7.49 (t, J = 8.9 Hz, 1H), 7.07 (dd, J = 11.3, 2.8 Hz, 1H), 6.87 (ddd, J = 9.0, 2.9, 1.2 Hz, 1H), 4.48 (s, 2H), 2.74 (s, 3H), 2.33 (s, 6H) | MS (APCI$^+$) m/z 466 (M + H)$^+$ |
| Example 799 | N-{3-[2-(4-chloro-3-fluorophenoxy)acetamido]bicyclo[1.1.1]pentan-1-yl}-6-(ethylsulfanyl)pyrazine-2-carboxamide (Compound 898) | $^1$H NMR (400 MHz, DMSO-$d_6$_$D_2O$) δ ppm 8.77 (s, 1H), 8.72 (s, 1H), 7.50 (t, J = 8.8 Hz, 1H), 7.07 (dd, J = 11.3, 2.9 Hz, 1H), 6.88 (ddd, J = 8.9, 2.8, 1.2 Hz, 1H), 4.50 (s, 2H), 3.33 (q, J = 7.3 Hz, 2H), 2.40 (s, 6H), 1.31 (t, J = 7.3 Hz, 3H) | MS (APCI$^+$) m/z 451 (M + H)$^+$ |
| Example 800 | 3-chloro-N-{3-[2-(4-chloro-3-fluorophenoxy)acetamido]bicyclo[1.1.1]pentan-1-yl}pyridine-2-carboxamide (Compound 899) | $^1$H NMR (400 MHz, DMSO-$d_6$_$D_2O$) δ ppm 8.53 (dd, J = 4.6, 1.3 Hz, 1H), 8.01 (dd, J = 8.2, 1.4 Hz, 1H), 7.54 (dd, J = 8.2, 4.6 Hz, 1H), 7.50 (t, J = 8.9 Hz, 1H), 7.07 (dd, J = 11.3, 2.9 Hz, 1H), 6.88 (ddd, J = 8.9, 2.9, 1.2 Hz, 1H), 4.49 (s, 2H), 2.36 (s, 6H) | MS (APCI$^+$) m/z 424 (M + H)$^+$ |
| Example 801 | N-{3-[2-(4-chloro-3-fluorophenoxy)acetamido]bicyclo[1.1.1]pentan-1-yl}-5-cyclopropyl-1,2-oxazole-4-carboxamide (Compound 900) | $^1$H NMR (400 MHz DMSO-$d_6$_$D_2O$) δ ppm 8.77 (s, 1H), 7.49 (t, J = 8.9 Hz, 1H), 7.07 (dd, J = 11.3, 2.8 Hz, 1H), 6.87 (ddd, J = 9.0, 2.9, 1.2 Hz, 1H), 4.49 (s, 2H), 3.00-2.81 (m, 1H), 2.34 (s, 6H), 1.25-1.15 (m, 2H), 1.13-1.06 (m, 2H) | MS (APCI$^+$) m/z 420 (M + H)$^+$ |
| Example 802 | N-{3-[2-(4-chloro-3-fluorophenoxy)acetamido]bicyclo[1.1.1]pentan-1-yl}-4,5-dimethyl-1,2-oxazole-3-carboxamide (Compound 901) | $^1$H NMR (501 MHz, DMSO-$d_6$_$D_2O$) δ ppm 9.22 (s, 1H), 8.84 (s, 1H), 7.49 (t, J = 8.9 Hz, 1H), 7.07 (dd, J = 11.3, 2.8 Hz, 1H), 6.87 (ddd, J = 9.0, 2.9, 1.2 Hz, 1H), 4.48 (s, 2H), 2.35 (s, 3H), 2.33 (s, 6H), 2.02 (s, 3H) | MS (APCI$^+$) m/z 408 (M + H)$^+$ |
| Example 803 | N-{3-[2-(4-chloro-3-fluorophenoxy)acetamido]bicyclo[1.1.1]pentan-1-yl}-3-(4H-1,2,4-triazol-4-yl)benzamide (Compound 902) | $^1$H NMR (501 MHz, DMSO-$d_6$_$D_2O$) δ ppm 9.15 (s, 2H), 8.08 (t, J = 2.0 Hz, 1H), 7.87 (dddd, J = 14.7, 8.0, 2.0, 1.0 Hz, 2H), 7.68 (t, J = 7.9 Hz, 1H), 7.50 (t, J = 8.9 Hz, 1H), 7.08 (dd, J = 11.3, 2.9 Hz, 1H), 6.88 (ddd, J = 8.9, 2.9, 1.2 Hz, 1H), 4.50 (s, 2H), 2.38 (s, 6H) | MS (APCI$^+$) m/z 456 (M + H)$^+$ |
| Example 804 | N-{3-[2-(4-chloro-3-fluorophenoxy)acetamido]bicyclo[1.1.1]pentan-1-yl}-4,5,6,7-tetrahydropyrazolo[1,5-a]pyridine-3-carboxamide (Compound 903) | $^1$H NMR (400 MHz, DMSO-$d_6$_$D_2O$) δ ppm 8.80 (s, 1H), 8.50 (s, 1H), 7.85 (s, 1H), 7.49 (t, J = 8.9 Hz, 1H), 7.07 (dd, J = 11.3, 2.8 Hz, 1H), 6.87 (ddd, J = 9.0, 2.9, 1.2 Hz, 1H), 4.48 (s, 2H), 4.04 (t, J = 6.0 Hz, 2H), 2.94 (t, J = 6.4 Hz, 2H), 2.30 (s, 6H), 2.03-1.86 (m, 2H), 1.85-1.67 (m, 2H) | MS (APCI$^+$) m/z 433 (M + H)$^+$ |

| Example | Name (Compound Number) | NMR | MS |
|---|---|---|---|
| Example 805 | N-{3-[2-(4-chloro-3-fluorophenoxy)acetamido]bicyclo[1.1.1]pentan-1-yl}-1-methyl-1H-imidazole-2-carboxamide (Compound 904) | $^1$H NMR (400 MHz, DMSO-$d_6$_D$_2$O) δ ppm 7.49 (t, J = 8.9 Hz, 1H), 7.43 (d, J = 1.2 Hz, 1H), 7.17 (d, J = 1.2 Hz, 1H), 7.07 (dd, J = 11.3, 2.9 Hz, 1H), 6.87 (ddd, J = 9.0, 2.9, 1.2 Hz, 1H), 4.49 (s, 2H), 3.94 (s, 3H), 2.35 (s, 6H) | MS (APCI$^+$) m/z 393 (M + H)$^+$ |
| Example 806 | N-{3-[2-(4-chloro-3-fluorophenoxy)acetamido]bicyclo[1.1.1]pentan-1-yl}-5-sulfamoylfuran-2-carboxamide (Compound 905) | $^1$H NMR (400 MHz, DMSO-$d_6$_D$_2$O) δ ppm 7.49 (t, J = 8.9 Hz, 1H), 7.20 (d, J = 3.6 Hz, 1H), 7.07 (td, J = 5.3, 2.9 Hz, 2H), 6.87 (ddd, J = 9.0, 2.9, 1.2 Hz, 1H), 4.49 (s, 2H), 2.35 (s, 6H) | MS (APCI$^+$) m/z 458 (M + H)$^+$ |
| Example 807 | N-{3-[2-(4-chloro-3-fluorophenoxy)acetamido]bicyclo[1.1.1]pentan-1-yl}-2-ethyl-4-methyl-1,3-oxazole-5-carboxamide (Compound 906) | $^1$H NMR (501 MHz, DMSO-$d_6$_D$_2$O) δ ppm 7.49 (t, J = 8.9 Hz, 1H), 7.07 (dd, J = 11.3, 2.8 Hz, 1H), 6.87 (ddd, J = 9.0, 2.8, 1.1 Hz, 1H), 4.48 (s, 2H), 2.75 (q, J = 7.6 Hz, 2H), 2.32 (s, 6H), 2.30 (s, 3H), 1.25 (t, J = 7.6 Hz, 3H) | MS (APCI$^+$) m/z 422 (M + H)$^+$ |
| Example 808 | N-{3-[2-(4-chloro-3-fluorophenoxy)acetamido]bicyclo[1.1.1]pentan-1-yl}-1,3-benzothiazole-2-carboxamide (Compound 907) | $^1$H NMR (501 MHz, DMSO-$d_6$_D$_2$O) δ ppm 9.79 (s, 1H), 8.87 (s, 1H), 8.21 (dt, J = 7.9, 0.9 Hz, 1H), 8.18-8.09 (m, 1H), 7.62 (dddd, J = 27.0, 8.3, 7.2, 1.3 Hz, 2H), 7.50 (t, J = 8.9 Hz, 1H), 7.08 (dd, J = 11.3, 2.9 Hz, 1H), 6.88 (ddd, J = 8.8, 2.8, 1.1 Hz, 1H), 4.50 (s, 2H), 2.40 (s, 6H) | MS (APCI$^+$) m/z 446 (M + H)$^+$ |
| Example 809 | N-{3-[2-(4-chloro-3-fluorophenoxy)acetamido]bicyclo[1.1.1]pentan-1-yl}-5-methyl-1,2-oxazole-4-carboxamide (Compound 908) | $^1$H NMR (501 MHz, DMSO-$d_6$_D$_2$O) δ ppm 8.80 (d, J = 0.8 Hz, 1H), 7.49 (t, J = 8.9 Hz, 1H), 7.07 (dd, J = 11.3, 2.9 Hz, 1H), 6.87 (ddd, J = 9.0, 2.9, 1.2 Hz, 1H), 4.49 (s, 2H), 2.62 (d, J = 0.8 Hz, 3H), 2.33 (s, 6H) | MS (APCI$^+$) m/z 394 (M + H)$^+$ |
| Example 810 | N-{3-[2-(4-chloro-3-fluorophenoxy)acetamido]bicyclo[1.1.1]pentan-1-yl}-5-methyl-1,3-oxazole-4-carboxamide (Compound 909) | $^1$H NMR (400 MHz, DMSO-$d_6$_D$_2$O) δ ppm 8.24 (s, 1H), 7.49 (t, J = 8.9 Hz, 1H), 7.07 (dd, J = 11.3, 2.9 Hz, 1H), 6.87 (ddd, J = 9.0, 2.9, 1.2 Hz, 1H), 4.48 (s, 2H), 2.55 (s, 3H), 2.33 (s, 6H) | MS (APCI$^+$) m/z 394 (M + H)$^+$ |
| Example 811 | N-{3-[2-(4-chloro-3-fluorophenoxy)acetamido]bicyclo[1.1.1]pentan-1-yl}-3,5-difluoropyridine-2-carboxamide (Compound 910) | $^1$H NMR (400 MHz, DMSO-$d_6$_D$_2$O) δ ppm 8.52 (d, J = 2.3 Hz, 1H), 7.98 (ddd, J = 11.1, 9.0, 2.3 Hz, 1H), 7.50 (t, J = 8.9 Hz, 1H), 7.07 (dd, J = 11.3, 2.8 Hz, 1H), 6.87 (ddd, J = 9.0, 2.9, 1.2 Hz, 1H), 4.49 (s, 2H), 2.36 (s, 6H) | MS (APCI$^+$) m/z 426 (M + H)$^+$ |
| Example 812 | N-{4-[2-(4-chloro-3-fluorophenoxy)acetamido]-3-hydroxybicyclo[2.2.2]octan-1-yl}-6-(propan-2-yl)pyridine-2-carboxamide (Compound 911) | | |
| Example 813 | N-{4-[2-(4-chloro-3-fluorophenoxy)acetamido]-3-hydroxybicyclo[2.2.2]octan-1-yl}-5-[(propan-2-yl)oxy]pyridine-2-carboxamide (Compound 912) | | |

-continued

| Example | Name (Compound Number) | NMR | MS |
|---|---|---|---|
| Example 814 | N-{3-[2-(4-chloro-3-fluorophenoxy)acetamido]bicyclo[1.1.1]pentan-1-yl}-1-(difluoromethyl)-3-methyl-1H-pyrazole-5-carboxamide (Compound 913) | | |
| Example 815 | N-{4-[2-(4-chloro-3-fluorophenoxy)acetamido]-3-hydroxybicyclo[2.2.2]octan-1-yl}-6-methylpyridine-2-carboxamide (Compound 914) | | |
| Example 816 | N-{4-[2-(4-chloro-3-fluorophenoxy)acetamido]-3-hydroxybicyclo[2.2.2]octan-1-yl}-4-methylpyridine-2-carboxamide (Compound 915) | | |
| Example 817 | N-{4-[2-(4-chloro-3-fluorophenoxy)acetamido]-3-hydroxybicyclo[2.2.2]octan-1-yl}-5-cyano-6-methylpyridine-2-carboxamide (Compound 916) | | |
| Example 818 | N-{4-[2-(4-chloro-3-fluorophenoxy)acetamido]-3-hydroxybicyclo[2.2.2]octan-1-yl}-5-fluoro-6-methylpyridine-2-carboxamide (Compound 917) | | |
| Example 819 | N-{4-[2-(4-chloro-3-fluorophenoxy)acetamido]-3-hydroxybicyclo[2.2.2]octan-1-yl}-4-ethylpyridine-2-carboxamide (Compound 918) | | |
| Example 820 | N-{3-[2-(4-chloro-3-fluorophenoxy)acetamido]bicyclo[1.1.1]pentan-1-yl}-4-ethyl-1,3-thiazole-2-carboxamide (Compound 919) | | |
| Example 821 | N-{3-[2-(3,4-dichlorophenoxy)acetamido]bicyclo[1.1.1]pentan-1-yl}quinoxaline-2-carboxamide (Compound 920) | | |
| Example 822 | N-{3-[2-(3,4-dichlorophenoxy)acetamido]bicyclo[1.1.1]pentan-1-yl}-1,2-oxazole-4-carboxamide (Compound 921) | | |
| Example 823 | N-{4-[2-(4-chloro-3-fluorophenoxy)acetamido]-3-hydroxybicyclo[2.2.2]octan-1-yl}-5-methoxypyridine-2-carboxamide (Compound 922) | | |
| Example 824 | N-{4-[2-(4-chloro-3-fluorophenoxy)acetamido]-3-hydroxybicyclo[2.2.2]octan-1-yl}-6-methoxypyridine-2-carboxamide (Compound 923) | | |
| Example 825 | N-{4-[2-(4-chloro-3-fluorophenoxy)acetamido]-3-hydroxybicyclo[2.2.2]octan-1-yl}-4-methoxypyridine-2-carboxamide (Compound 924) | | |
| Example 826 | N-{3-[2-(3,4-dichlorophenoxy)acetamido]bicyclo[1.1.1]pentan-1-yl}- | | |

| Example | Name (Compound Number) | NMR | MS |
|---|---|---|---|
| | 2-(methoxymethyl)-1,3-thiazole-4-carboxamide (Compound 925) | | |
| Example 827 | N-{3-[2-(4-chloro-3-fluorophenoxy)acetamido]bicyclo[1.1.1]pentan-1-yl}-2-(methoxymethyl)-1,3-thiazole-4-carboxamide (Compound 926) | | |
| Example 828 | N-{3-[2-(3,4-dichlorophenoxy)acetamido]bicyclo[1.1.1]pentan-1-yl}-6-(difluoromethyl)pyridine-3-carboxamide (Compound 927) | | |
| Example 829 | N-{3-[2-(4-chloro-3-fluorophenoxy)acetamido]bicyclo[1.1.1]pentan-1-yl}-5-phenylpyridine-2-carboxamide (Compound 928) | | |
| Example 830 | N-{3-[2-(4-chloro-3-fluorophenoxy)acetamido]bicyclo[1.1.1]pentan-1-yl}-6-fluoroquinoline-2-carboxamide (Compound 929) | | |
| Example 831 | N-{(2S)-4-[2-(4-chloro-3-fluorophenoxy)acetamido]-2-hydroxybicyclo[2.2.2]octan-1-yl}-6-fluoroquinoline-2-carboxamide (Compound 930) | | |
| Example 832 | N-{(3S)-4-[2-(4-chloro-3-fluorophenoxy)acetamido]-3-hydroxybicyclo[2.2.2]octan-1-yl}-2-phenyl-1,3-oxazole-5-carboxamide (Compound 931) | | |
| Example 833 | N-{4-[2-(4-chloro-3-fluorophenoxy)acetamido]-3-hydroxybicyclo[2.2.2]octan-1-yl}-4-cyanopyridine-2-carboxamide (Compound 932) | | |
| Example 834 | N-{4-[2-(4-chloro-3-fluorophenoxy)acetamido]-3-hydroxybicyclo[2.2.2]octan-1-yl}-4-(trifluoromethyl)pyridine-2-carboxamide (Compound 933) | | |
| Example 835 | N-{4-[2-(4-chloro-3-fluorophenoxy)acetamido]-3-hydroxybicyclo[2.2.2]octan-1-yl}-4-(1H-imidazol-1-yl)pyridine-2-carboxamide (Compound 934) | | |
| Example 836 | N-{4-[2-(4-chloro-3-fluorophenoxy)acetamido]-3-hydroxybicyclo[2.2.2]octan-1-yl}-4-(morpholin-4-yl)pyridine-2-carboxamide (Compound 9335) | | |
| Example 837 | N-{4-[2-(4-chloro-3-fluorophenoxy)acetamido]-3-hydroxybicyclo[2.2.2]octan-1-yl}-4-fluoropyridine-2-carboxamide (Compound 936) | | |
| Example 838 | N-{4-[2-(4-chloro-3-fluorophenoxy)acetamido]-3-hydroxybicyclo[2.2.2]octan-1-yl}-5-cyanopyridine-2-carboxamide (Compound 937) | | |

-continued

| Example | Name (Compound Number) | NMR | MS |
|---|---|---|---|
| Example 839 | N-{4-[2-(4-chloro-3-fluorophenoxy)acetamido]-3-hydroxybicyclo[2.2.2]octan-1-yl}-5-cyclopropylpyridine-2-carboxamide (Compound 938) | | |
| Example 840 | N-{4-[2-(4-chloro-3-fluorophenoxy)acetamido]-3-hydroxybicyclo[2.2.2]octan-1-yl}-5-(4-fluorophenyl)pyridine-2-carboxamide (Compound 939) | | |
| Example 841 | N-{4-[2-(4-chloro-3-fluorophenoxy)acetamido]-3-hydroxybicyclo[2.2.2]octan-1-yl}-5-(pyrrolidin-1-yl)pyridine-2-carboxamide (Compound 940) | | |
| Example 842 | N-{4-[2-(4-chloro-3-fluorophenoxy)acetamido]-3-hydroxybicyclo[2.2.2]octan-1-yl}-6-(trifluoromethyl)pyridine-2-carboxamide (Compound 941) | | |
| Example 843 | N-{4-[2-(4-chloro-3-fluorophenoxy)acetamido]-3-hydroxybicyclo[2.2.2]octan-1-yl}-6-(morpholin-4-yl)pyridine-2-carboxamide (Compound 942) | | |
| Example 844 | N-{4-[2-(4-chloro-3-fluorophenoxy)acetamido]-3-hydroxybicyclo[2.2.2]octan-1-yl}-6-hydroxypyridine-2-carboxamide (Compound 943) | | |
| Example 845 | N-{4-[2-(4-chloro-3-fluorophenoxy)acetamido]-3-hydroxybicyclo[2.2.2]octan-1-yl}-1-oxo-1$\lambda^5$-pyridine-2-carboxamide (Compound 944) | | |
| Example 846 | N-{4-[2-(4-chloro-3-fluorophenoxy)acetamido]-3-hydroxybicyclo[2.2.2]octan-1-yl}-6-(hydroxymethyl)pyridine-2-carboxamide (Compound 945) | | |
| Example 847 | N-{3-[4-(3-chlorophenyl)butanamido]bicyclo[1.1.1]pentan-1-yl}-5-(difluoromethyl)pyrazine-2-carboxamide (Compound 946) | | |
| Example 848 | N-(3-{2-[(3-chlorophenyl)methoxy]acetamido}bicyclo[1.1.1]pentan-1-yl)-5-(difluoromethyl)pyrazine-2-carboxamide (Compound 947) | | |
| Example 849 | N-{3-[2-(4-chloro-3-fluorophenoxy)acetamido]bicyclo[1.1.1]pentan-1-yl}-5-ethylpyridine-3-carboxamide (Compound 948) | | |
| Example 850 | N-{3-[2-(3,4-dichlorophenoxy)acetamido]bicyclo[1.1.1]pentan-1-yl}-5-ethylpyridine-3-carboxamide (Compound 949) | | |

| Example | Name (Compound Number) | NMR | MS |
|---|---|---|---|
| Example 851 | N-{(2S)-4-[2-(4-chloro-3-fluorophenoxy)acetamido]-2-hydroxybicyclo[2.2.2]octan-1-yl}-6-fluoroquinoxaline-2-carboxamide (Compound 950) | | |
| Example 852 | N-{3-[2-(4-chloro-3-fluorophenoxy)acetamido]bicyclo[1.1.1]pentan-1-yl}-6-fluoroquinoxaline-2-carboxamide (Compound 951) | | |
| Example 853 | N-{4-[2-(4-chloro-3-fluorophenoxy)acetamido]-3-hydroxybicyclo[2.2.2]octan-1-yl}-6-(3-fluorophenyl)pyridine-2-carboxamide (Compound 952) | | |
| Example 854 | 2-(4-chloro-3-fluorophenoxy)-N-{3-[(3-cyanopyridin-4-yl)amino]bicyclo[1.1.1]pentan-1-yl}acetamide (Compound 953) | | |
| Example 855 | 2-(4-chloro-3-fluorophenoxy)-N-{3-[(2-oxo-2H-[1,2'-bipyridin]-6'-yl)amino]bicyclo[1.1.1]pentan-1-yl}acetamide (Compound 954) | | |
| Example 856 | 2-(4-chloro-3-fluorophenoxy)-N-(3-{[2-(1H-imidazol-1-yl)pyridin-4-yl]amino}bicyclo[1.1.1]pentan-1-yl)acetamide (Compound 955) | | |
| Example 857 | 2-(4-chloro-3-fluorophenoxy)-N-(3-{[2-(1H-pyrrol-1-yl)pyrimidin-5-yl]amino}bicyclo[1.1.1]pentan-1-yl)acetamide (Compound 956) | | |
| Example 858 | 2-(4-chloro-3-fluorophenoxy)-N-(3-{[6-(morpholin-4-yl)pyridin-2-yl]amino}bicyclo[1.1.1]pentan-1-yl)acetamide (Compound 957) | | |
| Example 859 | 2-(4-chloro-3-fluorophenoxy)-N-(3-{[4-(morpholin-4-yl)quinazolin-6-yl]amino}bicyclo[1.1.1]pentan-1-yl)acetamide (Compound 958) | | |
| Example 860 | 2-(4-chloro-3-fluorophenoxy)-N-(3-{[4-(4-methylpiperazin-1-yl)quinazolin-6-yl]amino}bicyclo[1.1.1]pentan-1-yl)acetamide (Compound 959) | | |
| Example 861 | methyl 4-({3-[2-(4-chloro-3-fluorophenoxy)acetamido]bicyclo[1.1.1]pentan-1-yl}amino)quinoline-6-carboxylate (Compound 960) | | |

| Example | Name (Compound Number) | NMR | MS |
|---|---|---|---|
| Example 862 | 6-({3-[2-(4-chloro-3-fluorophenoxy)acetamido]bicyclo[1.1.1]pentan-1-yl}amino)pyridine-2-carboxamide (Compound 961) | | |
| Example 863 | 2-(4-chloro-3-fluorophenoxy)-N-(3-{[4-(pyrrolidin-1-yl)pyridin-2-yl]amino}bicyclo[1.1.1]pentan-1-yl)acetamide (Compound 962) | | |
| Example 864 | 2-(4-chloro-3-fluorophenoxy)-N-(3-{[4-(morpholin-4-yl)pyridin-2-yl]amino}bicyclo[1.1.1]pentan-1-yl)acetamide (Compound 963) | | |
| Example 865 | methyl 2-({3-[2-(4-chloro-3-fluorophenoxy)acetamido]bicyclo[1.1.1]pentan-1-yl}amino)pyridine-4-carboxylate (Compound 964) | | |
| Example 866 | ethyl 5-({3-[2-(4-chloro-3-fluorophenoxy)acetamido]bicyclo[1.1.1]pentan-1-yl}amino)pyridine-3-carboxylate (Compound 965) | | |
| Example 867 | 2-(4-chloro-3-fluorophenoxy)-N-{3-[(pyrido[2,3-b]pyrazin-7-yl)amino]bicyclo[1.1.1]pentan-1-yl}acetamide (Compound 966) | | |

Example 868: Activity of Exemplary Compounds in an In Vitro Model of Vanishing Cell White Matter Disease (VWMD)

In order to test exemplary compounds of the invention in a cellular context, a stable VWMD cell line was first constructed. The ATF4 reporter was prepared by fusing the human full-length ATF4 5'-UTR (NCBI Accession No. BC022088.2) in front of the firefly luciferase (FLuc) coding sequence lacking the initiator methionine as described in Sidrauski et al (eLife 2013). The construct was used to produce recombinant retroviruses using standard methods and the resulting viral supernatant was used to transduce HEK293T cells, which were then subsequently selected with puromycin to generate a stable cell line.

HEK293T cells carrying the ATF4 luciferase reporter were plated on polylysine coated 384-well plates (Greiner Bio-one) at 30,000 cells per well. Cells were treated the next day with 1 μg/mL tunicamycin and 200 nM of a compound of Formula (I) for 7 hours. Luminescence was measured using One Glo (Promega) as specified by the manufacturer. Cells were maintained in DMEM with L-glutamine supplemented with 10% heat-inactivated FBS (Gibco) and Antibiotic-Antimycotic solution (Gibco).

Table 2 below summarizes the $EC_{50}$ data obtained using the ATF4-Luc assay for exemplary compounds of the invention. In this table, "A" represents an $EC_{50}$ of less than 50 nM; "B" an $EC_{50}$ of between 50 nM and 250 nM; "C" an $EC_{50}$ of between 250 nM and 1 μM; "D" an $EC_{50}$ of between 1 μM and 2 μM; "E" an $EC_{50}$ of greater than 2 μM; and "F" indicates that data is not available.

TABLE 2

$EC_{50}$ values of exemplary compounds of the invention in the ATF4-Luc assay.

| Compound No. | ATF4-Luc $EC_{50}$ |
|---|---|
| 100 | C |
| 101 | E |
| 102 | D |
| 103 | D |
| 104 | C |
| 105 | A |
| 106 | A |
| 107 | A |
| 108 | A |
| 109 | C |
| 110 | B |
| 111 | E |
| 112 | C |
| 113 | B |
| 114 | B |
| 115 | D |
| 116 | E |
| 117 | A |
| 118 | E |
| 119 | C |
| 120 | B |
| 121 | D |
| 122 | D |
| 123 | C |
| 124 | D |
| 125 | E |
| 126 | B |
| 127 | E |
| 128 | E |

TABLE 2-continued

EC$_{50}$ values of exemplary compounds of the invention in the ATF4-Luc assay.

| Compound No. | ATF4-Luc EC$_{50}$ |
|---|---|
| 129 | B |
| 130 | B |
| 131 | B |
| 132 | B |
| 133 | D |
| 134 | A |
| 135 | B |
| 136 | C |
| 137 | D |
| 138 | B |
| 139 | C |
| 140 | C |
| 141 | C |
| 142 | C |
| 143 | B |
| 144 | A |
| 145 | B |
| 146 | B |
| 147 | B |
| 148 | E |
| 149 | D |
| 150 | B |
| 151 | E |
| 152 | B |
| 153 | B |
| 154 | C |
| 155 | D |
| 156 | B |
| 157 | E |
| 158 | C |
| 159 | C |
| 160 | C |
| 161 | D |
| 162 | E |
| 163 | D |
| 164 | B |
| 165 | E |
| 166 | B |
| 167 | B |
| 168 | B |
| 169 | B |
| 170 | B |
| 171 | B |
| 172 | C |
| 173 | B |
| 174 | C |
| 175 | C |
| 176 | B |
| 177 | C |
| 178 | B |
| 179 | C |
| 180 | D |
| 181 | C |
| 182 | B |
| 183 | D |
| 184 | E |
| 185 | C |
| 186 | C |
| 187 | D |
| 188 | C |
| 189 | C |
| 190 | C |
| 191 | B |
| 192 | C |
| 193 | B |
| 194 | B |
| 195 | A |
| 196 | C |
| 197 | B |
| 198 | B |
| 199 | B |
| 200 | B |
| 201 | A |
| 202 | B |
| 203 | D |
| 204 | B |
| 205 | E |
| 206 | C |
| 207 | B |
| 208 | D |
| 209 | C |
| 210 | C |
| 211 | D |
| 212 | C |
| 213 | C |
| 214 | E |
| 215 | B |
| 216 | E |
| 217 | D |
| 218 | E |
| 219 | B |
| 220 | B |
| 221 | D |
| 222 | E |
| 223 | B |
| 224 | C |
| 225 | B |
| 226 | C |
| 227 | C |
| 228 | E |
| 229 | B |
| 230 | B |
| 231 | B |
| 232 | B |
| 233 | A |
| 234 | A |
| 235 | B |
| 236 | A |
| 237 | C |
| 238 | B |
| 239 | B |
| 240 | D |
| 241 | A |
| 242 | B |
| 243 | C |
| 244 | B |
| 245 | C |
| 246 | C |
| 247 | C |
| 248 | B |
| 249 | B |
| 250 | A |
| 251 | B |
| 252 | C |
| 253 | B |
| 254 | A |
| 255 | C |
| 256 | C |
| 257 | B |
| 258 | C |
| 259 | C |
| 260 | C |
| 261 | C |
| 262 | B |
| 263 | C |
| 264 | C |
| 265 | A |
| 266 | B |
| 267 | A |
| 268 | B |
| 269 | C |
| 270 | E |
| 271 | C |
| 272 | B |
| 273 | C |
| 274 | C |
| 275 | B |
| 276 | F |

TABLE 2-continued

EC$_{50}$ values of exemplary compounds of the invention in the ATF4-Luc assay.

| Compound No. | ATF4-Luc EC$_{50}$ |
|---|---|
| 277 | D |
| 278 | C |
| 279 | C |
| 280 | E |
| 281 | B |
| 282 | C |
| 283 | A |
| 284 | B |
| 285 | B |
| 286 | C |
| 287 | B |
| 288 | E |
| 289 | A |
| 290 | B |
| 291 | B |
| 292 | B |
| 293 | A |
| 294 | B |
| 295 | C |
| 296 | B |
| 297 | A |
| 298 | B |
| 299 | C |
| 300 | C |
| 301 | C |
| 302 | E |
| 303 | D |
| 304 | C |
| 305 | C |
| 306 | C |
| 307 | C |
| 308 | C |
| 309 | C |
| 310 | E |
| 311 | D |
| 312 | E |
| 313 | B |
| 314 | E |
| 315 | C |
| 316 | B |
| 317 | A |
| 318 | E |
| 319 | B |
| 320 | D |
| 321 | B |
| 322 | E |
| 323 | C |
| 324 | C |
| 325 | E |
| 326 | B |
| 327 | B |
| 328 | D |
| 329 | B |
| 330 | B |
| 331 | C |
| 332 | E |
| 333 | D |
| 334 | A |
| 335 | B |
| 336 | E |
| 337 | C |
| 338 | B |
| 339 | A |
| 340 | A |
| 341 | E |
| 342 | C |
| 343 | B |
| 344 | A |
| 345 | B |
| 346 | C |
| 347 | C |
| 348 | B |
| 349 | C |
| 350 | C |
| 351 | B |
| 352 | B |
| 353 | B |
| 354 | D |
| 355 | D |
| 356 | E |
| 357 | C |
| 358 | A |
| 359 | C |
| 360 | E |
| 361 | B |
| 362 | E |
| 363 | D |
| 364 | B |
| 365 | A |
| 366 | B |
| 367 | E |
| 368 | C |
| 369 | D |
| 370 | A |
| 371 | B |
| 372 | C |
| 373 | C |
| 374 | E |
| 375 | B |
| 376 | B |
| 377 | C |
| 378 | A |
| 379 | B |
| 380 | C |
| 381 | D |
| 382 | E |
| 383 | E |
| 384 | A |
| 385 | C |
| 386 | E |
| 387 | B |
| 388 | C |
| 389 | C |
| 390 | D |
| 391 | C |
| 392 | A |
| 393 | E |
| 394 | A |
| 395 | E |
| 396 | C |
| 397 | B |
| 398 | E |
| 399 | C |
| 400 | C |
| 401 | C |
| 402 | E |
| 403 | E |
| 404 | E |
| 405 | E |
| 406 | B |
| 407 | D |
| 408 | E |
| 409 | B |
| 410 | B |
| 411 | E |
| 412 | E |
| 413 | A |
| 414 | B |
| 415 | E |
| 416 | E |
| 417 | C |
| 418 | E |
| 419 | C |
| 420 | E |
| 421 | C |
| 422 | B |
| 423 | C |
| 424 | D |

TABLE 2-continued

EC$_{50}$ values of exemplary compounds of the invention in the ATF4-Luc assay.

| Compound No. | ATF4-Luc EC$_{50}$ |
|---|---|
| 425 | C |
| 426 | E |
| 427 | C |
| 428 | C |
| 429 | E |
| 430 | E |
| 431 | B |
| 432 | E |
| 433 | E |
| 434 | C |
| 435 | E |
| 436 | B |
| 437 | A |
| 438 | C |
| 439 | E |
| 440 | B |
| 441 | A |
| 442 | C |
| 443 | A |
| 444 | E |
| 445 | E |
| 446 | C |
| 447 | B |
| 448 | D |
| 449 | F |
| 450 | B |
| 451 | A |
| 452 | C |
| 453 | D |
| 454 | B |
| 455 | E |
| 456 | B |
| 457 | C |
| 458 | B |
| 459 | E |
| 460 | E |
| 461 | D |
| 462 | C |
| 463 | B |
| 464 | E |
| 465 | E |
| 466 | A |
| 467 | B |
| 468 | C |
| 469 | C |
| 470 | B |
| 471 | B |
| 472 | C |
| 473 | B |
| 474 | B |
| 475 | B |
| 476 | C |
| 477 | D |
| 478 | B |
| 479 | B |
| 480 | A |
| 481 | D |
| 482 | A |
| 483 | B |
| 484 | B |
| 485 | A |
| 486 | B |
| 487 | A |
| 488 | B |
| 489 | B |
| 490 | B |
| 491 | E |
| 492 | B |
| 493 | B |
| 494 | A |
| 495 | C |
| 496 | B |
| 497 | C |
| 498 | A |
| 499 | A |
| 500 | A |
| 501 | D |
| 502 | A |
| 503 | B |
| 504 | B |
| 505 | E |
| 506 | B |
| 507 | C |
| 508 | B |
| 509 | C |
| 510 | C |
| 511 | C |
| 512 | E |
| 513 | B |
| 514 | B |
| 515 | A |
| 516 | D |
| 517 | B |
| 518 | C |
| 519 | B |
| 520 | C |
| 521 | B |
| 522 | B |
| 523 | B |
| 524 | C |
| 525 | C |
| 526 | C |
| 527 | D |
| 528 | E |
| 529 | E |
| 530 | C |
| 531 | D |
| 532 | E |
| 533 | B |
| 534 | C |
| 535 | B |
| 536 | C |
| 537 | C |
| 538 | A |
| 539 | B |
| 540 | C |
| 541 | D |
| 542 | E |
| 543 | E |
| 544 | A |
| 545 | C |
| 546 | E |
| 547 | D |
| 548 | E |
| 549 | E |
| 550 | D |
| 551 | B |
| 552 | B |
| 553 | E |
| 554 | A |
| 555 | B |
| 556 | D |
| 557 | E |
| 558 | D |
| 559 | A |
| 560 | B |
| 561 | E |
| 562 | C |
| 563 | A |
| 564 | B |
| 565 | B |
| 566 | A |
| 567 | B |
| 568 | B |
| 569 | A |
| 570 | B |
| 571 | C |
| 572 | B |

TABLE 2-continued

EC$_{50}$ values of exemplary compounds of the invention in the ATF4-Luc assay.

| Compound No. | ATF4-Luc EC$_{50}$ |
|---|---|
| 573 | D |
| 574 | B |
| 575 | A |
| 576 | B |
| 577 | B |
| 578 | A |
| 579 | B |
| 580 | E |
| 581 | A |
| 582 | B |
| 583 | B |
| 584 | A |
| 585 | B |
| 586 | A |
| 587 | B |
| 588 | A |
| 589 | B |
| 590 | B |
| 591 | B |
| 592 | B |
| 593 | B |
| 594 | B |
| 595 | D |
| 596 | C |
| 597 | C |
| 598 | B |
| 599 | C |
| 600 | C |
| 601 | C |
| 602 | C |
| 603 | C |
| 604 | E |
| 605 | E |
| 606 | B |
| 607 | B |
| 608 | B |
| 609 | D |
| 610 | D |
| 611 | A |
| 612 | B |
| 613 | B |
| 614 | B |
| 615 | B |
| 616 | E |
| 617 | A |
| 618 | A |
| 619 | A |
| 620 | D |
| 621 | B |
| 622 | A |
| 623 | B |
| 624 | B |
| 625 | C |
| 626 | B |
| 627 | E |
| 628 | C |
| 629 | C |
| 630 | C |
| 631 | B |
| 632 | A |
| 633 | B |
| 634 | E |
| 635 | C |
| 636 | C |
| 637 | C |
| 638 | C |
| 639 | B |
| 640 | C |
| 641 | A |
| 642 | D |
| 643 | C |
| 644 | B |
| 645 | B |
| 646 | B |
| 647 | C |
| 648 | B |
| 649 | D |
| 650 | B |
| 651 | B |
| 652 | A |
| 653 | C |
| 654 | B |
| 655 | B |
| 656 | E |
| 657 | E |
| 658 | B |
| 659 | B |
| 660 | C |
| 661 | E |
| 662 | E |
| 663 | B |
| 664 | C |
| 665 | A |
| 666 | A |
| 667 | A |
| 668 | A |
| 669 | C |
| 670 | A |
| 671 | A |
| 672 | B |
| 673 | B |
| 674 | A |
| 675 | B |
| 676 | A |
| 677 | C |
| 678 | D |
| 679 | A |
| 680 | A |
| 681 | A |
| 682 | A |
| 683 | A |
| 684 | D |
| 685 | A |
| 686 | A |
| 687 | C |
| 688 | E |
| 689 | B |
| 690 | C |
| 691 | A |
| 692 | B |
| 693 | C |
| 694 | A |
| 695 | A |
| 696 | B |
| 697 | A |
| 698 | A |
| 699 | C |
| 700 | A |
| 701 | B |
| 702 | A |
| 703 | A |
| 704 | A |
| 705 | E |
| 706 | A |
| 707 | C |
| 708 | B |
| 709 | B |
| 710 | C |
| 711 | A |
| 712 | C |
| 713 | B |
| 714 | C |
| 715 | D |
| 716 | C |
| 717 | C |
| 718 | C |
| 719 | D |
| 720 | E |

TABLE 2-continued

EC$_{50}$ values of exemplary compounds of the invention in the ATF4-Luc assay.

| Compound No. | ATF4-Luc EC$_{50}$ |
|---|---|
| 721 | E |
| 722 | B |
| 723 | C |
| 724 | C |
| 725 | D |
| 726 | F |
| 727 | A |
| 728 | A |
| 729 | A |
| 730 | B |
| 731 | D |
| 732 | C |
| 733 | E |
| 734 | A |
| 735 | A |
| 736 | E |
| 737 | C |
| 738 | E |
| 739 | E |
| 740 | A |
| 741 | E |
| 742 | A |
| 743 | E |
| 744 | C |
| 745 | E |
| 746 | B |
| 747 | E |
| 748 | C |
| 749 | B |
| 750 | E |
| 751 | A |
| 752 | A |
| 753 | C |
| 754 | A |
| 755 | C |
| 756 | C |
| 757 | E |
| 758 | A |
| 759 | A |
| 760 | E |
| 761 | E |
| 762 | E |
| 763 | E |
| 764 | E |
| 765 | B |
| 766 | E |
| 767 | E |
| 768 | E |
| 769 | E |
| 770 | D |
| 771 | E |
| 772 | E |
| 773 | E |
| 774 | E |
| 775 | E |
| 776 | E |
| 777 | E |
| 778 | E |
| 779 | E |
| 780 | E |
| 781 | E |
| 782 | E |
| 783 | E |
| 784 | E |
| 785 | E |
| 786 | E |
| 787 | E |
| 788 | E |
| 789 | B |
| 790 | B |
| 791 | E |
| 792 | C |
| 793 | C |
| 794 | E |
| 795 | E |
| 796 | E |
| 797 | E |
| 798 | E |
| 799 | E |
| 800 | E |
| 801 | E |
| 802 | E |
| 803 | E |
| 804 | E |
| 805 | E |
| 806 | E |
| 807 | E |
| 808 | E |
| 809 | E |
| 810 | E |
| 811 | E |
| 812 | D |
| 813 | E |
| 814 | E |
| 815 | E |
| 816 | E |
| 817 | E |
| 818 | E |
| 819 | C |
| 820 | E |
| 821 | E |
| 822 | E |
| 823 | E |
| 824 | E |
| 825 | C |
| 826 | D |
| 827 | E |
| 828 | E |
| 829 | B |
| 830 | B |
| 831 | F |
| 832 | B |
| 833 | D |
| 834 | C |
| 835 | D |
| 836 | E |
| 837 | E |
| 838 | B |
| 839 | E |
| 840 | D |
| 841 | C |
| 842 | E |
| 843 | E |
| 844 | E |
| 845 | E |
| 846 | D |
| 847 | C |
| 848 | A |
| 849 | D |
| 850 | B |
| 851 | C |
| 852 | D |
| 853 | E |
| 854 | E |
| 855 | E |
| 856 | C |
| 857 | B |
| 858 | D |
| 859 | E |
| 860 | D |
| 861 | E |
| 862 | E |
| 863 | E |
| 864 | E |
| 865 | D |
| 866 | E |
| 867 | E |
| 868 | E |

TABLE 2-continued

EC$_{50}$ values of exemplary compounds of the invention in the ATF4-Luc assay.

| Compound No. | ATF4-Luc EC$_{50}$ |
|---|---|
| 869 | E |
| 870 | E |
| 871 | C |
| 872 | B |
| 873 | E |
| 874 | E |
| 875 | A |
| 876 | C |
| 877 | E |
| 878 | C |
| 879 | E |
| 880 | E |
| 881 | E |
| 882 | E |
| 883 | E |
| 884 | C |
| 885 | E |
| 886 | C |
| 887 | C |
| 888 | B |
| 889 | D |
| 890 | E |
| 891 | B |
| 892 | C |
| 893 | D |
| 894 | C |
| 895 | C |
| 896 | D |
| 897 | E |
| 898 | B |
| 899 | C |
| 900 | E |
| 901 | E |
| 902 | E |
| 903 | E |
| 904 | E |
| 905 | E |
| 906 | C |
| 907 | B |
| 908 | E |
| 909 | E |
| 910 | B |
| 911 | C |
| 912 | A |
| 913 | C |
| 914 | B |
| 915 | C |
| 916 | B |
| 917 | B |
| 918 | C |
| 919 | A |
| 920 | A |
| 921 | D |
| 922 | C |
| 923 | B |
| 924 | E |
| 925 | A |
| 926 | B |
| 927 | B |
| 928 | B |
| 929 | A |
| 930 | A |
| 931 | A |
| 932 | B |
| 933 | B |
| 934 | D |
| 935 | E |
| 936 | B |
| 937 | A |
| 938 | B |
| 939 | E |
| 940 | B |
| 941 | A |
| 942 | D |
| 943 | B |
| 944 | E |
| 945 | E |
| 946 | E |
| 947 | E |

VWMD mutations were introduced into the genome of the HEK293T ATF4-Fluc stable cell lines by using Gene Art CRISPR nuclease vector with OFP Reporter kit (ThermoFisher; see Table 3 below). Guide RNAs were designed using the CRISPR Design Tool (http://crispr.mit.edu) and ligated into the CRISPR OFP Nuclease Vector. To obtain homology directed repair (HDR) incorporating VWMD point mutations in the genome, 150 bp ssDNA ultramer oligos were synthesized by Integrated DNA Technologies containing specific mutations of interest. In addition to the VWMD mutations, the ssDNA HDR templates contained a silent mutation to the PAM site of the CRISPR gRNA sequence (to avoid further Cas9 cutting) and 75 bp of homology on each side of the mutation.

HEK293T ATF4-Fluc cells were transfected with 500 ng of the CRISPR OFP Nuclease Vector and 1 uL of 10 μM ssDNA HDR template using lipofectamine 3000 (ThermoFisher) or SF Cell Line 4D-nucleofector X Kit (Lonza) according to the manufacturer's instructions. After 2-3 days of recovery, single cells were sorted for positive OFP expression on a FACS Aria II (BD Biosciences) into wells of a 96 well plate and allowed to recover for 1-2 weeks.

The resulting clones were surveyed for CRISPR editing and HDR by harvesting the genomic DNA with the PureLink Genomic DNA kit (ThermoFisher), amplifying a ~500 bp locus near the editing site, and sequencing the amplicon. Clones that displayed an ambiguous chromatogram signal near the expected CRISPR editing site were further examined by TA cloning (Invitrogen) and sequencing of the amplicon, yielding the sequence of each allele in the clone. Typical clones obtained were hemizygous for the VWMD point mutation, with one or two alleles harboring the desired mutation, and the remaining alleles knocked out (edited to produce a premature stop codon).

TABLE 3

Exemplary VWMD point mutations introduced into eIF2B

| eIF2B Subunit | Mutation |
|---|---|
| eIF2B1 | V183F |
| eIF2B3 | H341Q |
| eIF2B3 | I346T |
| eIF2B4 | R483W |
| eIF2B5 | R113H |
| eIF2B5 | R195H |

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims are introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

We claim:
1. A compound of Formula (I):

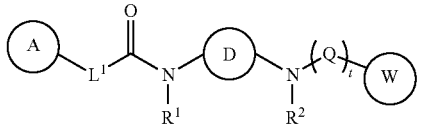

Formula (I)

or a pharmaceutically acceptable salt thereof, wherein:
D is selected from the group consisting of

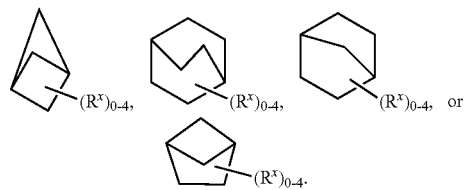

$L^1$ is $CH_2O$—*, wherein "—*" indicates the attachment point to A;
$R^1$ and $R^2$ are each independently hydrogen or $C_1$-$C_6$ alkyl;
Q is C(O) or $S(O)_2$;
A is phenyl and W is phenyl or 5-6 membered heteroaryl, wherein each phenyl or 5-6-membered heteroaryl is optionally substituted with 1-5 $R^Y$;
each $R^X$ is independently selected from the group consisting of $C_1$-$C_6$ alkyl, hydroxy-$C_1$-$C_6$ alkyl, halo-$C_1$-$C_6$ alkyl, amino-$C_1$-$C_6$ alkyl, cyano-$C_1$-$C_6$ alkyl, oxo, halo, cyano, —$OR^A$, —$NR^BR^C$, —$NR^BC(O)R^D$, —$C(O)NR^BR^C$, —$C(O)R^D$, —C(O)OH, —$C(O)OR^D$, —$SR^E$, —$S(O)R^B$, —$S(O)_2R^D$, and $G^2$;
each $R^Y$ is independently selected from the group consisting of hydrogen, $C_1$-$C_6$ alkyl, $C_1$-$C_6$ alkenyl, hydroxy-$C_1$-$C_6$ alkyl, hydroxy-$C_1$-$C_6$ alkenyl, halo-$C_1$-$C_6$ alkyl, halo-$C_1$-$C_6$ alkoxy, amino-$C_1$-$C_6$ alkyl, amido-$C_1$-$C_6$ alkyl, cyano-$C_1$-$C_6$ alkyl, siloxy-$C_1$-$C_6$ alkoxy, hydroxyl-$C_1$-$C_6$ alkoxy, $C_1$-$C_6$ alkoxy-$C_1$-$C_6$ alkyl, $C_1$-$C_6$ alkoxy-$C_1$-$C_6$ alkenyl, $C_1$-$C_6$ alkoxy-$C_1$-$C_6$ alkoxy, oxo, halo, cyano, —$OR^A$, —$NR^BR^C$, —$NR^BC(O)R^D$, —$C(O)NR^BR^C$, —$C(O)R^D$, —C(O)OH, —$C(O)OR^D$, —$S(R^F)_m$, —$S(O)R^D$, —$S(O)_2R^D$, —$S(O)NR^BR^C$, —$NR^BS(O)_2R^D$, —$OS(O)R^D$, —$OS(O)_2R^D$, $R^FS$—$C_1$-$C_6$ alkyl, $R^DC(O)NR^B$—$C_1$-$C_6$ alkyl, $(R^B)(R^C)N$—$C_1$-$C_6$ alkoxy, $R^DOC(O)NR^B$—$C_1$-$C_6$ alkyl, $G^1$, $G^1$-$C_1$-$C_6$ alkyl, $G^1$-$N(R^B)$, $G^1$-$C_1$-$C_6$ alkenyl, $G^1$-O—, $G^1C(O)NR^B$—$C_1$-$C_6$ alkyl, and $G^1$-$NR^BC(O)$; or
2 $R^Y$ groups on adjacent atoms, together with the atoms to which they are attached form a fused phenyl, a 3-7-membered fused cycloalkyl ring, a 3-7-membered fused heterocyclyl ring, or a 5-6-membered fused heteroaryl ring, each optionally substituted with 1-5 $R^X$;
each $G^1$ or $G^2$ is independently 3-7 membered cycloalkyl, 4-7-membered heterocyclyl, aryl, or 5-6-membered heteroaryl, wherein each 3-7 membered cycloalkyl, 4-7-membered heterocyclyl, aryl, or 5-6-membered heteroaryl is optionally substituted with 1-6 $R^Z$;
each $R^Z$ is independently selected from the group consisting of $OR^A$, $C(O)R^D$, halo, halo $C_1$-$C_6$ alkyl, $C_1$-$C_6$ alkyl, $C(O)R^D$, and $C(O)OR^D$;

$R^A$ is, at each occurrence, independently hydrogen, $C_1$-$C_6$ alkyl, halo-$C_1$-$C_6$ alkyl, —$ORA^1$, —$C(O)NR^BR^C$, —$C(O)R^D$, —$C(O)OH$, or —$C(O)OR^D$;

each of $R^B$ and $R^C$ is independently hydrogen, $C_1$-$C_6$ alkyl, hydroxy-$C_1$-$C_6$ alkyl, $G^1$-$C_1$-$C_6$ alkyl, 3-7 membered cycloalkyl, or 4-7-membered heterocyclyl, wherein each alkyl, cycloalkyl, or heterocyclyl is optionally substituted with 1-6 $R^Z$; or $R^B$ and $R^C$ together with the atom to which they are attached form a 3-7-membered cycloalkyl or heterocyclyl ring optionally substituted with 1-6 $R^Z$;

$R^D$ is, at each occurrence, independently $C_1$-$C_6$ alkyl, $C_1$-$C_6$ alkoxy-$C_1$-$C_6$ alkyl, or halo-$C_1$-$C_6$ alkyl;

each $R^E$ is independently hydrogen $C_1$-$C_6$ alkyl, or halo-$C_1$-$C_6$ alkyl;

each $R^F$ is independently hydrogen, $C_1$-$C_6$ alkyl, or halo;

each $RA^1$ is hydrogen, $C_1$-$C_6$ alkyl, halo-$C_1$-$C_6$ alkyl, 3-7 membered cycloalkyl, or 4-7-membered heterocyclyl;

m is 1, 3, or 5; and t is 0 or 1.

2. The compound of claim 1, wherein D is substituted with one $R^X$, and $R^X$ is OH.

3. The compound of claim 1, wherein D is substituted with 0 $R^X$.

4. The compound of claim 1, wherein D is

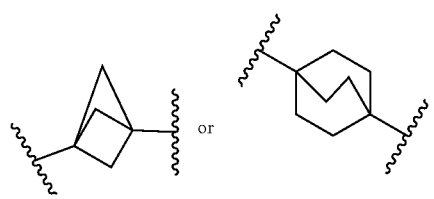

5. The compound of claim 1, wherein t is 1.
6. The compound of claim 1, wherein t is 0.
7. The compound of claim 1, wherein each of $R^1$ and $R^2$ is independently hydrogen.
8. The compound of claim 1, wherein one of $R^1$ and $R^2$ is independently hydrogen and the other of $R^1$ and $R^2$ is independently $CH_3$.
9. The compound of claim 1, wherein Q is C(O).
10. The compound of claim 1, wherein A is

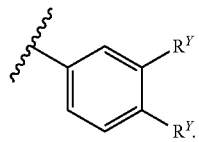

11. The compound of claim 1, wherein W is selected from the group consisting of:

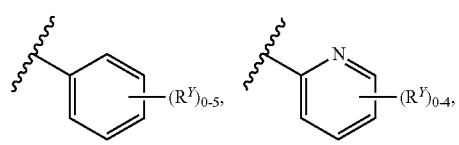

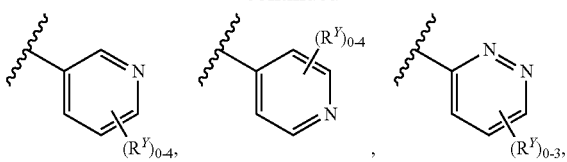
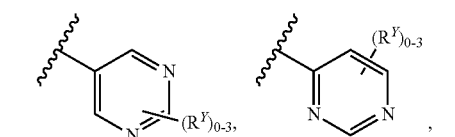
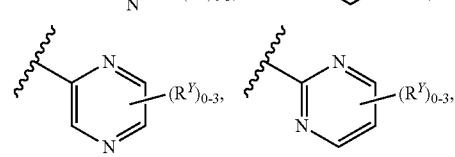
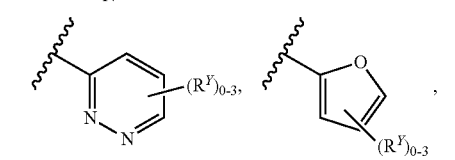
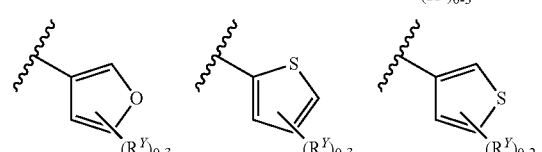
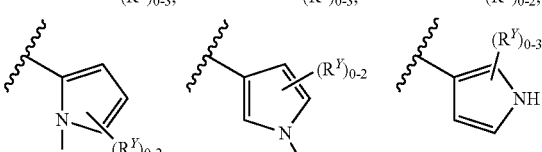
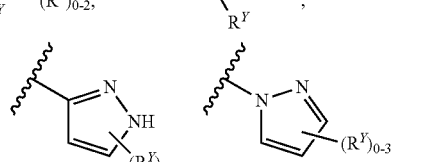
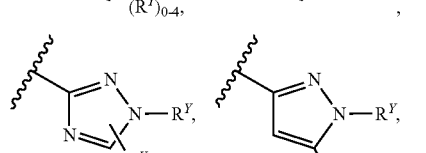
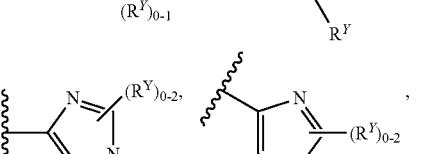
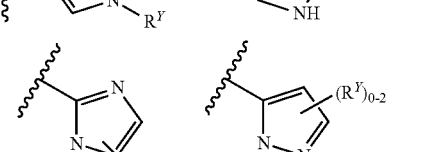
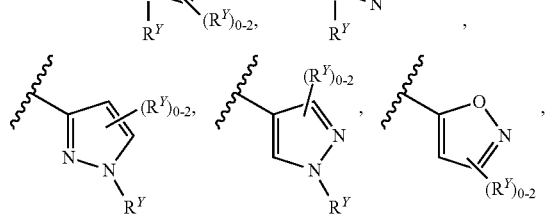

-continued

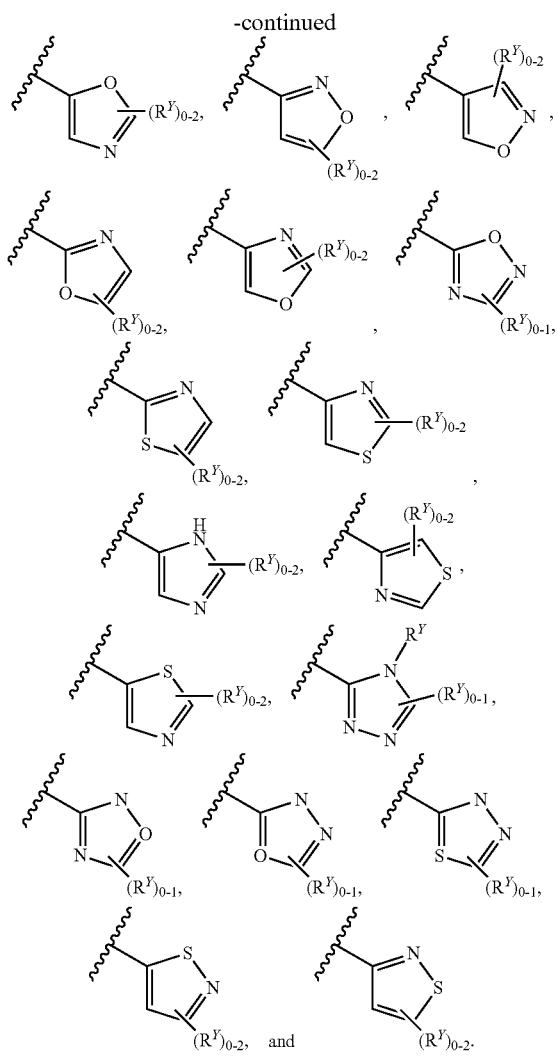

12. The compound of claim 1, wherein each $R^Y$ is independently selected from the group consisting of chloro, fluoro, oxo, CN, OH, CF$_3$, CHF$_2$, CH$_3$, CH$_2$CH$_3$, CH$_2$CH$_2$CH$_2$CH$_3$, CH=CHCH$_2$OH, CH$_2$CH$_2$OH, CH$_2$NH$_2$, NHCH$_3$, CH$_2$NHC(O)CH$_3$, N(CH$_2$CH$_3$)$_2$, CH$_2$N(CH$_3$)$_2$, C(CH$_3$)$_2$OH, CH(CH$_3$)$_2$, CH$_2$CH$_2$CH$_3$, C(CH$_3$)$_3$, CH$_2$CH(CH$_3$)$_2$, CH$_2$CH$_2$OH, CH(OH)CH$_3$, CH$_2$CH$_2$CH$_2$OCH$_3$, CH$_2$CF$_3$, CH$_2$C(CH$_3$)$_2$OH, CH$_2$SCH$_3$, CH$_2$CN, CH$_2$CH$_2$CN, CH$_2$CH$_2$C(CH$_3$)$_2$OH, CH$_2$NHC(O)CH$_3$, OCH$_3$, OCH$_2$CH$_3$, OCH$_2$CH$_2$CH$_3$, OCH$_2$CH$_2$OCH$_3$, OCH(CH$_3$)$_2$, OCF$_3$, OCH$_2$CF$_3$, OCH$_2$CH$_2$N(CH$_3$)$_2$, CH$_2$OH, CH$_2$OCH$_3$, OCH$_2$CH$_2$OH, OCHF$_2$, OCF$_3$, OCH$_3$, CH$_2$OH, C(O)OH, C(O)CH$_3$, C(O)OCH$_3$, C(O)NH$_2$, C(O)NHCH$_2$CH$_2$CH$_2$OH, CH$_2$CN, C(O)OCH$_2$CH$_3$, C(O)NHCH$_2$CH$_3$, OCH$_2$CH$_2$OSi(CH$_3$)$_2$C(CH$_3$)$_3$, CH$_2$N(CH$_3$)$_2$, CH$_2$NHC(O)CH$_3$, CH$_2$NHC(O)OC(CH$_3$)$_3$, CH=CHCH$_2$OCH$_3$, CH=CHC(CH$_3$)$_2$OH, N(CH$_3$)$_2$, N(CH$_2$CH$_3$)$_2$, NHCH$_2$CH$_3$, NHC(O)CH$_3$, NHC(O)CH$_2$OCH$_3$, NHS(O)$_2$CH$_3$, SCH$_3$, SCH$_2$CH$_3$, SO$_2$NH$_2$, S(O)CH$_3$, S(O)$_2$CH$_3$, C(O)NHG$^1$, N(CH$_3$)CH$_2$G$^1$, NHG$^1$, OG$^1$, CH$_2$G$^1$, CH$_2$CH$_2$G$^1$, CH$_2$NHC(O)G$^1$, and CH=CHG$^1$, or
2 $R^Y$ groups on adjacent atoms, together with the atoms to which they are attached, form a 5-7-membered fused heterocyclyl ring, 5-6-membered fused heteroaryl, a 5-6-membered fused cycloalkyl, or a fused phenyl, each optionally substituted with 1-5 Rx.

13. The compound of claim 11, wherein the 2 $R^Y$ together with the atoms to which they are attached form a dioxolanyl, hexahydropyrimidinyl, pyridyl, or pyrimidinyl ring, each of which is optionally substituted with 1-5 $R^X$.

14. The compound of claim 13, wherein each $R^X$ is independently C$_1$-C$_6$ alkyl, fluoro, chloro, oxo, OCH$_3$, C(O)OCH$_3$, or G$^2$.

15. The compound of claim 1, wherein G$^1$ is pyrrolidinyl, azetidinyl, cyclopropyl, cyclohexyl, cyclohexenyl, tetrahydropyranyl, dihydropyranyl, tetrahydropyridinyl, piperidinyl, phenyl, pyridyl, pyrimidinyl, pyridazinyl, pyrazolyl, morphilino, furanyl, triazolyl, oxetanyl, or pyrazinyl, each of which is optionally substituted with 1-5 $R^Z$.

16. The compound of claim 15, wherein each $R^Z$ is independently fluoro, chloro, OH, OCH$_3$, oxo, CH$_3$, CHF$_2$, CF$_3$, C(O)CH$_3$ or C(O)OC(CH$_3$)$_3$.

17. A compound represented by Formula (I-b):

Formula (I-b)

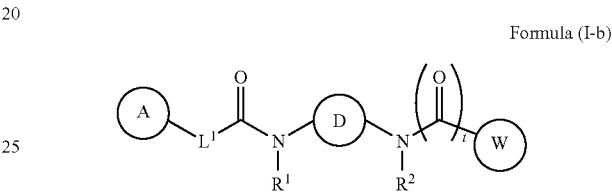

or a pharmaceutically acceptable salt thereof, wherein:
D is bicyclo[1.1.1]pentane, bicyclo[2.2.1]heptane, bicyclo[2.2.2]octane, or bicyclo[2.1.1]hexane, each of which is optionally substituted with 1-4 $R^X$;
L$^1$ CH$_2$O—*, wherein "—*" indicates the attachment point to A;
R$^1$ and R$^2$ are each independently hydrogen or C$_1$-C$_6$ alkyl;
A is phenyl optionally substituted with 1-2 $R^Y$;
W is phenyl or 5-6 membered heteroaryl, wherein each phenyl or 5-6-membered heteroaryl is optionally substituted with 1-5 $R^Y$;
each $R^X$ is independently C$_1$-C$_6$ alkyl, fluoro, chloro, oxo, OCH$_3$, C(O)OCH$_3$, or G$^2$;
each $R^Y$ is independently chloro, fluoro, oxo, CN, OH, CF$_3$, CHF$_2$, CH$_3$, CH$_2$CH$_3$, CH$_2$CH$_2$CH$_2$CH$_3$, CH=CHCH$_2$OH, CH$_2$CH$_2$OH, CH$_2$NH$_2$, NHCH$_3$, CH$_2$NHC(O)CH$_3$, N(CH$_2$CH$_3$)$_2$, CH$_2$N(CH$_3$)$_2$, C(CH$_3$)$_2$OH, CH(CH$_3$)$_2$, CH$_2$CH$_2$CH$_3$, C(CH$_3$)$_3$, CH$_2$CH(CH$_3$)$_2$, CH$_2$CH$_2$OH, CH(OH)CH$_3$, CH$_2$CH$_2$CH$_2$OCH$_3$, CH$_2$CF$_3$, CH$_2$C(CH$_3$)$_2$OH, CH$_2$SCH$_3$, CH$_2$CN, CH$_2$CH$_2$CN, CH$_2$CH$_2$C(CH$_3$)$_2$OH, CH$_2$NHC(O)CH$_3$, OCH$_3$, OCH$_2$CH$_3$, OCH$_2$CH$_2$CH$_3$, OCH$_2$CH$_2$OCH$_3$, OCH(CH$_3$)$_2$, OCF$_3$, OCH$_2$CF$_3$, OCH$_2$CH$_2$N(CH$_3$)$_2$, CH$_2$OH, CH$_2$OCH$_3$, OCH$_2$CH$_2$OH, OCHF$_2$, OCF$_3$, OCH$_3$, CH$_2$OH, C(O)OH, C(O)CH$_3$, C(O)OCH$_3$, C(O)NH$_2$, C(O)NHCH$_2$CH$_2$CH$_2$OH, CH$_2$CN, C(O)OCH$_2$CH$_3$, C(O)NHCH$_2$CH$_3$, OCH$_2$CH$_2$OSi(CH$_3$)$_2$C(CH$_3$)$_3$, CH$_2$N(CH$_3$)$_2$, CH$_2$NHC(O)CH$_3$, CH$_2$NHC(O)OC(CH$_3$)$_3$, CH=CHCH$_2$OCH$_3$, CH=CHC(CH$_3$)$_2$OH, N(CH$_3$)$_2$, N(CH$_2$CH$_3$)$_2$, NHCH$_2$CH$_3$, NHC(O)CH$_3$, NHC(O)CH$_2$OCH$_3$, NHS(O)$_2$CH$_3$, SCH$_3$, SCH$_2$CH$_3$, SO$_2$NH$_2$, S(O)CH$_3$, S(O)$_2$CH$_3$, G$^1$, C(O)NHG$^1$, N(CH$_3$)CH$_2$G$^1$, NHG$^1$, OG$^1$, CH$_2$G$^1$, CH$_2$CH$_2$G$^1$, CH$_2$NHC(O)G$^1$, or CH=CHG$^1$; or
2 $R^Y$ groups on adjacent atoms, together with the atoms to which they are attached form a 5-7-membered fused heterocyclyl ring, 5-6-membered fused heteroaryl, a 5-6-membered fused cycloalkyl, or a fused phenyl, each optionally substituted with 1-5 $R^X$;

$G^1$ and $G^2$ are each independently pyrrolidinyl, azetidinyl, cyclopropyl, cyclohexyl, cyclohexenyl, tetrahydropyranyl, dihydropyranyl, tetrahydropyridinyl, piperidinyl, phenyl, pyridyl, pyrimidinyl, pyridazinyl, pyrazolyl, morphilino, furanyl, triazolyl, oxetanyl, or pyrazinyl, each of which is optionally substituted with 1-5 $R^Z$;

each $R^Z$ is independently fluoro, chloro, OH, $OCH_3$, oxo, $CH_3$, $CHF_2$, $CF_3$, $C(O)CH_3$ or $C(O)OC(CH_3)_3$; and t is 0 or 1.

18. A compound selected from the group consisting of:

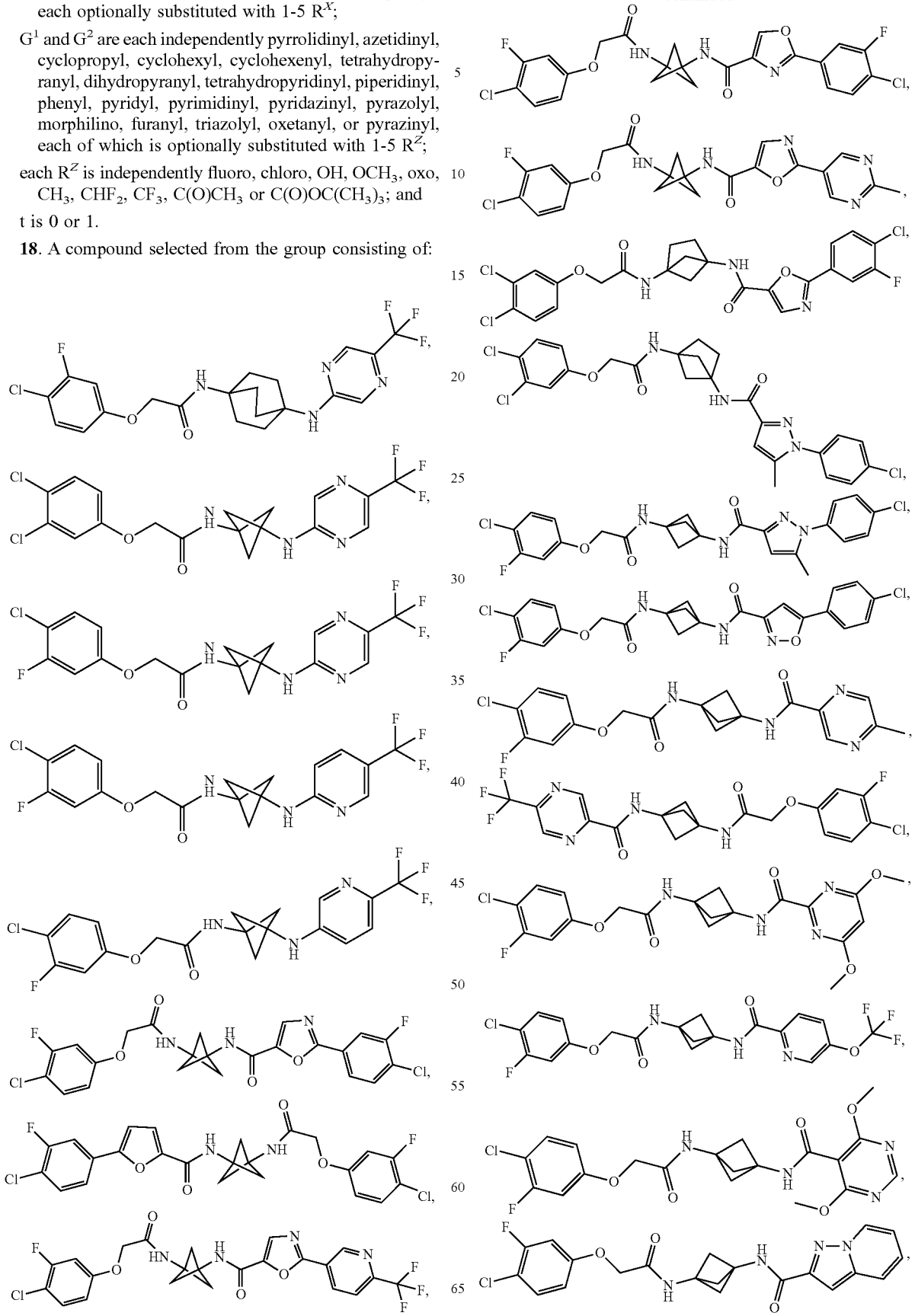

-continued
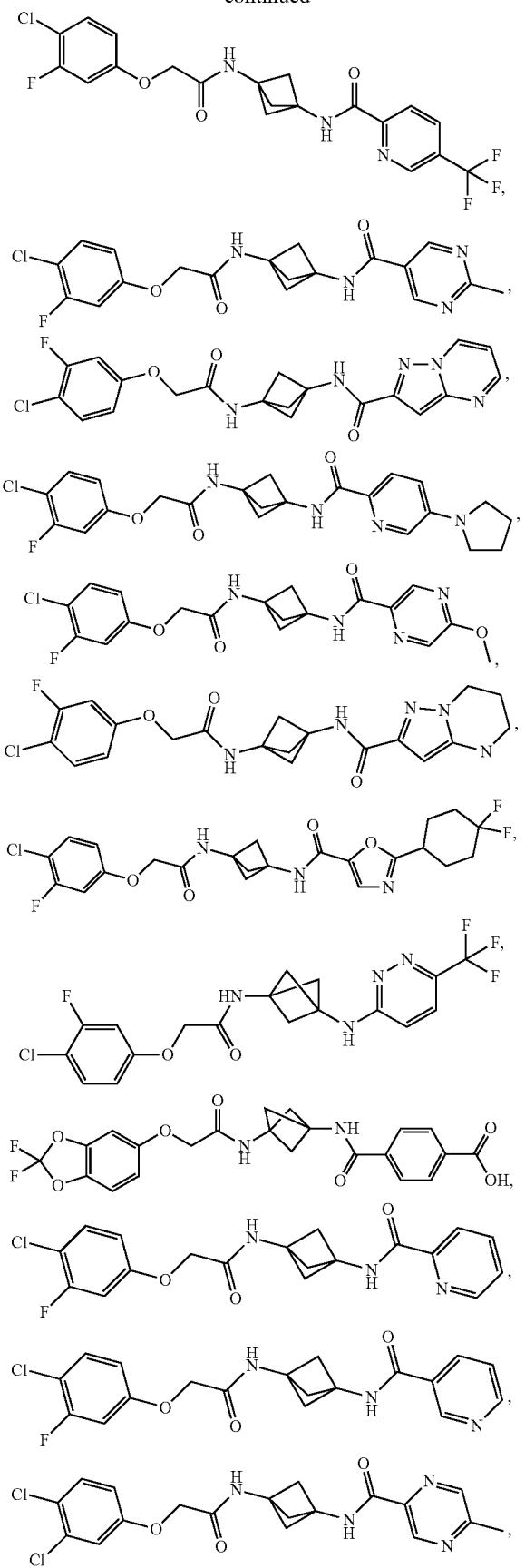
-continued
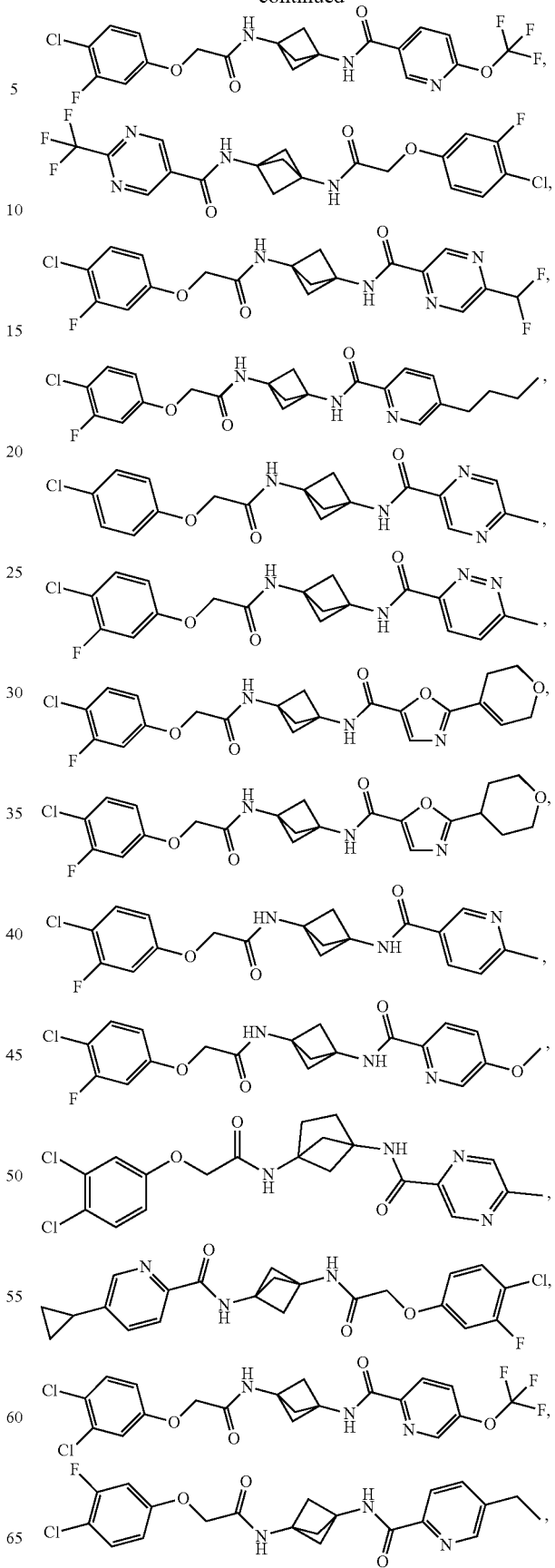

815
-continued
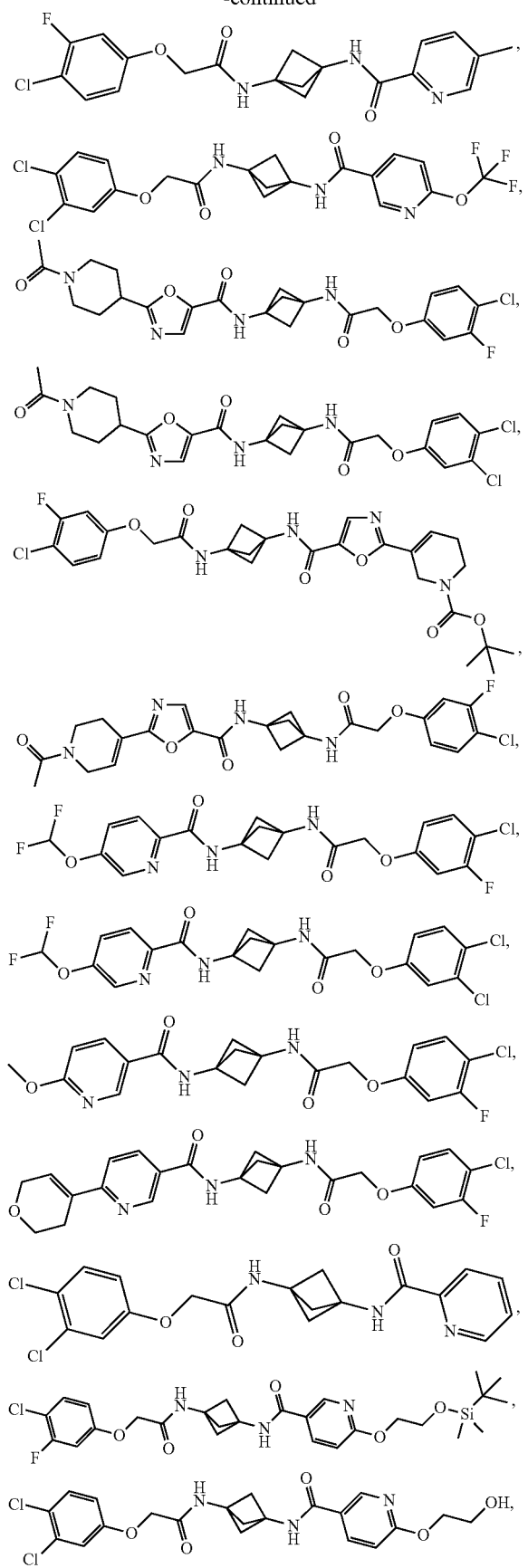
816
-continued
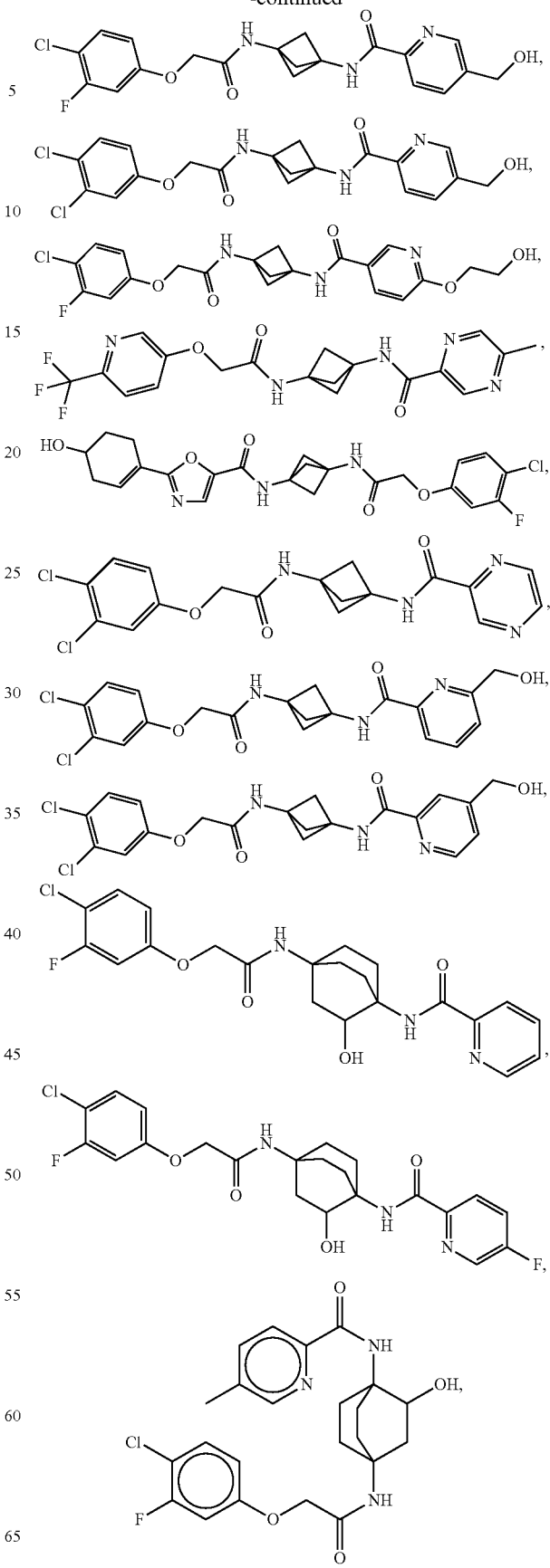

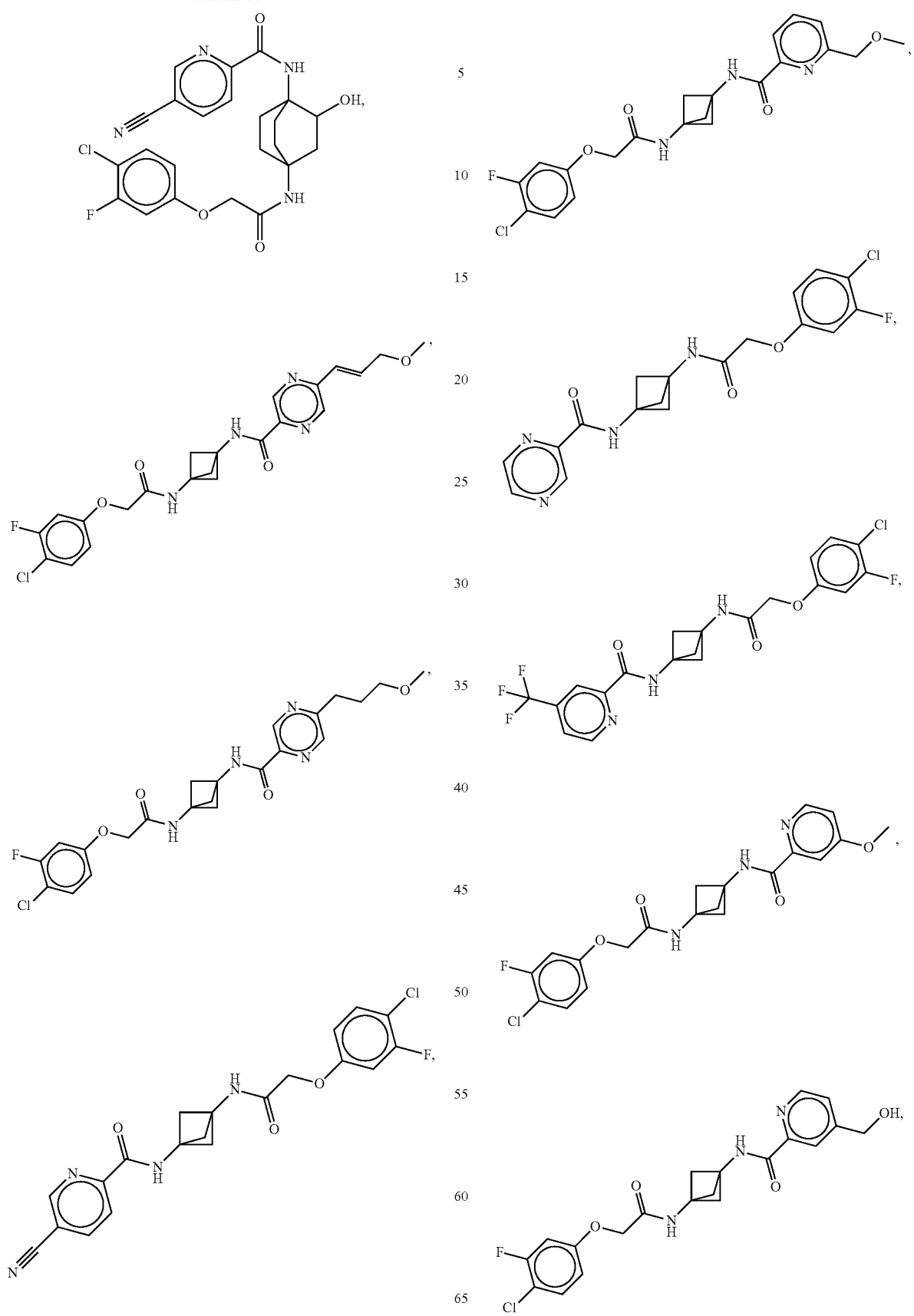

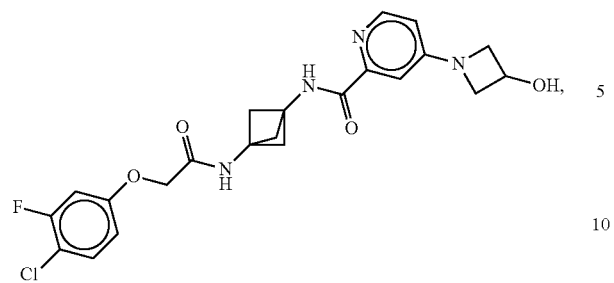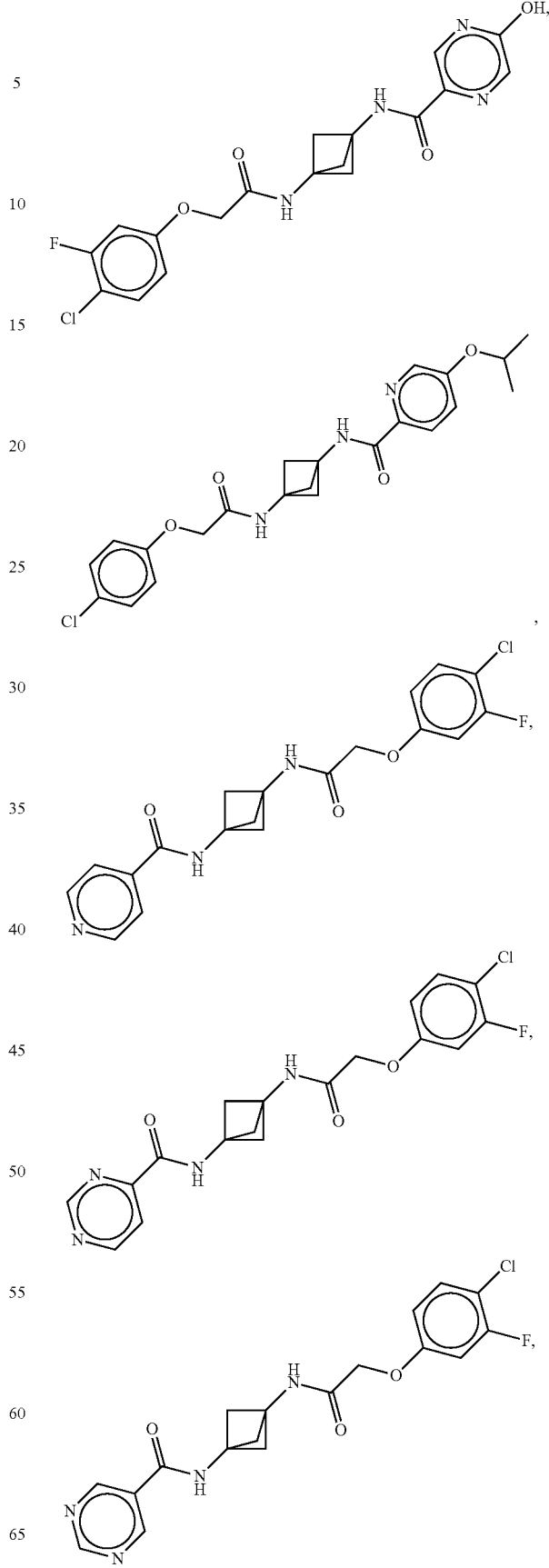

-continued
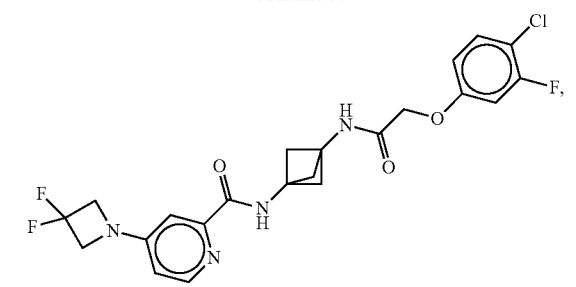
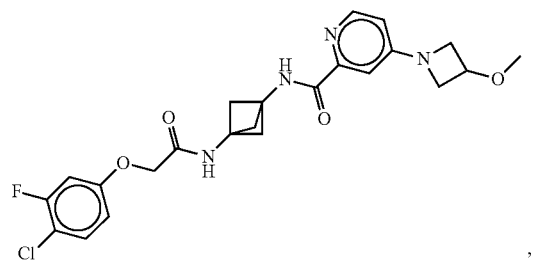
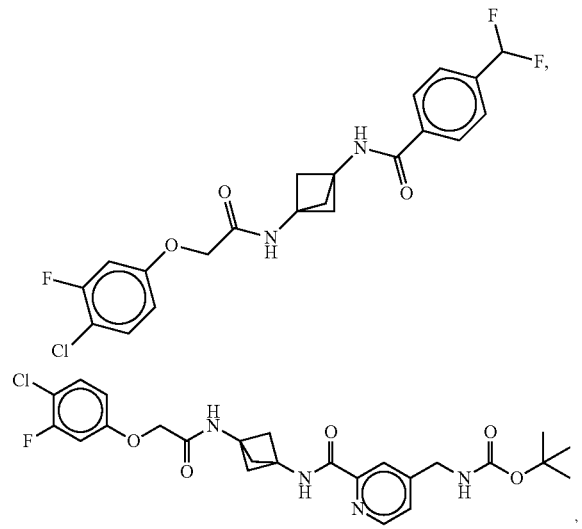
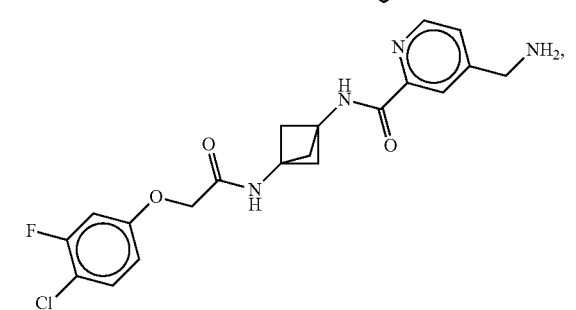
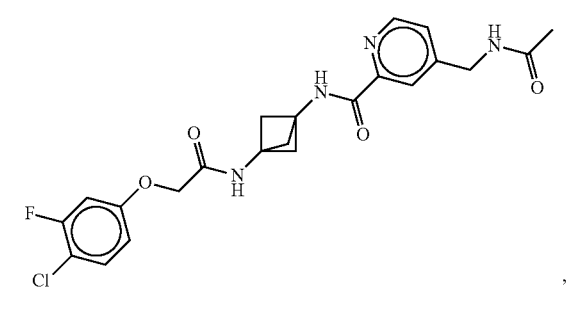
-continued
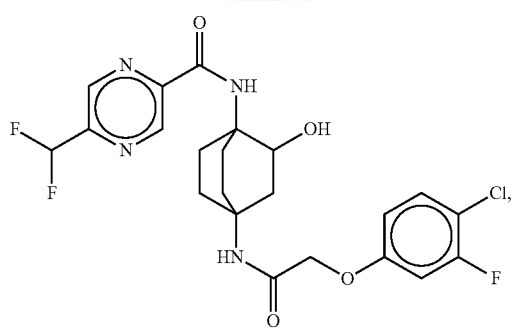
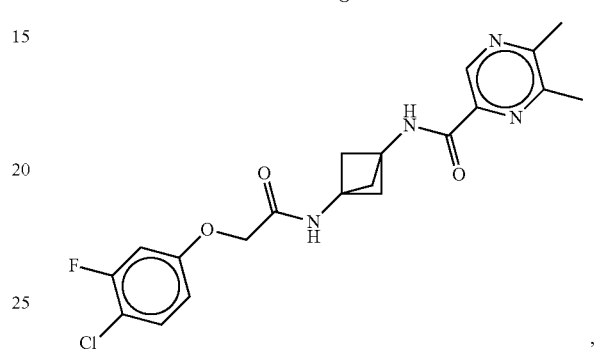
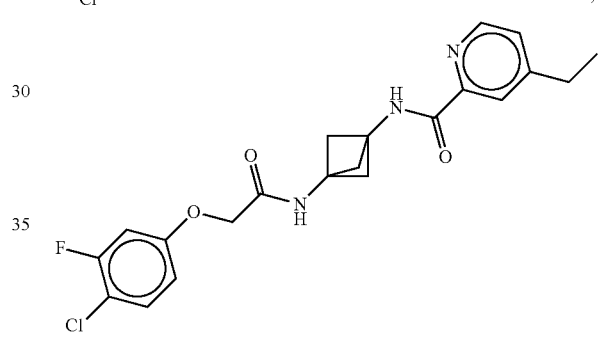
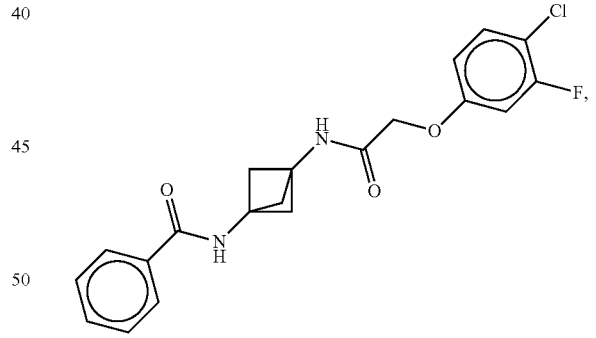
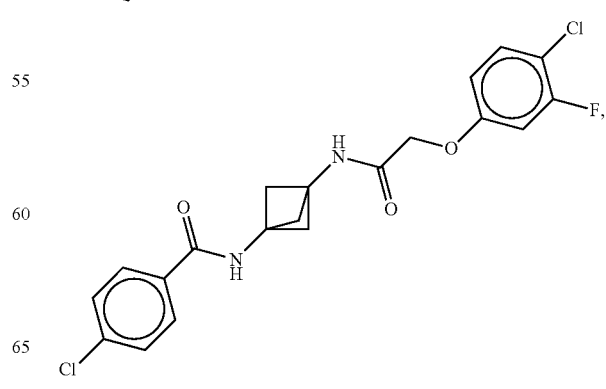

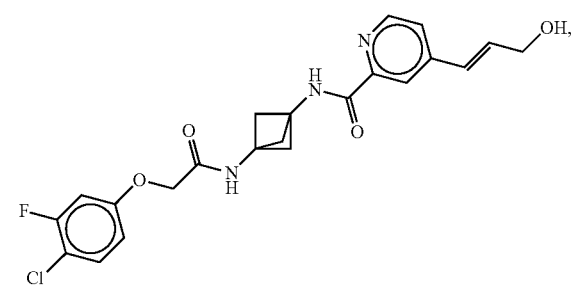
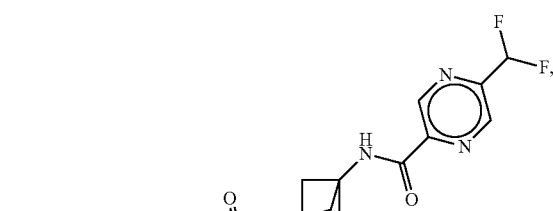
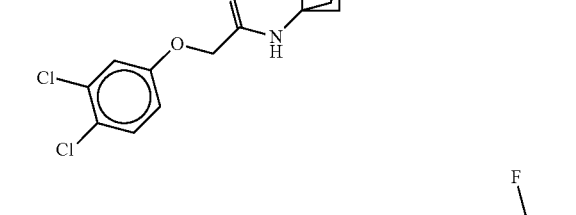
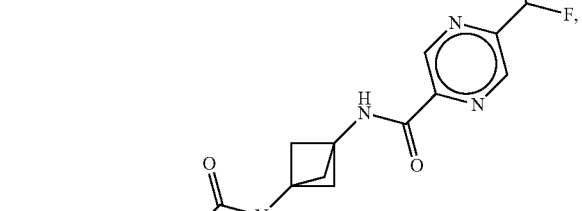
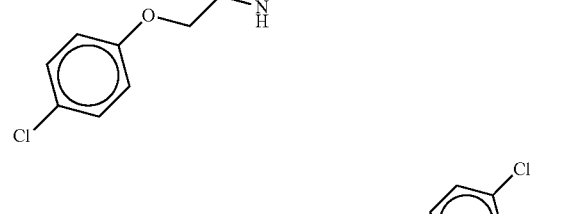
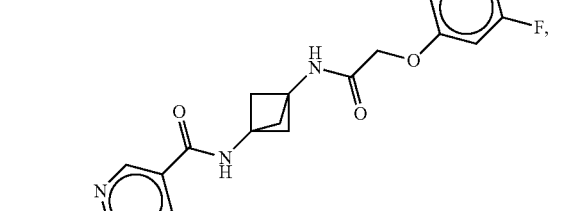
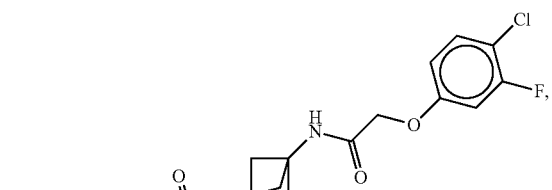
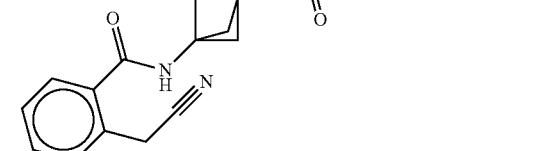

825
-continued
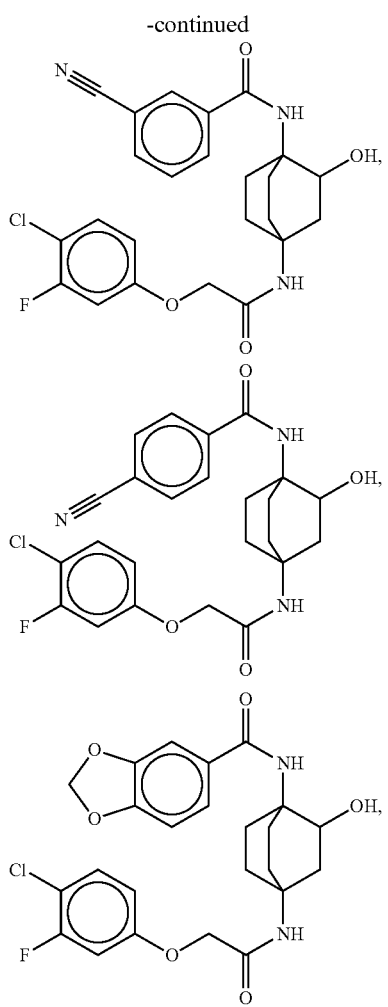
826
-continued
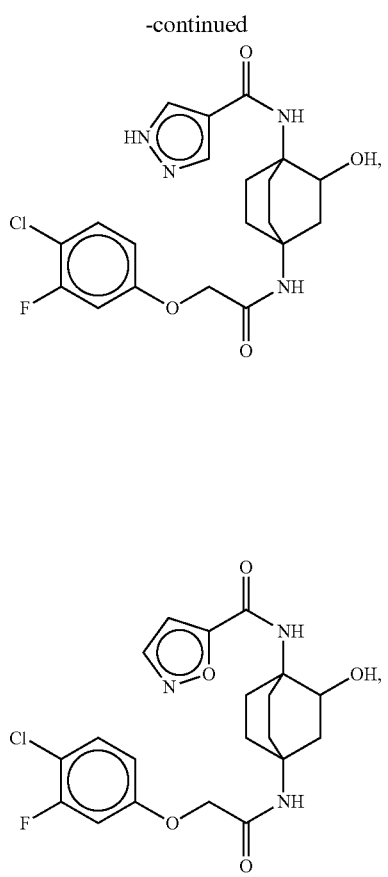
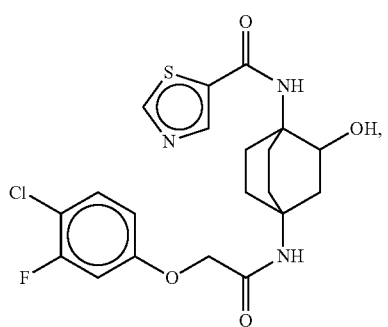

827
-continued
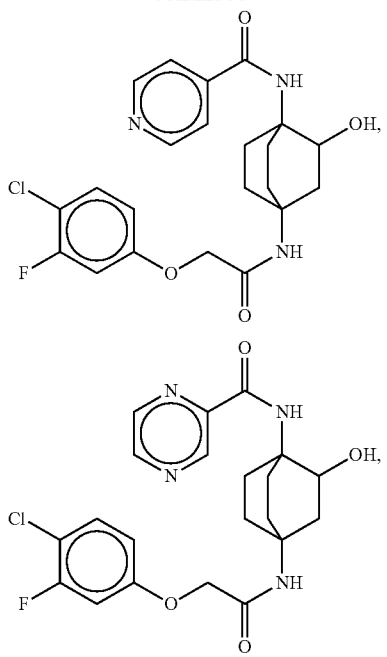
828
-continued
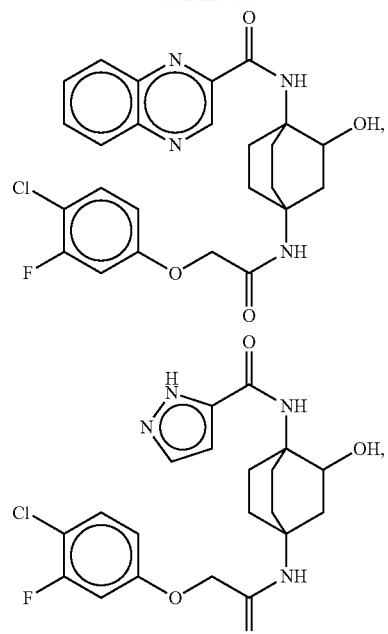
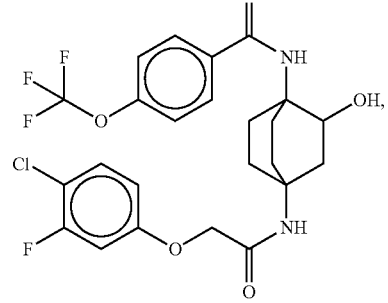
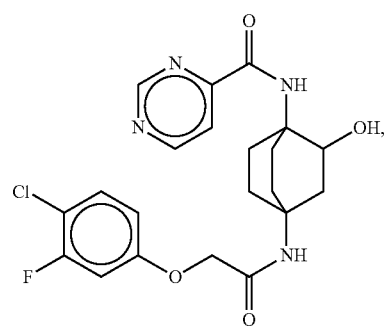
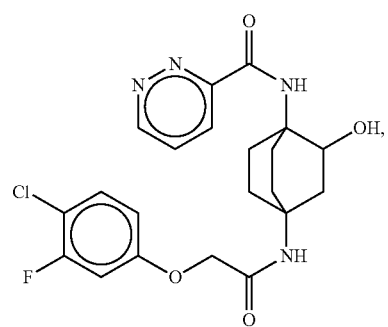

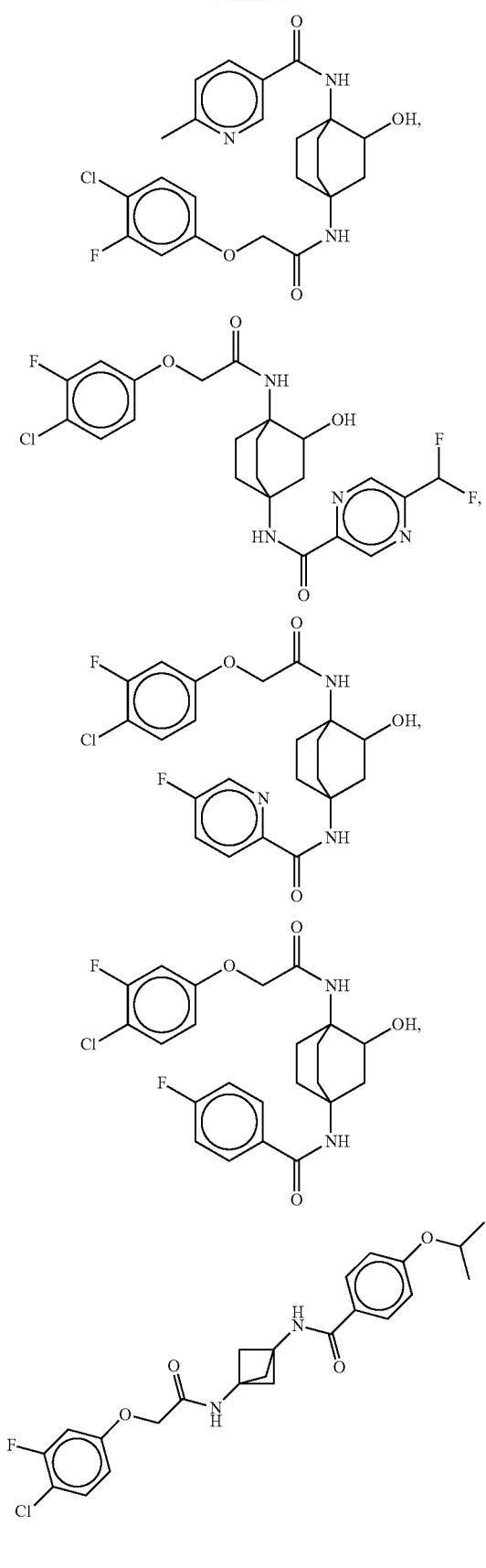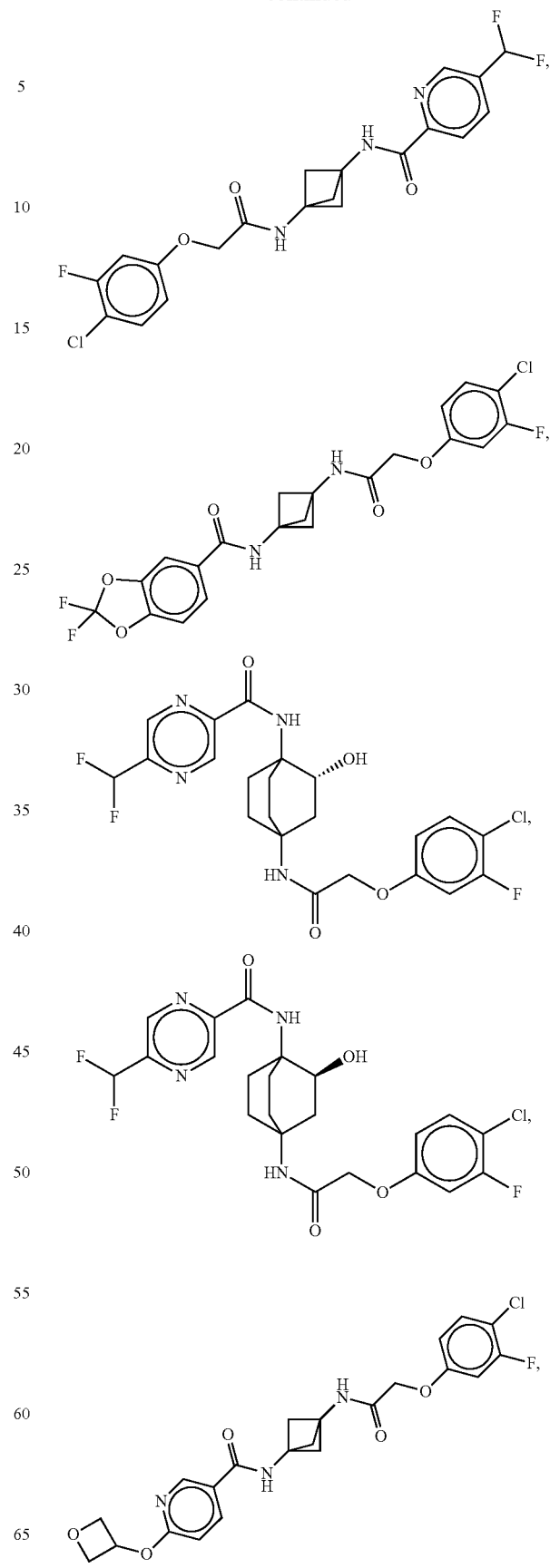

831
-continued
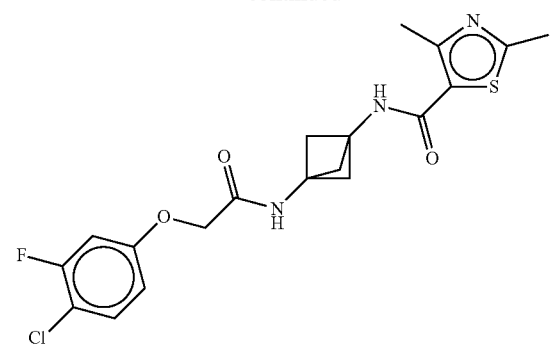
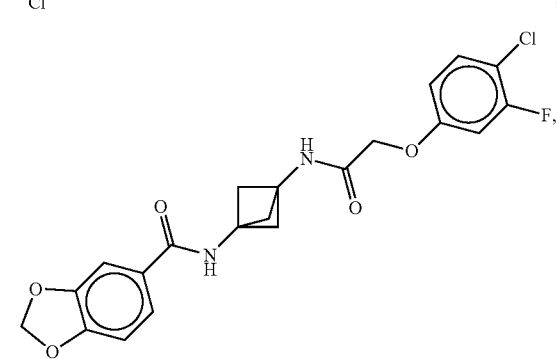
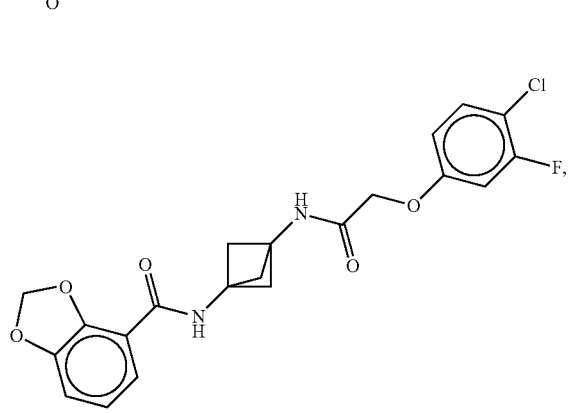
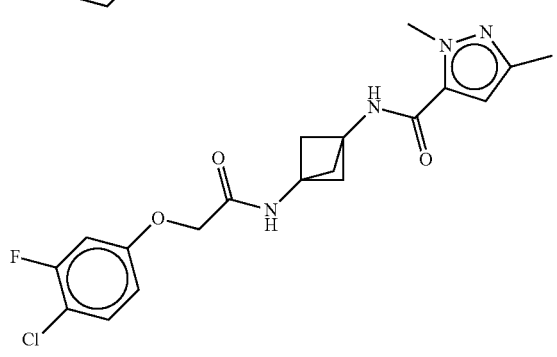
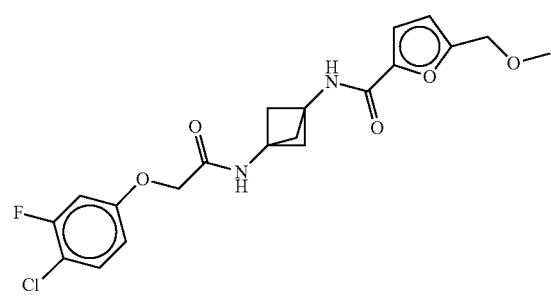
832
-continued
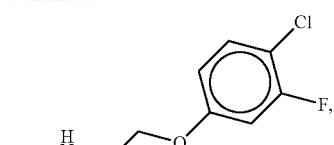
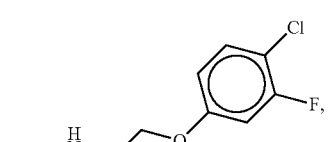
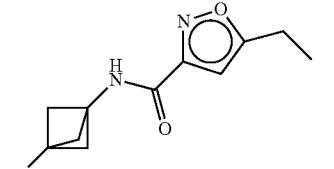

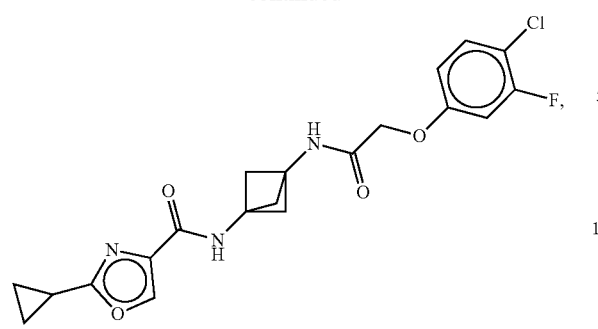
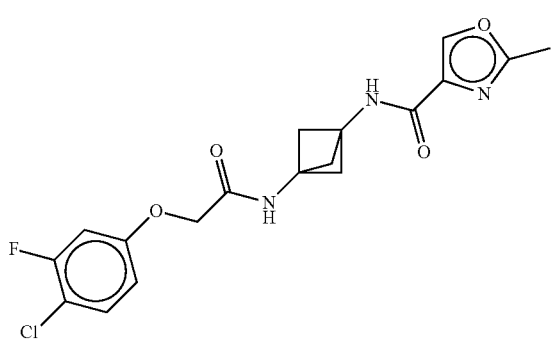
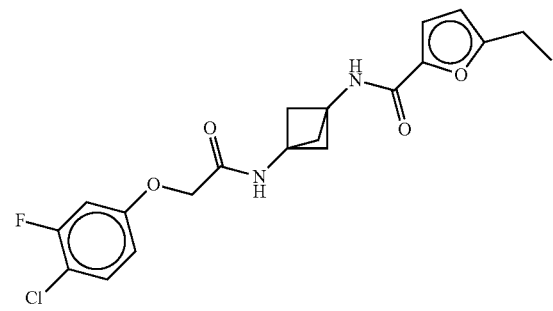
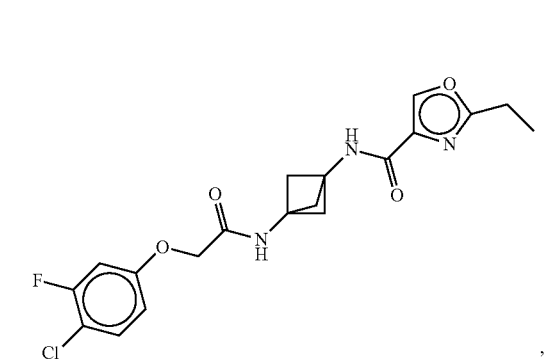
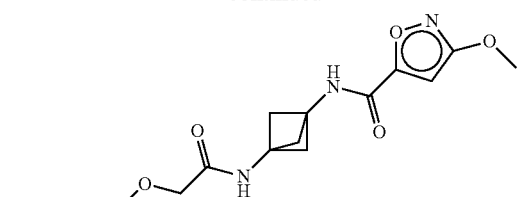
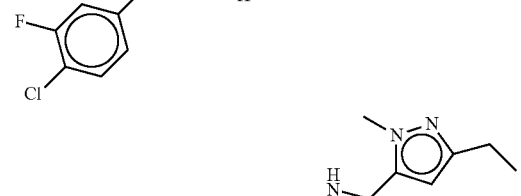
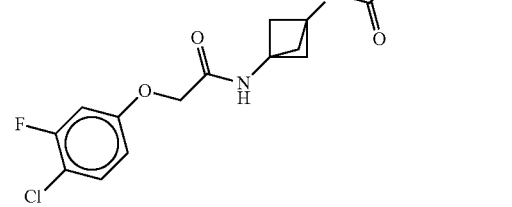
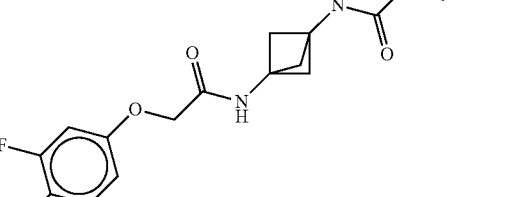
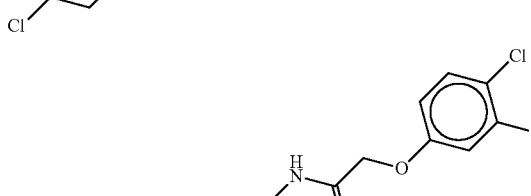
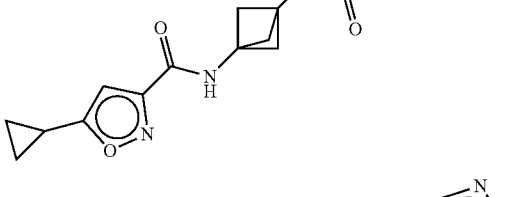

-continued
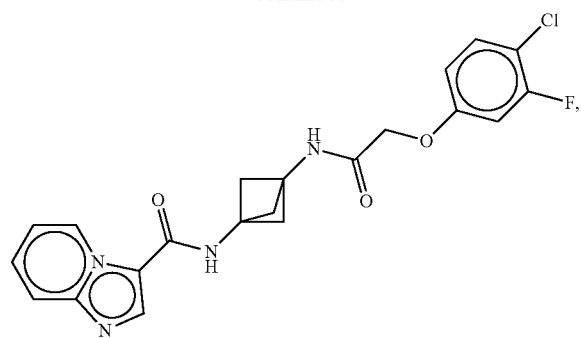
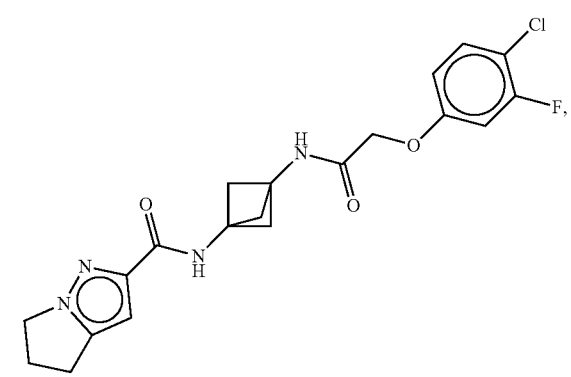
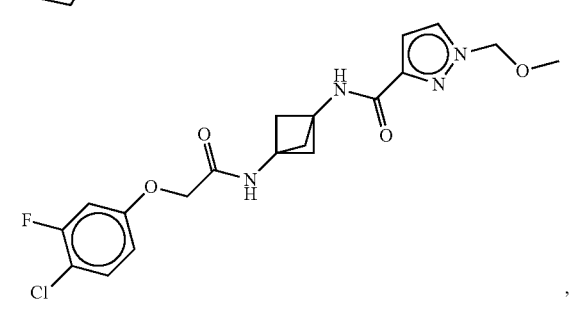
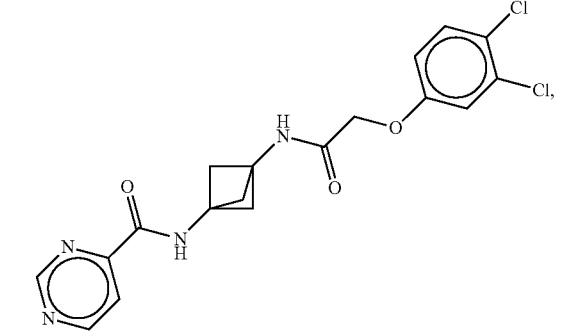
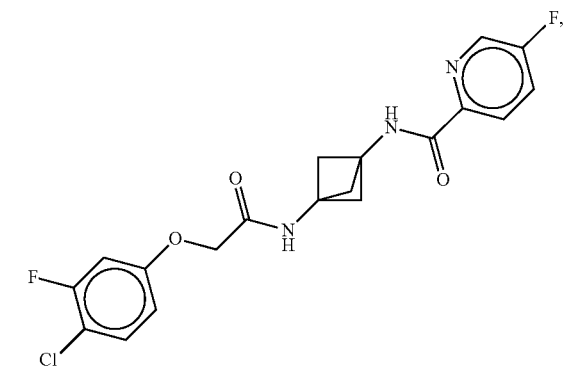
-continued
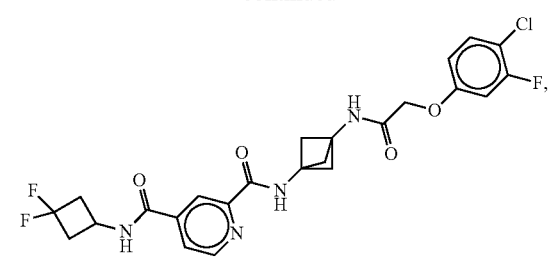
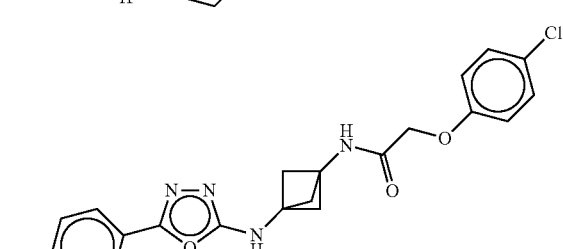
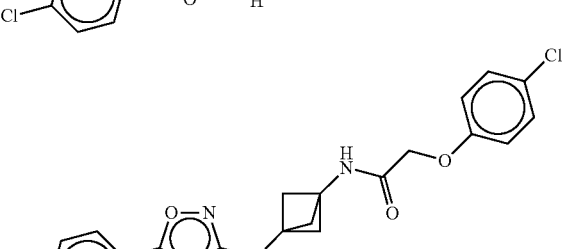
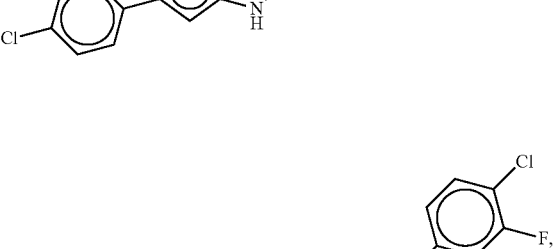
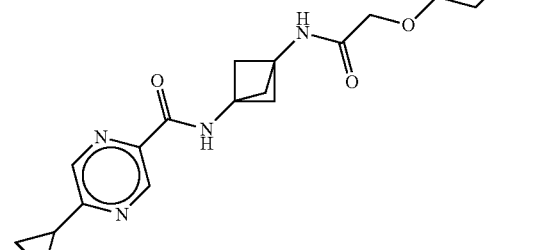
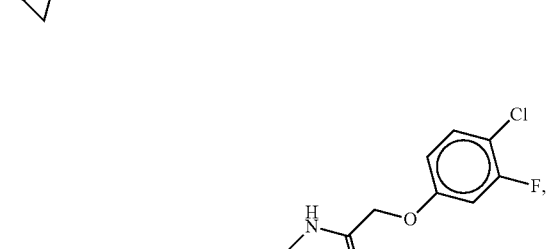

-continued
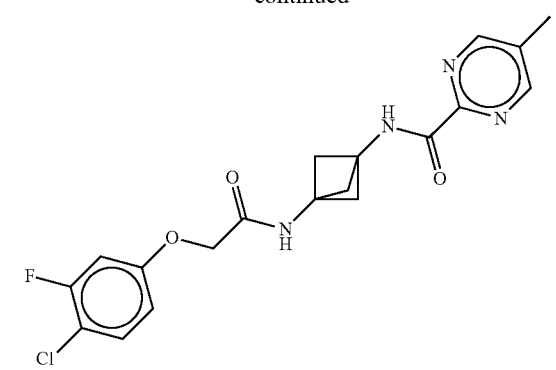
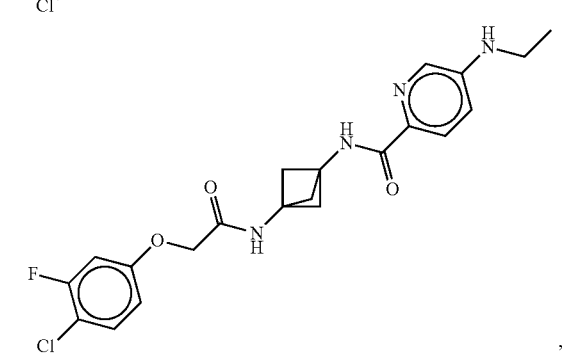
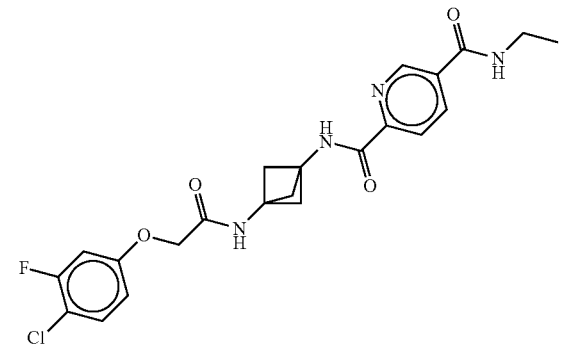
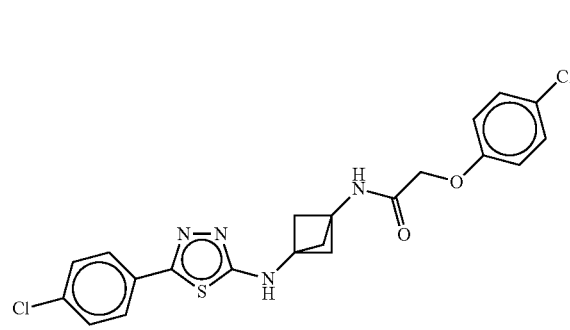
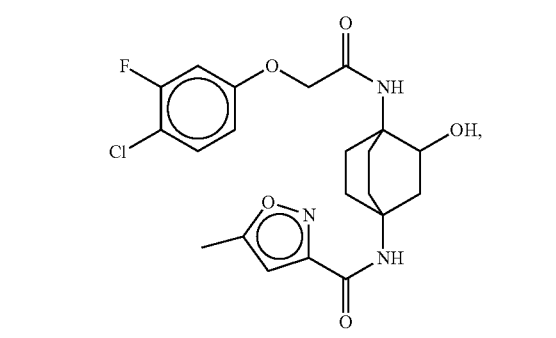
-continued
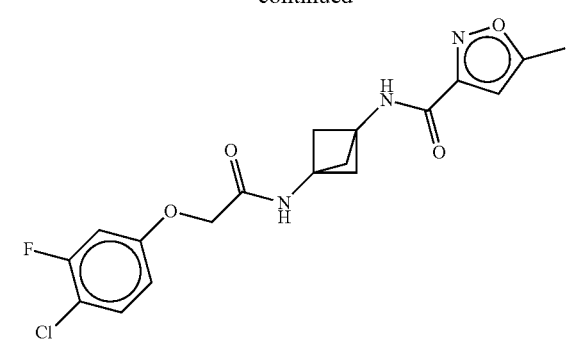
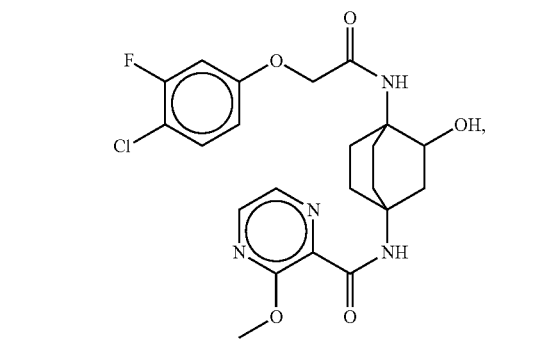
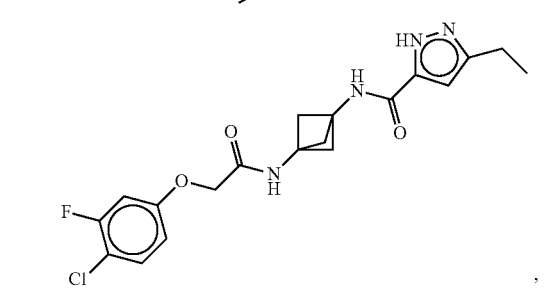
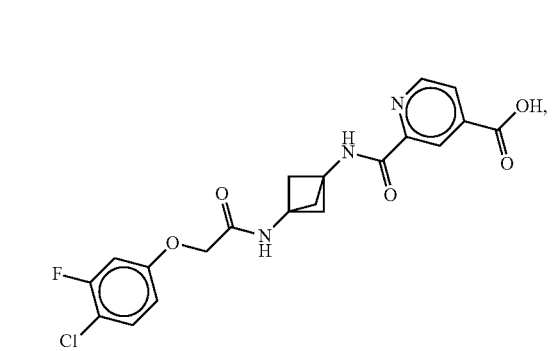
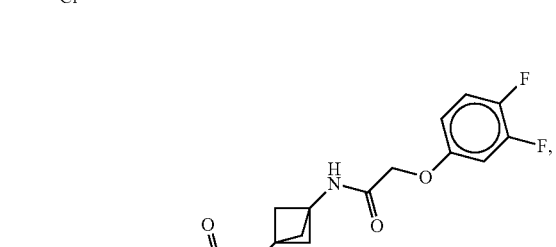
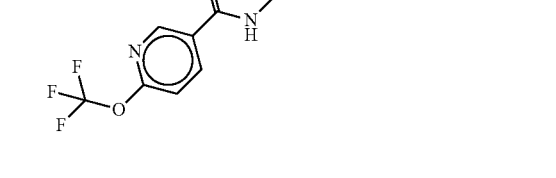

839
-continued
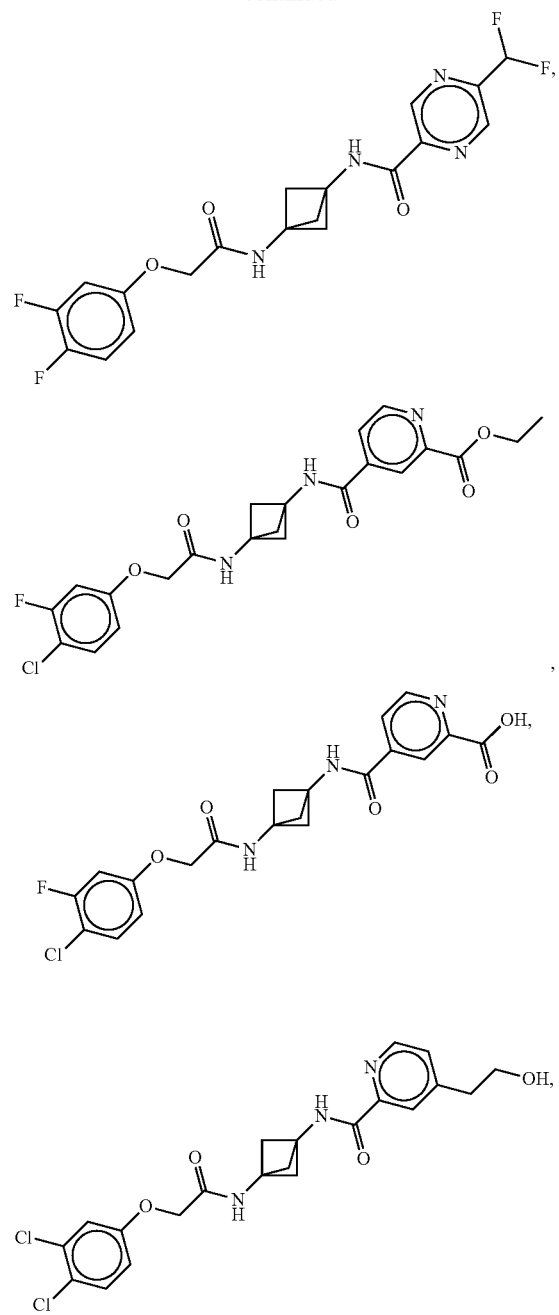
840
-continued
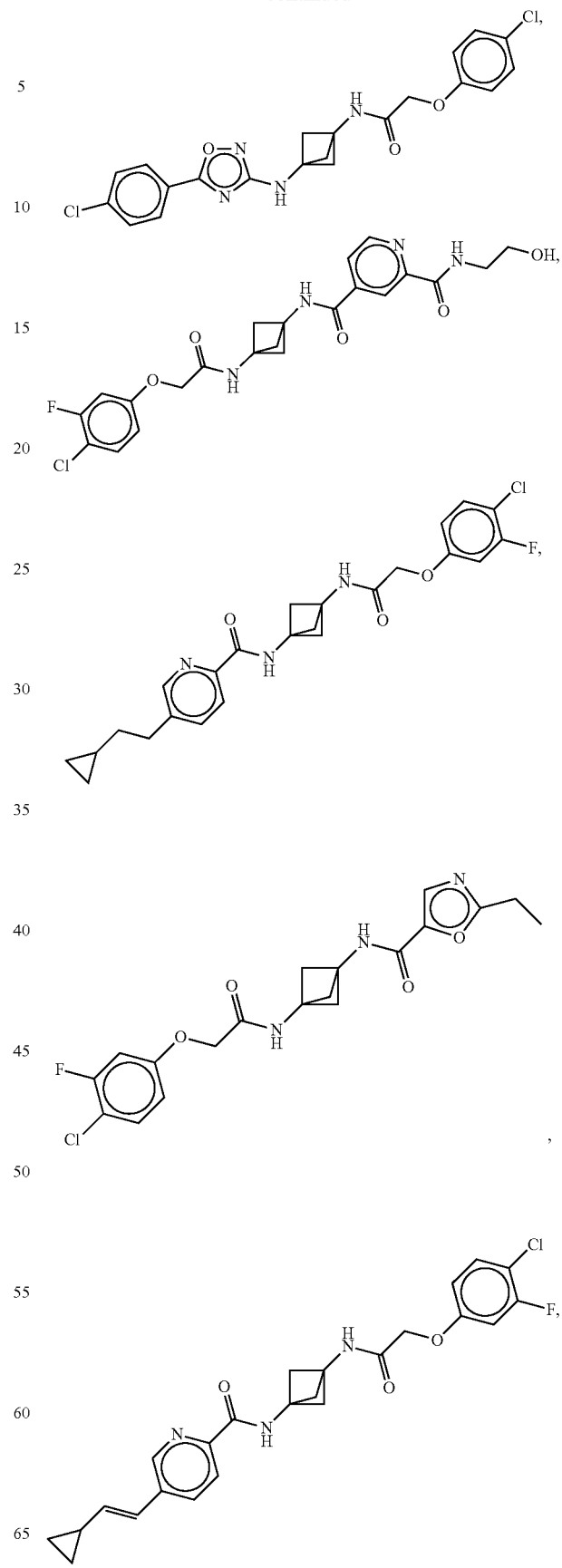

-continued
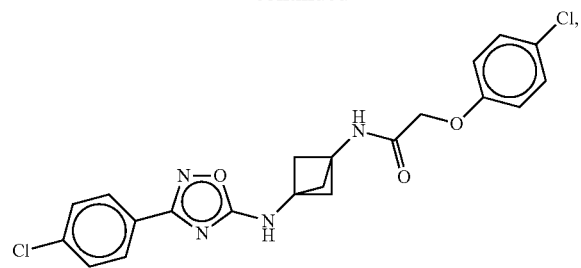
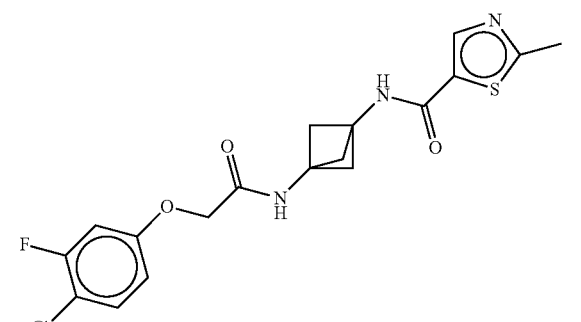
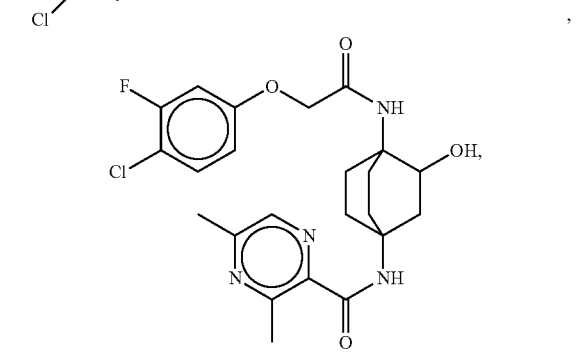
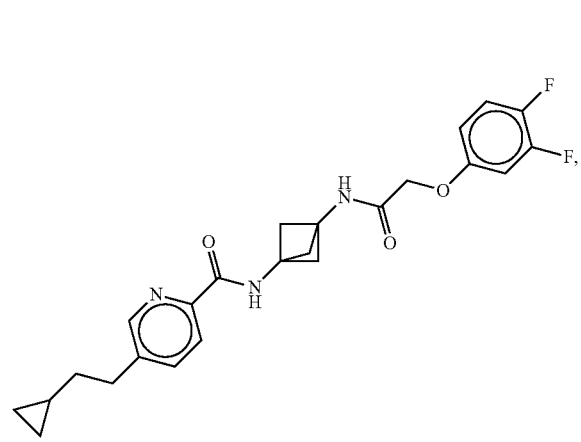
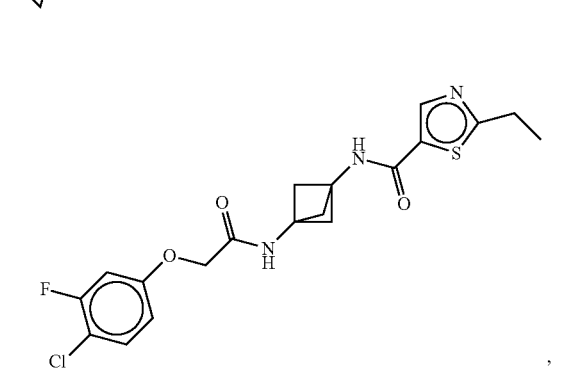
-continued
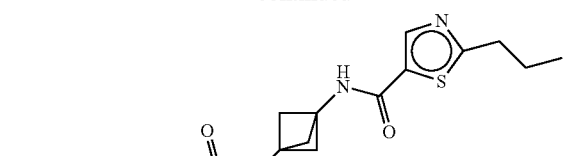
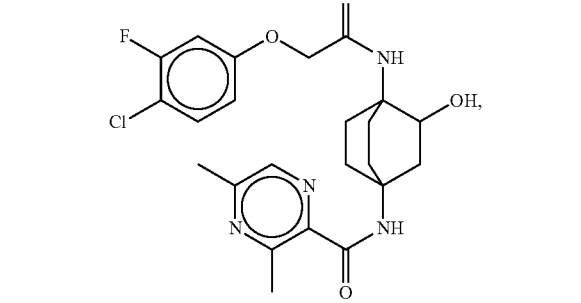
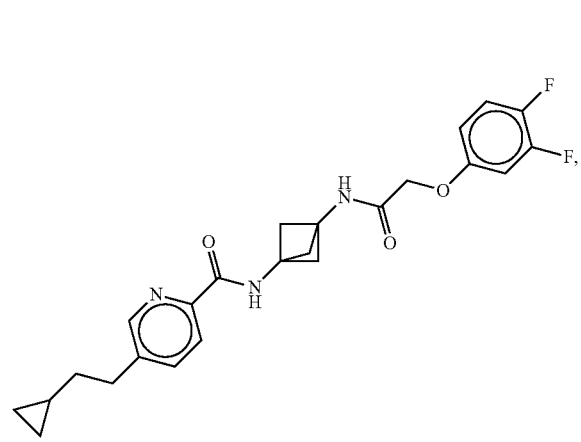
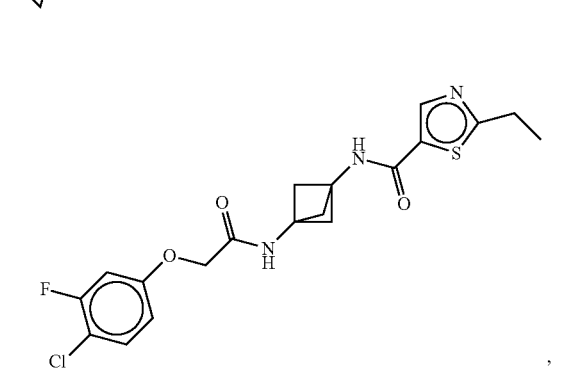

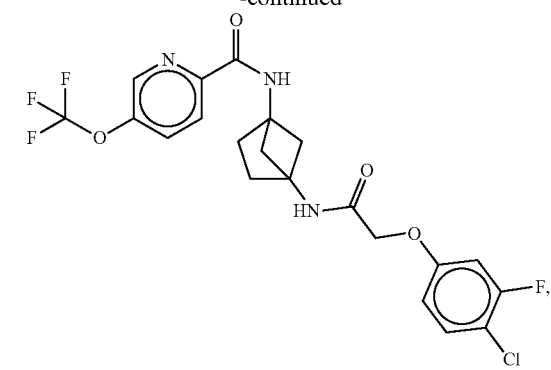
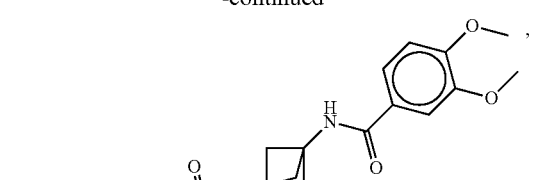
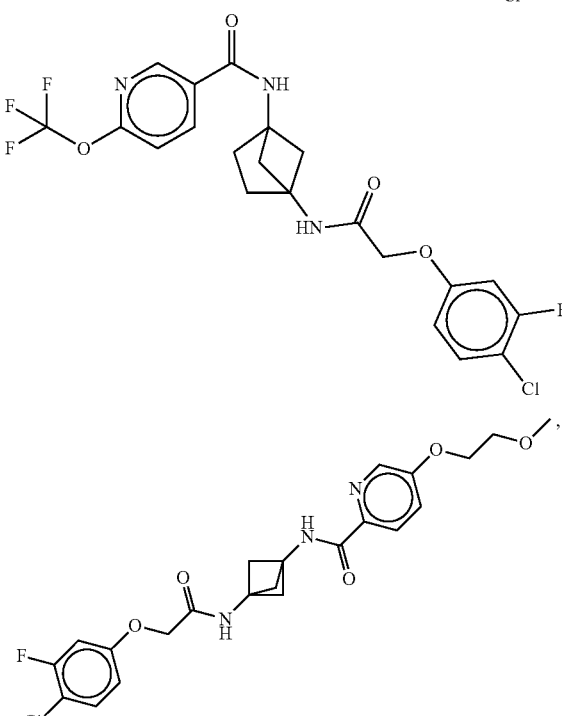
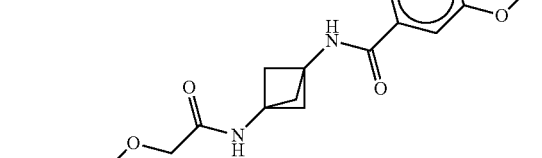
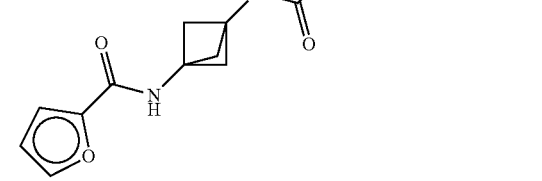
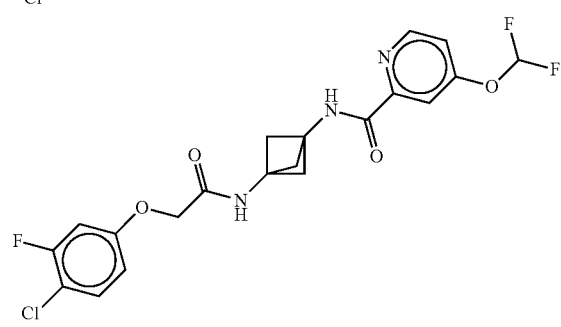
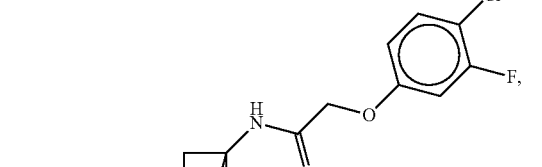
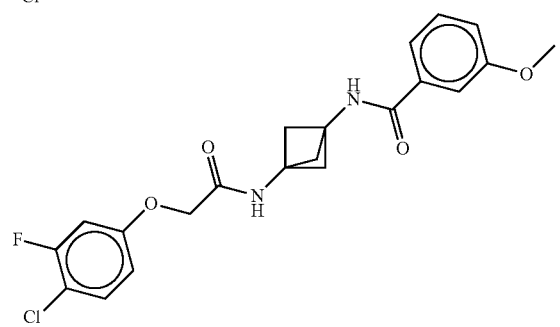
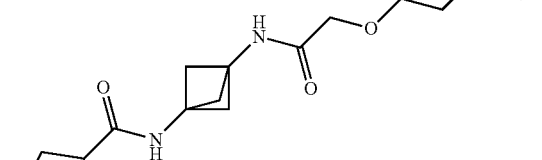

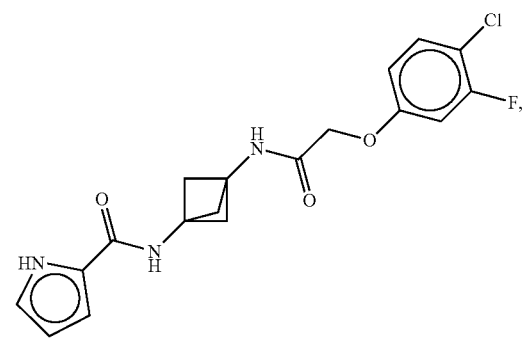
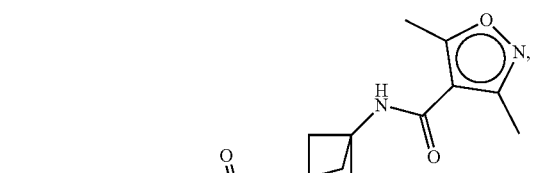
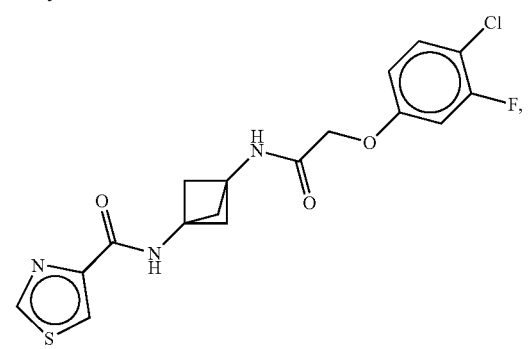
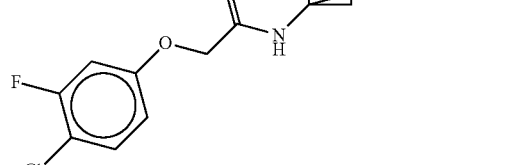
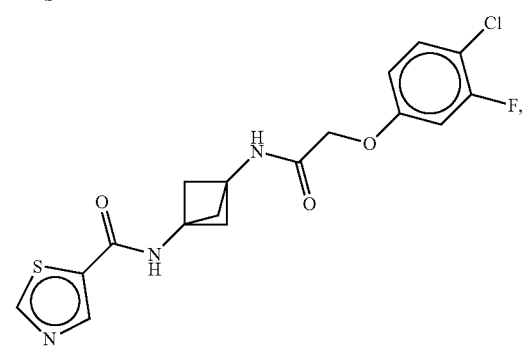
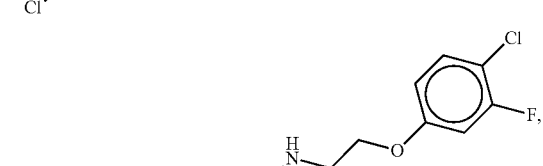
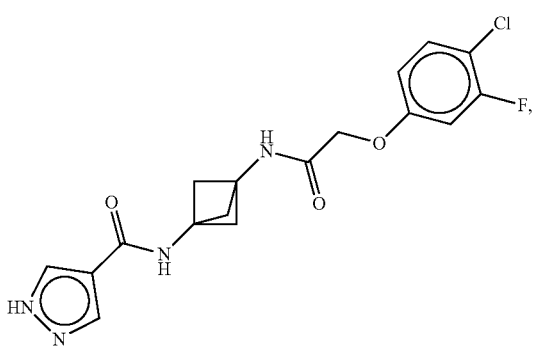
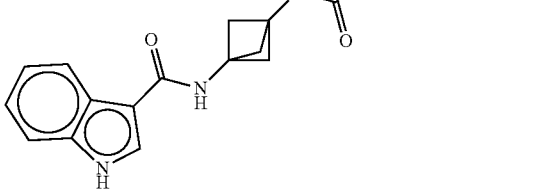
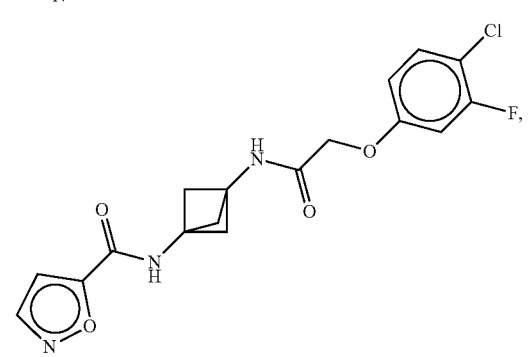
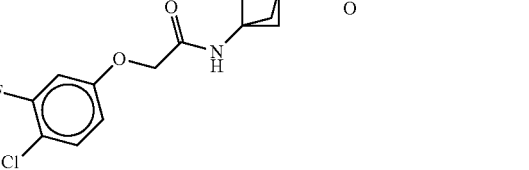

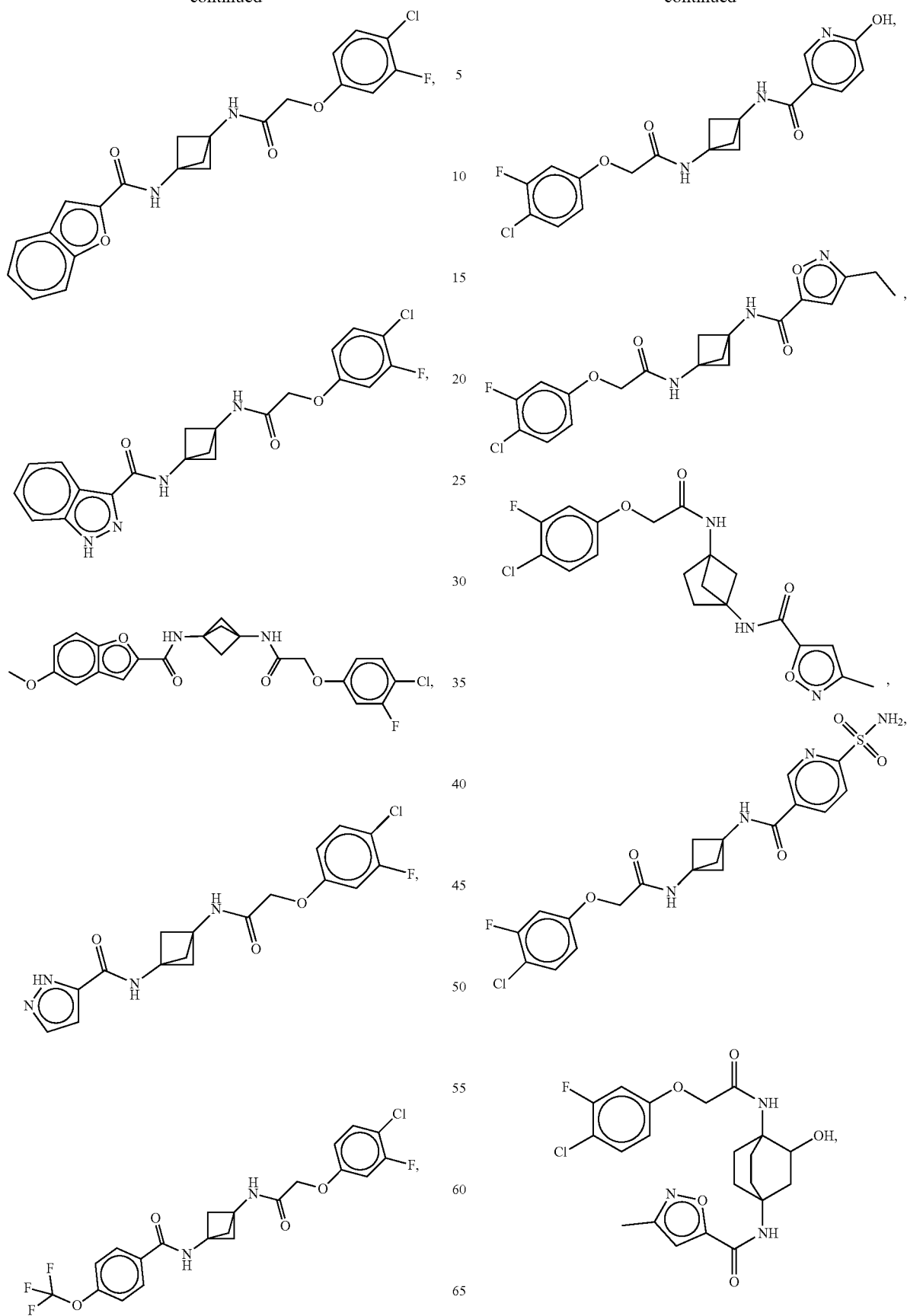

-continued
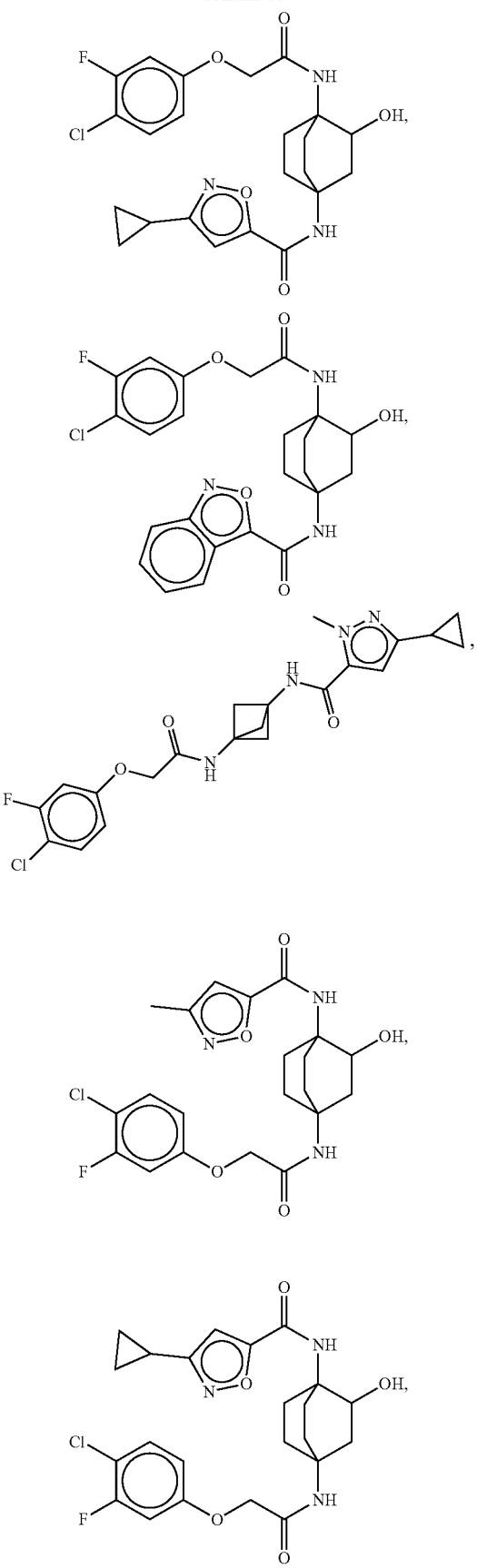
-continued
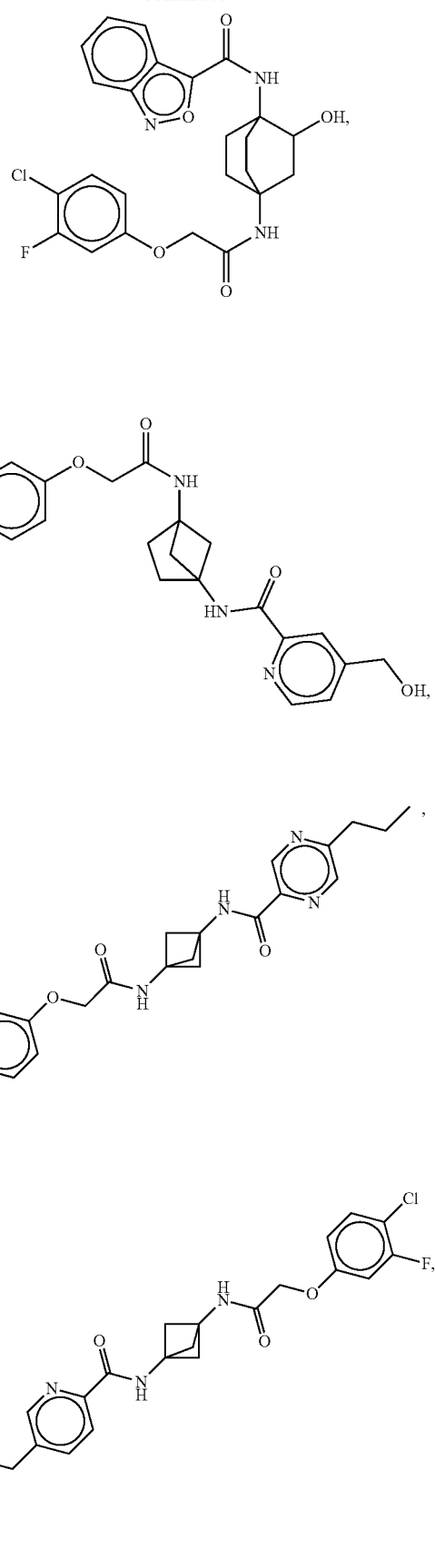

851
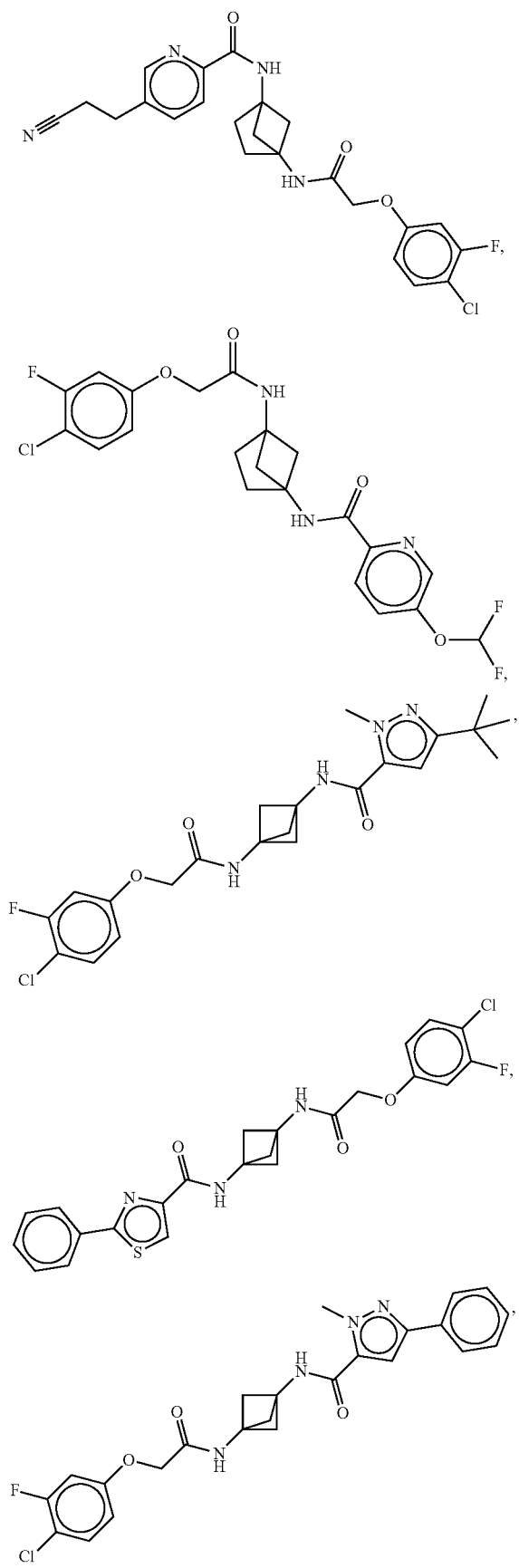
852
-continued
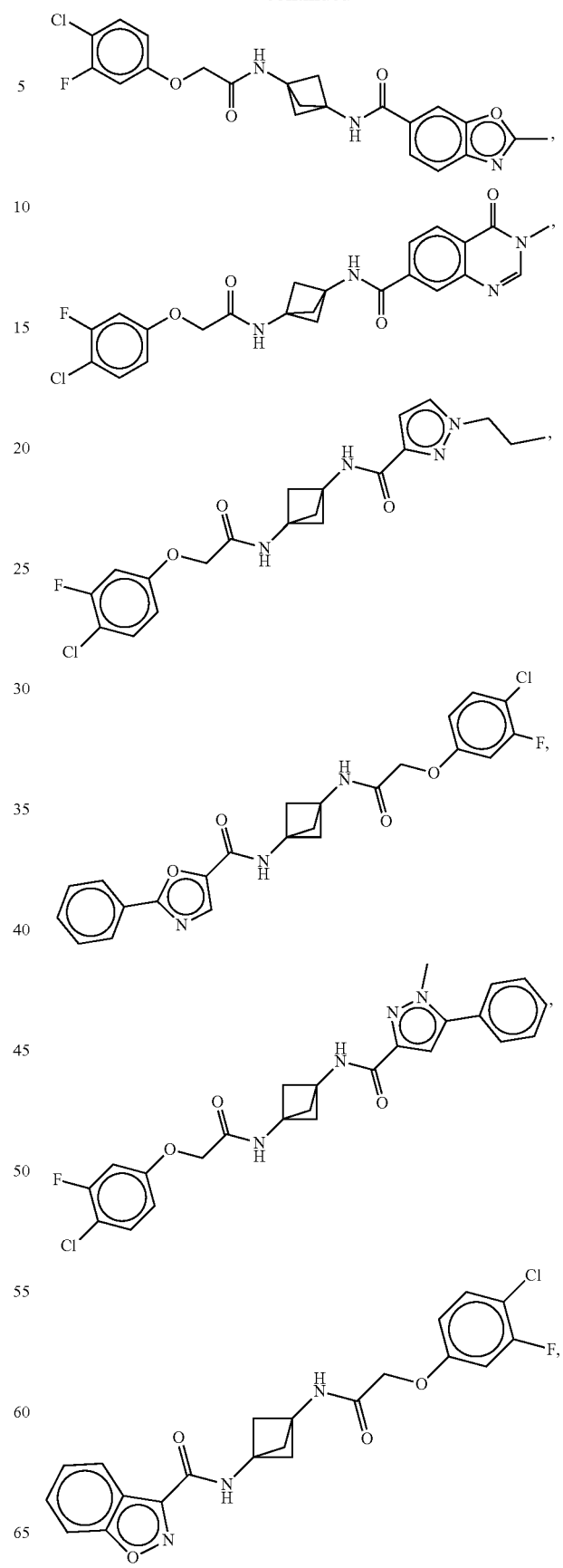

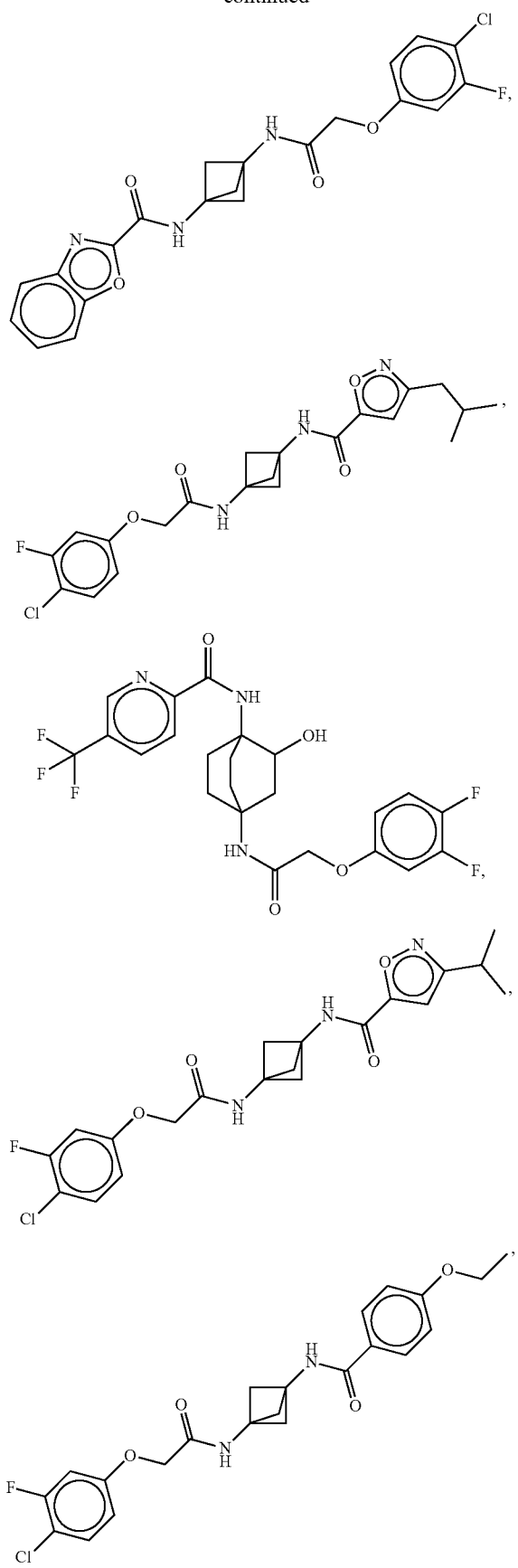
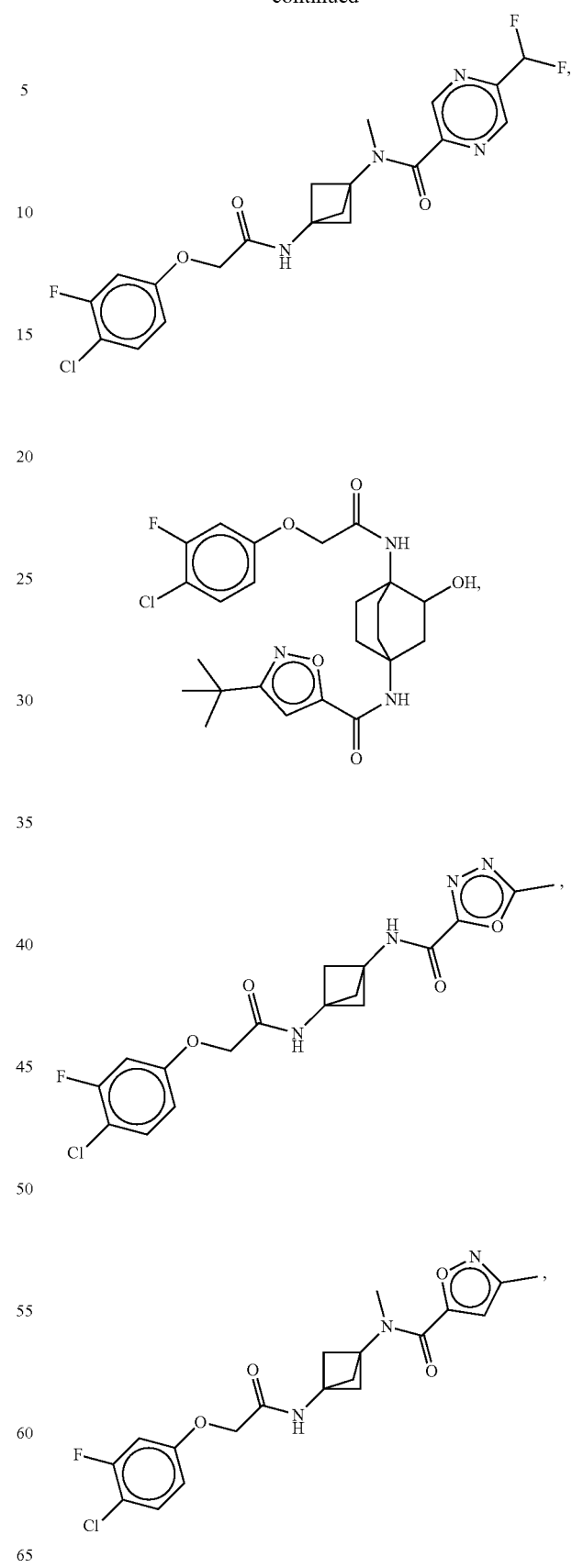

-continued
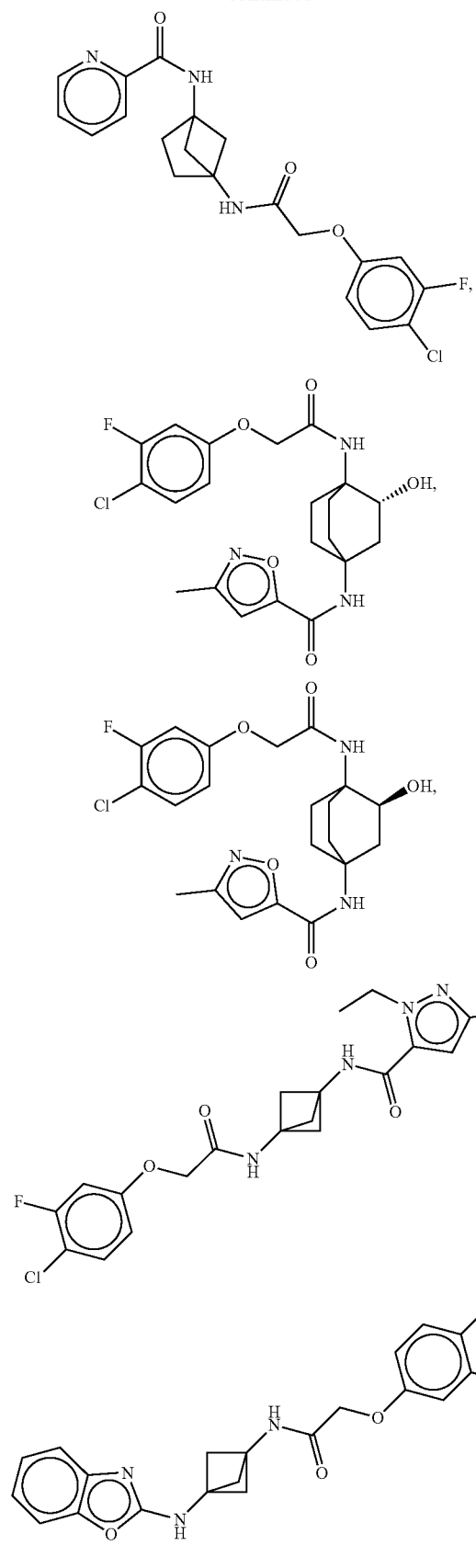
-continued
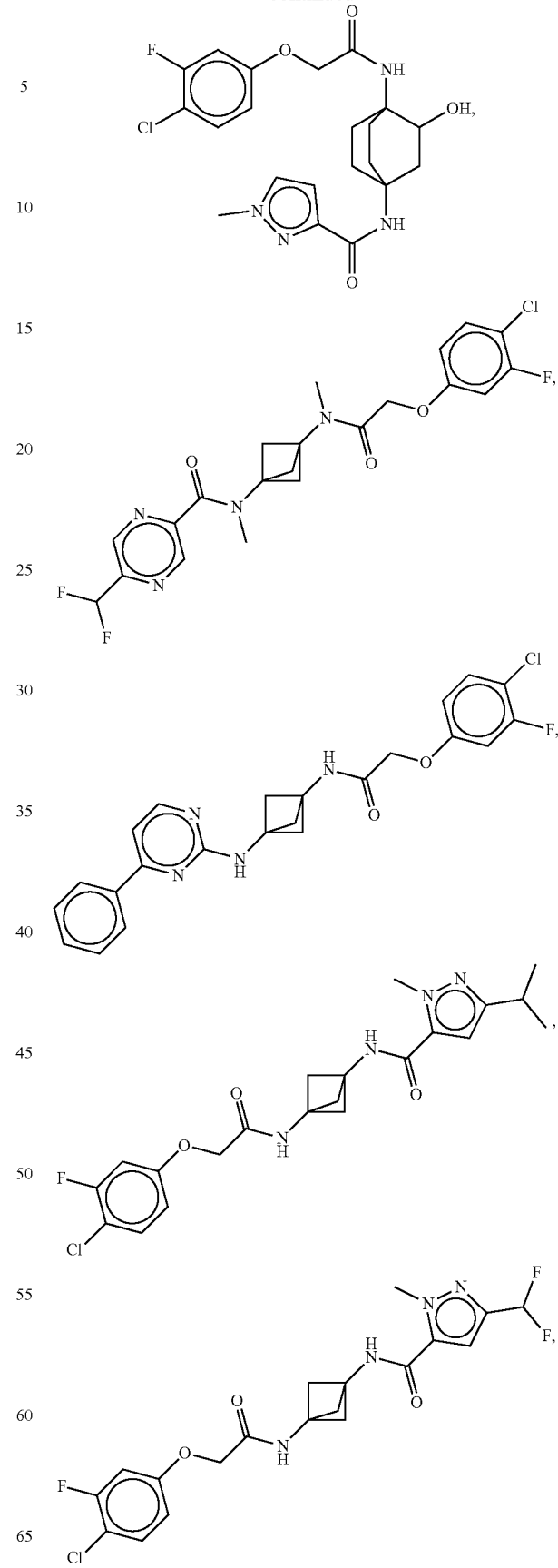

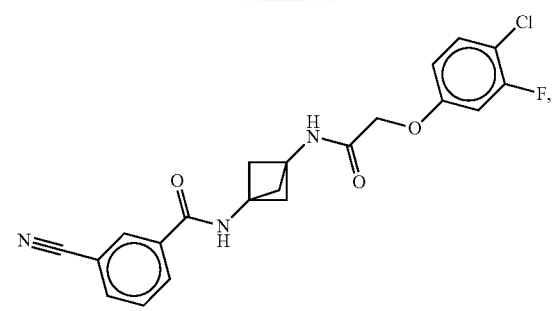
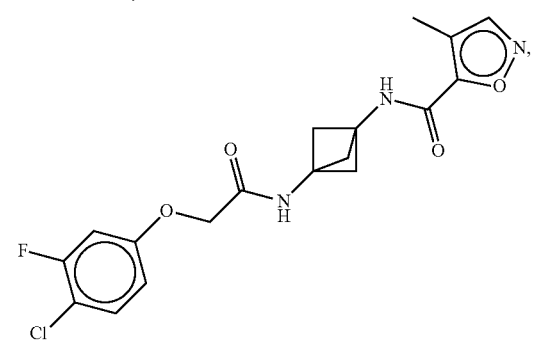
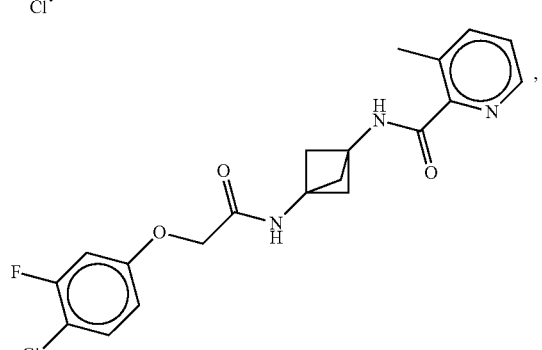
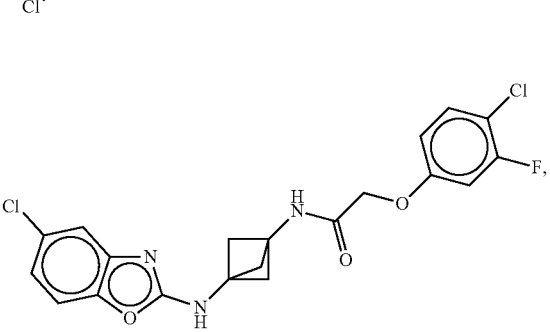
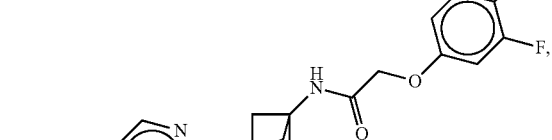
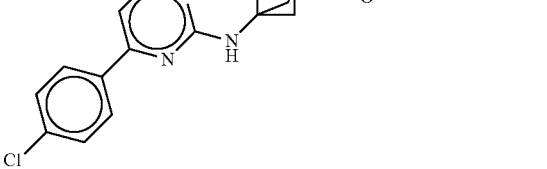
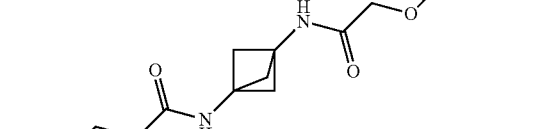
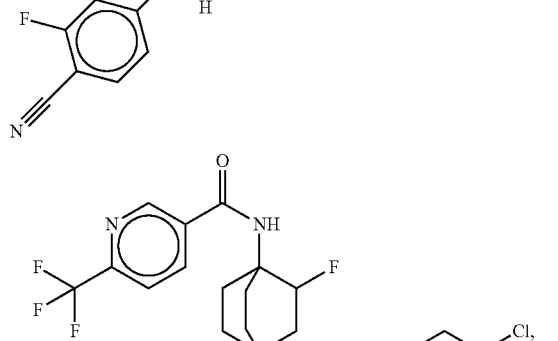
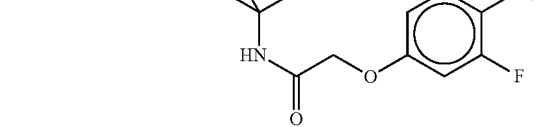
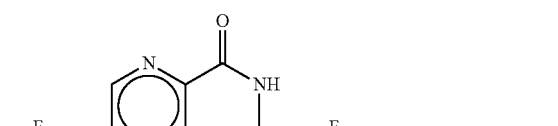
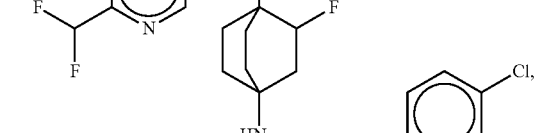
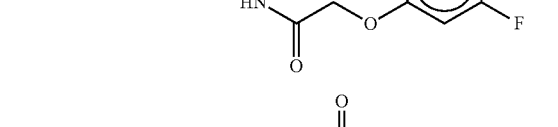
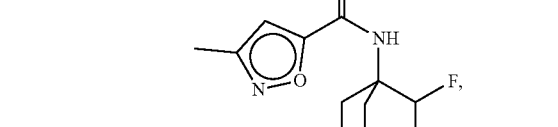
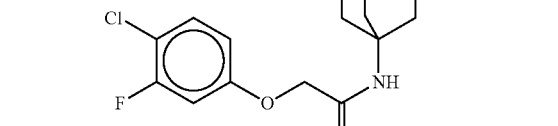
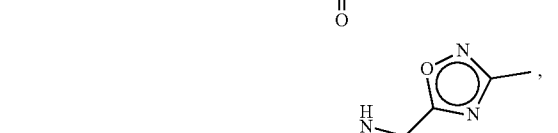
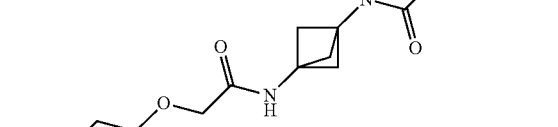

859
-continued
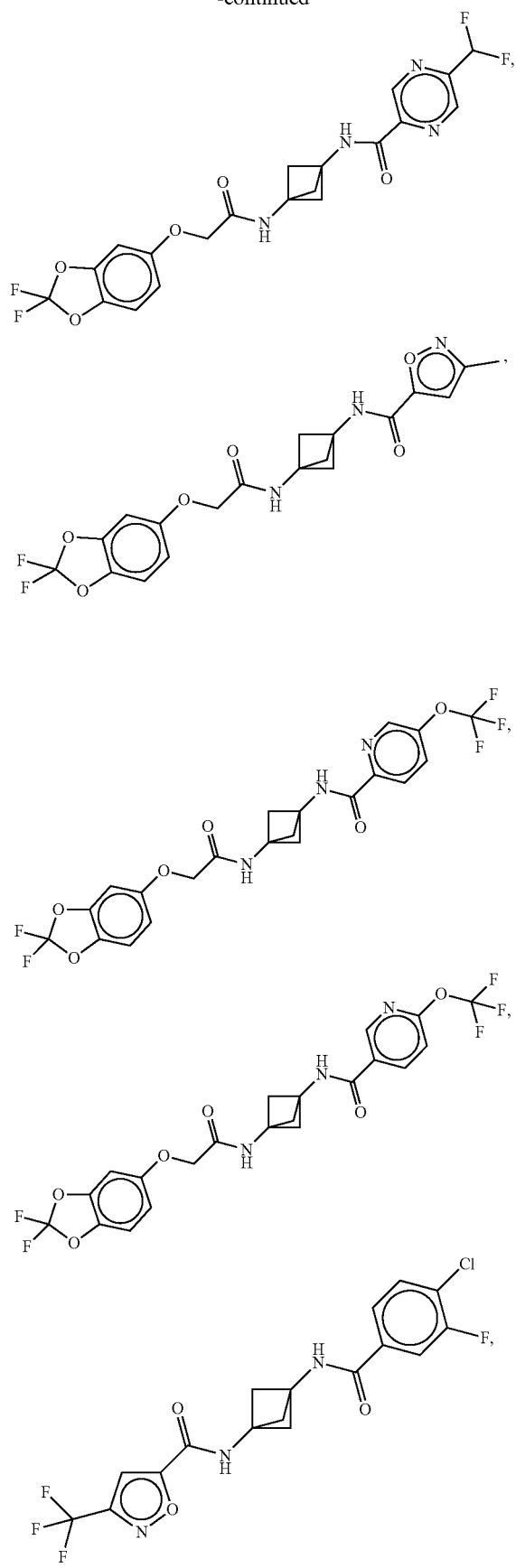
860
-continued
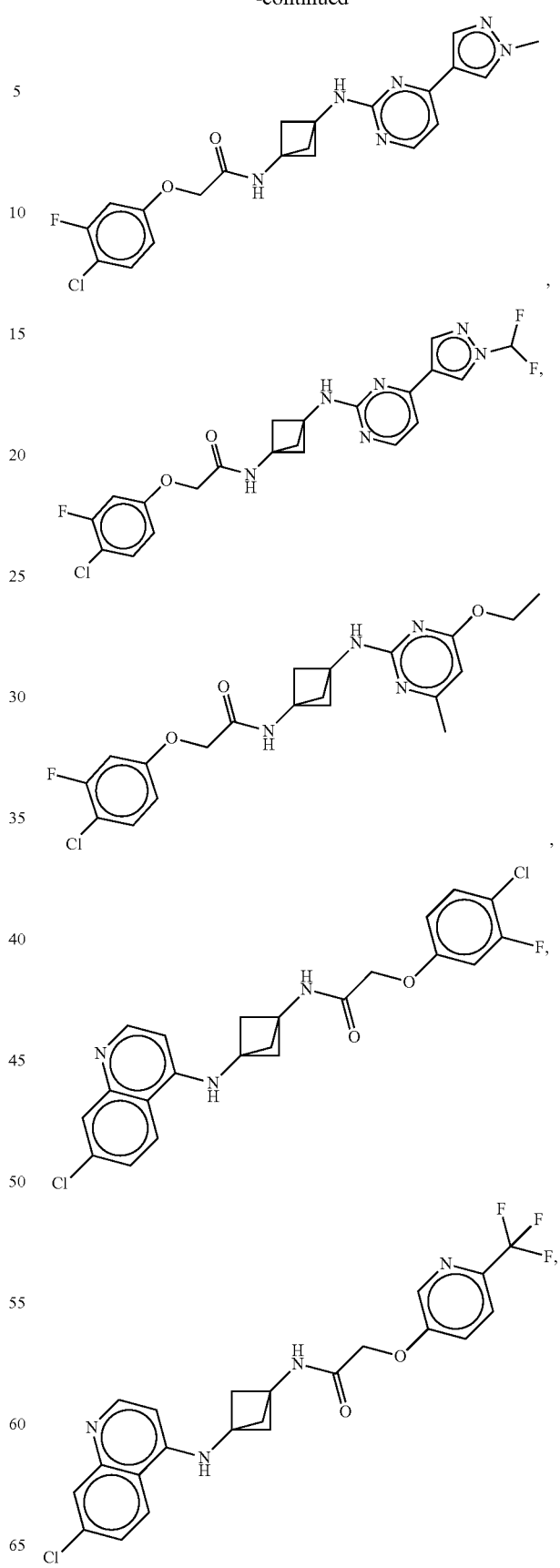

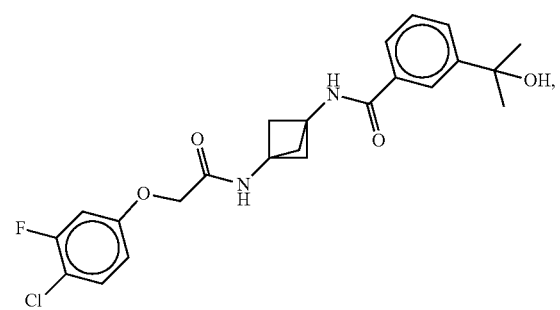
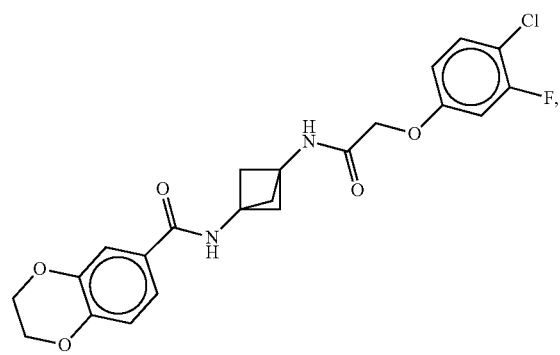
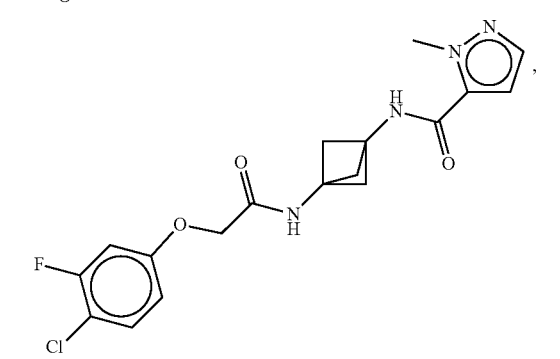
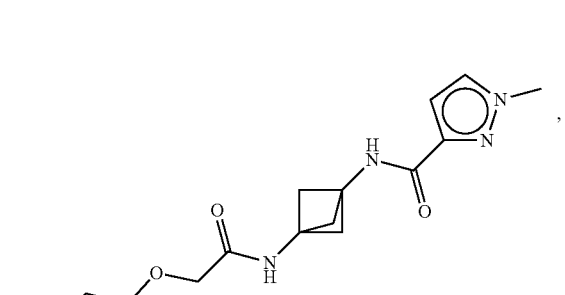
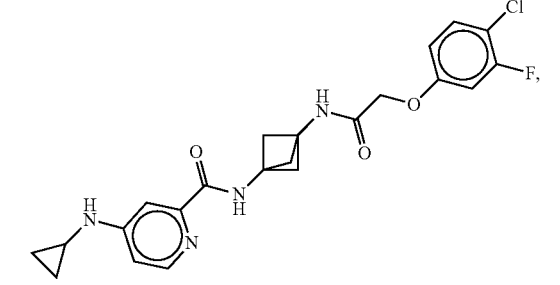
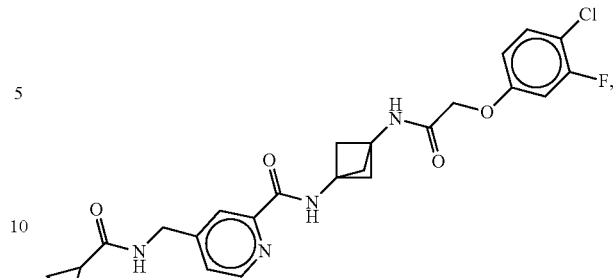
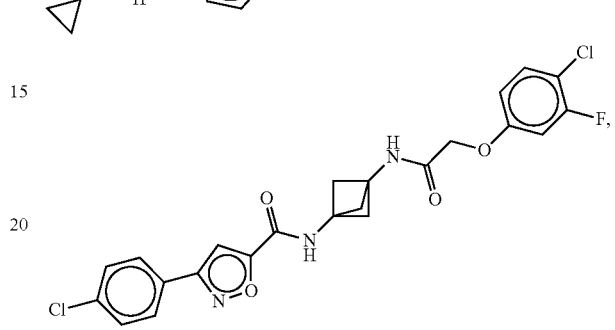
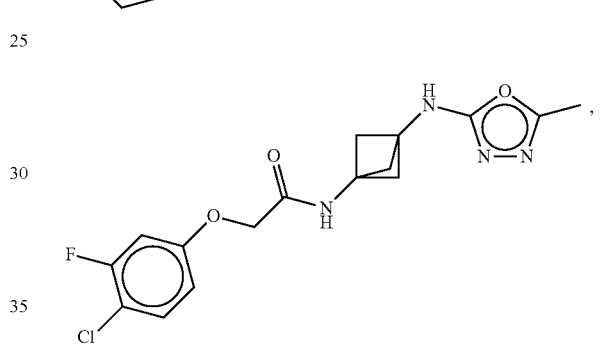
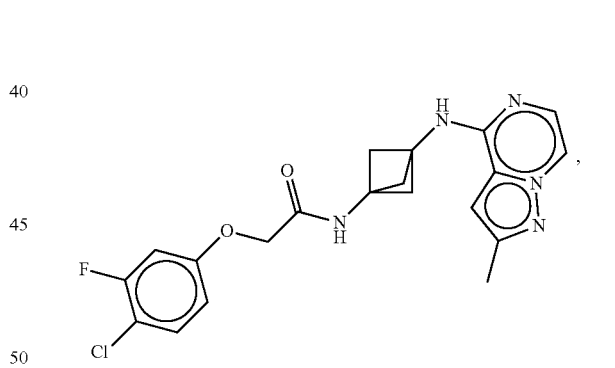
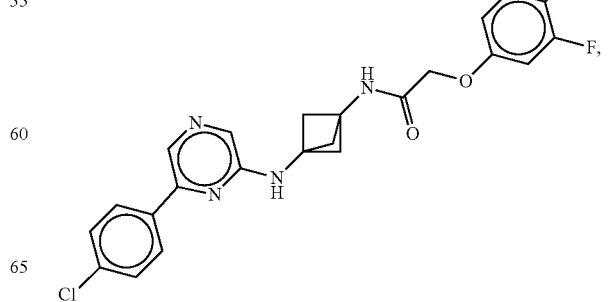

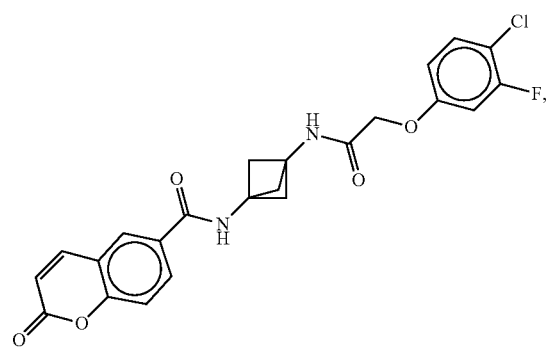
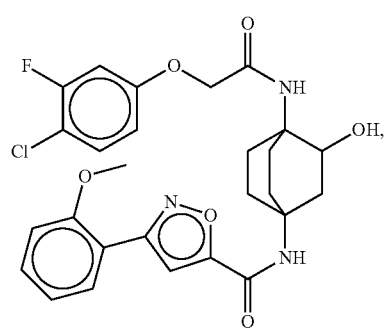
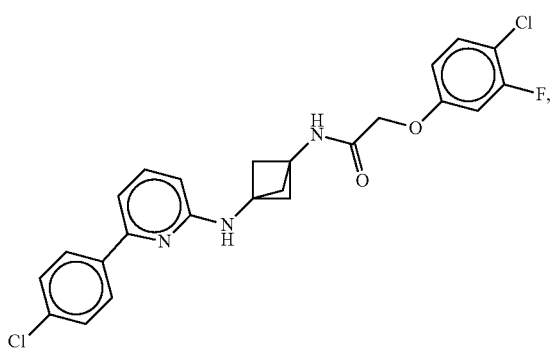
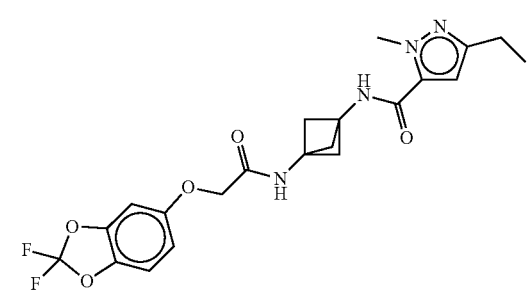
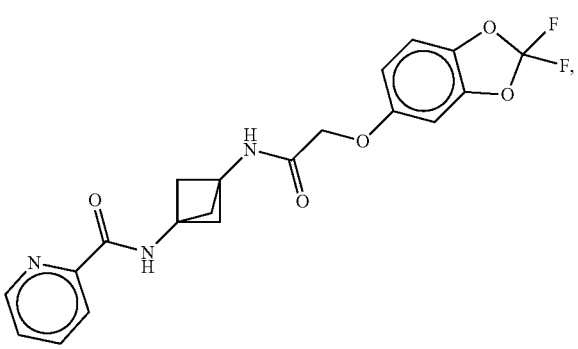
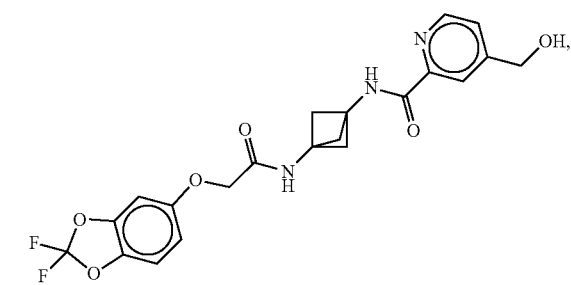
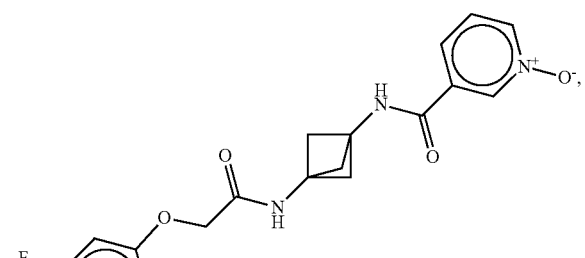
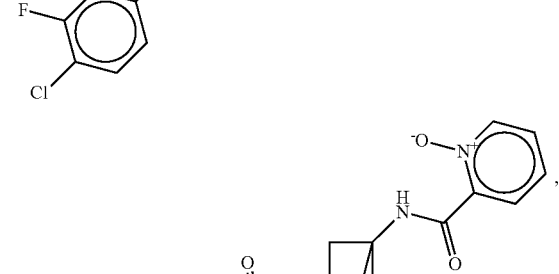
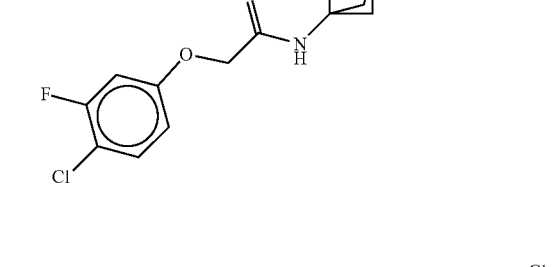
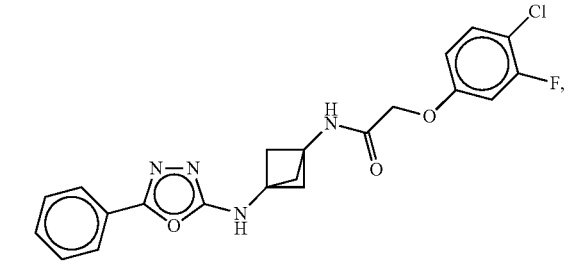
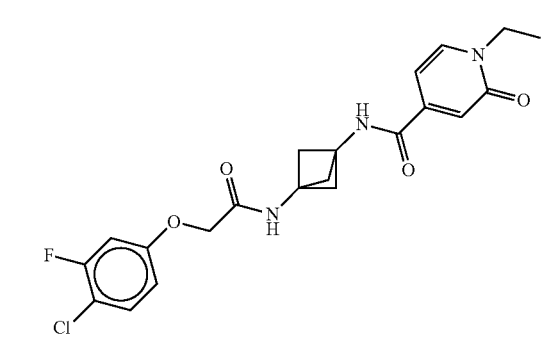

865
-continued
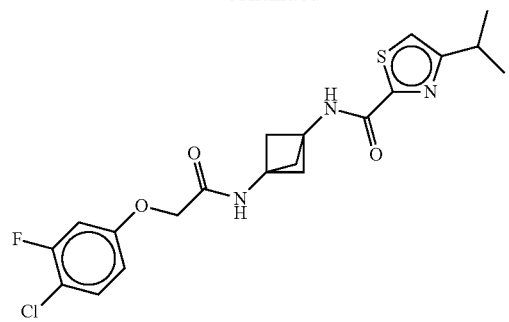
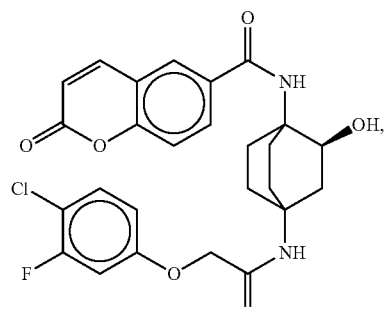
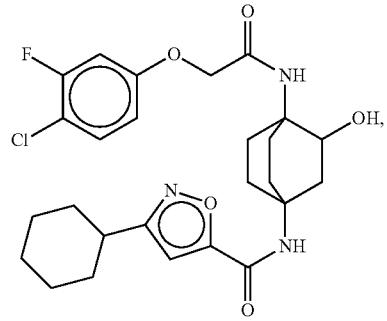
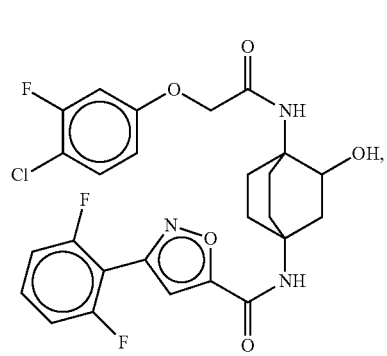
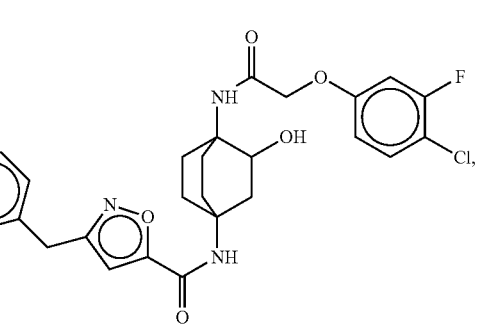
866
-continued
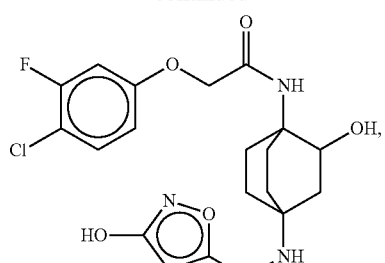
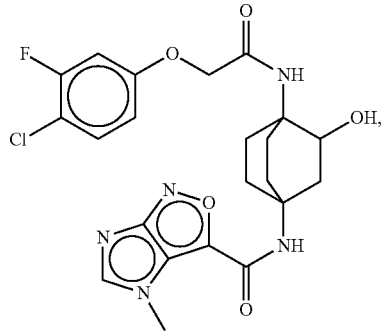
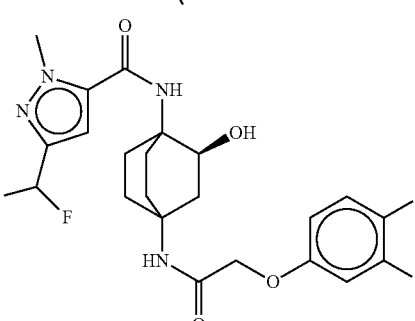
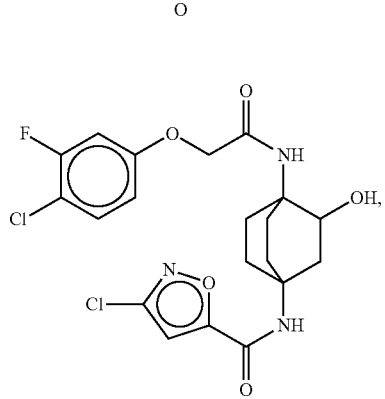
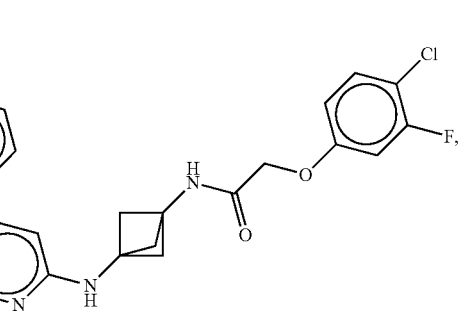

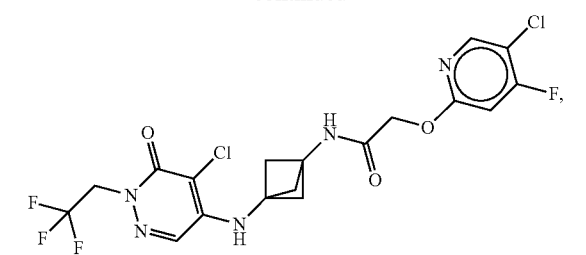
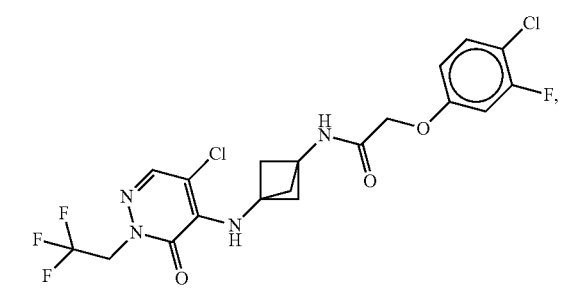
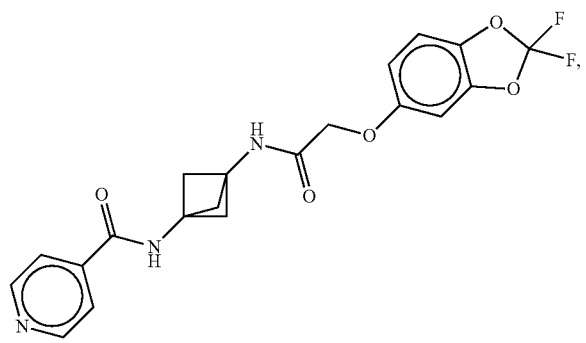
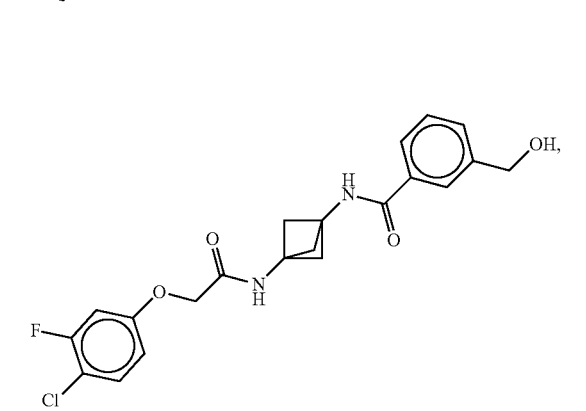
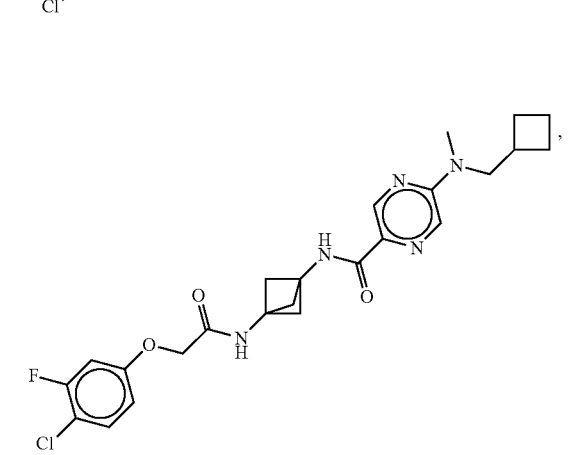
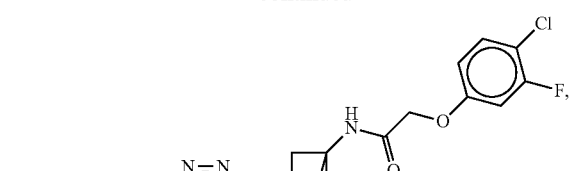
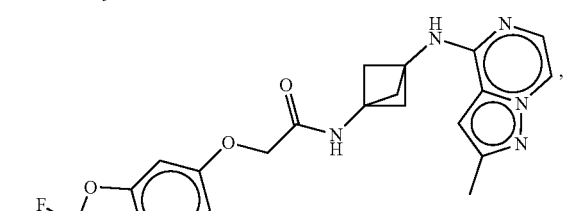
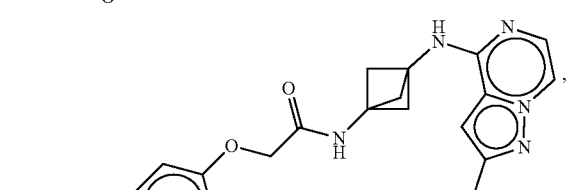
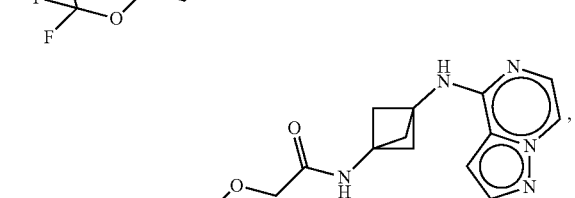
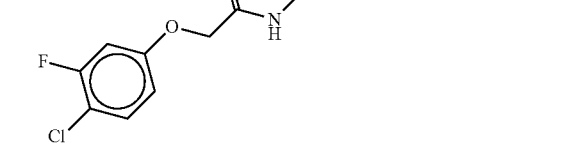
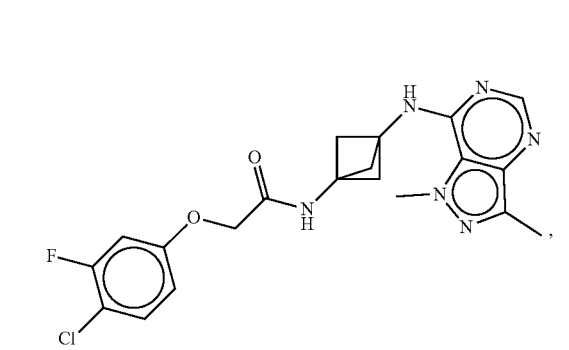

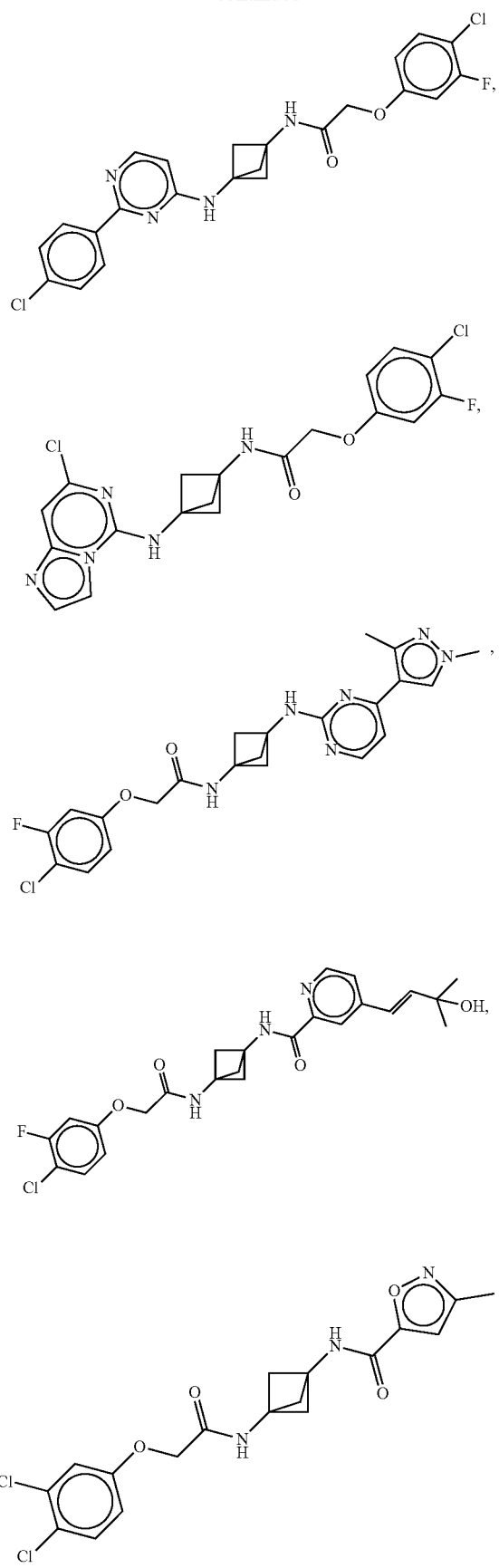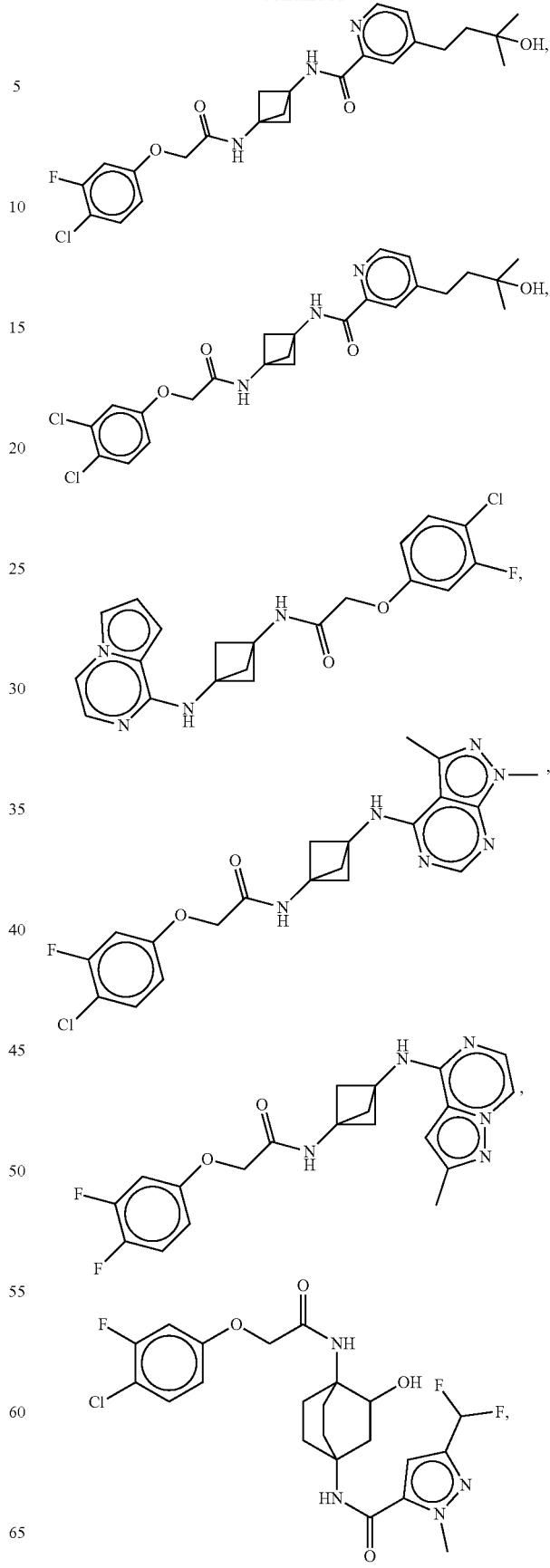

871
-continued
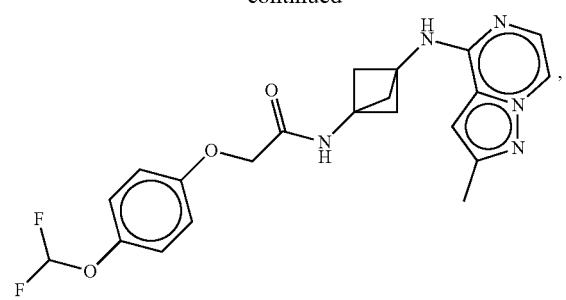
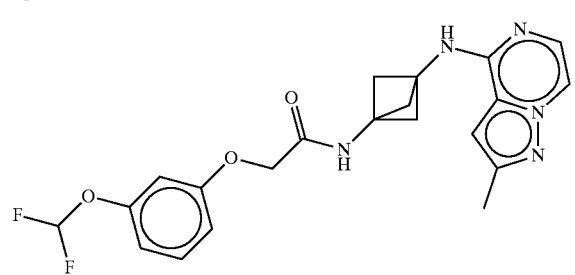
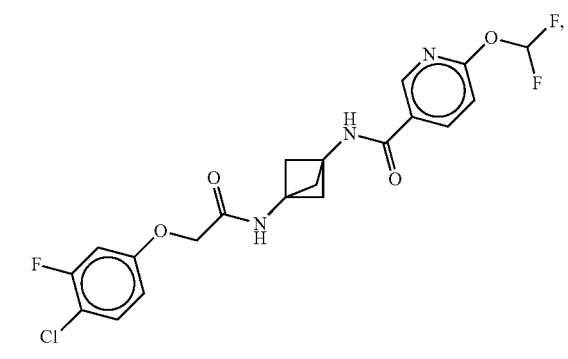
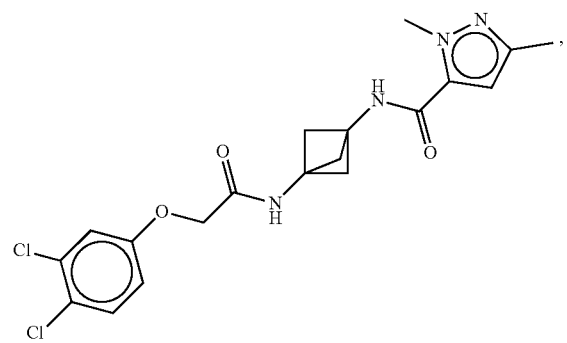
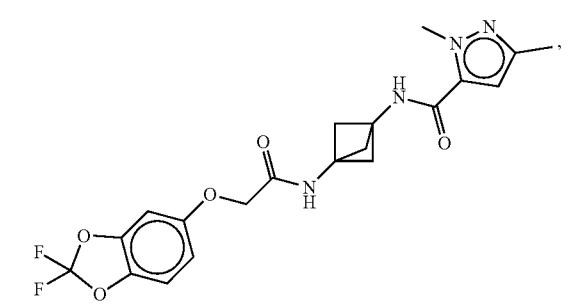
872
-continued
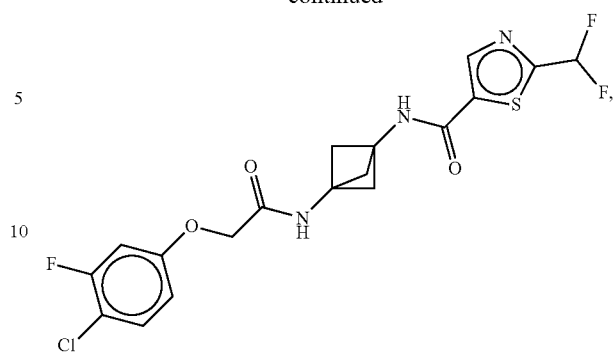
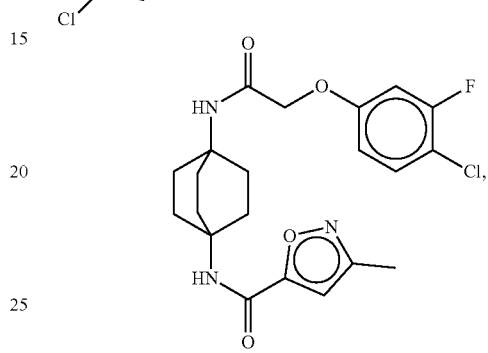
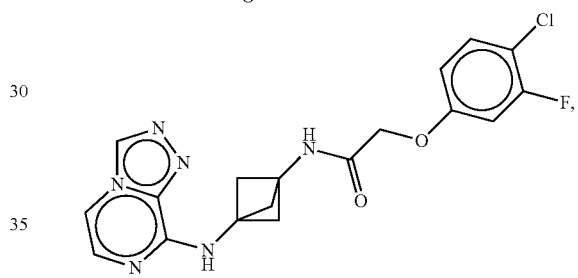
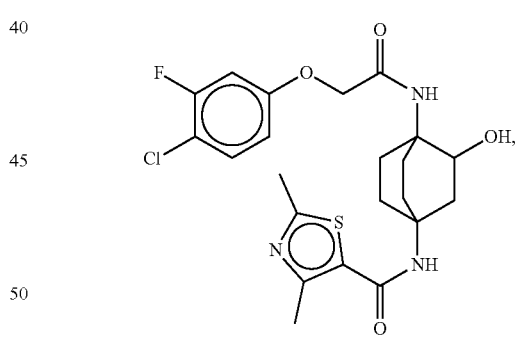
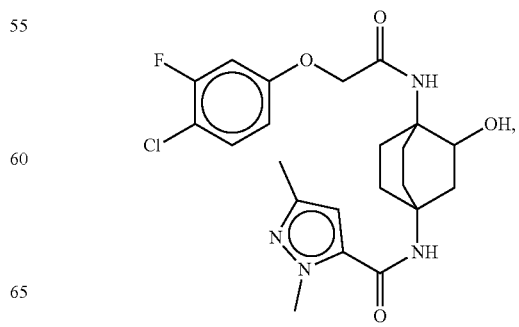

873
-continued
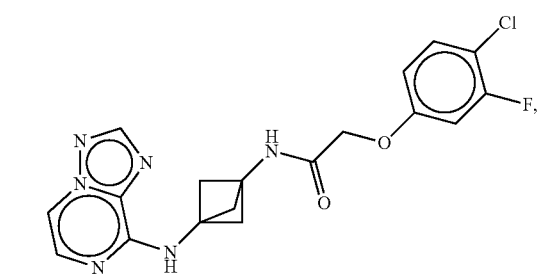
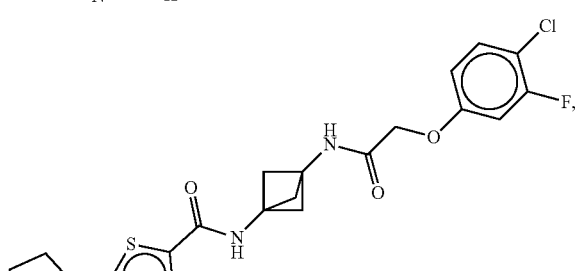
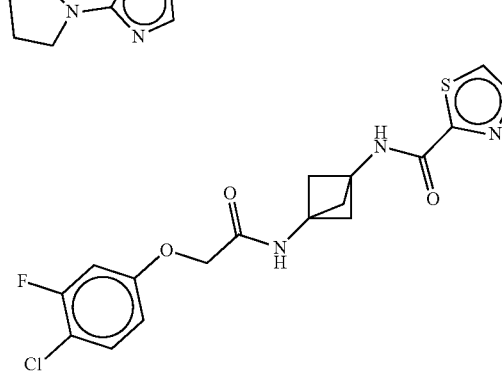
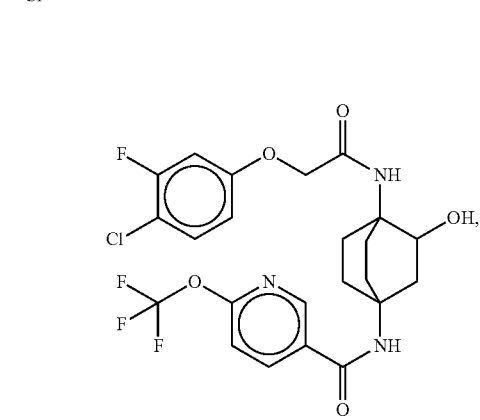
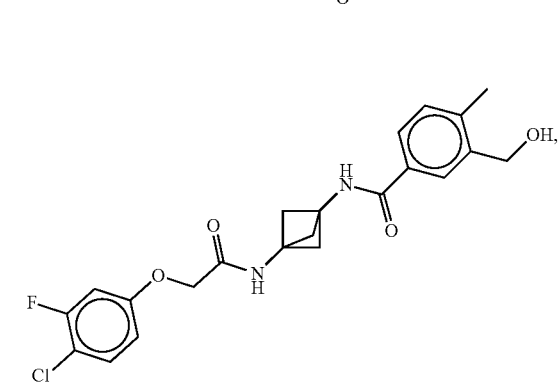
874
-continued
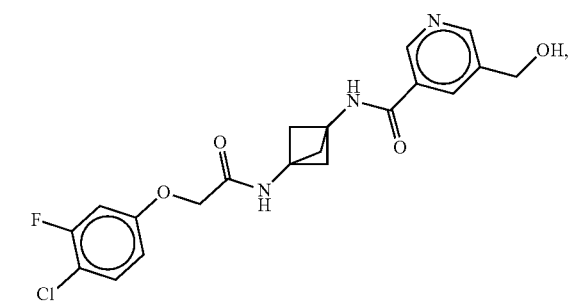
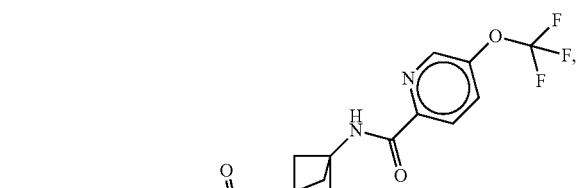
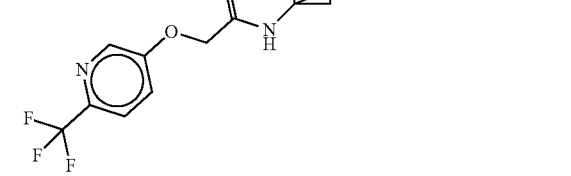
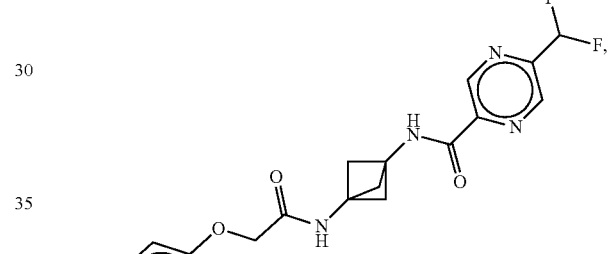
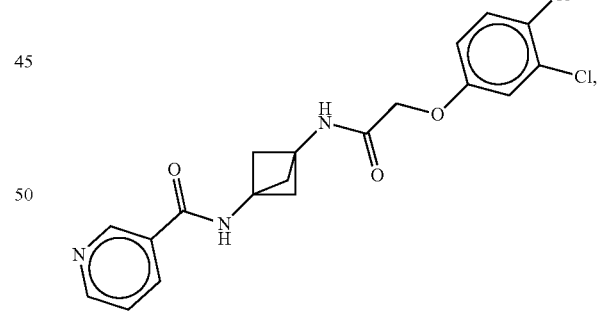
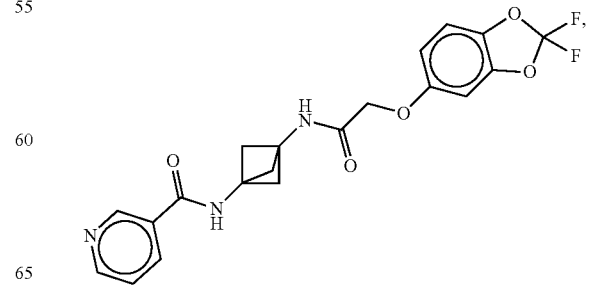

-continued
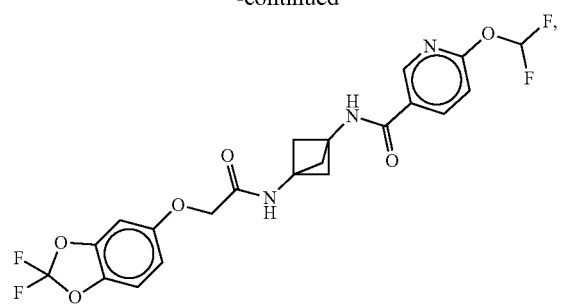
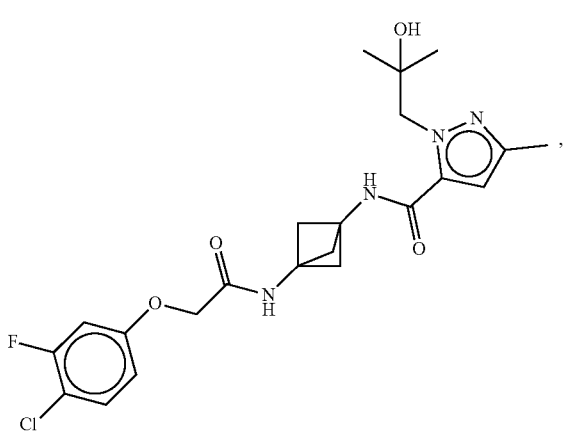
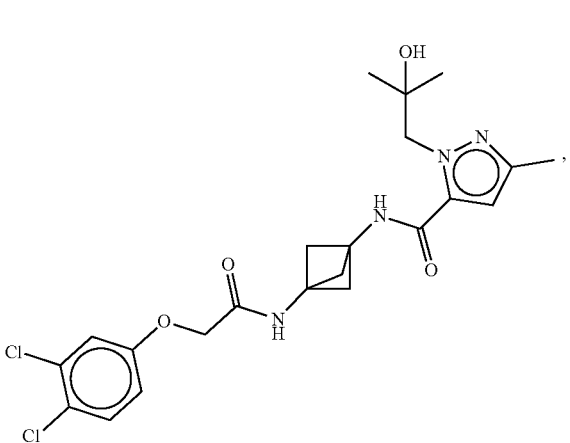
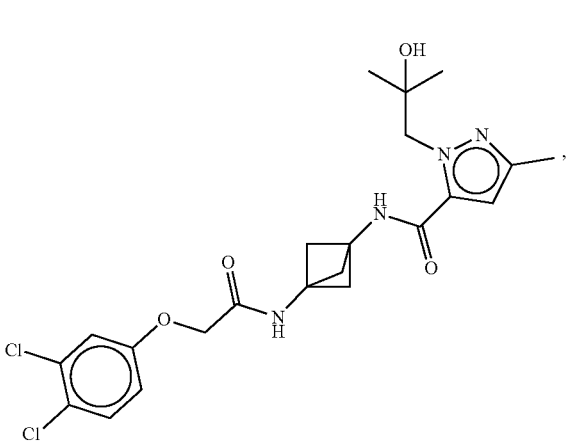
-continued
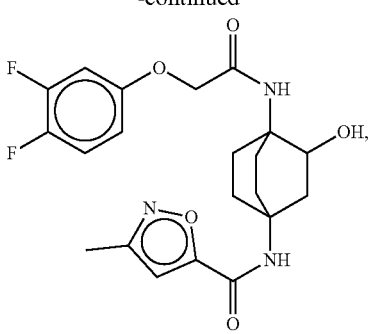
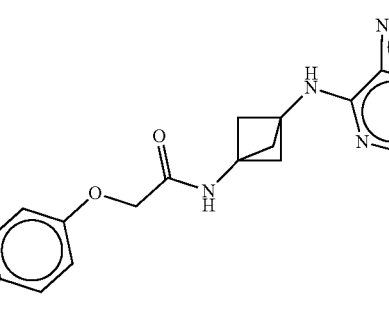
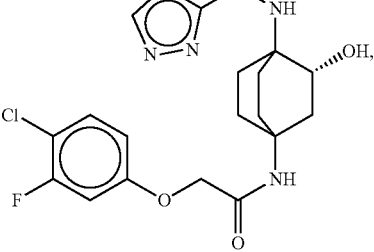
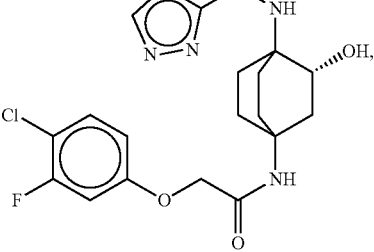

877
-continued
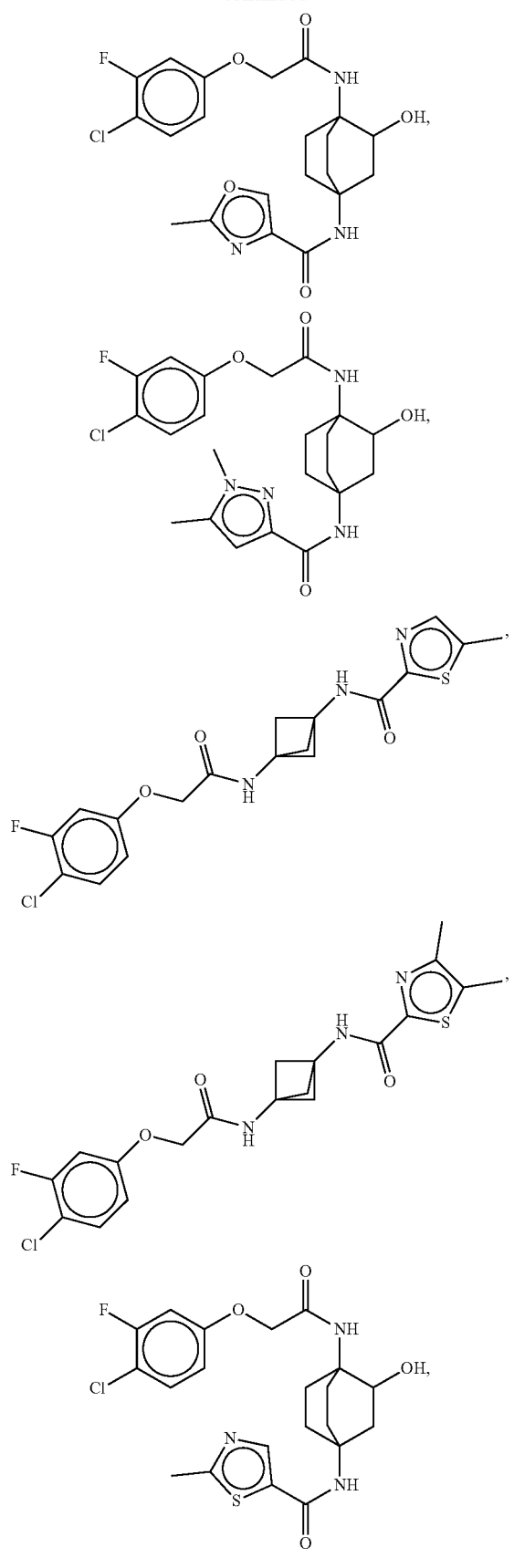
878
-continued
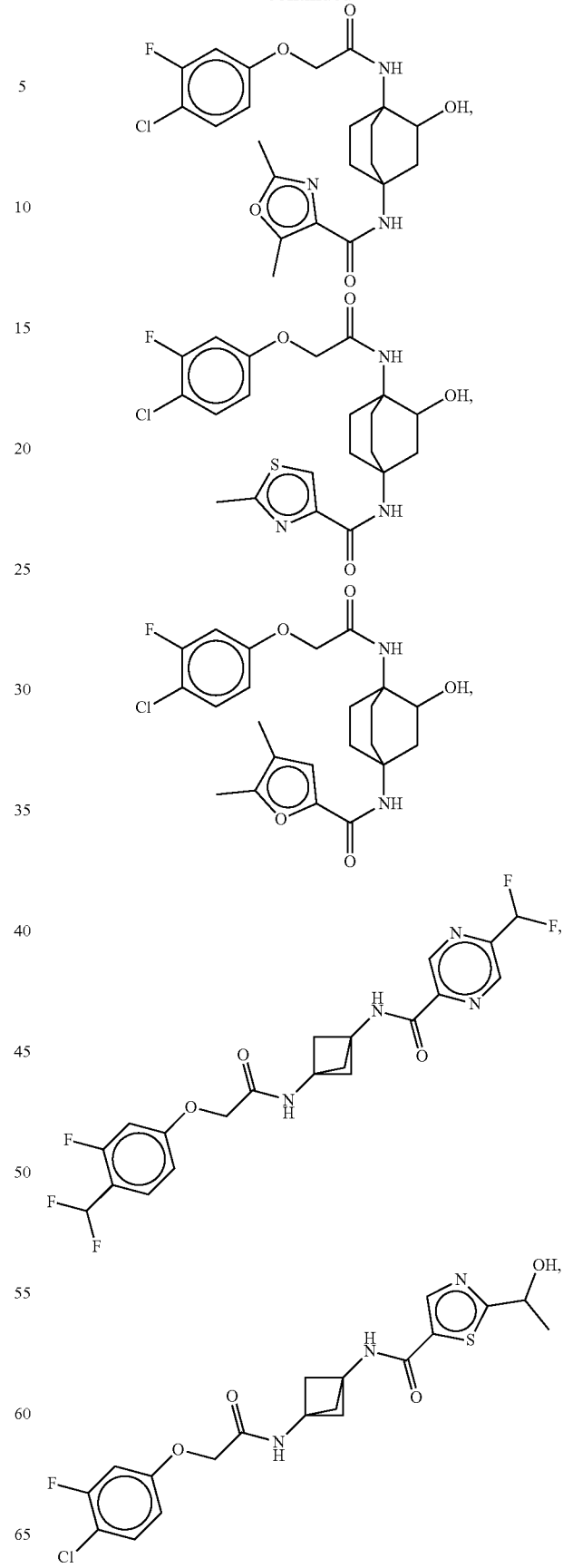

879
-continued
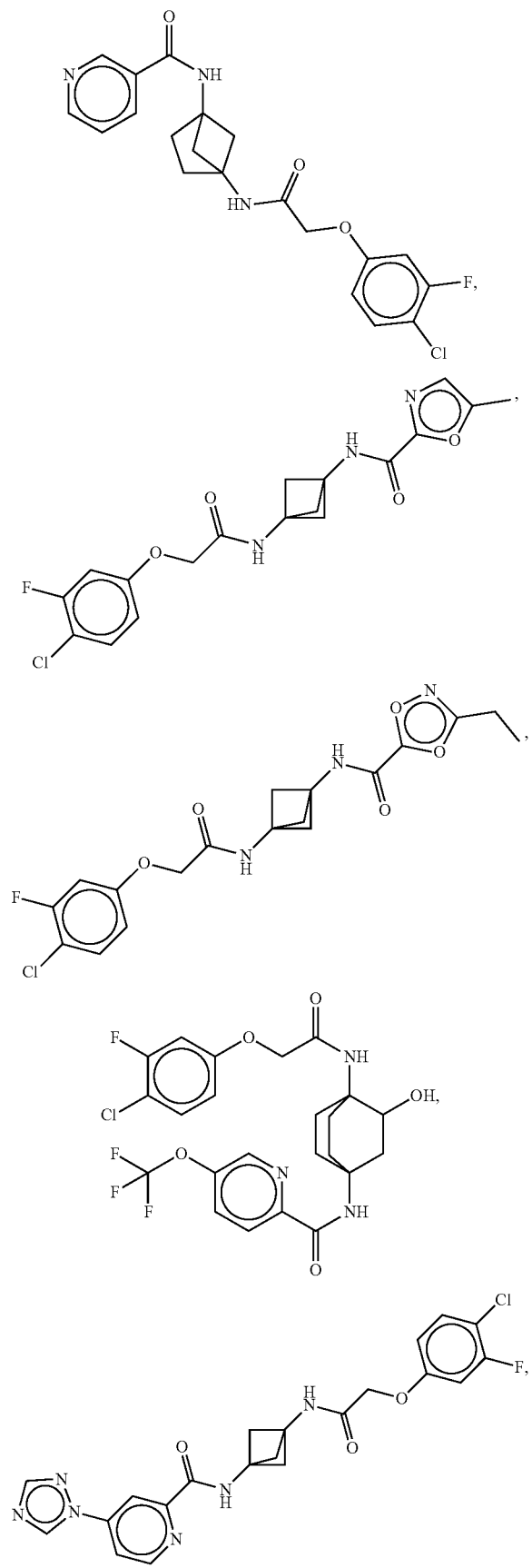
880
-continued
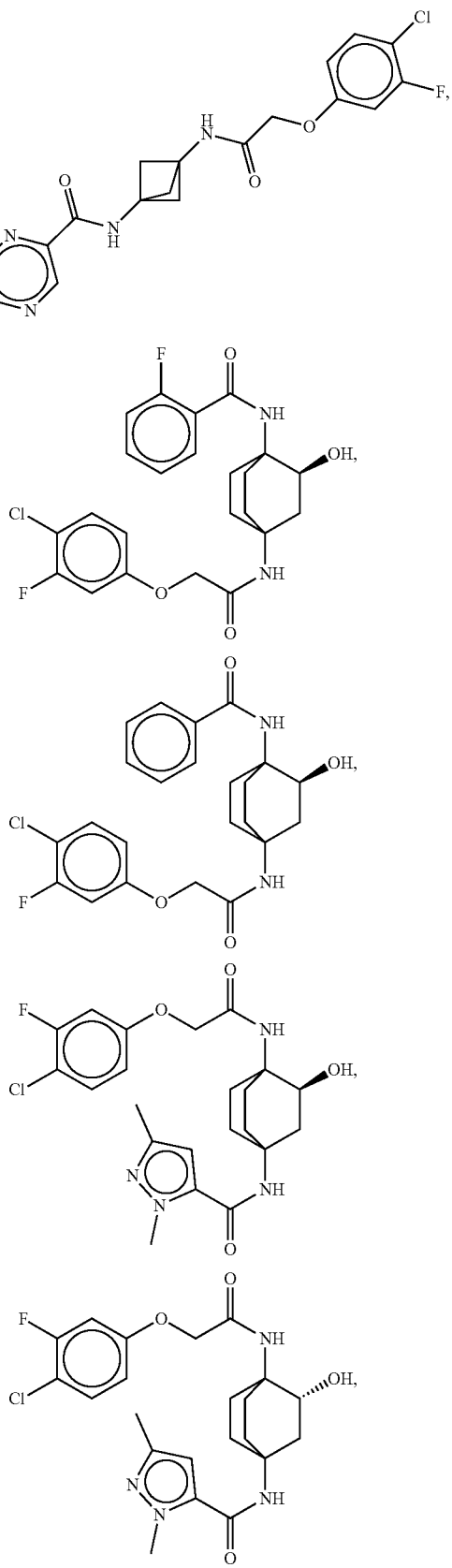

-continued
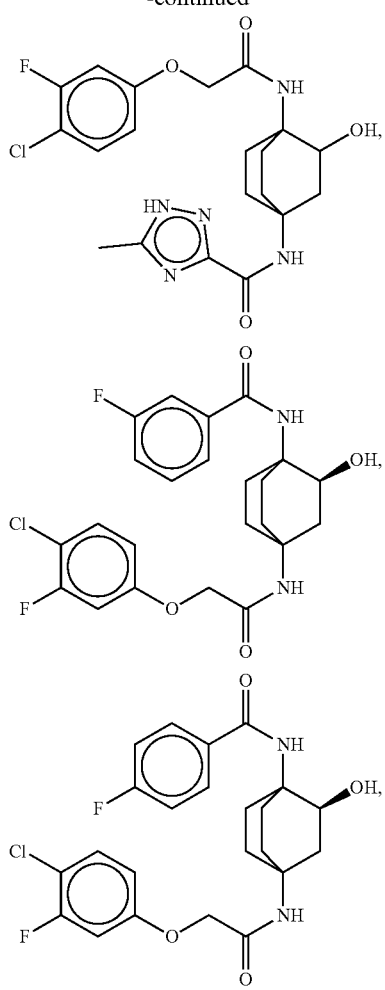
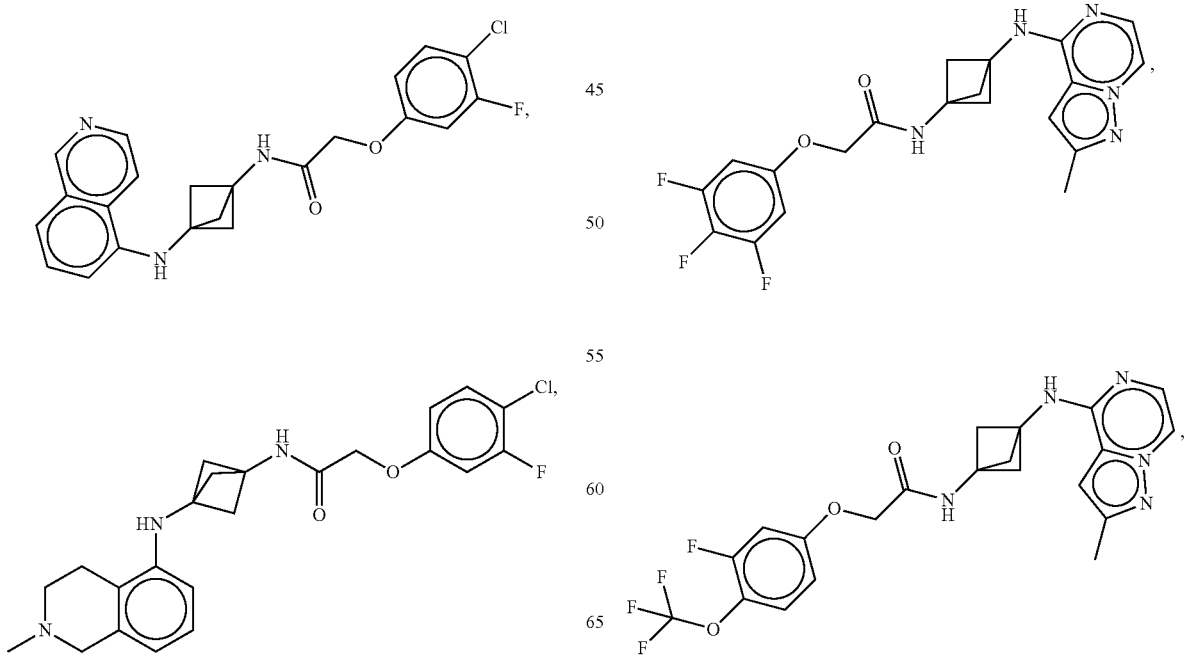

883
-continued
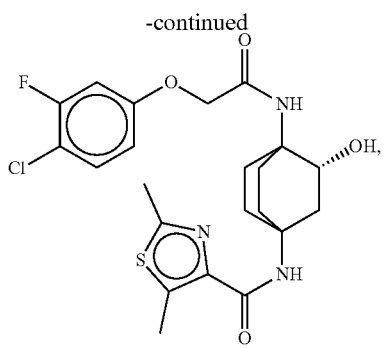
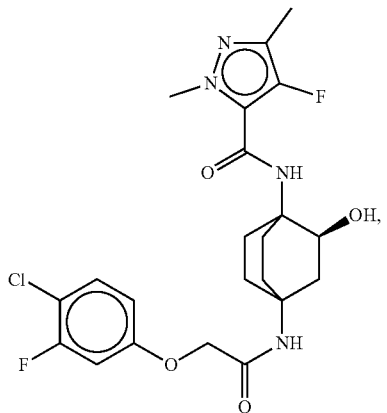
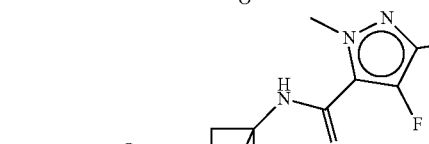
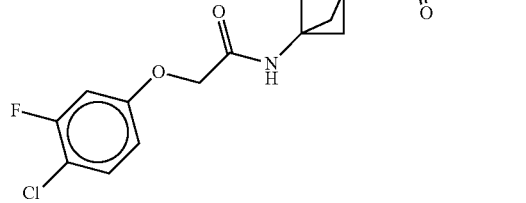
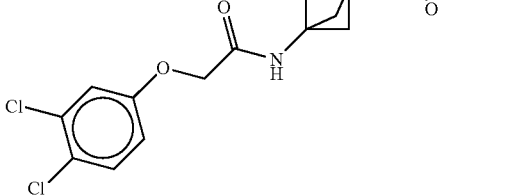
884
-continued
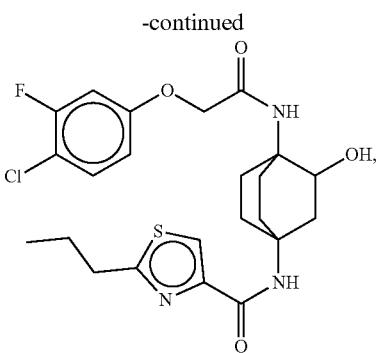
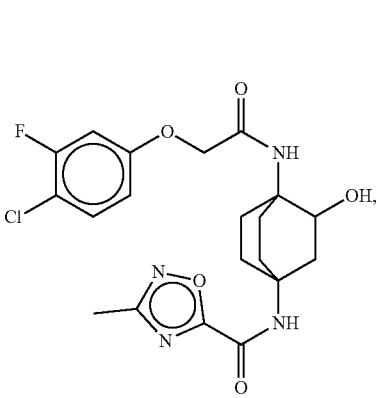
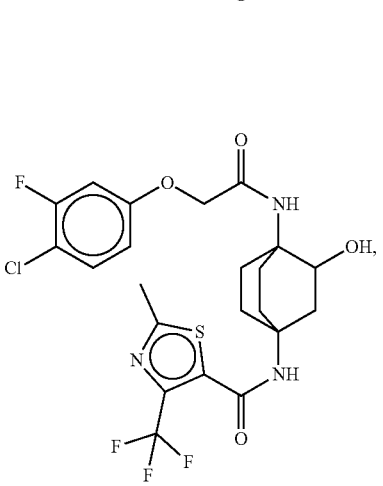
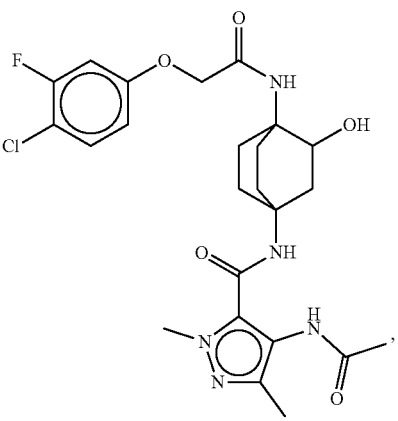

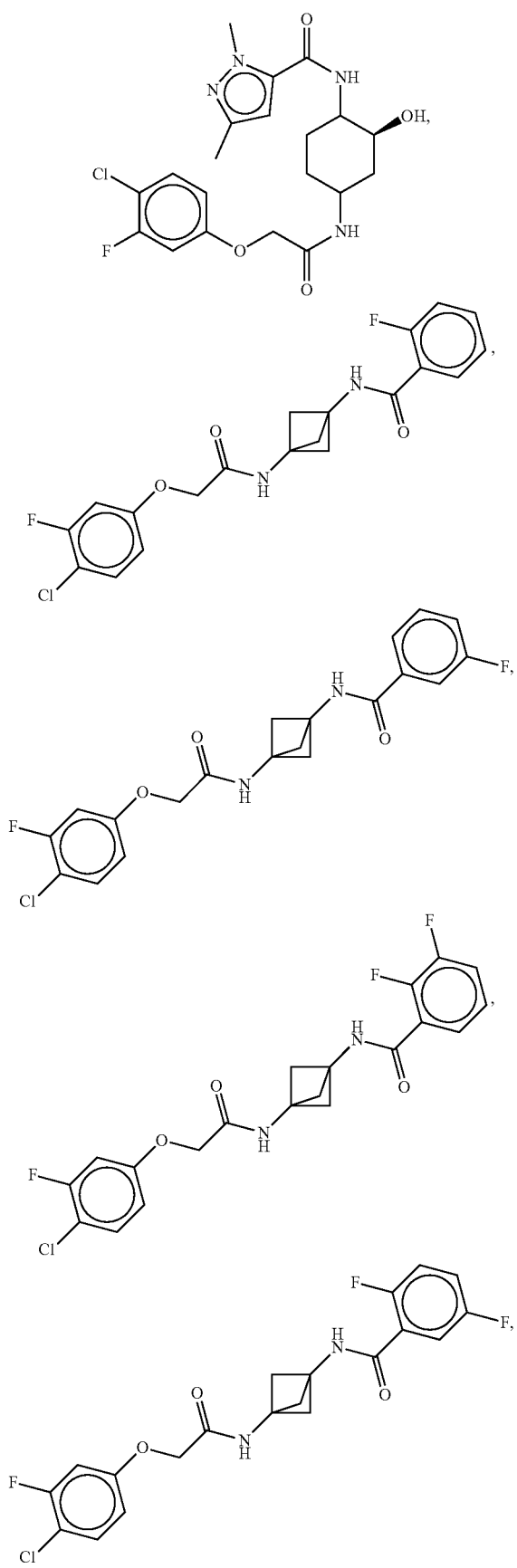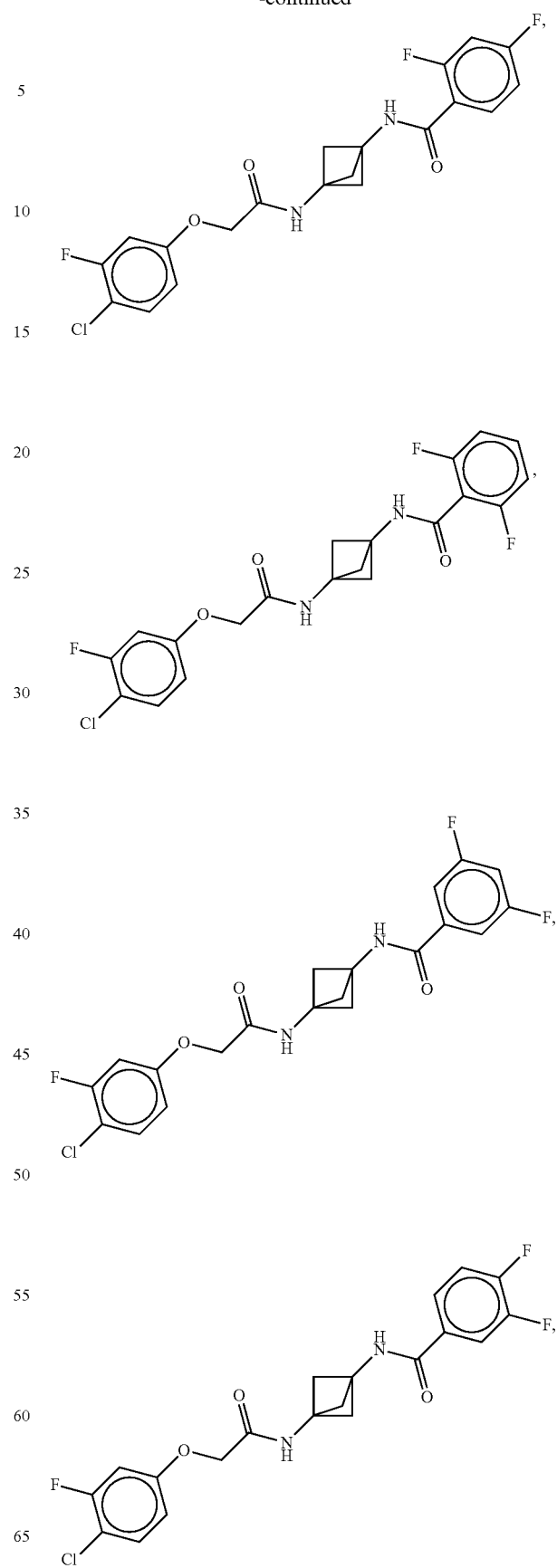

887
-continued
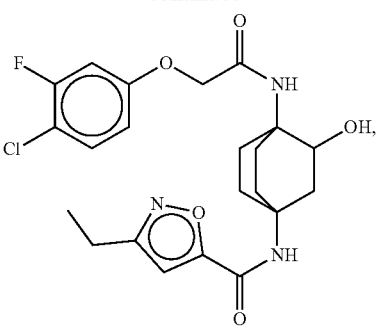
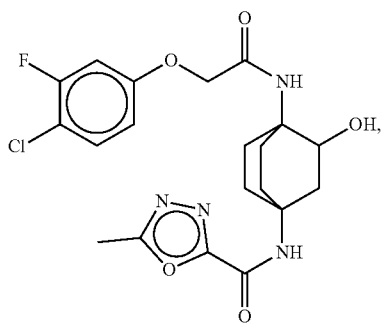
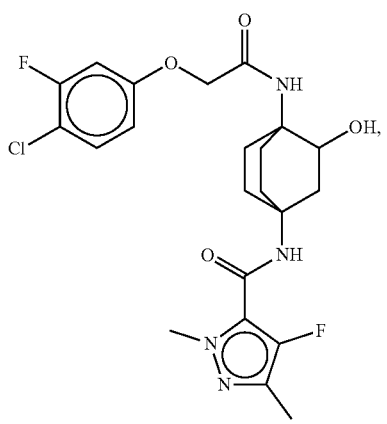
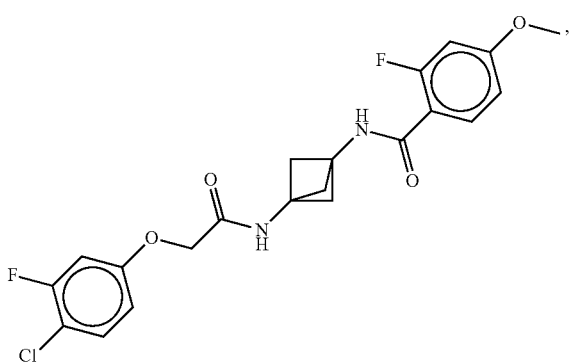
888
-continued
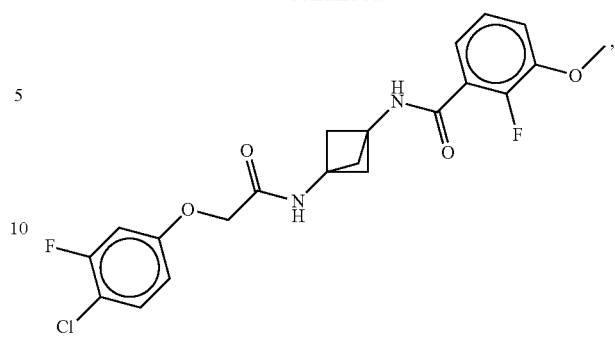
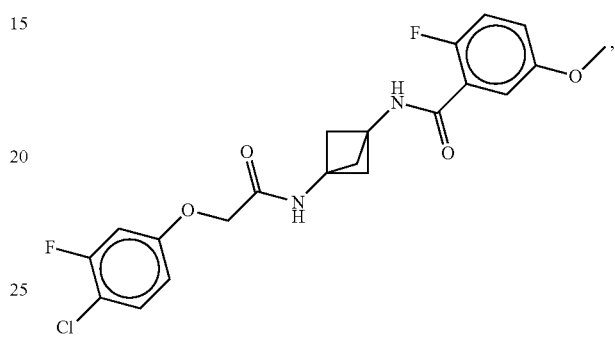
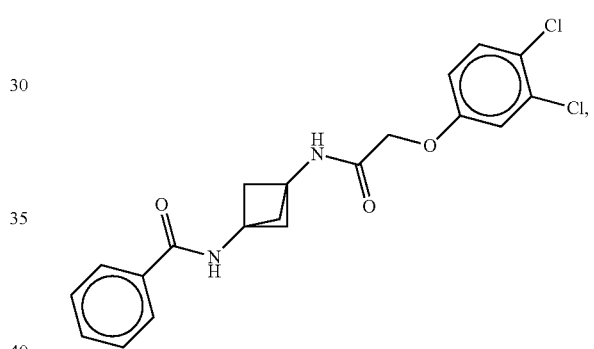
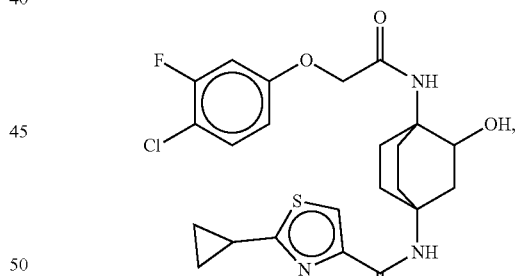
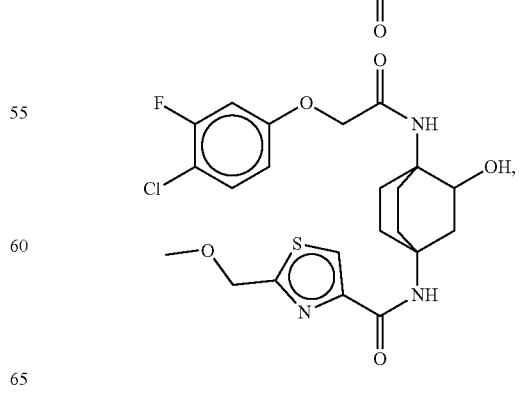

889
-continued
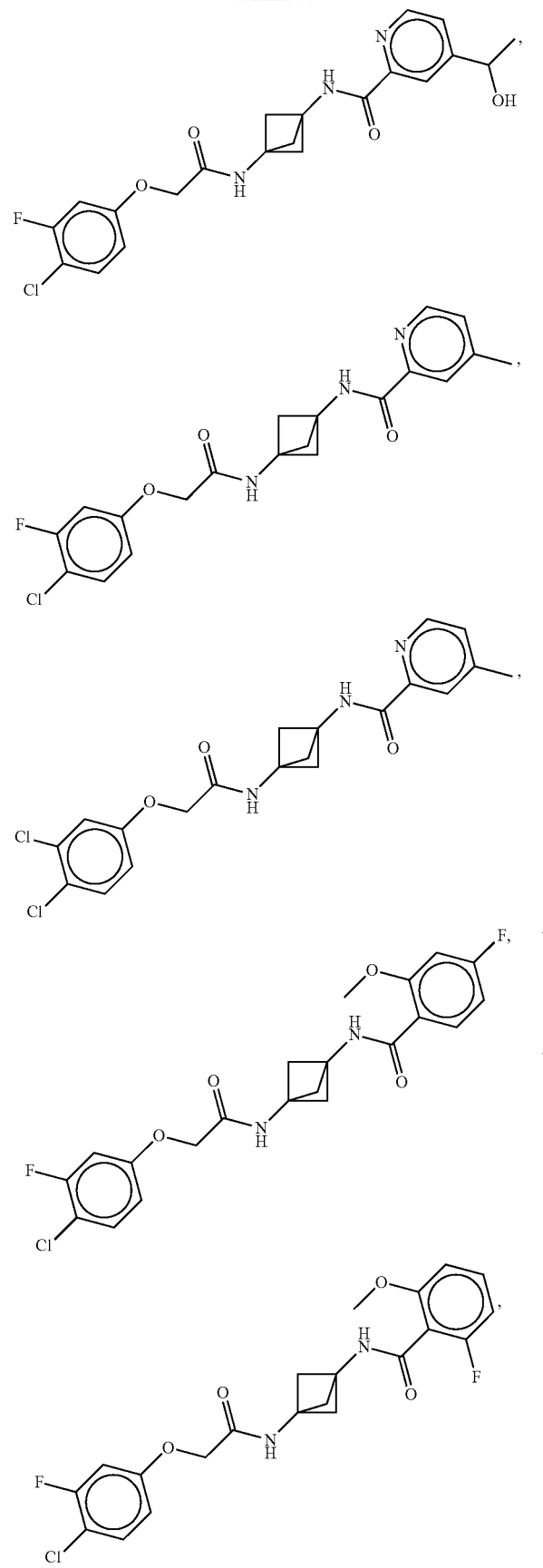
890
-continued
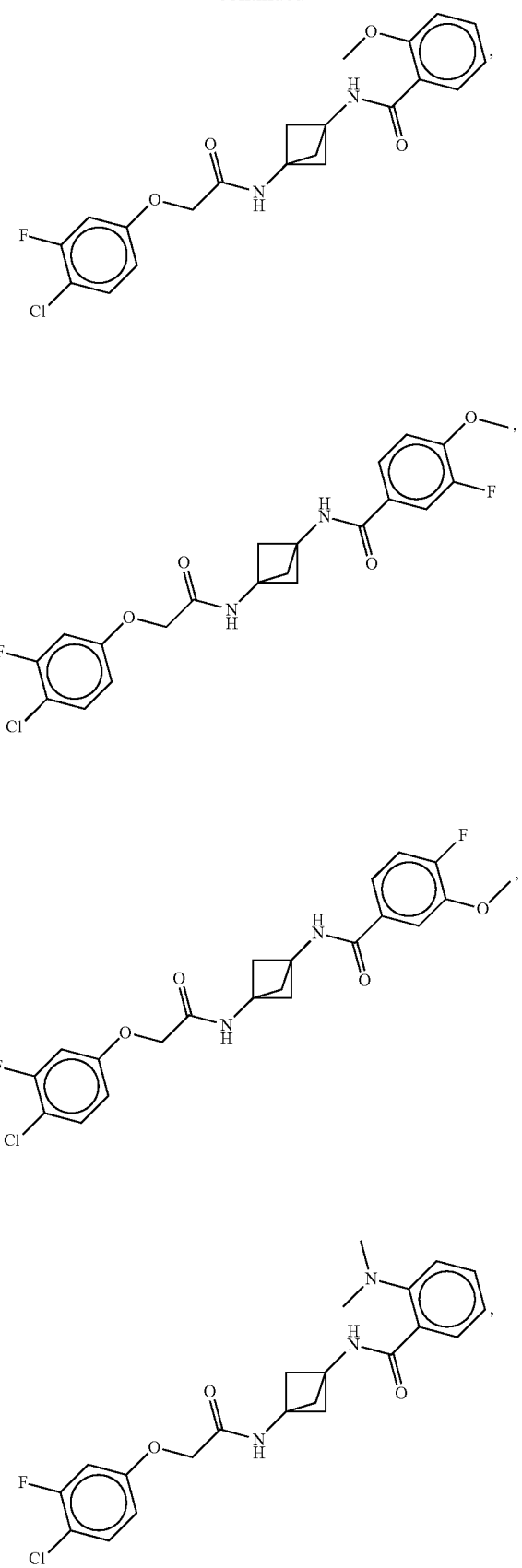

891
-continued
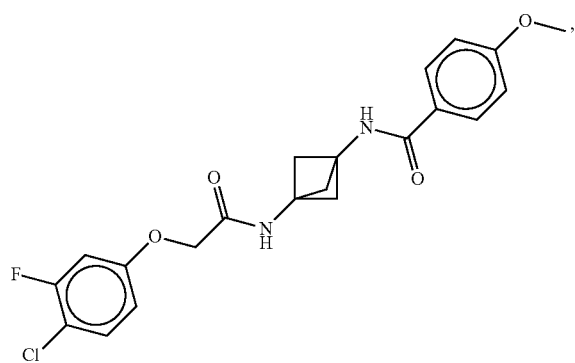
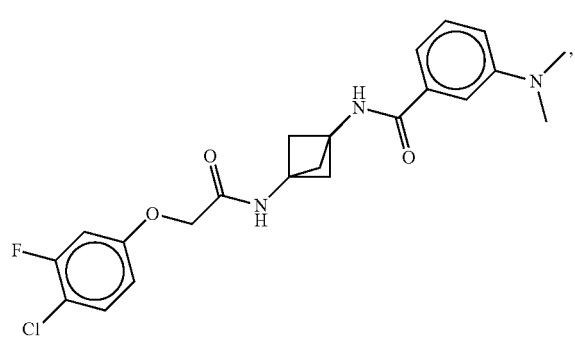
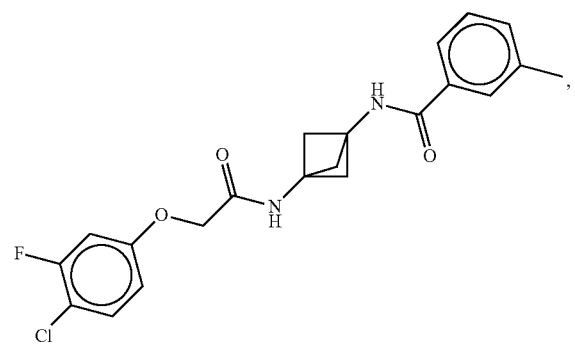
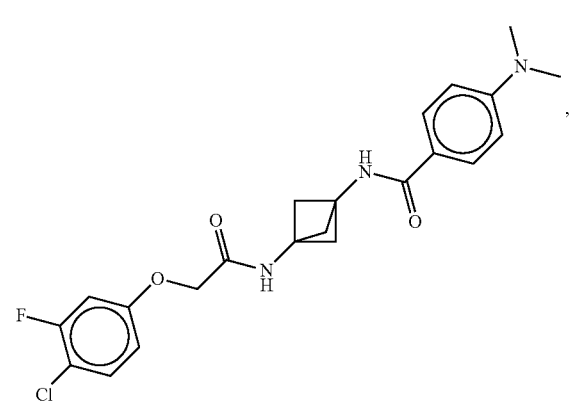
892
-continued
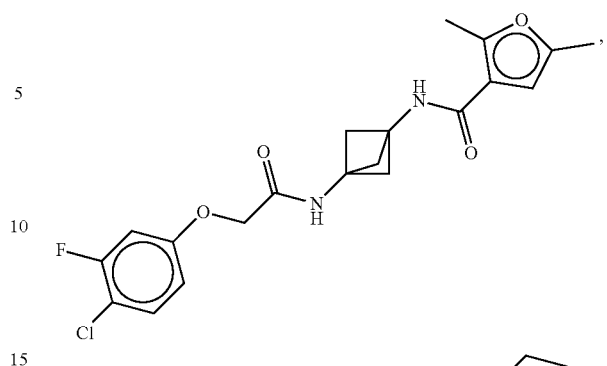
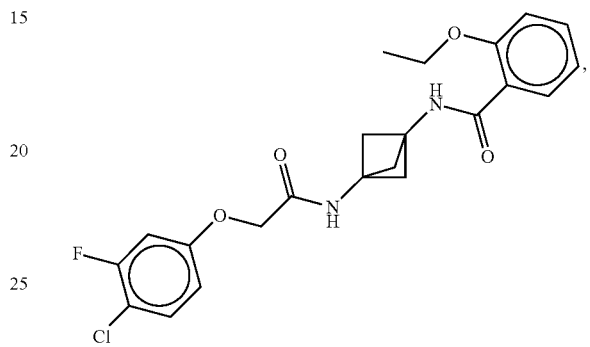
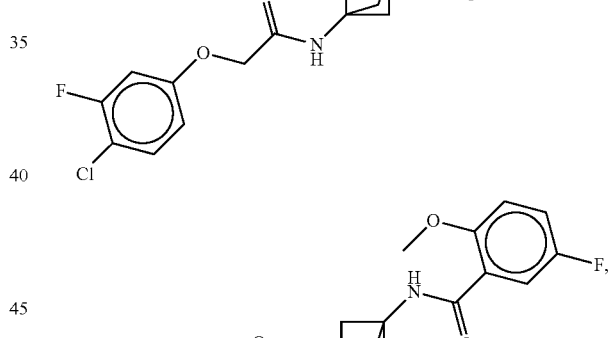
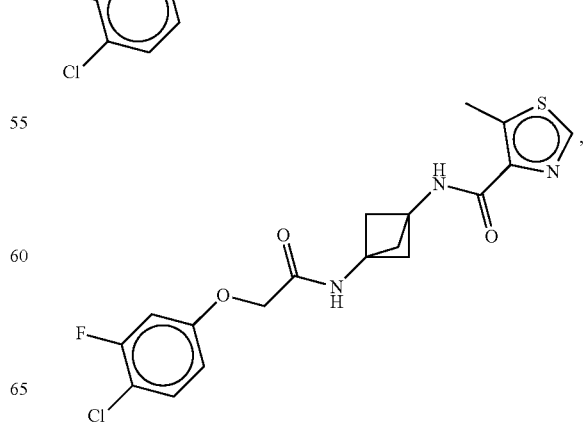

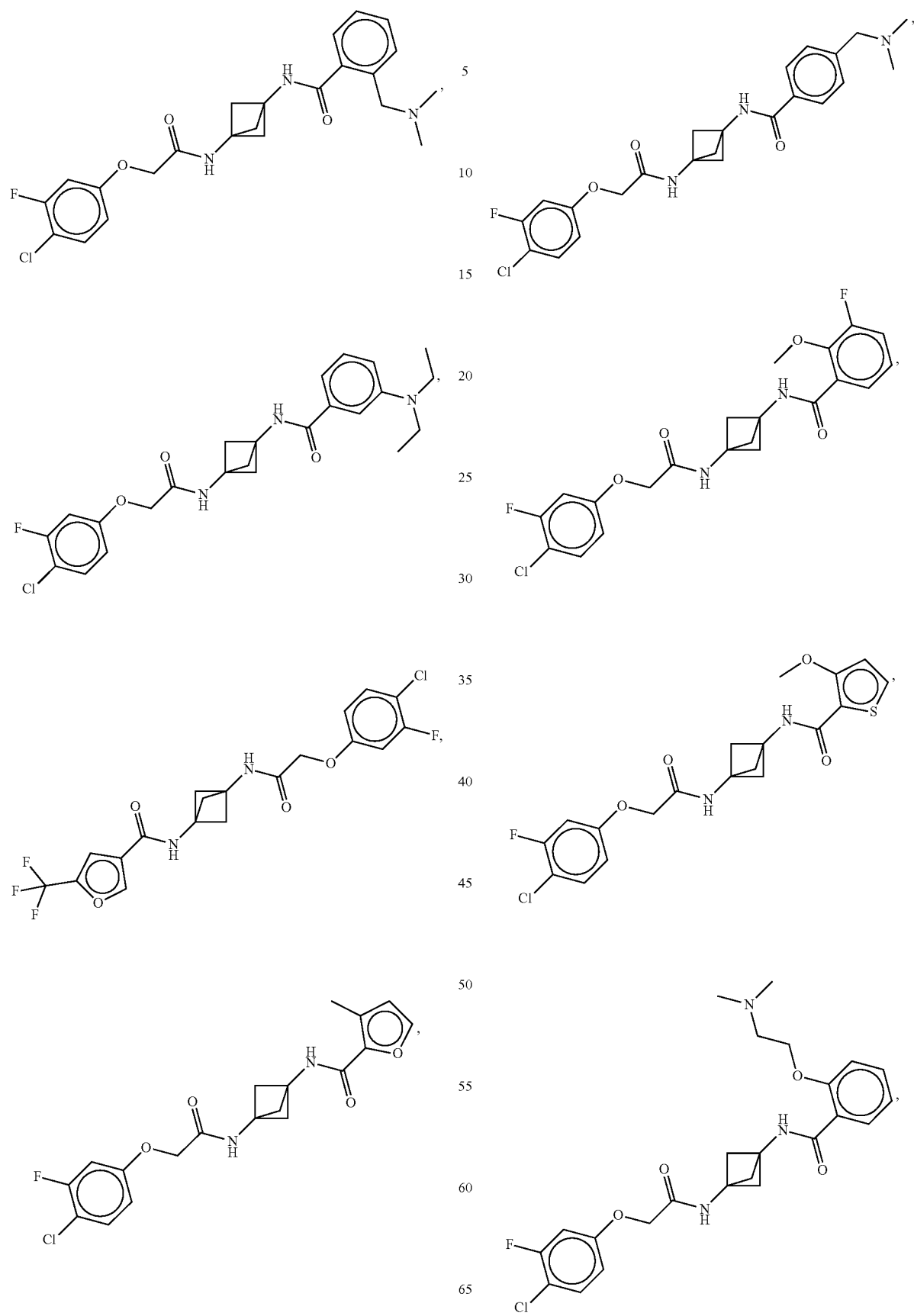

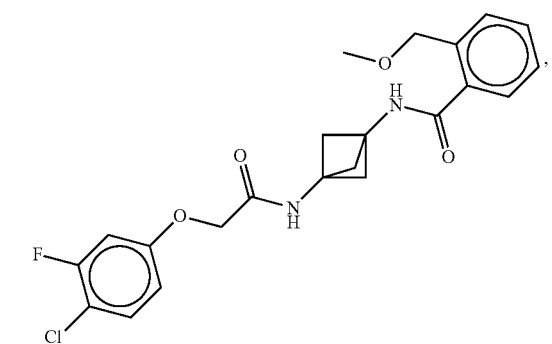
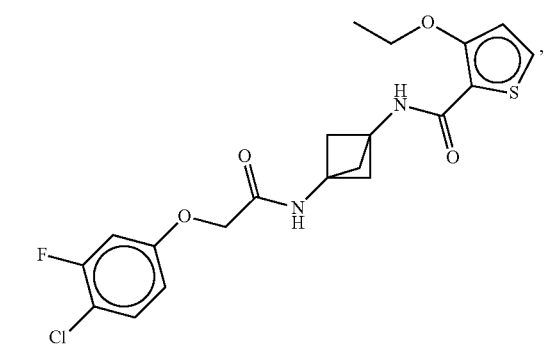
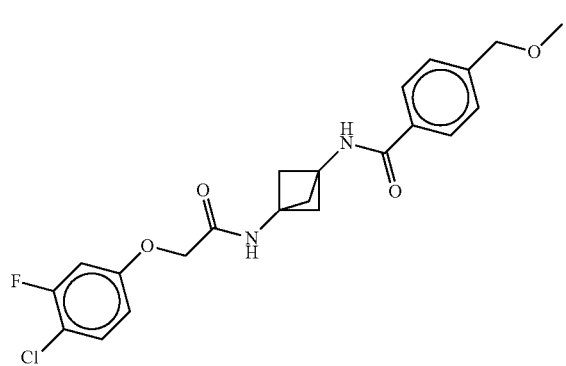
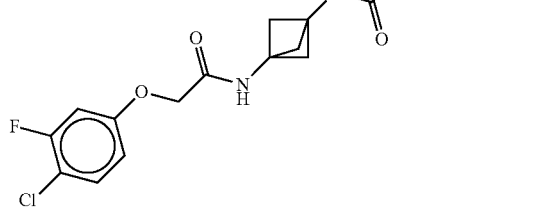
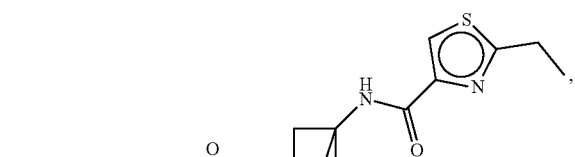
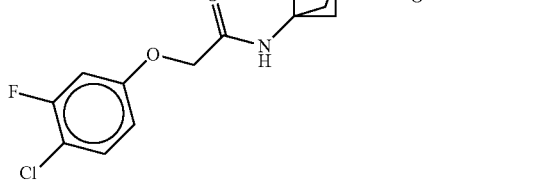
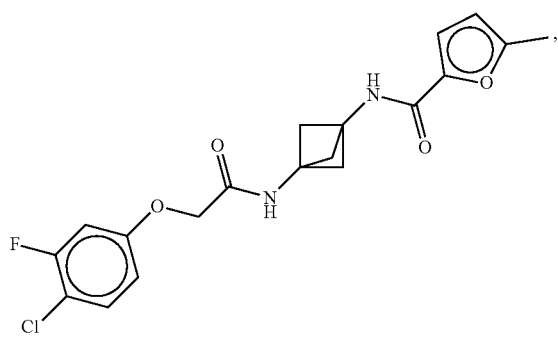
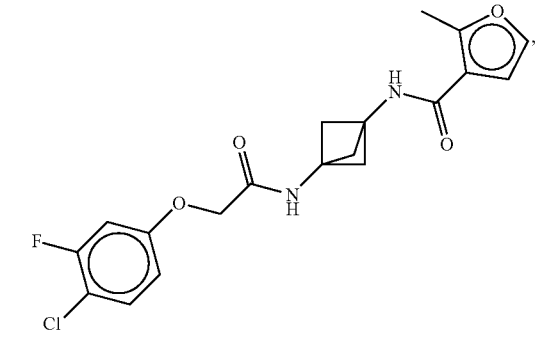
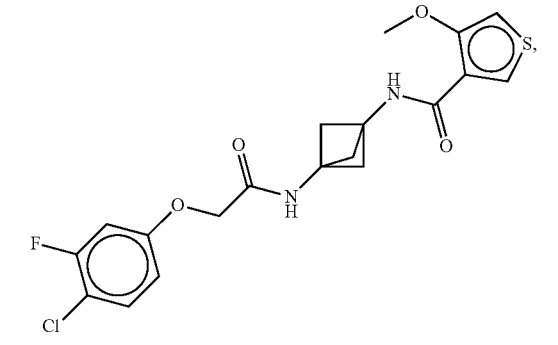
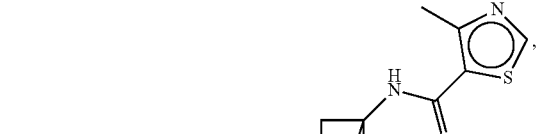
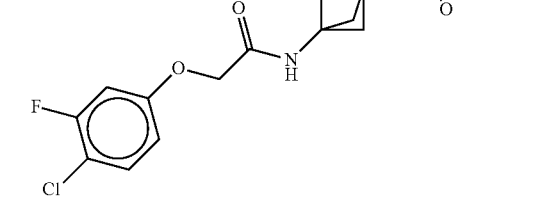
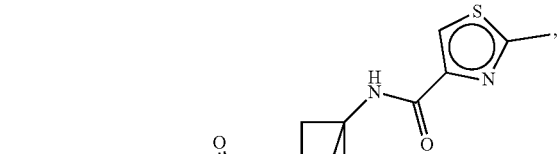
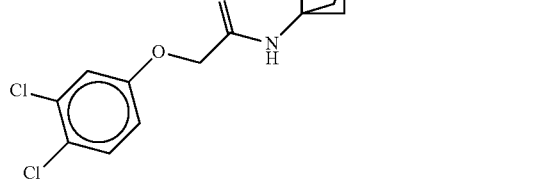

897
-continued
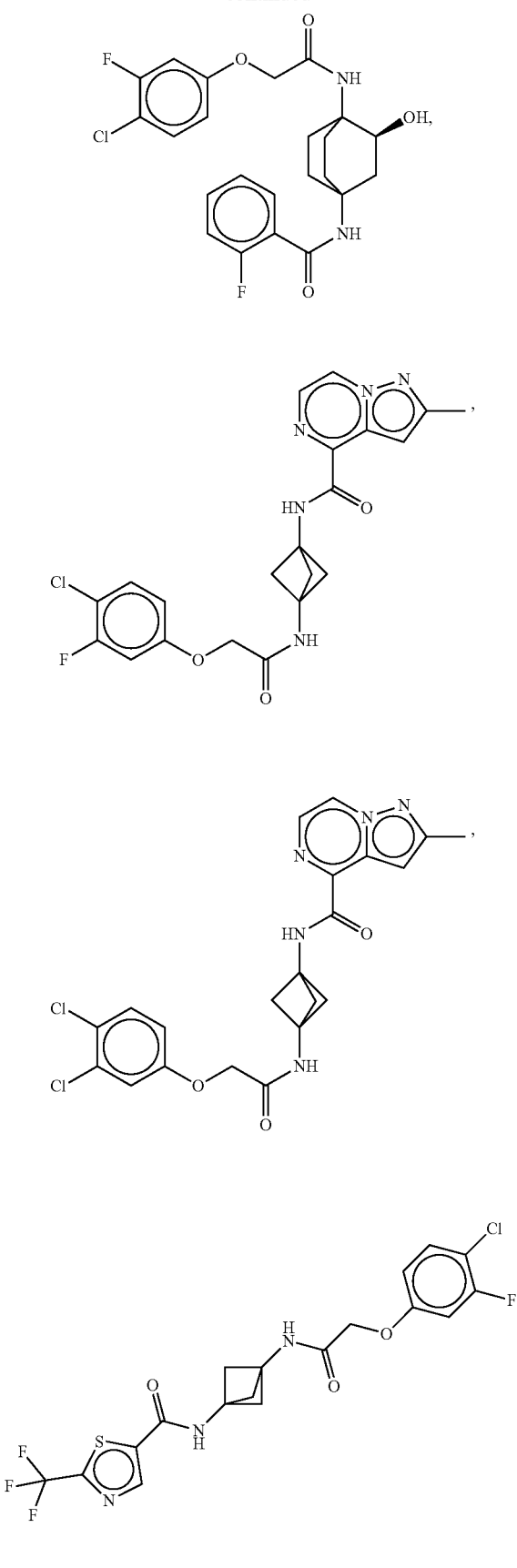
898
-continued
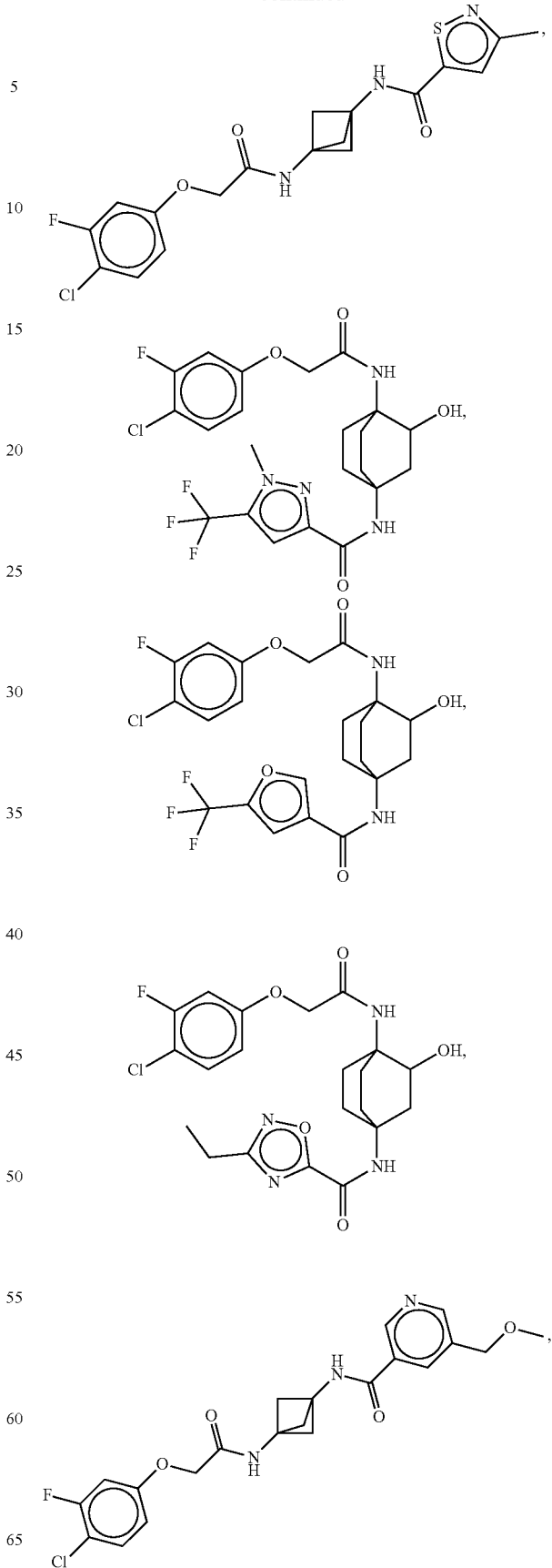

899
-continued
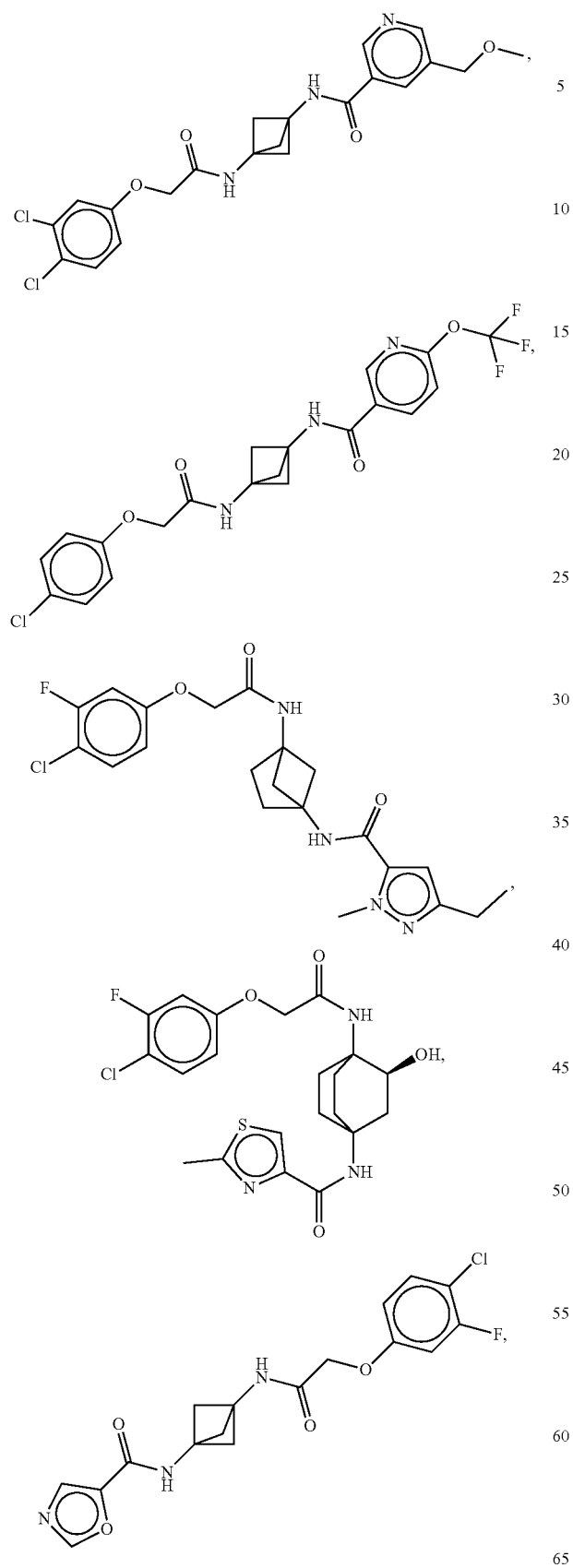
900
-continued
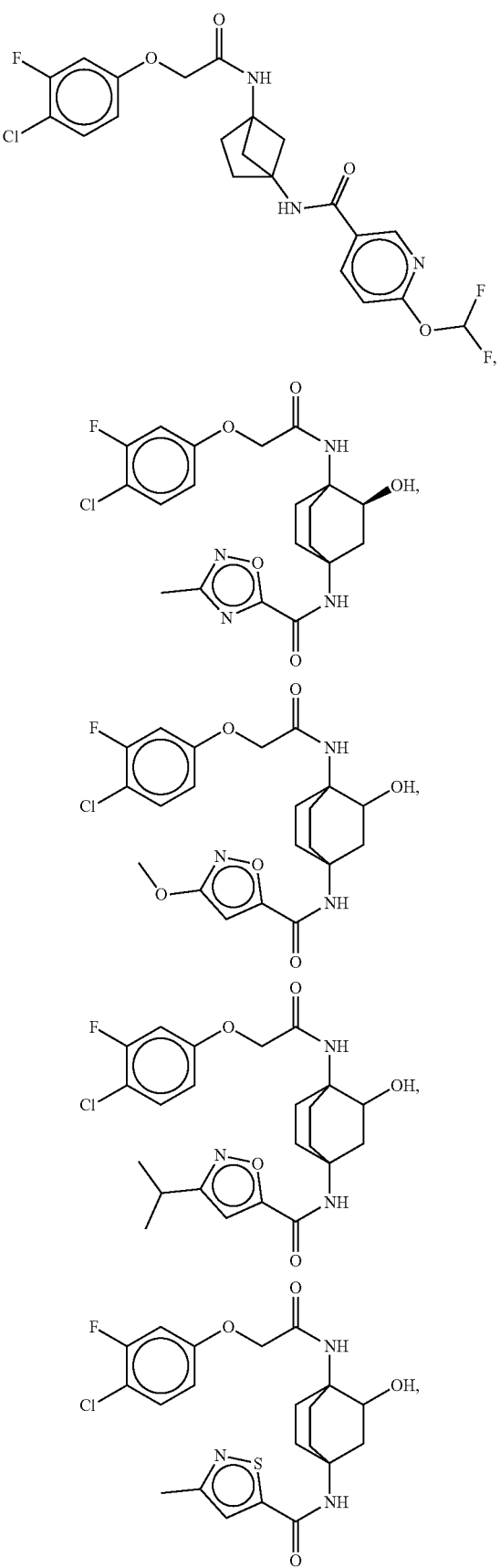

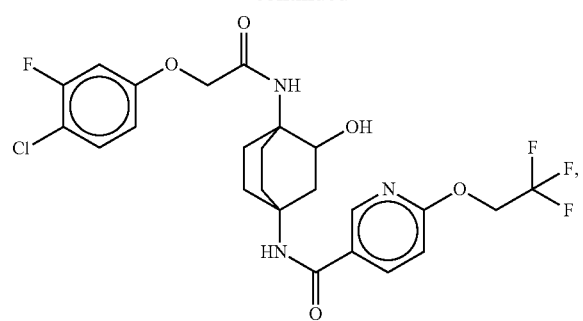
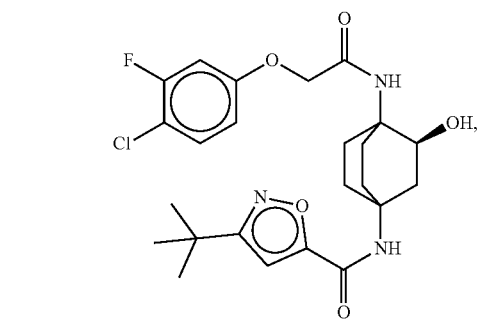
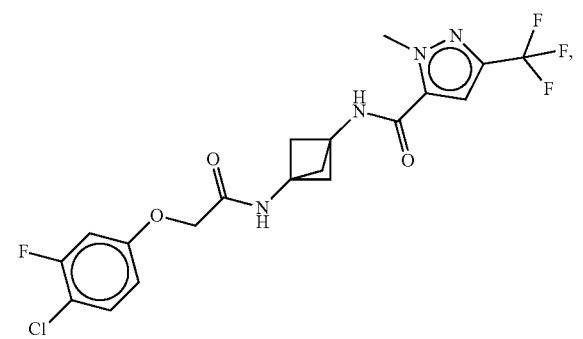
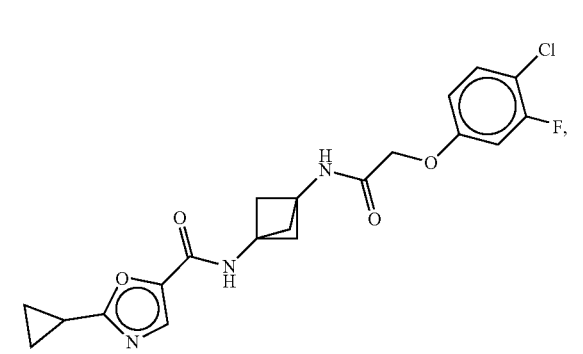
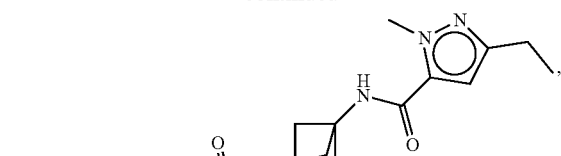
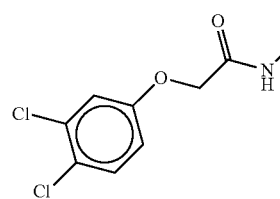
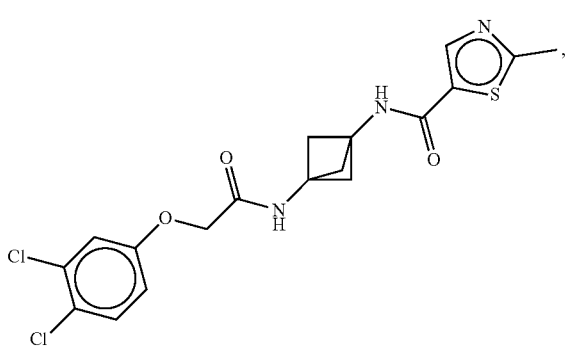
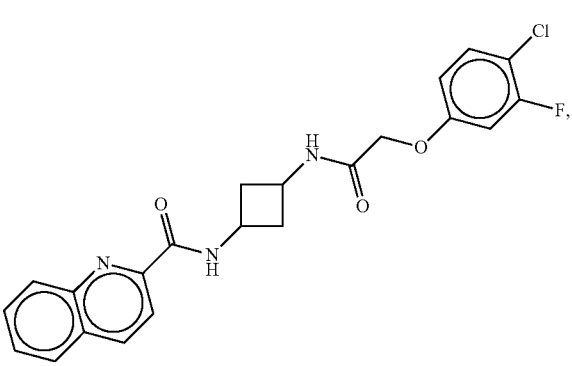
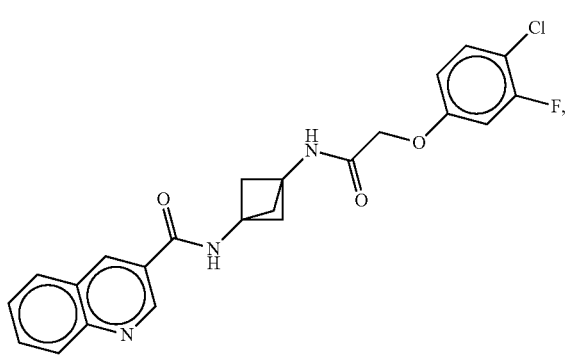

903
-continued
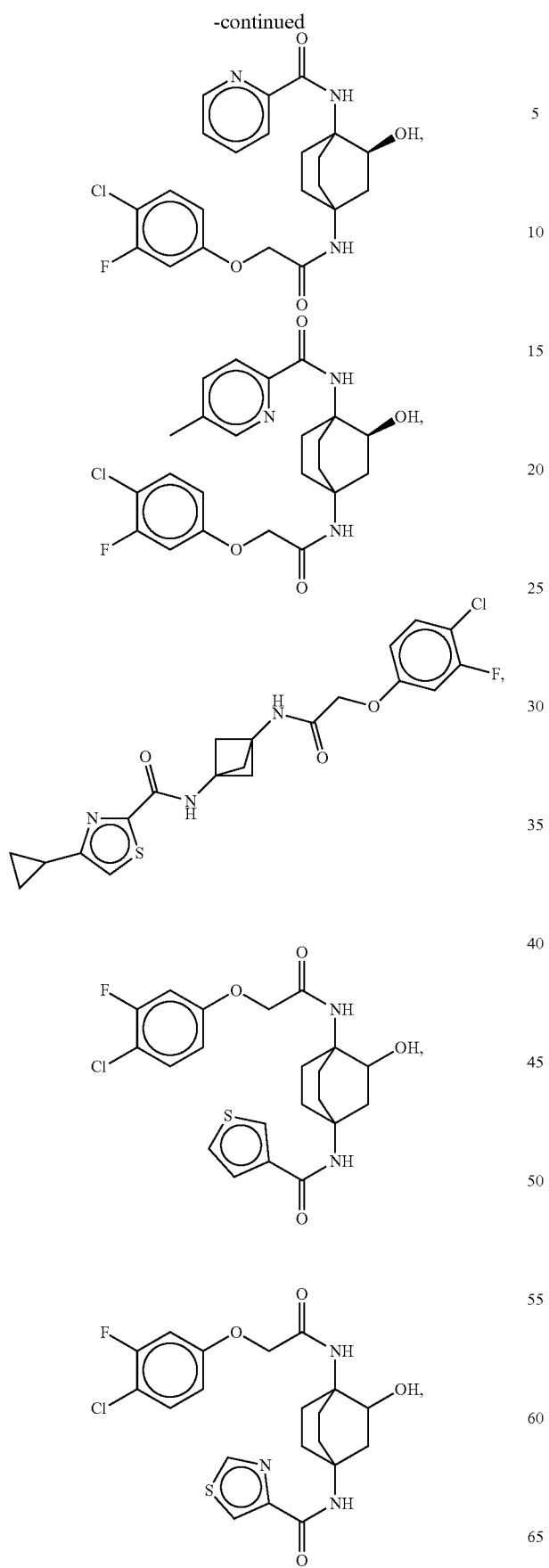
904
-continued
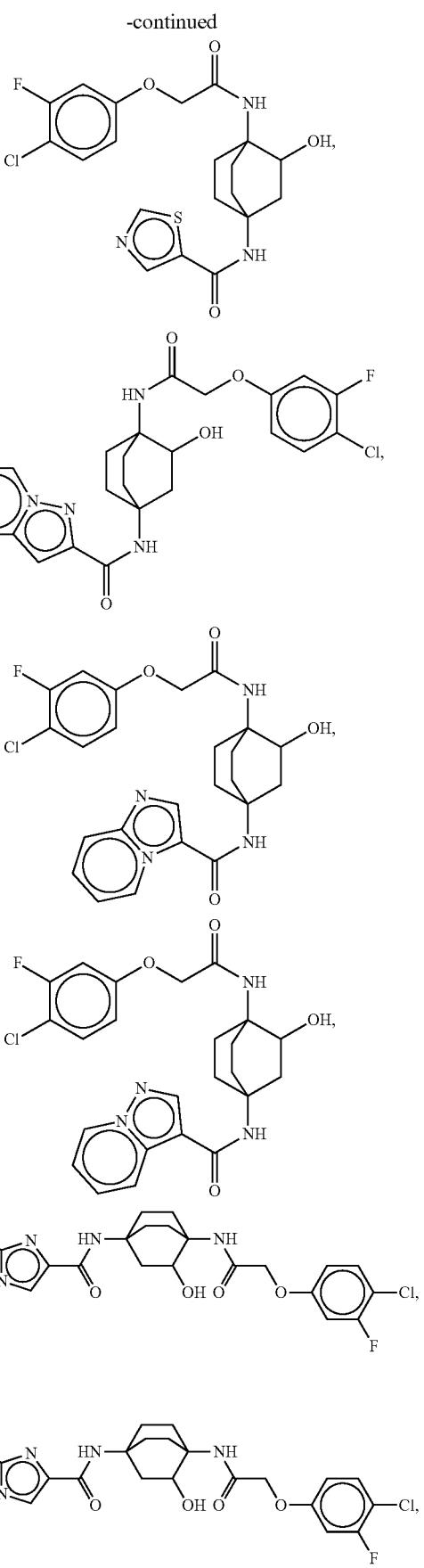

905
-continued
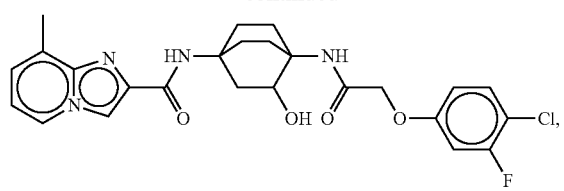
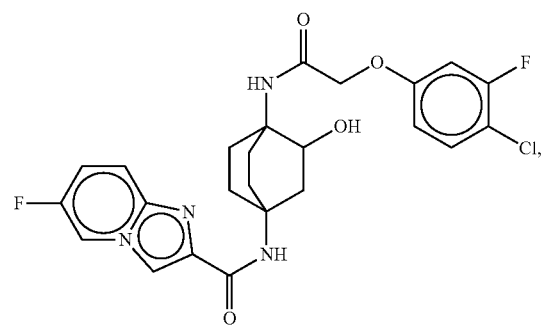
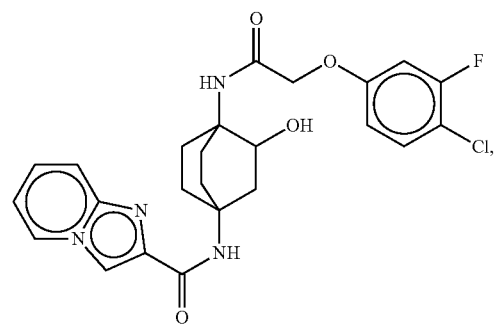
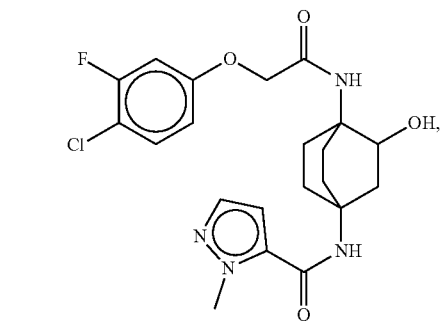
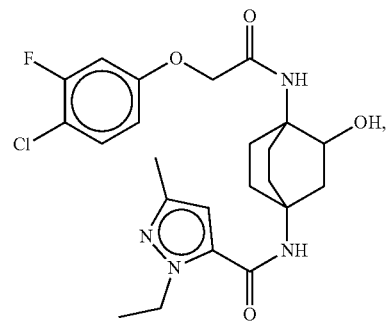
906
-continued
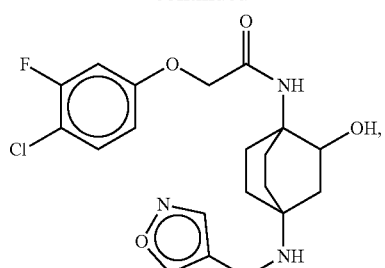
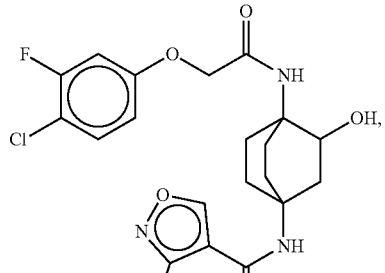
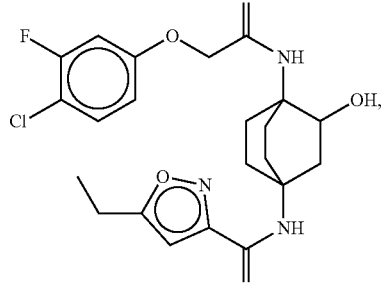
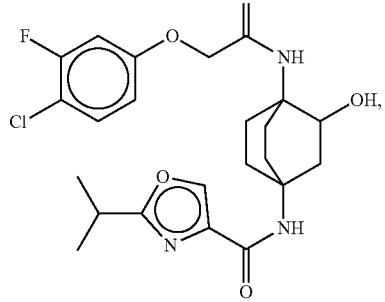
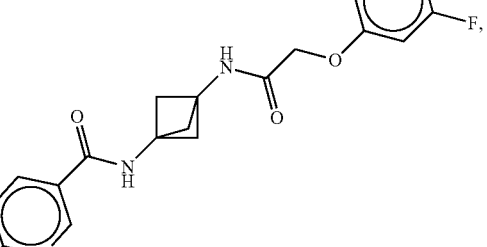

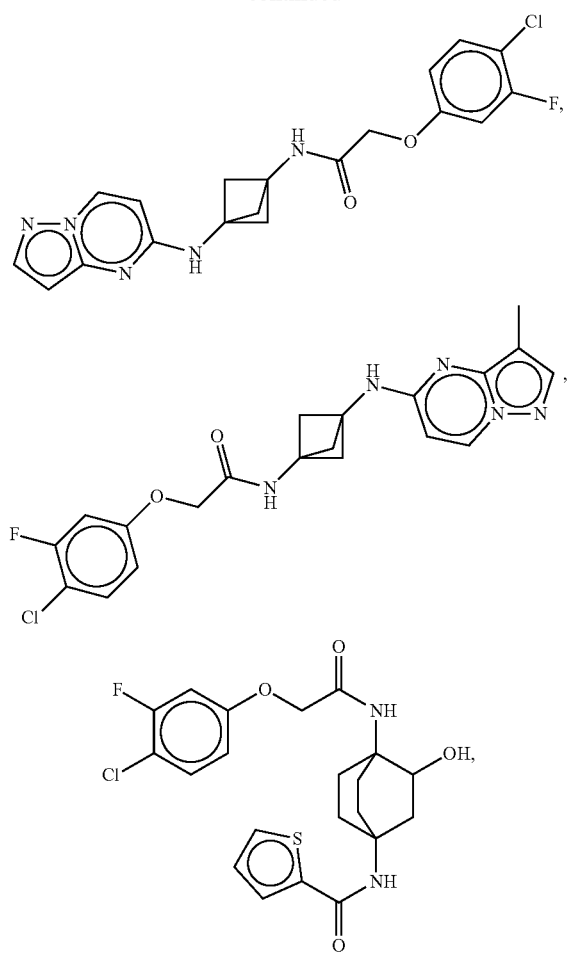
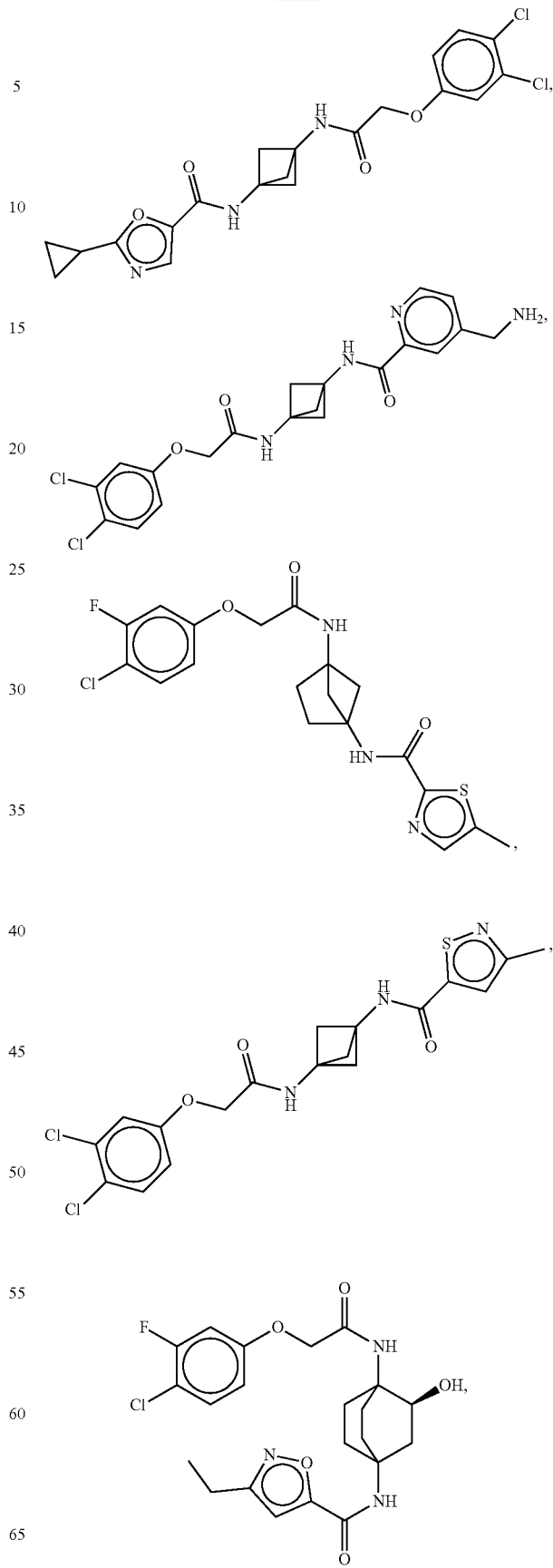

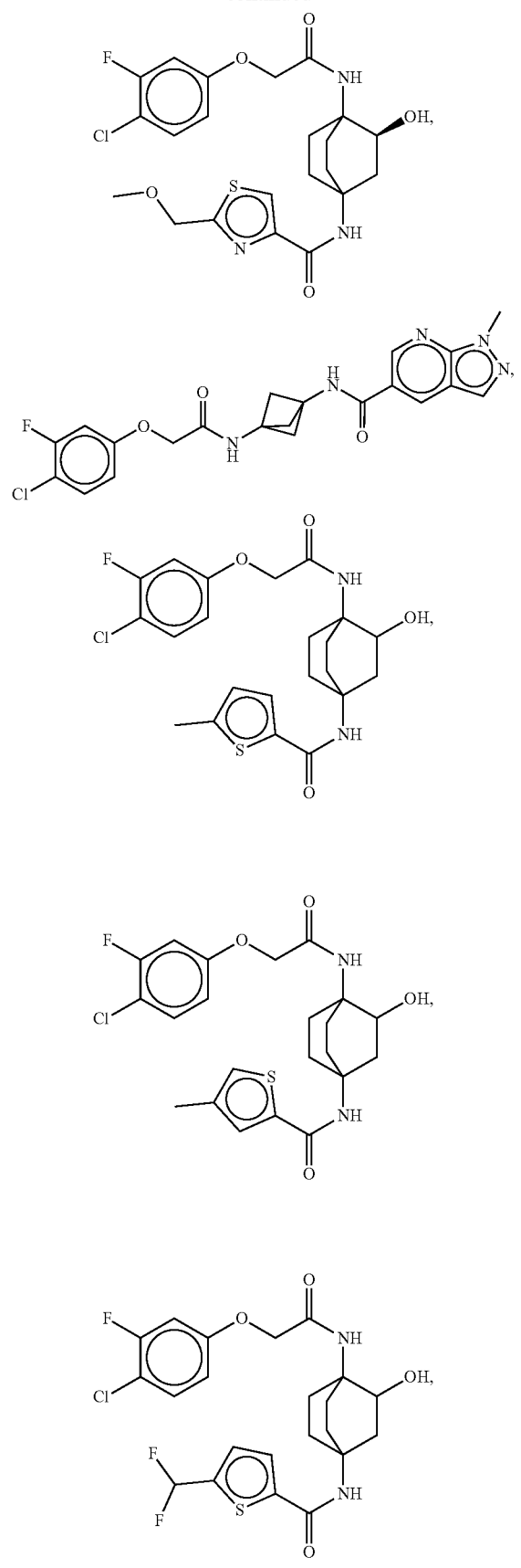
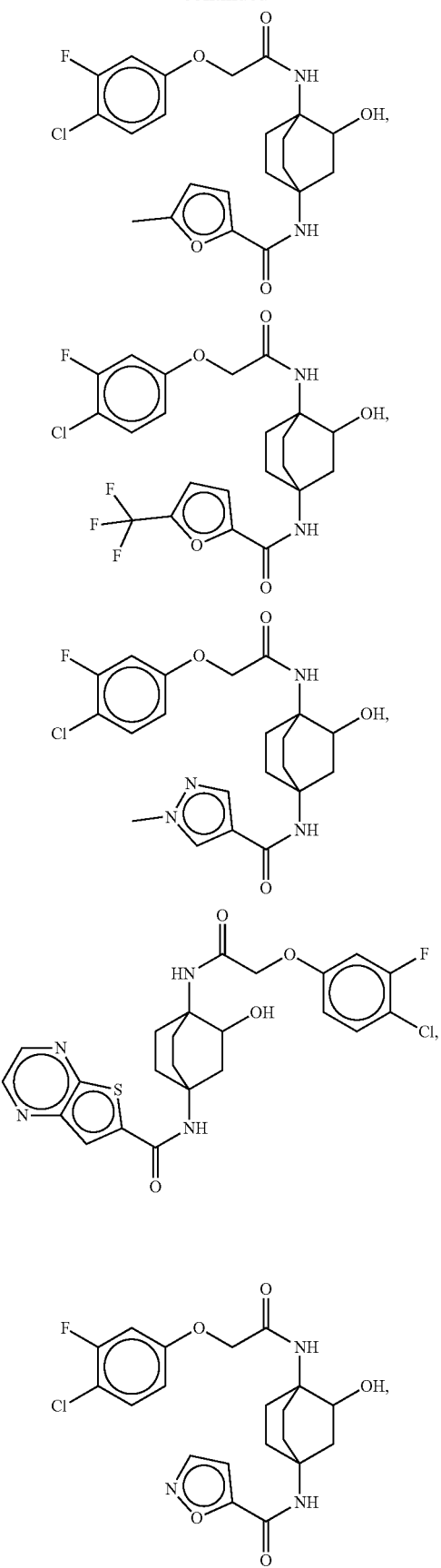

911
-continued
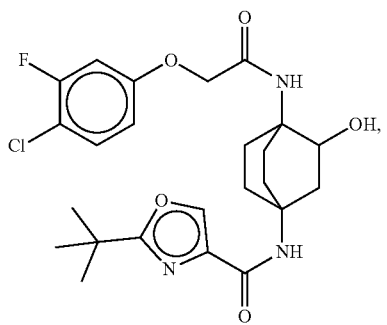
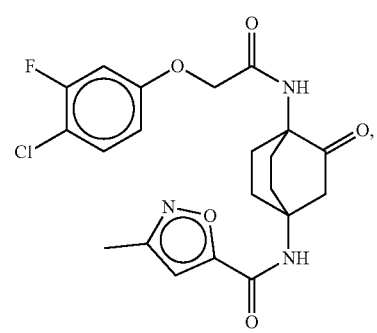
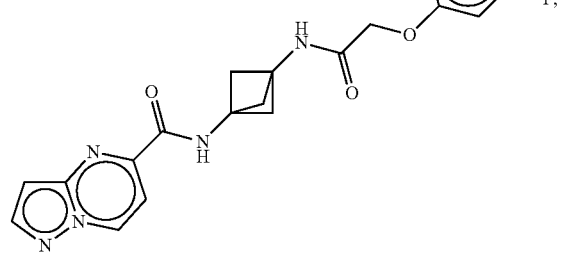
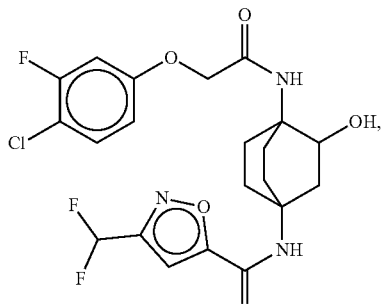
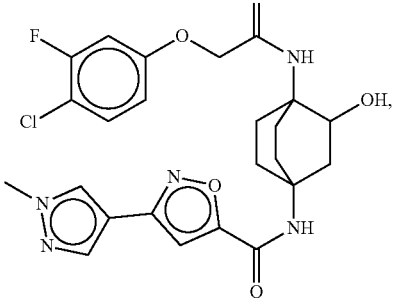
912
-continued
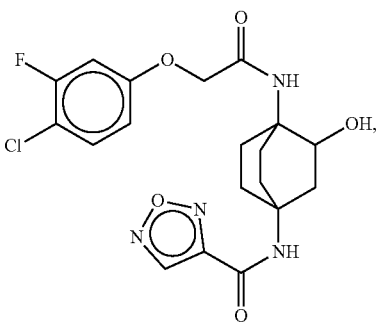
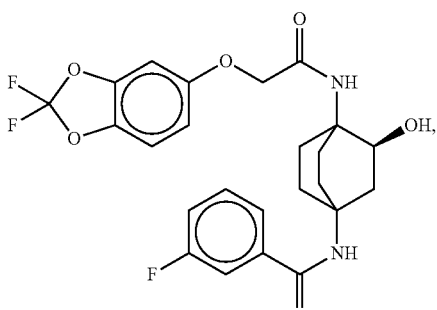
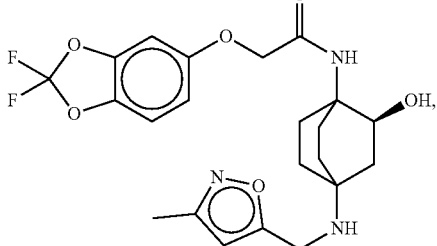
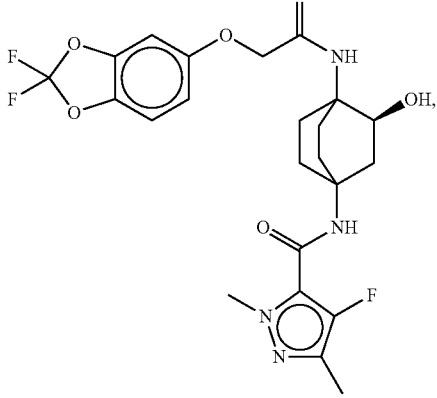
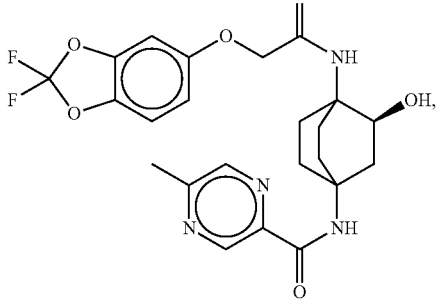

913
-continued
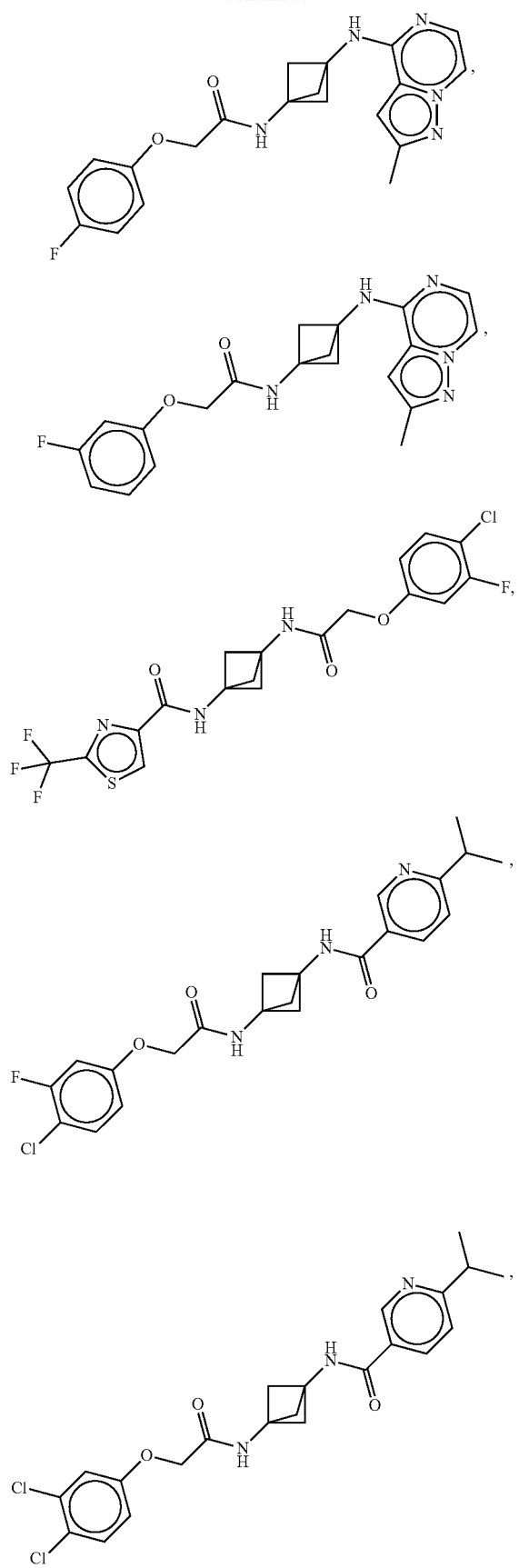
914
-continued
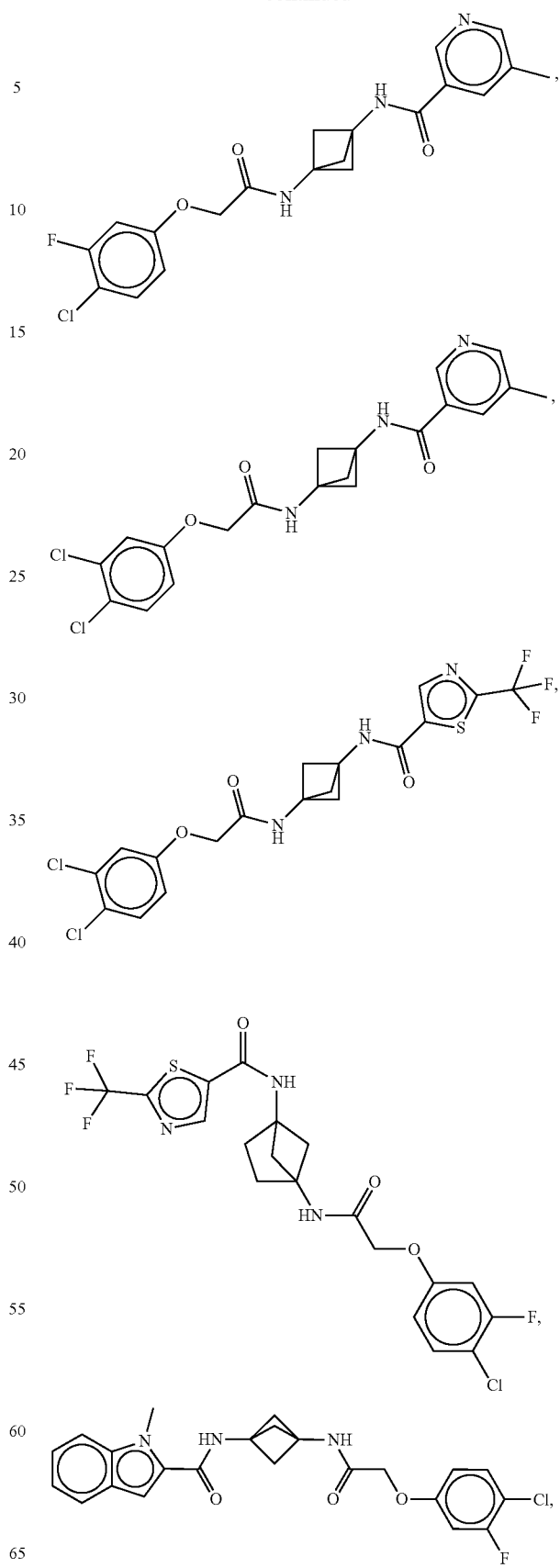

915
-continued
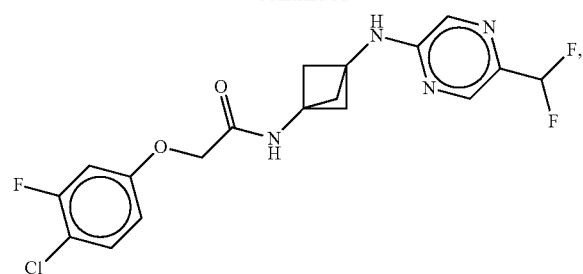
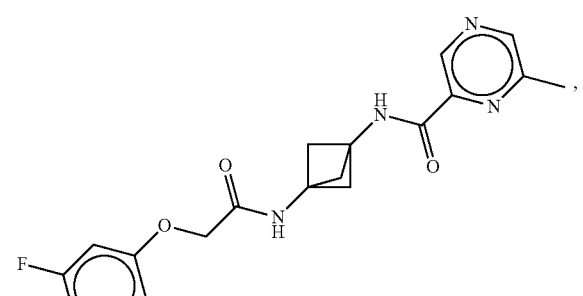
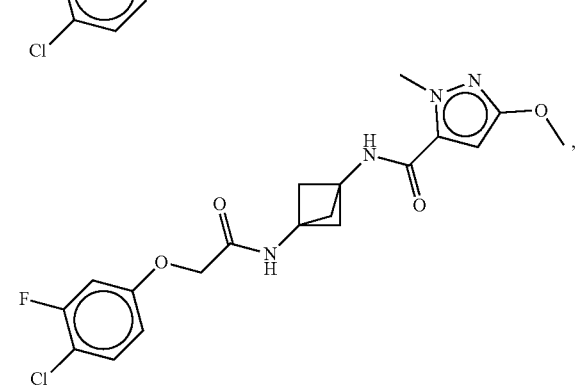
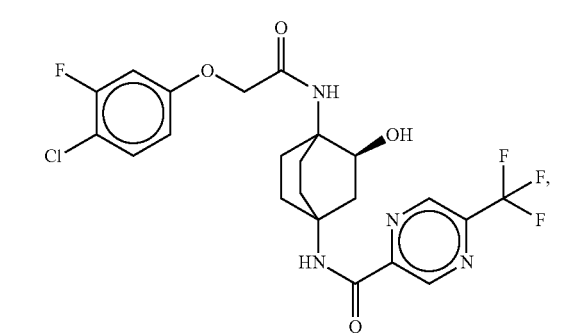
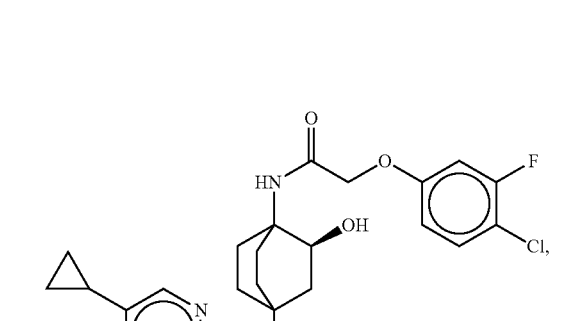
916
-continued
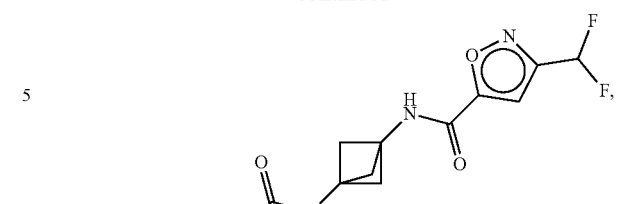
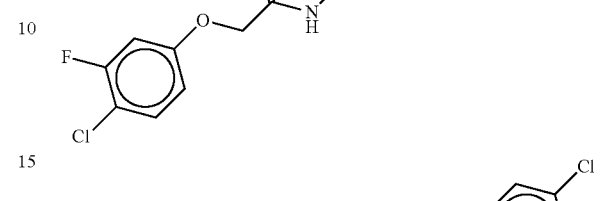
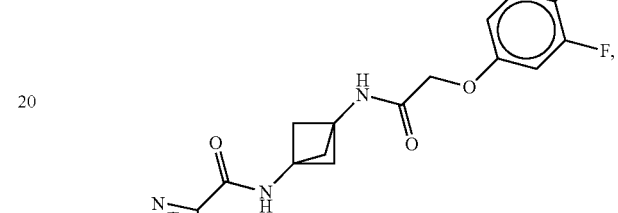
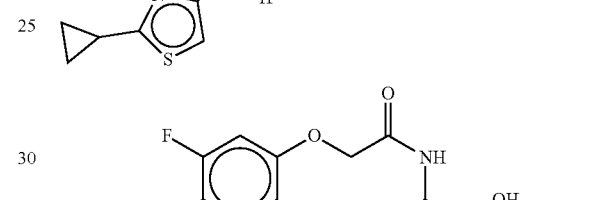
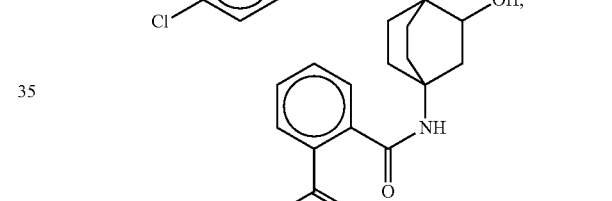
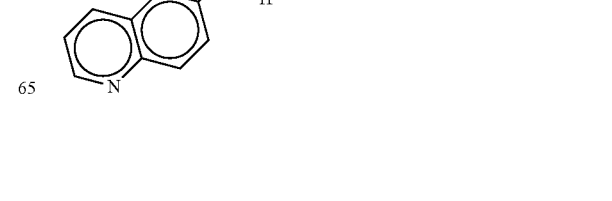

917
-continued
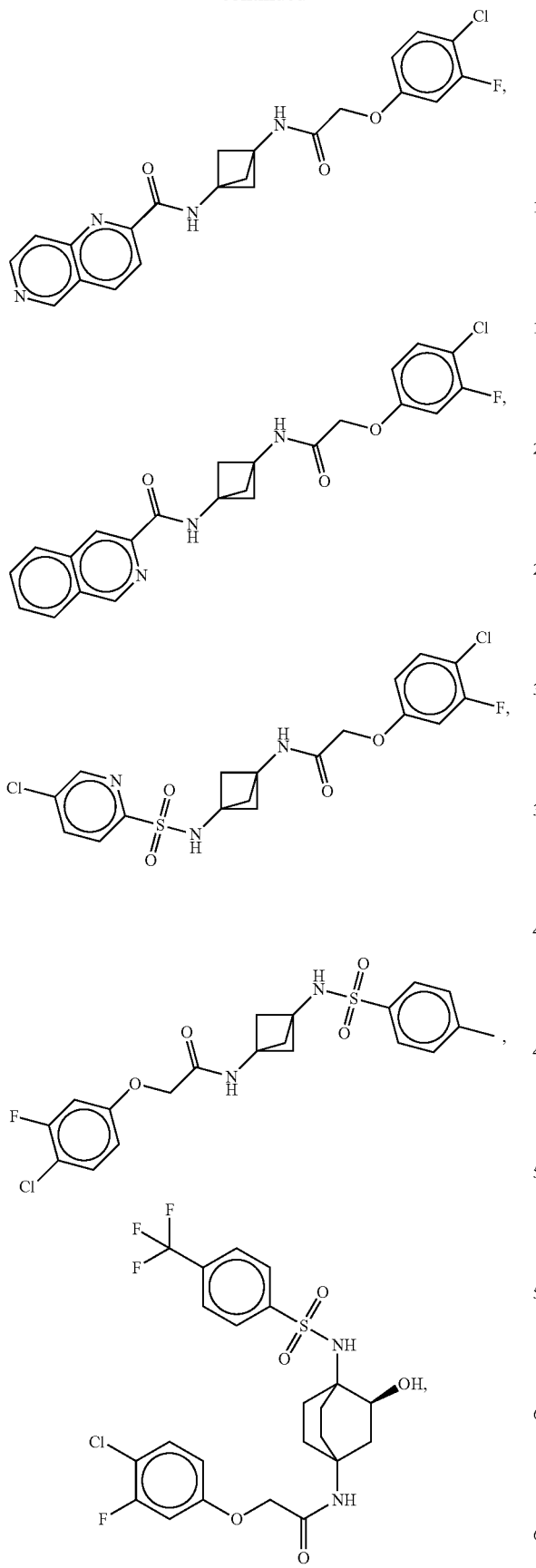
918
-continued
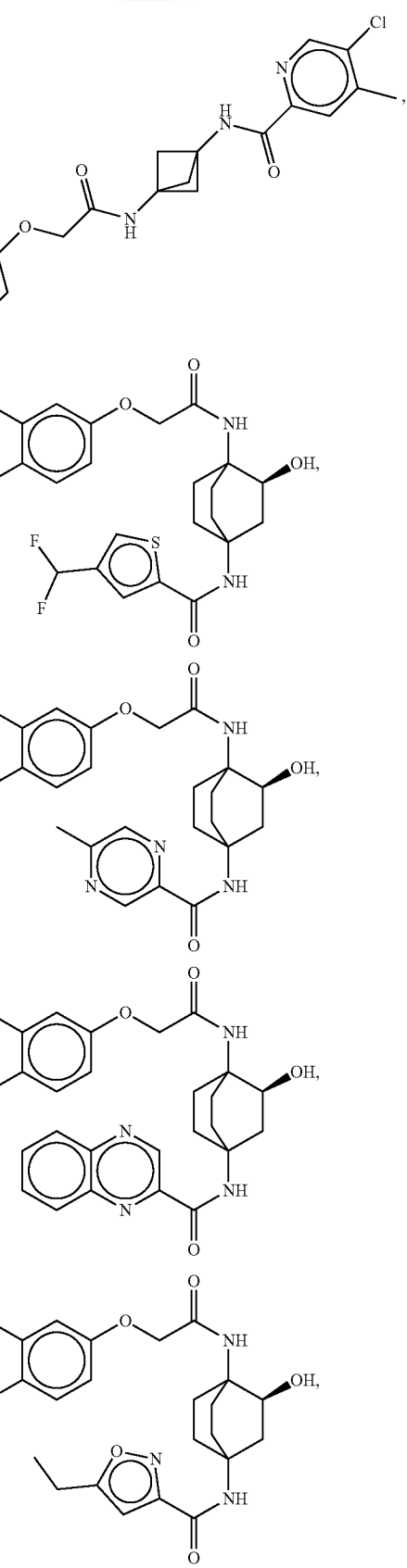

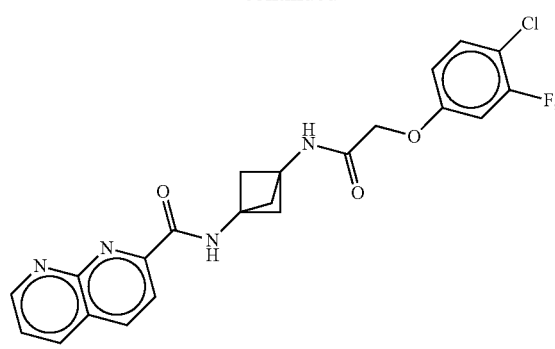
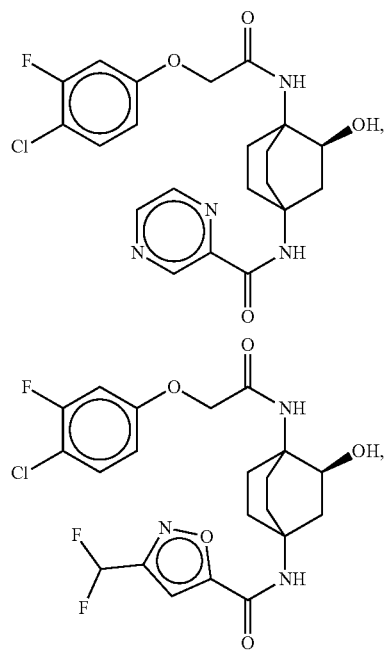
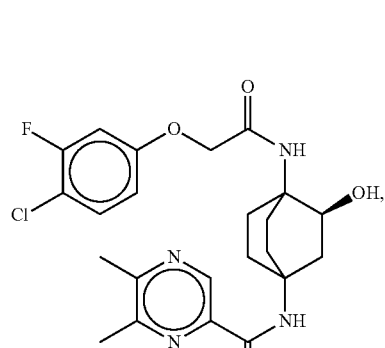
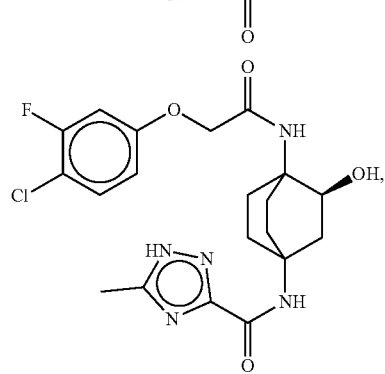
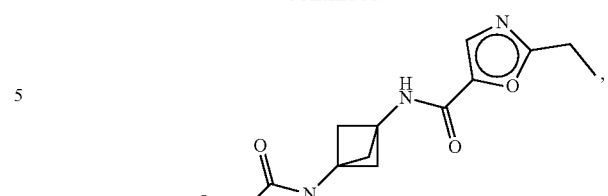
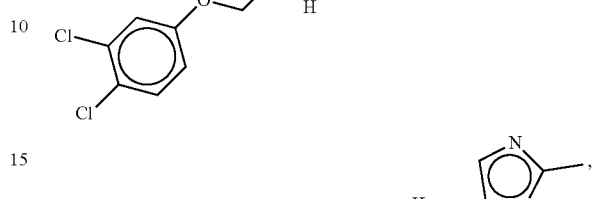
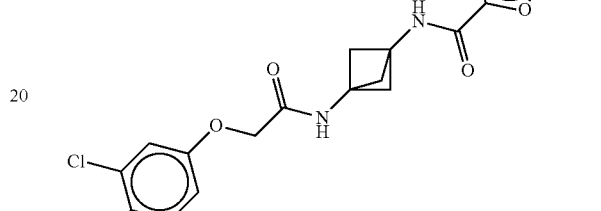
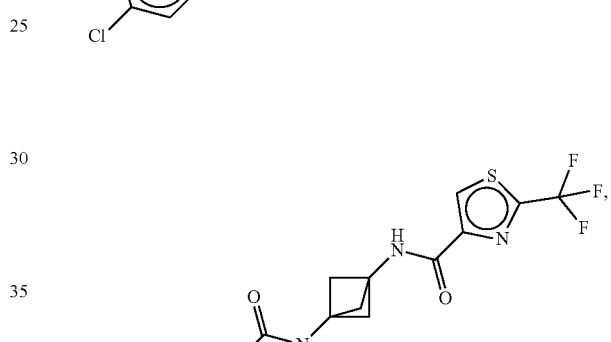
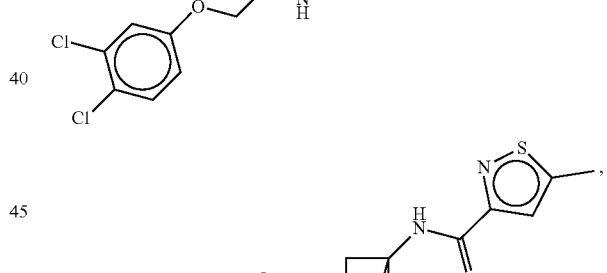
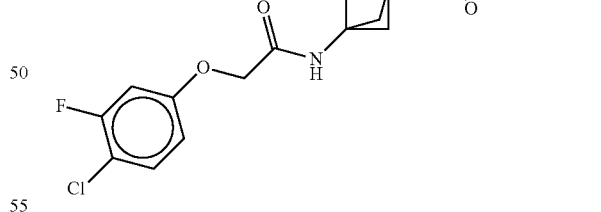
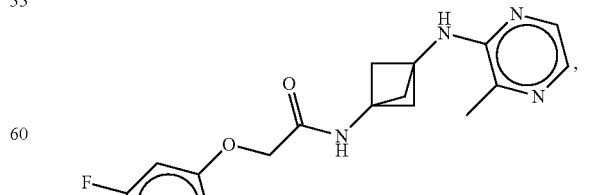

921
-continued
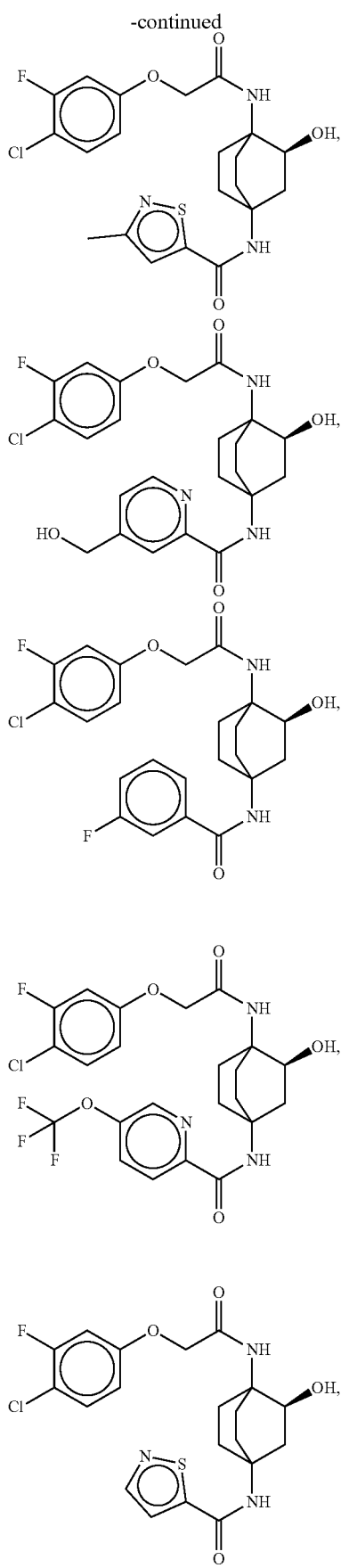
922
-continued
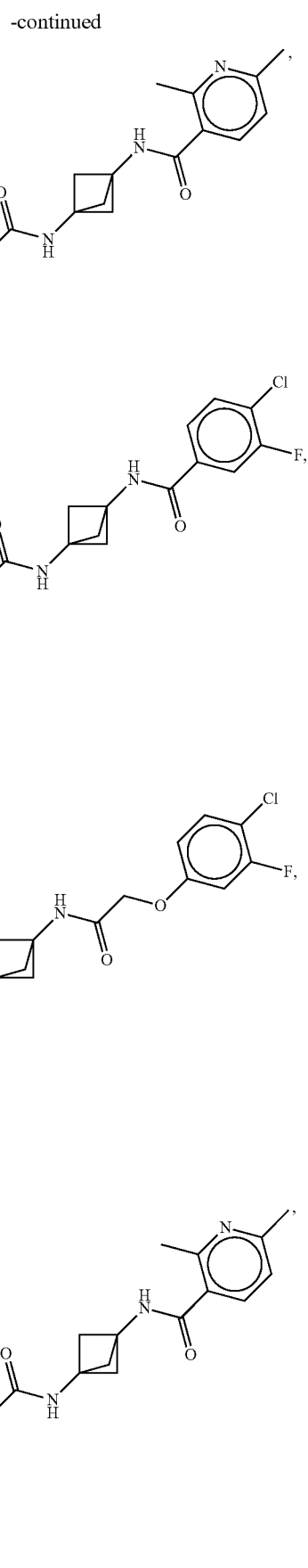

923
-continued
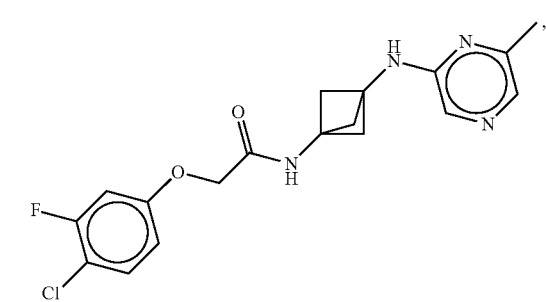
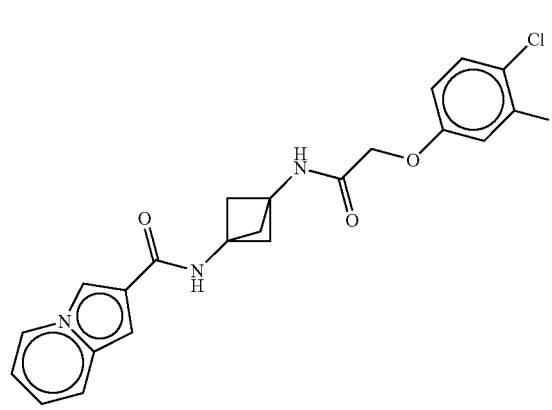
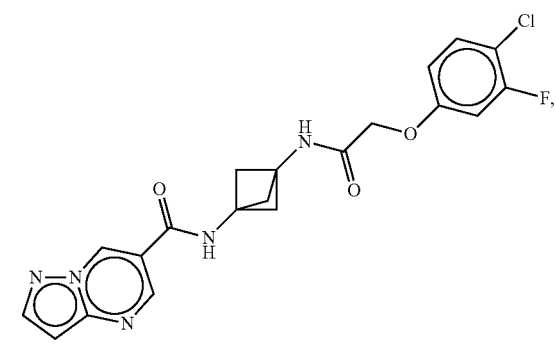
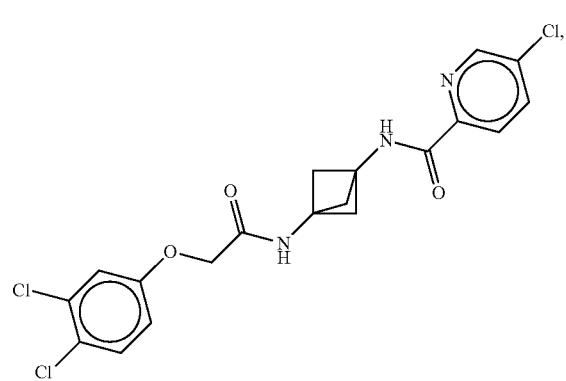
924
-continued
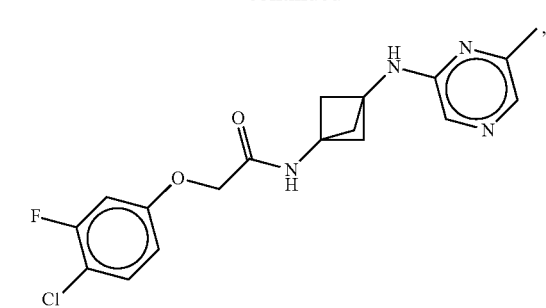
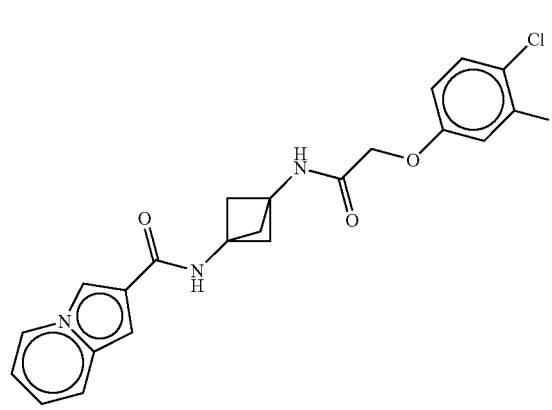
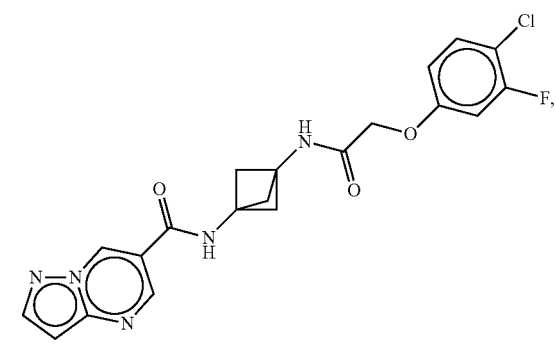

-continued
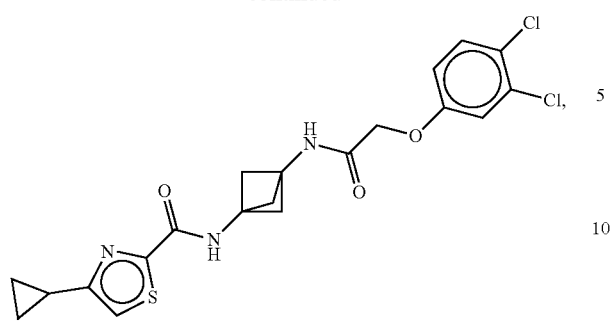
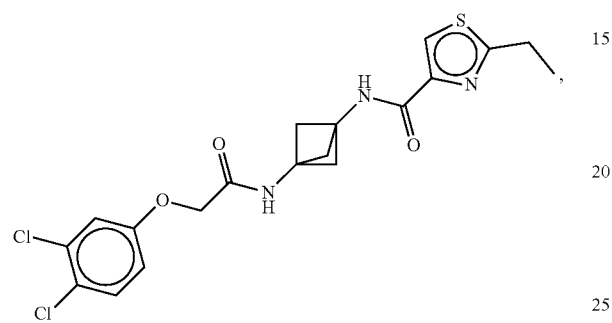
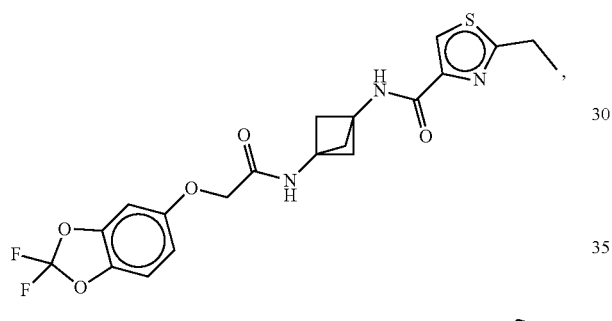
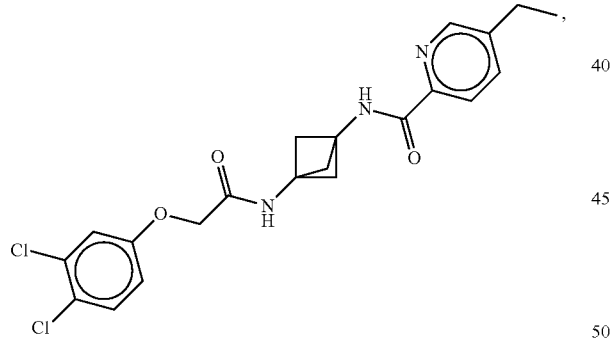
-continued
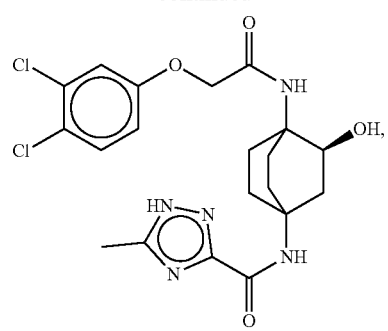
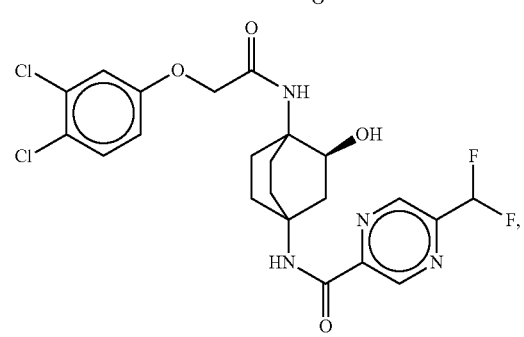
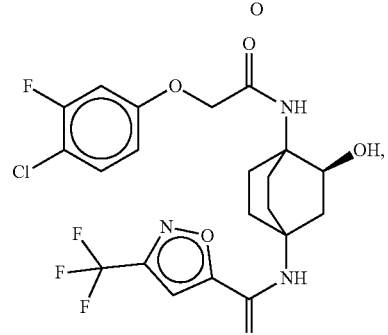
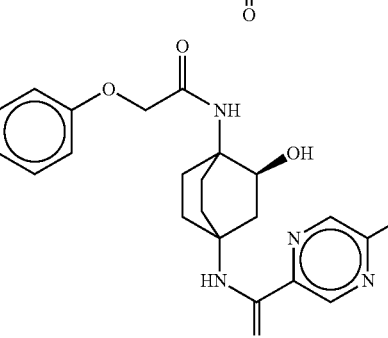

927
-continued
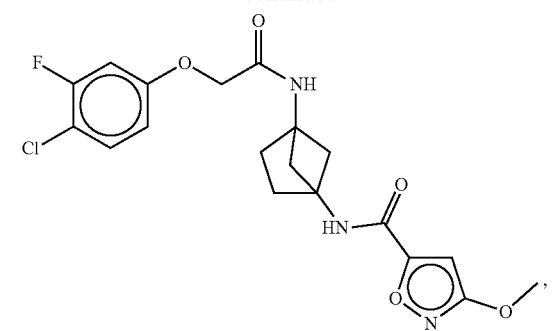
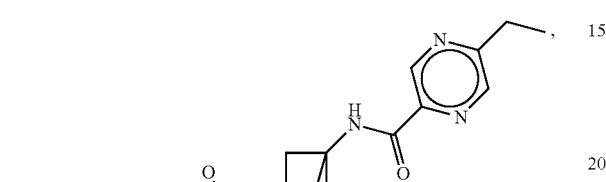
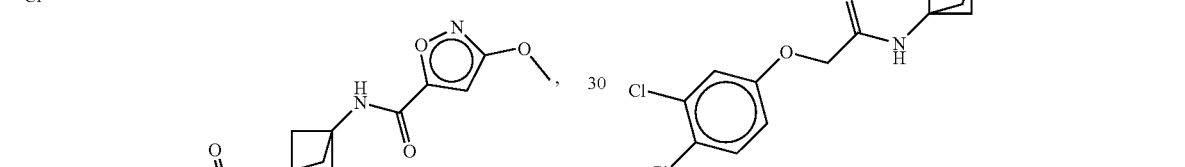
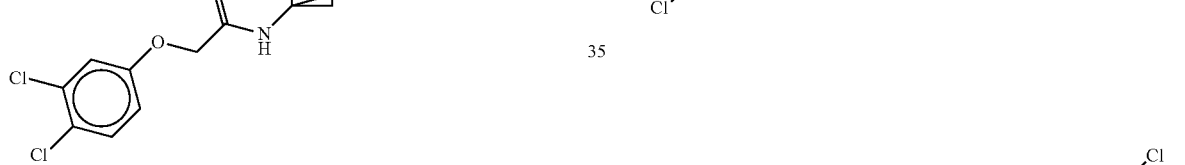
928
-continued
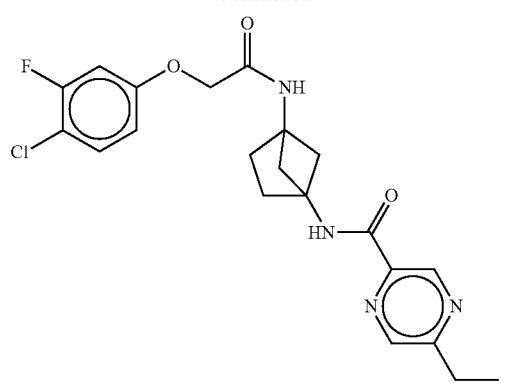
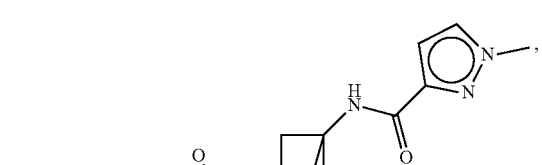
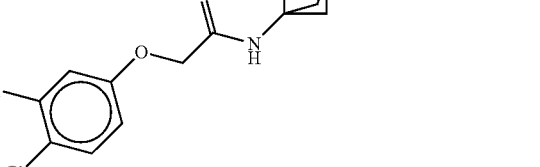
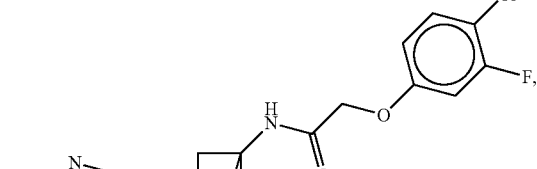
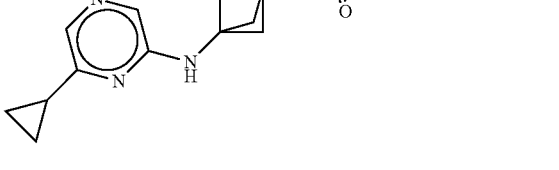

929
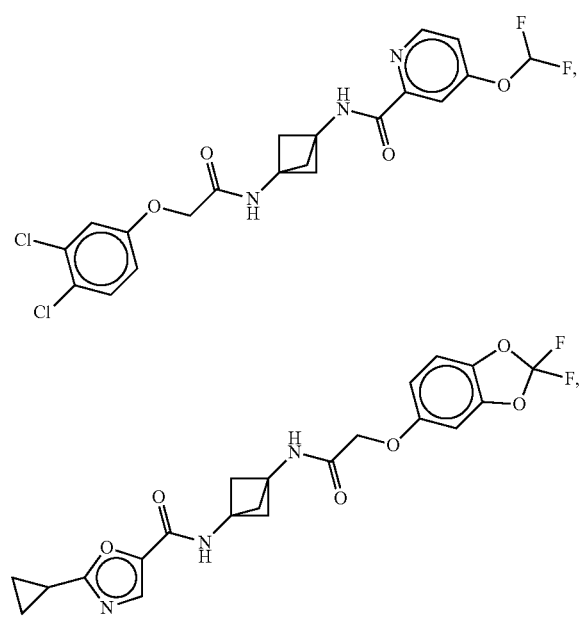
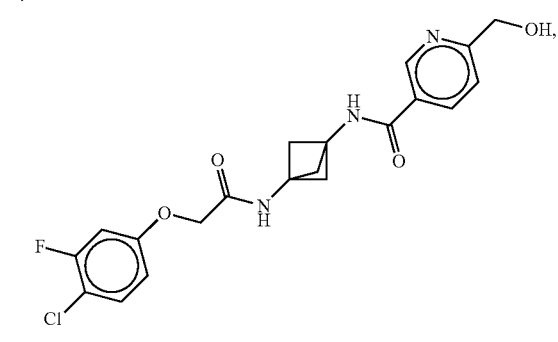
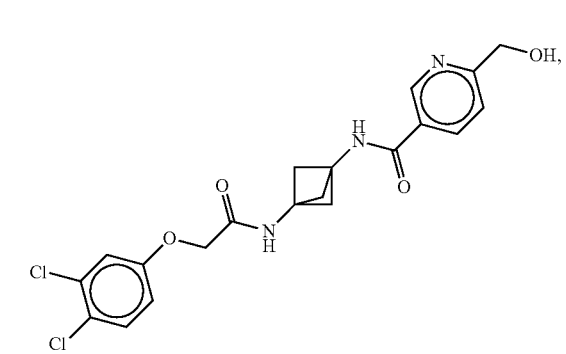
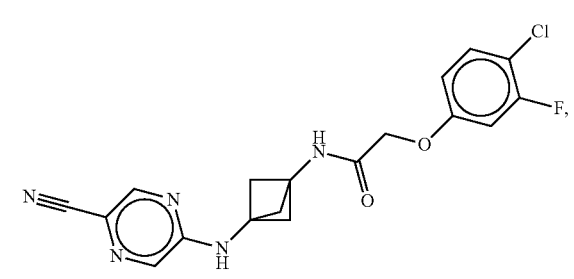
930
-continued
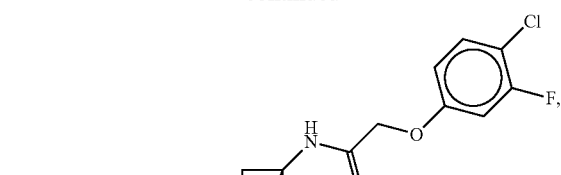
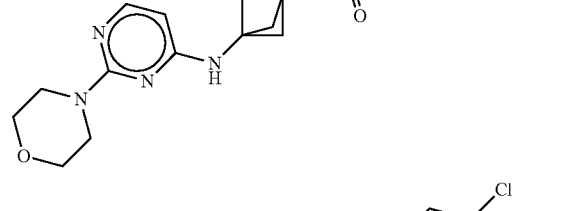
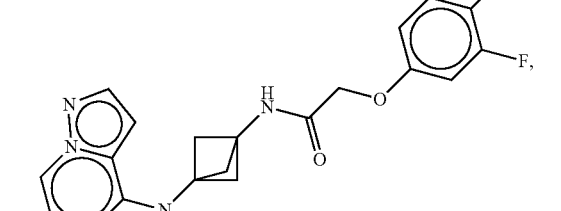
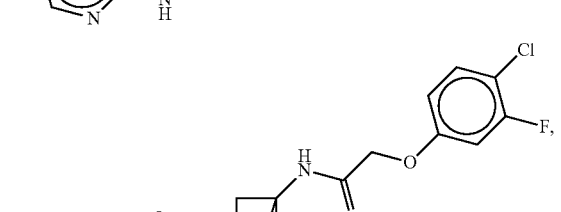
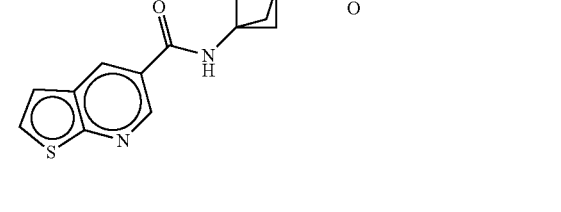
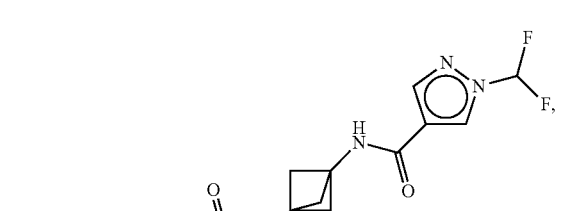

931
-continued
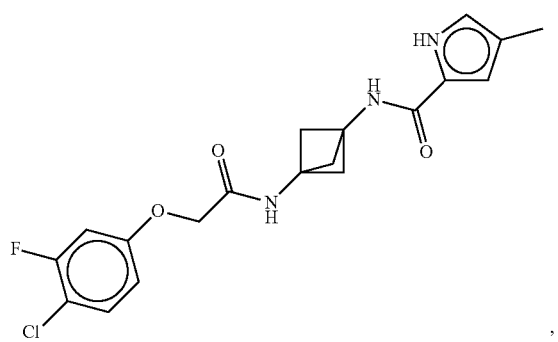
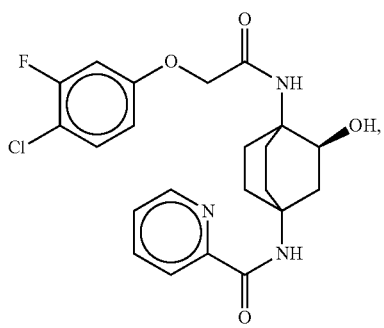
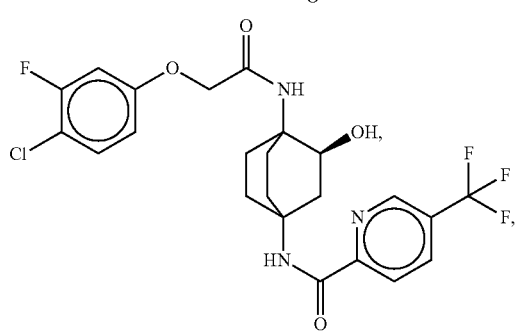
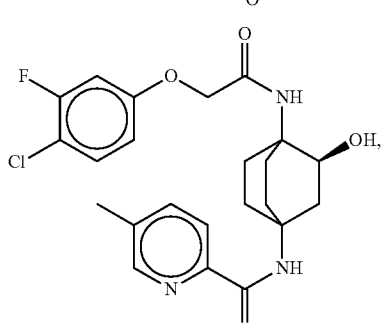
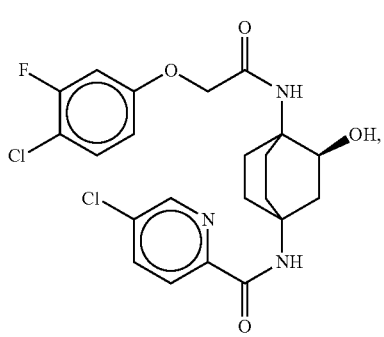
932
-continued
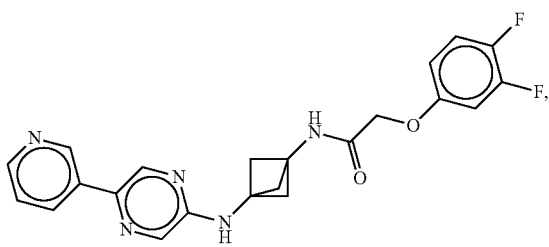
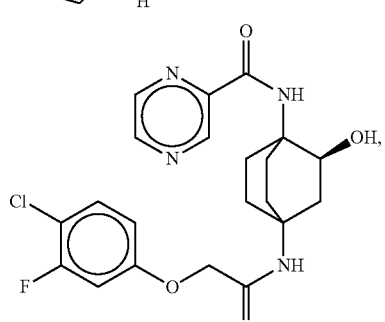
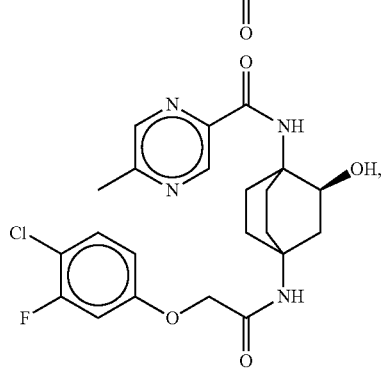
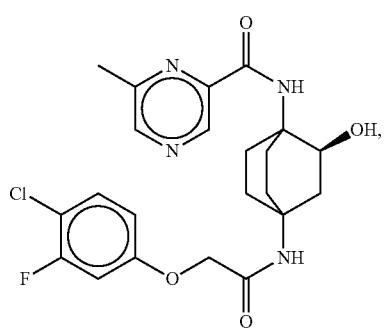
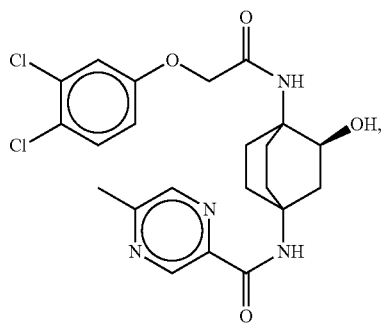

-continued
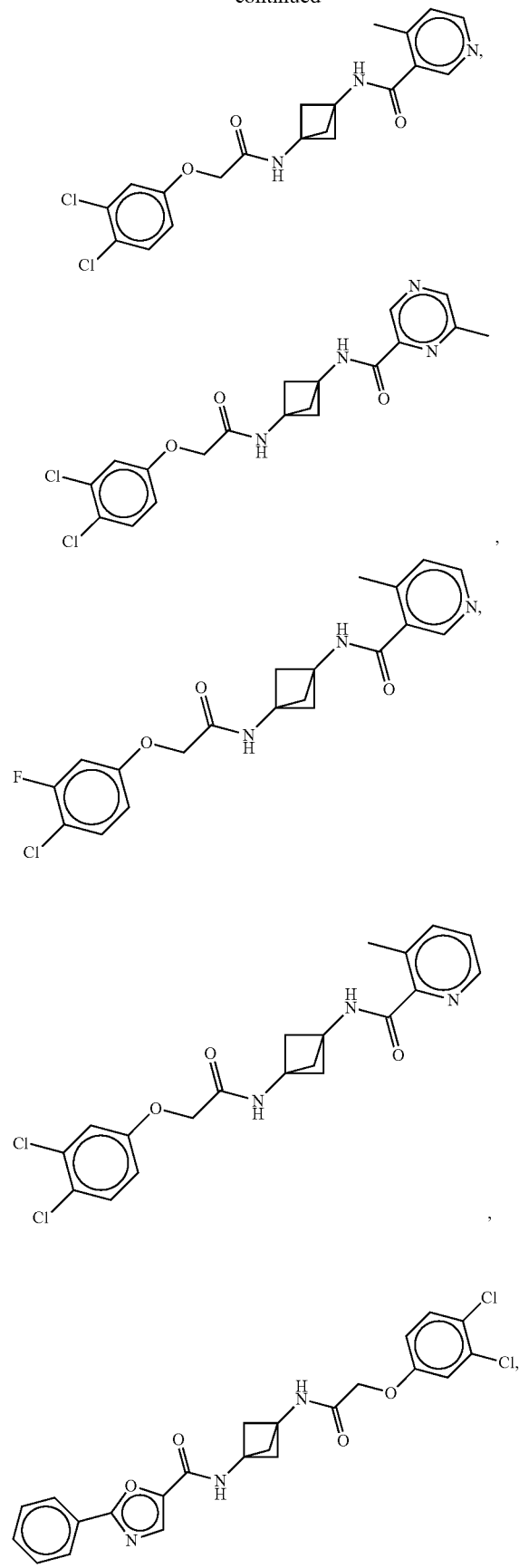
-continued
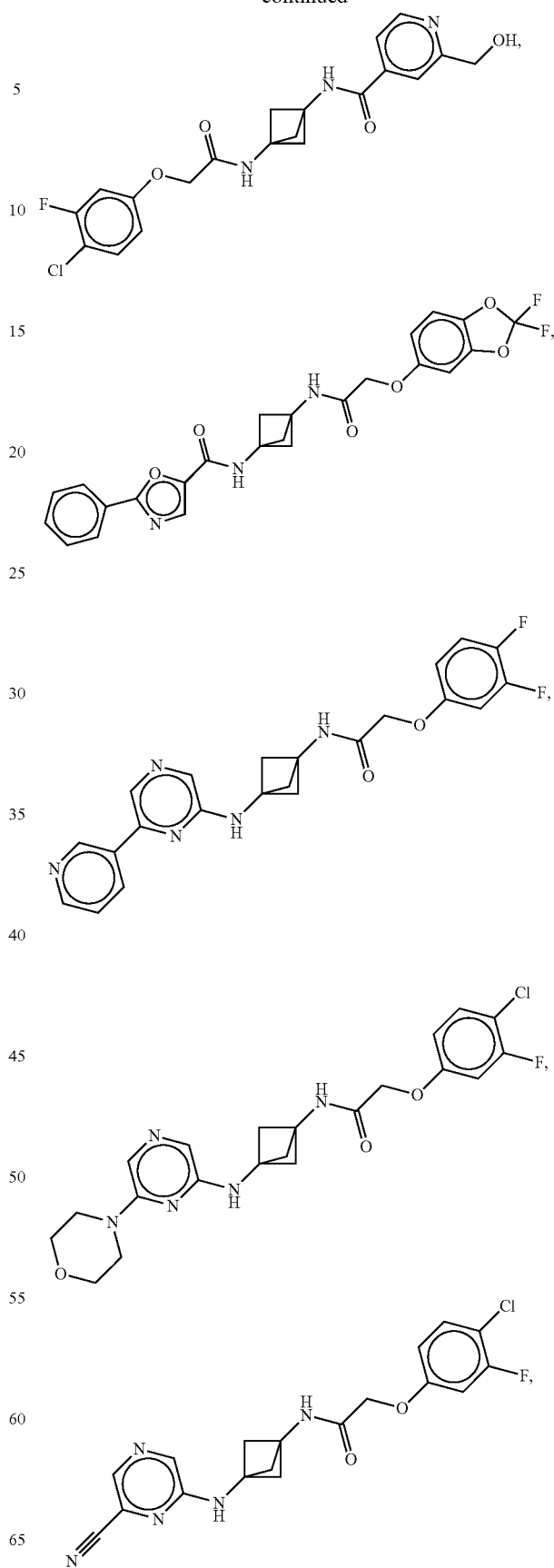

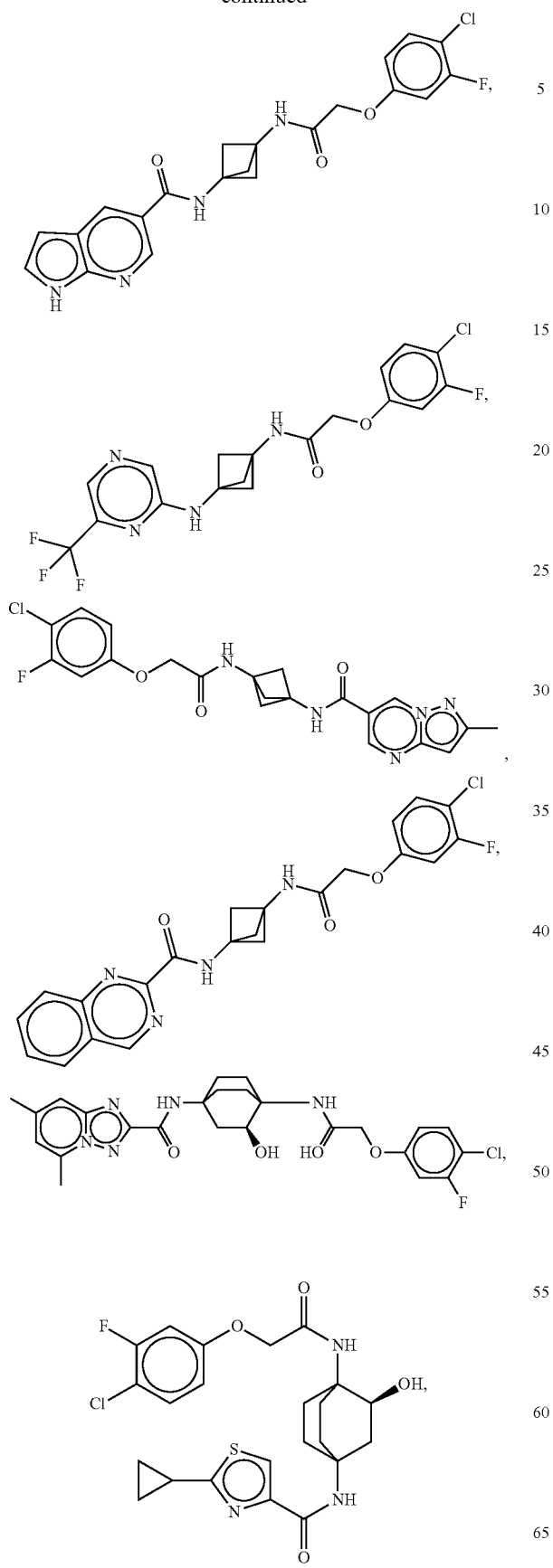
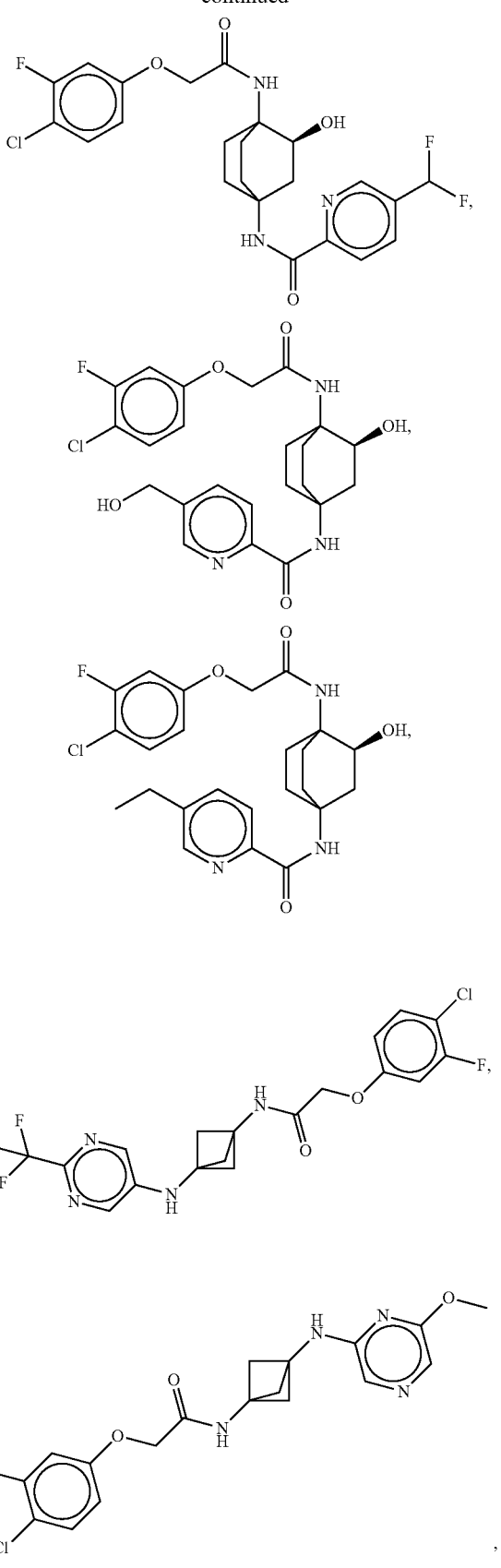

937
-continued
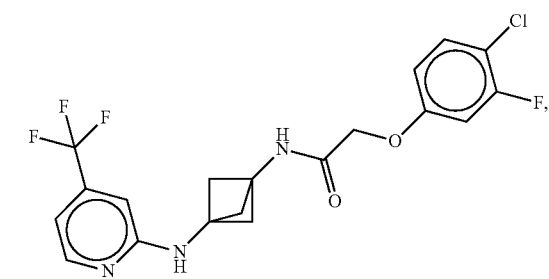
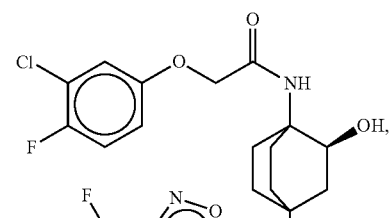
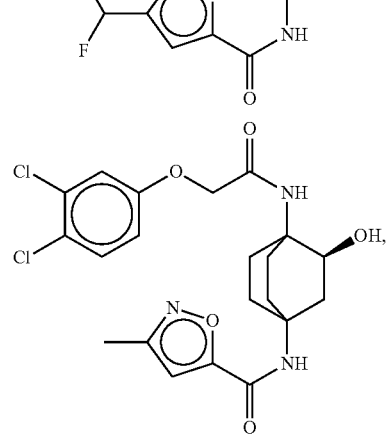
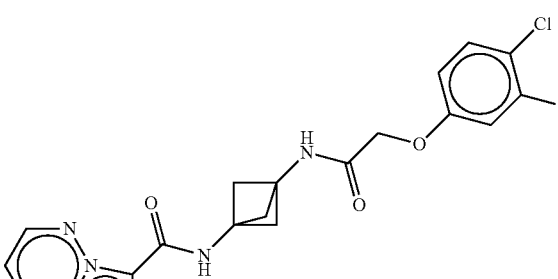
938
-continued
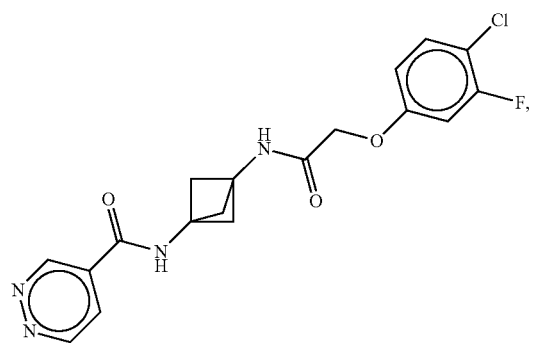
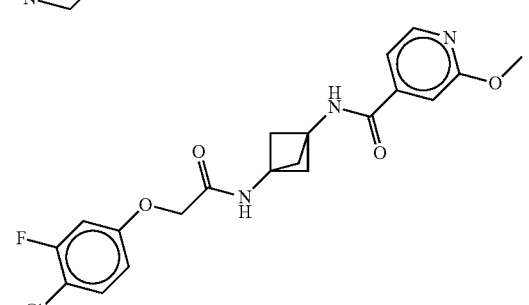
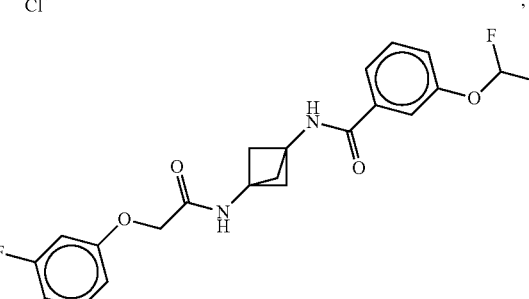
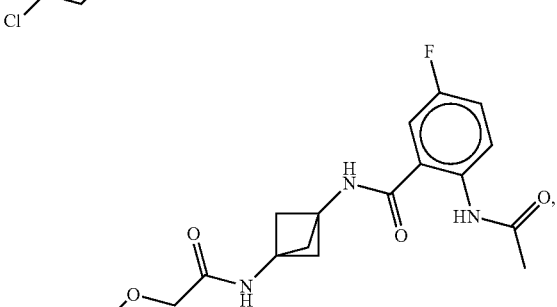
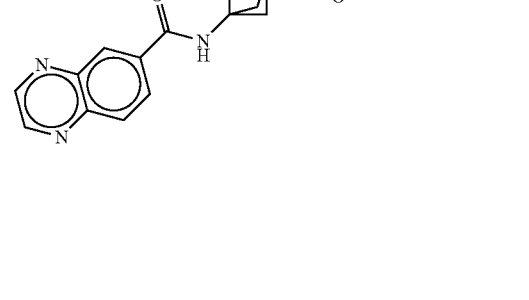

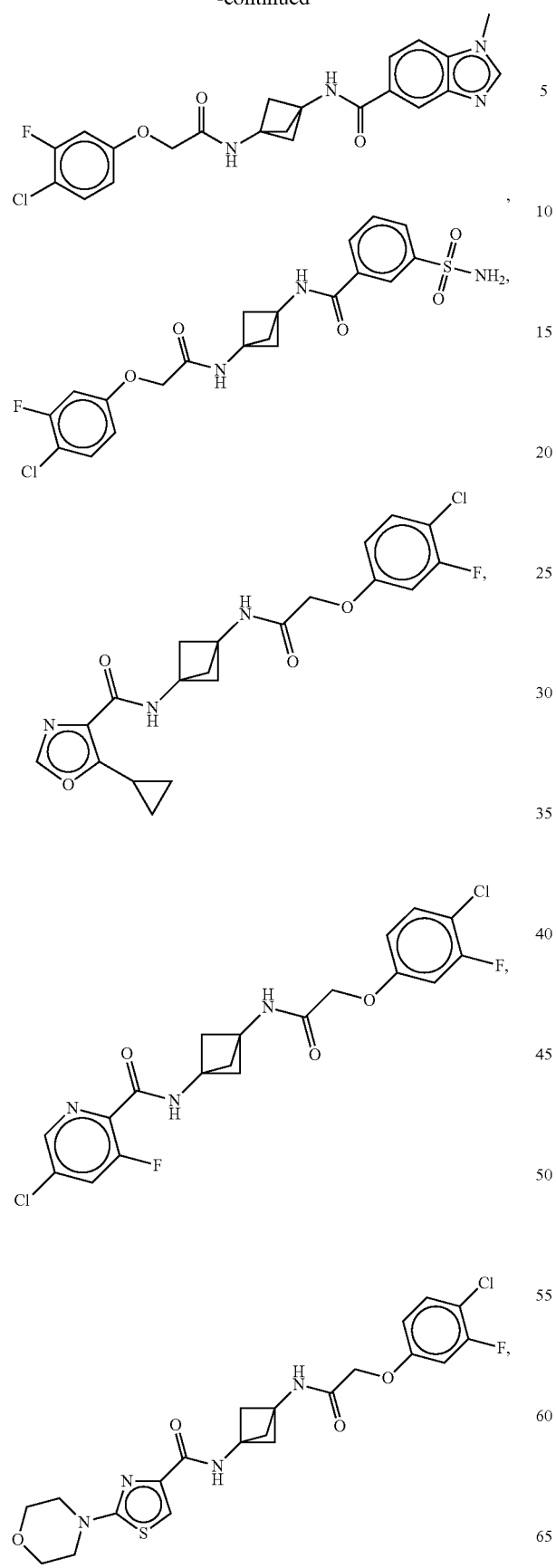
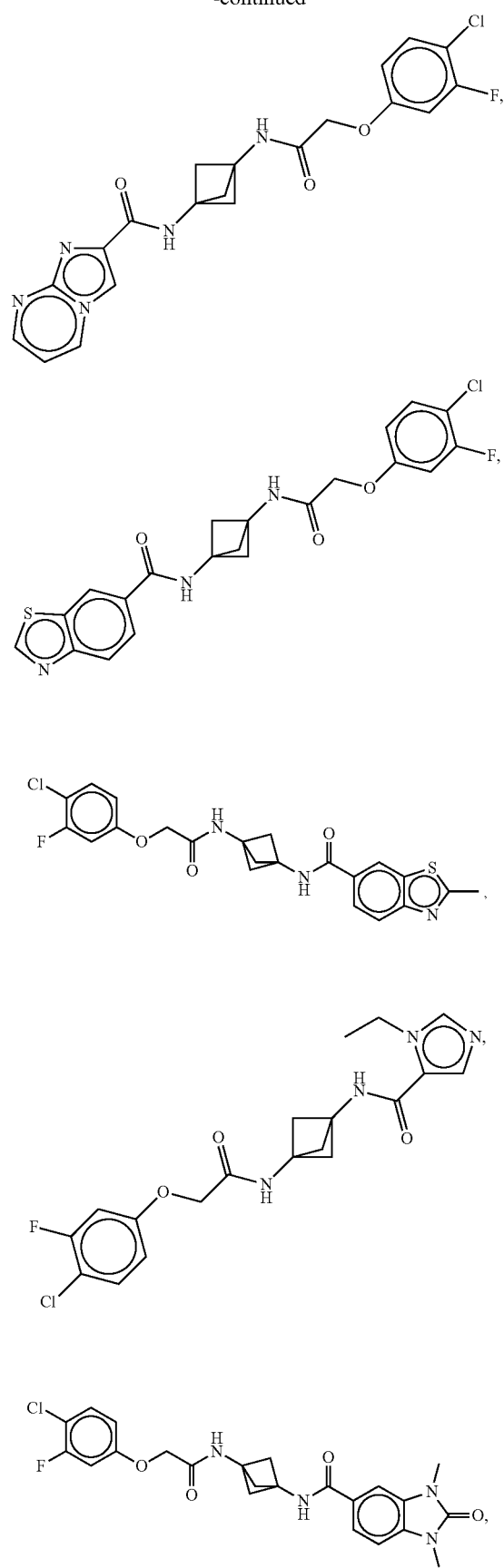

941
-continued
942
-continued
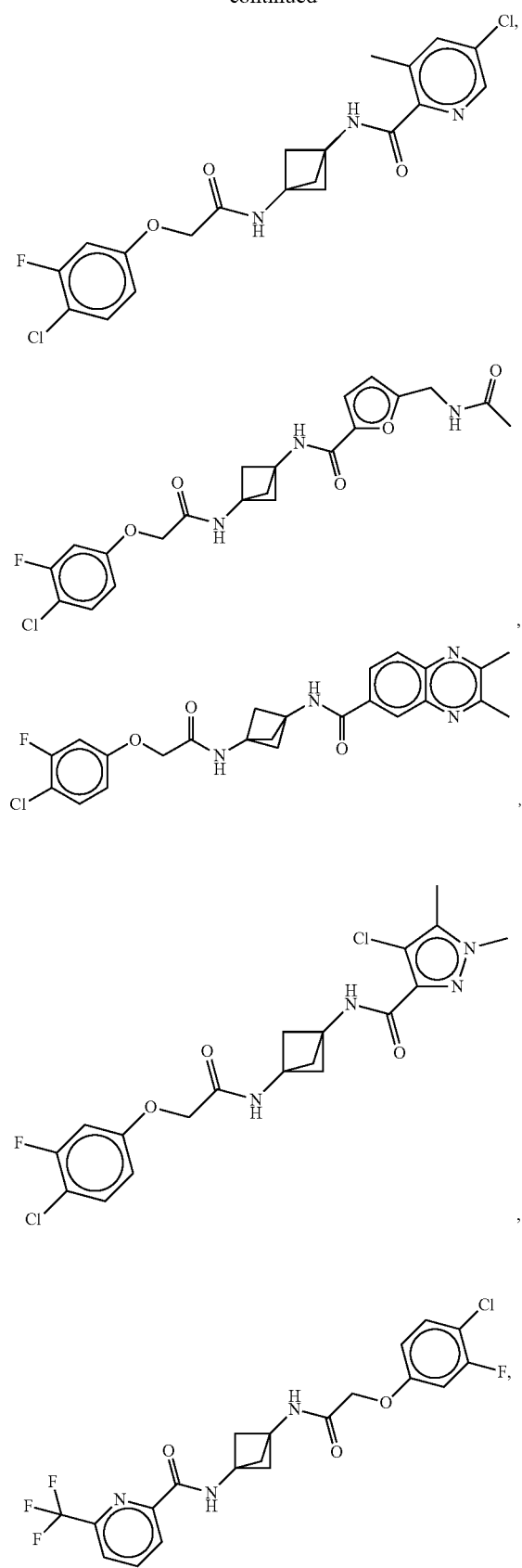
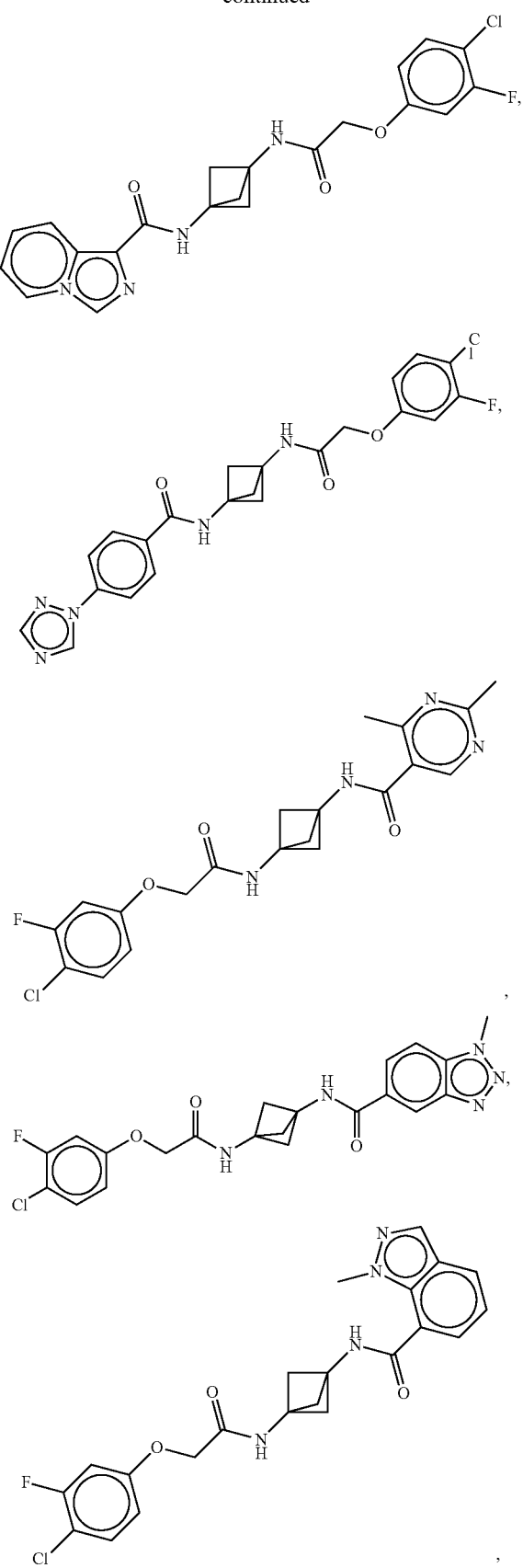

943
-continued
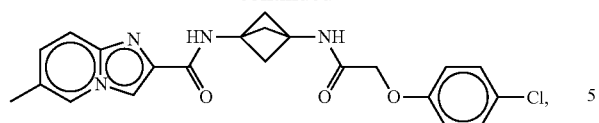
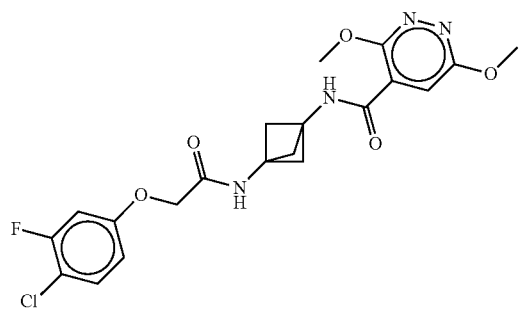
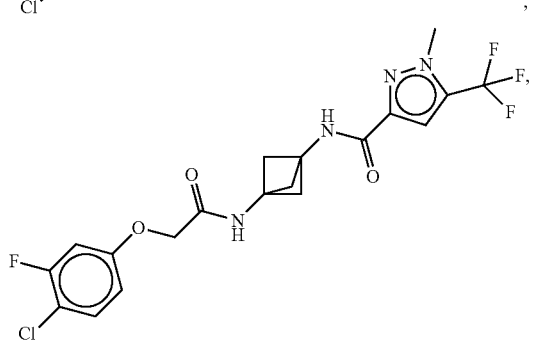
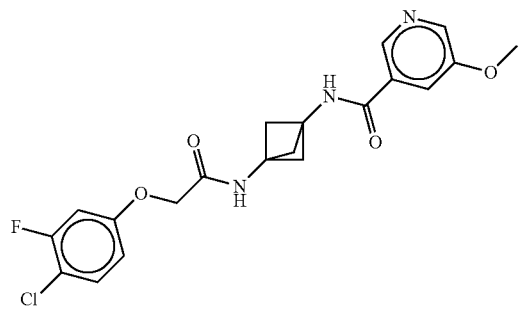
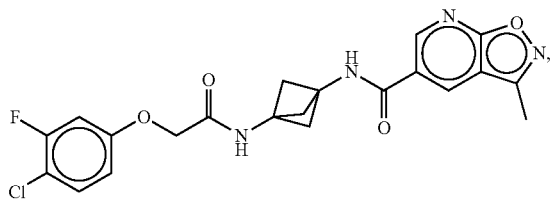
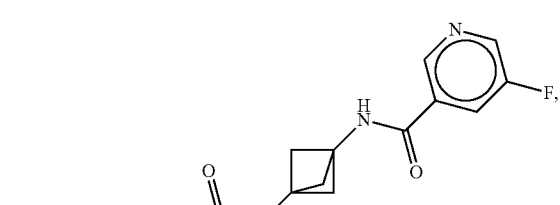
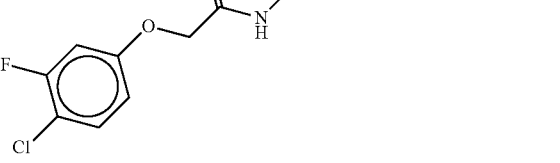
944
-continued
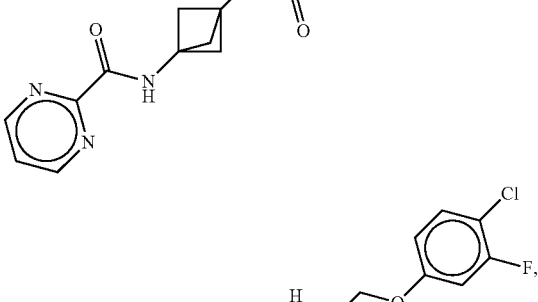
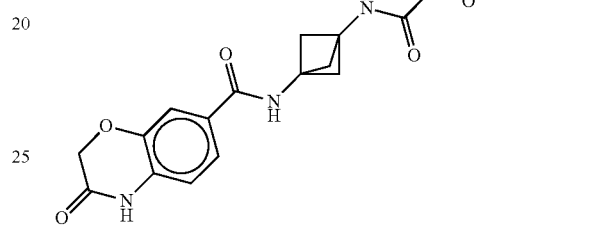
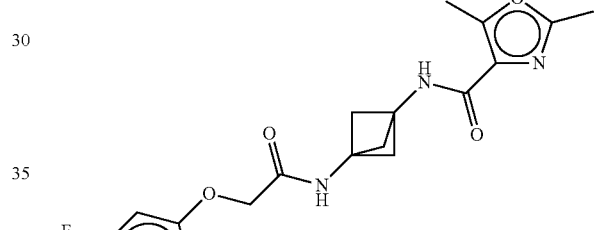
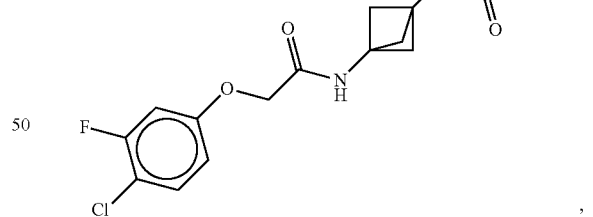
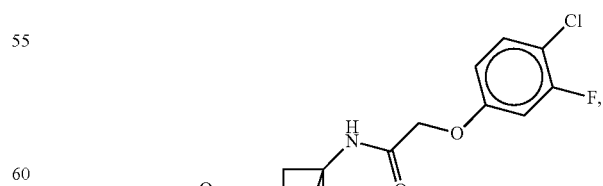
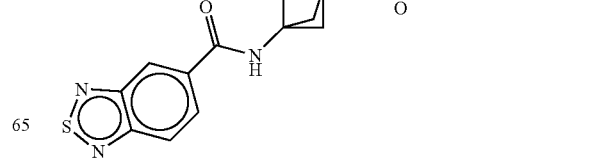

945
-continued
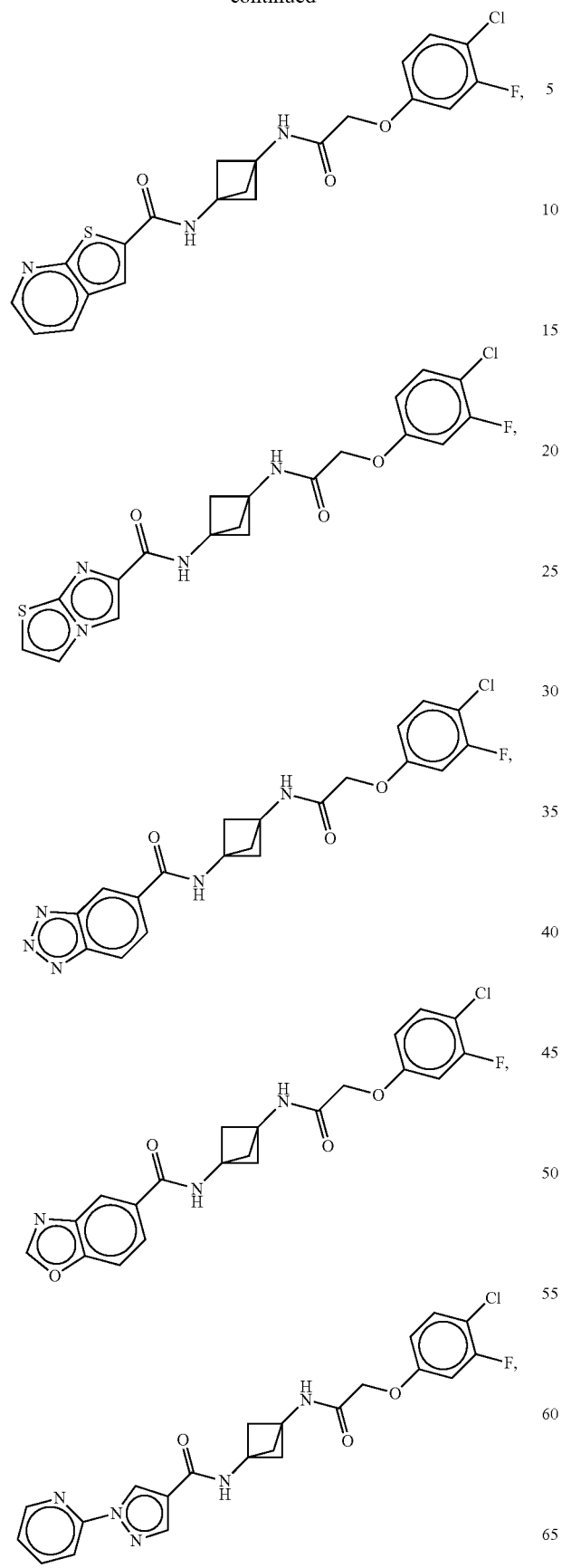
946
-continued
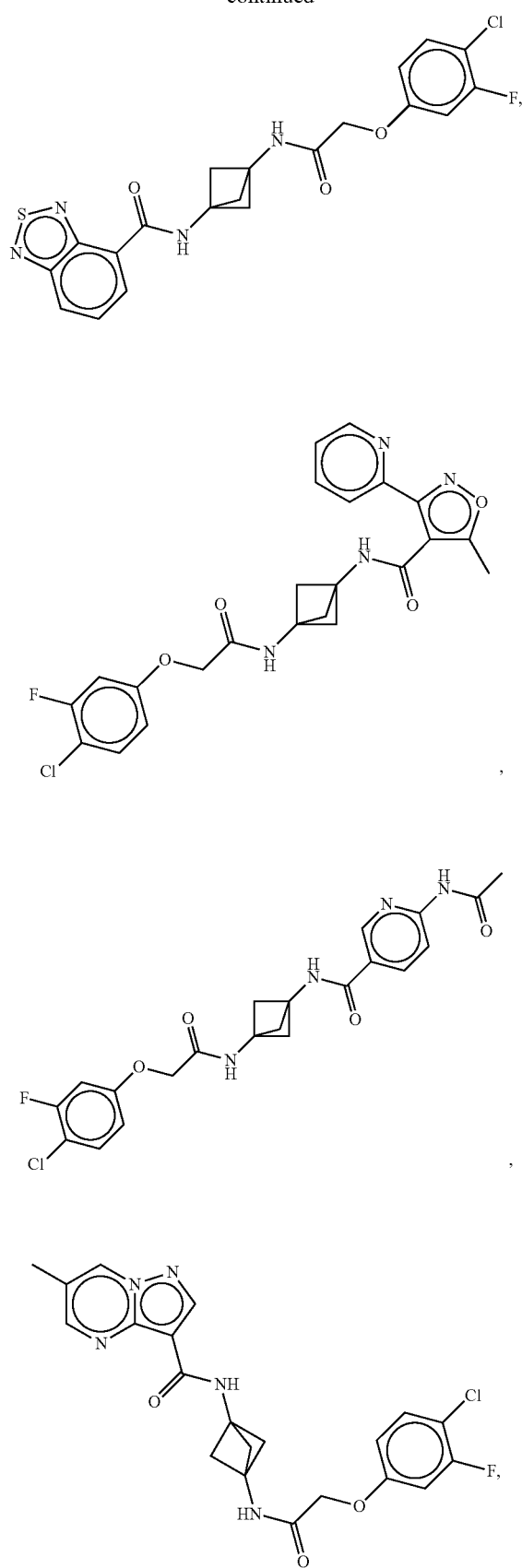

947
-continued
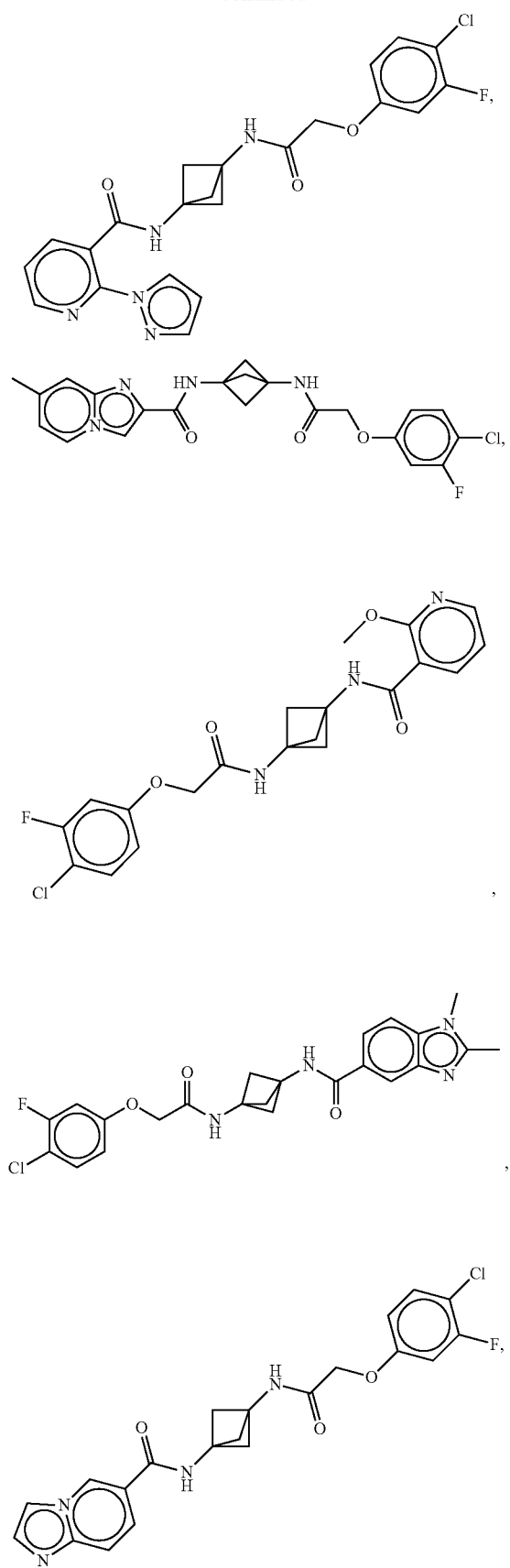
948
-continued
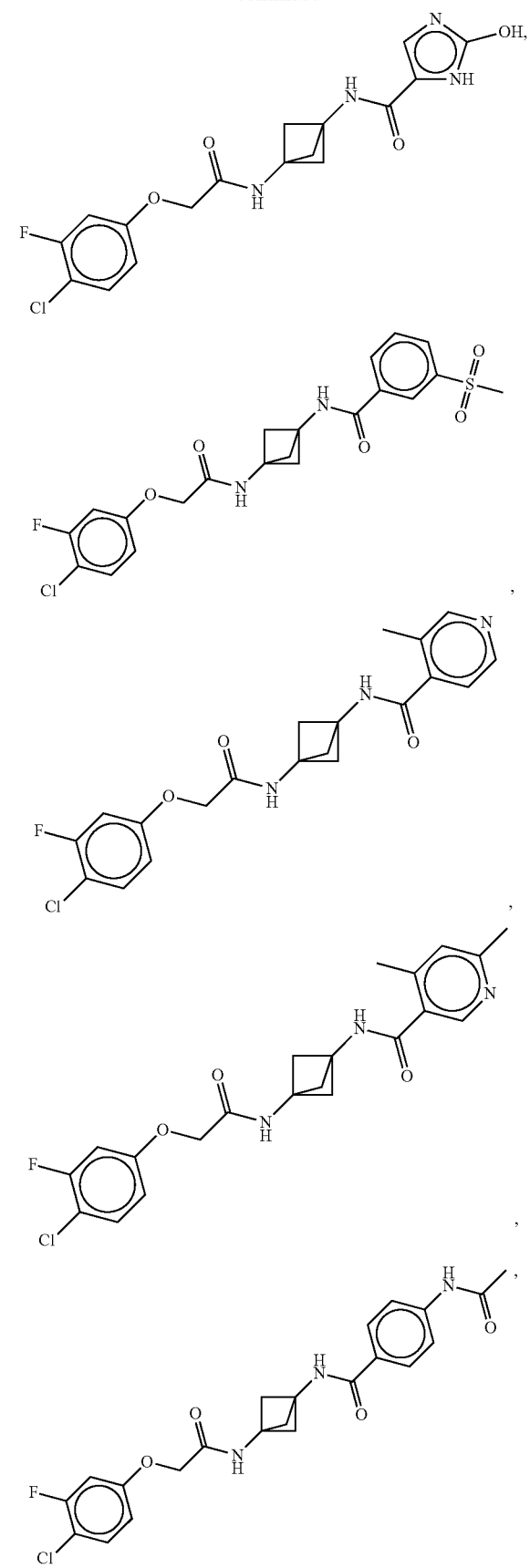

949
-continued
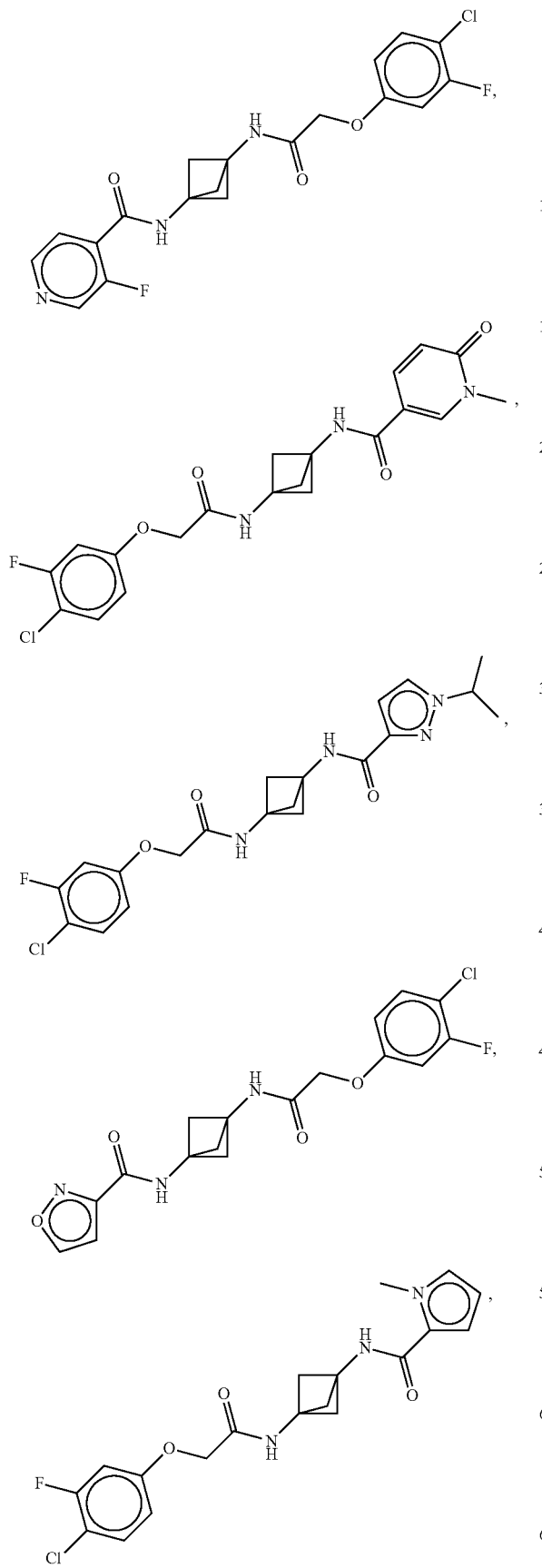
950
-continued
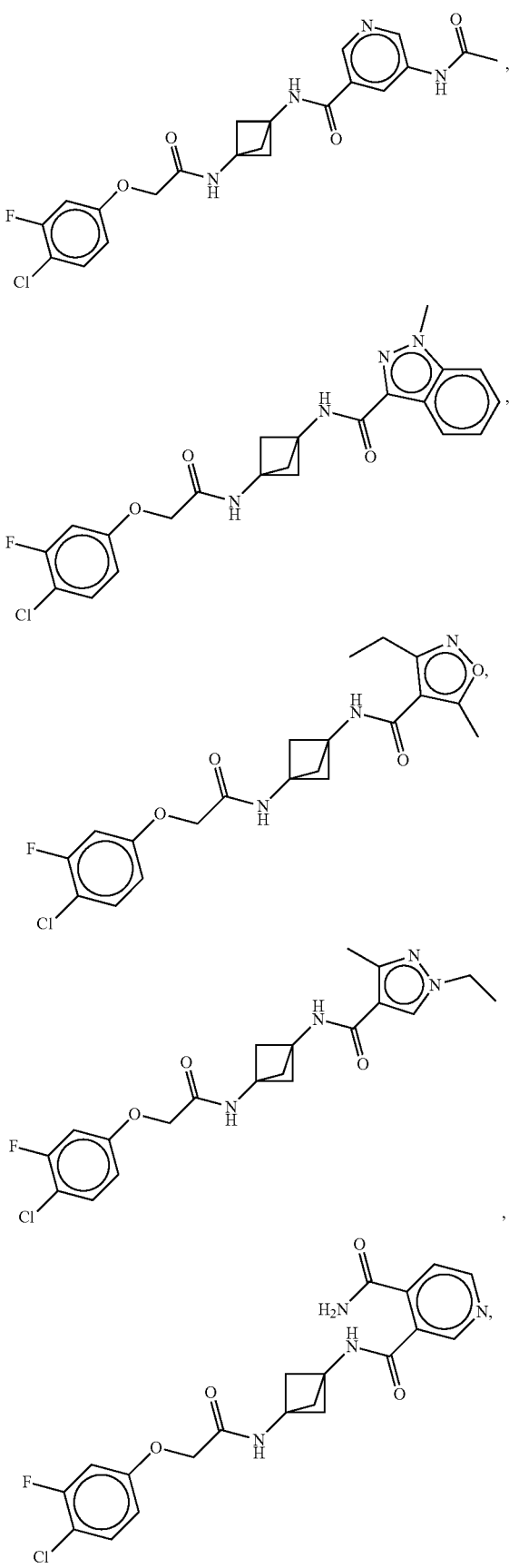

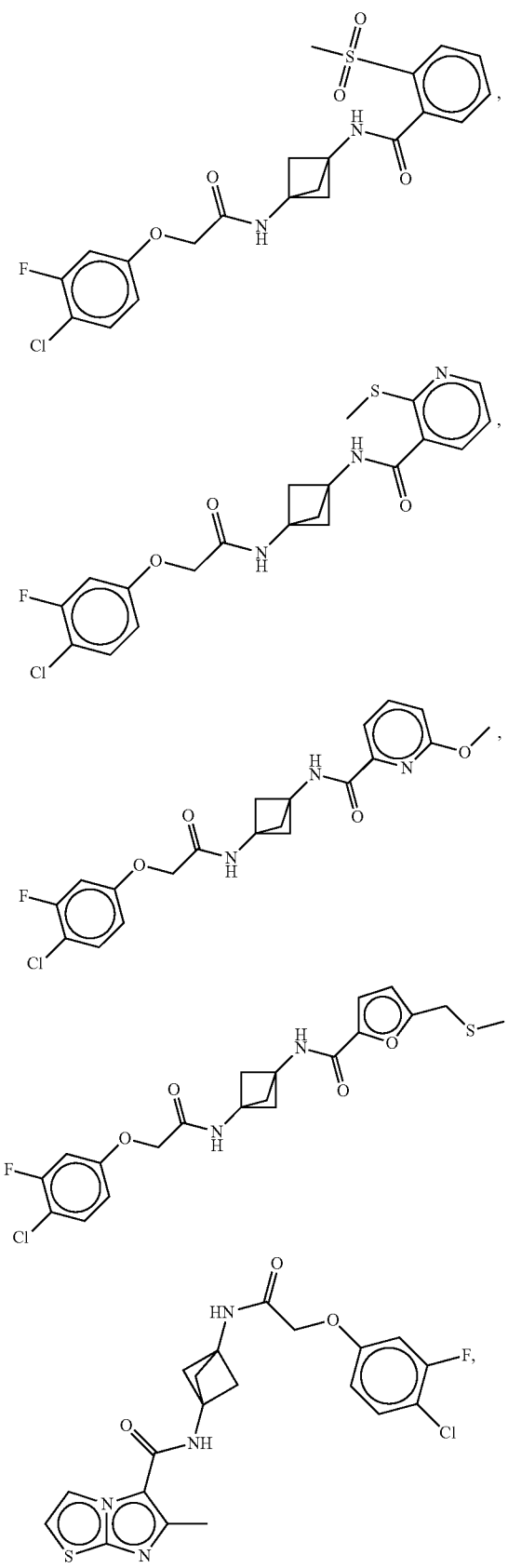
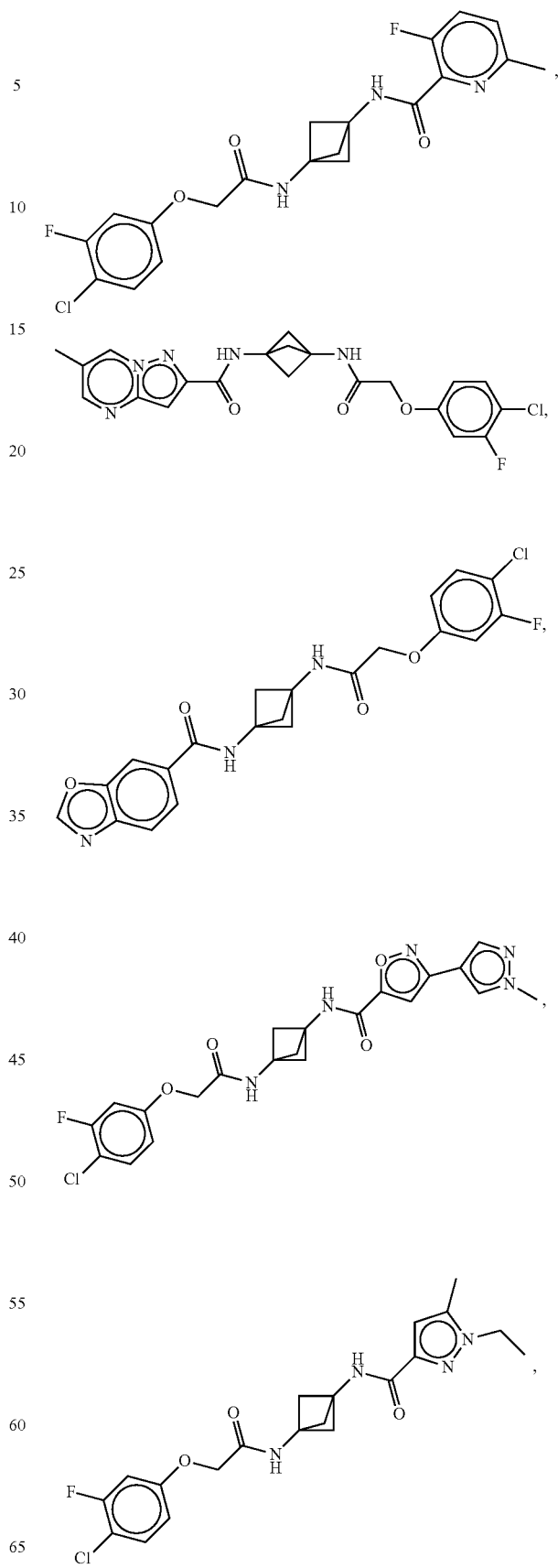

-continued
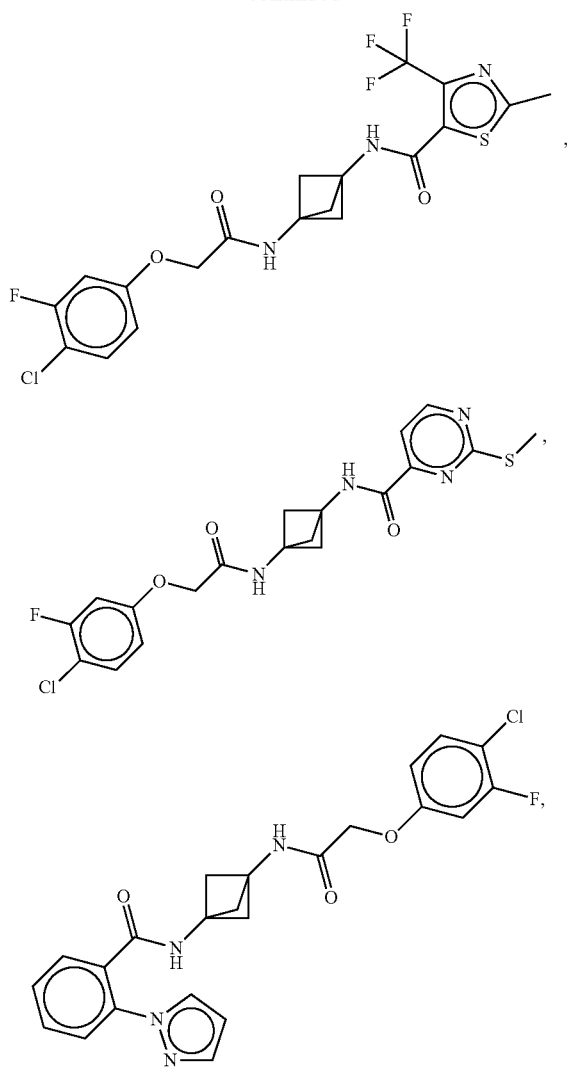
-continued
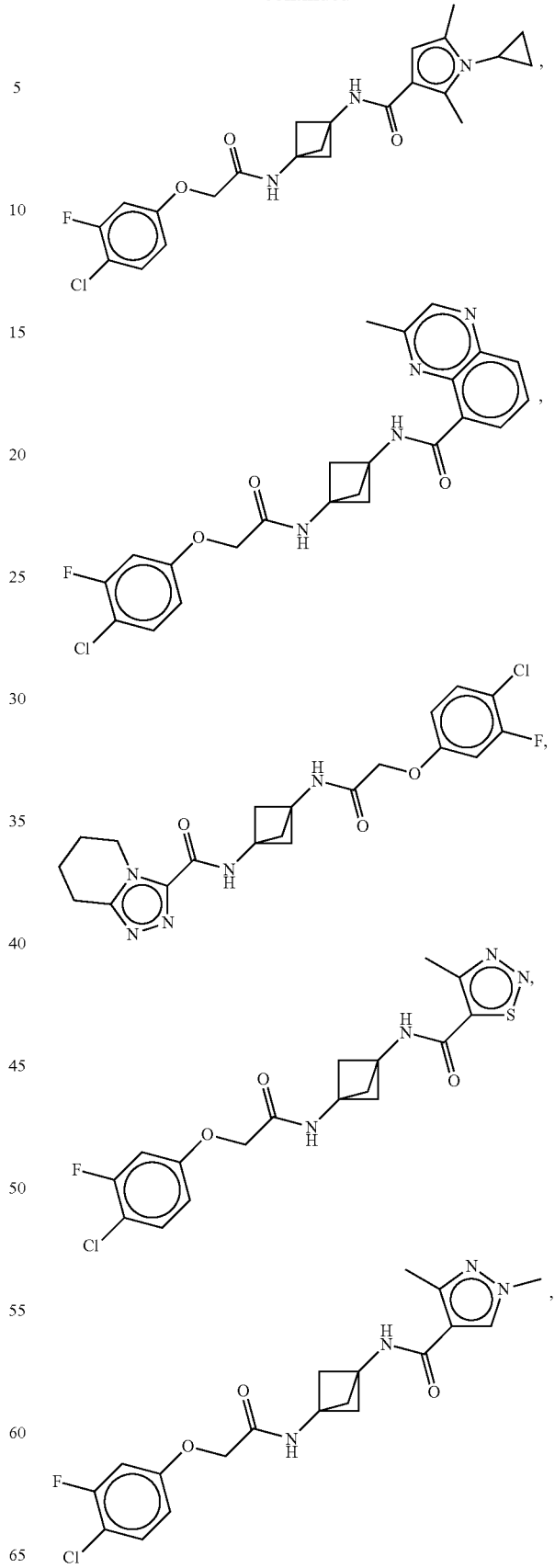

955
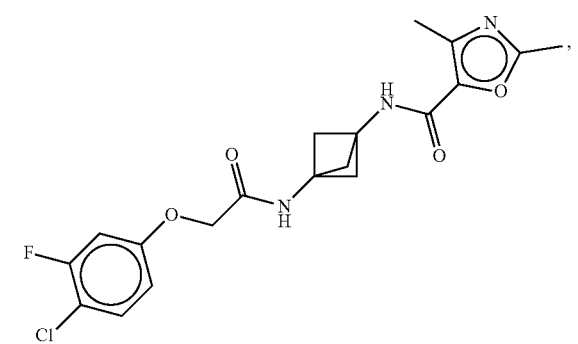
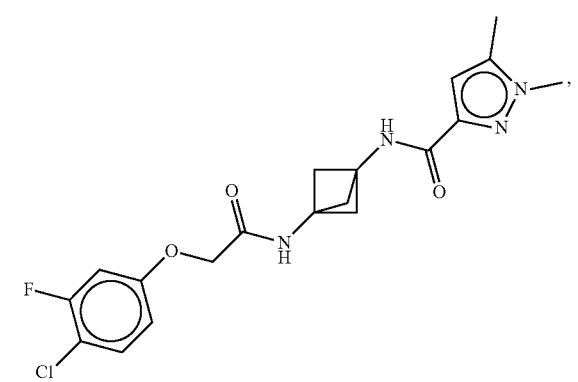
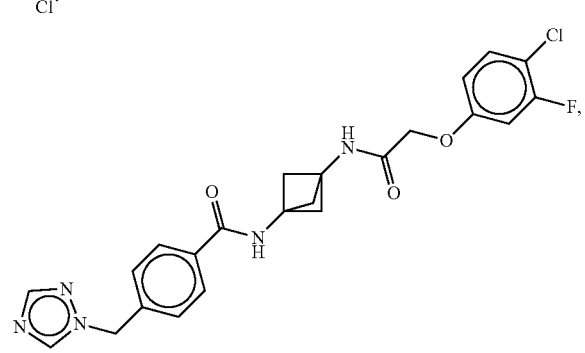
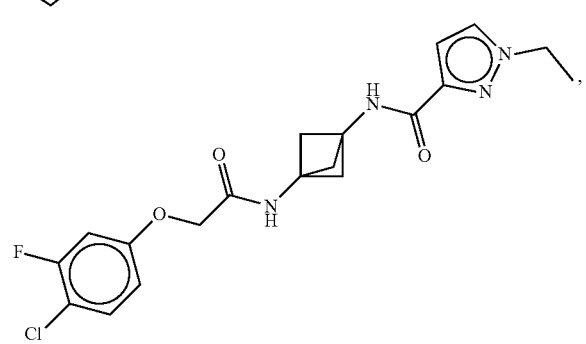
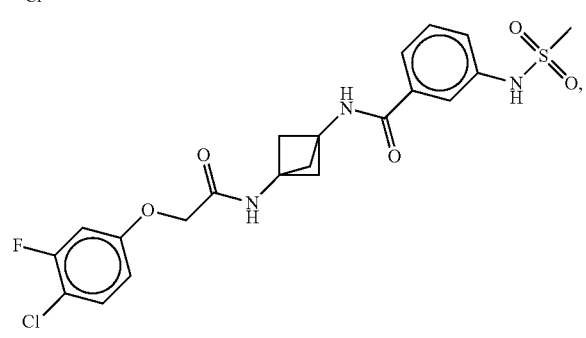
956
-continued
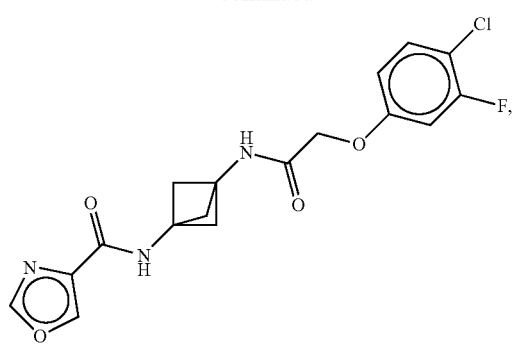
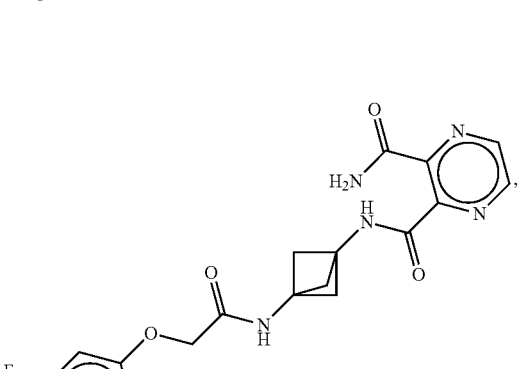
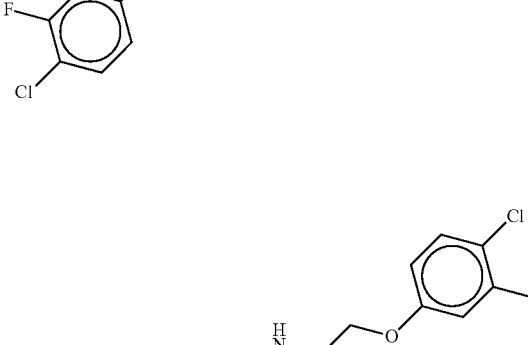
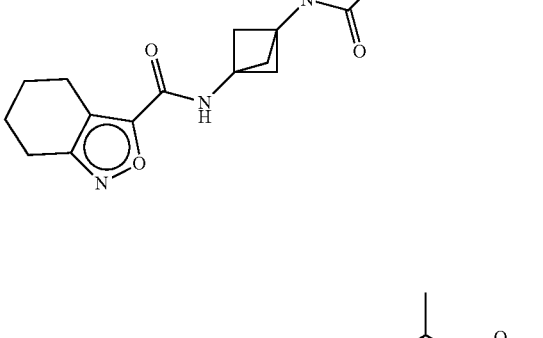
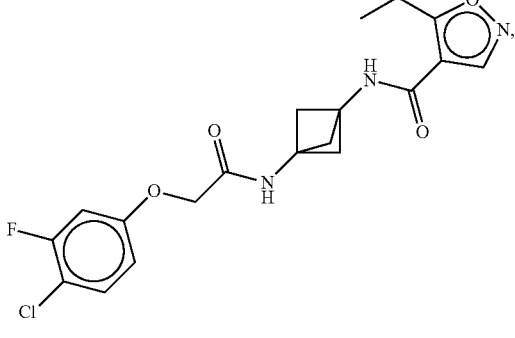

957
-continued
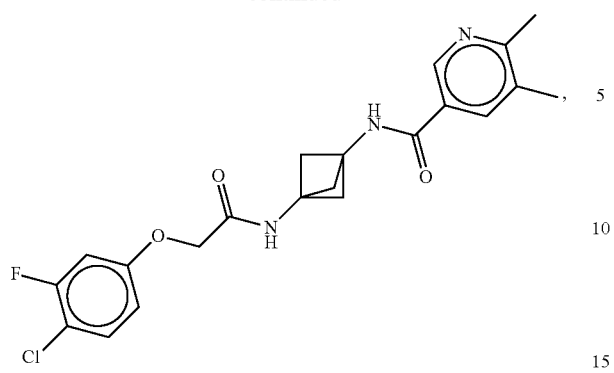
958
-continued
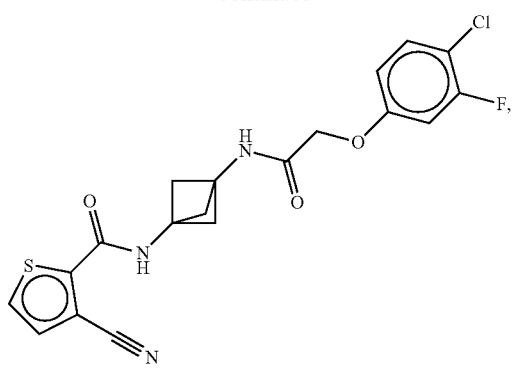
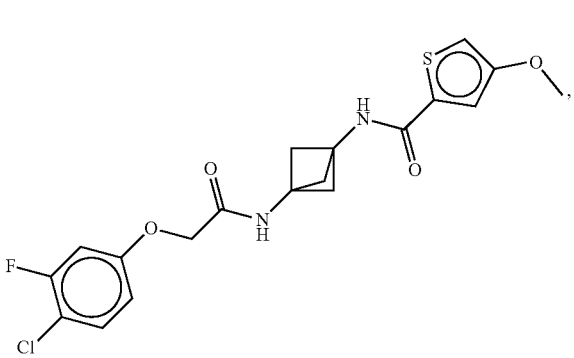
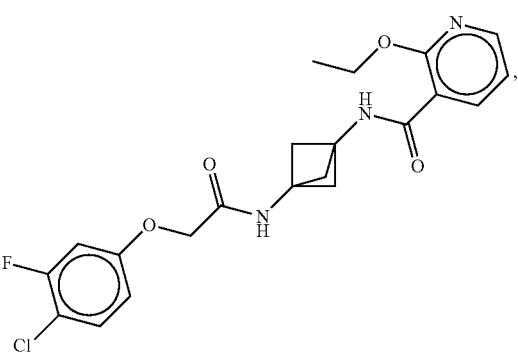
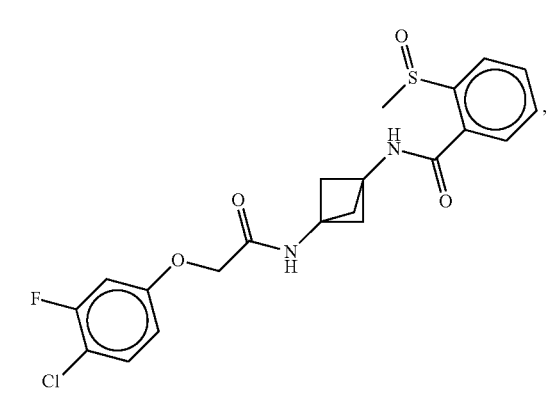
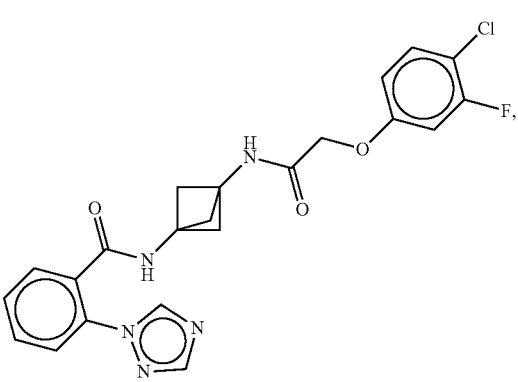
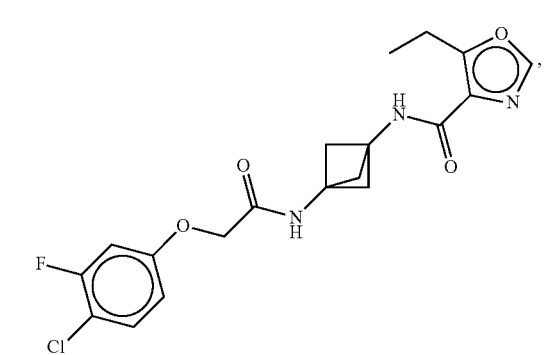
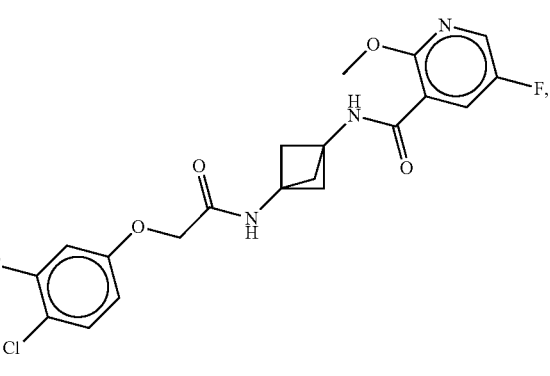

-continued
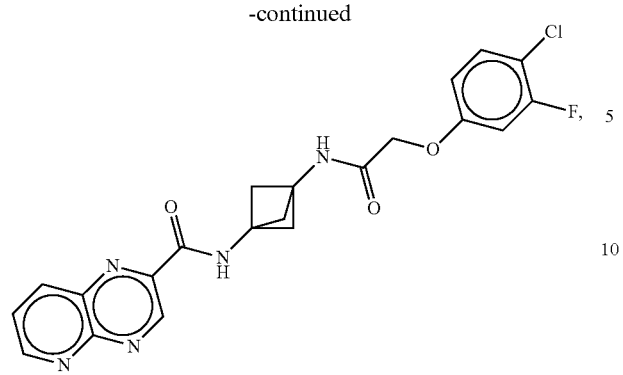
-continued
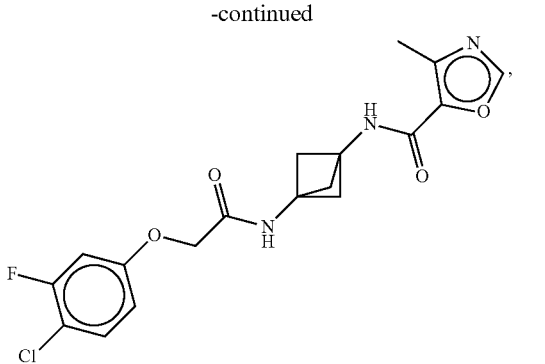

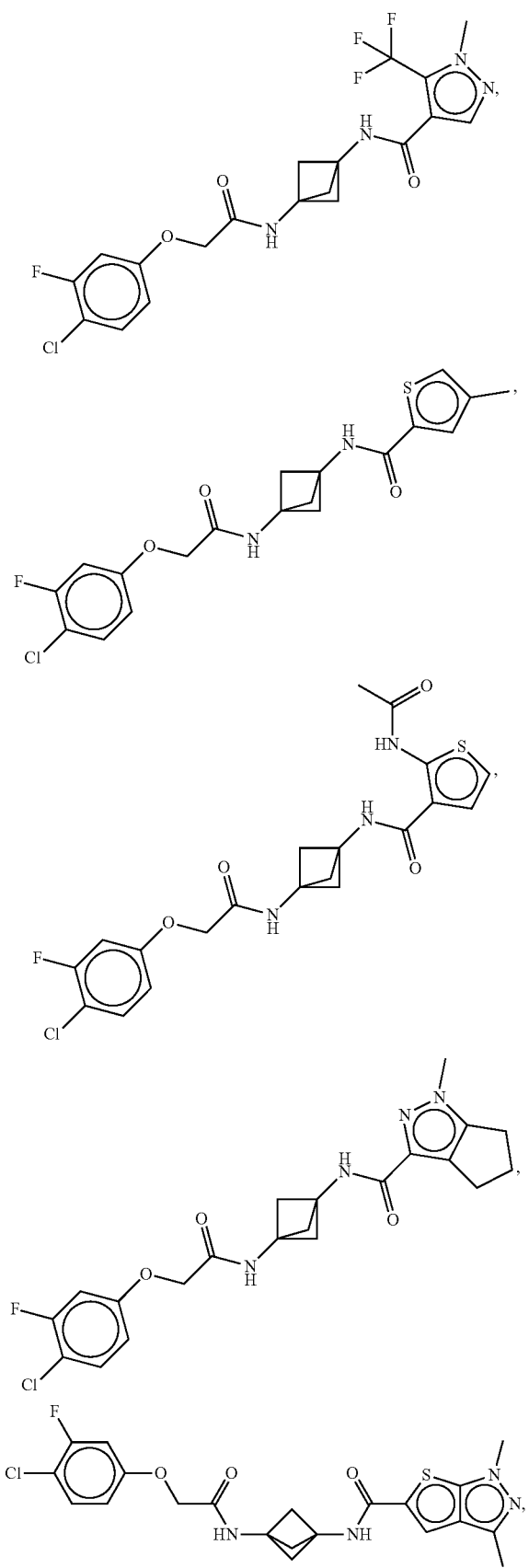
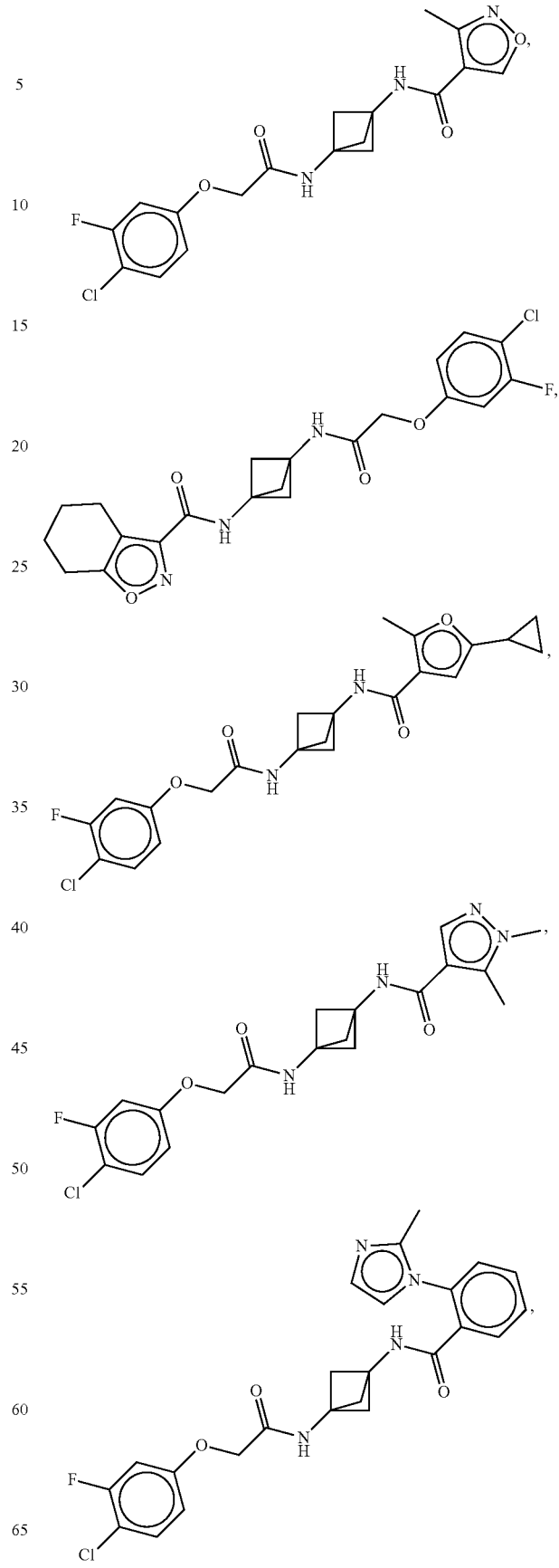

963
-continued
964
-continued
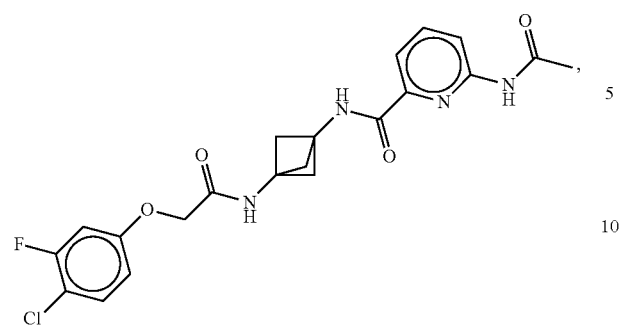
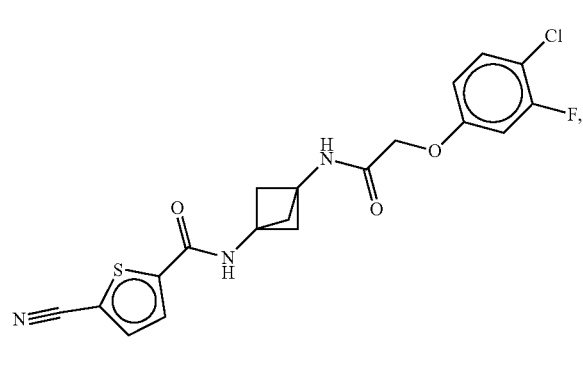
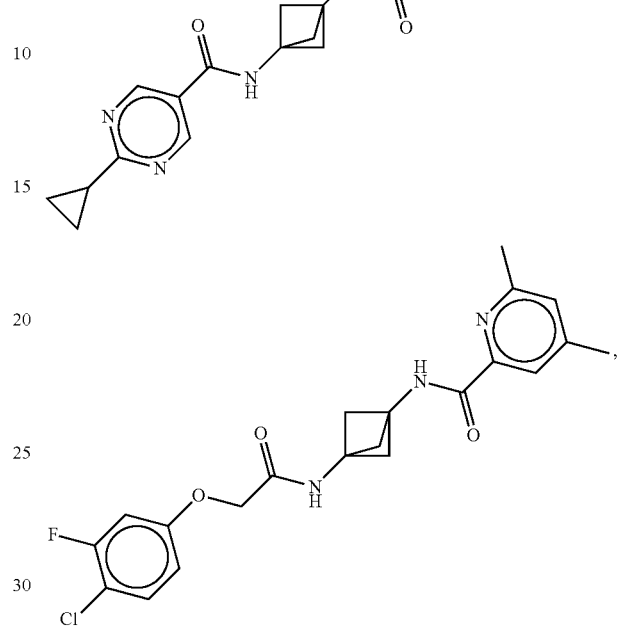
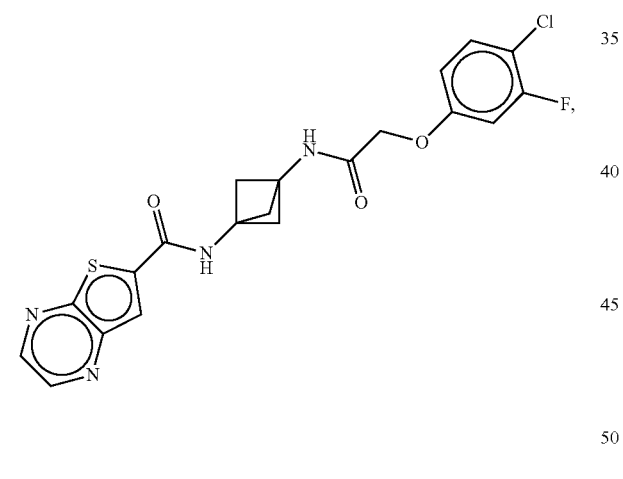
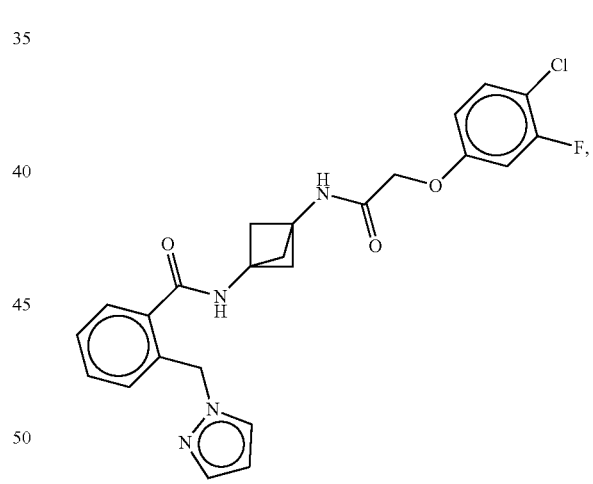
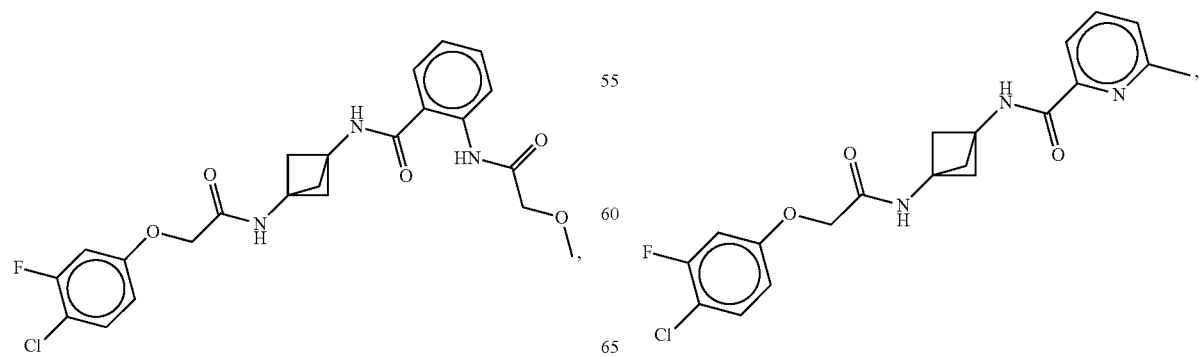
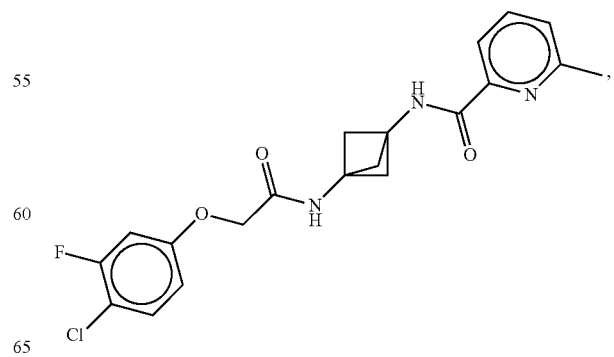

965
-continued
966
-continued
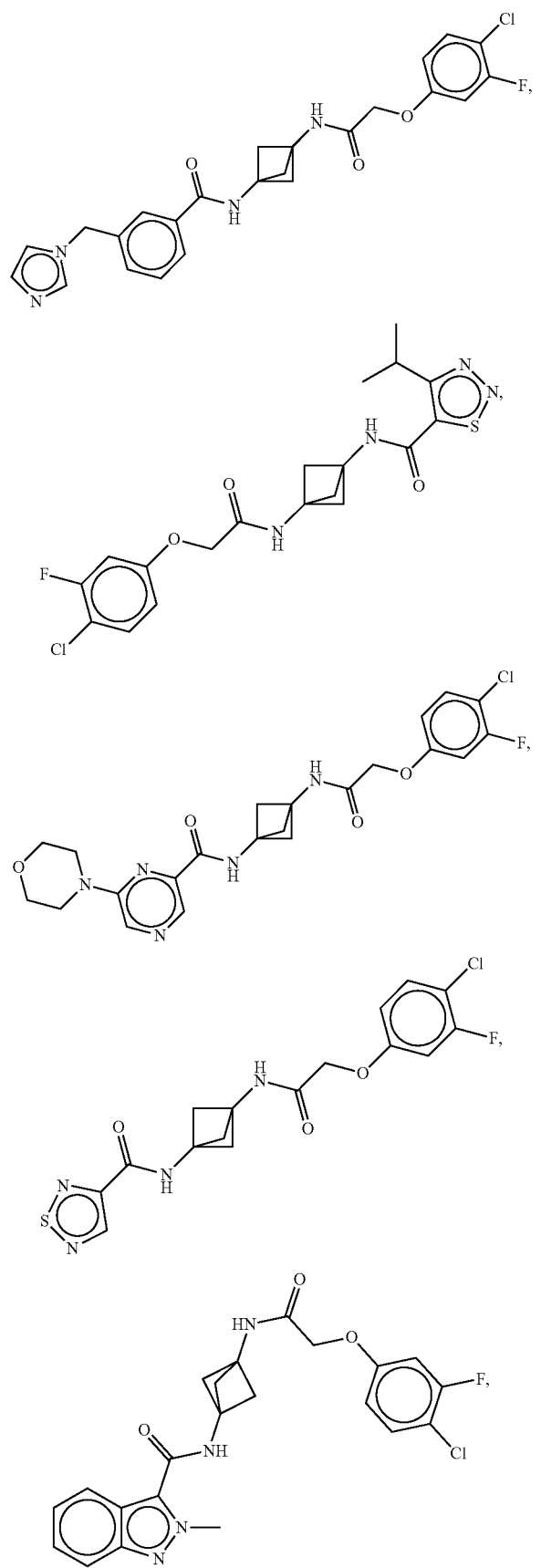
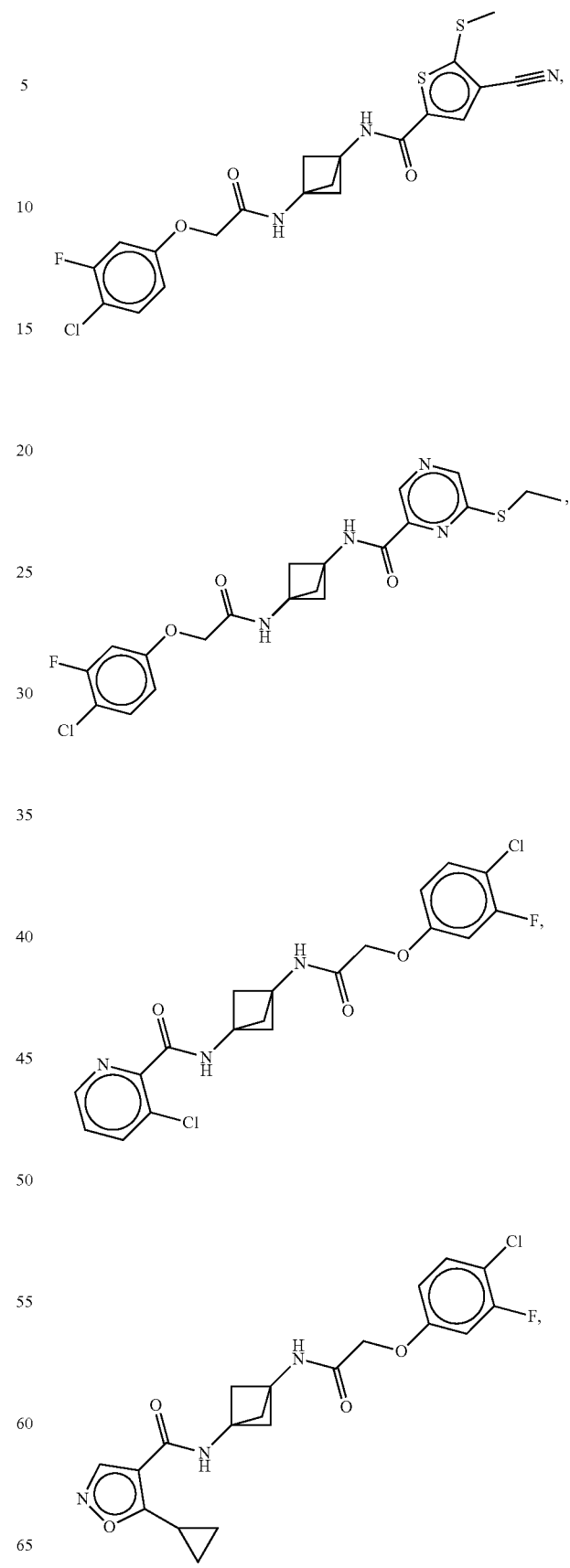

967
-continued
968
-continued
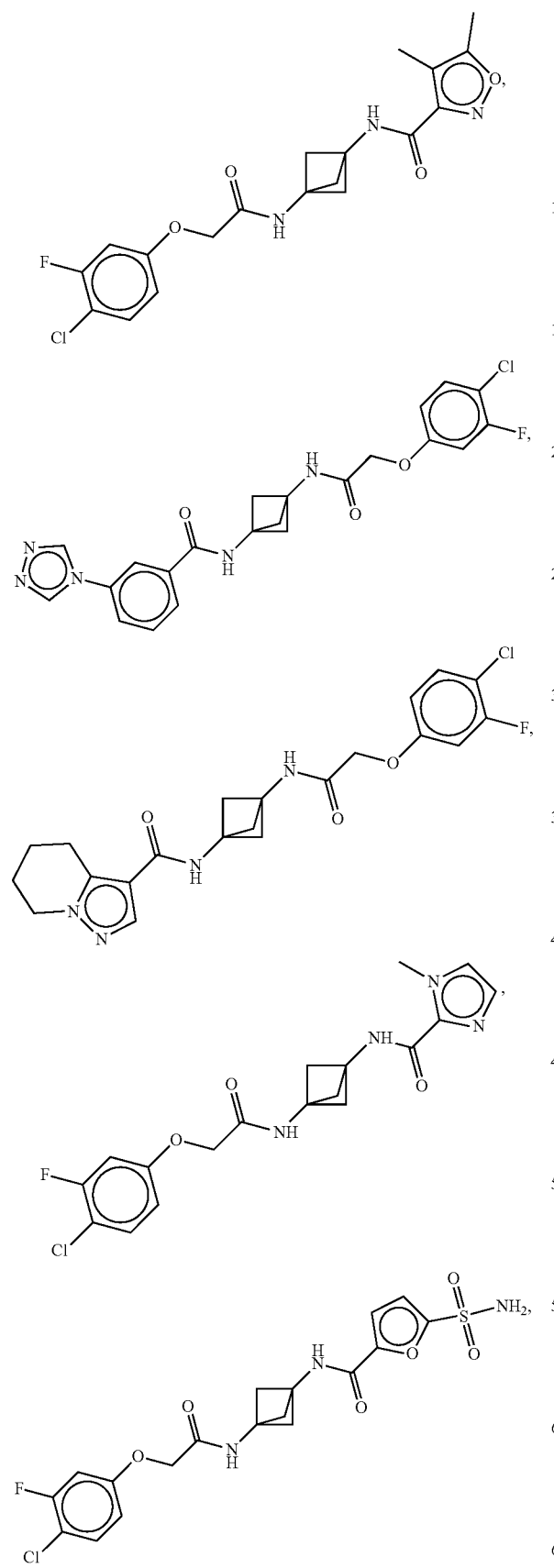
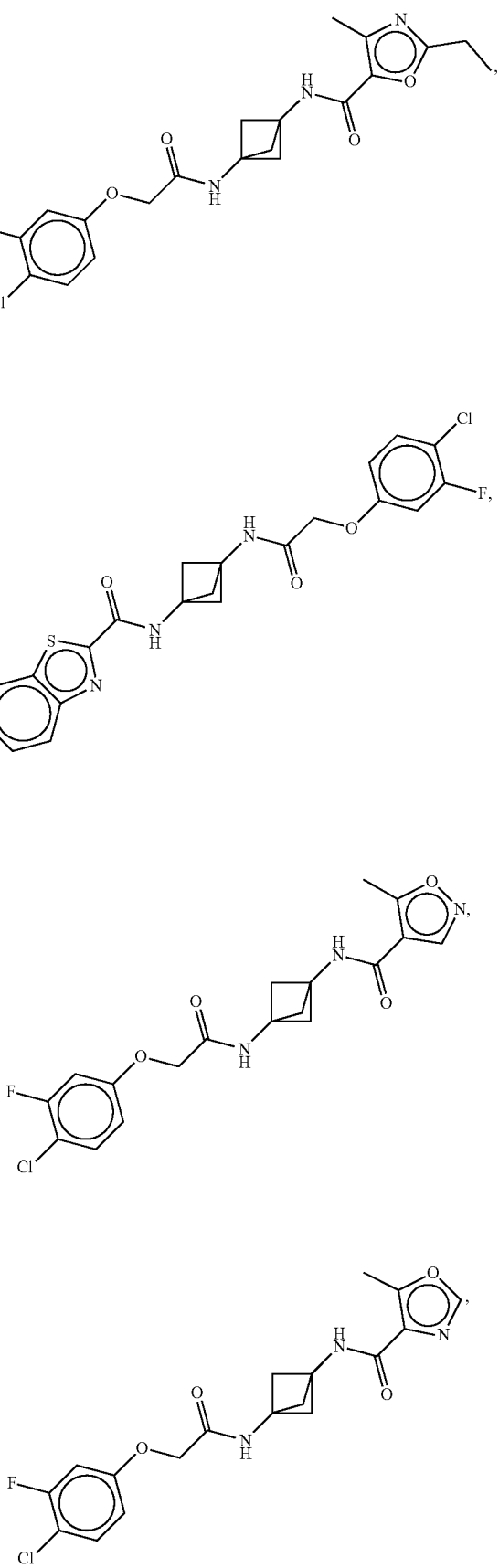

969
-continued
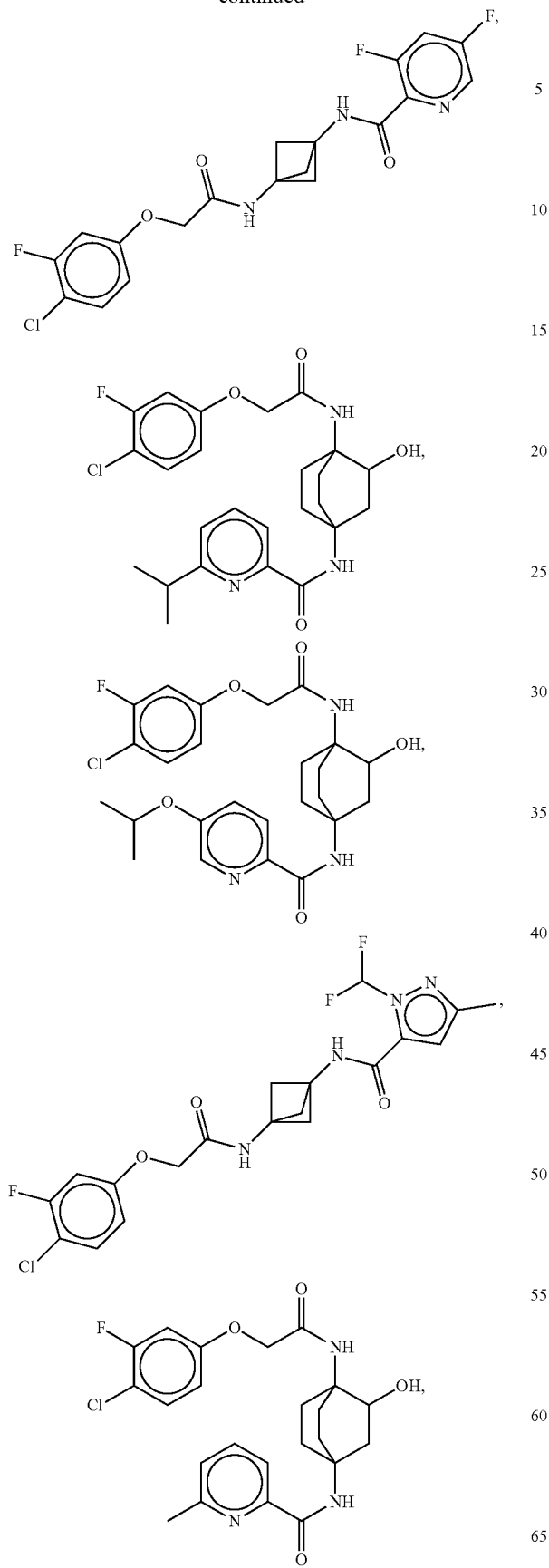
970
-continued
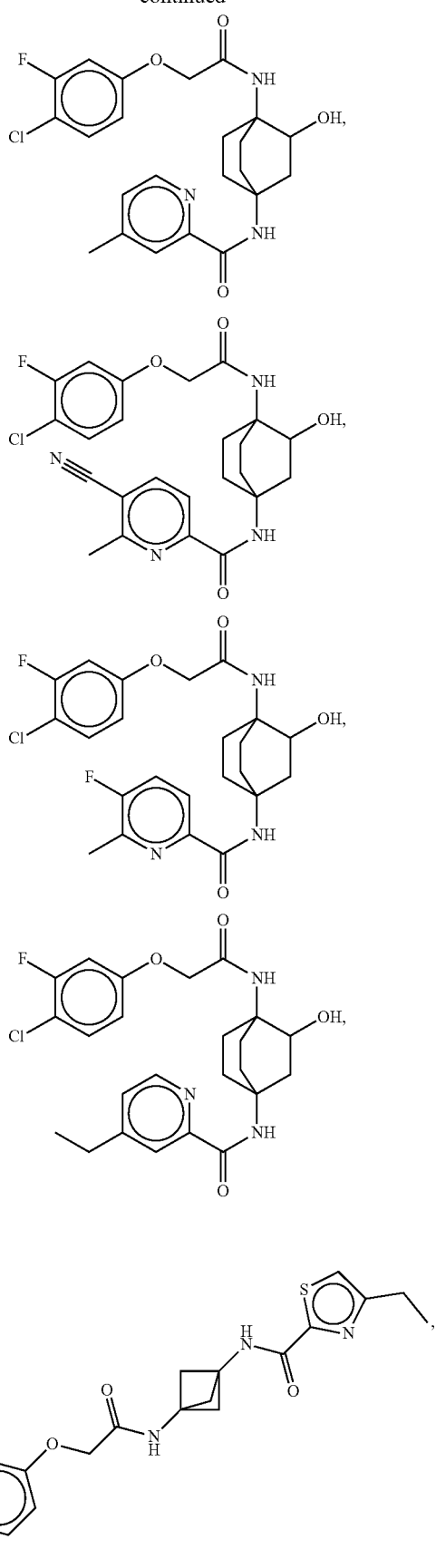

971
-continued
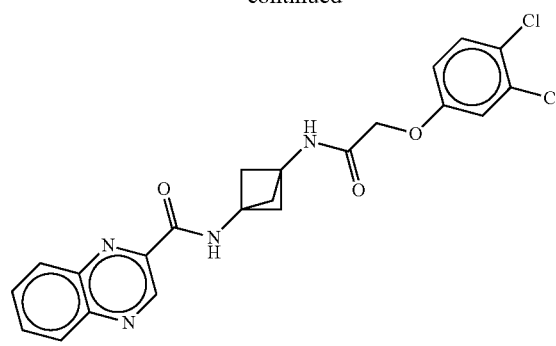
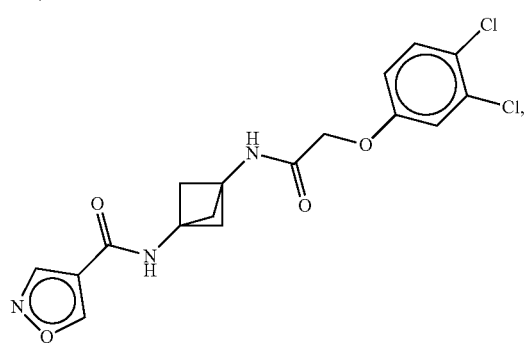
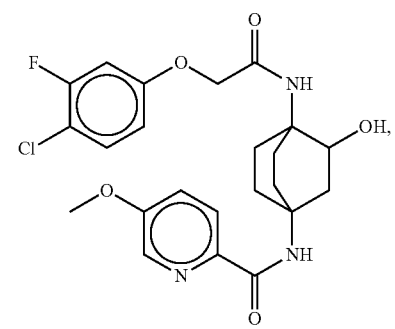
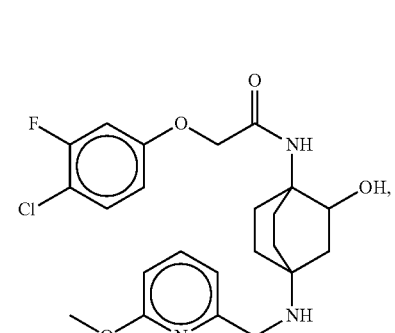
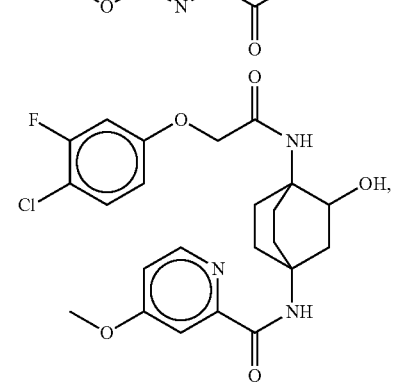
972
-continued
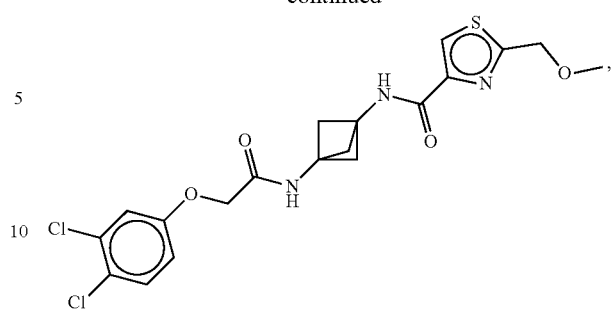
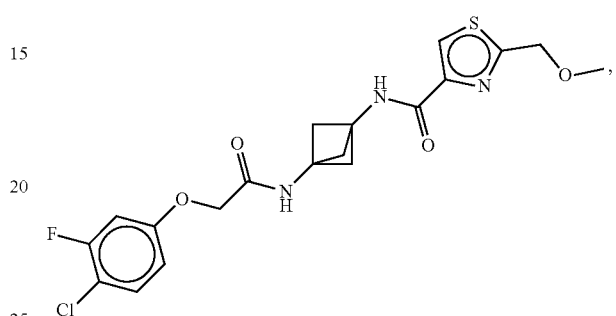
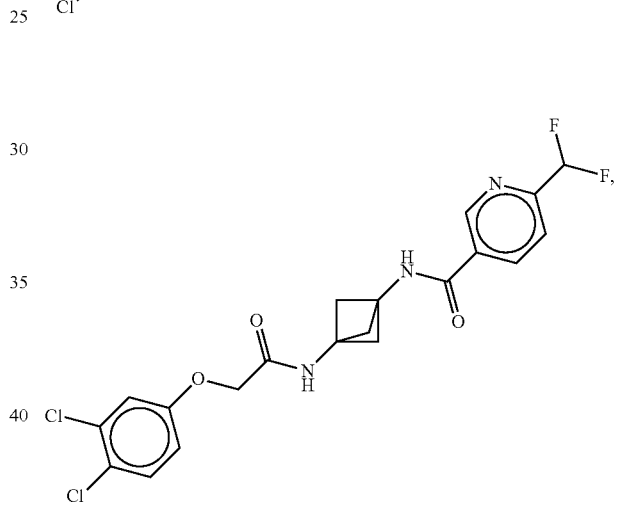
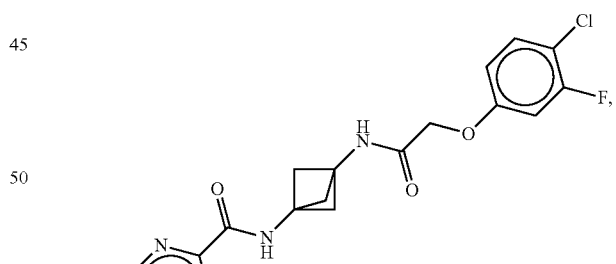
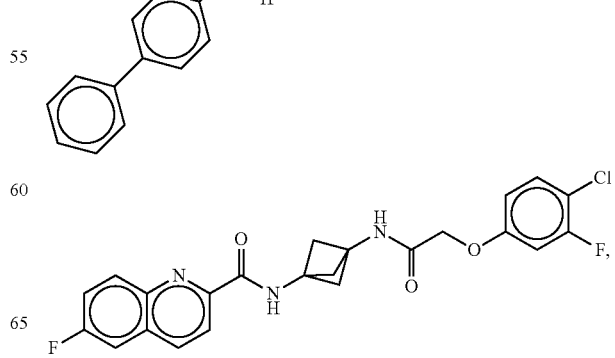

973
-continued
974
-continued
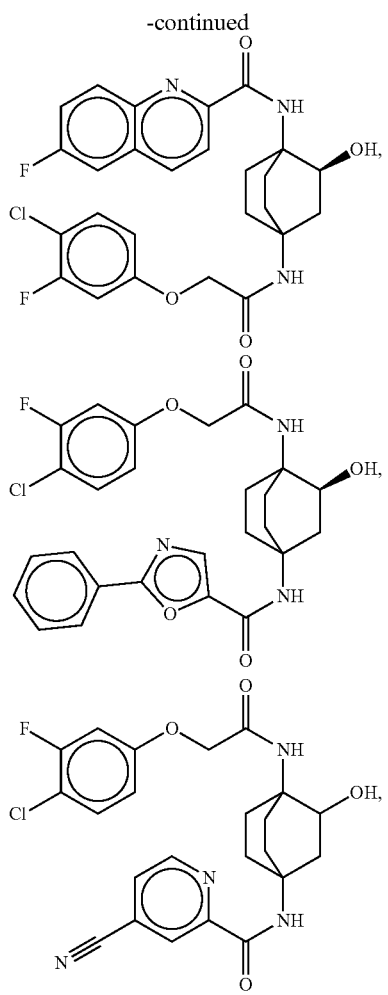
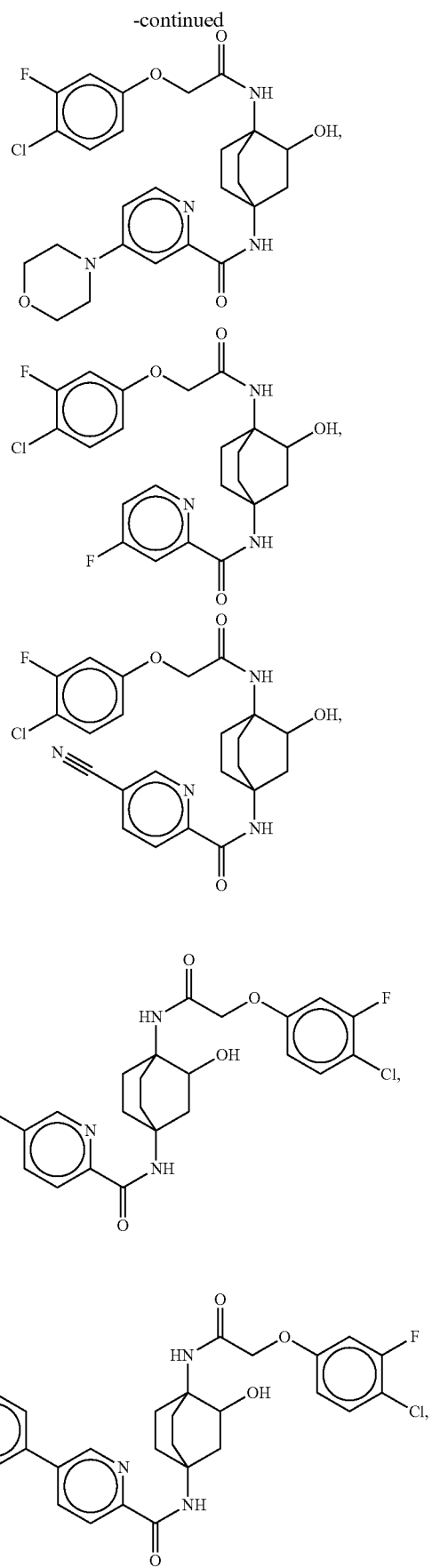

975
-continued
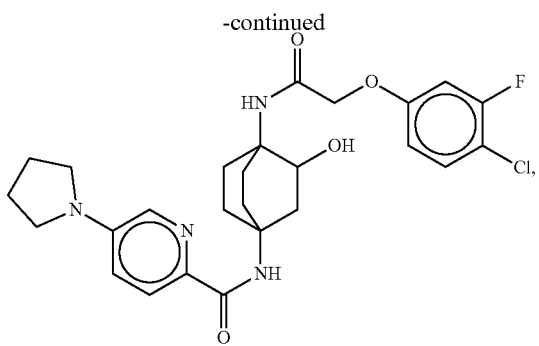
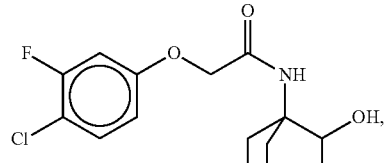
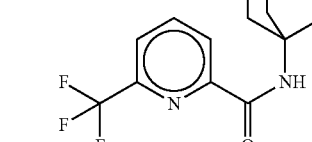
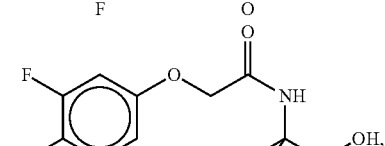
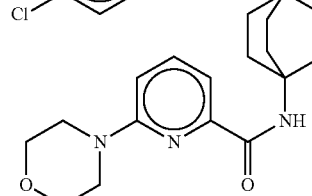
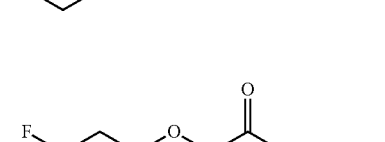
976
-continued
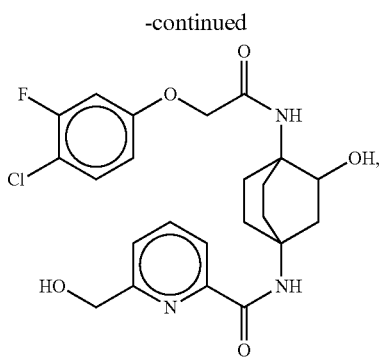
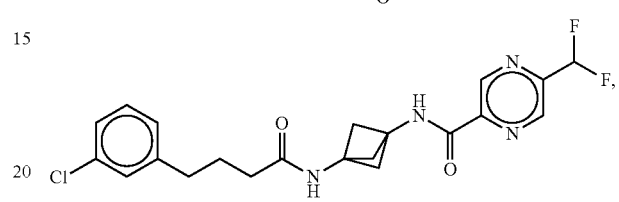
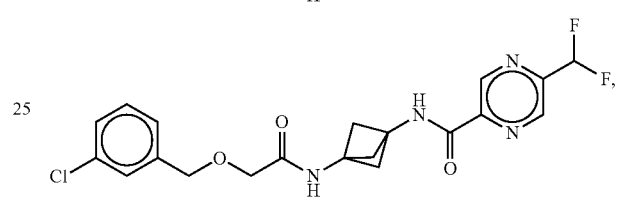
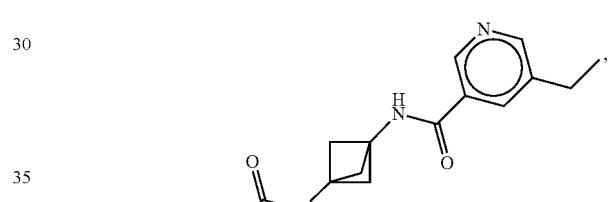
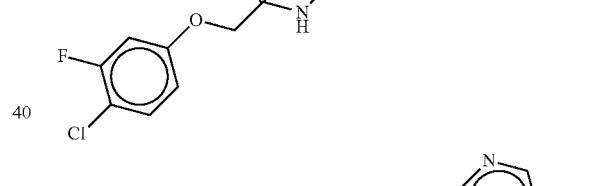
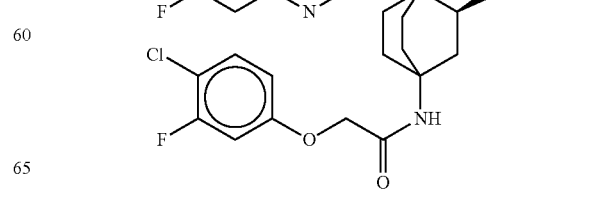

-continued

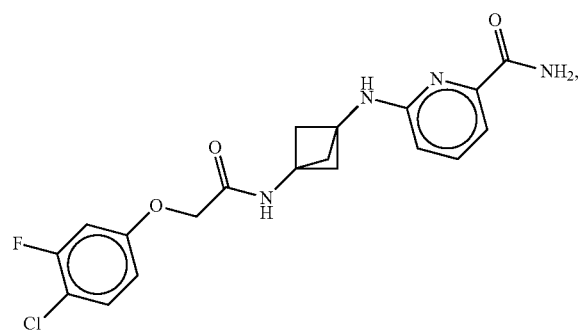
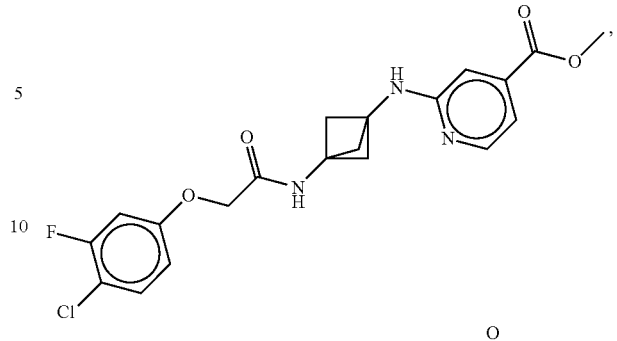
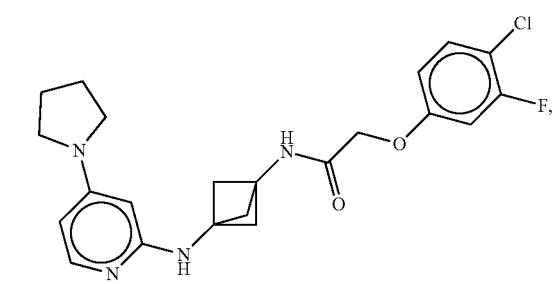
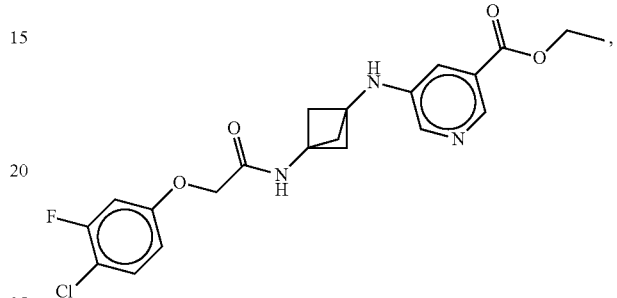
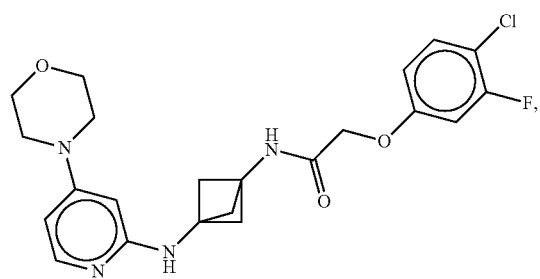
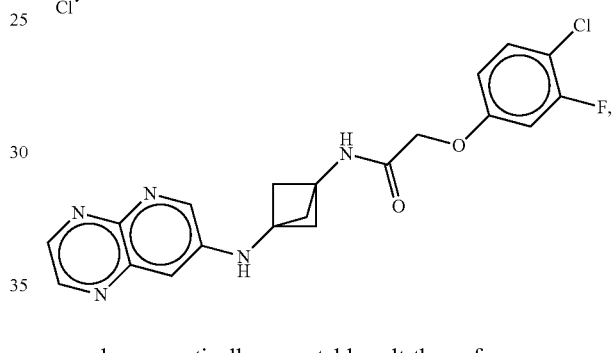
or a pharmaceutically acceptable salt thereof.
* * * * *